United States Patent
Sherer et al.

(10) Patent No.: US 9,988,391 B2
(45) Date of Patent: Jun. 5, 2018

(54) TBK/IKK INHIBITOR COMPOUNDS AND USES THEREOF

(71) Applicant: Merck Patent GmbH, Darmstadt (DE)

(72) Inventors: Brian A. Sherer, Nashua, NH (US); Srinivasa Karra, Pembroke, MA (US); Yufang Xiao, Lexington, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days. days.

(21) Appl. No.: 15/194,780

(22) Filed: Jun. 28, 2016

(65) Prior Publication Data

US 2016/0376283 A1    Dec. 29, 2016

Related U.S. Application Data

(60) Provisional application No. 62/185,788, filed on Jun. 29, 2015.

(51) Int. Cl.
    *C07D 491/048* (2006.01)
    *C07D 519/00* (2006.01)
    *C07D 405/04* (2006.01)

(52) U.S. Cl.
    CPC ....... *C07D 491/048* (2013.01); *C07D 405/04* (2013.01); *C07D 519/00* (2013.01)

(58) Field of Classification Search
    CPC .......................... C07D 491/048; C07D 519/00
    See application file for complete search history.

(56) References Cited

FOREIGN PATENT DOCUMENTS

WO    WO 2013117285 A1 *    8/2013    ........... C07D 495/04

OTHER PUBLICATIONS

Berge, Pharmaceutical Salts, Journal of Pharmaceutical Sciences, 1977, 66(1): 1-19.
Barbie et al., Nature Letters, 2009, 462: 108-114.
Boehm et al., Cell, 2007, 129: 1065-1079.
Chien et al., Cell, 2006, 127: 157-170.
Eddy et al., Cancer Res., 2005, 65 (24): 11375-11383.
Greene and Wuts, "Protective Groups in Organic Synthesis", Wiley Interscience, 3rd Edition, 1999.
Korherr et al., PNAS, 2006, 103(11): 4240-4245.
March's Advanced Organic Chemistry, 5th Ed., Ed: Smith, M.B. and March, J., John Wiley & Sons, New York: 2001.
Organic Chemistry, Thomas Sorrell, University Science Books, Sausalito, 1999.
Weinstein-Oppenheimer et al., Pharmacology and Therapeutics, 2000, 88: 229-279.

* cited by examiner

*Primary Examiner* — Sudhakar Katakam
(74) *Attorney, Agent, or Firm* — Dwight D. Kim; EMD Serono Research and Development Institute

(57) ABSTRACT

The present invention relates to compounds of Formula I and pharmaceutically acceptable compositions thereof, useful as TBK/IKKε inhibitors.

11 Claims, No Drawings

TBK/IKK INHIBITOR COMPOUNDS AND USES THEREOF

RELATED APPLICATION

This applications claims the benefit of U.S. Provisional Application 62/185,788, filed on Jun. 29, 2015, the contents of which are incorporated herein in its entirety by reference.

TECHNICAL FIELD OF THE INVENTION

The present invention provides for compounds of Formula (I) as dual inhibitors of TBK and IKKε that can be used to treat immunological disorders, TBK and/or IKKε inhibitors and their use in the treatment of cancer, and other diseases related to TBK and/or IKKε overexpression, including rheumatoid arthritis, systemic lupus erythematosus or lupus nephritis.

BACKGROUND OF THE INVENTION

Protein kinases regulate nearly every cellular process, including metabolism, cell proliferation, cell differentiation, and cell survival, so they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

One of the principal mechanisms by which cellular regulation is effected is through the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of disease states and/or diseases are attributable to either aberrant activation or functional mutations in the molecular components of kinase cascades. Consequently, considerable attention has been devoted to the characterisation of these proteins and compounds that are able to modulate their activity (for a review see: Weinstein-Oppenheimer et al. Pharma. &. Therap., 2000, 88, 229-279).

IKKε and TBK1 are serine/threonine kinases which are highly homologous to one another and other IkB kinases. The two kinases play an integral role in the innate immune system. Double-stranded RNA viruses are recognised by the Toll-like receptors 3 and 4 and the RNA helicases RIG-I and MDA-5 and result in activation of the TRIF-TBK1/IKKε-IRF3 signalling cascade, which results in a type I interferon response.

In 2007, Boehm et al. described IKKε as a novel breast cancer oncogene (J. S. Boehm et al., Cell 129, 1065-1079, 2007). 354 kinases were investigated with respect to their ability to recapitulate the Ras-transforming phenotype together with an activated form of the MAPK kinase Mek. IKKε was identified here as a cooperative oncogene. In addition, the authors were able to show that IKKε is amplified and overexpressed in numerous breast cancer cell lines and tumour samples. The reduction in gene expression by means of RNA interference in breast cancer cells induces apoptosis and impairs the proliferation thereof. Eddy et al. obtained similar findings in 2005, which underlines the importance of IKKε in breast cancer diseases (S. F. Eddy et al., Cancer Res. 2005; 65 (24), 11375-11383).

A protumorigenic effect of TBK1 was reported for the first time in 2006. In a screening of a gene library comprising 251,000 cDNA, Korherr et al. identified precisely three genes, TRIF, TBK1 and IRF3, which are typically involved in the innate immune defence as proangiogenic factors (C. Korherr et al., PNAS, 103, 4240-4245, 2006). In 2006, Chien et al. (Y. Chien et al., Cell 127, 157-170, 2006) published that TBK1-/- cells can only be transformed to a limited extent using oncogenic Ras, which suggests an involvement of TBK1 in the Ras-mediated transformation. Furthermore, they were able to show that an RNAi-mediated knock-down of TBK1 triggers apoptosis in MCF-7 and Panc-1 cells. Barbie et al. recently published that TBK1 is of essential importance in numerous cancer cell lines with mutated K-Ras, which suggests that TBK1 intervention could be of therapeutic importance in corresponding tumours (D. A. Barbie et al., Nature Letters 1-5, 2009).

Diseases caused by protein kinases are characterised by anomalous activity or hyperactivity of such protein kinases. Anomalous activity relates to either: (1) expression in cells which do not usually express these protein kinases; (2) increased kinase expression, which results in undesired cell proliferation, such as cancer; (3) increased kinase activity, which results in undesired cell proliferation, such as cancer, and/or in hyperactivity of the corresponding protein kinases. Hyperactivity relates either to amplification of the gene which encodes for a certain protein kinase, or the generation of an activity level which can be correlated with a cell proliferation disease (i.e. the severity of one or more symptoms of the cell proliferation disease increases with increasing kinase level). The bioavailability of a protein kinase may also be influenced by the presence or absence of a set of binding proteins of this kinase.

IKKε and TBK1 are highly homologous Ser/Thr kinases critically involved in the innate immune response through induction of type 1 interferons and other cytokines. These kinases are stimulated in response to viral/bacterial infection. Immune response to viral and bacterial infection involves the binding of antigens such as bacterial lipopolysaccharide (LPS), viral doublestranded RNS (dsRNA) to Toll like receptors, then subsequent activation of TBK1 pathway. Activated TBK1 and IKKε phosphorylate IRF3 and IRF7, which triggers the dimerization and nuclear translocation of those interferon regulatory transcription factors, ultimately inducing a signaling cascades leading to IFN production.

SUMMARY OF THE INVENTION

In one aspect, the invention provides a compound of Formula (I):

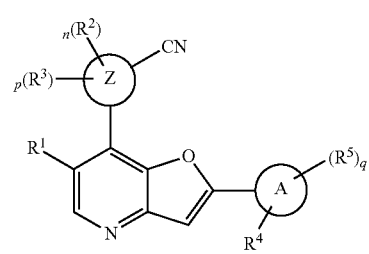

or a pharmaceutically acceptable derivative, solvate, salt, hydrate or stereoisomer thereof.

In another aspect, the invention provides compounds of Formula (I) which are suitable as a dual inhibitor of TBK and IKKε. The compounds of the invention have high solubility and high bioavailability.

In another aspect, the invention provides methods for the treatment and/or prevention of immunological disorders related to TBK and IKKε comprising administering a compound of Formula (I). In another aspect, the invention provides compounds which are able to modulate, especially inhibit the activity or function of TBK and IKKε in disease states in mammals.

In certain embodiments, the present invention provides compounds of Formula (I) which are selective for TBK and/or IKKε. In certain embodiments, the present invention provides compounds of Formula (I) which are selective for TBK and IKKε.

DETAILED DESCRIPTION OF CERTAIN EMBODIMENTS

1. General Description of Compounds of the Invention

In certain aspects, the present invention provides for dual inhibitors of TBK and IKKε. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl) alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

According to the invention, bivalent groups include substitution in both directions, and when inserted between any two groups, (e.g., the group "—OC(O)—" or "CO$_2$" inserted between X and Y), includes both

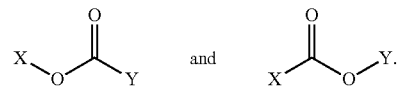

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

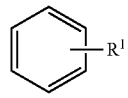

refers to at least

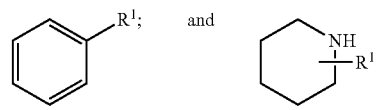

refers to at least

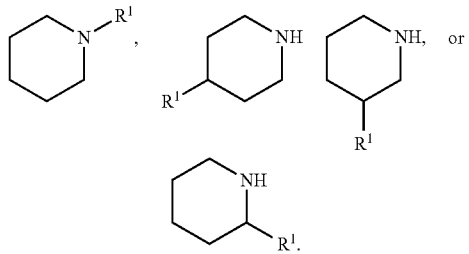

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which are optionally substituted with R°; —(CH$_2$)$_{0-4}$O(CH$_2$)$_{0-1}$Ph which is optionally substituted with R°; —CH=CHPh, which is optionally substituted with R°; —(CH$_2$)$_{0-4}$O(CH$_2$)$_{0-1}$-pyridyl which is optionally substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C (S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° is optionally substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —(CH$_2$)$_{0-2}$R•, -(haloR•), —(CH$_2$)$_{0-2}$OH, —(CH$_2$)$_{0-2}$OR•, —(CH$_2$)$_{0-2}$CH(OR•)$_2$; —O(haloR•), —CN, —N$_3$, —(CH$_2$)$_{0-2}$C(O)R•, —(CH$_2$)$_{0-2}$C(O)OH, —(CH$_2$)$_{0-2}$C(O)OR•, —(CH$_2$)$_{0-2}$SR•, —(CH$_2$)$_{0-2}$SH, —(CH$_2$)$_{0-2}$NH$_2$, —(CH$_2$)$_{0-2}$NHR•, —(CH$_2$)$_{0-2}$NR•$_2$, —NO$_2$, —SiR•$_3$, —OSiR•$_3$, —C(O)SR•, —(C$_{1-4}$ straight or branched alkylene)C(O)OR•, or —SSR• wherein each R• is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,
—OH, protected hydroxy, alkoxy, oxo, thiooxo,
—NO$_2$, —CN, CF$_3$, N$_3$,
—NH$_2$, protected amino, —NH alkyl, —NH alkenyl, —NH alkynyl, —NH cycloalkyl, —NH— aryl, —NH-heteroaryl, —NH-heterocyclic, -dialkylamino, -diarylamino, -diheteroarylamino,
—O— alkyl, —O— alkenyl, —O— alkynyl, —O— cycloalkyl, —O-aryl, —O-heteroaryl, —O-heterocyclic,
—C(O)— alkyl, —C(O)— alkenyl, —C(O)— alkynyl, —C(O)— carbocyclyl, —C(O)-aryl, —C(O)— heteroaryl, —C(O)-heterocyclyl,
—CONH$_2$, —CONH— alkyl, —CONH— alkenyl, —CONH— alkynyl, —CONH-carbocyclyl, —CONH-aryl, —CONH-heteroaryl, —CONH-heterocyclyl,
—OCO$_2$— alkyl, —OCO$_2$— alkenyl, —OCO$_2$— alkynyl, —OCO$_2$— carbocyclyl, —OCO$_2$-aryl, —OCO$_2$-heteroaryl, —OCO$_2$-heterocyclyl, —OCONH$_2$, —OCONH— alkyl, —OCONH— alkenyl, —OCONH— alkynyl, —OCONH— carbocyclyl, —OCONH— aryl, —OCONH— heteroaryl, —OCONH— heterocyclyl,
—NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —NHCO$_2$— alkyl, —NHCO$_2$— alkenyl, —NHCO$_2$— alkynyl, —NHCO$_2$— carbocyclyl, —NHCO$_2$— aryl, —NHCO$_2$— heteroaryl, —NHCO$_2$— heterocyclyl, —NHC(O)NH$_2$, —NHC(O)NH— alkyl, —NHC(O)NH— alkenyl, —NHC(O)NH— alkenyl, —NHC(O)NH— carbocyclyl, —NHC(O)NH-aryl, —NHC(O)NH-heteroaryl, —NHC(O)

NH— heterocyclyl, NHC(S)NH$_2$, —NHC(S)NH— alkyl, —NHC(S)NH— alkenyl, —NHC(S)NH— alkynyl, —NHC(S)NH— carbocyclyl, —NHC(S)NH-aryl, —NHC(S)NH-heteroaryl, —NHC(S)NH-heterocyclyl, —NHC(NH)NH$_2$, —NHC(NH)NH— alkyl, —NHC(NH)NH— -alkenyl, —NHC(NH)NH— alkenyl, —NHC(NH)NH— carbocyclyl, —NHC(NH)NH-aryl, —NHC(NH)NH-heteroaryl, —NHC(NH)NH— heterocyclyl, —NHC(NH)— alkyl, —NHC(NH)— alkenyl, —NHC(NH)— alkenyl, —NHC(NH)— carbocyclyl, —NHC(NH)-aryl, —NHC(NH)-heteroaryl, —NHC(NH)-heterocyclyl, —C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl, —S(O)— alkyl, —S(O)— alkenyl, —S(O)— alkynyl, —S(O)— carbocyclyl, —S(O)-aryl, —S(O)-heteroaryl, —S(O)-heterocyclyl —SO$_2$NH$_2$, —SO$_2$NH— alkyl, —SO$_2$NH— alkenyl, —SO$_2$NH— alkynyl, —SO$_2$NH— carbocyclyl, —SO$_2$NH— aryl, —SO$_2$NH— heteroaryl, —SO$_2$NH— heterocyclyl, —NHSO$_2$— alkyl, —NHSO$_2$— alkenyl, —NHSO$_2$— alkynyl, —NHSO$_2$— carbocyclyl, —NHSO$_2$-aryl, —NHSO$_2$-heteroaryl, —NHSO$_2$-heterocyclyl,

—CH$_2$NH$_2$, —CH$_2$SO$_2$CH$_3$,

-mono-, di-, or tri-alkyl silyl,

-alkyl, -alkenyl, -alkynyl, -aryl, -arylalkyl, -heteroaryl, -heteroarylalkyl, heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. In some embodiments, the group comprises one or more deuterium atoms.

Deuterium ($^2$H) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect (C$_{max}$), area under the dose response curve (AUC), and F; and in terms of reduced clearance, dose and materials costs.

As used herein, the term "modulator" is defined as a compound that binds to and/or inhibits the target with measurable affinity. In certain embodiments, a modulator has an IC$_{50}$ and/or binding constant of less about 50 μM, less than about 1 µM, less than about 500 nM, less than about 100 nM, or less than about 10 nM.

The terms "measurable affinity" and "measurably inhibit," as used herein, means a measurable change in TBK and/or IKKε activity between a sample comprising a compound of the present invention, or composition thereof, and TBK and/or IKKε, and an equivalent sample comprising TBK and/or IKKε, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

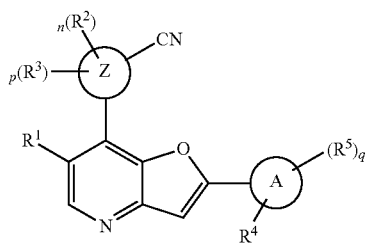

I or pharmaceutically acceptable derivatives, solvates, salts, hydrates, or stereoisomers thereof, wherein:
$R^1$ is hydrogen, optionally substituted $C_{1-6}$ aliphatic, optionally substituted 3-8 membered saturated or partially unsaturated carbocyclic ring, —OR, or halogen;
ring Z is phenyl, pyridine, or pyrimidine;
each $R^2$ is independently —R, halogen, —OR, —SR, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
each $R^3$ is independently —R, halogen, —OR, —SR, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
ring A is phenyl or a 5-6-membered heteroaryl having 1, 2, or 3 nitrogens;
$R^4$ is —R, halogen, —OR, —SR, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
each $R^5$ is independently —R, halogen, —OR, —SR, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
each R is independently hydrogen, $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, a 5-6 membered monocyclic heteroaryl ring having 1-4 heteroatoms independently selected from nitrogen, oxygen, or sulfur; or a 6-12 membered spiro, fused, or bridged bicyclic carbocyclic or heterocyclic ring having 1-4 heteroatoms independently selected from nitrogen, oxygen, or sulfur; each of which is optionally substituted; or
two R groups on the same atom are taken together with the atom to which they are attached to form a $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
n is 1 or 2;
p is 0, 1, or 2; and
q is 0, 1, or 2;
wherein the following compounds are excluded:
4-{7-[3-cyano-4-(tetrahydro-pyran-4-yloxy)-phenyl]-furo[3,2-b]pyridin-2-yl}-3-fluoro-N-(2-hydroxy-ethyl)-N-methyl-benzamide;
5-{2-[2-fluoro-4-(piperazine-1-carbonyl)-phenyl]-furo[3,2-b]pyridin-7-yl}-2-(tetrahydro-pyran-4-yloxy)-benzonitrile;
5-{2-[2-fluoro-4-(5-oxo-[1,4]diazepane-1-carbonyl)-phenyl]-furo[3,2-b]pyridin-7-yl}-2-(tetrahydro-pyran-4-yloxy)-benzonitrile;
5-{2-[2-fluoro-4-(4-hydroxy-piperidine-1-carbonyl)-phenyl]-furo[3,2-b]pyridin-7-yl}-2-(tetrahydro-pyran-4-yloxy)-benzonitrile;
5-{2-[2-fluoro-4-(morpholine-4-carbonyl)-phenyl]-furo[3,2-b]pyridin-7-yl}-2-(tetrahydro-pyran-4-yloxy)-benzonitrile;
4-{7-[3-cyano-4-(tetrahydro-pyran-4-yloxy)-phenyl]-furo[3,2-b]pyridin-2-yl}-N-(2-hydroxy-ethyl)-3-methoxy-N-methyl-benzamide;
5-{2-[4-(4-hydroxy-piperidine-1-carbonyl)-2-methoxy-phenyl]-furo[3,2-b]pyridin-7-yl}-2-(tetrahydro-pyran-4-yloxy)-benzonitrile;
4-{7-[3-cyano-4-(tetrahydro-pyran-4-yloxy)-phenyl]-furo[3,2-b]pyridin-2-yl}-3-methoxy-N,N-dimethyl-benzamide;
4-{7-[3-cyano-4-(tetrahydro-pyran-4-yloxy)-phenyl]-furo[3,2-b]pyridin-2-yl}-3-methoxy-N—(S)-piperidin-3-yl-benzamide; and
4-{7-[3-cyano-4-(tetrahydro-pyran-4-yloxy)-phenyl]-furo[3,2-b]pyridin-2-yl}-3-methoxy-N—(R)-piperidin-3-yl-benzamide.

In certain embodiments, $R^1$ is H.
In certain embodiments, $R^1$ is optionally substituted $C_{1-6}$ aliphatic, —OR, or halogen.
In certain embodiments, $R^1$ is $C_{1-6}$ aliphatic.
In certain embodiments, $R^1$ is methyl, ethyl, propyl, i-propyl, butyl, s-butyl, t-butyl, straight chain or branched pentyl, or straight chain or branched hexyl, each of which is optionally substituted. In certain embodiments, $R^1$ is methyl. In certain embodiments, $R^1$ is i-propyl.
In certain embodiments, $R^1$ is a 3-8 membered saturated or partially unsaturated carbocyclic ring.
In certain embodiments, $R^1$ is cyclopropyl, cyclobutyl, cyclopentyl, or cyclohexyl. In certain embodiments, $R^1$ is cyclopropyl.
In certain embodiments, $R^1$ is —OR. In certain embodiments, $R^1$ is —OMe.
In certain embodiments, $R^1$ is halogen.

In certain embodiments, R¹ is F or Cl.
In certain embodiments, R¹ is methyl, i-propyl, cyclopropyl, —OMe, F, or Cl.
In certain embodiments, ring Z is phenyl.
In certain embodiments, ring Z is pyridine.
In certain embodiments, ring Z is pyrimidine.
In certain embodiments, ring Z is

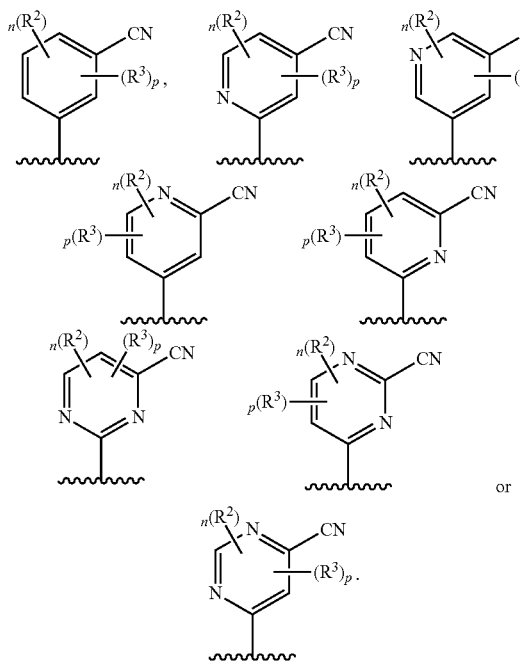

In certain embodiments, ring Z is

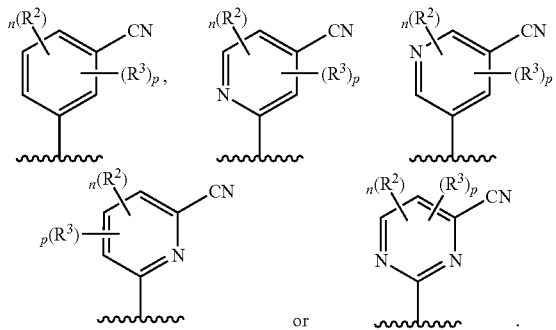

In certain embodiments, each R² is independently —R, halogen, —OR, or —N(R)₂.

In certain embodiments, each R² is independently $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or R² is halogen, —OR, or —N(R)₂.

In certain embodiments, each R² is independently methyl, ethyl, propyl, i-propyl, butyl, s-butyl, t-butyl, straight chain or branched pentyl, or straight chain or branched hexyl; each of which is optionally substituted.

In certain embodiments, each R² is independently phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, each R² is independently F, Cl, Br, or I.

In certain embodiments, each R² is independently —OR, or —N(R)₂.

In certain embodiments, each R² is independently —OH, —OCH₃, —F,

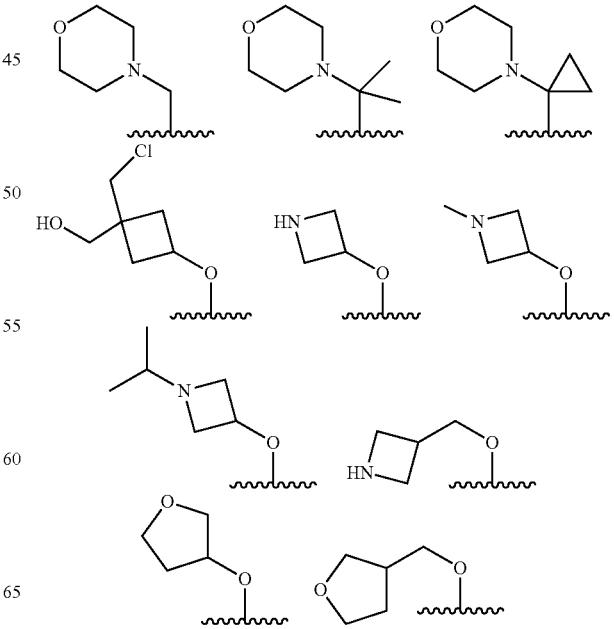

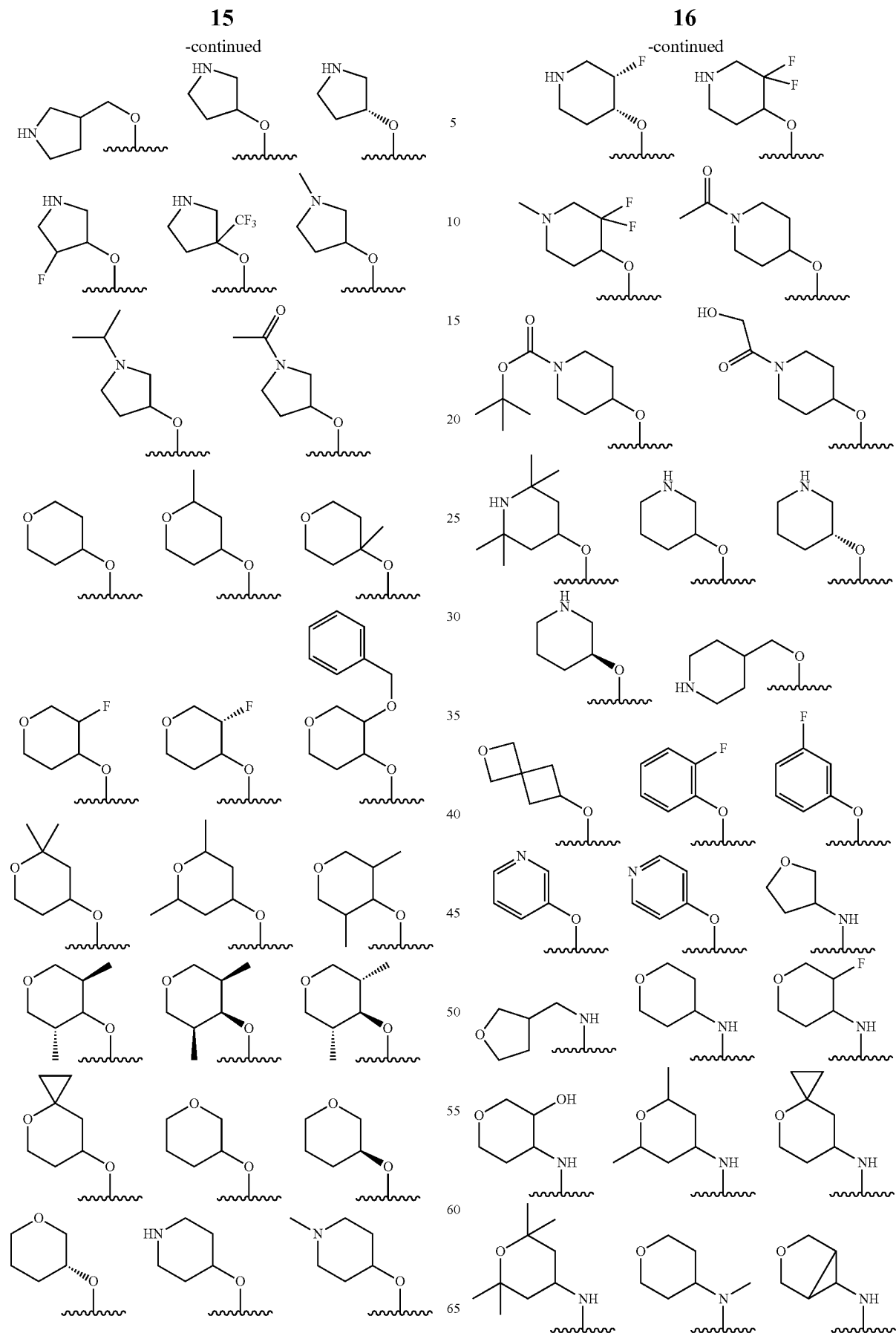

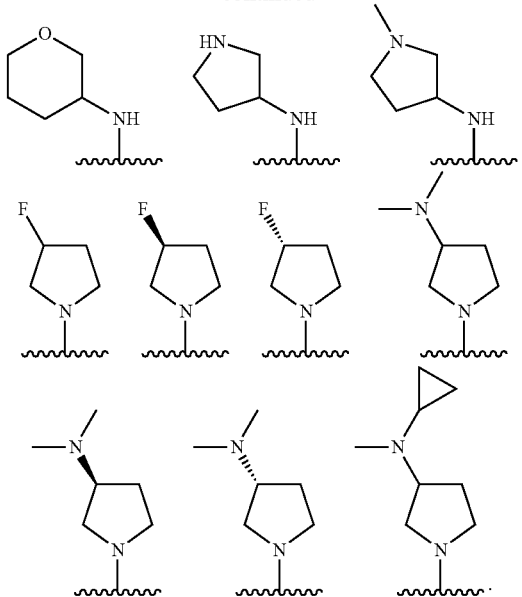

In certain embodiments, each R³ is independently —R, halogen, —OR, or —N(R)₂.

In certain embodiments, each R³ is independently H.

In certain embodiments, each R³ is independently an optionally substituted 3-8 membered saturated or partially unsaturated carbocyclic ring.

In certain embodiments, each R³ is independently halogen. In certain embodiments, each R³ is independently F.

In certain embodiments, each R³ is independently H, F, —OCH₃, or

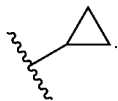 [SMILES: *C1CC1]

In certain embodiments, ring A is phenyl.

In certain embodiments, ring A is pyrrolyl, pyrazolyl, imidazolyl, pyridyl, pyridazinyl, pyrimidinyl, pyrizinyl, or triazinyl.

In certain embodiments, ring A is pyrazolyl, pyridyl, or pyridazinyl.

In certain embodiments, ring A is

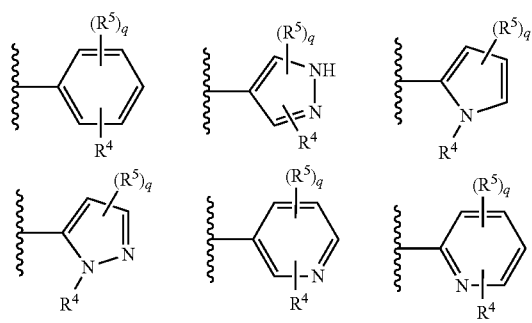

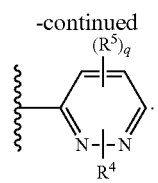

In certain embodiments, ring A is

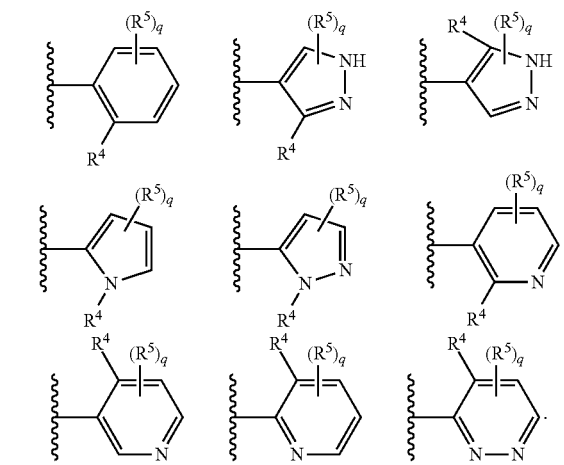

In certain embodiments, R⁴ is —R, halogen, —OR, —NRC(O)R, —NRC(O)N(R)₂, —NRSO₂R, or —N(R)₂. In certain embodiments, R⁴ is —R, halogen, or —OR.

In certain embodiments, R⁴ is H.

In certain embodiments, R⁴ is C₁₋₆ aliphatic, C₃₋₁₀ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, R⁴ is C₁₋₆ aliphatic which is optionally substituted.

In certain embodiments, R⁴ is an optionally substituted methyl, ethyl, propyl, i-propyl, butyl, s-butyl, t-butyl, straight chain or branched pentyl, or straight chain or branched hexyl.

In certain embodiments, R⁴ is —F, —Cl, —Br, or —I.

In certain embodiments, R⁴ is —OR, wherein R is H, C₁₋₆ aliphatic, C₃₋₁₀ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, R⁴ is -Me, -Et, —CF₃, —OH, —OCH₃, —OCF₃, —F, or —Cl.

In certain embodiments, each R⁵ is independently —R, —OR, —SR, —CN, —NO₂, —C(O)R, —CO₂R, —C(O)N(R)₂, —NRC(O)R, —NRC(O)N(R)₂, —NRSO₂R, or —N(R)₂.

In certain embodiments, each R⁵ is independently —R, —C(O)R, —CO₂R, —C(O)N(R)₂, —NRC(O)R, or —N(R)₂.

In certain embodiments, each R⁵ is independently C₁₋₆ aliphatic, C₃₋₁₀ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or $R^2$ is halogen, —OR, or —N(R)$_2$.

In certain embodiments, each $R^5$ is independently methyl, ethyl, propyl, i-propyl, butyl, s-butyl, t-butyl, straight chain or branched pentyl, or straight chain or branched hexyl; each of which is optionally substituted.

In certain embodiments, each $R^5$ is independently phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, each $R^5$ is independently —C(O)R, —CO$_2$R, —C(O)N(R)$_2$, —NRC(O)R, or —N(R)$_2$.

In certain embodiments, each $R^5$ is independently —NH$_2$, —NHC(O)Me,

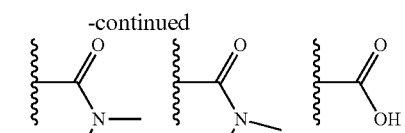
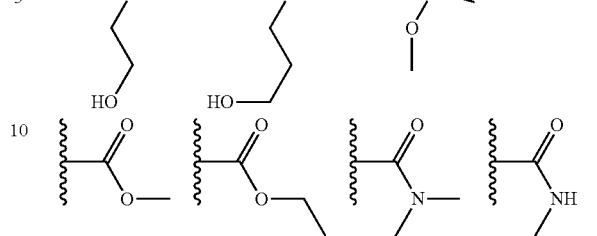
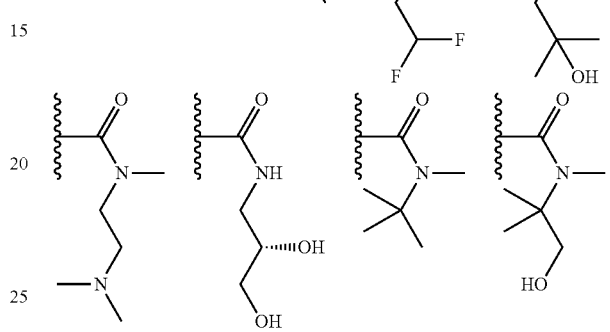
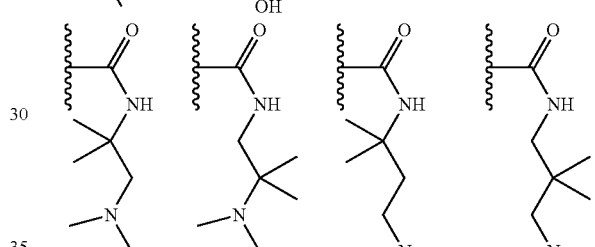
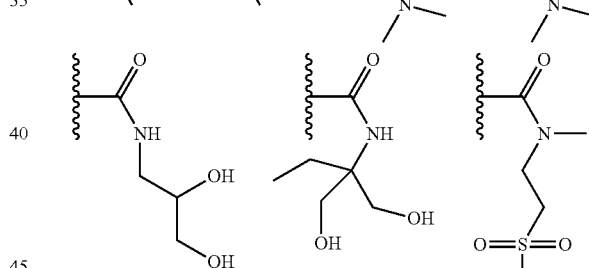
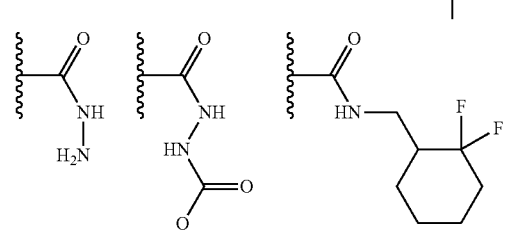
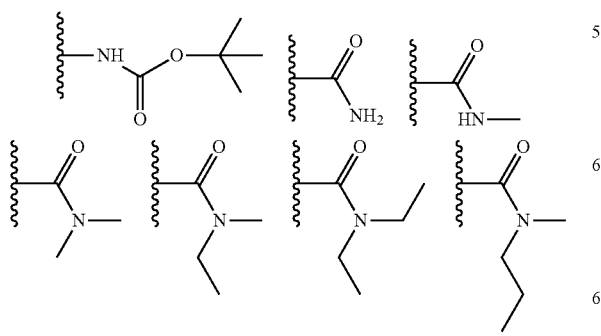
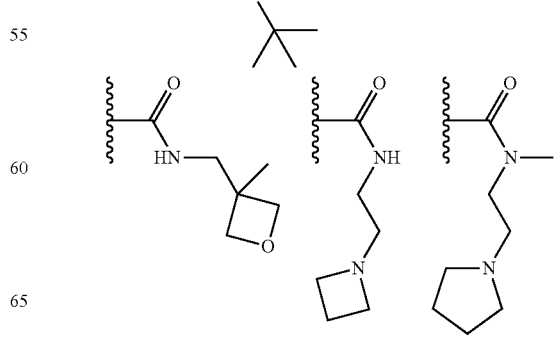

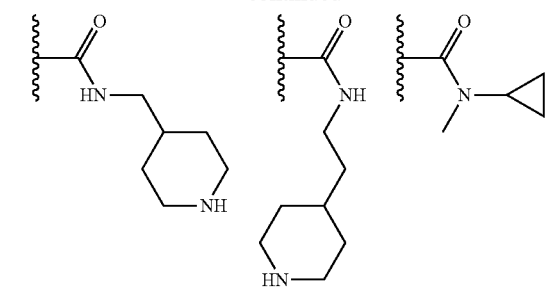
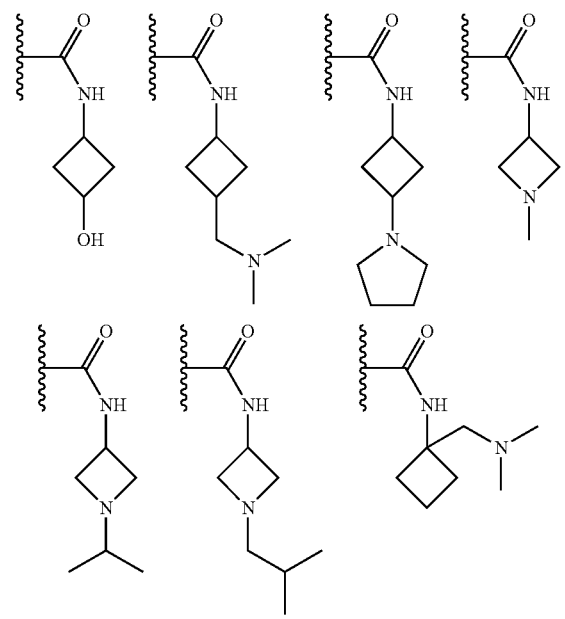
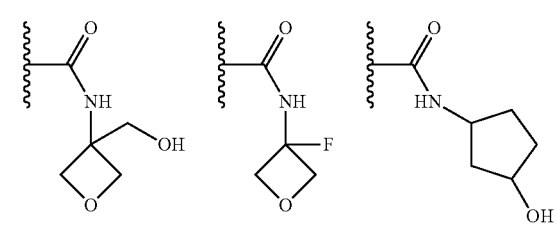
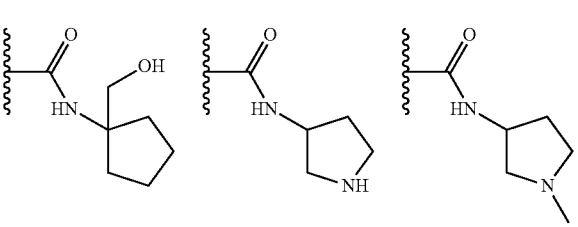
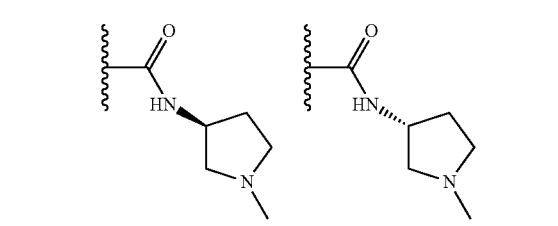
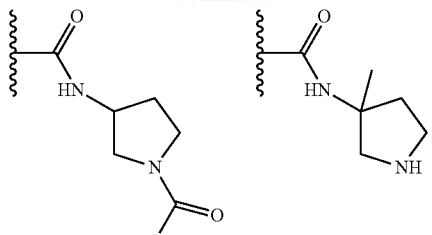
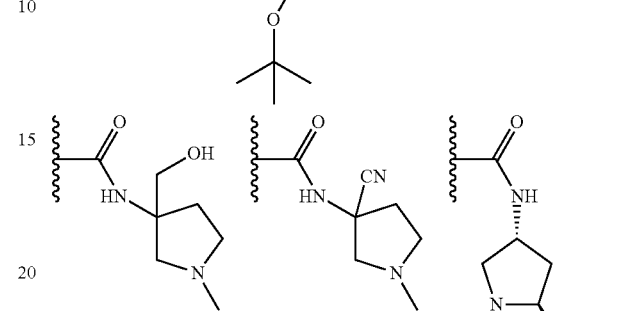
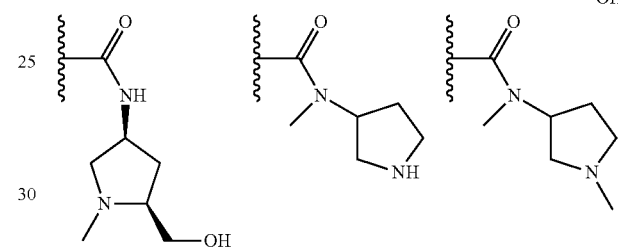
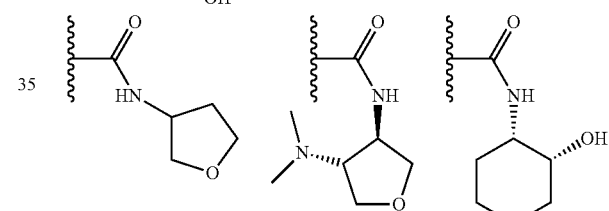
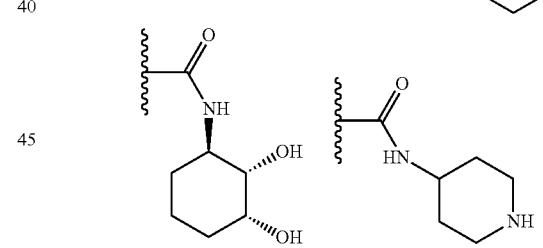
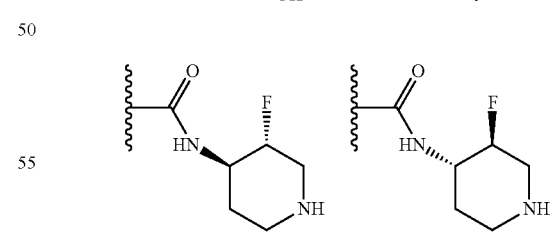
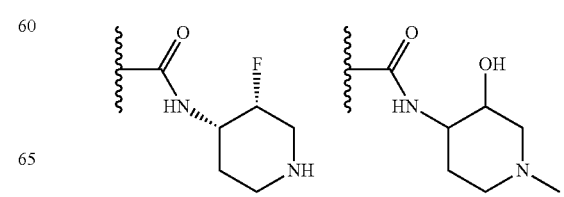

-continued
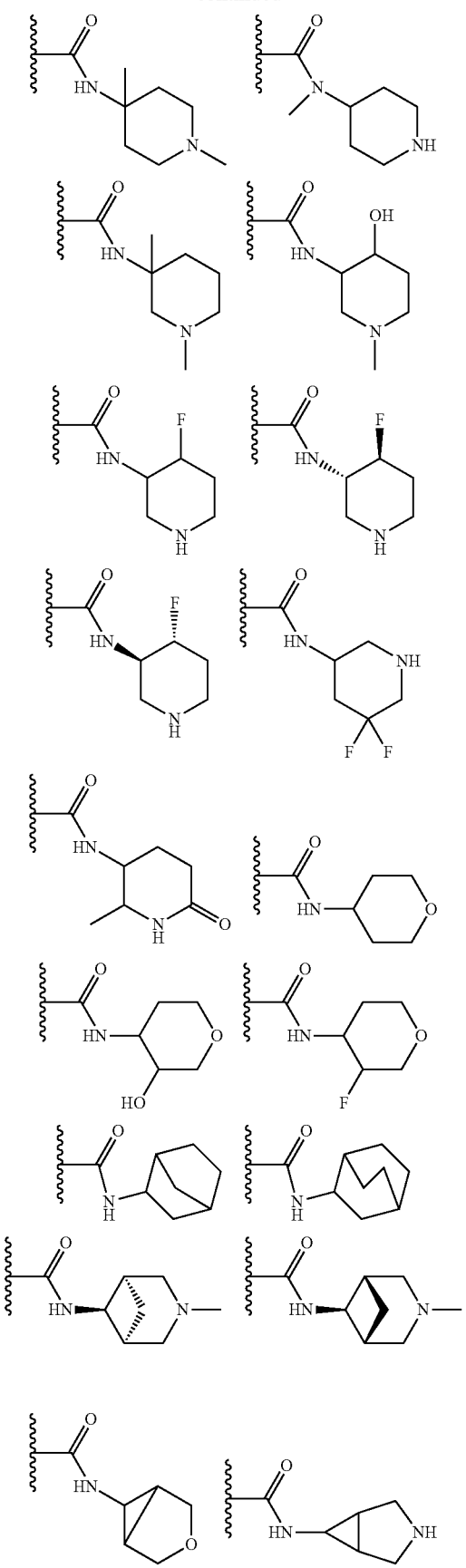
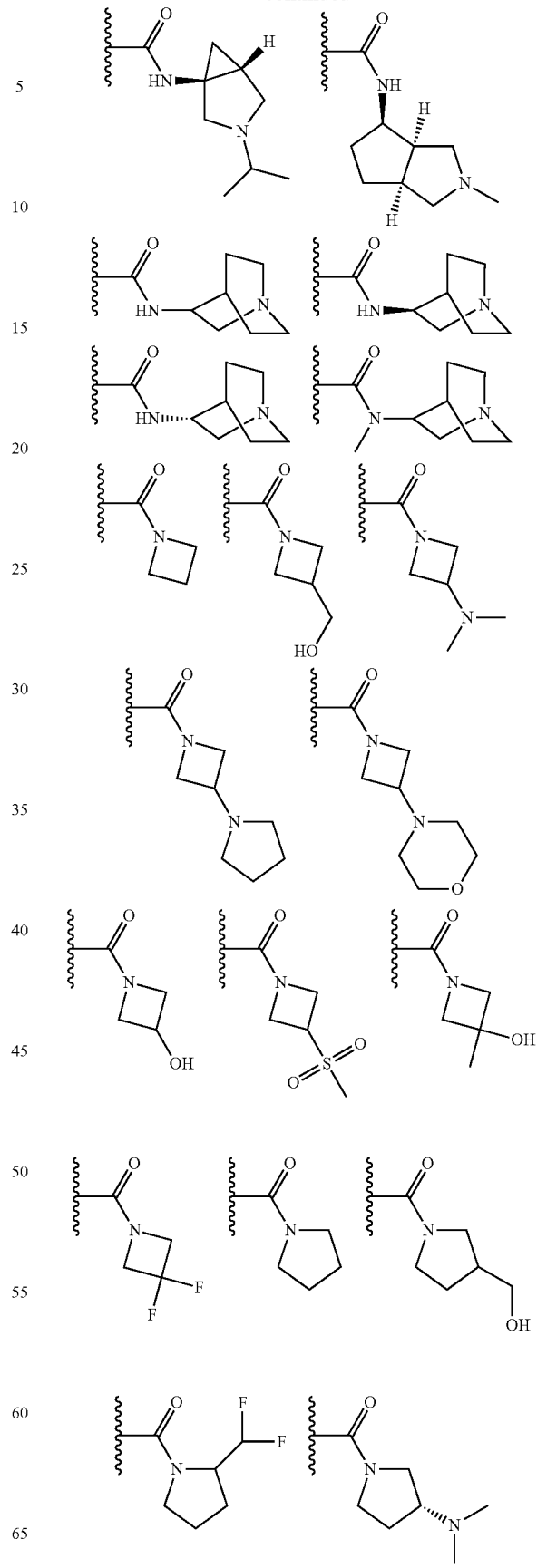

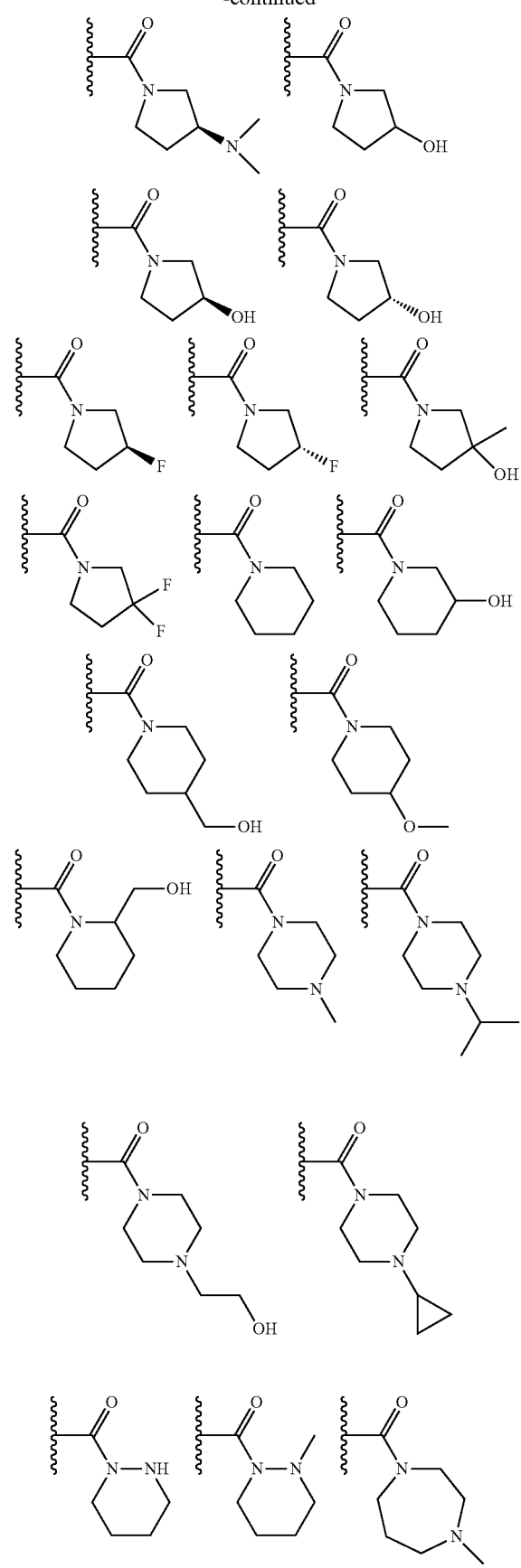
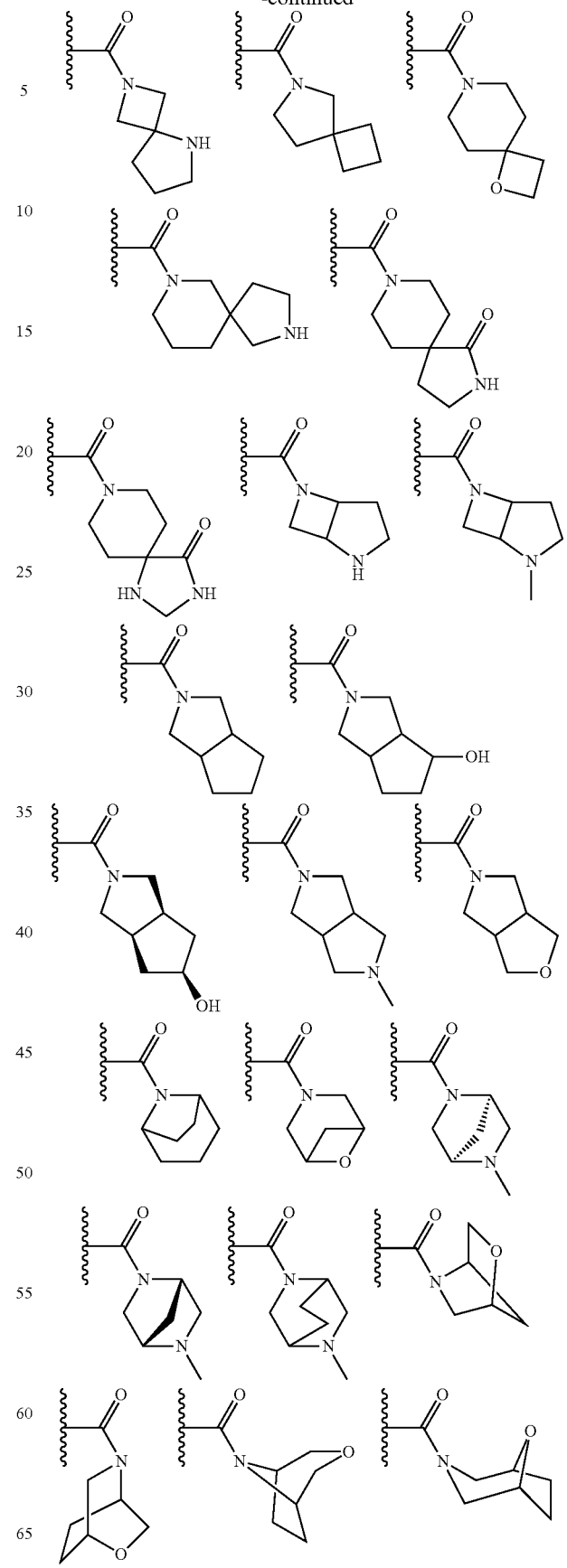

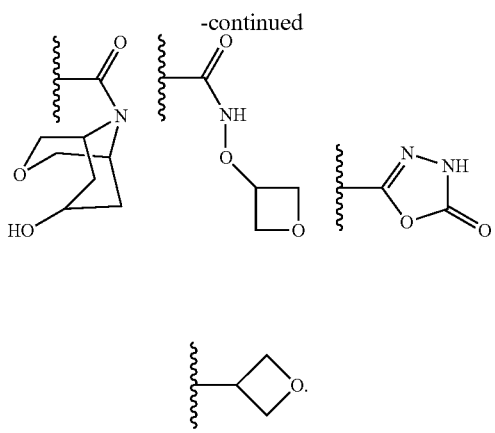

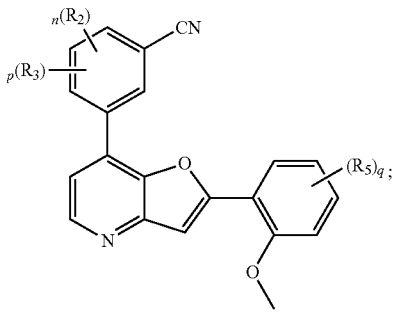

In certain embodiments, each of Ring A, Ring Z, R, $R^2$, $R^3$, $R^4$, $R^5$, n, p, and q, is as defined above and described in embodiments, classes and subclasses above and herein, singly or in combination.

In certain embodiments, the present invention provides a compound of formula II,

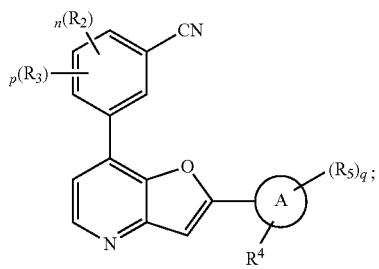

or a pharmaceutically acceptable salt thereof, wherein each of ring A, $R^2$, $R^3$, $R^4$, $R^5$, n, p, and q, is as defined above and described in embodiments, classes and subclasses above and herein, singly or in combination.

In certain embodiments, the present invention provides a compound of formula III,

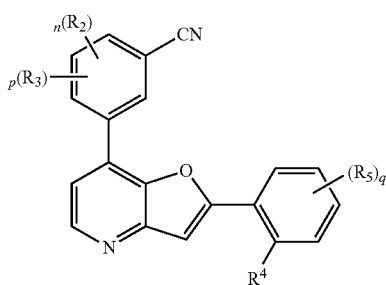

or a pharmaceutically acceptable salt thereof, wherein each of $R^2$, $R^3$, $R^4$, $R^5$, n, p, and q, is as defined above and described in embodiments, classes and subclasses above and herein, singly or in combination.

In certain embodiments, the present invention provides a compound of formula IV, or a pharmaceutically acceptable salt thereof, wherein each of $R^2$, $R^3$, $R^5$, n, p, and q, is as defined above and described in embodiments, classes and subclasses above and herein, singly or in combination.

In certain embodiments, the present invention provides a compound of formula V,

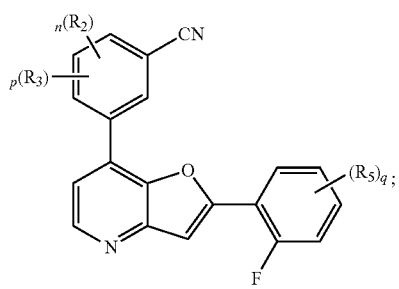

or a pharmaceutically acceptable salt thereof, wherein each of $R^2$, $R^3$, $R^5$, n, p, and q, is as defined above and described in embodiments, classes and subclasses above and herein, singly or in combination.

In certain embodiments, the present invention provides a compound of formula VI,

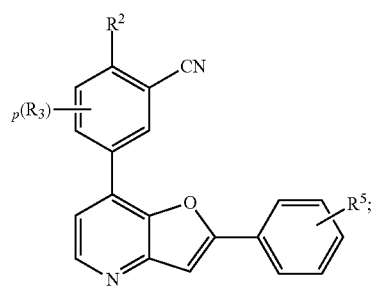

or a pharmaceutically acceptable salt thereof, wherein each of $R^2$, $R^3$, $R^5$, and p, is as defined above and described in embodiments, classes and subclasses above and herein, singly or in combination.

In certain embodiments, the present invention provides a compound of formula VII,

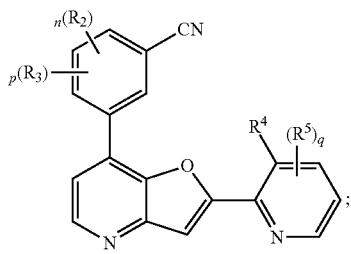

VII or a pharmaceutically acceptable salt thereof, wherein each of $R^2$, $R^3$, $R^4$, $R^5$, n, p, and q, is as defined above and described in embodiments, classes and subclasses above and herein, singly or in combination.

In certain embodiments, the present invention provides a compound of formula VIII,

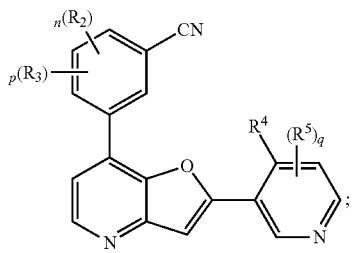

VIII or a pharmaceutically acceptable salt thereof, wherein each of $R^2$, $R^3$, $R^4$, $R^5$, n, p, and q, is as defined above and described in embodiments, classes and subclasses above and herein, singly or in combination.

In certain embodiments, the present invention provides a compound of formula IX,

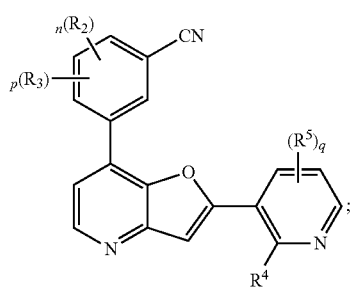

IX or a pharmaceutically acceptable salt thereof, wherein each of $R^2$, $R^3$, $R^4$, $R^5$, n, p, and q, is as defined above and described in embodiments, classes and subclasses above and herein, singly or in combination.

In certain embodiments, the present invention provides a compound of formula X,

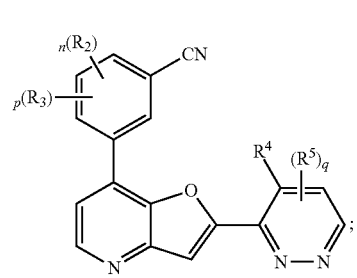

X or a pharmaceutically acceptable salt thereof, wherein each of $R^2$, $R^3$, $R^4$, $R^5$, n, p, and q, is as defined above and described in embodiments, classes and subclasses above and herein, singly or in combination.

In certain embodiments, the present invention provides a compound of formula XI,

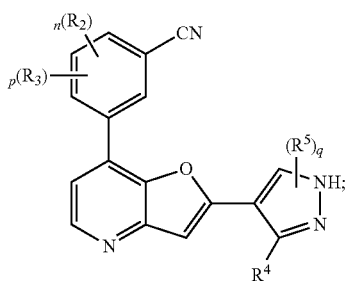

XI or a pharmaceutically acceptable salt thereof, wherein each of $R^2$, $R^3$, $R^4$, $R^5$, n, p, and q, is as defined above and described in embodiments, classes and subclasses above and herein, singly or in combination.

In certain embodiments, the present invention provides a compound of formula XII,

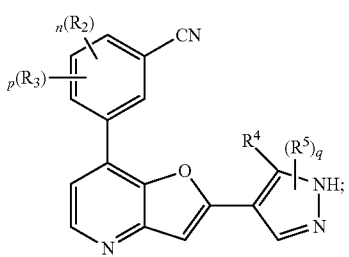

XII or a pharmaceutically acceptable salt thereof, wherein each of $R^2$, $R^3$, $R^4$, $R^5$, n, p, and q, is as defined above and described in embodiments, classes and subclasses above and herein, singly or in combination.

In certain embodiments, the present invention provides a compound of formula XIII,

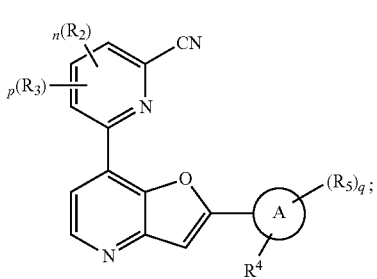

XIII or a pharmaceutically acceptable salt thereof, wherein each of Ring A, $R^2$, $R^3$, $R^4$, $R^5$, n, p, and q, is as defined above and described in embodiments, classes and subclasses above and herein, singly or in combination.

In certain embodiments, the present invention provides a compound of formula XIV,

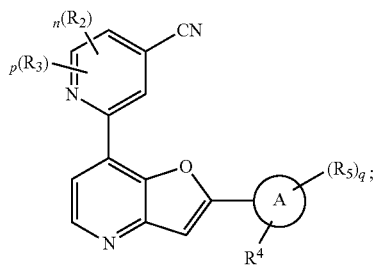

or a pharmaceutically acceptable salt thereof, wherein each of Ring A, $R^2$, $R^3$, $R^4$, $R^5$, n, p, and q, is as defined above and described in embodiments, classes and subclasses above and herein, singly or in combination.

In certain embodiments, the present invention provides a compound of formula XV,

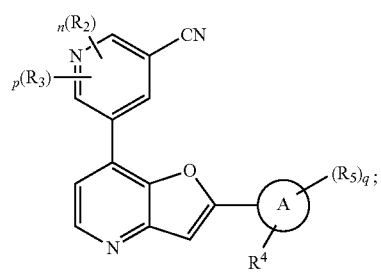

or a pharmaceutically acceptable salt thereof, wherein each of Ring A, $R^2$, $R^3$, $R^4$, $R^5$, n, p, and q, is as defined above and described in embodiments, classes and subclasses above and herein, singly or in combination.

In certain embodiments, the invention provides a compound selected from Table 1:

TABLE 1

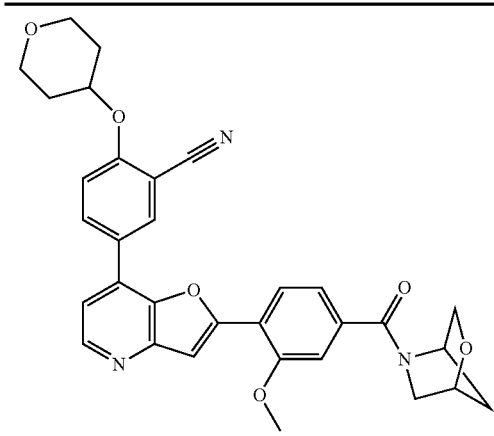
1

TABLE 1-continued

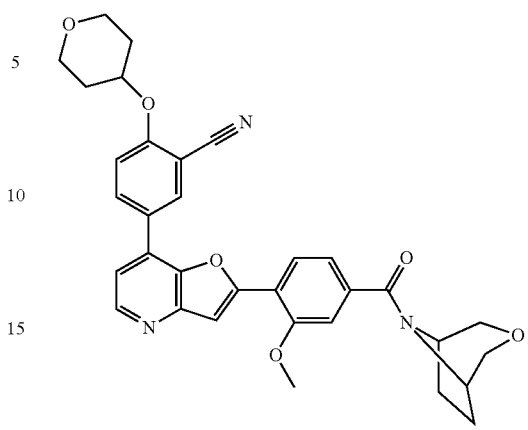
2

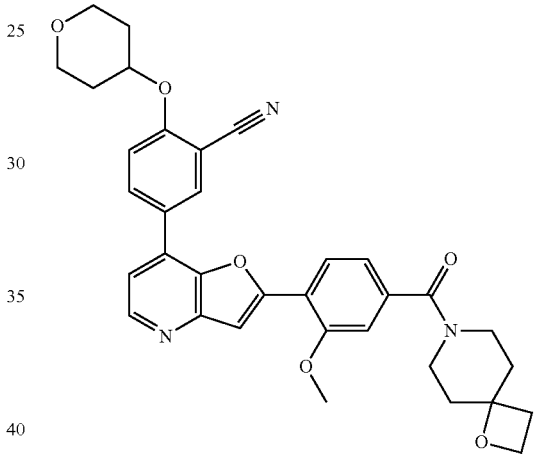
3

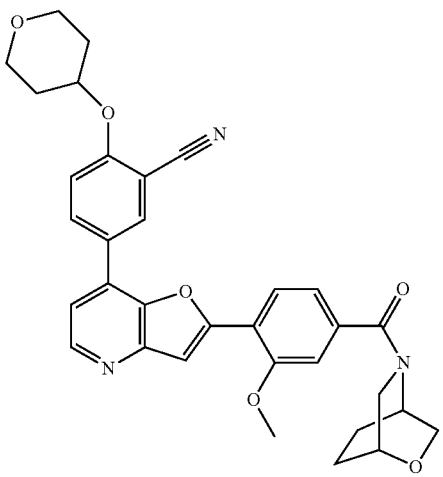 [SMILES: COc1cc(C(=O)N2CC3CCC2CO3)ccc1-c1cc2nccc(-c3ccc(OC4CCOCC4)c(C#N)c3)c2o1]
4

TABLE 1-continued
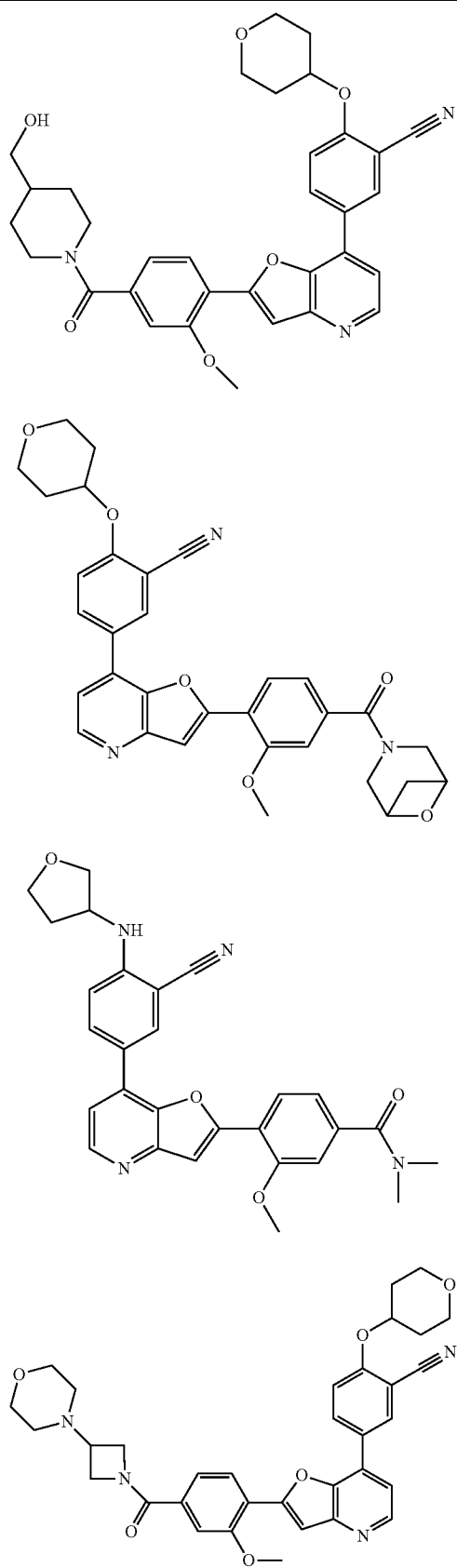
TABLE 1-continued
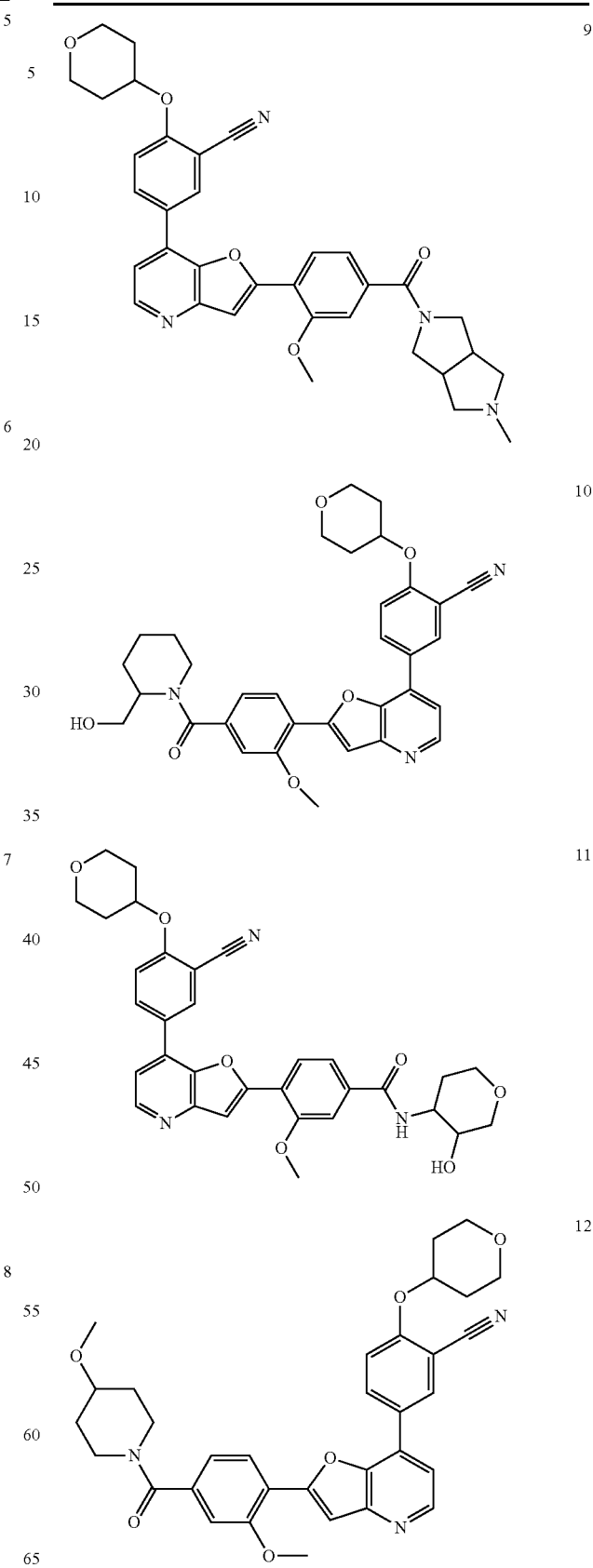

TABLE 1-continued
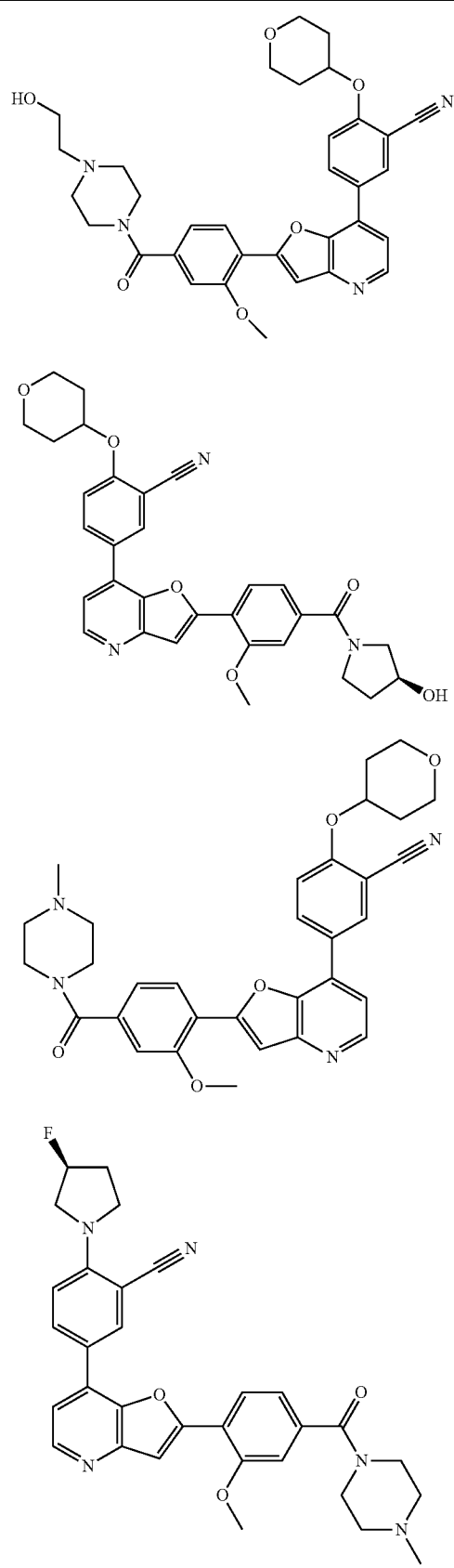
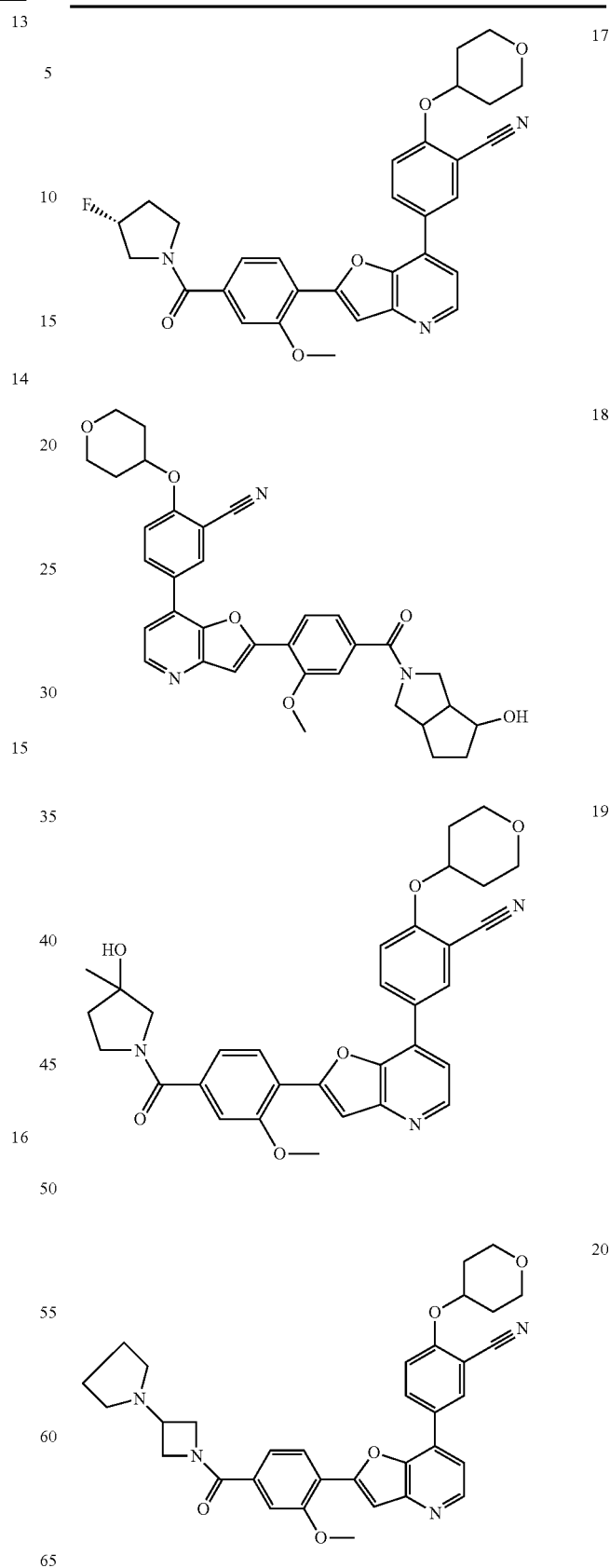

TABLE 1-continued
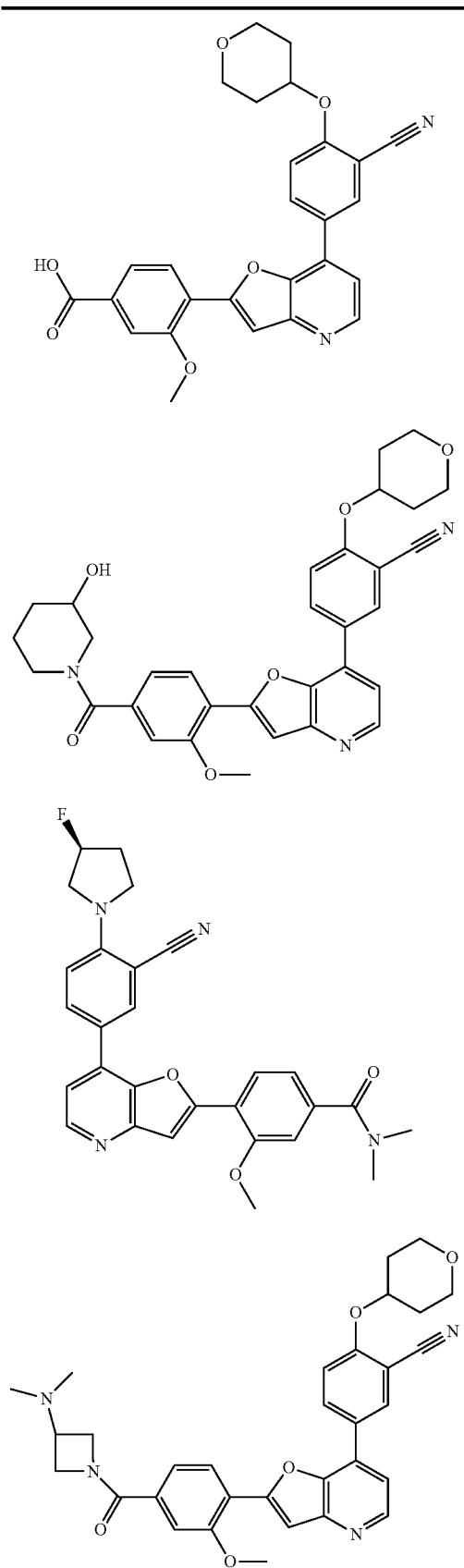
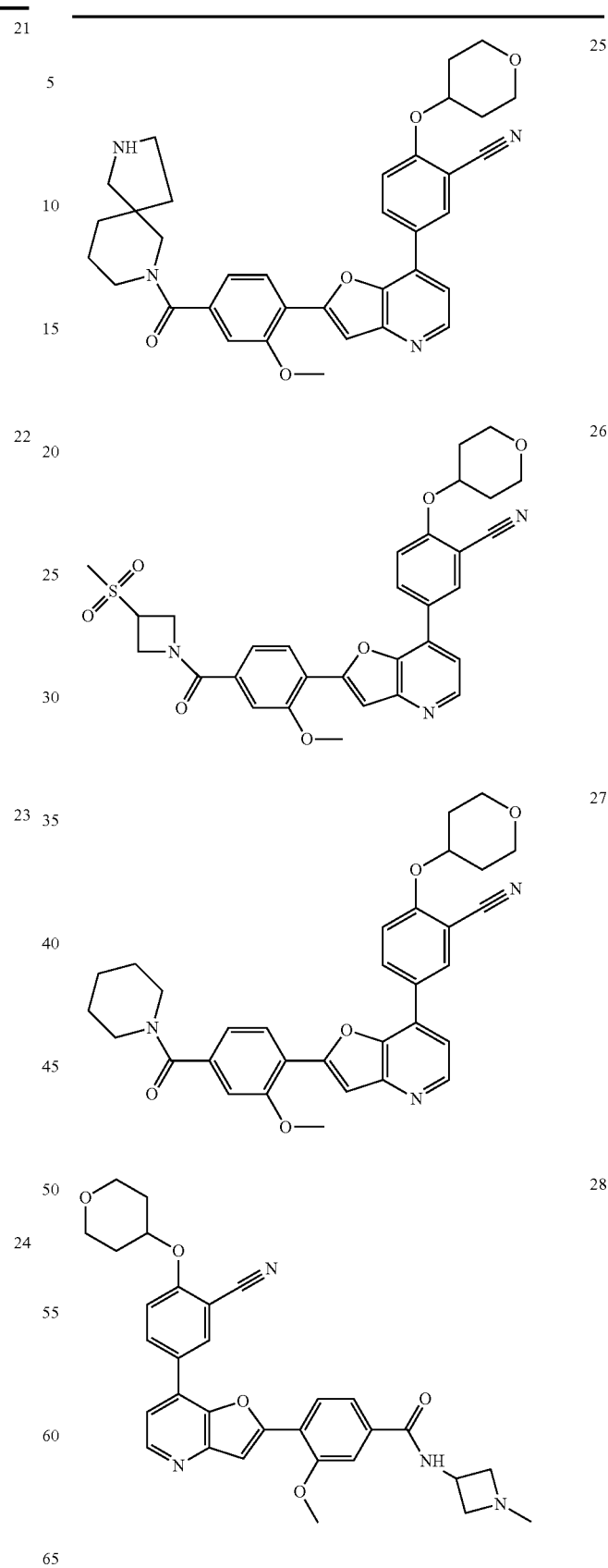

TABLE 1-continued
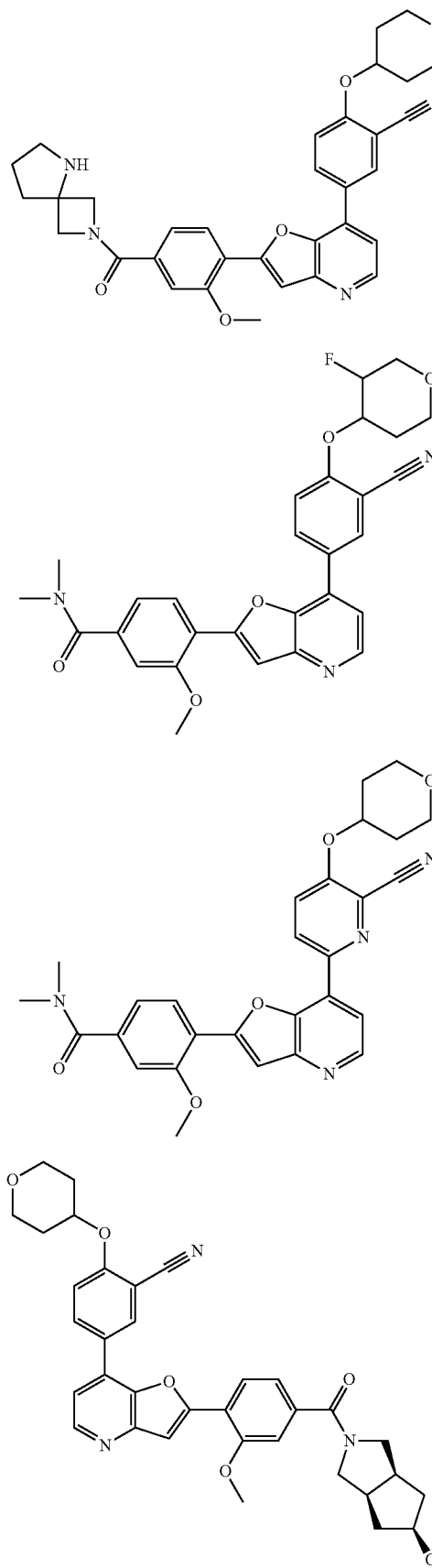
TABLE 1-continued
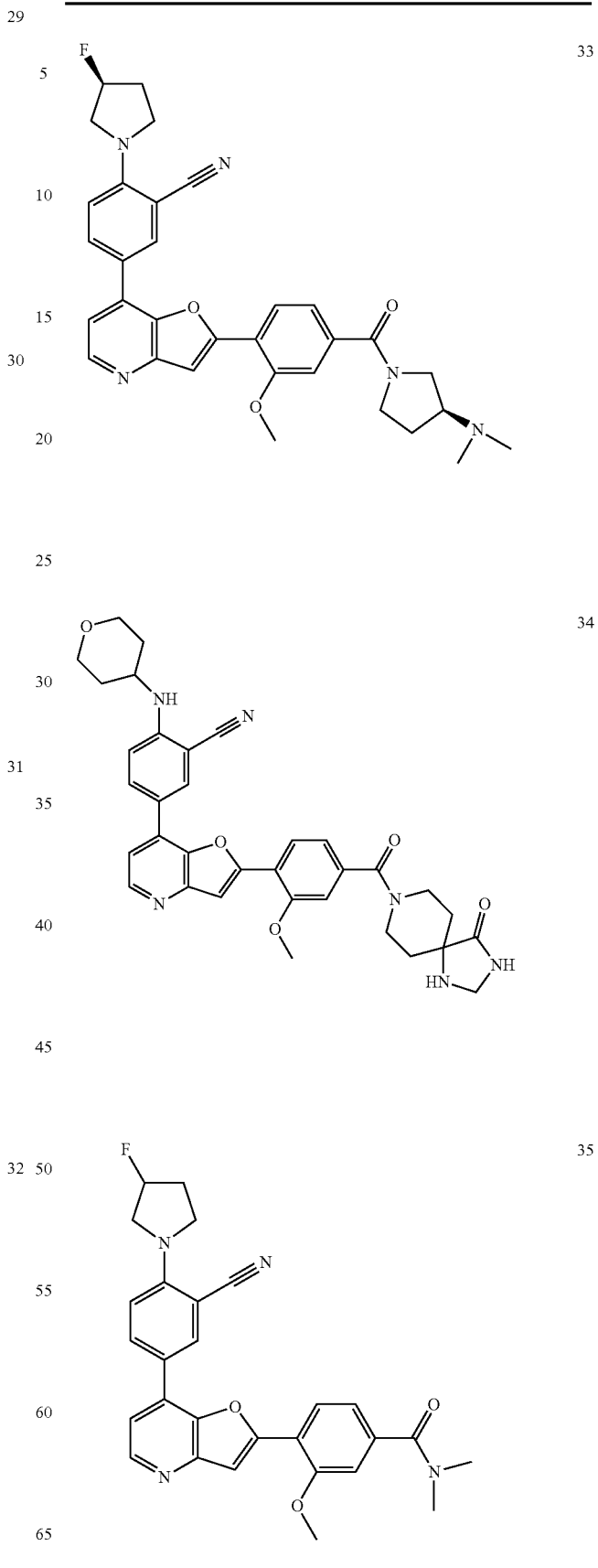

TABLE 1-continued
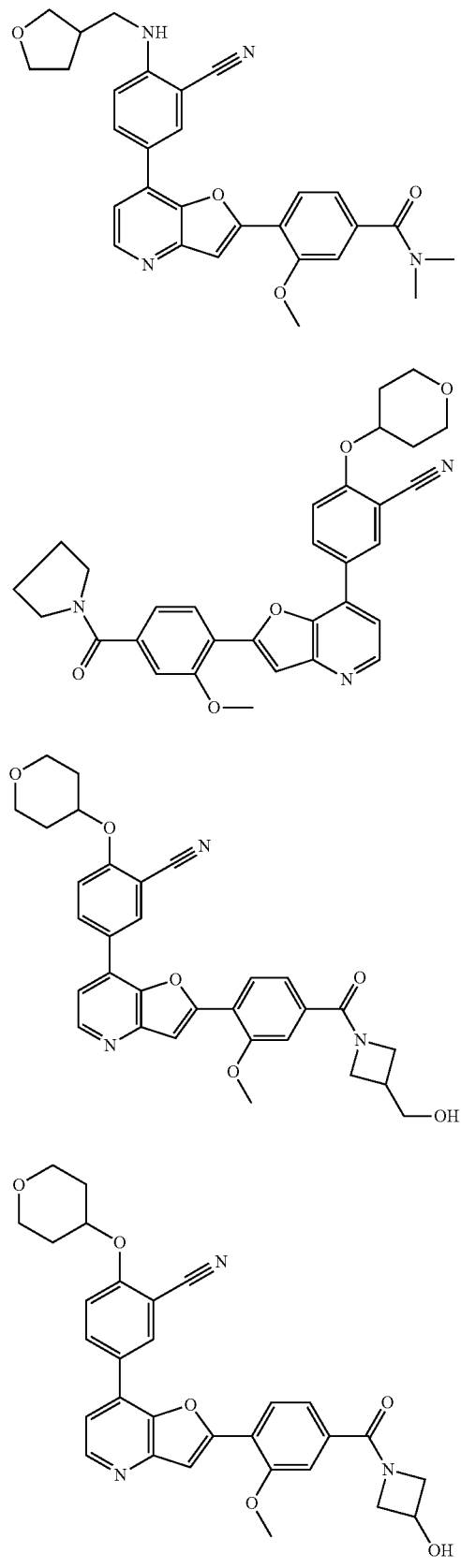
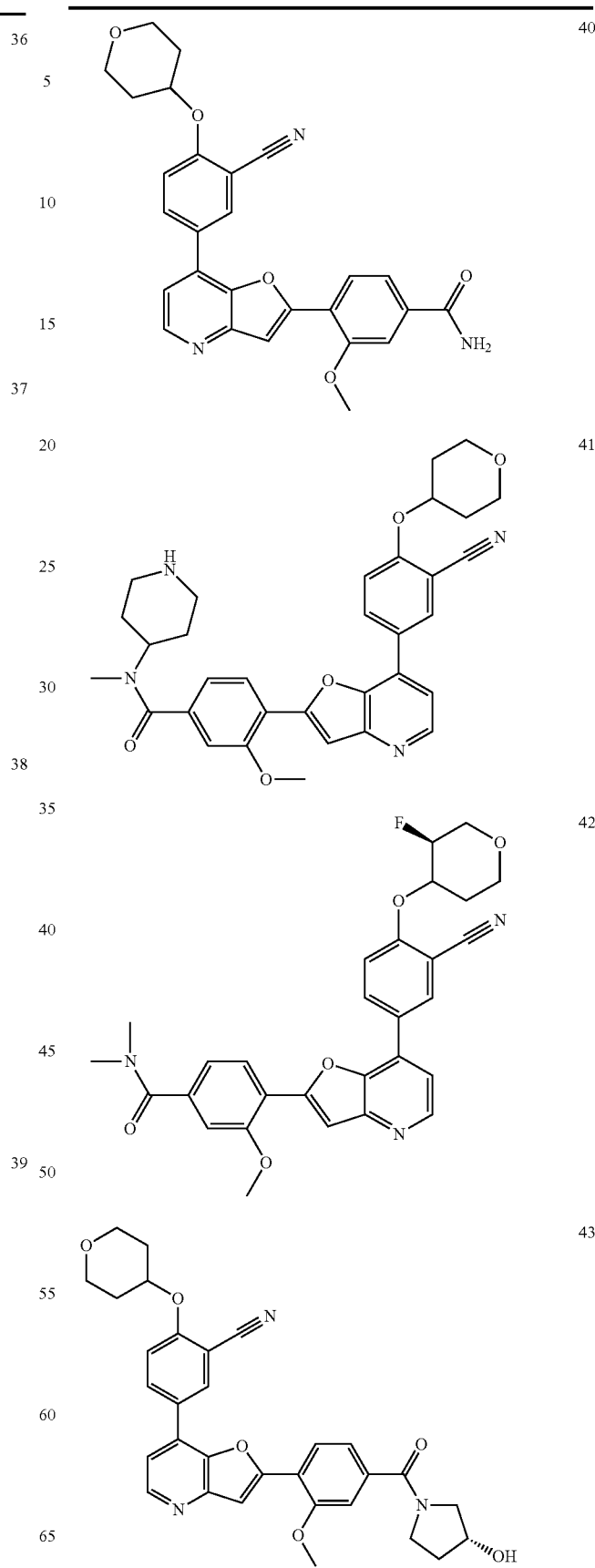

TABLE 1-continued
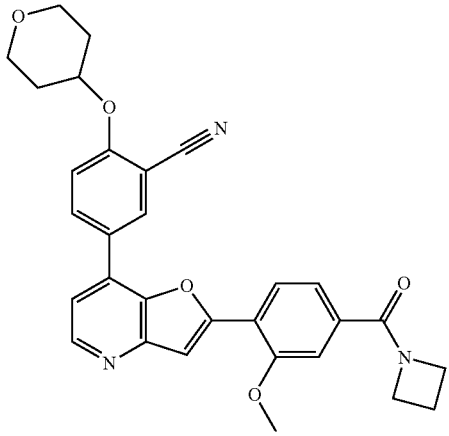 [SMILES: COc1cc(C(=O)N2CCC2)ccc1-c1cc2nccc(-c3ccc(OC4CCOCC4)c(C#N)c3)c2o1]
44
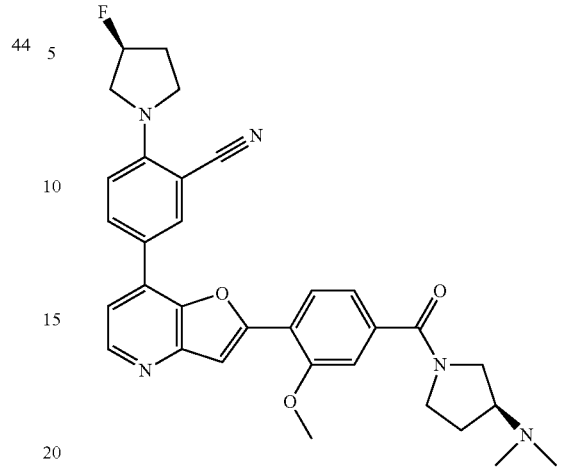
47
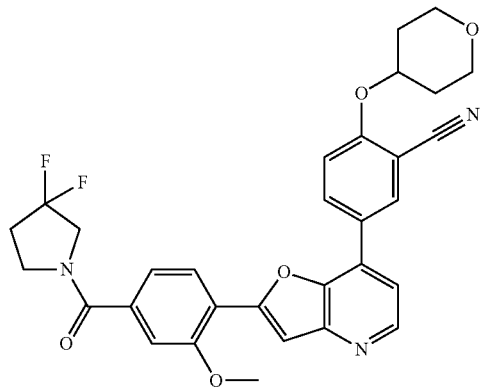 [SMILES: COc1cc(C(=O)N2CCC(F)(F)C2)ccc1-c1cc2nccc(-c3ccc(OC4CCOCC4)c(C#N)c3)c2o1]
45
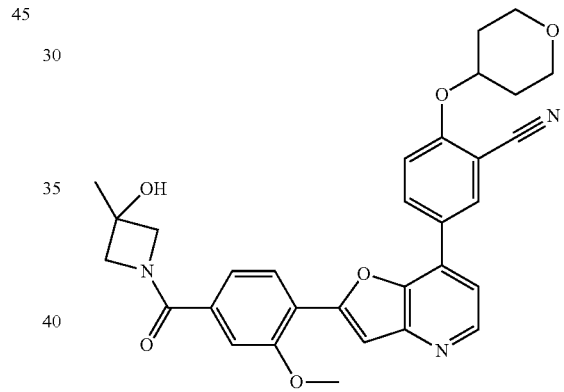
48
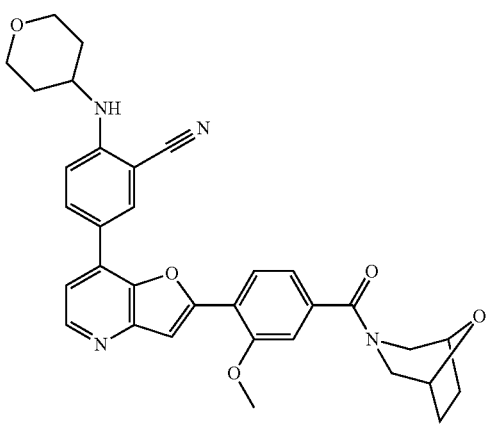
46
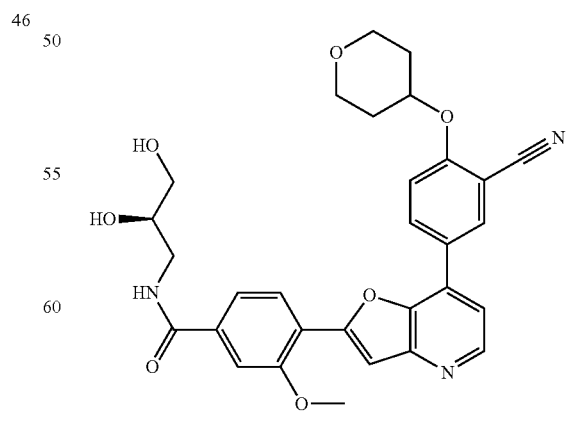
49

TABLE 1-continued
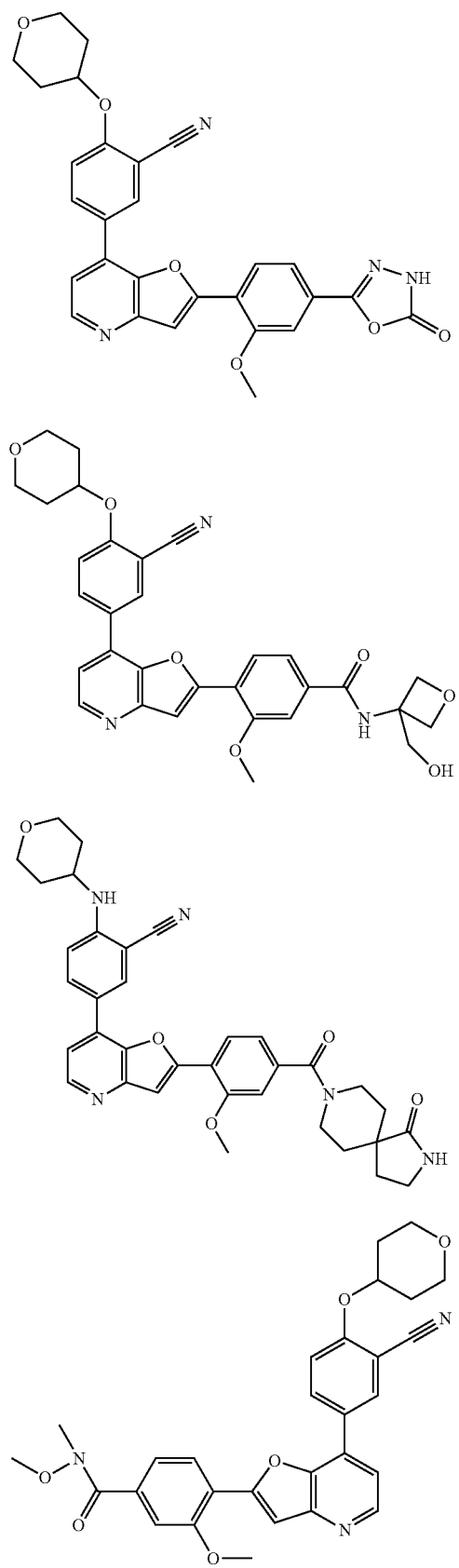
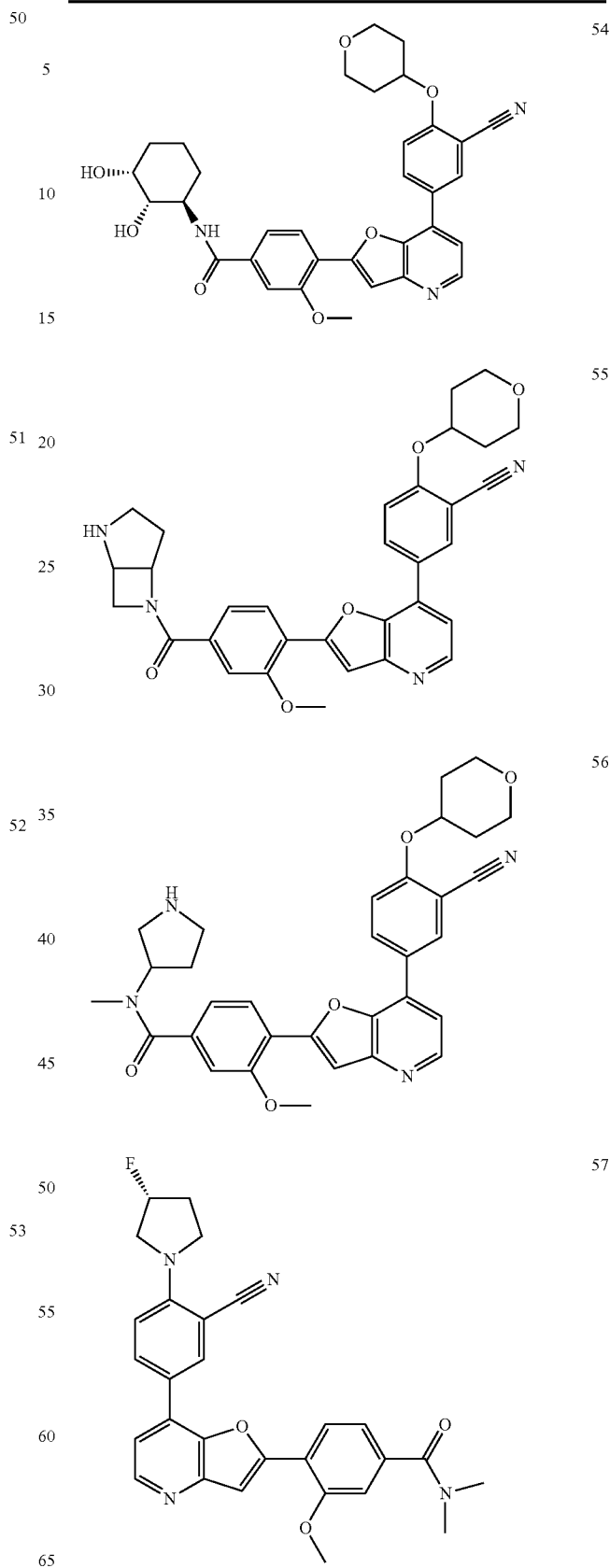

TABLE 1-continued
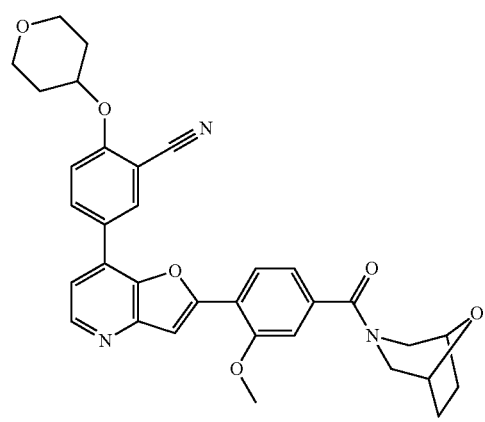 [SMILES: COc1cc(C(=O)N2CC3CCC(C2)O3)ccc1-c1cc2nccc(-c3ccc(OC4CCOCC4)c(C#N)c3)c2o1]
58
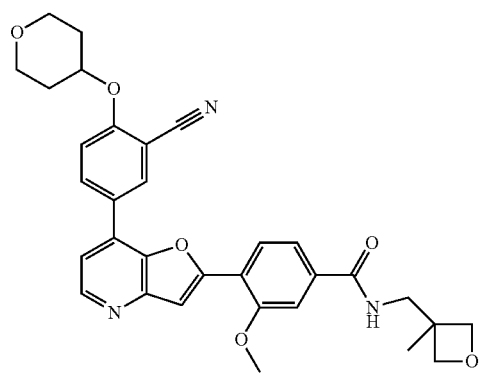 [SMILES: COc1cc(C(=O)NCC2(C)COC2)ccc1-c1cc2nccc(-c3ccc(OC4CCOCC4)c(C#N)c3)c2o1]
59
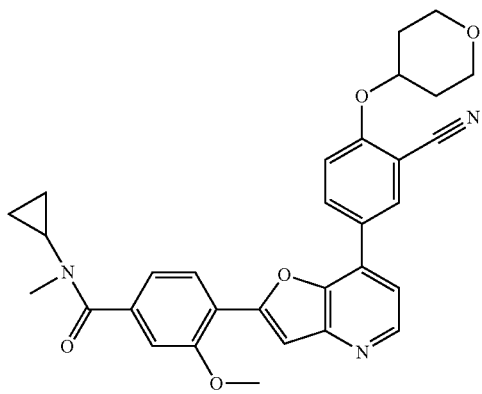 [SMILES: COc1cc(C(=O)N(C)C2CC2)ccc1-c1cc2nccc(-c3ccc(OC4CCOCC4)c(C#N)c3)c2o1]
60
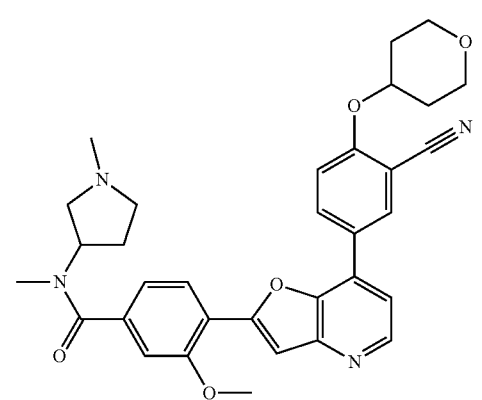 [SMILES: COc1cc(C(=O)N(C)C2CCN(C)C2)ccc1-c1cc2nccc(-c3ccc(OC4CCOCC4)c(C#N)c3)c2o1]
61
TABLE 1-continued
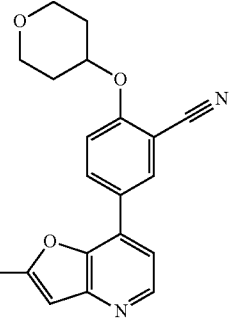
62
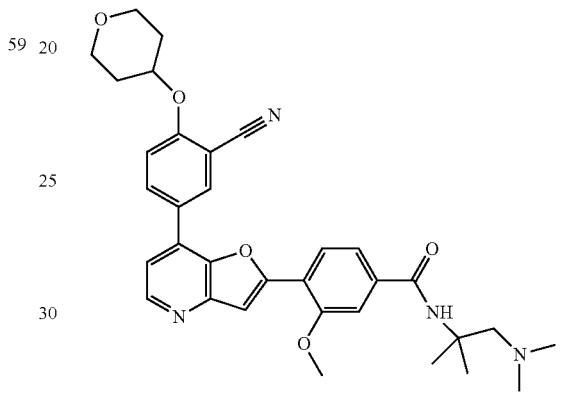
63
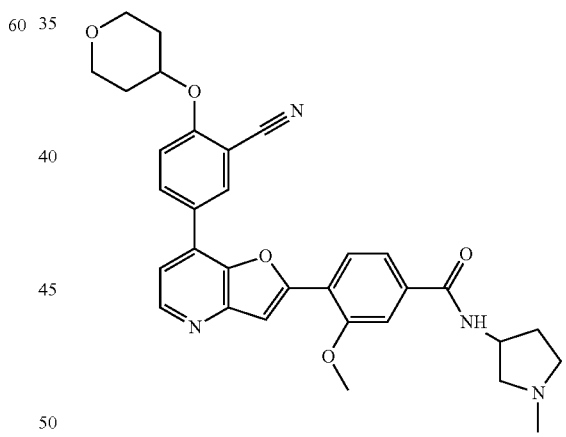
64
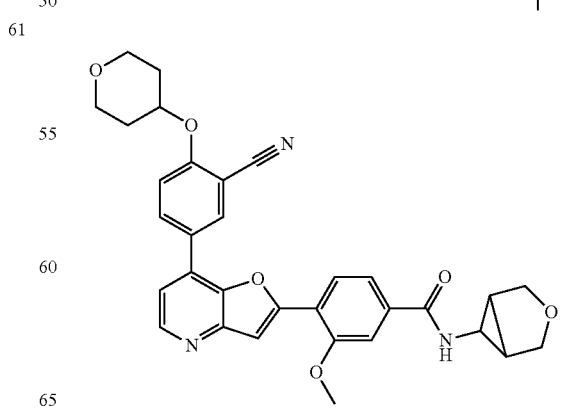
65

TABLE 1-continued
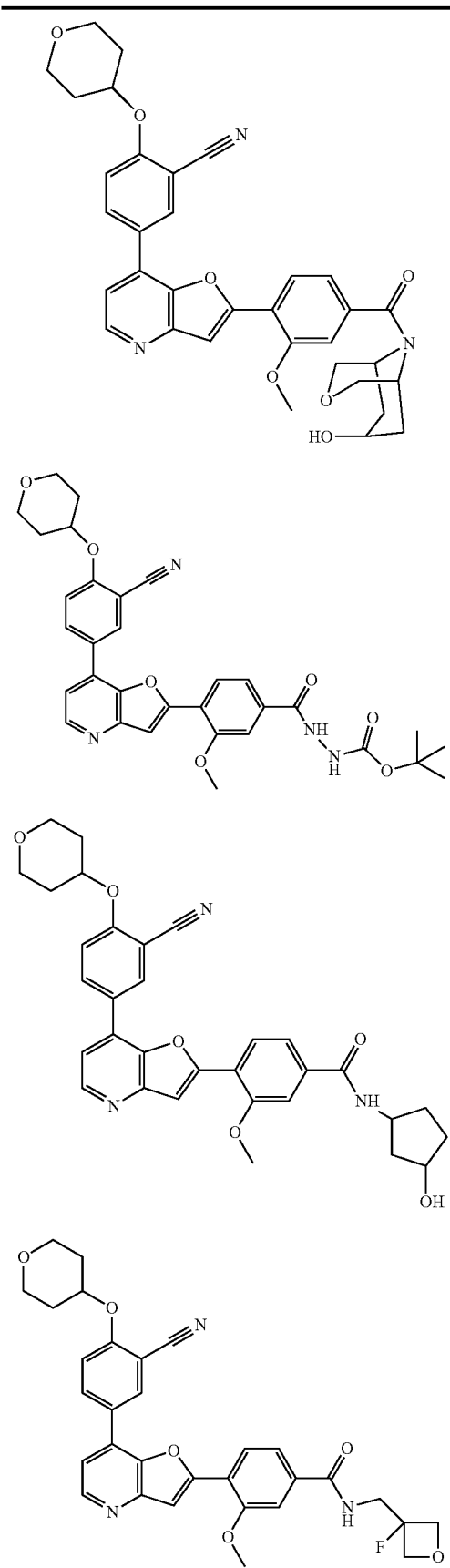
TABLE 1-continued
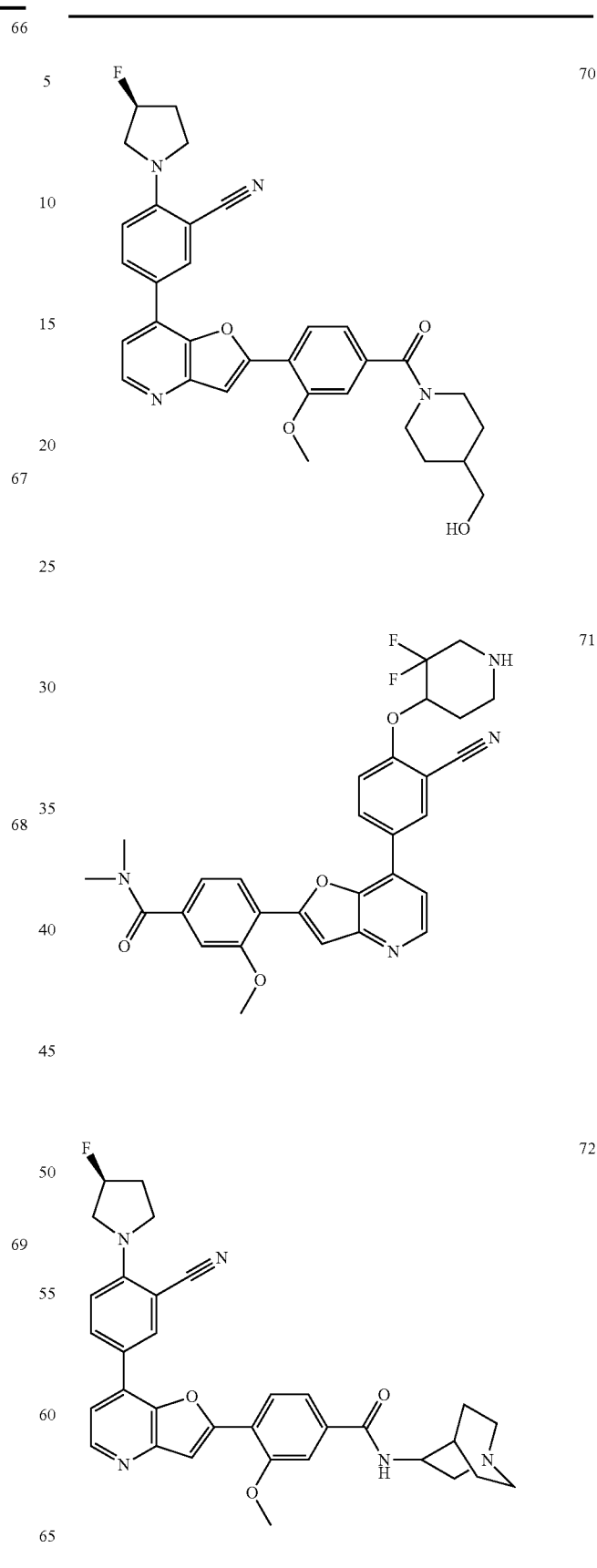

TABLE 1-continued
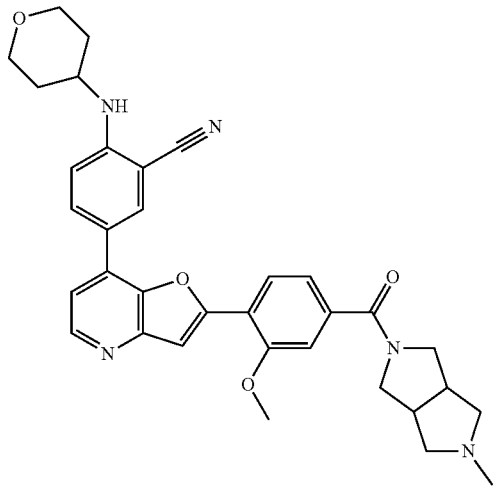 [SMILES: COc1cc(C(=O)N2CC3CN(C)CC3C2)ccc1-c1cc2nccc(-c3ccc(NC4CCOCC4)c(C#N)c3)c2o1]
73
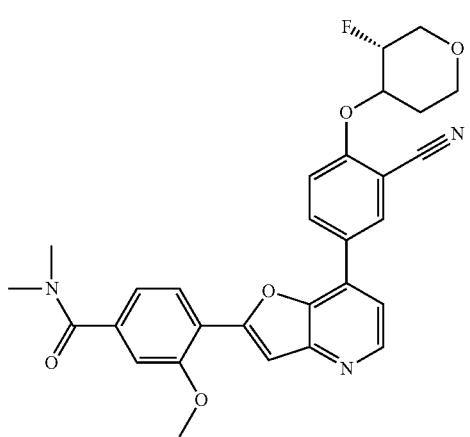 [SMILES: COc1cc(C(=O)N(C)C)ccc1-c1cc2nccc(-c3ccc(OC4CCOC[C@H]4F)c(C#N)c3)c2o1]
74
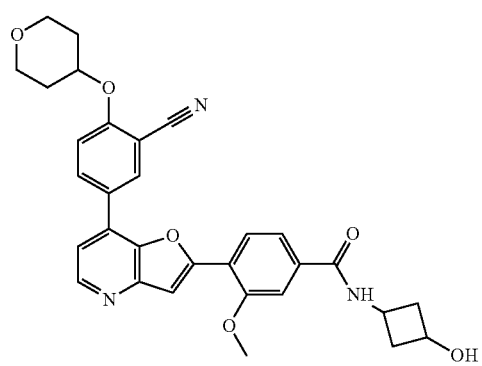 [SMILES: COc1cc(C(=O)NC2CC(O)C2)ccc1-c1cc2nccc(-c3ccc(OC4CCOCC4)c(C#N)c3)c2o1]
75
TABLE 1-continued
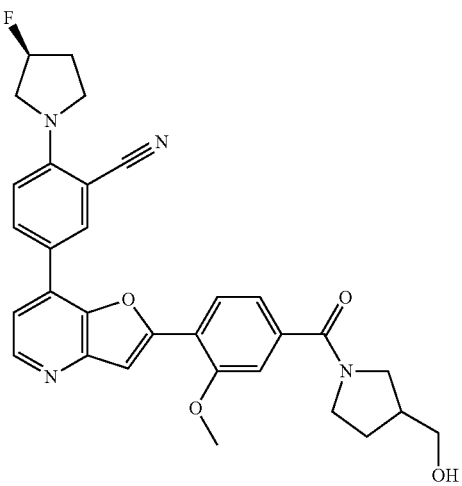 [SMILES: COc1cc(C(=O)N2CCC(CO)C2)ccc1-c1cc2nccc(-c3ccc(N4CC[C@H](F)C4)c(C#N)c3)c2o1]
76
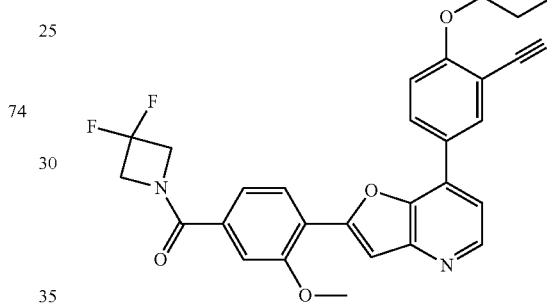
77
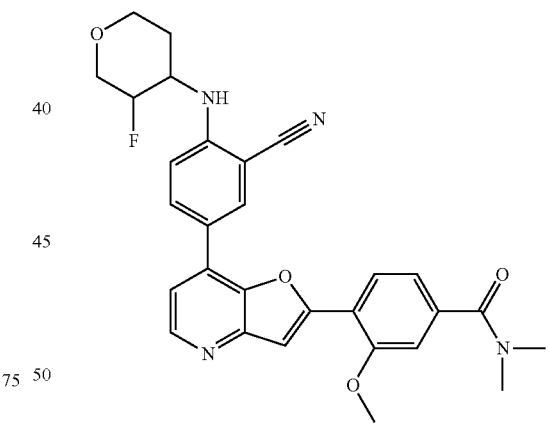
78
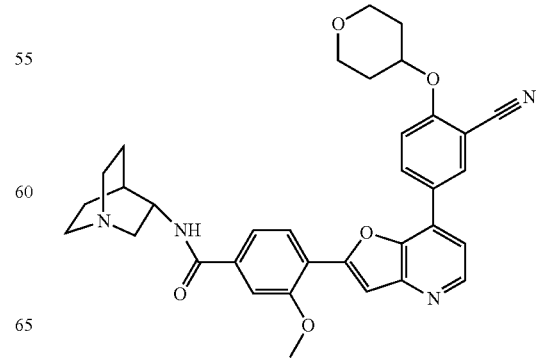
79

TABLE 1-continued
80 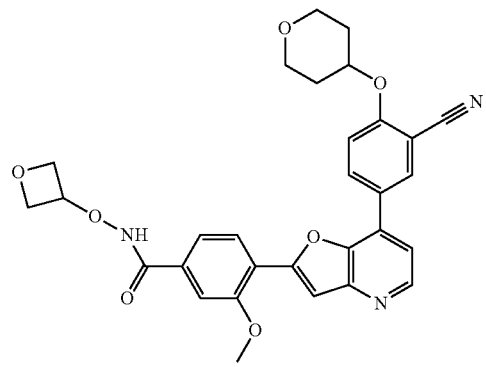 [SMILES: COc1cc(C(=O)NOC2COC2)ccc1-c1cc2nccc(-c3ccc(OC4CCOCC4)c(C#N)c3)c2o1]
81 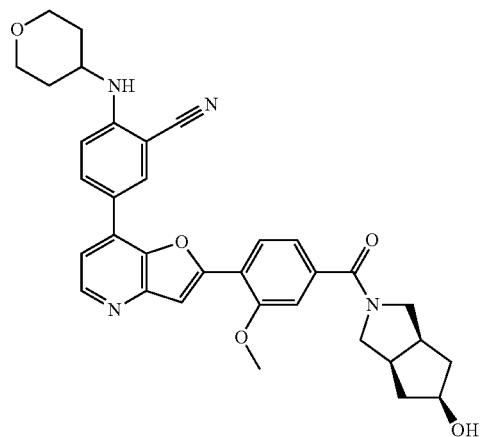 [SMILES: COc1cc(C(=O)N2C[C@H]3C[C@@H](O)C[C@H]3C2)ccc1-c1cc2nccc(-c3ccc(NC4CCOCC4)c(C#N)c3)c2o1]
82 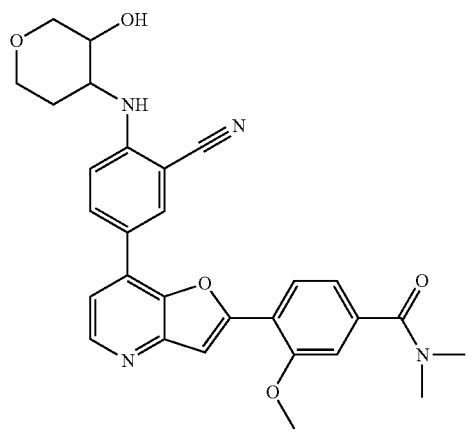 [SMILES: COc1cc(C(=O)N(C)C)ccc1-c1cc2nccc(-c3ccc(NC4CCOCC4O)c(C#N)c3)c2o1]
83 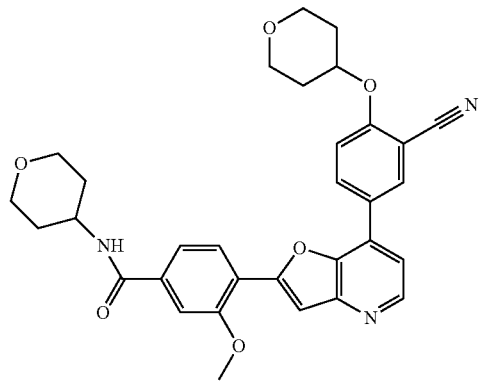 [SMILES: COc1cc(C(=O)NC2CCOCC2)ccc1-c1cc2nccc(-c3ccc(OC4CCOCC4)c(C#N)c3)c2o1]
TABLE 1-continued
84 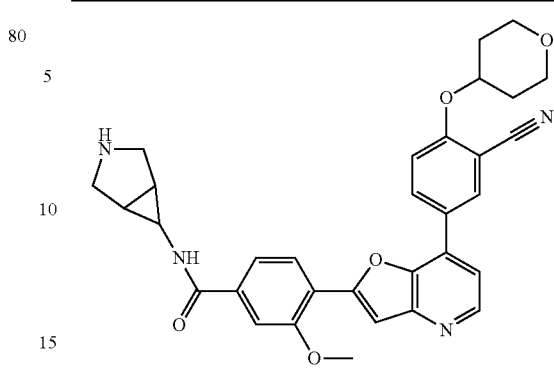
85 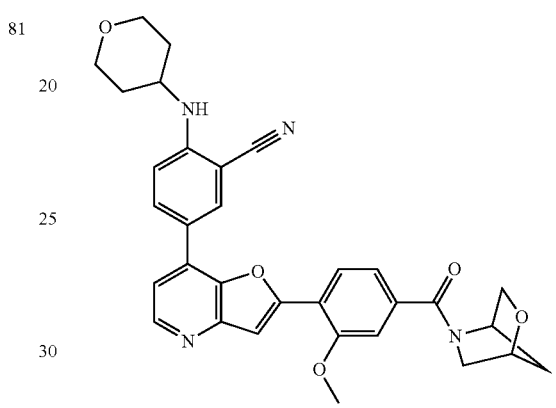
86 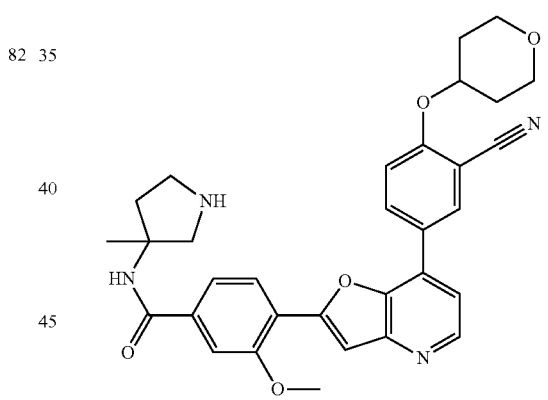
87 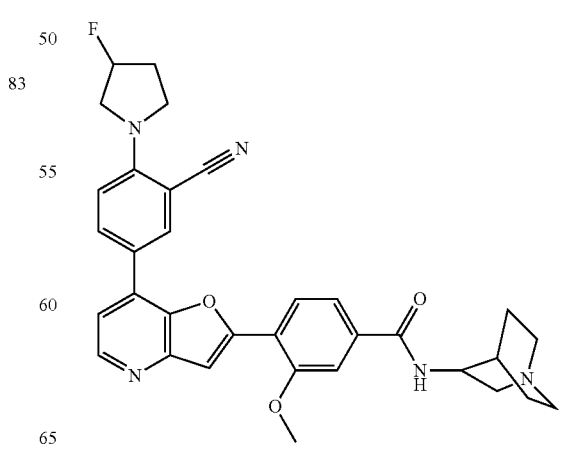

TABLE 1-continued
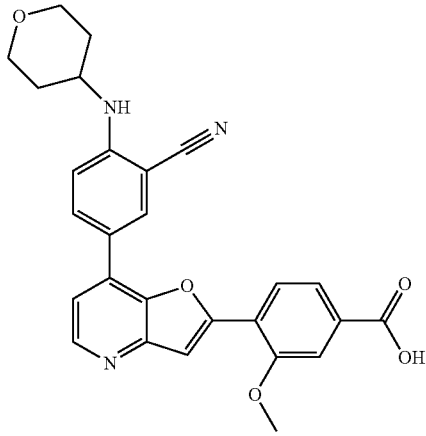 [SMILES: COc1cc(C(=O)O)ccc1-c1cc2nccc(-c3ccc(NC4CCOCC4)c(C#N)c3)c2o1]
88
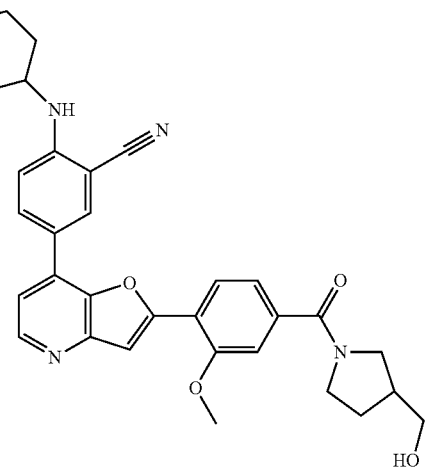
91
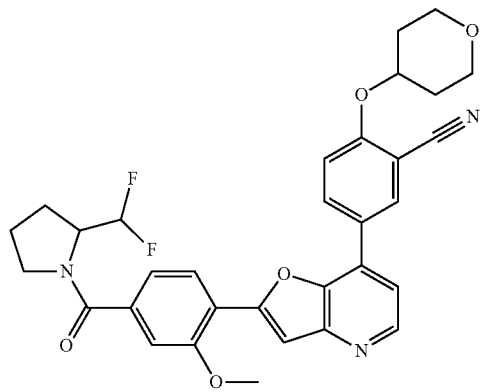 [SMILES: COc1cc(C(=O)N2CCCC2C(F)F)ccc1-c1cc2nccc(-c3ccc(OC4CCOCC4)c(C#N)c3)c2o1]
89
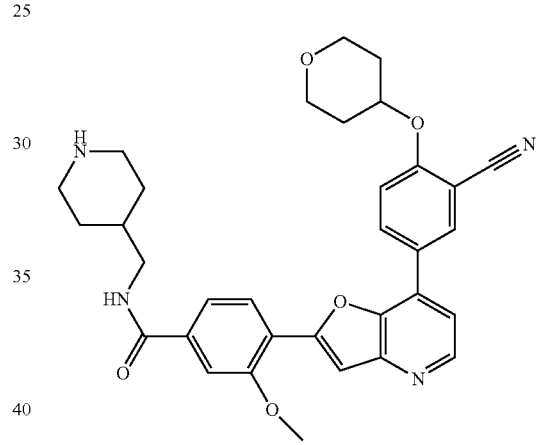
92
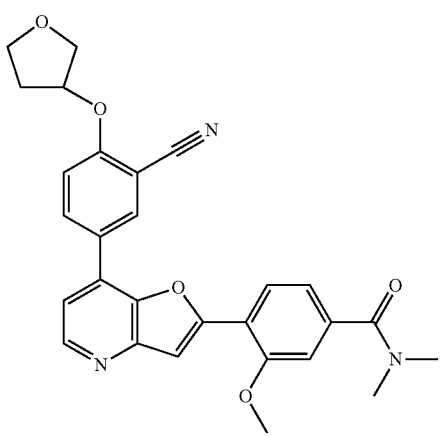 [SMILES: COc1cc(C(=O)N(C)C)ccc1-c1cc2nccc(-c3ccc(OC4CCOC4)c(C#N)c3)c2o1]
90
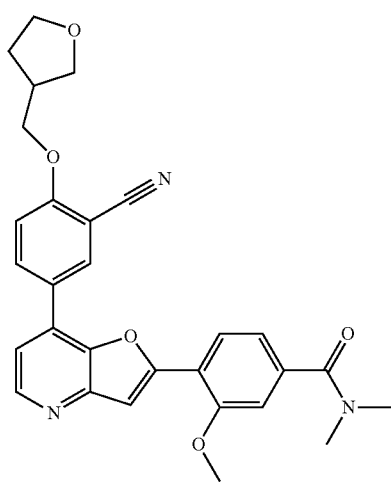 [SMILES: COc1cc(C(=O)N(C)C)ccc1-c1cc2nccc(-c3ccc(OCC4CCOC4)c(C#N)c3)c2o1]
93

TABLE 1-continued
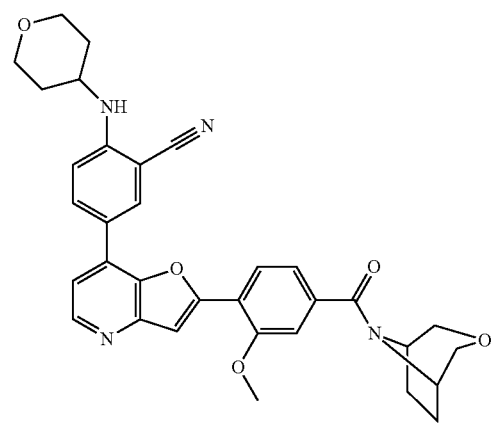 [SMILES: COc1cc(C(=O)N2C3CCC2COC3)ccc1-c1cc2nccc(-c3ccc(NC4CCOCC4)c(C#N)c3)c2o1]
94
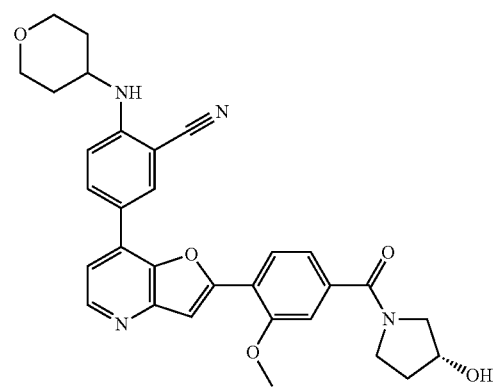 [SMILES: COc1cc(C(=O)N2CC[C@@H](O)C2)ccc1-c1cc2nccc(-c3ccc(NC4CCOCC4)c(C#N)c3)c2o1]
95
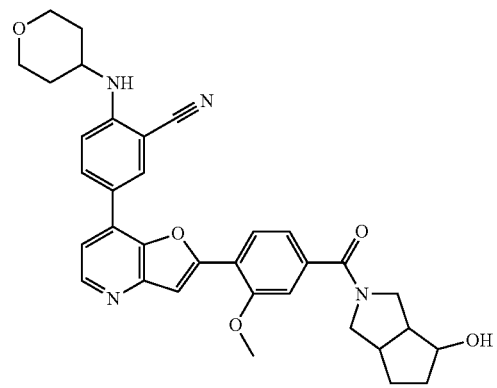 [SMILES: COc1cc(C(=O)N2CC3CCC(O)C3C2)ccc1-c1cc2nccc(-c3ccc(NC4CCOCC4)c(C#N)c3)c2o1]
96
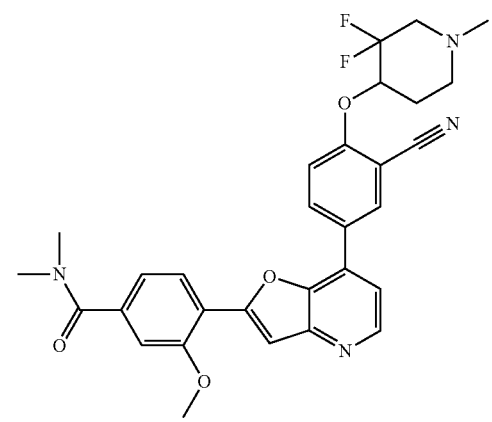
97
TABLE 1-continued
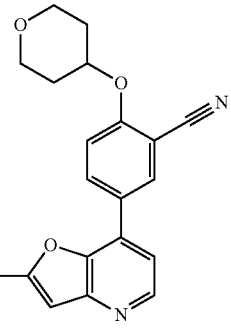
98
99
100

TABLE 1-continued
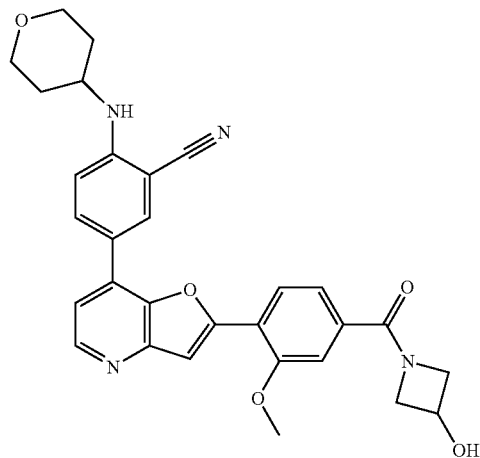 [SMILES: COc1cc(C(=O)N2CC(O)C2)ccc1-c1cc2nccc(-c3ccc(NC4CCOCC4)c(C#N)c3)c2o1]
101
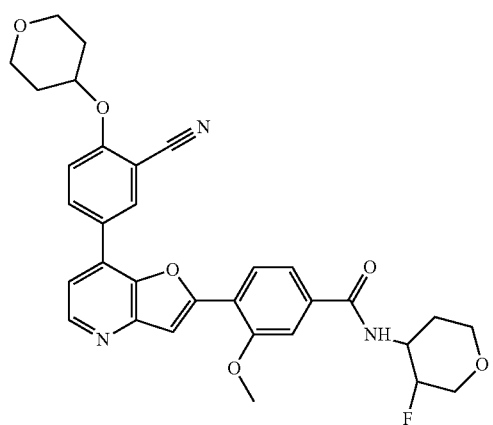 [SMILES: COc1cc(C(=O)NC2CCOCC2F)ccc1-c1cc2nccc(-c3ccc(OC4CCOCC4)c(C#N)c3)c2o1]
102
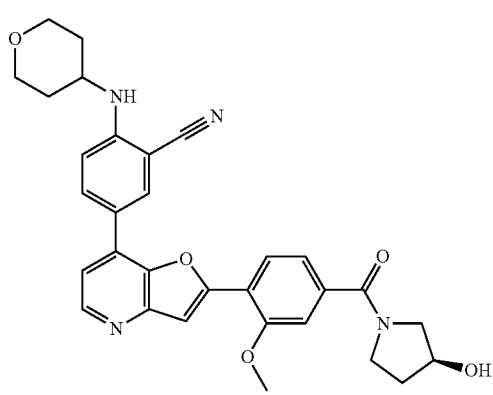 [SMILES: COc1cc(C(=O)N2CC[C@H](O)C2)ccc1-c1cc2nccc(-c3ccc(NC4CCOCC4)c(C#N)c3)c2o1]
103
TABLE 1-continued
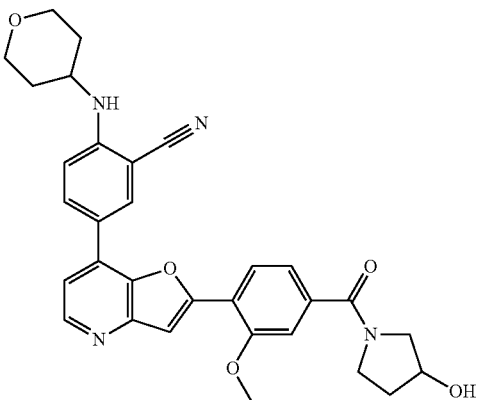 [SMILES: COc1cc(C(=O)N2CCC(O)C2)ccc1-c1cc2nccc(-c3ccc(NC4CCOCC4)c(C#N)c3)c2o1]
104
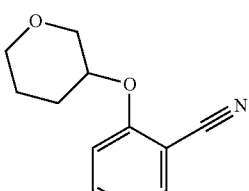
105
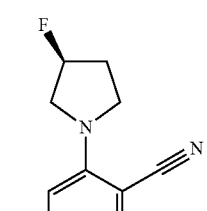
106
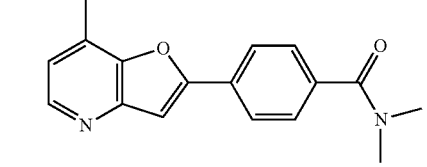
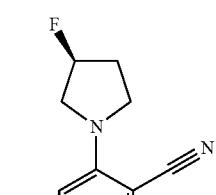
107
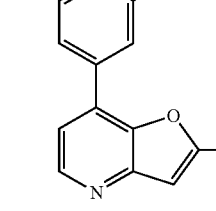

TABLE 1-continued
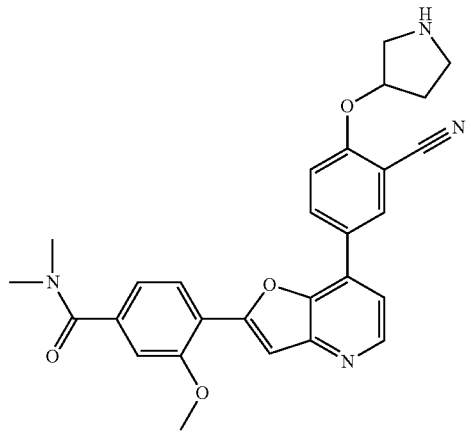 [SMILES: COc1cc(C(=O)N(C)C)ccc1-c1cc2nccc(-c3ccc(OC4CCNC4)c(C#N)c3)c2o1]
108
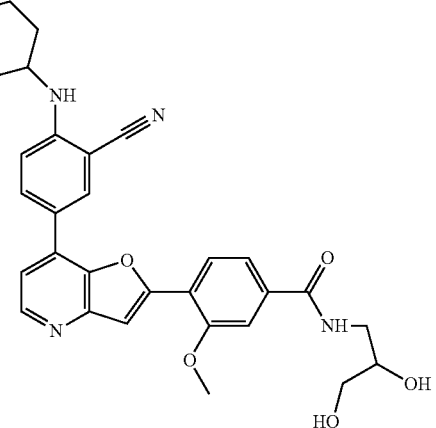
111
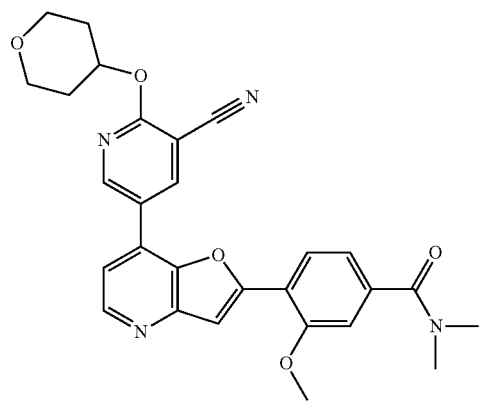 [SMILES: COc1cc(C(=O)N(C)C)ccc1-c1cc2nccc(-c3cnc(OC4CCOCC4)c(C#N)c3)c2o1]
109
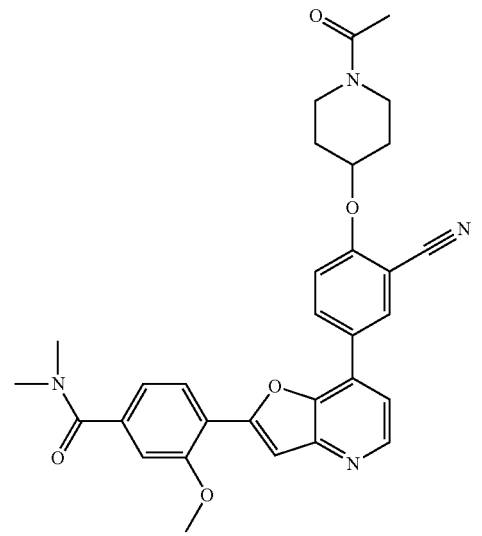
112
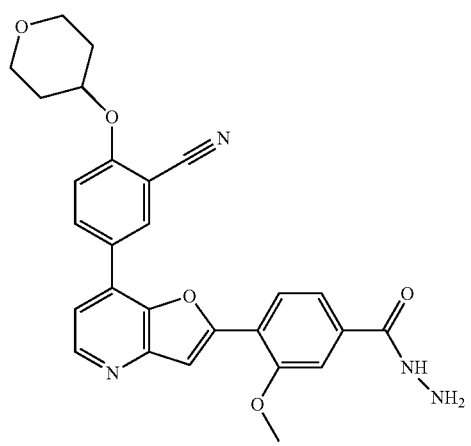 [SMILES: COc1cc(C(=O)NN)ccc1-c1cc2nccc(-c3ccc(OC4CCOCC4)c(C#N)c3)c2o1]
110
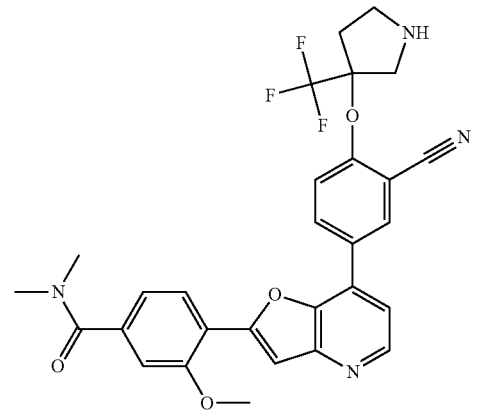 [SMILES: COc1cc(C(=O)N(C)C)ccc1-c1cc2nccc(-c3ccc(OC4(C(F)(F)F)CCNC4)c(C#N)c3)c2o1]
113

TABLE 1-continued
| | |
|---|---|
| 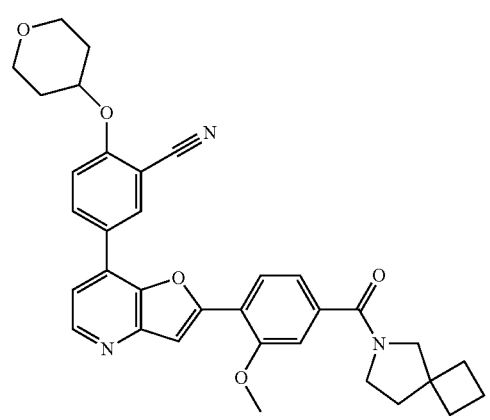 [SMILES: COc1cc(C(=O)N2CCC3(CCC3)C2)ccc1-c1cc2nccc(-c3ccc(OC4CCOCC4)c(C#N)c3)c2o1] 114 | 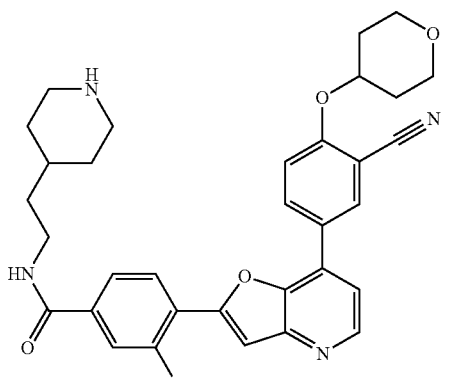 118 |
| 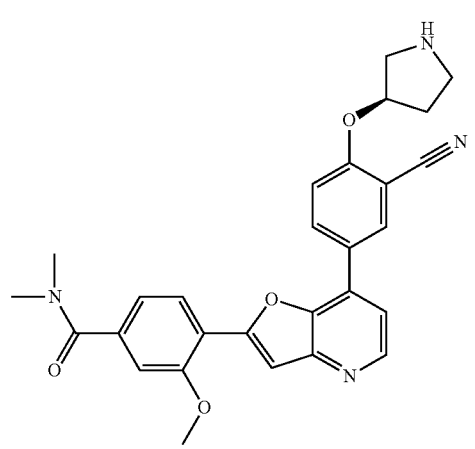 [SMILES: COc1cc(C(=O)N(C)C)ccc1-c1cc2nccc(-c3ccc(O[C@@H]4CCNC4)c(C#N)c3)c2o1] 115 | 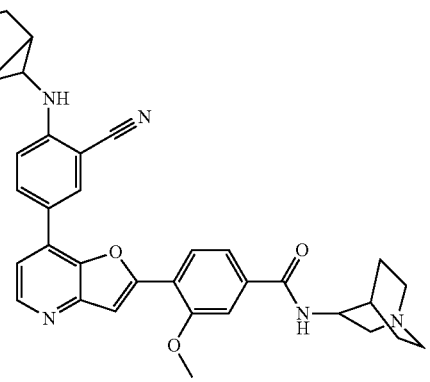 119 |
| 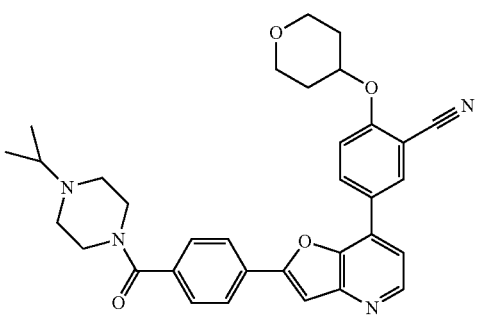 [SMILES: CC(C)N1CCN(C(=O)c2ccc(-c3cc4nccc(-c5ccc(OC6CCOCC6)c(C#N)c5)c4o3)cc2)CC1] 116 | 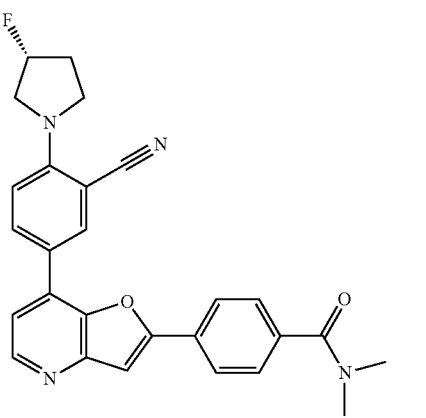 120 |
| 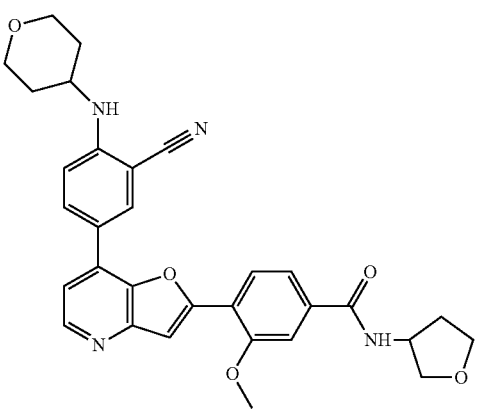 [SMILES: COc1cc(C(=O)NC2CCOC2)ccc1-c1cc2nccc(-c3ccc(NC4CCOCC4)c(C#N)c3)c2o1] 117 | 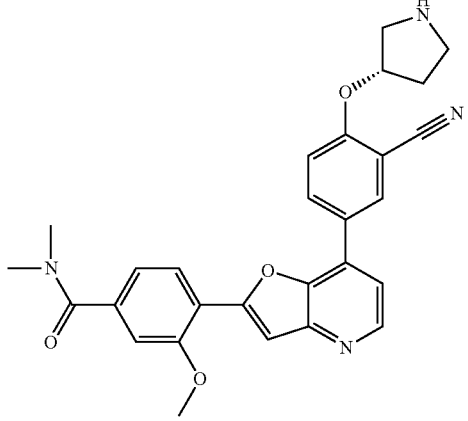 121 |

TABLE 1-continued
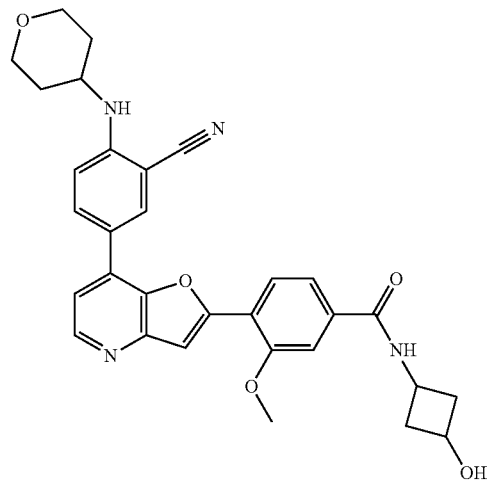 [SMILES: COc1cc(C(=O)NC2CC(O)C2)ccc1-c1cc2nccc(-c3ccc(NC4CCOCC4)c(C#N)c3)c2o1]
122
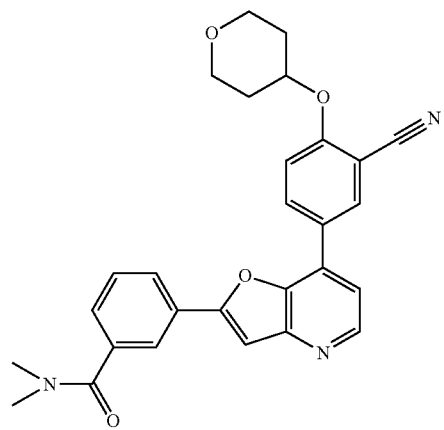 [SMILES: CN(C)C(=O)c1cccc(-c2cc3nccc(-c4ccc(OC5CCOCC5)c(C#N)c4)c3o2)c1]
123
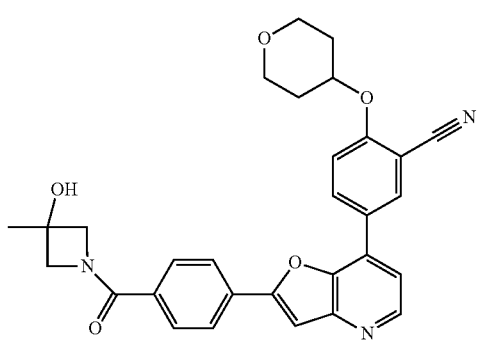 [SMILES: CC1(O)CN(C(=O)c2ccc(-c3cc4nccc(-c5ccc(OC6CCOCC6)c(C#N)c5)c4o3)cc2)C1]
124
TABLE 1-continued
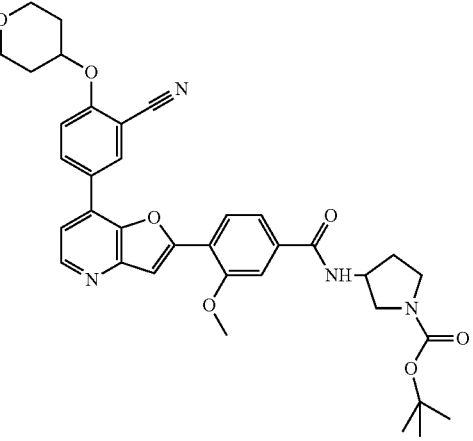
125
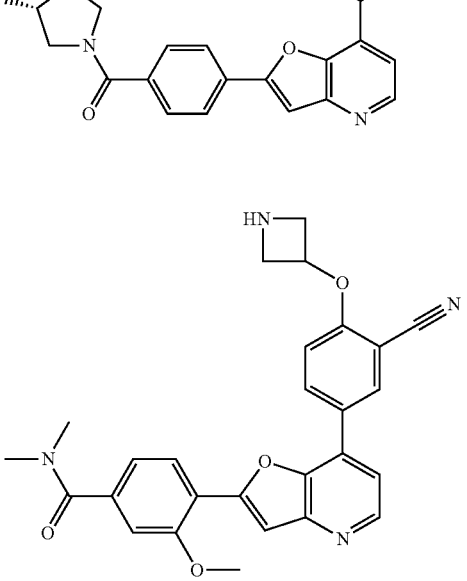
126
127
128

TABLE 1-continued
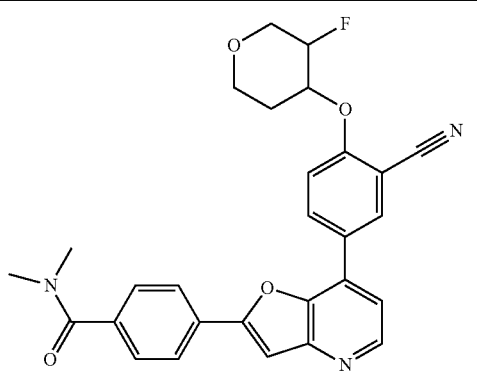
129
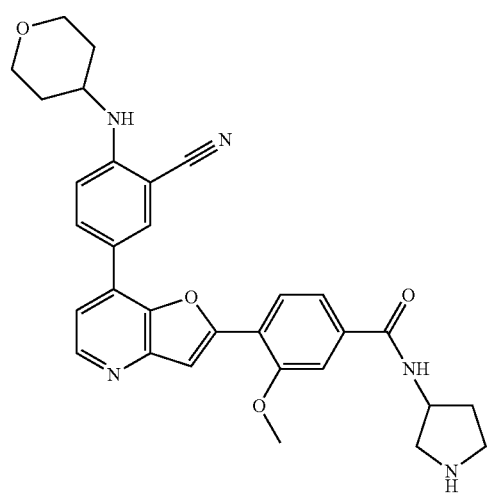 [SMILES: COc1cc(C(=O)NC2CCNC2)ccc1-c1cc2nccc(-c3ccc(NC4CCOCC4)c(C#N)c3)c2o1]
130
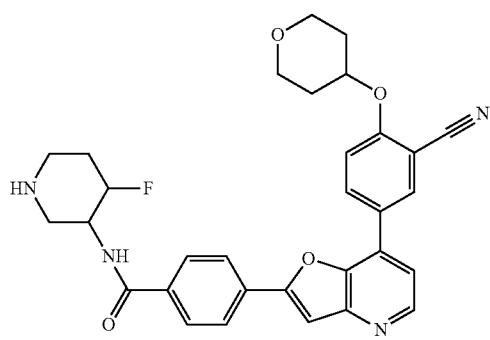 [SMILES: N#Cc1cc(-c2ccnc3cc(-c4ccc(C(=O)NC5CNCCC5F)cc4)oc23)ccc1OC1CCOCC1]
131
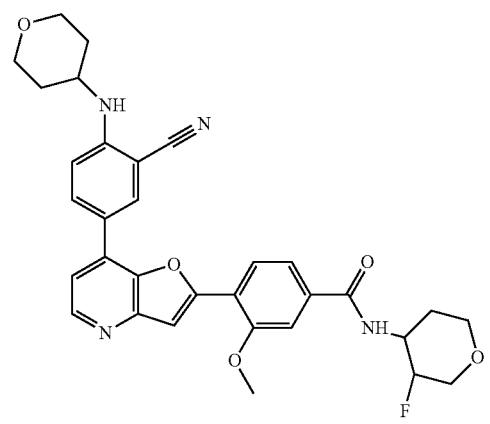 [SMILES: COc1cc(C(=O)NC2CCOCC2F)ccc1-c1cc2nccc(-c3ccc(NC4CCOCC4)c(C#N)c3)c2o1]
132
TABLE 1-continued
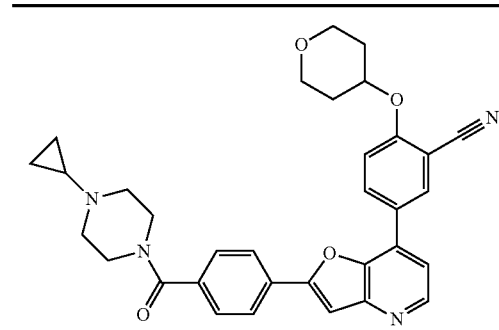
133
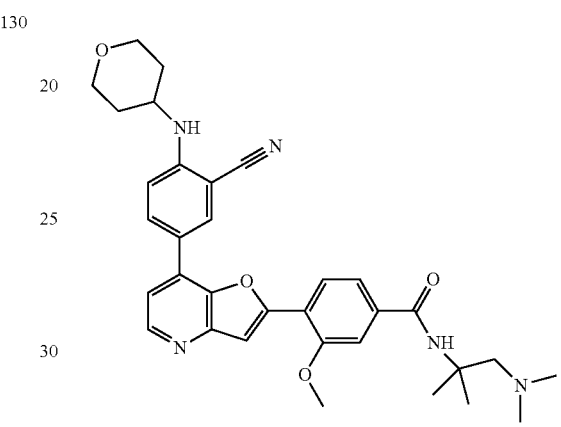
134
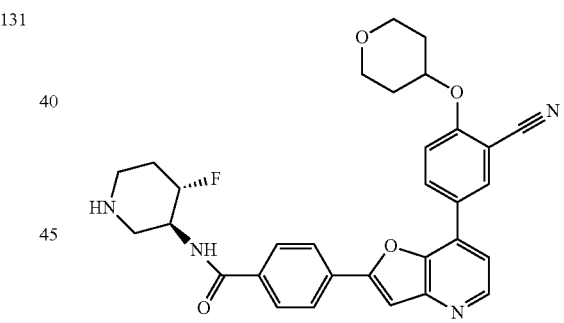
135
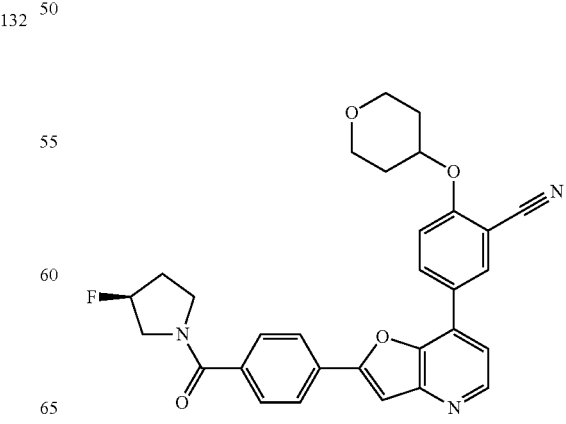
136

TABLE 1-continued
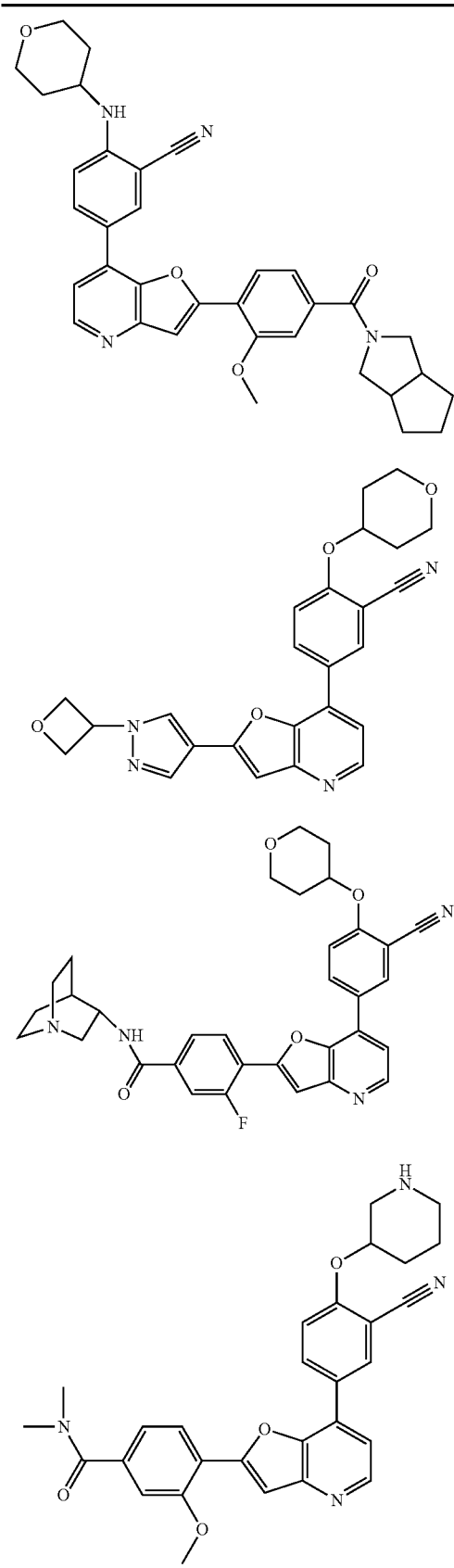
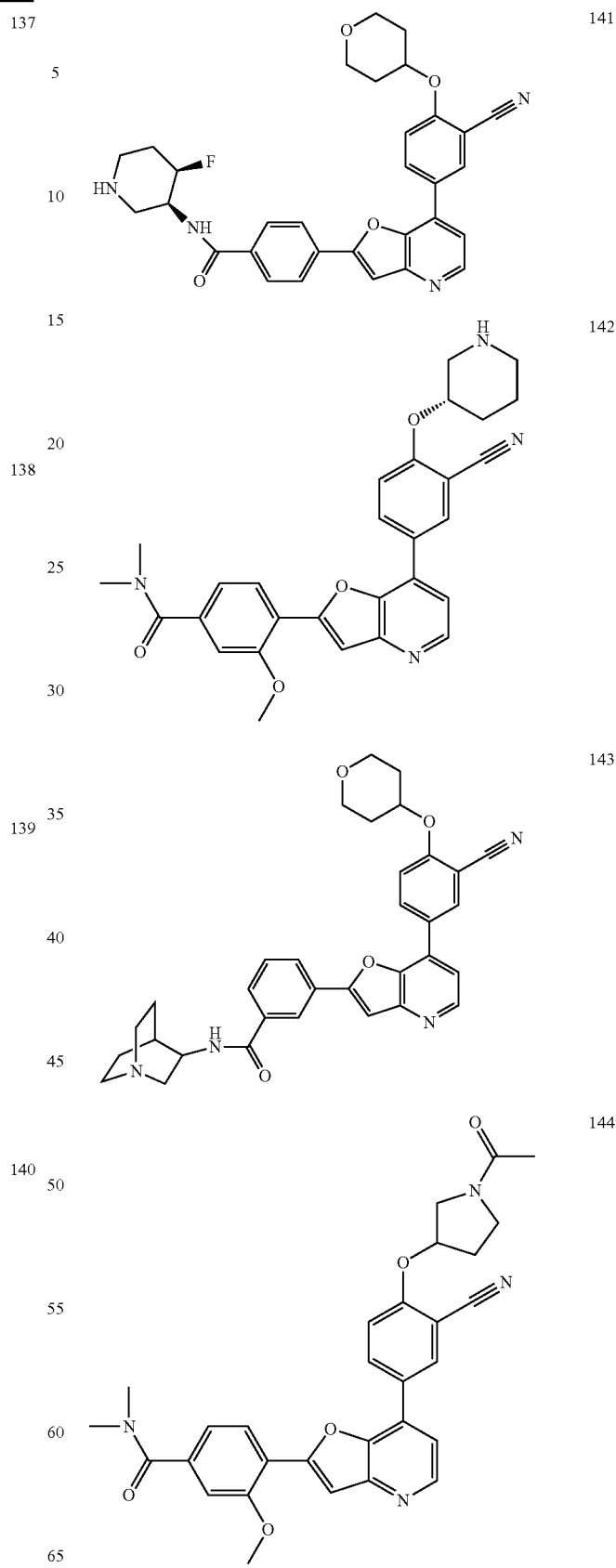

TABLE 1-continued
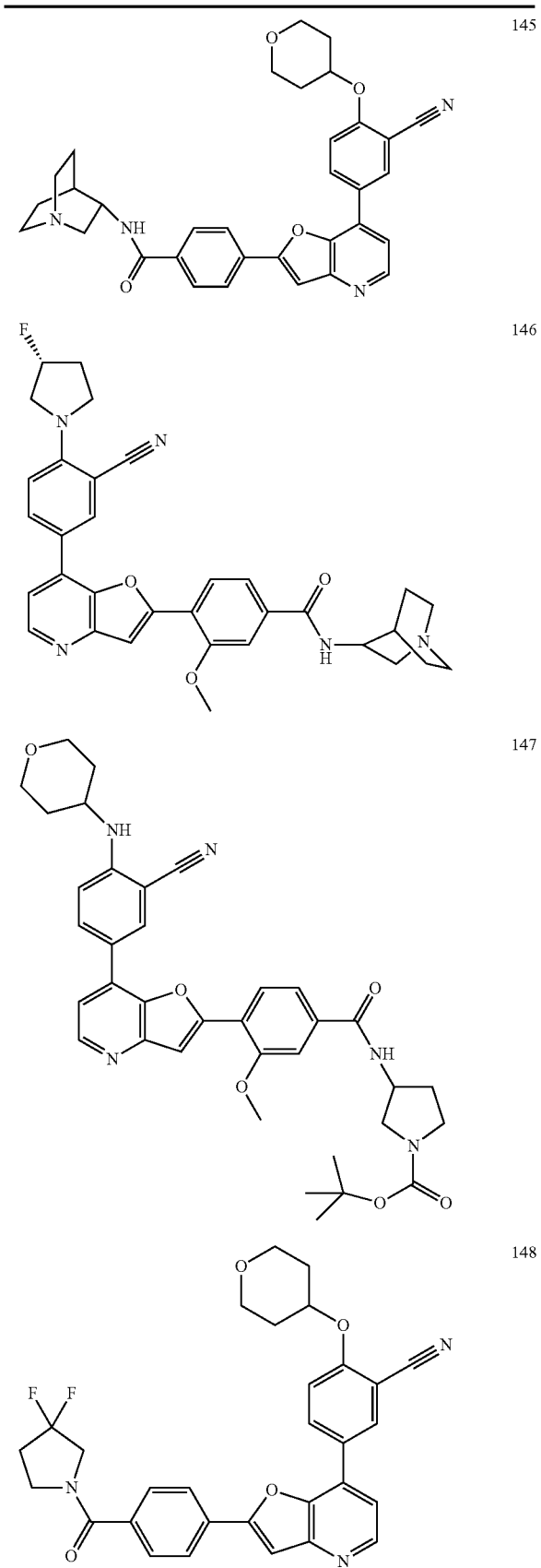
145
146
147
148
TABLE 1-continued
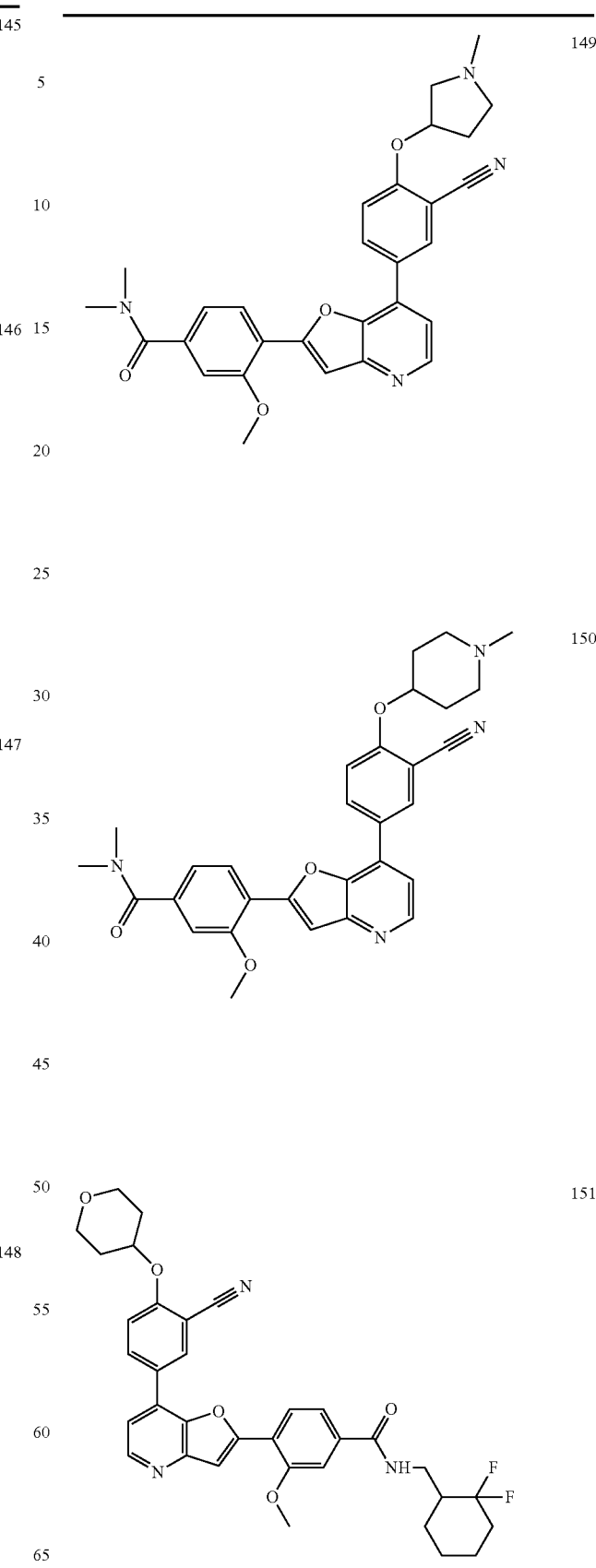
149
150
151

TABLE 1-continued
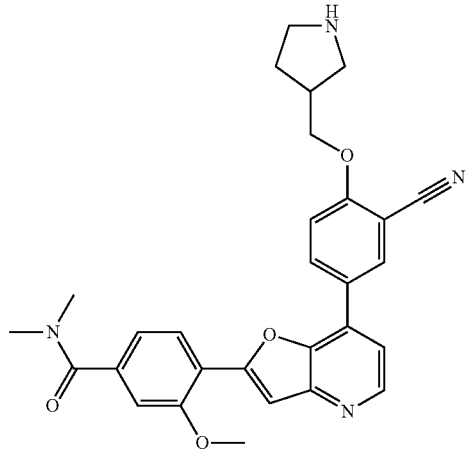 [SMILES: COc1cc(C(=O)N(C)C)ccc1-c1cc2nccc(-c3ccc(OCC4CCNC4)c(C#N)c3)c2o1]
152
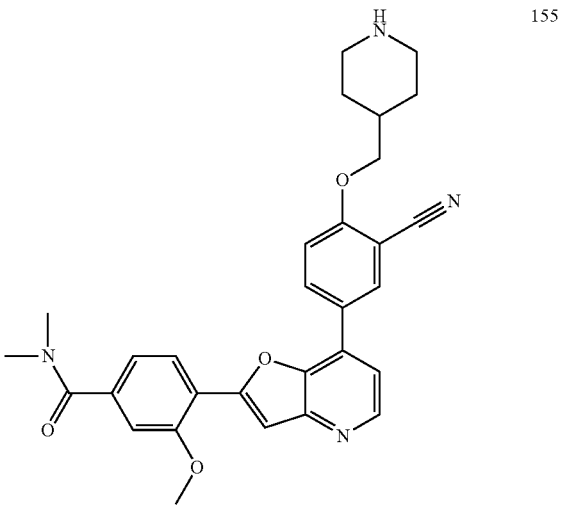
155
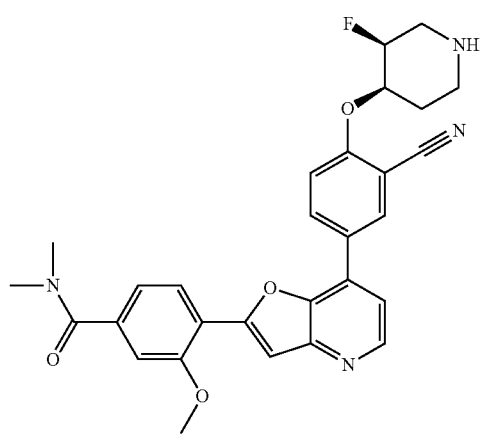 [SMILES: COc1cc(C(=O)N(C)C)ccc1-c1cc2nccc(-c3ccc(O[C@@H]4CCNC[C@@H]4F)c(C#N)c3)c2o1]
153
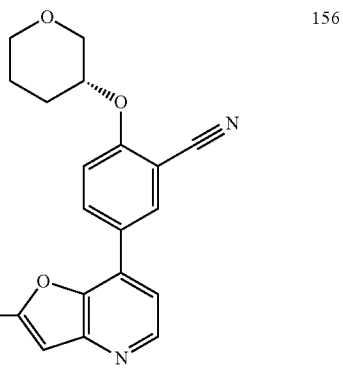
156
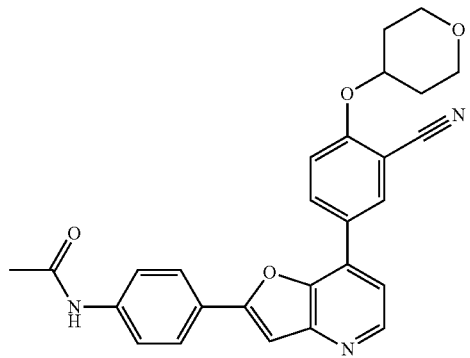 [SMILES: CC(=O)Nc1ccc(-c2cc3nccc(-c4ccc(OC5CCOCC5)c(C#N)c4)c3o2)cc1]
154
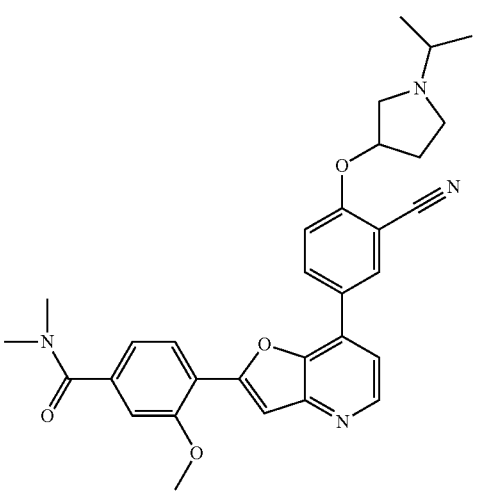 [SMILES: COc1cc(C(=O)N(C)C)ccc1-c1cc2nccc(-c3ccc(OC4CCN(C(C)C)C4)c(C#N)c3)c2o1]
157

TABLE 1-continued
158 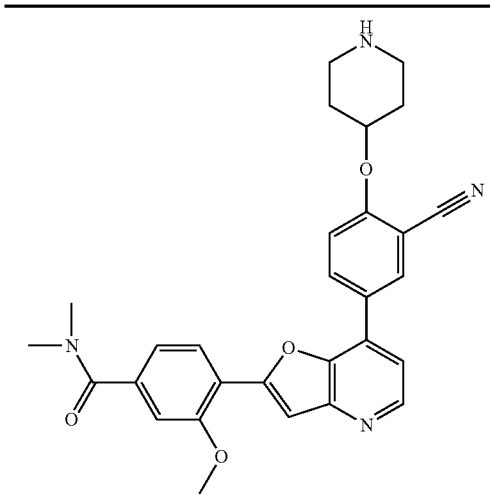
159 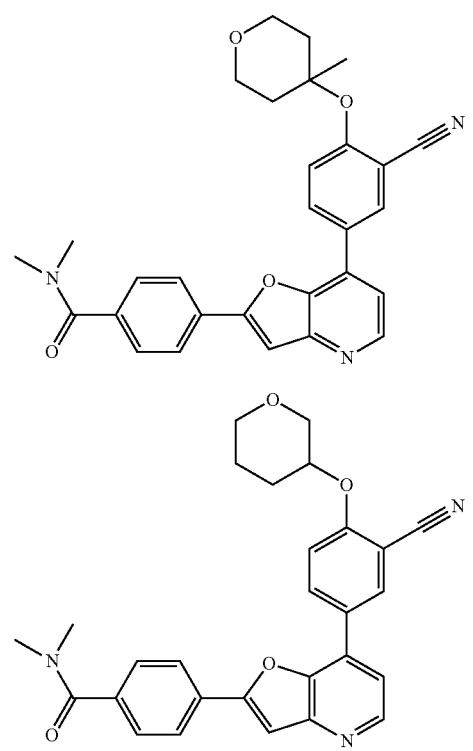
160 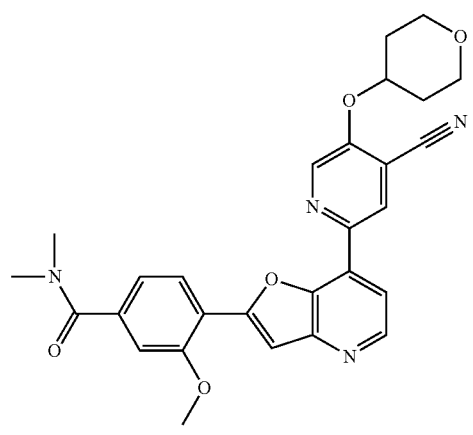 [SMILES: COc1cc(C(=O)N(C)C)ccc1-c1cc2nccc(-c3cc(C#N)c(OC4CCOCC4)cn3)c2o1]
161 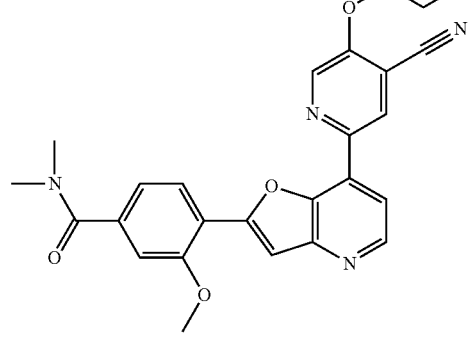
TABLE 1-continued
162 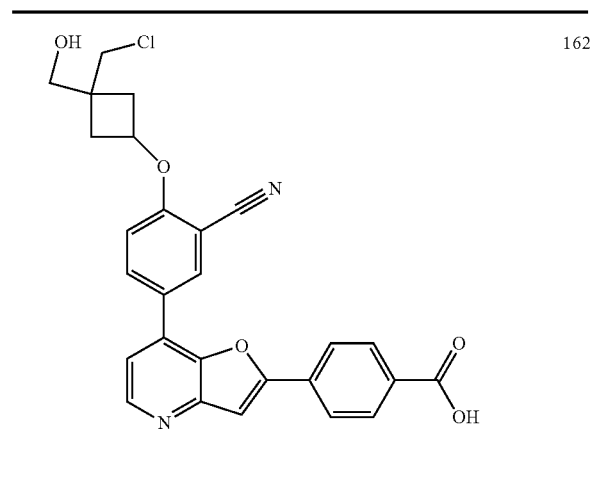
163 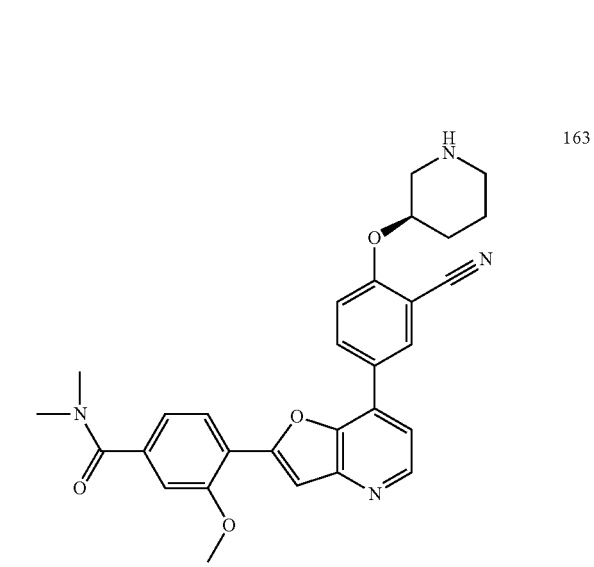
164 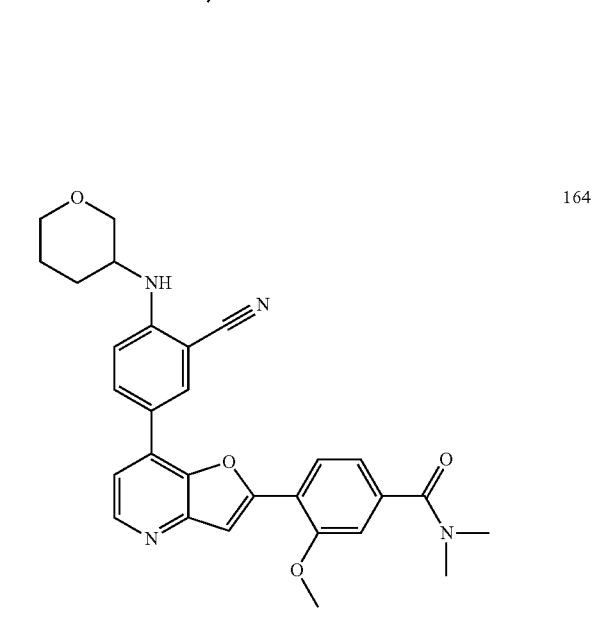

TABLE 1-continued
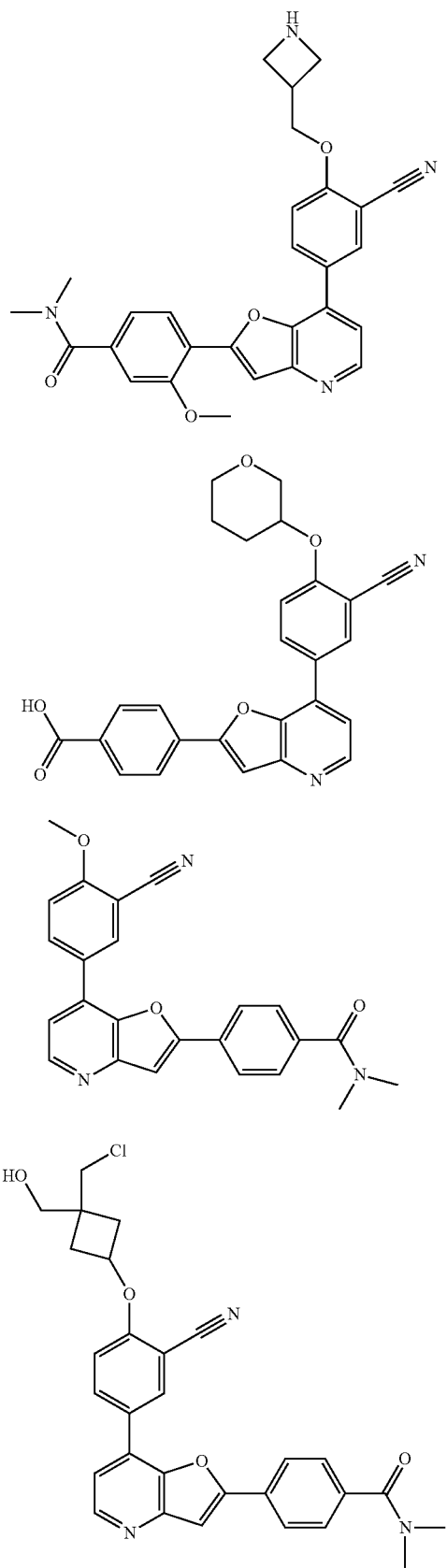
TABLE 1-continued
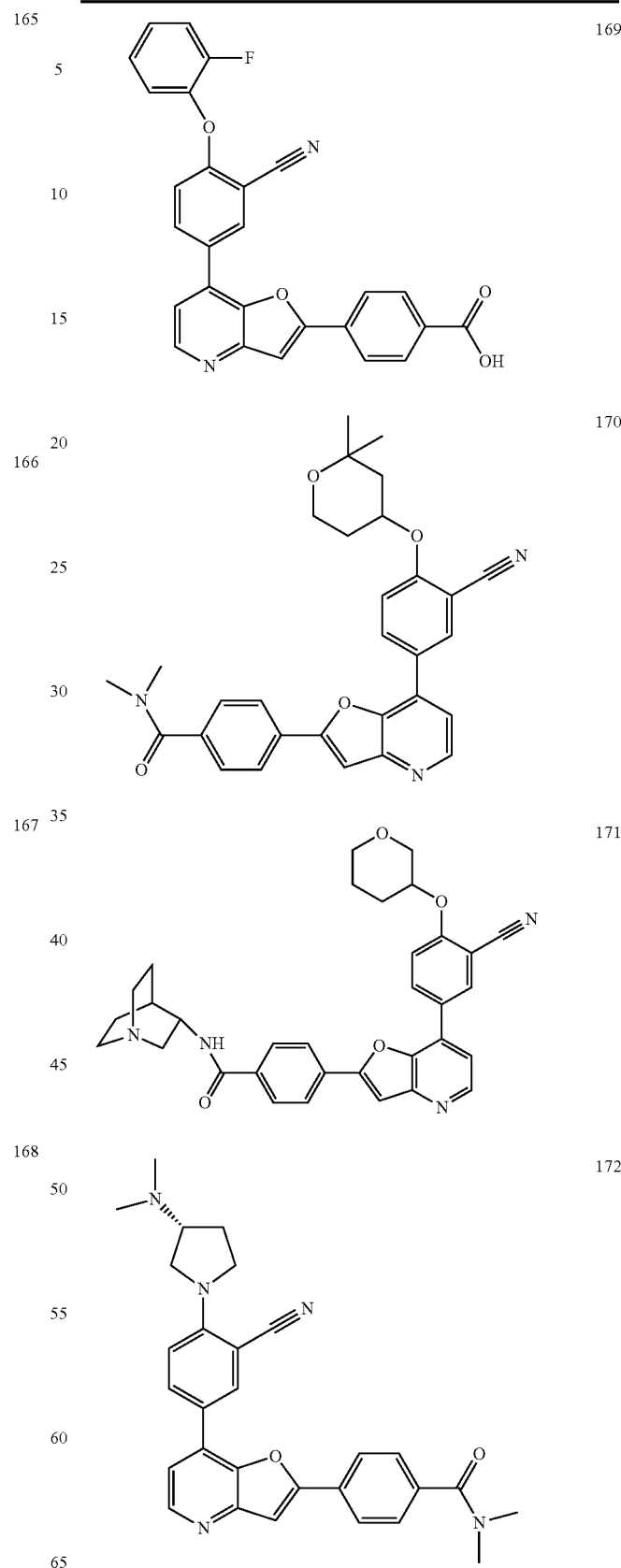

TABLE 1-continued
| | |
|---|---|
| 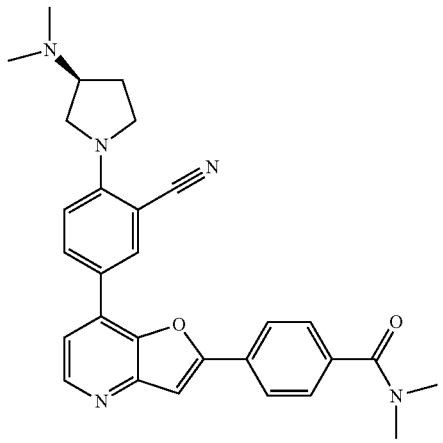 173 | 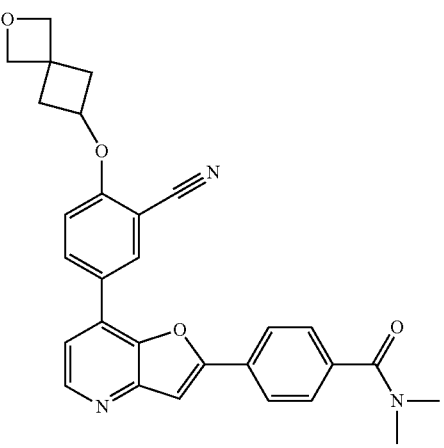 [SMILES: CN(C)C(=O)c1ccc(-c2cc3nccc(-c4ccc(OC5CC6(COC6)C5)c(C#N)c4)c3o2)cc1] 177 |
| 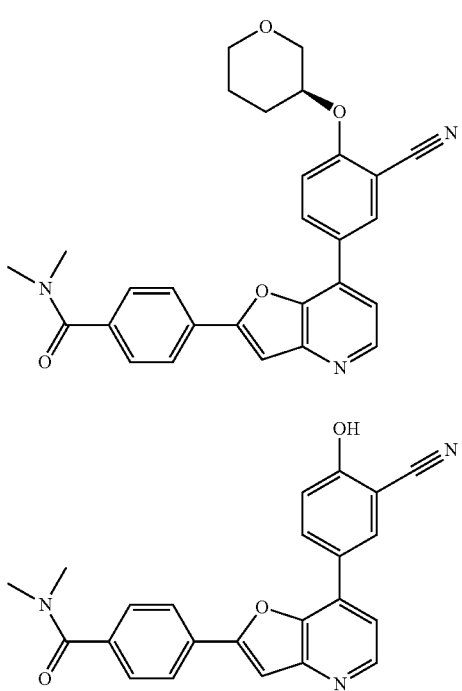 174 | 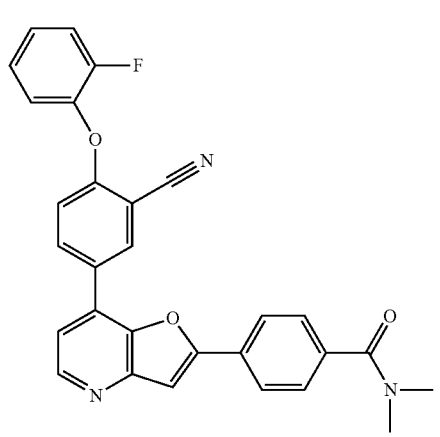 [SMILES: CN(C)C(=O)c1ccc(-c2cc3nccc(-c4ccc(Oc5ccccc5F)c(C#N)c4)c3o2)cc1] 178 |
| 175 | |
| 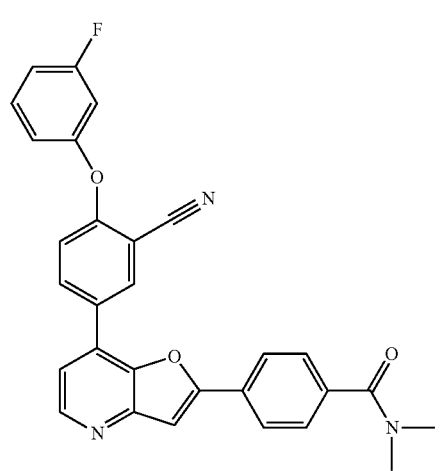 176 | 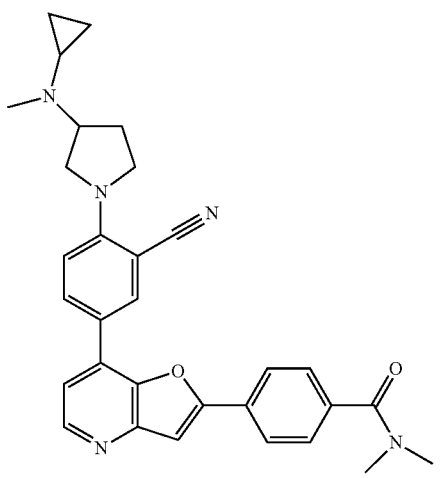 179 |

TABLE 1-continued
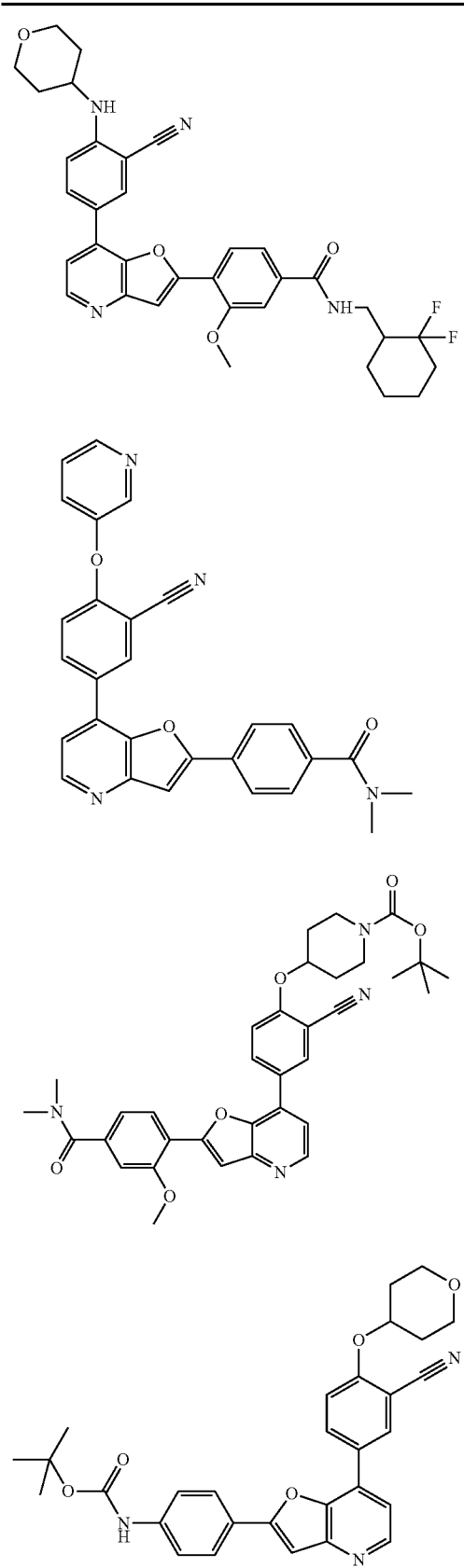
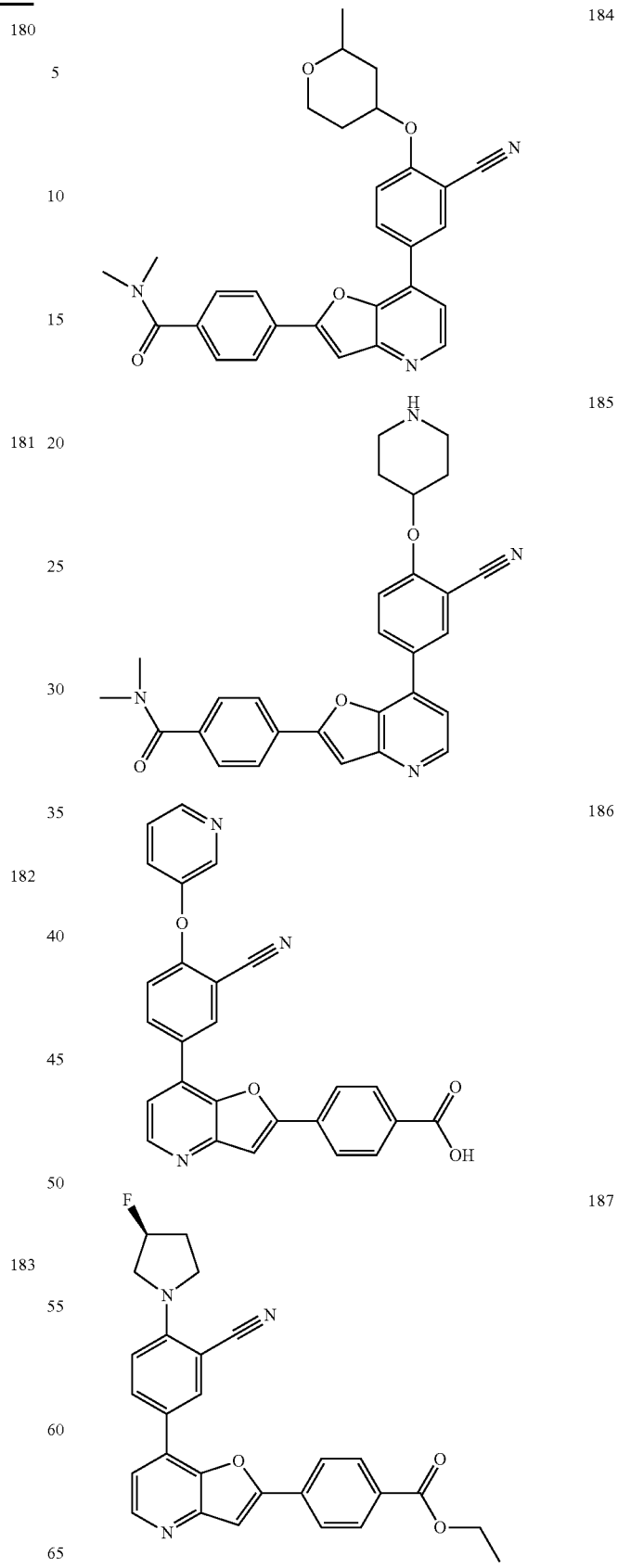

TABLE 1-continued
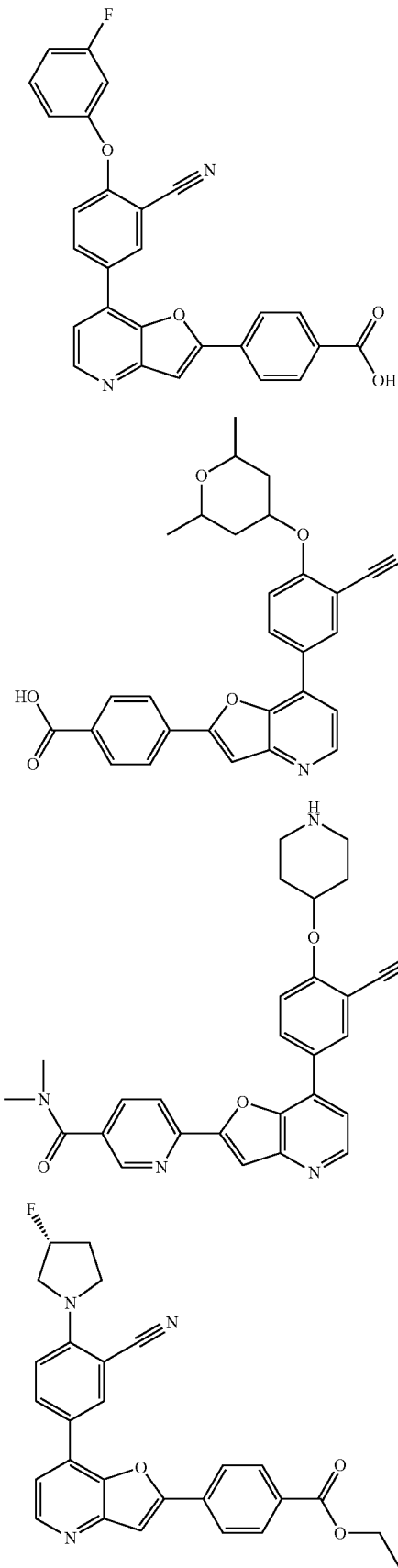
TABLE 1-continued
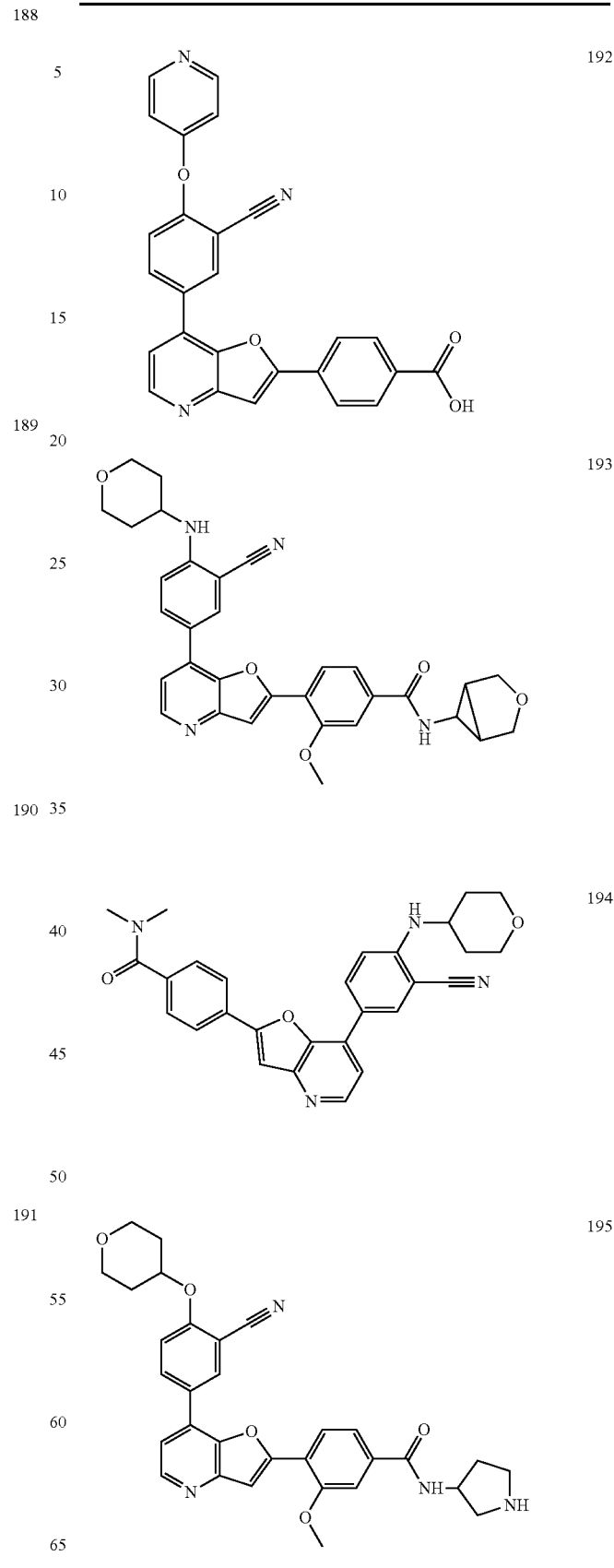

TABLE 1-continued
| | |
|---|---|
| 196 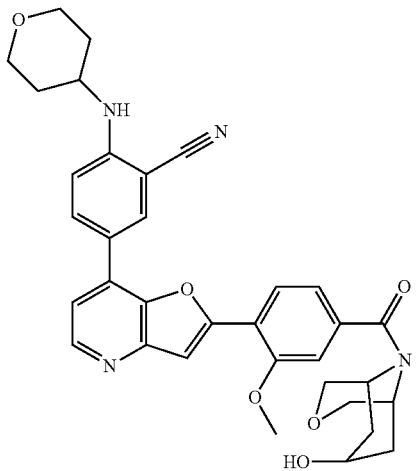 [SMILES: COc1cc(C(=O)N2C3COCC2CC(O)C3)ccc1-c1cc2nccc(-c3ccc(NC4CCOCC4)c(C#N)c3)c2o1] | 199 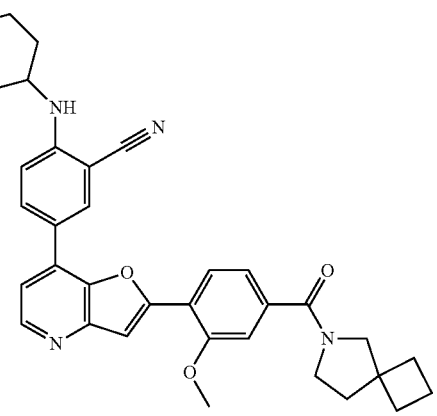 |
| 197 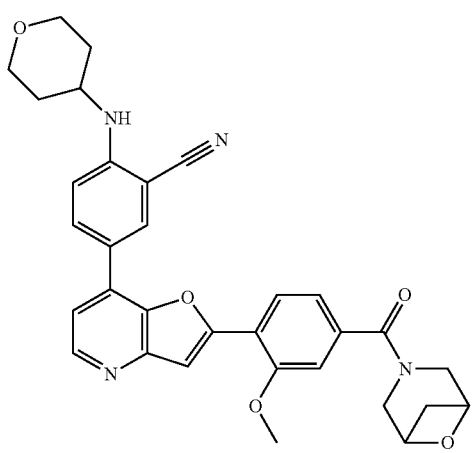 [SMILES: COc1cc(C(=O)N2CC3CC(C2)O3)ccc1-c1cc2nccc(-c3ccc(NC4CCOCC4)c(C#N)c3)c2o1] | 200 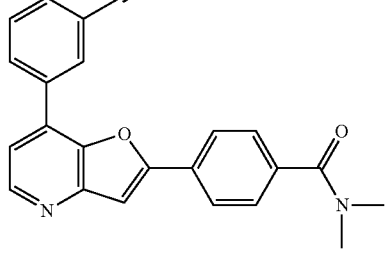 |
| 198 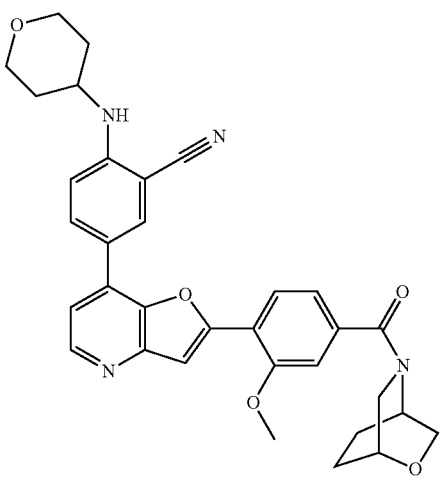 | 201 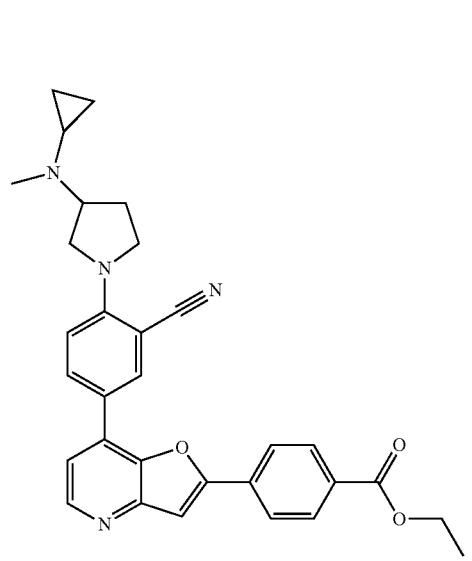 [SMILES: CCOC(=O)c1ccc(-c2cc3nccc(-c4ccc(N5CCC(N(C)C6CC6)C5)c(C#N)c4)c3o2)cc1] |

TABLE 1-continued
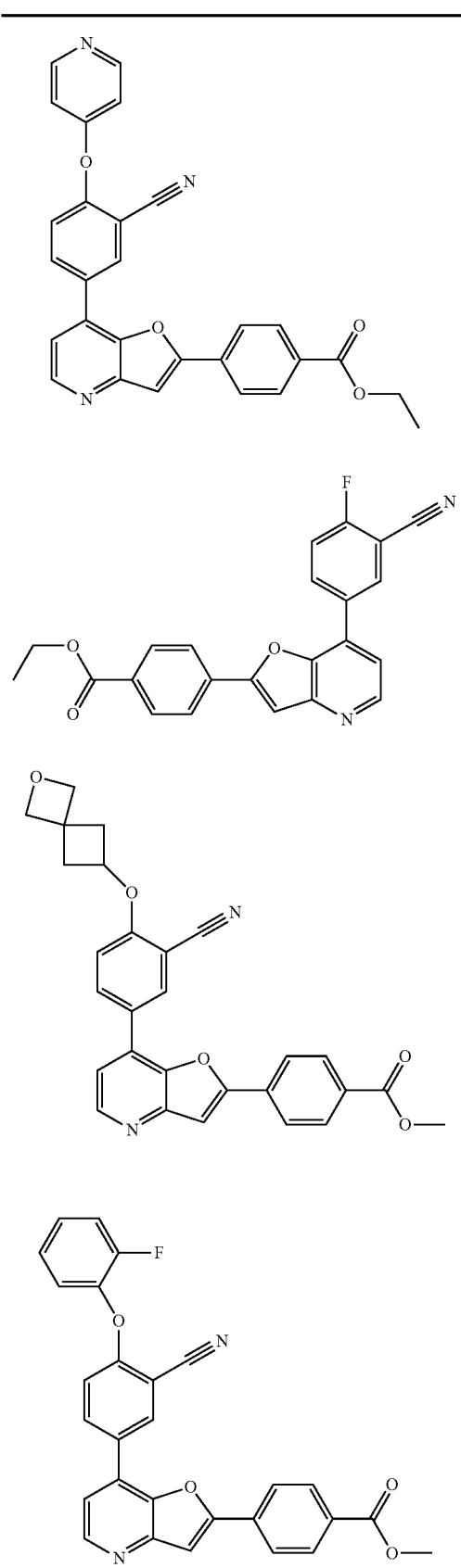
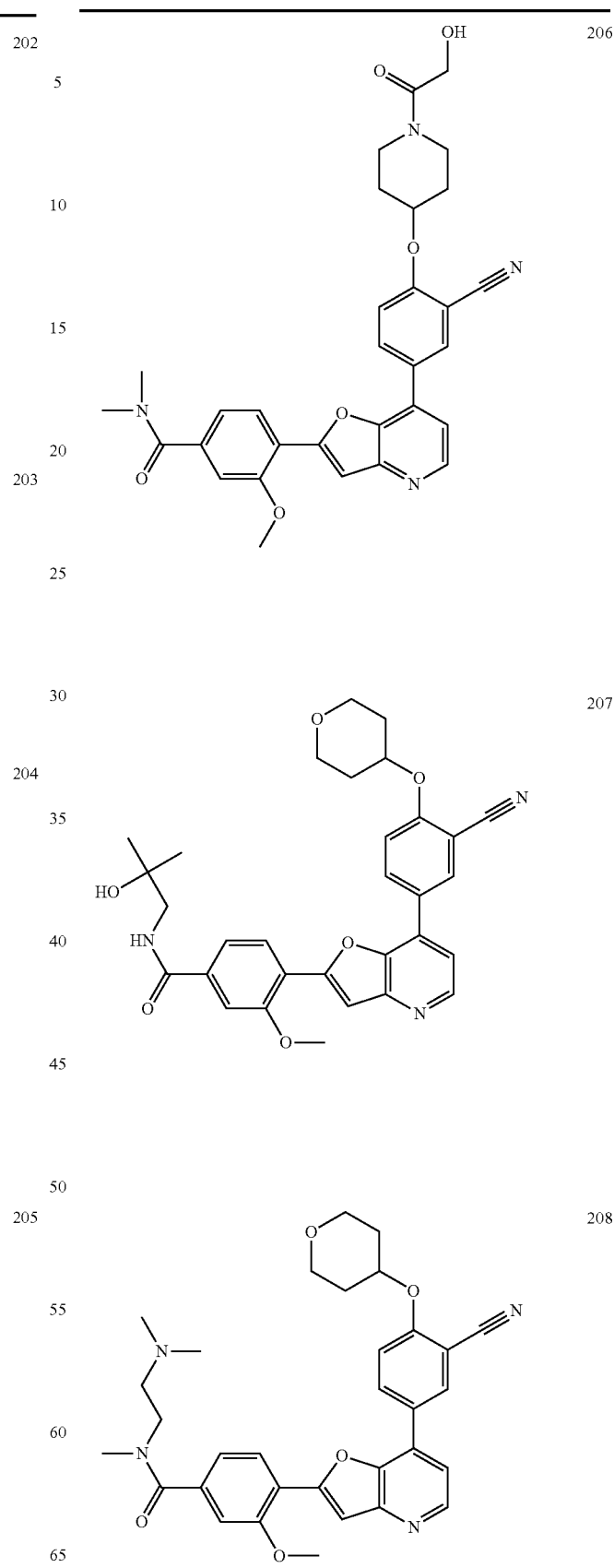

TABLE 1-continued
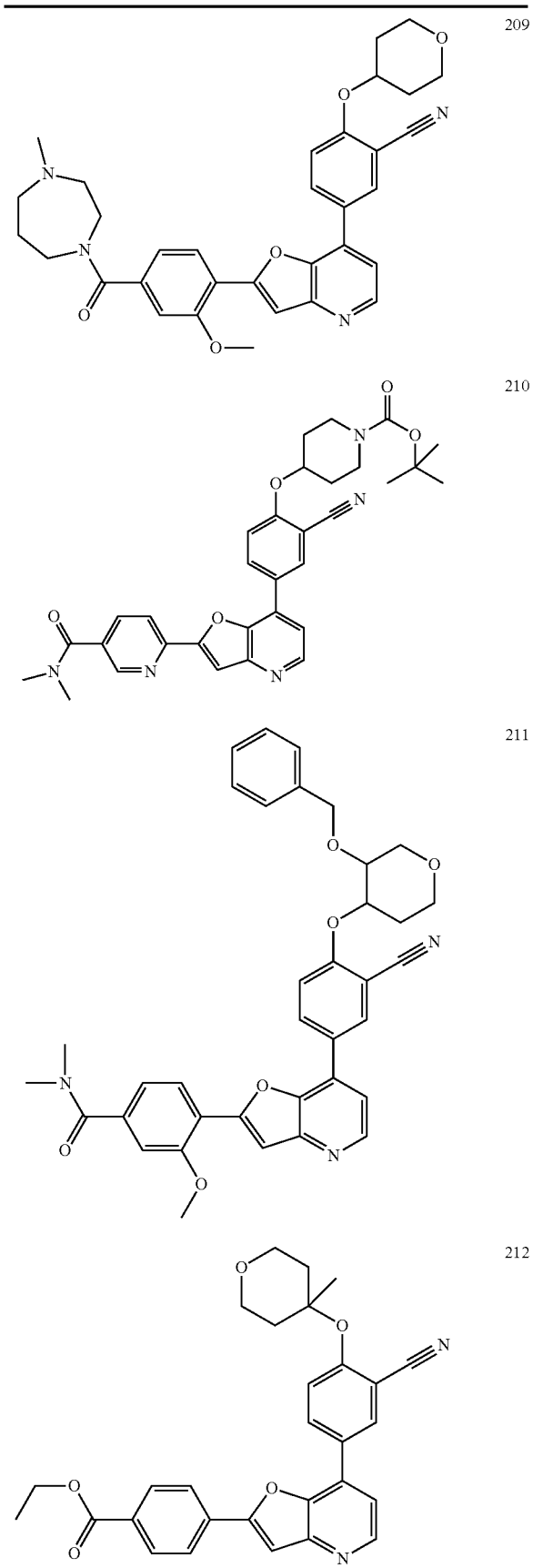

TABLE 1-continued
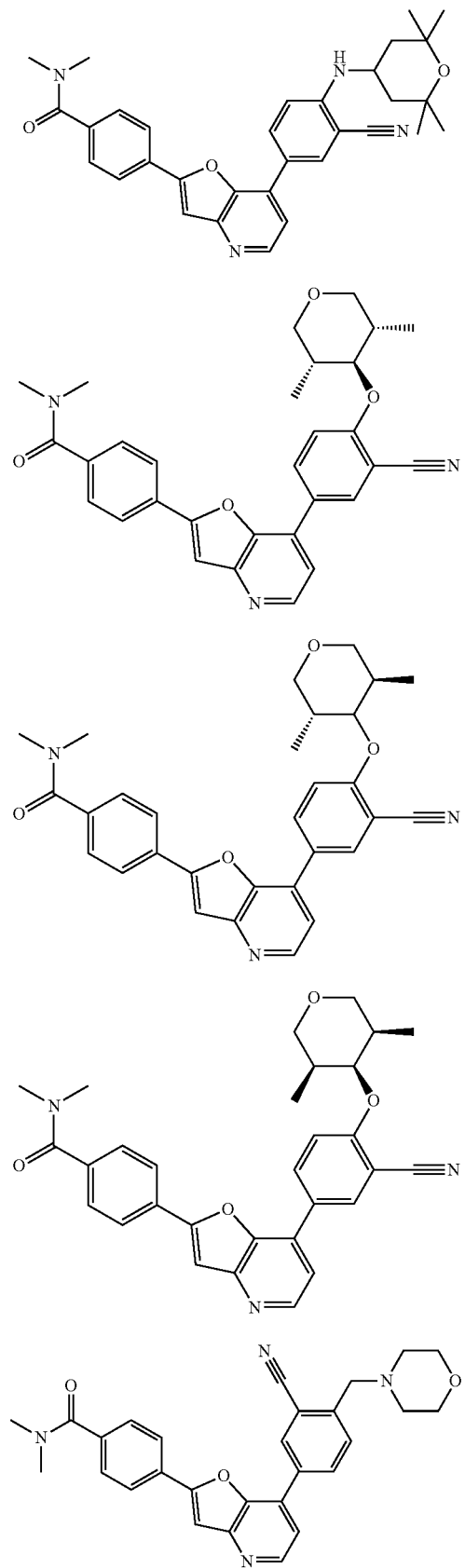
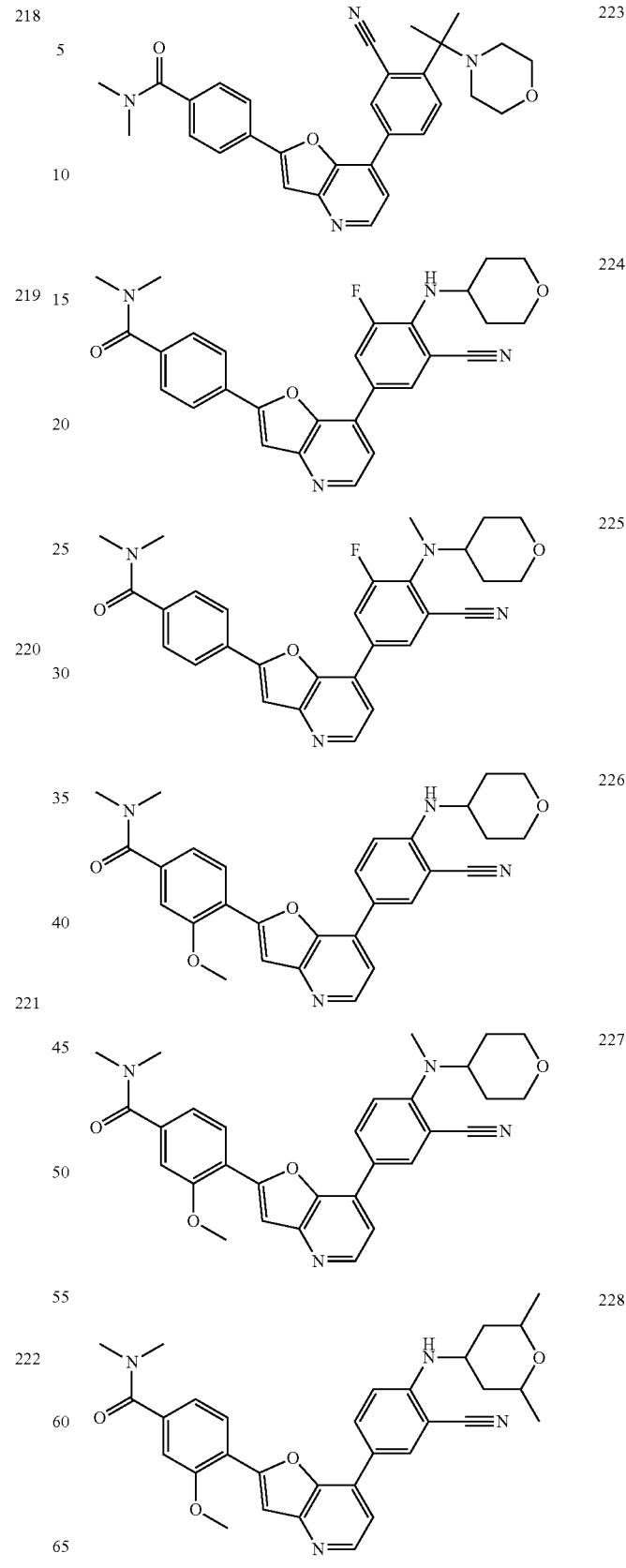

TABLE 1-continued
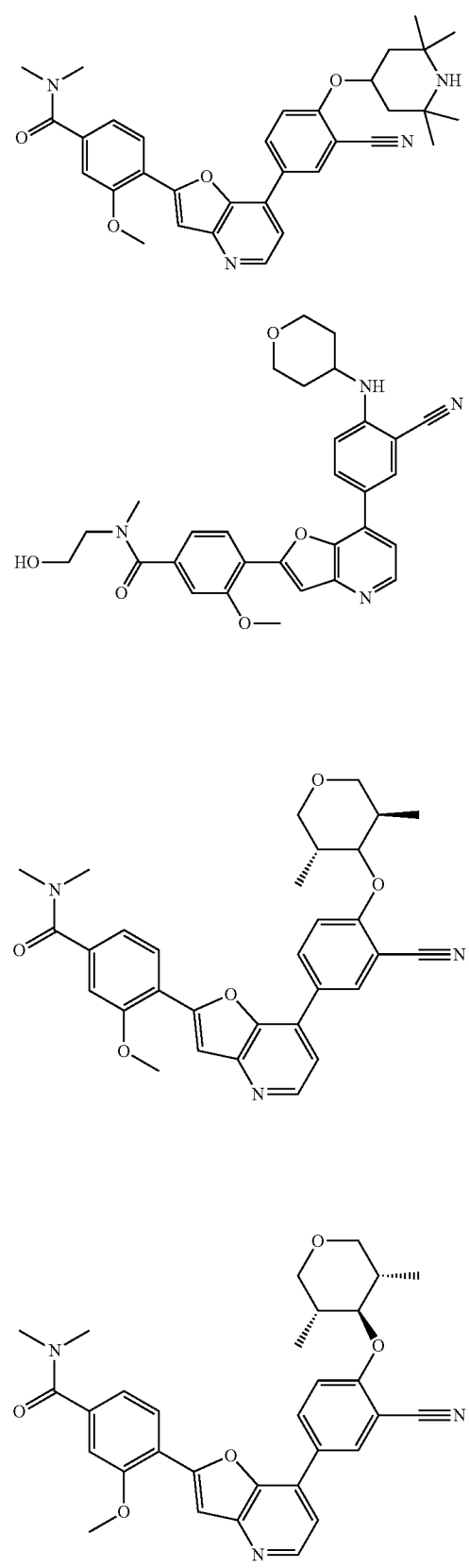
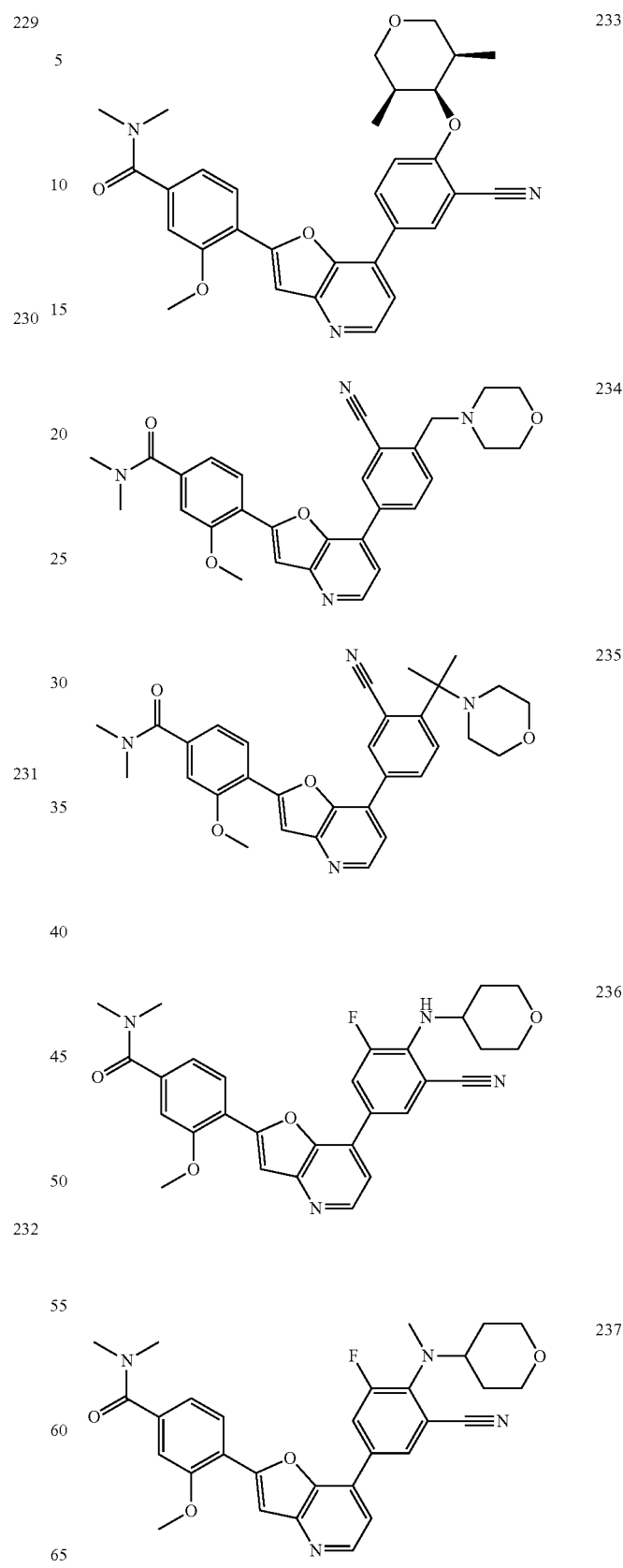

TABLE 1-continued
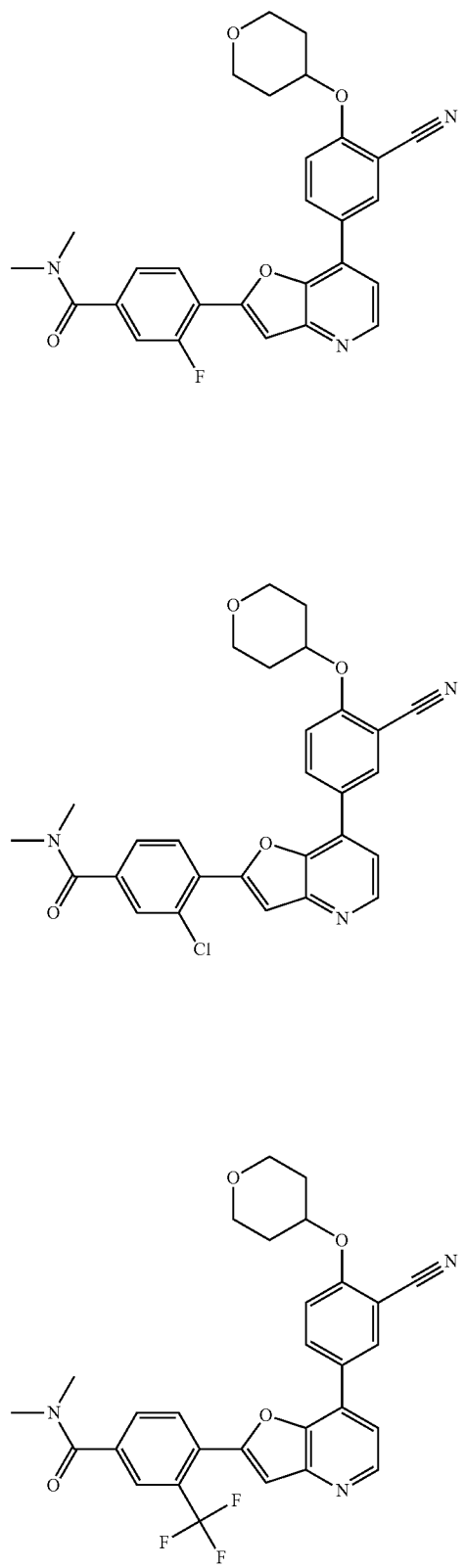
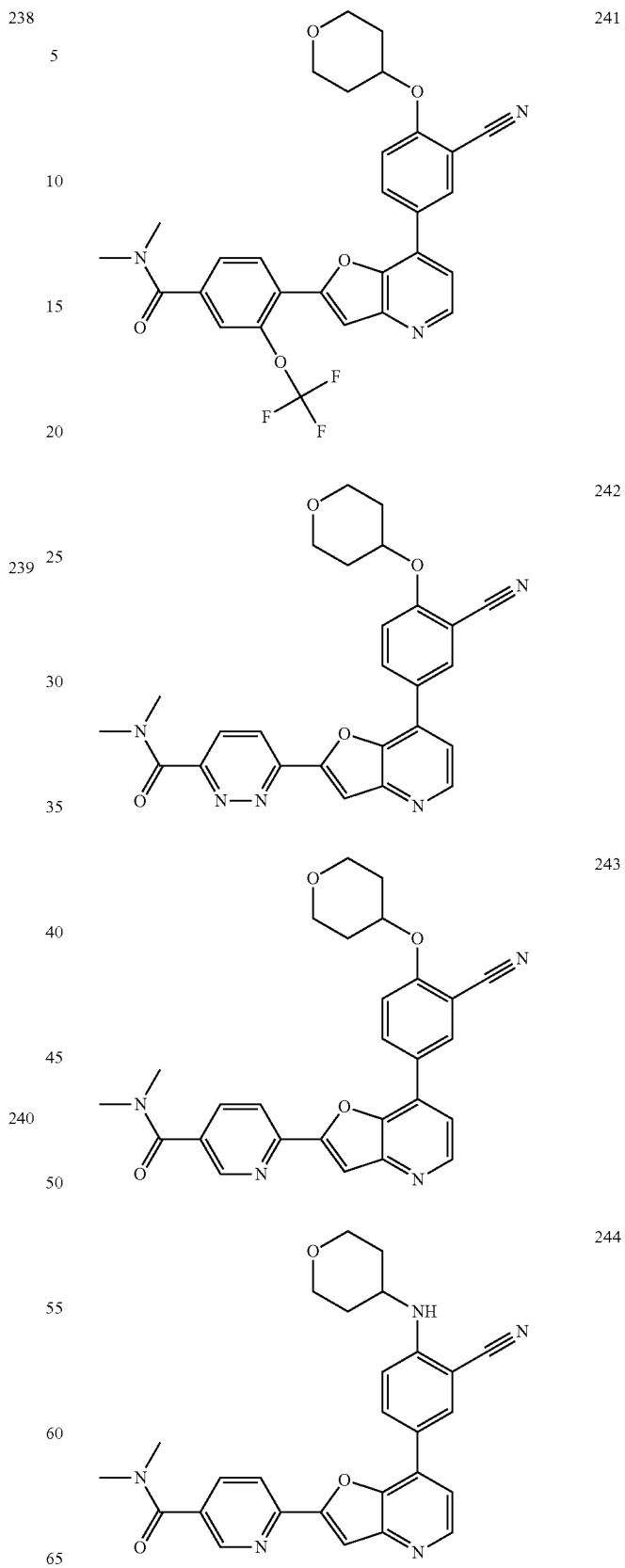

TABLE 1-continued
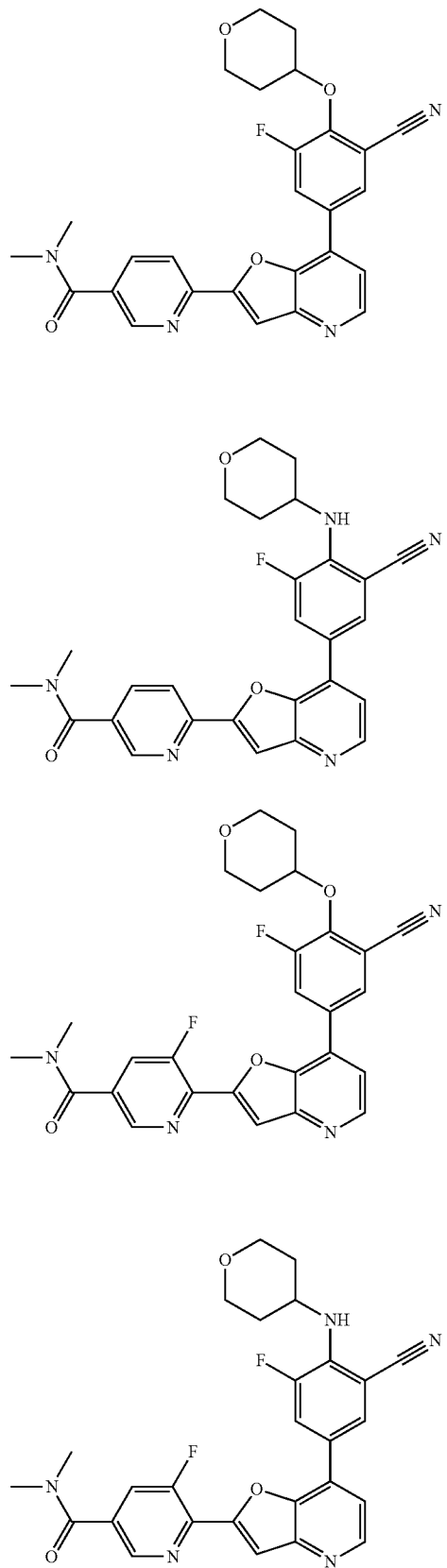
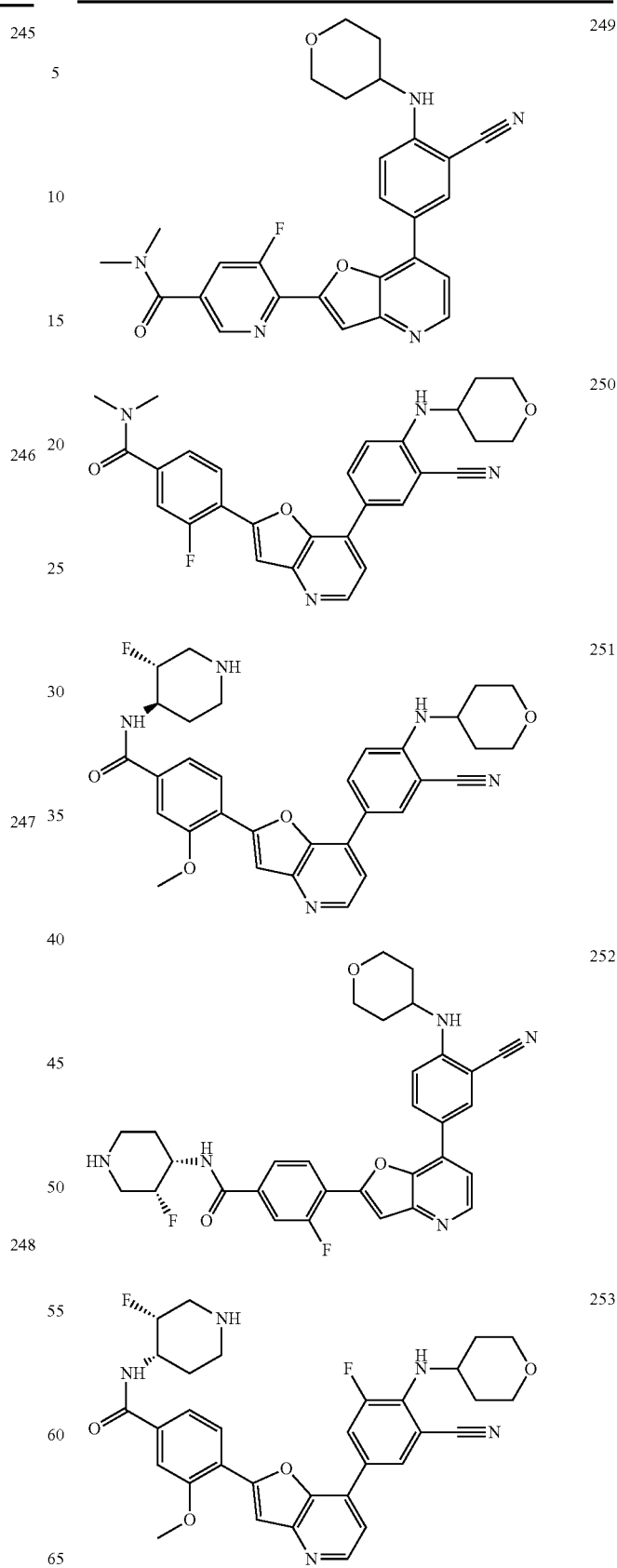

TABLE 1-continued
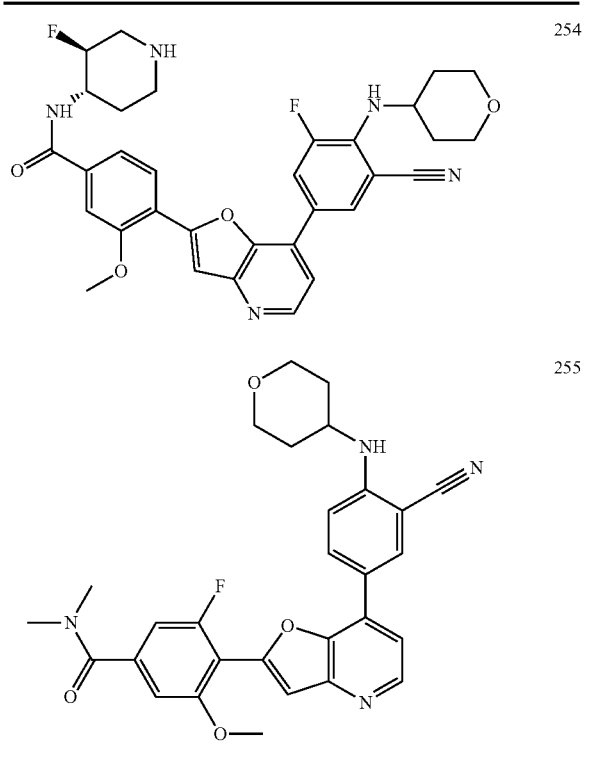
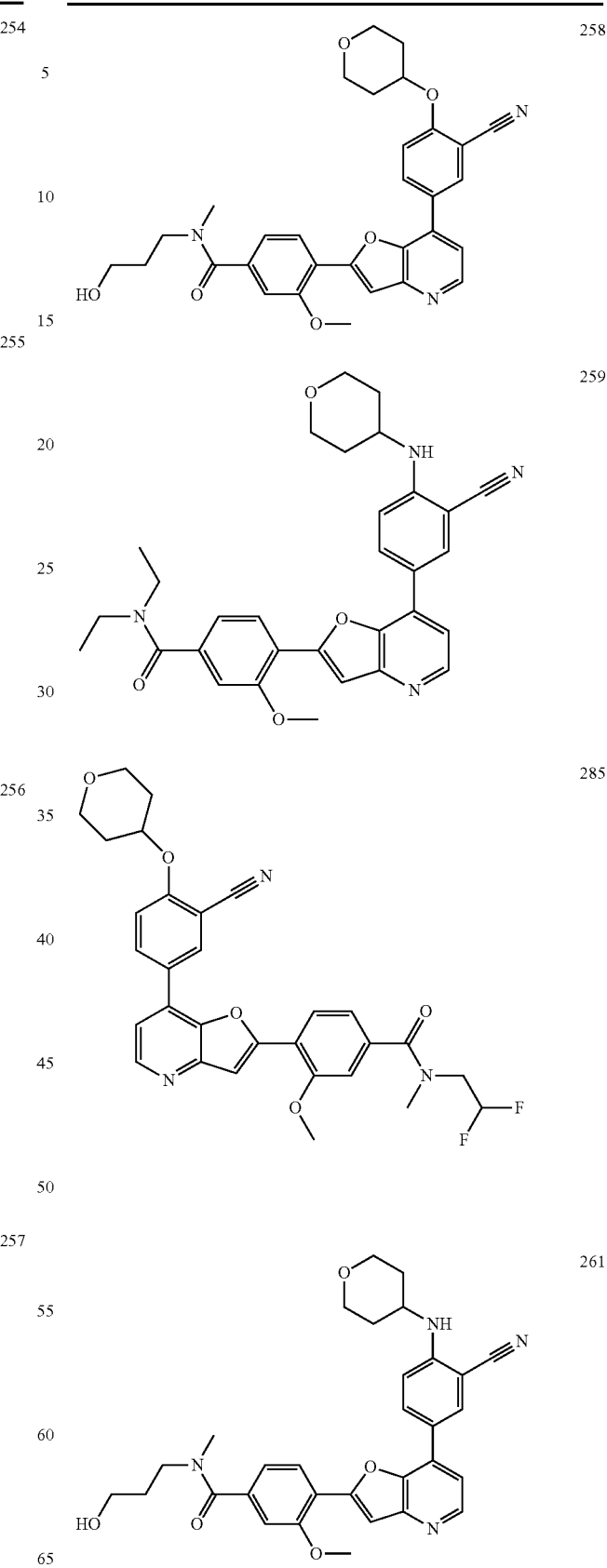

TABLE 1-continued
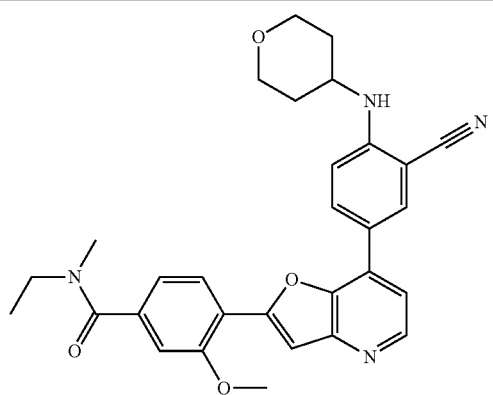 [SMILES: CCN(C)C(=O)c1ccc(-c2cc3nccc(-c4ccc(NC5CCOCC5)c(C#N)c4)c3o2)c(OC)c1]
262
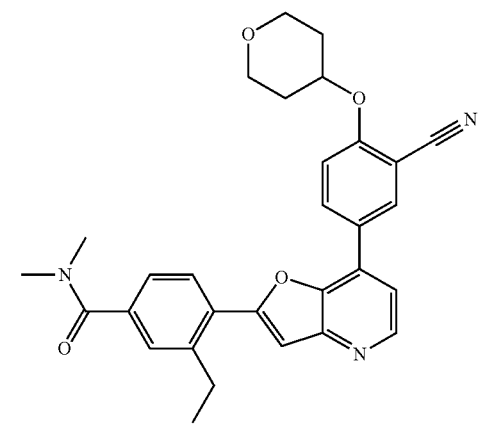 [SMILES: CCc1cc(C(=O)N(C)C)ccc1-c1cc2nccc(-c3ccc(OC4CCOCC4)c(C#N)c3)c2o1]
263
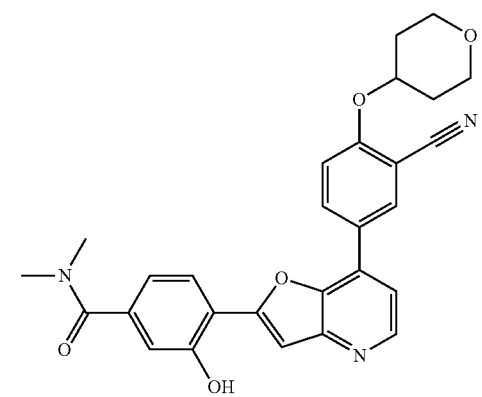 [SMILES: CN(C)C(=O)c1ccc(-c2cc3nccc(-c4ccc(OC5CCOCC5)c(C#N)c4)c3o2)c(O)c1]
264
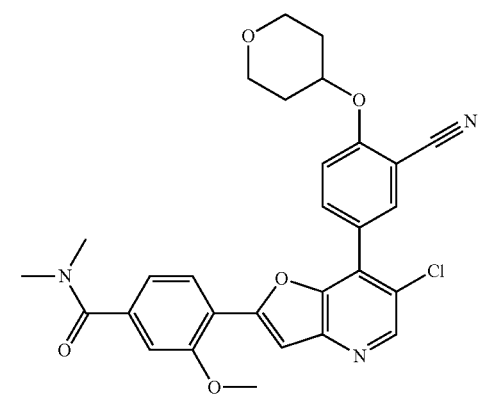 [SMILES: COc1cc(C(=O)N(C)C)ccc1-c1cc2ncc(Cl)c(-c3ccc(OC4CCOCC4)c(C#N)c3)c2o1]
265
TABLE 1-continued
266
267
268
269

TABLE 1-continued
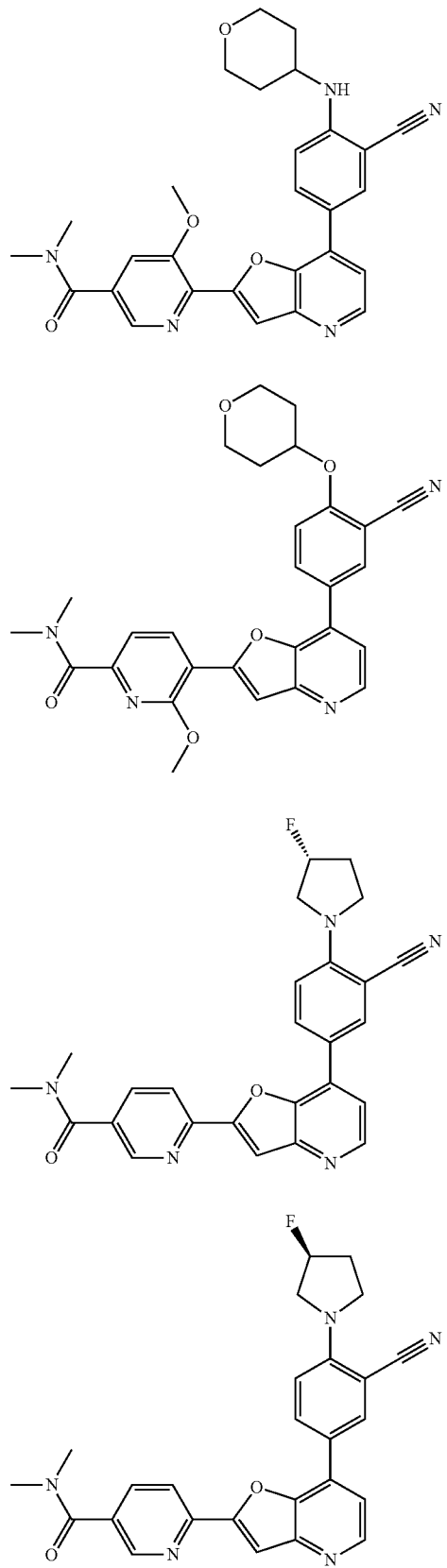
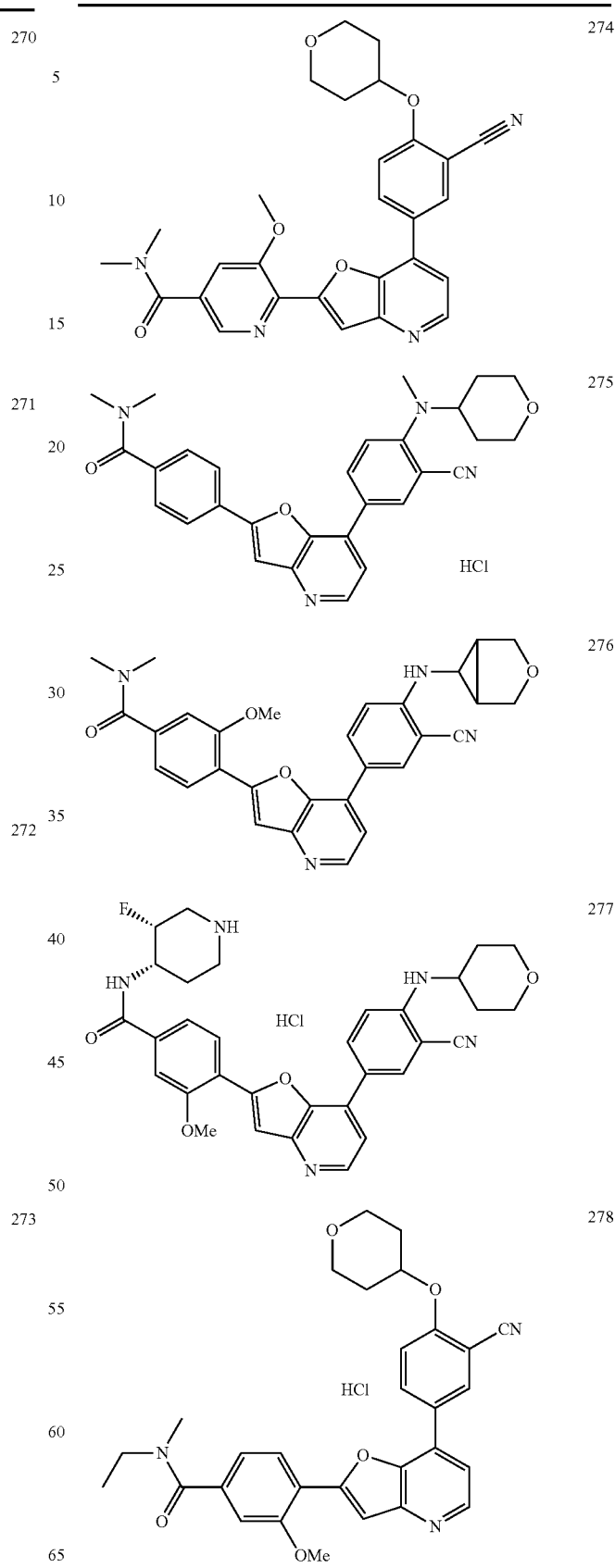

TABLE 1-continued
279
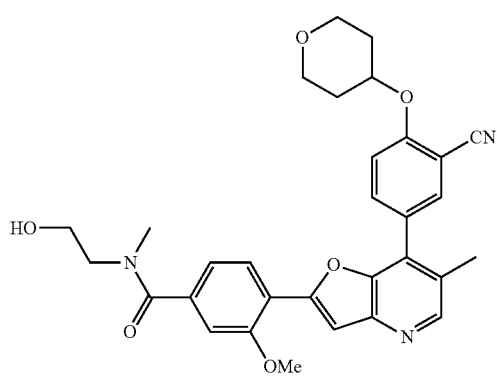 [SMILES: COc1cc(C(=O)N(C)CCO)ccc1-c1cc2ncc(C)c(-c3ccc(OC4CCOCC4)c(C#N)c3)c2o1]
280
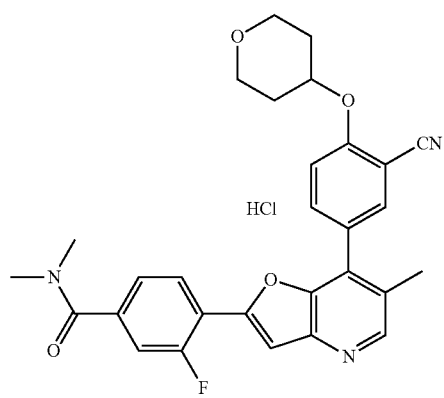 [SMILES: Cc1cnc2cc(-c3ccc(C(=O)N(C)C)cc3F)oc2c1-c1ccc(OC2CCOCC2)c(C#N)c1 ; Cl]
281
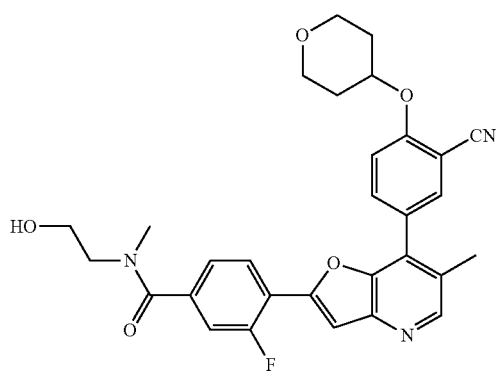 [SMILES: Cc1cnc2cc(-c3ccc(C(=O)N(C)CCO)cc3F)oc2c1-c1ccc(OC2CCOCC2)c(C#N)c1]
282
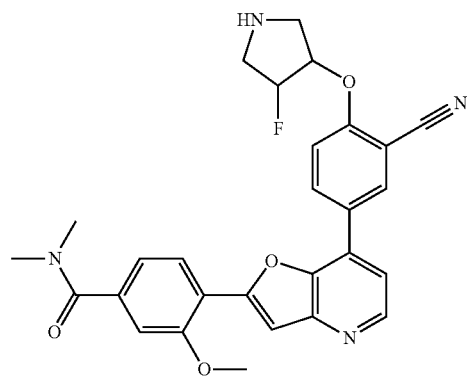 [SMILES: COc1cc(C(=O)N(C)C)ccc1-c1cc2nccc(-c3ccc(OC4CNCC4F)c(C#N)c3)c2o1]
TABLE 1-continued
283
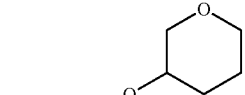
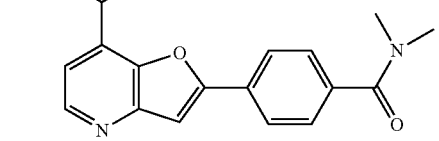
284
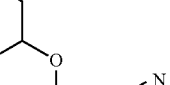
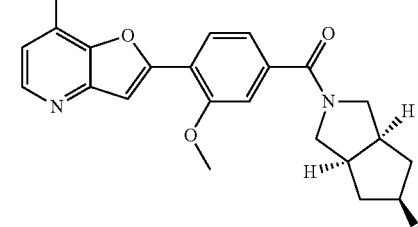
285
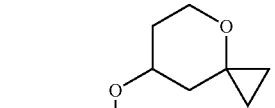
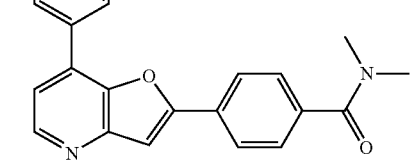
286
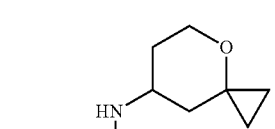
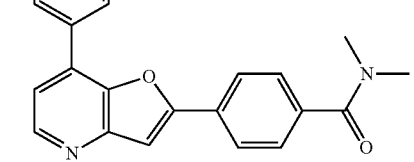

TABLE 1-continued
287
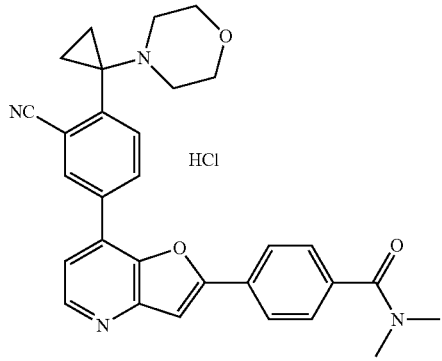 [SMILES: CN(C)C(=O)c1ccc(-c2cc3nccc(-c4ccc(C5(N6CCOCC6)CC5)c(C#N)c4)c3o2)cc1 ; Cl]
288
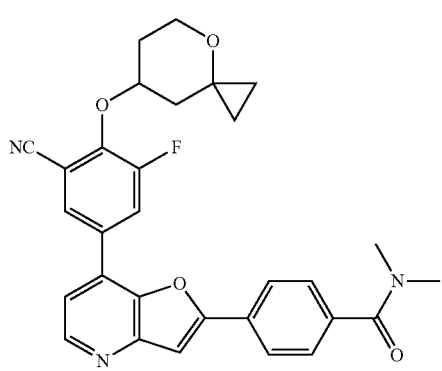 [SMILES: CN(C)C(=O)c1ccc(-c2cc3nccc(-c4cc(F)c(OC5CCOC6(CC6)C5)c(C#N)c4)c3o2)cc1]
289
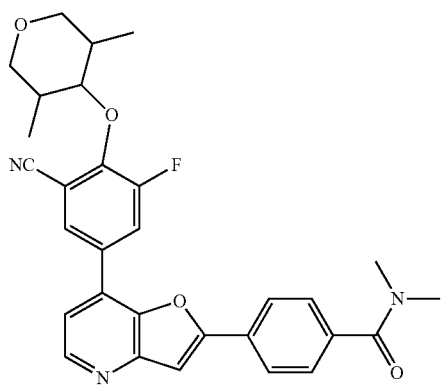 [SMILES: CC1COCC(C)C1Oc1c(F)cc(-c2ccnc3cc(-c4ccc(C(=O)N(C)C)cc4)oc23)cc1C#N]
290
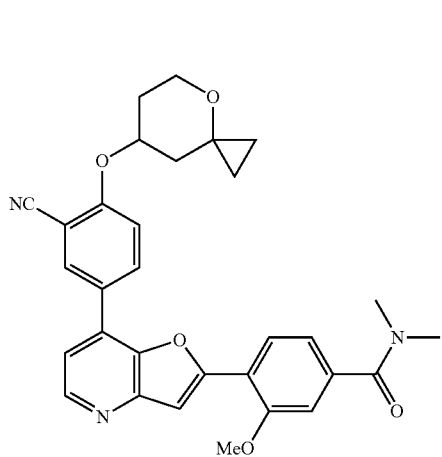 [SMILES: COc1cc(C(=O)N(C)C)ccc1-c1cc2nccc(-c3ccc(OC4CCOC5(CC5)C4)c(C#N)c3)c2o1]
TABLE 1-continued
291
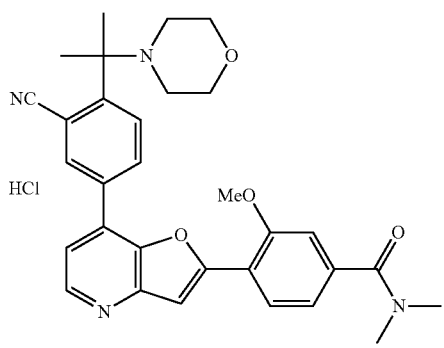 [SMILES: Cl ; COc1cc(C(=O)N(C)C)ccc1-c1cc2nccc(-c3ccc(C(C)(C)N4CCOCC4)c(C#N)c3)c2o1]
292
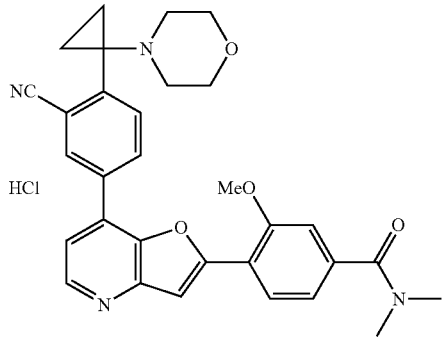 [SMILES: Cl ; COc1cc(C(=O)N(C)C)ccc1-c1cc2nccc(-c3ccc(C4(N5CCOCC5)CC4)c(C#N)c3)c2o1]
293
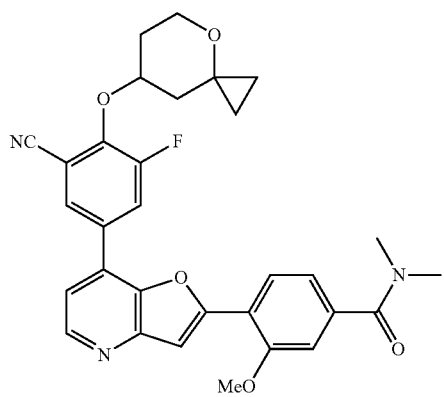 [SMILES: COc1cc(C(=O)N(C)C)ccc1-c1cc2nccc(-c3cc(F)c(OC4CCOC5(CC5)C4)c(C#N)c3)c2o1]
294
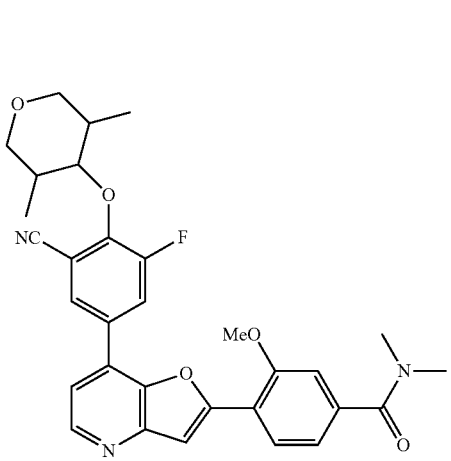 [SMILES: COc1cc(C(=O)N(C)C)ccc1-c1cc2nccc(-c3cc(F)c(OC4C(C)COCC4C)c(C#N)c3)c2o1]

TABLE 1-continued
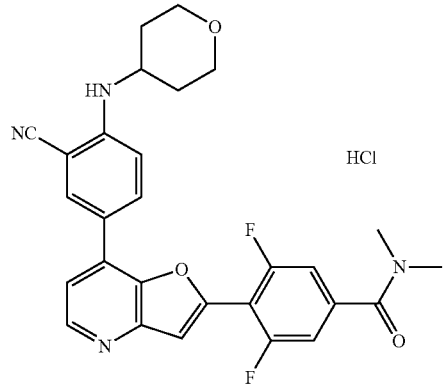 [SMILES: CN(C)C(=O)c1cc(F)c(-c2cc3nccc(-c4ccc(NC5CCOCC5)c(C#N)c4)c3o2)c(F)c1 ; Cl] 295 HCl
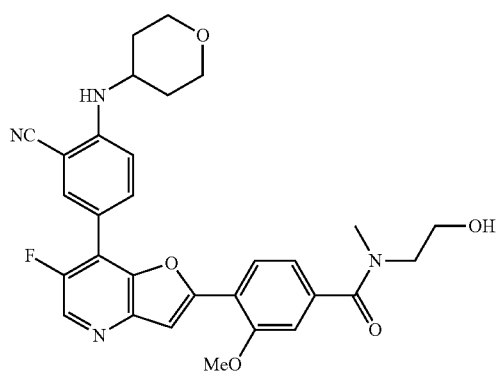 [SMILES: COc1cc(C(=O)N(C)CCO)ccc1-c1cc2ncc(F)c(-c3ccc(NC4CCOCC4)c(C#N)c3)c2o1] 296
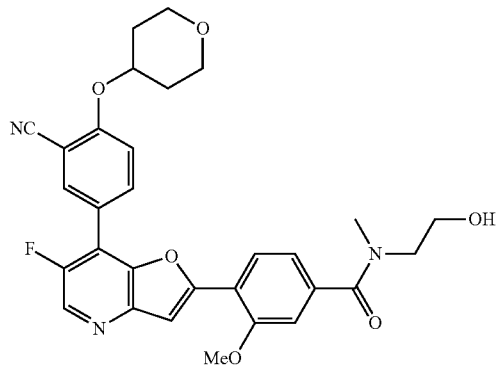 [SMILES: COc1cc(C(=O)N(C)CCO)ccc1-c1cc2ncc(F)c(-c3ccc(OC4CCOCC4)c(C#N)c3)c2o1] 297
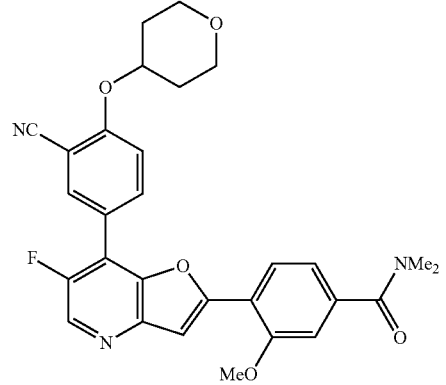 [SMILES: COc1cc(C(=O)N(C)C)ccc1-c1cc2ncc(F)c(-c3ccc(OC4CCOCC4)c(C#N)c3)c2o1] 298
TABLE 1-continued
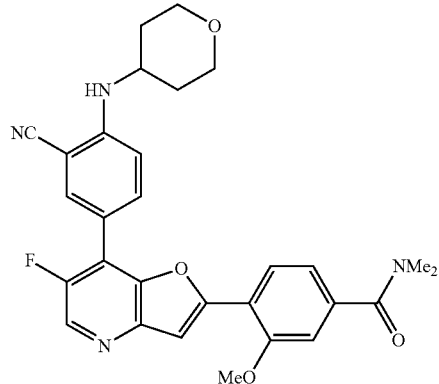 [SMILES: COc1cc(C(=O)N(C)C)ccc1-c1cc2ncc(F)c(-c3ccc(NC4CCOCC4)c(C#N)c3)c2o1] 299
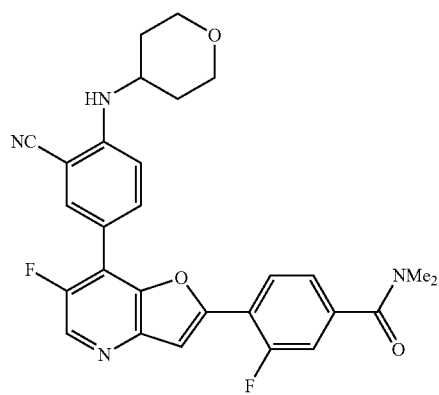 300
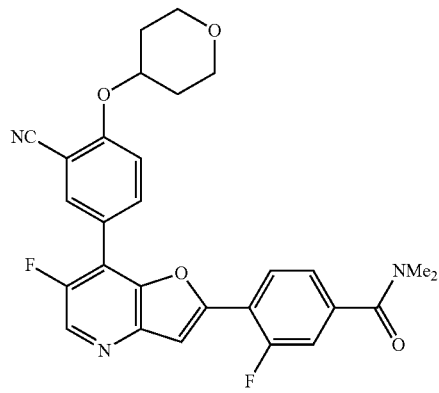 [SMILES: CN(C)C(=O)c1ccc(-c2cc3ncc(F)c(-c4ccc(OC5CCOCC5)c(C#N)c4)c3o2)c(F)c1] 301
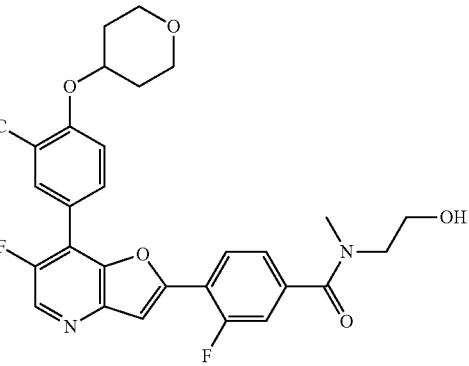 302

TABLE 1-continued
303
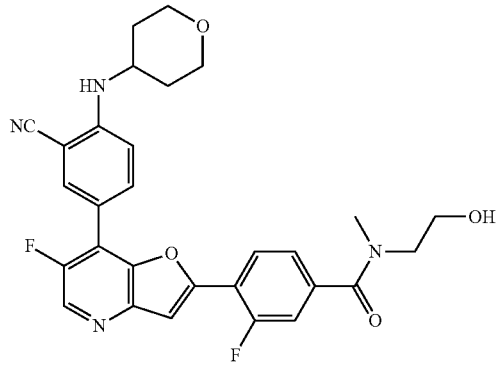 [SMILES: CN(CCO)C(=O)c1ccc(-c2cc3ncc(F)c(-c4ccc(NC5CCOCC5)c(C#N)c4)c3o2)c(F)c1]
304
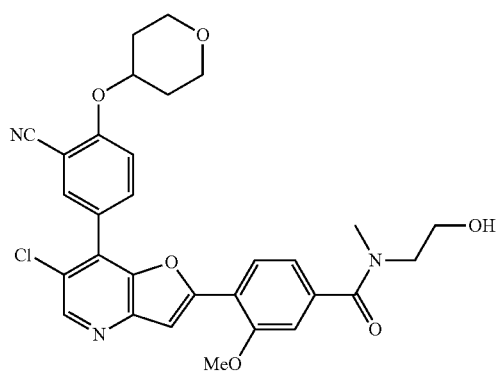 [SMILES: COc1cc(C(=O)N(C)CCO)ccc1-c1cc2ncc(Cl)c(-c3ccc(OC4CCOCC4)c(C#N)c3)c2o1]
305
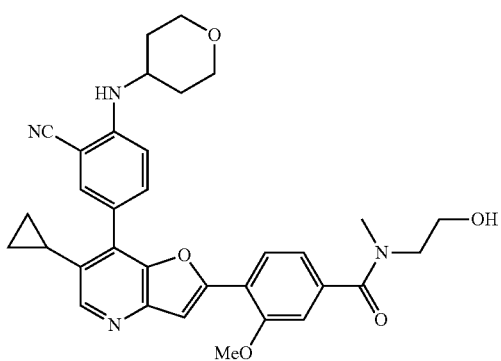 [SMILES: COc1cc(C(=O)N(C)CCO)ccc1-c1cc2ncc(C3CC3)c(-c3ccc(NC4CCOCC4)c(C#N)c3)c2o1]
306
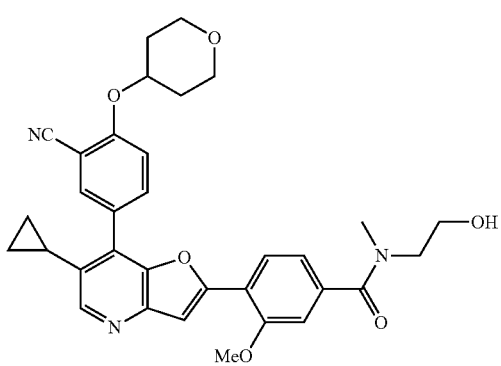 [SMILES: COc1cc(C(=O)N(C)CCO)ccc1-c1cc2ncc(C3CC3)c(-c3ccc(OC4CCOCC4)c(C#N)c3)c2o1]
TABLE 1-continued
307
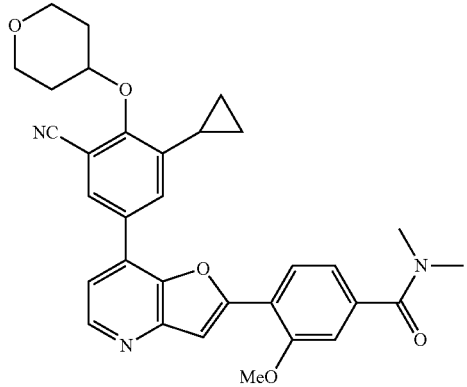 [SMILES: COc1cc(C(=O)N(C)C)ccc1-c1cc2nccc(-c3cc(C#N)c(OC4CCOCC4)c(C4CC4)c3)c2o1]
308
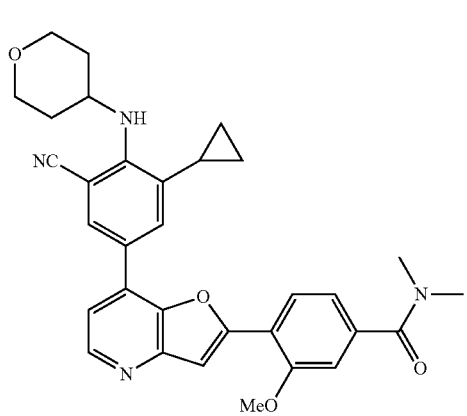
309
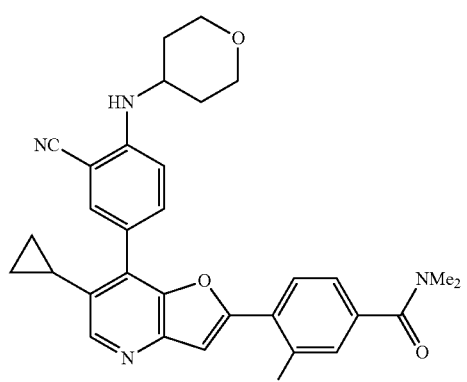
310
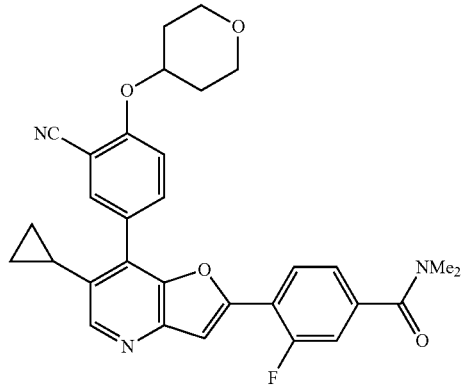 [SMILES: CN(C)C(=O)c1ccc(-c2cc3ncc(C4CC4)c(-c4ccc(OC5CCOCC5)c(C#N)c4)c3o2)c(F)c1]

TABLE 1-continued
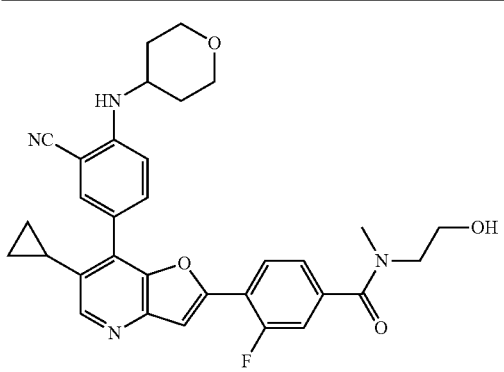 311
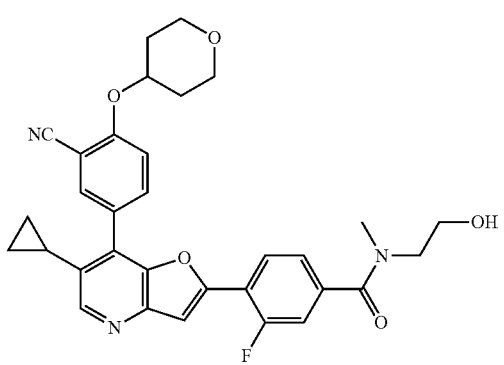 [SMILES: CN(CCO)C(=O)c1ccc(-c2cc3ncc(C4CC4)c(-c4ccc(OC5CCOCC5)c(C#N)c4)c3o2)c(F)c1] 312
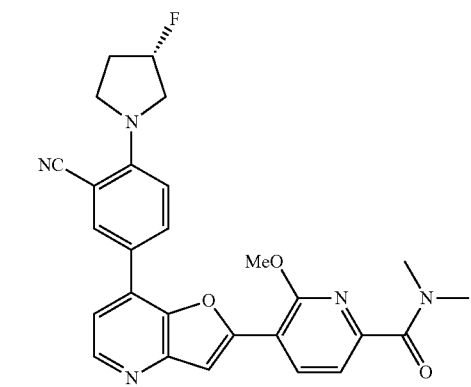 [SMILES: COc1nc(C(=O)N(C)C)ccc1-c1cc2nccc(-c3ccc(N4CC[C@H](F)C4)c(C#N)c3)c2o1] 313
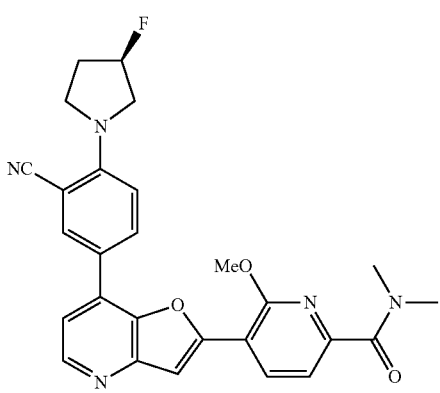 [SMILES: COc1nc(C(=O)N(C)C)ccc1-c1cc2nccc(-c3ccc(N4CC[C@@H](F)C4)c(C#N)c3)c2o1] 314
TABLE 1-continued
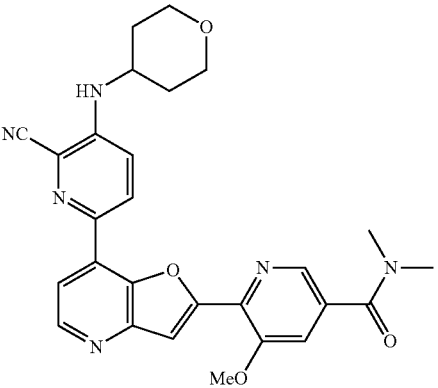 315
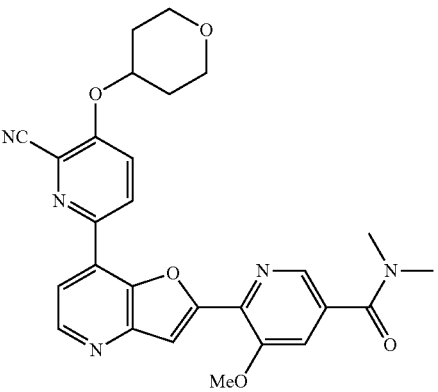 [SMILES: COc1cc(C(=O)N(C)C)cnc1-c1cc2nccc(-c3ccc(OC4CCOCC4)c(C#N)n3)c2o1] 316
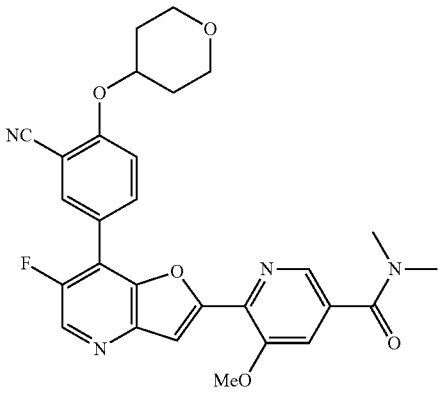 317
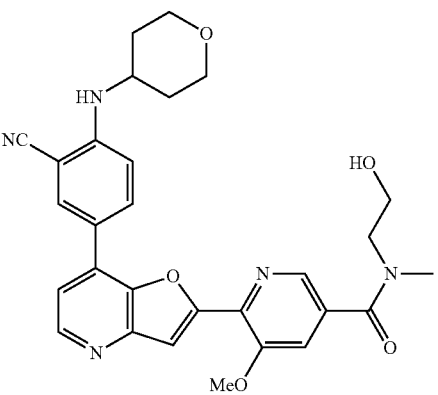 [SMILES: COc1cc(C(=O)N(C)CCO)cnc1-c1cc2nccc(-c3ccc(NC4CCOCC4)c(C#N)c3)c2o1] 318

TABLE 1-continued
| | |
|---|---|
| 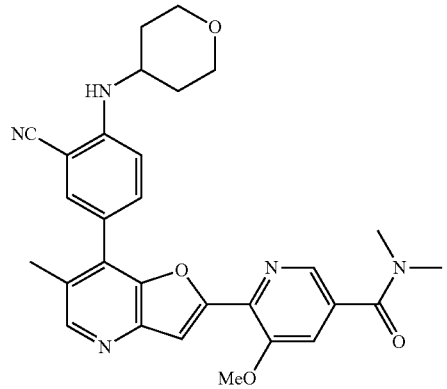 319 | 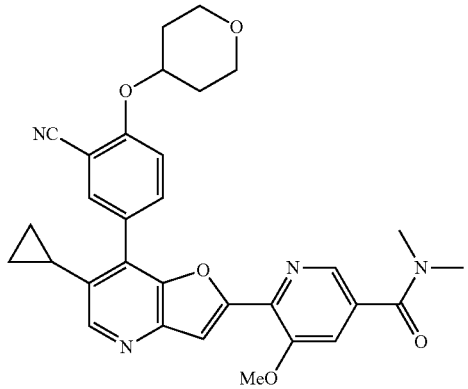 323 |
| 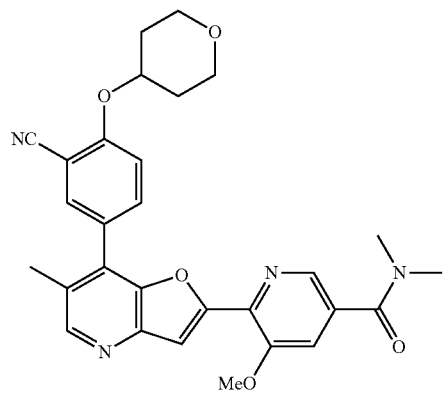 320 | 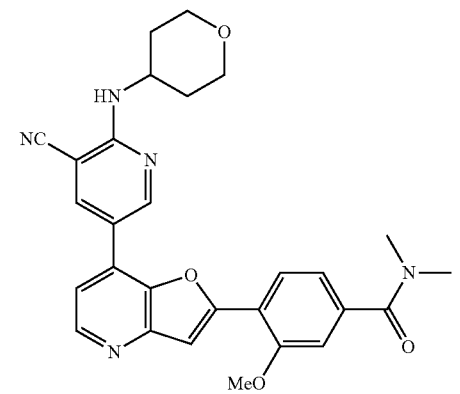 324 |
| 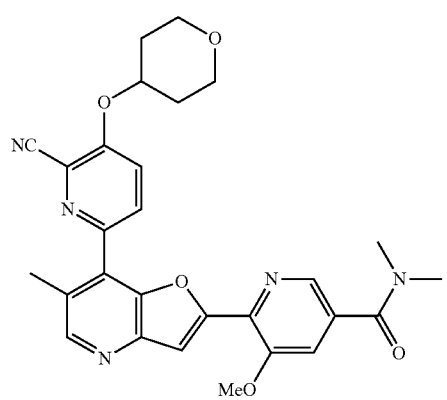 321 | 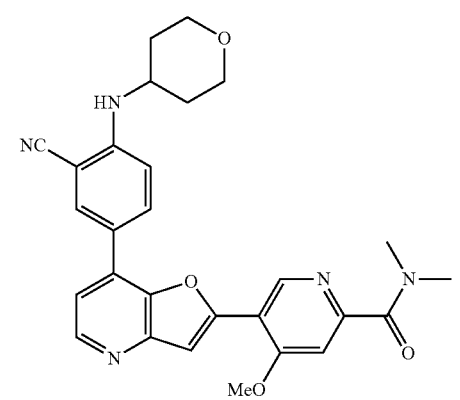 325 |
| 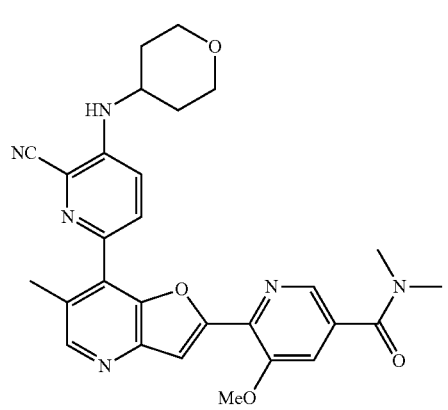 322 | 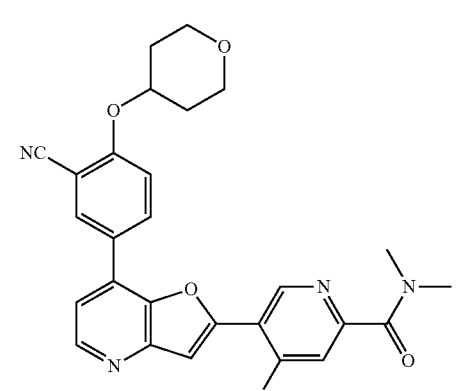 326 |

TABLE 1-continued
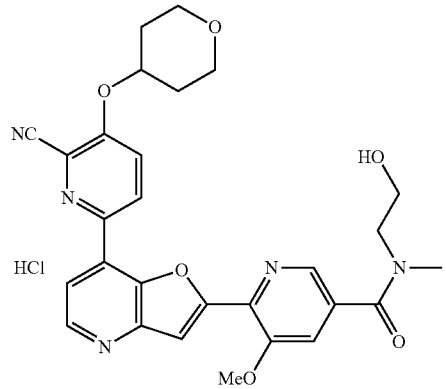 [SMILES: Cl ; COc1cc(C(=O)N(C)CCO)cnc1-c1cc2nccc(-c3ccc(OC4CCOCC4)c(C#N)n3)c2o1] 327
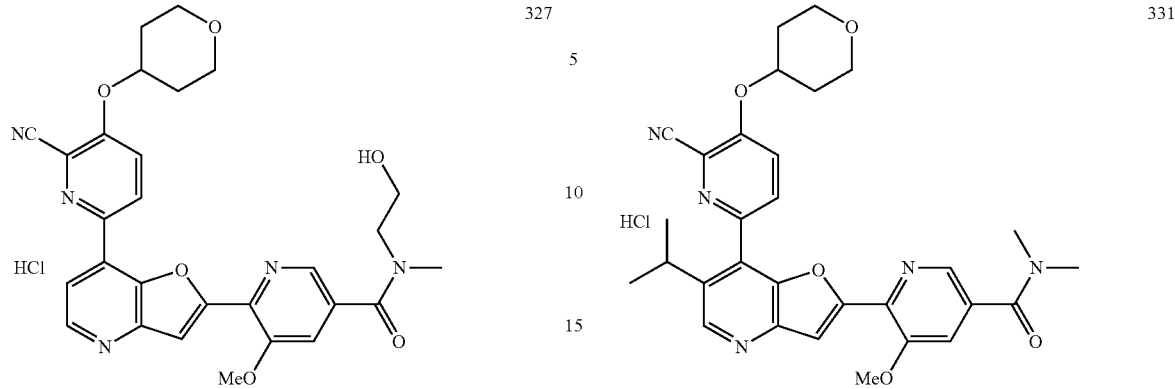 331
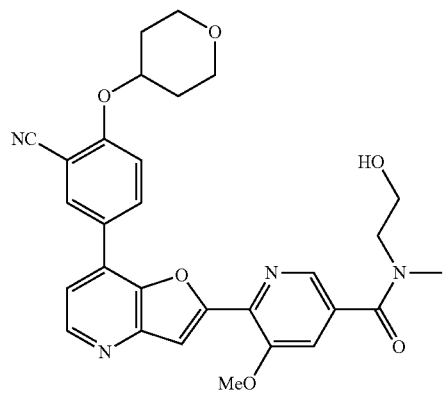 [SMILES: COc1cc(C(=O)N(C)CCO)cnc1-c1cc2nccc(-c3ccc(OC4CCOCC4)c(C#N)c3)c2o1] 328
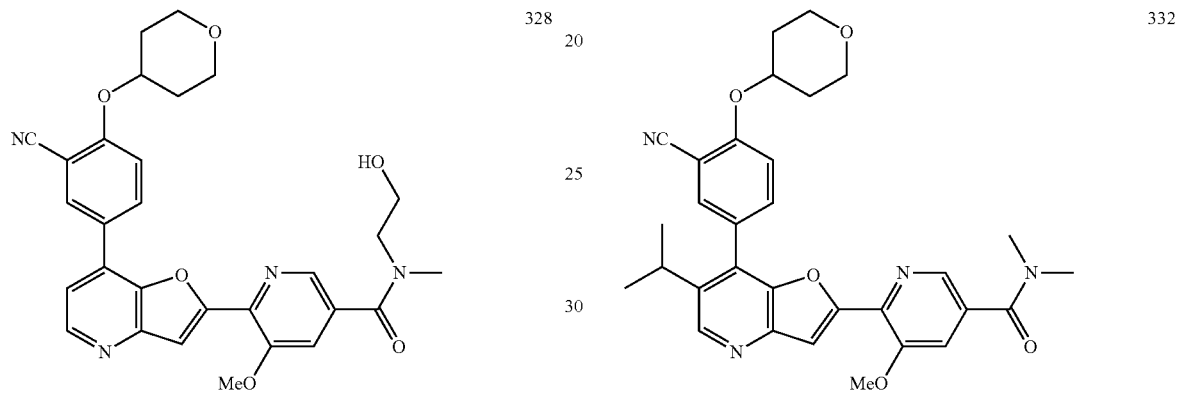 332
 329
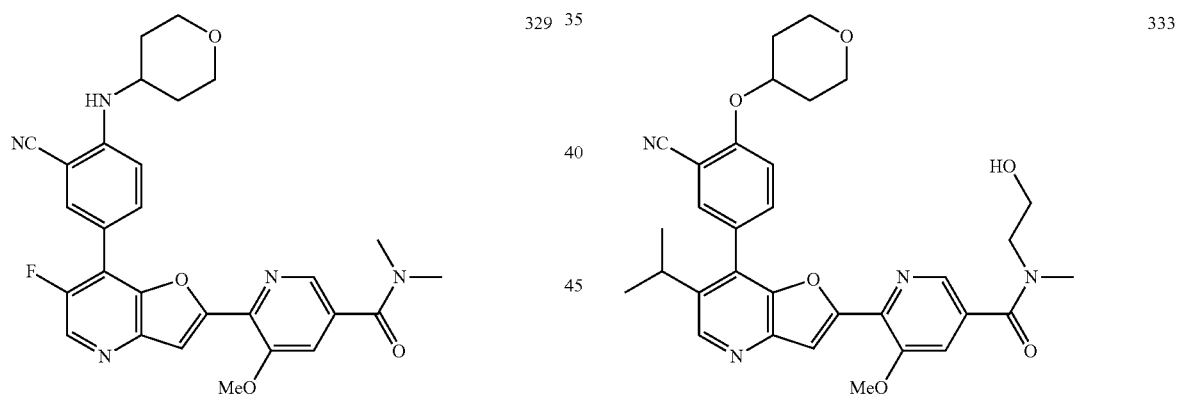 333
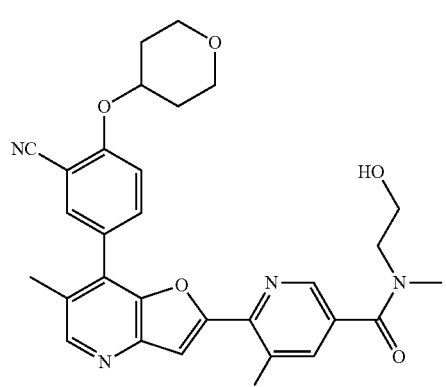 330
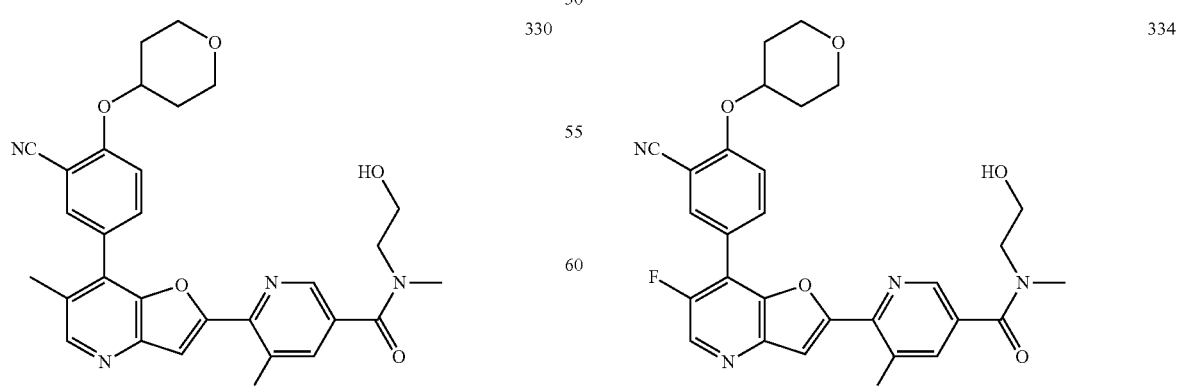 334

TABLE 1-continued
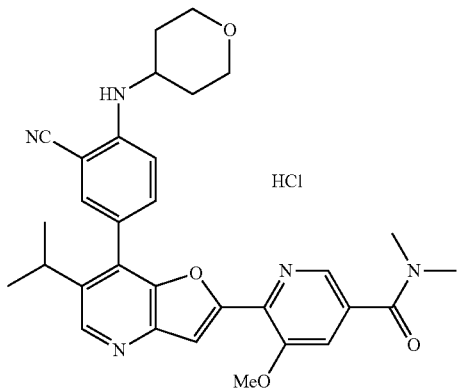 [SMILES: COc1cc(C(=O)N(C)C)cnc1-c1cc2ncc(C(C)C)c(-c3ccc(NC4CCOCC4)c(C#N)c3)c2o1 ; Cl] 335
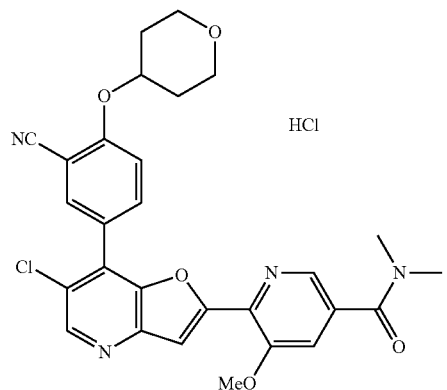 [SMILES: COc1cc(C(=O)N(C)C)cnc1-c1cc2ncc(Cl)c(-c3ccc(OC4CCOCC4)c(C#N)c3)c2o1 ; Cl] 336
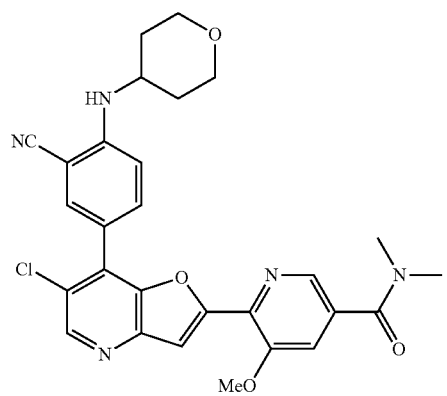 [SMILES: COc1cc(C(=O)N(C)C)cnc1-c1cc2ncc(Cl)c(-c3ccc(NC4CCOCC4)c(C#N)c3)c2o1] 337
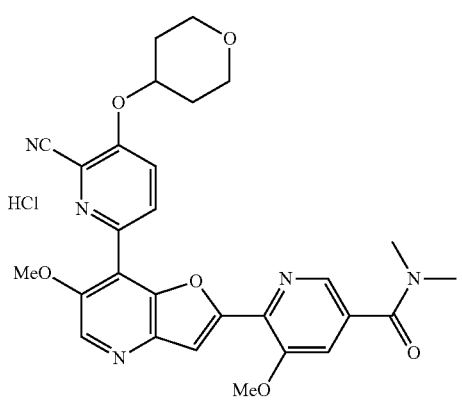 [SMILES: Cl ; COc1cc(C(=O)N(C)C)cnc1-c1cc2ncc(OC)c(-c3ccc(OC4CCOCC4)c(C#N)n3)c2o1] 338
TABLE 1-continued
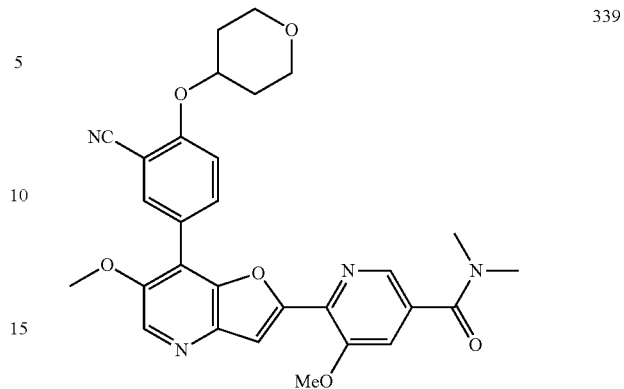 339
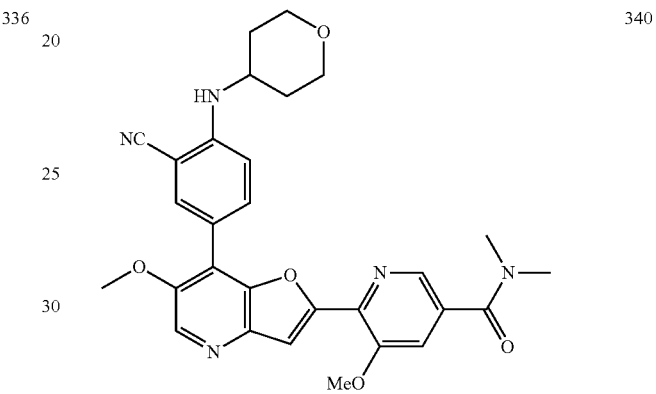 340
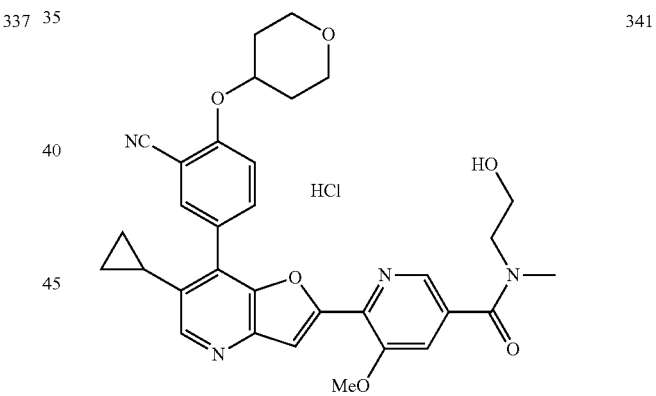 341
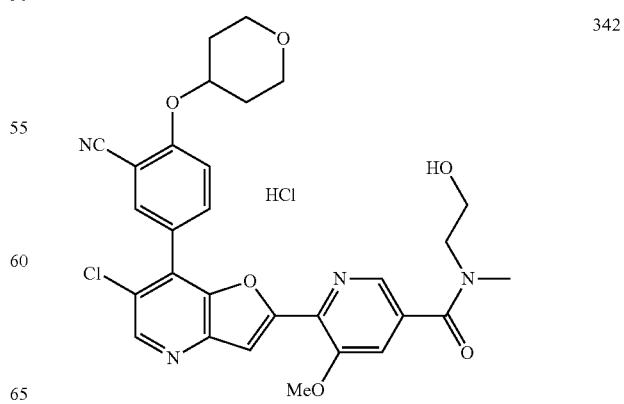 342

TABLE 1-continued
| | |
|---|---|
| 343 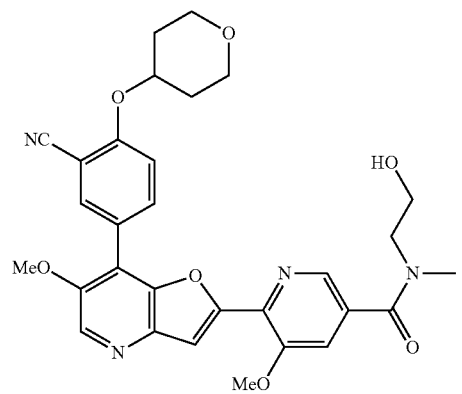 [SMILES: COc1cc(C(=O)N(C)CCO)cnc1-c1cc2ncc(OC)c(-c3ccc(OC4CCOCC4)c(C#N)c3)c2o1] | 347 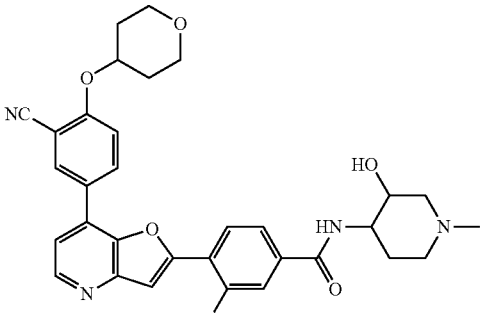 |
| 344 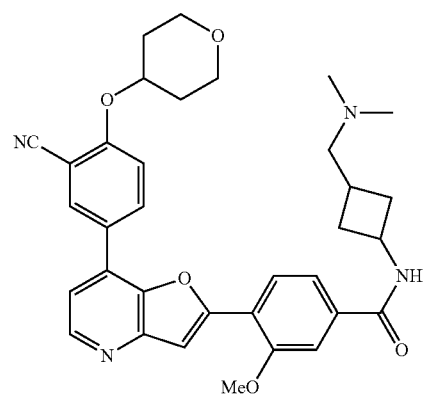 [SMILES: COc1cc(C(=O)NC2CC(CN(C)C)C2)ccc1-c1cc2nccc(-c3ccc(OC4CCOCC4)c(C#N)c3)c2o1] | 348 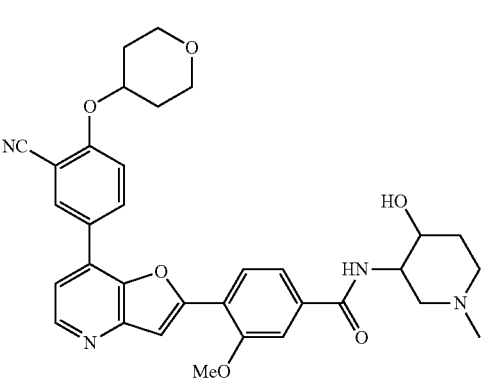 |
| 345 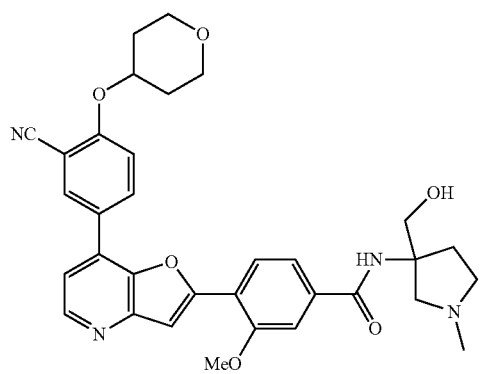 [SMILES: COc1cc(C(=O)NC2(CO)CCN(C)C2)ccc1-c1cc2nccc(-c3ccc(OC4CCOCC4)c(C#N)c3)c2o1] | 349 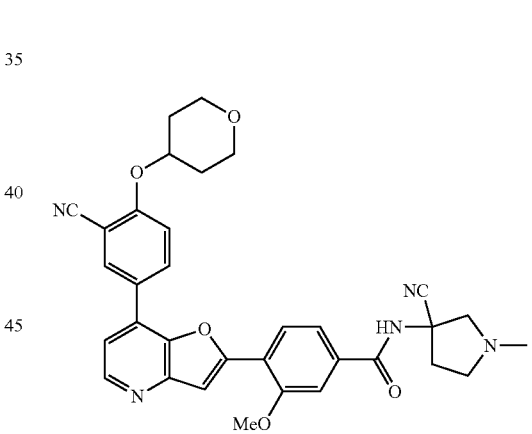 |
| 346 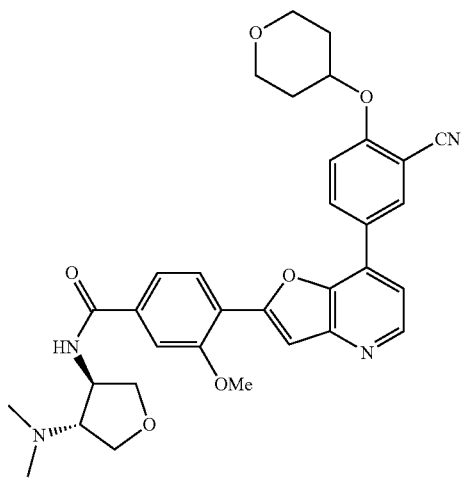 [SMILES: COc1cc(C(=O)N[C@H]2COC[C@@H]2N(C)C)ccc1-c1cc2nccc(-c3ccc(OC4CCOCC4)c(C#N)c3)c2o1] | 350 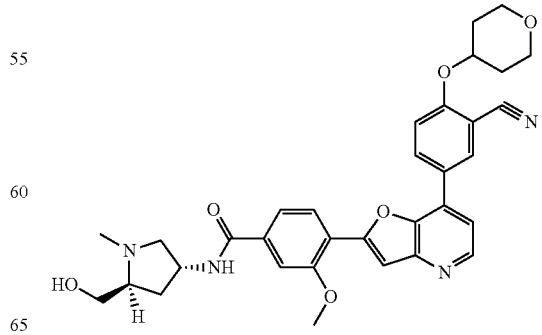 |

TABLE 1-continued
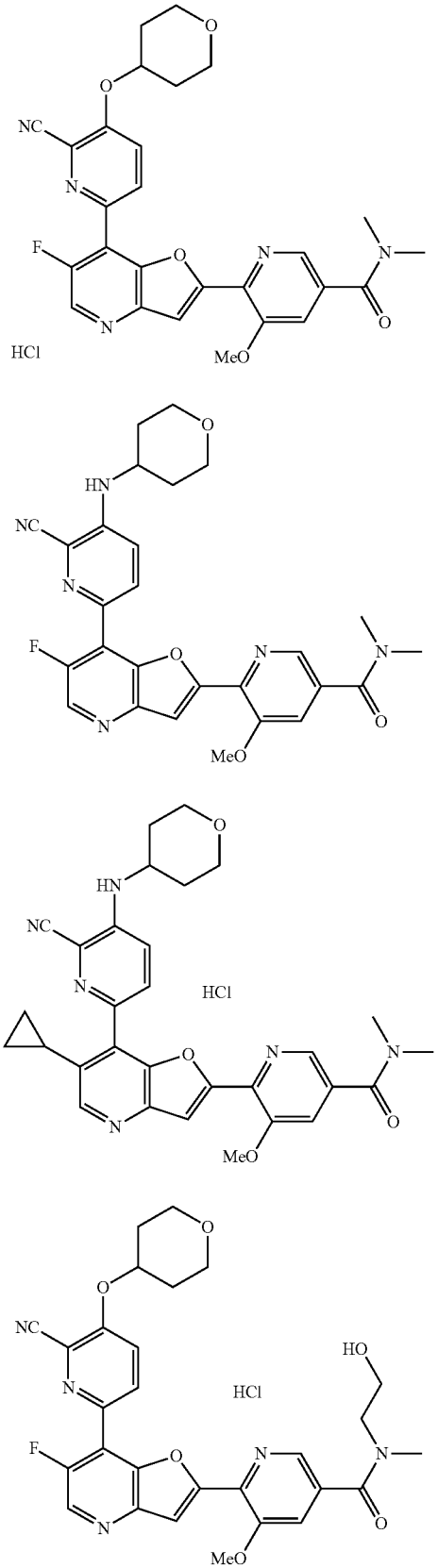
351
352
353
354
TABLE 1-continued
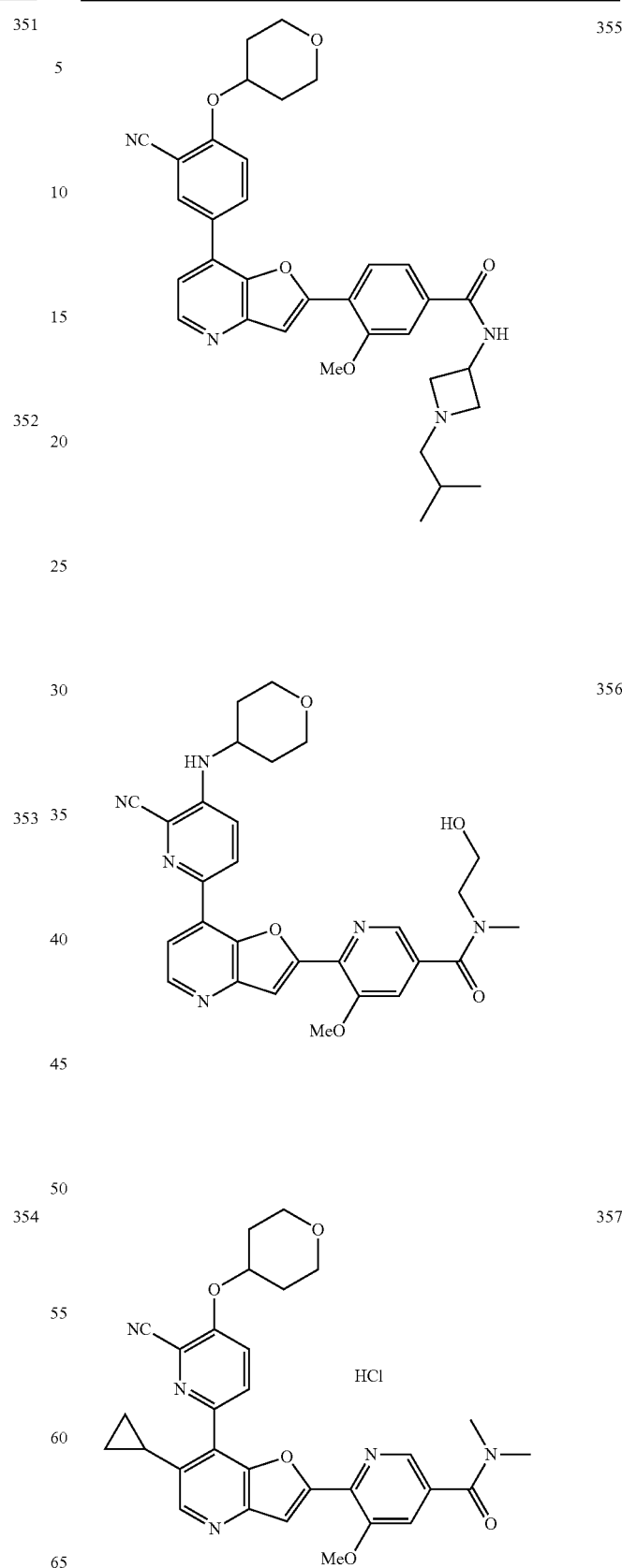
355
356
357

TABLE 1-continued
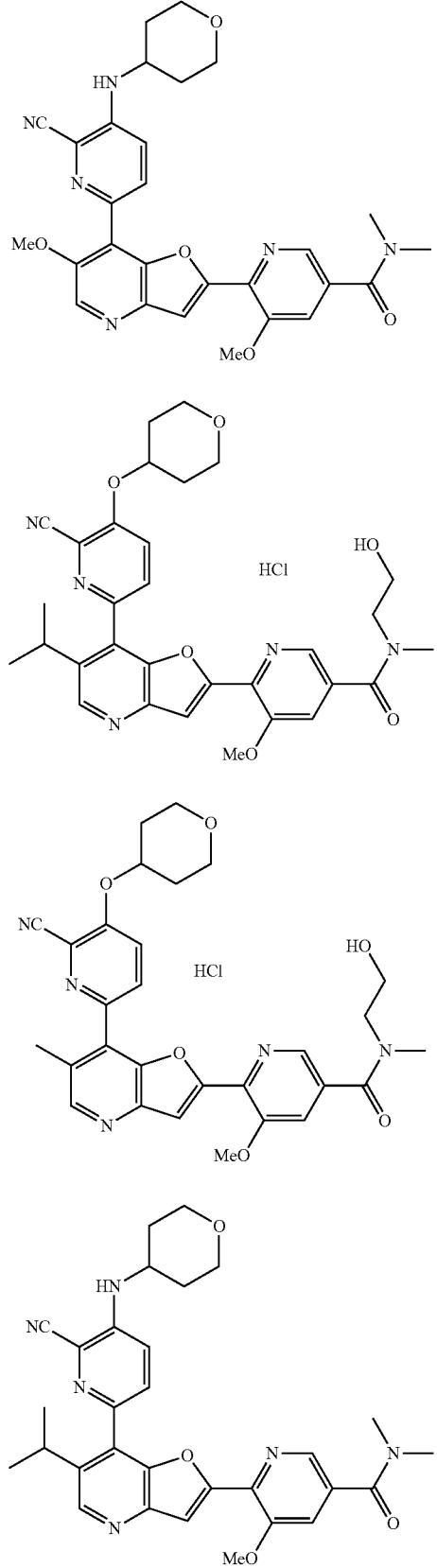
358
359
360
361
TABLE 1-continued
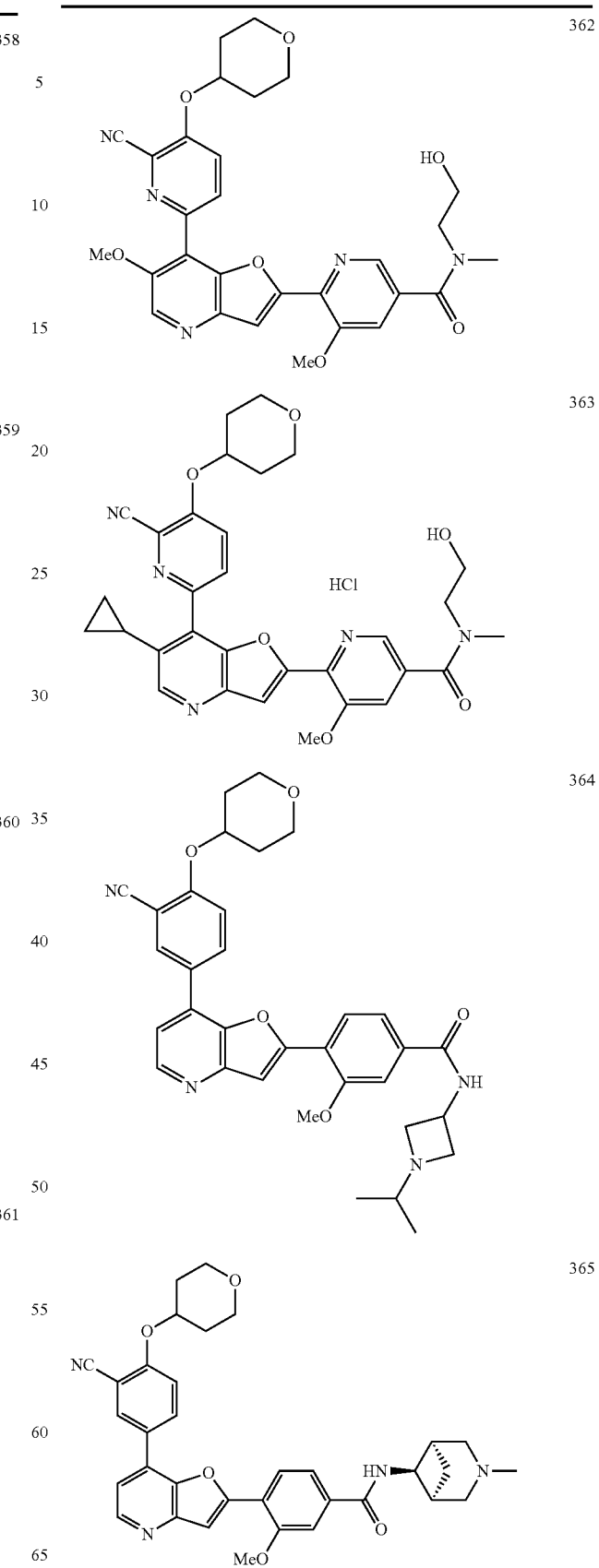
362
363
364
365

TABLE 1-continued
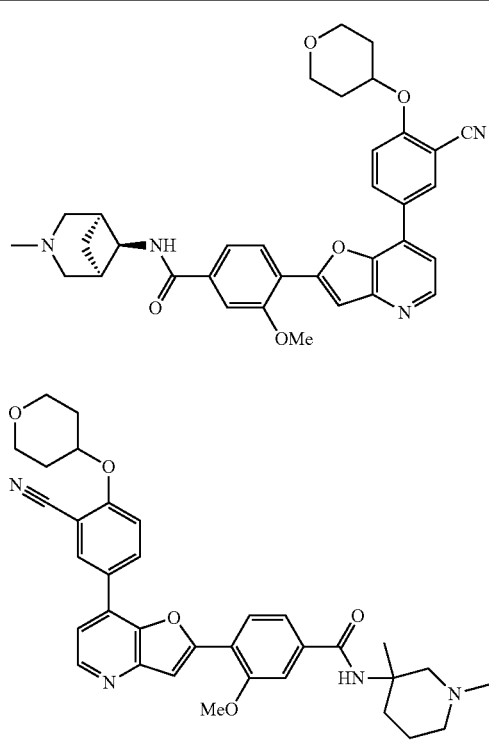
366
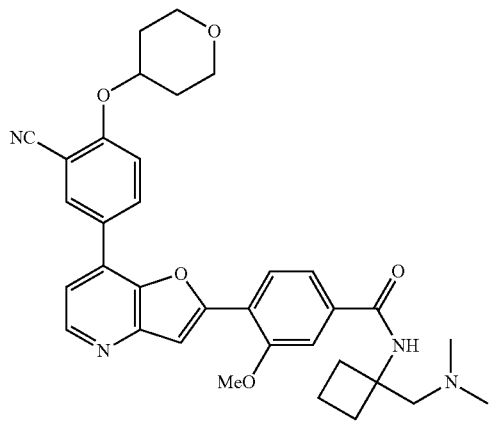 [SMILES: COc1cc(C(=O)NC2(CN(C)C)CCC2)ccc1-c1cc2nccc(-c3ccc(OC4CCOCC4)c(C#N)c3)c2o1]
367
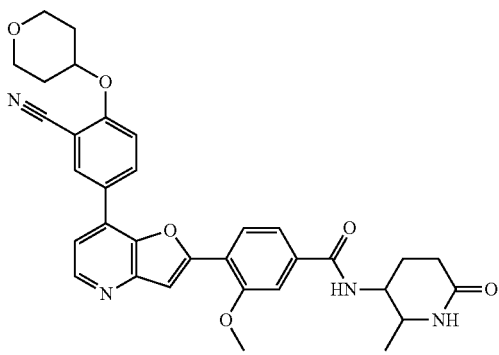 [SMILES: COc1cc(C(=O)NC2CCC(=O)NC2C)ccc1-c1cc2nccc(-c3ccc(OC4CCOCC4)c(C#N)c3)c2o1]
368
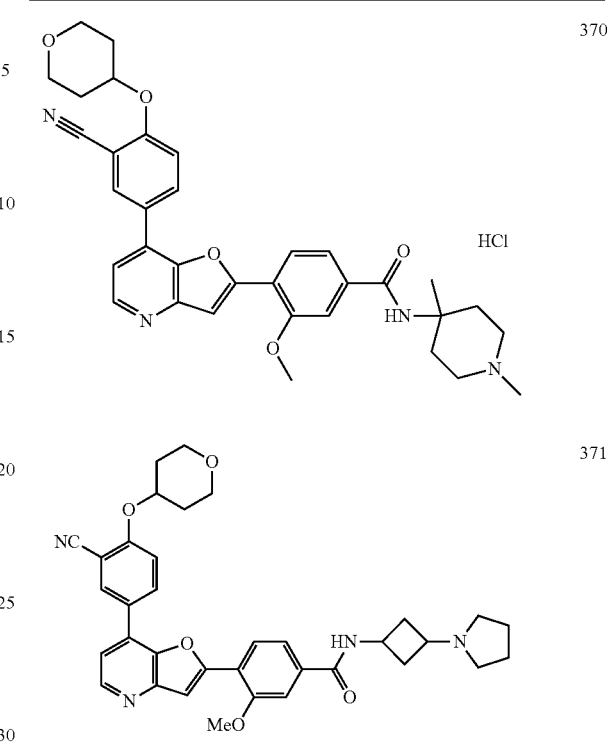
369
TABLE 1-continued
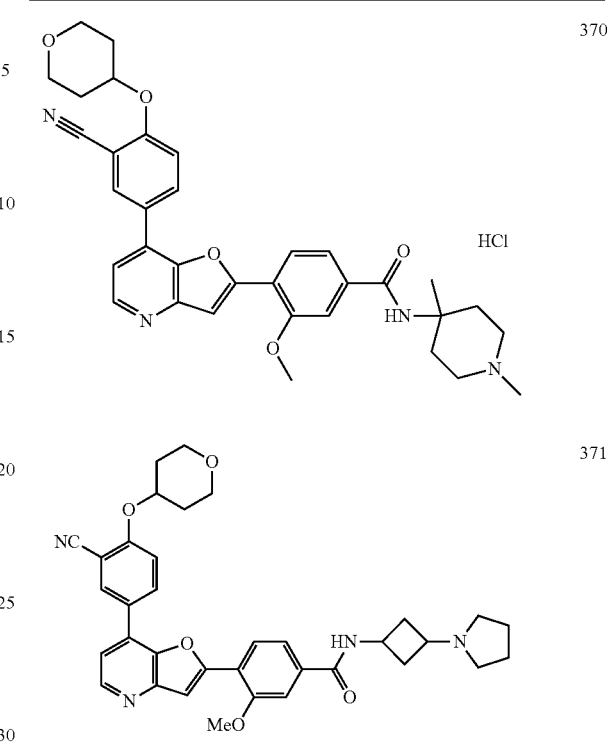
370
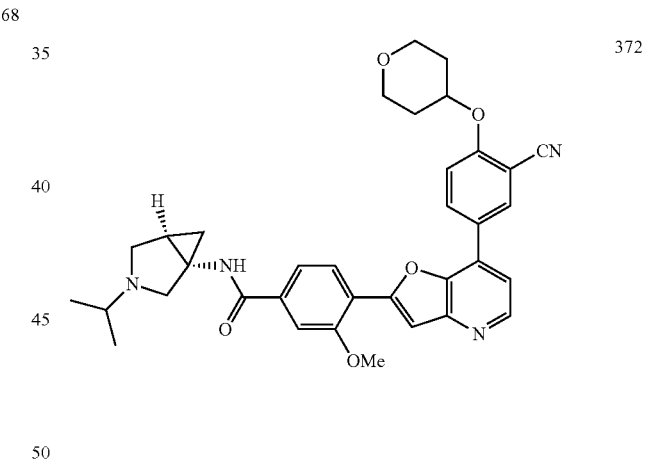
371
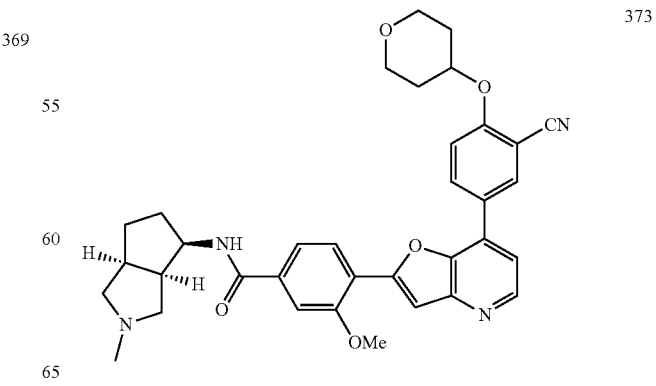
372
373

TABLE 1-continued
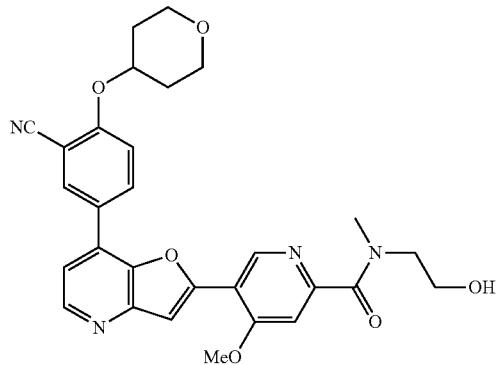 [SMILES: COc1cc(C(=O)N(C)CCO)ncc1-c1cc2nccc(-c3ccc(OC4CCOCC4)c(C#N)c3)c2o1]
374
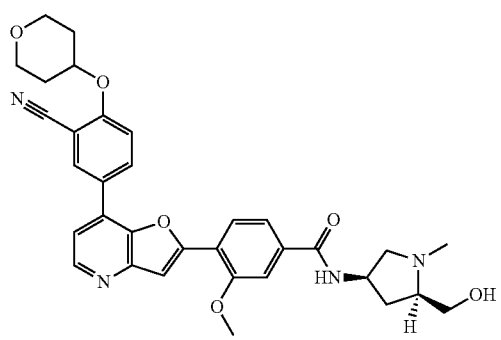 [SMILES: COc1cc(C(=O)N[C@@H]2C[C@H](CO)N(C)C2)ccc1-c1cc2nccc(-c3ccc(OC4CCOCC4)c(C#N)c3)c2o1]
375
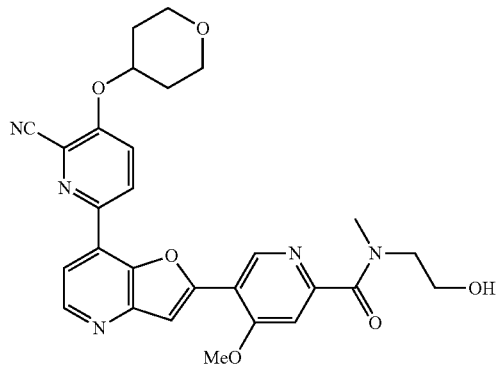
376
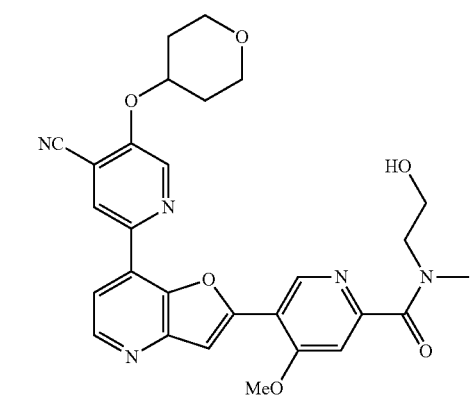 [SMILES: COc1cc(C(=O)N(C)CCO)ncc1-c1cc2nccc(-c3cc(C#N)c(OC4CCOCC4)cn3)c2o1]
377
TABLE 1-continued
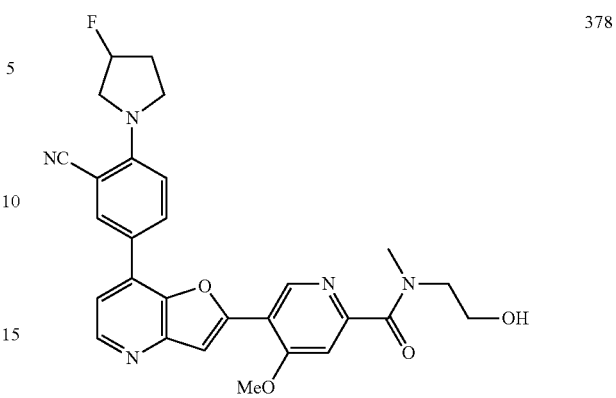
378
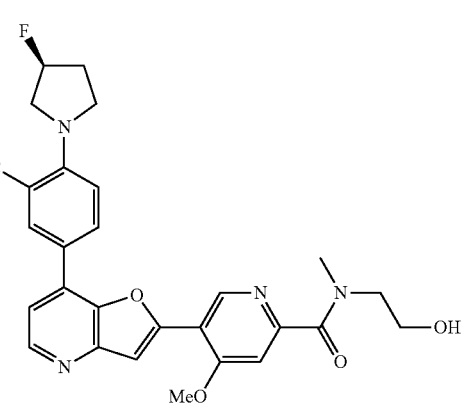
379
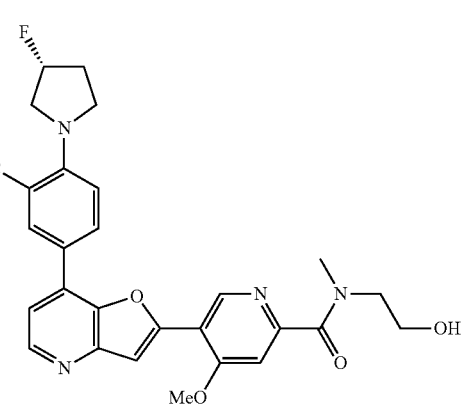
380
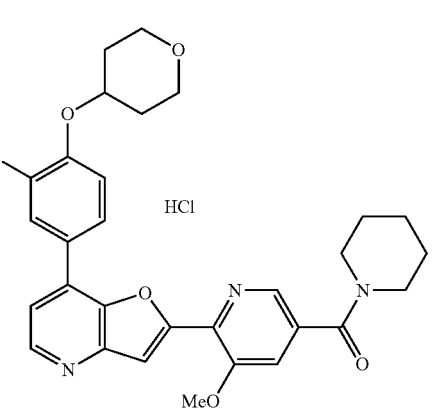
381

TABLE 1-continued
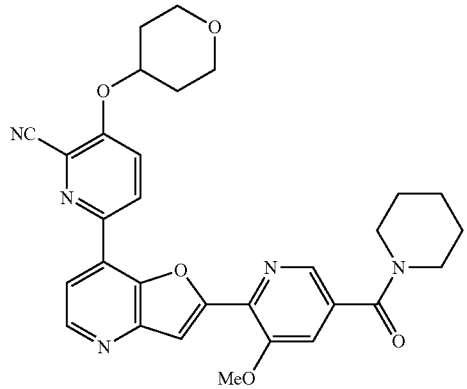 [SMILES: COc1cc(C(=O)N2CCCCC2)cnc1-c1cc2nccc(-c3ccc(OC4CCOCC4)c(C#N)n3)c2o1]
382
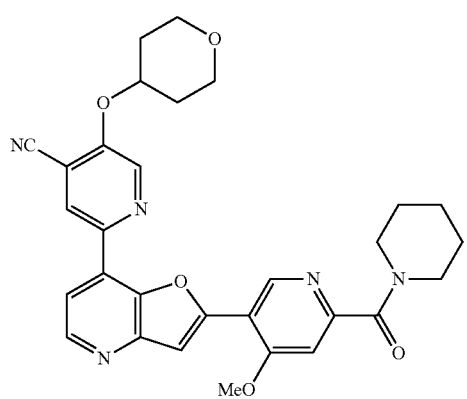 [SMILES: COc1cc(C(=O)N2CCCCC2)ncc1-c1cc2nccc(-c3cc(C#N)c(OC4CCOCC4)cn3)c2o1]
383
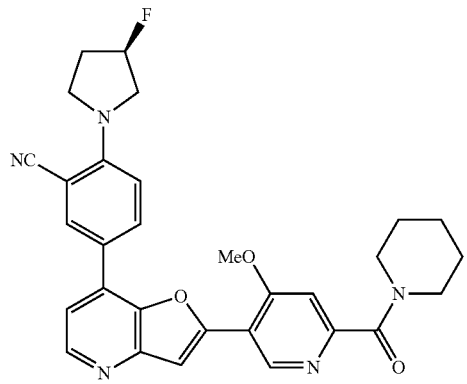 [SMILES: COc1cc(C(=O)N2CCCCC2)ncc1-c1cc2nccc(-c3ccc(N4CC[C@@H](F)C4)c(C#N)c3)c2o1]
384
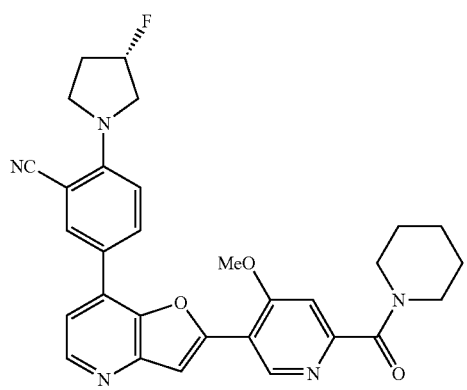 [SMILES: COc1cc(C(=O)N2CCCCC2)ncc1-c1cc2nccc(-c3ccc(N4CC[C@H](F)C4)c(C#N)c3)c2o1]
385
TABLE 1-continued
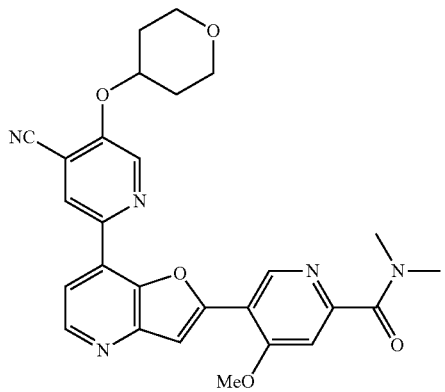 [SMILES: COc1cc(C(=O)N(C)C)ncc1-c1cc2nccc(-c3cc(C#N)c(OC4CCOCC4)cn3)c2o1]
386
387
388
389

TABLE 1-continued
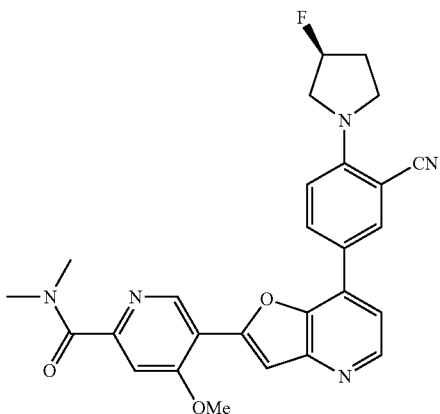 [SMILES: COc1cc(C(=O)N(C)C)ncc1-c1cc2nccc(-c3ccc(N4CC[C@H](F)C4)c(C#N)c3)c2o1] 390
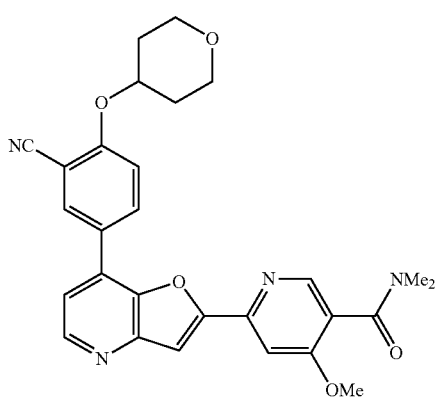 [SMILES: COc1cc(-c2cc3nccc(-c4ccc(OC5CCOCC5)c(C#N)c4)c3o2)ncc1C(=O)N(C)C] 391
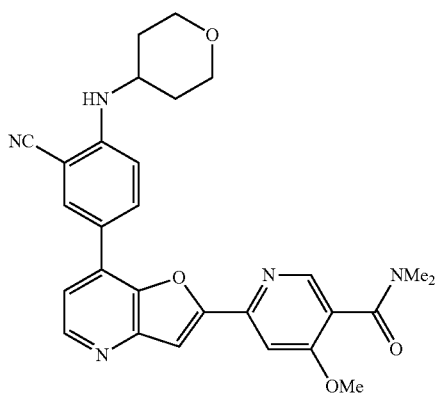 [SMILES: COc1cc(-c2cc3nccc(-c4ccc(NC5CCOCC5)c(C#N)c4)c3o2)ncc1C(=O)N(C)C] 392
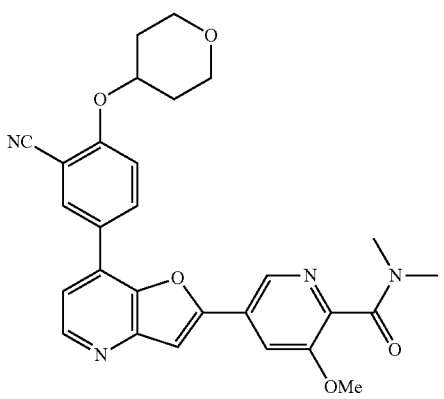 [SMILES: COc1cc(-c2cc3nccc(-c4ccc(OC5CCOCC5)c(C#N)c4)c3o2)cnc1C(=O)N(C)C] 393
TABLE 1-continued
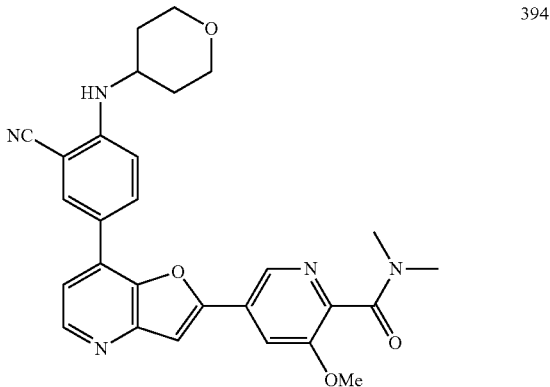 394
 395
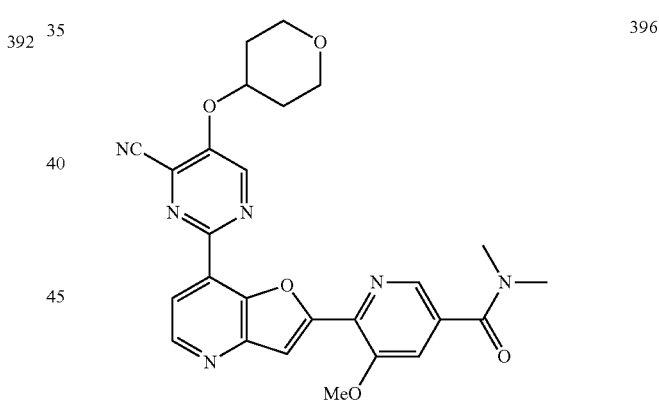 396
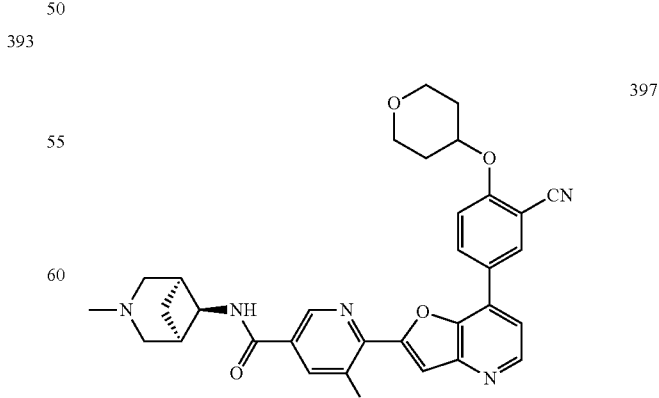 397

TABLE 1-continued
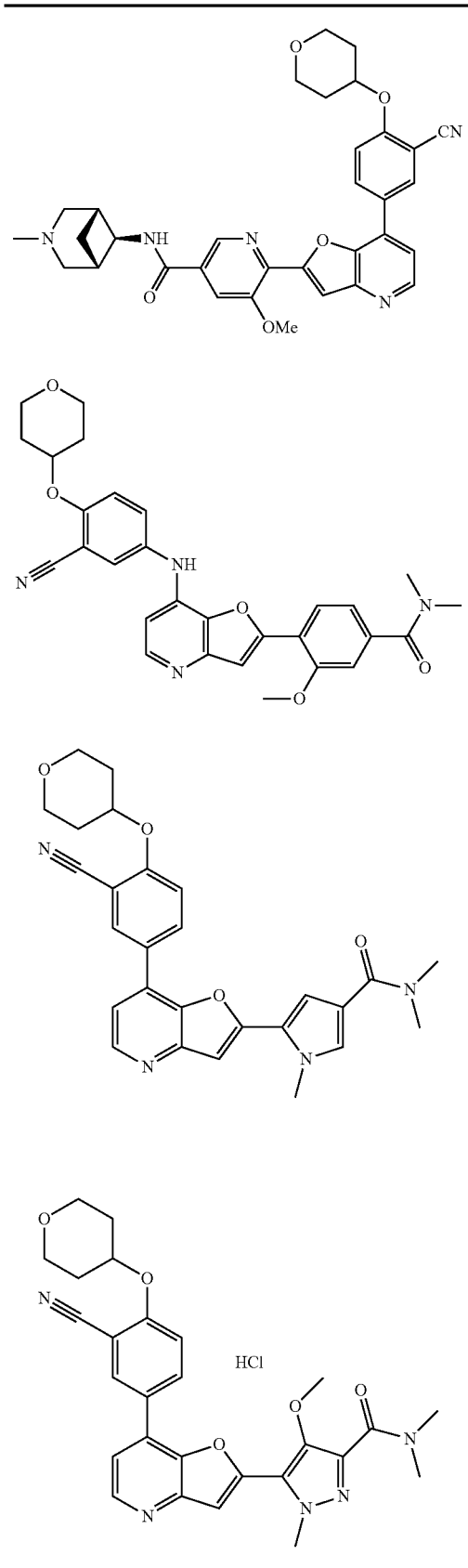
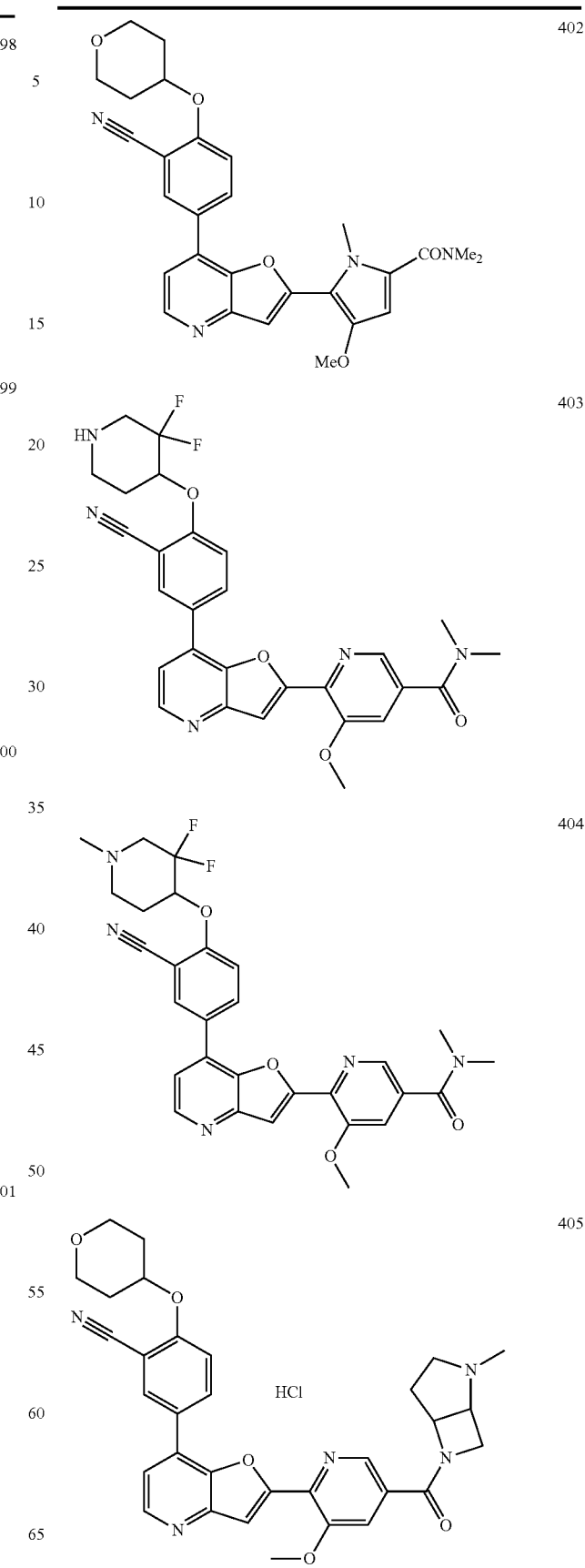

TABLE 1-continued
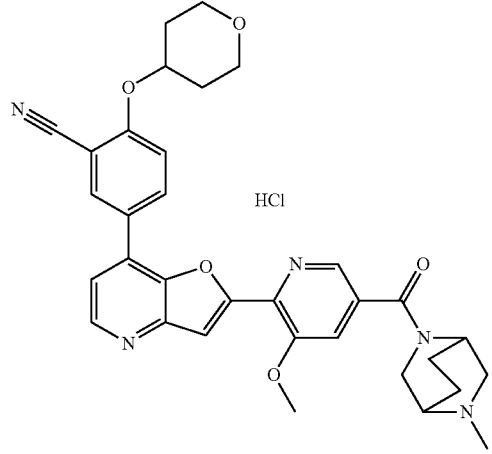 [SMILES: COc1cc(C(=O)N2CC3CCC2CN3C)cnc1-c1cc2nccc(-c3ccc(OC4CCOCC4)c(C#N)c3)c2o1 ; Cl]
406
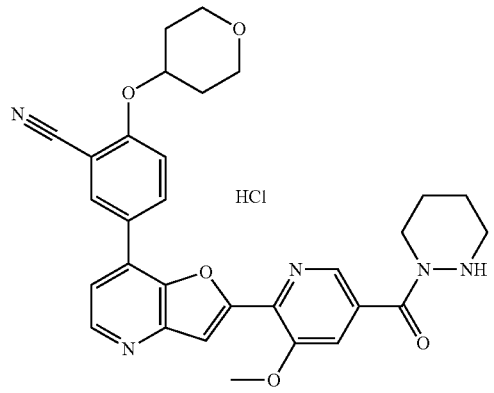 [SMILES: COc1cc(C(=O)N2CCCCN2)cnc1-c1cc2nccc(-c3ccc(OC4CCOCC4)c(C#N)c3)c2o1 ; Cl]
407
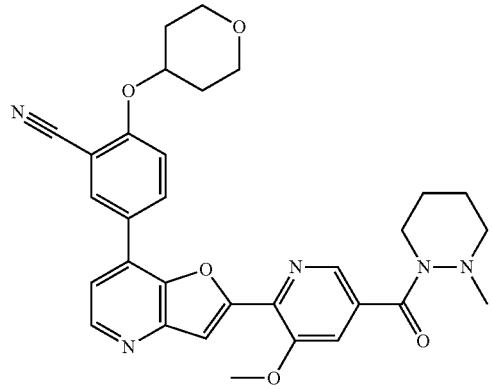
408
TABLE 1-continued
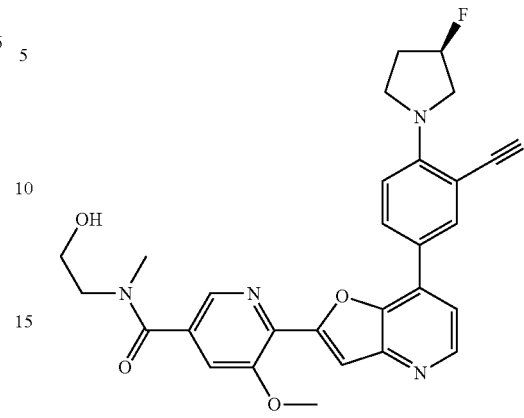
409
410
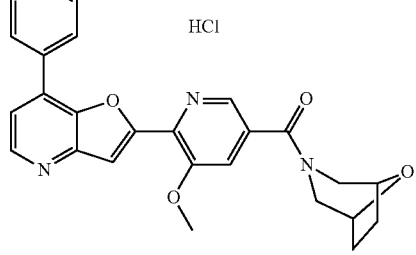
411

TABLE 1-continued
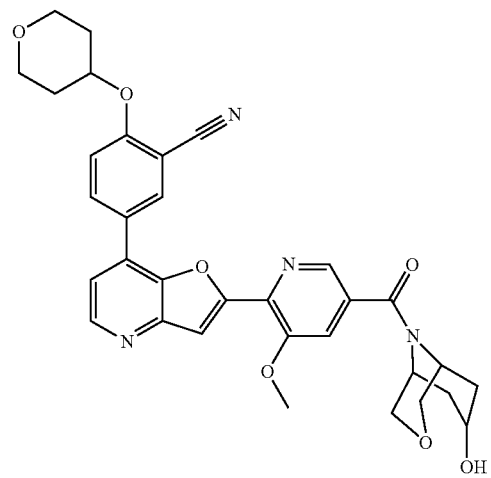 [SMILES: COc1cc(C(=O)N2C3COCC2CC(O)C3)cnc1-c1cc2nccc(-c3ccc(OC4CCOCC4)c(C#N)c3)c2o1] 412
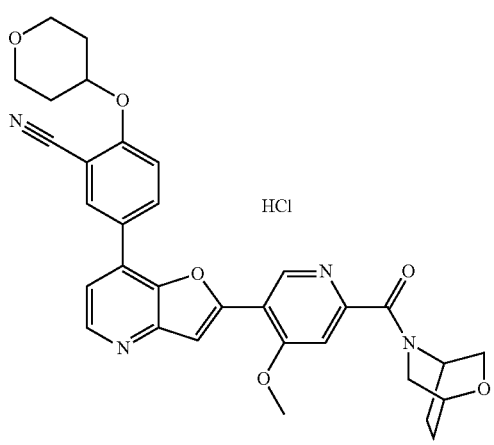 [SMILES: COc1cc(C(=O)N2CC3CCC2CO3)ncc1-c1cc2nccc(-c3ccc(OC4CCOCC4)c(C#N)c3)c2o1 ; Cl] 413
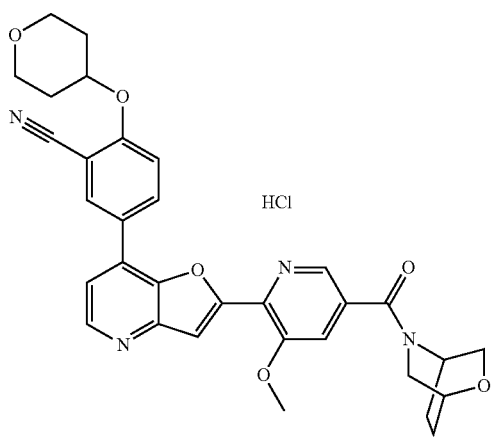 [SMILES: COc1cc(C(=O)N2CC3CCC2CO3)cnc1-c1cc2nccc(-c3ccc(OC4CCOCC4)c(C#N)c3)c2o1 ; Cl] 414
TABLE 1-continued
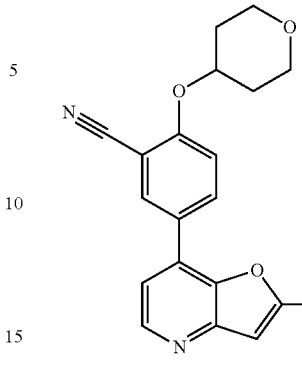 415
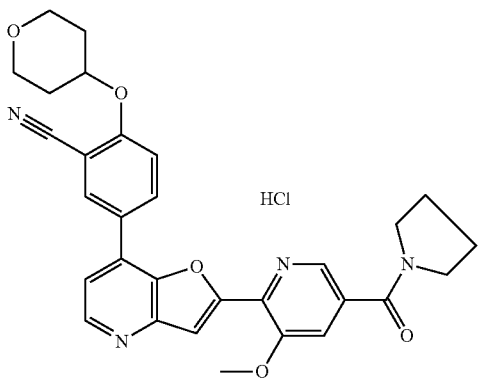 [SMILES: COc1cc(C(=O)N2CCCC2)cnc1-c1cc2nccc(-c3ccc(OC4CCOCC4)c(C#N)c3)c2o1 ; Cl] 416
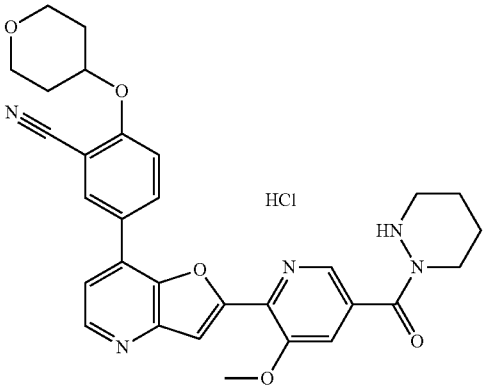 [SMILES: COc1cc(C(=O)N2CCCCN2)cnc1-c1cc2nccc(-c3ccc(OC4CCOCC4)c(C#N)c3)c2o1 ; Cl] 417
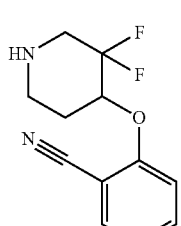
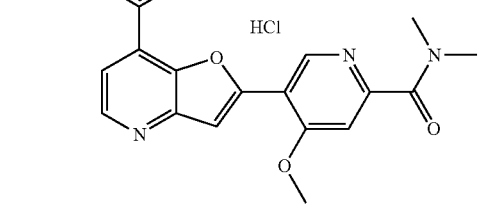 418

TABLE 1-continued
| | |
|---|---|
| 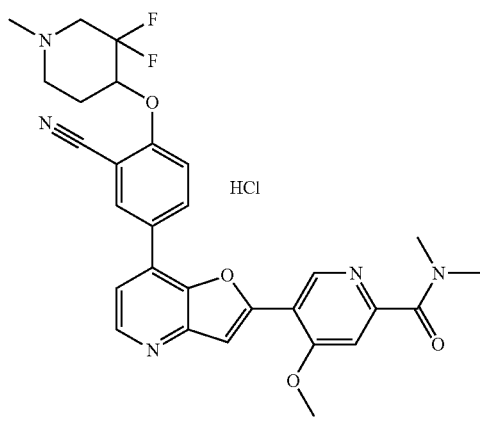 | 419 |
| 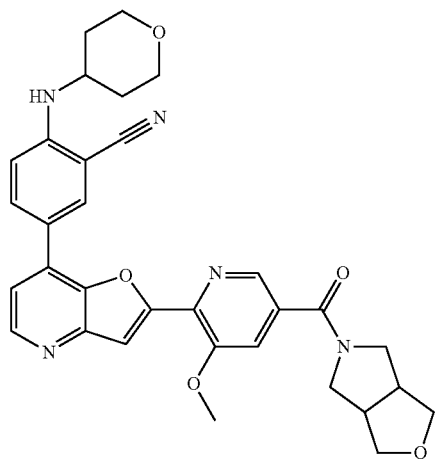 [SMILES: COc1cc(C(=O)N2CC3COCC3C2)cnc1-c1cc2nccc(-c3ccc(NC4CCOCC4)c(C#N)c3)c2o1] | 420 |
| 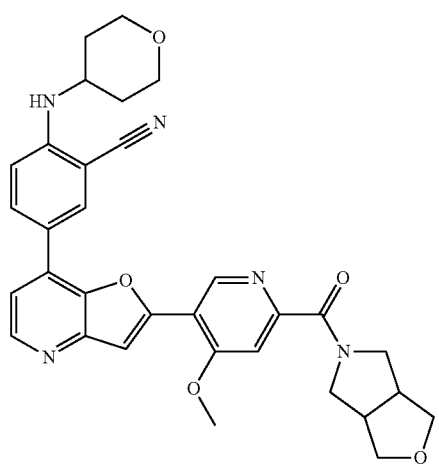 [SMILES: COc1cc(C(=O)N2CC3COCC3C2)ncc1-c1cc2nccc(-c3ccc(NC4CCOCC4)c(C#N)c3)c2o1] | 421 |
TABLE 1-continued
| | |
|---|---|
| 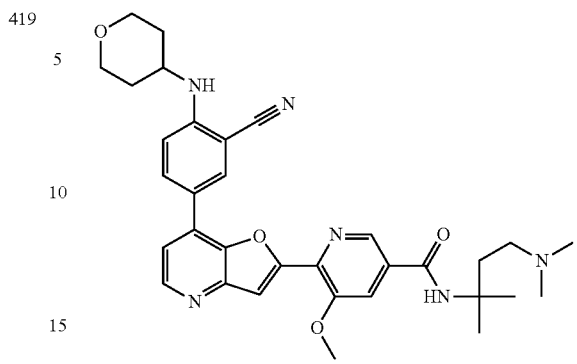 | 422 |
| 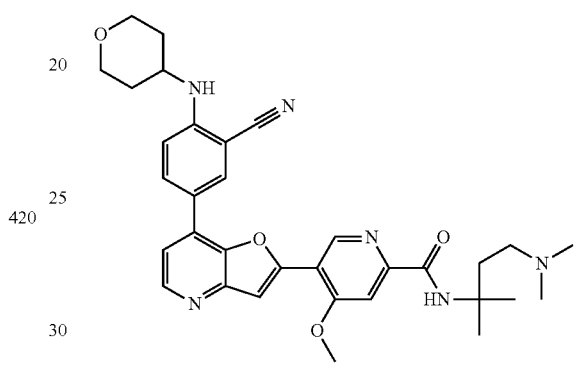 | 423 |
| 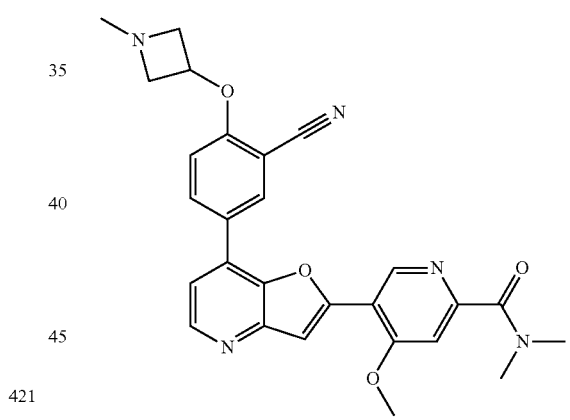 | 424 |
| 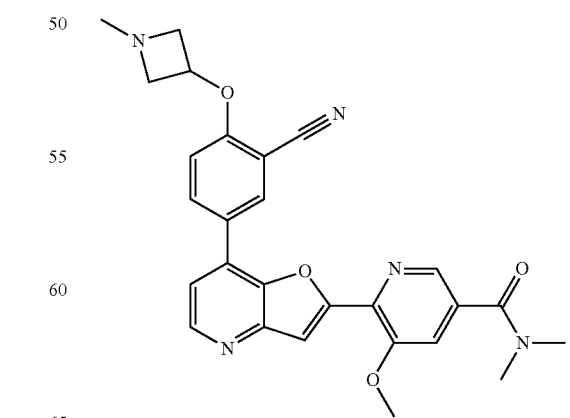 | 425 |

TABLE 1-continued
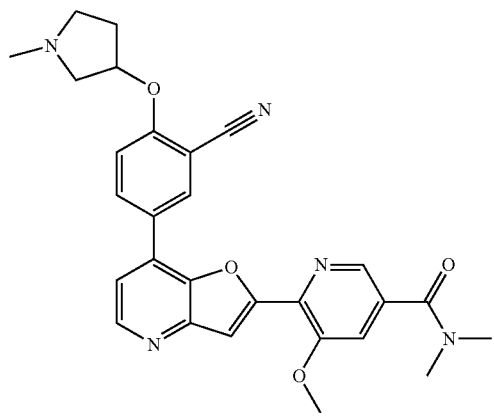 426
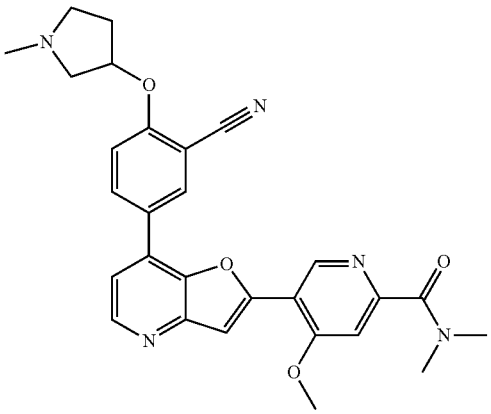 430
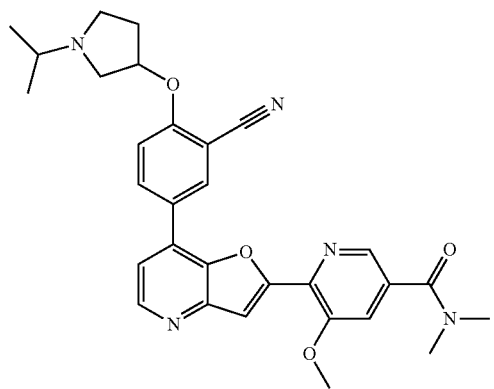 [SMILES: COc1cc(C(=O)N(C)C)cnc1-c1cc2nccc(-c3ccc(OC4CCN(C(C)C)C4)c(C#N)c3)c2o1] 427
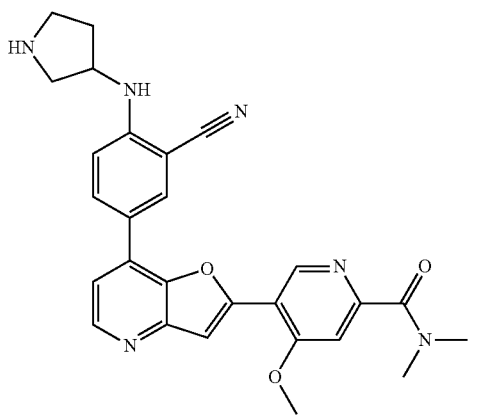 431
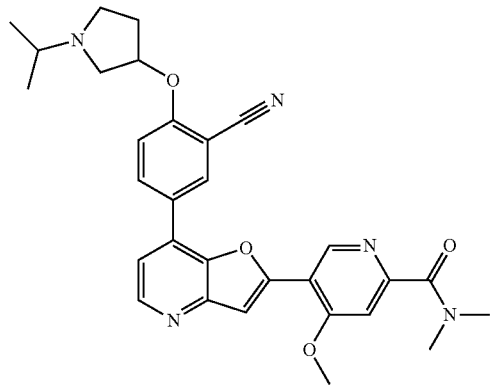 [SMILES: COc1cc(C(=O)N(C)C)ncc1-c1cc2nccc(-c3ccc(OC4CCN(C(C)C)C4)c(C#N)c3)c2o1] 428
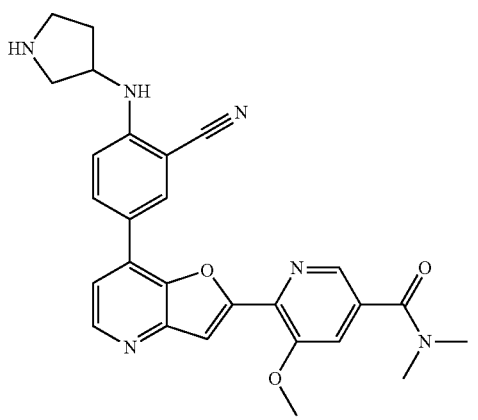 432
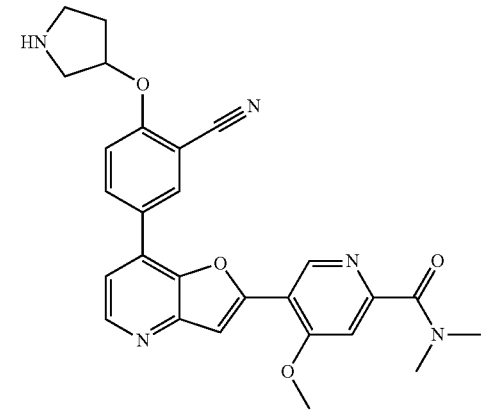 [SMILES: COc1cc(C(=O)N(C)C)ncc1-c1cc2nccc(-c3ccc(OC4CCNC4)c(C#N)c3)c2o1] 429
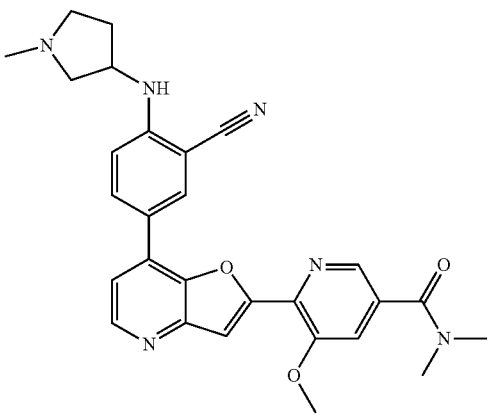 433

TABLE 1-continued
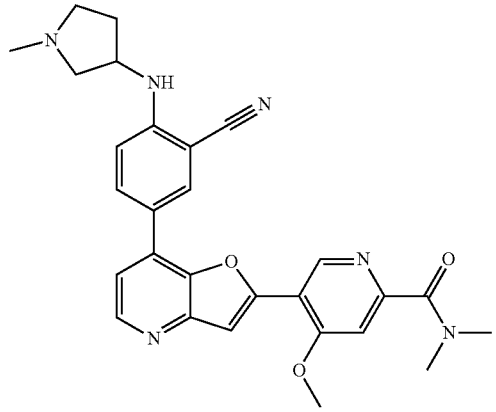
434
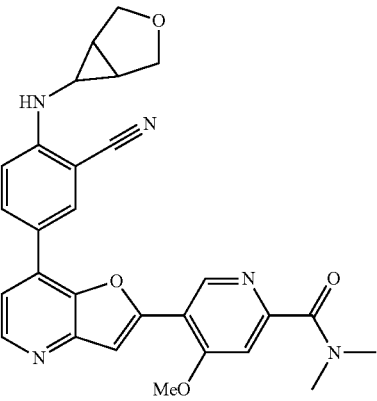
437
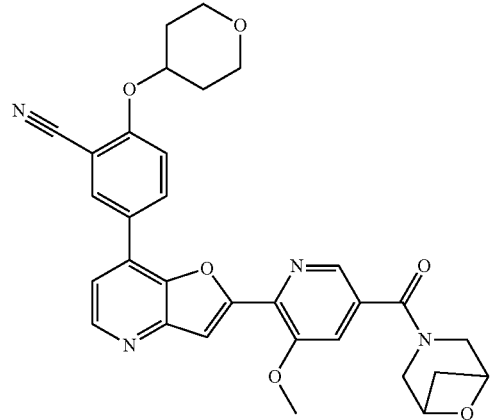 [SMILES: COc1cc(C(=O)N2CC3CC(C2)O3)cnc1-c1cc2nccc(-c3ccc(OC4CCOCC4)c(C#N)c3)c2o1]
435
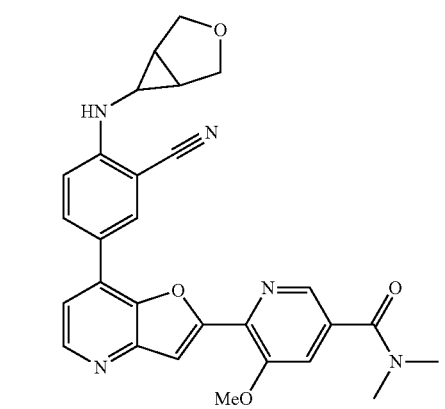 [SMILES: COc1cc(C(=O)N(C)C)cnc1-c1cc2nccc(-c3ccc(NC4C5COCC54)c(C#N)c3)c2o1]
436

TABLE 1-continued
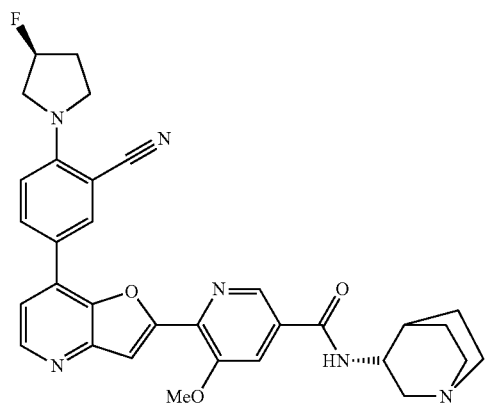
441
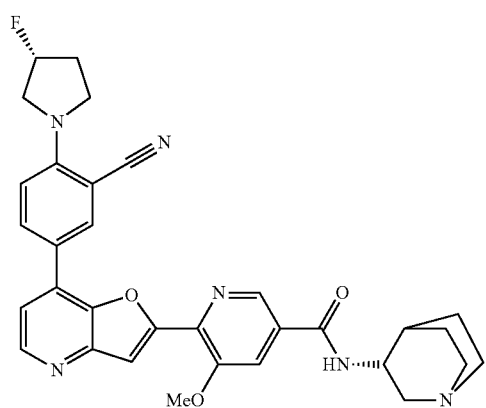
442
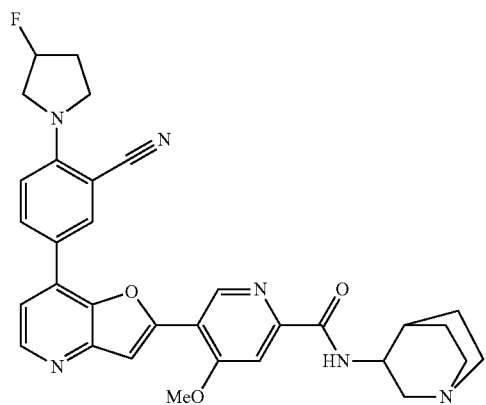 [SMILES: COc1cc(C(=O)NC2CN3CCC2CC3)ncc1-c1cc2nccc(-c3ccc(N4CCC(F)C4)c(C#N)c3)c2o1]
443
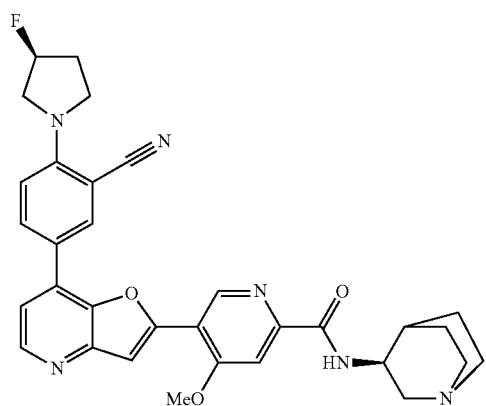 [SMILES: COc1cc(C(=O)N[C@@H]2CN3CCC2CC3)ncc1-c1cc2nccc(-c3ccc(N4CC[C@H](F)C4)c(C#N)c3)c2o1]
444
TABLE 1-continued
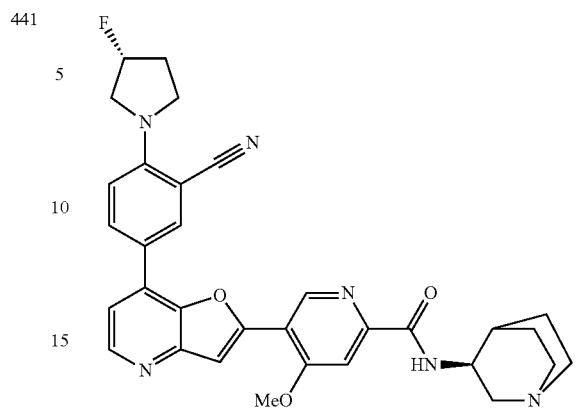
445
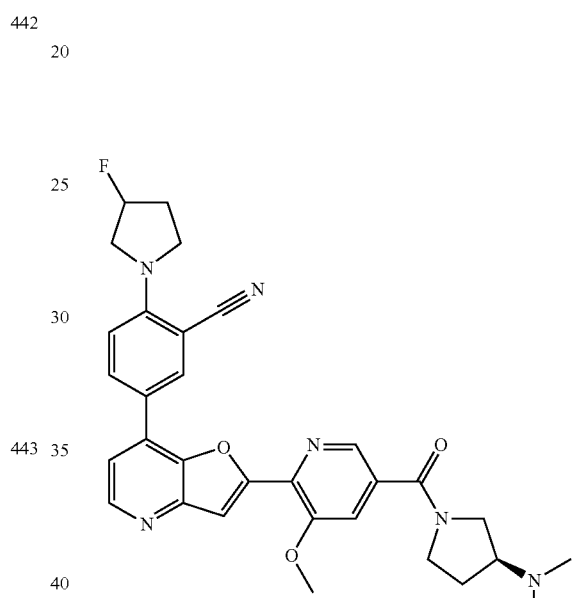
446
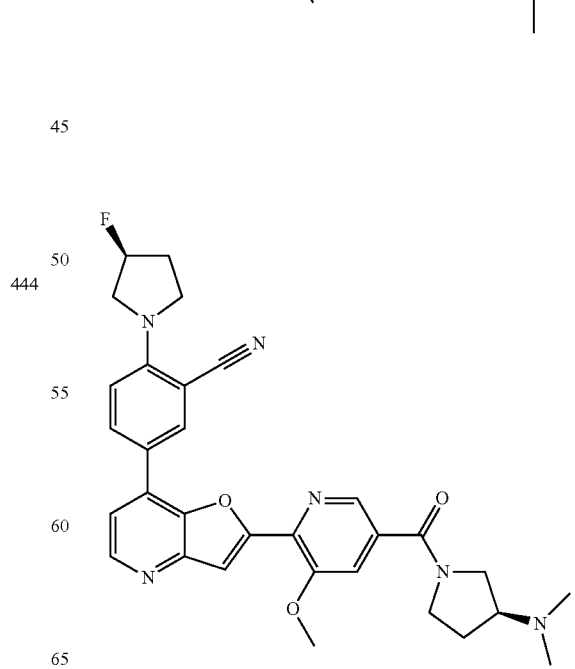
447

TABLE 1-continued
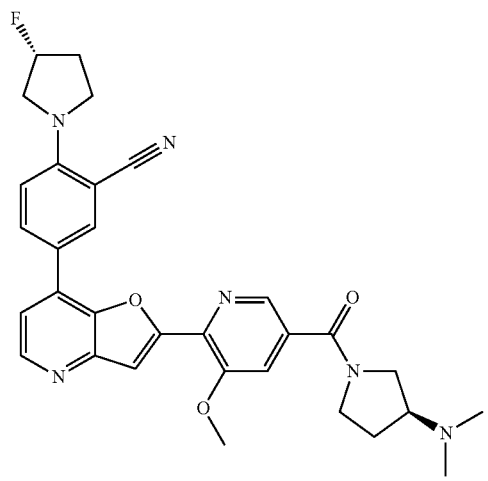 [SMILES: COc1cc(C(=O)N2CC[C@H](N(C)C)C2)cnc1-c1cc2nccc(-c3ccc(N4CC[C@@H](F)C4)c(C#N)c3)c2o1]
448
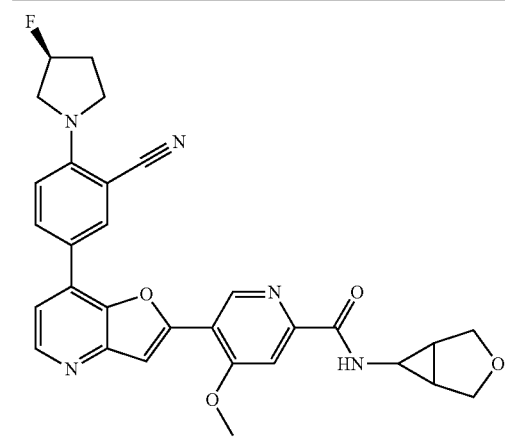
451
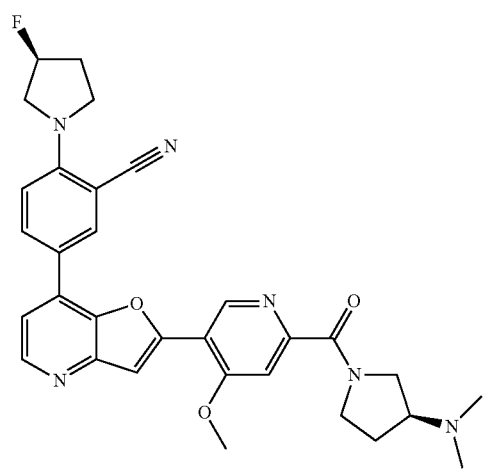 [SMILES: COc1cc(C(=O)N2CC[C@H](N(C)C)C2)ncc1-c1cc2nccc(-c3ccc(N4CC[C@H](F)C4)c(C#N)c3)c2o1]
449
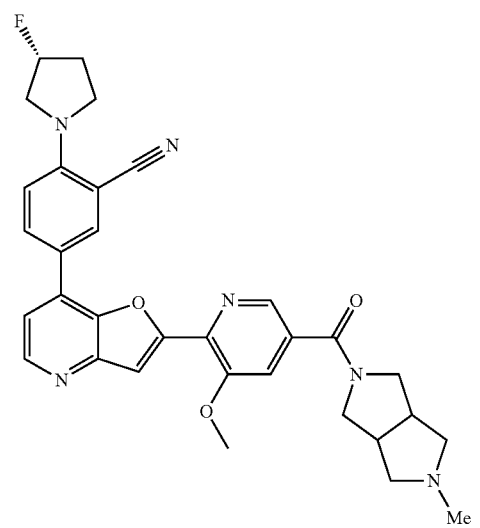 [SMILES: COc1cc(C(=O)N2CC3CN(C)CC3C2)cnc1-c1cc2nccc(-c3ccc(N4CC[C@@H](F)C4)c(C#N)c3)c2o1]
452
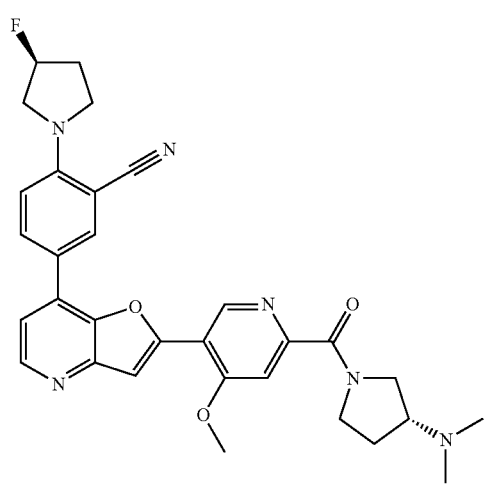
450
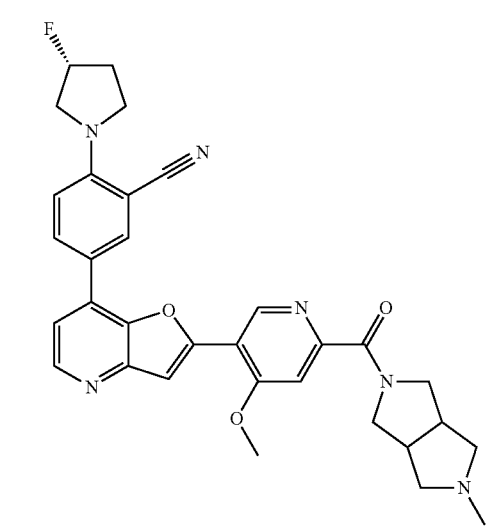 [SMILES: COc1cc(C(=O)N2CC3CN(C)CC3C2)ncc1-c1cc2nccc(-c3ccc(N4CC[C@@H](F)C4)c(C#N)c3)c2o1]
453

TABLE 1-continued
454
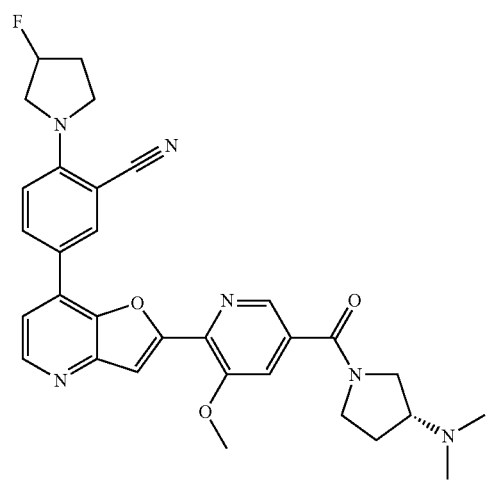 [SMILES: COc1cc(C(=O)N2CC[C@@H](N(C)C)C2)cnc1-c1cc2nccc(-c3ccc(N4CCC(F)C4)c(C#N)c3)c2o1]
455
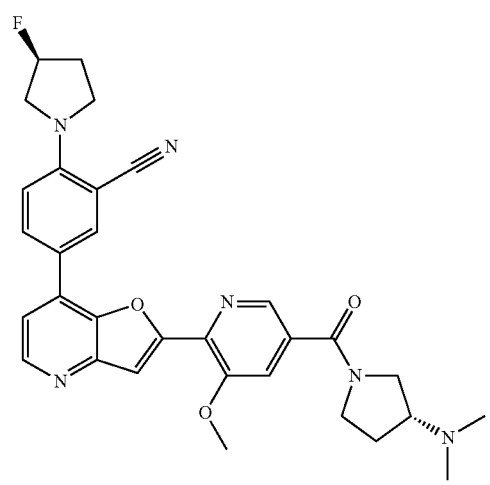 [SMILES: COc1cc(C(=O)N2CC[C@@H](N(C)C)C2)cnc1-c1cc2nccc(-c3ccc(N4CC[C@H](F)C4)c(C#N)c3)c2o1]
456
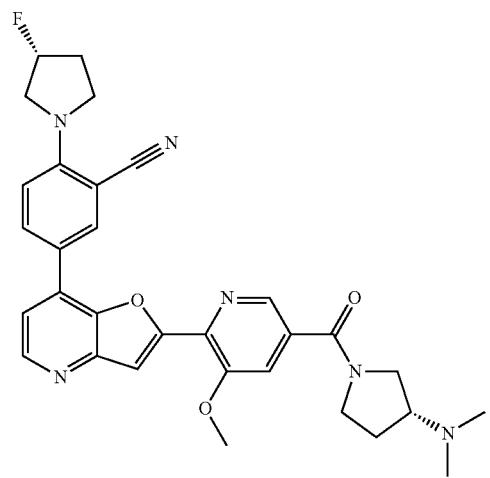 [SMILES: COc1cc(C(=O)N2CC[C@@H](N(C)C)C2)cnc1-c1cc2nccc(-c3ccc(N4CC[C@@H](F)C4)c(C#N)c3)c2o1]
TABLE 1-continued
457
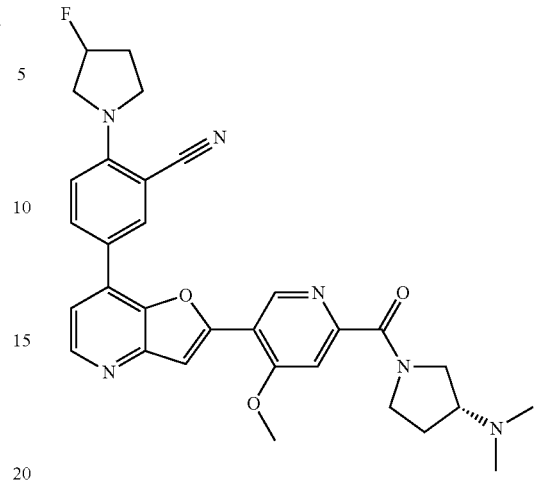
458
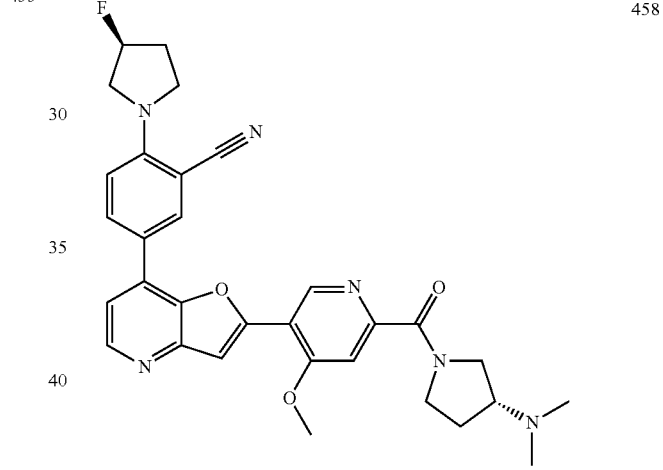
459
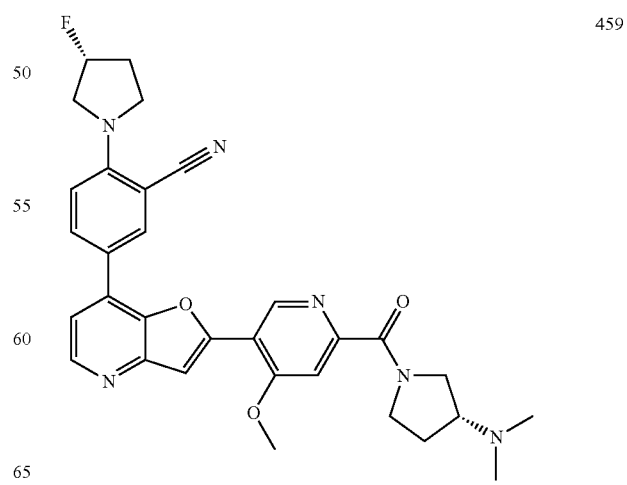

TABLE 1-continued
460
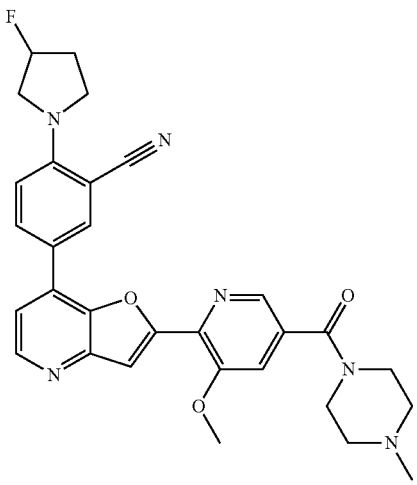 [SMILES: COc1cc(C(=O)N2CCN(C)CC2)cnc1-c1cc2nccc(-c3ccc(N4CCC(F)C4)c(C#N)c3)c2o1]
461
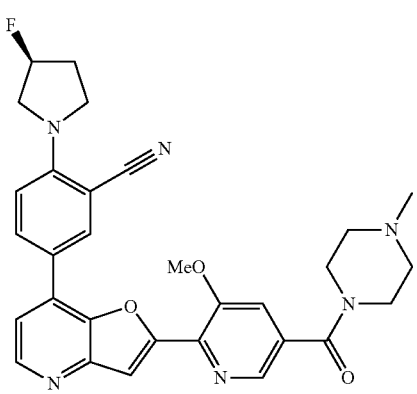 [SMILES: COc1cc(C(=O)N2CCN(C)CC2)cnc1-c1cc2nccc(-c3ccc(N4CC[C@H](F)C4)c(C#N)c3)c2o1]
462
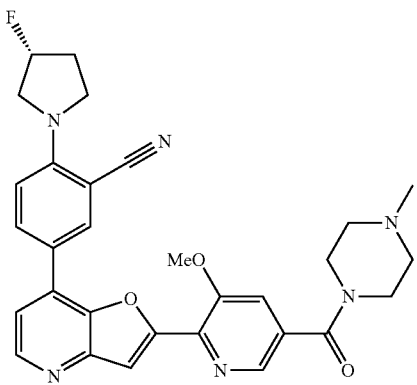 [SMILES: COc1cc(C(=O)N2CCN(C)CC2)cnc1-c1cc2nccc(-c3ccc(N4CC[C@@H](F)C4)c(C#N)c3)c2o1]
463
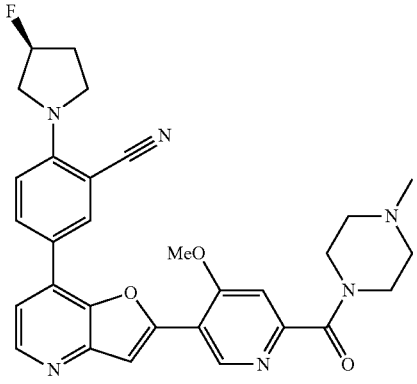 [SMILES: COc1cc(C(=O)N2CCN(C)CC2)ncc1-c1cc2nccc(-c3ccc(N4CC[C@H](F)C4)c(C#N)c3)c2o1]
TABLE 1-continued
464
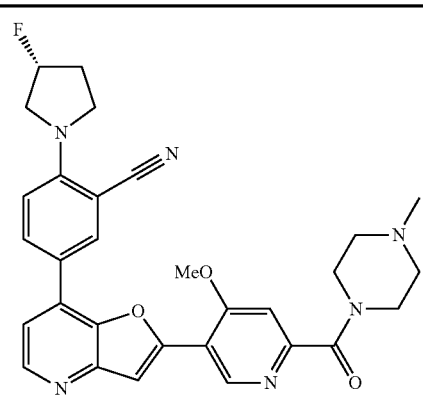
465
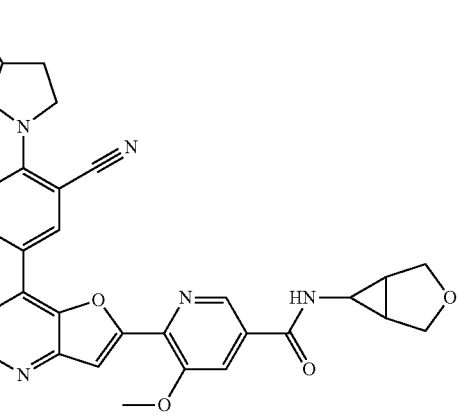
466
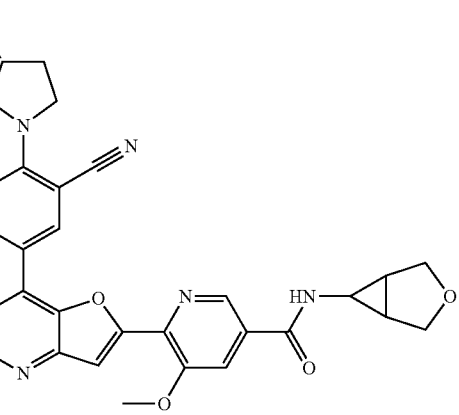
467
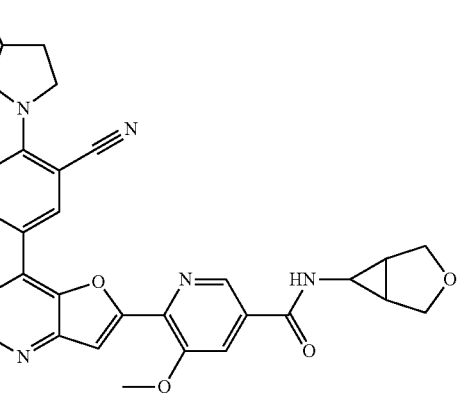

TABLE 1-continued
| 468 | 472 |
|---|---|
|  | 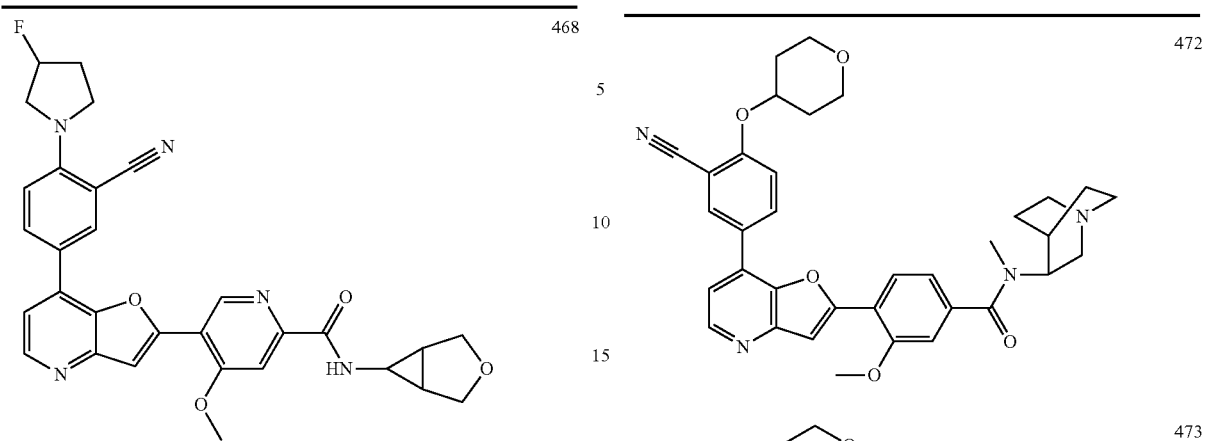 |
| 469 | 473 |
|  | 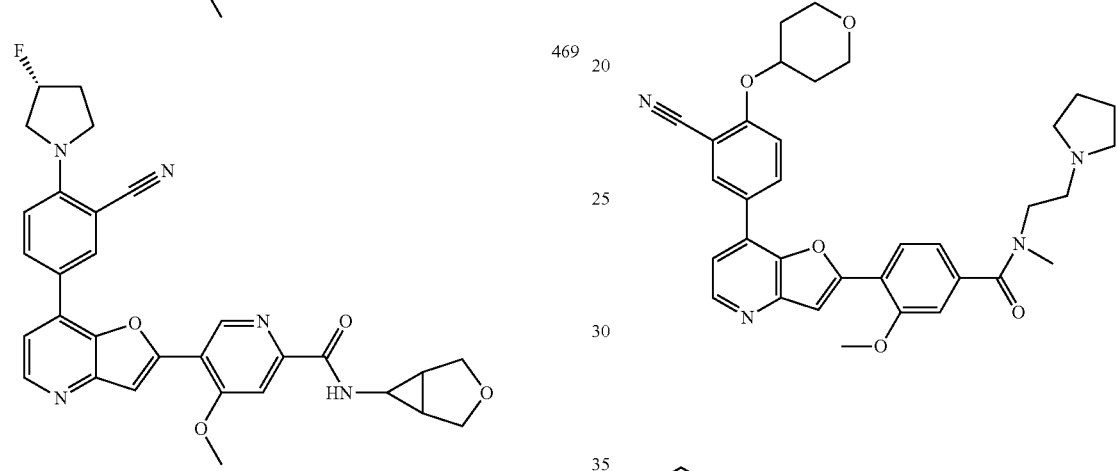 |
| 470 | 474 |
| 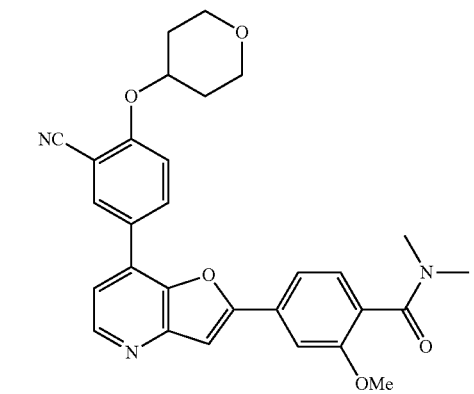 [SMILES: COc1cc(-c2cc3nccc(-c4ccc(OC5CCOCC5)c(C#N)c4)c3o2)ccc1C(=O)N(C)C] | 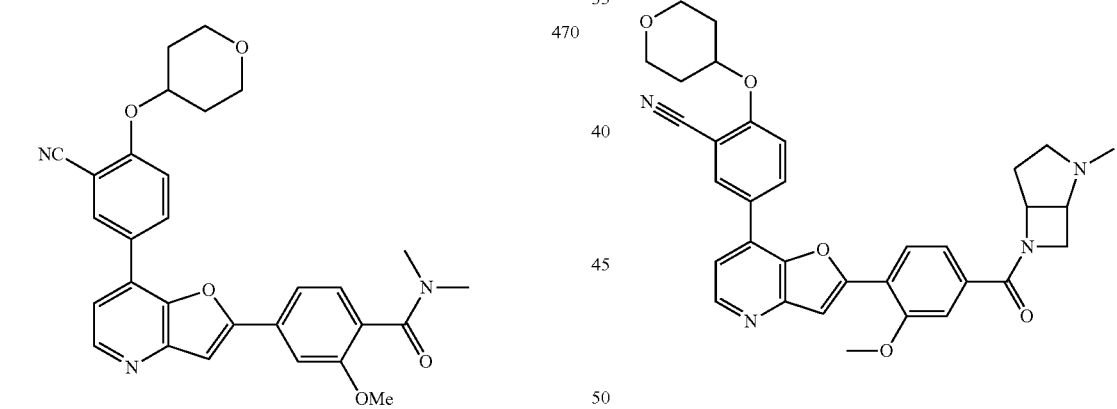 |
| 471 | 475 |
| 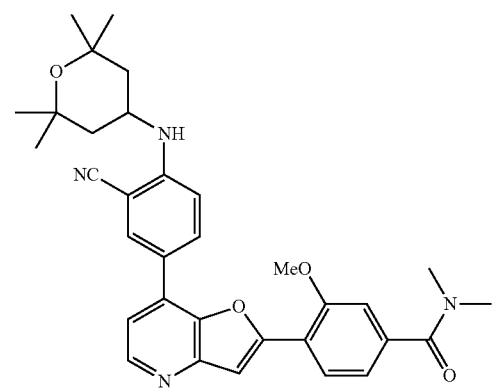 | 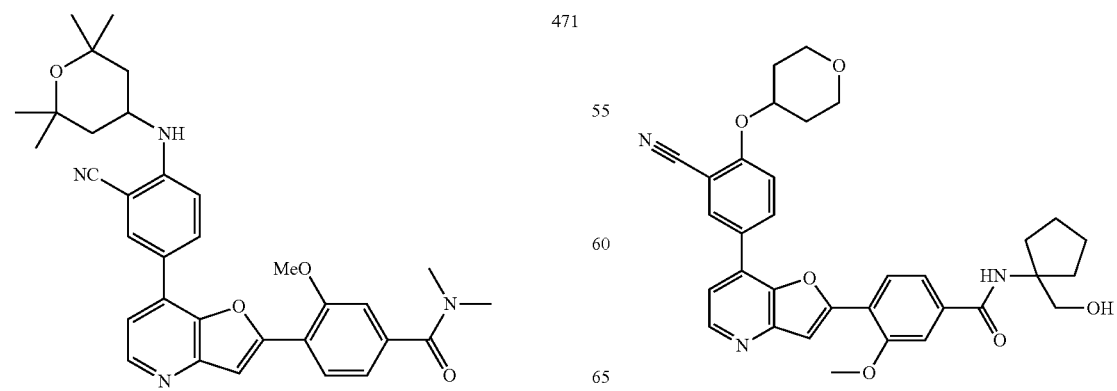 |

TABLE 1-continued
476
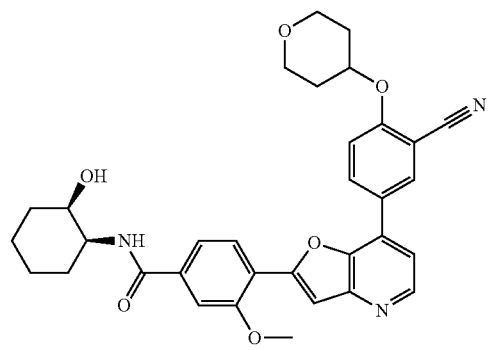 [SMILES: COc1cc(C(=O)N[C@H]2CCCC[C@H]2O)ccc1-c1cc2nccc(-c3ccc(OC4CCOCC4)c(C#N)c3)c2o1]
477
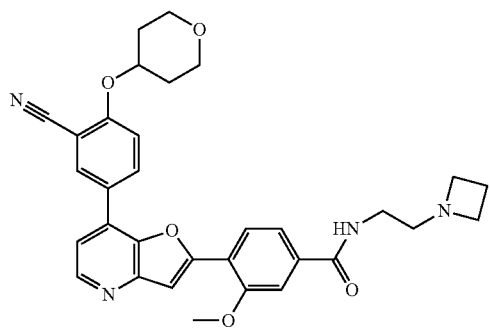 [SMILES: COc1cc(C(=O)NCCN2CCC2)ccc1-c1cc2nccc(-c3ccc(OC4CCOCC4)c(C#N)c3)c2o1]
478
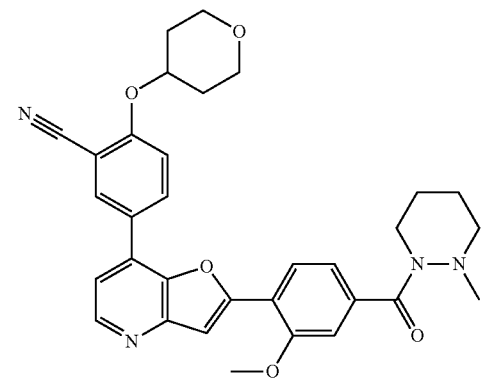 [SMILES: COc1cc(C(=O)N2CCCCN2C)ccc1-c1cc2nccc(-c3ccc(OC4CCOCC4)c(C#N)c3)c2o1]
479
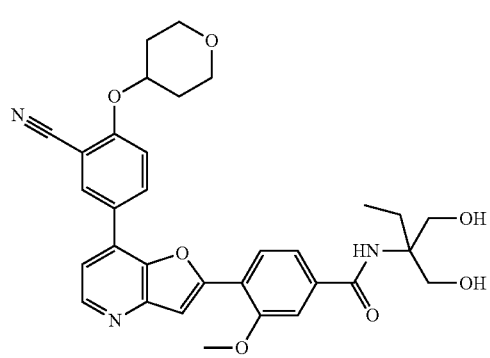 [SMILES: CCC(CO)(CO)NC(=O)c1ccc(-c2cc3nccc(-c4ccc(OC5CCOCC5)c(C#N)c4)c3o2)c(OC)c1]
TABLE 1-continued
480
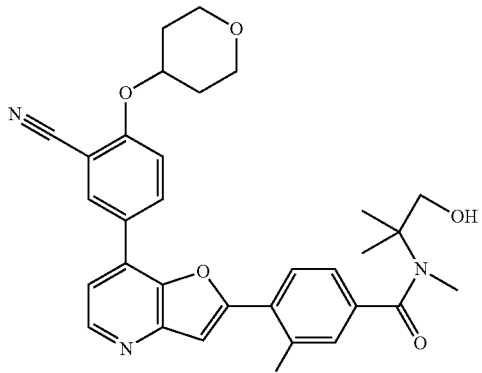
481
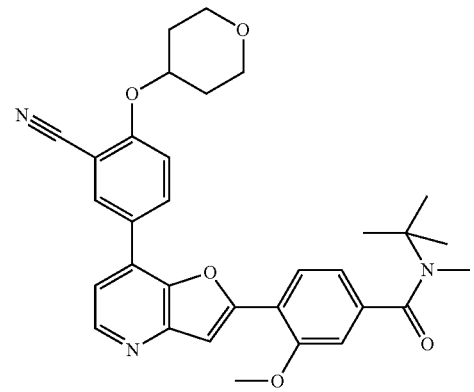 [SMILES: COc1cc(C(=O)N(C)C(C)(C)C)ccc1-c1cc2nccc(-c3ccc(OC4CCOCC4)c(C#N)c3)c2o1]
482
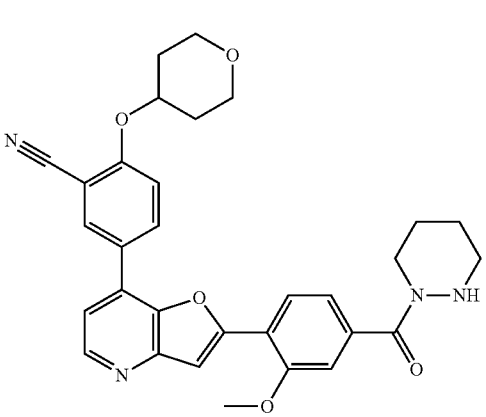 [SMILES: COc1cc(C(=O)N2CCCCN2)ccc1-c1cc2nccc(-c3ccc(OC4CCOCC4)c(C#N)c3)c2o1]
483
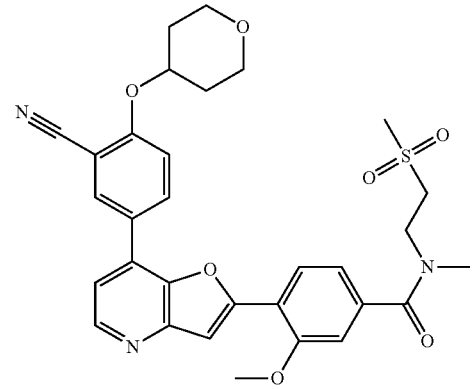 [SMILES: COc1cc(C(=O)N(C)CCS(C)(=O)=O)ccc1-c1cc2nccc(-c3ccc(OC4CCOCC4)c(C#N)c3)c2o1]

TABLE 1-continued
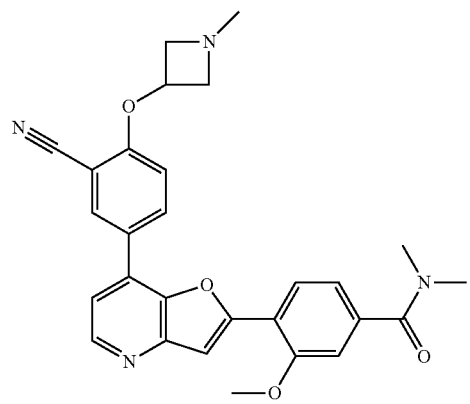 [SMILES: COc1cc(C(=O)N(C)C)ccc1-c1cc2nccc(-c3ccc(OC4CN(C)C4)c(C#N)c3)c2o1]
484
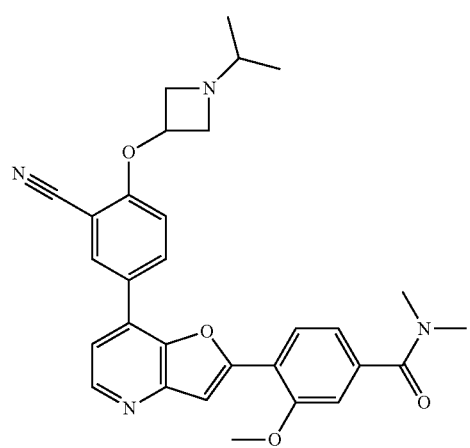 [SMILES: COc1cc(C(=O)N(C)C)ccc1-c1cc2nccc(-c3ccc(OC4CN(C(C)C)C4)c(C#N)c3)c2o1]
485
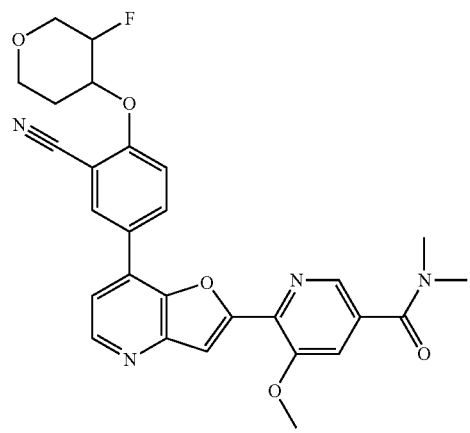 [SMILES: COc1cc(C(=O)N(C)C)cnc1-c1cc2nccc(-c3ccc(OC4CCOCC4F)c(C#N)c3)c2o1]
486
TABLE 1-continued
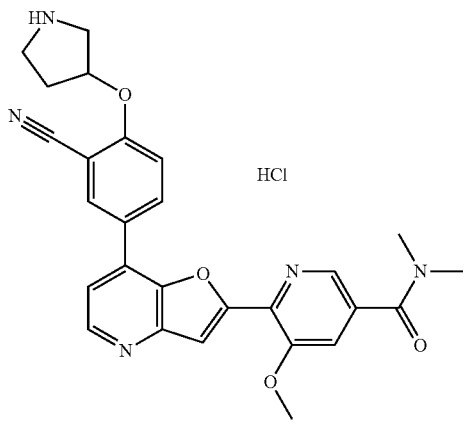 [SMILES: COc1cc(C(=O)N(C)C)cnc1-c1cc2nccc(-c3ccc(OC4CCNC4)c(C#N)c3)c2o1 ; Cl]
487
488
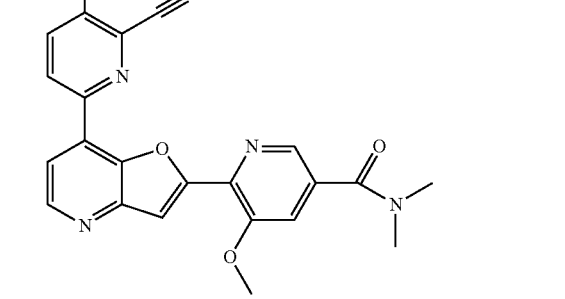
489
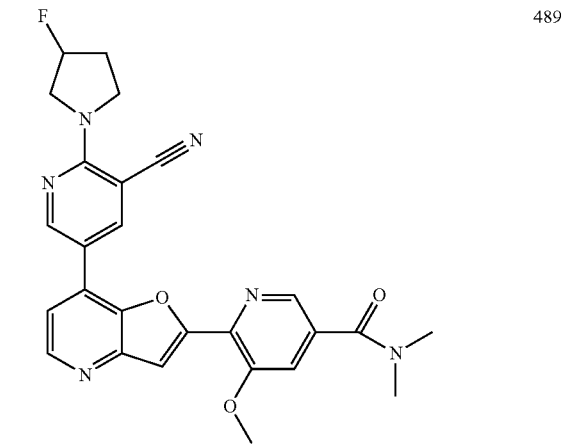
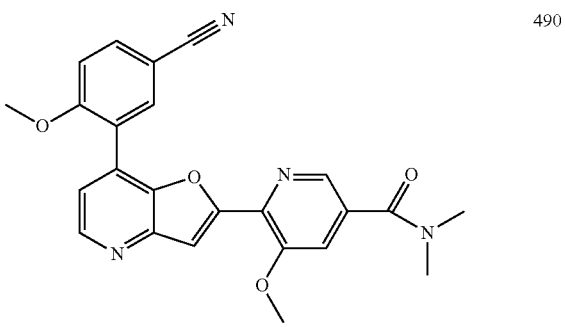
490

TABLE 1-continued
491
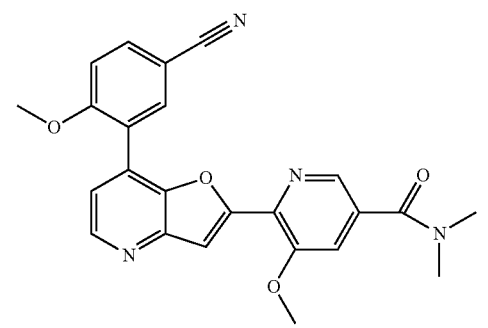
492
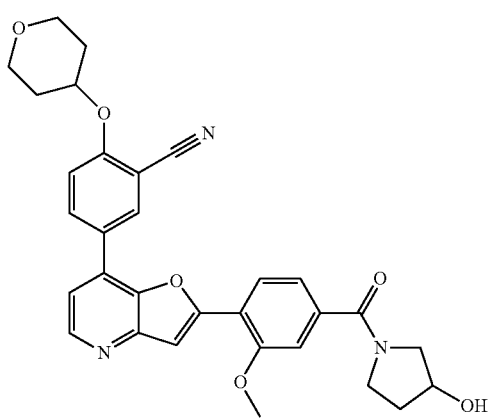 [SMILES: COc1cc(C(=O)N2CCC(O)C2)ccc1-c1cc2nccc(-c3ccc(OC4CCOCC4)c(C#N)c3)c2o1]
493
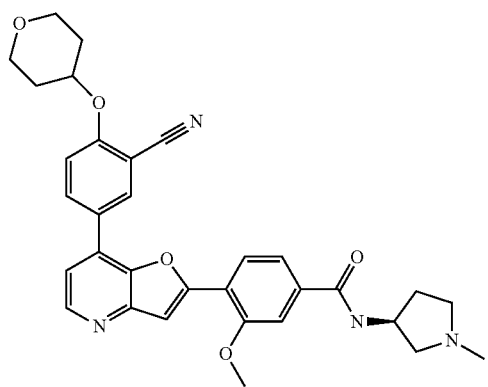
494
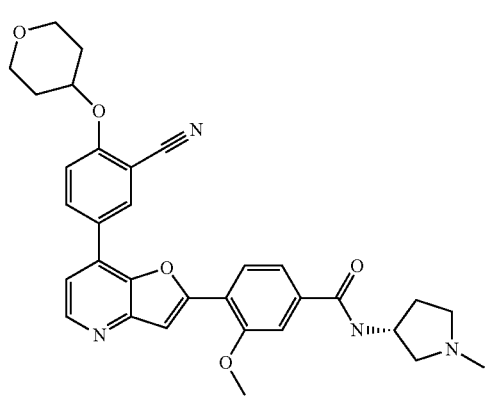 [SMILES: COc1cc(C(=O)N[C@@H]2CCN(C)C2)ccc1-c1cc2nccc(-c3ccc(OC4CCOCC4)c(C#N)c3)c2o1]
TABLE 1-continued
495
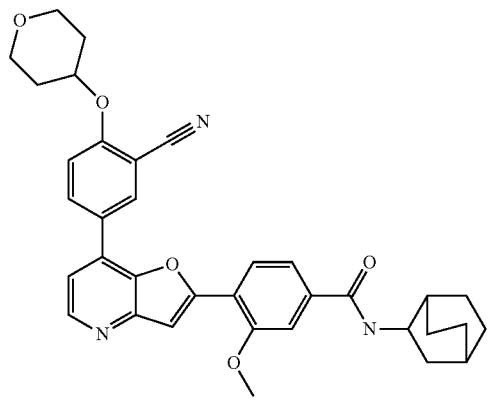 [SMILES: COc1cc(C(=O)NC2CC3CCC2CC3)ccc1-c1cc2nccc(-c3ccc(OC4CCOCC4)c(C#N)c3)c2o1]
496
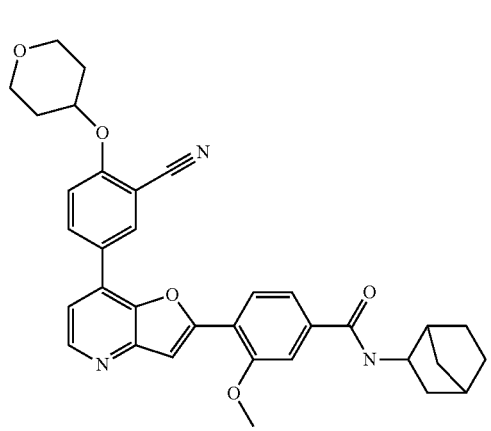 [SMILES: COc1cc(C(=O)NC2CC3CCC2C3)ccc1-c1cc2nccc(-c3ccc(OC4CCOCC4)c(C#N)c3)c2o1]
497 Chiral
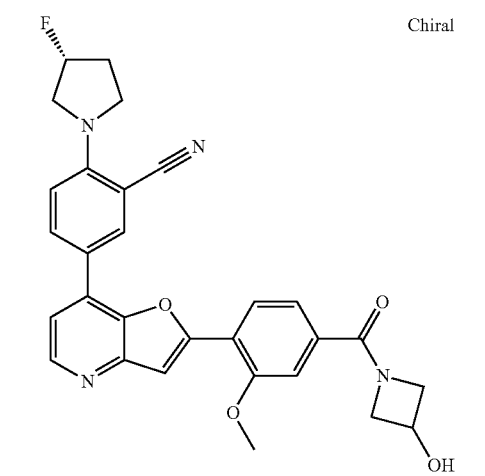 [SMILES: COc1cc(C(=O)N2CC(O)C2)ccc1-c1cc2nccc(-c3ccc(N4CC[C@@H](F)C4)c(C#N)c3)c2o1]

TABLE 1-continued
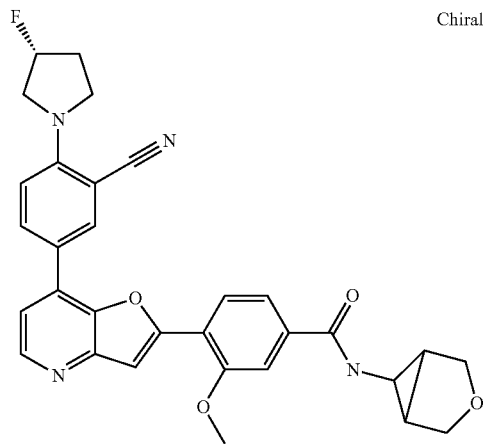 [SMILES: COc1cc(C(=O)NC2C3COCC32)ccc1-c1cc2nccc(-c3ccc(N4CC[C@@H](F)C4)c(C#N)c3)c2o1]
498 Chiral
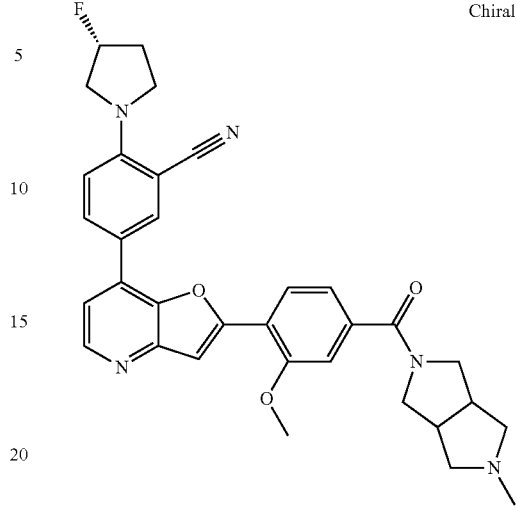
501 Chiral
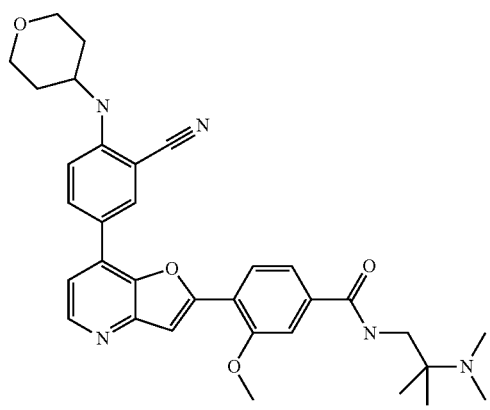 [SMILES: COc1cc(C(=O)NCC(C)(C)N(C)C)ccc1-c1cc2nccc(-c3ccc(NC4CCOCC4)c(C#N)c3)c2o1]
499
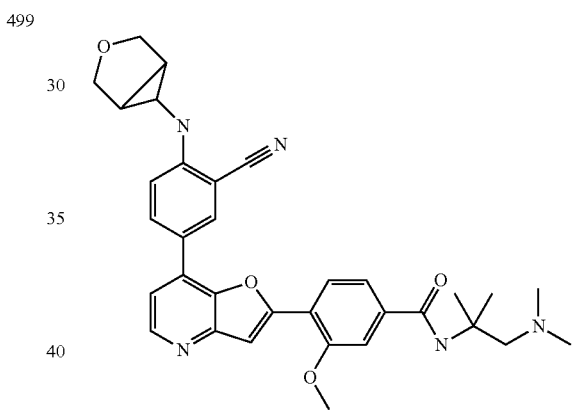
502
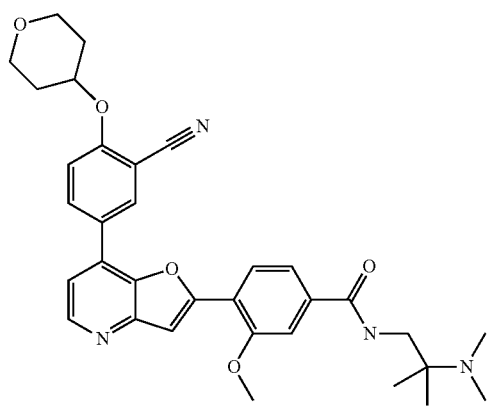 [SMILES: COc1cc(C(=O)NCC(C)(C)N(C)C)ccc1-c1cc2nccc(-c3ccc(OC4CCOCC4)c(C#N)c3)c2o1]
500
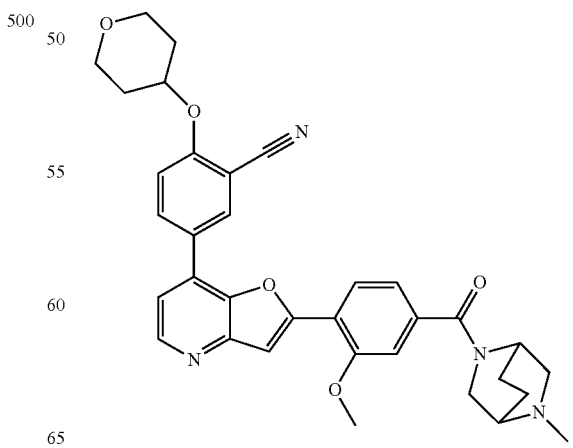
503

TABLE 1-continued
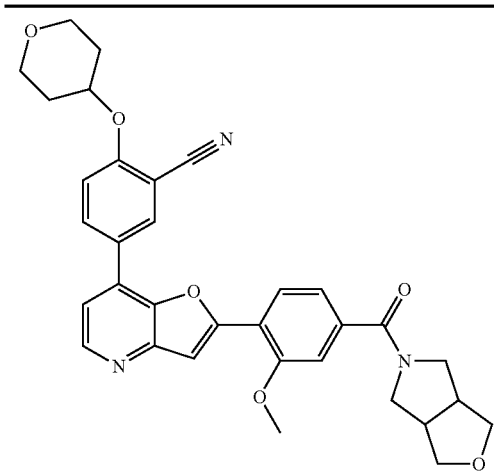
504
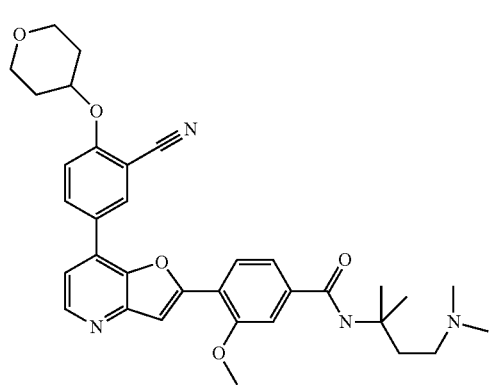 [SMILES: COc1cc(C(=O)NC(C)(C)CCN(C)C)ccc1-c1cc2nccc(-c3ccc(OC4CCOCC4)c(C#N)c3)c2o1]
505
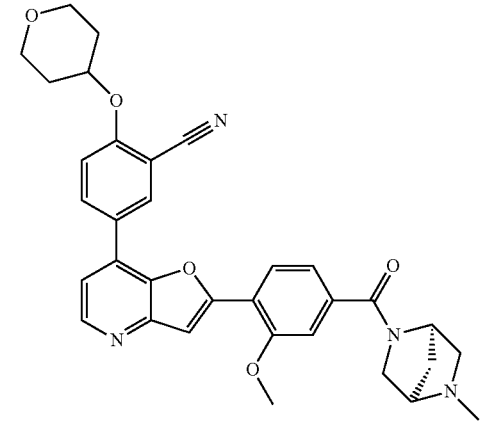
506
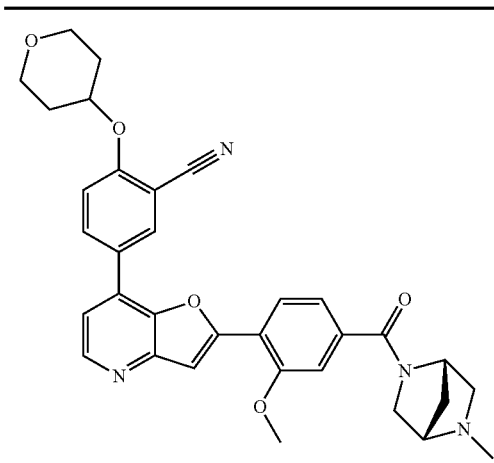
507
TABLE 1-continued
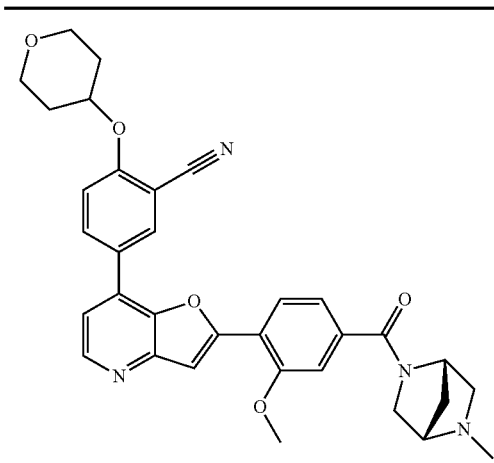
508
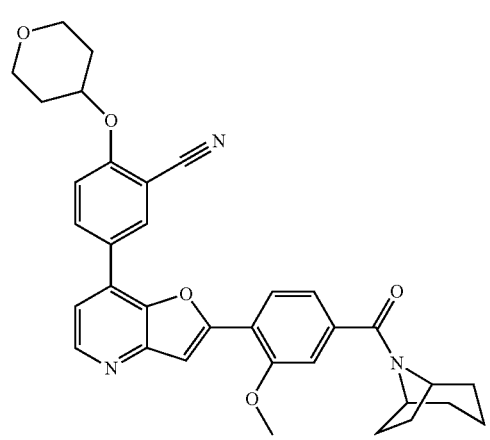 [SMILES: COc1cc(C(=O)N2C3CCCC2CC3)ccc1-c1cc2nccc(-c3ccc(OC4CCOCC4)c(C#N)c3)c2o1]
509
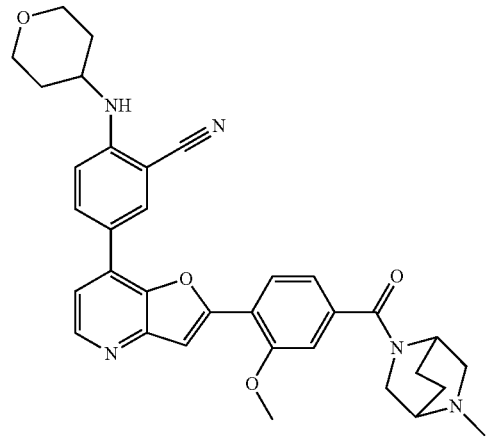 [SMILES: COc1cc(C(=O)N2CC3CCC2CN3C)ccc1-c1cc2nccc(-c3ccc(NC4CCOCC4)c(C#N)c3)c2o1]
510

TABLE 1-continued
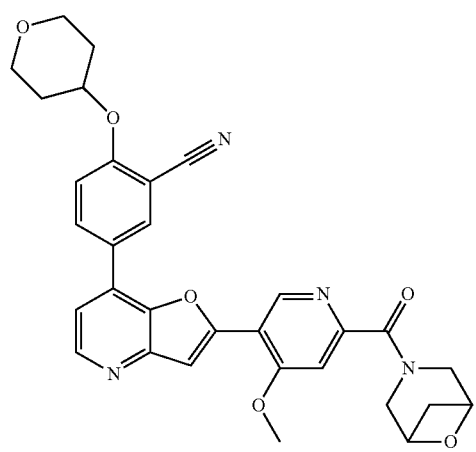 [SMILES: COc1cc(C(=O)N2CC3CC(C2)O3)ncc1-c1cc2nccc(-c3ccc(OC4CCOCC4)c(C#N)c3)c2o1] 511
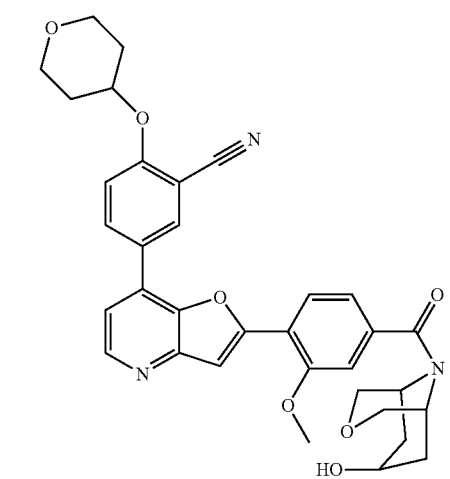 [SMILES: COc1cc(C(=O)N2C3COCC2CC(O)C3)ccc1-c1cc2nccc(-c3ccc(OC4CCOCC4)c(C#N)c3)c2o1] 512
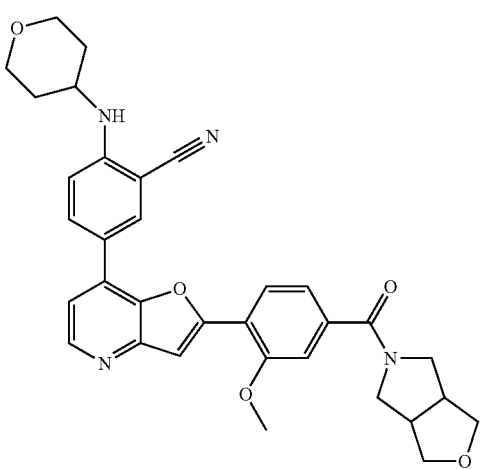 [SMILES: COc1cc(C(=O)N2CC3COCC3C2)ccc1-c1cc2nccc(-c3ccc(NC4CCOCC4)c(C#N)c3)c2o1] 513
TABLE 1-continued
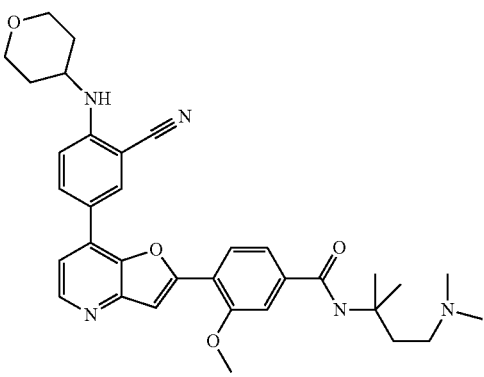 [SMILES: COc1cc(C(=O)NC(C)(C)CCN(C)C)ccc1-c1cc2nccc(-c3ccc(NC4CCOCC4)c(C#N)c3)c2o1] 514
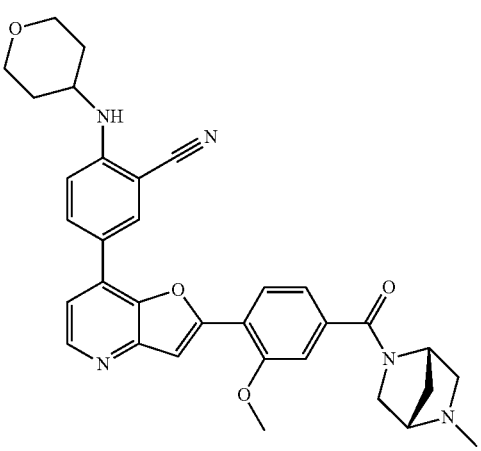 [SMILES: COc1cc(C(=O)N2C[C@@H]3C[C@H]2CN3C)ccc1-c1cc2nccc(-c3ccc(NC4CCOCC4)c(C#N)c3)c2o1] 515
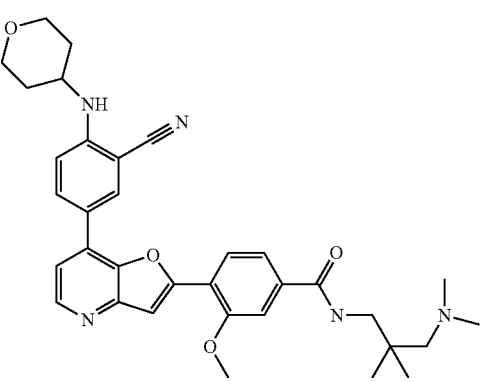 [SMILES: COc1cc(C(=O)NCC(C)(C)CN(C)C)ccc1-c1cc2nccc(-c3ccc(NC4CCOCC4)c(C#N)c3)c2o1] 516
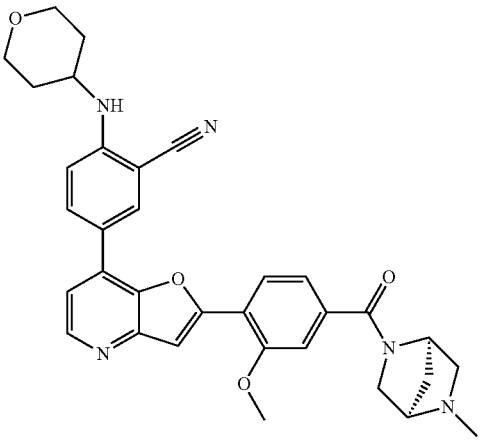 [SMILES: COc1cc(C(=O)N2C[C@H]3C[C@@H]2CN3C)ccc1-c1cc2nccc(-c3ccc(NC4CCOCC4)c(C#N)c3)c2o1] 517

TABLE 1-continued

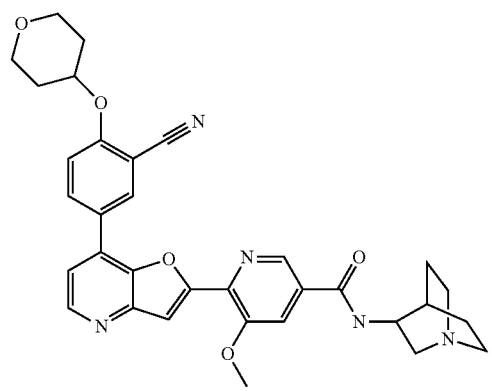 [SMILES: COc1cc(C(=O)NC2CN3CCC2CC3)cnc1-c1cc2nccc(-c3ccc(OC4CCOCC4)c(C#N)c3)c2o1]

518

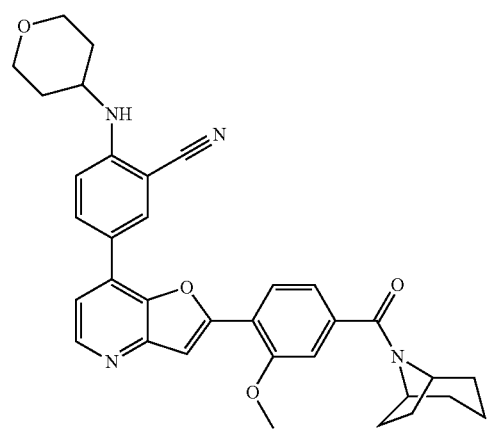 [SMILES: COc1cc(C(=O)N2C3CCCC2CC3)ccc1-c1cc2nccc(-c3ccc(NC4CCOCC4)c(C#N)c3)c2o1]

519

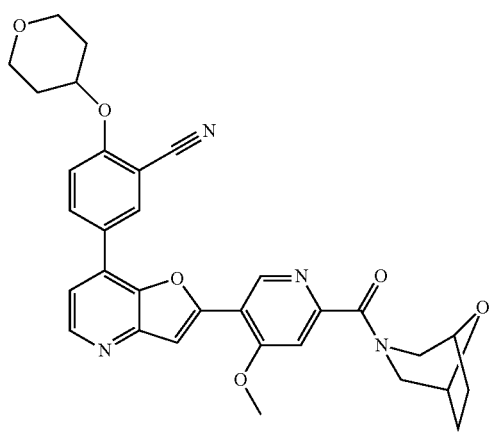 [SMILES: COc1cc(C(=O)N2CC3CCC(C2)O3)ncc1-c1cc2nccc(-c3ccc(OC4CCOCC4)c(C#N)c3)c2o1]

520

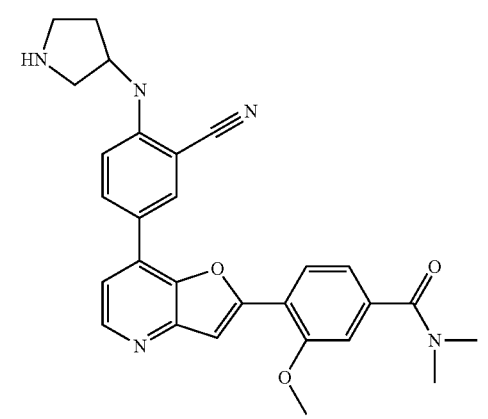 [SMILES: COc1cc(C(=O)N(C)C)ccc1-c1cc2nccc(-c3ccc(NC4CCNC4)c(C#N)c3)c2o1]

521

TABLE 1-continued

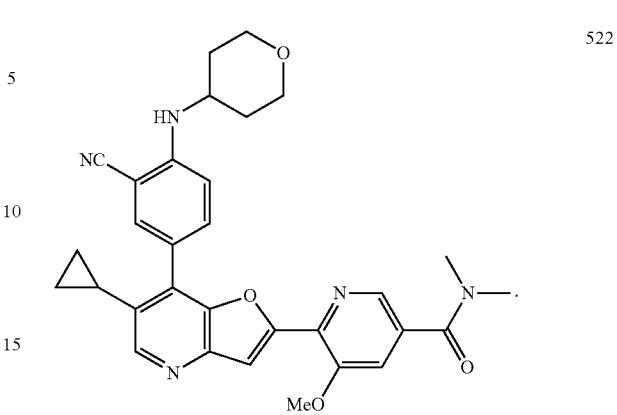

522

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g.,

is understood to be

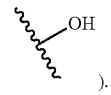

).

In certain embodiments, the compounds of the invention were synthesized in accordance with the schemes provided in the Examples below.

4. Uses, Formulation and Administration
Pharmaceutically Acceptable Compositions According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit TBK and IKKε, or a mutant thereof, in a biological sample or in a patient. In certain embodiments, the amount of compound in compositions of this invention is such that is effective to measurably inhibit TBK and IKKε, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The present invention furthermore relates to a method for treating a subject suffering from a TBK or IKKε related disorder, comprising administering to said subject an effective amount of a compound of formula I or any formulae presented herein.

The present invention preferably relates to a method, wherein the TBK or IKKε associated disorder is an autoimmune disorder or condition associated with an overactive immune response or cancer. The present invention furthermore relates to a method of treating a subject suffering from an immunoregulatory abnormality, comprising administering to said subject a compound of formula (I), and related formulae in an amount that is effective for treating said immunoregulatory abnormality.

The present invention preferably relates to a method wherein the immunoregulatory abnormality is an autoimmune or chronic inflammatory disease selected from the group consisting of: allergic diseases, amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

The present invention furthermore relates to a method wherein the immunoregulatory abnormality is bone marrow or organ transplant rejection or graft-versus-host disease.

The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, parkison diseases, trauma, and chronic bacterial infection.

In certain embodiments, disorders associated with TBK or IKKε are selected from Rheumatoid Arthritis, Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease (Cronh's Disease and Ulcerative Colitis), Hyperimmunoglobulinemia D and periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, Sepsis, Stroke, Atherosclerosis, Celiac disease, DIRA (Deficiency of IL-1 Receptor Antagonist), Alzheimer's disease, Parkinson's disease, and Cancer.

In certain embodiments, disorders associated with TBK or IKKε are selected from cancer, septic shock, Primary open Angle Glaucoma (POAG), hyperplasia, rheumatoid arthritis, psoriasis, artherosclerosis, retinopathy, osteoarthritis, endometriosis, chronic inflammation, and/or neurodegenerative diseases such as Alzheimers disease.

In certain embodiments, the cancer is selected from carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g., epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer.

In certain embodiments, the cancer is brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. In some embodiments, the cancer is metastatic cancer. In some embodiments, the cancer is colorectal cancer. In some embodiments, the cancer is colon cancer.

In certain aspects, the invention relates to the compounds of the invention for the use for the treatment of a disease or disorder described herein.

In certain aspects, the invention relates to the use of compounds of formula I, or any formulae presented herein, for the preparation of a medicament for the treatment or a disease or disorder described herein.

In various embodiments, compounds of formula (I), and related formulae exhibit a IC50 for the binding to TBK and/or IKKε of less than about 5 μM, preferably less than about 1 μM, preferably less than about 100 nM, preferably less than about 10 nM.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to inhibit TBK and/or IKKε activity, usually between about one hour and one week. In-vitro treatment can be carried out using cultivated cells from a biopsy sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing TBK and/or IKKε-dependent signal transduction pathways in animals and/or cell culture models or in the clinical diseases mentioned in this application.

Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of TBK and/or IKKε activity if expedient.

The invention also relates to the use of compounds according to formula (I) and/or physiologically acceptable salts thereof for the prophylactic or therapeutic treatment and/or monitoring of diseases that are caused, mediated and/or propagated by TBK and/or IKKε activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by TBK and/or IKKε activity. In certain embodiments, the invention provides the use of a compound according to formula I or physiologically acceptable salts thereof, for the production of a medicament for the prophylactic or therapeutic treatment of a TBK and/or IKKε-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with TBK and/or IKKε activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with TBK and/or IKKε activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor (TNF) antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib, XL-647[4];

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab, tabalumab[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin1,3, recombinant interferon beta-1a[4];

Drug Conjugates: such as denileukin diftitox, ibritumomab tiuxetan, iobenguane 1123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4].

([1] Prop. INN (Proposed International Nonproprietary Name); [2] Rec. INN (Recommended International Nonproprietary Names); [3] USAN (United States Adopted Name); [4] no INN).

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

In certain embodiments, a therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

In certain embodiments, the pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting TBK and/or IKKε activity in a biological sample comprising the step of contacting said biological sample with a compound of this invention, or a composition comprising said compound.

According to another embodiment, the invention relates to a method of inhibiting TBK and/or IKKε, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of TBK and/or IKKε, including the evaluation of the many factors thought to influence, and be influenced by, the production of TBK and/or IKKε and the interaction of TBK and/or IKKε. The present compounds are also useful in the development of other compounds that interact with TBK and/or IKKε since the present compounds provide important structure-activity relationship (SAR) information that facilitate that development. Compounds of the present invention that bind to TBK and/or IKKε can be used as reagents for detecting TBK and/or IKKε in living cells, fixed cells, in biological fluids, in tissue homogenates, in purified, natural biological materials, etc. For example, by labeling such compounds, one can identify cells expressing TBK and/or IKKε. In addition, based on their ability to bind TBK and/or IKKε, compounds of the present invention can be used in in-situ staining, FACS (fluorescence-activated cell sorting), sodium dodecyl sulfate polyacrylamide gel electrophoresis (SDS-PAGE), ELISA (enzyme-linked immunoadsorptive assay), etc., enzyme purification, or in purifying cells expressing TBK and/or IKKε inside permeabilized cells. The compounds of the invention can also be utilized as commercial research reagents for various medical research and diagnostic uses. Such uses can include but are not limited to: use as a calibration standard for quantifying the activities of candidate TBK and/or IKKε inhibitors in a variety of functional assays; use as blocking reagents in random compound screening, i.e. in looking for new families of TBK and/or IKKε ligands, the compounds can be used to block recovery of the presently claimed TBK and/or IKKε compounds; use in the co-crystallization with TBK and/or IKKε enzyme, i.e. the compounds of the present invention will allow formation of crystals of the compound bound to TBK and/or IKKε, enabling the determination of enzyme/compound structure by x-ray crystallography; other research and diagnostic applications, wherein TBK and/or IKKε is preferably activated or such activation is conveniently calibrated against a known quantity of an TBK and/or IKKε inhibitor, etc.; use in assays as probes for determining the expression of TBK and/or IKKε in cells; and developing assays for detecting compounds which bind to the same site as the TBK and/or IKKε binding ligands.

The compounds of the invention can be applied either themselves and/or in combination with physical measurements for diagnostics of treatment effectiveness. Pharmaceutical compositions containing said compounds and the use of said compounds to treat TBK and/or IKKε-mediated conditions is a promising, novel approach for a broad spectrum of therapies causing a direct and immediate improvement in the state of health, whether in human or in animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of TBK and/or IKKε, or a mutant thereof, activity in a biological sample is useful for a variety of purposes that are known to one of skill in the art. Examples of such purposes include, but are not limited to, blood transfusion, organ transplantation, biological specimen storage, and biological assays.

EXEMPLIFICATION

General Conditions and Analytical Methods

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

Unless otherwise indicated, all temperatures are expressed in ° C. (degrees Centigrade).

All reactions were conducted at room temperature unless otherwise noted. All compounds of the present invention were synthesized by processes developed by the inventors.

Compound numbers utilized in the Examples below correspond to compound numbers set forth supra.

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

All solvents used were commercially available and were used without further purification. Reactions were typically run using anhydrous solvents under an inert atmosphere of nitrogen. Flash column chromatography was generally carried out using Silica gel 60 (0.035-0.070 mm particle size).

All NMR experiments were recorded either on Bruker Mercury Plus 400 NMR Spectrometer equipped with a Bruker 400 BBFO probe at 400 MHz for proton NMR or on Bruker Mercury Plus 300 NMR Spectrometer equipped with a Bruker 300 BBFO probe at 300 MHz for proton NMR. All deuterated solvents contained typically 0.03% to 0.05% v/v tetramethylsilane, which was used as the reference signal (set at δ 0.00 for both $^1$H and $^{13}$C).

LC-MS analyses were performed on a SHIMADZU LC-MS machine consisting of an UFLC 20-AD system and LCMS 2020 MS detector. The column used was a Shim-pack XR-ODS, 2.2 μm, 3.0×50 mm. A linear gradient was applied, starting at 95% A (A: 0.05% TFA in water) and ending at 100% B (B: 0.05% TFA in acetonitrile) over 2.2 min with a total run time of 3.6 min. The column temperature was at 40° C. with the flow rate at 1.0 mL/min. The Diode Array detector was scanned from 200-400 nm. The mass spectrometer was equipped with an electro spray ion source (ES) operated in a positive or negative mode. The mass spectrometer was scanned between m/z 90-900 with a scan time of 0.6 s.

BPD is the abbreviation for 4,4,5,5-tetramethyl-2-(tetramethyl-1,3,2-dioxaborolan-2-yl)-1,3,2-dioxaborolane.

COMMON INTERMEDIATES

Intermediate 1: 7-chloro-2-iodofuro[3,2-b]pyridine

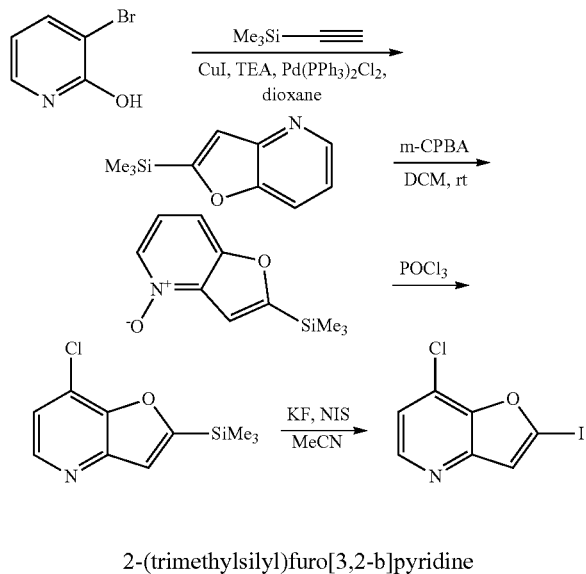

2-(trimethylsilyl)furo[3,2-b]pyridine

To a solution of 2-bromopyridin-3-ol (50.0 g, 287.4 mmol) in dioxane (750 mL) were added Pd(PPh$_3$)$_2$Cl$_2$ (30.3 g, 43.11 mmol), CuI (5.5 g, 28.72 mmol), ethynyltrimethylsilane (56.5 g, 574.74 mmol) and triethylamine (145.4 g, 1.44 mol) at room temperature. The resulting mixture was stirred for 6 h at 120° C. The reaction mixture was cooled to room temperature and the resulting solid in the reaction mixture was removed by filtration. The filtrate was concentrated under reduced pressure and the residue was purified by flash chromatography eluting with EtOAc in hexane (0% to 10% gradient) to yield 2-(trimethylsilyl)furo[3,2-b]pyridine as brown oil (50.0 g, 45%).

2-(trimethylsilyl)furo[3,2-b]pyridine 4-oxide

To a solution of 2-(trimethylsilyl) furo[3,2-b]pyridine (30.0 g, 156.82 mmol) in dichloromethane (260 mL) was added m-CPBA (40.6 g, 235.21 mmol) in portions at 0° C. The resulting solution was stirred for 30 min at 0° C., then warmed up to room temperature and stirred for another 2 h at room temperature. The reaction mixture was concentrated under reduced pressure, the resulting residue was diluted with water (400 mL) and the pH was adjusted to 8 with saturated sodium bicarbonate solution. The resulting mixture was then extracted with dichloromethane (800 mL×2). The organic phases were combined, washed with brine and dried over sodium sulfate. The solvent was removed under reduced pressure to yield 2-(trimethylsilyl)furo[3,2-b]pyridin-4-ium-4-olate as brown oil (30.0 g, 92%).

7-chloro-2-(trimethylsilyl)furo[3,2-b]pyridine

At 0° C., to the solution of 2-(trimethylsilyl)furo[3,2-b]pyridin-4-ium-4-olate (15.0 g, 72.36 mmol) in toluene (200 mL) was added POCl$_3$ (7.0 mL, 75.1 mmol) slowly. The resulting solution was stirred for 2 h at 95° C. After cooling to room temperature, the reaction mixture was concentrated under reduced pressure. The resulting residue was diluted with water (200 mL) and the pH was adjusted to 8 with saturated sodium bicarbonate solution. The resulting mixture was then extracted with dichloromethane (200 mL×2). The organic phases were combined, washed with brine and dried over sodium sulfate. The solvent was removed under reduced pressure and the residue was purified by flash chromatography eluting with EtOAc in hexane (0% to 10% gradient) to yield 7-chloro-2-(trimethylsilyl)furo[3,2-b]pyridine as brown oil (7.5 g, 46%). MS: m/z=226.0 [M+H]$^+$.

7-chloro-2-iodofuro[3,2-b]pyridine

To a solution of 7-chloro-2-(trimethylsilyl)furo[3,2-b]pyridine (1.0 g, 4.43 mmol) in acetonitrile (10 mL) was added potassium fluoride (309 mg, 5.32 mmol) and N-iodosuccinimide (10.0 g, 44.30 mmol) at room temperature. The resulting mixture was then stirred for 2 h at 55° C. The reaction mixture was cooled to room temperature and quenched by the addition of NaHSO$_3$ solution (50 mL, 4 M). The pH was adjusted to 8 with saturated sodium bicarbonate solution, and the resulting mixture was extracted with ethyl acetate (100 mL×2). The organic phases were combined, washed with brine and dried over sodium sulfate. The solvent was concentrated under reduced pressure to yield 7-chloro-2-iodofuro[3,2-b]pyridine as white solid (1.0 g, 81%). MS: m/z=280.0 [M+H]$^+$.

Intermediate 2: N,N-dimethyl-4-(4,4,5,5-tetramethyl-1,3,2-dioxaborolan-2-yl)benzamide

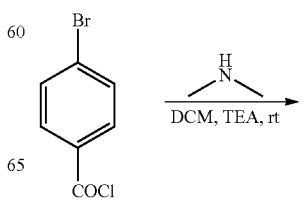

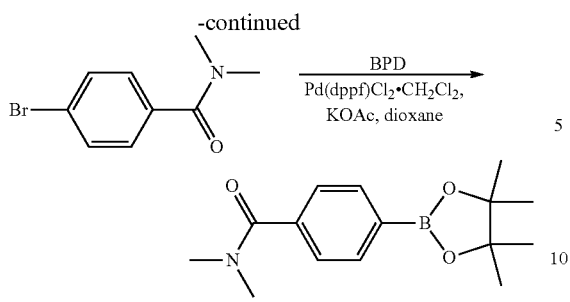

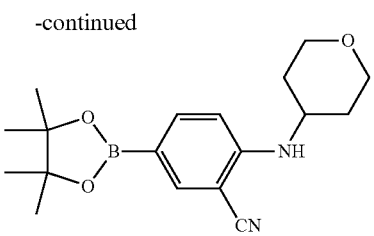

4-bromo-N,N-dimethylbenzamide

To a solution of 4-bromobenzoyl chloride (20.0 g, 91.13 mmol) in dichoromethane (400 mL) were added triethylamine (36.0 mL, 259.0 mmol) and dimethylamine hydrochloride (7.5 g, 91.36 mmol) at room temperature. The reaction mixture was stirred for 3 h at room temperature and then water (200 mL) was added. The resulting solution was extracted with ethyl acetate (300 mL×3). The organic phases were combined, washed with brine and dried over sodium sulfate. The solvent was removed under reduced pressure and the residue was recrystallized from dichloromethane to yield 4-bromo-N,N-dimethylbenzamide as off-white solid (10.0 g, 48%). MS: m/z=228.0 [M+H]$^+$.

N,N-dimethyl-4-(4,4,5,5-tetramethyl-1,3,2-dioxaborolan-2-yl)benzamide

To a solution of 4-bromo-N,N-dimethylbenzamide (11.0 g, 48.23 mmol) in dioxane (300 mL) were added 4,4,5,5-tetramethyl-2-(tetramethyl-1,3,2-dioxaborolan-2-yl)-1,3,2-dioxaborolane (14.7 g, 57.89 mmol), Pd(dppf)Cl$_2$ (3.5 g, 4.78 mmol) and potassium acetate (14.2 g, 144.69 mmol) at room temperature. The resulting mixture was stirred for 16 h at 100° C. The reaction mixture was cooled to room temperature and the resulting solid was removed by filtration. The filtrate was concentrated under reduced pressure and the resulting residue was purified by flash chromatography eluting with EtOAc in hexane (0% to 40% gradient) to yield N,N-dimethyl-4-(tetramethyl-1,3,2-dioxaborolan-2-yl)benzamide as orange solid (10.0 g, 70%). MS: m/z=276.0 [M+H]$^+$.

Intermediate 3: 2-(tetrahydro-2H-pyran-4-ylamino)-5-(4,4,5,5-tetramethyl-1,3,2-dioxaborolan-2-yl)benzonitrile

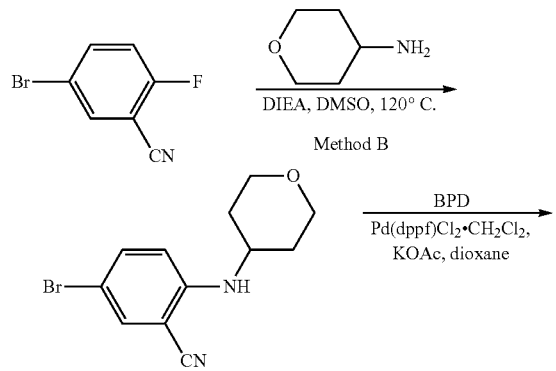

Method B

5-bromo-2-(tetrahydro-2H-pyran-4-ylamino)benzonitrile

To a solution of 5-bromo-2-fluorobenzonitrile (1.2 g, 6.00 mmol) in DMSO (40 mL) was added tetrahydro-2H-pyran-4-amine (1.2 g, 11.96 mmol) and DIEA (1.55 g, 11.99 mmol) at room temperature. The resulting solution was stirred for 16 h at 120° C. The reaction was cooled to room temperature and then treated with water (100 mL). The resulting mixture was extracted with ethyl acetate (50 mL×3). The organic phases were combined, washed with brine and dried over sodium sulfate to yield 5-bromo-2-[(oxan-4-yl)amino]benzonitrile as white solid (1.5 g, 89%). MS: m/z=281.0 [M+H]$^+$.

2-(tetrahydro-2H-pyran-4-ylamino)-5-(4,4,5,5-tetramethyl-1,3,2-dioxaborolan-2-yl)benzonitrile To a solution of 5-bromo-2-[(oxan-4-yl)amino]benzonitrile (1.7 g, 6.05 mmol) in dioxane (100 mL) was added 4,4,5,5-tetramethyl-2-(tetramethyl-1,3,2-dioxaborolan-2-yl)-1,3,2-dioxaborolane (1.8 g, 7.25 mmol), Pd(dppf)Cl$_2$—CH$_2$Cl$_2$ (245 mg, 0.30 mmol) and potassium acetate (1.7 g, 17.32 mmol) at room temperature. The reaction mixture was then irradiated with microwave for 2 h at 100° C. The reaction mixture was cooled to room temperature and then quenched by the addition of water (50 mL). The resulting solution was extracted with ethyl acetate (100 mL×3). The organic phases were combined, washed with brine and dried over sodium sulfate. The solvent was removed under reduced pressure and the residue was purified by flash chromatography eluting with ethyl acetate in hexane (0% to 45% gradient) to yield 2-[(oxan-4-yl)amino]-5-(tetramethyl-1,3,2-dioxaborolan-2-yl)benzonitrile as yellow solid (1.1 g, 49%). MS: m/z=329.0 [M+H]$^+$.

Intermediate 4: 2-(tetrahydro-2H-pyran-4-yloxy)-5-(4,4,5,5-tetramethyl-1,3,2-dioxaborolan-2-yl) benzonitrile

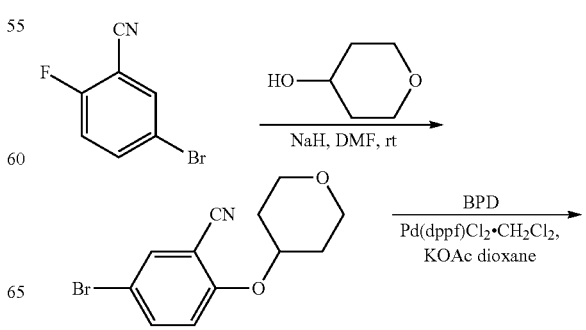

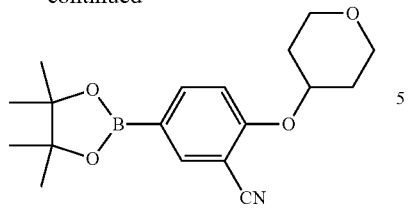

5-bromo-2-(tetrahydro-2H-pyran-4-yloxy)benzonitrile

At 0° C., to a suspension of sodium hydride (60% in oil, 11.2 g, 274.17 mmol) in DMF (400 mL) was added tetrahydro-2H-pyran-4-ol (20.0 g, 195.83 mmol) slowly. The resulting mixture was stirred at 0° C. for 10 min, and then was added by 5-bromo-2-fluorobenzonitrile (32.5 g, 162.54 mmol) slowly. The reaction mixture was warmed to room temperature and stirred for 2 h. The reaction mixture was quenched by the slow addition of water (200 mL). The solid that formed was collected by filtration and dried in oven under vacuum to yield 5-bromo-2-(oxan-4-yloxy)benzonitrile as off-white solid (40.0 g, 72%). MS: m/z=282.0 [M+H]$^+$.

2-(tetrahydro-2H-pyran-4-yloxy)-5-(4,4,5,5-tetramethyl-1,3,2-dioxaborolan-2-yl)benzonitrile To a solution of 5-bromo-2-(oxan-4-yloxy)benzonitrile (5.0 g, 17.72 mmol) in dioxane (100 mL) were added 4,4,5,5-tetramethyl-2-(tetramethyl-1,3,2-dioxaborolan-2-yl)-1,3,2-dioxaborolane (5.5 g, 21.58 mmol), Pd(dppf)Cl$_2$.CH$_2$Cl$_2$ (1.4 g, 1.73 mmol) and potassium acetate (5.2 g, 52.82 mmol) at room temperature. The resulting mixture was stirred overnight at 80° C. The reaction mixture was cooled to room temperature and quenched by the addition of water (100 mL). The resulting mixture was extracted with ethyl acetate (200 mL×3). The organic phases were combined, washed with brine and dried over sodium sulfate. The solvent was removed under reduced pressure and the residue was purified by flash chromatography eluting with ethyl acetate in hexane (0% to 15% gradient) to yield 2-(oxan-4-yloxy)-5-(tetramethyl-1,3,2-dioxaborolan-2-yl)benzonitrile as yellow solid (5.6 g, 96%). MS: m/z=330.0 [M+H]$^+$.

Intermediate 5: 4-(7-chlorofuro[3,2-b]pyridin-2-yl)-N,N-dimethylbenzamide

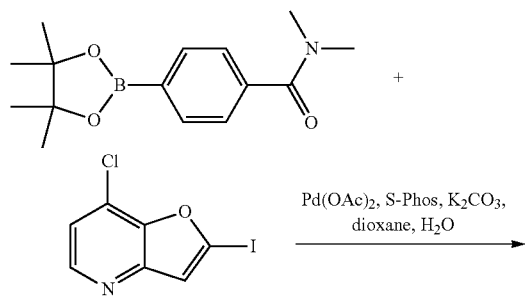

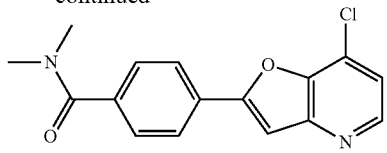

4-(7-chlorofuro[3,2-b]pyridin-2-yl)-N,N-dimethylbenzamide

To a solution of 7-chloro-2-iodofuro[3,2-b]pyridine (9.0 g, 32.2 mmol) in 1,4-dioxane (180 mL) was added N,N-dimethyl-4-(tetramethyl-1,3,2-dioxaborolan-2-yl)benzamide (10.0 g, 36.3 mmol), potassium carbonate (13.2 g, 95.5 mmol), Pd(OAc)$_2$ (720 mg, 3.21 mmol), S-Phos (3.9 g, 9.5 mmol) and water (22 mL) in sequence. The reaction mixture was then stirred for 3 h at 100° C. The reaction mixture was cooled to room temperature and was quenched the addition of water (100 mL). The resulting solution was extracted with ethyl acetate (300 mL×3). The organic phases were combined, washed with brine and dried over sodium sulfate. The solvent was removed under reduced pressure and the residue was purified by flash chromatography eluting with ethyl acetate in hexane (0% to 100% gradient) to yield 4-[7-chlorofuro[3,2-b]pyridin-2-yl]-N,N-dimethylbenzamide as yellow solid (4.0 g, 41%). MS: m/z=301.0 [M+H]$^+$.

Intermediate 6: 5-(5-bromo-1-(phenylsulfonyl)-1H-pyrrolo[2,3-b]pyridin-3-yl)-2-(tetrahydro-2H-pyran-4-yloxy)benzonitrile

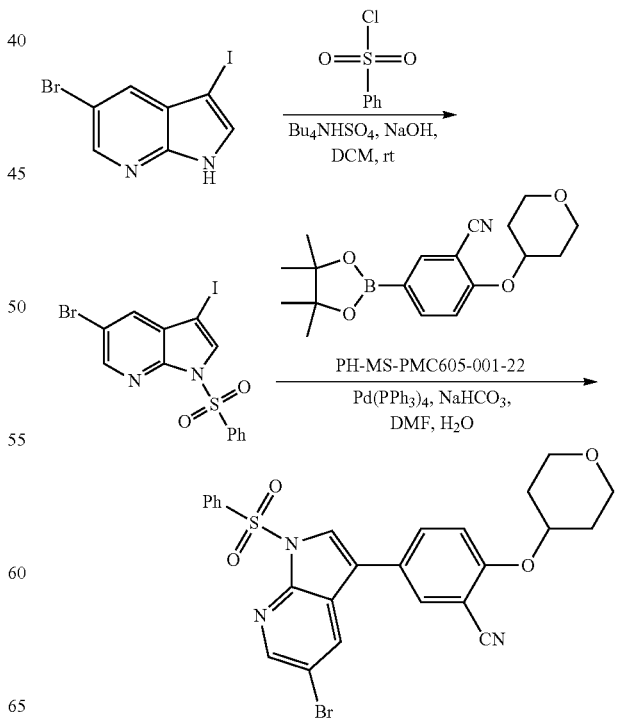

5-bromo-3-iodo-1-(phenylsulfonyl)-1H-pyrrolo[2,3-b]pyridine

To a solution of 5-bromo-3-iodo-1H-pyrrolo[2,3-b]pyridine (2.5 g, 7.7 mmol) in dichloromethane (35 mL) was added benzenesulfonyl chloride (2.2 g, 12.5 mmol) and Bu$_4$NHSO$_4$ (340 mg, 1.00 mmol) at room temperature. Then a solution of sodium hydroxide (2.5 g, 62.5 mmol) in water (5 mL) was added. The resulting mixture was then stirred for 2 h at room temperature. The reaction mixture was extracted with dichloromethane (10 mL×3). The organic phases were combined, washed with brine and dried over sodium sulfate. The solvent was removed under reduced pressure and the residue was recrystallized from methanol to yield 1-(benzenesulfonyl)-5-bromo-3-iodo-1H-pyrrolo[2,3-b]pyridine as brown solid (2.2 g, 61%). MS: m/z=462.0 [M+H]$^+$.

5-(5-bromo-1-(phenylsulfonyl)-1H-pyrrolo[2,3-b]pyridin-3-yl)-2-(tetrahydro-2H-pyran-4-yloxy) benzonitrile To a solution of 2-(oxan-4-yloxy)-5-(tetramethyl-1,3,2-dioxaborolan-2-yl)benzonitrile (7.8 g, 23.75 mmol) and 1-(benzenesulfonyl)-5-bromo-3-iodo-1H-pyrrolo[2,3-b]pyridine (10.0 g, 21.59 mmol) in N,N-dimethylformamide (300 mL) were added sodium bicarbonate (1.8 g, 21.55 mmol) and Pd(PPh$_3$)$_2$Cl$_2$ (303 mg, 0.43 mmol) at room temperature. The resulting mixture was stirred for 2 h at 80° C. The reaction mixture was cooled to room temperature and quenched by the addition of water (100 mL). The resulting mixture was extracted with ethyl acetate (200 mL×3). The organic phases were combined, washed with brine and dried over sodium sulfate. The solvent was removed under reduced pressure and the resulting residue was purified by flash chromatography eluting with EtOAc in hexane (0% to 100% gradient) to yield 5-[1-(benzenesulfonyl)-5-bromo-1H-pyrrolo[2,3-b]pyridin-3-yl]-2-(oxan-4-yloxy)benzonitrile as a off-white solid (8 g, 69%). MS: m/z=538.0 [M+H]$^+$.

Intermediate 7: 4-(7-chlorofuro[3,2-b]pyridin-2-yl)-3-methoxy-N,N-dimethylbenzamide

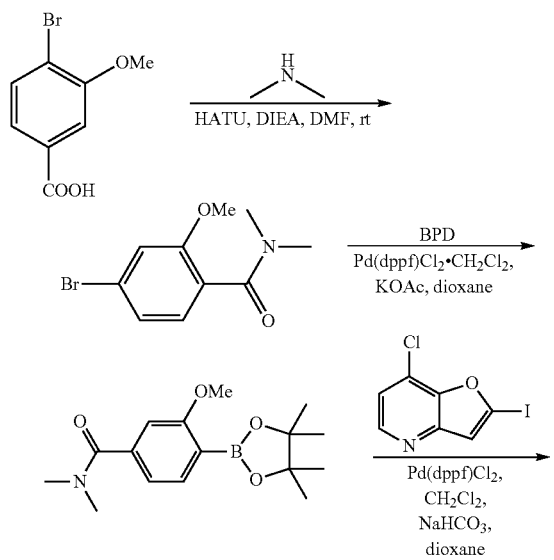

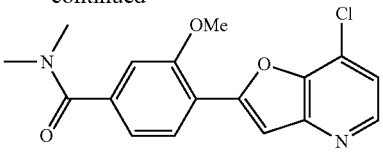

4-bromo-2-methoxy-N,N-dimethylbenzamide

To a solution of 4-bromo-3-methoxybenzoic acid (6.0 g, 26.0 mmol) in N,N-dimethylformamide (100 mL) was added DIEA (10.0 g, 77.4 mmol), dimethylamine hydrochloride (2.3 g, 28.2 mmol) and HATU (13.0 g, 34.2 mmol) in sequence. The resulting solution was stirred for 16 h at room temperature and then quenched by the addition of water (100 mL). The resulting mixture was extracted with ethyl acetate (200 mL×3). The organic phases were combined, washed with brine and dried over sodium sulfate. The solvent was removed under reduced pressure and the residue was purified by flash chromatography eluting with ethyl acetate in hexane (0% to 35% gradient) to yield 4-bromo-3-methoxy-N,N-dimethylbenzamide as brown solid (4.7 g, 50%). MS: m/z=258.0 [M+H]$^+$.

3-methoxy-N,N-dimethyl-4-(4,4,5,5-tetramethyl-1,3,2-dioxaborolan-2-yl)benzamide To a solution of 4-bromo-3-methoxy-N,N-dimethylbenzamide (5.0 g, 19.37 mmol) in dioxane (30 mL) was added 4,4,5,5-tetramethyl-2-(tetramethyl-1,3,2-dioxaborolan-2-yl)-1,3,2-dioxaborolane (5.9 g, 23.23 mmol), Pd(dppf)Cl$_2$·CH$_2$Cl$_2$ (1.6 g, 1.96 mmol) and potassium acetate (5.7 g, 58.08 mmol) at room temperature. The reaction mixture was stirred for 2 h at 100° C. The reaction mixture was cooled to room temperature and then was quenched by the addition of water (100 mL). The resulting mixture was extracted with ethyl acetate (200 mL×3). The organic phases were combined, washed with brine and dried over sodium sulfate. The solvent was removed under reduced pressure and the residue was purified by flash chromatography eluting with ethyl acetate in hexane (0% to 35% gradient) to yield 3-methoxy-N,N-dimethyl-4-(tetramethyl-1,3,2-dioxaborolan-2-yl)benzamide as orange oil (3.5 g, 59%). MS: m/z=306.0 [M+H]$^+$.

4-(7-chlorofuro[3,2-b]pyridin-2-yl)-3-methoxy-N,N-dimethylbenzamide

To a solution of 3-methoxy-N,N-dimethyl-4-(tetramethyl-1,3,2-dioxaborolan-2-yl)benzamide (2.5 g, 8.2 mmol) in dioxane (20 mL) was added 7-chloro-2-iodofuro[3,2-b]pyridine (1.9 g, 6.8 mmol), sodium bicarbonate (600 mg, 7.1 mmol) and Pd(dppf)Cl$_2$·CH$_2$Cl$_2$ (560 mg, 0.69 mmol) at room temperature. The resulting mixture was stirred for 3 h at 100° C. The reaction mixture was cooled to room temperature and quenched by the addition of water (100 mL). The mixture was extracted with ethyl acetate (150 mL×3). The organic phases were combined, washed with brine and dried over sodium sulfate. The solvent was removed under reduced pressure and the residue was purified by flash chromatography eluting with ethyl acetate in hexane (0% to 45% gradient) to yield 4-[7-chlorofuro[3,2-b]pyridin-2-yl]-3-methoxy-N,N-dimethylbenzamide as brown solid (1.3 g, 58%). MS: m/z=331.0 [M+H]$^+$.

Intermediate 8: 6-(7-chlorofuro[3,2-b]pyridin-2-yl)-N,N-dimethylnicotinamide

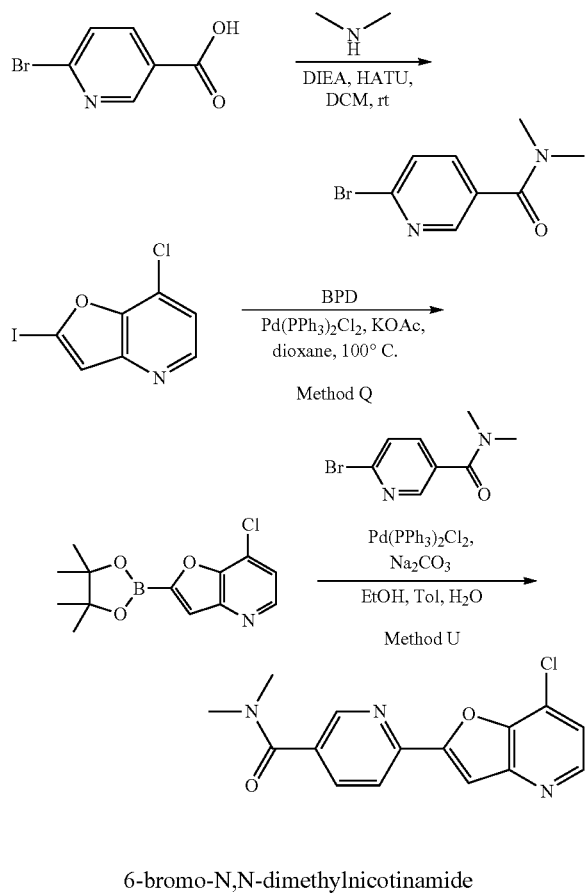

6-bromo-N,N-dimethylnicotinamide

To a solution of 6-bromopyridine-3-carboxylic acid (200 mg, 0.99 mmol) in dicholormethane (5 mL) were added dimethylamine hydrochloride (97 mg, 1.19 mmol), HATU (564 mg, 1.48 mmol) and DIEA (639 mg, 4.94 mmol) at room temperature. The resulting mixture was stirred overnight at room temperature and then was quenched by the addition of water (20 mL). The reaction mixture was extracted with ethyl acetate (50 mL×3). The organic phases were combined, washed with brine and dried over sodium sulfate. The solvent was removed under reduced pressure and the residue was purified by flash chromatography eluting with ethyl acetate in hexane (0% to 50% gradient) to yield 6-bromo-N,N-dimethylpyridine-3-carboxamide as colorless oil (203 mg, 90%). MS: m/z=229.0 [M+H]$^+$.

Method Q

7-chloro-2-(tetramethyl-1,3,2-dioxaborolan-2-yl)furo[3,2-b]pyridine

To a solution of 7-chloro-2-iodofuro[3,2-b]pyridine (270 mg, 0.97 mmol) in dioxane (6 mL) was added 4,4,5,5-tetramethyl-2-(tetramethyl-1,3,2-dioxaborolan-2-yl)-1,3,2-dioxaborolane (313 mg, 1.23 mmol), Pd(dppf)Cl$_2$.CH$_2$Cl$_2$ (95 mg, 0.12 mmol) and potassium acetate (285 mg, 2.90 mmol) at room temperature. The resulting mixture was irradiated with microwave for 3 h at 100° C. After cooling to room temperature, the reaction mixture was concentrated under reduced pressure to yield 7-chloro-2-(tetramethyl-1,3,2-dioxaborolan-2-yl)furo[3,2-b]pyridine, which was used directly in next step without further purification.

Method U

6-(7-chlorofuro[3,2-b]pyridin-2-yl)-N,N-dimethylnicotinamide

To a solution of 7-chloro-2-(tetramethyl-1,3,2-dioxaborolan-2-yl)furo[3,2-b]pyridine prepared above in toluene (20 mL) were added 6-bromo-N,N-dimethylpyridine-3-carboxamide (889 mg, 3.88 mmol), Pd(PPh$_3$)$_2$Cl$_2$ (70 mg, 0.1 mmol), sodium bicarbonate (308 mg, 2.91 mmol), water (1.5 mL) and ethanol (1.5 mL). The resulting mixture was stirred for 2 h at 110° C. The reaction mixture was cooled to room temperature and water (50 mL) was added. The resulting mixture was extracted with ethyl acetate (50 mL×3). The organic phases were combined, washed with brine and dried over sodium sulfate. The solvent was removed under reduced pressure and the residue was purified by flash chromatography eluting with ethyl acetate in hexane (0% to 100% gradient) to yield 6-[7-chlorofuro[3,2-b]pyridin-2-yl]-N,N-dimethylpyridine-3-carboxamide as brown solid (108 mg, 37%). MS: m/z=302.0 [M+H]$^+$.

Intermediate 9: 5-bromo-2-(morpholinomethyl)benzonitrile

5-bromo-2-(bromomethyl)benzonitrile

To a solution of 5-bromo-2-methylbenzonitrile (392 mg, 2.00 mmol) in chloroform (10 mL) were added benzoperoxide (484 mg, 1.89 mmol) and NBS (36 mg, 0.20 mmol). The resulting solution was stirred for 6 h at 60° C. The reaction mixture was cooled to room temperature and the solid that formed were removed by filtration. The filtrate was diluted with water (20 mL) and extracted with ethyl acetate (50 mL×3). The organic phases were combined, washed with brine and dried over sodium sulfate. The solvent was removed under reduced pressure and the residue was purified by flash chromatography eluting with ethyl acetate in hexane (0% to 2% gradient) to yield 5-bromo-2-(bromomethyl)benzonitrile as yellow oil (200 mg, 36%). MS: m/z=274.0 [M+H]$^+$.

5-bromo-2-(morpholinomethyl)benzonitrile

To a solution of 5-bromo-2-(bromomethyl)benzonitrile (318 mg, 1.16 mmol) in methanol (10 mL) were added morpholine (100 mg, 1.15 mmol) and triethylamine (116 mg, 1.15 mmol) at room temperature. The resulting solution was stirred for 8 h at room temperature and then treated with water (20 mL). The resulting mixture was extracted with ethyl acetate (50 mL×3). The organic phases were combined, washed with brine and dried over sodium sulfate. The solvent was removed under reduced pressure to yield 5-bromo-2-(morpholin-4-ylmethyl)benzonitrile as yellow solid (80 mg, 25%). MS: m/z=281.0 [M+H]$^+$.

Intermediate 10:
5-bromo-3-fluoro-2-(morpholinomethyl)benzonitrile

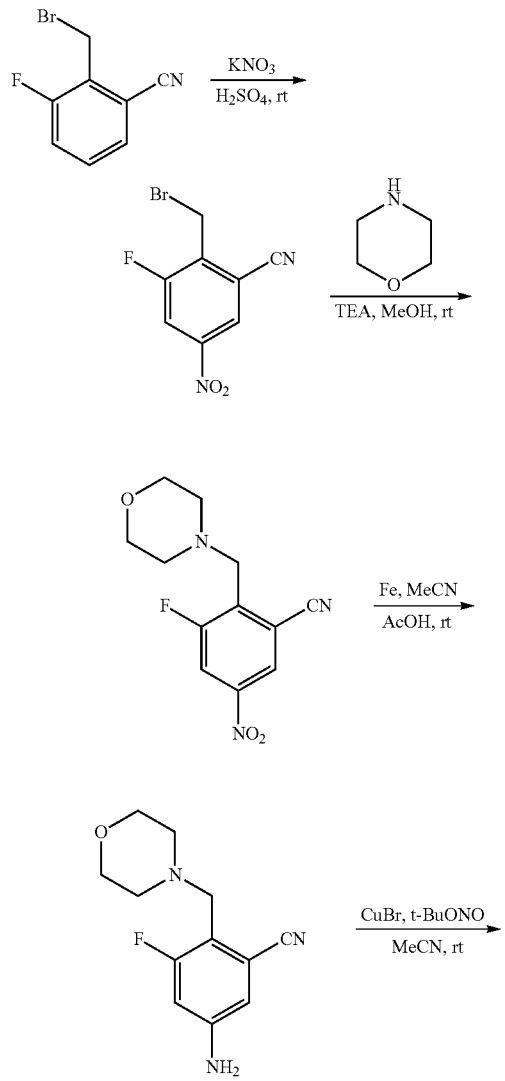

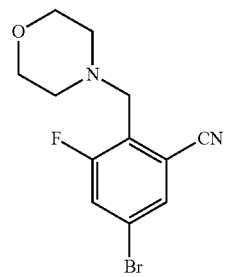

2-(bromomethyl)-3-fluoro-5-nitrobenzonitrile

To a solution of 2-(bromomethyl)-3-fluorobenzonitrile (2.0 g, 9.34 mmol) in sulfuric acid (20 mL) was added potassium nitrate (9.45 g, 93.47 mmol) in portions at 0° C. The resulting solution was stirred for 10 h at room temperature and then water/ice (100 mL) was added. The reaction mixture was extracted with ethyl acetate (100 mL×2). The organic phases were combined, washed with brine and dried over sodium sulfate The solvent was removed under reduced pressure to yield 2-(bromomethyl)-3-fluoro-5-nitrobenzonitrile as yellow solid (1.5 g, 62%).

3-fluoro-2-(morpholinomethyl)-5-nitrobenzonitrile

To a solution of 2-(bromomethyl)-3-fluoro-5-nitrobenzonitrile (160 mg, 0.62 mmol) in methanol (10 mL) were added triethylamine (222 mg, 2.20 mmol) and morpholine (128 mg, 1.47 mmol) at room temperature. The resulting solution was stirred for 8 h at room temperature and then treated with water (10 mL). The resulting mixture was extracted with ethyl acetate (30 mL×3). The organic phases were combined, washed with brine and dried over sodium sulfate. The solvent was removed under reduced pressure and the residue was purified by flash chromatography eluting with ethyl acetate in hexane (0% to 20% gradient) to yield 3-fluoro-2-(morpholin-4-ylmethyl)-5-nitrobenzonitrile as off-white solid (100 mg, 61%).

5-amino-3-fluoro-2-(morpholinomethyl)benzonitrile

To a solution of 3-fluoro-2-(morpholin-4-ylmethyl)-5-nitrobenzonitrile (3.3 g, 12.59 mmol) in acetonitrile (50 mL) was added acetic acid (15.1 g, 251.46 mmol) and iron powder (4.9 g, 88.46 mmol) at room temperature. The resulting mixture was stirred for 2 h at room temperature and the solid that formed were removed by filtration. The filtrate was diluted with water (100 mL) and the pH value of the mixture was adjusted to 9 with saturated sodium carbonate solution. The resulting mixture was extracted with ethyl acetate (200 mL×3) and the organic phases were combined, washed with brine and dried over sodium sulfate. The solvent was removed under reduced pressure to yield 5-amino-3-fluoro-2-(morpholin-4-ylmethyl)benzonitrile as light yellow solid (2 g, 68%). MS: m/z=236.0 [M+H]$^+$.

5-bromo-3-fluoro-2-(morpholinomethyl)benzonitrile

To a solution of 5-amino-3-fluoro-2-(morpholin-4-ylmethyl)benzonitrile (400 mg, 1.70 mmol) in acetonitrile (50 mL) was added copper (I) bromide (1.2 g, 8.50 mmol) and tert-Butyl nitrite (877 mg, 8.50 mmol) in sequence. The resulting mixture was stirred for 8 h at room temperature and then treated with water (30 mL). The resulting solution was extracted with ethyl acetate (50 mL×3). The organic phases were combined, washed with brine and dried over sodium sulfate. The solvent was removed under reduced pressure and the residue was purified by flash chromatography eluting with ethyl acetate in hexane (0% to 2% gradient) to yield 5-bromo-3-fluoro-2-(morpholin-4-ylmethyl)benzonitrile as off-white solid (150 mg, 29%). MS: m/z=299.0 [M+H]⁺.

Intermediate 11: 4-(7-(3-cyano-4,5-difluorophenyl) furo[3,2-b]pyridin-2-yl)-N,N-dimethylbenzamid

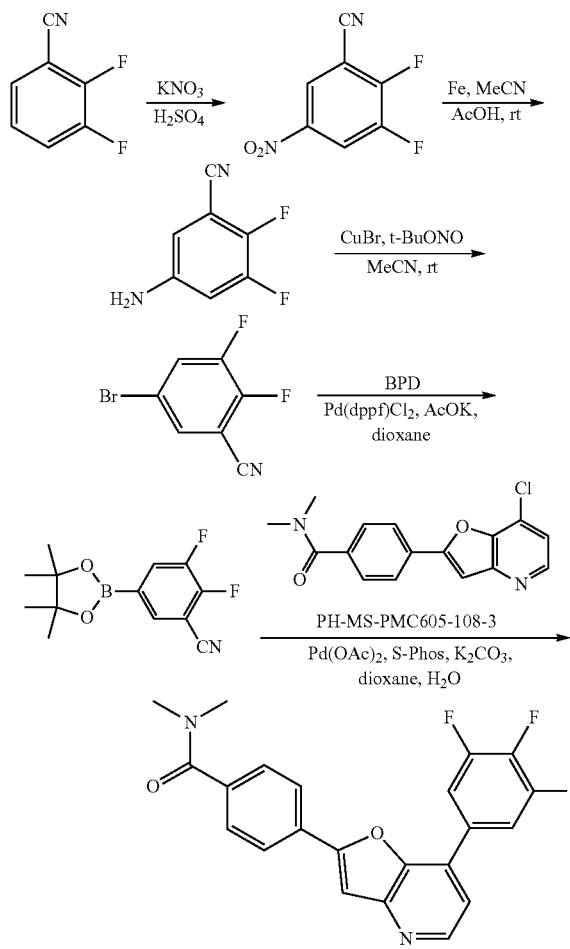

2,3-difluoro-5-nitrobenzonitrile

At 0° C., to a solution of 2,3-difluorobenzonitrile (20.8 g, 149.82 mmol) in sulfuric acid (100 mL) was added potassium nitrate (30.3 g, 299.59 mmol) in portions over 1 h period. The resulting solution was kept stirring for 2 h at 0° C. and then ice water (500 mL) was added. The resulting mixture was extracted with ethyl acetate (300 mL×3). The organic phases were combined, washed with brine and dried over sodium sulfate. The solvent was removed under reduced pressure and the residue was purified by flash chromatography eluting with ethyl acetate in hexane (0% to 10% gradient) to yield 2,3-difluoro-5-nitrobenzonitrile as brown solid (3.6 g, 13%).

5-amino-2,3-difluorobenzonitrile

To a solution of 2,3-difluoro-5-nitrobenzonitrile (920 mg, 5.00 mmol) in acetonitrile (25 mL) was added iron powder (1.96 g, 35.10 mmol) and acetic acid (6.0 g, 99.91 mmol). The resulting mixture was stirred for 2 h at room temperature and the solid that formed in the reaction mixture were removed by filtration. The filtrate was diluted with water (100 mL) and the pH value of the mixture was adjusted to 8 with saturated sodium bicarbonate solution. The resulting mixture was extracted with ethyl acetate (150 mL×2) and the organic phases were combined, washed with brine and dried over sodium sulfate. The solvent was removed under reduced pressure and the residue was purified by a neutral alumina column with ethyl acetate in hexane (0% to 65% gradient) to yield 5-amino-2,3-difluorobenzonitrile as yellow solid (660 mg, 86%).

5-bromo-2,3-difluorobenzonitrile

At room temperature, copper bromide (6.1 g, 42.80 mmol) was added to the solution of 5-amino-2,3-difluorobenzonitrile (660 mg, 4.28 mmol) in acetonitrile (33 mL). The reaction mixture was then added dropwise by a solution of tert-butyl nitrite (4.4 g, 42.77 mmol) in acetonitrile (33 mL) over 1.5 h period at room temperature. The resulting mixture was stirred for 3 h at room temperature and then treated with water (50 mL). The resulting solution was extracted with ethyl acetate (150 mL×3). The organic phases were combined, washed with brine and dried over sodium sulfate. The solvent was removed under reduced pressure and the residue was purified by flash chromatography eluting with ethyl acetate in hexane (0% to 10% gradient) to yield 5-bromo-2,3-difluorobenzonitrile as light yellow solid (660 mg, 71%).

2,3-difluoro-5-(4,4,5,5-tetramethyl-1,3,2-dioxaborolan-2-yl)benzonitrile

To a solution of 5-bromo-2,3-difluorobenzonitrile (140 mg, 0.64 mmol) in 1,4-dioxane (7 mL) were added 4,4,5,5-tetramethyl-2-(tetramethyl-1,3,2-dioxaborolan-2-yl)-1,3,2-dioxaborolane (179.4 mg, 0.71 mmol), Pd(dppf)Cl₂ (26.2 mg, 0.04 mmol) and potassium acetate (126 mg, 1.28 mmol) at room temperature. The resulting mixture was stirred for 2 h at 120° C. and then water (10 mL) was added. The mixture was extracted with ethyl acetate (30 mL×3). The organic phases were combined, washed with brine and dried over sodium sulfate. The solvent was removed under reduced pressure to yield 2,3-difluoro-5-(tetramethyl-1,3,2-dioxaborolan-2-yl)benzonitrile as brown oil (200 mg, crude). MS: m/z=266.0 [M+H]⁺.

4-(7-(3-cyano-4,5-difluorophenyl)furo[3,2-b]pyridin-2-yl)-N,N-dimethylbenzamide

To a solution of 4-[7-chlorofuro[3,2-b]pyridin-2-yl]-N,N-dimethylbenzamide (200 mg, crude) in 1,4-dioxane (12 mL) were added 2,3-difluoro-5-(tetramethyl-1,3,2-dioxaborolan-2-yl)benzonitrile (181 mg, 0.64 mmol), Pd(AcO)₂ (16 mg, 0.06 mmol), SPhos (84 mg, 0.19 mmol), potassium carbonate (283 mg, 1.92 mmol) and water (1 mL) at room temperature. The resulting mixture was stirred for 2 h at 110° C. The reaction mixture was cooled to room temperature and diluted with water (30 mL). The mixture was extracted with ethyl acetate (50 mL×3) and the organic phases were combined, washed with brine and dried over sodium sulfate. The solvent was removed under reduced pressure and the residue was purified by flash chromatography eluting with ethyl acetate in hexane (0% to 10% gradient) to yield 4-[7-(3-cyano-4,5-difluorophenyl)furo[3,2-b]pyridin-2-yl]-N,N-dimethylbenzamide as brown solid (238 mg, 70%). MS: m/z=404.0 [M+H]⁺.

Intermediate 12: 4-(7-(3-cyano-4,5-difluorophenyl)furo[3,2-b]pyridin-2-yl)-3-methoxy-N,N-dimethylbenzamide

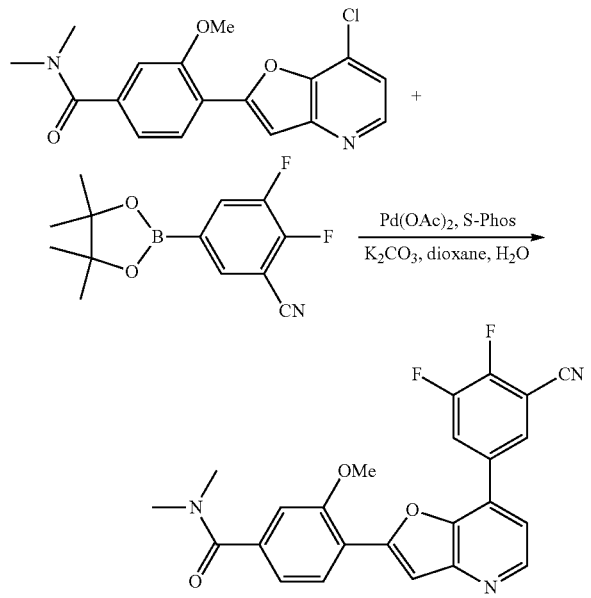

4-(7-(3-cyano-4,5-difluorophenyl)furo[3,2-b]pyridin-2-yl)-3-methoxy-N,N-dimethylbenzamide To a solution of 4-[7-chlorofuro[3,2-b]pyridin-2-yl]-3-methoxy-N,N-dimethylbenzamide (279 mg, 0.84 mmol) in 1,4-dioxane (18 mL) was added 2,3-difluoro-5-(tetramethyl-1,3,2-dioxaborolan-2-yl)benzonitrile (219 mg, 0.83 mmol), Pd(OAc)₂ (20.6 mg, 0.09 mmol), S-Phos (108 mg, 0.26 mmol), water (1.2 mL) and potassium carbonate (361 mg, 2.61 mmol) at room temperature. The resulting mixture was stirred for 3 h at 110° C. The reaction mixture was cooled to room temperature, concentrated under reduced pressure and the residue was purified by flash chromatography eluting with ethyl acetate in hexane (0% to 100% gradient) to yield 4-[7-(3-cyano-4,5-difluorophenyl)furo[3,2-b]pyridin-2-yl]-3-methoxy-N,N-dimethylbenzamide as yellow solid (220 mg, 50%). MS: m/z=434.0 [M+H]⁺.

Intermediate 13: 4-(7-chlorofuro[3,2-b]pyridin-2-yl)-3-fluoro-N,N-dimethylbenzamide

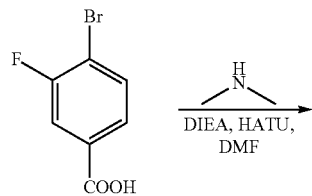

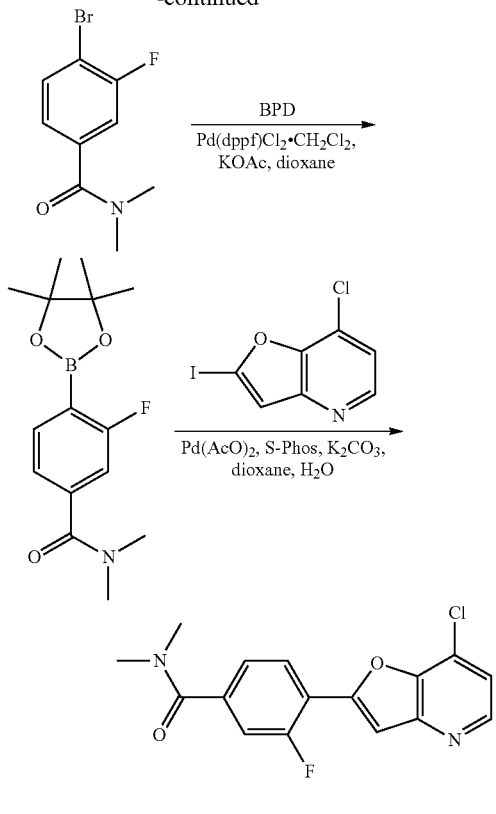

4-bromo-3-fluoro-N,N-dimethylbenzamide

To a solution of 4-bromo-3-fluorobenzoic acid (1.0 g, 4.57 mmol) in DMF (15 mL) were added dimethylamine (440 mg, 9.76 mmol), DIEA (1.7 g, 13.15 mmol) and HATU (2.0 g, 5.26 mmol) at room temperature. The resulting solution was stirred for 18 h at 50° C. and diluted with water (60 mL). The mixture was extracted with ethyl acetate (30 mL×3) and the organic phases were combined, washed with brine and dried over sodium sulfate. The solvent was removed under reduced pressure and the residue was purified by flash chromatography eluting with ethyl acetate in hexane (0% to 30% gradient) to yield 4-bromo-3-fluoro-N,N-dimethylbenzamide as yellow oil (800 mg, 71%). MS: m/z=246.0 [M+H]⁺.

3-fluoro-N,N-dimethyl-4-(4,4,5,5-tetramethyl-1,3,2-dioxaborolan-2-yl)benzamide

To a solution of 4-bromo-3-fluoro-N,N-dimethylbenzamide (2.5 g, 10.16 mmol) in 1,4-dioxane (50 mL) were added 4,4,5,5-tetramethyl-2-(tetramethyl-1,3,2-dioxaborolan-2-yl)-1,3,2-dioxaborolane (2.6 g, 10.16 mmol), potassium acetate (2.0 g, 20.28 mmol) and Pd(dppf)Cl₂ (370 mg, 0.51 mmol). The resulting mixture was stirred for 18 h at 100° C. The reaction mixture was cooled to room temperature, concentrated under reduced pressure and the resulting residue was purified by flash chromatography eluting with ethyl acetate in hexane (0% to 100% gradient) to yield 3-fluoro-N,N-dimethyl-4-(tetramethyl-1,3,2-dioxaborolan-2-yl)benzamide as brown solid (2.6 g, 87%). MS: m/z=294.0 [M+H]⁺.

4-(7-chlorofuro[3,2-b]pyridin-2-yl)-3-fluoro-N,N-dimethylbenzamide

To a solution of 3-fluoro-N,N-dimethyl-4-(tetramethyl-1,3,2-dioxaborolan-2-yl)benzamide (105 mg, 0.36 mmol) in 1,4-dioxane (2 mL) were added 7-chloro-2-iodofuro[3,2-b]pyridine (100 mg, 0.36 mmol), S-phos (20 mg, 0.05 mmol), Pd(OAc)$_2$ (20 mg, 0.09 mmol), potassium carbonate (150 mg, 1.09 mmol) and water (0.25 mL) at room temperature. The resulting mixture was stirred for 3 h at 100° C. in an oil bath. The reaction mixture was cooled to room temperature, concentrated under reduced pressure and the residue was purified by flash chromatography eluting with ethyl acetate in hexane (0% to 100% gradient) to yield 4-[7-chlorofuro[3,2-b]pyridin-2-yl]-3-fluoro-N,N-dimethylbenzamide as yellow solid (80 mg, 70%). MS: m/z=319.0 [M+H]$^+$.

Intermediate 14: 4-(7-(3-cyano-4-(tetrahydro-2H-pyran-4-yloxy)phenyl)furo[3,2-b]pyridin-2-yl)-3-methoxybenzoic acid

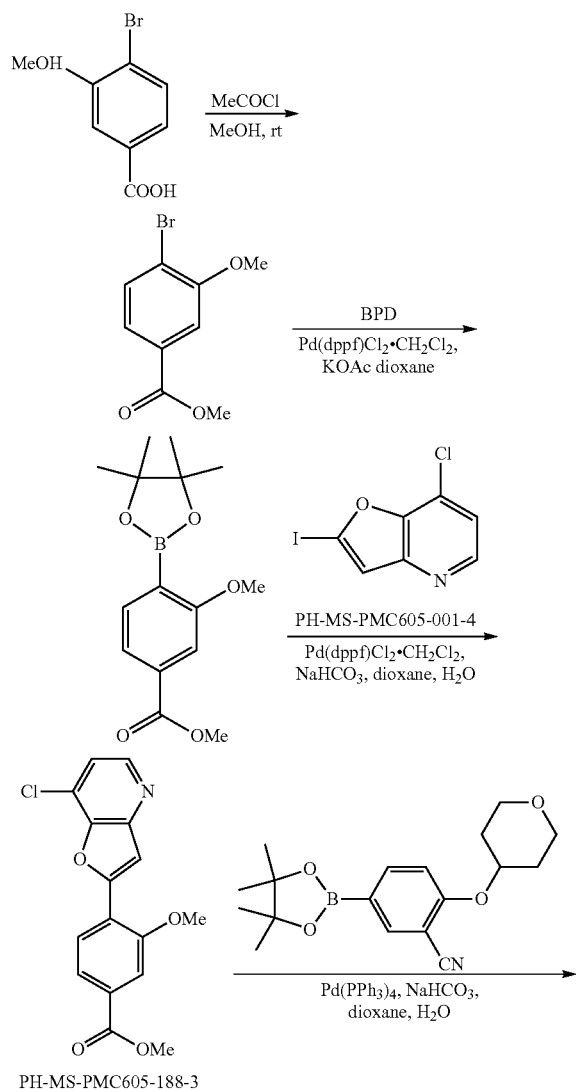

PH-MS-PMC605-188-3

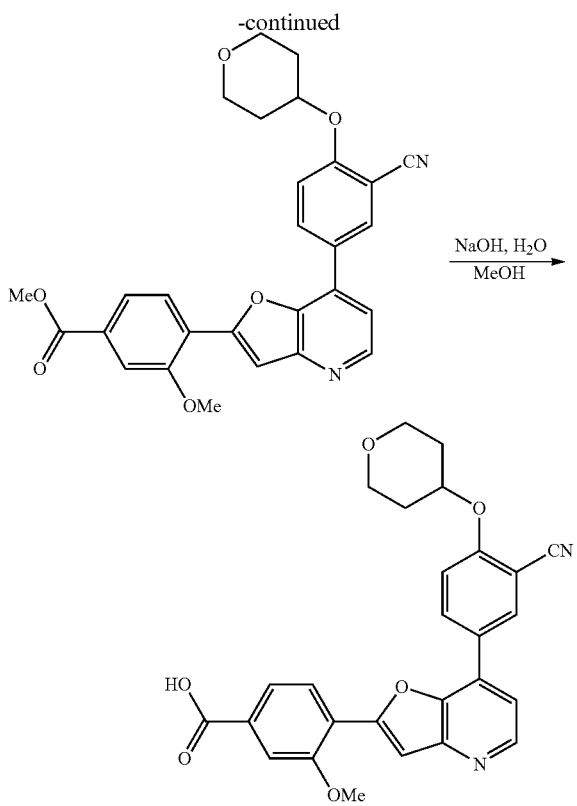

Methyl 4-bromo-3-methoxybenzoate

To a solution of 4-bromo-3-methoxybenzoic acid (10.0 g, 43.28 mmol) in methanol (400 mL) was added acetyl chloride (19 mL, 266.25 mmol) dropwise at 0° C. The resulting solution was then stirred for 16 h at room temperature. The reaction mixture was concentrated under reduced pressure and the residue was purified by flash chromatography eluting with ethyl aceate in hexane (0% to 5% gradient) to yield methyl 4-bromo-3-methoxybenzoate as white solid (7.3 g, 69%). MS: m/z=245.0 [M+H]$^+$.

methyl 3-methoxy-4-(4,4,5,5-tetramethyl-1,3,2-dioxaborolan-2-yl)benzoate

To a solution of methyl 4-bromo-3-methoxybenzoate (7.3 g, 29.79 mmol) in dioxane (150 mL) was added 4,4,5,5-tetramethyl-2-(tetramethyl-1,3,2-dioxaborolan-2-yl)-1,3,2-dioxaborolane (8.3 g, 32.69 mmol), Pd(dppf)Cl$_2$.CH$_2$Cl$_2$ (2.4 g, 2.94 mmol) and potassium acetate (8.76 g, 89.26 mmol) at room temperature. The reaction mixture was stirred for 16 h at 80° C., cooled to room temperature, and treated with water (100 mL). The resulting solution was extracted with ethyl acetate (250 mL×3). The organic phases were combined, washed with brine and dried over sodium sulfate. The solvent was removed under reduced pressure and the residue was purified by flash chromatography eluting with ethyl acetate in hexane (0% to 10% gradient) to yield methyl 3-methoxy-4-(tetramethyl-1,3,2-dioxaborolan-2-yl)benzoate as yellow oil (6.0 g, 69%). MS: m/z=293.0 [M+H]$^+$.

methyl 4-(7-chlorofuro[3,2-b]pyridin-2-yl)-3-methoxybenzoate

To a solution of methyl 3-methoxy-4-(tetramethyl-1,3,2-dioxaborolan-2-yl)benzoate (5.0 g, 17.12 mmol) in dioxane (210 mL) were added 7-chloro-2-iodofuro[3,2-b]pyridine (4.7 g, 16.82 mmol), Pd(dppf)Cl$_2$.CH$_2$Cl$_2$ (1.4 g, 1.71 mmol), sodium bicarbonate (1.5 g, 17.86 mmol) and water (70 mL) at room temperature. The reaction mixture was stirred for 10 h at 100° C. After cooling to room temperature, it was quenched by the addition of water (150 mL). The resulting solution was extracted with ethyl acetate (250 mL×3). The organic phases were combined, washed with brine and dried over sodium sulfate. The solvent was removed under reduced pressure and the residue was purified by flash chromatography eluting with methanol in dichloromethane (0% to 10% gradient) to yield methyl 4-[7-chlorofuro[3,2-b]pyridin-2-yl]-3-methoxybenzoate as brown solid (4.3 g, 79%). MS: m/z=318.0 [M+H]$^+$.

Methyl 4-(7-(3-cyano-4-(tetrahydro-2H-pyran-4-yloxy)phenyl)furo[3,2-b]pyridin-2-yl)-3-methoxy benzoate To a solution of methyl 4-[7-chlorofuro[3,2-b]pyridin-2-yl]-3-methoxybenzoate (1.2 g, 3.62 mmol) in dioxane (100 mL) were added 2-(oxan-4-yloxy)-5-(tetramethyl-1,3,2-dioxaborolan-2-yl)benzonitrile (1.2 g, 3.65 mmol), Pd(PPh$_3$)$_4$ 4-(7-(3-cyano-4-(tetrahydro-2H-pyran-4-yloxy)phenyl)furo[3,2-b]pyridin-2-yl)-3-methoxybenzoic acid At room temperature, to a solution of methyl 4-[7-[3-cyano-4-(oxan-4-yloxy)phenyl]furo[3,2-b]pyridin-2-yl]-3-methoxybenzoate (1.3 g, 2.68 mmol) in methanol (80 mL) was added a solution of sodium hydroxide (1.1 g, 27.50 mmol) in water (27 mL) at room temperature. The resulting solution was stirred for 16 h at room temperature and then concentrated under reduced pressure. The residue was diluted with water (50 mL) and the pH value of the mixture was adjusted to 2 with hydrochloric acid solution (2 M). The precipitate that formed were collected by filtration and dried in oven under vacuum to yield 4-[7-[3-cyano-4-(oxan-4-yloxy)phenyl]furo[3,2-b]pyridin-2-yl]-3-methoxybenzoic acid as yellow solid (1.2 g, 86%). MS: m/z=471.0 [M+H]$^+$.

Intermediate 15: 4-(7-(3-cyano-4-(tetrahydro-2H-pyran-4-ylamino)phenyl)furo[3,2-b]pyridin-2-yl)-3-methoxybenzoic acid

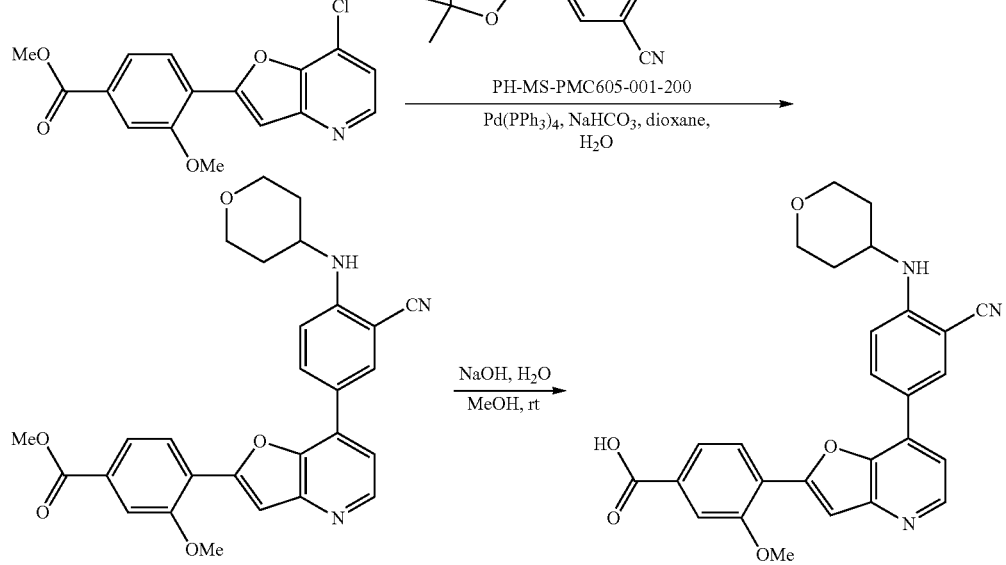

(420 mg, 0.36 mmol), sodium bicarbonate (300 mg, 3.57 mmol) and water (33 mL) at room temperature. The resulting mixture was stirred for 2 h at 100° C., cooled to room temperature, and treated with water (50 mL). The mixture was extracted with ethyl acetate (150 mL×3). The organic phases were combined, washed with brine and dried over sodium sulfate. The solvent was removed under reduced pressure and the residue was purified by flash chromatography eluting with ethyl acetate in hexane (0% to 100% gradient) to yield methyl 4-[7-[3-cyano-4-(oxan-4-yloxy) phenyl]furo[3,2-b]pyridin-2-yl]-3-methoxybenzoate as yellow solid (1.4 g, 80%). MS: m/z=485.0 [M+H]$^+$.

methyl 4-(7-(3-cyano-4-(tetrahydro-2H-pyran-4-ylamino)phenyl)furo[3,2-b]pyridin-2-yl)-3-methoxybenzoate To a solution of methyl 4-[7-chlorofuro[3,2-b]pyridin-2-yl]-3-methoxybenzoate (700 mg, 2.20 mmol) in DMF (18 mL) were added 2-[(oxan-4-yl)amino]-5-(tetramethyl-1,3,2-dioxaborolan-2-yl)benzonitrile (724 mg, 2.21 mmol), potassium acetate (418 mg, 4.26 mmol), Pd(PCy$_3$)$_2$Cl$_2$ (81 mg, 0.11 mmol) and water (2 mL) at room temperature. The resulting mixture was stirred for 16 h at 100° C., cooled to room temperature, and treated water (20 mL). The mixture was extracted with ethyl acetate (30 mL×3). The organic phases were combined, washed with brine and dried over sodium sulfate. The solvent was removed under reduced pressure and the residue was purified by flash chromatography eluting with ethyl acetate in hexane (0% to 10% gradient) to yield methyl 4-(7-[3-cyano-4-[(oxan-4-yl)amino]phenyl]furo[3,2-b]pyridin-2-yl)-3-methoxybenzoate as brown oil (350 mg, 33%). MS: m/z=484.0 [M+H]$^+$.

4-(7-(3-cyano-4-(tetrahydro-2H-pyran-4-ylamino)phenyl)furo[3,2-b]pyridin-2-yl)-3-methoxybenzoic acid To a solution of methyl 4-(7-[3-cyano-4-[(oxan-4-yl)amino]phenyl]furo[3,2-b]pyridin-2-yl)-3-methoxybenzoate (300 mg, 0.62 mmol) in methanol (12 mL) was added a solution of sodium hydroxide (244 mg, 6.10 mmol) in water (2 mL) at room temperature. The resulting mixture was stirred for 16 h at room temperature, concentrated under reduced pressure, and the resulting residue was diluted with water (5 mL). The pH value of the mixture was adjusted to 2 with hydrochloric acid solution (2 M). The precipitate that formed was collected by filtration and dried in oven under vacuum to yield 4-(7-[3-cyano-4-[(oxan-4-yl)amino]phenyl]furo[3,2-b]pyridin-2-yl)-3-methoxybenzoic acid as yellow solid (160 mg, 55%). MS: m/z=470.0 [M+H]$^+$.

Intermediate 16:
6,7-dichloro-2-iodofuro[3,2-b]pyridine

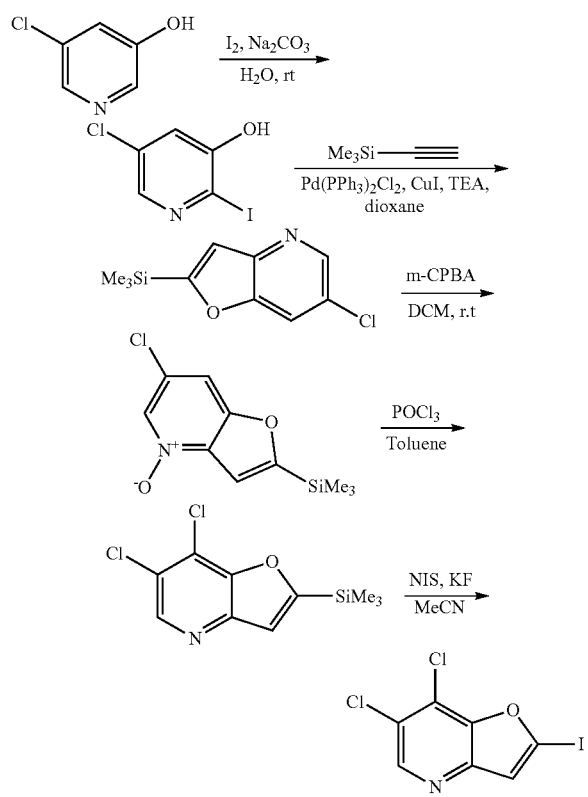

5-chloro-2-iodopyridin-3-ol

To a solution of sodium carbonate (1.6 g, 15.47 mmol) in water (15 mL) was added 5-chloropyridin-3-ol (1.0 g, 7.72 mmol) and I2 (2.0 g, 7.72 mmol) at room temperature. The resulting mixture was stirred for 5 h at room temperature and then treated with a hydrochloric acid solution (30 mL, 2 M). The precipitate that formed was collected by filtration and re-dissolved in ethyl acetate (300 mL). The mixture was washed with brine (20 mL×2) and the organic phase was dried over sodium sulfate. The solvent was removed under reduced pressure to yield 5-chloro-2-iodopyridin-3-ol as yellow solid (1.9 g, 96%). MS: m/z=256.0 [M+H]$^+$.

6-chloro-2-(trimethylsilyl)furo[3,2-b]pyridine

To a solution of 5-chloro-2-iodopyridin-3-ol (800 mg, 3.13 mmol) in dioxane (12.8 mL, 151.1 mmol) was added ethynyltrimethylsilane (667 mg, 6.79 mmol), Pd(PPh$_3$)$_2$Cl$_2$ (238 mg, 0.34 mmol), CuI (8 mg, 0.04 mmol) and triethylamine (1.7 g, 16.80 mmol) at room temperature. The resulting mixture was stirred for 6 h at 120° C., cooled to room temperature, and treated with water (50 mL). The resulting mixture was extracted with ethyl acetate (150 mL×3). The organic phases were combined, washed with brine and dried over sodium sulfate. The solvent was removed under reduced pressure and the residue was purified by flash chromatography eluting with ethyl acetate in hexane (0% to 5% gradient) to yield 6-chloro-2-(trimethylsilyl)furo[3,2-b]pyridine as brown solid (580 mg, 82%). MS: m/z=226.0 [M+H]$^+$.

6-chloro-2-(trimethylsilyl)furo[3,2-b]pyridine 4-oxide

At 0° C., to a solution of 6-chloro-2-(trimethylsilyl)furo[3,2-b]pyridine (5.5 g, 24.36 mmol, 1.00 equiv) in dichloromethane (260 mL) was added m-CPBA (6.3 g, 36.51 mmol) in portions. The resulting solution was stirred for 30 min at 0° C., then warmed up to room temperature and stirred for another 16 h at room temperature. The reaction mixture was treated with water (100 mL) and The pH value of the mixture was adjusted to 8 with saturated sodium bicarbonate. The resulting mixture was then extracted with dichloromethane (800 mL×2) and the organic phases were combined, washed with brine and dried over sodium sulfate. The solvent was removed under reduced pressure to yield 6-chloro-2-(trimethylsilyl)furo[3,2-b]pyridin-4-ium-4-olate as brown oil (7.0 g, crude).

6,7-dichloro-2-(trimethylsilyl)furo[3,2-b]pyridine

To a solution of 6-chloro-2-(trimethylsilyl)furo[3,2-b]pyridin-4-ium-4-olate (7.0 g, crude) in toluene (200 mL) was added POCl$_3$ (6.3 g, 41.09 mmol) at room temperature. The resulting solution was then stirred for 3 h at 95° C. After cooling to room temperature, the reaction mixture was concentrated under reduced pressure and the resulting residue was diluted by water (200 mL). The pH value of the mixture was adjusted to 9 with saturated sodium carbonate solution. The resulting mixture was then extracted with dichloromethane (200 mL×3). The solvent was removed under reduced pressure and the residue was purified by flash chromatography eluting with ethyl acetate in hexane (0% to 2% gradient) to yield 6,7-dichloro-2-(trimethylsilyl)furo[3,2-b]pyridine as brown oil (3 g, 48% for 2 steps). MS: m/z=260.0 [M+H]$^+$.

6,7-dichloro-2-iodofuro[3,2-b]pyridine

To a solution of 6,7-dichloro-2-(trimethylsilyl)furo[3,2-b]pyridine (600 mg, 2.3 mmol) in CH$_3$CN (80 mL) were added potassium fluoride (380 mg, 6.54 mmol) and NIS (5.2 g, 23 mmol) at room temperature. The resulting solution was stirred for 3 h at 55° C. The reaction mixture was cooled to room temperature and treated with NaHSO₃ solution (100 mL, 4 M). The resulting mixture was extracted with ethyl acetate (50 mL×3). The organic phases were combined, washed with brine and dried over sodium sulfate. The solvent was removed under reduced pressure to yield 6,7-dichloro-2-iodofuro[3,2-b]pyridine as white solid (500 mg, 51%). MS: m/z=314.0 [M+H]⁺.

Intermediate 17: 7-chloro-2-iodo-6-methylfuro[3,2-b]pyridine

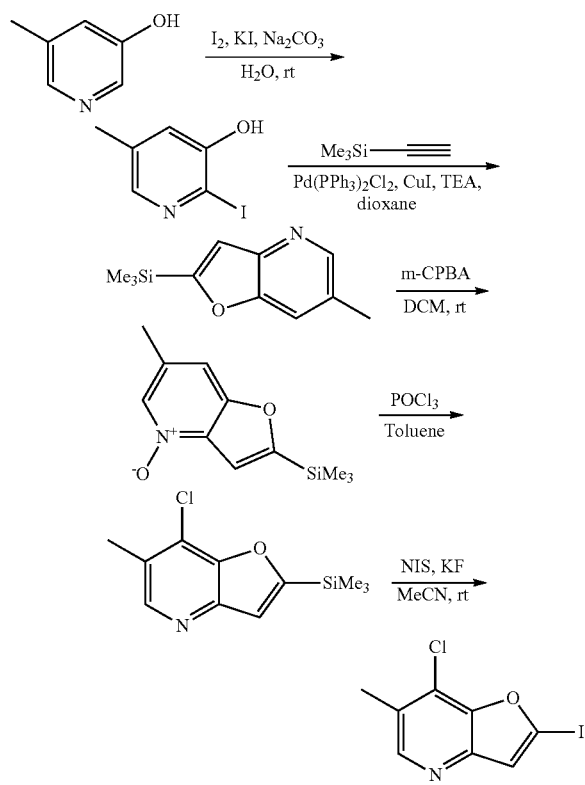

2-iodo-5-methylpyridin-3-ol

To a solution of sodium carbonate (7.0 g, 65.95 mmol) in water (200 mL) was added 5-methylpyridin-3-ol (3.42 g, 31.34 mmol) at room temperature. To the reaction mixture was added a solution of potassium iodide (5.21 g, 31.36 mmol) and iodine (7.95 g, 31.33 mmol) in water (200 mL) dropwise over 1.2 h period. The resulting solution was stirred for 2 h at room temperature and then the pH value of the reaction mixture was adjusted to 1 with hydrochloric acid solution (1 M). The solid that formed was removed by filtration. The pH value of the filtrate was adjusted to 9 with saturated sodium carbonate solution. The resulting solution was extracted with ethyl acetate (200 mL×3) and the organic phases were combined, washed with brine and dried over sodium sulfate. The solvent was removed under reduced pressure to yield 2-iodo-5-methylpyridin-3-ol as yellow solid (5.0 g, 68%). MS: m/z=236.0 [M+H]⁺.

6-methyl-2-(trimethylsilyl)furo[3,2-b]pyridine

To a solution of sodium 2-iodo-5-methylpyridin-3-ol (7.2 g, 30.64 mmol) in dioxane (130 mL) was added ethynyltrimethylsilane (6.4 g, 64.71 mmol), Pd(PPh₃)₂Cl₂ (3.4 g, 4.85 mmol), copper iodide (616 mg, 3.23 mmol) and triethylamine (16.2 g, 160.73 mmol) at room temperature. The resulting mixture was stirred for 5 h at 120° C. The reaction mixture was cooled to room temperature and treated with water (100 mL). The resulting mixture was extracted with ethyl acetate (200 mL×3). The organic phases were combined, washed with brine and dried over sodium sulfate. The solvent was removed under reduced pressure and the residue was purified by flash chromatography eluting with ethyl acetate in hexane (0% to 10% gradient) to yield 6-methyl-2-(trimethylsilyl)furo[3,2-b]pyridine as brown oil (4.0 g, 57%). MS: m/z=206.0 [M+H]⁺.

6-methyl-2-(trimethylsilyl)furo[3,2-b]pyridine 4-oxide

At 0° C., to a solution of 6-methyl-2-(trimethylsilyl)furo[3,2-b]pyridine (3.0 g, 14.61 mmol) in dichloromethane (30 mL) was added m-CPBA (5.0 g, 28.97 mmol) in portions. The resulting solution was stirred for 30 min at 0° C., then warmed up to room temperature and stirred for another 5 h at room temperature. The solid that formed in the reaction mixture were removed by filtration and the filtrate was washed with saturated sodium bicarbonate (20 mL×3). The organic phase was dried over anhydrous sodium sulfate and concentrated under reduced pressure to yield 6-methyl-2-(trimethylsilyl)furo[3,2-b]pyridin-4-ium-4-olate as brown oil (4.3 g, crude). MS: m/z=222.0 [M+H]⁺.

7-chloro-6-methyl-2-(trimethylsilyl)furo[3,2-b]pyridine

To a solution of 6-methyl-2-(trimethylsilyl)furo[3,2-b]pyridin-4-ium-4-olate (4.3 g, crude) in toluene (40 mL) was added POCl₃ (2.7 g, 17.53 mmol) dropwise at 0-5° C. The resulting mixture was stirred for 3 h at 60° C. The reaction mixture was cooled to room temperature and then treated with water (50 mL). The resulting solution was extracted with ethyl acetate (150 mL×3). The organic phases were combined, washed with brine and dried over sodium sulfate. The solvent was removed under reduced pressure and the residue was purified by flash chromatography eluting with ethyl acetate in hexane (0% to 10% gradient) to yield 7-chloro-6-methyl-2-(trimethylsilyl)furo[3,2-b]pyridine as brown oil (800 mg, 23% for 2 steps). MS: m/z=240.0 [M+H]⁺.

7-chloro-2-iodo-6-methylfuro[3,2-b]pyridine

To a solution of 7-chloro-6-methyl-2-(trimethylsilyl)furo[3,2-b]pyridine (860 mg, 3.59 mmol) in acetonitrile (20 mL) were added potassium fluoride (228 mg, 3.92 mmol) and NIS (8.9 g, 39.69 mmol). The resulting solution was stirred for 3 h at 55° C. The reaction mixture was cooled to room temperature and treated with NaHSO₃ (20 mL, 4M). The solid that formed was removed by filtration and the filtrate was concentrated under reduced pressure to yield 7-chloro- 2-iodo-6-methylfuro[3,2-b]pyridine as yellow solid (800 mg, 68%). MS: m/z=294.0 [M+H]+.

Intermediate 18: 5-(7-chlorofuro[3,2-b]pyridin-2-yl)-6-methoxy-N,N-dimethylpicolinamide

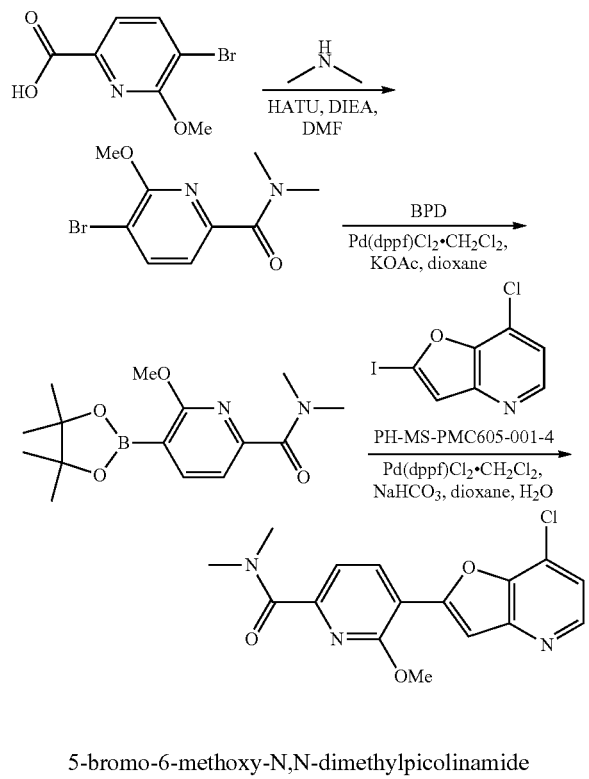

5-bromo-6-methoxy-N,N-dimethylpicolinamide

To a solution of 5-bromo-6-methoxypyridine-2-carboxylic acid (1.0 g, 4.31 mmol) in DMF (10 mL) were added dimethylamine (1.5 g, 33.27 mmol), HATU (2.0 g, 5.13 mmol) and DIEA (1.7 g, 12.77 mmol) at room temperature. The resulting solution was stirred for 2 h at 100° C. The reaction mixture was cooled to room temperature and treated with water (50 mL). The resulting mixture was extracted with ethyl acetate (100 mL×3). The organic phases were combined, washed with brine and dried over sodium sulfate. The solvent was removed under reduced pressure to yield 5-bromo-6-methoxy-N,N-dimethylpyridine-2-carboxamide as black oil (1.2 g, crude). MS: m/z=259.0 [M+H]+.

6-methoxy-N,N-dimethyl-5-(4,4,5,5-tetramethyl-1,3,2-dioxaborolan-2-yl)picolinamide To a solution of 5-bromo-6-methoxy-N,N-dimethylpyridine-2-carboxamide (600 mg, crude) in dioxane (8 mL) were added 4,4,5,5-tetramethyl-2-(tetramethyl-1,3,2-dioxaborolan-2-yl)-1,3,2-dioxaborolane (822 mg, 0.95 mmol), Pd(dppf)Cl₂.CH₂Cl₂ (777 mg, 0.95 mmol) and potassium acetate (220 mg, 2.25 mmol) at room temperature. The resulting mixture was stirred for 2 h at 100° C. After the reaction mixture was cooled to room temperature, the solid that formed were removed by filtration and the filtrate was concentrated under reduced pressure to yield [6-(dimethylcarbamoyl)-2-methoxypyridin-3-yl]boronic acid as brown oil (2.4 g, crude). MS: m/z=307.0 [M+H]+.

5-(7-chlorofuro[3,2-b]pyridin-2-yl)-6-methoxy-N,N-dimethylpicolinamide

To a solution of [6-(dimethylcarbamoyl)-2-methoxypyridin-3-yl]boronic acid (2400 mg, crude) in dioxane (10 mL), were added 7-chloro-2-iodofuro[3,2-b]pyridine (1400 mg, 5 mmol), Pd(dppf)Cl₂.CH₂Cl₂ (408 mg, 0.5 mmol), sodium bicarbonate (116 mg, 1.1 mmol) and water (1 mL) at room temperature. The resulting mixture was stirred for 2 h at 100° C. After the reaction mixture was cooled to room temperature, the solid that formed were removed by filtration the filtrate was concentrated under reduced pressure. The resulting residue was purified by flash chromatography eluting with ethyl acetate in hexane (0% to 1% gradient) to yield 5-[7-chlorofuro[3,2-b]pyridin-2-yl]-6-methoxy-N,N-dimethylpyridine-2-carboxamide as brown solid (200 mg, 28% for 3 steps). MS: m/z=332.0 [M+H]+.

EXAMPLES

Example 1: Synthesis of 5-(2-cyclohexyl-2-fluoro-ethyl)-5H-imidazo[5,1-a]isoindole hydrochloride (194)

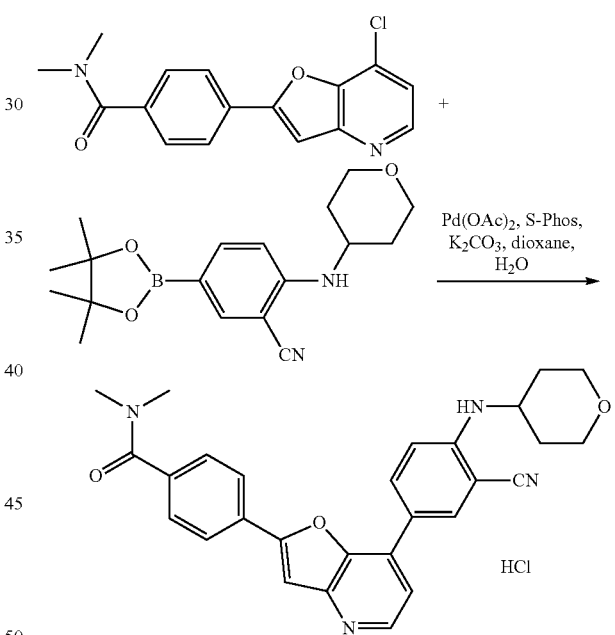

4-(7-(3-cyano-4-(tetrahydro-2H-pyran-4-ylamino) phenyl)furo[3,2-b]pyridin-2-yl)-N,N-dimethylbenzamide hydrochloride To a solution of 4-[7-chlorofuro[3,2-b]pyridin-2-yl]-N,N-dimethylbenzamide (206 mg, 0.68 mmol) in 1,4-dioxane (16 ml) was added 2-[(oxan-4-yl)amino]-5-(tetramethyl-1,3,2-dioxaborolan-2-yl)benzonitrile (410 mg, 1.25 mmol), Pd(OAc)₂ (5.1 mg, 0.02 mmol), S-Phos (28 mg, 0.08 mmol), potassium carbonate (189 mg, 1.37 mmol) and water (2 mL) at room temperature. The resulting mixture was stirred for 5 h at 100° C. The reaction mixture was cooled to room temperature and treated with water (50 mL). The resulting mixture was extracted with ethyl acetate (50 mL×2). The organic phases were combined, washed with brine and dried over sodium sulfate. The solvent was removed under reduced pressure and the resulting residue was purified by prep-HPLC under the following conditions: column, Gemini-NX C18, 21.2×150 mm 5 um; mobile phase, acetonitrile in water (with 0.02% HCl), 15% to 50% gradient in 10 min; detector, UV 254/220 nm. 4-(7-(3-cyano-4-(methyl(tetrahydro-2H-pyran-4-yl)amino)phenyl)furo[3,2-b]pyridin-2-yl)-N,N-dimethylbenzamide hydrochloride was obtained as brown solid (50 mg, 8%). HPLC: 98.4% purity, RT=1.03 min. MS: m/z=467.0 [M+H]$^+$. $^1$H NMR (300 MHz, DMSO, ppm) δ 8.67 (br s, 1H), 8.50-8.35 (m, 2H), 8.20 (d, J=7.8 Hz, 2H), 8.00 (br s, 1H), 7.95 (s, 1H), 7.65 (d, J=7.2 Hz, 2H), 7.26 (d, J=8.7 Hz, 1H), 6.67 (s, 1H), 3.94-3.75 (m, 3H), 3.55-3.40 (m, 2H), 3.01 (s, 3H), 2.96 (s, 3H), 1.95-1.80 (m, 2H), 1.79-1.58 (m, 2H).

Example 2: 4-(7-(3-cyano-4-(methyl(tetrahydro-2H-pyran-4-yl)amino)phenyl)furo[3,2-b]pyridin-2-yl)-N,N-dimethylbenzamide hydrochloride (275)

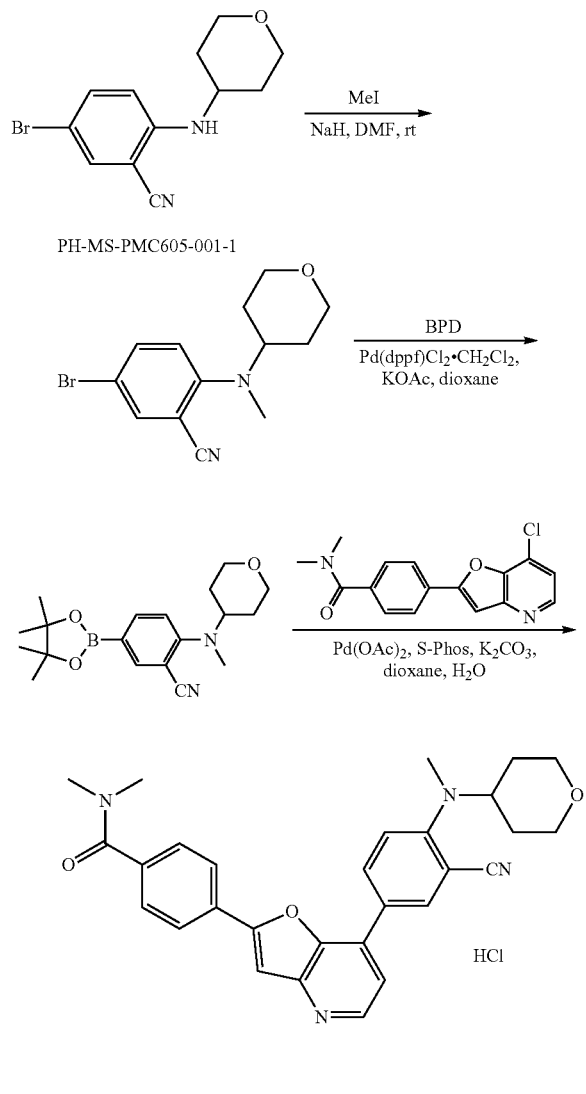

5-bromo-2-(methyl(tetrahydro-2H-pyran-4-yl)amino)benzonitrile

To a suspension of sodium hydride (60% in oil, 182 mg, 4.46 mmol) in DMF (10 mL) was added 5-bromo-2-[(oxan-4-yl)amino]benzonitrile (500 mg, 1.78 mmol) at 0° C. The resulting mixture was stirred at 0° C. for 10 min, and then added iodomethane (303 mg, 2.13 mmol). The reaction mixture was then stirred for 16 h at room temperature and then treated with ice/water (2 mL). The mixture was extracted with ethyl acetate (30 mL×3). The organic phases were combined, washed with brine and dried over sodium sulfate. The solvent was removed under reduced pressure to yield 5-bromo-2-[methyl(oxan-4-yl)amino]benzonitrile as brown oil (570 mg, crude). MS: m/z=295.0 [M+H]$^+$.

2-(methyl(tetrahydro-2H-pyran-4-yl)amino)-5-(4,4,5,5-tetramethyl-1,3,2-dioxaborolan-2-yl)benzonitrile To a solution of 5-bromo-2-[methyl(oxan-4-yl)amino]benzonitrile (570 mg, crude) in 1,4-dioxane (18 mL) were added 4,4,5,5-tetramethyl-2-(tetramethyl-1,3,2-dioxaborolan-2-yl)-1,3,2-dioxaborolane (537 mg, 2.12 mmol), Pd(dppf)Cl$_2$CH$_2$Cl$_2$ (79 mg, 0.10 mmol) and potassium acetate (379 mg, 3.86 mmol) at room temperature. The resulting mixture was stirred for 4 h at 100° C., cooled to room temperature, and treated with water (30 mL). The resulting mixture was extracted with ethyl acetate (50 mL×3). The organic phases were combined, washed with brine and dried over sodium sulfate. The solvent was removed under reduced pressure to yield 2-[methyl(oxan-4-yl)amino]-5-(tetramethyl-1,3,2-dioxaborolan-2-yl)benzonitrile as brown solid (790 mg, crude). MS: m/z=343.0 [M+H]$^+$.

4-(7-(3-cyano-4-(methyl(tetrahydro-2H-pyran-4-yl)amino)phenyl)furo[3,2-b]pyridin-2-yl)-N,N-dimethylbenzamide hydrochloride To a solution of 4-[7-chlorofuro[3,2-b]pyridin-2-yl]-N,N-dimethylbenzamide (132 mg, crude) in 1,4-dioxane (8 mL) was added 2-[methyl(oxan-4-yl)amino]-5-(tetramethyl-1,3,2-dioxaborolan-2-yl)benzonitrile (180 mg, 0.53 mmol), Pd(OAc)$_2$ (5.0 mg, 0.02 mmol), S-Phos (10 mg, 0.02 mmol), potassium carbonate (182 mg, 1.31 mmol) and water (1 mL) at room temperature. The resulting mixture was stirred for 2 h at 100° C. in an oil bath, cooled to room temperature, and treated with water (10 mL). The resulting mixture was extracted with ethyl acetate (50 mL×2). The solvent was removed under reduced pressure and the residue was purified by prep-HPLC under the following conditions: column, Gemini-NX C18, 21.2×150 mm 5 um; mobile phase, acetonitrile in water (with 0.02% HCl), 15% to 50% gradient in 10 min; detector, UV 254/220 nm. 4-(7-(3-cyano-4-(methyl(tetrahydro-2H-pyran-4-yl)amino)phenyl)furo[3,2-b]pyridin-2-yl)-N,N-dimethylbenzamide hydrochloride was obtained as brown solid (52 mg, 36% for 3 steps). HPLC: 90.2% purity, RT=2.60 min. MS: m/z=481.0 [M+H]$^+$. $^1$H NMR (300 MHz, DMSO, ppm) δ 8.71 (d, J=6.0 Hz, 1H), 8.51 (s, 1H), 8.45 (d, J=9.0 Hz, 1H), 8.20 (d, J=8.0 Hz, 2H), 8.09 (br s, 1H), 7.97 (s, 1H), 7.72 (d, J=5.4 Hz, 2H), 7.38 (d, J=9.0 Hz, 1H), 4.19-4.03 (m, 1H), 3.98 (d, J=9.0 Hz, 2H), 3.48-3.35 (m, 2H), 3.08-2.90 (m, 9H), 2.00-1.82 (m, 2H), 1.79-1.68 (m, 2H).

Example 3: 4-(7-(3-cyano-4-(2,6-dimethyl-tetra-hydro-2H-pyran-4-ylamino)phenyl)furo[3,2-b]pyridin-2-yl)-N,N-dimethylbenzamide hydrochloride (215)

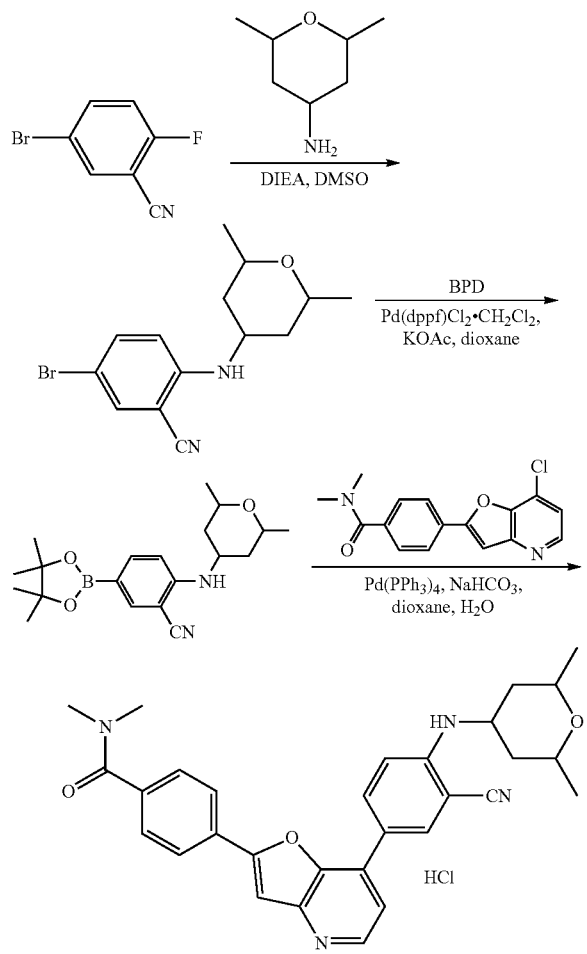

5-bromo-2-(2,6-dimethyl-tetrahydro-2H-pyran-4-ylamino)benzonitrile

To a solution of 5-bromo-2-fluorobenzonitrile (1.1 g, 5.42 mmol) in DMSO (50 mL) was added DIEA (1.1 g, 8.12 mmol) and 2,6-dimethyloxan-4-amine (700 mg, 5.42 mmol) at room temperature. The resulting solution was stirred for 16 h at 120° C. in an oil bath. After cooling to room temperature, the reaction mixture was diluted with water (300 mL). The mixture was extracted with ethyl acetate (100 mL×3). The organic phases were combined, washed with brine and dried over sodium sulfate. The solvent was removed under reduced pressure to yield 5-bromo-2-[(2,6-dimethyloxan-4-yl)amino]benzonitrile as yellow solid (900 mg, 51%). MS: m/z=309.0 [M+H]$^+$.

2-(2,6-dimethyl-tetrahydro-2H-pyran-4-ylamino)-5-(4,4,5,5-tetramethyl-1,3,2-dioxaborolan-2-yl)benzonitrile To a solution of 5-bromo-2-[(2,6-dimethyloxan-4-yl)amino]benzonitrile (300 mg, 0.97 mmol) in dioxane (12 mL) were added 4,4,5,5-tetramethyl-2-(tetramethyl-1,3,2-dioxaborolan-2-yl)-1,3,2-dioxaborolane (296 mg, 1.17 mmol), Pd(dppf)Cl$_2$·CH$_2$Cl$_2$ (70 mg, 0.09 mmol) and potassium acetate (285 mg, 2.90 mmol) at room temperature. The reaction mixture was irradiated with microwave for 2 h at 100° C., cooled to room temperature, and treated with water (30 mL). The resulting mixture was extracted with ethyl acetate (50 mL×3). The organic phases were combined, washed with brine and dried over sodium sulfate. The solvent was removed under reduced pressure and the residue was purified by flash chromatography eluting with ethyl acetate in hexane (0% to 25% gradient) to yield 2-[(2,6-dimethyloxan-4-yl)amino]-5-(tetramethyl-1,3,2-dioxaborolan-2-yl)benzonitrile as yellow solid (298 mg, 86%). MS: m/z=357.0 [M+H]$^+$.

4-(7-(3-cyano-4-(methyl(tetrahydro-2H-pyran-4-yl)amino)phenyl)furo[3,2-b]pyridin-2-yl)-N,N-dimethylbenzamide hydrochloride To a solution of 2-[(2,6-dimethyloxan-4-yl)amino]-5-(tetramethyl-1,3,2-dioxaborolan-2-yl)benzonitrile (300 mg, 0.84 mmol) in dioxane (12 mL) were added 4-[7-chlorofuro[3,2-b]pyridin-2-yl]-N,N-dimethylbenzamide (303 mg, 1.01 mmol), Pd(PPh$_3$)$_4$ (100 mg, 0.09 mmol), sodium bicarbonate (75 mg, 0.89 mmol) and water (4 mL) at room temperature. The resulting mixture was stirred for 16 h at 90° C. After cooling to room temperature, the reaction mixture was concentrated under reduced pressure. The residue was purified by prep-HPLC under the following conditions: column, Gemini-NX C18, 21.2×150 mm 5 um; mobile phase, acetonitrile in water (with 0.02% HCl), 20% to 50% gradient in 10 min; detector, UV 254/220 nm. 4-(7-(3-cyano-4-(methyl(tetrahydro-2H-pyran-4-yl)amino)phenyl)furo[3,2-b]pyridin-2-yl)-N,N-dimethylbenzamide hydrochloride was obtained as brown solid (21 mg, 5%). HPLC: 97.2% purity, RT=1.14 min. MS: m/z=495.0 [M+H]$^+$. $^1$H NMR (400 MHz, DMSO, ppm) δ 8.68 (s, 1H), 8.50-8.38 (m, 2H), 8.30-8.20 (m, 2H), 8.01 (br s, 1H), 7.95 (s, 1H), 7.64 (d, J=8.0 Hz, 2H), 7.29 (d, J=9.2 Hz, 0.5H), 7.14 (d, J=9.2 Hz, 0.5H), 6.70-6.35 (m, 1H), 4.14 (br s, 0.5H), 3.86 (br s, 0.5H), 3.80-3.73 (m, 1H), 3.62-3.52 (m, 1H), 3.03 (s, 3H), 2.96 (m, 3H), 1.95-1.82 (m, 2H), 1.50-1.37 (m, 1H), 1.35-1.18 (m, 1H), 1.17-0.97 (m, 6H).

Example 4: 4-(7-(3-cyano-4-(2,2,6,6-tetramethylpiperidin-4-yloxy)phenyl)furo[3,2-b]pyridin-2-yl)-N,N-dimethylbenzamide (216)

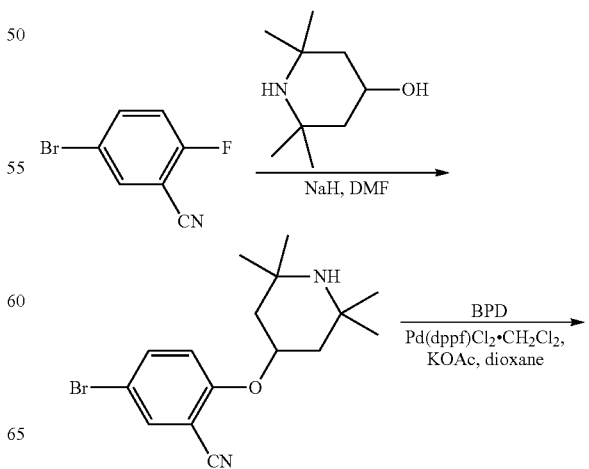

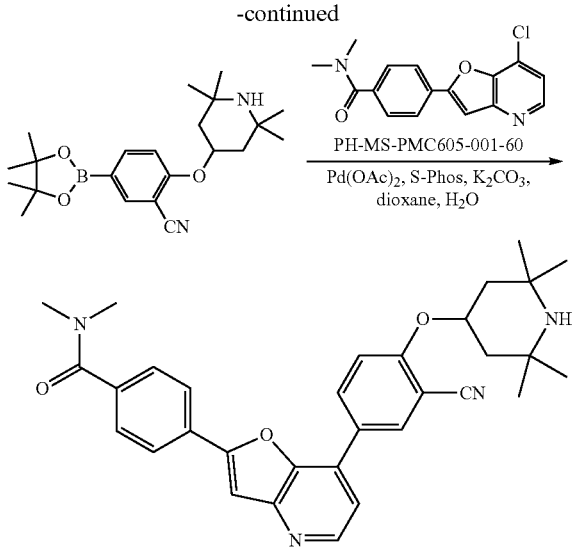

5-bromo-2-(2,2,6,6-tetramethylpiperidin-4-yloxy) benzonitrile to a suspension of sodium hydride (60% in oil, 74 mg, 1.80 mmol) in DMF (10 mL) was added 2,2,6,6-tetramethylpiperidin-4-ol (652 mg, 4.15 mmol) slowly at 0° C. After stirring for 10 min at 0° C., to the mixture was added 5-bromo-2-fluorobenzonitrile (1.0 g, 5.00 mmol) slowly. The reaction mixture was then stirred for 2 h at 50° C., cooled to room temperature, and treated with water (10 mL). The mixture was extracted with ethyl acetate (30 mL×3). The organic phases were combined, washed with brine and dried over sodium sulfate. The solvent was removed under reduced pressure to yield 5-bromo-2-[(2,2,6,6-tetramethylpiperidin-4-yl)oxy]benzonitrile as light yellow solid (1.6 g, 95%). MS: m/z=337.0 [M+H]$^+$.

5-(4,4,5,5-tetramethyl-1,3,2-dioxaborolan-2-yl)-2-(2,2,6,6-tetramethylpiperidin-4-yloxy)benzonitrile To a solution of 5-bromo-2-[(2,2,6,6-tetramethylpiperidin-4-yl)oxy]benzonitrile (200 mg, 0.59 mmol) in dioxane (10 mL) was added 4,4,5,5-tetramethyl-2-(tetramethyl-1,3,2-dioxaborolan-2-yl)-1,3,2-dioxaborolane (181 mg, 0.71 mmol), Pd(dppf)Cl$_2$ (43 mg, 0.06 mmol) and potassium acetate (174 mg, 1.78 mmol) at room temperature. The resulting mixture was stirred for 2 h at 90° C., cooled to room temperature, and treated with water (10 mL). The resulting solution was extracted with ethyl acetate (30 mL×3). The organic phases were combined, washed with brine and dried over sodium sulfate. The solvent was removed under reduced pressure and the residue was purified by flash chromatography eluting with ethyl acetate in hexane (0% to 17% gradient) to yield 5-(tetramethyl-1,3,2-dioxaborolan-2-yl)-2-[(2,2,6,6-tetramethylpiperidin-4-yl)oxy]benzonitrile as brown solid (200 mg, 88%). MS: m/z=385.0 [M+H]$^+$.

4-(7-(3-cyano-4-(2,2,6,6-tetramethylpiperidin-4-yloxy)phenyl)furo[3,2-b]pyridin-2-yl)-N,N-dimethylbenzamide To a solution of 4-[7-chlorofuro[3,2-b]pyridin-2-yl]-N,N-dimethylbenzamide (200 mg, 0.67 mmol) in DMF (10 mL) was added 5-(tetramethyl-1,3,2-dioxaborolan-2-yl)-2-[(2,2,6,6-tetramethylpiperidin-4-yl)oxy]benzonitrile (268 mg, 0.70 mmol), Pd(OAc)$_2$ (15 mg, 0.07 mmol), S-phos (81 mg, 0.20 mmol) and potassium carbonate (276 mg, 2.00 mmol) at room temperature. The resulting mixture was stirred for 2 h at 80° C., cooled to room temperature, and treated with water (10 mL). The resulting solution was extracted with ethyl acetate (30 mL×3). The organic phases were combined, washed with brine and dried over sodium sulfate. The solvent was removed under reduced pressure and the residue was purified by prep-HPLC under the following conditions: column, Gemini-NX C18, 21.2×150 mm 5 um; mobile phase, acetonitrile in water (with 0.02% HCl), 15% to 45% gradient in 10 min; detector, UV 254/220 nm. 4-(7-(3-cyano-4-(2,2,6,6-tetramethylpiperidin-4-yloxy)phenyl)furo[3,2-b]pyridin-2-yl)-N,N-dimethylbenzamide was obtained as white solid (20 mg, 6%). HPLC: 99.1% purity, RT=1.43 min. MS: m/z=523.0 [M+H]$^+$. $^1$H NMR (400 MHz, DMSO, ppm) δ 8.59 (d, J=5.2 Hz, 1H), 8.50-8.41 (m, 2H), 8.09 (d, J=8.4 Hz, 2H), 7.83 (s, 1H), 7.68 (d, J=5.2 Hz, 1H), 7.62-7.56 (m, 3H), 5.19-5.02 (m, 1H), 3.02 (s, 3H), 2.96 (m, 3H), 2.07-1.97 (m, 2H), 1.40 (br s, 1H), 1.31-1.25 (m, 2H), 1.24 (s, 6H), 1.13 (s, 6H).

Example 5: 4 4-(7-(4-(3-oxa-bicyclo[3.1.0]hexan-6-ylamino)-3-cyanophenyl)furo[3,2-b]pyridin-2-yl)-N,N-dimethylbenzamide hydrochloride (217)

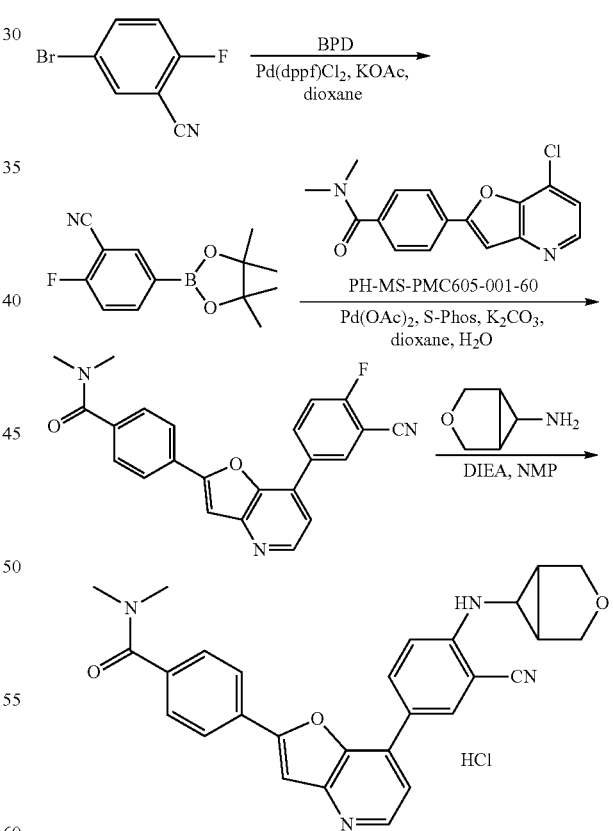

2-fluoro-5-(4,4,5,5-tetramethyl-1,3,2-dioxaborolan-2-yl)benzonitrile

To a solution of 5-bromo-2-fluorobenzonitrile (3.0 g, 15.00 mmol) in 1,4-dioxane (50 mL) was added 4,4,5,5- tetramethyl-2-(tetramethyl-1,3,2-dioxaborolan-2-yl)-1,3,2-dioxaborolane (3.8 g, 15.00 mmol), potassium acetate (2.9 g, 30.00 mmol) and Pd(dppf)Cl₂ (100 mg, 0.14 mmol) at room temperature. The resulting mixture was stirred for 16 h at 100° C., cooled to room temperature, and treated with water (100 mL). The mixture was extracted with ethyl acetate (200 mL×3). The organic phases were combined, washed with brine and dried over sodium sulfate. The solvent was removed under reduced pressure and the residue was purified by flash chromatography eluting with ethyl acetate in hexane (0% to 100% gradient) to yield 2-fluoro-5-(tetramethyl-1,3,2-dioxaborolan-2-yl)benzonitrile as a white solid (2.3 g, 62%).

4-(7-(3-cyano-4-fluorophenyl)furo[3,2-b]pyridin-2-yl)-N,N-dimethylbenzamide

To a solution of 4-[7-chlorofuro[3,2-b]pyridin-2-yl]-N,N-dimethylbenzamide (500 mg, 1.66 mmol) in 1,4-dioxane (10 mL) was added 2-fluoro-5-(tetramethyl-1,3,2-dioxaborolan-2-yl)benzonitrile (411 mg, 1.66 mmol), potassium carbonate (690 mg, 4.99 mmol), SPhos (205 mg, 0.50 mmol), Pd(OAc)₂ (41 mg, 0.18 mmol) and water (2 mL) at room temperature. The resulting mixture was stirred for 6 h at 100° C., cooled to room temperature, and treated with water (50 mL). The resulting solution was extracted with dichloromethane (100 mL×3). The organic phases were combined, washed with brine and dried over sodium sulfate. The solvent was removed under reduced pressure and the residue was purified by flash chromatography eluting with ethyl acetate in dichloromethane (0% to 100% gradient) to yield 4-[7-(3-cyano-4-fluorophenyl)furo[3,2-b]pyridin-2-yl]-N,N-dimethylbenzamide as a yellow solid (440 mg, 69%). MS: m/z=386.0 [M+H]⁺.

4-(7-(4-(3-oxa-bicyclo[3.1.0]hexan-6-ylamino)-3-cyanophenyl)furo[3,2-b]pyridin-2-yl)-N,N-dimethylbenzamide hydrochloride To a solution of 4-[7-(3-cyano-4-fluorophenyl)furo[3,2-b]pyridin-2-yl]-N,N-dimethylbenzamide (14 mg, 0.04 mmol) in NMP (2 mL) were added 3-oxabicyclo[3.1.0]hexan-6-amine hydrochloride (10 mg, 0.07 mmol) and DIEA (48 mg, 0.37 mmol) at room temperature. The resulting mixture was stirred for 2 h at 160° C., cooled to room temperature, and treated with water (20 mL). The mixture was extracted with ethyl acetate (30 mL×3). The organic phases were combined, washed with brine and dried over sodium sulfate. The solvent was removed under reduced pressure and the residue was purified by prep-HPLC under the following conditions: column, Atlantis Prep T3 OBD column, 19×150 mm 5 um 10 nm; mobile phase, acetonitrile in water (with 0.02% HCl), 20% to 35% gradient in 10 min; detector, UV 254/220 nm. 4-(7-(4-(3-oxa-bicyclo[3.1.0]hexan-6-ylamino)-3-cyanophenyl)furo[3,2-b]pyridin-2-yl)-N,N-dimethylbenzamide hydrochloride was obtained as light yellow solid (12 mg, 11%). HPLC: 94.6% purity, RT=1.57 min. MS: m/z=465.0 [M+H]⁺. ¹H NMR (400 MHz, DMSO, ppm) δ 8.53 (d, J=4.8 Hz, 1H), 8.32 (d, J=8.4 Hz, 1H), 8.27 (s, 1H), 8.08 (d, J=7.6 Hz, 2H), 7.78 (s, 1H), 7.72-7.52 (m, 3H), 7.20 (d, J=9.4 Hz, 1H), 7.03 (s, 1H), 4.02 (d, J=8.0 Hz, 2H), 3.71 (d, J=8.0 Hz, 2H), 3.02 (s, 3H), 2.97 (m, 3H), 2.51 (s, 1H), 2.00 (s, 2H).

Example 6: 4-(7-(3-cyano-4-(2,2,6,6-tetramethyl-tetrahydro-2H-pyran-4-ylamino)phenyl)furo[3,2-b]pyridin-2-yl)-N,N-dimethylbenzamide (218)

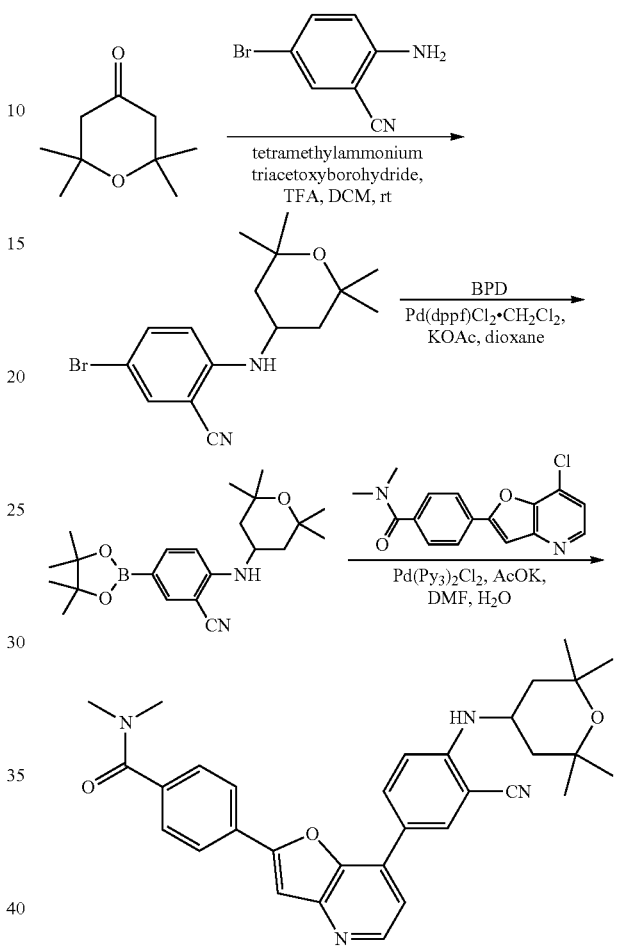

5-bromo-2-(2,2,6,6-tetramethyl-tetrahydro-2H-pyran-4-ylamino)benzonitrile

To a solution of 2,2,6,6-tetramethyloxan-4-one (350 mg, 2.24 mmol) in dichloromethane (60 mL) was added 2-amino-5-bromobenzonitrile (500 mg, 2.54 mmol), tetramethylammonium triacetoxyborohydride (700 mg, 2.66 mmol) and trifluoroacetic acid (0.375 mL) at room temperature. The resulting solution was stirred for 4 h at room temperature and then water (50 mL) was added. The mixture was extracted with ethyl acetate (50 mL×3). The organic phases were combined, washed with brine and dried over sodium sulfate. The solvent was removed under reduced pressure and the residue was purified by flash chromatography eluting with ethyl acetate in hexane (0% to 70% gradient) to yield 5-bromo-2-[(2,2,6,6-tetramethyloxan-4-yl)amino]benzonitrile as yellow solid (180 mg, 24%).

5-(4,4,5,5-tetramethyl-1,3,2-dioxaborolan-2-yl)-2-(2,2,6,6-tetramethyl-tetrahydro-2H-pyran-4-ylamino)benzonitrile To a solution of 5-bromo-2-[(2,2,6,6-tetramethyloxan-4-yl)amino]benzonitrile (743 mg, 2.20 mmol) in dioxane (12 mL) were added 4,4,5,5-tetramethyl-2-(tetramethyl-1,3,2-dioxaborolan-2-yl)-1,3,2-dioxaborolane (666 mg, 2.62 mmol), Pd(dppf)Cl$_2$·CH$_2$Cl$_2$ (179 mg, 0.22 mmol) and potassium acetate (629 mg, 6.41 mmol) at room temperature. The reaction mixture was irradiated with microwave for 2 h at 90° C., cooled to room temperature, and treated with water (50 mL). The resulting mixture was extracted with ethyl acetate (50 mL×3). The organic phases were combined, washed with brine and dried over sodium sulfate. The solvent was removed under reduced pressure and the residue was purified by flash chromatography eluting with ethyl acetate in hexane (0% to 100% gradient) to yield 5-(tetramethyl-1,3,2-dioxaborolan-2-yl)-2-[(2,2,6,6-tetramethyloxan-4-yl)amino]benzonitrile as brown solid (300 mg, 35%). MS: m/z=385.0 [M+H]$^+$.

4-(7-(3-cyano-4-(2,2,6,6-tetramethyl-tetrahydro-2H-pyran-4-ylamino)phenyl)furo[3,2-b]pyridin-2-yl)-N,N-dimethylbenzamide To a solution of 5-(tetramethyl-1,3,2-dioxaborolan-2-yl)-2-[(2,2,6,6-tetramethyloxan-4-yl)amino]benzonitrile (300 mg, 0.78 mmol) in dioxane (12 mL) were added 4-[7-chlorofuro[3,2-b]pyridin-2-yl]-N,N-dimethylbenzamide (196 mg, 0.65 mmol), Pd(PCy$_3$)$_2$Cl$_2$ (70 mg, 0.09 mmol), potassium acetate (160 mg, 1.63 mmol) and water (4 mL) at room temperature. The reaction mixture was irradiated with microwave for 2 h at 100° C., cooled to room temperature, and treated with water (50 mL). The resulting mixture was extracted with ethyl acetate (50 mL×3). The organic phases were combined, washed with brine and dried over sodium sulfate. The solvent was removed under reduced pressure and the residue was purified by prep-HPLC under the following conditions: column, Gemini-NX C18, 21.2×150 mm 5 um; mobile phase, acetonitrile in water, 20% to 55% gradient in 10 min; detector, UV 254/220 nm. 4-(7-(3-cyano-4-(2,2,6,6-tetramethyl-tetrahydro-2H-pyran-4-ylamino)phenyl)furo[3,2-b]pyridin-2-yl)-N,N-dimethylbenzamide was obtained as off-white solid (13 mg, 3%). HPLC: 98.1% purity, RT=1.46 min. MS: m/z=523.0 [M+H]$^+$. $^1$H NMR (400 MHz, CDCl$_3$, ppm) δ 8.52 (d, J=5.6 Hz, 1H), 8.23 (s, 1H), 8.16 (d, J=8.4 Hz, 1H), 7.98 (d, J=8.0 Hz, 2H), 7.68-7.53 (m, 3H), 7.46 (d, J=5.2 Hz, 1H), 6.94 (d, J=8.8 Hz, 1H), 4.78 (d, J=7.6 Hz, 1H), 4.09-3.95 (m, 1H), 3.16 (s, 3H), 3.04 (s, 3H), 2.08 (dd, J=12.4, 2.8 Hz, 2H), 1.43 (s, 6H), 1.42-1.31 (m, 2H), 1.30 (s, 6H).

Example 7: 4-(7-(3-cyano-4-(3,5-dimethyl-tetrahydro-2H-pyran-4-yloxy)phenyl)furo[3,2-b]pyridin-2-yl)-N,N-dimethylbenzamide hydrochloride (219, 220, and 221)

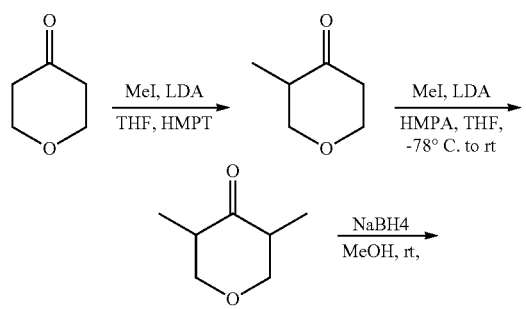

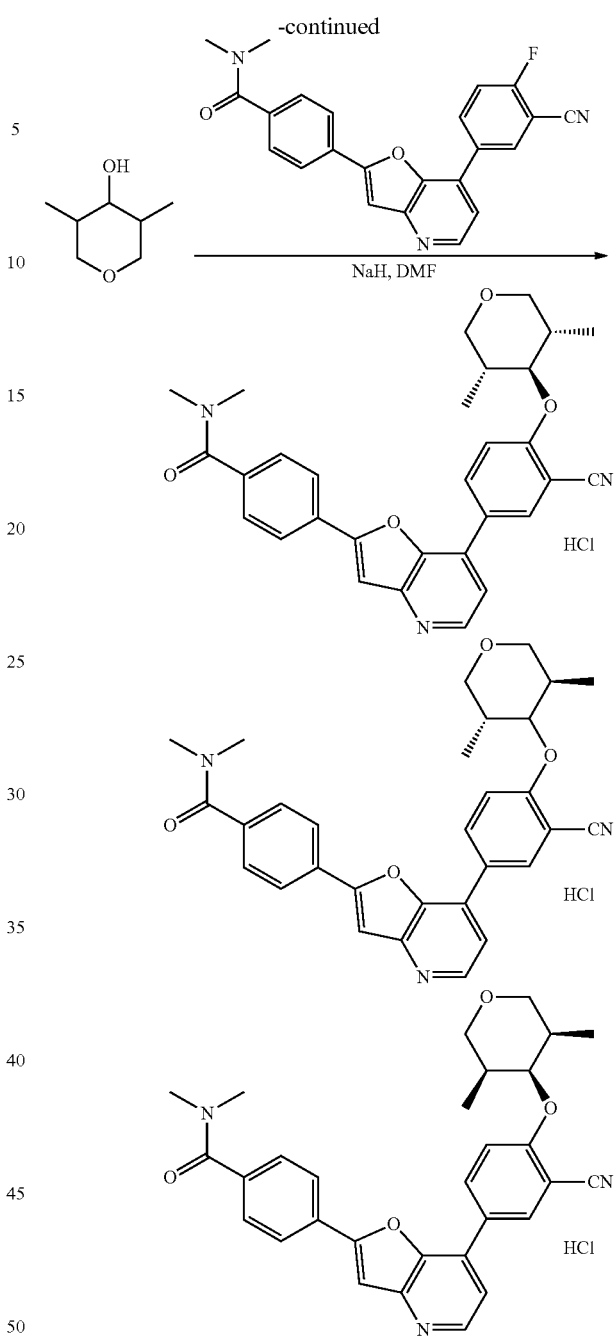

3-methyl-tetrahydropyran-4-one

At −78° C., to a solution of oxan-4-one (11.2 g, 112 mmol) in tetrahydrofuran (300 mL) was added HMPT (18.2 g, 112 mmol). While stirring at −78° C., to the mixture was added LDA (2 M in THF, 280 mL, 559 mmol) dropwise over 30 min period. The resulting solution was stirred for 15 minutes at −78° C. Then iodomethane (76.7 g, 540 mmol) was added. The reaction mixture was stirred at −78° C. for 20 minutes, then warmed up to 0° C. gradually and stirred for another 2 h at 0° C. The reaction mixture was quenched by the addition of saturated ammonium chloride solution (200 mL) and warmed to room temperature. The resulting mixture was extracted with diethyl ether (200 mL×3). The organic phases were combined, washed with brine and dried over sodium sulfate. The solvent was removed under reduced pressure and the residue was purified by distillation at 169-171° C. under standard atmospheric pressure to yield 3-methyloxan-4-one as colorless oil (3.6 g, 28%). GCMS: m/z=114.0 [M]+.

3,5-dimethyl-tetrahydropyran-4-one

At −78° C., to a solution of 3-methyloxan-4-one (546 mg, 4.78 mmol) in tetrahydrofuran (50 mL) was added HMPT (1.2 g, 6.5 mmol). While stirring at −78° C., to the mixture was added LDA (2M in THF, 2.9 mL, 5.7 mmol) over 30 min period. The resulting solution was stirred for 15 minutes at −78° C. Then iodomethane (4.61 g, 32.46 mmol) was added. The reaction mixture was stirred at −78° C. for 60 min, warmed up to room temperature gradually and stirred for another 12 h at room temperature. The reaction mixture was quenched by the addition of saturated ammonium chloride solution (20 mL). The resulting solution was extracted with diethyl ether (30 mL×3). The organic phases were combined, washed with brine and dried over sodium sulfate. The solvent was removed under reduced pressure to yield 3,5-dimethyloxan-4-one as brown oil (0.9 g, crude). GCMS: m/z=128.0 [M]+.

3,5-dimethyl-tetrahydro-2H-pyran-4-ol

At 5° C., to a solution of 3,5-dimethyloxan-4-one (420 mg, crude) in methanol (20 mL) was added sodium borohydride (295 mg, 7.79 mmol). The resulting solution was stirred for 4 h at room temperature and treated with water (10 mL). The pH value of the mixture was adjusted to 6 with hydrochloric acid (3 M). The resulting mixture was extracted with dichloromethane (50 mL×3). The organic phases were combined, washed with brine and dried over sodium sulfate. The solvent was removed under reduced pressure to yield 3,5-dimethyloxan-4-ol as colorless oil (300 mg, crude). GCMS: m/z=130.0 [M]+.

4-(7-(3-cyano-4-(3,5-dimethyl-tetrahydro-2H-pyran-4-yloxy)phenyl)furo[3,2-b]pyridin-2-yl)-N,N-dimethylbenzamide hydrochloride At 0° C., to a suspension of sodium hydride (60% in oil, 18 mg, 0.44 mmol) in N,N-dimethylformamide (2 mL) was added 3,5-dimethyloxan-4-ol (30 mg, 0.23 mmol) slowly. The resulting mixture was stirred at 0° C. for 10 min and was added by 4-[7-(3-cyano-4-fluorophenyl)furo[3,2-b]pyridin-2-yl]-N,N-dimethylbenzamide (98 mg, 0.25 mmol). The reaction mixture was heated to 50° C. and stirred at 50° C. for 16 h. The reaction mixture was cooled to room temperature and then quenched by the addition of water (20 mL). The mixture was extracted with ethyl acetate (30 mL×3). The organic phases were combined, washed with brine and dried over sodium sulfate. The solvent was removed under reduced pressure and the residue was purified by prep-HPLC under the following conditions: column, Gemini-NX C18, 21.2×150 mm 5 um; mobile phase, acetonitrile in water (with 0.02% HCl), 20% to 50% gradient in 10 min; detector, UV 254/220 nm. Three diastereomeric products of 4-(7-(3-cyano-4-(3,5-dimethyl-tetrahydro-2H-pyran-4-yloxy)phenyl)furo[3,2-b]pyridin-2-yl)-N,N-dimethylbenzamide hydrochloride were obtained after separation.

Compound 219:

(20 mg, 18% for 3 steps, light yellow solid) HPLC: 99.4% purity, RT=1.52 min. MS: m/z=496.0 [M+H]+. 1H NMR (300 MHz, CD3OD, ppm) δ 8.54 (d, J=5.1 Hz, 1H), 8.48-8.36 (m, 2H), 8.08 (d, J=7.8 Hz, 2H), 7.70-7.58 (m, 3H), 7.57-7.45 (m, 2H), 4.67-4.50 (m, 1H), 4.02-3.90 (m, 1H), 3.83-3.60 (m, 2H), 3.42-3.30 (m, 1H), 3.15 (s, 3H), 3.07 (s, 3H), 2.45-2.30 (m, 1H), 2.29-2.10 (m, 1H), 1.25-1.00 (m, 6H).

Compound 220:

(8 mg, 5% for 3 steps, light yellow solid) HPLC: 99.0% purity, RT=1.49 min. MS: m/z=496.0 [M+H]+. 1H NMR (300 MHz, CD3OD, ppm) δ 8.55 (br s, 1H), 8.47-8.30 (m, 2H), 8.10 (d, J=8.1 Hz, 2H), 7.75-7.55 (m, 4H), 7.52 (s, 1H), 4.35-4.20 (m, 1H), 3.97 (d, J=4.8 Hz, 1H), 3.93 (d, J=4.8 Hz, 1H), 3.29-3.20 (m, 2H), 3.15 (s, 3H), 3.07 (s, 3H), 2.45-2.30 (m, 1H), 2.20-1.96 (m, 2H), 0.96 (s, 3H), 0.94 (s, 3H).

Compound 221:

(5 mg, 3% for 3 steps, light yellow solid) HPLC: 93.9% purity, RT=3.00 min. MS: m/z=496.0 [M+H]+. 1H NMR (300 MHz, CD3OD, ppm) δ 8.54 (d, J=5.4 Hz, 1H), 8.48-8.35 (m, 2H), 8.10 (d, J=8.4 Hz, 2H), 7.70-7.59 (m, 4H), 7.54 (s, 1H), 5.00 (s, 1H), 3.78-3.60 (m, 4H), 3.15 (s, 3H), 3.07 (s, 3H), 2.30-2.10 (m, 2H), 0.93 (s, 3H), 0.90 (s, 3H).

Example 8: 4-(7-(3-cyano-4-(morpholinomethyl)phenyl)furo[3,2-b]pyridin-2-yl)-N,N-dimethylbenzamide (222)

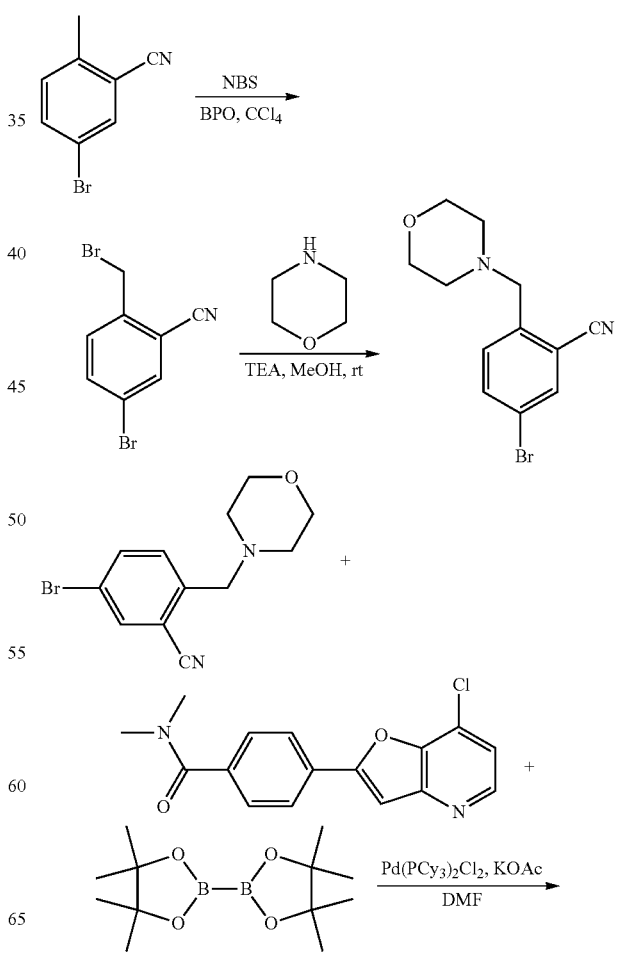

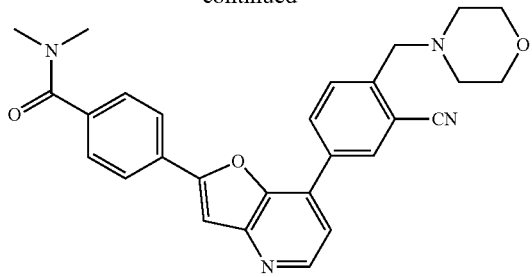

5-bromo-2-(bromomethyl)benzonitrile

To a solution of 5-bromo-2-methylbenzonitrile (10.0 g, 51.0 mmol) in chloroform (150 mL) was added benzoperoxide (1.3 g, 5.07 mmol) and NBS (9.0 g, 50.0 mmol) at room temperature. The resulting solution was stirred for 16 h at 60° C., cooled to room temperature, and treated with water (100 mL). The resulting solution was extracted with ethyl acetate (300 mL×3). The organic phases were combined, washed with brine and dried over sodium sulfate. The solvent was removed under reduced pressure and the residue was purified by flash chromatography eluting with ethyl acetate in hexane (0% to 5% gradient) to yield 5-bromo-2-(bromomethyl)benzonitrile as purple solid (6.0 g, 43%).

5-bromo-2-(morpholinomethyl)benzonitrile

To a solution of 5-bromo-2-(bromomethyl)benzonitrile (520 mg, 1.89 mmol) in methanol (20 mL) was added triethylamine (600 mg, 5.93 mmol) and morpholine (1.5 g, 17.2 mmol) at room temperature. The resulting solution was stirred for 8 h at room temperature, the reaction mixture was concentrated under reduced pressure and the residue was purified by flash chromatography eluting with ethyl acetate in hexane (0% to 2% gradient) to yield 5-bromo-2-(morpholin-4-ylmethyl)benzonitrile as yellow solid (400 mg, 8%).

4-(7-(3-cyano-4-(morpholinomethyl)phenyl)furo[3,2-b]pyridin-2-yl)-N,N-dimethylbenzamide To a solution of 5-bromo-2-(morpholin-4-ylmethyl)benzonitrile (200 mg, 0.71 mmol) in DMF (10 mL) was added 4,4,5,5-tetramethyl-2-(tetramethyl-1,3,2-dioxaborolan-2-yl)-1,3,2-dioxaborolane (217 mg, 0.85 mmol), 4-[7-chlorofuro[3,2-b]pyridin-2-yl]-N,N-dimethylbenzamide (235 mg, 0.78 mmol), Pd(PCy$_3$)$_2$Cl$_2$ (53 mg, 0.07 mmol), potassium acetate (244 mg, 2.49 mmol) at room temperature. The reaction mixture was irradiated with microwave radiation for 1 h at 100° C., cooled to room temperature, and treated with water (20 mL). The resulting mixture was extracted with ethyl acetate (50 mL×3). The organic phases were combined, washed with brine and dried over sodium sulfate. The solvent was removed under reduced pressure and the residue was purified by prep-HPLC under the following conditions: column, Gemini-NX C18, 21.2×150 mm 5 um; mobile phase, acetonitrile in water (with 10 mmol/L NH$_4$HCO$_3$), 20% to 45% gradient in 10 min; detector, UV 254/220 nm. 4-(7-(3-cyano-4-(morpholinomethyl)phenyl)furo[3,2-b]pyridin-2-yl)-N,N-dimethylbenzamide was obtained as off-white solid (15 mg, 5%). HPLC: 94.8% purity, RT=2.24 min. MS: m/z=467.0 [M+H]$^+$. $^1$H NMR (400 MHz, DMSO, ppm) δ 8.62 (d, J=5.2 Hz, 1H), 8.55 (s, 1H), 8.47 (d, J=8.0 Hz, 1H), 8.09 (d, J=8.4 Hz, 2H), 7.91-7.82 (m, 2H), 7.72 (d, J=4.8 Hz, 1H), 7.60 (d, J=8.4 Hz, 2 H), 3.75 (s, 2H), 3.69-3.50 (m, 4H), 3.01 (s, 3H), 2.95 (s, 3H), 2.60-2.50 (m, 2H), 2.10-1.70 (m, 2H).

Example 9: 4-(7-(3-cyano-4-(2-morpholinopropan-2-yl)phenyl)furo[3,2-b]pyridin-2-yl)-N,N-dimethylbenzamide hydrochloride hydrochloride (223)

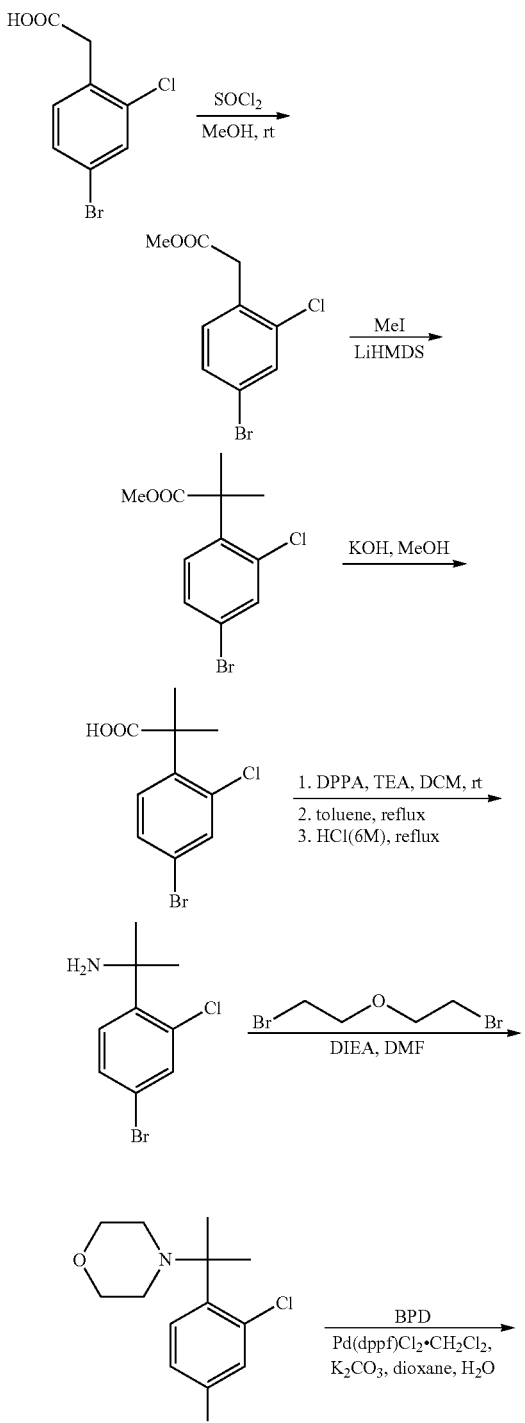

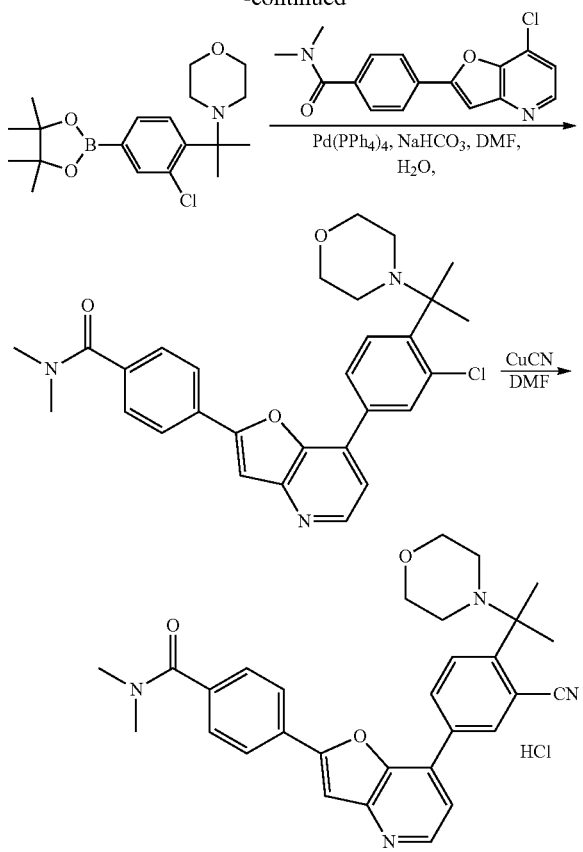

Methyl 2-(4-bromo-2-chlorophenyl)acetate

To a solution of 2-(4-bromo-2-chlorophenyl)acetic acid (1.9 g, 7.62 mmol) in methanol (100 mL) was added thionyl chloride (2.7 g, 22.85 mmol) at room temperature. The resulting solution was stirred for 4 h at room temperature. The reaction mixture was concentrated under reduced pressure to yield methyl 2-(4-bromo-2-chlorophenyl)acetate as colorless oil (1.9 g, 95%). MS: m/z=263.0 [M+H]$^+$.

Methyl 2-(4-bromo-2-chlorophenyl)-2-methylpropanoate

At 0° C., to a solution of methyl 2-(4-bromo-2-chlorophenyl)acetate (475 mg, 1.80 mmol) in tetrahydrofuran (48 mL) was added a solution of lithiobis(trimethylsilyl)amine (666 mg, 3.98 mmol) in tetrahydrofuran (2 mL) dropwise over 5 min period. The resulting solution was stirred for 30 min at 0° C., and then added iodomethane (616 mg, 4.34 mmol). The reaction mixture was stirred for 4 h at room temperature. The reaction mixture was quenched by addition of saturated ammonium chloride solution. The resulting mixture was extracted with ether (50×3 mL). The organic layers were combined and dried over sodium sulfate. The solvent was removed under reduced pressure to yield methyl 2-(4-bromo-2-chlorophenyl)-2-methylpropanoate as colorless oil (500 mg, 88%). MS: m/z=291.0 [M+H]$^+$.

2-(4-bromo-2-chlorophenyl)-2-methylpropanoic acid

At room temperature, methyl 2-(4-bromo-2-chlorophenyl)-2-methylpropanoate (500 mg, 1.55 mmol) was dissolved in ethanol (30 mL) in a 100 mL sealed tube. Then potassium hydroxide (280 mg, 4.99 mmol) was added. The resulting mixture was stirred overnight at 120° C. After cooling to room temperature, the reaction mixture was concentrated under reduced pressure. The residue was diluted with water (25 mL) and the pH value of the mixture was adjusted to 3 with hydrogen chloride (6 M). The resulting mixture was extracted with ethyl acetate (30 mL×3). The organic layers were combined and dried over sodium sulfate. The solvent was removed under reduced pressure to yield 2-(4-bromo-2-chlorophenyl)-2-methylpropanoic acid as light yellow solid (300 mg, 66%). MS: m/z=276.0 [M+H]$^+$.

2-(4-bromo-2-chlorophenyl)propan-2-amine

To a solution of 2-(4-bromo-2-chlorophenyl)-2-methylpropanoic acid (400 mg, 1.44 mmol) in dichloromethane (20 mL) was added DPPA (571 mg, 2.08 mmol) and triethylamine (225 mg, 2.22 mmol) at room temperature. The resulting solution was stirred for 2 h at room temperature. The reaction mixture was concentrated under reduced pressure and the residue was diluted with toluene (20 mL). The resulting solution was then heated to reflux and stirred for 2 h. After cooling to room temperature, an aqueous solution of hydrogen chloride (6 M, 5 mL) was added. The resulting mixture was stirred for another 4 h at reflux. After cooling to room temperature, the reaction mixture was concentrated under reduced pressure and was diluted with water (50 mL). The pH value of the resulting mixture was adjusted to 8 with sodium hydroxide solution (5 M). The mixture was extracted with ethyl acetate (100 mL×3). The organic phases were combined, washed with brine and dried over sodium sulfate. The solvent was removed under reduced pressure and the residue was purified by flash chromatography eluting with ethyl acetate in hexane (0% to 10% gradient) to yield 2-(4-bromo-2-chlorophenyl)propan-2-amine as white solid (250 mg, 70%). MS: m/z=248.0 [M+H]$^+$.

4-(2-(4-bromo-2-chlorophenyl)propan-2-yl)morpholine

To a solution of 2-(4-bromo-2-chlorophenyl)propan-2-amine (200 mg, 0.80 mmol) in DIEA (10 mL) was added 1-bromo-2-(2-bromoethoxy)ethane (224 mg, 0.97 mmol) at room temperature. The resulting solution was stirred overnight at 120° C., cooled to room temperature, and treated with When water (10 mL). The resulting mixture was extracted with ethyl acetate (30 mL×3). The organic phases were combined, washed with brine and dried over sodium sulfate. The solvent was removed under reduced pressure and the residue was purified by flash chromatography eluting with ethyl acetate in hexane (0% to 8% gradient) to yield 4-[2-(4-bromo-2-chlorophenyl)propan-2-yl]morpholine as light yellow solid (200 mg, 78%). MS: m/z=318.0 [M+H]$^+$.

4-(2-(2-chloro-4-(4,4,5,5-tetramethyl-1,3,2-dioxaborolan-2-yl)phenyl)propan-2-yl)morpholine To a solution of 4-[2-(4-bromo-2-chlorophenyl)propan-2-yl]morpholine (160 mg, 0.50 mmol) in dioxane (10 mL) was added 4,4,5,5-tetramethyl-2-(tetramethyl-1,3,2-dioxaborolan-2-yl)-1,3,2-dioxaborolane (153 mg, 0.60 mmol), Pd(dppf)Cl$_2$·CH$_2$Cl$_2$ (82 mg, 0.10 mmol) and potassium acetate (148 mg, 1.51 mmol) at room temperature. The resulting mixture was stirred for 2 h at 100° C. in an oil bath, cooled to room temperature, and the reaction mixture was concentrated under reduced pressure to yield 4-[2-[2-chloro-4-(tetramethyl-1,3,2-dioxaborolan-2-yl)phenyl]propan-2-yl]morpholine as brown solid (500 mg, crude). MS: m/z=366.0 [M+H]$^+$. The crude product was used on next step without further purification.

4-(7-(3-chloro-4-(2-morpholinopropan-2-yl)phenyl)furo[3,2-b]pyridin-2-yl)-N,N-dimethylbenzamide To a solution of 4-[2-[2-chloro-4-(tetramethyl-1,3,2-dioxaborolan-2-yl)phenyl]propan-2-yl]morpholine (500 mg, crude) in DMF (20 mL) was added 4-[7-chlorofuro[3,2-b]pyridin-2-yl]-N,N-dimethylbenzamide (90 mg, 0.30 mmol), Pd(PPh$_3$)$_4$ (69 mg, 0.06 mmol), sodium bicarbonate (75 mg, 0.89 mmol) and water (1.5 mL) at room temperature. The resulting solution was stirred for 2 h at 100° C., cooled to room temperature, and treated with water (20 mL). The resulting mixture was extracted with dichloromethane (60 mL×3). The organic phases were combined, washed with brine and dried over sodium sulfate. The solvent was removed under reduced pressure and the residue was purified by flash chromatography eluting with methanol in dichloromethane (0% to 5% gradient) to yield 4-(7-[3-chloro-4-[2-(morpholin-4-yl)propan-2-yl]phenyl]furo[3,2-b]pyridin-2-yl)-N,N-dimethylbenzamide as a light yellow solid (100 mg, 66% for 2 steps). MS: m/z=504.0 [M+H]$^+$.

4-(7-(3-cyano-4-(2-morpholinopropan-2-yl)phenyl)furo[3,2-b]pyridin-2-yl)-N,N-dimethylbenzamide hydrochloride To a solution of 4-(7-[3-chloro-4-[2-(morpholin-4-yl)propan-2-yl]phenyl]furo[3,2-b]pyridin-2-yl)-N,N-dimethylbenzamide (90 mg, 0.18 mmol) in DMF (3 mL) was added copper cyanide (77 mg, 0.85 mmol) at room temperature. The resulting mixture was stirred for 18 h at 150° C. and cooled to room temperature. The solid that formed were removed by filtration and the filtrate was diluted with water (10 mL). The resulting mixture was extracted with dichloromethane (30 mL×3). The organic phases were combined, washed with brine and dried over sodium sulfate. The solvent was removed under reduced pressure and the residue was purified by prep-HPLC under the following conditions: column, Gemini-NX, 5u C18 110A, AXIA Packed 150×21.2 mm; mobile phase, acetonitrile in water (with 0.02% HCl), 20% to 40% gradient in 10 min; detector, UV 254/220 nm. 4-(7-(3-cyano-4-(2-morpholinopropan-2-yl)phenyl)furo[3,2-b]pyridin-2-yl)-N,N-dimethyl benzamide hydrochloride was obtained as off-white solid (10 mg, 11%). HPLC: 98.3% purity, RT=1.26 min. MS: m/z=495.0 [M+H]$^+$. $^1$H NMR (300 MHz, CD$_3$OD, ppm) δ 8.57 (br s, 1H), 8.46 (s, 1H), 8.34 (dd, J=8.4, 2.1 Hz, 1H), 8.07 (d, J=8.4 Hz, 2H), 7.77 (d, J=8.4 Hz, 1H), 7.70-7.45 (m, 4H), 3.80-3.65 (m, 4H), 3.11 (s, 3H), 3.03 (s, 3H), 2.65-2.45 (m, 4H), 1.53 (s, 6H).

Example 10: 4-(7-(3-cyano-5-fluoro-4-(tetrahydro-2H-pyran-4-ylamino)phenyl)furo[3,2-b]pyridin-2-yl)-N,N-dimethylbenzamide hydrochloride (224)

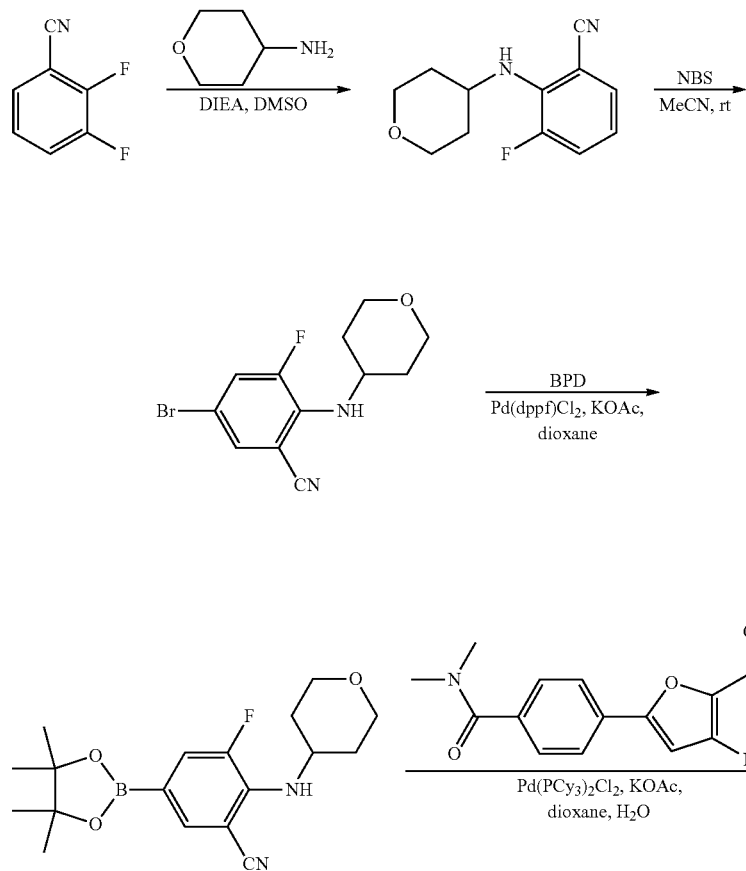

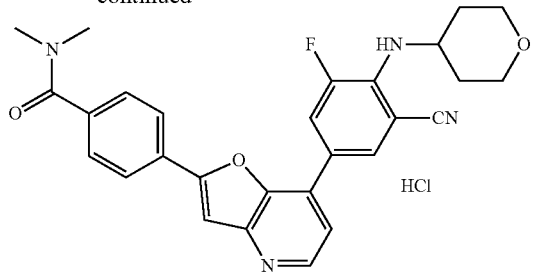

3-fluoro-2-(tetrahydro-2H-pyran-4-ylamino)benzonitrile

To a solution of 2,3-difluorobenzonitrile (2.8 g, 19.99 mmol) in DMSO (40 mL) was added oxan-4-amine (2.0 g, 19.77 mmol) and DIEA (6.5 g, 49.91 mmol) at room temperature. The resulting solution was stirred overnight at 120° C., cooled to room temperature, and treated with water (80 mL). The resulting solution was extracted with ethyl acetate (100 mL×3). The organic phases were combined, washed with brine and dried over sodium sulfate. The solvent was removed under reduced pressure to yield 3-fluoro-2-[(oxan-4-yl)amino]benzonitrile as black solid (3.3 g, 76%). MS: m/z=221.0 [M+H]$^+$.

5-bromo-3-fluoro-2-(tetrahydro-2H-pyran-4-ylamino)benzonitrile

To a solution of 3-fluoro-2-[(oxan-4-yl)amino]benzonitrile (3.3 g, 15.12 mmol) in acetonitrile (70 mL) was added NBS (2.7 g, 15.06 mmol) at room temperature. The resulting solution was stirred for 1 h at room temperature and then treated with water (60 mL). The resulting solution was extracted with ethyl acetate (100 mL×3). The organic phases were combined, washed with brine and dried over sodium sulfate. The solvent was removed under reduced pressure to yield 5-bromo-3-fluoro-2-[(oxan-4-yl)amino]benzonitrile as brown solid (4.5 g, 99%). MS: m/z=299.0 [M+H]$^+$.

3-fluoro-2-(tetrahydro-2H-pyran-4-ylamino)-5-(4,4,5,5-tetramethyl-1,3,2-dioxaborolan-2-yl)benzonitrile To a solution of 5-bromo-3-fluoro-2-[(oxan-4-yl)amino] benzonitrile (200 mg, 0.67 mmol) in dioxan (10 mL) was added 4,4,5,5-tetramethyl-2-(tetramethyl-1,3,2-dioxaborolan-2-yl)-1,3,2-dioxaborolane (204 mg, 0.80 mmol), Pd(dppf)Cl$_2$ (58 mg, 0.08 mmol) and potassium acetate (197 mg, 2.01 mmol) at room temperature. The resulting mixture was stirred for 5 h at 90° C., cooled to room temperature and treated with water (50 mL). The mixture was extracted with ethyl acetate (50 mL×3). The organic phases were combined, washed with brine and dried over sodium sulfate. The solvent was removed under reduced pressure and the residue was purified by flash chromatography eluting with ethyl acetate in hexane (0% to 100% gradient) to yield 3-fluoro-2-[(oxan-4-yl)amino]-5-(tetramethyl-1,3,2-dioxaborolan-2-yl)benzonitrile as black solid (200 mg, 86%). MS: m/z=347.0 [M+H]$^+$.

4-(7-(3-cyano-5-fluoro-4-(tetrahydro-2H-pyran-4-ylamino)phenyl)furo[3,2-b]pyridin-2-yl)-N,N-dimethylbenzamide hydrochloride To a solution of 3-fluoro-2-[(oxan-4-yl)amino]-5-(tetramethyl-1,3,2-dioxaborolan-2-yl)benzonitrile (200 mg, 0.58 mmol) in dioxane (10 mL) were added 4-[7-chlorofuro[3,2-b]pyridin-2-yl]-N,N-dimethylbenzamide (144 mg, 0.48 mmol), Pd(PCy$_3$)$_2$Cl$_2$ (35 mg, 0.05 mmol), potassium acetate (94 mg, 0.96 mmol) and water (2 mL) at room temperature. The resulting mixture was stirred for 4 h at 80° C., cooled to room temperature, and treated with water (30 mL). The mixture was extracted with ethyl acetate (30 mL×3). The organic phases were combined, washed with brine and dried over sodium sulfate. The solvent was removed under reduced pressure and the residue was purified by prep-HPLC under the following conditions: column, Atlantis Prep T3 OBD column, 19×150 mm 5 um 10 nm; mobile phase, acetonitrile in water (with 0.02% HCl), 20% to 45% gradient in 10 min; detector, UV 254/220 nm. 4-(7-(3-cyano-5-fluoro-4-(tetrahydro-2H-pyran-4-ylamino)phenyl)furo[3,2-b]pyridin-2-yl)-N,N-dimethylbenzamide hydrochloride was obtained as yellow solid (35 mg, 13%). HPLC: 99.7% purity, RT=1.75 min. MS: m/z=485.0 [M+H]$^+$. $^1$H NMR (400 MHz, CD$_3$OD, ppm) δ 8.65 (d, J=6.4 Hz, 1H), 8.38 (s, 1H), 8.33-8.15 (m, 3H), 8.08 (d, J=6.4 Hz, 1H), 7.82 (s, 1H), 7.70 (d, J=8.4 Hz, 2H), 4.50-4.37 (m, 1H), 4.04 (dd, J=12.0, 2.4 Hz, 2H), 3.62-3.50 (m, 2H), 3.21 (s, 3H), 3.14 (s, 3H), 2.15-2.00 (m, 2H), 1.85-1.68 (m, 2H).

Example 11: 4-(7-(3-cyano-5-fluoro-4-(methyl(tetrahydro-2H-pyran-4-yl)amino)phenyl)furo[3,2-b]pyridin-2-yl)-N,N-dimethylbenzamide hydrochloride (225)

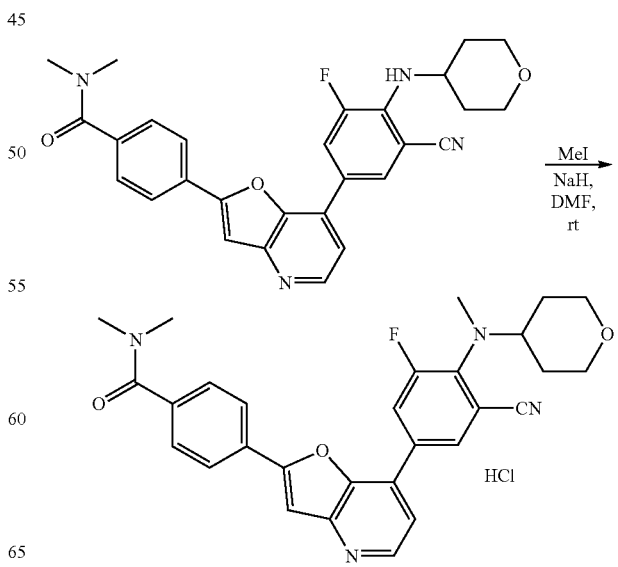

4-(7-[3-cyano-5-fluoro-4-[methyl(oxan-4-yl)amino]phenyl]furo[3,2-b]pyridin-2-yl)-N,N-dimethylbenzamide hydrochloride To a suspension of sodium hydride (60% in oil, 24 mg, 0.58 mmol) in DMF (3 mL) was added 4-(7-[3-cyano-5-fluoro-4-[(oxan-4-yl)amino]phenyl]furo[3,2-b]pyridin-2-yl)-N,N-dimethylbenzamide (100 mg, 0.21 mmol) at 0° C. The resulting mixture was stirred at 0° C. for 10 min and iodomethane (88 mg, 0.62 mmol) was added. The reaction mixture was then stirred at room temperature for 30 min and then treated with water (20 mL). The resulting solution was extracted with ethyl acetate (30 mL×3). The organic phases were combined, washed with brine and dried over sodium sulfate. The solvent was removed under reduced pressure and the residue was purified by prep-HPLC under the following conditions: column, Gemini-NX C18 AXAI Packed, 21.2×150 mm 5 um 11 nm; mobile phase, acetonitrile in water (with 0.02% HCl), 15% to 50% gradient in 10 min; detector, UV 254/220 nm. 4-(7-[3-cyano-5-fluoro-4-[methyl(oxan-4-yl)amino]phenyl]furo[3,2-b]pyridin-2-yl)-N,N-dimethylbenzamide hydrochloride was obtained as yellow solid (60 mg, 53%). HPLC: 97.1% purity, RT=1.31 min. MS: m/z=499.0 [M+H]$^+$. $^1$H NMR (400 MHz, CD$_3$OD, ppm) δ 8.73 (d, J=6.0 Hz, 1H), 8.42 (s, 1H), 8.32 (d, J=11.6 Hz, 1H), 8.23 (d, J=8.4 Hz, 2H), 8.07 (d, J=5.2 Hz, 1H), 7.83 (s, 1H), 7.71 (d, J=8.0 Hz, 2H), 4.07 (dd, J=11.2 Hz, 2H), 3.80-3.69 (m, 1H), 3.58-3.40 (m, 2H), 3.25-2.80 (m, 9H), 2.10-1.95 (m, 2H), 1.94-1.80 (m, 2H).

Example 12: 4-(7-(3-cyano-4-(tetrahydro-2H-pyran-4-ylamino)phenyl)furo[3,2-b]pyridin-2-yl)-3-methoxy-N,N-dimethylbenzamide (226)

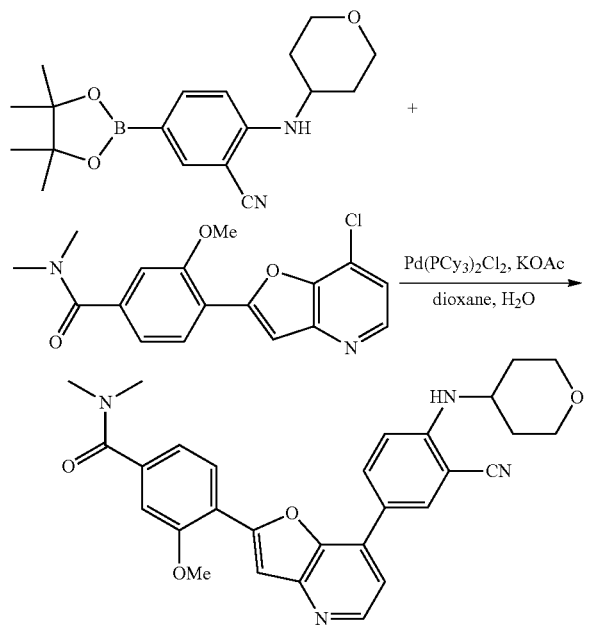

4-(7-(3-cyano-4-(tetrahydro-2H-pyran-4-ylamino)phenyl)furo[3,2-b]pyridin-2-yl)-3-methoxy-N,N-dimethylbenzamide To a solution of 4-[7-chlorofuro[3,2-b]pyridin-2-yl]-3-methoxy-N,N-dimethylbenzamide (1.5 g, 4.53 mmol) in dioxane (80 mL) was added 2-[(oxan-4-yl)amino]-5-(tetramethyl-1,3,2-dioxaborolan-2-yl)benzonitrile (1.5 g, 4.57 mmol), Pd(PCy$_3$)$_2$Cl$_2$ (300 mg, 0.41 mmol), potassium acetate (1.4 g, 14.27 mmol) and water (10 mL). The resulting mixture was stirred for 16 h at 100° C., cooled to room temperature, and treated with water (60 mL). The mixture was extracted with dichloromethane (150 mL×3). The organic phases were combined, washed with brine and dried over sodium sulfate. The solvent was removed under reduced pressure and the residue was purified by prep-HPLC under the following conditions: column, Gemini-NX C18 AXAI Packed, 21.2×150 mm 5 um 11 nm; mobile phase, acetonitrile in water (with 10 mmol/L NH$_4$HCO$_3$), 20% to 55% gradient in 8 min; detector, UV 254/220 nm. 4-(7-(3-cyano-4-(tetrahydro-2H-pyran-4-ylamino)phenyl)furo[3,2-b]pyridin-2-yl)-3-methoxy-N,N-dimethylbenzamide was obtained as yellow solid (220 mg, 10%). HPLC: 98.5% purity, RT=1.30 min. MS: m/z=497.0 [M+H]$^+$. $^1$H NMR (400 MHz, DMSO, ppm) δ 8.51 (d, J=2.8 Hz, 1H), 8.37-8.23 (m, 2H), 8.03 (d, J=8.0 Hz, 1H), 7.62 (d, J=5.2 Hz, 1H), 7.60 (s, 1H), 7.26 (s, 1H), 7.22-7.15 (m, 2H), 6.29 (d, J=8.0 Hz, 1H), 4.07 (s, 3H), 3.92 (d, J=10.0 Hz, 2H), 3.88-3.72 (m, 1H), 3.51-3.40 (m, 2H), 3.03 (s, 3H), 2.97 (s, 3H), 1.91-1.88 (d, J=10.4 Hz, 2H), 1.75-1.60 (m, 2H).

Example 13: 4-(7-(3-cyano-4-(methyl(tetrahydro-2H-pyran-4-yl)amino)phenyl)furo[3,2-b]pyridin-2-yl)-3-methoxy-N,N-dimethylbenzamide (227)

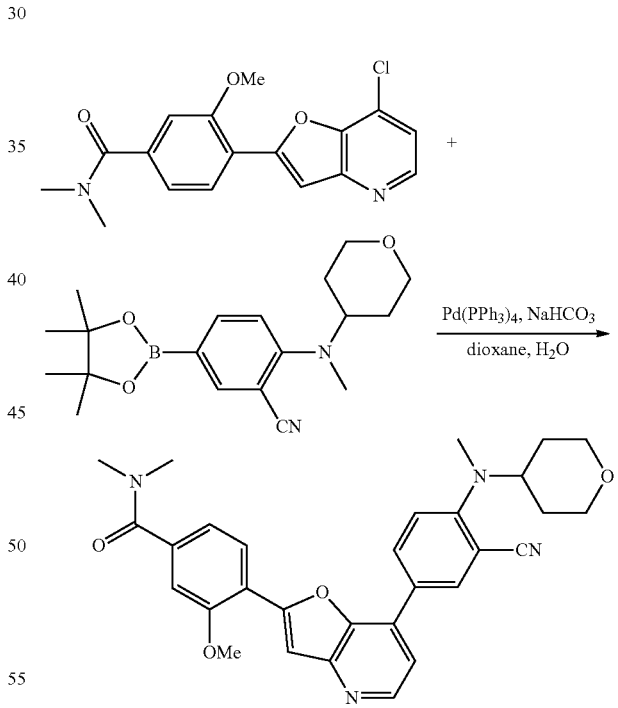

4-(7-(3-cyano-4-(methyl(tetrahydro-2H-pyran-4-yl)amino)phenyl)furo[3,2-b]pyridin-2-yl)-3-methoxy-N,N-dimethylbenzamide To a solution of 2-[methyl(oxan-4-yl)amino]-5-(tetramethyl-1,3,2-dioxaborolan-2-yl)benzonitrile (160 mg, 0.47 mmol) in dioxane (9 mL) was added 4-[7-chlorofuro[3,2-b]pyridin-2-yl]-3-methoxy-N,N-dimethylbenzamide (160 mg, 0.48 mmol) and Pd(PPh$_3$)$_4$ (50 mg, 0.04 mmol) at room temperature. Then a solution of sodium bicarbonate (40 mg, 0.48 mmol) in water (3 mL) was added. The resulting mixture was stirred for 16 h at 100° C., cooled to room temperature, and treated with water (10 mL). The mixture was extracted with dichloromethane (30 mL×3). The organic phases were combined, washed with brine and dried over sodium sulfate. The solvent was removed under reduced pressure and the residue was purified by prep-HPLC under the following conditions: column, Atlantis Prep T$_3$ OBD column, 19×150 mm 5 um 10 nm; mobile phase, acetonitrile in water (with 10 mmol/L NH$_4$HCO$_3$), 30% to 60% gradient in 8 min; detector, UV 254/220 nm. 4-(7-(3-cyano-4-(methyl (tetrahydro-2H-pyran-4-yl)amino)phenyl)furo[3,2-b]pyridin-2-yl)-3-methoxy-N,N-dimethylbenzamide was obtained as yellow solid (25 mg, 10%). HPLC: 97.2% purity, RT=1.33 min. MS: m/z=497.0 [M+H]$^+$. $^1$H NMR (400 MHz, DMSO, ppm) δ 8.54 (d, J=5.2 Hz, 1H), 8.40-8.30 (m, 2H), 8.04 (d, J=8.0 Hz, 1H), 7.66 (d, J=5.2 Hz, 1H), 7.62 (s, 1H), 7.37 (d, J=9.2 Hz, 1H), 7.26 (s, 1H), 7.18 (d, J=8.0 Hz, 1H), 4.06 (s, 3H), 4.04-3.90 (m, 3H), 3.48-3.37 (m, 2H), 3.03 (s, 3H), 2.96 (s, 3H), 2.94 (s, 3H), 2.00-1.80 (m, 2H), 1.74-1.71 (d, J=10.4 Hz, 2H).

Example 14: 4-(7-(3-cyano-4-(2,6-dimethyl-tetrahydro-2H-pyran-4-ylamino)phenyl)furo[3,2-b]pyridin-2-yl)-3-methoxy-N,N-dimethylbenzamide (228)

sodium bicarbonate (100 mg, 1.19 mmol) and water (4 mL) at room temperature. The resulting mixture was stirred for 4 h at 90° C., cooled to room temperature, and treated with water (10 mL). The mixture was extracted with ethyl acetate (30 mL×3). The organic phases were combined, washed with brine and dried over sodium sulfate. The solvent was removed under reduced pressure and the residue was purified by prep-HPLC under the following conditions: column, Gemini-NX C18, 21.2×150 mm 5 um; mobile phase, acetonitrile in water (with 10 mmol/L NH$_4$HCO$_3$), 20% to 40% gradient in 10 min; detector, UV 254/220 nm. 4-(7-(3-cyano-4-(2,6-dimethyl-tetrahydro-2H-pyran-4-ylamino)phenyl)furo[3,2-b]pyridin-2-yl)-3-methoxy-N,N-dimethylbenzamide was obtained as yellow solid (25 mg, 8%). HPLC: 98.9% purity, RT=1.39 min. MS: m/z=525.0 [M+H]$^+$. $^1$H NMR (400 MHz, CDCl$_3$, ppm) δ 8.54 (d, J=5.2 Hz, 1H), 8.20 (d, J=7.6 Hz, 1H), 8.16-8.06 (m, 1H), 8.06 (d, J=22.4 Hz, 1H), 7.70 (s, 1H), 7.33 (d, J=5.2 Hz, 1H), 7.20-7.10 (m, 2H), 6.98-6.82 (m, 1H), 5.20-4.66 (m, 1H), 4.12-3.58 (m, 5H), 3.15 (s, 3H), 3.05 (s, 3H), 2.13 (dd, J=12.4, 4.0 Hz, 2H), 1.90-1.80 (m, 1H), 1.70-1.55 (m, 1H), 1.33-1.20 (m, 7H).

Example 15: 4-(7-(3-cyano-4-(2,2,6,6-tetramethylpiperidin-4-yloxy)phenyl)furo[3,2-b]pyridin-2-yl)-3-methoxy-N,N-dimethylbenzamide (229)

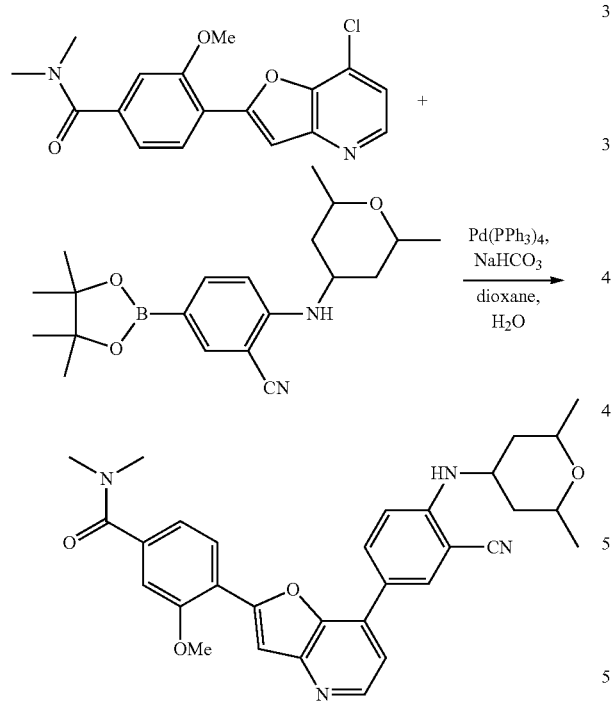

4-(7-(3-cyano-4-(2,6-dimethyl-tetrahydro-2H-pyran-4-ylamino)phenyl)furo[3,2-b]pyridin-2-yl)-3-methoxy-N,N-dimethylbenzamide

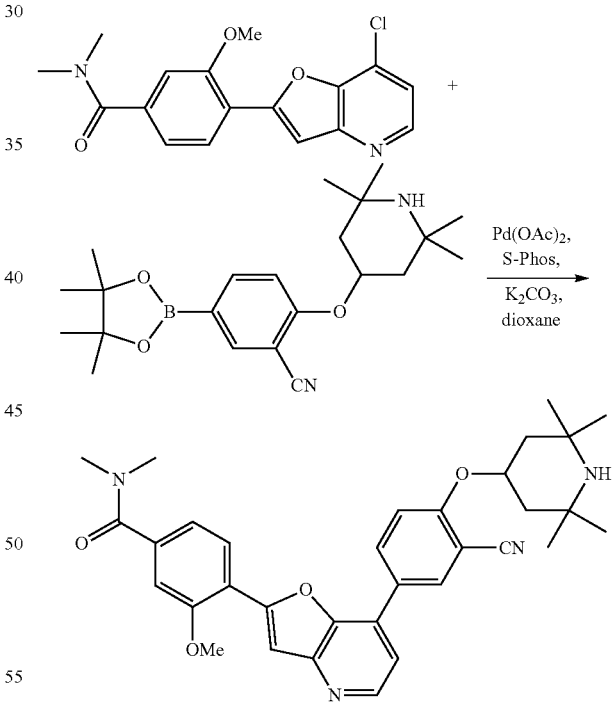

4-(7-(3-cyano-4-(2,2,6,6-tetramethylpiperidin-4-yloxy)phenyl)furo[3,2-b]pyridin-2-yl)-3-methoxy-N,N-dimethylbenzamide To a solution of 2-[(2,6-dimethyloxan-4-yl)amino]-5-(tetramethyl-1,3,2-dioxaborolan-2-yl)benzonitrile (200 mg, 0.56 mmol) in dioxane (12 mL) was added 4-[7-chlorofuro[3,2-b]pyridin-2-yl]-3-methoxy-N,N-dimethylbenzamide (200 mg, 0.60 mmol), Pd(PPh$_3$)$_4$ (60 mg, 0.05 mmol), To a solution of 4-[7-chlorofuro[3,2-b]pyridin-2-yl]-3-methoxy-N,N-dimethylbenzamide (200 mg, 0.60 mmol) in DMF (8 mL) was added 5-(tetramethyl-1,3,2-dioxaborolan-2-yl)-2-[(2,2,6,6-tetramethylpiperidin-4-yl)oxy]benzonitrile (244 mg, 0.63 mmol), Pd(OAc)$_2$ (14 mg, 0.06 mmol), S-Phos (75 mg, 0.18 mmol) and potassium carbonate (250 mg, 1.81 mmol) at room temperature. The resulting mixture was stirred for 2 h at 80° C., cooled to room temperature, and treated with water (10 mL). The mixture was extracted with dichloromethane (30 mL×3). The organic phases were combined, washed with brine and dried over sodium sulfate. The solvent was removed under reduced pressure and the residue was purified by prep-HPLC under the following conditions: column, Gemini-NX C18, 21.2×150 mm 5 um; mobile phase, acetonitrile in water (with 10 mmol/L $NH_4HCO_3$), 20% to 50% gradient in 8 min; detector, UV 254/220 nm. 4-(7-(3-cyano-4-(2,2,6,6-tetramethylpiperidin-4-yloxy)phenyl)furo[3,2-b]pyridin-2-yl)-3-methoxy-N,N-dimethylbenzamide was obtained as white solid (40 mg, 12%). HPLC: 97.6% purity, RT=1.43 min. MS: m/z=553.0 [M+H]$^+$. $^1$H NMR (400 MHz, DMSO, ppm) δ 8.58 (d, J=4.8 Hz, 1H), 8.53-8.20 (m, 2H), 8.04 (d, J=7.6 Hz, 1H), 7.89-7.53 (m, 3H), 7.26 (s, 1H), 7.18 (d, J=8.0 Hz, 1H), 5.20-5.07 (m, 1H), 4.06 (s, 3H), 3.02 (s, 3H), 2.96 (s, 3H), 2.04 (d, J=10.0 Hz, 2H), 1.40-1.00 (m, 14H).

Example 16: 4-(7-(4-(3-oxa-bicyclo[3.1.0]hexan-6-ylamino)-3-cyanophenyl)furo[3,2-b]pyridin-2-yl)-3-methoxy-N,N-dimethylbenzamide (276)

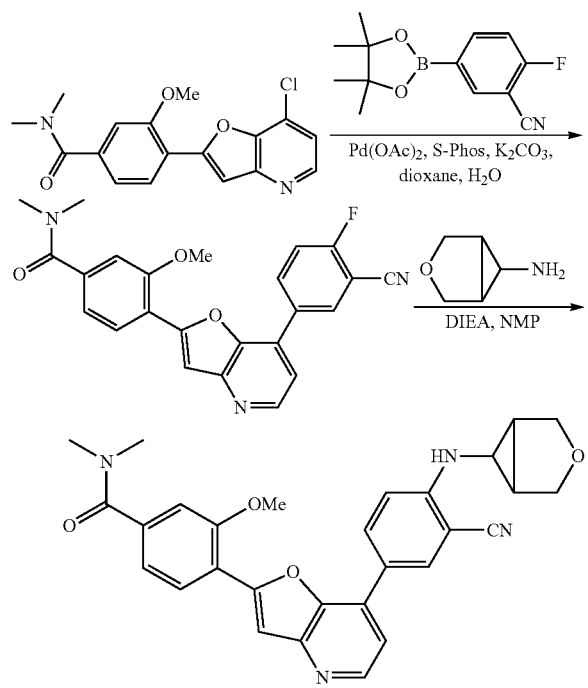

4-(7-(3-cyano-4-fluorophenyl)furo[3,2-b]pyridin-2-yl)-3-methoxy-N,N-dimethylbenzamide To a solution of 4-[7-chlorofuro[3,2-b]pyridin-2-yl]-3-methoxy-N,N-dimethylbenzamide (300 mg, 0.91 mmol) in 1,4-dioxane (15 mL) was added 2-fluoro-5-(tetramethyl-1,3,2-dioxaborolan-2-yl)benzonitrile (235 mg, 0.95 mmol), Pd(OAc)$_2$ (20 mg, 0.09 mmol), S-Phos (112 mg, 0.27 mmol), potassium carbonate (376 mg, 2.72 mmol) and water (3 mL) at room temperature. The reaction mixture was stirred for 1.5 h at 100° C., cooled to room temperature, and treated with water (10 mL). The mixture was extracted with ethyl acetate (30 mL×3). The organic phases were combined, washed with brine and dried over sodium sulfate. The solvent was removed under reduced pressure and the residue was purified by flash chromatography eluting with ethyl acetate in hexane (0% to 100% gradient) to yield 4-[7-(3-cyano-4-fluorophenyl)furo[3,2-b]pyridin-2-yl]-3-methoxy-N,N-dimethylbenzamide as yellow solid (340 mg, 69%). MS: m/z=416.0 [M+H]$^+$.

4-(7-(4-(3-oxa-bicyclo[3.1.0]hexan-6-ylamino)-3-cyanophenyl)furo[3,2-b]pyridin-2-yl)-3-methoxy-N,N-dimethylbenzamide To a solution of 4-[7-(3-cyano-4-fluorophenyl)furo[3,2-b]pyridin-2-yl]-3-methoxy-N,N-dimethylbenzamide (92 mg, 0.22 mmol) in NMP (12 mL) were added 3-oxabicyclo[3.1.0]hexan-6-amine hydrochloride (60 mg, 0.44 mmol) and DIEA (286 mg, 2.21 mmol) at room temperature. The resulting solution was stirred for 40 h at 120° C., cooled to room temperature, and treated with water (10 mL). The mixture was extracted with dichloromethane (30 mL×3). The organic phases were combined, washed with brine and dried over sodium sulfate. The solvent was removed under reduced pressure and the residue was purified by prep-HPLC under the following conditions: column, Gemini-NX C18 AXAI Packed, 21.2×150 mm 5 um 11 nm; mobile phase, acetonitrile in water (with 10 mmol/L $NH_4HCO_3$), 20% to 50% gradient in 8 min; detector, UV 254/220 nm. 4-(7-(4-(3-oxa-bicyclo[3.1.0]hexan-6-ylamino)-3-cyanophenyl)furo[3,2-b]pyridin-2-yl)-3-methoxy-N,N-dimethylbenzamide was obtained as yellow solid (29 mg, 25%). HPLC: 95.3% purity, RT=2.44 min. MS: m/z=495.0 [M+H]$^+$. $^1$H NMR (400 MHz, DMSO, ppm) δ 8.51 (d, J=5.1 Hz, 1H), 8.39-8.22 (m, 2H), 8.04 (d, J=7.8 Hz, 1H), 7.70-7.56 (m, 2H), 7.30-7.12 (m, 3H), 7.04 (s, 1H), 4.16-3.96 (m, 5H), 3.70 (d, J=8.4 Hz, 2H), 3.02 (s, 3H), 2.97 (s, 3H), 2.35 (s, 1H), 1.99 (s, 2H).

Example 17: 4-(7-(3-cyano-4-(3,5-dimethyl-tetrahydro-2H-pyran-4-yloxy)phenyl)furo[3,2-b]pyridin-2-yl)-3-methoxy-N,N-dimethylbenzamide (231, 232, 233

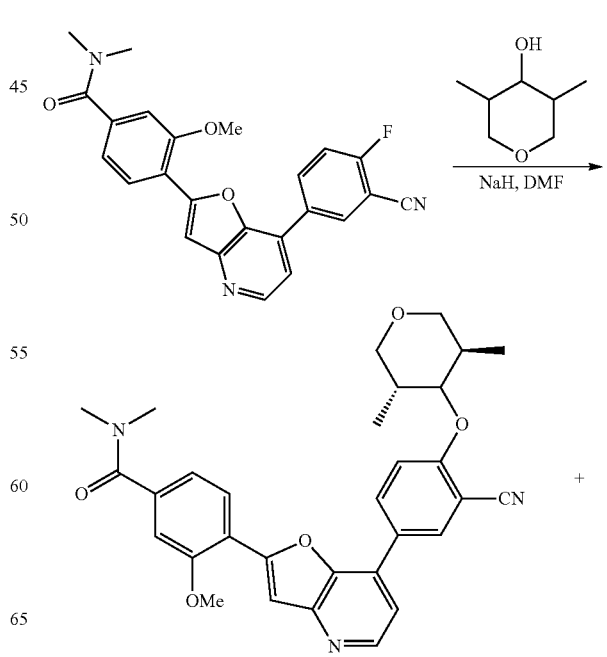

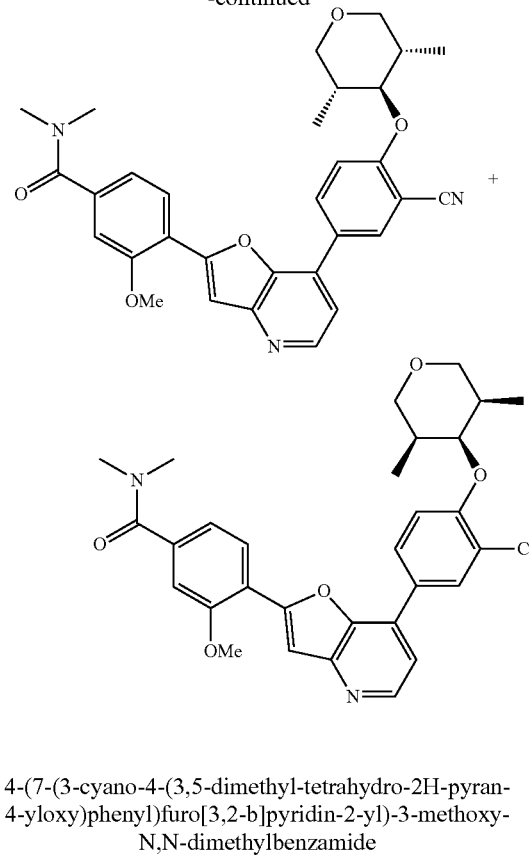

4-(7-(3-cyano-4-(3,5-dimethyl-tetrahydro-2H-pyran-4-yloxy)phenyl)furo[3,2-b]pyridin-2-yl)-3-methoxy-N,N-dimethylbenzamide At 0° C., to a suspension of sodium hydride (60% in oil, 55 mg, 1.35 mmol) in DMF (7 ml) was added 3,5-dimethyloxan-4-ol (170 mg, 1.31 mmol). The resulting mixture was stirred at 0° C. for 10 min. To this stirring mixture was added a solution of 4-[7-(3-cyano-4-fluorophenyl)furo[3,2-b]pyridin-2-yl]-3-methoxy-N,N-dimethylbenzamide (406 mg, 0.98 mmol) in DMF (12 mL) dropwise over 10 min period at 0° C. The reaction mixture was heated to 50° C. and stirred at 50° C. for 3 h. The reaction mixture was cooled to room temperature and treated with water (10 mL). The mixture was extracted with dichloromethane (30 mL×3). The organic phases were combined, washed with brine and dried over sodium sulfate. The solvent was removed under reduced pressure and the residue was purified by prep-HPLC under the following conditions: column, XBridge Prep C18 OBD column, 5 um, 19×150 mm; mobile phase, acetonitrile in water (with 10 mmol/L NH$_4$HCO$_3$), 5% to 72% gradient in 30 min; detector, UV 254/220 nm. Three diastereomeric products of 4-(7-(3-cyano-4-(3,5-dimethyl-tetrahydro-2H-pyran-4-yloxy)phenyl)furo[3,2-b]pyridin-2-yl)-3-methoxy-N,N-dimethyl benzamide were obtained after separation.

Compound 231:
(62 mg, 9%, off-white solid) HPLC: 97.2% purity, RT=2.63 min. MS: m/z=526.0 [M+H]$^+$. $^1$H NMR (300 MHz, CD$_3$OD, ppm) δ 8.45 (d, J=24.0 Hz, 1H), 8.45-8.35 (m, 2H), 8.07 (d, J=8.1 Hz, 1H), 7.62-7.42 (m, 3H), 7.27 (s, 1H), 7.18 (d, J=7.8 Hz, 1H), 4.65-4.50 (m, 1H), 4.10 (s, 3H), 3.95 (dd, J=11.4, 3.9 Hz, 1H), 3.82-3.60 (m, 2H), 3.42-3.32 (m, 1H), 3.15 (s, 3H), 3.08 (s, 3H), 2.45-2.10 (m, 2H), 1.20-1.00 (m, 6H).

Compound 232:
(20 mg, 5%, light yellow solid) HPLC: 97.4% purity, RT=2.59 min. MS: m/z=526.0 [M+H]$^+$. $^1$H NMR (300 MHz, CD$_3$OD, ppm) δ 8.51 (d, J=5.4 Hz, 1H), 8.47-8.35 (m, 2H), 8.10 (d, J=7.8 Hz, 1H), 7.67-7.55 (m, 3H), 7.27 (s, 1H), 7.19 (d, J=7.8 Hz, 1H), 4.35-4.20 (m, 1H), 4.11 (s, 3H), 3.94 (dd, J=11.7, 4.5 Hz, 2H), 3.30-3.20 (m, 2H), 3.15 (s, 3H), 3.08 (s, 3H), 2.20-2.00 (m, 2H), 0.96 (s, 3H), 0.94 (s, 3H).

Compound 233:
(12 mg, 4%, light yellow solid) HPLC: 94.8% purity, RT=2.53 min. MS: m/z=526.0 [M+H]$^+$. $^1$H NMR (300 MHz, DMSO, ppm) δ 8.58 (d, J=5.1 Hz, 1H), 8.52-8.40 (m, 2H), 8.05 (d, J=8.1 Hz, 2H), 7.80-7.59 (m, 3H), 7.26 (s, 1H), 7.18 (d, J=8.1 Hz, 2H), 5.01 (s, 1H), 4.07 (s, 3H), 3.70-3.55 (m, 2H), 3.51-3.37 (m, 2H), 3.02 (s, 3H), 2.96 (s, 3H), 2.20-2.00 (m, 2H), 0.82 (s, 3H), 0.79 (s, 3H).

Example 18: 4-(7-(3-cyano-4-(morpholinomethyl)phenyl)furo[3,2-b]pyridin-2-yl)-3-methoxy-N,N-dimethylbenzamide (234)

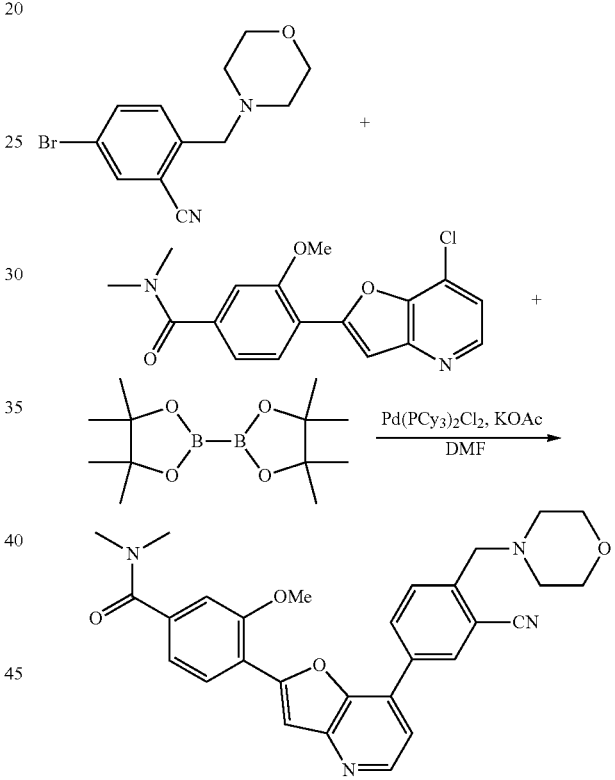

4-(7-(3-cyano-4-(morpholinomethyl)phenyl)furo[3,2-b]pyridin-2-yl)-3-methoxy-N,N-dimethylbenzamide To a solution of 5-bromo-2-(morpholin-4-ylmethyl)benzonitrile (300 mg, 1.07 mmol) in DMF (10 mL) was added 4,4,5,5-tetramethyl-2-(tetramethyl-1,3,2-dioxaborolan-2-yl)-1,3,2-dioxaborolane (325 mg, 1.28 mmol), 4-[7-chlorofuro[3,2-b]pyridin-2-yl]-3-methoxy-N,N-dimethylbenzamide (349 mg, 1.06 mmol), Pd(PCy$_3$)$_2$Cl$_2$ (78.77 mg, 0.11 mmol) and potassium acetate (320 mg, 3.27 mmol) at room temperature. The reaction mixture was irradiated with microwave radiation for 1 h at 100° C., cooled to room temperature, and treated with water (10 mL). The mixture was extracted with dichloromethane (30 mL×3). The organic phases were combined, washed with brine and dried over sodium sulfate. The solvent was removed under reduced pressure and the residue was purified by prep-HPLC under the following conditions: column, Gemini-NX C18, 21.2×150 mm 5 um; mobile phase, acetonitrile in water (with 10 mmol/L NH$_4$HCO$_3$), 20% to 50% gradient in 8 min; detector, UV 254/220 nm. 4-(7-(3-cyano-4-(morpholinomethyl)phenyl)furo[3,2-b]pyridin-2-yl)-3-methoxy-N,N-dimethylbenzamide was obtained as off-white solid (70 mg, 13%). HPLC: 99.8% purity, RT=1.32 min. MS: m/z=497.0 [M+H]$^+$. $^1$H NMR (400 MHz, DMSO, ppm) δ 8.61 (d, J=5.2 Hz, 1H), 8.52 (s, 1H), 8.46 (dd, J=8.0, 2.0 Hz, 1H), 8.04 (d, J=8.0 Hz, 1H), 7.86 (d, J=8.4 Hz, 1H), 7.71 (d, J=5.2 Hz, 1H), 7.64 (s, 1H), 7.25 (s, 1H), 7.18 (dd, J=8.0, 1.2 Hz, 1H), 4.06 (s, 3H), 3.75 (s, 2H), 3.69-3.50 (m, 4H), 3.02 (s, 3H), 2.96 (s, 3H), 2.60-2.40 (m, 4H).

Example 19: 4-(7-(3-cyano-4-(2-morpholinopropan-2-yl)phenyl)furo[3,2-b]pyridin-2-yl)-3-methoxy-N,N-dimethylbenzamide hydrochloride (235)

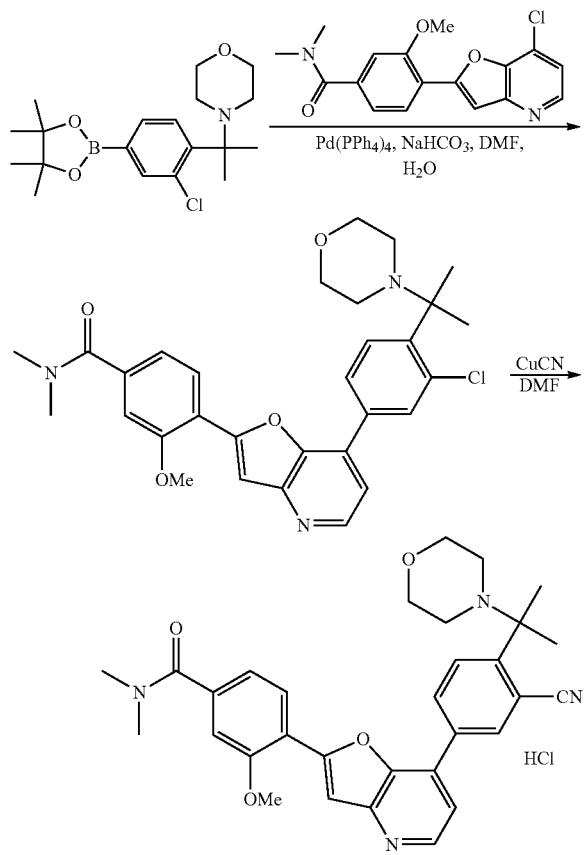

4-(7-(3-chloro-4-(2-morpholinopropan-2-yl)phenyl)furo[3,2-b]pyridin-2-yl)-3-methoxy-N,N-dimethylbenzamide To a solution of 4-[7-chlorofuro[3,2-b]pyridin-2-yl]-2-methoxy-N,N-dimethylbenzamide (80 mg, 0.24 mmol) in DMF (6 mL) was added 4-[2-[2-chloro-4-(tetramethyl-1,3,2-dioxaborolan-2-yl)phenyl]propan-2-yl]morpholine (108 mg, 0.30 mmol), Pd(PPh$_3$)$_4$ (57 mg, 0.05 mmol), sodium bicarbonate (66 mg, 0.79 mmol) and water (2 mL) at room temperature. The resulting mixture was stirred for 2 h at 100° C., cooled to room temperature, and treated with water (20 mL). The mixture was extracted with dichloromethane (60 mL×3). The organic phases were combined, washed with brine and dried over sodium sulfate. The solvent was removed under reduced pressure and the residue was purified by flash chromatography eluting with methanol in dichloromethane (0% to 2% gradient) to yield 4-(7-(3-chloro-4-(2-morpholinopropan-2-yl)phenyl)furo[3,2-b]pyridin-2-yl)-3-methoxy-N,N-dimethyl benzamide as light yellow solid (90 mg, 51%). MS: m/z=534.0 [M+H]$^+$.

4-(7-(3-cyano-4-(2-morpholinopropan-2-yl)phenyl)furo[3,2-b]pyridin-2-yl)-3-methoxy-N,N-dimethyl benzamide hydrochloride To a solution of 4-(7-(3-chloro-4-(2-morpholinopropan-2-yl)phenyl)furo[3,2-b]pyridin-2-yl)-3-methoxy-N,N-dimethylbenzamide (90 mg, 0.17 mmol) in DMF (3 mL) was added copper cyanide (77 mg, 0.85 mmol) at room temperature. The resulting solution was then stirred for 18 h at 150° C. and then cooled to room temperature. The solid that formed in the reaction mixture was removed by filtration and the filtrate was concentrated under reduced pressure. The resulting residue was diluted with water (10 mL) and the resulting mixture was extracted with dichloromethane (30 mL×3). The organic phases were combined, washed with brine and dried over sodium sulfate. The solvent was removed under reduced pressure and the residue was purified by prep-HPLC under the following conditions: column, Gemini-NX, 5u C18 110A, AXIA Packed 150×21.2 mm; mobile phase, acetonitrile in water (with 0.02% HCl), 20% to 40% gradient in 10 min; detector, UV 254/220 nm. 4-(7-(3-cyano-4-(2-morpholinopropan-2-yl)phenyl)furo[3,2-b]pyridin-2-yl)-3-methoxy-N,N-dimethyl benzamide hydrochloride was obtained as yellow solid (30 mg, 16%). HPLC: 95.1% purity, RT=1.28 min. MS: m/z=525.0 [M+H]$^+$. $^1$H NMR (300 MHz, CD$_3$OD+HCl, ppm) δ 8.90-8.40 (m, 4H), 8.33-8.10 (m, 2H), 7.88 (s, 1H), 7.32 (s, 1H), 7.29-7.10 (m, 1H), 5.10-4.90 (m, 2H), 4.25-3.95 (m, 6H), 3.61-3.20 (m, 3H), 3.12 (s, 3H), 3.03 (s, 3H), 2.23 (s, 6H).

Example 20: 4-(7-(3-cyano-5-fluoro-4-(tetrahydro-2H-pyran-4-ylamino)phenyl)furo[3,2-b]pyridin-2-yl)-3-methoxy-N,N-dimethylbenzamide (236)

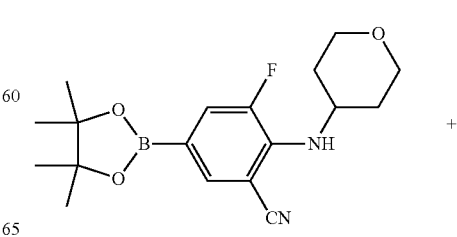

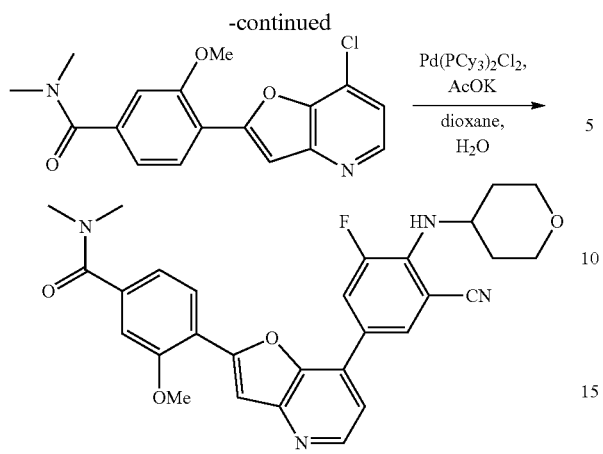
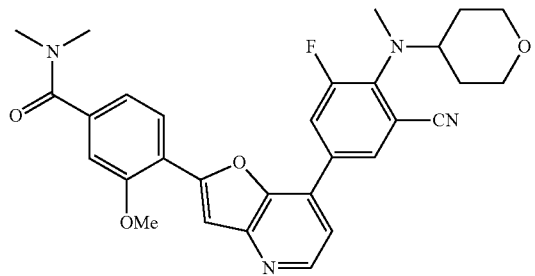

4-(7-(3-cyano-5-fluoro-4-(tetrahydro-2H-pyran-4-ylamino)phenyl)furo[3,2-b]pyridin-2-yl)-3-methoxy-N,N-dimethylbenzamide To a solution of 4-[7-chlorofuro[3,2-b]pyridin-2-yl]-3-methoxy-N,N-dimethylbenzamide (300 mg, 0.91 mmol) in dioxane (8 mL) was added 3-fluoro-2-[(oxan-4-yl)amino]-5-(tetramethyl-1,3,2-dioxaborolan-2-yl)benzonitrile (327 mg, 0.94 mmol), Pd(PCy₃)₂Cl₂ (67 mg, 0.09 mmol), potassium acetate (196 mg, 2.00 mmol) and water (2 mL) at room temperature. The resulting mixture was then stirred for 2 h at 100° C., cooled to room temperature, and treated with water (30 mL). The mixture was extracted with dichloromethane (80 mL×3). The organic phases were combined, washed with brine and dried over sodium sulfate. The solvent was removed under reduced pressure and the residue was purified by prep-HPLC under the following conditions: column, Gemini-NX 5u C18 110A, AXIA Packed, 150×21.2 mm; mobile phase, acetonitrile in water (with 10 mmol/L NH₄HCO₃), 20% to 55% gradient in 8 min; detector, UV 254/220 nm. 4-(7-(3-cyano-5-fluoro-4-(tetrahydro-2H-pyran-4-ylamino)phenyl)furo[3,2-b]pyridin-2-yl)-3-methoxy-N,N-dimethylbenzamide was obtained as yellow solid (100 mg, 21%). HPLC: 99.0% purity, RT=1.14 min. MS: m/z=515.0 [M+H]⁺. ¹H NMR (300 MHz, CD₃OD, ppm) δ 8.52 (d, J=2.8 Hz, 1H), 8.20 (s, 1H), 8.08 (d, J=13.8 Hz, 1H), 8.15-7.85 (m, 2H), 7.62 (s, 1H), 7.27 (s, 1H), 7.16 (d, J=8.1 Hz, 1H), 4.42-4.27 (m, 1H), 4.20-3.90 (m, 5H), 3.60-3.40 (m, 2H), 3.13 (s, 3H), 3.02 (s, 3H), 2.10-1.90 (m, 2H), 1.80-1.60 (m, 2H), 1.40-1.20 (m, 1H).

Example 21: 4-(7-(3-cyano-5-fluoro-4-(methyl(tetrahydro-2H-pyran-4-yl)amino)phenyl)furo[3,2-b]pyridin-2-yl)-3-methoxy-N,N-dimethylbenzamide (237)

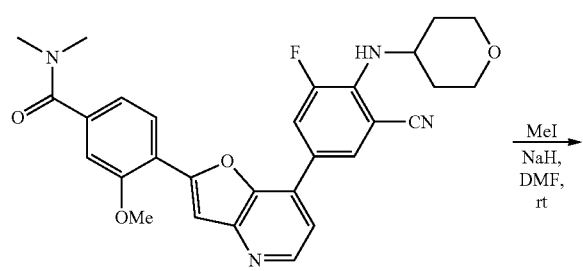

4-(7-(3-cyano-5-fluoro-4-(methyl(tetrahydro-2H-pyran-4-yl)amino)phenyl)furo[3,2-b]pyridin-2-yl)-3-methoxy-N,N-dimethylbenzamide To a suspension of sodium hydride (60% in oil, 17 mg, 0.42 mmol, 2.14 equiv) in DMF (3 mL) was added 4-(7-[3-cyano-5-fluoro-4-[(oxan-4-yl)amino]phenyl]furo[3,2-b]pyridin-2-yl)-3-methoxy-N,N-dimethylbenzamide (100 mg, 0.19 mmol) at 0° C. The resulting mixture was stirred at 0° C. for 10 min and iodomethane (83 mg, 0.58 mmol, 3.01 equiv) was added. The reaction mixture was then stirred for 30 min at room temperature and then treated with water (20 mL). The mixture was extracted with dichloromethane (30 mL×3). The organic phases were combined, washed with brine and dried over sodium sulfate. The solvent was removed under reduced pressure and the residue was purified by prep-HPLC under the following conditions: column, Gemini-NX C18 AXAI Packed, 21.2×150 mm 5 um 11 nm; mobile phase, acetonitrile in water (with 10 mmol/L NH₄HCO₃), 20% to 50% gradient in 10 min; detector, UV 254/220 nm. 4-(7-(3-cyano-5-fluoro-4-(methyl(tetrahydro-2H-pyran-4-yl)amino)phenyl)furo[3,2-b]pyridin-2-yl)-3-methoxy-N,N-dimethyl benzamide was obtained as yellow solid (25 mg, 23%). HPLC: 97.3% purity, RT=1.35 min. MS: m/z=529.0 [M+H]⁺. ¹H NMR (300 MHz, CD₃OD, ppm) δ 8.63 (d, J=6.0 Hz, 1H), 8.39-8.30 (m, 1H), 8.24 (dd, J=13.5, 2.1 Hz, 1H), 8.12 (d, J=8.1 Hz, 1H), 7.93 (d, J=6.3 Hz, 1H), 7.71 (s, 1H), 7.30 (s, 1H), 7.22 (d, J=8.1 Hz, 1H), 4.11 (s, 3 h), 4.01 (dd, J=10.8, 2.4 Hz, 2H), 3.75-3.59 (m, 1H), 3.52-3.38 (m, 2H), 3.20-2.90 (m, 9H), 2.05-1.75 (m, 4H).

Example 22: 4-(7-(3-cyano-4-(tetrahydro-2H-pyran-4-yloxy)phenyl)furo[3,2-b]pyridin-2-yl)-3-fluoro-N,N-dimethylbenzamide (238)

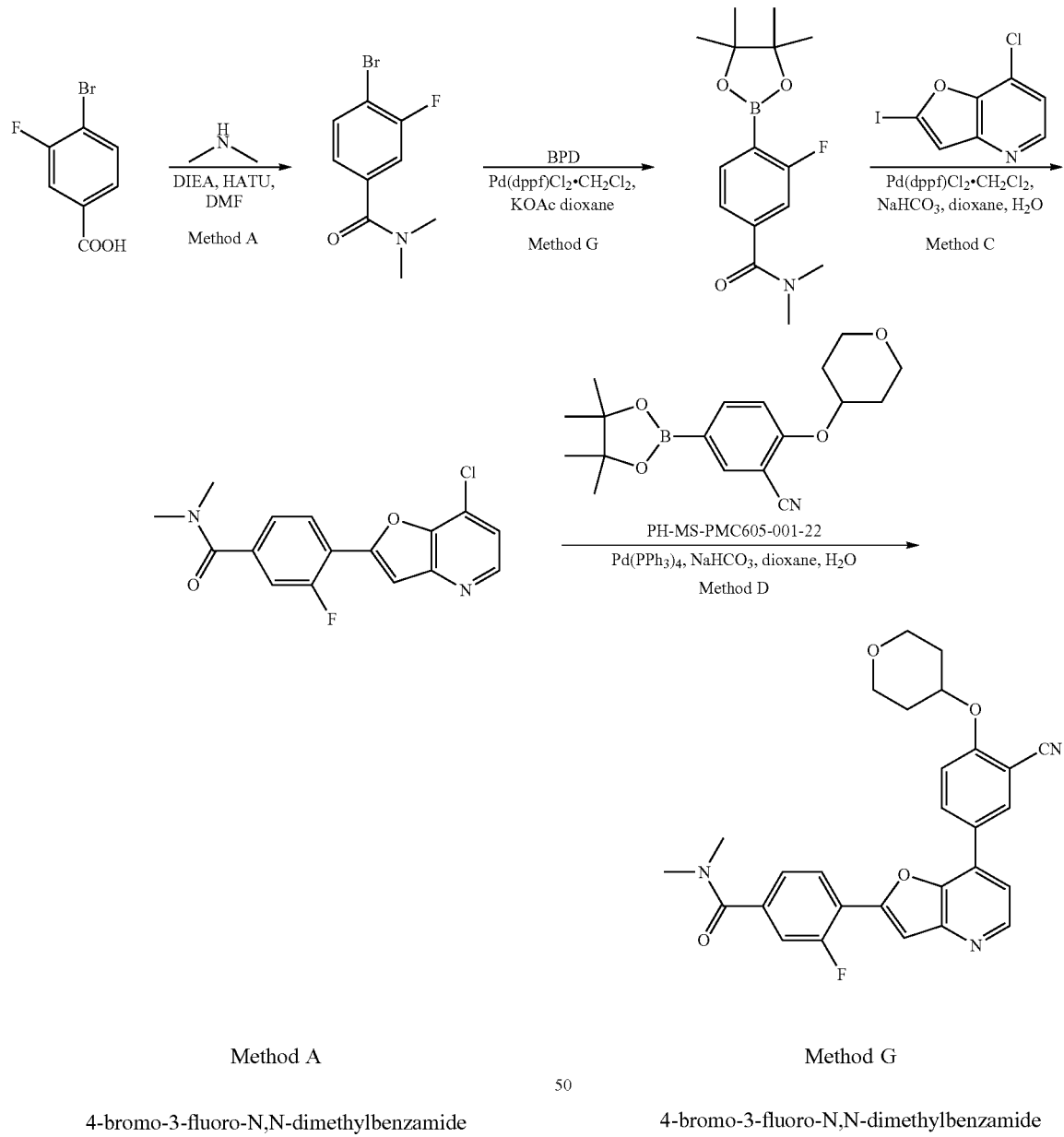

Method A 4-bromo-3-fluoro-N,N-dimethylbenzamide

At room temperature, to a solution of 4-bromo-3-fluorobenzoic acid (5.0 g, 22.83 mmol) in DMF (100 mL) was added dimethylamine (3.2 g, 70.98 mmol), DIEA (8.9 g, 68.86 mmol) and HATU (10.5 g, 27.61 mmol) in sequence. The resulting solution was then stirred for 18 h at 50° C., cooled to room temperature, and treated with water (150 mL). The resulting solution was extracted with ethyl acetate (250 mL×3). The organic phases were combined, washed with brine and dried over sodium sulfate. The solvent was removed under reduced pressure and the residue was purified by flash chromatography eluting with ethyl acetate in hexane (0% to 30% gradient) to yield 4-bromo-3-fluoro-N,N-dimethylbenzamide as yellow oil (2.5 g, 45%). MS: m/z=246.0 [M+H]$^+$.

Method G 4-bromo-3-fluoro-N,N-dimethylbenzamide

To a solution of 4-bromo-3-fluoro-N,N-dimethylbenzamide (2.5 g, 10.16 mmol) in 1,4-dioxane (50 mL) was added 4,4,5,5-tetramethyl-2-(tetramethyl-1,3,2-dioxaborolan-2-yl)-1,3,2-dioxaborolane (2.6 g, 10.16 mmol), potassium acetate (2.0 g, 20.28 mmol) and Pd(dppf)Cl$_2$ (370 mg, 0.51 mmol) at room temperature. The resulting mixture was then stirred for 18 h at 100° C., cooled to room temperature, and treated with water (100 mL). The mixture was extracted with ethyl acetate (250 mL×3). The organic phases were combined, washed with brine and dried over sodium sulfate. The solvent was removed under reduced pressure and the residue was purified by flash chromatography eluting with ethyl acetate in hexane (0% to 100% gradient) to yield 3-fluoro-N,N-dimethyl-4-(tetramethyl-1,3,2-dioxaborolan-2-yl)benzamide as brown solid (2.6 g, 87%). MS: m/z=246.0 [M+H]⁺.

Method C

4-(7-chlorofuro[3,2-b]pyridin-2-yl)-3-fluoro-N,N-dimethylbenzamide

To a solution of 7-chloro-2-iodofuro[3,2-b]pyridine (600 mg, 2.15 mmol) in dioxane (25 mL) was added 3-fluoro-N,N-dimethyl-4-(tetramethyl-1,3,2-dioxaborolan-2-yl)benzamide (629 mg, 2.15 mmol), water (9 mL), sodium bicarbonate (216 mg, 2.58 mmol) and Pd(dppf)Cl₂ (157 mg, 0.21 mmol) at room temperature. The resulting mixture was then stirred for 3 h at 80° C., cooled to room temperature, and treated with water (50 mL). The mixture was extracted with ethyl acetate (150 mL×3). The organic phases were combined, washed with brine and dried over sodium sulfate. The solvent was removed under reduced pressure and the residue was purified by flash chromatography eluting with ethyl acetate in hexane (0% to 100% gradient) to yield 4-[7-chlorofuro[3,2-b]pyridin-2-yl]-3-fluoro-N,N-dimethylbenzamide as brown solid (500 mg, 73%). MS: m/z=319.0 [M+H]⁺.

Method D

4-(7-(3-cyano-4-(tetrahydro-2H-pyran-4-yloxy)phenyl)furo[3,2-b]pyridin-2-yl)-3-fluoro-N,N-dimethyl benzamide To a solution of 4-[7-chlorofuro[3,2-b]pyridin-2-yl]-3-fluoro-N,N-dimethylbenzamide (130 mg, 0.41 mmol) in dioxane (6 mL) was added 2-(oxan-4-yloxy)-5-(tetramethyl-1,3,2-dioxaborolan-2-yl)benzonitrile (134 mg, 0.41 mmol), Pd(PPh₃)₄ (47 mg, 0.04 mmol), sodium bicarbonate (41 mg, 0.49 mmol) and water (2 mL) at room temperature. The reaction mixture was irradiated with microwave for 2 h at 100° C., cooled to room temperature, and treated with water (10 mL). The mixture was extracted with dichloromethane (30 mL×3). The organic phases were combined, washed with brine and dried over sodium sulfate. The solvent was removed under reduced pressure and the residue was purified by prep-HPLC under the following conditions: column, Gemini-NX C18, 21.2×150 mm 5 um; mobile phase, acetonitrile in water (with 10 mmol/L NH₄HCO₃), 15% to 50% gradient in 10 min; detector, UV 254/220 nm. 4-(7-(3-cyano-4-(tetrahydro-2H-pyran-4-yloxy)phenyl)furo[3,2-b]pyridin-2-yl)-3-fluoro-N,N-dimethylbenzamide was obtained as yellow solid (38 mg, 19%). HPLC: 96.4% purity, RT=1.89 min. MS: m/z=486.0 [M+H]⁺. ¹H NMR (400 MHz, CD₃OD, ppm) δ 8.55 (br s, 1H), 8.40 (br s, 2H), 8.13 (d, J=6.4 Hz, 1H), 7.80-7.40 (m, 5H), 4.96 (br s, 1H), 4.17-3.95 (m, 2H), 3.80-3.60 (m, 2H), 3.06 (s, 3H), 3.02 (s, 3H), 2.25-2.10 (m, 2H), 1.99-1.80 (m, 2H).

Example 23: 3-chloro-4-(7-(3-cyano-4-(tetrahydro-2H-pyran-4-yloxy)phenyl)furo[3,2-b]pyridin-2-yl)-N,N-dimethylbenzamide (239)

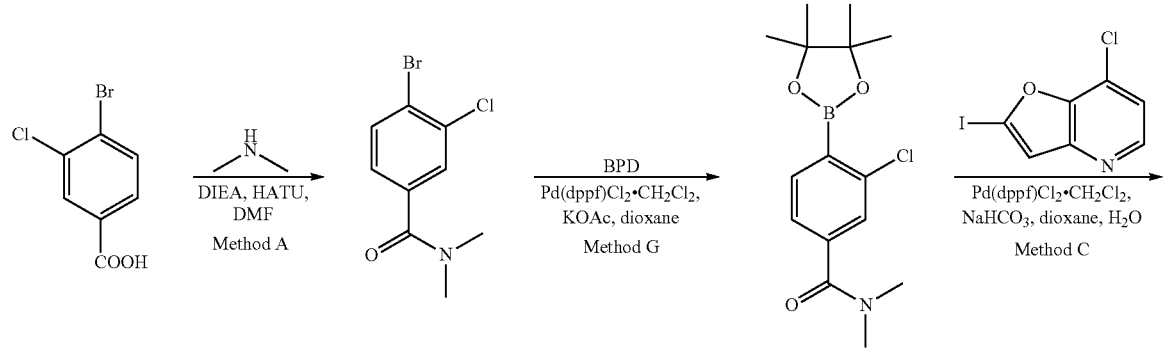

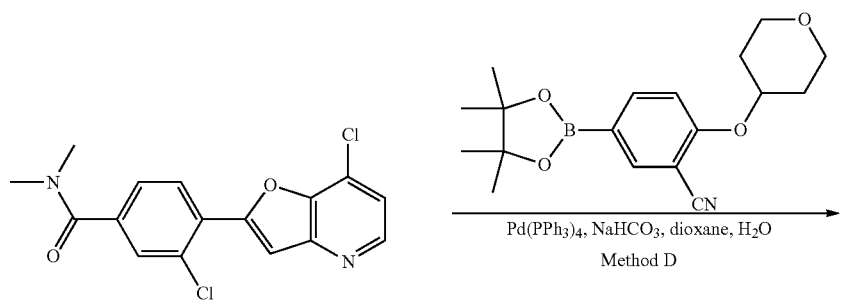

-continued

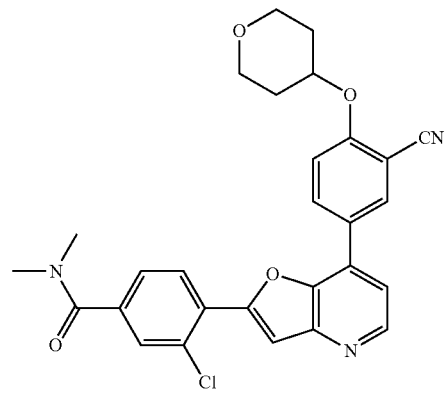

3-chloro-4-(7-(3-cyano-4-(tetrahydro-2H-pyran-4-yloxy)phenyl)furo[3,2-b]pyridin-2-yl)-N,N-dimethylbenzamide 3-chloro-4-(7-(3-cyano-4-(tetrahydro-2H-pyran-4-yloxy)phenyl)furo[3,2-b]pyridin-2-yl)-N,N-dimethylbenzamide was prepared from 4-bromo-3-chlorobenzoic acid, 4,4,5,5-tetramethyl-2-(tetramethyl-1,3,2-dioxaborolan-2-yl)-1,3,2-dioxaborolane, 7-chloro-2-iodofuro[3,2-b]pyridine, 2-(oxan-4-yloxy)-5-(tetramethyl-1,3,2-dioxaborolan-2-yl)benzonitrile using Method A, G, C and D. The final product was purified by prep-HPLC under the following conditions: Gemini-NX C18, 21.2×150 mm 5 um; mobile phase, acetonitrile in water (with 10 mmol/L $NH_4HCO_3$), 15% to 50% gradient in 10 min; detector, UV 254/220 nm. 3-chloro-4-(7-(3-cyano-4-(tetrahydro-2H-pyran-4-yloxy)phenyl)furo[3,2-b]pyridin-2-yl)-N,N-dimethylbenzamide was obtained as yellow solid (68 mg, 2.1% for 4 steps). HPLC: 97.0% purity, RT=5.06 min. MS: m/z=502.0 $[M+H]^+$. $^1$H NMR (300 MHz, DMSO, ppm) δ 8.71 (d, J=5.1 Hz, 1H), 8.62-8.40 (m, 2H), 8.14 (d, J=8.1 Hz, 1H), 7.99-7.80 (m, 2H), 7.76 (s, 1H), 7.70-7.50 (m, 2H), 5.05-4.90 (br s, 1H), 4.00-3.80 (m, 2H), 3.03 (s, 3H), 2.97 (s, 3H), 2.19-2.00 (m, 2H), 1.81-1.60 (m, 2H).

Example 24: 4-(7-(3-cyano-4-(tetrahydro-2H-pyran-4-yloxy)phenyl)furo[3,2-b]pyridin-2-yl)-N,N-dimethyl-3-(trifluoromethyl)benzamide (240)

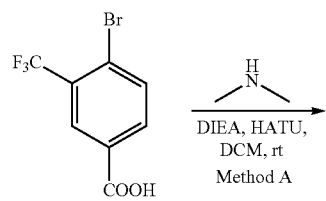

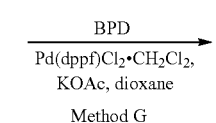

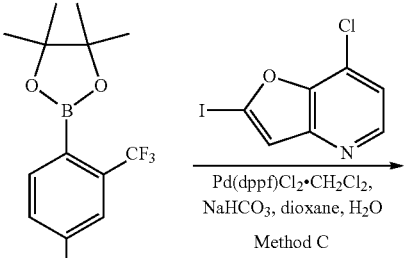

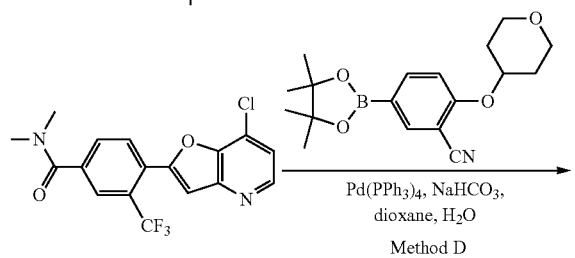

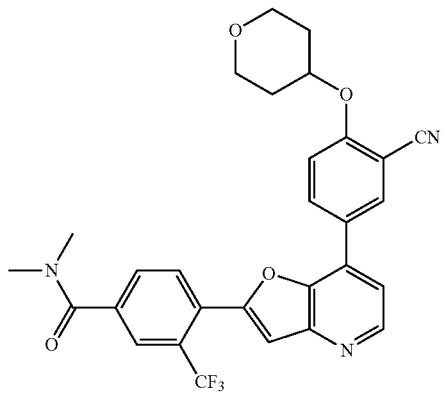

4-(7-(3-cyano-4-(tetrahydro-2H-pyran-4-yloxy)phenyl)furo[3,2-b]pyridin-2-yl)-N,N-dimethyl-3-(trifluoromethyl)benzamide 4-(7-(3-cyano-4-(tetrahydro-2H-pyran-4-yloxy) phenyl)furo[3,2-b]pyridin-2-yl)-N,N-dimethyl-3-(trifluoromethyl)benzamide was prepared from 4-bromo-3-(trifluoromethyl)benzoic acid, 4,4,5,5-tetramethyl-2-(tetramethyl-1,3,2- dioxaborolan-2-yl)-1,3,2-dioxaborolane, 7-chloro-2-iodofuro[3,2-b]pyridine, 2-(oxan-4-yloxy)-5-(tetramethyl-1,3,2-dioxaborolan-2-yl)benzonitrile using Method A, G, C and D. The final product was purified by prep-HPLC under the following conditions: Gemini-NX C18, 21.2×150 mm 5 um; mobile phase, acetonitrile in water (with 10 mmol/L NH$_4$HCO$_3$), 20% to 55% gradient in 10 min; detector, UV 254/220 nm. 4-(7-(3-cyano-4-(tetrahydro-2H-pyran-4-yloxy)phenyl)furo[3,2-b]pyridin-2-yl)-N,N-dimethyl-3-(trifluoromethyl) benzamide was obtained as yellow solid (30 mg, 4.8% for 4 steps). HPLC: 98.3% purity, RT=3.38 min. MS: m/z=536.0 [M+H]$^+$. $^1$H NMR (300 MHz, DMSO, ppm) δ 8.72 (d, J=5.4 Hz, 1H), 8.50 (s, 1H), 8.41-8.37 (m, 1H), 8.15 (d, J=8.1 Hz, 1H), 8.01 (s, 1H), 7.99-7.80 (m, 2H), 7.71 (s, 1H), 7.62 (d, J=9.3 Hz, 1H), 5.05-4.90 (m, 1H), 4.00-3.80 (m, 2H), 3.70-3.60 (m, 2H), 3.05 (s, 3H), 2.97 (s, 3H), 2.13-1.90 (m, 2H), 1.79-1.60 (m, 2H).

Example 25: 4-(7-(3-cyano-4-(tetrahydro-2H-pyran-4-yloxy)phenyl)furo[3,2-b]pyridin-2-yl)-N,N-dimethyl-3-(trifluoromethoxy)benzamide (241)

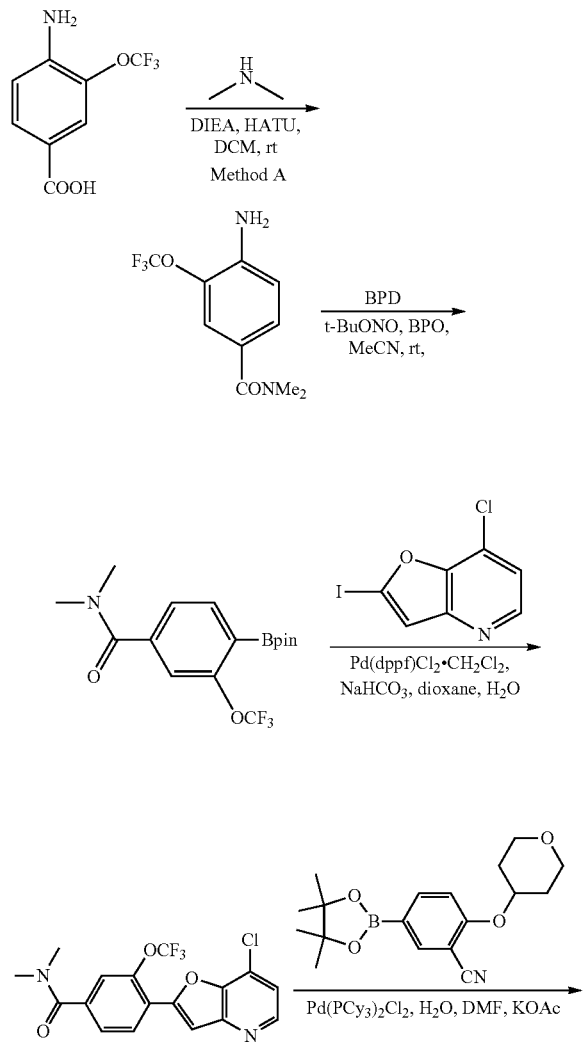

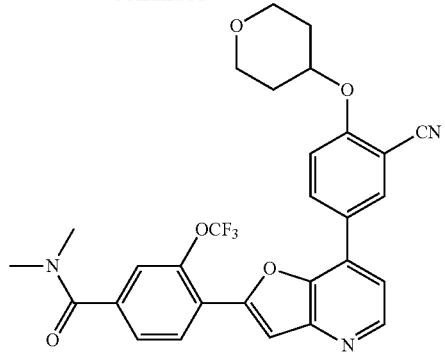

4-amino-N,N-dimethyl-3-(trifluoromethoxy)benzamide 4-amino-N,N-dimethyl-3-(trifluoromethoxy)benzamide was prepared from 4-amino-3-(trifluoromethoxy)benzoic acid using Method A to yield 4-amino-N,N-dimethyl-3-(trifluoromethoxy)benzamide as light brown oil (206 mg, crude).

4-amino-N,N-dimethyl-3-(trifluoromethoxy)benzamide

At room temperature, to a solution of 4-amino-N,N-dimethyl-3-(trifluoromethoxy)benzamide (206 mg, crude) in acetonitrile (10 mL) was added 4,4,5,5-tetramethyl-2-(tetramethyl-1,3,2-dioxaborolan-2-yl)-1,3,2-dioxaborolane (307 mg, 1.21 mmol), benzoperoxide (6 mg, 0.02 mmol) and 2-methyl-2-nitropropane (186 mg, 1.80 mmol). The resulting solution was stirred for 5 h at room temperature and then diluted with water (10 mL). The mixture was extracted with ethyl acetate (30 mL×3). The organic phases were combined, washed with brine and dried over sodium sulfate. The solvent was removed under reduced pressure and the residue was purified by flash chromatography eluting with ethyl acetate in hexane (0% to 20% gradient) to yield N,N-dimethyl-4-(tetramethyl-1,3,2-dioxaborolan-2-yl)-3-(trifluoromethoxy) benzamide as light brown oil (200 mg, 49% for 2 steps). MS: m/z=360.0 [M+H]$^+$.

4-(7-chlorofuro[3,2-b]pyridin-2-yl)-N,N-dimethyl-3-(trifluoromethoxy)benzamide

To a solution of 7-chloro-2-iodofuro[3,2-b]pyridine (200 mg, 0.72 mmol) in dioxane (10 mL) was added N,N-dimethyl-4-(tetramethyl-1,3,2-dioxaborolan-2-yl)-3-(trifluoromethoxy)benzamide (400 mg, 1.12 mmol), Pd(dppf)Cl$_2$.CH$_2$Cl$_2$ (120 mg, 0.14 mmol), sodium bicarbonate (180 mg, 2.14 mmol) and water (2 mL) at room temperature. The resulting mixture was stirred for 2 h at 100° C., cooled to room temperature, and diluted with water (10 mL). The mixture was extracted with ethyl acetate (30 mL×3). The organic phases were combined, washed with brine and dried over sodium sulfate. The solvent was removed under reduced pressure and the residue was purified by flash chromatography eluting with ethyl acetate in hexane (0% to 100% gradient) to yield 4-[7-chlorofuro[3,2-b]pyridin-2-yl]-N,N-dimethyl-3-(trifluoromethoxy) benzamide as light brown solid (150 mg, 54%). MS: m/z=385.0 [M+H]$^+$.

4-(7-(3-cyano-4-(tetrahydro-2H-pyran-4-yloxy)phenyl)furo[3,2-b]pyridin-2-yl)-N,N-dimethyl-3-(trifluoromethoxy)benzamide To a solution of 4-[7-chlorofuro[3,2-b]pyridin-2-yl]-N,N-dimethyl-3-(trifluoromethoxy)benzamide (150 mg) in DMF (6 mL) was added 2-(oxan-4-yloxy)-5-(tetramethyl-1,3,2-dioxaborolan-2-yl)benzonitrile (141 mg, 0.43 mmol), Pd(PCy$_3$)$_2$Cl$_2$ (29 mg, 0.04 mmol), potassium acetate (115 mg, 1.17 mmol) and water (2 mL) at room temperature. The resulting mixture was stirred for 2 h at 100° C., cooled to room temperature, and diluted with water (10 mL). The mixture was extracted with dichloromethane (30 mL×3). The organic phases were combined, washed with brine and dried over sodium sulfate. The solvent was removed under reduced pressure and the residue was purified by prep-HPLC under the following conditions: column, XBridge Prep C18 OBD column, 19×150 mm 5 um 13 nm; mobile phase, acetonitrile in water (with 10 mmol/L NH$_4$HCO$_3$), 20% to 40% gradient in 10 min; detector, UV 254/220 nm. 4-(7-(3-cyano-4-(tetrahydro-2H-pyran-4-yloxy)phenyl)furo[3,2-b]pyridin-2-yl)-N,N-dimethyl-3-(trifluoromethoxy)benzamide was obtained as yellow solid (16 mg, 7%). HPLC: 97.9% purity, RT=1.38 min. MS: m/z=552.0 [M+H]$^+$. $^1$H NMR (300 MHz, CD$_3$OD, ppm) δ 8.68 (d, J=5.4 Hz, 1H), 8.55-8.40 (m, 2H), 8.26 (d, J=8.4 Hz, 1H), 7.92 (d, J=5.7 Hz, 1H), 7.75-7.59 (m, 3H), 7.54 (d, J=9.0 Hz, 1H), 5.05-4.90 (m, 1H), 4.08-3.90 (m, 2H), 3.75-3.60 (m, 2H), 3.12 (s, 3H), 3.02 (s, 3H), 2.21-2.05 (m, 2H), 1.93-1.75 (m, 2H).

Example 26: 6-(7-(3-cyano-4-(tetrahydro-2H-pyran-4-yloxy)phenyl)furo[3,2-b]pyridin-2-yl)-N,N-dimethylpyridazine-3-carboxamide hydrochloride (242)

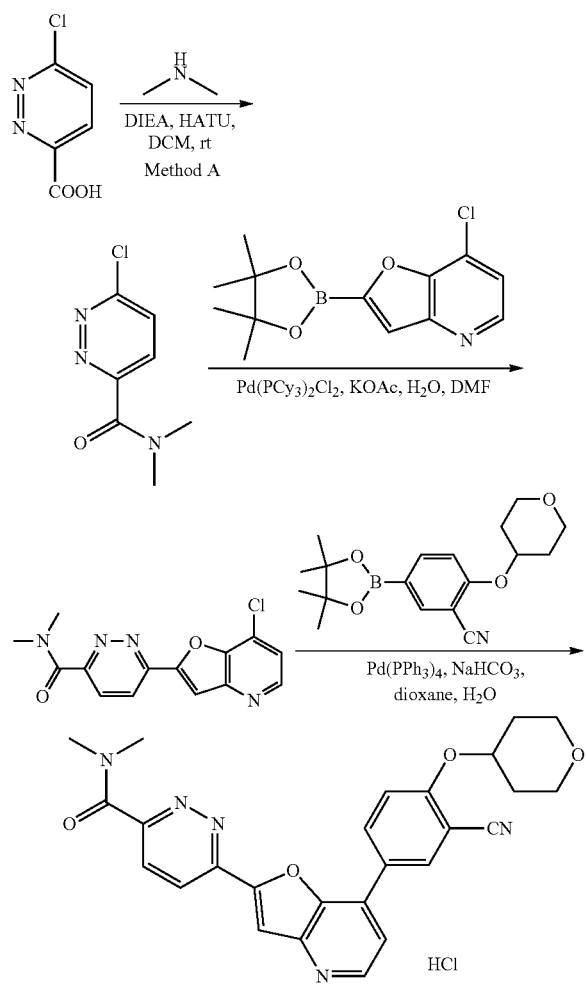

6-chloro-N,N-dimethylpyridazine-3-carboxamide 6-chloro-N,N-dimethyl pyridazine-3-carboxamide was prepared from 6-chloropyridazine-3-carboxylic acid using Method A to yield 6-chloro-N,N-dimethylpyridazine-3-carboxamide as light brown oil (1.3 g, crude). MS: m/z=186.0 [M+H]$^+$.

6-(7-chlorofuro[3,2-b]pyridin-2-yl)-N,N-dimethyl-pyridazine-3-carboxamide

To a solution of 6-chloro-N,N-dimethylpyridazine-3-carboxamide (300 mg, crude) in DMF (6 mL) was added 7-chloro-2-(tetramethyl-1,3,2-dioxaborolan-2-yl)furo[3,2-b]pyridine (542 mg, 1.94 mmol), potassium acetate (475 mg, 4.84 mmol), Pd(PCy$_3$)$_2$Cl$_2$ (119 mg, 0.16 mmol) and water (2 mL) at room temperature. The reaction mixture was irradiated with microwave for 45 min at 70° C., cooled to room temperature, and diluted with water (50 mL). The mixture was extracted with ethyl acetate (15 mL×3). The organic phases were combined, washed with brine and dried over sodium sulfate. The solvent was removed under reduced pressure and the residue was purified by flash chromatography eluting with ethyl acetate in hexane (0% to 100% gradient) to yield 6-[7-chlorofuro[3,2-b]pyridin-2-yl]-N,N-dimethylpyridazine-3-carboxamide as light yellow solid (151 mg, 31%). MS: m/z=303.0 [M+H]$^+$.

6-(7-(3-cyano-4-(tetrahydro-2H-pyran-4-yloxy)phenyl)furo[3,2-b]pyridin-2-yl)-N,N-dimethyl pyridazine-3-carboxamide hydrochloride To a solution of 6-[7-chlorofuro[3,2-b]pyridin-2-yl]-N,N-dimethylpyridazine-3-carboxamide (130 mg, 0.43 mmol) in dioxane (4 mL) was added 2-(oxan-4-yloxy)-5-(tetramethyl-1,3,2-dioxaborolan-2-yl)benzonitrile (170 mg, 0.52 mmol), Pd(PPh$_3$)$_4$ (99 mg, 0.09 mmol), sodium bicarbonate (108 mg, 1.29 mmol) and water (1 mL) at room temperature. The reaction mixture was irradiated with microwave for 2 h at 100° C., cooled to room temperature, and diluted with water (10 mL). The mixture was extracted with dichloromethane (30 mL×3). The organic phases were combined, washed with brine and dried over sodium sulfate. The solvent was removed under reduced pressure and the residue was purified by prep-HPLC under the following conditions: column, Gemini-NX C18, 21.2×150 mm 5 um; mobile phase, acetonitrile in water (with 0.02% HCl), 15% to 50% gradient in 10 min; detector, UV 254/220 nm. 6-(7-(3-cyano-4-(tetrahydro-2H-pyran-4-yloxy)phenyl) furo[3,2-b]pyridin-2-yl)-N,N-dimethyl pyridazine-3-carboxamide hydrochloride was obtained as yellow solid (17 mg, 8%). HPLC: 99.7% purity, RT=1.62 min. MS: m/z=470.0 [M+H]$^+$. $^1$H NMR (300 MHz, DMSO, ppm) δ 8.75 (d, J=19.8 Hz, 1H), 8.62-8.40 (m, 3H), 8.25-8.00 (m, 2H), 7.87 (d, J=5.1 Hz, 1H), 7.64 (d, J=8.7 Hz, 1H), 5.05-4.90 (m, 1H), 4.03-3.80 (m, 2H), 3.75-3.60 (m, 2H), 3.10 (s, 3H), 3.03 (s, 3H), 2.15-1.90 (m, 2H), 1.80-1.60 (m, 2H).

Example 27: 6-(7-(3-cyano-4-(tetrahydro-2H-pyran-4-yloxy)phenyl)furo[3,2-b]pyridin-2-yl)-N,N-dimethylnicotinamide (243)

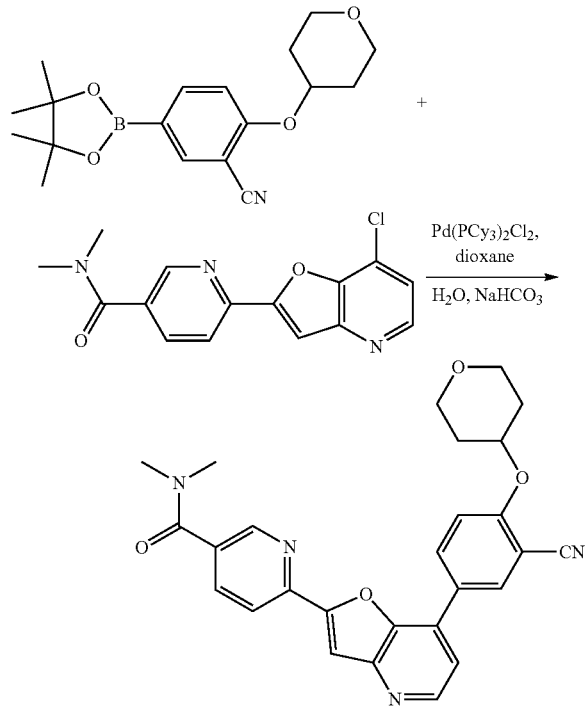

6-(7-(3-cyano-4-(tetrahydro-2H-pyran-4-yloxy)phenyl)furo[3,2-b]pyridin-2-yl)-N,N-dimethylnicotinamide To a solution of 6-[7-chlorofuro[3,2-b]pyridin-2-yl]-N,N-dimethylpyridine-3-carboxamide (600 mg, 1.99 mmol) in dioxane (10 mL) was added 2-(oxan-4-yloxy)-5-(tetramethyl-1,3,2-dioxaborolan-2-yl)benzonitrile (784 mg, 2.38 mmol), Pd(PCy$_3$)$_2$Cl$_2$ (148 mg, 0.20 mmol), sodium bicarbonate (504 mg, 6.00 mmol) and water (3 mL) at room temperature. The reaction mixture was then stirred for 2 h at 100° C. in an oil bath, cooled to room temperature, and then diluted with water (10 mL). The mixture was extracted with dichloromethane (30 mL×3). The organic phases were combined, washed with brine and dried over sodium sulfate. The solvent was removed under reduced pressure and the residue was purified by prep-HPLC under the following conditions: column, Gemini-NX C18 AXAI Packed, 21.2, 100 mm 5 um 11 nm; mobile phase, acetonitrile in water (with 10 mmol/L NH$_4$HCO$_3$), 20% to 40% gradient in 10 min; detector, UV 254/220 nm. 6-(7-(3-cyano-4-(tetrahydro-2H-pyran-4-yloxy)phenyl)furo[3,2-b]pyridin-2-yl)-N,N-dimethylnicotinamide was obtained as yellow solid (300 mg, 32%). HPLC: 98.9% purity, RT=1.08 min. MS: m/z=469.0 [M+H]$^+$. $^1$H NMR (400 MHz, DMSO, ppm) δ 8.82 (s, 1H), 8.73 (d, J=5.2 Hz, 1H), 8.60-8.50 (m, 2H), 8.19 (d, J=8.0 Hz, 1H), 8.12 (dd, J=8.0, 2.4 Hz, 1H), 7.98-7.85 (m, 2H), 7.69 (d, J=9.2 Hz, 1H), 5.05-4.90 (m, 1H), 3.98-3.80 (m, 2H), 3.68-3.50 (m, 2H), 3.05 (s, 3H), 3.00 (s, 3H), 2.11-2.08 (dd, J$_1$=3.6 Hz, J$_2$=9.2 Hz, 1H), 1.80-1.63 (m, 2H).

Example 28: 6-(7-(3-cyano-4-(tetrahydro-2H-pyran-4-ylamino)phenyl)furo[3,2-b]pyridin-2-yl)-N,N-dimethylnicotinamide (244)

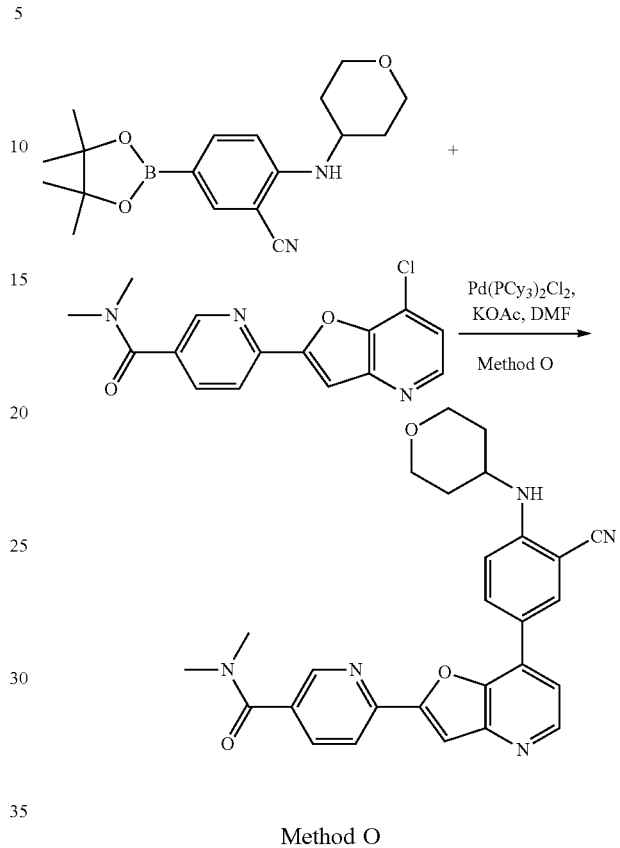

Method O 6-(7-(3-cyano-4-(tetrahydro-2H-pyran-4-ylamino)phenyl)furo[3,2-b]pyridin-2-yl)-N,N-dimethylnicotinamide To a solution of 6-[7-chlorofuro[3,2-b]pyridin-2-yl]-N,N-dimethylpyridine-3-carboxamide (140 mg, 0.46 mmol) in DMF (6 mL) was added 2-(morpholin-4-ylmethyl)-5-(tetramethyl-1,3,2-dioxaborolan-2-yl)benzonitrile (153 mg, 0.47 mmol), Pd(PCy$_3$)$_2$Cl$_2$ (35 mg, 0.05 mmol) and potassium acetate (136 mg, 1.39 mmol) at room temperature. The reaction mixture was irradiated with microwave for 1 h at 100° C., cooled to room temperature, and diluted with water (10 mL). The mixture was extracted with dichloromethane (30 mL×3). The organic phases were combined, washed with brine and dried over sodium sulfate. The solvent was removed under reduced pressure and the residue was purified by prep-HPLC under the following conditions: column, Atlantis Prep T$_3$ OBD column, 19×150 mm 5 um 10 nm; mobile phase, acetonitrile in water (with 10 mmol/L NH$_4$HCO$_3$), 20% to 50% gradient in 8 min; detector, UV 254/220 nm. 6-(7-(3-cyano-4-(tetrahydro-2H-pyran-4-ylamino)phenyl)furo[3,2-b]pyridin-2-yl)-N,N-dimethylnicotinamide was obtained as yellow solid (30 mg, 14%). HPLC: 99.9% purity, RT=1.53 min. MS: m/z=468.0 [M+H]$^+$. $^1$H NMR (400 MHz, DMSO, ppm) δ 8.79 (s, 1H), 8.56 (d, J=5.2 Hz, 1H), 8.38-8.28 (m, 2H), 8.18-8.08 (m, 2H), 7.81 (s, 1H), 7.68 (d, J=5.2 Hz, 1H), 7.19 (d, J=8.8 Hz, 1H), 6.29 (d, J=8.0 Hz, 1H), 3.92 (d, J=10.0 Hz, 2H), 3.88-3.75 (m, 1H), 3.05 (s, 3H), 3.00 (s, 3H), 2.09 (dd, J=9.2, 3.6 Hz, 1H), 1.80-1.63 (m, 2H).

Example 29: 6-(7-(3-cyano-5-fluoro-4-(tetrahydro-2H-pyran-4-yloxy)phenyl)furo[3,2-b]pyridin-2-yl)-N,N-dimethylnicotinamide hydrochloride (245)

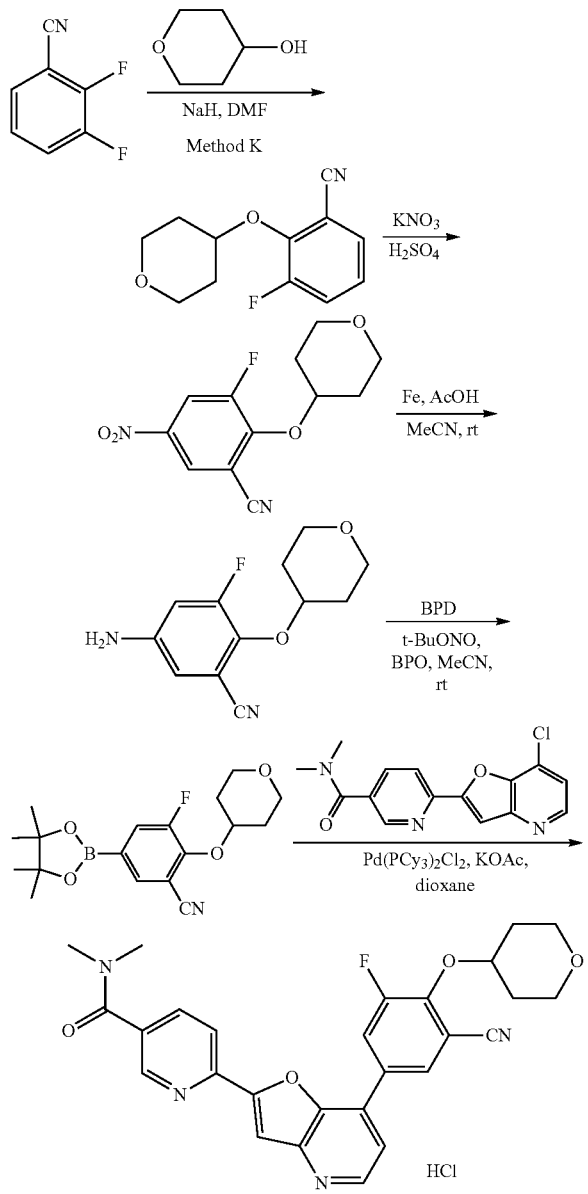

3-fluoro-2-(tetrahydro-2H-pyran-4-yloxy)benzonitrile 3-fluoro-2-(tetrahydro-2H-pyran-4-yloxy)benzonitrile was prepared from 2,3-difluorobenzonitrile and tetrahydro-2H-pyran-4-ol using Method K. The product was purified by flash chromatography eluting with EtOAc in hexane (0% to 8% gradient) to yield 3-fluoro-2-(oxan-4-yloxy)benzonitrile as white solid (780 mg, 98%). MS: m/z=222.0 [M+H]$^+$.

3-fluoro-5-nitro-2-(tetrahydro-2H-pyran-4-yloxy)benzonitrile

At 0° C., to a solution of 3-fluoro-2-(oxan-4-yloxy)benzonitrile (7.0 g, 31.64 mmol) in sulfuric acid (50 mL) was added potassium nitrate (6.4 g, 63.30 mmol) slowly. The resulting solution was stirred for 2 h at 0° C. and then treated with ice water (50 mL). The solid that formed in the reaction mixture was removed by filtration and the filtrate was extracted with ethyl acetate (50 mL×3). The organic phases were combined, washed with brine and dried over sodium sulfate. The solvent was removed under reduced pressure to yield 3-fluoro-5-nitro-2-(oxan-4-yloxy)benzonitrile as white solid (8.0 g, 95%).

5-amino-3-fluoro-2-(tetrahydro-2H-pyran-4-yloxy)benzonitrile

To a solution of 3-fluoro-5-nitro-2-(oxan-4-yloxy)benzonitrile (8.0 g, 30.05 mmol) in acetonitrile (100 mL) was added iron powder (11.8 g, 210.40 mmol) and acetic acid (36.1 g, 600.98 mmol) at room temperature. The resulting mixture was stirred for 2 h at room temperature and then diluted with water (40 mL). The pH value of the mixture was adjusted to 8 with saturated sodium bicarbonate solution. The resulting mixture was then extracted with ethyl acetate (50 mL×3). The organic phases were combined, washed with brine and dried over sodium sulfate. The solvent was removed under reduced pressure to yield 5-amino-3-fluoro-2-(oxan-4-yloxy)benzonitrile as a light brown solid (6 g, 85%).

3-fluoro-2-(tetrahydro-2H-pyran-4-yloxy)-5-(4,4,5,5-tetramethyl-1,3,2-dioxaborolan-2-yl)benzonitrile To a solution of 5-amino-3-fluoro-2-(oxan-4-yloxy)benzonitrile (1.0 g, 4.23 mmol) in acetonitrile (20 mL) was added 4,4,5,5-tetramethyl-2-(tetramethyl-1,3,2-dioxaborolan-2-yl)-1,3,2-dioxaborolane (1.2 g, 4.65 mmol), benzoperoxide (50 mg, 0.20 mmol), tert-butyl nitrite (870 mg, 8.44 mmol) at room temperature. The resulting mixture was stirred for 4 h at room temperature and then diluted with water (30 mL). The resulting mixture was extracted with ethyl acetate (50 mL×3). The organic phases were combined, washed with brine and dried over sodium sulfate. The solvent was removed under reduced pressure and the residue was purified by flash chromatography eluting with ethyl acetate in hexane (0% to 10% gradient) to yield 3-fluoro-2-(oxan-4-yloxy)-5-(tetramethyl-1,3,2-dioxaborolan-2-yl)benzonitrile as yellow oil (500 mg, 34%).

6-(7-(3-cyano-5-fluoro-4-(tetrahydro-2H-pyran-4-yloxy)phenyl)furo[3,2-b]pyridin-2-yl)-N,N-dimethylnicotinamide hydrochloride To a solution of 6-[7-chlorofuro[3,2-b]pyridin-2-yl]-N,N-dimethylpyridine-3-carboxamide (100 mg, 0.33 mmol) in dioxane (5 mL) was added 3-fluoro-2-(oxan-4-yloxy)-5-(tetramethyl-1,3,2-dioxaborolan-2-yl)benzonitrile (127 mg, 0.36 mmol), Pd(PCy$_3$)$_2$Cl$_2$ (25 mg, 0.03 mmol) and potassium acetate (98 mg, 0.99 mmol) at room temperature. The resulting mixture was then stirred for 2 h at 80° C., cooled to room temperature, and diluted with water (10 mL). The mixture was extracted with dichloromethane (30 mL×3). The organic phases were combined, washed with brine and dried over sodium sulfate. The solvent was removed under reduced pressure and the residue was purified by prep-HPLC under the following conditions: column, Gemini-NX C18, 21.2×150 mm 5 um; mobile phase, acetonitrile in water (with 0.02% HCl), 20% to 50% gradient in 8 min; detector, UV 254/220 nm. 6-[7-chlorofuro[3,2-b]pyridin-2-yl]-N,N-dimethylpyridine-3-carboxamide was obtained as yellow solid (20 mg, 11%). HPLC: 94.2% purity, RT=3.46 min. MS: m/z=487.0 [M+H]+. ¹H NMR (400 MHz, DMSO, ppm) δ 8.80 (s, 1H), 8.72 (d, J=5.2 Hz, 1H), 8.55-8.41 (m, 2H), 8.21-8.10 (m, 2H), 7.90 (s, 1H), 7.85 (d, J=5.2 Hz, 1H), 4.85-4.63 (m, 1H), 4.00-3.85 (m, 2H), 3.58-3.40 (m, 2H), 3.04 (s, 3H), 2.99 (s, 3H), 2.11-1.90 (m, 2H), 1.85-1.73 (m, 2H).

Example 30: 6-(7-(3-cyano-5-fluoro-4-(tetrahydro-2H-pyran-4-yloxy)phenyl)furo[3,2-b]pyridin-2-yl)-N,N-dimethylnicotinamide (246)

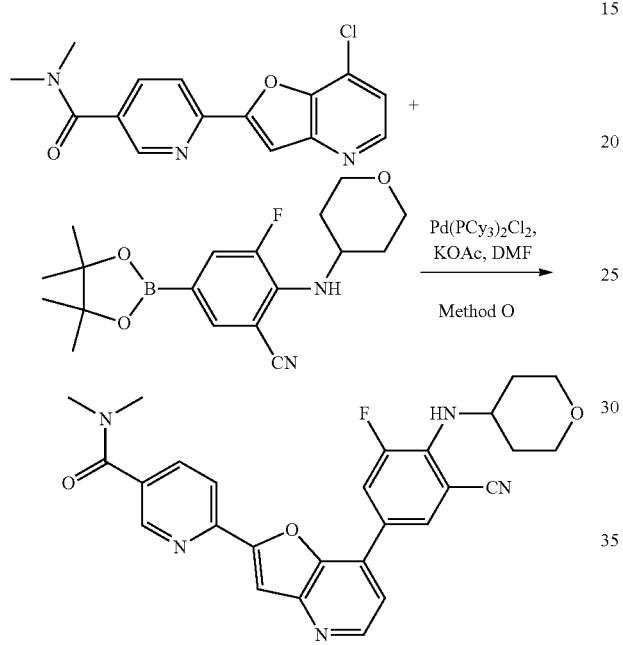

6-(7-(3-cyano-5-fluoro-4-(tetrahydro-2H-pyran-4-yloxy)phenyl)furo[3,2-b]pyridin-2-yl)-N,N-dimethylnicotinamide 6-(7-(3-cyano-5-fluoro-4-(tetrahydro-2H-pyran-4-yloxy)phenyl)furo[3,2-b]pyridin-2-yl)-N,N-dimethylnicotinamide was prepared from 3-fluoro-2-(tetrahydro-2H-pyran-4-ylamino)-5-(4,4,5,5-tetramethyl-1,3,2-dioxaborolan-2-yl)benzonitrile and 6-[7-chlorofuro[3,2-b]pyridin-2-yl]-N,N-dimethylpyridine-3-carboxamide using Method O. The product was purified by prep-HPLC under the following conditions: column Atlantis Prep T₃ OBD column, 19×150 mm 5 um 10 nm; mobile phase, acetonitrile in water (with 10 mmol/L NH₄HCO₃), 20% to 50% gradient in 8 min; detector, UV 254/220 nm. 6-(7-(3-cyano-5-fluoro-4-(tetrahydro-2H-pyran-4-yloxy)phenyl)furo[3,2-b]pyridin-2-yl)-N,N-dimethylnicotinamide was obtained as light yellow solid (30 mg, 13%). HPLC: 94.2% purity, RT=3.46 min. MS: m/z=486.0 [M+H]+. ¹H NMR (400 MHz, DMSO, ppm) δ 8.80 (s, 1H), 8.59 (d, J=5.2 Hz, 1H), 8.21 (d, J=2.0 Hz, 1H), 8.18 (s, 1H), 8.10 (s, 2H), 7.83 (s, 1H), 7.72 (d, J=5.2 Hz, 1H), 6.48 (dd, J=9.2, 3.6 Hz, 1H), 4.28-4.13 (m, 1H), 3.94 (d, J=10.4 Hz, 2H), 3.35-3.20 (m, 2H), 3.04 (s, 3H), 3.00 (s, 3H), 1.93 (d, J=10.0 Hz, 2H), 1.78-1.63 (m, 2H).

Example 31: 6-(7-(3-cyano-5-fluoro-4-(tetrahydro-2H-pyran-4-yloxy)phenyl)furo[3,2-b]pyridin-2-yl)-5-fluoro-N,N-dimethylnicotinamide (247)

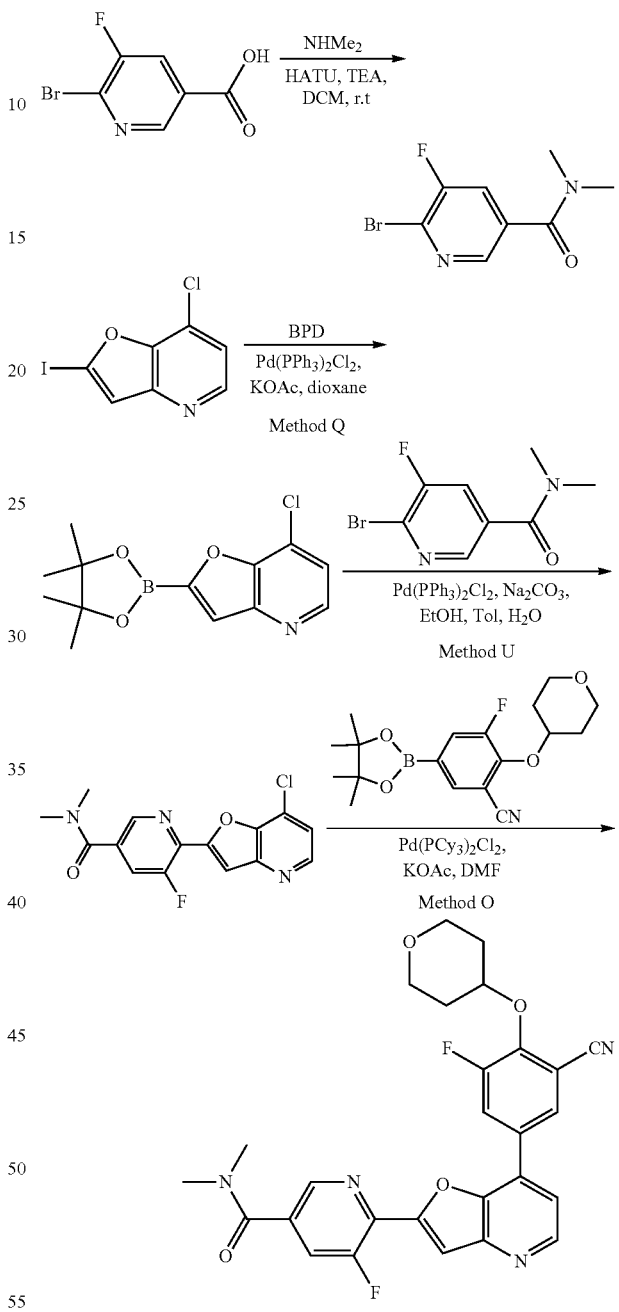

6-bromo-5-fluoro-N,N-dimethylnicotinamide

At room temperature, to a solution of 6-bromo-5-fluoropyridine-3-carboxylic acid (900.0 mg, 4.09 mmol) and dimethylamine hydrochloride (667 mg, 8.18 mmol) in dichloromethane (10 mL) were added triethylamine (2.07 g, 20.45 mmol) and HATU (1.86 g, 4.91 mmol) in sequence. The resulting solution was stirred for 18 h at room temperature and then diluted with water (50 mL). The resulting solution was extracted with ethyl acetate (100 mL×3). The organic phases were combined, washed with brine and dried over sodium sulfate. The solvent was removed under reduced pressure and the residue was purified by flash chromatography eluting with ethyl acetate in hexane (0% to 9% gradient) to yield 6-bromo-5-fluoro-N,N-dimethylpyridine-3-carboxamide as brown oil (800 mg, 80%). MS: m/z=247.0 [M+H]+.

6-(7-(3-cyano-5-fluoro-4-(tetrahydro-2H-pyran-4-yloxy)phenyl)furo[3,2-b]pyridin-2-yl)-5-fluoro-N,N-dimethylnicotinamide 6-(7-(3-cyano-5-fluoro-4-(tetrahydro-2H-pyran-4-yloxy)phenyl)furo[3,2-b]pyridin-2-yl)-5-fluoro-N,N-dimethylnicotinamide was prepared from 7-chloro-2-(tetramethyl-1,3,2-dioxaborolan-2-yl)furo[3,2-b]pyridine, 6-bromo-5-fluoro-N,N-dimethylnicotinamide and 3-fluoro-2-(tetrahydro-2H-pyran-4-yloxy)-5-(4,4,5,5-tetramethyl-1,3,2-dioxaborolan-2-yl)benzonitrile using Method Q, U, and O. The final product was purified by prep-HPLC under the following conditions: column XBridge Prep C18 OBD column, 19×150 mm 5 um 13 nm; mobile phase, acetonitrile in water (with 10 mmol/L NH4HCO3), 20% to 50% gradient in 8 min; detector, UV 254/220 nm. 6-(7-(3-cyano-5-fluoro-4-(tetrahydro-2H-pyran-4-yloxy)phenyl)furo[3,2-b]pyridin-2-yl)-5-fluoro-N,N-dimethylnicotinamide was obtained as light yellow solid (5 mg, 4.5% for 3 steps) HPLC: 93.6% purity, RT=1.24 min. MS: m/z=505.0 [M+H]+. 1H NMR (400 MHz, CD3OD, ppm) δ 8.85-8.65 (m, 2H), 8.50-8.35 (m, 2H), 8.10-7.90 (m, 2H), 7.74 (s, 1H), 5.05-4.90 (m, 1H), 4.12-3.95 (m, 2H), 3.70-3.50 (m, 2H), 3.16 (s, 3H), 3.10 (s, 3H), 2.18-2.05 (m, 2H), 1.97-1.85 (m, 2H).

Example 32: 6-(7-(3-cyano-5-fluoro-4-(tetrahydro-2H-pyran-4-ylamino)phenyl)furo[3,2-b]pyridin-2-yl)-5-fluoro-N,N-dimethylnicotinamide (248)

Method R 6-(7-(3-cyano-5-fluoro-4-(tetrahydro-2H-pyran-4-ylamino)phenyl)furo[3,2-b]pyridin-2-yl)-5-fluoro-N,N-dimethylnicotinamide To a solution of 6-[7-chlorofuro[3,2-b]pyridin-2-yl]-5-fluoro-N,N-dimethylpyridine-3-carboxamide (90 mg, 0.28 mmol) in DMF (3 mL) was added 3-fluoro-2-[(oxan-4-yl)amino]-5-(tetramethyl-1,3,2-dioxaborolan-2-yl)benzonitrile (99 mg, 0.29 mmol), Pd(Pcy3)2Cl2 (21 mg, 0.03 mmol), sodium bicarbonate (10 mg, 0.12 mmol) and water (1 mL) at room temperature. The resulting mixture was then stirred for 2 h at 90° C., cooled to room temperature, and diluted with water (10 mL). The mixture was extracted with dichloromethane (30 mL×3). The organic phases were combined, washed with brine and dried over sodium sulfate. The solvent was removed under reduced pressure and the residue was purified by prep-HPLC under the following conditions: column, Gemini-NX C18, 21.2×150 mm 5 um; mobile phase, acetonitrile in water (with 10 mmol/L NH4HCO3), 20% to 60% gradient in 8 min; detector, UV 254/220 nm. 6-(7-(3-cyano-5-fluoro-4-(tetrahydro-2H-pyran-4-ylamino)phenyl)furo[3,2-b]pyridin-2-yl)-5-fluoro-N,N-dimethylnicotinamide was obtained as light yellow solid (20 mg, 14%). HPLC: 98.8% purity, RT=1.15 min. MS: m/z=504.0 [M+H]+. 1H NMR (400 MHz, DMSO, ppm) δ 8.69 (d, J=1.6 Hz, 1H), 8.62 (d, J=9.2 Hz, 1H), 8.30-8.20 (m, 2H), 8.12 (dd, J=11.6, 1.6 Hz, 1H), 7.84-7.75 (m, 2H), 6.51 (dd, J=8.8, 3.2 Hz, 1H), 4.28-4.12 (m, 1H), 3.93 (dd, J=12.0, 2.4 Hz, 2H), 3.45-3.30 (m, 2H), 3.04 (s, 3H), 3.00 (s, 3H), 1.98-1.86 (m, 2H), 1.80-162 (m, 2H).

Example 33: 6-(7-(3-cyano-4-(tetrahydro-2H-pyran-4-ylamino)phenyl)furo[3,2-b]pyridin-2-yl)-5-fluoro-N,N-dimethylnicotinamide (249)

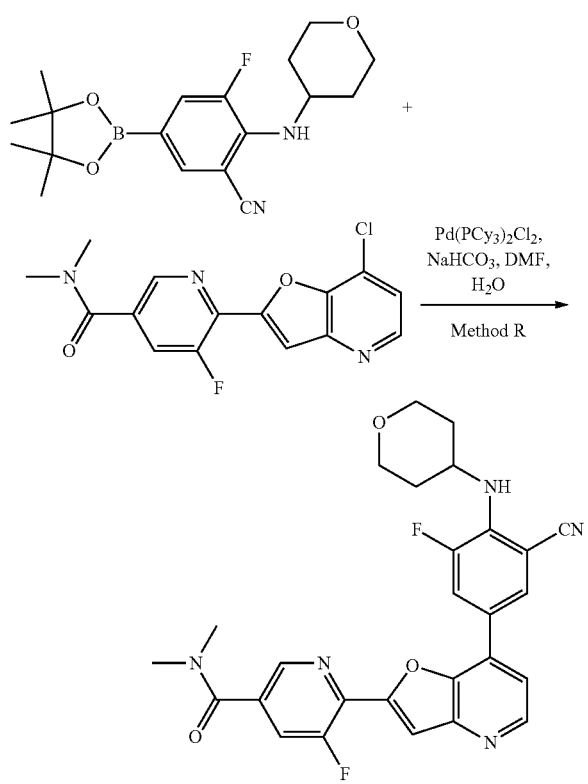
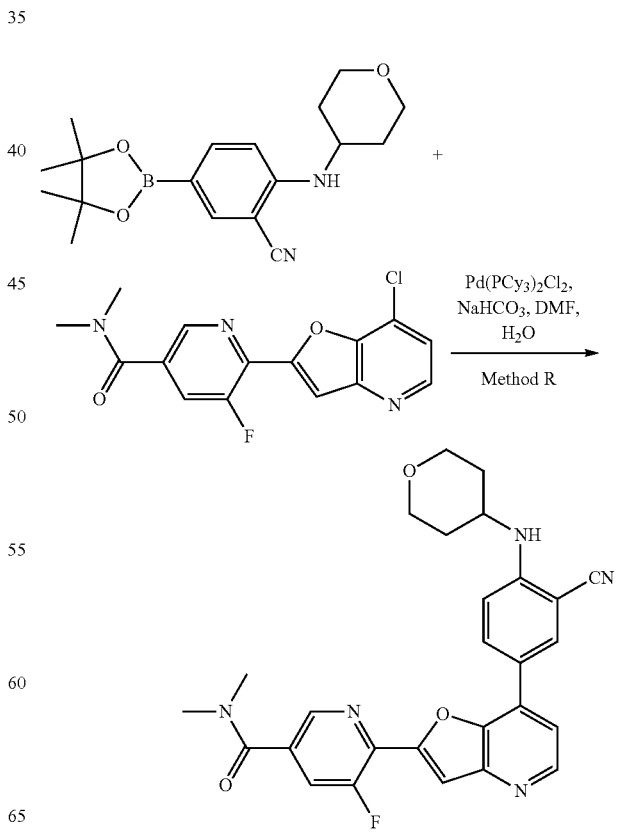

6-(7-(3-cyano-4-(tetrahydro-2H-pyran-4-ylamino)phenyl)furo[3,2-b]pyridin-2-yl)-5-fluoro-N,N-dimethylnicotinamide 6-(7-(3-cyano-4-(tetrahydro-2H-pyran-4-ylamino)phenyl)furo[3,2-b]pyridin-2-yl)-5-fluoro-N,N-dimethylnicotinamide was prepared from 6-(7-chlorofuro[3,2-b]pyridin-2-yl)-5-fluoro-N,N-dimethylnicotinamide and 2-(tetrahydro-2H-pyran-4-ylamino)-5-(4,4,5,5-tetramethyl-1,3,2-dioxaborolan-2-yl)benzonitrile using Method R. The final product was purified by prep-HPLC under the following conditions: column Gemini-NX C18, 21.2×150 mm 5 um; mobile phase, acetonitrile in water (with 10 mmol/L NH$_4$HCO$_3$), 20% to 50% gradient in 8 min; detector, UV 254/220 nm. 6-(7-(3-cyano-4-(tetrahydro-2H-pyran-4-ylamino)phenyl)furo[3,2-b]pyridin-2-yl)-5-fluoro-N,N-dimethylnicotinamide was obtained as yellow solid (15 mg, 16%). HPLC: 99.9% purity, RT=1.00 min. MS: m/z=486.0 [M+H]$^+$. $^1$H NMR (400 MHz, DMSO, ppm) δ 8.68 (s, 1H), 8.60 (d, J=5.2 Hz, 1H), 8.36 (s, 1H), 8.29 (dd, J=8.8, 2.0 Hz, 1H), 8.12 (dd, J=11.2, 1.2 Hz, 1H), 7.80-7.70 (m, 2H), 7.18 (d, J=9.6 Hz, 1 H), 6.34 (d, J=8.4 Hz, 1H), 3.98-3.75 (m, 3H), 3.45-3.30 (m, 2H), 3.04 (s, 3H), 3.00 (s, 3H), 1.87 (d, J=10.4 Hz, 2H), 1.72-160 (m, 2H).

Example 34: 4-(7-(3-cyano-4-(tetrahydro-2H-pyran-4-ylamino)phenyl)furo[3,2-b]pyridin-2-yl)-3-fluoro-N,N-dimethylbenzamide (250)

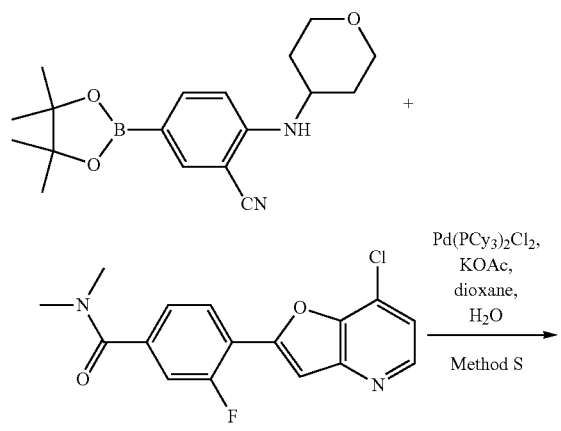

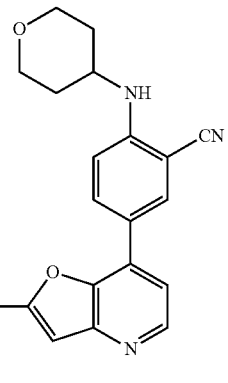

Method S

4-(7-(3-cyano-4-(tetrahydro-2H-pyran-4-ylamino)phenyl)furo[3,2-b]pyridin-2-yl)-3-fluoro-N,N-dimethylbenzamide To a solution of 4-[7-chlorofuro[3,2-b]pyridin-2-yl]-3-fluoro-N,N-dimethylbenzamide (150 mg, 0.47 mmol) in dioxane (8 mL) was added 2-[(oxan-4-yl)amino]-5-(tetramethyl-1,3,2-dioxaborolan-2-yl)benzonitrile (186 mg, 0.57 mmol), potassium acetate (92 mg, 0.94 mmol), Pd(Pcy$_3$)$_2$Cl$_2$ (40 mg, 0.05 mmol) and water (1 mL) at room temperature. The resulting mixture was stirred for 16 h at 80° C., cooled to room temperature, and diluted with water (10 mL). The mixture was extracted with dichloromethane (30 mL×3). The organic phases were combined, washed with brine and dried over sodium sulfate. The solvent was removed under reduced pressure and the residue was purified by flash chromatography eluting with methanol in dichloromethane (0% to 5% gradient). 4-(7-[3-cyano-4-[(oxan-4-yl)amino]phenyl]furo[3,2-b]pyridin-2-yl)-3-fluoro-N,N-dimethylbenzamide was obtained as light yellow solid (43 mg, 19%). HPLC: 99.9% purity, RT=1.12 min. MS: m/z=485.0 [M+H]$^+$. $^1$H NMR (300 MHz, DMSO, ppm) δ 8.55 (d, J=5.1 Hz, 1H), 8.36-8.20 (m, 2H), 8.17-8.05 (m, 1H), 7.67 (d, J=5.1 Hz, 1H), 7.62-7.42 (m, 3H), 7.18 (d, J=9.9 Hz, 1H), 6.30 (d, J=8.4 Hz, 1H), 3.98-3.70 (m, 3H), 3.52-3.40 (m, 2H), 3.02 (s, 3H), 2.96 (s, 3H), 1.89 (d, J=11.1 Hz, 2H), 1.80-1.60 (m, 2H).

Example 35: 4-(7-(3-cyano-4-(tetrahydro-2H-pyran-4-ylamino)phenyl)furo[3,2-b]pyridin-2-yl)-N-(3-fluoropiperidin-4-yl)-3-methoxybenzamide hydrochloride (277, 251)

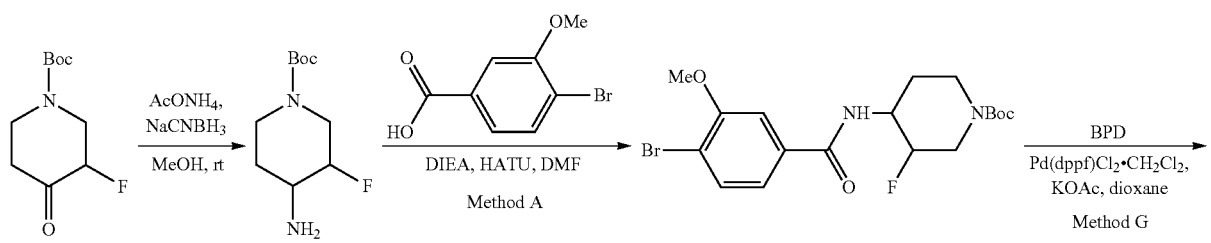

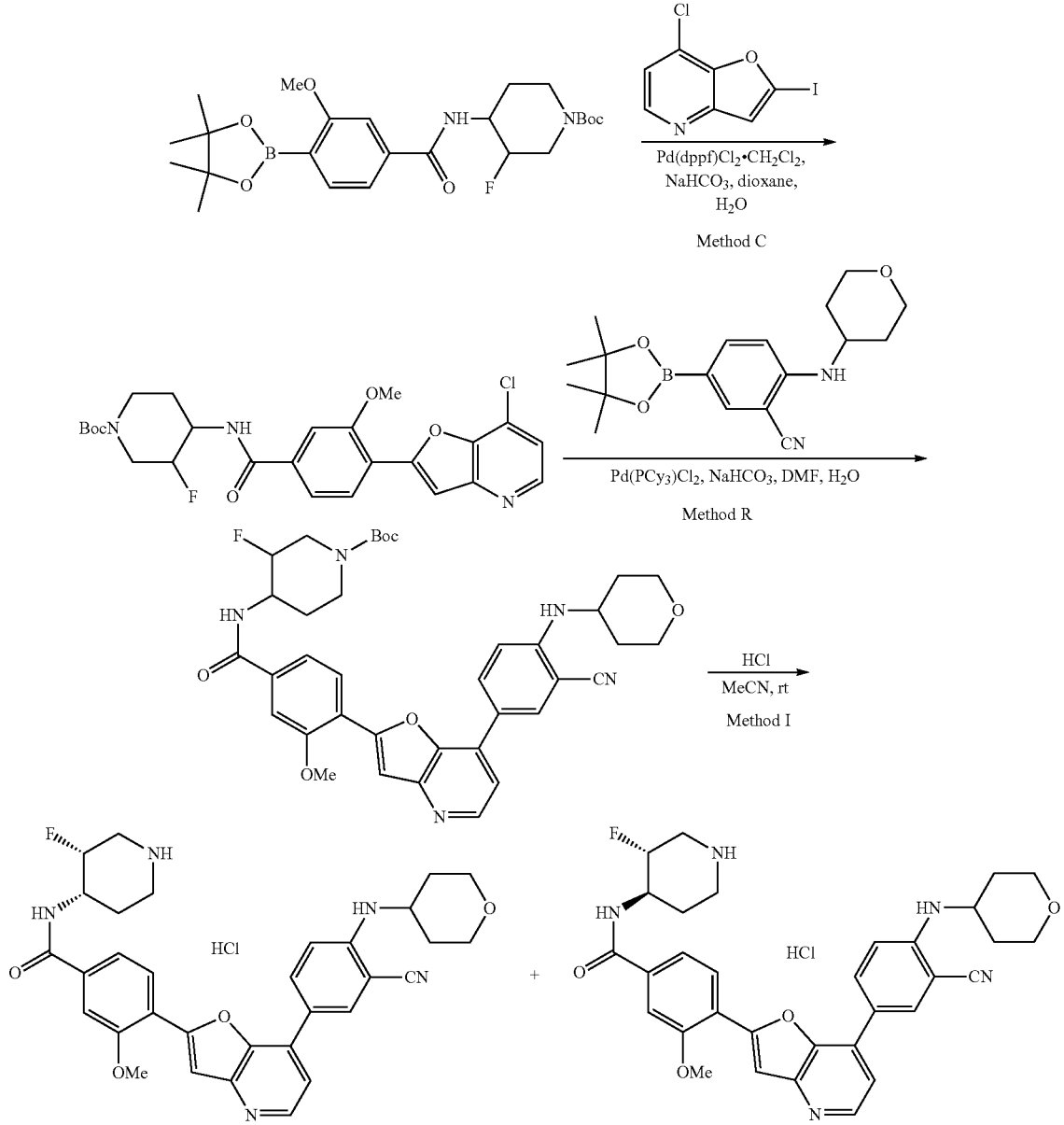

tert-Butyl 4-amino-3-fluoropiperidine-1-carboxylate

At room temperature, to a solution of tert-butyl 3-fluoro-4-oxopiperidine-1-carboxylate (5.10 g, 23.02 mmol) in methanol (100 mL) were added ammonium acetate (12.51 g, 162.29 mmol) and sodium cyanoborohydride (1.90 g, 29.92 mmol) in sequence. The resulting solution was stirred for 18 h at room temperature and then treated with sodium carbonate (50 mL, 1%). The resulting mixture was extracted with ethyl acetate (100 mL×3) and the organic layers were combined, dried over anhydrous sodium sulfate and concentrated under reduced pressure to yield tert-butyl 4-amino-3-fluoropiperidine-1-carboxylate as yellow solid (4.9 g, 98%).

4-(7-(3-cyano-4-(tetrahydro-2H-pyran-4-ylamino) phenyl)furo[3,2-b]pyridin-2-yl)-N-(3-fluoropiperidin-4-yl)-3-methoxybenzamide hydrochloride 4-(7-(3-cyano-4-(tetrahydro-2H-pyran-4-ylamino)phenyl)furo[3,2-b]pyridin-2-yl)-N-(3-fluoropiperidin-4-yl)-3-methoxybenzamide hydrochloride was prepared from tert-butyl 3-fluoro-4-oxopiperidine-1-carboxylate, 4-bromo-3-methoxybenzoic acid, 4,4,5,5-tetramethyl-2-(tetramethyl-1,3,2-dioxaborolan-2-yl)-1,3,2-dioxaborolane, 7-chloro-2-iodofuro[3,2-b]pyridine and 2-(tetrahydro-2H-pyran-4-ylamino)-5-(4,4,5,5-tetramethyl-1,3,2-dioxaborolan-2-yl) benzonitrile using Method A, G, C, R and I. The final product was purified by prep-HPLC under the following conditions: column XBridge Prep C18 OBD column, 5 um, 19×50 mm; mobile phase, acetonitrile in water (with 0.02% HCl), 20% to 50% gradient in 8 min; detector, UV 254/220 nm. Two diastereomeric products of 4-(7-(3-cyano-4-(tetrahydro-2H-pyran-4-ylamino)phenyl)furo[3,2-b]pyridin-2-yl)-N-(3-fluoropiperidin-4-yl)-3-methoxybenzamide hydrochloride were obtained.

277:

(25 mg, 0.8% for 5 steps, orange solid) HPLC: 96.6% purity, RT=1.45 min. MS: m/z=570.0 [M+H]⁺. ¹H NMR (400 MHz, CD₃OD, ppm) δ 8.62 (d, J=4.8 Hz, 1H), 8.51 (s, 1H), 8.45 (br s, 1H), 8.35-8.15 (m, 1H), 8.07 (d, J=4.0 Hz, 1H), 7.90-7.70 (m, 3H), 7.35-7.20 (m, 1H), 5.20-5.00 (m, 1H), 4.60-4.45 (m, 1H), 4.22 (s, 3H), 4.15-3.85 (m, 3H), 3.84-3.20 (m, 6H), 2.45-2.30 (m, 1H), 2.20-2.00 (m, 3H), 1.85-1.70 (m, 2H).

251:

(15 mg, 0.6% for 5 steps, orange solid) HPLC: 95.4% purity, RT=3.40 min. MS: m/z=570.0 [M+H]⁺. ¹H NMR (400 MHz, CD₃OD, ppm) δ 8.60 (d, J=6.4 Hz, 1H), 8.51-8.39 (m, 2H), 8.12 (d, J=8.4 Hz, 1H), 8.04 (d, J=6.8 Hz, 1H), 7.82-7.63 (m, 3H), 7.25 (d, J=9.2 Hz, 1H), 5.30-5.10 (m, 1H), 4.58-4.40 (m, 1H), 4.18 (s, 3H), 4.06 (d, J=10.0 Hz, 2H), 3.98-3.88 (m, 1H), 3.85-3.75 (m, 1H), 3.70-3.45 (m, 4H), 3.40-3.30 (m, 1H), 2.45-2.30 (m, 1H), 2.20-2.00 (m, 3H), 1.83-1.70 (m, 2H).

Example 36: 4-(7-(3-cyano-4-(tetrahydro-2H-pyran-4-ylamino)phenyl)furo[3,2-b]pyridin-2-yl)-3-fluoro-N-(3-fluoropiperidin-4-yl)benzamide hydrochloride (252)

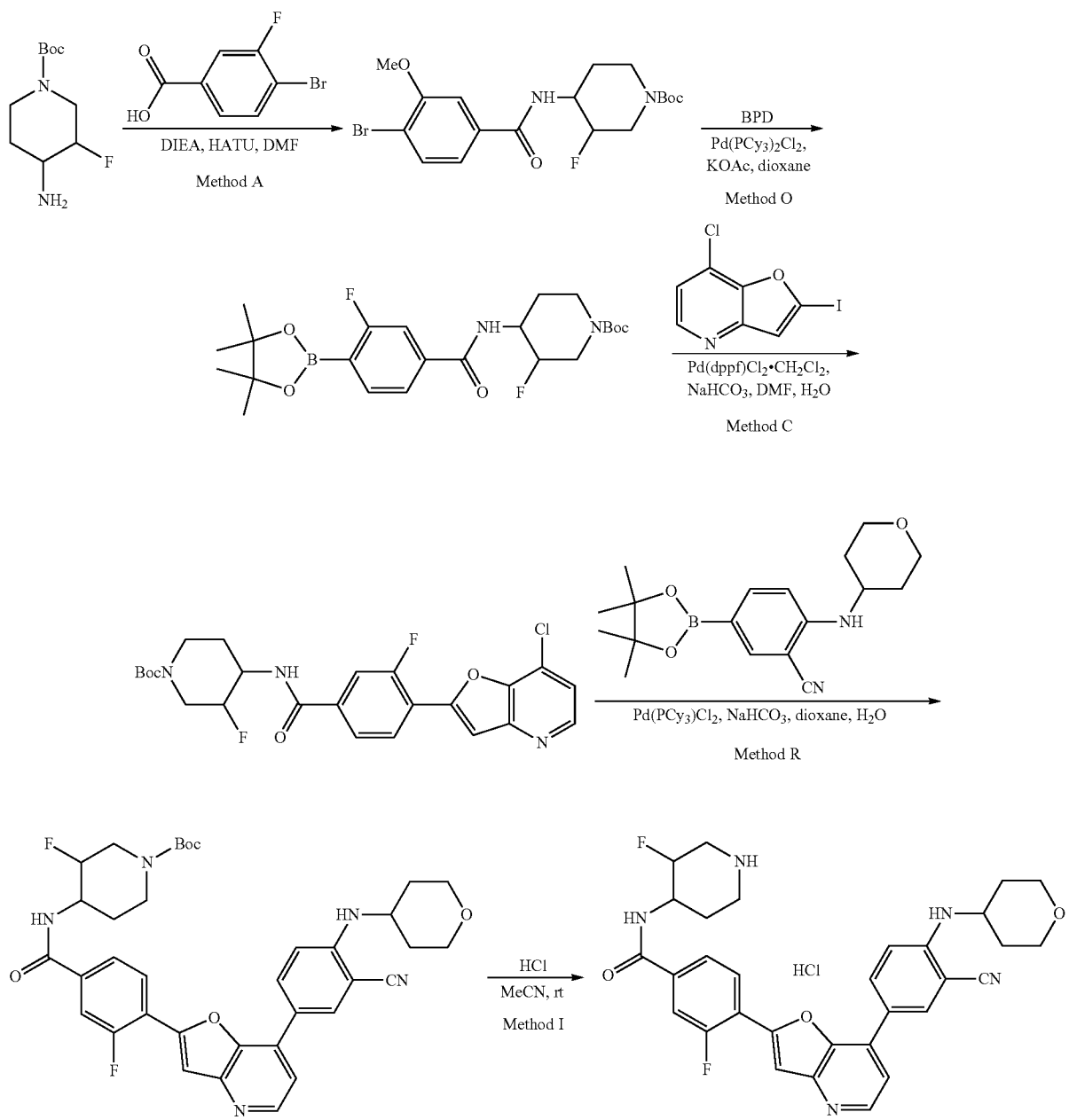

4-(7-(3-cyano-4-(tetrahydro-2H-pyran-4-ylamino) phenyl)furo[3,2-b]pyridin-2-yl)-3-fluoro-N-(3-fluoropiperidin-4-yl)benzamide hydrochloride 4-(7-(3-cyano-4-(tetrahydro-2H-pyran-4-ylamino)phenyl)furo[3,2-b]pyridin-2-yl)-3-fluoro-N-(3-fluoropiperidin-4-yl)benzamide hydrochloride was prepared from tert-butyl 4-amino-3-fluoropiperidine-1-carboxylate, 4-bromo-3-fluorobenzoic acid, 4,4,5,5-tetramethyl-2-(tetramethyl-1,3,2-dioxaborolan-2-yl)-1,3,2-dioxaborolane, 7-chloro-2-iodofuro[3,2-b]pyridine and 2-(tetrahydro-2H-pyran-4-ylamino)-5-(4,4,5,5-tetramethyl-1,3,2-dioxaborolan-2-yl)benzonitrile using Method A, O, C, R and I. The final product was purified by prep-HPLC under the following conditions: column Gemini-NX 5u C18, 110A, AXIA Packed 150×21.2 mm; mobile phase, acetonitrile in water (with 0.02% HCl), 20% to 40% gradient in 10 min; detector, UV 254/220 nm. 4-(7-(3-cyano-4-(tetrahydro-2H-pyran-4-ylamino)phenyl)furo[3,2-b]pyridin-2-yl)-3-fluoro-N-(3-fluoropiperidin-4-yl)benzamide hydrochloride was obtained as yellow solid (20 mg, 3.4% for 5 steps). HPLC: 96.5% purity, RT=1.15 min. MS: m/z=558.0 [M+H]$^+$. $^1$H NMR (400 MHz, CD$_3$OD, ppm) δ 8.66 (s, 1H), 8.54 (d, J=1.2 Hz, 1H), 8.46 (d, J=7.6 Hz, 1H), 8.38-8.25 (m, 1H), 8.12 (d, J=6.4 Hz, 1H), 8.01 (d, J=7.6 Hz, 1H), 7.95 (d, J=12.0 Hz, 1H), 7.74 (d, J=2.4 Hz, 1H), 7.25 (d, J=8.8 Hz, 1H), 5.15-4.90 (m, 1H), 4.52-4.41 (m, 1H), 4.04 (d, J=9.2 Hz, 1H), 4.00-3.85 (m, 1H), 3.80-3.20 (m, 6H), 2.43-2.30 (m, 1H), 2.15-2.00 (m, 3H), 1.85-1.68 (m, 2H).

Example 37: 4-(7-(3-cyano-5-fluoro-2H-pyran-4-ylamino)phenyl)furo[3,2-b]pyridin-2-yl)-N-(3-fluoropiperidin-4-yl)-3-methoxybenzamide hydrochloride (253, 254)

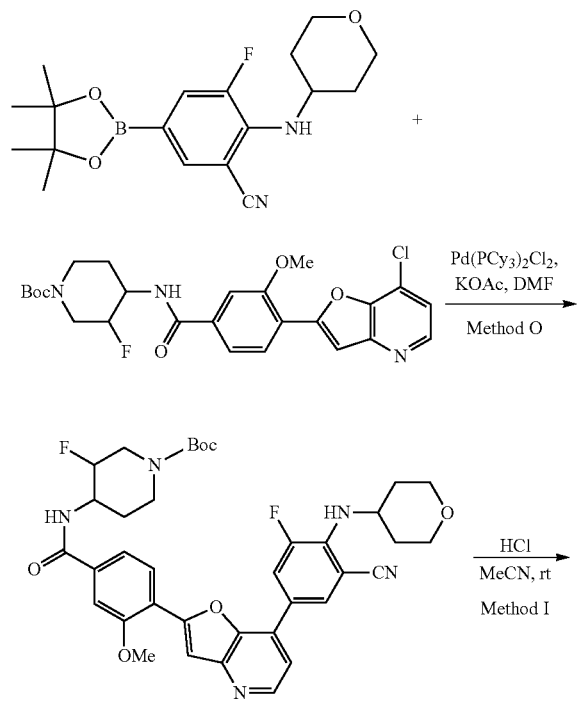

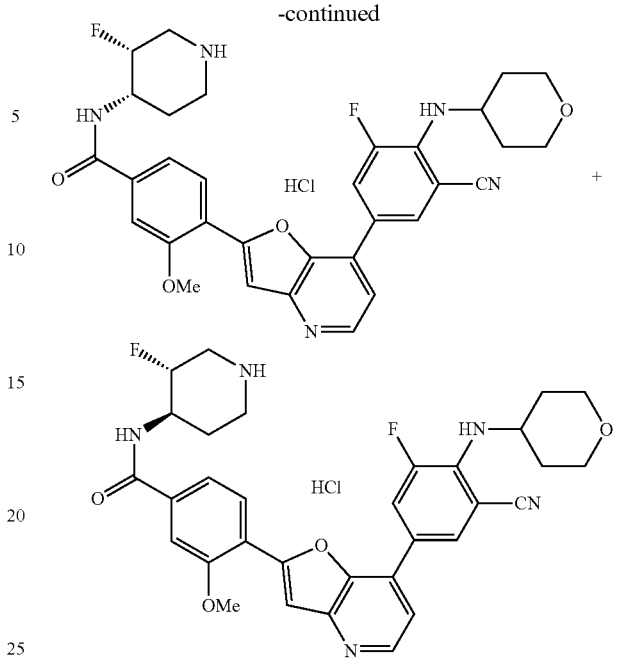

4-(7-(3-cyano-5-fluoro-4-(tetrahydro-2H-pyran-4-ylamino)phenyl)furo[3,2-b]pyridin-2-yl)-N-(3-fluoropiperidin-4-yl)-3-methoxybenzamide hydrochloride 4-(7-(3-cyano-5-fluoro-4-(tetrahydro-2H-pyran-4-ylamino)phenyl)furo[3,2-b]pyridin-2-yl)-N-(3-fluoropiperidin-4-yl)-3-methoxybenzamide hydrochloride was prepared from tert-butyl 4-(4-(7-chlorofuro[3,2-b]pyridin-2-yl)-3-methoxybenzamido)-3-fluoropiperidine-1-carboxylate and 3-fluoro-2-(tetrahydro-2H-pyran-4-ylamino)-5-(4,4,5,5-tetramethyl-1,3,2-dioxaborolan-2-yl)benzonitrile using Method O and I. The final product was purified by prep-HPLC under the following conditions: column Gemini-NX 5u C18 110A, AXIA Packed, 150×21.2 mm; mobile phase, acetonitrile in water (with 0.02% HCl), 30% to 60% gradient in 10 min; detector, UV 254/220 nm. Two diastereomeric products of 4-(7-(3-cyano-5-fluoro-4-(tetrahydro-2H-pyran-4-ylamino)phenyl)furo[3,2-b]pyridin-2-yl)-N-(3-fluoropiperidin-4-yl)-3-methoxy benzamide hydrochloride were obtained.

Compound 253:

(10 mg, 4% for 2 steps, yellow solid) HPLC: 95.4% purity, RT=1.46 min. MS: m/z=588.0 [M+H]$^+$. $^1$H NMR (400 MHz, CD$_3$OD, ppm) δ 8.70-8.55 (m, 1H), 8.36 (s, 1H), 8.28-8.15 (m, 2H), 8.03-7.96 (m, 1H), 7.82-7.69 (m, 3H), 5.25-5.10 (m, 1H), 4.55-4.35 (m, 2H), 4.19 (s, 3H), 4.10-3.99 (m, 2H), 3.80-3.70 (m, 1H), 3.65-3.20 (m, 5H), 2.40-2.25 (m, 1H), 2.15-2.00 (m, 3H), 1.85-1.70 (m, 2H).

Compound 254:

(10 mg, 4% for 2 steps, yellow solid) HPLC: 99.2% purity, RT=0.88 min. MS: m/z=588.0 [M+H]$^+$. $^1$H NMR (400 MHz, CD$_3$OD, ppm) δ 8.61 (s, 1H), 8.36 (s, 1H), 8.28-8.15 (m, 2H), 8.01 (s, 1H), 7.82-7.69 (m, 3H), 5.20-4.95 (m, 1H), 4.55-4.35 (m, 2H), 4.19 (s, 3H), 4.10-3.99 (m, 2H), 3.80-3.60 (m, 1H), 3.59-3.20 (m, 5H), 2.45-2.30 (m, 1H), 2.15-2.00 (m, 3H), 1.85-1.70 (m, 2H).

Example 38: 4-(7-(3-cyano-4-(tetrahydro-2H-pyran-4-ylamino)phenyl)furo[3,2-b]pyridin-2-yl)-3-fluoro-5-methoxy-N,N-dimethylbenzamide (255)

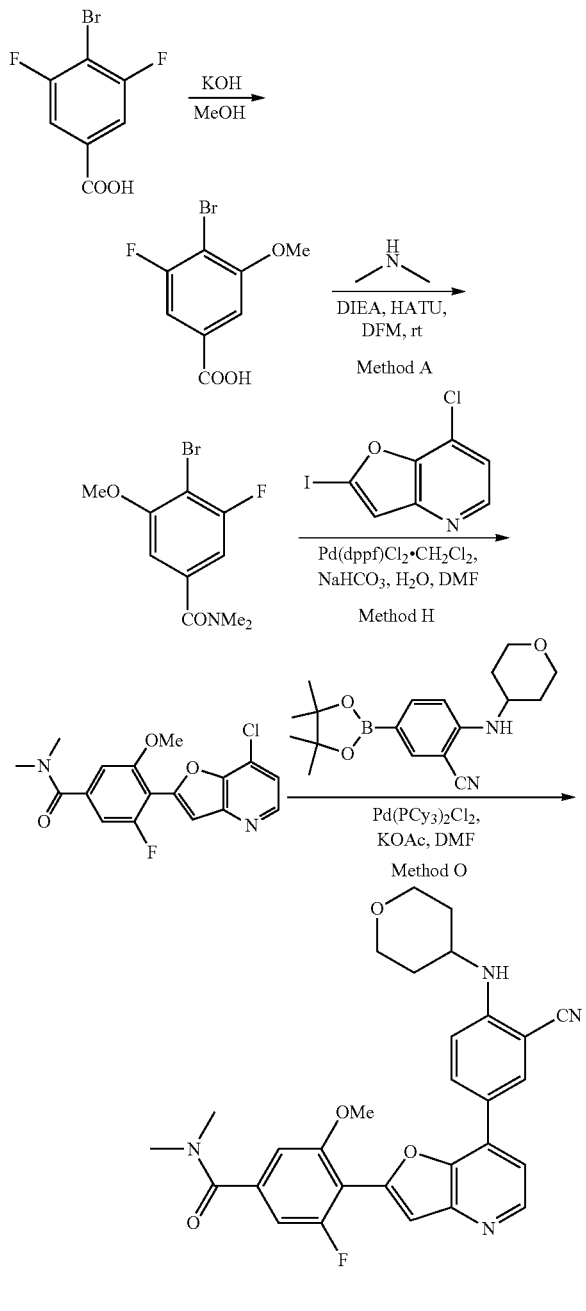

4-bromo-3-fluoro-5-methoxybenzoic acid

To a solution of 4-bromo-3,5-difluorobenzoic acid (2.37 g, 10.00 mmol) in methanol (10 mL) was added potassium hydroxide (1.68 g, 29.9 mmol) at room temperature. The reaction mixture was stirred for 10 h at 90° C., cooled to room temperature and diluted with water (50 mL). The pH value of the mixture was adjusted to 3-4 with hydrogen chloride solution (4 M). The solid that formed was collected by filtration and were dried in oven under vacuum to yield 4-bromo-3-fluoro-5-methoxybenzoic acid as an off-white solid (2.3 g, 92%). MS: m/z=249.0 [M+H]+.

4-(7-(3-cyano-4-(tetrahydro-2H-pyran-4-ylamino)phenyl)furo[3,2-b]pyridin-2-yl)-3-fluoro-5-methoxy-N,N-dimethylbenzamide 4-(7-(3-cyano-4-(tetrahydro-2H-pyran-4-ylamino)phenyl)furo[3,2-b]pyridin-2-yl)-3-fluoro-5-methoxy-N,N-dimethylbenzamide was prepared from 4-bromo-3,5-difluorobenzoic acid, 7-chloro-2-iodofuro[3,2-b]pyridine and 2-(tetrahydro-2H-pyran-4-ylamino)-5-(4,4,5,5-tetramethyl-1,3,2-dioxaborolan-2-yl)benzonitrile using Method A, H and O. The final product was purified by prep-HPLC under the following conditions: column Gemini-NX 5u C18 110A, AXIA Packed, 150×21.2 mm; mobile phase, acetonitrile in water (with 10 mmol/L NH$_4$HCO$_3$), 20% to 45% gradient in 8 min; detector, UV 254/220 nm. 4-(7-(3-cyano-4-(tetrahydro-2H-pyran-4-ylamino)phenyl)furo[3,2-b]pyridin-2-yl)-3-fluoro-5-methoxy-N,N-dimethylbenzamide was obtained as light brown solid (10 mg, 1.3% for 3 steps). HPLC: 98.1% purity, RT=1.10 min. MS: m/z=515.0 [M+H]+. $^1$H NMR (400 MHz, DMSO, ppm) δ 8.55 (d, J=5.2 Hz, 1H), 8.36 (d, J=2.0 Hz, 1H), 8.24 (dd, J=9.2, 2.0 Hz, 1H), 7.68 (d, J=5.2 Hz, 1H), 7.49 (s, 1H), 7.19-7.08 (m, 3H), 6.30 (d, J=8.4 Hz, 1H), 4.02 (s, 3H), 3.90 (dd, J=11.6, 2.4 Hz, 2H), 3.85-3.73 (m, 1H), 3.50-3.40 (m, 2H), 3.02 (s, 3H), 2.97 (s, 3H), 1.86 (d, J=10.4 Hz, 2H), 1.72-1.58 (m, 2H).

Example 39: 4-(7-(3-cyano-4-(tetrahydro-2H-pyran-4-yloxy)phenyl)furo[3,2-b]pyridin-2-yl)-N,N-diethyl-3-methoxybenzamide hydrochloride (256)

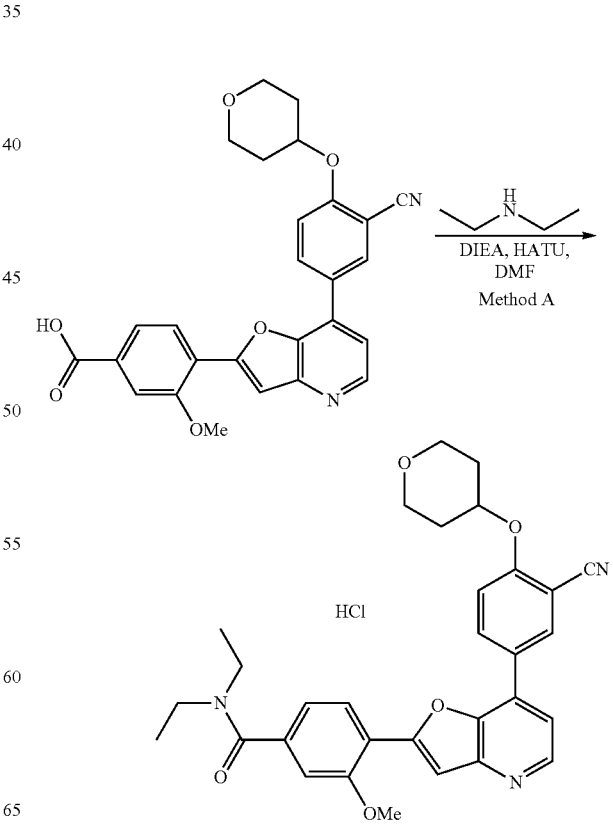

4-(7-(3-cyano-4-(tetrahydro-2H-pyran-4-yloxy)phenyl)furo[3,2-b]pyridin-2-yl)-N,N-diethyl-3-methoxybenzamide hydrochloride 4-(7-(3-cyano-4-(tetrahydro-2H-pyran-4-yloxy)phenyl)furo[3,2-b]pyridin-2-yl)-N,N-diethyl-3-methoxybenzamide hydrochloride was prepared from 4-(7-(3-cyano-4-(tetrahydro-2H-pyran-4-yloxy)phenyl)furo[3,2-b]pyridin-2-yl)-3-methoxybenzoic acid and diethylamine using Method A. The product was purified by prep-HPLC under the following conditions: column X Bridge C18, 19×150 mm, 5 um; mobile phase, acetonitrile in water (with 0.02% HCl), 20% to 50% gradient in 10 min; detector, UV 254/220 nm. 4-(7-(3-cyano-4-(tetrahydro-2H-pyran-4-yloxy)phenyl)furo[3,2-b]pyridin-2-yl)-N,N-diethyl-3-methoxybenzamide hydrochloride was obtained as yellow solid (25 mg, 10%). HPLC: 98.5% purity, RT=1.40 min. MS: m/z=526.0 [M+H]+. 1H NMR (400 MHz, DMSO, ppm) δ 8.69 (s, 1H), 8.60-8.50 (m, 2H), 8.07 (d, J=8.0 Hz, 1H), 7.89 (d, J=5.6 Hz, 1H), 7.75-7.65 (m, 2H), 7.29 (s, 1H), 7.14 (dd, J=8.0, 1.2 Hz, 1H), 5.10-4.95 (m, 1H), 4.08 (s, 3H), 3.95-3.85 (m, 2H), 3.66-3.40 (m, 4H), 3.30-3.15 (m, 2H), 2.12-2.02 (m, 2H), 1.80-1.65 (m, 2H), 1.18 (s, 3H), 1.10 (s, 3H).

Example 40: 4-(7-(3-cyano-4-(tetrahydro-2H-pyran-4-yloxy)phenyl)furo[3,2-b]pyridin-2-yl)-3-methoxy-N-methyl-N-propylbenzamide hydrochloride (257)

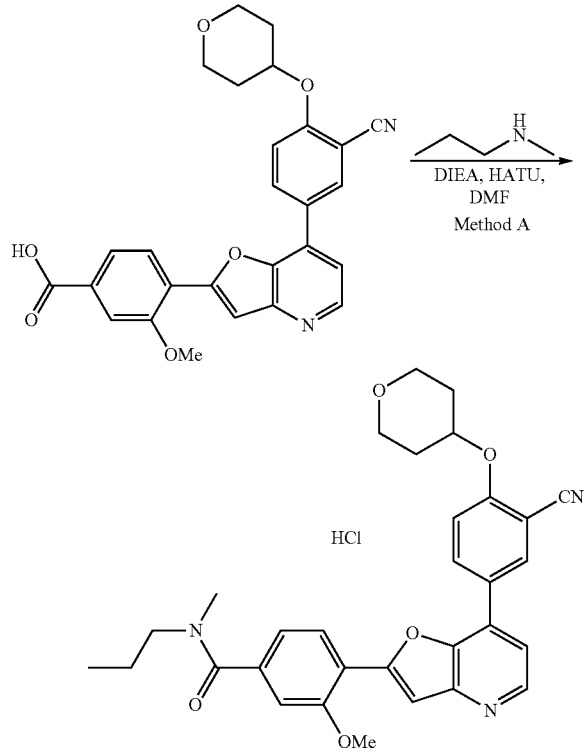

4-(7-(3-cyano-4-(tetrahydro-2H-pyran-4-yloxy)phenyl)furo[3,2-b]pyridin-2-yl)-3-methoxy-N-methyl-N-propylbenzamide hydrochloride 4-(7-(3-cyano-4-(tetrahydro-2H-pyran-4-yloxy)phenyl)furo[3,2-b]pyridin-2-yl)-3-methoxy-N-methyl-N-propylbenzamide hydrochloride was prepared from 4-(7-(3-cyano-4-(tetrahydro-2H-pyran-4-yloxy)phenyl)furo[3,2-b]pyridin-2-yl)-3-methoxybenzoic acid and N-methylpropan-1-amine using Method A. The product was purified by prep-HPLC under the following conditions: column X Bridge C18, 19×150 mm, 5 um; mobile phase, acetonitrile in water (with 0.02% HCl), 20% to 50% gradient in 10 min; detector, UV 254/220 nm. 4-(7-(3-cyano-4-(tetrahydro-2H-pyran-4-yloxy)phenyl)furo[3,2-b]pyridin-2-yl)-3-methoxy-N-methyl-N-propylbenzamide hydrochloride was obtained as yellow solid (25 mg, 10%). HPLC: 97.1% purity, RT=2.85 min. MS: m/z=526.0 [M+H]+. 1H NMR (400 MHz, DMSO, ppm) δ 8.71 (s, 1H), 8.63-8.50 (m, 2H), 8.08 (d, J=7.6 Hz, 1H), 7.92 (d, J=5.6 Hz, 1H), 7.78-7.52 (m, 3H), 7.25 (s, 1H), 7.21-7.09 (m 1H), 5.10-4.95 (m, 1H), 4.08 (s, 3H), 3.95-3.85 (m, 2H), 3.63-3.52 (m, 2H), 3.50-3.38 (s, 1H), 3.28-3.12 (m, 2H), 2.99 (s, 1.5H), 2.92 (s, 1.5H), 2.15-2.05 (m, 2H), 1.80-1.50 (m, 4H), 1.00-0.65 (m, 3H).

Example 41: 4-(7-(3-cyano-4-(tetrahydro-2H-pyran-4-yloxy)phenyl)furo[3,2-b]pyridin-2-yl)-N-(3-hydroxypropyl)-3-methoxy-N-methylbenzamide hydrochloride (258)

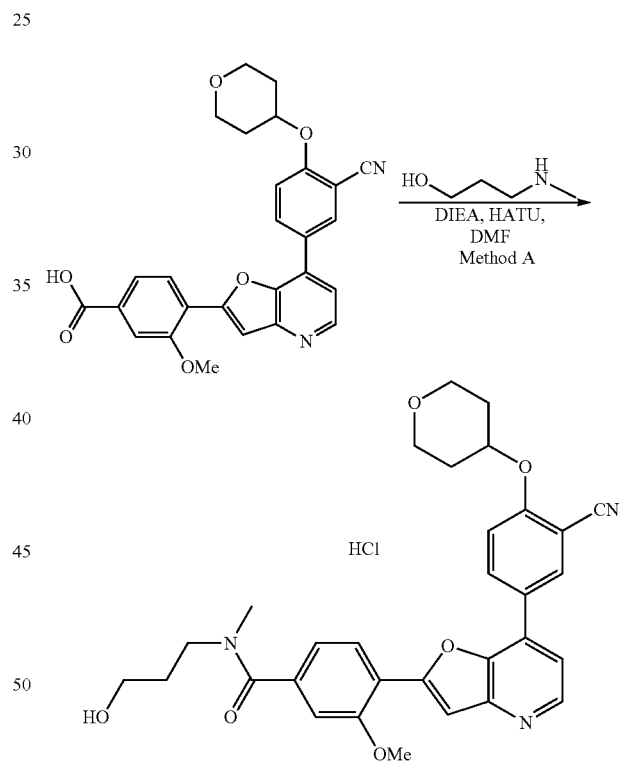

4-(7-(3-cyano-4-(tetrahydro-2H-pyran-4-yloxy)phenyl)furo[3,2-b]pyridin-2-yl)-N-(3-hydroxypropyl)-3-methoxy-N-methylbenzamide hydrochloride 4-(7-(3-cyano-4-(tetrahydro-2H-pyran-4-yloxy)phenyl)furo[3,2-b]pyridin-2-yl)-N-(3-hydroxypropyl)-3-methoxy-N-methylbenzamide hydrochloride was prepared from 4-(7-(3-cyano-4-(tetrahydro-2H-pyran-4-yloxy)phenyl)furo[3,2-b]pyridin-2-yl)-3-methoxybenzoic acid and 3-(methylamino)propan-1-ol using Method A. The product was purified by prep-HPLC under the following conditions: column XBridge BEH C18 OBD 5 um, 19 mm 250 mm;

mobile phase, acetonitrile in water (with 0.02% HCl), 20% to 40% gradient in 8 min; detector, UV 254/220 nm. 4-(7-(3-cyano-4-(tetrahydro-2H-pyran-4-yloxy)phenyl)furo[3,2-b]pyridin-2-yl)-N-(3-hydroxy propyl)-3-methoxy-N-methylbenzamide hydrochloride was obtained as yellow solid (20 mg, 16%). HPLC: 96.2% purity, RT=2.37 min. MS: m/z=542.0 [M+H]⁺. ¹H NMR (400 MHz, DMSO, ppm) δ 8.75-8.63 (m, 1H), 8.60-8.50 (m, 2H), 8.06 (d, J=8.0 Hz, 1H), 7.92-7.80 (m, 1H), 7.78-7.65 (m, 2H), 7.26 (s, 1H), 7.22-7.12 (m 1H), 5.10-4.95 (m, 1H), 4.08 (s, 3H), 3.97-3.85 (m, 2H), 3.65-3.45 (m, 4H), 3.40-3.22 (m, 2H), 2.99 (s, 1.5H), 2.94 (s, 1.5H), 2.15-2.05 (m, 2H), 1.85-1.65 (m, 4H).

Example 42: 4-(7-(3-cyano-4-(tetrahydro-2H-pyran-4-yloxy)phenyl)furo[3,2-b]pyridin-2-yl)-N-ethyl-3-methoxy-N-methylbenzamide hydrochloride (278)

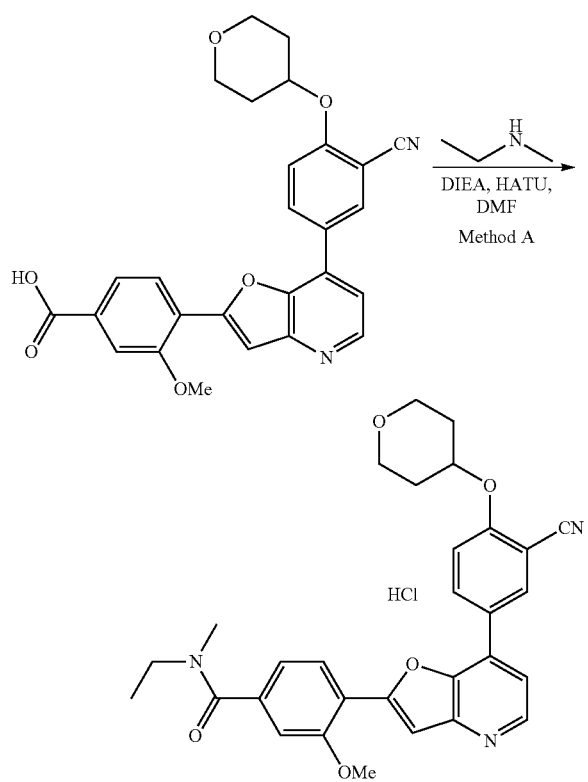

4-(7-(3-cyano-4-(tetrahydro-2H-pyran-4-yloxy)phenyl)furo[3,2-b]pyridin-2-yl)-N-ethyl-3-methoxy-N-methylbenzamide hydrochloride 4-(7-(3-cyano-4-(tetrahydro-2H-pyran-4-yloxy)phenyl)furo[3,2-b]pyridin-2-yl)-N-ethyl-3-methoxy-N-methylbenzamide hydrochloride was prepared from 4-(7-(3-cyano-4-(tetrahydro-2H-pyran-4-yloxy)phenyl)furo[3,2-b]pyridin-2-yl)-3-methoxybenzoic acid and N-methylethanamine using Method A. The product was purified by prep-HPLC under the following conditions: column X Bridge C18, 19×150 mm, 5 um; mobile phase, acetonitrile in water (with 0.02% HCl), 20% to 50% gradient in 8 min; detector, UV 254/220 nm. 4-(7-(3-cyano-4-(tetrahydro-2H-pyran-4-yloxy)phenyl)furo[3,2-b]pyridin-2-yl)-N-ethyl-3-methoxy-N-methylbenzamide hydrochloride was obtained as yellow solid (41 mg, 17%). HPLC: 98.4% purity, RT=1.36 min. MS: m/z=512.0 [M+H]⁺. ¹H NMR (400 MHz, DMSO, ppm) δ 8.72 (d, J=5.6 Hz, 1H), 8.60-8.50 (m, 2H), 8.05 (d, J=8.0 Hz, 1H), 7.92 (d, J=5.6 Hz, 1H), 7.75-7.65 (m, 2H), 7.27 (s, 1H), 7.22-7.12 (m 1H), 5.10-4.95 (m, 1H), 4.08 (s, 3H), 3.97-3.85 (m, 2H), 3.62-3.45 (m, 3H), 3.30-3.20 (m, 2H), 2.99 (s, 1.5H), 2.94 (s, 1.5H), 2.15-2.05 (m, 2H), 1.80-1.65 (m, 2H), 1.25-1.05 (m, 2H).

Example 43: 4-(7-(3-cyano-4-(tetrahydro-2H-pyran-4-ylamino)phenyl)furo[3,2-b]pyridin-2-yl)-N-(2-hydroxyethyl)-3-methoxy-N-methylbenzamide (230)

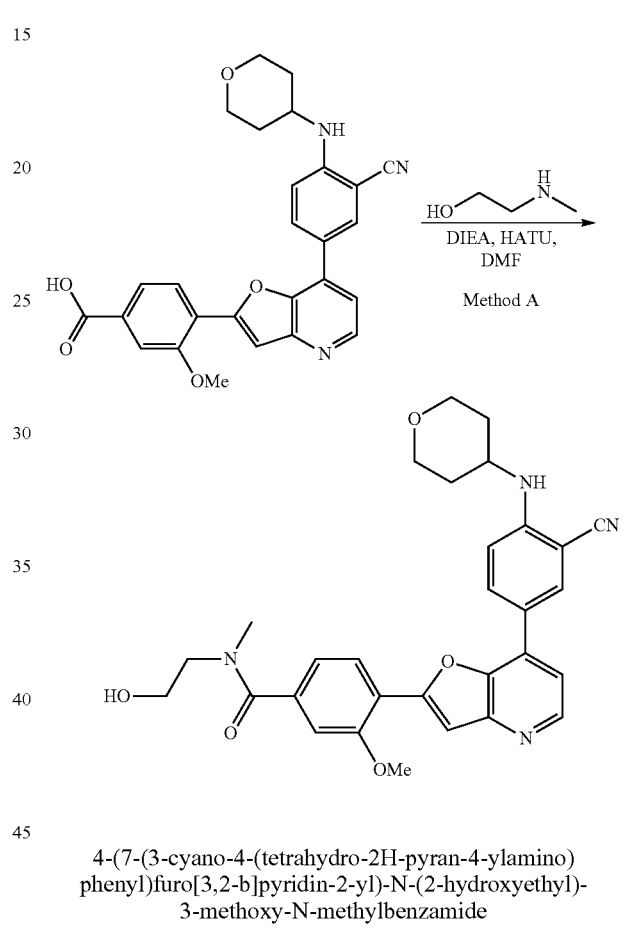

4-(7-(3-cyano-4-(tetrahydro-2H-pyran-4-ylamino)phenyl)furo[3,2-b]pyridin-2-yl)-N-(2-hydroxyethyl)-3-methoxy-N-methylbenzamide 4-(7-(3-cyano-4-(tetrahydro-2H-pyran-4-ylamino)phenyl)furo[3,2-b]pyridin-2-yl)-N-(2-hydroxyethyl)-3-methoxy-N-methylbenzamide was prepared from 4-(7-(3-cyano-4-(tetrahydro-2H-pyran-4-ylamino)phenyl)furo[3,2-b]pyridin-2-yl)-3-methoxybenzoic acid and 2-(methylamino)ethanol using Method A. The product was purified by prep-HPLC under the following conditions: column Gemini-NX 5u C18, 110A, AXIA Packed 150×21.2 mm; mobile phase, acetonitrile in water (with 10 mmol/L NH₄HCO₃), 20% to 50% gradient in 10 min; detector, UV 254/220 nm. 4-(7-(3-cyano-4-(tetrahydro-2H-pyran-4-ylamino)phenyl)furo[3,2-b]pyridin-2-yl)-N-(2-hydroxyethyl)-3-methoxy-N-methylbenzamide was obtained as yellow solid (40 mg, 71%). HPLC: 99.8% purity, RT=1.46 min. MS: m/z=527.0 [M+H]⁺. ¹H NMR (400 MHz, DMSO, ppm) δ 8.51 (d, J=5.2 Hz, 1H), 8.27 (br s, 2H), 8.02 (d, J=7.2 Hz, 1H), 7.70-7.55 (m, 2H), 7.38-7.12 (m, 3H), 6.28 (d, J=8.0 Hz, 1H), 4.92-4.78 (m, 1H), 4.05 (s, 3H), 3.92 (d, J=9.6 Hz, 2H), 3.81 (d, J=4.0 Hz, 2H), 3.71-3.40 (m, 5H), 3.02 (s, 3H), 1.95-1.82 (m, 2H), 1.75-1.68 (m, 2H).

Example 44: 4-(7-(3-cyano-4-(tetrahydro-2H-pyran-4-ylamino)phenyl)furo[3,2-b]pyridin-2-yl)-N,N-diethyl-3-methoxybenzamide (259)

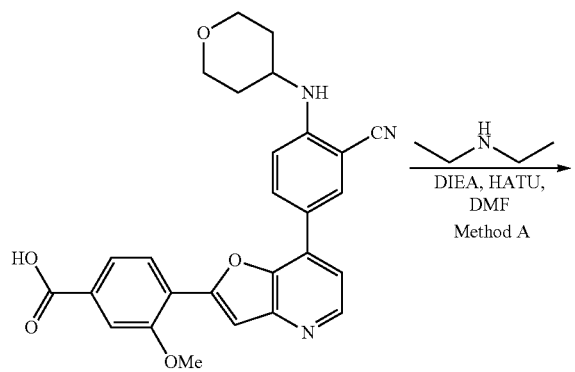

4-(7-(3-cyano-4-(tetrahydro-2H-pyran-4-ylamino)phenyl)furo[3,2-b]pyridin-2-yl)-N,N-diethyl-3-methoxybenzamide 4-(7-(3-cyano-4-(tetrahydro-2H-pyran-4-ylamino)phenyl)furo[3,2-b]pyridin-2-yl)-N,N-diethyl-3-methoxybenzamide was prepared from 4-(7-(3-cyano-4-(tetrahydro-2H-pyran-4-ylamino)phenyl)furo[3,2-b]pyridin-2-yl)-3-methoxybenzoic acid and diethylamine using Method A. The product was purified by prep-HPLC under the following conditions: column Gemini-NX C18 AXAI Packed, 21.2× 150 mm 5 um 11 nm; mobile phase, acetonitrile in water (with 10 mmol/L NH$_4$HCO$_3$), 20% to 50% gradient in 8 min; detector, UV 254/220 nm. 4-(7-(3-cyano-4-(tetrahydro-2H-pyran-4-ylamino)phenyl)furo[3,2-b]pyridin-2-yl)-N,N-diethyl-3-methoxybenzamide was obtained as yellow solid (41 mg, 52%). HPLC: 99.9% purity, RT=1.16 min. MS: m/z=525.0 [M+H]$^+$. $^1$H NMR (300 MHz, DMSO, ppm) δ 8.51 (d, J=5.1 Hz, 1H), 8.33-8.20 (m, 2H), 8.07 (d, J=7.8 Hz, 1H), 7.67-7.55 (m, 2H), 7.25-7.05 (m, 3H), 6.28 (d, J=8.1 Hz, 1H), 4.06 (s, 3H), 3.92 (d, J=9.6 Hz, 2H), 3.88-3.70 (m, 1H), 3.60-3.10 (m, 6H), 1.95-1.82 (m, 2H), 1.80-1.55 (m, 2H), 1.30-1.03 (m, 6H).

Example 46: 4-(7-(3-cyano-4-(tetrahydro-2H-pyran-4-ylamino)phenyl)furo[3,2-b]pyridin-2-yl)-N-(3-hydroxypropyl)-3-methoxy-N-methylbenzamide (261)

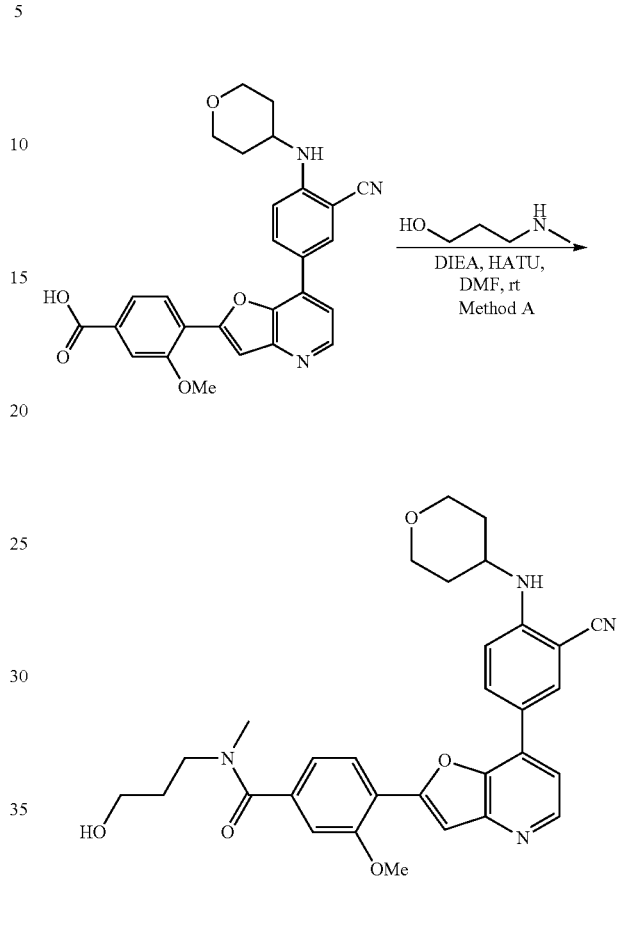

4-(7-(3-cyano-4-(tetrahydro-2H-pyran-4-ylamino)phenyl)furo[3,2-b]pyridin-2-yl)-N-(3-hydroxypropyl)-3-methoxy-N-methylbenzamide 4-(7-(3-cyano-4-(tetrahydro-2H-pyran-4-ylamino)phenyl)furo[3,2-b]pyridin-2-yl)-N-(3-hydroxypropyl)-3-methoxy-N-methylbenzamide was prepared from 4-(7-(3-cyano-4-(tetrahydro-2H-pyran-4-yloxy)phenyl)furo[3,2-b]pyridin-2-yl)-3-methoxybenzoic acid and 3-(methylamino)propan-1-ol using Method A. The residue was purified by flash chromatography eluting with EtOAc in hexane (0% to 100% gradient). 4-(7-(3-cyano-4-(tetrahydro-2H-pyran-4-ylamino)phenyl)furo[3,2-b]pyridin-2-yl)-N-(3-hydroxypropyl)-3-methoxy-N-methylbenzamide was obtained as light yellow solid (36 mg, 39%). HPLC: 99.1% purity, RT=1.56 min. MS: m/z=541.0 [M+H]$^+$. $^1$H NMR (300 MHz, DMSO, ppm) δ 8.51 (d, J=5.1 Hz, 1H), 8.35-8.25 (m, 2H), 8.03 (d, J=8.1 Hz, 1H), 7.67-7.55 (m, 2H), 7.30-7.10 (m, 3H), 6.29 (d, J=8.1 Hz, 1H), 4.59-4.35 (m, 1H), 4.06 (s, 3H), 3.92 (d, J=9.0 Hz, 2H), 3.88-3.70 (m, 1H), 3.60-3.39 (m, 4H), 2.99 (s, 1.5H), 2.95 (s, 1.5H), 1.95-1.58 (m, 6H).

Example 47: 4-(7-(3-cyano-4-(tetrahydro-2H-pyran-4-ylamino)phenyl)furo[3,2-b]pyridin-2-yl)-N-ethyl-3-methoxy-N-methylbenzamide (262)

4-(7-(3-cyano-4-(tetrahydro-2H-pyran-4-ylamino)phenyl)furo[3,2-b]pyridin-2-yl)-N-ethyl-3-methoxy-N-methylbenzamide 4-(7-(3-cyano-4-(tetrahydro-2H-pyran-4-ylamino)phenyl)furo[3,2-b]pyridin-2-yl)-N-ethyl-3-methoxy-N-methylbenzamide was prepared from 4-(7-(3-cyano-4-(tetrahydro-2H-pyran-4-ylamino)phenyl)furo[3,2-b]pyridin-2-yl)-3-methoxybenzoic acid and N-methylethanamine using Method A. The product was purified by prep-HPLC under the following conditions: column Gemini-NX 5u C18 110A, AXIA Packed, 150×21.2 mm; mobile phase, acetonitrile in water (with 10 mmol/L $NH_4HCO_3$), 20% to 50% gradient in 8 min; detector, UV 254/220 nm. 4-(7-(3-cyano-4-(tetrahydro-2H-pyran-4-ylamino)phenyl)furo[3,2-b]pyridin-2-yl)-N-ethyl-3-methoxy-N-methylbenzamide was obtained as yellow solid (35 mg, 40%). HPLC: 99.6% purity, RT=1.64 min. MS: m/z=511.0 $[M+H]^+$. $^1H$ NMR (300 MHz, DMSO, ppm) δ 8.51 (d, J=5.4 Hz, 1H), 8.32-8.22 (m, 2H), 8.02 (d, J=7.8 Hz, 1H), 7.67-7.55 (m, 2H), 7.30-7.10 (m, 3H), 6.29 (d, J=8.1 Hz, 1H), 4.06 (s, 3H), 3.92 (d, J=9.3 Hz, 2H), 3.88-3.71 (m, 1H), 3.60-3.40 (m, 3H), 3.35-3.15 (m, 1H), 3.10-2.90 (m, 3H), 1.89 (d, J=10.5 Hz, 2H), 1.79-1.59 (m, 2H), 1.30-1.05 (m, 3H).

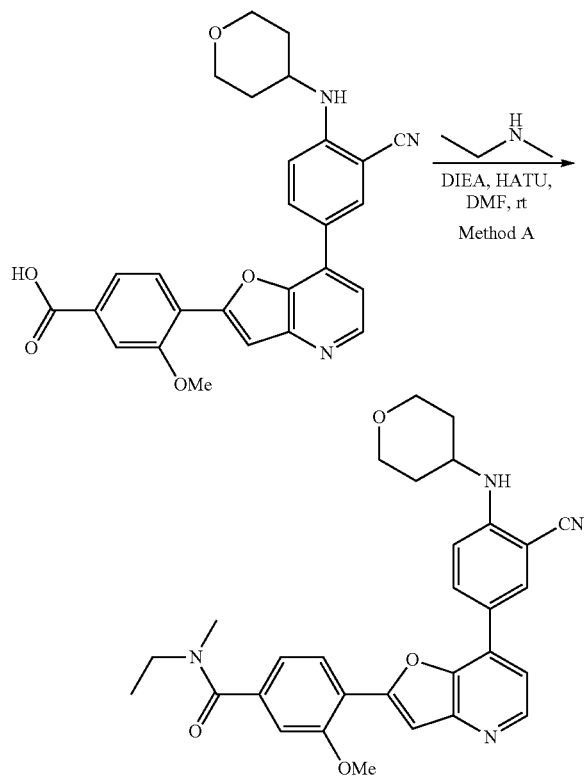

Example 48: 4-(7-(3-cyano-4-(tetrahydro-2H-pyran-4-yloxy)phenyl)furo[3,2-b]pyridin-2-yl)-3-ethyl-N,N-dimethylbenzamide (263)

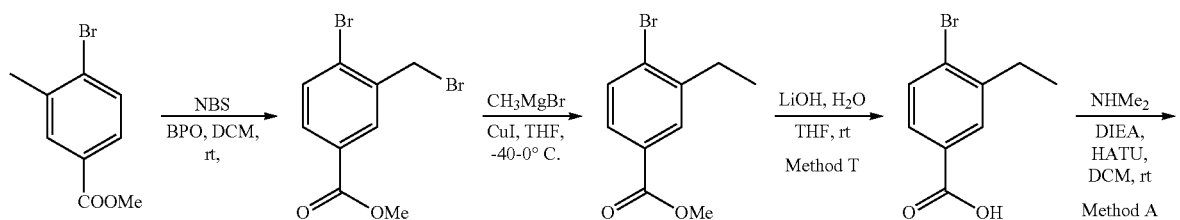

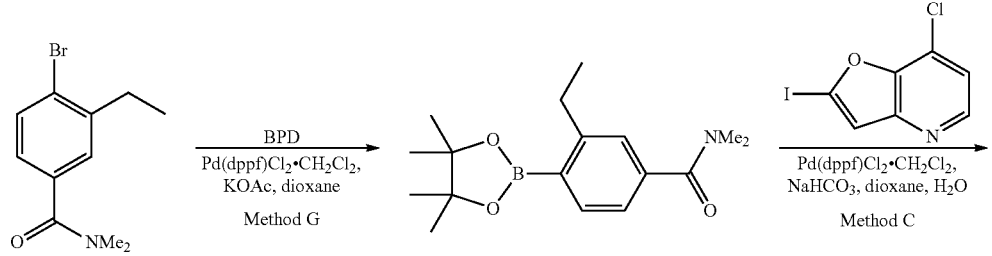

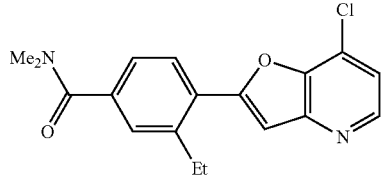
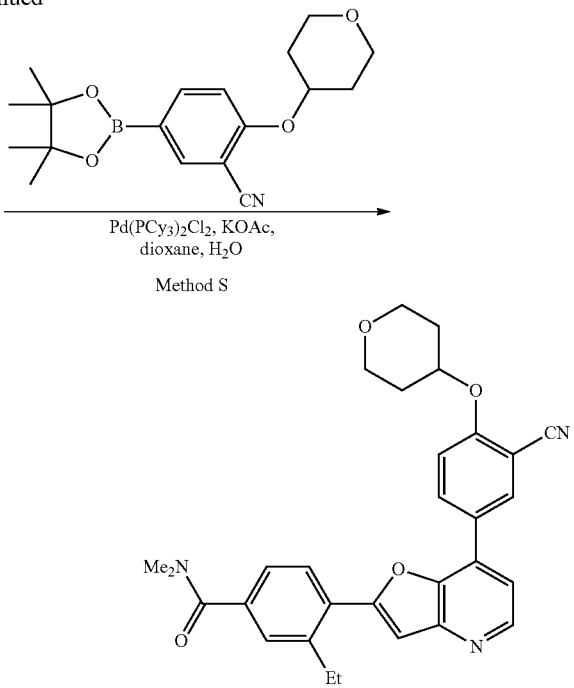

Method S

Methyl 4-bromo-3-(bromomethyl)benzoate

To a solution of methyl 4-bromo-3-methylbenzoate (5.00 g, 21.83 mmol) in dichloromethane (30 mL) was added NBS (4.66 g, 26.18 mmol) and benzoperoxide (110 mg, 0.43 mmol) at room temperature. The resulting solution was stirred overnight at room temperature and then diluted with water (50 mL). The mixture was extracted with ethyl acetate (100 mL×3). The organic phases were combined, washed with brine and dried over sodium sulfate. The solvent was removed under reduced pressure and the residue was purified by flash chromatography eluting with ethyl acetate in hexane (0% to 10% gradient) to yield methyl 4-bromo-3-(bromomethyl)benzoate as brown solid (2.2 g, 33%).

Methyl 4-bromo-3-ethylbenzoate

At −40° C., to a solution of methyl 4-bromo-3-(bromomethyl)benzoate (1.31 g, 4.22 mmol) in tetrahydrofuran (20 mL) was added copper iodide (80 mg, 0.42 mmol). To this stirring mixture was added bromo(methyl)magnesium (2 mL, 5.03 mmol) dropwise at −40° C. over 10 min period. The resulting mixture was then stirred for 60 min at −40° C., warmed to room temperature and the treated with saturated ammonium chloride solution (30 mL). The mixture was extracted with ethyl acetate (60 mL×3). The organic phases were combined, washed with brine and dried over sodium sulfate. The solvent was removed under reduced pressure and the residue was purified by flash chromatography eluting with ethyl acetate in hexane (0% to 20% gradient) to yield methyl 4-bromo-3-ethylbenzoate as a yellow solid (200 mg, 19%).

Method T

4-bromo-3-ethylbenzoic acid

To a solution of methyl 4-bromo-3-ethylbenzoate (430 mg, 1.77 mmol) in tetrahydrofuran (8 mL) and water (4 mL) was added lithium hydroxide (127 mg, 5.30 mmol) at 0° C. The reaction mixture was stirred for 3 h at room temperature and then diluted with water (15 mL). The pH value of the mixture was adjusted to 2 with hydrogen chloride solution (1 M). The resulting mixture was extracted with dichloromethane (35 mL×3). The organic phases were combined, washed with brine and dried over sodium sulfate. The solvent was removed under reduced pressure and the residue was purified by flash chromatography eluting with ethyl acetate in hexane (0% to 100% gradient) to yield 4-bromo-3-ethylbenzoic acid as brown solid (300 mg, 74%). MS: m/z=228.0 [M+H]$^+$.

4-(7-(3-cyano-4-(tetrahydro-2H-pyran-4-yloxy)phenyl)furo[3,2-b]pyridin-2-yl)-3-ethyl-N,N-dimethylbenzamide 4-(7-(3-cyano-4-(tetrahydro-2H-pyran-4-yloxy)phenyl)furo[3,2-b]pyridin-2-yl)-3-ethyl-N,N-dimethylbenzamide was prepared from 4-bromo-3-ethylbenzoic acid, dimethylamine, 4,4,5,5-tetramethyl-2-(tetramethyl-1,3,2-dioxaborolan-2-yl)-1,3,2-dioxaborolane, 7-chloro-2-iodofuro[3,2-b]pyridine and 2-(tetrahydro-2H-pyran-4-ylamino)-5-(4,4,5,5-tetramethyl-1,3,2-dioxaborolan-2-yl)benzonitrile using Method A, G, C, and S. The final product was purified by prep-HPLC under the following conditions: column Gemini-NX 5u C18 110A, AXIA Packed, 150×21.2 mm; mobile phase, acetonitrile in water (with 10 mmol/L NH$_4$HCO$_3$), 20% to 50% gradient in 8 min; detector, UV 254/220 nm. 4-(7-(3-cyano-4-(tetrahydro-2H-pyran-4-yloxy)phenyl)furo[3,2-b]pyridin-2-yl)-3-ethyl-N,N-dimethylbenzamide was obtained as off-white solid (25 mg, 1.6% for 5 steps). HPLC: 97.3% purity, RT=1.15 min. MS: m/z=496.0 [M+H]$^+$. $^1$H NMR (400 MHz, DMSO, ppm) δ 8.60 (s, 1H), 8.45 (d, J=2.0 Hz, 1H), 8.36 (dd, J=8.8, 2.0 Hz, 1H), 7.89 (d, J=8.0 Hz, 1H), 7.68 (d, J=5.2 Hz, 1H), 7.62 (d, J=9.2 Hz, 1H), 7.54 (s, 1H), 7.47 (d, J=1.2 Hz, 1H), 7.41 (dd, J=8.0, 1.6 Hz, 1H), 5.01-4.90 (m, 1H), 3.95-3.82 (m, 2H), 3.65-3.50 (m, 2H), 3.10-2.90 (m, 8H), 2.10-1.98 (m, 2H), 1.79-1.65 (m, 2H), 1.30-1.20 (m, 3H).

Example 49: 4-(7-(3-cyano-4-(tetrahydro-2H-pyran-4-yloxy)phenyl)furo[3,2-b]pyridin-2-yl)-3-hydroxy-N,N-dimethylbenzamide (264)
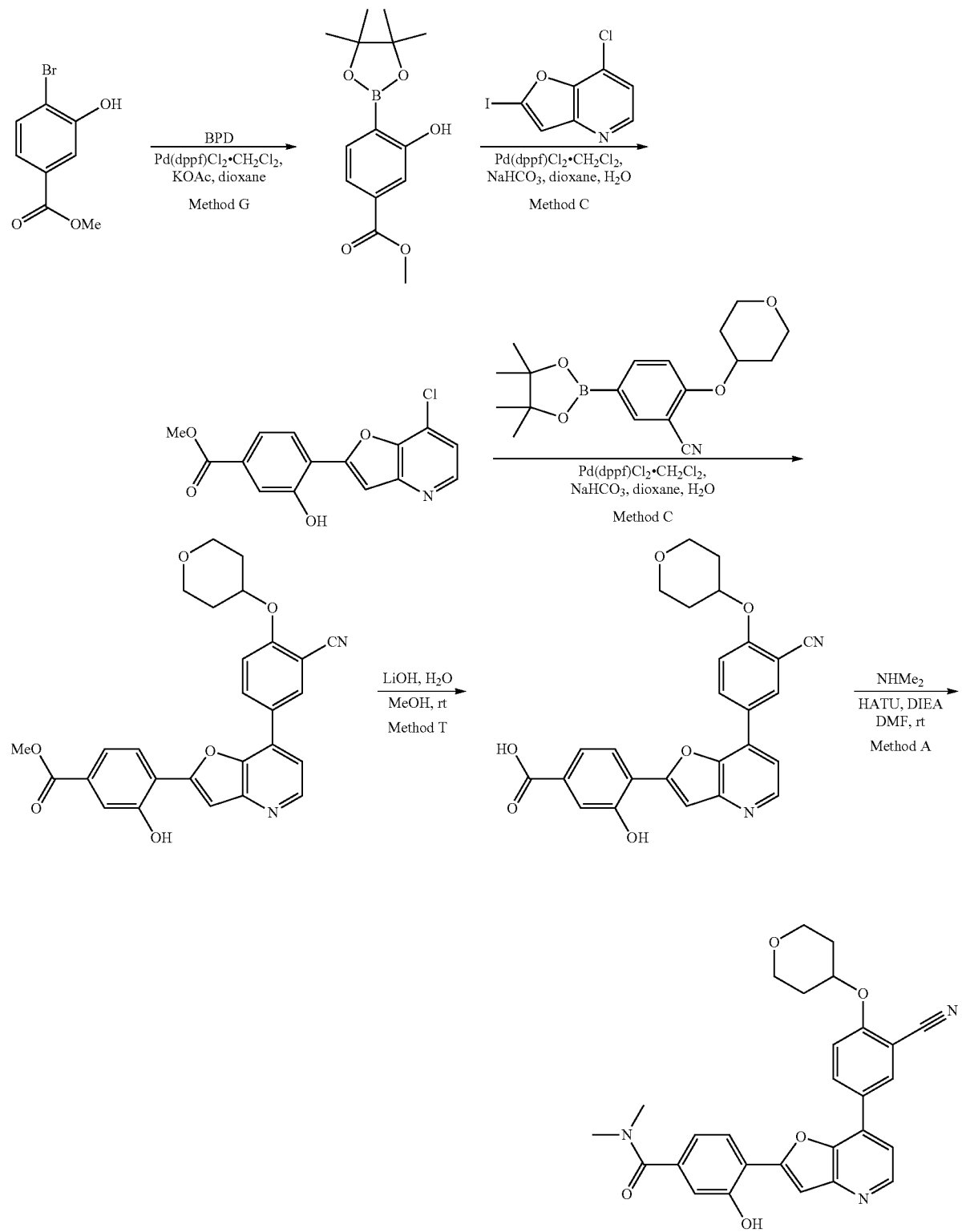

4-(7-(3-cyano-4-(tetrahydro-2H-pyran-4-yloxy)phenyl)furo[3,2-b]pyridin-2-yl)-3-hydroxy-N,N-dimethylbenzamide 4-(7-(3-cyano-4-(tetrahydro-2H-pyran-4-yloxy)phenyl) furo[3,2-b]pyridin-2-yl)-3-hydroxy-N,N-dimethylbenzamide was prepared from methyl 4-bromo-3-hydroxybenzoate, 4,4,5,5-tetramethyl-2-(tetramethyl-1,3,2-dioxaborolan-2-yl)-1,3,2-dioxaborolane, 7-chloro-2-iodofuro[3,2-b]pyridine, 2-(tetrahydro-2H-pyran-4-yloxy)-5-(4,4,5,5-tetramethyl-1,3,2-dioxaborolan-2-yl)benzonitrile and dimethylamine using Method G, C, C, T and A. The final product was purified by prep-HPLC under the following conditions: column Gemini-NX 5u C18 110A, AXIA Packed, 150×21.2 mm; mobile phase, acetonitrile in water (with 10 mmol/L NH$_4$HCO$_3$), 20% to 60% gradient in 8 min; detector, UV 254/220 nm. 4-(7-(3-cyano-4-(tetrahydro-2H-pyran-4-yloxy)phenyl)furo[3,2-b]pyridin-2-yl)-3-hydroxy-N,N-dimethylbenzamide was obtained as off-white solid (20 mg, 1.2% for 5 steps). HPLC: 98.0% purity, RT=1.25 min. MS: m/z=484.0 [M+H]$^+$. $^1$H NMR (400 MHz, DMSO, ppm) δ 8.56 (d, J=4.8 Hz, 1H), 8.51-8.45 (m, 2H), 7.93 (d, J=8.4 Hz, 1H), 7.72-7.60 (m, 3H), 7.04 (s, 1H), 6.98 (d, J=7.2 Hz, 1H), 5.02-4.92 (m, 1H), 3.95-3.84 (m, 2H), 3.63-3.52 (m, 2H), 2.98 (s, 3H), 2.95 (s, 3H), 2.12-2.04 (m, 2H), 1.79-1.65 (m, 2H).

Example 50: 4-(6-chloro-7-(3-cyano-4-(tetrahydro-2H-pyran-4-yloxy)phenyl)furo[3,2-b]pyridin-2-yl)-3-methoxy-N,N-dimethylbenzamide (265)

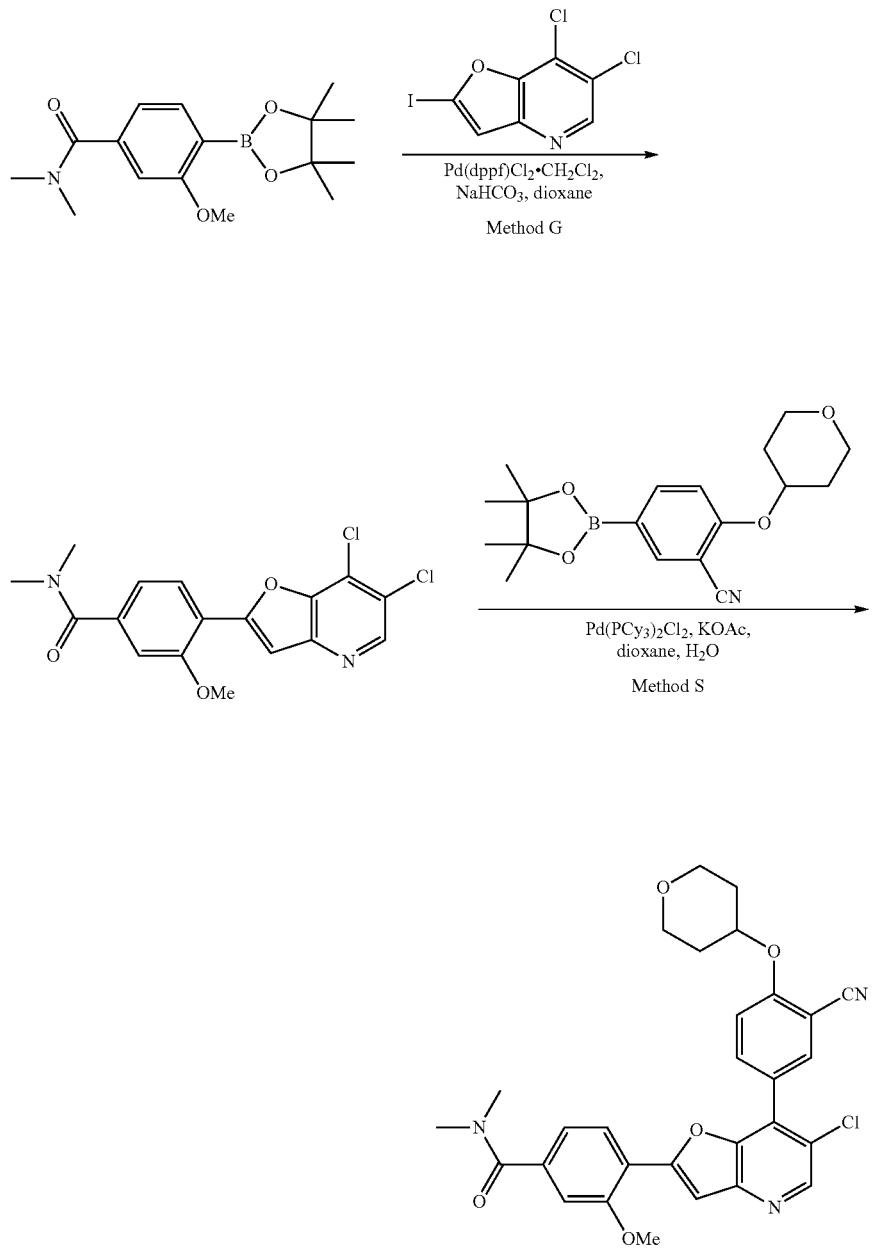

4-(6-chloro-7-(3-cyano-4-(tetrahydro-2H-pyran-4-yloxy)phenyl)furo[3,2-b]pyridin-2-yl)-3-methoxy-N,N-dimethylbenzamide 4-(6-chloro-7-(3-cyano-4-(tetrahydro-2H-pyran-4-yloxy)phenyl)furo[3,2-b]pyridin-2-yl)-3-methoxy-N,N-dimethylbenzamide was prepared from 3-methoxy-N,N-dimethyl-4-(4,4,5,5-tetramethyl-1,3,2-dioxaborolan-2-yl)benzamide, 6,7-dichloro-2-iodofuro[3,2-b]pyridine and 2-(tetrahydro-2H-pyran-4-yloxy)-5-(4,4,5,5-tetramethyl-1,3,2-dioxaborolan-2-yl)benzonitrile using Method G and S. The final product was purified by prep-HPLC under the following conditions: column Gemini-NX 5u C18 110A, AXIA Packed, 150×21.2 mm; mobile phase, acetonitrile in water (with 10 mmol/L NH$_4$HCO$_3$), 20% to 45% gradient in 8 min; detector, UV 254/220 nm. 4-(6-chloro-7-(3-cyano-4-(tetrahydro-2H-pyran-4-yloxy)phenyl)furo[3,2-b]pyridin-2-yl)-3-methoxy-N,N-dimethylbenzamide was obtained as white solid (40 mg, 12% for 2 steps). HPLC: 99.3% purity, RT=2.17 min. MS: m/z=532.0 [M+H]$^+$. $^1$H NMR (400 MHz, DMSO, ppm) δ 8.70 (s, 1H), 8.17 (s, 1H), 8.03 (d, J=8.4 Hz, 1H), 7.78 (d, J=7.6 Hz, 1H), 7.70-7.57 (m, 2H), 7.23 (s, 1H), 7.12 (d, J=8.0 Hz, 1H), 5.02-4.90 (m, 1H), 4.05 (s, 3H), 3.98-3.82 (m, 2H), 3.65-3.50 (m, 2H), 3.00 (s, 3H), 2.93 (s, 3H), 2.15-2.05 (m, 2H), 1.79-1.67 (m, 2H).

Example 51: 4-(6-chloro-7-(3-cyano-4-(tetrahydro-2H-pyran-4-ylamino)phenyl)furo[3,2-b]pyridin-2-yl)-3-methoxy-N,N-dimethylbenzamide (266)

4-(6-chloro-7-(3-cyano-4-(tetrahydro-2H-pyran-4-ylamino)phenyl)furo[3,2-b]pyridin-2-yl)-3-methoxy-N,N-dimethylbenzamide 4-(6-chloro-7-(3-cyano-4-(tetrahydro-2H-pyran-4-ylamino)phenyl)furo[3,2-b]pyridin-2-yl)-3-methoxy-N,N-dimethylbenzamide was prepared from 4-(6,7-dichlorofuro[3,2-b]pyridin-2-yl)-3-methoxy-N,N-dimethylbenzamide and 2-(tetrahydro-2H-pyran-4-ylamino)-5-(4,4,5,5-tetramethyl-1,3,2-dioxaborolan-2-yl)benzonitrile using Method S. The final product was purified by prep-HPLC under the following conditions: column Gemini-NX 5u C18 110A, AXIA Packed, 150×21.2 mm; mobile phase, acetonitrile in water (with 10 mmol/L NH$_4$HCO$_3$), 20% to 45% gradient in 8 min; detector, UV 254/220 nm. 4-(6-chloro-7-(3-cyano-4-(tetrahydro-2H-pyran-4-ylamino)phenyl)furo[3,2-b]pyridin-2-yl)-3-methoxy-N,N-dimethylbenzamide was obtained as light yellow solid (50 mg, 23% for 2 steps). HPLC: 99.1% purity, RT=2.19 min. MS: m/z=531.0 [M+H]$^+$. $^1$H NMR (400 MHz, DMSO, ppm) δ 8.64 (s, 1H), 7.91 (d, J=2.0 Hz, 1H), 7.80 (d, J=8.0 Hz, 2H), 7.60 (s, 1H), 7.23 (s, 1H), 7.20-7.10 (m, 2H), 6.29 (d, J=8.0 Hz, 1H), 4.04 (s, 3H), 3.92 (d, J=9.2 Hz, 2H), 3.83-3.70 (m, 1H), 3.50-3.40 (m, 2H), 3.00 (s, 3H), 2.93 (s, 3H), 1.92-1.85 (m, 2H), 1.75-1.60 (m, 2H).

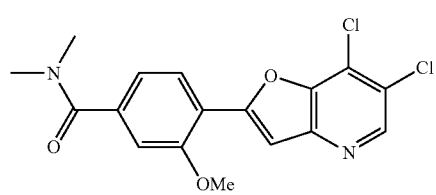
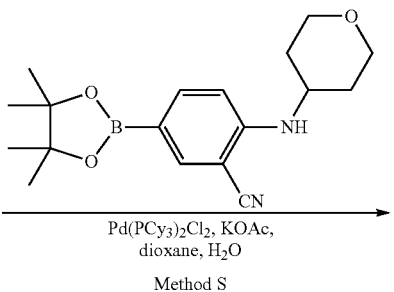

Pd(PCy$_3$)$_2$Cl$_2$, KOAc, dioxane, H$_2$O
Method S

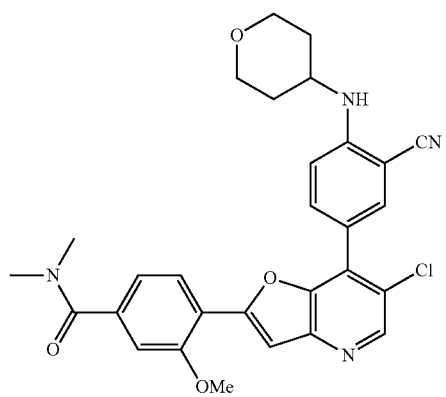

Example 52: 4-(6-chloro-7-(3-cyano-4-(tetrahydro-2H-pyran-4-yloxy)phenyl)furo[3,2-b]pyridin-2-yl)-3-fluoro-N-(2-hydroxyethyl)-N-methylbenzamide (267)

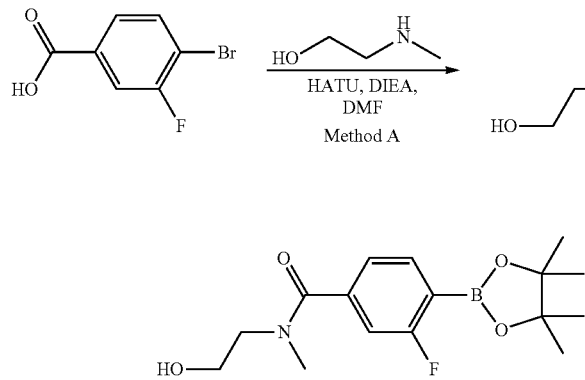
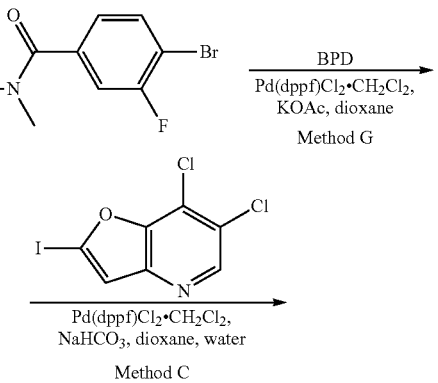
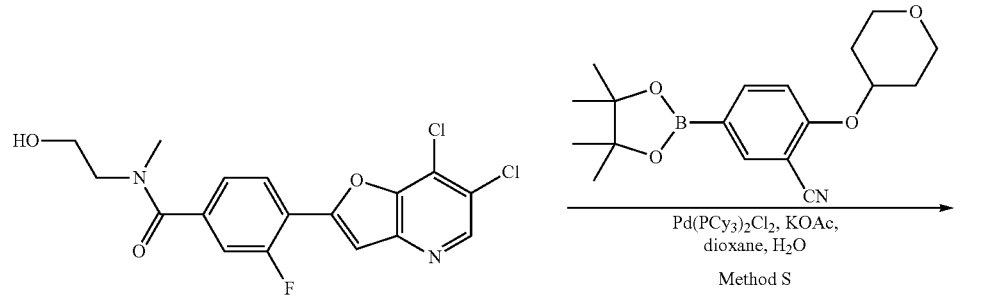
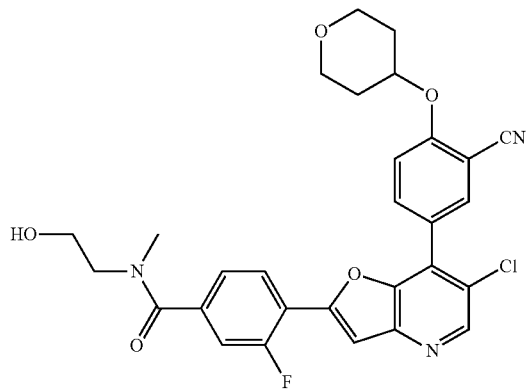

4-(6-chloro-7-(3-cyano-4-(tetrahydro-2H-pyran-4-yloxy)phenyl)furo[3,2-b]pyridin-2-yl)-3-fluoro-N-(2-hydroxyethyl)-N-methylbenzamide 4-(6-chloro-7-(3-cyano-4-(tetrahydro-2H-pyran-4-yloxy)phenyl)furo[3,2-b]pyridin-2-yl)-3-fluoro-N-(2-hydroxyethyl)-N-methylbenzamide was prepared from 4-bromo-3-fluorobenzoic acid, 2-(methylamino)ethanol, 4,4,5,5-tetramethyl-2-(tetramethyl-1,3,2-dioxaborolan-2-yl)-1,3,2-dioxaborolane, 6,7-dichloro-2-iodofuro[3,2-b]pyridine, 2-(tetrahydro-2H-pyran-4-ylamino)-5-(4,4,5,5-tetramethyl-1,3,2-dioxaborolan-2-yl)benzonitrile using Method A, G, C, S. The final product was purified by prep-HPLC under the following conditions: column Gemini-NX 5u C18 110A, AXIA Packed, 150×21.2 mm; mobile phase, acetonitrile in water (with 10 mmol/L $NH_4HCO_3$), 20% to 50% gradient in 8 min; detector, UV 254/220 nm. 4-(6-chloro-7-(3-cyano-4-(tetrahydro-2H-pyran-4-yloxy)phenyl)furo[3,2-b]pyridin-2-yl)-3-fluoro-N-(2-hydroxyethyl)-N-methylbenzamide was obtained as white solid (15 mg, 4.7% for 4 steps). HPLC: 99.2% purity, RT=2.14 min. MS: m/z=550.0 [M+H]$^+$. $^1$H NMR (400 MHz, DMSO, ppm) δ 8.75 (s, 1H), 8.18 (s, 1H), 8.04 (d, J=8.4 Hz, 1H), 7.98-7.80 (m, 1H), 7.78-7.30 (m, 4H), 4.98 (br s, 1H), 4.85 (br s, 1H), 3.99-3.80 (m, 2H), 3.71-3.45 (m, 5H), 3.30-3.15 (m, 1H), 3.10-2.90 (m, 3H), 2.15-1.99 (m, 2H), 1.82-1.66 (m, 2H).

Example 53: 4-(7-(3-cyano-4-(tetrahydro-2H-pyran-4-ylamino)phenyl)-6-methylfuro[3,2-b]pyridin-2-yl)-N-(2-hydroxyethyl)-3-methoxy-N-methylbenzamide (268)

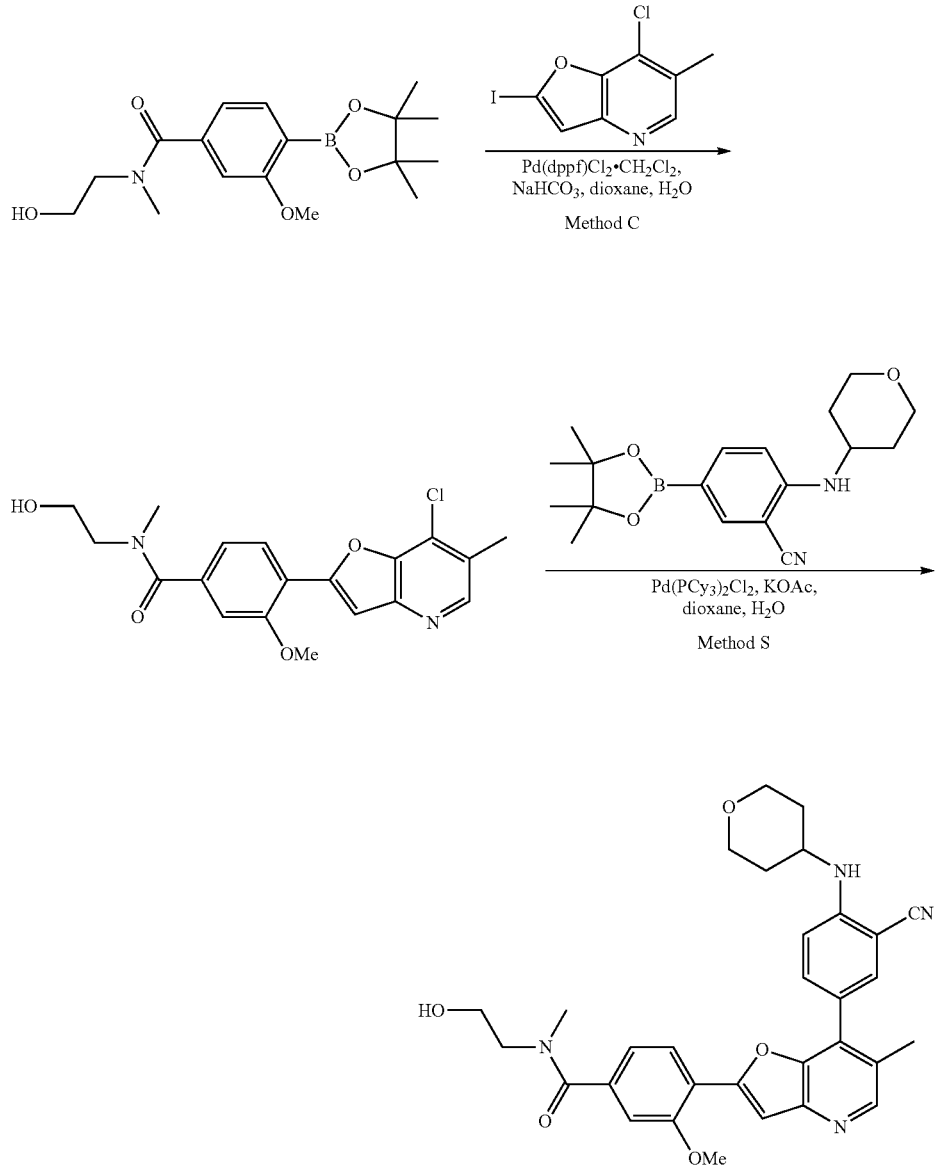

4-(7-(3-cyano-4-(tetrahydro-2H-pyran-4-ylamino)phenyl)-6-methylfuro[3,2-b]pyridin-2-yl)-N-(2-hydroxyethyl)-3-methoxy-N-methylbenzamide 4-(7-(3-cyano-4-(tetrahydro-2H-pyran-4-ylamino)phenyl)-6-methylfuro[3,2-b]pyridin-2-yl)-N-(2-hydroxyethyl)-3-methoxy-N-methylbenzamide was prepared from N-(2-hydroxyethyl)-3-methoxy-N-methyl-4-(4,4,5,5-tetramethyl-1,3,2-dioxaborolan-2-yl)benzamide, 7-chloro-2-iodo-6-methylfuro[3,2-b]pyridine and 2-(tetrahydro-2H-pyran-4-ylamino)-5-(4,4,5,5-tetramethyl-1,3,2-dioxaborolan-2-yl)benzonitrile using Method C and S. The final product was purified by prep-HPLC under the following conditions: column Gemini-NX 5u C18 110A, AXIA Packed, 150×21.2 mm; mobile phase, acetonitrile in water (with 10 mmol/L $NH_4HCO_3$), 20% to 50% gradient in 8 min; detector, UV 254/220 nm. 4-(7-(3-cyano-4-(tetrahydro-2H-pyran-4-ylamino)phenyl)-6-methylfuro[3,2-b]pyridin-2-yl)-N-(2-hydroxyethyl)-3-methoxy-N-methylbenzamide was obtained as off-white solid (28 mg, 8.4% for 2 steps). HPLC: 99.8% purity, RT=1.49 min. MS: m/z=541.0 [M+H]$^+$. $^1$H NMR (400 MHz, DMSO, ppm) δ 8.46 (s, 1H), 7.85-7.72 (m, 2H), 7.70 (dd, J=9.2, 2.0 Hz, 1H), 7.53 (s, 1H), 7.29-7.17 (m, 1H), 7.18-7.05 (m, 2H), 6.14 (d, J=8.0 Hz, 1H), 4.88-4.77 (m, 1H), 4.02 (s, 3H), 3.92 (d, J=9.6 Hz, 2H), 3.82-3.70 (m, 3H), 3.69-3.40 (m, 5H), 3.35-3.20 (m, 1H), 3.06-2.90 (m, 3H), 2.37 (s, 3H), 1.91-1.89 (d, J=10.4 Hz, 2H), 1.73-1.58 (m, 2H).

Example 54: 4-(7-(3-cyano-4-(tetrahydro-2H-pyran-4-yloxy)phenyl)-6-methylfuro[3,2-b]pyridin-2-yl)-N-(2-hydroxyethyl)-3-methoxy-N-methylbenzamide (279)

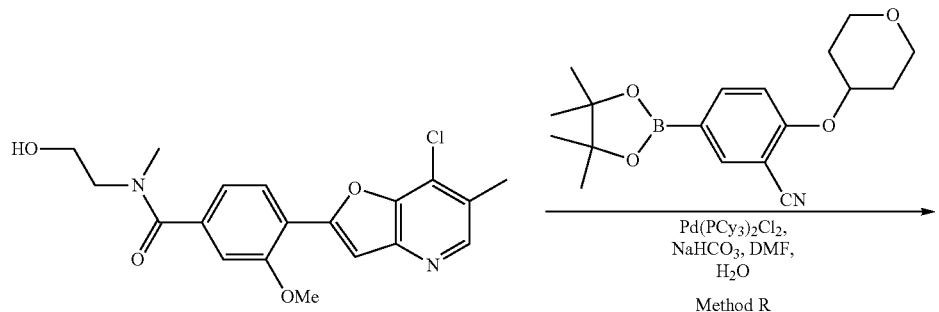

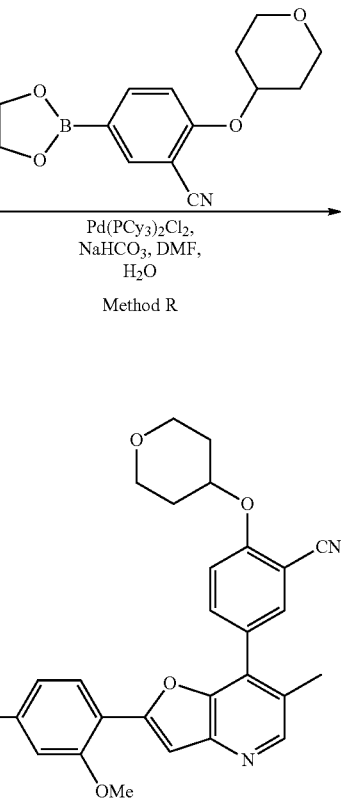

4-(7-(3-cyano-4-(tetrahydro-2H-pyran-4-yloxy)phenyl)-6-methylfuro[3,2-b]pyridin-2-yl)-N-(2-hydroxyethyl)-3-methoxy-N-methylbenzamide 4-(7-(3-cyano-4-(tetrahydro-2H-pyran-4-yloxy)phenyl)-6-methylfuro[3,2-b]pyridin-2-yl)-N-(2-hydroxyethyl)-3-methoxy-N-methylbenzamide was prepared from 4-(7-chloro-6-methylfuro[3,2-b]pyridin-2-yl)-N-(2-hydroxyethyl)-3-methoxy-N-methylbenzamide and 2-(tetrahydro-2H-pyran-4-yloxy)-5-(4,4,5,5-tetramethyl-1,3,2-dioxaborolan-2-yl)benzonitrile using Method R. The product was purified by prep-HPLC under the following conditions: column Gemini-NX 5u C18 110A, AXIA Packed, 150×21.2 mm; mobile phase, acetonitrile in water (with 10 mmol/L NH$_4$HCO$_3$), 20% to 50% gradient in 8 min; detector, UV 254/220 nm. 4-(7-(3-cyano-4-(tetrahydro-2H-pyran-4-yloxy)phenyl)-6-methylfuro[3,2-b]pyridin-2-yl)-N-(2-hydroxyethyl)-3-methoxy-N-methylbenzamide was obtained as white solid (23 mg, 12%). HPLC: 96.7% purity, RT=1.54 min. MS: m/z=542.0 [M+H]$^+$. $^1$H NMR (300 MHz, CD$_3$OD, ppm) δ 8.43 (s, 1H), 7.95-7.80 (m, 3H), 7.58-7.41 (m, 2H), 7.28 (d, J=11.1 Hz, 1H), 7.10 (dd, J=7.8, 1.2 Hz, 1H), 5.00-4.88 (m, 1H), 4.15-3.95 (m, 5H), 3.89-3.79 (m, 1H), 3.75-3.55 (m, 4H), 3.50-3.39 (m, 1H), 3.10 (d, J=13.5 Hz, 3H), 2.40 (s, 3H), 2.22-2.08 (m, 2H), 1.97-1.80 (m, 2H).

Example 55: 4-(7-(3-cyano-4-(tetrahydro-2H-pyran-4-yloxy)phenyl)-6-methylfuro[3,2-b]pyridin-2-yl)-3-methoxy-N,N-dimethylbenzamide hydrochloride (269)

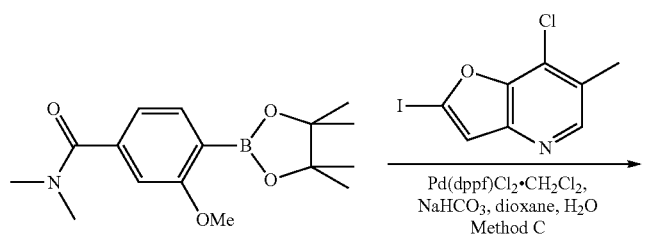

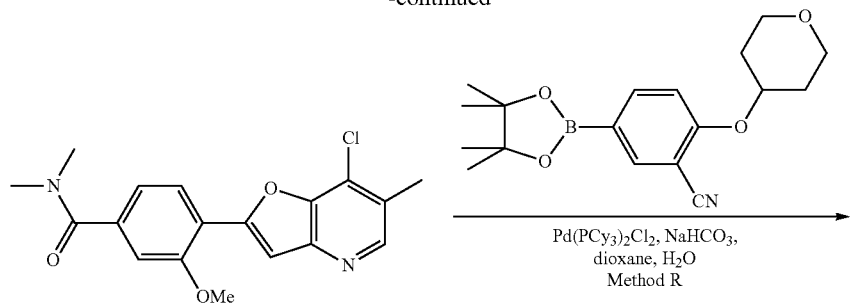

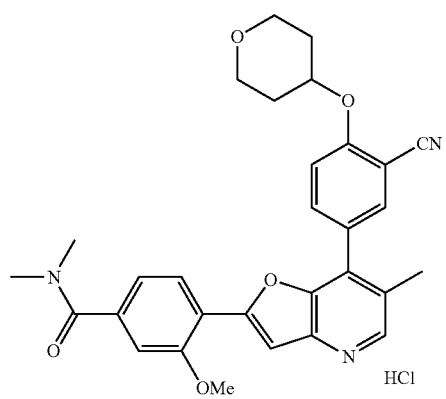

4-(7-(3-cyano-4-(tetrahydro-2H-pyran-4-yloxy)phenyl)-6-methylfuro[3,2-b]pyridin-2-yl)-3-methoxy-N,N-dimethylbenzamide hydrochloride 4-(7-(3-cyano-4-(tetrahydro-2H-pyran-4-yloxy)phenyl)-6-methylfuro[3,2-b]pyridin-2-yl)-3-methoxy-N,N-dimethylbenzamide hydrochloride was prepared from 3-methoxy-N,N-dimethyl-4-(4,4,5,5-tetramethyl-1,3,2-dioxaborolan-2-yl)benzamide, 7-chloro-2-iodo-6-methylfuro[3,2-b]pyridine and 2-(tetrahydro-2H-pyran-4-ylamino)-5-(4,4,5,5-tetramethyl-1,3,2-dioxaborolan-2-yl)benzonitrile using Method C and R. The final product was purified by prep-HPLC under the following conditions: column Gemini-NX 5u C18 110A, AXIA Packed, 150×21.2 mm; mobile phase, acetonitrile in water (with 0.02% HCl), 20% to 50% gradient in 10 min; detector, UV 254/220 nm. 4-(7-(3-cyano-4-(tetrahydro-2H-pyran-4-yloxy)phenyl)-6-methylfuro[3,2-b]pyridin-2-yl)-3-methoxy-N,N-dimethylbenzamide hydrochloride was obtained as light yellow solid (15 mg, 9.5% for 2 steps). HPLC: 98.3% purity, RT=1.17 min. MS: m/z=512.0 [M+H]+. $^1$H NMR (400 MHz, CD$_3$OD, ppm) δ 8.60 (s, 1H), 8.02 (d, J=2.4 Hz, 1H), 8.00-7.90 (m, 2H), 7.67 (s, 1H), 7.55 (d, J=9.2 Hz, 1H), 7.29 (s, 1H), 7.15 (dd, J=8.0, 1.2 Hz, 1H), 5.04-4.90 (m, 1H), 4.12 (s, 3H), 4.10-4.00 (m, 2H), 3.78-3.66 (m, 2H), 3.14 (s, 3H), 3.05 (s, 3H), 2.51 (s, 3H), 2.25-2.15 (m, 2H), 1.99-1.85 (m, 2H).

Example 56: 4-(7-(3-cyano-4-(tetrahydro-2H-pyran-4-yloxy)phenyl)-6-methylfuro[3,2-b]pyridin-2-yl)-3-fluoro-N,N-dimethylbenzamide hydrochloride (280)

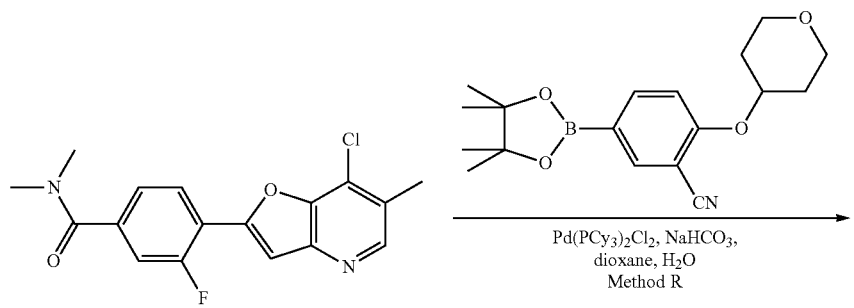

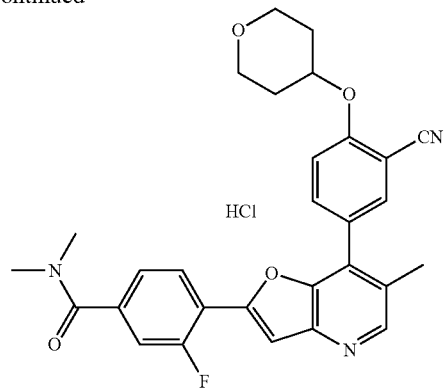

4-(7-(3-cyano-4-(tetrahydro-2H-pyran-4-yloxy)phenyl)-6-methylfuro[3,2-b]pyridin-2-yl)-3-fluoro-N,N-dimethylbenzamide hydrochloride 4-(7-(3-cyano-4-(tetrahydro-2H-pyran-4-yloxy)phenyl)-6-methylfuro[3,2-b]pyridin-2-yl)-3-fluoro-N,N-dimethylbenzamide hydrochloride was prepared from 4-(7-chloro-6-methylfuro[3,2-b]pyridin-2-yl)-3-fluoro-N,N-dimethylbenzamide and 2-(tetrahydro-2H-pyran-4-yloxy)-5-(4,4,5,5-tetramethyl-1,3,2-dioxaborolan-2-yl)benzonitrile using Method R. The final product was purified by prep-HPLC under the following conditions: column Gemini-NX 5u C18 110A, AXIA Packed, 150×21.2 mm; mobile phase, acetonitrile in water (with 0.02% HCl), 20% to 50% gradient in 8 min; detector, UV 254/220 nm. 4-(7-(3-cyano-4-(tetrahydro-2H-pyran-4-yloxy)phenyl)-6-methylfuro[3,2-b]pyridin-2-yl)-3-fluoro-N,N-dimethylbenzamide hydrochloride was obtained as white solid (10 mg, 8%). HPLC: 98.8% purity, RT=1.24 min. MS: m/z=500.0 [M+H]$^+$. $^1$H NMR (400 MHz, DMSO, ppm) δ 8.71 (s, 1H), 8.10-7.95 (m, 3H), 7.62 (d, J=2.1 Hz, 1H), 7.57 (d, J=8.8 Hz, 1H), 7.51-7.40 (m, 2H), 5.04-4.90 (m, 1H), 4.10-4.00 (m, 2H), 3.78-3.69 (m, 2H), 3.14 (s, 3H), 3.04 (s, 3H), 2.55 (s, 3H), 2.23-2.12 (m, 2H), 1.99-1.87 (m, 2H).

Example 57: 4-(7-(3-cyano-4-(tetrahydro-2H-pyran-4-yloxy)phenyl)-6-methylfuro[3,2-b]pyridin-2-yl)-3-fluoro-N-(2-hydroxyethyl)-N-methylbenzamide (281)

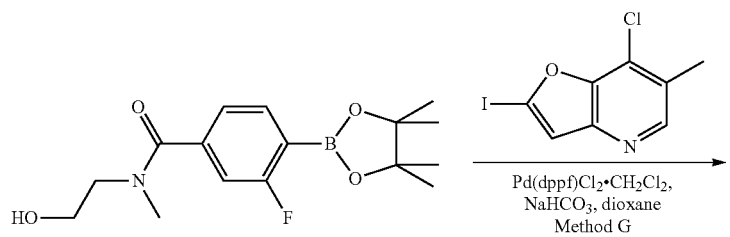

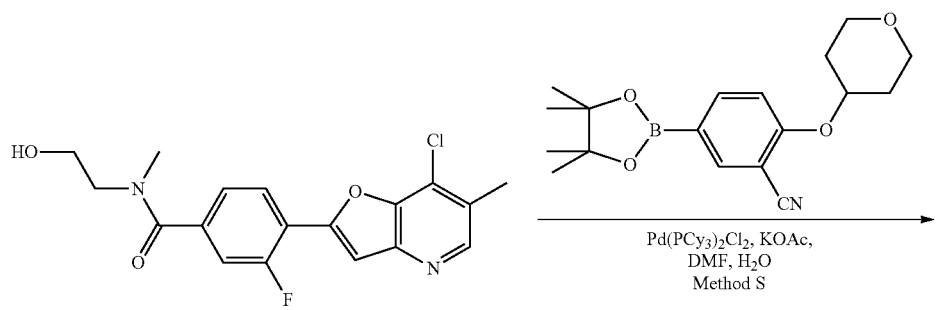

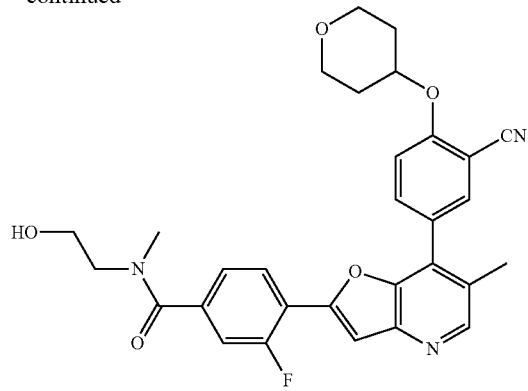

4-(7-(3-cyano-4-(tetrahydro-2H-pyran-4-yloxy)phenyl)-6-methylfuro[3,2-b]pyridin-2-yl)-3-fluoro-N-(2-hydroxyethyl)-N-methylbenzamide 4-(7-(3-cyano-4-(tetrahydro-2H-pyran-4-yloxy)phenyl)-6-methylfuro[3,2-b]pyridin-2-yl)-3-fluoro-N-(2-hydroxyethyl)-N-methylbenzamide was prepared from 3-fluoro-N-(2-hydroxyethyl)-N-methyl-4-(4,4,5,5-tetramethyl-1,3,2-dioxaborolan-2-yl)benzamide, 7-chloro-2-iodo-6-methylfuro[3,2-b]pyridine and 2-(tetrahydro-2H-pyran-4-yloxy)-5-(4,4,5,5-tetramethyl-1,3,2-dioxaborolan-2-yl)benzonitrile using Method G and S. The final product was purified by prep-HPLC under the following conditions: column Gemini-NX 5u C18 110A, AXIA Packed, 150×21.2 mm; mobile phase, acetonitrile in water (with 10 mmol/L NH$_4$HCO$_3$), 20% to 50% gradient in 8 min; detector, UV 254/220 nm. 4-(7-(3-cyano-4-(tetrahydro-2H-pyran-4-yloxy)phenyl)-6-methylfuro[3,2-b]pyridin-2-yl)-3-fluoro-N-(2-hydroxyethyl)-N-methylbenzamide was obtained as white solid (25 mg, 13% for 2 steps). HPLC: 99.2% purity, RT=1.09 min. MS: m/z=530.0 [M+H]$^+$. $^1$H NMR (300 MHz, DMSO, ppm) δ 8.68 (s, 1H), 8.08 (d, J=2.1 Hz, 1H), 7.94 (dd, J=8.7, 2.1 Hz, 1H), 7.90-7.80 (m, 1H), 7.58 (d, J=9.0 Hz, 1H), 7.56-7.45 (m, 2H), 7.40 (d, J=8.1 Hz, 1H), 5.01-4.89 (m, 1H), 4.90-4.75 (m, 1H), 3.97-3.80 (m, 2H), 3.70-3.40 (m, 5H), 3.30-3.20 (m, 1H), 3.05-2.90 (m, 3H), 2.34 (s, 3H), 2.15-1.99 (m, 2H), 1.82-1.66 (m, 2H).

Example 58: 5-(7-(3-cyano-4-(tetrahydro-2H-pyran-4-yloxy)phenyl)furo[3,2-b]pyridin-2-yl)-6-methoxy-N,N-dimethylpicolinamide (271)

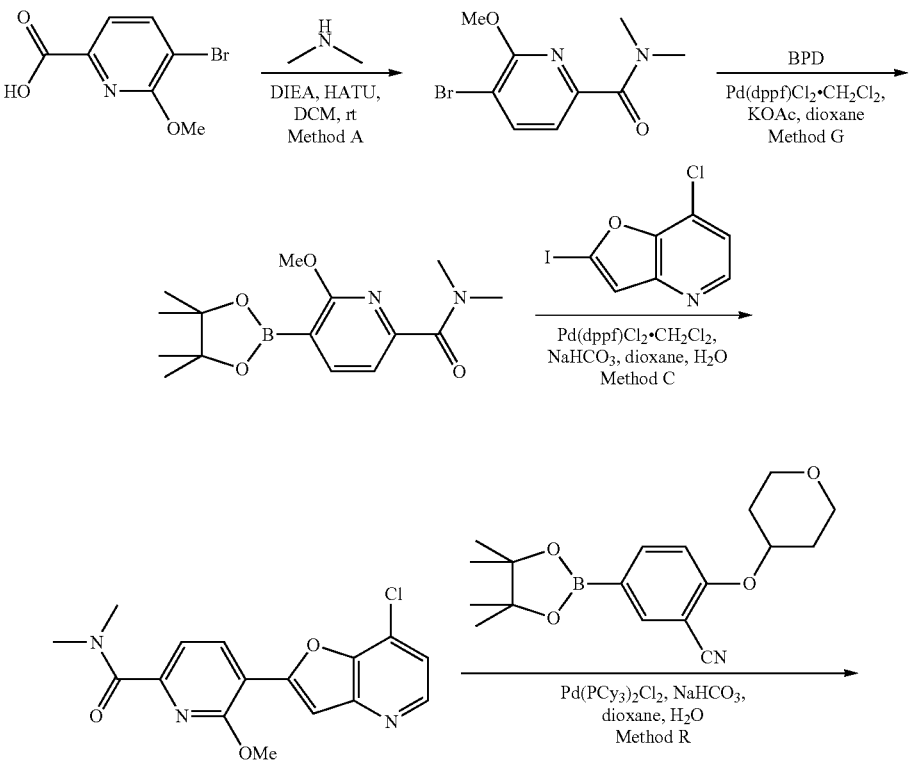

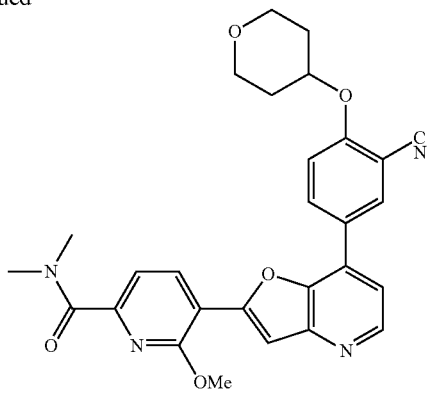

5-(7-(3-cyano-4-(tetrahydro-2H-pyran-4-yloxy)phenyl)furo[3,2-b]pyridin-2-yl)-6-methoxy-N,N-dimethylpicolinamide 5-(7-(3-cyano-4-(tetrahydro-2H-pyran-4-yloxy)phenyl)furo[3,2-b]pyridin-2-yl)-6-methoxy-N,N-dimethylpicolinamide was prepared from 5-bromo-6-methoxypicolinic acid, dimethylamine, 4,4,5,5-tetramethyl-2-(tetramethyl-1,3,2-dioxaborolan-2-yl)-1,3,2-dioxaborolane, 6,7-dichloro-2-iodofuro[3,2-b]pyridine, 2-(tetrahydro-2H-pyran-4-ylamino)-5-(4,4,5,5-tetramethyl-1,3,2-dioxaborolan-2-yl)benzonitrile using Method A, G, C and R. The final product was purified by prep-HPLC under the following conditions: column Gemini-NX 5u C18 110A, AXIA Packed, 150×21.2 mm; mobile phase, acetonitrile in water (with 10 mmol/L $NH_4HCO_3$), 20% to 50% gradient in 8 min; detector, UV 254/220 nm. 5-(7-(3-cyano-4-(tetrahydro-2H-pyran-4-yloxy)phenyl)furo[3,2-b]pyridin-2-yl)-6-methoxy-N,N-dimethylpicolinamide was obtained as white solid (15 mg, 7.3% for 4 steps). HPLC: 96.0% purity, RT=1.22 min. MS: m/z=499.0 [M+H]$^+$. $^1$H NMR (300 MHz, DMSO, ppm) δ 8.60 (d, J=8.1 Hz, 1H), 8.52-8.42 (m, 3H), 7.76-7.69 (m, 2H), 7.64 (d, J=9.6 Hz, 1H), 7.41 (d, J=7.8 Hz, 1H), 5.05-4.90 (m, 1H), 4.13 (s, 3H), 3.98-3.80 (m, 2H), 3.65-3.50 (m, 2H), 2.50 (m, 3H), 2.49 (s, 3H), 2.15-2.00 (m, 2H), 1.80-1.62 (m, 2H).

Example 59: 6-(7-(3-cyano-4-(3-fluoropyrrolidin-1-yl)phenyl)furo[3,2-b]pyridin-2-yl)-N,N-dimethylnicotinamide hydrochloride (272, 273)

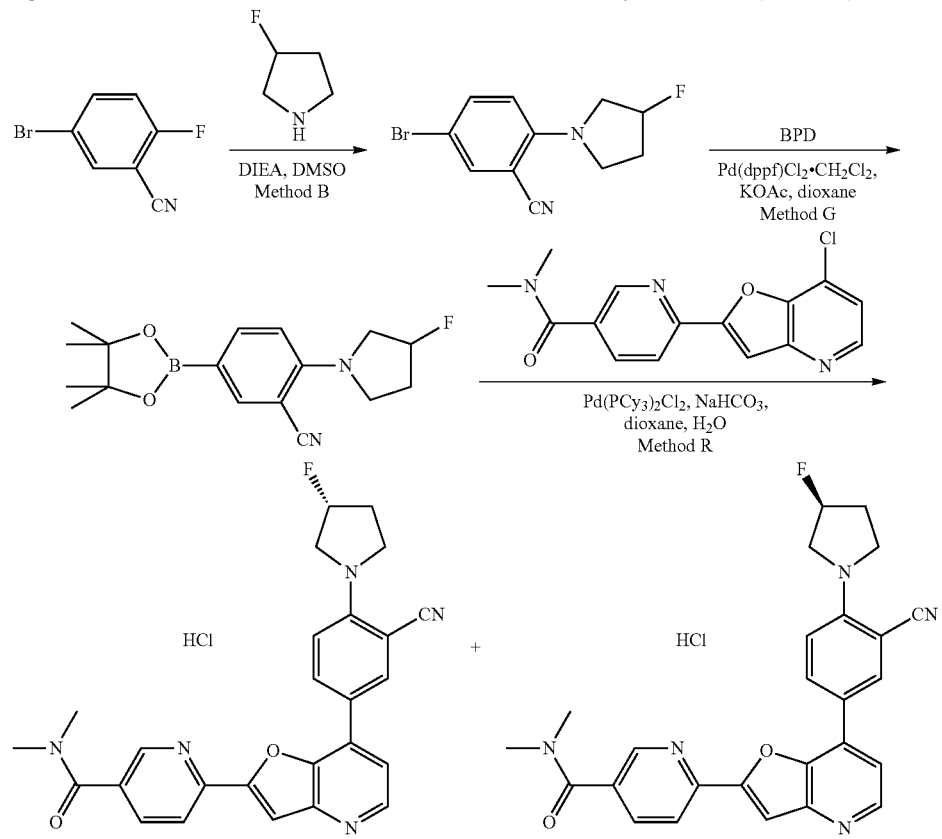

6-(7-(3-cyano-4-(3-fluoropyrrolidin-1-yl)phenyl)furo[3,2-b]pyridin-2-yl)-N,N-dimethylnicotinamide hydrochloride 6-(7-(3-cyano-4-(3-fluoropyrrolidin-1-yl)phenyl)furo[3,2-b]pyridin-2-yl)-N,N-dimethylnicotinamide hydrochloride was prepared from 5-bromo-2-fluorobenzonitrile, 3-fluoropyrrolidine, 4,4,5,5-tetramethyl-2-(tetramethyl-1,3,2-dioxaborolan-2-yl)-1,3,2-dioxaborolane and 6-(7-chlorofuro[3,2-b]pyridin-2-yl)-N,N-dimethylnicotinamide using Method B, G, and R. The final product was first purified by prep-HPLC under the following conditions: column Atlantis Prep T₃ OBD column, 19×150 mm 5 um 10 nm; mobile phase, acetonitrile in water (with 0.02% HCl), 20% to 50% gradient in 8 min; detector, UV 254/220 nm. Then the two enantiomeric products of 6-(7-(3-cyano-4-(3-fluoropyrrolidin-1-yl)phenyl)furo[3,2-b]pyridin-2-yl)-N,N-dimethylnicotinamide hydrochloride were obtained by separation on chiral prep-HPLC under the following conditions: column CHIRALPAK AD-H SFC, 5×25 cm, 5 um; mobile phase, EtOH in hexane (0.1% DEA) in 36 min; detector, UV 330 nm.

Compound 272:
(15 mg, 3.3% for 3 steps, yellow solid) HPLC: 96.1% purity, RT=1.07 min. MS: m/z=456.0 [M+H]⁺. ¹H NMR (300 MHz, CD₃OD, ppm) δ 8.82 (s, 1H), 8.60 (d, J=8.4 Hz, 1H), 8.49 (d, J=2.4 Hz, 1H), 8.37 (dd, J=9.3, 2.4 Hz, 1H), 8.22 (d, J=8.4 Hz, 1 H), 8.11 (dd, J=8.1, 2.1 Hz, 1H), 7.98 (d, J=8.0 Hz, 1H), 7.83 (s, 1H), 7.07 (d, J=9.3 Hz, 1H), 5.55-5.32 (m, 1H), 4.18-3.85 (m, 4H), 3.14 (s, 3H), 3.06 (s, 3H), 2.50-2.10 (m, 2H).

Compound 273:
(15 mg, 3.3% for 3 steps, yellow solid) HPLC: 93.6% purity, RT=1.06 min. MS: m/z=456.0 [M+H]⁺. ¹H NMR (300 MHz, CD₃OD, ppm) δ 8.81 (s, 1H), 8.60 (d, J=8.0 Hz, 1H), 8.49 (d, J=2.4 Hz, 1H), 8.37 (dd, J=9.3, 2.4 Hz, 1H), 8.22 (d, J=8.7 Hz, 1H), 8.11 (dd, J=8.1, 2.1 Hz, 1H), 7.98 (d, J=8.0 Hz, 1H), 7.85 (s, 1H), 7.08 (d, J=9.6 Hz, 1H), 5.55-5.32 (m, 1H), 4.18-3.85 (m, 4H), 3.14 (s, 3H), 3.06 (s, 3H), 2.50-2.10 (m, 2H).

Example 60: 6-(7-(3-cyano-4-(tetrahydro-2H-pyran-4-yloxy)phenyl)furo[3,2-b]pyridin-2-yl)-5-methoxy-N,N-dimethylnicotinamide hydrochloride (274)

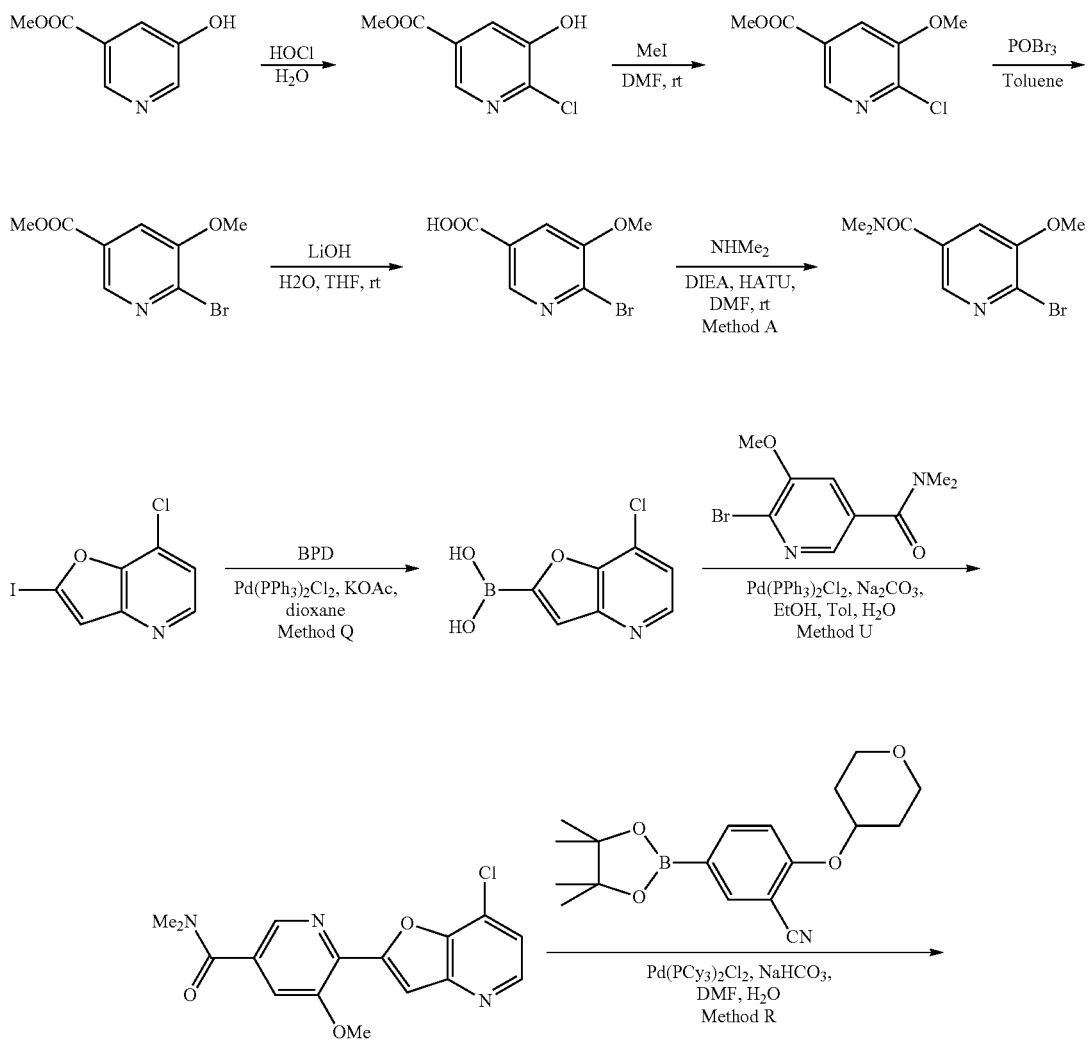

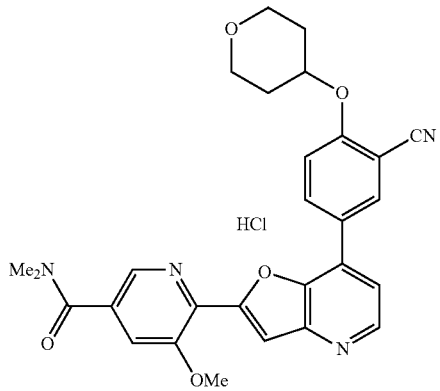

Methyl 6-chloro-5-hydroxynicotinate

At 0° C., to a solution of methyl 5-hydroxypyridine-3-carboxylate (1.8 g, 11.75 mmol) in water (15 mL) was added HClO (651 mg, 12.4 mmol) in portions over 10 min period. The resulting solution was stirred for 1 h at 0° C., warmed to room temperature and treated with hydrochloric acid solution (2 M, 20 mL). The precipitate that formed were collected by filtration and dried in oven under vacuum to yield methyl 6-chloro-5-hydroxynicotinate as off-white solid (800 mg, 33%).

Methyl 6-chloro-5-methoxynicotinate

To a solution of methyl 6-chloro-5-hydroxypyridine-3-carboxylate (720 mg, 3.84 mmol) in DMF (10 mL) was added methyl iodide (635 mg, 4.46 mmol) at room temperature. The resulting solution was stirred for 8 h at room temperature and diluted with water (30 mL). The mixture was extracted with ethyl acetate (50 mL×3). The organic phases were combined, washed with brine and dried over sodium sulfate. The solvent was concentrated under reduced pressure to yield methyl 6-chloro-5-methoxypyridine-3-carboxylate as yellow solid (600 mg, 66%).

Methyl 6-bromo-5-methoxynicotinate

To a solution of 6-chloro-5-methoxypyridine-3-carboxylate (850 mg, 4.22 mmol) in toluene (50 mL) was added POBr$_3$ (2.9 g, 10.37 mmol) at room temperature. The resulting solution was then stirred for 16 h at 90° C., cooled to room temperature and diluted with water (30 mL). The resulting mixture was extracted with ethyl acetate (60 mL×3). The organic phases were combined, washed with brine and dried over sodium sulfate. The solvent was removed under reduced pressure and the residue was purified by flash chromatography eluting with ethyl acetate in hexane (0% to 100% gradient) to yield methyl 6-bromo-5-methoxypyridine-3-carboxylate as off-white solid (800 mg, 116%). MS: m/z=246.0 [M+H]$^+$.

6-bromo-5-methoxynicotinic acid

To a solution of methyl 6-bromo-5-methoxypyridine-3-carboxylate (1.0 g, 4.15 mmol) in tetrahydrofuran (10 mL) was added a solution of lithium hydroxide (298 mg, 12.42 mmol) in water (2.5 mL) at room temperature. The resulting mixture was stirred overnight at room temperature and then diluted with water (20 mL). The pH value of the mixture was adjusted to 1 with hydrochloric acid solution (2 M). The resulting mixture was extracted with ethyl acetate (80 mL×3). The organic phases were combined, washed with brine and dried over sodium sulfate. The solution was removed under reduced pressure and the residue was purified by flash chromatography eluting with methanol in dichloromethane (0% to 10% gradient) to yield 6-bromo-5-methoxypyridine-3-carboxylic acid as off-white solid (850 mg, 88%). MS: m/z=232.0 [M+H]$^+$.

6-bromo-5-methoxy-N,N-dimethylnicotinamide

At room temperature, to a solution of 6-bromo-5-methoxypyridine-3-carboxylic acid (2.7 g, 11.81 mmol) and dimethylamine hydrochloride (1.1 g, 12.93 mmol) in DMF (30 mL) were added DIEA (5.0 g, 38.66 mmol) and HATU (7.4 g, 19.36 mmol) in sequence. The resulting solution was stirred for 16 h at 60° C., cooled to room temperature and diluted with water (100 mL). The resulting mixture was extracted with ethyl acetate (200 mL×3). The organic phases were combined, washed with brine and dried over sodium sulfate. The solvent was removed under reduced pressure and the residue was purified by flash chromatography eluting with ethyl acetate in hexane (0% to 70% gradient) to yield 6-bromo-5-methoxy-N,N-dimethylpyridine-3-carboxamide as red oil (2.3 g, 75%). MS: m/z=259.0 [M+H]$^+$.

6-(7-(3-cyano-4-(tetrahydro-2H-pyran-4-yloxy)phenyl)furo[3,2-b]pyridin-2-yl)-5-methoxy-N,N-dimethylnicotinamide hydrochloride 6-(7-(3-cyano-4-(tetrahydro-2H-pyran-4-yloxy)phenyl) furo[3,2-b]pyridin-2-yl)-5-methoxy-N,N-dimethylnicotinamide hydrochloride was prepared from 7-chloro-2-iodofuro[3,2-b]pyridine, 6-bromo-5-methoxy-N,N-dimethylnicotinamide and 2-(tetrahydro-2H-pyran-4-yloxy)-5-(4,4,5,5-tetramethyl-1,3,2-dioxaborolan-2-yl)benzonitrile using Method Q, U and R. The final product was purified by prep-HPLC under the following conditions: column Gemini-NX 5u C18 110A, AXIA Packed, 150×21.2 mm; mobile phase, acetonitrile in water (with 0.02% HCl), 20% to 40% gradient in 8 min; detector, UV 254/220 nm. 6-(7-(3-cyano-4-(tetrahydro-2H-pyran-4-yloxy)phenyl)furo[3,2-b]pyridin-2-yl)-5-methoxy-N,N-dimethylnicotinamide hydrochloride was obtained as yellow solid (20 mg, 1.3% for 3 steps). HPLC: 99.2% purity, RT=1.57 min. MS: m/z=499.0 [M+H]$^+$. $^1$H NMR (400 MHz, CD$_3$OD, ppm) δ 8.82 (d, J=1.6 Hz, 1H), 8.79-8.61 (m, 1H), 8.48 (d, J=4.4 Hz, 1H), 8.52-8.42 (m, 1H), 8.29-8.20 (m, 1H), 8.00 (d, J=4.8

Hz, 1H), 7.88 (s, 1H), 7.69-7.58 (m, 1H), 5.12-5.00 (br s, 1H), 4.24 (s, 3H), 4.09-3.95 (m, 2H), 3.79-3.65 (m, 2H), 3.20 (m, 3H), 3.12 (s, 3H), 2.25-2.10 (m, 2H), 1.99-1.80 (m, 2H).

Example 61: 6-(7-(3-cyano-4-(tetrahydro-2H-pyran-4-ylamino)phenyl)furo[3,2-b]pyridin-2-yl)-5-methoxy-N,N-dimethylnicotinamide hydrochloride (270)

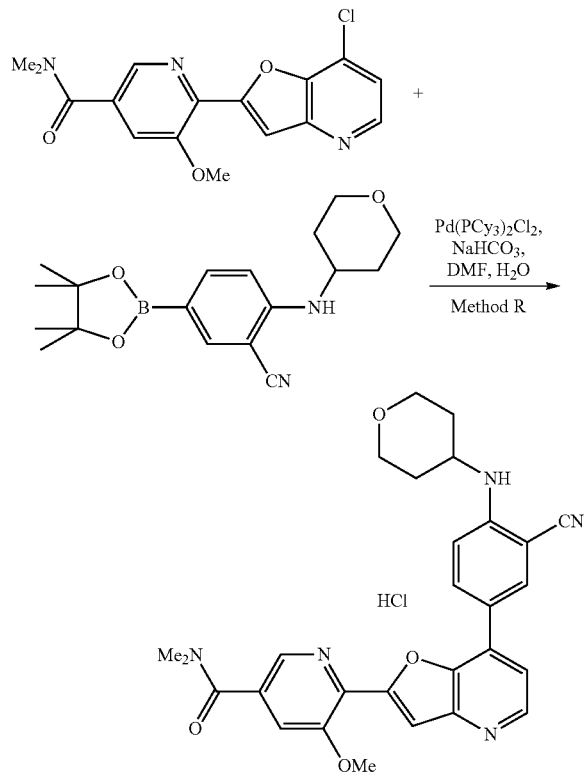

6-(7-(3-cyano-4-(tetrahydro-2H-pyran-4-ylamino) phenyl)furo[3,2-b]pyridin-2-yl)-5-methoxy-N,N-dimethylnicotinamide hydrochloride 6-(7-(3-cyano-4-(tetrahydro-2H-pyran-4-ylamino)phenyl)furo[3,2-b]pyridin-2-yl)-5-methoxy-N,N-dimethylnicotinamide hydrochloride was prepared from 6-(7-chlorofuro[3,2-b]pyridin-2-yl)-5-methoxy-N,N-dimethylnicotinamide and 2-(tetrahydro-2H-pyran-4-ylamino)-5-(4,4,5,5-tetramethyl-1,3,2-dioxaborolan-2-yl)benzonitrile using Method R. The product was purified by prep-HPLC under the following conditions: column Gemini-NX 5u C18 110A, AXIA Packed, 150×21.2 mm; mobile phase, acetonitrile in water (with 0.02% HCl), 20% to 50% gradient in 8 min; detector, UV 254/220 nm. 6-(7-(3-cyano-4-(tetrahydro-2H-pyran-4-ylamino)phenyl)furo[3,2-b]pyridin-2-yl)-5-methoxy-N,N-dimethylnicotinamide hydrochloride was obtained as yellow solid (230 mg, 21%). HPLC: 98.9% purity, RT=0.95 min. MS: m/z=498.0 [M+H]$^+$. $^1$H NMR (300 MHz, DMSO, ppm) δ 8.56 (d, J=5.1 Hz, 1H), 8.45-8.35 (m, 2H), 8.30 (d, J=9.0 Hz, 1H), 8.85-8.66 (m, 3H), 7.18 (d, J=9.3 Hz, 1H), 6.31 (d, J=8.1 Hz, 1H), 4.11 (s, 3H), 3.99-3.72 (m, 3H), 3.40-3.39 (m, 2H), 3.04 (m, 3H), 3.00 (s, 3H), 1.97-1.80 (m, 2H), 1.78-1.50 (m, 2H).

Example 62: 4-[7-(3-Cyano-4-hydroxy-phenyl)-furo[3,2-b]pyridin-2-yl]-N,N-dimethyl-benzamide (175)

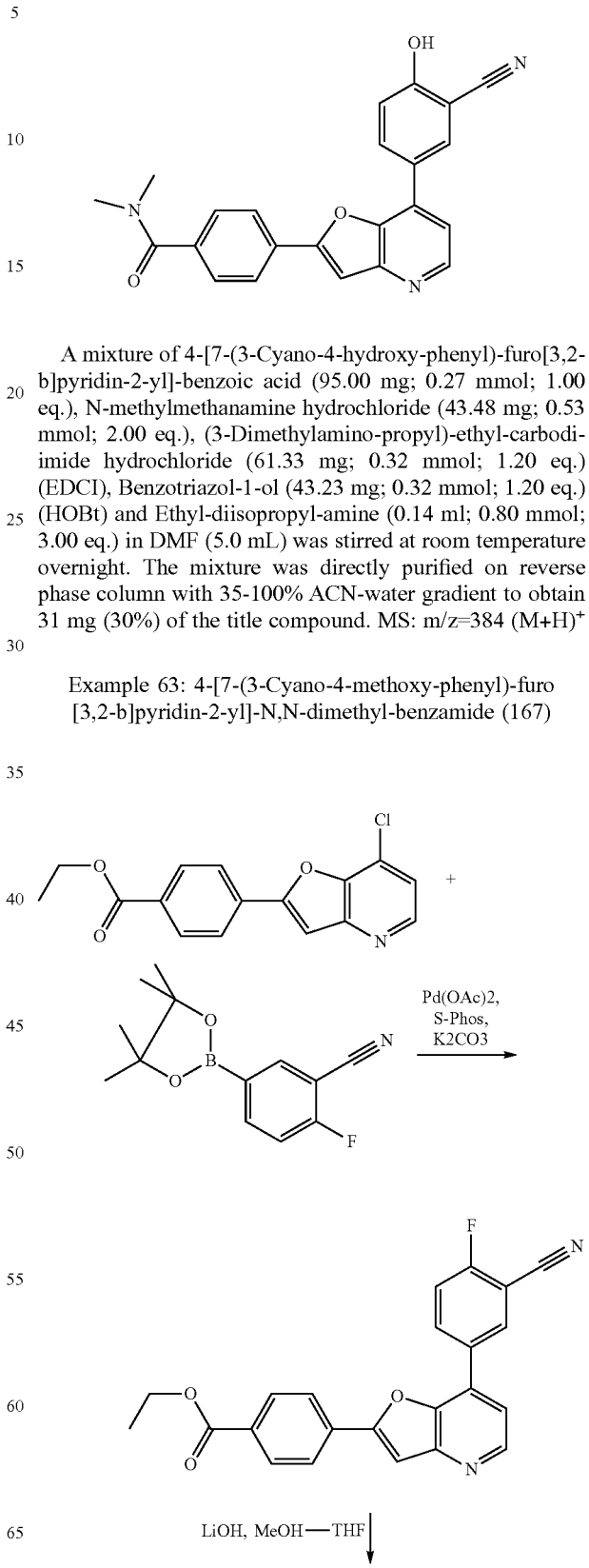

A mixture of 4-[7-(3-Cyano-4-hydroxy-phenyl)-furo[3,2-b]pyridin-2-yl]-benzoic acid (95.00 mg; 0.27 mmol; 1.00 eq.), N-methylmethanamine hydrochloride (43.48 mg; 0.53 mmol; 2.00 eq.), (3-Dimethylamino-propyl)-ethyl-carbodiimide hydrochloride (61.33 mg; 0.32 mmol; 1.20 eq.) (EDCI), Benzotriazol-1-ol (43.23 mg; 0.32 mmol; 1.20 eq.) (HOBt) and Ethyl-diisopropyl-amine (0.14 ml; 0.80 mmol; 3.00 eq.) in DMF (5.0 mL) was stirred at room temperature overnight. The mixture was directly purified on reverse phase column with 35-100% ACN-water gradient to obtain 31 mg (30%) of the title compound. MS: m/z=384 (M+H)$^+$ Example 63: 4-[7-(3-Cyano-4-methoxy-phenyl)-furo[3,2-b]pyridin-2-yl]-N,N-dimethyl-benzamide (167)

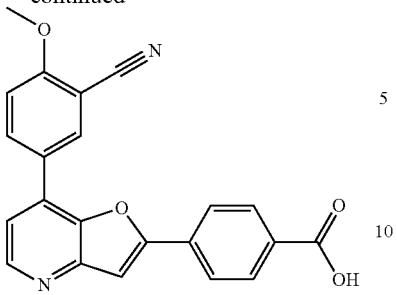

2-Fluoro-5-(4,4,5,5-tetramethyl-[1,3,2]dioxaborolan-2-yl)-benzonitrile

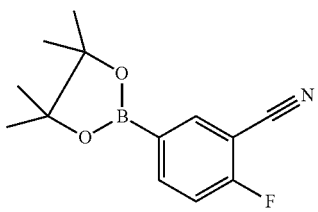 [SMILES: CC1(C)OB(c2ccc(F)c(C#N)c2)OC1(C)C]

A mixture of 5-Bromo-2-fluoro-benzonitrile (1000.00 mg; 5.00 mmol; 1.00 eq.), 4,4,5,5,4',4',5',5'-Octamethyl-[2,2']bi[[1,3,2]dioxaborolanyl] (1396.61 mg; 5.50 mmol; 1.10 eq.), potassium acetate (1472.07 mg; 15.00 mmol; 3.00 eq.) in dioxane (10 mL) and DMf (1 mL) was degassed, then [1,1']-bis(diphenyl phosphino) ferrocene]dichloropalladium (II), complex with dichloromethane(1:) (366.85 mg; 0.50 mmol; 0.10 eq.) was added and the sealed vial was heated at 100° C. for overnight. The reaction mixture was cooled and filtered through a pad of Celite. The solvent was removed and the crude product was purified through flash chromatography on silica gel (EtOAc:hexanes from 0% to 5%) to obtain 2-Fluoro-5-(4,4,5,5-tetramethyl-[1,3,2]dioxaborolan-2-yl)-benzonitrile (1.0 g, 81%)

4-[7-(3-Cyano-4-fluoro-phenyl)-furo[3,2-b]pyridin-2-yl]-benzoic acid ethyl ester

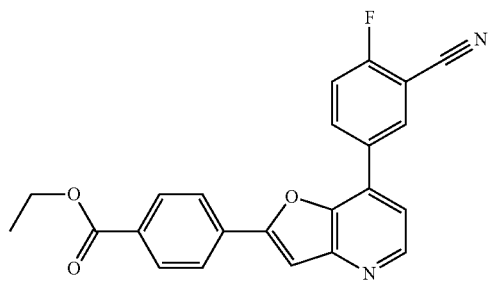 [SMILES: CCOC(=O)c1ccc(-c2cc3nccc(-c4ccc(F)c(C#N)c4)c3o2)cc1]

The mixture of 4-(7-Chloro-furo[3,2-b]pyridin-2-yl)-benzoic acid ethyl ester (500.00 mg; 1.66 mmol; 1.00 eq.), 2-Fluoro-5-(4,4,5,5-tetramethyl-[1,3,2]dioxaborolan-2-yl)-benzonitrile (532.27 mg; 2.15 mmol; 1.30 eq.), Dicyclohexyl-(2',6'-dimethoxy-biphenyl-2-yl)-phosphane (204.09 mg; 0.50 mmol; 0.30 eq.) and dipotassium carbonate (458.05 mg; 3.31 mmol; 2.00 eq.) in 1,4-dioxane (9 mL) and water (0.5 mL) in a sealed vial was stirred at 100 for 6 h. The hot solution was filtered through a pad of Celite to obtain 4-[7-(3-Cyano-4-fluoro-phenyl)-furo[3,2-b]pyridin-2-yl]-benzoic acid ethyl ester as a solid (500 mg, 78%). MS: m/z=387 (M+H)+.

4-[7-(3-Cyano-4-methoxy-phenyl)-furo[3,2-b]pyridin-2-yl]-benzoic acid

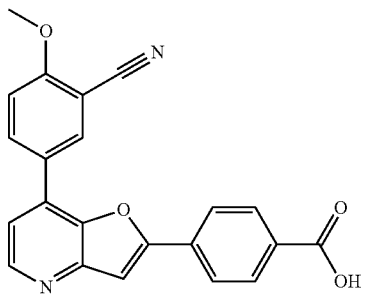 [SMILES: COc1ccc(-c2ccnc3cc(-c4ccc(C(=O)O)cc4)oc23)cc1C#N]

The mixture of 4-[7-(3-Cyano-4-fluoro-phenyl)-furo[3,2-b]pyridin-2-yl]-benzoic acid ethyl ester (100.00 mg; 0.26 mmol; 1.00 eq.) and lithium hydroxide (18.59 mg; 0.78 mmol; 3.00 eq.) in THF/MeOH/water (5/5/3 mL) was irradiated at microwave vial at 100° C. for 15 minutes. aq. HCl (1N) was added to adjust pH to 5. After removal of the solvent, the product was precipitated from water. The solid was filtered and purified through reverse phase HPLC to obtain 4-[7-(3-Cyano-4-methoxy-phenyl)-furo[3,2-b]pyridin-2-yl]-benzoic acid (59 mg, 62%).

4-[7-(3-Cyano-4-methoxy-phenyl)-furo[3,2-b]pyridin-2-yl]-N,N-dimethyl-benzamide

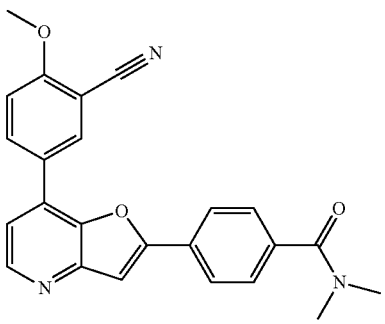 [SMILES: COc1ccc(-c2ccnc3cc(-c4ccc(C(=O)N(C)C)cc4)oc23)cc1C#N]

A mixture of 4-[7-(3-Cyano-4-methoxy-phenyl)-furo[3,2-b]pyridin-2-yl]-benzoic acid (24.00 mg; 0.06 mmol; 1.00 eq.), N-methylmethanamine hydrochloride (10.57 mg; 0.13 mmol; 2.00 eq.), (3-Dimethylamino-propyl)-ethyl-carbodiimide hydrochloride (14.91 mg; 0.08 mmol; 1.20 eq.) (EDCI), Benzotriazol-1-ol (10.51 mg; 0.08 mmol; 1.20 eq.) (HOBt) and Ethyl-diisopropyl-amine (25.13 mg; 0.19 mmol; 3.00 eq.) in DMF (5.0 mL) was stirred at room temperature overnight. The mixture was purified on reverse phase HPLC column to get 4-[7-(3-Cyano-4-methoxy-phenyl)-furo[3,2-b]pyridin-2-yl]-N,N-dimethyl-benzamide (12 mg). MS: m/z: 398 (M+H)+.

Example 64: 4-{7-[4-(Azetidin-3-yloxy)-3-cyano-phenyl]-furo[3,2-b]pyridin-2-yl}-3-methoxy-N,N-dimethyl-benzamide (128)

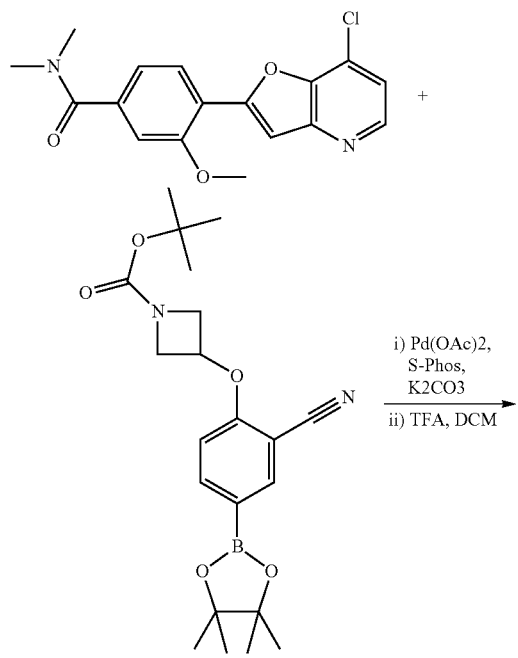

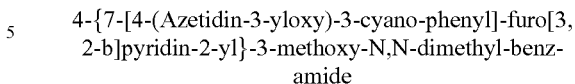

3-{2-Cyano-4-[2-(4-dimethylcarbamoyl-2-methoxy-phenyl)-furo[3,2-b]pyridin-7-yl]-phenoxy}-azetidine-1-carboxylic acid tert-butyl ester To a mixture of 4-(7-Chloro-furo[3,2-b]pyridin-2-yl)-3-methoxy-N,N-dimethyl-benzamide (200.00 mg; 0.60 mmol; 1.00 eq.), 3-[2-Cyano-4-(4,4,5,5-tetramethyl-[1,3,2]dioxaborolan-2-yl)-phenoxy]-azetidine-1-carboxylic acid tert-butyl ester (290.44 mg; 0.73 mmol; 1.20 eq.), Dicyclohexyl-(2',6'-dimethoxy-biphenyl-2-yl)-phosphane (74.47 mg; 0.18 mmol; 0.30 eq.) and dipotassium carbonate (167.13 mg; 1.21 mmol; 2.00 eq.) in a MW oven vial were added 1,4-dioxane (20 ml) and water (2 ml). The reaction mixture was sparged with Argon for 15 min. and then diacetoxypalladium (27.15 mg; 0.12 mmol; 0.20 eq.) was added. The reaction mixture was heated with microwave radiation at 120° C. for 1 h. The reaction mixture was diluted with methanol, filtered over celite. The filtrate was concentrated and purified on Biotage using EtOAc-methanol gradient on 100 g column to obtain 3-{2-Cyano-4-[2-(4-dimethylcarbamoyl-2-methoxy-phenyl)-furo[3,2-b]pyridin-7-yl]-phenoxy}-azetidine-1-carboxylic acid tert-butyl ester (203 mg).

4-{7-[4-(Azetidin-3-yloxy)-3-cyano-phenyl]-furo[3,2-b]pyridin-2-yl}-3-methoxy-N,N-dimethyl-benzamide To a solution of 3-{2-Cyano-4-[2-(4-dimethylcarbamoyl-2-methoxy-phenyl)-furo[3,2-b]pyridin-7-yl]-phenoxy}-azetidine-1-carboxylic acid tert-butyl ester (203.00 mg; 0.36 mmol; 1.00 eq.) none (contained some DIEA impurity) in Dichloro-methane (15.00 ml) was added Trifluoro-acetic acid (0.14 ml; 1.79 mmol; 5.00 eq.). Stirred at room temperature for 3 h. The solvent was removed and the crude was purified on with ethylacetate-methanol mixture to obtain the title compound (88 mg, 42%); MS: m/z=469 [M+H]$^+$. $^1$H NMR (400 MHz, Chloroform-d) δ 8.36 (d, J=4.9 Hz, 1H), 8.16-7.93 (m, 2H), 7.80 (d, J=7.8 Hz, 1H), 7.48 (s, 1H), 7.09 (q, J=6.3, 4.8 Hz, 3H), 6.83 (d, J=8.7 Hz, 1H), 5.29 (t, J=6.2 Hz, 1H), 4.69 (d, J=8.7 Hz, 2H), 4.38-4.21 (m, 2H), 4.05 (s, 3H), 3.08 (d, J=40.2 Hz, 6H).

Example 65: 4-{7-[3-Cyano-4-(tetrahydro-furan-3-yloxy)-phenyl]-furo[3,2-b]pyridin-2-yl}-3-methoxy-N,N-dimethyl-benzamide (90)

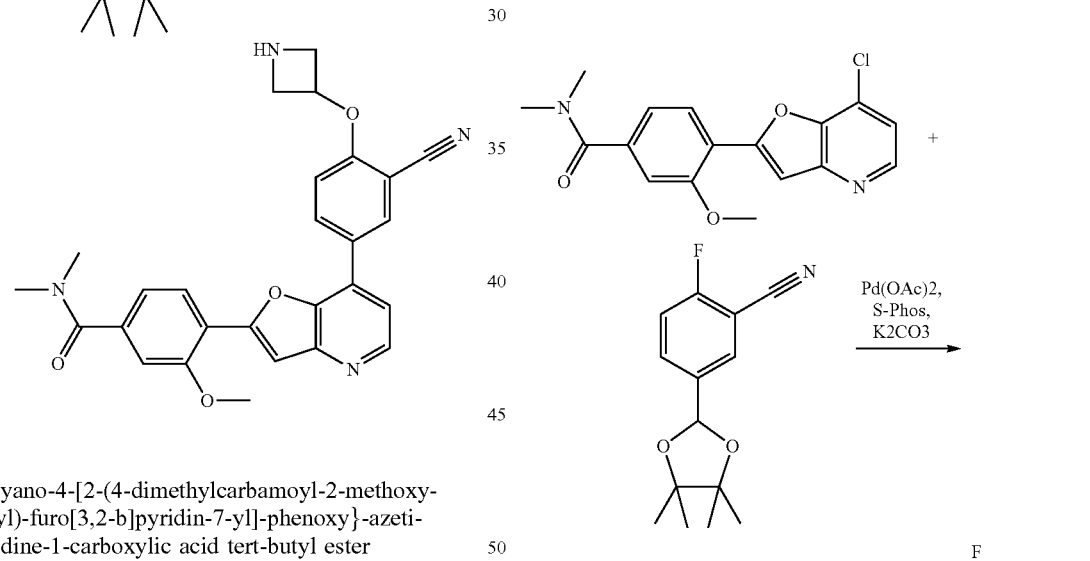

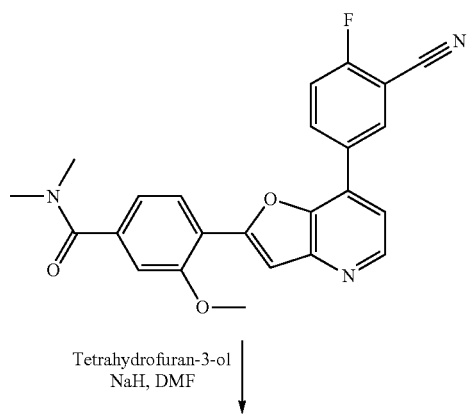

311
-continued

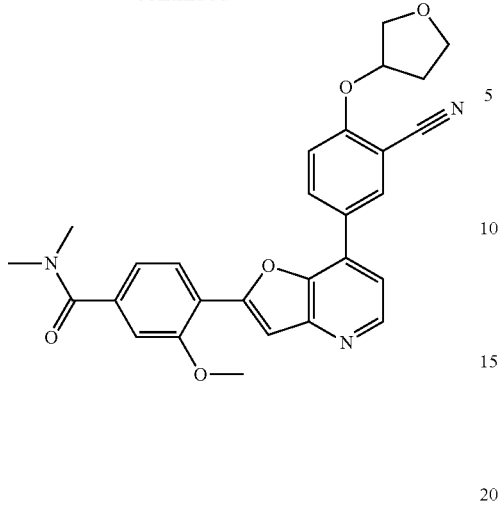

4-[7-(3-Cyano-4-fluoro-phenyl)-furo[3,2-b]pyridin-2-yl]-3-methoxy-N,N-dimethyl-benzamide The mixture of 4-(7-Chloro-furo[3,2-b]pyridin-2-yl)-3-methoxy-N,N-dimethyl-benzamide (1500.00 mg; 4.53 mmol; 1.00 eq.), 2-Fluoro-5-(4,4,5,5-tetramethyl-[1,3,2]dioxaborolan-2-yl)-benzonitrile (1232.51 mg; 4.99 mmol; 1.10 eq.), Dicyclohexyl-(2',6'-dimethoxy-biphenyl-2-yl)-phosphane (558.52 mg; 1.36 mmol; 0.30 eq.) and dipotassium carbonate (1253.51 mg; 9.07 mmol; 2.00 eq.) in 1,4-dioxane (9 mL) and water (0.5 mL) in the sealed vial was stirred at 100 for 6 h. The hot solution was filtered through a pad of Celite. 4-[7-(3-Cyano-4-fluoro-phenyl)-furo[3,2-b]pyridin-2-yl]-3-methoxy-N,N-dimethyl-benzamide was precipitated from the solution and the solid was filtered, washed with EtOAc and dried (500 mg, 26%). MS: m/z=416 (M+H)$^+$.

4-{7-[3-Cyano-4-(tetrahydro-furan-3-yloxy)-phenyl]-furo[3,2-b]pyridin-2-yl}-3-methoxy-N,N-dimethyl-benzamide Tetrahydro-furan-3-ol (42.42 mg; 0.48 mmol; 2.00 eq.) was added to a stirred suspension of sodium hydride (60% in mineral oil) (23.11 mg; 0.58 mmol; 2.40 eq.) in N,N-Dimethyl-formamide (10 mL) at 0° C. The reaction mixture was brought to RT and stirred for 1 h. 4-[7-(3-Cyano-4-fluoro-phenyl)-furo[3,2-b]pyridin-2-yl]-3-methoxy-N,N-dimethyl-benzamide (100.00 mg; 0.24 mmol; 1.00 eq.) in DMF (35 ml) was added dropwise to the reaction mixture at 0° C. Allowed to come to RT and stirred at 50° C. overnight. The reaction was quenched carefully with addition of ice water. The separated solid was filtered, washed with water and dried under vacuum. The crude mixture was purified through reverse phase HPLC to provide the title compound (40 mg, 35%). MS: m/z=484 (M+H)$^+$.

312

Example 66: 4-{7-[3-Cyano-4-(pyrrolidin-3-yloxy)-phenyl]-furo[3,2-b]pyridin-2-yl}-3-methoxy-N,N-dimethyl-benzamide (108)

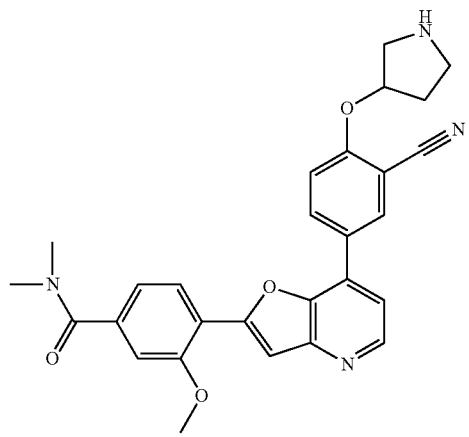 [SMILES: COc1cc(C(=O)N(C)C)ccc1-c1cc2nccc(-c3ccc(OC4CCNC4)c(C#N)c3)c2o1]

The title compound was synthesized according to the procedure described in example 64 using 4-(7-Chloro-furo[3,2-b]pyridin-2-yl)-3-methoxy-N,N-dimethyl-benzamide (500.00 mg; 1.51 mmol; 1.00 eq.), 3-[2-Cyano-4-(4,4,5,5-tetramethyl-[1,3,2]dioxaborolan-2-yl)-phenoxy]-pyrrolidine-1-carboxylic acid tert-butyl ester (814.16 mg; 1.97 mmol; 1.30 eq.), Dicyclohexyl-(2',6'-dimethoxy-biphenyl-2-yl)-phosphane (186.17 mg; 0.45 mmol; 0.30 eq.), dipotassium carbonate (417.84 mg; 3.02 mmol; 2.00 eq.) in diacetoxypalladium (67.88 mg; 0.30 mmol; 0.20 eq.) 1,4-dioxane (20 ml) and water (2 ml) to obtain 3-{2-Cyano-4-[2-(4-dimethylcarbamoyl-2-methoxy-phenyl)-furo[3,2-b]pyridin-7-yl]-phenoxy}-pyrrolidine-1-carboxylic acid tert-butyl ester (682 mg, 77%). The boc group was deprotected in DCM by treating with hydrogen chloride in Ether (5.58 ml; 11.16 mmol; 10.00 eq.) to obtain 4-{7-[3-Cyano-4-(pyrrolidin-3-yloxy)-phenyl]-furo[3,2-b]pyridin-2-yl}-3-methoxy-N,N-dimethyl-benzamide (501 mg, 85%). MS: m/z: 483 [M+H]$^+$ 1H NMR (400 MHz, Methanol-d$_4$) δ 8.74 (d, J=4.6 Hz, 1H), 8.64 (d, J=13.4 Hz, 1H), 8.19 (dd, J=8.0, 2.9 Hz, 1H), 7.82 (s, 1H), 7.70 (t, J=2.1 Hz, 1H), 7.42-6.95 (m, 4H), 5.63 (s, 1H), 4.16 (s, 3H), 3.77 (s, 2H), 3.63 (s, 2H), 3.33 (s, 3H), 3.18 (s, 3H), 2.53 (m, 2H).

Example 67: 4-{7-[3-Cyano-4-((R)-pyrrolidin-3-yloxy)-phenyl]-furo[3,2-b]pyridin-2-yl}-3-methoxy-N,N-dimethyl-benzamide (115)

Chiral

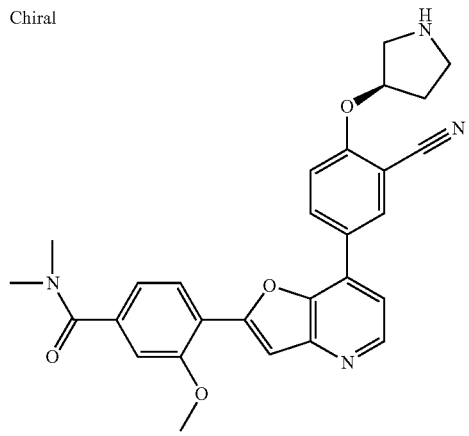 [SMILES: COc1cc(C(=O)N(C)C)ccc1-c1cc2nccc(-c3ccc(O[C@@H]4CCNC4)c(C#N)c3)c2o1]

150 mg of racemic 4-{7-[3-Cyano-4-(pyrrolidin-3-yloxy)-phenyl]-furo[3,2-b]pyridin-2-yl}-3-methoxy-N,N-dimethyl-benzamide was separated to obtain 62 mg of (R) and 52 mg (S) isomers. MS: m/z=483 [M+H]$^+$. $^1$H NMR (400 MHz, Chloroform-d) δ 8.74 (d, J=4.6 Hz, 1H), 8.34-8.14 (m, 2H), 8.02 (dd, J=8.0, 2.9 Hz, 1H), 7.67 (t, J=2.1 Hz, 1H), 7.42-6.95 (m, 4H), 5.12 (s, 1H), 4.09 (s, 3H), 3.35 (dt, J=29.2, 13.1 Hz, 4H), 3.17 (s, 3H), 3.07 (s, 3H), 2.25 (m, 2H).

Example 68: 4-{7-[3-Cyano-4-((S)-pyrrolidin-3-yloxy)-phenyl]-furo[3,2-b]pyridin-2-yl}-3-methoxy-N,N-dimethyl-benzamide (121)

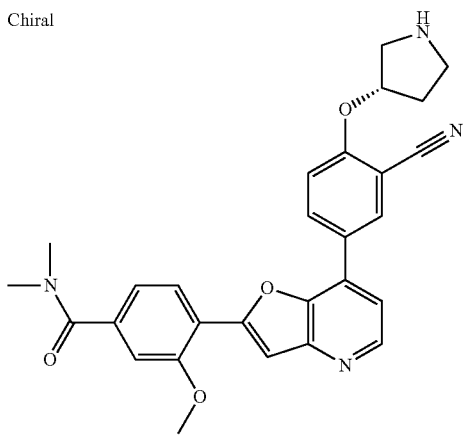 [SMILES: COc1cc(C(=O)N(C)C)ccc1-c1cc2nccc(-c3ccc(O[C@H]4CCNC4)c(C#N)c3)c2o1]

MS: m/z: 483 [M+H]$^+$. $^1$H NMR (400 MHz, Chloroform-d) δ 8.60 (t, J=3.8 Hz, 1H), 8.36-8.17 (m, 2H), 8.02 (d, J=8.0 Hz, 1H), 7.66 (d, J=10.3 Hz, 1H), 7.30 (dd, J=12.8, 3.3 Hz, 2H), 7.16 (d, J=10.0 Hz, 2H), 5.12 (s, 1H), 4.09 (s, 3H), 3.43-3.23 (m, 4H), 3.17 (s, 3H), 3.07 (s, 3H), 2.25 (m, 2H).

Example 69: 4-{7-[4-(Azetidin-3-ylmethoxy)-3-cyano-phenyl]-furo[3,2-b]pyridin-2-yl}-3-methoxy-N,N-dimethyl-benzamide (165)

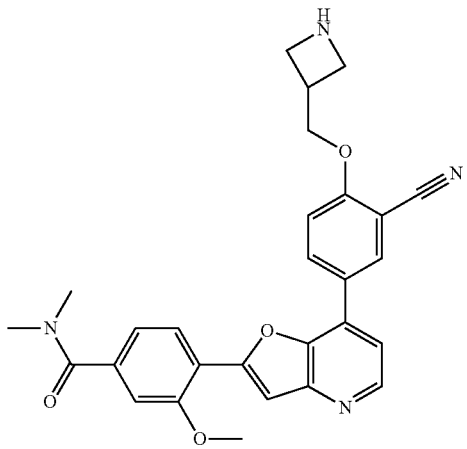 [SMILES: COc1cc(C(=O)N(C)C)ccc1-c1cc2nccc(-c3ccc(OCC4CNC4)c(C#N)c3)c2o1]

The title compound was synthesized according to the procedure described in example 64 using 4-(7-Chloro-furo [3,2-b]pyridin-2-yl)-3-methoxy-N,N-dimethyl-benzamide (200.00 mg; 0.60 mmol; 1.00 eq.), 3-[2-Cyano-4-(4,4,5,5-tetramethyl-[1,3,2]dioxaborolan-2-yl)-phenoxymethyl]-azetidine-1-carboxylic acid tert-butyl ester (300.61 mg; 0.73 mmol; 1.20 eq.), Dicyclohexyl-(2',6'-dimethoxy-biphenyl-2-yl)-phosphane (74.47 mg; 0.18 mmol; 0.30 eq.), dipotassium carbonate (167.13 mg; 1.21 mmol; 2.00 eq.), and diacetoxypalladium (27.15 mg; 0.12 mmol; 0.20 eq.) to obtain 3-{2-Cyano-4-[2-(4-dimethylcarbamoyl-2-methoxy-phenyl)-furo[3,2-b]pyridin-7-yl]-phenoxymethyl}-azetidine-1-carboxylic acid tert-butyl ester (208 mg, 59%). This Boc-compound (100.00 mg; 0.07 mmol; 1.00 eq.) in Dichloro-methane (15.00 ml) was treated with trifluoro-acetic acid (0.05 ml; 0.69 mmol) to get the title compound (15 mg, 37%). $^1$H NMR (400 MHz, Chloroform-d) δ 8.48 (d, J=5.0 Hz, 1H), 8.13 (dd, J=14.3, 5.8 Hz, 2H), 7.89 (d, J=8.2 Hz, 1H), 7.55 (d, J=3.2 Hz, 1H), 7.32-6.98 (m, 4H), 4.37 (q, J=9.6, 7.5 Hz, 4H), 4.22 (t, J=8.8 Hz, 2H), 4.04 (d, J=2.8 Hz, 3H), 3.54 (m, 2H), 3.14 (s, 3H) 3.04 (s, 3H)

Example 70: 4-{7-[3-Cyano-4-(4-fluoro-pyrrolidin-3-yloxy)-phenyl]-furo[3,2-b]pyridin-2-yl}-3-methoxy-N,N-dimethyl-benzamide (282)

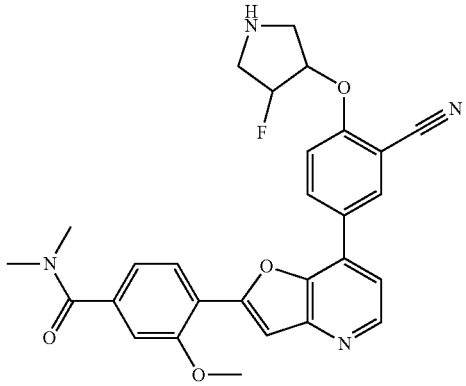 [SMILES: COc1cc(C(=O)N(C)C)ccc1-c1cc2nccc(-c3ccc(OC4CNCC4F)c(C#N)c3)c2o1]

The title compound was synthesized according to the procedure described in example 64 using 4-(7-Chloro-furo [3,2-b]pyridin-2-yl)-3-methoxy-N,N-dimethyl-benzamide (300.00 mg; 0.91 mmol; 1.00 eq.), 3-[2-Cyano-4-(4,4,5,5-tetramethyl-[1,3,2]dioxaborolan-2-yl)-phenoxy]-4-fluoro-pyrrolidine-1-carboxylic acid tert-butyl ester (996.83 mg; 1.36 mmol; 1.50 eq.), (crude) Dicyclohexyl-(2',6'-dimethoxy-biphenyl-2-yl)-phosphane (111.70 mg; 0.27 mmol; 0.30 eq.), dipotassium carbonate (250.70 mg; 1.81 mmol; 2.00 eq.) and diacetoxypalladium (40.73 mg; 0.18 mmol; 0.20 eq.) to obtain 3-{2-Cyano-4-[2-(4-dimethylcarbamoyl-2-methoxy-phenyl)-furo[3,2-b]pyridin-7-yl]-phenoxy}-4-fluoro-pyrrolidine-1-carboxylic acid tert-butyl ester (232 mg, 34%). The boc group was removed by treating with Trifluoro-acetic acid (0.30 ml; 3.86 mmol; 10.00). MS: m/z=501 [M+H]$^+$. $^1$H NMR (400 MHz, Chloroform-d) δ 8.56 (d, J=4.1 Hz, 1H), 8.25-8.14 (m, 1H), 7.98-7.86 (m, 1H), 7.60 (d, J=2.2 Hz, 1H), 7.33-7.19 (m, 3H), 7.22-7.04 (m, 2H), 5.41 (d, J=49.8 Hz, 1H), 5.23 (d, J=11.9 Hz, 1H), 4.08 (d, J=2.1 Hz, 3H), 3.98-3.48 (m, 4H), 3.10 (d, J=42.6 Hz, 6H).

Example 71: 4-(7-{3-Cyano-4-[(tetrahydro-pyran-3-yl)oxy]-phenyl}-furo[3,2-b]pyridin-2-yl)-N,N-dimethyl-benzamide (283)

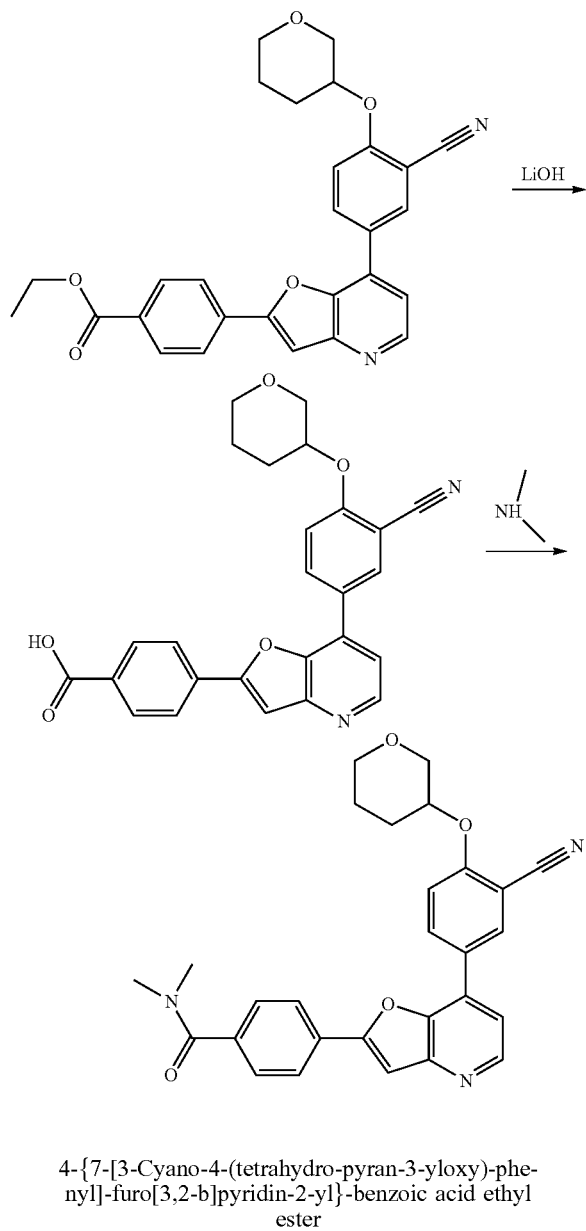

4-{7-[3-Cyano-4-(tetrahydro-pyran-3-yloxy)-phenyl]-furo[3,2-b]pyridin-2-yl}-benzoic acid ethyl ester The title compound was synthesized according to the procedures described in intermediate 14 and example 64 using Tetrahydro-pyran-3-ol (0.61 g; 6.00 mmol; 1.20 eq.) and 5-Bromo-2-fluoro-benzonitrile (1.00 g; 5.00 mmol; 1.00 eq.), 4,4,5,5,4',4',5',5'-Octamethyl-[2,2']bi[[1,3,2]dioxaborolanyl] (2.93 g; 11.52 mmol; 1.30 eq.) and 4-(7-Chloro-furo[3,2-b]pyridin-2-yl)-benzoic acid ethyl ester (200.00 mg; 0.66 mmol; 1.00 eq.).

4-{7-[3-Cyano-4-(3-methyl-tetrahydro-pyran-4-yloxy)-phenyl]-furo[3,2-b]pyridin-2-yl}-benzoic acid To a stirred solution of 4-{7-[3-Cyano-4-(tetrahydro-pyran-3-yloxy)-phenyl]-furo[3,2-b]pyridin-2-yl}-benzoic acid ethyl ester (80.00 mg; 0.17 mmol; 1.00 eq.) in THF (5.00 ml) Methanol (5 ml) water (1 ml) in a microwave vial was added lithium hydroxide (12.27 mg; 0.51 mmol; 3.00 eq). The mixture was heated under microwave for 10 min. The solvent was evaporated and the neutralized with 2N HCl to get a solid (75 mg). The solid was filtered and washed with water.

4-{7-[3-Cyano-4-(tetrahydro-pyran-3-yloxy)-phenyl]-furo[3,2-b]pyridin-2-yl}-3-methoxy-N,N-dimethyl-benzamide To a stirred solution of 4-{7-[3-Cyano-4-(3-methyl-tetrahydro-pyran-4-yloxy)-phenyl]-furo[3,2-b]pyridin-2-yl}-benzoic acid (55.00 mg; 0.06 mmol; 1.00 eq.) in Dichloromethane (10.00 ml) were added Ethyl-diisopropyl-amine (0.06 ml; 0.37 mmol; 3.00 eq.), Dimethyl-amine (0.12 ml; 0.25 mmol; 2.00 eq.) and 2,4,6-Tripropyl-[1,3,5,2,4,6]trioxatriphosphinane 2,4,6-trioxide (0.11 ml; 0.37 mmol; 3.00 eq.). The reaction mixture was stirred overnight. DCM was evaporated and the crude was purified on silica gel column to get the title compound (19 mg, 33%). MS: m/z=468 [M+H]$^+$. $^1$H NMR (400 MHz, Chloroform-d) δ 8.33-8.15 (m, 2H), 7.95 (d, J=7.7 Hz, 2H), 7.59 (d, J=7.7 Hz, 2H), 7.50-7.22 (m, 4H), 4.58 (dt, J=7.8, 3.7 Hz, 1H), 4.17-3.99 (m, 1H), 3.84 (dd, J=11.2, 5.6 Hz, 1H), 3.66 (ddd, J=23.0, 11.6, 8.1 Hz, 2H), 3.05 (s, 3H), 3.16 (s, 3H), 2.26 (dd, J=12.1, 5.9 Hz, 1H), 2.13-1.89 (m, 2H), 1.75 (dt, J=12.8, 8.9 Hz, 1H).

Example 72: 4-(7-{3-Cyano-4-[(S)-(tetrahydro-pyran-3-yl)oxy]-phenyl}-furo[3,2-b]pyridin-2-yl)-N,N-dimethyl-benzamide (174)

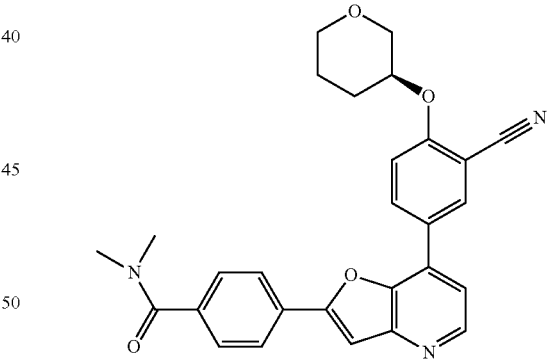

The title compound (48 mg) was separated from 150 mg of racemic 4-(7-{3-Cyano-4-[(tetrahydro-pyran-3-yl)oxy]-phenyl}-furo[3,2-b]pyridin-2-yl)-N,N-dimethyl-benzamide. MS: m/z=468 (M+H)$^+$. $^1$H NMR (400 MHz, Chloroform-d) δ 8.36 (d, J=2.3 Hz, 2H), 8.29 (dd, J=8.9, 2.4 Hz, 2H), 8.07-7.95 (m, 2H), 7.71-7.56 (m, 2H), 7.33 (d, J=9.0 Hz, 1H), 7.28 (s, 1H), 4.64 (td, J=7.5, 3.7 Hz, 1H), 4.08 (ddd, J=11.6, 3.7, 1.6 Hz, 1H), 3.86 (dt, J=11.7, 4.5 Hz, 1H), 3.79-3.60 (m, 2H), 3.18 (s, 3H), 3.05 (s, 3H), 2.26 (dd, J=11.8, 5.8 Hz, 1H), 1.99 (ddt, J=17.5, 8.9, 4.8 Hz, 2H), 1.77 (ddt, J=13.0, 8.4, 4.3 Hz, 1H).

Example 73: 4-(7-{3-Cyano-4-[(R)-(tetrahydro-pyran-3-yl)oxy]-phenyl}-furo[3,2-b]pyridin-2-yl)-N,N-dimethyl-benzamide (156)

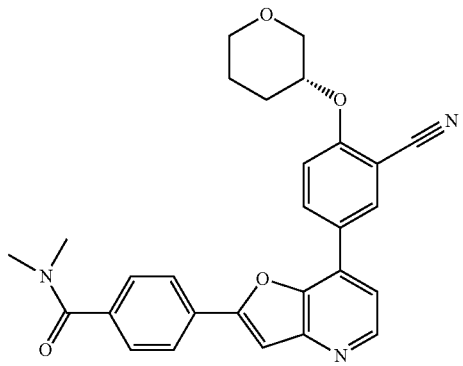 [SMILES: CN(C)C(=O)c1ccc(-c2cc3nccc(-c4ccc(O[C@@H]5CCCOC5)c(C#N)c4)c3o2)cc1]

The title compound (53 mg) was separated from 150 mg of racemic 4-(7-{3-Cyano-4-[(tetrahydro-pyran-3-yl)oxy]-phenyl}-furo[3,2-b]pyridin-2-yl)-N,N-dimethyl-benzamide. MS: m/z=468 (M+H)$^+$. $^1$H NMR (400 MHz, Chloroform-d) δ 8.34 (d, J=2.3 Hz, 2H), 8.27 (dd, J=8.9, 2.4 Hz, 2H), 8.00 (d, J=8.2 Hz, 2H), 7.63 (d, J=8.0 Hz, 2H), 7.31 (d, J=17.7 Hz, 2H), 4.63 (dt, J=7.7, 3.9 Hz, 1H), 4.08 (ddd, J=11.6, 3.7, 1.6 Hz, 1H), 3.90-3.82 (m, 1H), 3.77-3.59 (m, 2H), 3.50 (s, 3H), 2.26 (dd, J=11.9, 5.9 Hz, 1H), 1.99 (dddt, J=17.3, 12.9, 8.6, 5.2 Hz, 2H), 1.75 (tt, J=9.4, 4.8 Hz, 1H).

Example 74: 4-{7-[3-Cyano-4-(tetrahydro-pyran-3-yloxy)-phenyl]-furo[3,2-b]pyridin-2-yl}-3-methoxy-N,N-dimethyl-benzamide (105)

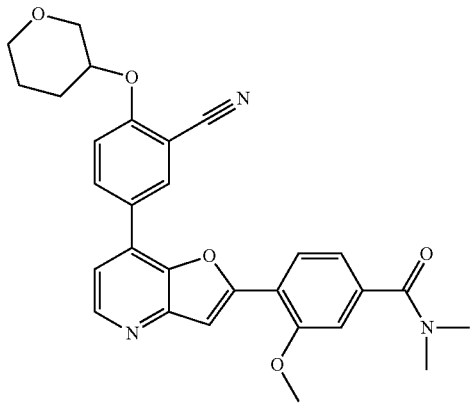 [SMILES: COc1cc(C(=O)N(C)C)ccc1-c1cc2nccc(-c3ccc(OC4CCCOC4)c(C#N)c3)c2o1]

The title compound was synthesized according to the procedure described in example 1 using 4-(7-Chloro-furo[3,2-b]pyridin-2-yl)-3-methoxy-N,N-dimethyl-benzamide (500.00 mg; 1.51 mmol; 1.00 eq.), 2-(Tetrahydro-pyran-3-yloxy)-5-(4,4,5,5-tetramethyl-[1,3,2]dioxaborolan-2-yl)-benzonitrile (547.39 mg; 1.66 mmol; 1.10 eq.), Dicyclohexyl-(2',6'-dimethoxy-biphenyl-2-yl)-phosphane (186.17 mg; 0.45 mmol; 0.30 eq.) and dipotassium carbonate (417.84 mg; 3.02 mmol; 2.00 eq.) and palladium acetate (68 mg, 0.3 mmol, 0.2 eq) in dioxane-water solvent (195 mg, 26%). MS: m/z=498 (M+H)+.

Example 75: 4-{7-[3-Cyano-4-(tetrahydro-furan-3-ylmethoxy)-phenyl]-furo[3,2-b]pyridin-2-yl}-3-methoxy-N,N-dimethyl-benzamide (93)

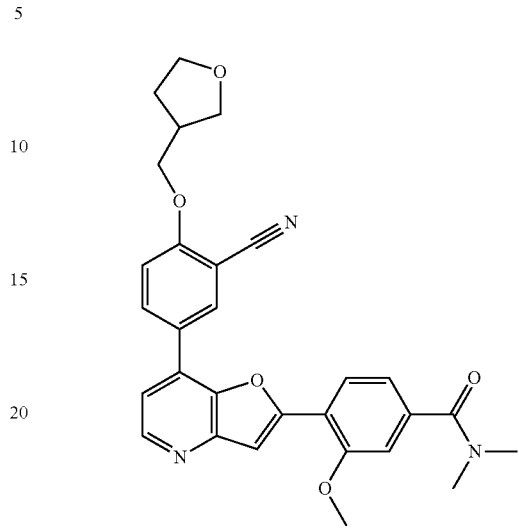

The title compound was synthesized (27 mg, 23%) according to the procedure described in example 65 using (Tetrahydro-furan-3-yl)-methanol (49.17 mg; 0.48 mmol; 2.00 eq.) and 4-[7-(3-Cyano-4-fluoro-phenyl)-furo[3,2-b]pyridin-2-yl]-3-methoxy-N,N-dimethyl-benzamide (100.00 mg; 0.24 mmol; 1.00 eq.). MS: m/z=498 (M+H)$^+$.

Example 76: 4-{7-[3-Cyano-4-((S)-3-fluoro-tetrahydro-pyran-4-yloxy)-phenyl]-furo[3,2-b]pyridin-2-yl}-3-methoxy-N,N-dimethyl-benzamide (30)

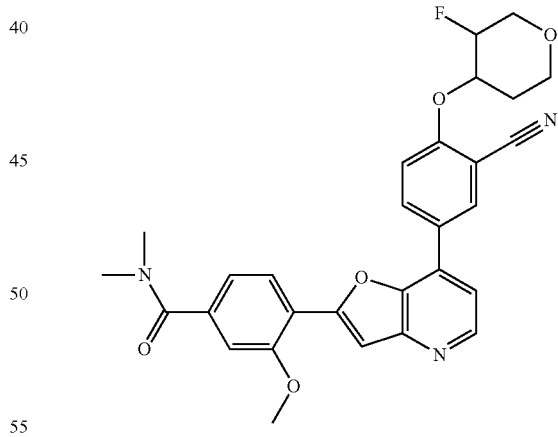

The title compound was synthesized according to the procedure described in example 64 using 4-(7-Chloro-furo[3,2-b]pyridin-2-yl)-3-methoxy-N,N-dimethyl-benzamide (200.00 mg; 0.60 mmol; 1.00 eq.), 2-(3-Fluoro-tetrahydro-pyran-4-yloxy)-5-(4,4,5,5-tetramethyl-[1,3,2]dioxaborolan-2-yl)-benzonitrile (272.91 mg; 0.79 mmol; 1.30 eq.), Dicyclohexyl-(2',6'-dimethoxy-biphenyl-2-yl)-phosphane (74.47 mg; 0.18 mmol; 0.30 eq.) dipotassium carbonate (167.13 mg; 1.21 mmol; 2.00 eq.) and diacetoxypalladium (27.15 mg; 0.12 mmol; 0.20 eq.) in dioxane-water (189 mg, 47%). MS: m/z=516 [M+H]$^+$. $^1$H NMR (400 MHz, Chloroform-d)

δ 8.59 (d, J=5.1 Hz, 1H), 8.30 (d, J=1.9 Hz, 1H), 8.23 (dt, J=8.9, 2.0 Hz, 1H), 8.00 (dd, J=7.8, 1.5 Hz, 1H), 7.72 (d, J=1.8 Hz, 1H), 7.44-7.27 (m, 2H), 7.20-7.09 (m, 2H), 4.80 (q, J=7.3, 5.6 Hz, 1H), 4.68 (q, J=5.5 Hz, 1H), 4.18 (ddd, J=21.3, 12.1, 3.3 Hz, 1H), 4.07 (s, 3H), 4.02-3.89 (m, 1H), 3.81-3.61 (m, 2H), 3.16 (s, 3H), 3.06 (s, 3H), 2.35 (ddd, J=15.2, 7.4, 3.9 Hz, 1H), 2.02 (dt, J=13.9, 5.8 Hz, 1H).

Example 77: 4-{7-[3-Cyano-4-((S)-3-fluoro-tetrahydro-pyran-4-yloxy)-phenyl]-furo[3,2-b]pyridin-2-yl}-3-methoxy-N,N-dimethyl-benzamide (42)

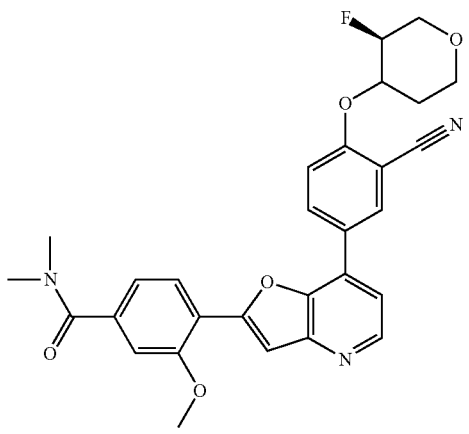 [SMILES: COc1cc(C(=O)N(C)C)ccc1-c1cc2nccc(-c3ccc(OC4CCOC[C@@H]4F)c(C#N)c3)c2o1]

The title compound (40 mg) was separated from racemic 4-{7-[3-Cyano-4-((S)-3-fluoro-tetrahydro-pyran-4-yloxy)-phenyl]-furo[3,2-b]pyridin-2-yl}-3-methoxy-N,N-dimethyl-benzamide. MS: m/z=516 [M+H]$^+$. $^1$H NMR (400 MHz, Chloroform-d) δ 8.62 (s, 1H), 8.39-8.20 (m, 2H), 8.02 (d, J=7.8 Hz, 1H), 7.82 (d, J=3.4 Hz, 1H), 7.48 (d, J=5.1 Hz, 1H), 7.37 (d, J=8.8 Hz, 1H), 7.17 (d, J=10.3 Hz, 2H), 4.81 (d, J=6.6 Hz, 1H), 4.75-4.59 (m, 1H), 4.32 (m, 1H), 4.09 (s, 3H), 4.02 (m, 1H), 3.83-3.59 (m, 2H), 3.17 (s, 3H), 3.07 (s, 3H), 2.36 (d, J=13.9 Hz, 1H), 2.03 (d, J=11.4 Hz, 1H), Example 78: 4-{7-[3-Cyano-4-((R)-3-fluoro-tetrahydro-pyran-4-yloxy)-phenyl]-furo[3,2-b]pyridin-2-yl}-N,N-dimethyl-benzamide (74)

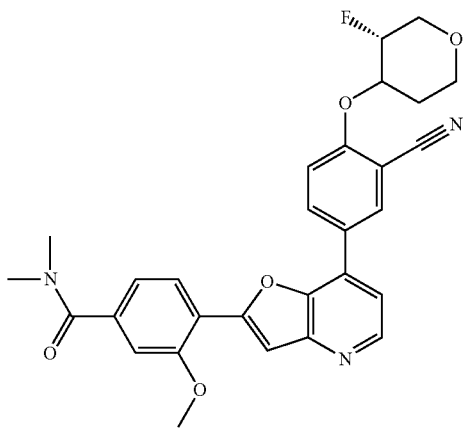

The title compound (38 mg) was separated from racemic 4-{7-[3-Cyano-4-((S)-3-fluoro-tetrahydro-pyran-4-yloxy)-phenyl]-furo[3,2-b]pyridin-2-yl}-3-methoxy-N,N-dimethyl-benzamide. MS: m/z=516 [M+H]$^+$. $^1$H NMR (400 MHz, Chloroform-d) δ 8.72 (s, 1H), 8.42-8.17 (m, 2H), 8.02 (d, J=7.7 Hz, 1H), 7.81 (d, J=3.4 Hz, 1H), 7.46 (d, J=5.1 Hz, 1H), 7.37 (d, J=8.7 Hz, 1H), 7.17 (d, J=10.2 Hz, 2H), 4.82 (s, 1H), 4.71-4.67 (m, 1H), 4.34-3.87 (m, 1H), 4.09 (s, 3H), 4.02 (m, 1H), 3.85-3.59 (m, 2H), 3.17 (s, 3H), 3.07 (s, 3H), 2.36 (d, J=14.0 Hz, 1H), 2.03 (d, J=11.4 Hz, 1H)

Example 79: 4-{7-[3-Cyano-4-(1-methyl-pyrrolidin-3-yloxy)-phenyl]-furo[3,2-b]pyridin-2-yl}-3-methoxy-N,N-dimethyl-benzamide (149)

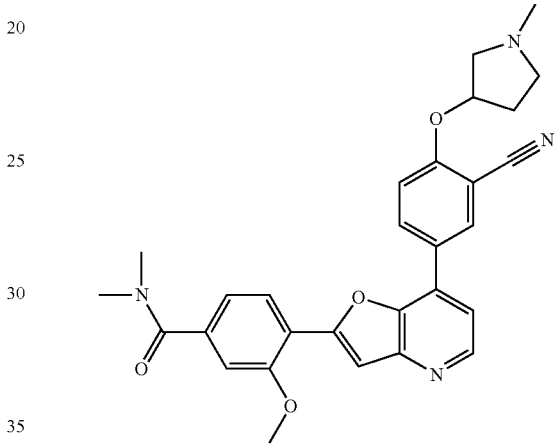

To a solution of 4-{7-[3-Cyano-4-(pyrrolidin-3-yloxy)-phenyl]-furo[3,2-b]pyridin-2-yl}-3-methoxy-N,N-dimethyl-benzamide; Hydrochloride (50.00 mg; 0.10 mmol; 1.00 eq.) in Methanol (30.00 ml) were added Formaldehyde (78.18 mg; 0.96 mmol; 10.00 eq.) solution followed by palladium on activated carbon (20.51 mg; 0.02 mmol; 0.20 eq.). The reaction mixture was stirred for 3 h under hydrogen atmosphere. The catalyst was filtered and washed with methanol. Methanol was concentrated and the crude was purified on a C18 reverse phase column to obtain the title compound (25 mg, 52%). MS: m/z=497 [M+H]$^+$.

Example 80: 4-{7-[3-Cyano-4-(piperidin-3-yloxy)-phenyl]-furo[3,2-b]pyridin-2-yl}-3-methoxy-N,N-dimethyl-benzamide Hydrochloride (140)

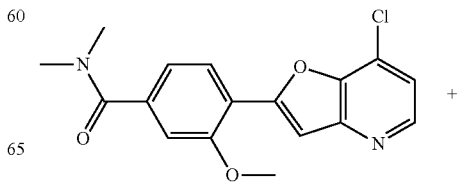

321

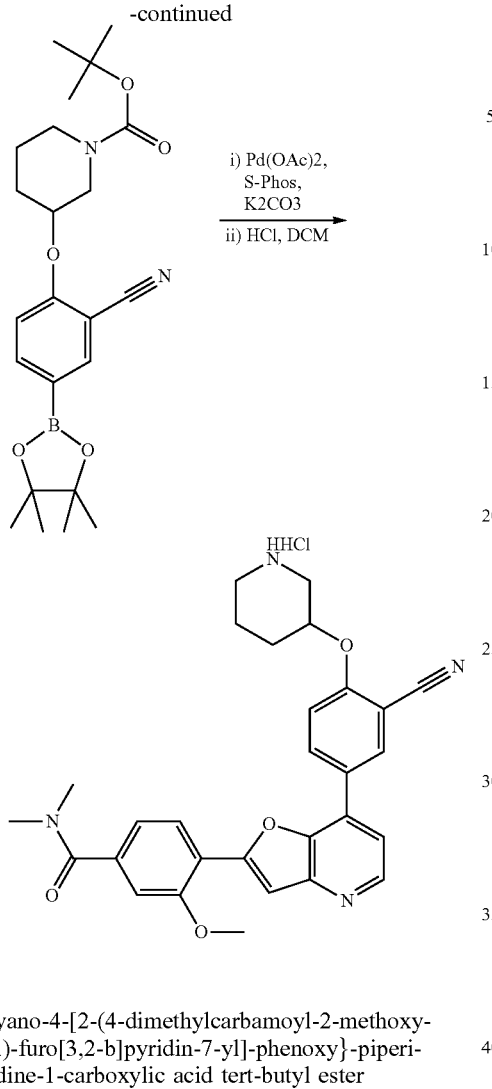

3-{2-Cyano-4-[2-(4-dimethylcarbamoyl-2-methoxy-phenyl)-furo[3,2-b]pyridin-7-yl]-phenoxy}-piperidine-1-carboxylic acid tert-butyl ester The title compound was synthesized according to the procedure described in example 64 using 4-(7-Chloro-furo[3,2-b]pyridin-2-yl)-3-methoxy-N,N-dimethyl-benzamide (200.00 mg; 0.60 mmol; 1.00 eq.), 3-[2-Cyano-4-(4,4,5,5-tetramethyl-[1,3,2]dioxaborolan-2-yl)-phenoxy]-piperidine-1-carboxylic acid tert-butyl ester (310.79 mg; 0.73 mmol; 1.20 eq.), Dicyclohexyl-(2',6'-dimethoxy-biphenyl-2-yl)-phosphane (74.47 mg; 0.18 mmol; 0.30 eq.), dipotassium carbonate (167.13 mg; 1.21 mmol; 2.00 eq.) and diacetoxypalladium (27.15 mg; 0.12 mmol; 0.20 eq.) in dioxin-water (250 mg, 69%). MS: m/z=597 [M+H]$^+$.

4-{7-[3-Cyano-4-(piperidin-3-yloxy)-phenyl]-furo[3,2-b]pyridin-2-yl}-3-methoxy-N,N-dimethyl-benzamide hydrochloride To a solution of 3-{2-Cyano-4-[2-(4-dimethylcarbamoyl-2-methoxy-phenyl)-furo[3,2-b]pyridin-7-yl]-phenoxy}-piperidine-1-carboxylic acid tert-butyl ester (250.00 mg; 0.42 mmol; 1.00 eq.) in dichloromethane (10 ml) was added hydrogen chloride in Ether (2.09 ml; 4.19 mmol; 10.00 eq). The mixture was stirred for 4 h to get a yellow solid which was filtered dried under vacuum to get an yellow colored solid (186 mg, 83%). MS: m/z=497 [M+H]$^+$. $^1$H NMR (400 MHz, Methanol-d$_4$) δ 8.71 (d, J=43.9 Hz, 3H), 8.20 (d, J=25.7 Hz, 2H), 7.80 (d, J=43.7 Hz, 2H), 7.32 (d, J=35.7 Hz, 2H), 5.22 (s, 1H), 4.17 (s, 3H), 3.62 (m, 2H), 3.33 (m, 2H), 3.17 (s, 3H), 3.07 (s, 3H), 2.37-1.84 (m, 4H).

Example 81: 4-{7-[3-Cyano-4-((R)-piperidin-3-yloxy)-phenyl]-furo[3,2-b]pyridin-2-yl}-3-methoxy-N,N-dimethyl-benzamide (163)

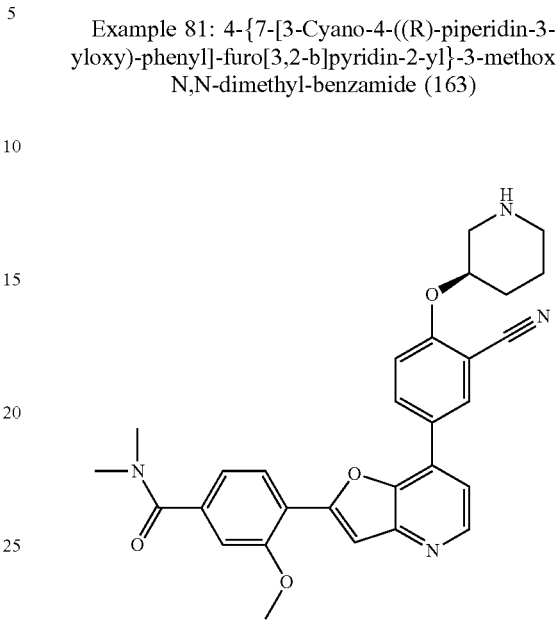

The title compound (50 mg) was separated from 140 mg of racemic 4-{7-[3-Cyano-4-(piperidin-3-yloxy)-phenyl]-furo[3,2-b]pyridin-2-yl}-3-methoxy-N,N-dimethyl-benzamide. MS: m/z=497 [M+H]$^+$.

Example 82: 4-{7-[3-Cyano-4-((S)-piperidin-3-yloxy)-phenyl]-furo[3,2-b]pyridin-2-yl}-3-methoxy-N,N-dimethyl-benzamide (142)

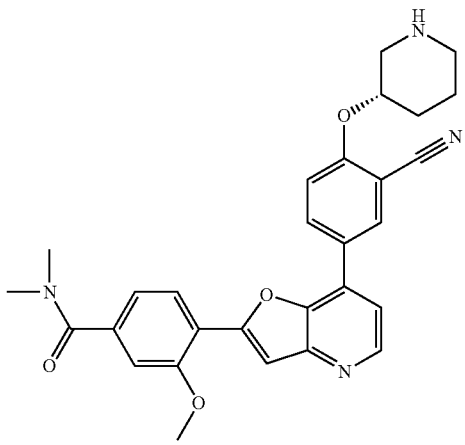 [SMILES: COc1cc(C(=O)N(C)C)ccc1-c1cc2nccc(-c3ccc(O[C@H]4CCCNC4)c(C#N)c3)c2o1]

The title compound (66 mg) was separated from 140 mg of racemic 4-{7-[3-Cyano-4-(piperidin-3-yloxy)-phenyl]-furo[3,2-b]pyridin-2-yl}-3-methoxy-N,N-dimethyl-benzamide. MS: m/z=497 [M+H]$^+$.

Example 83: 4-{7-[3-Cyano-4-(piperidin-4-yloxy)-phenyl]-furo[3,2-b]pyridin-2-yl}-N,N-dimethyl-benzamide hydrochloride (185)

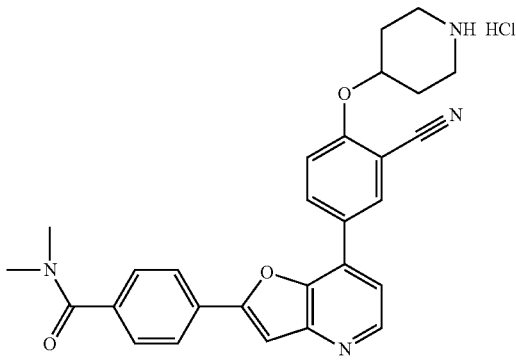 [SMILES: CN(C)C(=O)c1ccc(-c2cc3nccc(-c4ccc(OC5CCNCC5)c(C#N)c4)c3o2)cc1 ; Cl]

The title compound was synthesized according to the procedure described in example 64 using 4-(7-Chloro-furo[3,2-b]pyridin-2-yl)-N,N-dimethyl-benzamide (200.00 mg; 0.67 mmol; 1.00 eq.), 4-[2-Cyano-4-(4,4,5,5-tetramethyl-[1,3,2]dioxaborolan-2-yl)-phenoxy]-piperidine-1-carboxylic acid tert-butyl ester (341.82 mg; 0.80 mmol; 1.20 eq.), Dicyclohexyl-(2',6'-dimethoxy-biphenyl-2-yl)-phosphane (81.90 mg; 0.20 mmol; 0.30 eq.), dipotassium carbonate (183.82 mg; 1.33 mmol; 2.00 eq.) and diacetoxypalladium (29.86 mg; 0.13 mmol; 0.20 eq.) followed by treatment of the 4-{2-Cyano-4-[2-(4-dimethylcarbamoyl-phenyl)-furo[3,2-b]pyridin-7-yl]-phenoxy}-piperidine-1-carboxylic acid tert-butyl ester (150.00 mg; 0.26 mmol; 1.00 eq.) with hydrogen chloride in ether (1.32 ml; 2.65 mmol; 10.00 eq.) in DCM (130 mg, 39%). MS: m/z=467 [M+H]$^+$. $^1$H NMR (400 MHz, Methanol-d$_4$) δ 8.76-8.68 (m, 1H), 8.59 (dd, J=7.8, 2.0 Hz, 2H), 8.20 (d, J=7.8 Hz, 2H), 8.04 (dd, J=6.1, 1.9 Hz, 1H), 7.81 (d, J=1.9 Hz, 1H), 7.78-7.58 (m, 3H), 5.19 (m, 1H), 3.51 (t, J=10.8 Hz, 2H), 3.40 (dt, J=11.7, 5.0 Hz, 2H), 3.17 (s, 3H), 3.07 (s, 3H), 2.47-2.13 (m, 4H).

Example 84: 4-{7-[3-Cyano-4-(piperidin-4-yloxy)-phenyl]-furo[3,2-b]pyridin-2-yl}-3-methoxy-N,N-dimethyl-benzamide Hydrochloride (158)

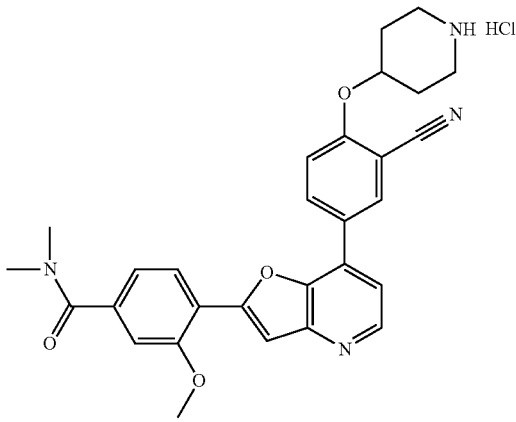 [SMILES: COc1cc(C(=O)N(C)C)ccc1-c1cc2nccc(-c3ccc(OC4CCNCC4)c(C#N)c3)c2o1 ; Cl]

The title compound was synthesized according to the procedure described in example 64 using 4-(7-Chloro-furo[3,2-b]pyridin-2-yl)-3-methoxy-N,N-dimethyl-benzamide (200.00 mg; 0.60 mmol; 1.00 eq.), 4-[2-Cyano-4-(4,4,5,5-tetramethyl-[1,3,2]dioxaborolan-2-yl)-phenoxy]-piperidine-1-carboxylic acid tert-butyl ester (310.79 mg; 0.73 mmol; 1.20 eq.), Dicyclohexyl-(2',6'-dimethoxy-biphenyl-2-yl)-phosphane (74.47 mg; 0.18 mmol; 0.30 eq.) and dipotassium carbonate (167.13 mg; 1.21 mmol; 2.00 eq.) and diacetoxypalladium (27.15 mg; 0.12 mmol; 0.20 eq.) in dioxane-water followed by treatment of 4-{2-Cyano-4-[2-(4-dimethylcarbamoyl-phenyl)-furo[3,2-b]pyridin-7-yl]-phenoxy}-piperidine-1-carboxylic acid tert-butyl ester (150.00 mg; 0.26 mmol; 1.00 eq.) in dichloromethane with hydrogen chloride in ether (1.58 ml; 3.17 mmol; 10.00 eq.) to get an yellow solid (125 mg, 43%). 497 [M+H]$^+$. $^1$H NMR (400 MHz, Methanol-d$_4$) δ 8.75 (dd, J=6.5, 1.6 Hz, 1H), 8.63 (d, J=7.2 Hz, 2H), 8.30-8.08 (m, 2H), 7.85 (d, J=1.7 Hz, 1H), 7.74 (d, J=8.8 Hz, 1H), 7.35 (s, 1H), 7.26 (d, J=7.9 Hz, 1H), 5.21 (s, 1H), 4.16 (s, 3H), 3.45 (ddd, J=34.6, 11.7, 5.5 Hz, 4H), 3.17 (s, 3H), 3.07 (s, 3H), 2.56-2.09 (m, 4H).

Example 85: 4-{7-[3-Cyano-4-(pyrrolidin-3-yl-methoxy)-phenyl]-furo[3,2-b]pyridin-2-yl}-3-methoxy-N,N-dimethyl-benzamide hydrochloride (152)

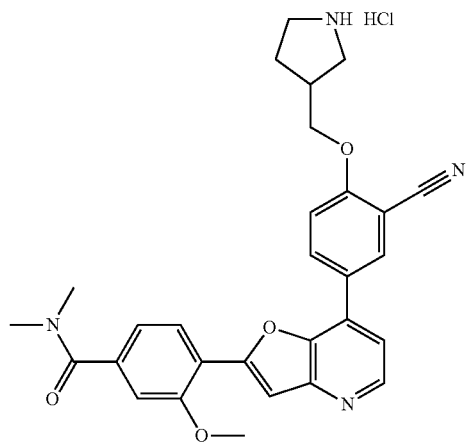 [SMILES: Cl ; COc1cc(C(=O)N(C)C)ccc1-c1cc2nccc(-c3ccc(OCC4CCNC4)c(C#N)c3)c2o1]

The title compound was synthesized according to the procedure described in example 64 using 4-(7-Chloro-furo[3,2-b]pyridin-2-yl)-3-methoxy-N,N-dimethyl-benzamide (200.00 mg; 0.60 mmol; 1.00 eq.), 3-[2-Cyano-4-(4,4,5,5-tetramethyl-[1,3,2]dioxaborolan-2-yl)-phenoxymethyl]-pyrrolidine-1-carboxylic acid tert-butyl ester (310.79 mg; 0.73 mmol; 1.20 eq.), Dicyclohexyl-(2',6'-dimethoxy-biphenyl-2-yl)-phosphane (74.47 mg; 0.18 mmol; 0.30 eq.), dipotassium carbonate (167.13 mg; 1.21 mmol; 2.00 eq.) and diacetoxypalladium (27.15 mg; 0.12 mmol; 0.20 eq.) in dioxane-water followed by treatment of 3-{2-Cyano-4-[2-(4-dimethylcarbamoyl-2-methoxy-phenyl)-furo[3,2-b]pyridin-7-yl]-phenoxymethyl}-pyrrolidine-1-carboxylic acid tert-butyl ester (265.00 mg; 0.44 mmol; 1.00 eq.) in dichloromethane (15.00 ml) was added hydrogen chloride in ether (2.22 ml; 4.44 mmol; 10.00 eq.) as an yellow solid (185 mg, 53%). MS: m/z=497 [M+H]$^+$. $^1$H NMR (400 MHz, Chloroform-d) δ 8.66 (dd, J=6.5, 1.6 Hz, 1H), 8.38 (d, J=7.2 Hz, 2H), 8.11-7.90 (m, 2H), 7.83 (d, J=1.7 Hz, 1H), 7.61 (d, J=8.8 Hz, 1H), 7.34-7.24 (m, 1H), 7.14 (d, J=7.9 Hz, 1H), 5.28 (s, 1H), 4.08 (s, 2H), 3.64 (m, 4H), 3.41 (s, 3H), 3.11 (s, 3H), 3.00 (s, 3H), 2.39 (m, 2H).

Example 86: 4-{7-[3-Cyano-4-((3S,4R)-3-fluoro-piperidin-4-yloxy)-phenyl]-furo[3,2-b]pyridin-2-yl}-3-methoxy-N,N-dimethyl-benzamide hydrochloride (153)

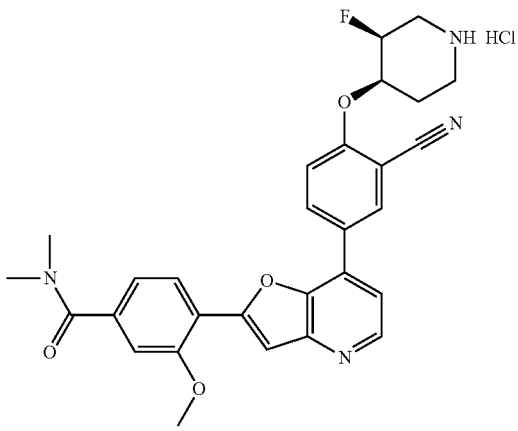 [SMILES: COc1cc(C(=O)N(C)C)ccc1-c1cc2nccc(-c3ccc(O[C@@H]4CCNC[C@@H]4F)c(C#N)c3)c2o1 ; Cl]

The title compound was synthesized according to the procedure described in example 64 using 4-(7-Chloro-furo[3,2-b]pyridin-2-yl)-3-methoxy-N,N-dimethyl-benzamide (200.00 mg; 0.60 mmol; 1.00 eq.), (3S,4R)-4-[2-Cyano-4-(4,4,5,5-tetramethyl-[1,3,2]dioxaborolan-2-yl)-phenoxy]-3-fluoro-piperidine-1-carboxylic acid tert-butyl ester (323.85 mg; 0.73 mmol; 1.20 eq.), Dicyclohexyl-(2',6'-dimethoxy-biphenyl-2-yl)-phosphane (74.47 mg; 0.18 mmol; 0.30 eq.), dipotassium carbonate (167.13 mg; 1.21 mmol; 2.00 eq) and diacetoxypalladium (27.15 mg; 0.12 mmol; 0.20 eq.) (palladium acetate) in dioxane-water followed by treatment of (3S,4R)-4-{2-Cyano-4-[2-(4-dimethylcarbamoyl-2-methoxy-phenyl)-furo[3,2-b]pyridin-7-yl]-phenoxy}-3-fluoro-piperidine-1-carboxylic acid tert-butyl ester (215.00 mg; 0.35 mmol; 1.00 eq.) in dichloro-methane (9.00 ml) with hydrogen chloride in Ether (1.75 ml; 3.50 mmol; 10.00 eq.) afforded an yellow solid. (185 mg, 49%). MS: m/z=516 [M+H]$^+$. $^1$H NMR (400 MHz, Chloroform-d) δ 8.66 (d, J=5.6 Hz, 1H), 8.38 (m, 2H), 8.02 (d, J=7.7 Hz, 1H), 7.97 (d, J=1.7 Hz, 1H), 7.82 (d, J=3.4 Hz, 1H), 7.61 (d, J=5.1 Hz, 1H), 7.14 (d, J=10.2 Hz, 2H), 5.40 (m, 1H), 5.28 (m, 1H), 4.08 (s, 3H), 3.58 (m, 4H), 3.11 (s, 3H), 3.06 (s, 3H), 2.39 (m, 2H).

Example 87: 4-{7-[3-Cyano-4-(3,3-difluoro-piperidin-4-yloxy)-phenyl]-furo[3,2-b]pyridin-2-yl}-3-methoxy-N,N-dimethyl-benzamide hydrochloride (71)

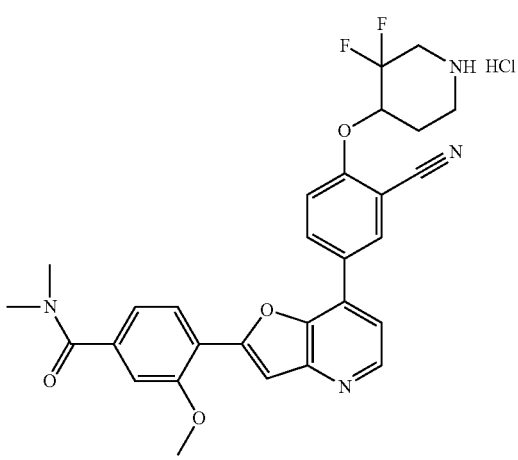 [SMILES: COc1cc(C(=O)N(C)C)ccc1-c1cc2nccc(-c3ccc(OC4CCNCC4(F)F)c(C#N)c3)c2o1 ; Cl]

The title compound was synthesized according to the procedure described in example 64 using 4-(7-Chloro-furo[3,2-b]pyridin-2-yl)-3-methoxy-N,N-dimethyl-benzamide (200.00 mg; 0.60 mmol; 1.00 eq.), 4-[2-Cyano-4-(4,4,5,5-tetramethyl-[1,3,2]dioxaborolan-2-yl)-phenoxy]-3,3-difluoro-piperidine-1-carboxylic acid tert-butyl ester (336.90 mg; 0.73 mmol; 1.20 eq.), Dicyclohexyl-(2',6'-dimethoxy-biphenyl-2-yl)-phosphane (74.47 mg; 0.18 mmol; 0.30 eq.), dipotassium carbonate (167.13 mg; 1.21 mmol; 2.00 eq.) and diacetoxypalladium (27.15 mg; 0.12 mmol; 0.20 eq.) in dioxane-water followed by treatment of 4-{2-Cyano-4-[2-(4-dimethylcarbamoyl-2-methoxy-phenyl)-furo[3,2-b]pyridin-7-yl]-phenoxy}-3,3-difluoro-piperidine-1-carboxylic acid tert-butyl ester (285.00 mg; 0.45 mmol; 1.00 eq.) in Dichloro-methane (15.00 ml) with hydrogen chloride in Ether (2.25 ml; 4.50 mmol; 10.00 eq.) to obtain an yellow solid (227 mg, 51%). MS: m/z=532 [M]$^+$. $^1$H NMR (400 MHz, Chloroform-d) δ 8.66-8.52 (m, 1H), 8.29 (s, 1H), 8.22 (d, J=9.1 Hz, 1H), 8.01 (d, J=7.8 Hz, 1H), 7.66 (s, 1H), 7.39-7.24 (m, 3H), 7.15 (d, J=10.4 Hz, 1H), 4.84 (s, 1H), 4.08 (s, 3H), 3.47 (td, J=20.2, 17.5, 10.2 Hz, 2H), 3.16 (s, 3H) 3.0 (s, 3H), 2.97 (d, J=14.1 Hz, 2H), 2.19 (m, 2H).

Example 88: 4-{7-[3-Cyano-4-(3-trifluoromethyl-pyrrolidin-3-yloxy)-phenyl]-furo[3,2-b]pyridin-2-yl}-3-methoxy-N,N-dimethyl-benzamide (113)

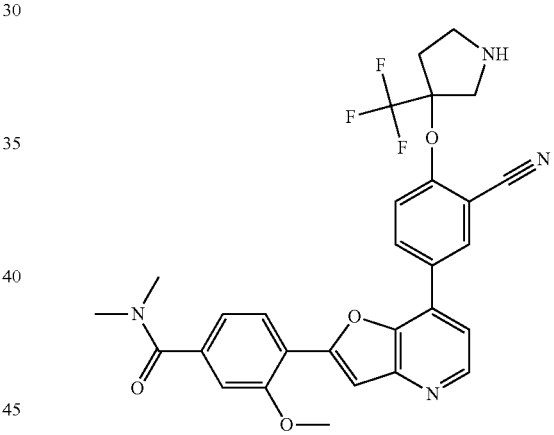

The title compound was synthesized according to the procedure described in example 64 using 4-(7-Chloro-furo[3,2-b]pyridin-2-yl)-3-methoxy-N,N-dimethyl-benzamide (150.00 mg; 0.45 mmol; 1.00 eq.), 3-[2-Cyano-4-(4,4,5,5-tetramethyl-[1,3,2]dioxaborolan-2-yl)-phenoxy]-3-trifluoromethyl-pyrrolidine-1-carboxylic acid tert-butyl ester (262.46 mg; 0.54 mmol; 1.20 eq.), Dicyclohexyl-(2',6'-dimethoxy-biphenyl-2-yl)-phosphane (55.85 mg; 0.14 mmol; 0.30 eq.), dipotassium carbonate (125.35 mg; 0.91 mmol; 2.00 eq.) and diacetoxypalladium (20.36 mg; 0.09 mmol; 0.20 eq.) in dioxane-water followed by treatment of 3-{2-Cyano-4-[2-(4-dimethylcarbamoyl-2-methoxy-phenyl)-furo[3,2-b]pyridin-7-yl]-phenoxy}-3-trifluoromethyl-pyrrolidine-1-carboxylic acid tert-butyl ester (28.00 mg; 0.04 mmol; 1.00 eq.) in Dichloro-methane (15.00 ml) with Trifluoro-acetic acid (0.03 ml; 0.43 mmol; 10.00 eq.) in 7% yield. MS: m/z=551 [M+H]$^+$. $^1$H NMR (400 MHz, Chloroform-d) δ 8.65 (d, J=4.8 Hz, 1H), 8.42-8.11 (m, 2H), 8.12-7.96 (m, 1H), 7.69 (t, J=2.1 Hz, 1H), 7.57 (dd, J=9.0, 2.4 Hz, 1H), 7.34 (d, J=4.2 Hz, 1H), 7.18 (d, J=9.3 Hz, 2H), 4.09 (s, 3H), 3.60 (m, 2H), 3.50-3.29 (m, 2H), 3.17 (s, 3H), 3.08 (s, 3H), 2.55-2.26 (m, 2H), Example 89: 4-{7-[3-Cyano-4-(2-methyl-tetrahydro-pyran-4-yloxy)-phenyl]-furo[3,2-b]pyridin-2-yl}-N,N-dimethyl-benzamide (184)

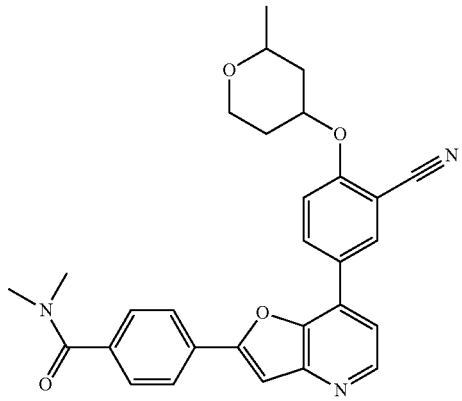 [SMILES: CC1CC(Oc2ccc(-c3ccnc4cc(-c5ccc(C(=O)N(C)C)cc5)oc34)cc2C#N)CCO1]

The title compound was synthesized according to the procedure described in example 71 starting from 4-(7-Chloro-furo[3,2-b]pyridin-2-yl)-benzoic acid ethyl ester (175.00 mg; 0.58 mmol; 1.00 eq.), 2-(2-Methyl-tetrahydro-pyran-4-yloxy)-5-(4,4,5,5-tetramethyl-[1,3,2]dioxaborolan-2-yl)-benzonitrile (218.98 mg; 0.64 mmol; 1.10 eq.) and Dimethyl-amine (4.96 mg; 0.11 mmol; 2.00 eq.) as an off-white solid. (8 mg). MS: m/z=482 [M+H]$^+$. $^1$H NMR (400 MHz, Chloroform-d) δ 8.30 (s, 1H), 8.24 (d, J=8.6 Hz, 2H), 7.99 (d, J=7.6 Hz, 2H), 7.60 (d, J=6.7 Hz, 2H), 7.32-7.21 (m, 3H), 4.76-4.57 (m, 1H), 4.16 (dd, J=12.1, 4.7 Hz, 1H), 3.69-3.50 (m, 2H), 3.17 (s, 3H), 3.07 (s, 3H), 2.21 (ddd, J=27.2, 12.6, 3.9 Hz, 2H), 1.90 (dd, J=11.9, 4.7 Hz, 1H), 1.64 (q, J=11.5 Hz, 1H), 1.32 (d, J=6.1 Hz, 3H).

Example 90: 4-{7-[3-Cyano-4-(4-methyl-tetrahydro-pyran-4-yloxy)-phenyl]-furo[3,2-b]pyridin-2-yl}-N,N-dimethyl-benzamide (159)

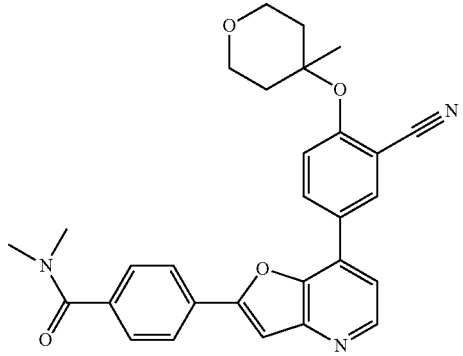 [SMILES: CN(C)C(=O)c1ccc(-c2cc3nccc(-c4ccc(OC5(C)CCOCC5)c(C#N)c4)c3o2)cc1]

The title compound was synthesized according to the procedure described in example 71 starting from 4-(7-Chloro-furo[3,2-b]pyridin-2-yl)-benzoic acid ethyl ester (250.00 mg; 0.83 mmol; 1.00 eq.), 2-(4-Methyl-tetrahydro-pyran-4-yloxy)-5-(4,4,5,5-tetramethyl-[1,3,2]dioxaborolan-2-yl)-benzonitrile (312.83 mg; 0.91 mmol; 1.10 eq.) and Dimethyl-amine (0.33 ml; 0.66 mmol; 2.00 eq.) as a white solid (25 mg). MS: m/z=482 M$^+$. $^1$H NMR (400 MHz, Chloroform-d) δ 8.30 (s, 1H), 8.18 (d, J=8.9 Hz, 1H), 7.96 (d, J=7.8 Hz, 2H), 7.60 (d, J=7.8 Hz, 2H), 7.43 (d, J=8.3 Hz, 2H), 7.36 (d, J=8.8 Hz, 1H), 7.29 (s, 1H), 3.96 (t, J=10.9 Hz, 2H), 3.80 (dd, J=11.6, 4.9 Hz, 2H), 3.16 (s, 3H), 3.05 (s, 3H), 2.24 (d, J=14.0 Hz, 2H), 1.99-1.85 (m, 2H), 1.63 (s, 3H).

Example 91: 4-{7-[3-Cyano-4-(2-oxa-spiro[3.3]hept-6-yloxy)-phenyl]-furo[3,2-b]pyridin-2-yl}-N,N-dimethyl-benzamide (177)

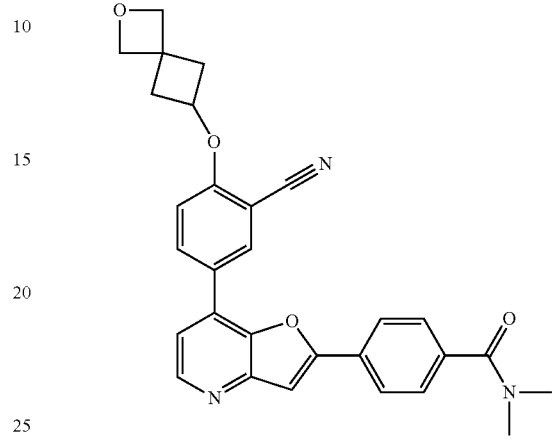

The title compound was synthesized according to the procedure described in example 71 starting from 4-(7-Chloro-furo[3,2-b]pyridin-2-yl)-benzoic acid methyl ester (200.00 mg; 0.70 mmol; 1.00 eq.), 2-(2-Oxa-spiro[3.3]hept-6-yloxy)-5-(4,4,5,5-tetramethyl-[1,3,2]dioxaborolan-2-yl)-benzonitrile (284.64 mg; 0.83 mmol; 1.20 eq.), and N-methylmethanamine hydrochloride (10.81 mg; 0.13 mmol; 2.00 eq.). The amide coupling was accomplished using (3-Dimethylamino-propyl)-ethyl-carbodiimide hydrochloride (15.25 mg; 0.08 mmol; 1.20 eq.) (EDCI), Benzotriazol-1-ol (10.75 mg; 0.08 mmol; 1.20 eq.) (HOBt) and Ethyl-diisopropyl-amine (25.71 mg; 0.20 mmol; 3.00 eq.) in DMF (5.0 mL) to obtain the title compound (8 mg). MS: m/z=480 [M+H]$^+$.

Example 92: 4-{7-[4-(3-Chloromethyl-3-hydroxymethyl-cyclobutoxy)-3-cyano-phenyl]-furo[3,2-b]pyridin-2-yl}-N,N-dimethyl-benzamide (168)

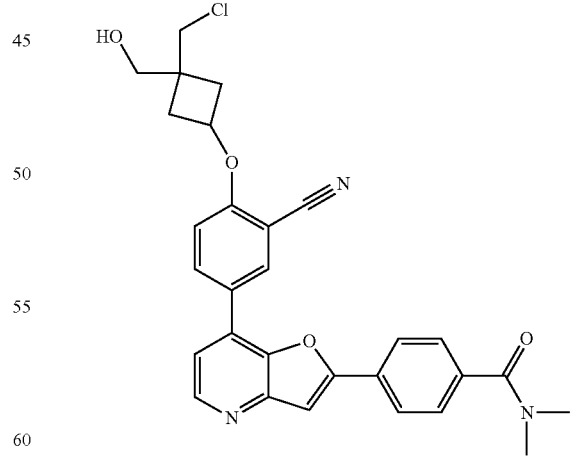

The title compound was synthesized according to the procedure described in example 71 starting from 4-(7-Chloro-furo[3,2-b]pyridin-2-yl)-benzoic acid methyl ester (200.00 mg; 0.70 mmol; 1.00 eq.), 2-(2-Oxa-spiro[3.3]hept-6-yloxy)-5-(4,4,5,5-tetramethyl-[1,3,2]dioxaborolan-2-yl)-benzonitrile (284.64 mg; 0.83 mmol; 1.20 eq.), and N-methylmethanamine hydrochloride (13.34 mg; 0.16 mmol; 2.00 eq.). The amide coupling was done using (3-Dimethylamino-propyl)-ethyl-carbodiimide hydrochloride (18.82 mg; 0.10 mmol; 1.20 eq.) (EDCI), Benzotriazol-1-ol (13.27 mg; 0.10 mmol; 1.20 eq.) (HOBt) and Ethyl-diisopropyl-amine (31.72 mg; 0.25 mmol; 3.00 eq.) in DMF (5.0 mL) to obtain the title compound (25 mg). MS: m/z=517 [M+H]$^+$.

Example 93: 4-{7-[3-Cyano-4-(1-methyl-piperidin-4-yloxy)-phenyl]-furo[3,2-b]pyridin-2-yl}-3-methoxy-N,N-dimethyl-benzamide (150)

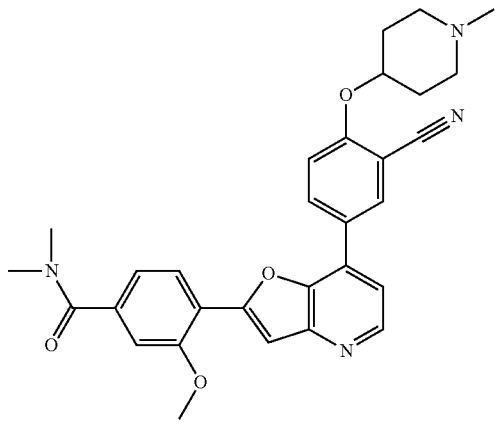

The title compound was synthesized according to the procedure described in example 71 using 4-(7-Chloro-furo[3,2-b]pyridin-2-yl)-3-methoxy-N,N-dimethyl-benzamide (200.00 mg; 0.60 mmol; 1.00 eq.), 2-(1-Methyl-piperidin-4-yloxy)-5-(4,4,5,5-tetramethyl-[1,3,2]dioxaborolan-2-yl)-benzonitrile (269.02 mg; 0.79 mmol; 1.30 eq.), Dicyclohexyl-(2',6'-dimethoxy-biphenyl-2-yl)-phosphane (74.47 mg; 0.18 mmol; 0.30 eq.), dipotassium carbonate (167.13 mg; 1.21 mmol; 2.00 eq.) and diacetoxypalladium (27.15 mg; 0.12 mmol; 0.20 eq.) (palladium acetate) in dioxane-water (45 mg, 15%). MS: m/z=511 [M+H]$^+$. $^1$H NMR (400 MHz, Chloroform-d) δ 8.61 (s, 1H), 8.39-8.14 (m, 2H), 8.03 (d, J=7.8 Hz, 1H), 7.67 (s, 1H), 7.46-6.86 (m, 4H), 4.71 (m, 1H), 4.09 (s, 3H), 3.17 (s, 3H), 3.08 (s, 3H), 2.81 (m, 2H), 2.59 (m, 2H), 2.44 (s, 3H), 2.14 (m, 4H).

Example 94: 4-{7-[3-Cyano-4-(piperidin-4-ylmethoxy)-phenyl]-furo[3,2-b]pyridin-2-yl}-3-methoxy-N,N-dimethyl-benzamide (155)

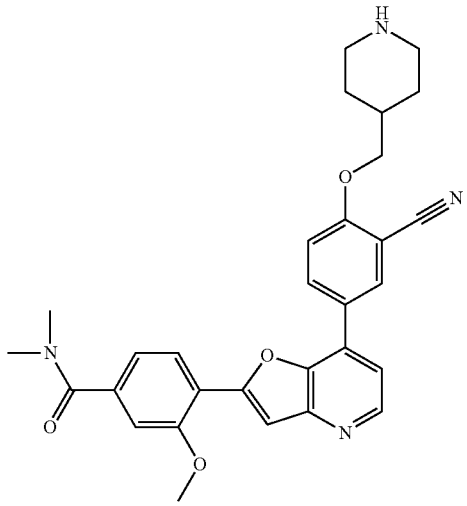 [SMILES: COc1cc(C(=O)N(C)C)ccc1-c1cc2nccc(-c3ccc(OCC4CCNCC4)c(C#N)c3)c2o1]

The title compound was synthesized according to the procedure described in example 64 using 4-(7-Chloro-furo[3,2-b]pyridin-2-yl)-3-methoxy-N,N-dimethyl-benzamide (130.00 mg; 0.39 mmol; 1.00 eq.), 4-[2-Cyano-4-(4,4,5,5-tetramethyl-[1,3,2]dioxaborolan-2-yl)-phenoxymethyl]-piperidine-1-carboxylic acid tert-butyl ester (191.24 mg; 0.43 mmol; 1.10 eq.)), Dicyclohexyl-(2',6'-dimethoxy-biphenyl-2-yl)-phosphane (48.40 mg; 0.12 mmol; 0.30 eq.), and dipotassium carbonate (108.64 mg; 0.79 mmol; 2.00 eq.). Diacetoxypalladium (17.65 mg; 0.08 mmol; 0.20 eq.) in dioxane-water followed by treatment of 4-{2-Cyano-4-[2-(4-dimethylcarbamoyl-2-methoxy-phenyl)-furo[3,2-b]pyridin-7-yl]-phenoxymethyl}-piperidine-1-carboxylic acid tert-butyl ester (150.00 mg; 0.25 mmol; 1.00 eq.) in Dichloro-methane (9.00 ml) with hydrogen chloride in Ether (1.23 ml; 2.46 mmol; 10.00 eq.) to obtain an yellow solid (32 mg, 13%). MS: m/z=511 [M+H]$^+$. $^1$H NMR (400 MHz, Chloroform-d) δ 8.57 (d, J=5.1 Hz, 1H), 8.31-8.14 (m, 2H), 8.00 (d, J=7.9 Hz, 1H), 7.64 (s, 1H), 7.39-7.26 (m, 1H), 7.25-7.04 (m, 3H), 4.06 (s, 3H) 4.04 (d, J=4.0 Hz, 2H), 3.27-3.21 (m, 2H), 3.15 (s, 3H), 3.06 (s, 3H), 2.75 (t, 1H), 2.52 (s, 2H), 2.13 (m, 1H), 1.97 (d, J=13.1 Hz, 2H), 1.45 (m, 2H).

Example 95: 4-{7-[3-Cyano-4-(3,3-difluoro-1-methyl-piperidin-4-yloxy)-phenyl]-furo[3,2-b]pyridin-2-yl}-3-methoxy-N,N-dimethyl-benzamide (97)

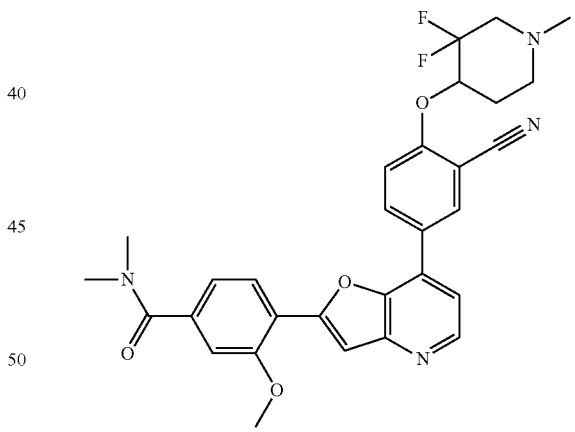

The title compound was synthesized according to the procedure described in example 79 using 4-{7-[3-Cyano-4-(3,3-difluoro-piperidin-4-yloxy)-phenyl]-furo[3,2-b]pyridin-2-yl}-3-methoxy-N,N-dimethyl-benzamide; (65.00 mg; 0.11 mmol; 1.00 eq.), Formaldehyde (37% w/w Aq. solution) (0.50 ml) and palladium on activated carbon (24.31 mg; 0.02 mmol; 0.20 eq.) in Methanol (27 mg, 43%). MS: m/z=547 [M+H]$^+$. $^1$H NMR (400 MHz, Chloroform-d) δ 8.61 (t, J=3.9 Hz, 1H), 8.29 (d, J=2.9 Hz, 1H), 8.23 (d, J=8.7 Hz, 1H), 8.09-7.89 (m, 1H), 7.76-7.59 (m, 1H), 7.40-7.00 (m, 4H), 4.76 (s, 1H), 4.08 (s, 3H), 3.17 (s, 3H), 3.07 (s, 3H), 3.02-2.85 (m, 2H), 2.70 (m, 2H), 2.47 (s, 3H), 2.36-2.04 (m, 2H).

Example 96: 4-{7-[3-Cyano-4-(1-isopropyl-pyrrolidin-3-yloxy)-phenyl]-furo[3,2-b]pyridin-2-yl}-3-methoxy-N,N-dimethyl-benzamide (157)

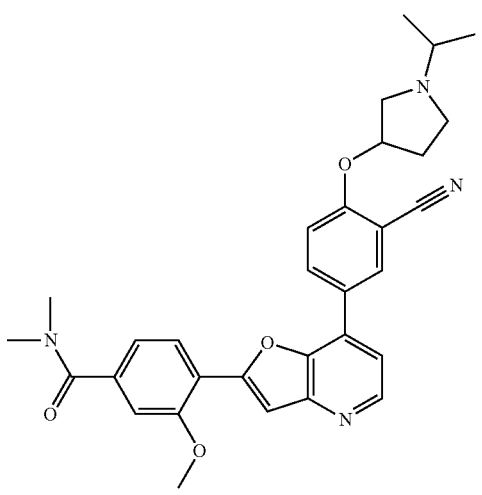 [SMILES: COc1cc(C(=O)N(C)C)ccc1-c1cc2nccc(-c3ccc(OC4CCN(C(C)C)C4)c(C#N)c3)c2o1]

The title compound was synthesized according to the procedure described in example 79 using 4-{7-[3-Cyano-4-(pyrrolidin-3-yloxy)-phenyl]-furo[3,2-b]pyridin-2-yl}-3-methoxy-N,N-dimethyl-benzamide; hydrochloride (50.00 mg; 0.10 mmol; 1.00 eq.), Acetone and palladium on activated carbon (20.51 mg; 0.02 mmol; 0.20 eq.) in Methanol (15 mg, 30%). MS: m/z=525 [M+H]$^+$. $^1$H NMR (400 MHz, Chloroform-d) δ 8.62 (dd, J=5.4, 2.5 Hz, 1H), 8.31 (q, J=2.1 Hz, 1H), 8.28-8.16 (m, 1H), 8.11-7.91 (m, 1H), 7.68 (t, J=1.8 Hz, 1H), 7.33 (dt, J=4.3, 1.7 Hz, 1H), 7.29 (d, J=1.8 Hz, 1H), 7.21-7.10 (m, 2H), 5.12 (s, 1H), 4.15 (s, 3H), 3.64-3.42 (m, 2H), 3.17 (s, 3H), 3.08 (s, 3H), 2.93 (t, J=9.4 Hz, 2H), 2.48 (m, 1H), 2.29-2.14 (m, 2H), 1.26 (d, J=6.8 Hz, 6H).

Example 97: 4-{7-[4-(1-Acetyl-pyrrolidin-3-yloxy)-3-cyano-phenyl]-furo[3,2-b]pyridin-2-yl}-3-methoxy-N,N-dimethyl-benzamide (144)

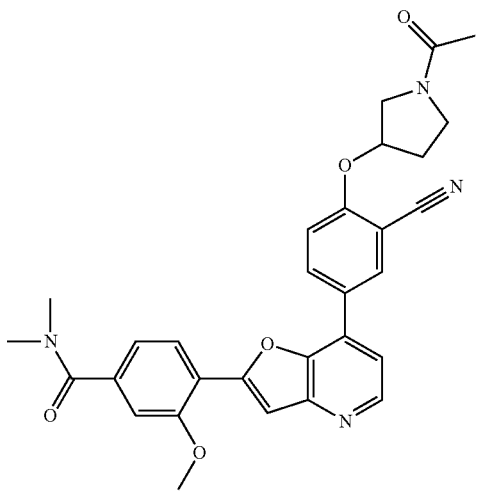 [SMILES: COc1cc(C(=O)N(C)C)ccc1-c1cc2nccc(-c3ccc(OC4CCN(C(C)=O)C4)c(C#N)c3)c2o1]

Ethyl-diisopropyl-amine (0.08 ml; 0.48 mmol; 5.00 eq.) was added to a suspension of 4-{7-[3-Cyano-4-(pyrrolidin-3-yloxy)-phenyl]-furo[3,2-b]pyridin-2-yl}-3-methoxy-N,N-dimethyl-benzamide; hydrochloride (50.00 mg; 0.10 mmol; 1.00 eq.), in Dichloro-methane (10 ml). The resulting homogeneous solution was treated with Acetyl chloride (0.01 ml; 0.19 mmol; 2.00 eq.) and stirred at room temperature for 1 h. The solvent was removed and the residue was purified on a reverse phase with Acetonitrile and water (0.1% NH$_4$OH) gradient to obtain the title compound. (35 mg, 69%). MS: m/z=525 [M+H]$^+$. $^1$H NMR (400 MHz, Chloroform-d) δ 8.61 (t, J=3.4 Hz, 1H), 8.37-8.17 (m, 3H), 8.14-7.98 (m, 1H), 7.71 (d, J=3.2 Hz, 1H), 7.47-7.29 (m, 2H), 7.18 (dd, J=7.1, 3.4 Hz, 1H), 5.18 (d, J=4.5 Hz, 1H), 4.09 (s, 3H), 4.03-3.57 (m, 4H), 3.17 (s, 3H), 3.08 (s, 3H), 2.54 (d, J=13.0 Hz, 2H), 2.16 (s, 3H).

Example 98: 4-{7-[3-Cyano-4-(2,6-dimethyl-tetrahydro-pyran-4-yloxy)-phenyl]-furo[3,2-b]pyridin-2-yl}-N,N-dimethyl-benzamide (213)

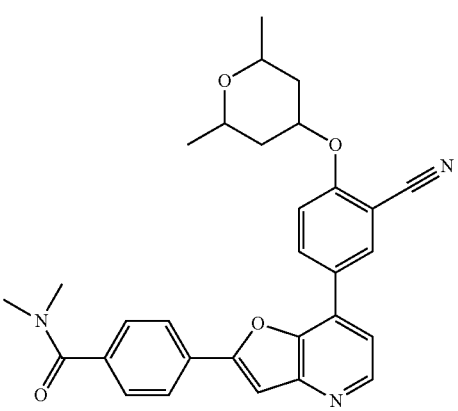 [SMILES: CC1CC(Oc2ccc(-c3ccnc4cc(-c5ccc(C(=O)N(C)C)cc5)oc34)cc2C#N)CC(C)O1]

The title compound was synthesized according to the procedure described in example 71 starting from 4-(7-Chloro-furo[3,2-b]pyridin-2-yl)-benzoic acid ethyl ester (200.00 mg; 0.66 mmol; 1.00 eq), 2-(2,6-Dimethyl-tetrahydro-pyran-4-yloxy)-5-(4,4,5,5-tetramethyl-[1,3,2]dioxaborolan-2-yl)-benzonitrile (260.49 mg; 0.73 mmol; 1.10 eq.), and Dimethyl-amine (0.19 ml; 0.38 mmol; 2.00 eq.) as a white solid (24 mg, 11%). MS: m/z=496 [M+H]$^+$. $^1$H NMR (400 MHz, Chloroform-d) δ 8.63 (s, 1H), 8.39-8.18 (m, 2H), 7.99 (d, J=8.0 Hz, 2H), 7.74-7.52 (m, 3H), 7.39-7.18 (m, 2H), 4.71 (dt, J=11.2, 6.1 Hz, 1H), 3.64 (m, 2H), 3.18 (s, 3H), 3.06 (s, 3H), 2.22 (dd, J=12.9, 4.4 Hz, 2H), 1.58 (q, J=11.6 Hz, 2H), 1.34 (s, 3H), 1.32 (s, 3H).

Example 99: 4-{7-[3-Cyano-4-(2,2-dimethyl-tetrahydro-pyran-4-yloxy)-phenyl]-furo[3,2-b]pyridin-2-yl}-N,N-dimethyl-benzamide (170)

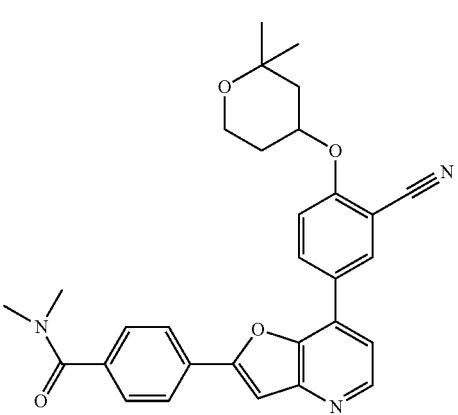 [SMILES: CN(C)C(=O)c1ccc(-c2cc3nccc(-c4ccc(OC5CCOC(C)(C)C5)c(C#N)c4)c3o2)cc1]

The title compound was synthesized according to the procedure described in example 71 starting from 4-(7-Chloro-furo[3,2-b]pyridin-2-yl)-benzoic acid methyl ester (200.00 mg; 0.70 mmol; 1.00 eq.), 2-(2,2-Dimethyl-tetrahydro-pyran-4-yloxy)-5-(4,4,5,5-tetramethyl-[1,3,2]dioxaborolan-2-yl)-benzonitrile (410.47 mg; 0.86 mmol; 1.30 eq.), and Dimethyl-amine (0.31 ml; 0.62 mmol; 2.00 eq.) to get a white solid (41 mg, 27%). MS: m/z=496 [M+H]$^+$. $^1$H NMR (400 MHz, Chloroform-d) δ 8.62 (d, J=5.3 Hz, 1H), 8.30 (d, J=1.9 Hz, 1H), 8.23 (dt, J=8.8, 1.9 Hz, 1H), 7.96 (dd, J=8.2, 1.6 Hz, 2H), 7.60 (dd, J=8.2, 1.5 Hz, 2H), 7.48 (s, 1H), 7.43 (d, J=5.2 Hz, 1H), 7.27-7.20 (m, 1H), 4.86 (m, 1H), 4.04 (m, 1H), 3.86-3.72 (m, 1H), 3.17 (s, 3H), 3.06 (s, 3H), 2.21-2.00 (m, 2H), 1.98-1.76 (m, 2H), 1.41 (s, 3H), 1.34 (s, 3H).

Example 100: 4-{7-[4-(1-Acetyl-piperidin-4-yloxy)-3-cyano-phenyl]-furo[3,2-b]pyridin-2-yl}-3-methoxy-N,N-dimethyl-benzamide (112)

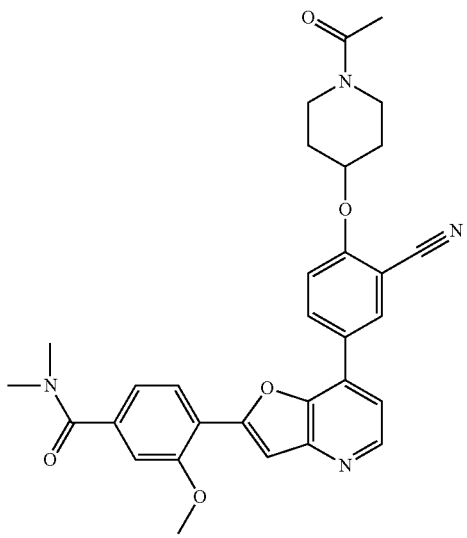 [SMILES: COc1cc(C(=O)N(C)C)ccc1-c1cc2nccc(-c3ccc(OC4CCN(C(C)=O)CC4)c(C#N)c3)c2o1]

The title compound was synthesized according to the procedure described in example 97 using 4-{7-[3-Cyano-4-(piperidin-4-yloxy)-phenyl]-furo[3,2-b]pyridin-2-yl}-3-methoxy-N,N-dimethyl-benzamide, Hydrochloride (25.00 mg; 0.05 mmol; 1.00 eq.), Acetyl chloride (0.01 ml; 0.09 mmol; 2.00 eq.) and Ethyl-diisopropyl-amine (0.04 ml; 0.23 mmol; 5.00 eq.) in dichloromethane to get a white solid (15 mg, 59%). MS: m/z=539 [M+H]$^+$. $^1$H NMR (400 MHz, Chloroform-d) δ 8.71-8.50 (m, 1H), 8.40-8.14 (m, 2H), 8.02 (dd, J=7.8, 2.7 Hz, 1H), 7.79 (d, J=5.4 Hz, 1H), 7.45 (s, 1H), 7.34-7.00 (m, 3H), 5.00-4.80 (m, 1H), 4.09 (s, 3H), 4.00-3.90 (m, 1H), 3.87-3.73 (m, 1H), 3.64 (m, 2H), 3.17 (s, 3H), 3.07 (s, 3H), 2.17 (s, 3H), 2.11-1.86 (m, 4H).

Example 101: 4-(7-{3-Cyano-4-[1-(2-hydroxy-acetyl)-piperidin-4-yloxy]-phenyl}-furo[3,2-b]pyridin-2-yl)-3-methoxy-N,N-dimethyl-benzamide (206)

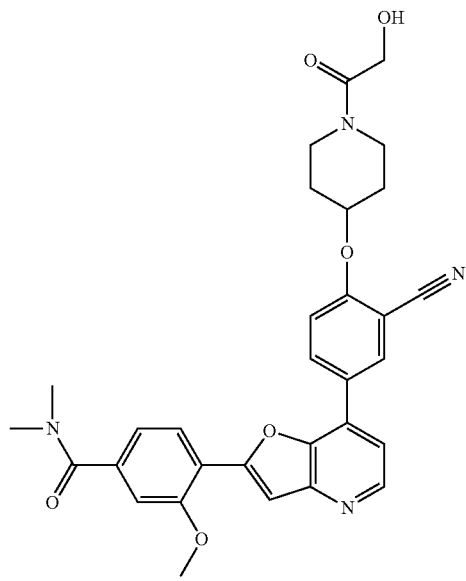 [SMILES: COc1cc(C(=O)N(C)C)ccc1-c1cc2nccc(-c3ccc(OC4CCN(C(=O)CO)CC4)c(C#N)c3)c2o1]

A mixture of 4-{7-[3-Cyano-4-(piperidin-4-yloxy)-phenyl]-furo[3,2-b]pyridin-2-yl}-3-methoxy-N,N-dimethyl-benzamide hydrochloride (50.00 mg; 0.09 mmol; 1.00 eq.), Hydroxy-acetic acid (8.56 mg; 0.11 mmol; 1.20 eq.), [Dimethylamino-([1,2,3]triazolo[4,5-b]pyridin-3-yloxy)-methylene]-dimethyl-ammonium; hexafluoro phosphate (HATU) (42.80 mg; 0.11 mmol; 1.20 eq.), and Ethyl-diisopropyl-amine (0.05 ml; 0.28 mmol; 5.00 eq.) in DMF (3.0 mL) was stirred at room temperature overnight. The reaction mixture was purified on a reverse phase column with 10-100% ACN-Water (0.1% NH$_4$OH) gradient for 40 min at a flow rate of 40 ml/min to obtain the title compound as a white solid (30 mg, 58%). MS: m/z=555 [M+H]$^+$. $^1$H NMR (400 MHz, Methanol-d$_4$) δ 8.24 (dd, J=5.1, 2.9 Hz, 1H), 8.15-8.08 (m, 1H), 8.05 (d, J=2.8 Hz, 1H), 7.76 (dd, J=8.1, 2.5 Hz, 1H), 7.32-7.23 (m, 3H), 7.15 (d, J=2.4 Hz, 1H), 7.07 (dd, J=8.0, 2.2 Hz, 1H), 4.93-4.85 (m, 1H), 4.30 (d, J=2.3 Hz, 2H), 4.01 (s, 3H), 3.89-3.57 (m, 2H), 3.57-3.41 (m, 1H), 3.40-3.30 (m, 1H), 3.14 (s, 3H), 3.08 (s, 3H), 2.26-1.71 (m, 4H).

Example 102: 4-{7-[3-Cyano-4-(pyridin-3-yloxy)-phenyl]-furo[3,2-b]pyridin-2-yl}-N,N-dimethyl-benzamide (181)

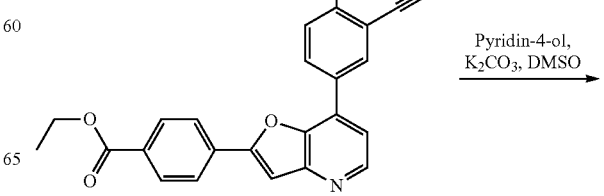

-continued

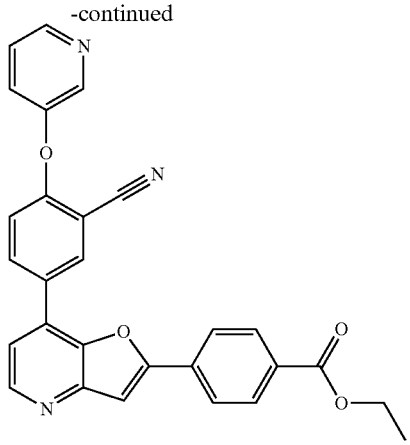

i) LiOH, MeOH ↓ ii) Me₂NH, EDC, HOBT·DIEA

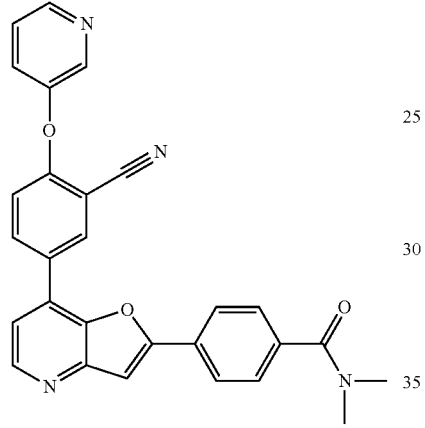

4-{7-[3-Cyano-4-(pyridin-3-yloxy)-phenyl]-furo[3,2-b]pyridin-2-yl}-benzoic acid ethyl ester A mixture of 4-[7-(3-Cyano-4-fluoro-phenyl)-furo[3,2-b]pyridin-2-yl]-benzoic acid ethyl ester (60.94 mg; 0.16 mmol; 1.00 eq.), and Pyridin-3-ol in DMSO (3 mL) was heated to 140° C. for 30 minutes under microwave irradiation. The mixture was poured into water, extracted with ether, dried over MgSO4. The title compound was obtained after purification through flash chromatography on silica gel (hexanes: ethyl acetate=100:0 to 95:5) (58 mg, 80% yield). MS: m/z=462 (M+H)⁺

4-{7-[3-Cyano-4-(pyridin-3-yloxy)-phenyl]-furo[3,2-b]pyridin-2-yl}-benzoic acid (186)

A mixture of 4-{7-[3-Cyano-4-(pyridin-3-yloxy)-phenyl]-furo[3,2-b]pyridin-2-yl}-benzoic acid ethyl ester (50.00 mg; 0.11 mmol; 1.00 eq.) and lithium hydroxide (7.78 mg; 0.33 mmol; 3.00 eq.) in THF/MeOH/water (5/5/3 mL) was stirred at room temperature for 2 h. Aqueous HCl (1N) was added to adjust pH to 5. After removal of the solvent, the product was precipitated from water. The crude solid was filtered, dissolved in DMF and purified through reverse phase HPLC to obtain the product (36 mg, 76% yield). MS: m/z=444 (M+H)⁺. ¹H NMR (DMSO-d6): 8.67 (1H), 8.60 (1H), 8.58 (1H), 8.52 (1H), 8.09 (2H), 7.85 (2H), 7.73 (2H), 7.56 (3H), 7.25 (1H).

4-{7-[3-Cyano-4-(pyridin-3-yloxy)-phenyl]-furo[3,2-b]pyridin-2-yl}-N,N-dimethyl-benzamide (181)

A mixture of 4-{7-[3-Cyano-4-(pyridin-3-yloxy)-phenyl]-furo[3,2-b]pyridin-2-yl}-benzoic acid (28.00 mg; 0.06 mmol; 1.00 eq.), N-methylmethanamine hydrochloride (10.54 mg; 0.13 mmol; 2.00 eq.), (3-Dimethylamino-propyl)-ethyl-carbodiimide hydrochloride (14.86 mg; 0.08 mmol; 1.20 eq.) (EDCI), Benzotriazol-1-ol (10.48 mg; 0.08 mmol; 1.20 eq.) (HOBt) and Ethyl-diisopropyl-amine (25.05 mg; 0.19 mmol; 3.00 eq.) in DMF (5.0 mL) was stirred at room temperature overnight. The mixture was purified on reverse phase HPLC to obtain the title compound (7 mg, 10% yield). MS: M/Z=385 (M+H). H NMR (DMSO-d6): 8.67 (1H), 8.60 (1H), 8.58 (1H), 8.52 (1H), 8.09 (2H), 7.85 (2H), 7.73 (2H), 7.56 (3H), 7.25 (1H), 2.9 (3H), 2.94 (3H).

Example 103: 4-{7-[3-Cyano-4-(pyridin-4-yloxy)-phenyl]-furo[3,2-b]pyridin-2-yl}-N,N-dimethyl-benzamide (200)

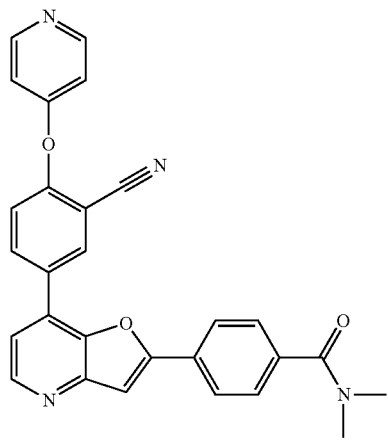 [SMILES: CN(C)C(=O)c1ccc(-c2cc3nccc(-c4ccc(Oc5ccncc5)c(C#N)c4)c3o2)cc1]

4-{7-[3-Cyano-4-(pyridin-4-yloxy)-phenyl]-furo[3,2-b]pyridin-2-yl}-benzoic acid ethyl ester (202)

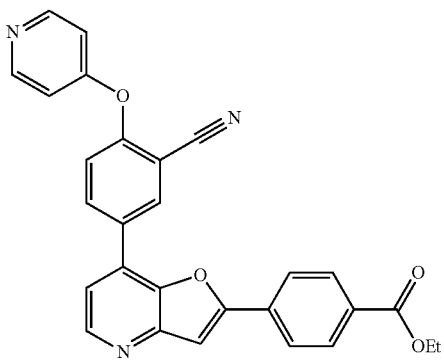 [SMILES: CCOC(=O)c1ccc(-c2cc3nccc(-c4ccc(Oc5ccncc5)c(C#N)c4)c3o2)cc1]

The title compound was synthesized according to the procedure described in example 102 using 4-[7-(3-Cyano-4-fluoro-phenyl)-furo[3,2-b]pyridin-2-yl]-benzoic acid ethyl ester (60.94 mg; 0.16 mmol; 1.00 eq.), dipotassium carbonate (43.60 mg; 0.32 mmol; 2.00 eq.) and Pyridin-4-ol (30.00 mg; 0.32 mmol; 2.00 eq.) in DMSO. (40 mg, 58% yield). MS: m/z=462 (M+H)

4-{7-[3-Cyano-4-(pyridin-4-yloxy)-phenyl]-furo[3,2-b]pyridin-2-yl}-benzoic acid (192)

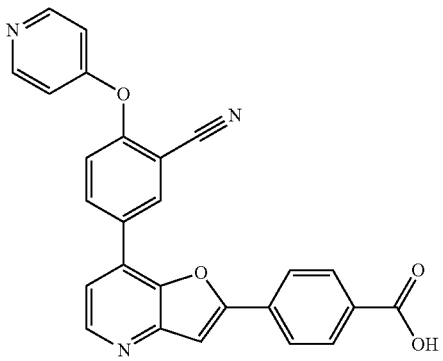 [SMILES: N#Cc1cc(-c2ccnc3cc(-c4ccc(C(=O)O)cc4)oc23)ccc1Oc1ccncc1]

The title compound was synthesized according to the procedure described in example 102 using 4-{7-[3-Cyano-4-(pyridin-4-yloxy)-phenyl]-furo[3,2-b]pyridin-2-yl}-benzoic acid ethyl ester (70.00 mg; 0.15 mmol; 1.00 eq.) and lithium hydroxide (10.90 mg; 0.46 mmol; 3.00 eq.) in THF/MeOH/water (5/5/3 mL). (34 mg, 52% yield). MS: m/z=462 (M+H)+

4-{7-[3-Cyano-4-(pyridin-4-yloxy)-phenyl]-furo[3,2-b]pyridin-2-yl}-N,N-dimethyl-benzamide (200)

The title compound was synthesized according to the procedure described in example 102 using 4-{7-[3-Cyano-4-(pyridin-4-yloxy)-phenyl]-furo[3,2-b]pyridin-2-yl}-benzoic acid (21.00 mg; 0.05 mmol; 1.00 eq.), N-methylmethanamine hydrochloride (7.90 mg; 0.10 mmol; 2.00 eq.), (3-Dimethylamino-propyl)-ethyl-carbodiimide hydrochloride (11.15 mg; 0.06 mmol; 1.20 eq.) (EDCI), Benzotriazol-1-ol (7.86 mg; 0.06 mmol; 1.20 eq.) (HOBt) and Ethyl-diisopropyl-amine (18.79 mg; 0.15 mmol; 3.00 eq.) in DMF (5.0 mL), (2.6 mg, 10% yield). MS: m/z=385 (M+H). H NMR (DMSO-d6): 8.67 (1H), 8.60 (1H), 8.58 (1H), 8.52 (1H), 8.09 (2H), 7.85 (2H), 7.73 (2H), 7.56 (3H), 7.25 (1H), 2.9 (3H), 2.94 (3H).

Example 104: 4-{7-[3-Cyano-4-(2-fluoro-phenoxy)-phenyl]-furo[3,2-b]pyridin-2-yl}-N,N-dimethyl-benzamide (178)

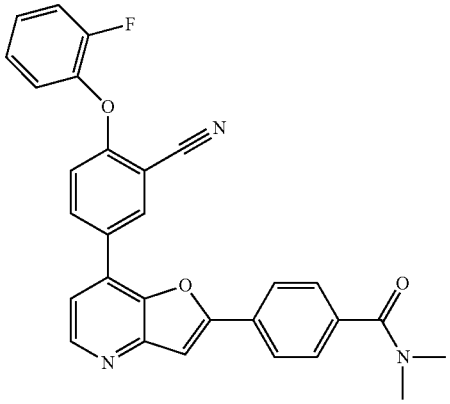 [SMILES: CN(C)C(=O)c1ccc(-c2cc3nccc(-c4ccc(Oc5ccccc5F)c(C#N)c4)c3o2)cc1]

4-{7-[3-Cyano-4-(2-fluoro-phenoxy)-phenyl]-furo[3,2-b]pyridin-2-yl}-benzoic acid (169)

The title compound was synthesized according to the procedure described in example 102 using 4-{7-[3-Cyano-4-(2-fluoro-phenoxy)-phenyl]-furo[3,2-b]pyridin-2-yl}-benzoic acid methyl ester (140.00 mg; 0.30 mmol; 1.00 eq.) and lithium hydroxide (21.66 mg; 0.90 mmol; 3.00 eq.) in THF/MeOH/water (5/5/3 mL). (70 mg, 51% yield). MS: m/z=451 (M+H)+.

4-{7-[3-Cyano-4-(2-fluoro-phenoxy)-phenyl]-furo[3,2-b]pyridin-2-yl}-N,N-dimethyl-benzamide (178)

The title compound was synthesized according to the procedure described in example 102 using 4-{7-[3-Cyano-4-(2-fluoro-phenoxy)-phenyl]-furo[3,2-b]pyridin-2-yl}-benzoic acid (40.00 mg; 0.09 mmol; 1.00 eq.), N-methyl-methanamine hydrochloride (14.48 mg; 0.18 mmol; 2.00 eq.), (3-Dimethylamino-propyl)-ethyl-carbodiimide hydrochloride (20.43 mg; 0.11 mmol; 1.20 eq.) (EDCI), Benzotriazol-1-ol (14.40 mg; 0.11 mmol; 1.20 eq.) (HOBt) and Ethyl-diisopropyl-amine (34.43 mg; 0.27 mmol; 3.00 eq.) in DMF (5.0 mL) (20.7 mg, 35% yield). MS: m/z=478 (M+H). H NMR (DMSO-d6): 8.67 (1H), 8.61 (1H), 8.52 (1H), 8.11 (2H), 7.84 (1H), 7.59 (1H), 7.44 (2H), 7.41 (2H), 7.14 (1H), 3.03 (3H), 2.98 (3H).

Example 105: 4-{7-[3-Cyano-4-(3-fluoro-phenoxy)-phenyl]-furo[3,2-b]pyridin-2-yl}-N,N-dimethyl-benzamide (176)

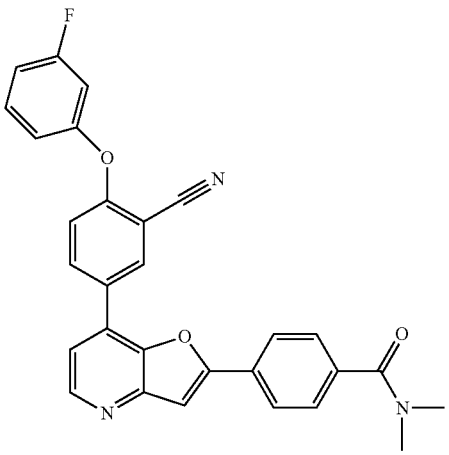 [SMILES: CN(C)C(=O)c1ccc(-c2cc3nccc(-c4ccc(Oc5cccc(F)c5)c(C#N)c4)c3o2)cc1]

4-{7-[3-Cyano-4-(3-fluoro-phenoxy)-phenyl]-furo[3,2-b]pyridin-2-yl}-benzoic acid (188)

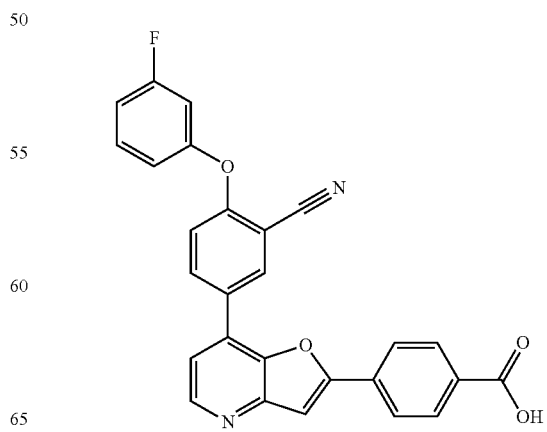

The title compound was synthesized according to the procedure described in example 102 using 4-{7-[3-Cyano-4-(2-fluoro-phenoxy)-phenyl]-furo[3,2-b]pyridin-2-yl}-benzoic acid methyl ester (140.00 mg; 0.30 mmol; 1.00 eq.) and lithium hydroxide (10.83 mg; 0.45 mmol; 3.00 eq.) in THF/MeOH/water (5/5/3 mL). (50 mg, 74% yield). MS: m/z=451 (M+H)+

4-{7-[3-Cyano-4-(3-fluoro-phenoxy)-phenyl]-furo[3,2-b]pyridin-2-yl}-N,N-dimethyl-benzamide (176)

The title compound was synthesized according to the procedure described in example 102 using 4-{7-[3-Cyano-4-(3-fluoro-phenoxy)-phenyl]-furo[3,2-b]pyridin-2-yl}-benzoic acid (30.00 mg; 0.07 mmol; 1.00 eq.), N-methyl-methanamine hydrochloride (10.86 mg; 0.13 mmol; 2.00 eq.), (3-Dimethylamino-propyl)-ethyl-carbodiimide hydrochloride (15.32 mg; 0.08 mmol; 1.20 eq.) (EDCI), Benzotriazol-1-ol (10.80 mg; 0.08 mmol; 1.20 eq.) (HOBt) and Ethyl-diisopropyl-amine (25.82 mg; 0.20 mmol; 3.00 eq.) in DMF (5.0 mL) (12.7 mg, 15% yield). MS: m/z=478 (M+H)+. ¹H NMR (DMSO-d6): 8.67 (1H), 8.61 (1H), 8.52 (1H), 8.11 (2H), 7.84 (1H), 7.59 (1H), 7.44 (2H), 7.41 (2H), 7.14 (1H), 3.03 (3H), 2.98 (3H).

Example 106: 4-{7-[3-Cyano-4-((S)-3-fluoro-pyrrolidin-1-yl)-phenyl]-furo[3,2-b]pyridin-2-yl}-N,N-dimethyl-benzamide (106)

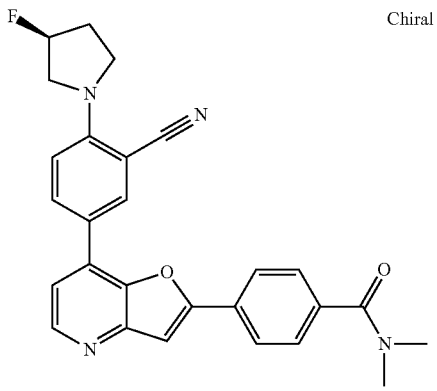 [SMILES: CN(C)C(=O)c1ccc(-c2cc3nccc(-c4ccc(N5CC[C@H](F)C5)c(C#N)c4)c3o2)cc1]

4-{7-[3-Cyano-4-((S)-3-fluoro-pyrrolidin-1-yl)-phenyl]-furo[3,2-b]pyridin-2-yl}-benzoic acid ethyl ester (187)

The title compound was synthesized according to the procedure described in example 102 using 4-[7-(3-Cyano-4-fluoro-phenyl)-furo[3,2-b]pyridin-2-yl]-benzoic acid ethyl ester (60.94 mg; 0.16 mmol; 1.00 eq.), and (S)-3-Fluoro-pyrrolidine (42.17 mg; 0.47 mmol; 3.00 eq.) in DMSO (55 mg, 77% yield). MS: m/z=456 (M+H).

4-{7-[3-Cyano-4-((S)-3-fluoro-pyrrolidin-1-yl)-phenyl]-furo[3,2-b]pyridin-2-yl}-benzoic acid (107)

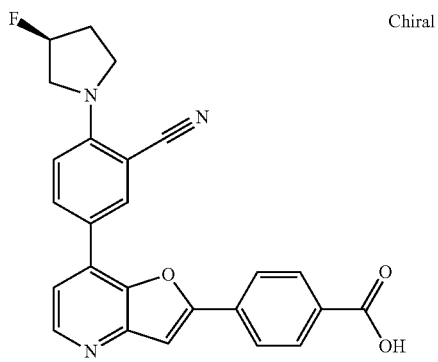 [SMILES: N#Cc1cc(-c2ccnc3cc(-c4ccc(C(=O)O)cc4)oc23)ccc1N1CC[C@H](F)C1]

The title compound was synthesized according to the procedure described in example 102 using 4-{7-[3-Cyano-4-((S)-3-fluoro-pyrrolidin-1-yl)-phenyl]-furo[3,2-b]pyridin-2-yl}-benzoic acid ethyl ester (50.00 mg; 0.11 mmol; 1.00 eq.) and lithium hydroxide (7.89 mg; 0.33 mmol; 3.00 eq.) in THF/MeOH/water (5/5/3 mL) stirred at room temperature for 2 hours (40 mg, 85% yield). MS: m/z=428 (M+H)

4-{7-[3-Cyano-4-((S)-3-fluoro-pyrrolidin-1-yl)-phenyl]-furo[3,2-b]pyridin-2-yl}-N,N-dimethyl-benzamide (106)

The title compound was synthesized according to the procedure described in example 102 using 4-{7-[3-Cyano-4-((S)-3-fluoro-pyrrolidin-1-yl)-phenyl]-furo[3,2-b]pyridin-2-yl}-benzoic acid (15.00 mg; 0.04 mmol; 1.00 eq.), N-methylmethanamine hydrochloride (5.72 mg; 0.07 mmol; 2.00 eq.), (3-Dimethylamino-propyl)-ethyl-carbodiimide hydrochloride (8.07 mg; 0.04 mmol; 1.20 eq.) (EDCI), Benzotriazol-1-ol (5.69 mg; 0.04 mmol; 1.20 eq.) (HOBt) and Ethyl-diisopropyl-amine (13.61 mg; 0.11 mmol; 3.00 eq.) in DMF (5.0 mL), (13.1 mg, 27% yield). MS: m/z=456 (M+H)+. H NMR (DMSO-d6): 8.51 (1H), 8.31 (2H), 8.08 (2H), 7.77 (1H), 7.66 (1H), 7.56 (2H), 7.08 (1H), 5.59-5.45 (1H), 3.82-4.04 (4H), 3.03 (3H), 2.98 (3H), 2.20-2.32 (2H).

Example 107: 4-{7-[3-Cyano-4-((R)-3-fluoro-pyrrolidin-1-yl)-phenyl]-furo[3,2-b]pyridin-2-yl}-N,N-dimethyl-benzamide (120)

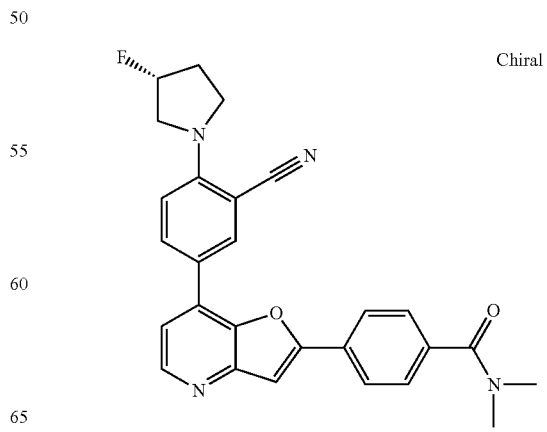

4-{7-[3-Cyano-4-((R)-3-fluoro-pyrrolidin-1-yl)-phenyl]-furo[3,2-b]pyridin-2-yl}-benzoic acid ethyl ester (191)

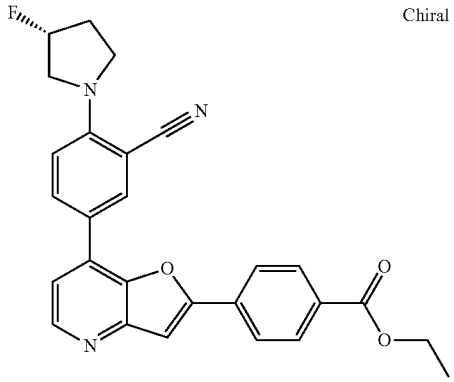 [SMILES: CCOC(=O)c1ccc(-c2cc3nccc(-c4ccc(N5CC[C@@H](F)C5)c(C#N)c4)c3o2)cc1]

The title compound was synthesized according to the procedure described in example 102 using 4-[7-(3-Cyano-4-fluoro-phenyl)-furo[3,2-b]pyridin-2-yl]-benzoic acid ethyl ester (60.94 mg; 0.16 mmol; 1.00 eq.), and (R)-3-Fluoro-pyrrolidine (42.17 mg; 0.47 mmol; 3.00 eq.) in DMSO (3 mL) (63 mg, 83% yield). MS: m/z=456 (M+H)⁺.

4-{7-[3-Cyano-4-((R)-3-fluoro-pyrrolidin-1-yl)-phenyl]-furo[3,2-b]pyridin-2-yl}-N,N-dimethyl-benzamide (120)

The title compound was synthesized according to the procedure described in example 102 using 4-{7-[3-Cyano-4-((R)-3-fluoro-pyrrolidin-1-yl)-phenyl]-furo[3,2-b]pyridin-2-yl}-benzoic acid (35.00 mg; 0.08 mmol; 1.00 eq.), N-methylmethanamine hydrochloride (13.35 mg; 0.16 mmol; 2.00 eq.), (3-Dimethylamino-propyl)-ethyl-carbodiimide hydrochloride (18.84 mg; 0.10 mmol; 1.20 eq.) (EDCI), Benzotriazol-1-ol (13.28 mg; 0.10 mmol; 1.20 eq.) (HOBt) and Ethyl-diisopropyl-amine (31.75 mg; 0.25 mmol; 3.00 eq.) in DMF (5.0 mL), (34.70 mg, 78% yield). MS: m/z=456 (M+H). H NMR (DMSO-d6): 8.51 (1H), 8.31 (2H), 8.08 (2H), 7.77 (1H), 7.66 (1H), 7.56 (2H), 7.08 (1H), 5.59-5.45 (1H), 3.82-4.04 (4H), 3.03 (3H), 2.98 (3H), 2.20-2.32 (2H).

Example 108: 4-(7-{3-Cyano-4-[3-(cyclopropyl-methyl-amino)-pyrrolidin-1-yl]-phenyl}-furo[3,2-b]pyridin-2-yl)-N,N-dimethyl-benzamide (179)

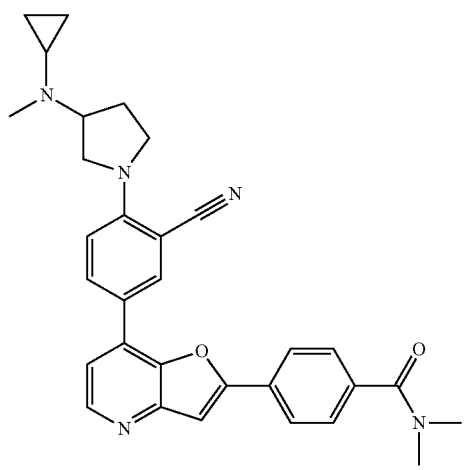

4-(7-{3-Cyano-4-[3-(cyclopropyl-methyl-amino)-pyrrolidin-1-yl]-phenyl}-furo[3,2-b]pyridin-2-yl)-benzoic acid ethyl ester (201)

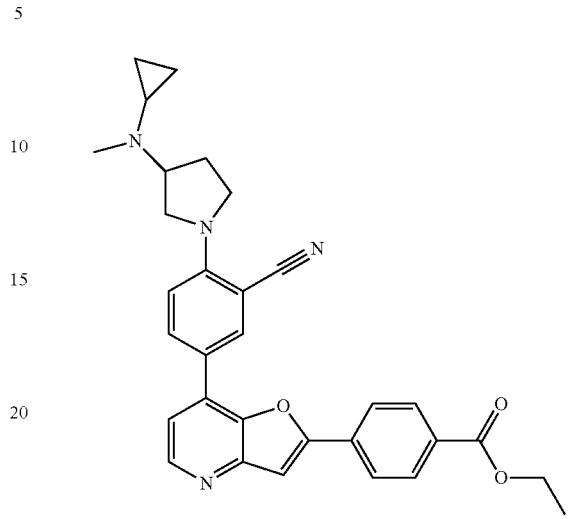

The title compound was synthesized according to the procedure described in example 102 using 4-[7-(3-Cyano-4-fluoro-phenyl)-furo[3,2-b]pyridin-2-yl]-benzoic acid ethyl ester (60.94 mg; 0.16 mmol; 1.00 eq.), and Cyclopropyl-methyl-pyrrolidin-3-yl-amine (44.24 mg; 0.32 mmol; 2.00 eq.) in DMSO (3 mL) (76 mg, 90% yield). MS: m/z=507 (M+H)⁺

4-(7-{3-Cyano-4-[3-(cyclopropyl-methyl-amino)-pyrrolidin-1-yl]-phenyl}-furo[3,2-b]pyridin-2-yl)-N,N-dimethyl-benzamide (179)

The title compound was synthesized according to the procedure described in example 102 using 4-(7-{3-Cyano-4-[3-(cyclopropyl-methyl-amino)-pyrrolidin-1-yl]-phenyl}-furo[3,2-b]pyridin-2-yl)-benzoic acid (40.00 mg; 0.08 mmol; 1.00 eq.), N-methylmethanamine hydrochloride (13.63 mg; 0.17 mmol; 2.00 eq.), (3-Dimethylamino-propyl)-ethyl-carbodiimide hydrochloride (19.23 mg; 0.10 mmol; 1.20 eq.) (EDCI), Benzotriazol-1-ol (13.55 mg; 0.10 mmol; 1.20 eq.) (HOBt) and Ethyl-diisopropyl-amine (32.41 mg; 0.25 mmol; 3.00 eq.) in DMF (5.0 mL) (11.1 mg, 24% yield). MS: m/z=406 (M+H)⁺. ¹H NMR (DMSO-d6): 8.53 (1H), 8.30 (2H), 8.08 (2H), 7.77 (1H), 7.66 (1H), 7.56 (2H), 7.08 (1H), 3.82-4.04 (4H), 3.03 (3H), 2.98 (3H), 2.26 (1H), 2.32 (2H), 1.7-1.90 (4H), 0.38-0.51 (4H).

Example 109: 4-{7-[3-Cyano-4-((S)-3-dimethyl-amino-pyrrolidin-1-yl)-phenyl]-furo[3,2-b]pyridin-2-yl}-N,N-dimethyl-benzamide (173)-EDC-HOBT Method

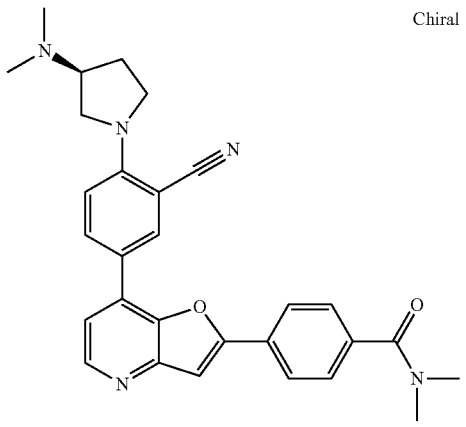

A mixture of 4-{7-[3-Cyano-4-((S)-3-dimethylamino-pyrrolidin-1-yl)-phenyl]-furo[3,2-b]pyridin-2-yl}-benzoic acid (30.00 mg; 0.07 mmol; 1.00 eq.), N-methylmethanamine hydrochloride (10.81 mg; 0.13 mmol; 2.00 eq.), (3-Dimethylamino-propyl)-ethyl-carbodiimide hydrochloride (15.25 mg; 0.08 mmol; 1.20 eq.) (EDCI), Benzotriazol-1-ol (10.75 mg; 0.08 mmol; 1.20 eq.) (HOBt) and Ethyl-diisopropyl-amine (25.71 mg; 0.20 mmol; 3.00 eq.) in DMF (5.0 mL) was stirred at room temperature overnight. The reaction mixture was purified on reverse phase HPLC to obtain the title compound. (21.1 mg, 50% yield). MS: m/z=456 (M+H). H NMR (DMSO-d6): 8.51 (1H), 8.31 (2H), 8.08 (2H), 7.77 (1H), 7.66 (1H), 7.56 (2H), 7.08 (1H), 5.59-5.45 (1H), 3.87-3.76 (3H), 3.48 (1H), 3.18 (1H), 2.22 (6H), 3.03 (3H), 2.98 (3H), 1.85 (1H), 1.67 (1H), 1.14 (1H).

Example 110: 4-{7-[3-Cyano-4-((R)-3-dimethyl-amino-pyrrolidin-1-yl)-phenyl]-furo[3,2-b]pyridin-2-yl}-N,N-dimethyl-benzamide (172)

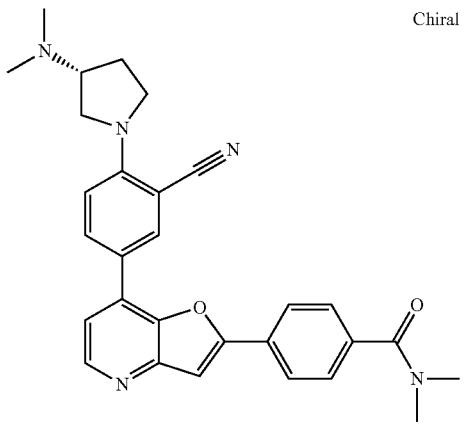

The title compound was synthesized according to the procedure described in example 109 using 4-{7-[3-Cyano-4-((R)-3-dimethylamino-pyrrolidin-1-yl)-phenyl]-furo[3,2-b]pyridin-2-yl}-benzoic acid (30.00 mg; 0.07 mmol; 1.00 eq.), N-methylmethanamine hydrochloride (10.81 mg; 0.13 mmol; 2.00 eq.), (3-Dimethylamino-propyl)-ethyl-carbodiimide hydrochloride (15.25 mg; 0.08 mmol; 1.20 eq.) (EDCI), Benzotriazol-1-ol (10.75 mg; 0.08 mmol; 1.20 eq.) (HOBt) and Ethyl-diisopropyl-amine (25.71 mg; 0.20 mmol; 3.00 eq.) in DMF (5.0 mL), (22.2 mg, 57% yield). MS: m/z=456 (M+H)$^+$. $^1$H NMR (DMSO-d6): 8.51 (1H), 8.31 (2H), 8.08 (2H), 7.77 (1H), 7.66 (1H), 7.56 (2H), 7.08 (1H), 5.59-5.45 (1H), 3.87-3.76 (3H), 3.48 (1H), 3.18 (1H), 2.22 (6H), 3.03 (3H), 2.98 (3H), 2.92 (1H), 1.85 (1H), 1.67 (1H), 1.14 (1H).

Example 111: N-(1-Aza-bicyclo[2.2.2]oct-3-yl)-4-{7-[3-cyano-4-((S)-3-fluoro-pyrrolidin-1-yl)-phenyl]-furo[3,2-b]pyridin-2-yl}-3-methoxy-benzamide (72)

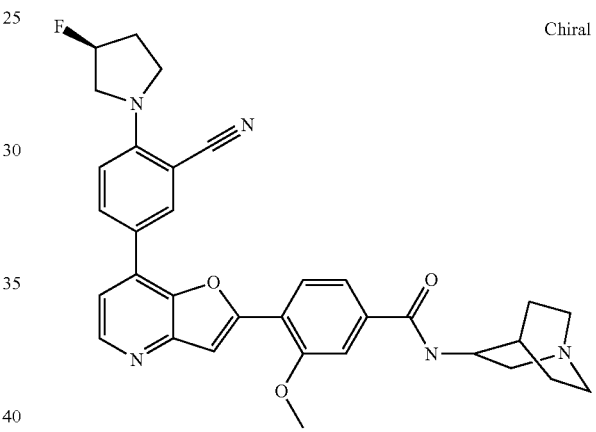

The title compound was synthesized according to the procedure described in example 109 using 4-{7-[3-Cyano-4-((S)-3-fluoro-pyrrolidin-1-yl)-phenyl]-furo[3,2-b]pyridin-2-yl}-3-methoxy-benzoic acid (30.00 mg; 0.07 mmol; 1.00 eq.), 1-Aza-bicyclo[2.2.2]oct-3-ylamine (16.55 mg; 0.13 mmol; 2.00 eq.), (3-Dimethylamino-propyl)-ethyl-carbodiimide hydrochloride (15.09 mg; 0.08 mmol; 1.20 eq.) (EDCI), Benzotriazol-1-ol (10.63 mg; 0.08 mmol; 1.20 eq.) (HOBt) and Ethyl-diisopropyl-amine (25.43 mg; 0.20 mmol; 3.00 eq.) in DMF (5.0 mL), (8.2 mg, 17% yield). MS: m/z=566 (M+H). H NMR (DMSO-d6): 8.51 (1H), 8.31 (2H), 8.08 (2H), 7.77 (1H), 7.66 (1H), 7.56 (2H), 7.08 (1H), 5.59-5.45 (1H), 3.87-3.76 (3H), 3.48 (1H), 3.18 (1H), 2.22 (6H), 3.03 (3H), 2.98 (3H), 2.92 (1H), 1.85 (1H), 1.67 (1H), 1.14 (1H).

Example 112: 2-((S)-3-Fluoro-pyrrolidin-1-yl)-5-{2-[2-methoxy-4-(4-methyl-piperazine-1-carbonyl)-phenyl]-furo[3,2-b]pyridin-7-yl}-benzonitrile (16)

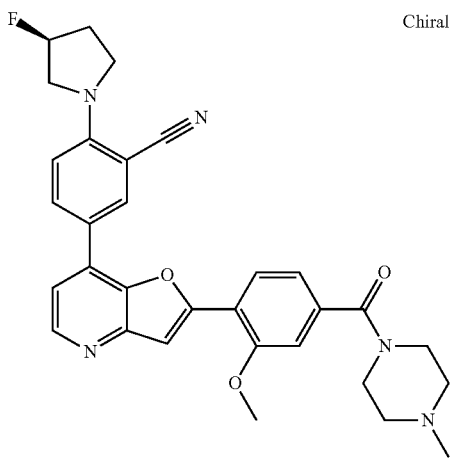 [SMILES: COc1cc(C(=O)N2CCN(C)CC2)ccc1-c1cc2nccc(-c3ccc(N4CC[C@H](F)C4)c(C#N)c3)c2o1]

The title compound was synthesized according to the procedure described in example 109 using 4-{7-[3-Cyano-4-((S)-3-fluoro-pyrrolidin-1-yl)-phenyl]-furo[3,2-b]pyridin-2-yl}-3-methoxy-benzoic acid (30.00 mg; 0.07 mmol; 1.00 eq.), 1-Methyl-piperazine (13.14 mg; 0.13 mmol; 2.00 eq.), (3-Dimethylamino-propyl)-ethyl-carbodiimide hydrochloride (15.09 mg; 0.08 mmol; 1.20 eq.) (EDCI), Benzotriazol-1-ol (10.63 mg; 0.08 mmol; 1.20 eq.) (HOBt) and Ethyl-diisopropyl-amine (25.43 mg; 0.20 mmol; 3.00 eq.) in DMF (5.0 mL), (9.1 mg, 17% yield). MS: m/z=540 (M+H). H NMR (DMSO-d6): 8.51 (1H), 8.31 (2H), 8.08 (2H), 7.77 (1H), 7.66 (1H), 7.56 (2H), 7.08 (1H), 5.59-5.45 (1H), 3.87-3.76 (3H), 3.48 (1H), 3.18 (1H), 2.22 (6H), 3.03 (3H), 2.98 (3H), 2.92 (1H), 1.85 (1H), 1.67 (1H), 1.14 (1H).

Example 113: 4-{7-[3-Cyano-4-((S)-3-fluoro-pyrrolidin-1-yl)-phenyl]-furo[3,2-b]pyridin-2-yl}-3-methoxy-N,N-dimethyl-benzamide (23)

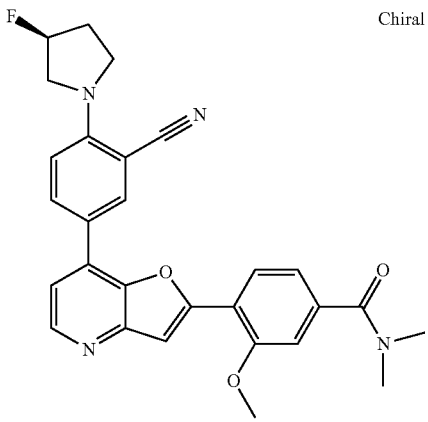 [SMILES: COc1cc(C(=O)N(C)C)ccc1-c1cc2nccc(-c3ccc(N4CC[C@H](F)C4)c(C#N)c3)c2o1]

The title compound was synthesized according to the procedure described in example 109 using 4-{7-[3-Cyano-4-((S)-3-fluoro-pyrrolidin-1-yl)-phenyl]-furo[3,2-b]pyridin-2-yl}-3-methoxy-benzoic acid (30.00 mg; 0.07 mmol; 1.00 eq.), N-methylmethanamine hydrochloride (10.70 mg; 0.13 mmol; 2.00 eq.), (3-Dimethylamino-propyl)-ethyl-carbodiimide hydrochloride (15.09 mg; 0.08 mmol; 1.20 eq.) (EDCI), Benzotriazol-1-ol (10.63 mg; 0.08 mmol; 1.20 eq.) (HOBt) and Ethyl-diisopropyl-amine (25.43 mg; 0.20 mmol; 3.00 eq.) in DMF (5.0 mL), (10.9 mg, 27% yield). MS: m/z=485 (M+H). 1H NMR (DMSO-d6): 8.51 (1H), 8.31 (2H), 8.01 (2H), 7.67 (1H), 7.60 (1H), 7.26 (1H), 7.17 (1H), 7.08 (1H), 5.59-5.45 (1H), 4.05 (3H), 3.82-4.04 (4H), 3.03 (3H), 2.98 (3H), 2.20-2.32 (2H).

Example 114: N-(1-Aza-bicyclo[2.2.2]oct-3-yl)-4-{7-[3-cyano-4-((R)-3-fluoro-pyrrolidin-1-yl)-phenyl]-furo[3,2-b]pyridin-2-yl}-3-methoxy-benzamide (146)

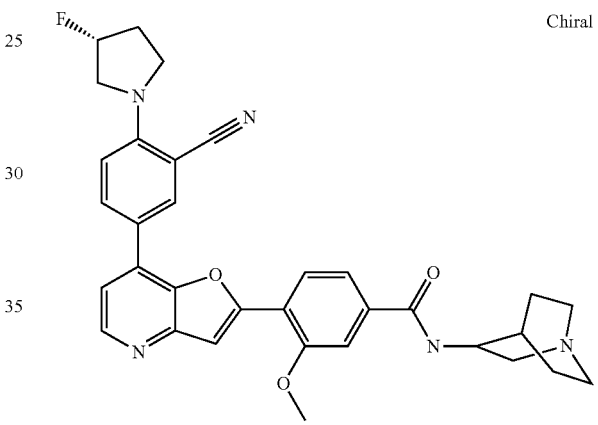

The title compound was synthesized according to the procedure described in example 109 using 4-{7-[3-Cyano-4-((R)-3-fluoro-pyrrolidin-1-yl)-phenyl]-furo[3,2-b]pyridin-2-yl}-3-methoxy-benzoic acid (30.00 mg; 0.07 mmol; 1.00 eq.), 1-Aza-bicyclo[2.2.2]oct-3-ylamine (16.55 mg; 0.13 mmol; 2.00 eq.), (3-Dimethylamino-propyl)-ethyl-carbodiimide hydrochloride (15.09 mg; 0.08 mmol; 1.20 eq.) (EDCI), Benzotriazol-1-ol (10.63 mg; 0.08 mmol; 1.20 eq.) (HOBt) and Ethyl-diisopropyl-amine (25.43 mg; 0.20 mmol; 3.00 eq.) in DMF (5.0 mL), (10.2 mg, 27% yield). MS: m/z=566 (M+H). H NMR (DMSO-d6): 8.51 (1H), 8.31 (2H), 8.08 (2H), 7.77 (1H), 7.66 (1H), 7.56 (2H), 7.08 (1H), 5.59-5.45 (1H), 3.87-3.76 (3H), 3.48 (1H), 3.18 (1H), 2.22 (6H), 3.03 (3H), 2.98 (3H), 2.92 (1H), 1.85 (1H), 1.67 (1H), 1.14 (1H).

Example 115: N-(1-Aza-bicyclo[2.2.2]oct-3-yl)-4-{7-[3-cyano-4-(3-fluoro-pyrrolidin-1-yl)-phenyl]-furo[3,2-b]pyridin-2-yl}-3-methoxy-benzamide (87)

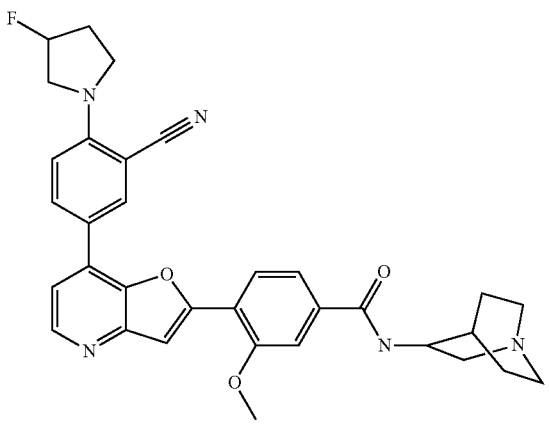 [SMILES: COc1cc(C(=O)NC2CN3CCC2CC3)ccc1-c1cc2nccc(-c3ccc(N4CCC(F)C4)c(C#N)c3)c2o1]

The title compound was synthesized according to the procedure described in example 109 using 4-{7-[3-Cyano-4-(3-fluoro-pyrrolidin-1-yl)-phenyl]-furo[3,2-b]pyridin-2-yl}-3-methoxy-benzoic acid (30.00 mg; 0.07 mmol; 1.00 eq.), 1-Aza-bicyclo[2.2.2]oct-3-ylamine (16.55 mg; 0.13 mmol; 2.00 eq.), (3-Dimethylamino-propyl)-ethyl-carbodiimide hydrochloride (15.09 mg; 0.08 mmol; 1.20 eq.) (EDCI), Benzotriazol-1-ol (10.63 mg; 0.08 mmol; 1.20 eq.) (HOBt) and Ethyl-diisopropyl-amine (25.43 mg; 0.20 mmol; 3.00 eq.) in DMF (5.0 mL), (14.9 mg, 43% yield). MS: m/z=566 (M+H). H NMR (DMSO-d6): 8.51 (1H), 8.31 (2H), 8.08 (2H), 7.77 (1H), 7.66 (1H), 7.56 (2H), 7.08 (1H), 5.59-5.45 (1H), 3.87-3.76 (3H), 3.48 (1H), 3.18 (1H), 2.22 (6H), 3.03 (3H), 2.98 (3H), 2.92 (1H), 1.85 (1H), 1.67 (1H), 1.14 (1H).

Example 116: 4-{7-[3-Cyano-4-((R)-3-fluoro-pyrrolidin-1-yl)-phenyl]-furo[3,2-b]pyridin-2-yl}-3-methoxy-N,N-dimethyl-benzamide (57)

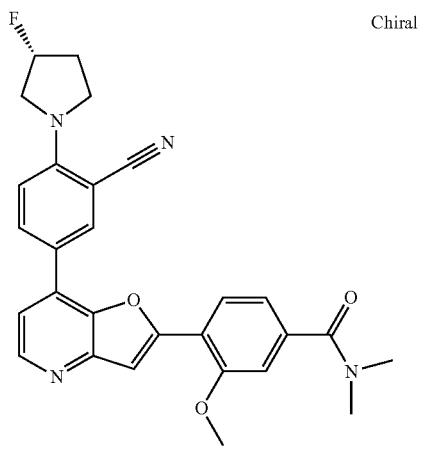 [SMILES: COc1cc(C(=O)N(C)C)ccc1-c1cc2nccc(-c3ccc(N4CC[C@@H](F)C4)c(C#N)c3)c2o1]

Chiral

The title compound was synthesized according to the procedure described in example 109 using 4-{7-[3-Cyano-4-((R)-3-fluoro-pyrrolidin-1-yl)-phenyl]-furo[3,2-b]pyridin-2-yl}-3-methoxy-benzoic acid (30.00 mg; 0.07 mmol; 1.00 eq.), N-methylmethanamine hydrochloride (10.70 mg; 0.13 mmol; 2.00 eq.), (3-Dimethylamino-propyl)-ethyl-carbodiimide hydrochloride (15.09 mg; 0.08 mmol; 1.20 eq.) (EDCI), Benzotriazol-1-ol (10.63 mg; 0.08 mmol; 1.20 eq.) (HOBt) and Ethyl-diisopropyl-amine (25.43 mg; 0.20 mmol; 3.00 eq.) in DMF (5.0 mL) (4.1 mg, 17% yield). MS: m/z=485 (M+H). H NMR (DMSO-d6): 8.51 (1H), 8.31 (2H), 8.01 (2H), 7.67 (1H), 7.60 (1H), 7.26 (1H), 7.17 (1H), 7.08 (1H), 5.59-5.45 (1H), 4.05 (3H), 3.82-4.04 (4H), 3.03 (3H), 2.98 (3H), 2.20-2.32 (2H).

Example 117: 4-{7-[3-Cyano-4-((3-fluoro-pyrrolidin-1-yl)-phenyl]-furo[3,2-b]pyridin-2-yl}-3-methoxy-N,N-dimethyl-benzamide (35)

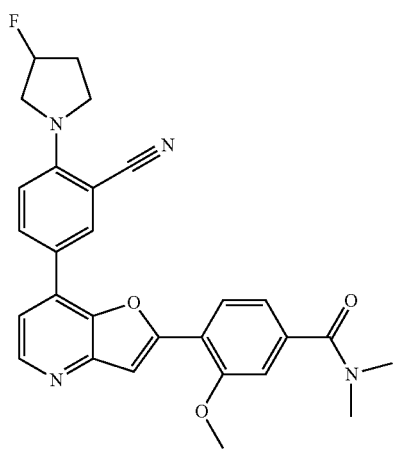 [SMILES: COc1cc(C(=O)N(C)C)ccc1-c1cc2nccc(-c3ccc(N4CCC(F)C4)c(C#N)c3)c2o1]

The title compound was synthesized according to the procedure described in example 109 using 4-{7-[3-Cyano-4-(3-fluoro-pyrrolidin-1-yl)-phenyl]-furo[3,2-b]pyridin-2-yl}-3-methoxy-benzoic acid (30.00 mg; 0.07 mmol; 1.00 eq.), N-methylmethanamine hydrochloride (10.70 mg; 0.13 mmol; 2.00 eq.), (3-Dimethylamino-propyl)-ethyl-carbodiimide hydrochloride (15.09 mg; 0.08 mmol; 1.20 eq.) (EDCI), Benzotriazol-1-ol (10.63 mg; 0.08 mmol; 1.20 eq.) (HOBt) and Ethyl-diisopropyl-amine (25.43 mg; 0.20 mmol; 3.00 eq.) in DMF (5.0 mL) (8.30 mg, 35% yield). MS: m/z=485 (M+H). H NMR (DMSO-d6): 8.51 (1H), 8.31 (2H), 8.01 (2H), 7.67 (1H), 7.60 (1H), 7.26 (1H), 7.17 (1H), 7.08 (1H), 5.59-5.45 (1H), 4.05 (3H), 3.82-4.04 (4H), 3.03 (3H), 2.98 (3H), 2.20-2.32 (2H).

Example 118: 2-((S)-3-Fluoro-pyrrolidin-1-yl)-5-{2-[4-(3-hydroxymethyl-pyrrolidine-1-carbonyl)-2-methoxy-phenyl]-furo[3,2-b]pyridin-7-yl}-benzonitrile (76)

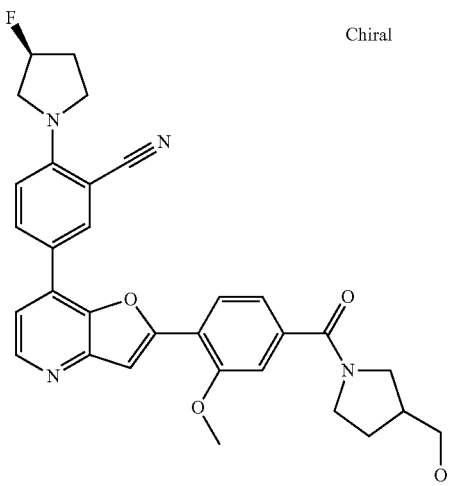 [SMILES: COc1cc(C(=O)N2CCC(CO)C2)ccc1-c1cc2nccc(-c3ccc(N4CC[C@H](F)C4)c(C#N)c3)c2o1]

The title compound was synthesized according to the procedure described in example 109 using 4-{7-[3-Cyano-4-((S)-3-fluoro-pyrrolidin-1-yl)-phenyl]-furo[3,2-b]pyridin-2-yl}-3-methoxy-benzoic acid (30.00 mg; 0.07 mmol; 1.00 eq.), Pyrrolidin-3-yl-methanol (19.90 mg; 0.20 mmol; 3.00 eq.), (3-Dimethylamino-propyl)-ethyl-carbodiimide hydrochloride (15.09 mg; 0.08 mmol; 1.20 eq.) (EDCI), Benzotriazol-1-ol (10.63 mg; 0.08 mmol; 1.20 eq.) (HOBt) and Ethyl-diisopropyl-amine (25.43 mg; 0.20 mmol; 3.00 eq.) in DMF (5.0 mL), (5.6 mg, 16% yield). MS: m/z=541 (M+H).

Example 119: 5-{2-[4-((S)-3-Dimethylamino-pyrrolidine-1-carbonyl)-2-methoxy-phenyl]-furo[3,2-b]pyridin-7-yl}-2-((S)-3-fluoro-pyrrolidin-1-yl)-benzonitrile (47)

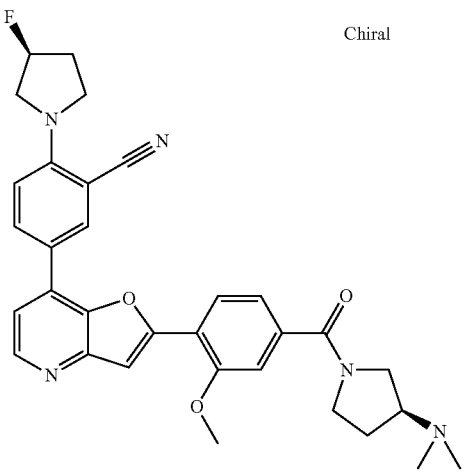 [SMILES: COc1cc(C(=O)N2CC[C@H](N(C)C)C2)ccc1-c1cc2nccc(-c3ccc(N4CC[C@H](F)C4)c(C#N)c3)c2o1]

The title compound was synthesized according to the procedure described in example 109 using 4-{7-[3-Cyano-4-((S)-3-fluoro-pyrrolidin-1-yl)-phenyl]-furo[3,2-b]pyridin-2-yl}-3-methoxy-benzoic acid (30.00 mg; 0.07 mmol; 1.00 eq.), Dimethyl-(S)-pyrrolidin-3-yl-amine (22.47 mg; 0.20 mmol; 3.00 eq.), (3-Dimethylamino-propyl)-ethyl-carbodiimide hydrochloride (15.09 mg; 0.08 mmol; 1.20 eq.) (EDCI), Benzotriazol-1-ol (10.63 mg; 0.08 mmol; 1.20 eq.) (HOBt) and Ethyl-diisopropyl-amine (25.43 mg; 0.20 mmol; 3.00 eq.) in DMF (5.0 mL), (6.6 mg, 18% yield). MS: m/z=554 (M+H).

Example 120: 5-{2-[4-((R)-3-Dimethylamino-pyrrolidine-1-carbonyl)-2-methoxy-phenyl]-furo[3,2-b]pyridin-7-yl}-2-((S)-3-fluoro-pyrrolidin-1-yl)-benzonitrile (33)

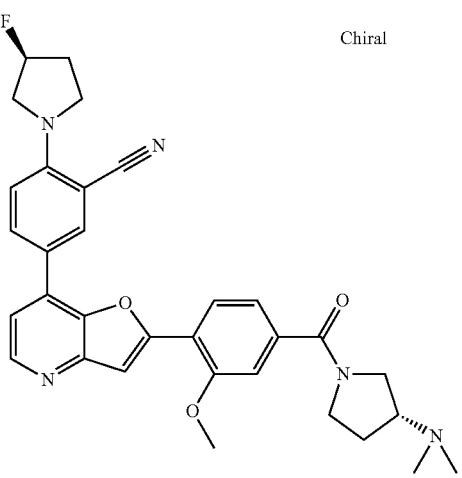 [SMILES: COc1cc(C(=O)N2CC[C@@H](N(C)C)C2)ccc1-c1cc2nccc(-c3ccc(N4CC[C@H](F)C4)c(C#N)c3)c2o1]

The title compound was synthesized according to the procedure described in example 109 using 4-{7-[3-Cyano-4-((S)-3-fluoro-pyrrolidin-1-yl)-phenyl]-furo[3,2-b]pyridin-2-yl}-3-methoxy-benzoic acid (30.00 mg; 0.07 mmol; 1.00 eq.), Dimethyl-(R)-pyrrolidin-3-yl-amine (22.47 mg; 0.20 mmol; 3.00 eq.), (3-Dimethylamino-propyl)-ethyl-carbodiimide hydrochloride (15.09 mg; 0.08 mmol; 1.20 eq.) (EDCI), Benzotriazol-1-ol (10.63 mg; 0.08 mmol; 1.20 eq.) (HOBt) and Ethyl-diisopropyl-amine (25.43 mg; 0.20 mmol; 3.00 eq.) in DMF (5.0 mL), (4.4 mg, 12% yield). MS: m/z=554 (M+H).

Example 121: 5-{2-[2-Methoxy-4-(1-oxo-2,8-diaza-spiro[4.5]decane-8-carbonyl)-phenyl]-furo[3,2-b]pyridin-7-yl}-2-(tetrahydro-pyran-4-ylamino)-benzonitrile (52)

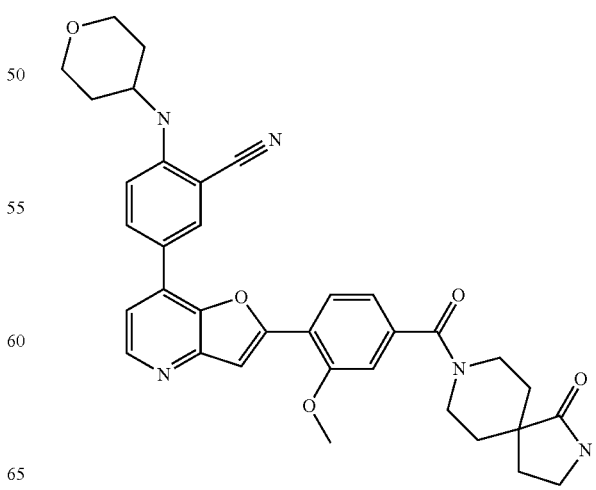

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 2,8-Diaza-spiro[4.5]decan-1-one hydrochloride (48.73 mg; 0.26 mmol; 3.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL), (22.9 mg, 44% yield). MS: m/z=606 (M+H). H NMR (DMSO-d6): 8.51 (1H), 8.31 (2H), 8.08 (2H), 7.60 (2H), 7.26 (1H), 7.18 (1H), 6.25 (1H), 4.29 (1H), 4.08 (3H), 3.94 (2H), 3.80 (1H), 3.65 (1H), 3.48 (2H), 3.18 (3H), 2.02 (2H) 1.95 (2H), 1.65 (3H).

Example 122: 5-{2-[2-Methoxy-4-(4-oxo-1,3,8-triaza-spiro[4.5]decane-8-carbonyl)-phenyl]-furo[3,2-b]pyridin-7-yl}-2-(tetrahydro-pyran-4-ylamino)-benzonitrile (34)

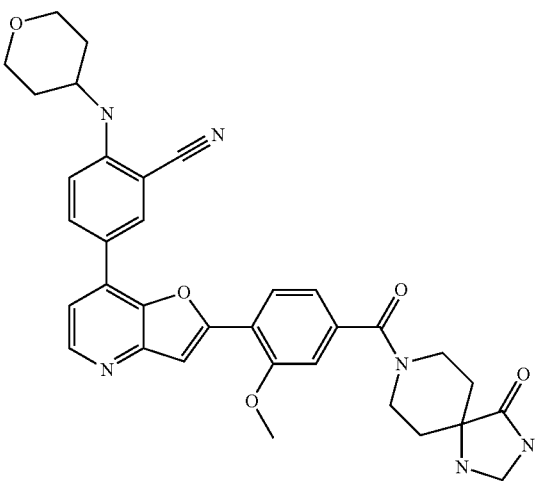 [SMILES: COc1cc(C(=O)N2CCC3(CC2)NCNC3=O)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 1,3,8-Triaza-spiro[4.5]decan-4-one hydrochloride (48.99 mg; 0.26 mmol; 3.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (13.5 mg, 26% yield). MS: m/z=607 (M+H). H NMR (DMSO-d6): 8.51 (1H), 8.31 (2H), 8.08 (2H), 7.60 (2H), 7.26 (1H), 7.18 (1H), 6.25 (1H), 4.39 (1H), 4.08 (3H), 3.94 (2H), 3.84 (1H), 3.48 (2H), 3.18 (1H), 1.90 (2H), 1.67 (3H).

Example 123: 2-((S)-3-Fluoro-pyrrolidin-1-yl)-5-{2-[4-(4-hydroxymethyl-piperidine-1-carbonyl)-2-methoxy-phenyl]-furo[3,2-b]pyridin-7-yl}-benzonitrile (70)

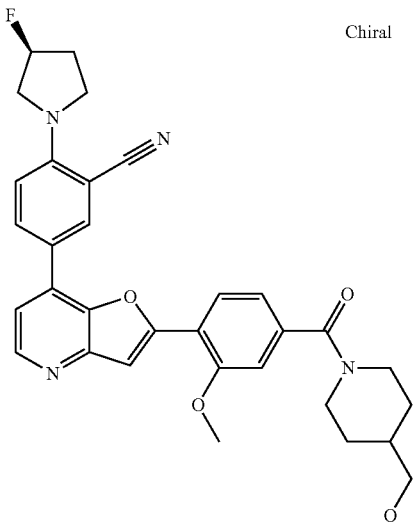 [SMILES: COc1cc(C(=O)N2CCC(CO)CC2)ccc1-c1cc2nccc(-c3ccc(N4CC[C@H](F)C4)c(C#N)c3)c2o1]

The title compound was synthesized according to the procedure described in example 109 using 4-{7-[3-Cyano-4-((S)-3-fluoro-pyrrolidin-1-yl)-phenyl]-furo[3,2-b]pyridin-2-yl}-3-methoxy-benzoic acid (30.00 mg; 0.07 mmol; 1.00 eq.), Piperidin-4-yl-methanol (22.66 mg; 0.20 mmol; 3.00 eq.), (3-Dimethylamino-propyl)-ethyl-carbodiimide hydrochloride (15.09 mg; 0.08 mmol; 1.20 eq.) (EDCI), Benzotriazol-1-ol (10.63 mg; 0.08 mmol; 1.20 eq.) (HOBt) and Ethyl-diisopropyl-amine (25.43 mg; 0.20 mmol; 3.00 eq.) in DMF (5.0 mL), (9.4 mg, 27% yield). MS: m/z=555 (M+H).

Example 124: 4-{7-[5-Cyano-6-(tetrahydro-pyran-4-yloxy)-pyridin-3-yl]-furo[3,2-b]pyridin-2-yl}-3-methoxy-N,N-dimethyl-benzamide (109)

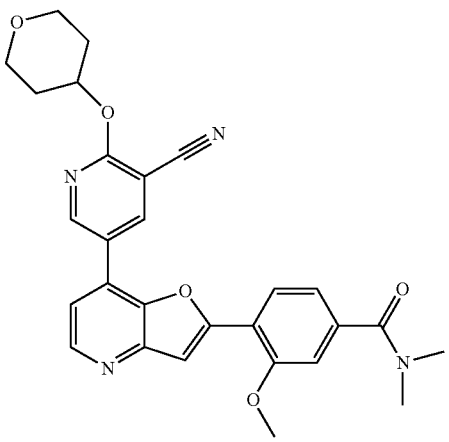 [SMILES: COc1cc(C(=O)N(C)C)ccc1-c1cc2nccc(-c3cnc(OC4CCOCC4)c(C#N)c3)c2o1]

The title compound was synthesized according to the procedure described in example 109 using 4-{7-[5-Cyano-6-(tetrahydro-pyran-4-yloxy)-pyridin-3-yl]-furo[3,2-b]pyridin-2-yl}-3-methoxy-benzoic acid (40.00 mg; 0.08 mmol; 1.00 eq.), N-methylmethanamine hydrochloride (13.84 mg; 0.17 mmol; 2.00 eq.), (3-Dimethylamino-propyl)-ethyl-carbodiimide hydrochloride (19.52 mg; 0.10 mmol; 1.20 eq.) (EDCI), Benzotriazol-1-ol (13.76 mg; 0.10 mmol; 1.20 eq.) (HOBt) and Ethyl-diisopropyl-amine (32.90 mg; 0.25 mmol; 3.00 eq.) in DMF (5.0 mL) (10.6 mg, 25% yield).

MS: m/z=499 (M+H). H NMR (DMSO-d6): 9.25 (1H), 8.99 (1H), 8.61 (1H), 8.08 (1H), 7.72 (1H), 7.65 (1H), 7.25 (1H), 7.19 (1H), 5.50 (1H), 4.09 (1H), 4.05 (3H), 3.94 (2H), 3.60 (2H), 3.08 (2H), 2.97 (3H), 1.81 (2H), 1.55 (1H), 1.03 (1H).

Example 125: 5-{2-[4-(3-Hydroxy-azetidine-1-carbonyl)-2-methoxy-phenyl]-furo[3,2-b]pyridin-7-yl}-2-(tetrahydro-pyran-4-ylamino)-benzonitrile (101)

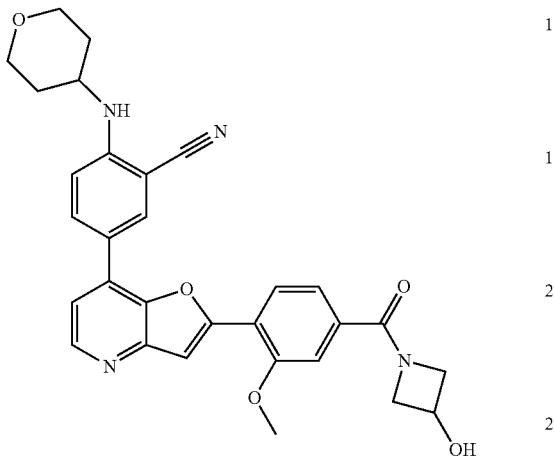

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), azetidin-3-ol hydrochloride (37.34 mg; 0.34 mmol; 4.00 eq.), (3-dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (19.9 mg, 45% yield). MS: m/z=525 (M+H). H NMR (DMSO-d6): 8.55 (1H), 8.30 (2H), 8.05 (1H), 7.66 (2H), 7.43 (2H), 7.20 (1H), 6.25 (1H), 5.77 (1H), 4.54 (2H), 4.29 (1H), 4.07 (1H), 4.05 (3H), 3.92 (2H), 3.80 (2H), 3.37 (2H), 1.89 (1H), 1.70 (1H).

Example 126: 5-{2-[4-(3-Hydroxy-pyrrolidine-1-carbonyl)-2-methoxy-phenyl]-furo[3,2-b]pyridin-7-yl}-2-(tetrahydro-pyran-4-ylamino)-benzonitrile (104)

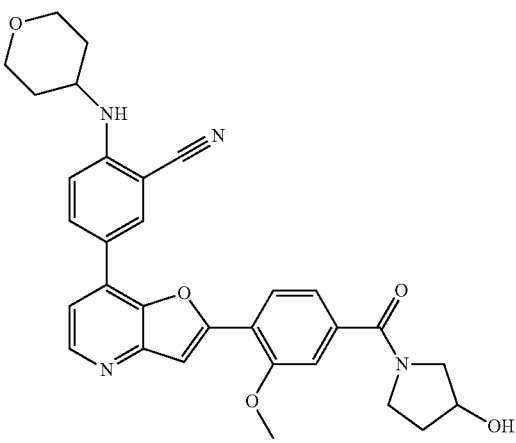 [SMILES: COc1cc(C(=O)N2CCC(O)C2)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), Pyrrolidin-3-ol (29.69 mg; 0.34 mmol; 4.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (38.8 mg, 85% yield). MS: m/z=553 (M+H). H NMR (DMSO-d6): 8.55 (1H), 8.30 (2H), 8.05 (1H), 7.66 (2H), 7.43 (2H), 7.20 (1H), 6.27 (1H), 5.07-4.97 (1H), 4.34-4.28 (2H), 4.08 (3H), 3.92 (2H), 3.81 (2H), 3.61 (2H), 3.47 (2H), 1.89 (4H), 1.67 (2H).

Example 127: 5-{2-[4-(3-Hydroxymethyl-pyrrolidine-1-carbonyl)-2-methoxy-phenyl]-furo[3,2-b]pyridin-7-yl}-2-(tetrahydro-pyran-4-ylamino)-benzonitrile (91)

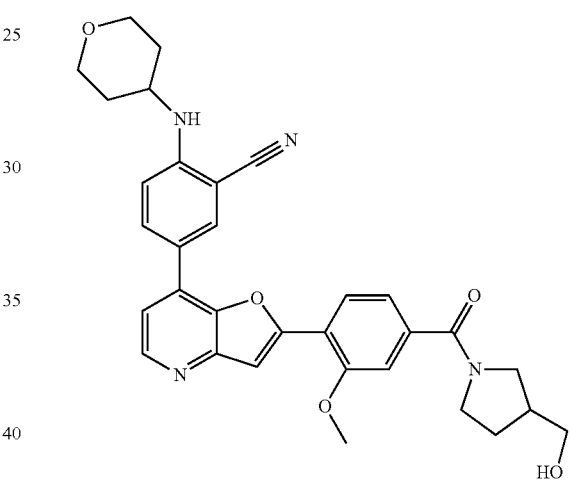

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), Pyrrolidin-3-yl-methanol (25.85 mg; 0.26 mmol; 3.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (22 mg, 47% yield). MS: m/z=553 (M+H). H NMR (DMSO-d6): 8.55 (1H), 8.30 (2H), 8.05 (1H), 7.66 (2H), 7.43 (2H), 7.20 (1H), 6.27 (1H), 5.07-4.97 (1H), 4.34-4.28 (2H), 4.08 (3H), 3.92 (2H), 3.81 (2H), 3.61 (2H), 3.47 (2H), 1.89 (4H), 1.67 (4H), 1.13 (1H).

Example 128: 4-{7-[3-Cyano-4-(tetrahydro-pyran-4-ylamino)-phenyl]-furo[3,2-b]pyridin-2-yl}-N-(2,3-dihydroxy-propyl)-3-methoxy-benzamide (111)

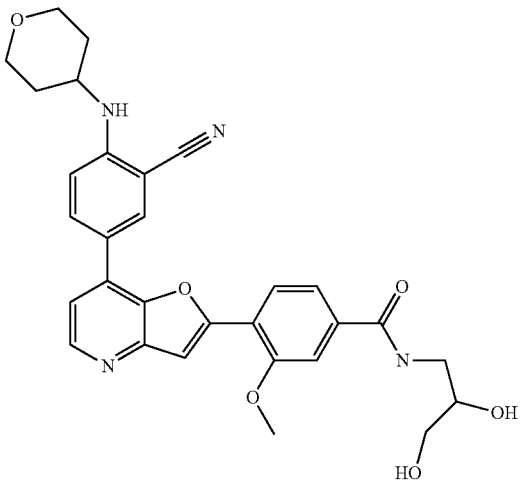 [SMILES: COc1cc(C(=O)NCC(O)CO)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 3-Amino-propane-1,2-diol (23.29 mg; 0.26 mmol; 3.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (9.7 mg, 21% yield). MS: m/z=543 (M+H). H NMR (DMSO-d6): 8.55 (1H), 8.30 (2H), 8.05 (1H), 7.66 (2H), 7.43 (2H), 7.20 (1H), 6.27 (1H), 5.07-4.97 (1H), 4.34-4.28 (2H), 4.08 (3H), 3.92 (2H), 3.81 (2H), 3.61 (2H), 3.47 (2H), 1.89 (4H), 1.67 (2H).

Example 129: 4-{7-[3-Cyano-4-(tetrahydro-pyran-4-ylamino)-phenyl]-furo[3,2-b]pyridin-2-yl}-3-methoxy-N-(tetrahydro-furan-3-yl)-benzamide (117)

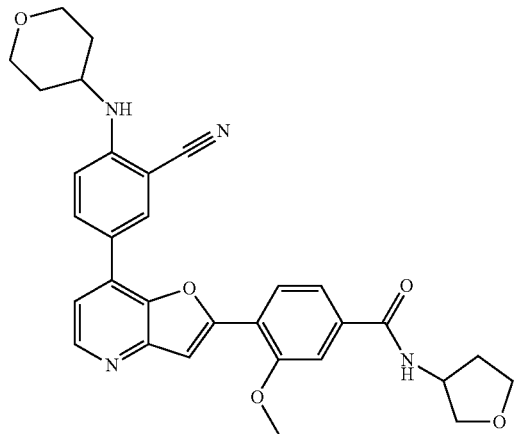 [SMILES: COc1cc(C(=O)NC2CCOC2)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), Tetrahydro-furan-3-ylamine (22.27 mg; 0.26 mmol; 3.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (25 mg, 55% yield). MS: m/z=539 (M+H). H NMR (DMSO-d6): 8.55 (1H), 8.30 (2H), 8.05 (1H), 7.66 (2H), 7.43 (2H), 7.18 (1H), 6.31 (1H), 4.51 (1H), 4.08 (3H), 3.89 (3H), 3.75 (2H), 3.67 (1H), 3.47 (2H), 2.19 (1H), 1.96 (1H), 1.90 (2H), 1.99 (2H).

Example 130: 5-{2-[2-Methoxy-4-(5-methyl-hexahydro-pyrrolo[3,4-c]pyrrole-2-carbonyl)-phenyl]-furo[3,2-b]pyridin-7-yl}-2-(tetrahydro-pyran-4-ylamino)-benzonitrile (73)

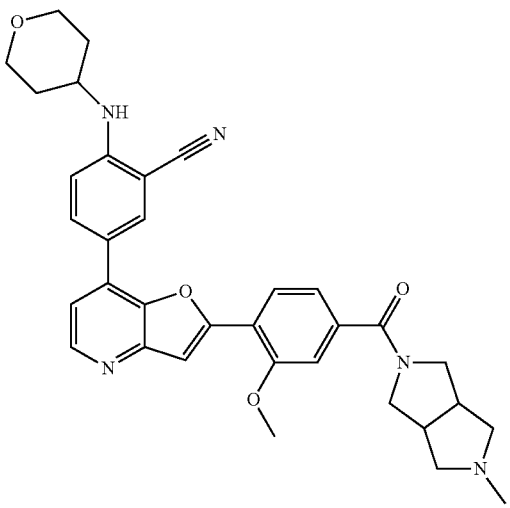 [SMILES: COc1cc(C(=O)N2CC3CN(C)CC3C2)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 2-Methyl-octahydro-pyrrolo[3,4-c]pyrrole (32.26 mg; 0.26 mmol; 3.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (20.4 mg, 41% yield). MS: m/z=578 (M+H). H NMR (DMSO-d6): 8.55 (1H), 8.30 (2H), 8.05 (1H), 7.66 (2H), 7.30 (1H), 7.24 (1H), 7.18 (1H), 6.28 (1H), 4.08 (3H), 3.89 (2H), 3.80 (2H), 3.71 (1H), 3.47 (4H), 2.79 (2H), 2.39 (2H), 2.23 (3H), 1.88 (2H), 1.65 (2H).

Example 131: 4-{7-[3-Cyano-4-(tetrahydro-pyran-4-ylamino)-phenyl]-furo[3,2-b]pyridin-2-yl}-N-(3-hydroxy-cyclobutyl)-3-methoxy-benzamide (122)

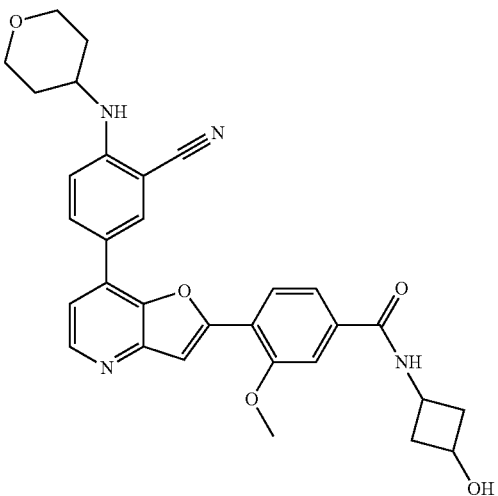 [SMILES: COc1cc(C(=O)NC2CC(O)C2)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 3-Amino-cyclobutanol (22.27 mg; 0.26 mmol; 3.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (34.6 mg, 76% yield). MS: m/z=539 (M+H). H NMR (DMSO-d6): 8.51 (1H), 8.25 (2H), 8.05 (1H), 7.64 (2H), 7.43 (2H), 7.20 (1H), 6.27 (1H), 5.15 (1H), 4.48-4.37 (1H), 4.11 (3H), 3.92 (3H), 3.81 (1H), 3.47 (2H), 2.66 (2H), 2.32 (1H), 2.22 (1H), 1.94-1.89 (3H), 1.65 (2H).

Example 132: N-(1-Aza-bicyclo[2.2.2]oct-3-yl)-4-{7-[3-cyano-4-(3-oxa-bicyclo[3.1.0]hex-6-ylamino)-phenyl]-furo[3,2-b]pyridin-2-yl}-3-methoxy-benzamide (119)

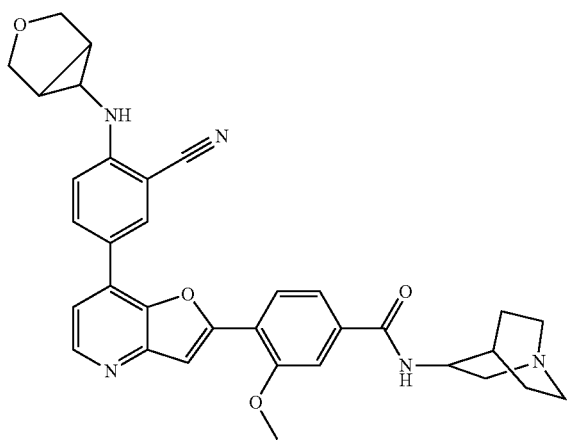 [SMILES: COc1cc(C(=O)NC2CN3CCC2CC3)ccc1-c1cc2nccc(-c3ccc(NC4C5COCC54)c(C#N)c3)c2o1]

The title compound was synthesized according to the procedure described in example 109 using 4-{7-[3-Cyano-4-(3-oxa-bicyclo[3.1.0]hex-6-ylamino)-phenyl]-furo[3,2-b]pyridin-2-yl}-3-methoxy-benzoic acid (40.00 mg; 0.09 mmol; 1.00 eq.), 1-Aza-bicyclo[2.2.2]oct-3-ylamine (21.60 mg; 0.17 mmol; 2.00 eq.), (3-Dimethylamino-propyl)-ethyl-carbodiimide hydrochloride (19.68 mg; 0.10 mmol; 1.20 eq.) (EDCI), Benzotriazol-1-ol (13.87 mg; 0.10 mmol; 1.20 eq.) (HOBt) and Ethyl-diisopropyl-amine (33.18 mg; 0.26 mmol; 3.00 eq.) in DMF (5.0 mL) (31.3 mg, 64% yield). MS: m/z=576 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 4.11 (3H), 4.03 (3H), 3.72 (2H), 3.17 (2H), 2.96 (2H), 2.72 (4H), 2.32 (1H), 2.02 (2H), 1.94 (1H), 1.89 (1H), 1.61 (2H), 1.32 (2H).

Example 133: 4-{7-[3-Cyano-4-(tetrahydro-pyran-4-yloxy)-phenyl]-furo[3,2-b]pyridin-2-yl}-3-methoxy-N-(3-oxa-bicyclo[3.1.0]hex-6-yl)-benzamide (65)

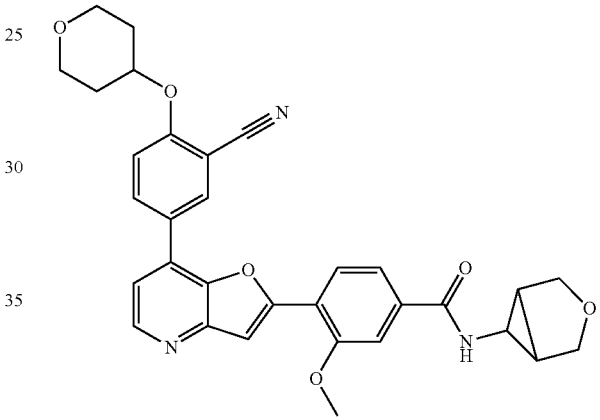

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (40.00 mg; 0.09 mmol; 1.00 eq.), 3-Oxa-bicyclo[3.1.0]hex-6-ylamine hydrochloride (34.58 mg; 0.26 mmol; 3.00 eq.), (3-Dimethylamino-propyl)-ethyl-carbodiimide hydrochloride (19.56 mg; 0.10 mmol; 1.20 eq.) (EDCI), Benzotriazol-1-ol (13.79 mg; 0.10 mmol; 1.20 eq.) (HOBt) and Ethyl-diisopropyl-amine (32.97 mg; 0.26 mmol; 3.00 eq.) in DMF (5.0 mL) (25.9 mg, 55% yield). MS: m/z=552 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 4.97 (1H), 4.11 (3H), 4.03 (3H), 3.91 (3H), 3.66 (2H), 3.61 (2H), 2.65 (1H), 2.08 (2H), 1.94 (1H), 1.73 (2H).

Example 134: 5-{2-[2-Methoxy-4-(1-oxa-7-aza-spiro[3.5]nonane-7-carbonyl)-phenyl]-furo[3,2-b]pyridin-7-yl}-2-(tetrahydro-pyran-4-yloxy)-benzonitrile (3)

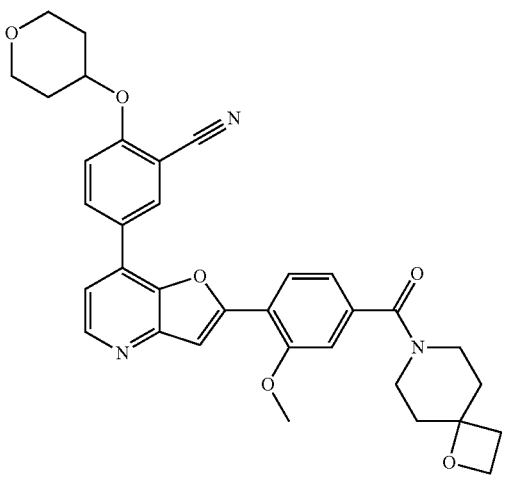 [SMILES: COc1cc(C(=O)N2CCC3(CCO3)CC2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (40.00 mg; 0.09 mmol; 1.00 eq.), 2-Oxa-7-aza-spiro[3.5]nonane (32.44 mg; 0.26 mmol; 3.00 eq.), (3-Dimethylamino-propyl)-ethyl-carbodiimide hydrochloride (19.56 mg; 0.10 mmol; 1.20 eq.) (EDCI), Benzotriazol-1-ol (13.79 mg; 0.10 mmol; 1.20 eq.) (HOBt) and Ethyl-diisopropyl-amine (32.97 mg; 0.26 mmol; 3.00 eq.) in DMF (5.0 mL) (14.2 mg, 29% yield). MS: m/z=580 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 4.97 (1H), 4.43 (2H), 4.03 (3H), 3.91 (2H), 3.57 (2H), 3.01 (1H), 2.48 (2H), 2.09 (2H), 1.94 (4H), 1.73 (2H).

Example 135: 4-{7-[3-Cyano-4-(tetrahydro-pyran-4-yloxy)-phenyl]-furo[3,2-b]pyridin-2-yl}-N-(3-hydroxymethyl-oxetan-3-yl)-3-methoxy-benzamide (51)

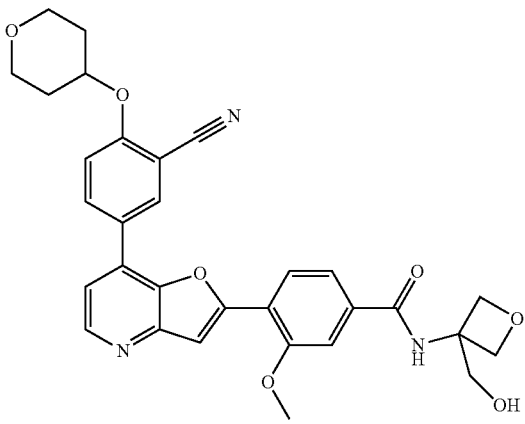 [SMILES: COc1cc(C(=O)NC2(CO)COC2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (40.00 mg; 0.09 mmol; 1.00 eq.), (3-Amino-oxetan-3-yl)-methanol (26.30 mg; 0.26 mmol; 3.00 eq.), (3-Dimethylamino-propyl)-ethyl-carbodiimide hydrochloride (19.56 mg; 0.10 mmol; 1.20 eq.) (EDCI), Benzotriazol-1-ol (13.79 mg; 0.10 mmol; 1.20 eq.) (HOBt) and Ethyl-diisopropyl-amine (32.97 mg; 0.26 mmol; 3.00 eq.) in DMF (5.0 mL) (17.5 mg, 37% yield). MS: m/z=556 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 5.19 (1H), 4.98 (1H), 4.66 (2H), 4.58 (2H), 4.13 (3H), 3.91 (2H), 3.81 (2H), 3.59 (2H), 2.15 (2H), 1.74 (2H).

Example 136: 4-{7-[3-Cyano-4-(tetrahydro-pyran-4-yloxy)-phenyl]-furo[3,2-b]pyridin-2-yl}-3-methoxy-N-(3-methyl-oxetan-3-ylmethyl)-benzamide (59)

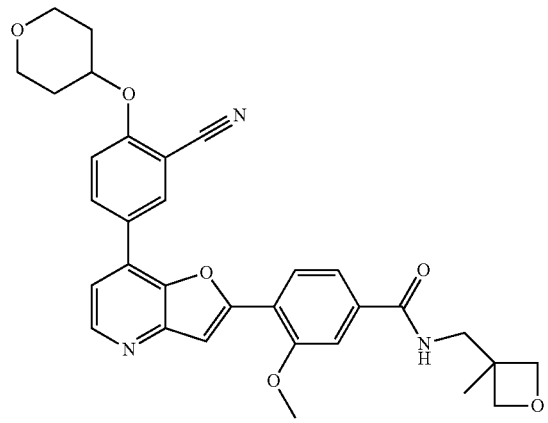 [SMILES: COc1cc(C(=O)NCC2(C)COC2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (40.00 mg; 0.09 mmol; 1.00 eq.), C-(3-Methyl-oxetan-3-yl)-methylamine (25.80 mg; 0.26 mmol; 3.00 eq.), (3-Dimethylamino-propyl)-ethyl-carbodiimide hydrochloride (19.56 mg; 0.10 mmol; 1.20 eq.) (EDCI), Benzotriazol-1-ol (13.79 mg; 0.10 mmol; 1.20 eq.) (HOBt) and Ethyl-diisopropyl-amine (32.97 mg; 0.26 mmol; 3.00 eq.) in DMF (5.0 mL) (25.7 mg, 55% yield). MS: m/z=554 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 4.98 (1H), 4.52 (2H), 4.24 (2H), 4.13 (3H), 3.91 (2H), 3.59 (2H), 3.52 (2H), 3.02 (2H), 1.72 (2H), 1.29 (3H).

Example 137: 4-{7-[3-Cyano-4-(tetrahydro-pyran-4-yloxy)-phenyl]-furo[3,2-b]pyridin-2-yl}-N-(3-fluoro-oxetan-3-ylmethyl)-3-methoxy-benzamide (69)

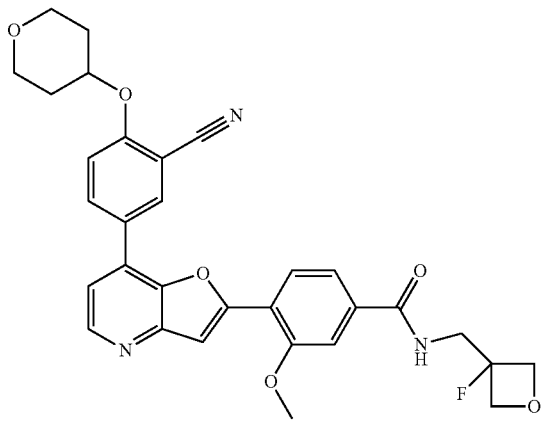 [SMILES: COc1cc(C(=O)NCC2(F)COC2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (40.00 mg; 0.09 mmol; 1.00 eq.), C-(3-Fluoro-oxetan-3-yl)-methylamine (26.81 mg; 0.26 mmol; 3.00 eq.), (3-Dimethylamino-propyl)-ethyl-carbodiimide hydrochloride (19.56 mg; 0.10 mmol; 1.20 eq.) (EDCI), Benzotriazol-1-ol (13.79 mg; 0.10 mmol; 1.20 eq.) (HOBt) and Ethyl-diisopropyl-amine (32.97 mg; 0.26 mmol; 3.00 eq.) in DMF (5.0 mL) (8 mg, 17% yield). MS: m/z=558 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 4.94 (1H), 4.72-4.63 (4H), 4.13 (3H), 3.91 (2H), 3.85 (1H), 3.59 (2H), 2.15 (2H), 1.72 (2H).

Example 138: 4-{7-[3-Cyano-4-(tetrahydro-pyran-4-yloxy)-phenyl]-furo[3,2-b]pyridin-2-yl}-N-(3-hydroxy-tetrahydro-pyran-4-yl)-3-methoxy-benzamide (11)

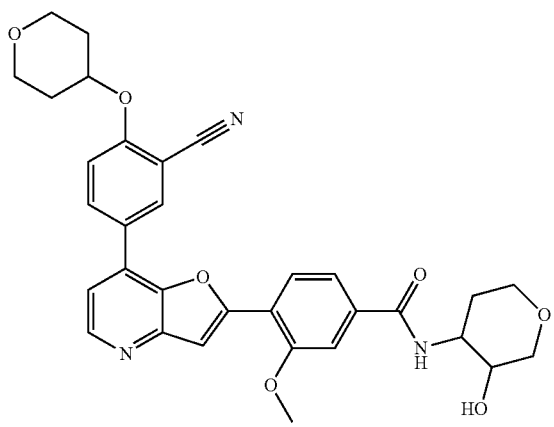 [SMILES: COc1cc(C(=O)NC2CCOCC2O)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (40.00 mg; 0.09 mmol; 1.00 eq.), 4-Amino-tetrahydro-pyran-3-ol (29.88 mg; 0.26 mmol; 3.00 eq.), (3-Dimethylamino-propyl)-ethyl-carbodiimide hydrochloride (19.56 mg; 0.10 mmol; 1.20 eq.) (EDCI), Benzotriazol-1-ol (13.79 mg; 0.10 mmol; 1.20 eq.) (HOBt) and Ethyl-diisopropyl-amine (32.97 mg; 0.26 mmol; 3.00 eq.) in DMF (5.0 mL) (17.9 mg, 37% yield). MS: m/z=570 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 4.94 (1H), 4.13 (3H), 3.89 (4H), 3.59 (2H), 3.35 (1H), 3.09 (2H), 2.15 (2H), 1.88 (1H), 1.74 (2H), 1.58 (2H).

Example 139: 4-{7-[3-Cyano-4-(tetrahydro-pyran-4-yloxy)-phenyl]-furo[3,2-b]pyridin-2-yl}-3-methoxy-N-(1-methyl-pyrrolidin-3-yl)-benzamide (64)

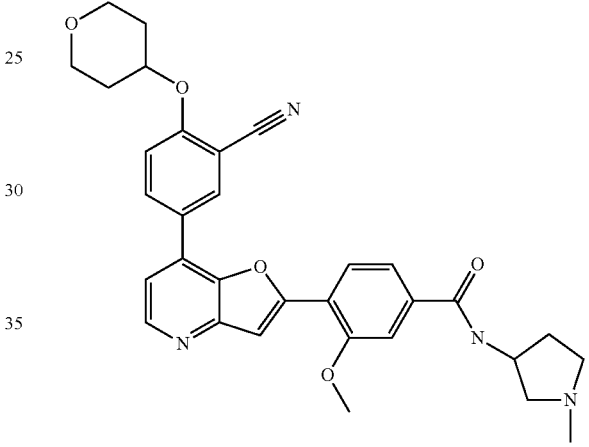

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (40.00 mg; 0.09 mmol; 1.00 eq.), 1-Methyl-pyrrolidin-3-ylamine hydrochloride (34.85 mg; 0.26 mmol; 3.00 eq.), (3-Dimethylamino-propyl)-ethyl-carbodiimide hydrochloride (19.56 mg; 0.10 mmol; 1.20 eq.) (EDCI), Benzotriazol-1-ol (13.79 mg; 0.10 mmol; 1.20 eq.) (HOBt) and Ethyl-diisopropyl-amine (32.97 mg; 0.26 mmol; 3.00 eq.) in DMF (5.0 mL) (18.8 mg, 40% yield). MS: m/z=553 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 4.97 (1H), 4.49 (2H), 4.13 (3H), 3.89 (2H), 3.59 (2H), 2.68 (3H) 2.45 (1H), 2.27 (3H), 2.14 (1H), 2.08 (2H), 1.80 (3H).

Example 140: 4-{7-[3-Cyano-4-(tetrahydro-pyran-4-yloxy)-phenyl]-furo[3,2-b]pyridin-2-yl}-N-(2-dimethylamino-1,1-dimethyl-ethyl)-3-methoxy-benzamide (63)

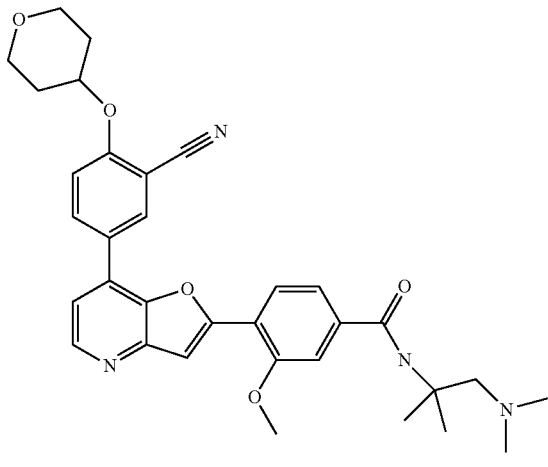 [SMILES: COc1cc(C(=O)NC(C)(C)CN(C)C)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (80.00 mg; 0.17 mmol; 1.00 eq.), 2,N1,N1-Trimethyl-propane-1,2-diamine (39.52 mg; 0.34 mmol; 2.00 eq.), (3-Dimethylamino-propyl)-ethyl-carbodiimide hydrochloride (39.12 mg; 0.20 mmol; 1.20 eq.) (EDCI), Benzotriazol-1-ol (27.57 mg; 0.20 mmol; 1.20 eq.) (HOBt) and Ethyl-diisopropyl-amine (65.93 mg; 0.51 mmol; 3.00 eq.) in DMF (5 mL) (55 mg, 56% yield). MS: m/z=569 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 4.97 (1H), 4.13 (3H), 3.92 (2H), 3.59 (2H), 2.26 (6H), 2.08 (2H), 1.74 (2H), 1.39 (6H)

Example 141: 4-{7-[3-Cyano-4-(tetrahydro-pyran-4-ylamino)-phenyl]-furo[3,2-b]pyridin-2-yl}-3-methoxy-N-pyrrolidin-3-yl-benzamide (130)

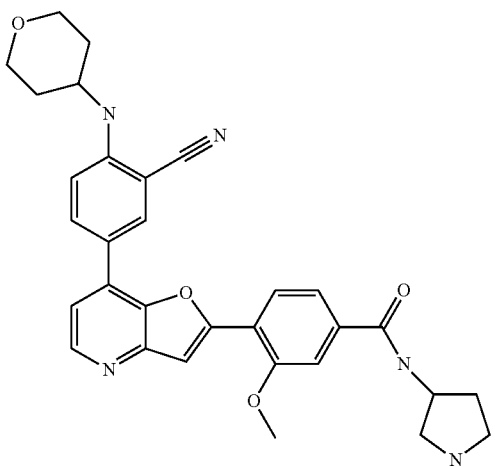 [SMILES: COc1cc(C(=O)NC2CCNC2)ccc1-c1cc2nccc(-c3ccc(NC4CCOCC4)c(C#N)c3)c2o1]

3-(4-{7-[3-Cyano-4-(tetrahydro-pyran-4-ylamino)-phenyl]-furo[3,2-b]pyridin-2-yl}-3-methoxy-benzoylamino)-pyrrolidine-1-carboxylic acid tert-butyl ester (147)

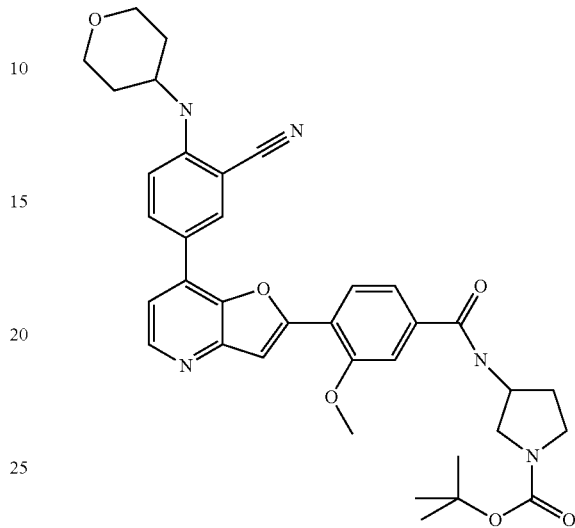

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (80.00 mg; 0.17 mmol; 1.00 eq.), 3-Amino-pyrrolidine-1-carboxylic acid tert-butyl ester (95.21 mg; 0.51 mmol; 3.00 eq.), (3-Dimethylamino-propyl)-ethyl-carbodiimide hydrochloride (39.20 mg; 0.20 mmol; 1.20 eq.) (EDCI), Benzotriazol-1-ol (27.63 mg; 0.20 mmol; 1.20 eq.) (HOBt) and Ethyl-diisopropyl-amine (66.07 mg; 0.51 mmol; 3.00 eq.) in DMF (5.0 mL) (90 mg, 80% yield). MS: m/z=638 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 6.28 (1H), 4.37 (1H), 4.13 (3H), 3.92 (2H), 3.80 (2H), 3.49 (2H), 3.02 (1H), 2.95 (1H), 2.79 (1H), 2.73 (1H), 2.01 (1H), 1.90 (2H), 1.70 (2H) 1.09 (9H).

4-{7-[3-Cyano-4-(tetrahydro-pyran-4-ylamino)-phenyl]-furo[3,2-b]pyridin-2-yl}-3-methoxy-N-pyrrolidin-3-yl-benzamide (130)

A mixture of 90 mg of 3-(4-{7-[3-Cyano-4-(tetrahydro-pyran-4-ylamino)-phenyl]-furo[3,2-b]pyridin-2-yl}-3-methoxy-benzoylamino)-pyrrolidine-1-carboxylic acid tert-butyl ester in TFA (2 mL) was stirred for 10 minutes, then the TFA was removed, the mixture was purified through reverse phase HPLC to provide the title compound (46 mg, 78% yield). MS: m/z=538 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 6.28 (1H), 4.37 (1H), 4.13 (3H), 3.92 (2H), 3.80 (2H), 3.49 (2H), 3.02 (1H), 2.95 (1H), 2.79 (1H), 2.73 (1H), 2.01 (1H), 1.90 (2H), 1.70 (2H).

Example 142: 4-{7-[3-Cyano-4-(tetrahydro-pyran-4-yloxy)-phenyl]-furo[3,2-b]pyridin-2-yl}-3-methoxy-benzamide (40)

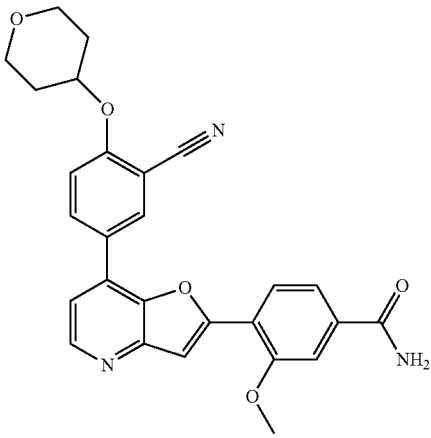 [SMILES: COc1cc(C(N)=O)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (80.00 mg; 0.17 mmol; 1.00 eq.), ammonia (28.96 mg; 1.70 mmol; 10.00 eq. 0.5 m in 1,4-dioxane 3.4 mL), (3-Dimethylamino-propyl)-ethyl-carbodiimide hydrochloride (39.12 mg; 0.20 mmol; 1.20 eq.) (EDCI), Benzotriazol-1-ol (27.57 mg; 0.20 mmol; 1.20 eq.) (HOBt) and Ethyl-diisopropyl-amine (65.93 mg; 0.51 mmol; 3.00 eq.) in DMF (5.0 mL) (54 mg, 67% yield). MS: m/z=470 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 4.98 (1H), 4.13 (3H), 3.92 (2H), 3.57 (2H), 3.02 (1H), 2.11 (2H), 1.74 (2H).

Example 143: 4-{7-[3-Cyano-4-(tetrahydro-pyran-4-yloxy)-phenyl]-furo[3,2-b]pyridin-2-yl}-3-methoxy-benzoic acid hydrazide (110)

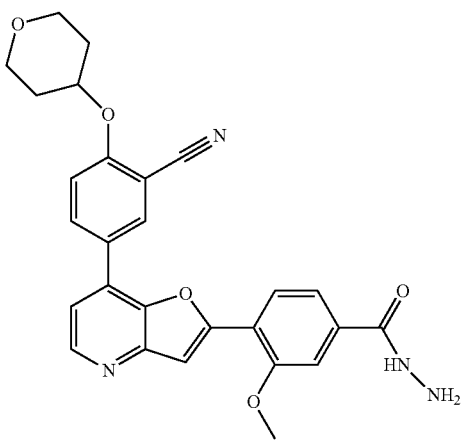 [SMILES: COc1cc(C(=O)NN)ccc1-c1cc2nccc(-c3ccc(OC4CCOCC4)c(C#N)c3)c2o1]

N'-(4-{7-[3-Cyano-4-(tetrahydro-pyran-4-yloxy)-phenyl]-furo[3,2-b]pyridin-2-yl}-3-methoxy-benzoyl)-hydrazinecarboxylic acid tert-butyl ester (67)

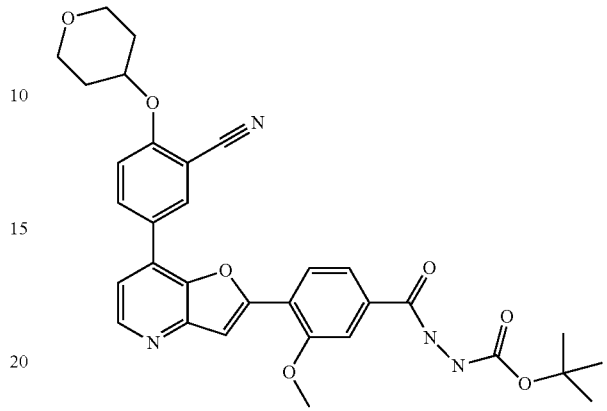

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (2000.00 mg; 4.25 mmol; 1.00 eq.), Hydrazinecarboxylic acid tert-butyl ester (842.73 mg; 6.38 mmol; 1.50 eq.), (3-Dimethylamino-propyl)-ethyl-carbodiimide hydrochloride (977.91 mg; 5.10 mmol; 1.20 eq.) (EDCI), Benzotriazol-1-ol (689.30 mg; 5.10 mmol; 1.20 eq.) (HOBt) and Ethyl-diisopropyl-amine (1648.25 mg; 12.75 mmol; 3.00 eq.) in DMF (5.0 mL) (1500 mg, 67% yield). MS: m/z=585 (M+H). H NMR (DMSO-d6): 10.36 (1H), 8.51 (1H), 8.40 (1H), 8.30 (2H), 8.09 (1H), 7.72 (1H), 7.63 (2H), 7.20 (1H), 7.06 (1H), 4.98 (1H), 4.13 (3H), 3.92 (2H), 3.57 (2H), 2.11 (2H), 1.74 (2H), 1.48 (9H)

4-{7-[3-Cyano-4-(tetrahydro-pyran-4-yloxy)-phenyl]-furo[3,2-b]pyridin-2-yl}-3-methoxy-benzoic acid hydrazide (110)

The mixture of 100 mg of N'-(4-{7-[3-Cyano-4-(tetrahydro-pyran-4-yloxy)-phenyl]-furo[3,2-b]pyridin-2-yl}-3-methoxy-benzoyl)-hydrazinecarboxylic acid tert-butyl ester in TFA (5 mL) was stirred for 10 minutes, then the TFA was removed. The mixture was purified through reverse phase HPLC to provide the product (32 mg, 70%). MS: m/z=485 (M+H). H NMR (DMSO-d6): 10.36 (1H), 8.51 (1H), 8.40 (1H), 8.30 (2H), 8.09 (1H), 7.72 (1H), 7.63 (2H), 7.20 (1H), 7.06 (1H), 4.98 (1H), 4.13 (3H), 3.92 (2H), 3.57 (2H), 2.11 (2H), 1.74 (2H).

Example 144: 4-{7-[3-Cyano-4-(tetrahydro-pyran-4-yloxy)-phenyl]-furo[3,2-b]pyridin-2-yl}-N-(3-hydroxy-cyclobutyl)-3-methoxy-benzamide (75)

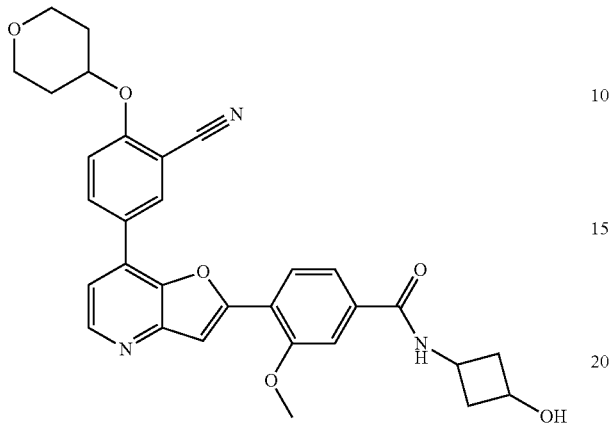

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), 3-Amino-cyclobutanol; hydrochloride (52.53 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (74 mg, 65% yield). MS: m/z=540 (M+H). H NMR (DMSO-d6): 8.51 (1H), 8.25 (2H), 8.05 (1H), 7.64 (2H), 7.43 (2H), 7.20 (1H), 6.27 (1H), 5.75 (1H), 4.54 (2H), 4.29 (1H), 4.10 (1H), 4.08 (3H), 3.92 (2H), 3.81 (2H), 3.61 (1H), 3.47 (2H), 2.96 (1H), 2.20 (1H), 1.89 (2H), 1.67 (2H).

Example 145: 4-{7-[3-Cyano-4-(tetrahydro-pyran-4-ylamino)-phenyl]-furo[3,2-b]pyridin-2-yl}-N-(2-dimethylamino-1,1-dimethyl-ethyl)-3-methoxy-benzamide (134)

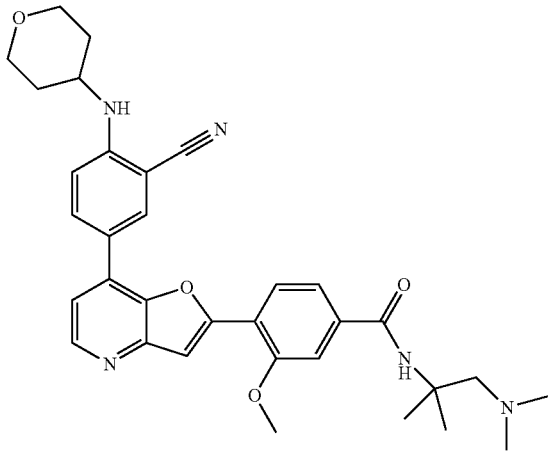

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 2,N1,N1-Trimethyl-propane-1,2-diamine (19.80 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (42 mg, 87% yield). MS: m/z=568 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 4.97 (1H), 4.13 (3H), 3.92 (2H), 3.59 (2H), 2.26 (6H), 2.08 (2H), 1.74 (2H), 1.39 (6H)

Example 146: 4-{7-[3-Cyano-4-(tetrahydro-pyran-4-yloxy)-phenyl]-furo[3,2-b]pyridin-2-yl}-N-(3-hydroxy-cyclopentyl)-3-methoxy-benzamide (68)

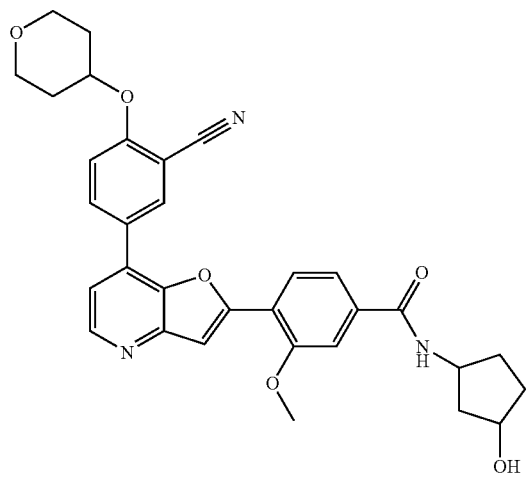 [SMILES: COc1cc(C(=O)NC2CCC(O)C2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), 3-Amino-cyclopentanol hydrochloride (58.50 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (100 mg, 85% yield). MS: m/z=554 (M+H). H NMR (DMSO-d6): 8.55 (1H), 8.30 (2H), 8.05 (1H), 7.66 (2H), 7.43 (2H), 7.20 (1H), 6.27 (1H), 5.07-4.97 (1H), 4.34-4.28 (2H), 4.08 (3H), 3.92 (2H), 3.81 (2H), 3.61 (2H), 3.47 (2H), 1.89 (4H), 1.67 (2H).

Example 147: 5-{2-[4-(3-Hydroxy-azetidine-1-carbonyl)-2-methoxy-phenyl]-furo[3,2-b]pyridin-7-yl}-2-(tetrahydro-pyran-4-yloxy)-benzonitrile (39)

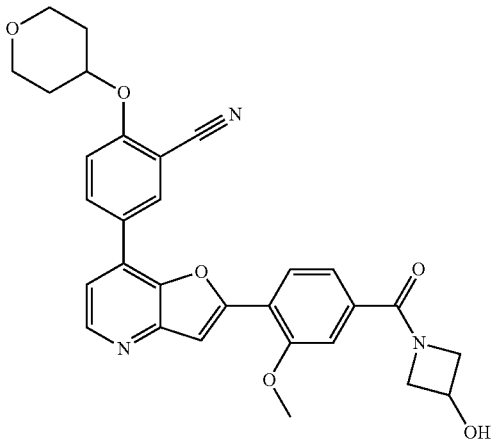 [SMILES: COc1cc(C(=O)N2CC(O)C2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), Azetidin-3-ol hydrochloride (46.57 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (45 mg, 47% yield). MS: m/z=526 (M+H). H NMR (DMSO-d6): 8.51 (1H), 8.25 (2H), 8.05 (1H), 7.64 (2H), 7.43 (2H), 7.20 (1H), 6.27 (1H), 5.75 (1H), 4.54 (2H), 4.29 (1H), 4.10 (1H), 4.08 (3H), 3.92 (2H), 3.81 (2H), 3.61 (1H), 3.47 (2H), 2.96 (1H), 2.20 (1H), 1.89 (2H), 1.67 (2H).

Example 148: 5-{2-[2-Methoxy-4-(5-methyl-hexahydro-pyrrolo[3,4-c]pyrrole-2-carbonyl)-phenyl]-furo[3,2-b]pyridin-7-yl}-2-(tetrahydro-pyran-4-yloxy)-benzonitrile (9)

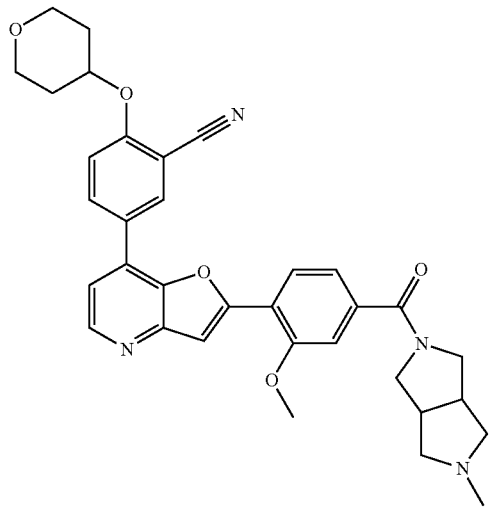 [SMILES: COc1cc(C(=O)N2CC3CN(C)CC3C2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), 2-Methyl-octahydro-pyrrolo[3,4-c]pyrrole hydrochloride (69.15 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (84 mg, 68% yield). MS: m/z=578 (M+H). H NMR (DMSO-d6): 8.55 (1H), 8.30 (2H), 8.05 (1H), 7.66 (2H), 7.30 (1H), 7.24 (1H), 7.18 (1H), 6.28 (1H), 4.08 (3H), 3.89 (2H), 3.80 (2H), 3.71 (1H), 3.47 (4H), 2.79 (2H), 2.39 (2H), 2.23 (3H), 1.88 (2H), 1.65 (2H).

Example 149: 4-{7-[3-Cyano-4-(tetrahydro-pyran-4-yloxy)-phenyl]-furo[3,2-b]pyridin-2-yl}-3-methoxy-N-pyrrolidin-3-yl-benzamide (195)

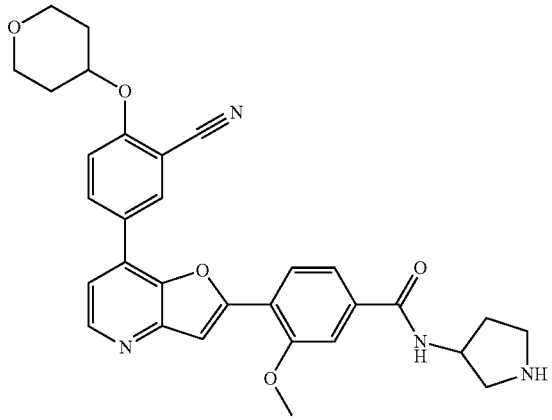 [SMILES: COc1cc(C(=O)NC2CCNC2)ccc1-c1cc2nccc(-c3ccc(OC4CCOCC4)c(C#N)c3)c2o1]

3-(4-{7-[3-Cyano-4-(tetrahydro-pyran-4-yloxy)-phenyl]-furo[3,2-b]pyridin-2-yl}-3-methoxy-benzoylamino)-pyrrolidine-1-carboxylic acid tert-butyl ester (125)

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), 3-Amino-pyrrolidine-1-carboxylic acid tert-butyl ester (79.18 mg; 0.43 mmol; 2.00 eq.), 3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (105 mg, 77% yield). MS: m/z=639 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 6.28 (1H), 4.37 (1H), 4.13 (3H), 3.92 (2H), 3.80 (2H), 3.49 (2H), 3.02 (1H), 2.95 (1H), 2.79 (1H), 2.73 (1H), 2.01 (1H), 1.90 (2H), 1.70 (2H) 1.09 (9H).

4-{7-[3-Cyano-4-(tetrahydro-pyran-4-yloxy)-phenyl]-furo[3,2-b]pyridin-2-yl}-3-methoxy-N-pyrrolidin-3-yl-benzamide (195)

The mixture of 3-(4-{7-[3-Cyano-4-(tetrahydro-pyran-4-yloxy)-phenyl]-furo[3,2-b]pyridin-2-yl}-3-methoxy-benzoylamino)-pyrrolidine-1-carboxylic acid tert-butyl ester (70.00 mg; 0.11 mmol; 1.00 eq.) in 2 mL of TFA was stirred for 10 minutes. The solvent was removed and the residue was dissolved in 2 mL of DMF and the solution was loaded at reverse phase HPLC and the pure product was obtained with the eluent of water/MeOH (from 40% of MeOH to 100% MeOH) in 10 minutes. (52.8 mg, 89% yield). MS: m/z=539 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 6.28 (1H), 4.37 (1H), 4.13 (3H), 3.92 (2H), 3.80 (2H), 3.49 (2H), 3.02 (1H), 2.95 (1H), 2.89 (1H), 2.09 (2H), 1.86 (1H), 1.70 (2H).

Example 150: 5-{2-[4-(3-Hydroxymethyl-azetidine-1-carbonyl)-2-methoxy-phenyl]-furo[3,2-b]pyridin-7-yl}-2-(tetrahydro-pyran-4-yloxy)-benzonitrile (38)

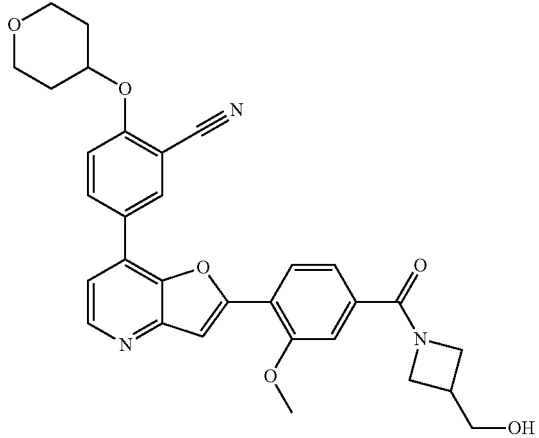 [SMILES: COc1cc(C(=O)N2CC(CO)C2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), Azetidin-3-yl-methanol (52.53 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (50 mg, 44% yield). MS: m/z=540 (M+H). H NMR (DMSO-d6): 8.51 (1H), 8.25 (2H), 8.05 (1H), 7.64 (2H), 7.43 (2H), 7.20 (1H), 5.00 (1H), 4.84 (1H), 4.41 (1H), 4.10 (3H), 3.92 (2H), 3.81 (2H), 3.58 (4H), 3.03 (2H), 2.76 (1H), 2.20 (1H), 1.89 (2H), 1.67 (2H).

Example 151: 5-{2-[4-((S)-3-Hydroxy-pyrrolidine-1-carbonyl)-2-methoxy-phenyl]-furo[3,2-b]pyridin-7-yl}-2-(tetrahydro-pyran-4-yloxy)-benzonitrile (14)

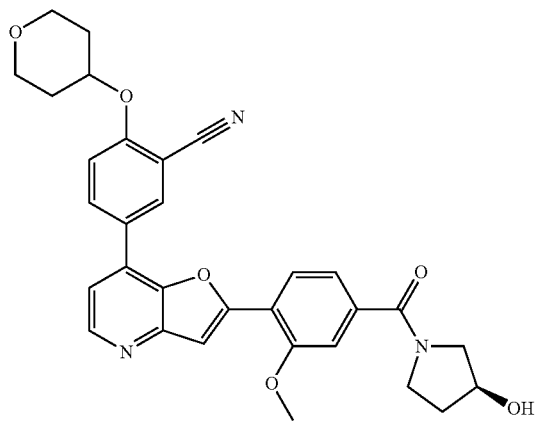 [SMILES: COc1cc(C(=O)N2CC[C@H](O)C2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), (S)-Pyrrolidin-3-ol (37.04 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (61 mg, 53% yield). MS: m/z=540 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.20 (1H), 2.09 (2H), 1.74 (2H).

Example 152: 5-{2-[4-((R)-3-Hydroxy-pyrrolidine-1-carbonyl)-2-methoxy-phenyl]-furo[3,2-b]pyridin-7-yl}-2-(tetrahydro-pyran-4-yloxy)-benzonitrile (43)

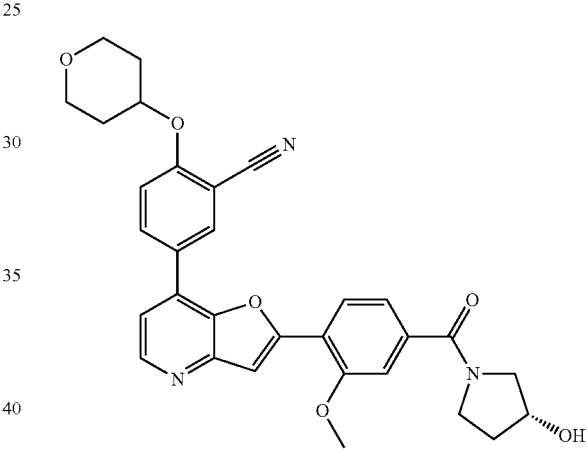

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), (R)-Pyrrolidin-3-ol (37.04 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (4.2 mg, 3.2% yield). MS: m/z=540 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.20 (1H), 2.09 (2H), 1.74 (2H).

Example 153: 5-{2-[4-(4-Hydroxy-hexahydro-cyclopenta[c]pyrrole-2-carbonyl)-2-methoxy-phenyl]-furo[3,2-b]pyridin-7-yl}-2-(tetrahydro-pyran-4-yloxy)-benzonitrile (18)

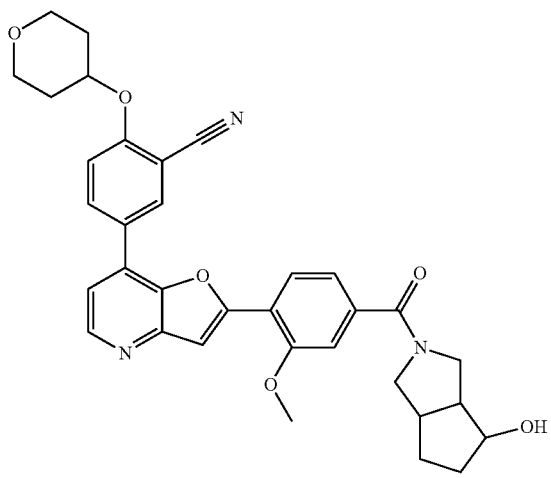 [SMILES: COc1cc(C(=O)N2CC3CCC(O)C3C2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), Octahydro-cyclopenta[c]pyrrol-4-ol (54.07 mg; 0.43 mmol; 2.00 eq.), 3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (99 mg, 80% yield). MS: m/z=580 (M+H). H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.70 (1H), 3.61 (2H), 2.61 (2H), 2.09 (2H), 1.74 (2H), 1.65 (2H)

Example 154: 5-{2-[4-((3aR,5R,6aS)-5-Hydroxy-hexahydro-cyclopenta[c]pyrrole-2-carbonyl)-2-methoxy-phenyl]-furo[3,2-b]pyridin-7-yl}-2-(tetrahydro-pyran-4-yloxy)-benzonitrile (32)

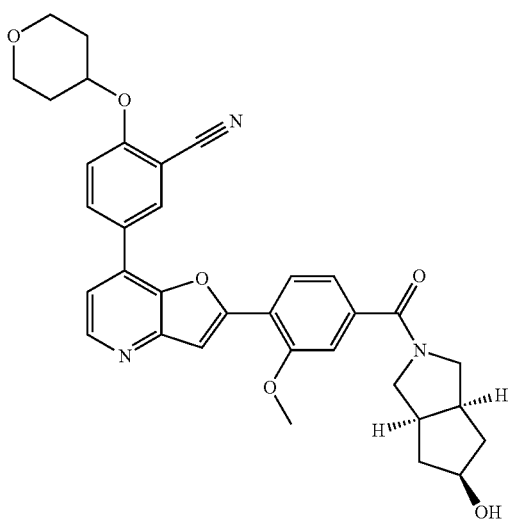 [SMILES: COc1cc(C(=O)N2C[C@H]3C[C@@H](O)C[C@H]3C2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), (3aR,5R,6aS)-Octahydro-cyclopenta[c]pyrrol-5-ol (69.57 mg; 0.43 mmol; 2.00 eq.) (relative stereochemistry), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (97 mg, 78% yield). MS: m/z=580 (M+H). H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.40 (1H), 2.61 (2H), 2.09 (2H), 1.96 (1H), 1.74 (2H), 1.40 (1H), 1.32 (1H).

Example 155: 4-{7-[3-Cyano-4-(tetrahydro-pyran-4-yloxy)-phenyl]-furo[3,2-b]pyridin-2-yl}-3-methoxy-N-(1-methyl-azetidin-3-yl)-benzamide (28)

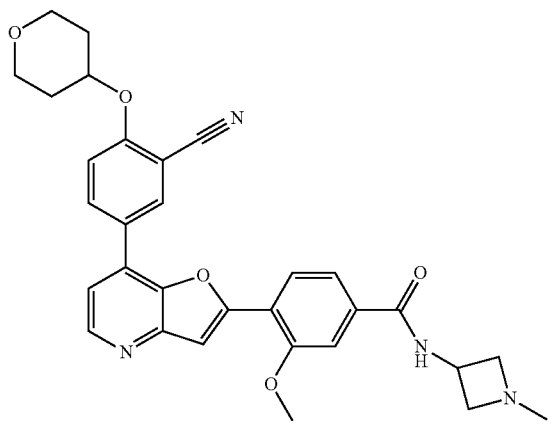 [SMILES: COc1cc(C(=O)NC2CN(C)C2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), 1-Methyl-azetidin-3-ylamine hydrochloride (52.12 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (44 mg, 38% yield). MS: m/z=539 (M+H). H NMR (DMSO-d6): 8.51 (1H), 8.40 (1H), 8.30 (2H), 8.09 (1H), 7.72 (1H), 7.63 (2H), 7.20 (1H), 7.06 (1H), 4.97 (1H), 4.49 (1H), 4.16 (1H), 4.13 (3H), 4.09 (1H), 3.89 (2H), 3.79 (1H), 3.56 (3H), 3.02 (1H), 2.25 (3H), 2.08 (2H), 1.80 (2H).

Example 156: 5-{2-[2-Methoxy-4-(8-oxa-3-azabicyclo[3.2.1]octane-3-carbonyl)-phenyl]-furo[3,2-b]pyridin-7-yl}-2-(tetrahydro-pyran-4-ylamino)-benzonitrile (46)

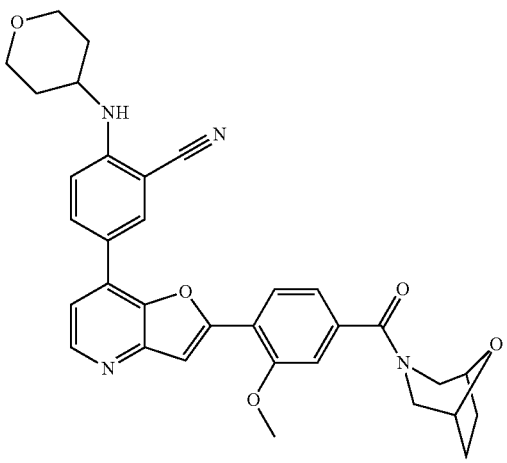 [SMILES: COc1cc(C(=O)N2CC3CCC(C2)O3)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.) 8-Oxa-3-aza-bicyclo[3.2.1]octane; hydrochloride (25.49 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (20 mg, 42% yield). MS: m/z=565 (M+H). H NMR (DMSO-d6): 8.51 (1H), 8.40 (1H), 8.30 (2H), 8.09 (1H), 7.72 (1H), 7.63 (2H), 7.20 (1H), 7.19 (1H), 6.28 (1H), 4.42 (1H), 4.16 (1H), 4.13 (3H), 4.09 (1H), 3.89 (2H), 3.79 (1H), 3.56 (3H), 3.02 (1H), 1.89 (2H), 1.70 (2H).

Example 157: 5-{2-[2-Methoxy-4-(8-oxa-3-azabicyclo[3.2.1]octane-3-carbonyl)-phenyl]-furo[3,2-b]pyridin-7-yl}-2-(tetrahydro-pyran-4-yloxy)-benzonitrile (58)

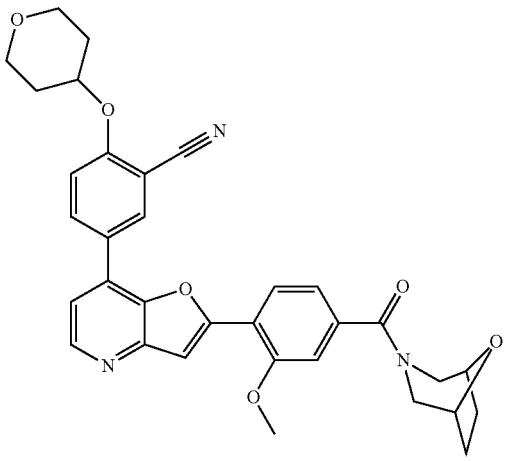 [SMILES: COc1cc(C(=O)N2CC3CCC(C2)O3)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), 8-Oxa-3-aza-bicyclo[3.2.1]octane (63.60 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (100 mg, 83% yield). MS: m/z=566 (M+H). H NMR (DMSO-d6): 8.51 (1H), 8.40 (1H), 8.30 (2H), 8.09 (1H), 7.72 (1H), 7.63 (2H), 7.20 (1H), 7.19 (1H), 4.99 (1H), 4.44 (1H), 4.16 (1H), 4.13 (3H), 4.09 (1H), 3.89 (2H), 3.79 (1H), 3.56 (3H), 3.02 (1H), 1.89 (2H), 1.70 (2H).

Example 158: 5-{2-[2-Methoxy-4-(3-oxa-8-azabicyclo[3.2.1]octane-8-carbonyl)-phenyl]-furo[3,2-b]pyridin-7-yl}-2-(tetrahydro-pyran-4-yloxy)-benzonitrile (2)

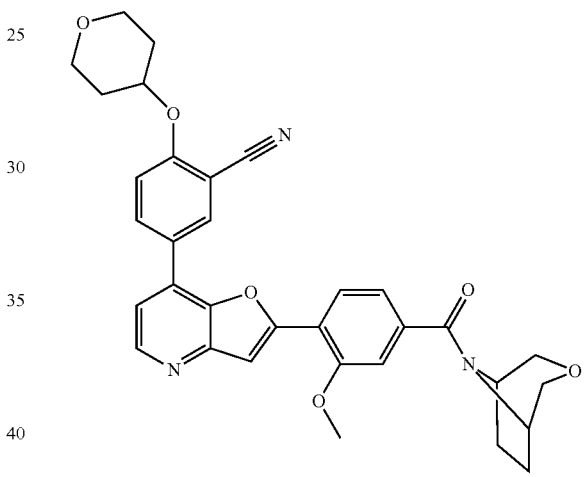

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.)), 3-Oxa-8-aza-bicyclo[3.2.1]octane (63.60 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (110 mg, 91% yield). MS: m/z=566 (M+H). H NMR (DMSO-d6): 8.51 (1H), 8.40 (1H), 8.30 (2H), 8.09 (1H), 7.72 (1H), 7.63 (2H), 7.20 (1H), 7.19 (1H), 4.99 (1H), 4.54 (1H), 4.13 (3H), 4.09 (1H), 3.89 (2H), 3.79 (2H), 3.56 (4H), 2.09 (2H), 1.92 (4), 1.70 (2H).

Example 159: 5-{2-[2-Methoxy-4-(2-oxa-5-aza-bicyclo[2.2.1]heptane-5-carbonyl)-phenyl]-furo[3,2-b]pyridin-7-yl}-2-(tetrahydro-pyran-4-yloxy)-benzonitrile (1)

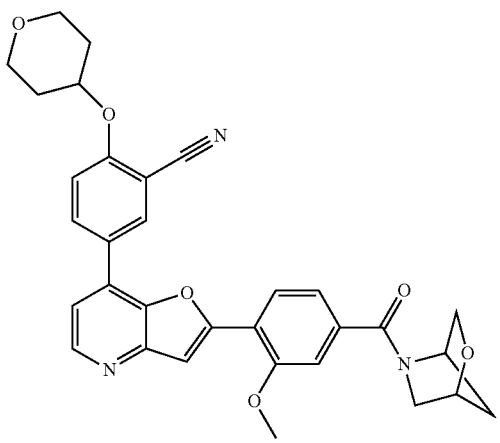 [SMILES: COc1cc(C(=O)N2CC3CC2CO3)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), 2-Oxa-5-aza-bicyclo[2.2.1]heptane hydrochloride (57.64 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (113 mg, 96% yield). MS: m/z=552 (M+H). H NMR (DMSO-d6): 8.51 (1H), 8.40 (1H), 8.30 (2H), 8.09 (1H), 7.72 (1H), 7.63 (2H), 7.20 (1H), 7.19 (1H), 4.99 (1H), 4.54 (1H), 4.13 (3H), 4.09 (1H), 3.89 (2H), 3.79 (2H), 3.56 (4H), 2.09 (2H), 1.92 (4), 1.70 (2H).

Example 160: 5-{2-[2-Methoxy-4-(5-oxo-4,5-di-hydro-[1,3,4]oxadiazol-2-yl)-phenyl]-furo[3,2-b]pyridin-7-yl}-2-(tetrahydro-pyran-4-yloxy)-benzonitrile (50)

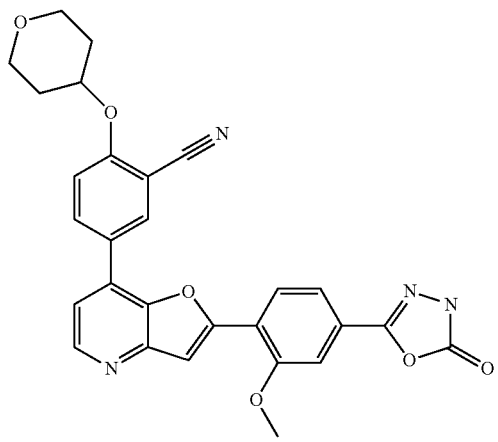 [SMILES: COc1cc(-c2n[nH]c(=O)o2)ccc1-c1cc2nccc(-c3ccc(OC4CCOCC4)c(C#N)c3)c2o1]

The mixture of 4-{7-[3-Cyano-4-(tetrahydro-pyran-4-yloxy)-phenyl]-furo[3,2-b]pyridin-2-yl}-3-methoxy-benzoic acid hydrazide (40.00 mg; 0.08 mmol; 1.00 eq.), Di-imidazol-1-yl-methanone (26.77 mg; 0.17 mmol; 2.00 eq.) and Ethyl-diisopropyl-amine (21.34 mg; 0.17 mmol; 2.00 eq.) in THF (10 mL) was stirred for 5 h, after reaction was complete, the solvent was removed and the residue was purified through reverse phase HPLC to provide the product (33 mg, 78% yield). MS: m/z=511 (M+H). H NMR (DMSO-d6): 8.51 (1H), 8.40 (1H), 8.30 (2H), 8.09 (1H), 7.72 (1H), 7.63 (2H), 7.20 (1H), 7.19 (1H), 4.99 (1H), 4.13 (3H), 3.93 (2H), 3.59 (2H), 2.06 (2H), 1.70 (2H).

Example 161: 5-{2-[2-Methoxy-4-(2-oxa-5-aza-bicyclo[2.2.1]heptane-5-carbonyl)-phenyl]-furo[3,2-b]pyridin-7-yl}-2-(tetrahydro-pyran-4-ylamino)-benzonitrile (85)

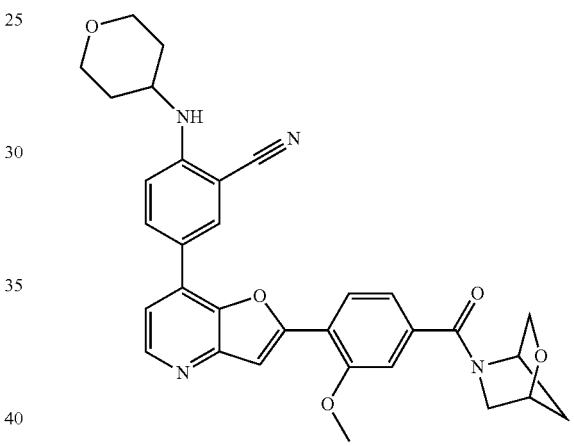

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 2-Oxa-5-aza-bicyclo[2.2.1]heptane (23.10 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (17.9 mg, 38% yield). MS: m/z=551 (M+H). H NMR (DMSO-d6): 8.51 (1H), 8.40 (1H), 8.30 (2H), 8.09 (1H), 7.72 (1H), 7.63 (2H), 7.20 (1H), 7.19 (1H), 4.99 (1H), 4.54 (1H), 4.13 (3H), 4.09 (1H), 3.89 (2H), 3.79 (2H), 3.56 (4H), 2.09 (2H), 1.92 (4), 1.70 (2H).

379

Example 162: 5-{2-[2-Methoxy-4-(3-oxa-8-aza-bicyclo[3.2.1]octane-8-carbonyl)-phenyl]-furo[3,2-b]pyridin-7-yl}-2-(tetrahydro-pyran-4-ylamino)-benzonitrile (94)

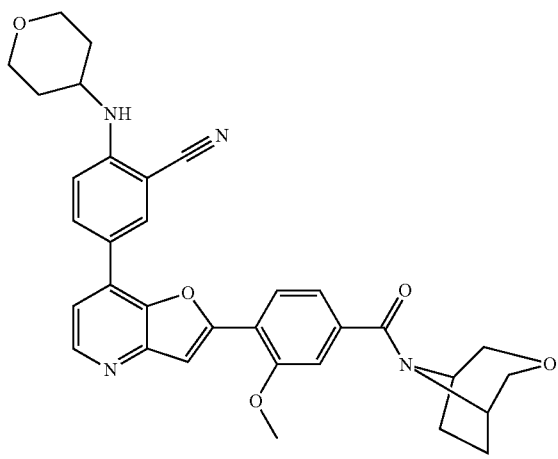 [SMILES: COc1cc(C(=O)N2C3CCC2COC3)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 3-Oxa-8-aza-bicyclo[3.2.1]octane (25.49 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (33 mg, 68% yield). MS: m/z=565 (M+H). H NMR (DMSO-d6): 8.51 (1H), 8.40 (1H), 8.30 (2H), 8.09 (1H), 7.72 (1H), 7.63 (2H), 7.20 (1H), 7.19 (1H), 4.99 (1H), 4.54 (1H), 4.13 (3H), 4.09 (1H), 3.89 (2H), 3.79 (2H), 3.56 (4H), 2.09 (2H), 1.92 (4), 1.70 (2H).

Example 163: 5-{2-[4-(4-Hydroxy-hexahydro-cyclopenta[c]pyrrole-2-carbonyl)-2-methoxy-phenyl]-furo[3,2-b]pyridin-7-yl}-2-(tetrahydro-pyran-4-ylamino)-benzonitrile (284)

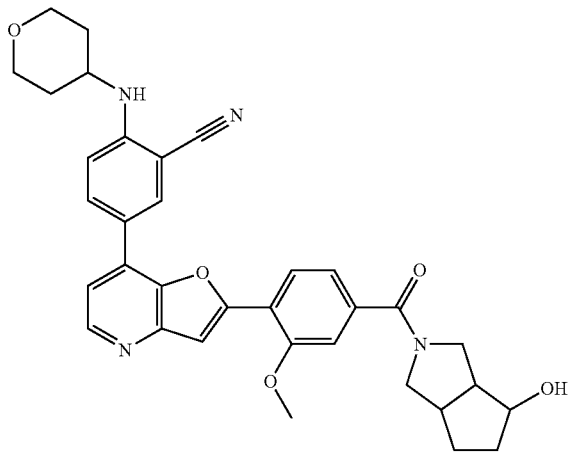 [SMILES: COc1cc(C(=O)N2CC3CCC(O)C3C2)ccc1-c1cc2nccc(-c3ccc(NC4CCOCC4)c(C#N)c3)c2o1]

380

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), Octahydro-cyclopenta[c]pyrrol-4-ol (21.67 mg; 0.17 mmol; 2.00 eq.), 3-Dimethylamino-propyl)-ethyl-carbodiimide hydrochloride (48.90 mg; 0.26 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (27 mg, 55% yield). MS: m/z=579 (M+H). H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.70 (1H), 3.61 (2H), 2.61 (2H), 2.09 (2H), 1.74 (2H), 1.65 (2H).

Example 164: 5-{2-[4-((3aR,5R,6aS)-5-Hydroxy-hexahydro-cyclopenta[c]pyrrole-2-carbonyl)-2-methoxy-phenyl]-furo[3,2-b]pyridin-7-yl}-2-(tetrahydro-pyran-4-ylamino)-benzonitrile (81)

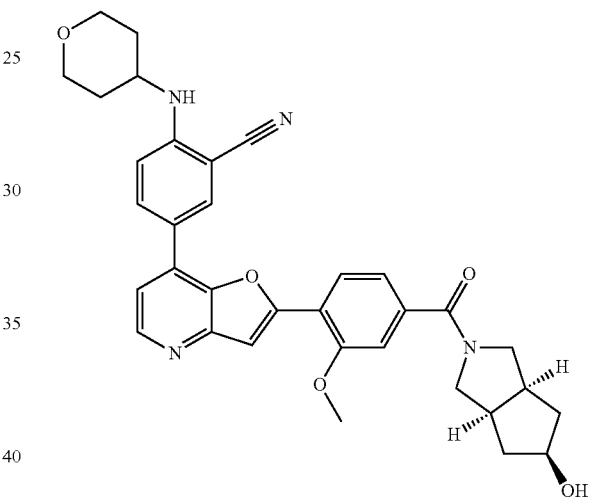

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), (3aR,5R,6aS)-Octahydro-cyclopenta[c]pyrrol-5-ol (27.88 mg; 0.17 mmol; 2.00 eq.) (relative stereochemistry), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (27 mg, 53% yield). MS: m/z=579 (M+H). H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.40 (1H), 2.61 (2H), 2.09 (2H), 1.96 (1H), 1.74 (2H), 1.40 (1H), 1.32 (1H).

Example 165: 5-{2-[4-(Azetidine-1-carbonyl)-2-methoxy-phenyl]-furo[3,2-b]pyridin-7-yl}-2-(tetrahydro-pyran-4-yloxy)-benzonitrile (44)

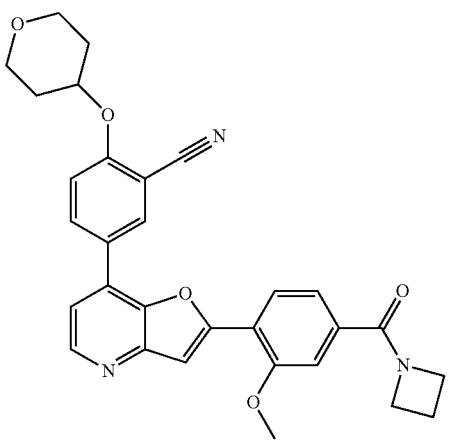 [SMILES: COc1cc(C(=O)N2CCC2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), Azetidine (24.27 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (7 mg, 6% yield). MS: m/z=510 (M+H). H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.40 (1H), 2.61 (2H), 2.09 (2H0, 1.75 (2H), 1.32 (2H).

Example 166: 4-{7-[3-Cyano-4-(tetrahydro-pyran-4-yloxy)-phenyl]-furo[3,2-b]pyridin-2-yl}-3-methoxy-N-methyl-benzamide (100)

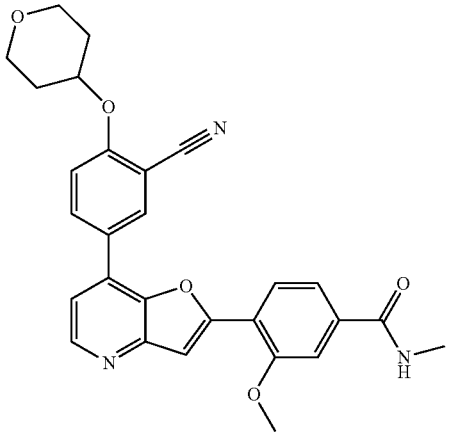 [SMILES: CNC(=O)c1ccc(-c2cc3nccc(-c4ccc(OC5CCOCC5)c(C#N)c4)c3o2)c(OC)c1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), Methylamine (1.07 ml; 2.13 mmol; 10.00 eq.), 1.07 mL, 2M in THF, (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (34 mg, 33% yield). MS: m/z=484 (M+H). H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.40 (1H), 2.61 (2H), 2.09 (2H), 1.75 (2H).

Example 167: 5-{2-[4-((R)-3-Hydroxy-pyrrolidine-1-carbonyl)-2-methoxy-phenyl]-furo[3,2-b]pyridin-7-yl}-2-(tetrahydro-pyran-4-ylamino)-benzonitrile (95)

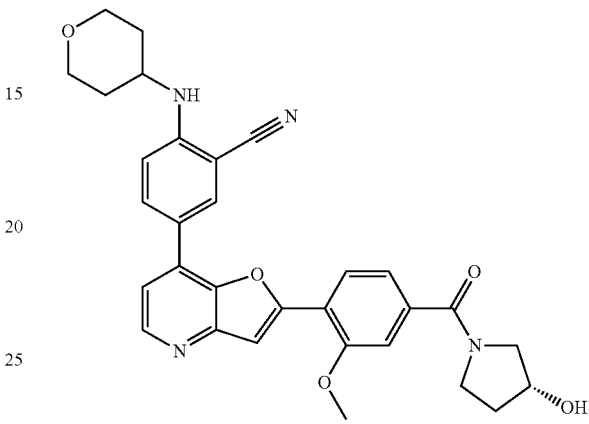

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), (R)-Pyrrolidin-3-ol (14.85 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (20 mg, 44% yield). MS: m/z=539 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.20 (1H), 2.09 (2H), 1.74 (2H).

Example 168: 5-{2-[4-((S)-3-Hydroxy-pyrrolidine-1-carbonyl)-2-methoxy-phenyl]-furo[3,2-b]pyridin-7-yl}-2-(tetrahydro-pyran-4-ylamino)-benzonitrile (103)

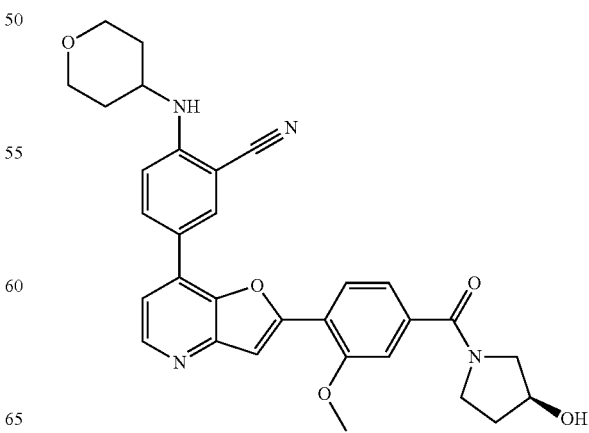

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), (S)-Pyrrolidin-3-ol (14.85 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (11.2 mg, 24% yield). MS: m/z=539 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.20 (1H), 2.09 (2H), 1.74 (2H).

Example 169: 5-{2-[4-(Hexahydro-cyclopenta[c]pyrrole-2-carbonyl)-2-methoxy-phenyl]-furo[3,2-b]pyridin-7-yl}-2-(tetrahydro-pyran-4-yloxy)-benzonitrile (99)

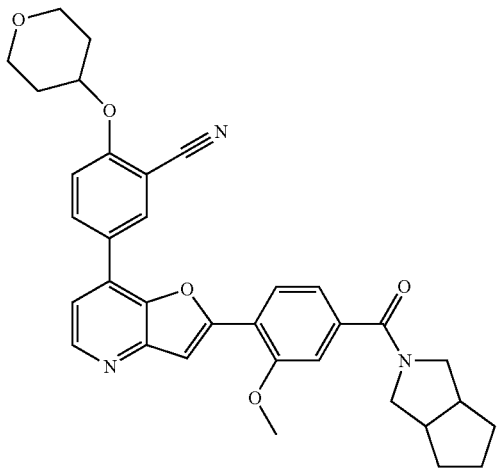 [SMILES: COc1cc(C(=O)N2CC3CCCC3C2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.)), Octahydro-cyclopenta[c]pyrrole (47.27 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (93 mg, 77% yield). MS: m/z=564 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.20 (1H), 2.09 (2H), 1.74 (2H), 1.58 (4H), 1.38 (2H).

Example 170: 4-{7-[3-Cyano-4-(tetrahydro-pyran-4-yloxy)-phenyl]-furo[3,2-b]pyridin-2-yl}-N-(3-fluoro-tetrahydro-pyran-4-yl)-3-methoxy-benzamide (102)

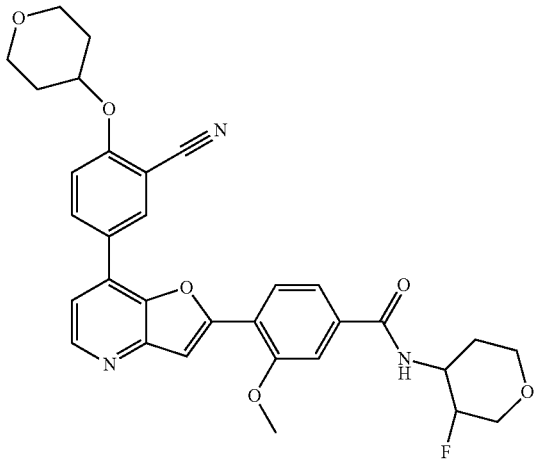 [SMILES: COc1cc(C(=O)NC2CCOCC2F)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.)), 3-Fluoro-tetrahydro-pyran-4-ylamine (50.65 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (97 mg, 79% yield). MS: m/z=572 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.20 (1H), 2.09 (2H), 1.74 (2H), 1.66 (2H).

Example 171: 4-{7-[3-Cyano-4-(tetrahydro-pyran-4-yloxy)-phenyl]-furo[3,2-b]pyridin-2-yl}-N-(2,2-difluoro-cyclohexylmethyl)-3-methoxy-benzamide (151)

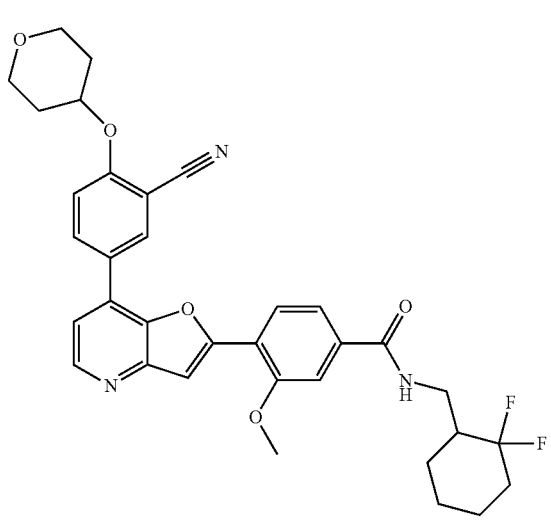 [SMILES: COc1cc(C(=O)NCC2CCCCC2(F)F)ccc1-c1cc2nccc(-c3ccc(OC4CCOCC4)c(C#N)c3)c2o1]

The title compound was synthesized according to the procedure described in example 109 using 4-{7-[3-Cyano- 4-(tetrahydro-pyran-4-yloxy)-phenyl]-furo[3,2-b]pyridin-2-yl}-3-methoxy-benzoic acid (100.00 mg; 0.21 mmol; 1.00 eq.)), C-(3,3-Difluoro-cyclohexyl)-methylamine (78.92 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (94 mg, 73% yield). MS: m/z=602 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.20 (1H), 2.09 (2H), 1.74 (2H), 1.66 (2H), 1.06 (2H).

Example 172: 5-{2-[4-(6-Aza-spiro[3.4]octane-6-carbonyl)-2-methoxy-phenyl]-furo[3,2-b]pyridin-7-yl}-2-(tetrahydro-pyran-4-yloxy)-benzonitrile (114)

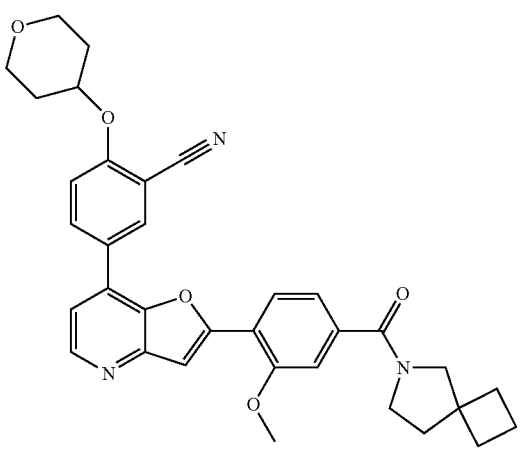 [SMILES: COc1cc(C(=O)N2CCC3(CCC3)C2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), 6-Aza-spiro[3.4]octane (47.27 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (87.8 mg, 73% yield). MS: m/z=564 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.20 (1H), 2.09 (2H), 1.90 (4H), 1.74 (2H), 1.66 (2H).

Example 173: 5-{2-[2-Methoxy-4-(2-oxa-5-aza-bicyclo[2.2.2]octane-5-carbonyl)-phenyl]-furo[3,2-b]pyridin-7-yl}-2-(tetrahydro-pyran-4-yloxy)-benzonitrile (4)

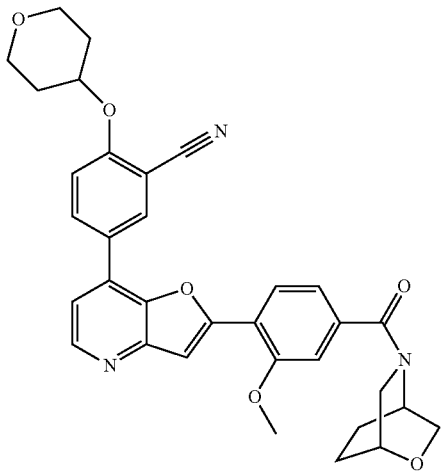 [SMILES: COc1cc(C(=O)N2CC3CCC2CO3)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), 2-Oxa-5-aza-bicyclo[2.2.2]octane (48.10 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (100 mg, 83% yield). MS: m/z=566 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.20 (1H), 2.09 (2H), 1.90 (2H), 1.80 (4H), 1.74 (2H).

Example 174: 5-{2-[2-Methoxy-4-(6-oxa-3-aza-bicyclo[3.1.1]heptane-3-carbonyl)-phenyl]-furo[3,2-b]pyridin-7-yl}-2-(tetrahydro-pyran-4-yloxy)-benzonitrile (6)

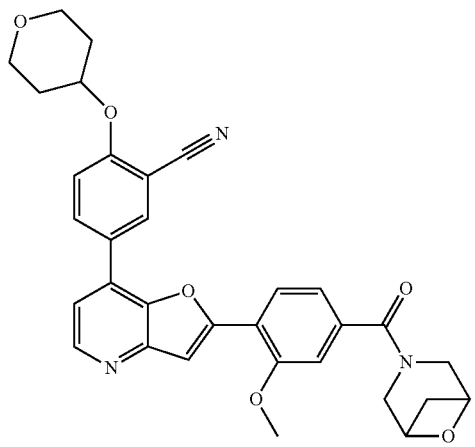 [SMILES: COc1cc(C(=O)N2CC3CC(C2)O3)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), 6-Oxa-3-aza-bicyclo[3.1.1]heptane (42.14 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (105 mg, 89% yield). MS: m/z=552 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.70 (1H), 4.51 (1H), 4.08 (3H), 4.00 (1H), 3.92 (2H), 3.81 (1H), 3.61 (2H), 3.47 (2H), 3.10 (1H), 2.20 (1H), 2.09 (2H), 1.90 (2H), 1.74 (2H).

Example 175: 5-{2-[4-(7-Hydroxy-3-oxa-9-aza-bicyclo[3.3.1]nonane-9-carbonyl)-2-methoxy-phenyl]-furo[3,2-b]pyridin-7-yl}-2-(tetrahydro-pyran-4-yloxy)-benzonitrile (66)

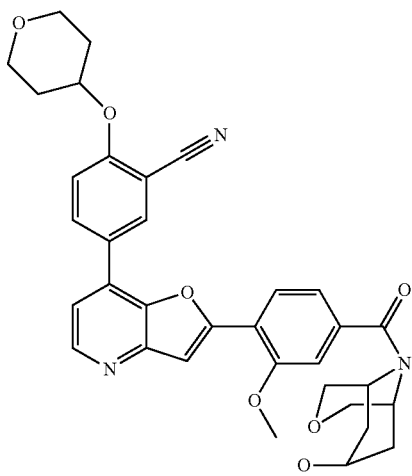 [SMILES: COc1cc(C(=O)N2C3COCC2CC(O)C3)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), 3-Oxa-9-aza-bicyclo[3.3.1]nonan-7-ol hydrochloride salt (76.37 mg; 0.43 mmol; 2.00 eq.)), (3-Dimethylamino-propyl)-ethyl-carbodiimide hydrochloride (48.90 mg; 0.26 mmol; 1.20 eq.)(EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (106 mg, 84% yield). MS: m/z=596 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.70 (1H), 4.51 (1H), 4.08 (3H), 4.00 (1H), 3.92 (2H), 3.81 (1H), 3.61 (2H), 3.47 (2H), 3.10 (1H), 2.22 (1H), 2.09 (3H), 1.90-1.74 (4H).

Example 176: 5-{2-[4-(Hexahydro-cyclopenta[c]pyrrole-2-carbonyl)-2-methoxy-phenyl]-furo[3,2-b]pyridin-7-yl}-2-(tetrahydro-pyran-4-ylamino)-benzonitrile (137)

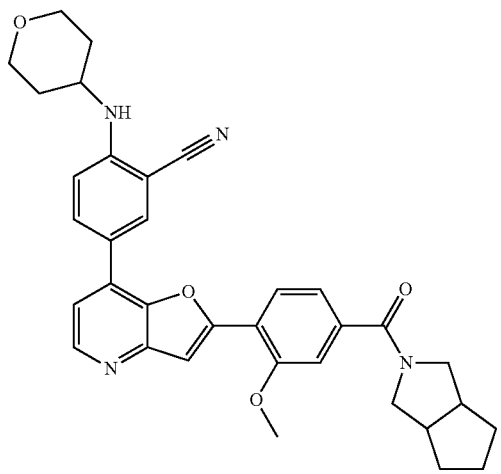 [SMILES: COc1cc(C(=O)N2CC3CCCC3C2)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), Octahydro-cyclopenta[c]pyrrole (18.95 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (27 mg, 56% yield). MS: m/z=563 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.20 (1H), 2.09 (2H), 1.74 (2H), 1.58 (4H), 1.07 (2H).

Example 177: 4-{7-[3-Cyano-4-(tetrahydro-pyran-4-ylamino)-phenyl]-furo[3,2-b]pyridin-2-yl}-N-(3-fluoro-tetrahydro-pyran-4-yl)-3-methoxy-benzamide (132)

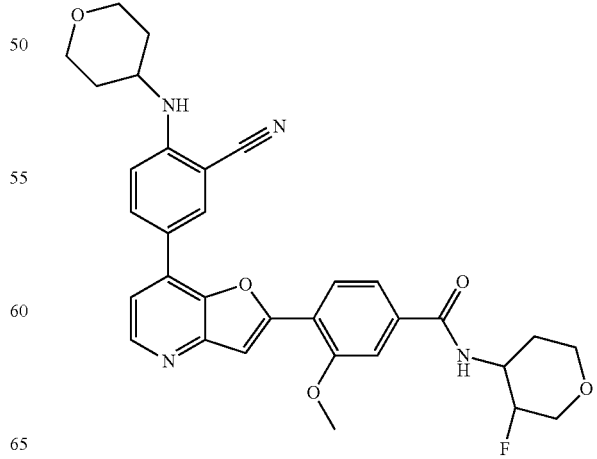

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 3-Fluoro-tetrahydro-pyran-4-ylamine (20.30 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (26 mg, 53% yield). MS: m/z=571 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.20 (1H), 2.09 (2H), 1.74 (2H), 1.66 (2H).

Example 178: 4-{7-[3-Cyano-4-(tetrahydro-pyran-4-ylamino)-phenyl]-furo[3,2-b]pyridin-2-yl}-N-(2,2-difluoro-cyclohexylmethyl)-3-methoxy-benzamide (180)

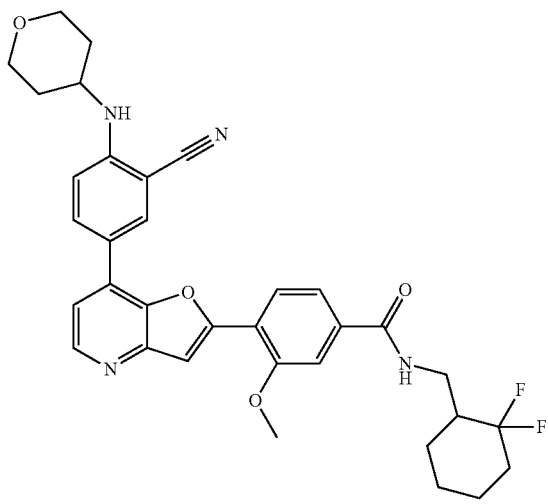 [SMILES: COc1cc(C(=O)NCC2CCCCC2(F)F)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), C-(3,3-Difluoro-cyclohexyl)-methylamine hydrochloride (31.63 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (36 mg, 70% yield). MS: m/z=601 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.20 (1H), 2.09 (2H), 1.74 (2H), 1.66 (2H), 1.06 (2H).

Example 179: 5-{2-[4-(6-Aza-spiro[3.4]octane-6-carbonyl)-2-methoxy-phenyl]-furo[3,2-b]pyridin-7-yl}-2-(tetrahydro-pyran-4-ylamino)-benzonitrile (199)

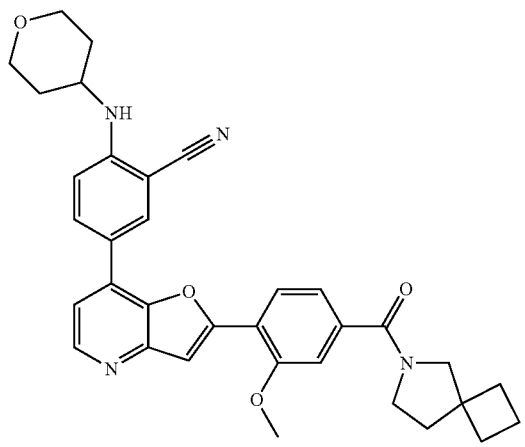 [SMILES: COc1cc(C(=O)N2CCC3(CCC3)C2)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 6-Aza-spiro[3.4]octane (18.95 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (38 mg, 79% yield). MS: m/z=563 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.20 (1H), 2.09 (2H), 1.90 (4H), 1.74 (2H), 1.64 (4H), 1.03 (4H).

Example 180: 5-{2-[2-Methoxy-4-(2-oxa-5-aza-bicyclo[2.2.2]octane-5-carbonyl)-phenyl]-furo[3,2-b]pyridin-7-yl}-2-(tetrahydro-pyran-4-ylamino)-benzonitrile (198)

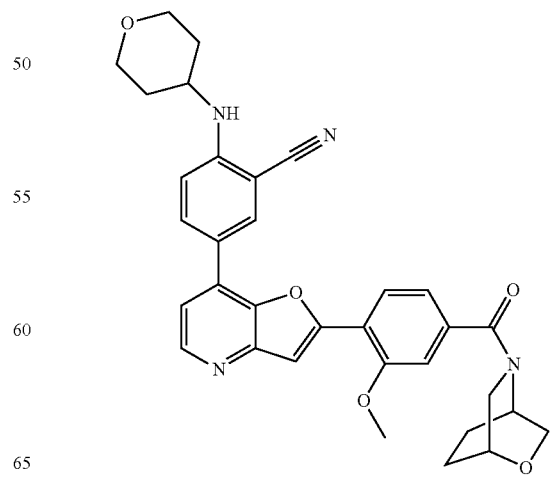

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 2-Oxa-5-aza-bicyclo[2.2.2]octane (19.28 mg; 0.17 mmol; 2.00 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (10.8 mg, 23% yield). MS: m/z=565 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.20 (1H), 2.09 (2H), 1.90 (2H), 1.80 (4H), 1.74 (2H).

Example 181: 5-{2-[2-Methoxy-4-(6-oxa-3-aza-bicyclo[3.1.1]heptane-3-carbonyl)-phenyl]-furo[3,2-b]pyridin-7-yl}-2-(tetrahydro-pyran-4-ylamino)-benzonitrile (197)

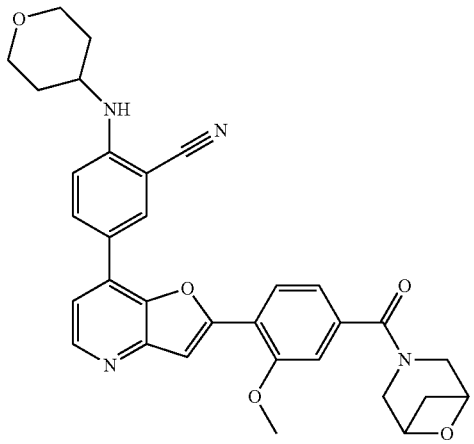 [SMILES: COc1cc(C(=O)N2CC3CC(C2)O3)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 6-Oxa-3-aza-bicyclo[3.1.1]heptane (16.89 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (19.1 mg, 47% yield). MS: m/z=551 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.70 (1H), 4.51 (1H), 4.08 (3H), 4.00 (1H), 3.92 (2H), 3.81 (1H), 3.61 (2H), 3.47 (2H), 3.07 (1H), 1.89 (2H), 1.69 (2H).

Example 182: 5-{2-[4-(7-Hydroxy-3-oxa-9-aza-bicyclo[3.3.1]nonane-9-carbonyl)-2-methoxy-phenyl]-furo[3,2-b]pyridin-7-yl}-2-(tetrahydro-pyran-4-ylamino)-benzonitrile (196)

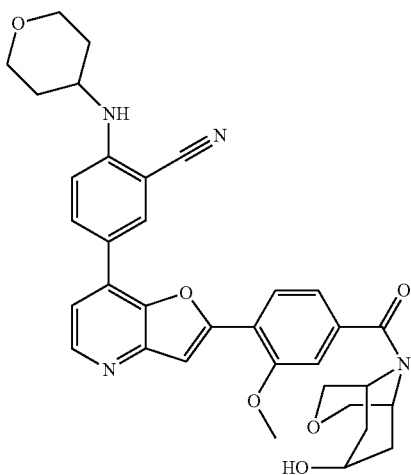 [SMILES: COc1cc(C(=O)N2C3COCC2CC(O)C3)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 3-Oxa-9-aza-bicyclo[3.3.1]nonan-7-ol hydrochloride (30.61 mg; 0.17 mmol; 2.00 eq.)), (3-Dimethylamino-propyl)-ethyl-carbodiimide hydrochloride (19.60 mg; 0.10 mmol; 1.20 eq.)(EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (7.8 mg, 15% yield). MS: m/z=595 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.70 (1H), 4.51 (1H), 4.08 (3H), 4.00 (1H), 3.92 (2H), 3.81 (1H), 3.61 (2H), 3.47 (2H), 3.10 (1H), 2.22 (1H), 2.09 (3H), 1.90-1.74 (4H).

Example 183: 4-{7-[3-Cyano-4-(tetrahydro-pyran-4-ylamino)-phenyl]-furo[3,2-b]pyridin-2-yl}-3-methoxy-N-(3-oxa-bicyclo[3.1.0]hex-6-yl)-benzamide (193)

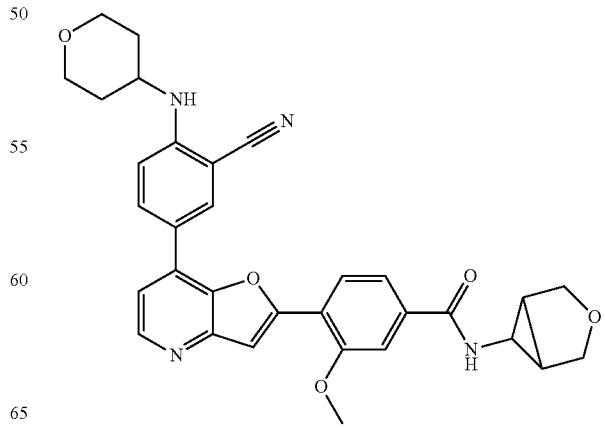

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 3-Oxa-bicyclo[3.1.0]hex-6-ylamine hydrochloride (34.66 mg; 0.26 mmol; 3.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (16.4 mg, 35% yield). MS: m/z=551 (M+H). H NMR (DMSO-d6): 8.55 (1H), 8.30 (2H), 8.05 (1H), 7.66 (2H), 7.43 (2H), 7.20 (1H), 6.27 (1H), 4.97 (2H), 4.70 (1H), 4.51 (1H), 4.08 (3H), 4.00 (1H), 3.92 (2H), 3.81 (1H), 3.61 (2H), 3.47 (2H), 3.10 (1H), 2.22 (1H), 2.09 (3H), 1.94 (1H), 1.90 (2H), 1.74 (2H), 1.06 (2H).

Example 184: 4-{7-[3-Cyano-4-(tetrahydro-pyran-4-yloxy)-phenyl]-furo[3,2-b]pyridin-2-yl}-N-(2,2-difluoro-ethyl)-3-methoxy-N-methyl-benzamide (285)

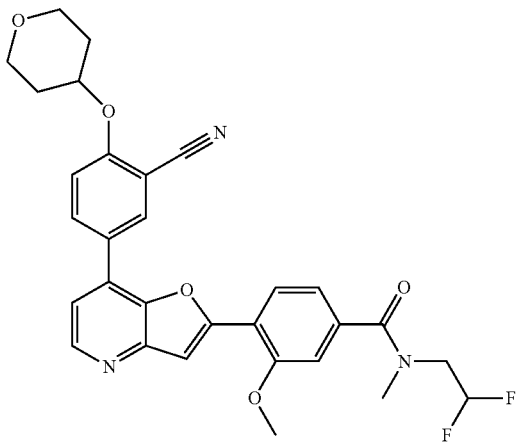 [SMILES: COc1cc(C(=O)N(C)CC(F)F)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), (2,2-Difluoro-ethyl)-methyl-amine hydrochloride (55.92 mg; 0.43 mmol; 2.00 eq.), (3-Dimethylamino-propyl)-ethyl-carbodiimide hydrochloride (48.90 mg; 0.26 mmol; 1.20 eq.)(EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (98 mg, 84% yield). MS: m/z=548 (M+H). H NMR (DMSO-d6): 8.55 (1H), 8.30 (2H), 8.05 (1H), 7.66 (2H), 7.43 (2H), 7.20 (1H), 6.27 (1H), 4.97 (1H), 4.08 (3H), 3.92 (2H), 3.61 (2H), 3.06 (2H), 2.09 (3H), 1.74 (2H).

Example 185: 5-{2-[4-((R)-2-Fluoro-pyrrolidine-1-carbonyl)-phenyl]-furo[3,2-b]pyridin-7-yl}-2-(tetrahydro-pyran-4-yloxy)-benzonitrile (127)

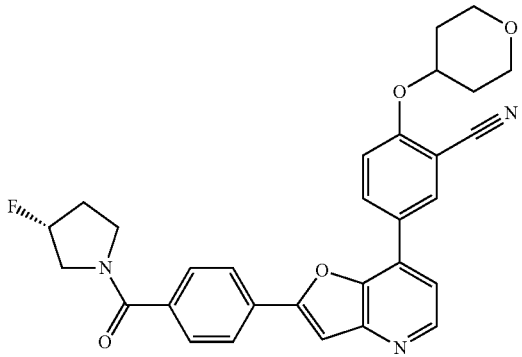 [SMILES: N#Cc1cc(-c2ccnc3cc(-c4ccc(C(=O)N5CC[C@@H](F)C5)cc4)oc23)ccc1OC1CCOCC1]

The title compound was synthesized according to the procedure described in example 109 using 4-{7-[3-Cyano-4-(tetrahydro-pyran-4-yloxy)-phenyl]-furo[3,2-b]pyridin-2-yl}-benzoic acid (50.00 mg; 0.11 mmol; 1.00 eq.), (R)-3-Fluoro-pyrrolidine hydrochloride (17.11 mg; 0.14 mmol; 1.20 eq.), (3-Dimethylamino-propyl)-ethyl-carbodiimide hydrochloride (26.11 mg; 0.14 mmol; 1.20 eq.) (EDCI), Benzotriazol-1-ol (18.41 mg; 0.14 mmol; 1.20 eq.) (HOBt) and Ethyl-diisopropyl-amine (0.06 ml; 0.34 mmol; 3.00 eq.) in DMF (2 mL) (20 mg, 34%) MS: m/z=512 (M+H)$^+$. $^1$H NMR (400 MHz, Chloroform-d) δ 8.63 (d, J=5.1 Hz, 1H), 8.29 (d, J=2.3 Hz, 1H), 8.21 (dd, J=8.8, 2.4 Hz, 1H), 7.97 (d, J=8.2 Hz, 2H), 7.71 (dd, J=18.5, 8.0 Hz, 2H), 7.41-7.33 (m, 2H), 7.23 (d, J=8.9 Hz, 1H), 5.33 (t, J=49.8 Hz, 1H), 4.81 (m, 1H), 4.22-3.53 (m, 8H), 2.53-2.25 (m, 2H), 2.24-2.07 (m, 2H), 2.00 (m, 2H).

Example 186: 5-{2-[4-((S)-3-Fluoro-pyrrolidine-1-carbonyl)-phenyl]-furo[3,2-b]pyridin-7-yl}-2-(tetrahydro-pyran-4-yloxy)-benzonitrile (136)

Chiral

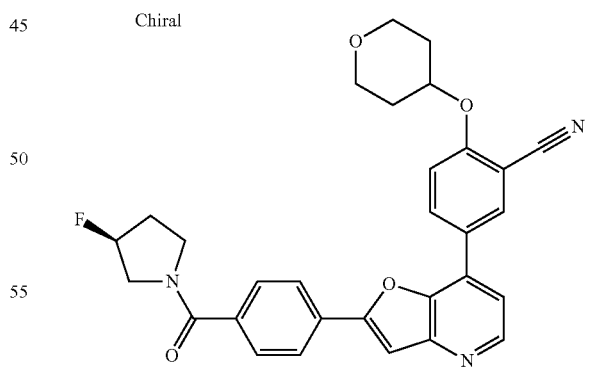

The title compound was synthesized according to the procedure described in example 109 using 4-{7-[3-Cyano-4-(tetrahydro-pyran-4-yloxy)-phenyl]-furo[3,2-b]pyridin-2-yl}-benzoic acid (50.00 mg; 0.11 mmol; 1.00 eq.), (S)-3-Fluoro-pyrrolidine hydrochloride (17.11 mg; 0.14 mmol; 1.20 eq.), (3-Dimethylamino-propyl)-ethyl-carbodiimide hydrochloride (26.11 mg; 0.14 mmol; 1.20 eq.) (EDCI), Benzotriazol-1-ol (18.41 mg; 0.14 mmol; 1.20 eq.) (HOBt)

and Ethyl-diisopropyl-amine (0.06 ml; 0.34 mmol; 3.00 eq.) in DMF (2 mL) (25 mg, 43%). MS: m/z=(M+H) 512. $^1$H NMR (400 MHz, Chloroform-d) δ 8.62 (d, J=5.0 Hz, 1H), 8.34-8.12 (m, 2H), 7.96 (d, J=8.2 Hz, 2H), 7.70 (dd, J=18.5, 8.0 Hz, 2H), 7.44-7.15 (m, 3H), 5.32 (t, J=49.5 Hz, 1H), 4.81 (dq, J=7.2, 3.6 Hz, 1H), 4.19-3.58 (m, 8H), 2.30 (d, J=20.9 Hz, 2H), 2.14 (m, 2H), 1.99 (m, 2H).

Example 187: 5-{2-[4-(3,3-Difluoro-pyrrolidine-1-carbonyl)-phenyl]-furo[3,2-b]pyridin-7-yl}-2-(tetrahydro-pyran-4-yloxy)-benzonitrile (148)

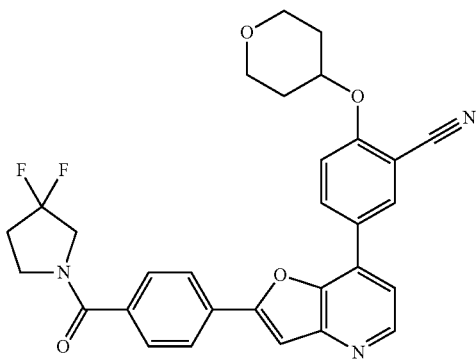 [SMILES: N#Cc1cc(-c2ccnc3cc(-c4ccc(C(=O)N5CCC(F)(F)C5)cc4)oc23)ccc1OC1CCOCC1]

The title compound was synthesized according to the procedure described in example 109 using 4-{7-[3-Cyano-4-(tetrahydro-pyran-4-yloxy)-phenyl]-furo[3,2-b]pyridin-2-yl}-benzoic acid (50.00 mg; 0.11 mmol; 1.00 eq.), 3,3-Difluoro-pyrrolidine hydrochloride (19.56 mg; 0.14 mmol; 1.20 eq.), (3-Dimethylamino-propyl)-ethyl-carbodiimide hydrochloride (26.11 mg; 0.14 mmol; 1.20 eq.) (EDCI), Benzotriazol-1-ol (18.41 mg; 0.14 mmol; 1.20 eq.) (HOBt) and Ethyl-diisopropyl-amine (0.06 ml; 0.34 mmol; 3.00 eq.) in DMF (2 mL) (36 mg, 60%). MS: m/z=(M+H) 530. $^1$H NMR (400 MHz, Chloroform-d) δ 8.62 (d, J=5.0 Hz, 1H), 8.28 (d, J=2.3 Hz, 1H), 8.19 (dd, J=8.9, 2.3 Hz, 1H), 7.97 (d, J=8.2 Hz, 2H), 7.68 (d, J=7.8 Hz, 2H), 7.38 (s, 1H), 7.34 (s, 1H), 7.23 (d, J=8.9 Hz, 1H), 4.81 (dt, J=7.2, 3.6 Hz, 1H), 3.89 (m, 8H), 2.45 (s, 2H), 2.15 (m, 2H), 1.98 (m, 2H).

Example 188: 5-{2-[4-(3-Hydroxy-3-methyl-azetidine-1-carbonyl)-phenyl]-furo[3,2-b]pyridin-7-yl}-2-(tetrahydro-pyran-4-yloxy)-benzonitrile (124)

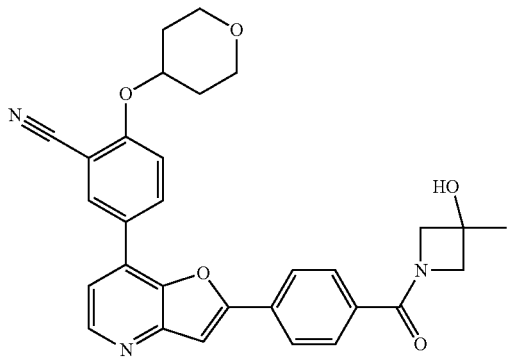 [SMILES: CC1(O)CN(C(=O)c2ccc(-c3cc4nccc(-c5ccc(OC6CCOCC6)c(C#N)c5)c4o3)cc2)C1]

The title compound was synthesized according to the procedure described in example 109 using 4-{7-[3-Cyano-4-(tetrahydro-pyran-4-yloxy)-phenyl]-furo[3,2-b]pyridin-2-yl}-benzoic acid (50.00 mg; 0.11 mmol; 1.00 eq.), 3-Methyl-azetidin-3-ol hydrochloride (16.83 mg; 0.14 mmol; 1.20 eq.)none, (3-Dimethylamino-propyl)-ethyl-carbodiimide hydrochloride (26.11 mg; 0.14 mmol; 1.20 eq.) (EDCI), Benzotriazol-1-ol (18.41 mg; 0.14 mmol; 1.20 eq.) (HOBt) and Ethyl-diisopropyl-amine (0.06 ml; 0.34 mmol; 3.00 eq.) in DMF (2 mL) (15 mg, 26%). MS: m/z=(M+H) 510. $^1$H NMR (400 MHz, Chloroform-d) δ 8.60 (d, J=5.1 Hz, 1H), 8.25 (d, J=2.3 Hz, 1H), 8.20 (dd, J=8.8, 2.3 Hz, 1H), 7.99-7.84 (m, 2H), 7.78 (d, J=8.3 Hz, 2H), 7.34 (d, J=2.3 Hz, 1H), 7.32 (s, 1H), 7.23 (d, J=8.9 Hz, 1H), 4.82 (m, 1H), 4.49-4.33 (m, 2H), 4.21 (m, 4H), 4.09 (m, 2H), 3.71 (m, 2H), 1.99 (m, 2H), 1.61 (s, 3H).

Example 189: 4-{7-[3-Cyano-4-(tetrahydro-pyran-4-yloxy)-phenyl]-furo[3,2-b]pyridin-2-yl}-N-(4-fluoro-piperidin-3-yl)-benzamide (131)

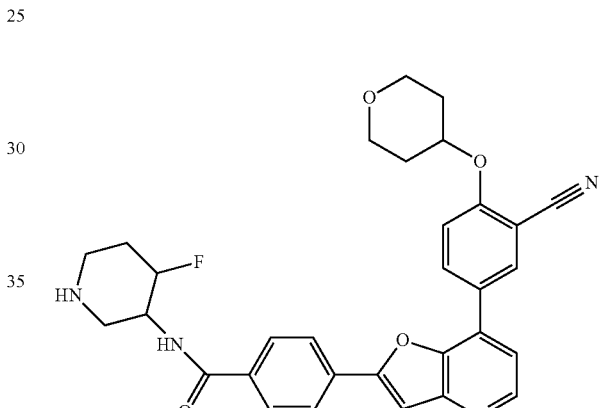

The title compound was synthesized according to the procedure described in example 109 using 4-{7-[3-Cyano-4-(tetrahydro-pyran-4-yloxy)-phenyl]-furo[3,2-b]pyridin-2-yl}-benzoic acid (100.00 mg; 0.23 mmol; 1.00 eq.), 4-Fluoro-piperidin-3-ylamine hydrochloride (2) (52.06 mg; 0.27 mmol; 1.20 eq.), (3-Dimethylamino-propyl)-ethyl-carbodiimide hydrochloride (52.23 mg; 0.27 mmol; 1.20 eq.) (EDCI), Benzotriazol-1-ol (36.81 mg; 0.27 mmol; 1.20 eq.) (HOBt) and Ethyl-diisopropyl-amine (0.12 ml; 0.68 mmol; 3.00 eq.) in DMF (2 mL) (22 mg, 18%). MS: m/z=541 (M+H)$^{+1}$H NMR (400 MHz, Chloroform-d) δ 8.55 (t, J=7.2 Hz, 1H), 8.25 (d, J=5.9 Hz, 1H), 8.22-8.13 (m, 1H), 7.94 (d, J=8.0 Hz, 2H), 7.55 (d, J=7.3 Hz, 2H), 7.35 (d, J=5.3 Hz, 2H), 7.22 (d, J=9.1 Hz, 1H), 4.80 (m, 1H), 4.49 (m, 2H), 4.04 (m, 2H), 3.67 (m, 2H), 3.20 (m, 2H), 2.80 (m, 2H), 2.11 (m, 4H), 2.01-1.84 (m, 2H).

Example 190: 4-{7-[3-Cyano-4-(tetrahydro-pyran-4-yloxy)-phenyl]-furo[3,2-b]pyridin-2-yl}-N-((3R,4R)-4-fluoro-piperidin-3-yl)-benzamide (141)

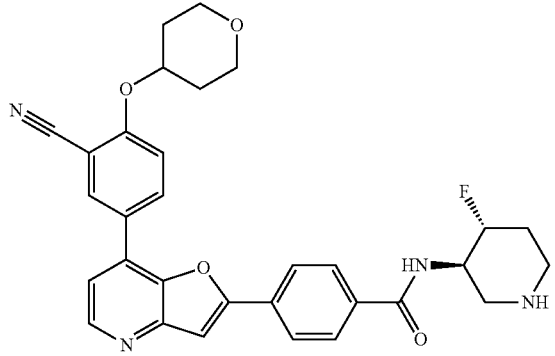 [SMILES: N#Cc1cc(-c2ccnc3cc(-c4ccc(C(=O)N[C@@H]5CNCC[C@H]5F)cc4)oc23)ccc1OC1CCOCC1]

The title compound (32 mg) was separated from 110 mg of racemic 4-{7-[3-Cyano-4-(tetrahydro-pyran-4-yloxy)-phenyl]-furo[3,2-b]pyridin-2-yl}-N-(4-fluoro-piperidin-3-yl)-benzamide. MS: m/z=(M+H) 541.

Example 191: 4-{7-[3-Cyano-4-(tetrahydro-pyran-4-yloxy)-phenyl]-furo[3,2-b]pyridin-2-yl}-N-((3S,4S)-4-fluoro-piperidin-3-yl)-benzamide (135)

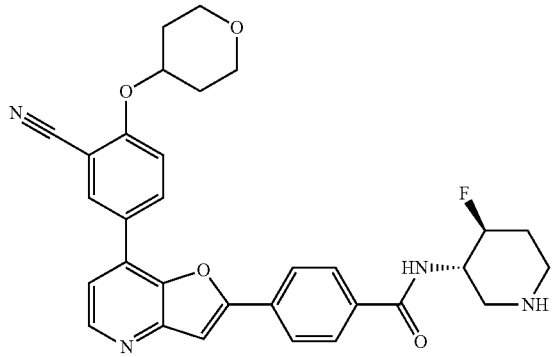 [SMILES: N#Cc1cc(-c2ccnc3cc(-c4ccc(C(=O)N[C@H]5CNCC[C@@H]5F)cc4)oc23)ccc1OC1CCOCC1]

The title compound (32 mg) was separated from 110 mg of racemic 4-{7-[3-Cyano-4-(tetrahydro-pyran-4-yloxy)-phenyl]-furo[3,2-b]pyridin-2-yl}-N-(4-fluoro-piperidin-3-yl)-benzamide. MS: m/z=(M+H) 541.

Example 192: 5-{2-[4-(4-Isopropyl-piperazine-1-carbonyl)-phenyl]-furo[3,2-b]pyridin-7-yl}-2-(tetrahydro-pyran-4-yloxy)-benzonitrile (116)

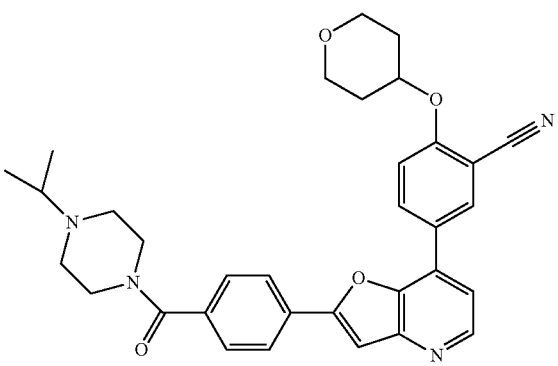 [SMILES: CC(C)N1CCN(C(=O)c2ccc(-c3cc4nccc(-c5ccc(OC6CCOCC6)c(C#N)c5)c4o3)cc2)CC1]

The title compound was synthesized according to the procedure described in example 109 using 4-{7-[3-Cyano-4-(tetrahydro-pyran-4-yloxy)-phenyl]-furo[3,2-b]pyridin-2-yl}-benzoic acid (50.00 mg; 0.11 mmol; 1.00 eq.), 1-Isopropyl-piperazine (17.47 mg; 0.14 mmol; 1.20 eq.), (3-Dimethylamino-propyl)-ethyl-carbodiimide hydrochloride (26.11 mg; 0.14 mmol; 1.20 eq.) (EDCI), Benzotriazol-1-ol (18.41 mg; 0.14 mmol; 1.20 eq.) (HOBt) and Ethyl-diisopropyl-amine (0.06 ml; 0.34 mmol; 3.00 eq.) in DMF (5.0 mL) (15 mg, 24%). MS: m/z=(M+H) 551.

Example 193: 5-{2-[4-(4-Cyclopropyl-piperazine-1-carbonyl)-phenyl]-furo[3,2-b]pyridin-7-yl}-2-(tetrahydro-pyran-4-yloxy)-benzonitrile (133)


The title compound was synthesized according to the procedure described in example 109 using 4-{7-[3-Cyano-4-(tetrahydro-pyran-4-yloxy)-phenyl]-furo[3,2-b]pyridin-2-yl}-benzoic acid (100.00 mg; 0.23 mmol; 1.00 eq.), 1-Cyclopropyl-piperazine (34.38 mg; 0.27 mmol; 1.20 eq.), (3-Dimethylamino-propyl)-ethyl-carbodiimide hydrochloride (52.23 mg; 0.27 mmol; 1.20 eq.) (EDCI), Benzotriazol-1-ol (36.81 mg; 0.27 mmol; 1.20 eq.) (HOBt) and Ethyl-diisopropyl-amine (0.12 ml; 0.68 mmol; 3.00 eq.) in DMF (5.0 mL) (84 mg, 67%). MS: m/z=(M+H) 549.

Example 194: N-(1-Aza-bicyclo[2.2.2]oct-3-yl)-4-{7-[3-cyano-4-(tetrahydro-pyran-4-yloxy)-phenyl]-furo[3,2-b]pyridin-2-yl}-benzamide (145)

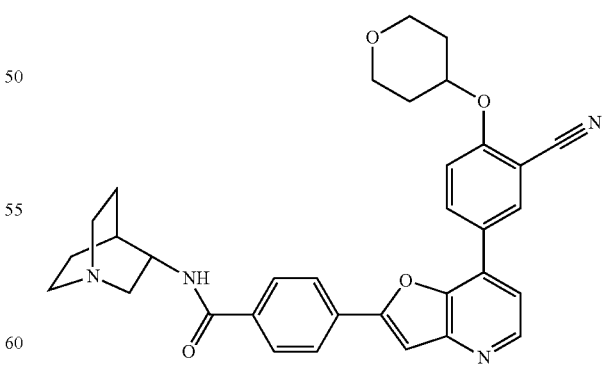

The title compound was synthesized according to the procedure described in example 109 using 4-{7-[3-Cyano-4-(tetrahydro-pyran-4-yloxy)-phenyl]-furo[3,2-b]pyridin-2-yl}-benzoic acid (85.00 mg; 0.19 mmol; 1.00 eq.), (3-Dimethylamino-propyl)-ethyl-carbodiimide hydrochloride (44.39 mg; 0.23 mmol; 1.20 eq.) (EDCI), Benzotriazol-1-ol (31.29 mg; 0.23 mmol; 1.20 eq.) (HOBt) and Ethyl-diisopropyl-amine (0.17 ml; 0.96 mmol; 5.00 eq.) in DMF (5.0 mL) (74 mg, 70%). MS: m/z=(M+H) 549. ¹H NMR (400 MHz, Chloroform-d) δ 8.64-8.57 (m, 1H), 8.29 (d, J=2.3 Hz, 1H), 8.19 (d, J=8.6 Hz, 1H), 7.95 (d, J=2.3 Hz, 4H), 7.39-7.31 (m, 2H), 7.22 (d, J=8.9 Hz, 1H), 4.82 (m, 1H), 4.22 (s, 1H), 4.16-4.03 (m, 2H), 3.78-3.64 (m, 2H), 3.56-3.24 (m, 2H), 3.10-2.63 (m, 5H), 2.20-2.08 (m, 2H), 2.01 (m, 2H), 1.89-1.51 (m, 5H).

Example 195: N-(1-Aza-bicyclo[2.2.2]oct-3-yl)-4-{7-[3-cyano-4-(tetrahydro-pyran-4-yloxy)-phenyl]-furo[3,2-b]pyridin-2-yl}-3-fluoro-benzamide (139)

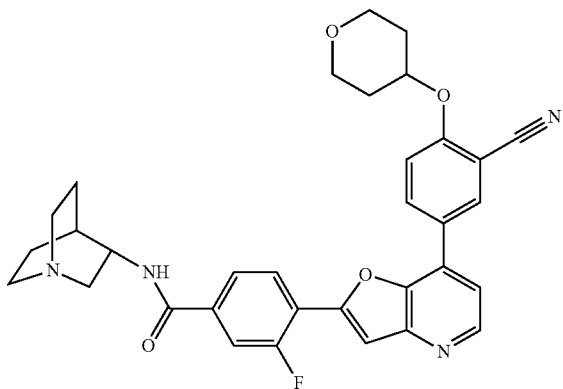 [SMILES: N#Cc1cc(-c2ccnc3cc(-c4ccc(C(=O)NC5CN6CCC5CC6)cc4F)oc23)ccc1OC1CCOCC1]

The title compound was synthesized according to the procedure described in example 109 using 4-{7-[3-Cyano-4-(tetrahydro-pyran-4-yloxy)-phenyl]-furo[3,2-b]pyridin-2-yl}-3-fluoro-benzoic acid (75.00 mg; 0.16 mmol; 1.00 eq.), (3-Dimethylamino-propyl)-ethyl-carbodiimide hydrochloride (37.63 mg; 0.20 mmol; 1.20 eq.) (EDCI), Benzotriazol-1-ol (26.53 mg; 0.20 mmol; 1.20 eq.) (HOBt) and Ethyl-diisopropyl-amine (0.14 ml; 0.82 mmol; 5.00 eq.) in DMF (3.0 mL) (17 mg, 13%). MS: m/z=(M+H) 567.

Example 196: 4-{7-[3-Cyano-4-(tetrahydro-pyran-4-yloxy)-phenyl]-furo[3,2-b]pyridin-2-yl}-3,N-dimethoxy-N-methyl-benzamide (53)

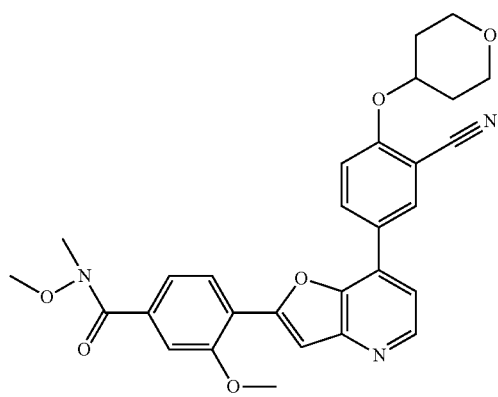 [SMILES: COc1cc(C(=O)N(C)OC)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), O,N-Dimethyl-hydroxylamine; Hydrochloride (37.32 mg; 0.38 mmol; 1.20 eq.), (3-Dimethylamino-propyl)-ethyl-carbodiimide hydrochloride (73.34 mg; 0.38 mmol; 1.20 eq.) (EDCI), Benzotriazol-1-ol (51.70 mg; 0.38 mmol; 1.20 eq.) (HOBt) and Ethyl-diisopropyl-amine (0.17 ml; 0.96 mmol; 3.00 eq.) in DMF (3.0 mL) (129 mg, 79%). MS: m/z=514 (M+H)⁺¹H NMR (400 MHz, Chloroform-d) δ 8.61 (d, J=4.0 Hz, 1H), 8.40-8.17 (m, 2H), 8.03 (dd, J=8.4, 2.7 Hz, 1H), 7.76 (d, J=3.9 Hz, 1H), 7.49 (d, J=2.3 Hz, 1H), 7.43 (d, J=2.4 Hz, 1H), 7.39 (s, 1H), 7.24 (dd, J=9.1, 2.7 Hz, 1H), 4.92-4.69 (m, 1H), 4.18-4.02 (m, 5H), 3.72 (dd, J=7.9, 3.7 Hz, 1H), 3.64 (d, J=2.4 Hz, 3H), 3.43 (d, J=2.8 Hz, 3H), 2.22-2.09 (m, 2H), 2.00 (dt, J=10.2, 3.6 Hz, 2H).

Example 197: 5-{2-[4-(3,3-Difluoro-azetidine-1-carbonyl)-2-methoxy-phenyl-furo[3,2-b]pyridin-7-yl}-2-(tetrahydro-pyran-4-yloxy)-benzonitrile (77)

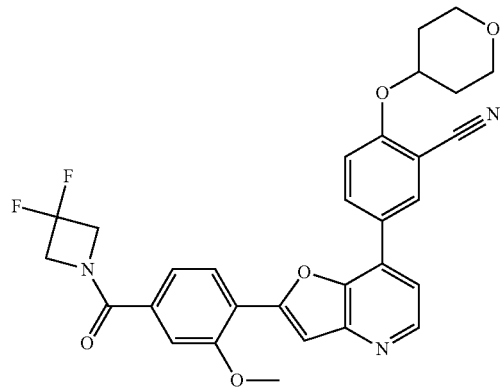 [SMILES: COc1cc(C(=O)N2CC(F)(F)C2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 3,3-Difluoro-azetidine (35.61 mg; 0.38 mmol; 1.20 eq.), (3-Dimethylamino-propyl)-ethyl-carbodiimide hydrochloride (73.34 mg; 0.38 mmol; 1.20 eq.) (EDCI), Benzotriazol-1-ol (51.70 mg; 0.38 mmol; 1.20 eq.) (HOBt) and Ethyl-diisopropyl-amine (0.28 ml; 1.59 mmol; 5.00 eq.) in DMF (3.0 mL) (110 mg, 63%). MS: m/z=546 (M+H)⁺¹H NMR (400 MHz, DMSO-d₆) δ 8.60-8.53 (m, 1H), 8.47-8.38 (m, 2H), 8.03 (dd, J=8.0, 2.3 Hz, 1H), 7.69-7.57 (m, 3H), 7.49-7.38 (m, 2H), 4.96 (m, 1H), 4.09 (d, J=2.4 Hz, 3H), 4.04 (s, 4H), 3.92 (m, 2H), 3.58 (m, 2H), 2.08 (m, 2H), 1.74 (m, 2H).

Example 198: 4-{7-[3-Cyano-4-(tetrahydro-pyran-4-yloxy)-phenyl]-furo[3,2-b]pyridin-2-yl}-N—((R)-2,3-dihydroxy-propyl)-3-methoxy-benzamide (49)

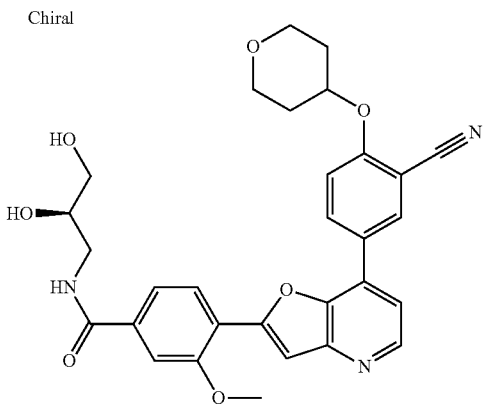 [SMILES: COc1cc(C(=O)NC[C@@H](O)CO)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (75.00 mg; 0.16 mmol; 1.00 eq.), (R)-3-Amino-propane-1,2-diol (17.43 mg; 0.19 mmol; 1.20 eq.), (3-Dimethylamino-propyl)-ethyl-carbodiimide hydrochloride (36.67 mg; 0.19 mmol; 1.20 eq.) (EDCI), Benzotriazol-1-ol (25.85 mg; 0.19 mmol; 1.20 eq.) (HOBt) and Ethyl-diisopropyl-amine (0.14 ml; 0.80 mmol; 5.00 eq.) in DMF (3.0 mL) (21, 24%). MS: m/z=545. $^1$H NMR (400 MHz, Chloroform-d) δ 8.48 (d, J=5.3 Hz, 1H), 8.31-8.10 (m, 2H), 7.95 (d, J=8.0 Hz, 1H), 7.64 (s, 1H), 7.58-7.37 (m, 2H), 7.22 (d, J=9.0 Hz, 2H), 4.78 (m, 1H), 4.04 (s, 5H), 3.79 (m, 1H), 3.80 (m, 2H), 3.54-3.22 (m, 4H), 2.08 (m, 2H), 1.98-1.79 (m, 2H).

Example 199: 4-{7-[3-Cyano-4-(tetrahydro-pyran-4-yloxy)-phenyl]-furo[3,2-b]pyridin-2-yl}-3-methoxy-N-(oxetan-3-yloxy)-benzamide (80)

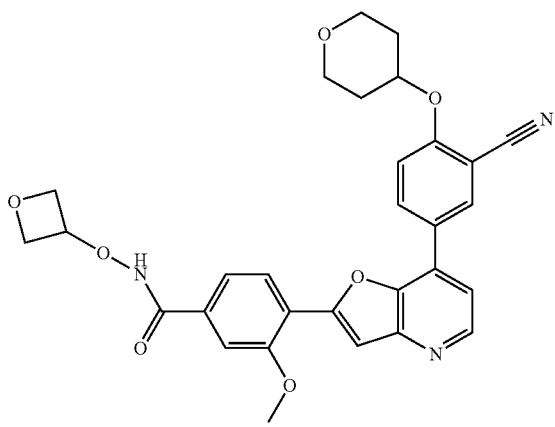 [SMILES: COc1cc(C(=O)NOC2COC2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (75.00 mg; 0.16 mmol; 1.00 eq.), O-Oxetan-3-yl-hydroxylamine (18.46 mg; 0.21 mmol; 1.30 eq.), (3-Dimethylamino-propyl)-ethyl-carbodiimide hydrochloride (36.67 mg; 0.19 mmol; 1.20 eq.) (EDCI), Benzotriazol-1-ol (25.85 mg; 0.19 mmol; 1.20 eq.) (HOBt) and Ethyl-diisopropyl-amine (0.14 ml; 0.80 mmol; 5.00 eq.) in DMF (3.0 mL) (12 mg, 14%). MS: m/z=(M+H) 542.

Example 200: 5-{2-[4-(3,3-Difluoro-pyrrolidine-1-carbonyl)-2-methoxy-phenyl]-furo[3,2-b]pyridin-7-yl}-2-(tetrahydro-pyran-4-yloxy)-benzonitrile (45)

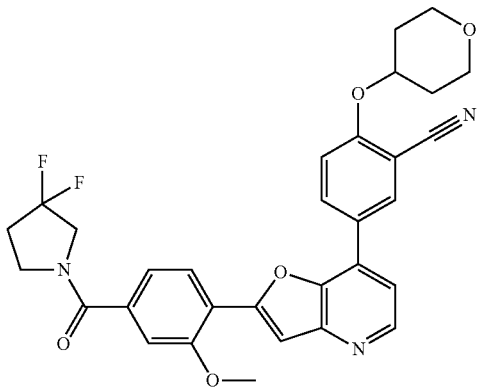 [SMILES: COc1cc(C(=O)N2CCC(F)(F)C2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 3,3-Difluoro-pyrrolidine; Hydrochloride (54.93 mg; 0.38 mmol; 1.20 eq.), (3-Dimethylamino-propyl)-ethyl-carbodiimide hydrochloride (73.34 mg; 0.38 mmol; 1.20 eq.) (EDCI), Benzotriazol-1-ol (51.70 mg; 0.38 mmol; 1.20 eq.) (HOBt) and Ethyl-diisopropyl-amine (0.28 ml; 1.59 mmol; 5.00 eq.) in DMF (3.0 mL) (110 mg, 62%). MS: m/z=560. $^1$H NMR (400 MHz, Chloroform-d) δ 8.60 (t, J=3.6 Hz, 1H), 8.30 (s, 1H), 8.18 (d, J=8.9 Hz, 1H), 8.08-7.99 (m, 1H), 7.69 (d, J=3.3 Hz, 1H), 7.37-7.31 (m, 1H), 7.28 (d, J=8.5 Hz, 1H), 7.25-7.16 (m, 2H), 4.81 (dt, J=7.5, 3.7 Hz, 1H), 4.09 (s, 3H), 4.10 (m, 2H), 3.87 (m, 4H), 3.70 (m, 2H), 2.45 (m, 2H), 2.14 (m, 2H), 2.06-1.87 (m, 2H).

Example 201: 4-{7-[3-Cyano-4-(tetrahydro-pyran-4-yloxy)-phenyl]-furo[3,2-b]pyridin-2-yl}-N-cyclopropyl-3-methoxy-N-methyl-benzamide (60) (HATU-Method)

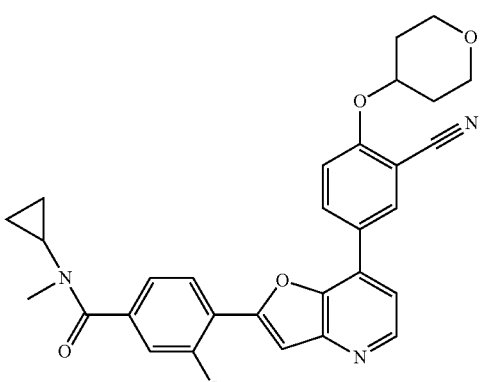

A mixture of 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), Cyclopropyl-methyl-amine (27.21 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) was stirred at room temperature overnight. The reaction mixture was purified on reverse phase HPLC to obtain the title compound (107 mg, 64%). MS: m/z=524 (M+H)+ $^1$H NMR (400 MHz, Chloroform-d) δ 8.59 (t, J=3.3 Hz, 1H), 8.30 (d, J=3.5 Hz, 1H), 8.25-8.11 (m, 1H), 8.00 (dd, J=8.3, 2.6 Hz, 1H), 7.74-7.59 (m, 1H), 7.33-7.27 (m, 2H), 7.25-7.18 (m, 2H), 4.80 (m, 1H), 4.13 (m, 2H), 4.07 (s, 3H), 3.69 (m, 2H), 3.14 (s, 3H), 2.13 (m, 2H), 1.98 (m, 2H), 1.27 (tt, J=7.2, 1.8 Hz, 1H), 0.69 (m, 2H), 0.56 (m, 2H).

Example 202: 5-{2-[2-Methoxy-4-(pyrrolidine-1-carbonyl)-phenyl]-furo[3,2-b]pyridin-7-yl}-2-(tetrahydro-pyran-4-yloxy)-benzonitrile (37)

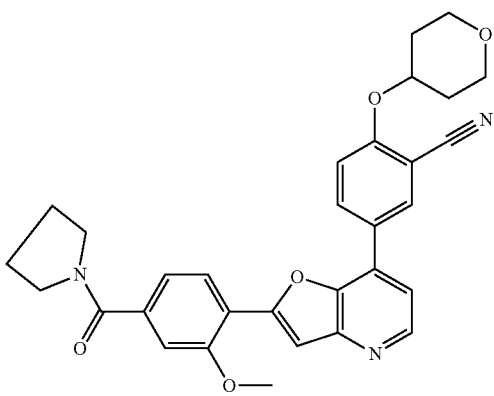 [SMILES: COc1cc(C(=O)N2CCCC2)ccc1-c1cc2nccc(-c3ccc(OC4CCOCC4)c(C#N)c3)c2o1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), Pyrrolidine (0.03 ml; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) (15 mg, 9%). MS: m/z=524 (M+H)+$^1$H NMR (400 MHz, Chloroform-d) δ 8.61 (dd, J=5.5, 2.6 Hz, 1H), 8.34 (t, J=2.7 Hz, 1H), 8.28-8.15 (m, 1H), 8.03 (dd, J=7.7, 2.6 Hz, 1H), 7.76 (d, J=5.6 Hz, 1H), 7.40 (d, J=5.9 Hz, 1H), 7.29 (d, J=3.0 Hz, 2H), 7.27-7.21 (m, 1H), 4.83 (m, 1H), 4.09 (s, 3H), 4.10-3.98 (m, 5H), 3.71 (td, J=7.7, 3.1 Hz, 4H), 3.59-3.43 (m, 2H), 2.16 (ddd, J=11.5, 7.5, 3.6 Hz, 2H), 2.08-1.89 (m, 6H).

Example 203: 5-{2-[4-((R)-3-Fluoro-pyrrolidine-1-carbonyl)-2-methoxy-phenyl]-furo[3,2-b]pyridin-7-yl}-2-(tetrahydro-pyran-4-yloxy)-benzonitrile (17)

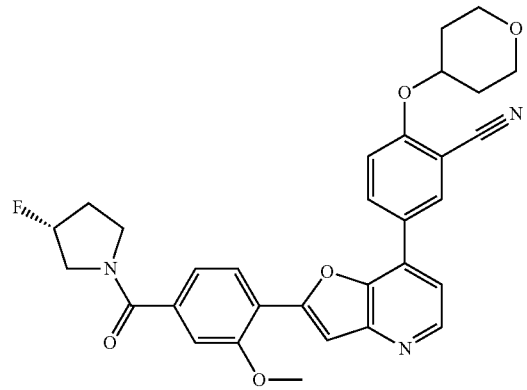 [SMILES: COc1cc(C(=O)N2CC[C@@H](F)C2)ccc1-c1cc2nccc(-c3ccc(OC4CCOCC4)c(C#N)c3)c2o1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), (R)-3-Fluoro-pyrrolidine; Hydrochloride (48.04 mg; 0.38 mmol; 1.20 eq.), [Dimethylamino-([1,2,3]triazolo[4,5-b]pyridin-3-yloxy)-methylene]-dimethyl-ammonium; hexafluoro phosphate (145.47 mg; 0.38 mmol; 1.20 eq.), and Ethyl-diisopropyl-amine (0.17 ml; 0.96 mmol; 3.00 eq.) in DMF (3.0 mL) (50 mg, 29%). MS: m/z=542 (M+H)+$^1$H NMR (400 MHz, Chloroform-d) δ 8.61 (d, J=5.1 Hz, 1H), 8.29 (d, J=2.3 Hz, 1H), 8.20 (dd, J=8.8, 2.4 Hz, 1H), 7.95 (d, J=8.2 Hz, 2H), 7.72 (dd, J=18.5, 8.0 Hz, 1H), 7.41-7.33 (m, 2H), 7.23 (d, J=8.9 Hz, 1H), 5.33 (t, J=49.8 Hz, 1H), 5.33 (m, 1H), 4.11 (s, 3H), 4.22-3.53 (m, 8H), 2.53-2.25 (m, 2H), 2.24-2.07 (m, 2H), 2.00 (m, 2H).

Example 204: 5-{2-[4-(3-Hydroxy-3-methyl-azetidine-1-carbonyl)-2-methoxy-phenyl]-furo[3,2-b]pyridin-7-yl}-2-(tetrahydro-pyran-4-yloxy)-benzonitrile (48)

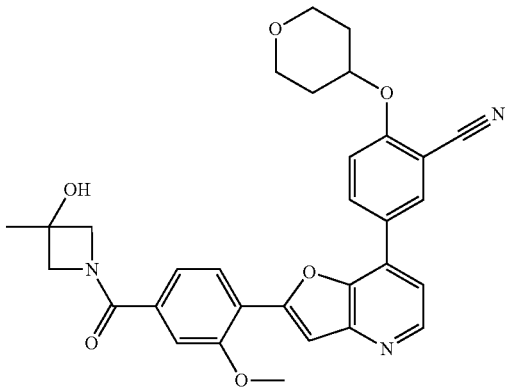 [SMILES: COc1cc(C(=O)N2CC(C)(O)C2)ccc1-c1cc2nccc(-c3ccc(OC4CCOCC4)c(C#N)c3)c2o1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 3-Methyl-azetidin-3-ol hydrochloride (47.28 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) (80 mg, 47%). MS: m/z=511 (M+H)$^+$ 1H NMR (400 MHz, Chloroform-d) δ 8.53 (dd, J=5.1, 2.4 Hz, 1H), 8.23 (d, J=2.8 Hz, 1H), 8.14 (d, J=8.8 Hz, 1H), 7.91 (dd, J=8.2, 2.3 Hz, 1H), 7.66-7.44 (m, 1H), 7.36 (d, J=2.4 Hz, 1H), 7.32-7.24 (m, 2H), 7.20 (dd, J=8.7, 2.3 Hz, 1H), 4.80 (m, 1H), 4.50-4.14 (m, 4H), 4.03 (s, 3H) 4.14-3.92 (m, 2H), 3.69 (m, 2H), 2.22-2.08 (m, 2H), 2.05-1.91 (m, 2H), 1.61 (d, J=2.5 Hz, 3H).

Example 205: 4-{7-[3-Cyano-4-(tetrahydro-pyran-4-yloxy)-phenyl]-furo[3,2-b]pyridin-2-yl}-N-(2-hydroxy-2-methyl-propyl)-3-methoxy-benzamide (207)

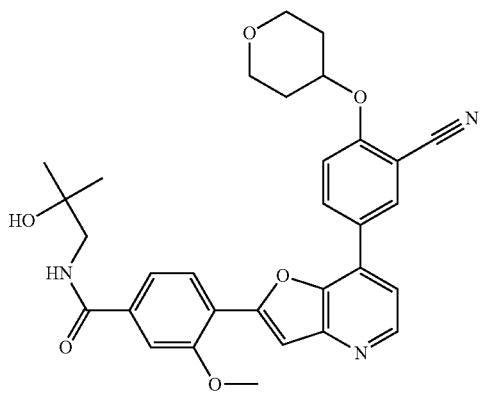 [SMILES: COc1cc(C(=O)NCC(C)(C)O)ccc1-c1cc2nccc(-c3ccc(OC4CCOCC4)c(C#N)c3)c2o1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 1-Amino-2-methyl-propan-2-ol (34.10 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) (105 mg, 61%). MS: m/z=511 (M+H)$^{+1}$H NMR (400 MHz, Chloroform-d) δ 8.50 (dd, J=5.3, 2.8 Hz, 1H), 8.21 (d, J=3.8 Hz, 1H), 8.14-8.05 (m, 1H), 7.94-7.80 (m, 1H), 7.55 (d, J=2.9 Hz, 2H), 7.41 (d, J=8.1 Hz, 1H), 7.26-7.21 (m, 1H), 7.19-7.13 (m, 1H), 7.06 (br s, 1H), 4.78 (m, 1H), 4.03 (s, 3H), 4.17-3.93 (m, 2H), 3.69 (m, 2H), 3.54 (m, 2H), 2.13 (m, 2H), 1.96 (m, 2H), 1.50-1.28 (m, 6H).

Example 206: 5-{2-[4-(3-Methanesulfonyl-azetidine-1-carbonyl)-2-methoxy-phenyl]-furo[3,2-b]pyridin-7-yl}-2-(tetrahydro-pyran-4-yloxy)-benzonitrile (26)

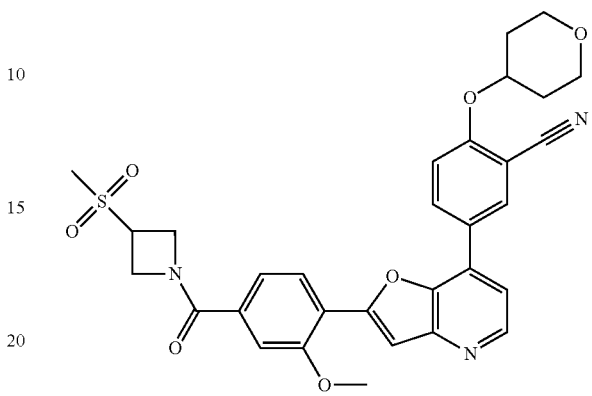

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 3-Methanesulfonyl-azetidine hydrochloride (65.67 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) (95 mg, 51%). MS: m/z=588 (M+H)$^{+1}$H NMR (400 MHz, Chloroform-d) δ 8.69-8.50 (m, 1H), 8.27 (q, J=2.3 Hz, 1H), 8.17 (d, J=8.5 Hz, 1H), 7.99 (dt, J=7.9, 2.3 Hz, 1H), 7.76-7.60 (m, 1H), 7.42 (d, J=3.0 Hz, 1H), 7.33-7.24 (m, 2H), 7.21 (dd, J=8.9, 2.6 Hz, 1H), 4.80 (m, 1H), 4.58 (m, 4H), 4.06 (s, 3H), 4.17-3.97 (m, 3H), 3.69 (m, 2H), 2.96 (s, 3H), 2.13 (m, 2H), 2.04-1.85 (m, 2H).

Example 207: 5-{2-[2-Methoxy-4-(piperidine-1-carbonyl)-phenyl]-furo[3,2-b]pyridin-7-yl}-2-(tetrahydro-pyran-4-yloxy)-benzonitrile (27)

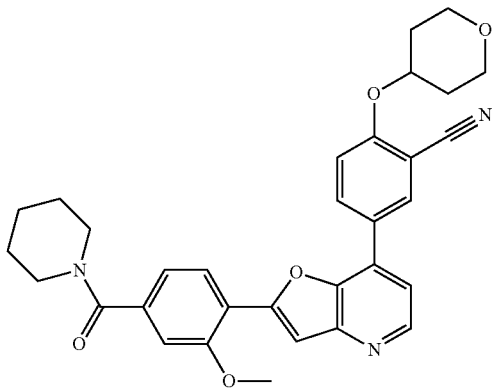 [SMILES: COc1cc(C(=O)N2CCCCC2)ccc1-c1cc2nccc(-c3ccc(OC4CCOCC4)c(C#N)c3)c2o1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), Piperidine (32.58 mg; 0.38 mmol; 1.20 eq.), [Dimethylamino-([1,2,3]triazolo[4,5-b]pyridin-3-yloxy)-methyl-ene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) (120 mg, 70%). MS: m/z=538 (M+H)+ ¹H NMR (400 MHz, Chloroform-d) δ 8.67-8.51 (m, 1H), 8.30 (s, 1H), 8.22 (d, J=8.8 Hz, 1H), 8.02 (dd, J=7.9, 2.4 Hz, 1H), 7.68 (d, J=2.8 Hz, 1H), 7.35 (t, J=4.0 Hz, 1H), 7.24 (dd, J=8.8, 2.5 Hz, 1H), 7.13 (d, J=9.7 Hz, 2H), 4.88-4.75 (m, 1H), 4.08 (s, 3H) 4.24-3.99 (m, 2H), 3.88-3.63 (m, 4H), 3.43 (m, 2H), 2.15 (m, 2H), 1.99 (m, 2H), 1.67 (m, 6H).

Example 208: 5-{2-[4-(2-Difluoromethyl-pyrrolidine-1-carbonyl)-2-methoxy-phenyl]-furo[3,2-b]pyridin-7-yl}-2-(tetrahydro-pyran-4-yloxy)-benzonitrile (89)

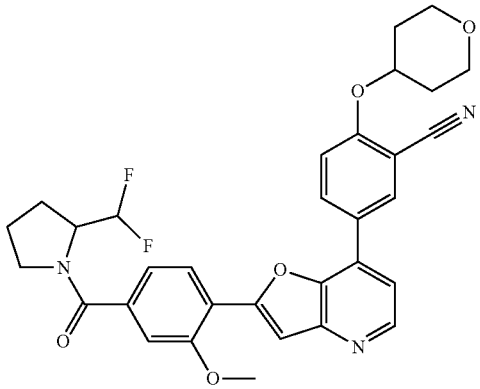 [SMILES: COc1cc(C(=O)N2CCCC2C(F)F)ccc1-c1cc2nccc(-c3ccc(OC4CCOCC4)c(C#N)c3)c2o1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), (R)-2-Difluoromethyl-pyrrolidine hydrochloride (40.20 mg; 0.26 mmol; 1.20 eq.), [Dimethylamino-([1,2,3]triazolo[4,5-b]pyridin-3-yloxy)-methylene]-dimethyl-ammonium; hexafluoro phosphate (HATU) (96.98 mg; 0.26 mmol; 1.20 eq.), and Ethyl-diisopropyl-amine (0.19 ml; 1.06 mmol; 5.00 eq.) in DMF (3.0 mL) (106 mg, 87%). MS: m/z=574 (M+H)+¹H NMR (400 MHz, Chloroform-d) δ 8.61 (d, J=4.2 Hz, 1H), 8.30 (d, J=3.1 Hz, 1H), 8.20 (d, J=8.9 Hz, 1H), 8.07-7.93 (m, 1H), 7.69 (d, J=3.3 Hz, 1H), 7.33 (d, J=4.3 Hz, 1H), 7.28 (d, J=7.7 Hz, 2H), 7.25-7.16 (m, 1H), 6.38 (t, J=57.2 Hz, 1H), 4.81 (m, 1H), 4.62 (m, 1H), 4.08 (s, 3H), 4.24-4.01 (m, 2H), 3.70 (m, 2H), 3.61 (m, 2H), 2.34-1.81 (m, 8H).

Example 209: 5-{2-[4-(3-Hydroxy-piperidine-1-carbonyl)-2-methoxy-phenyl]-furo[3,2-b]pyridin-7-yl}-2-(tetrahydro-pyran-4-yloxy)-benzonitrile (22)

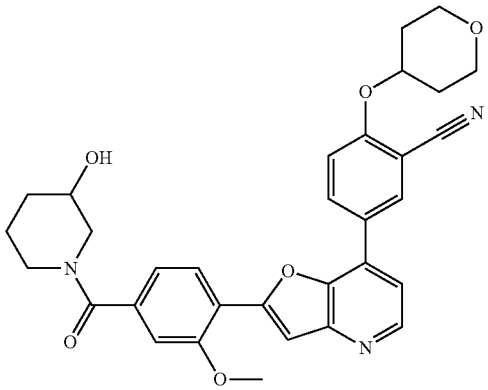 [SMILES: COc1cc(C(=O)N2CCCC(O)C2)ccc1-c1cc2nccc(-c3ccc(OC4CCOCC4)c(C#N)c3)c2o1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), Piperidin-3-ol hydrochloride (52.65 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) (106 mg, 60%). MS: m/z=574 (M+H)+¹H NMR (400 MHz, Chloroform-d) δ 8.52 (d, J=5.3 Hz, 1H), 8.30-8.07 (m, 2H), 7.93 (s, 1H), 7.58 (d, J=11.9 Hz, 1H), 7.27 (m, 1H), 7.15 (d, J=7.6 Hz, 2H), 4.8 (m, 1H), 4.06 (s, 3H), 4.05 (m, 2H), 3.83 (s, 1H), 3.68 (m, 2H), 3.64-3.12 (m, 4H), 2.21-2.06 (m, 2H), 1.96 (m, 4H), 1.70 (m, 2H).

Example 210: 5-{2-[4-(3-Hydroxy-3-methyl-pyrrolidine-1-carbonyl)-2-methoxy-phenyl]-furo[3,2-b]pyridin-7-yl}-2-(tetrahydro-pyran-4-yloxy)-benzonitrile (19)

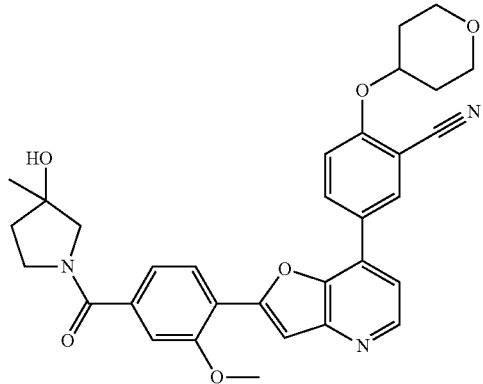 [SMILES: COc1cc(C(=O)N2CCC(C)(O)C2)ccc1-c1cc2nccc(-c3ccc(OC4CCOCC4)c(C#N)c3)c2o1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 3-Methyl-pyrrolidin-3-ol hydrochloride (52.65 mg; 0.38 mmol; 1.20 eq.), [Dimethylamino-([1,2,3]triazolo[4,5- b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) (115 mg, 65%). MS: m/z=574 (M+H)+ $^1$H NMR (400 MHz, Chloroform-d) δ 8.52 (d, J=4.7 Hz, 1H), 8.23 (s, 1H), 8.16 (d, J=8.4 Hz, 1H), 7.94 (dd, J=8.1, 3.2 Hz, 1H), 7.59 (d, J=3.4 Hz, 1H), 7.30-7.22 (m, 3H), 7.18 (d, J=9.0 Hz, 1H), 4.92-4.67 (m, 1H), 4.04 (s, 3H), 4.10-1.0 (m, 2H), 3.98-3.38 (m, 6H), 2.11 (m, 2H), 2.05-1.84 (m, 3H), 1.47 (m, 2H), 1.01 (s, 3H).

Example 211: 4-{7-[3-Cyano-4-(tetrahydro-pyran-4-yloxy)-phenyl]-furo[3,2-b]pyridin-2-yl}-3-methoxy-N-(tetrahydro-pyran-4-yl)-benzamide (83)

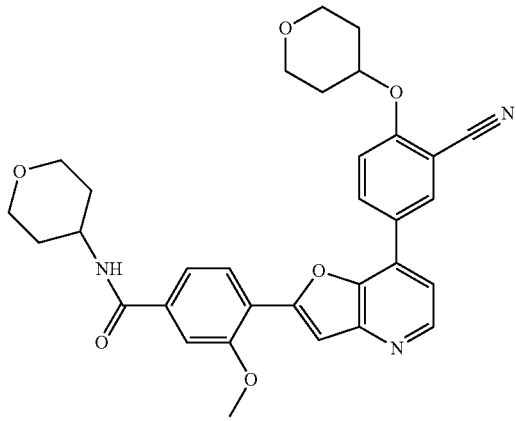 [SMILES: COc1cc(C(=O)NC2CCOCC2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (75.00 mg; 0.16 mmol; 1.00 eq.), Tetrahydro-pyran-4-ylamine (20.96 mg; 0.21 mmol; 1.30 eq.), (3-Dimethylamino-propyl)-ethyl-carbodiimide hydrochloride (36.67 mg; 0.19 mmol; 1.20 eq.) (EDCI), Benzotriazol-1-ol (25.85 mg; 0.19 mmol; 1.20 eq.) (HOBt) and Ethyl-diisopropyl-amine (0.14 ml; 0.80 mmol; 5.00 eq.) in DMF (3.0 mL) (25 mg, 28%). MS: m/z=554 (M+H)+. $^1$H NMR (400 MHz, Chloroform-d) δ 8.34 (s, 1H), 8.19 (dd, J=8.8, 2.2 Hz, 1H), 7.97 (d, J=7.9 Hz, 1H), 7.72 (s, 1H), 7.59 (s, 1H), 7.41 (d, J=8.2 Hz, 2H), 7.36-7.16 (m, 2H), 6.48 (d, J=7.6 Hz, 1H), 4.93-4.74 (m, 1H), 4.35-4.18 (m, 1H), 4.09 (s, 3H) 4.13-1.03 (m, 4H), 3.71 (m, 2H), 3.59 (t, J=11.6 Hz, 2H), 2.07 (m, 6H), 1.70 (m, 2H).

Example 212: 4-{7-[3-Cyano-4-(tetrahydro-pyran-4-yloxy)-phenyl]-furo[3,2-b]pyridin-2-yl}-3-methoxy-N-methyl-N-pyrrolidin-3-yl-benzamide (56)

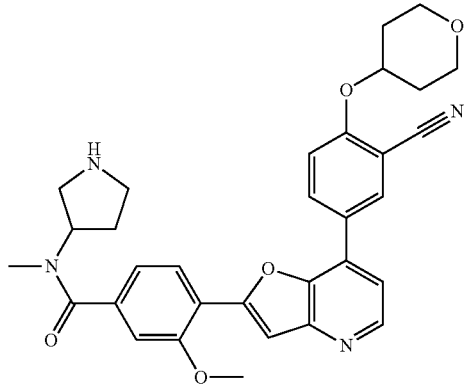 [SMILES: COc1cc(C(=O)N(C)C2CCNC2)ccc1-c1cc2nccc(-c3ccc(OC4CCOCC4)c(C#N)c3)c2o1]

3-[(4-{7-[3-Cyano-4-(tetrahydro-pyran-4-yloxy)-phenyl]-furo[3,2-b]pyridin-2-yl}-3-methoxy-benzoyl)-methyl-amino]-pyrrolidine-1-carboxylic acid tert-butyl ester The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (300.00 mg; 0.64 mmol; 1.00 eq.), 3-Methylamino-pyrrolidine-1-carboxylic acid tert-butyl ester (153.25 mg; 0.77 mmol; 1.20 eq.), [Dimethyl-amino-([1,2,3]triazolo[4,5-b]pyridin-3-yloxy)-methylene]-dimethyl-ammonium; hexafluoro phosphate (HATU) (290.95 mg; 0.77 mmol; 1.20 eq.), and Ethyl-diisopropyl-amine (0.56 ml; 3.19 mmol; 5.00 eq.) in DMF (3.0 mL) to get the title compound (500 mg) which was used as such deprotection of the boc group.

4-{7-[3-Cyano-4-(tetrahydro-pyran-4-yloxy)-phenyl]-furo[3,2-b]pyridin-2-yl}-3-methoxy-N-methyl-N-pyrrolidin-3-yl-benzamide To a solution of 3-[(4-{7-[3-Cyano-4-(tetrahydro-pyran-4-yloxy)-phenyl]-furo[3,2-b]pyridin-2-yl}-3-methoxy-benzoyl)-methyl-amino]-pyrrolidine-1-carboxylic acid tert-butyl ester (500.00 mg; 0.77 mmol; 1.00 eq.) in Dichloromethane (15.00 ml) was added hydrogen chloride in Ether (3.83 ml; 7.66 mmol; 10.00 eq.). Stirred for 3 h to obtain the title compound as a yellow colored solid (294 mg, 64%). MS: m/z=590 (M+H)+.

Example 213: 5-{2-[4-(3-Dimethylamino-azetidine-1-carbonyl)-2-methoxy-phenyl]-furo[3,2-b]pyridin-7-yl}-2-(tetrahydro-pyran-4-yloxy)-benzonitrile (24)

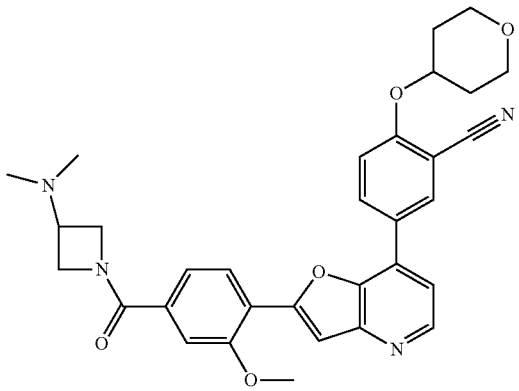 [SMILES: COc1cc(C(=O)N2CC(N(C)C)C2)ccc1-c1cc2nccc(-c3ccc(OC4CCOCC4)c(C#N)c3)c2o1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), N,N-dimethylazetidin-3-amine dihydrochloride (66.22 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) (60 mg, 34%). MS: m/z=553 (M+H)+.

Example 214: 4-{7-[3-Cyano-4-(tetrahydro-pyran-4-yloxy)-phenyl]-furo[3,2-b]pyridin-2-yl}-N-(2-dimethylamino-ethyl)-3-methoxy-N-methyl-benzamide (208)

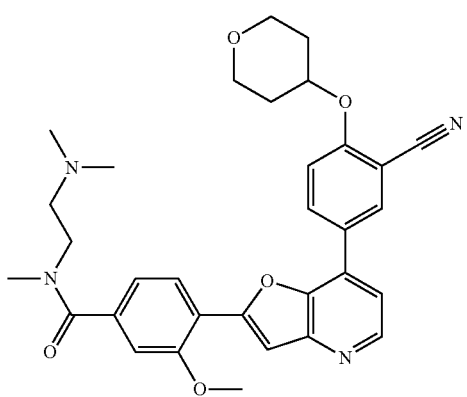 [SMILES: COc1cc(C(=O)N(C)CCN(C)C)ccc1-c1cc2nccc(-c3ccc(OC4CCOCC4)c(C#N)c3)c2o1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), N,N,N'-Trimethyl-ethane-1,2-diamine (39.09 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) (40 mg, 23%). MS: m/z=555 (M+H)+.

Example 215: 5-{2-[4-(2,6-Diaza-bicyclo[3.2.0]heptane-6-carbonyl)-2-methoxy-phenyl]-furo[3,2-b]pyridin-7-yl}-2-(tetrahydro-pyran-4-yloxy)-benzonitrile hydrochloride (55)

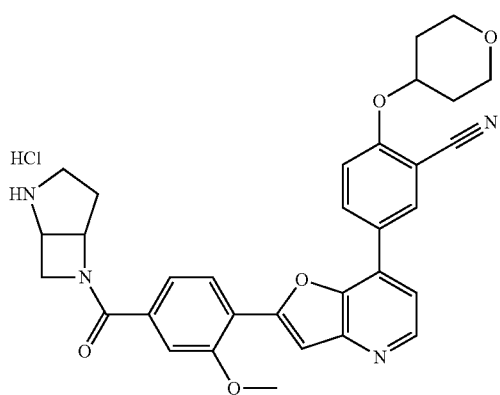 [SMILES: Cl ; COc1cc(C(=O)N2CC3NCCC32)ccc1-c1cc2nccc(-c3ccc(OC4CCOCC4)c(C#N)c3)c2o1]

The title compound was synthesized according to the procedure described in example 201 by stirring a mixture of 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 2,6-Diaza-bicyclo[3.2.0]heptane-2-carboxylic acid tert-butyl ester (75.85 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), (HATU), and Ethyl-diisopropyl-amine (0.28 ml; 1.59 mmol; 5.00 eq.) in DMF (3.0 mL) overnight at room temperature followed by treatment of 6-(4-{7-[3-Cyano-4-(tetrahydro-pyran-4-yloxy)-phenyl]-furo[3,2-b]pyridin-2-yl}-3-methoxy-benzoyl)-2,6-diaza-bicyclo[3.2.0]heptane-2-carboxylic acid tert-butyl ester (200.00 mg; 0.31 mmol; 1.00 eq.) with hydrogen chloride in Ether (1.54 ml; 3.07 mmol; 10.00 eq.) in Dichloro-methane (15.00 ml) to obtain the title compound (110 mg). MS: m/z=551 (M+H)+.

Example 216: 5-{2-[2-Methoxy-4-(4-methyl-piperazine-1-carbonyl)-phenyl]-furo[3,2-b]pyridin-7-yl}-2-(tetrahydro-pyran-4-yloxy)-benzonitrile (15)

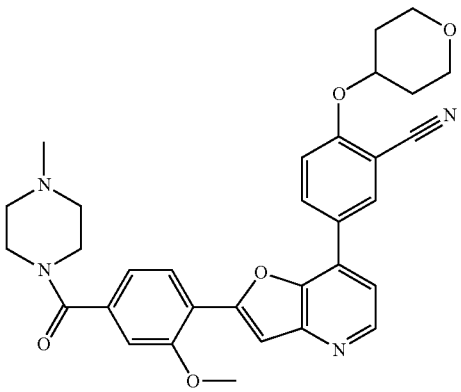 [SMILES: COc1cc(C(=O)N2CCN(C)CC2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 1-Methyl-piperazine (38.32 mg; 0.38 mmol; 1.20 eq.), (3-Dimethylamino-propyl)-ethyl-carbodiimide hydrochloride (73.34 mg; 0.38 mmol; 1.20 eq.) (EDCI), Benzotriazol-1-ol (51.70 mg; 0.38 mmol; 1.20 eq.) (HOBt) and Ethyl-diisopropyl-amine (0.28 ml; 1.59 mmol; 5.00 eq.) in DMF (3.0 mL) (50 mg, 28%). MS: m/z=553 (M+H)+.

Example 217: N-(3-Aza-bicyclo[3.1.0]hex-6-yl)-4-{7-[3-cyano-4-(tetrahydro-pyran-4-yloxy)-phenyl]-furo[3,2-b]pyridin-2-yl}-3-methoxy-benzamide hydrochloride (84)

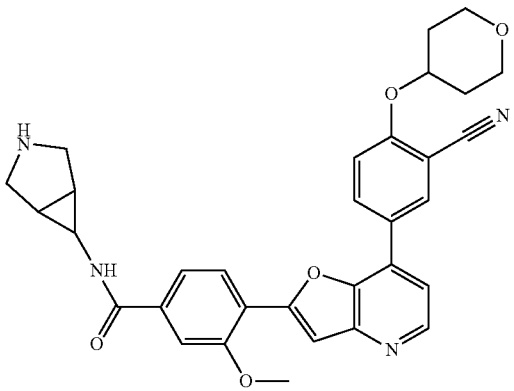 [SMILES: COc1cc(C(=O)NC2C3CNCC32)ccc1-c1cc2nccc(-c3ccc(OC4CCOCC4)c(C#N)c3)c2o1]

The title compound was synthesized according to the procedure described in example 109 by stirring a mixture of 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 6-Amino-3-aza-bicyclo[3.1.0]hexane-3-carboxylic acid tert-butyl ester (75.85 mg; 0.38 mmol; 1.20 eq.), (3-Dimethylamino-propyl)-ethyl-carbodiimide hydrochloride (73.34 mg; 0.38 mmol; 1.20 eq.) (EDCI), Benzotriazol-1-ol (51.70 mg; 0.38 mmol; 1.20 eq.) (HOBt) and Ethyl-diisopropyl-amine (0.17 ml; 0.96 mmol; 3.00 eq.) in DMF (3.0 mL) overnight followed by treatment of 6-(4-{7-[3-Cyano-4-(tetrahydro-pyran-4-yloxy)-phenyl]-furo[3,2-b]pyridin-2-yl}-3-methoxy-benzoylamino)-3-aza-bicyclo[3.1.0]hexane-3-carboxylic acid tert-butyl ester (120.00 mg; 0.18 mmol; 1.00 eq.) with hydrogen chloride in Ether (0.92 ml; 1.84 mmol; 10.00 eq.) in Dichloro-methane (15.00 ml) to obtain the title compound (98 mg). MS: m/z=551 (M+H)+.

Example 218: 4-{7-[3-Cyano-4-(tetrahydro-pyran-4-yloxy)-phenyl]-furo[3,2-b]pyridin-2-yl}-3-methoxy-N-piperidin-4-yl-benzamide hydrochloride (62)

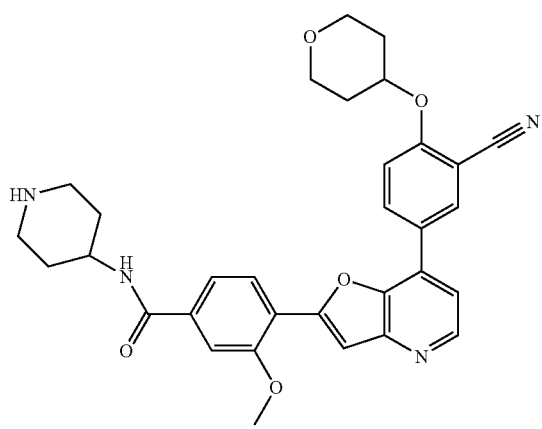 [SMILES: COc1cc(C(=O)NC2CCNCC2)ccc1-c1cc2nccc(-c3ccc(OC4CCOCC4)c(C#N)c3)c2o1]

The title compound was synthesized according to the procedure described in example 109 by stirring a mixture of 4-{7-[3-Cyano-4-(tetrahydro-pyran-4-yloxy)-phenyl]-furo[3,2-b]pyridin-2-yl}-3-methoxy-benzoic acid (75.00 mg; 0.16 mmol; 1.00 eq.), 4-Amino-piperidine-1-carboxylic acid tert-butyl ester (38.31 mg; 0.19 mmol; 1.20 eq.), (3-Dimethylamino-propyl)-ethyl-carbodiimide hydrochloride (36.67 mg; 0.19 mmol; 1.20 eq.) (EDCI), Benzotriazol-1-ol (25.85 mg; 0.19 mmol; 1.20 eq.) (HOBt) and Ethyl-diisopropyl-amine (0.14 ml; 0.80 mmol; 5.00 eq.) in DMF (2.0 mL) at room temperature overnight followed by treatment of 4-(4-{7-[3-Cyano-4-(tetrahydro-pyran-4-yloxy)-phenyl]-furo[3,2-b]pyridin-2-yl}-3-methoxy-benzoylamino)-piperidine-1-carboxylic acid tert-butyl ester (50.00 mg; 0.08 mmol; 1.00 eq.) with hydrogen chloride in Ether (0.38 ml; 0.77 mmol; 10.00 eq.) in Dichloro-methane (10 ml) to obtain the title compound (27 mg). MS: m/z=553 (M+H)+.

Example 219: 4-{7-[3-Cyano-4-(tetrahydro-pyran-4-yloxy)-phenyl]-furo[3,2-b]pyridin-2-yl}-3-methoxy-N-(3-methyl-pyrrolidin-3-yl)-benzamide hydrochloride (86)

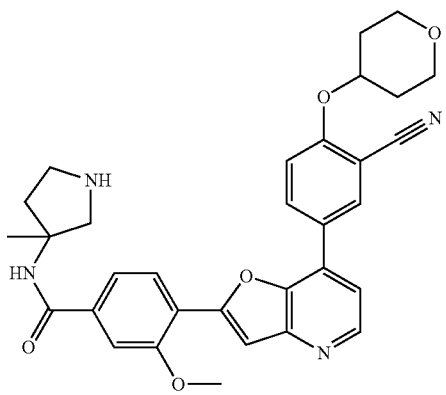 [SMILES: COc1cc(C(=O)NC2(C)CCNC2)ccc1-c1cc2nccc(-c3ccc(OC4CCOCC4)c(C#N)c3)c2o1]

The title compound was synthesized according to the procedure described in example 201 by stirring a mixture of 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 3-Amino-3-methyl-pyrrolidine-1-carboxylic acid tert-butyl ester (76.63 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) was stirred at room temperature overnight followed by treatment of 3-(4-{7-[3-Cyano-4-(tetrahydro-pyran-4-yloxy)-phenyl]-furo[3,2-b]pyridin-2-yl}-3-methoxy-benzoylamino)-3-methyl-pyrrolidine-1-carboxylic acid tert-butyl ester (135.00 mg; 0.21 mmol; 1.00 eq.) with hydrogen chloride in Ether (0.52 ml; 1.03 mmol; 5.00 eq.) in Dichloro-methane (15 ml) to obtain the title compound (70 mg). MS: m/z=553 (M+H)+.

Example 220: 4-{7-[3-Cyano-4-(tetrahydro-pyran-4-yloxy)-phenyl]-furo[3,2-b]pyridin-2-yl}-N-(5,5-difluoro-piperidin-3-yl)-3-methoxy-benzamide hydrochloride (98)

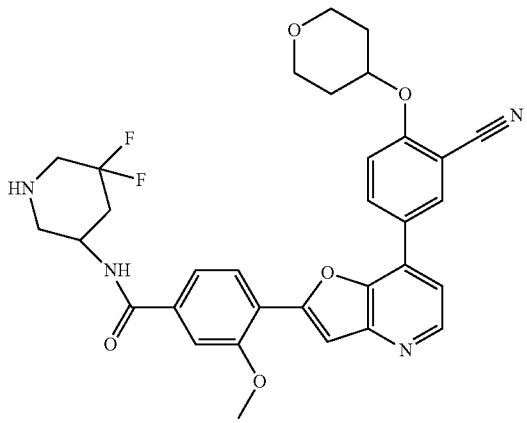 [SMILES: COc1cc(C(=O)NC2CNCC(F)(F)C2)ccc1-c1cc2nccc(-c3ccc(OC4CCOCC4)c(C#N)c3)c2o1]

The title compound was synthesized according to the procedure described in example 109 by stirring a mixture of 4-{7-[3-Cyano-4-(tetrahydro-pyran-4-yloxy)-phenyl]-furo[3,2-b]pyridin-2-yl}-3-methoxy-benzoic acid (75.00 mg; 0.16 mmol; 1.00 eq.), 5-Amino-3,3-difluoro-piperidine-1-carboxylic acid tert-butyl ester (48.96 mg; 0.21 mmol; 1.30 eq.), (3-Dimethylamino-propyl)-ethyl-carbodiimide hydrochloride (36.67 mg; 0.19 mmol; 1.20 eq.) (EDCI), Benzotriazol-1-ol (25.85 mg; 0.19 mmol; 1.20 eq.) (HOBt) and Ethyl-diisopropyl-amine (0.14 ml; 0.80 mmol; 5.00 eq.) in DMF (2.0 mL) was stirred at room temperature overnight followed by treatment of 5-(4-{7-[3-Cyano-4-(tetrahydro-pyran-4-yloxy)-phenyl]-furo[3,2-b]pyridin-2-yl}-3-methoxy-benzoylamino)-3,3-difluoro-piperidine-1-carboxylic acid tert-butyl ester (17.00 mg; 0.02 mmol; 1.00 eq.) with hydrogen chloride in Ether (0.12 ml; 0.25 mmol; 10.00 eq.) in Dichloro-methane (2.00 ml) to obtain the title compound (10 mg). MS: m/z=589 (M+H)$^+$.

Example 221: 5-{2-[4-(4-Hydroxymethyl-piperidine-1-carbonyl)-2-methoxy-phenyl]-furo[3,2-b]pyridin-7-yl}-2-(tetrahydro-pyran-4-yloxy)-benzonitrile (5)

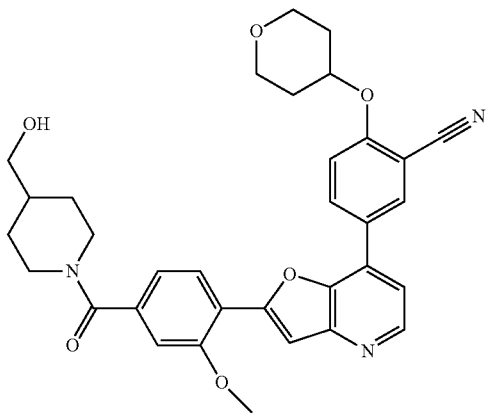 [SMILES: COc1cc(C(=O)N2CCC(CO)CC2)ccc1-c1cc2nccc(-c3ccc(OC4CCOCC4)c(C#N)c3)c2o1]

The title compound was synthesized according to the procedure described in example 109 using A mixture of 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), Piperidin-4-yl-methanol (44.06 mg; 0.38 mmol; 1.20 eq.), (3-Dimethylamino-propyl)-ethyl-carbodiimide hydrochloride (73.34 mg; 0.38 mmol; 1.20 eq.) (EDCI), Benzotriazol-1-ol (51.70 mg; 0.38 mmol; 1.20 eq.) (HOBt) and Ethyl-diisopropyl-amine (0.28 ml; 1.59 mmol; 5.00 eq.) in DMF (3.0 mL) (105 mg, 58%). MS: m/z=568 (M+H)$^+$.

Example 222: 5-{2-[4-(2-Hydroxymethyl-piperidine-1-carbonyl)-2-methoxy-phenyl]-furo[3,2-b]pyridin-7-yl}-2-(tetrahydro-pyran-4-yloxy)-benzonitrile

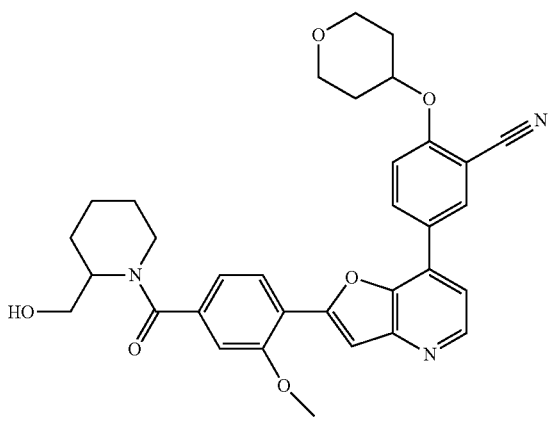 [SMILES: COc1cc(C(=O)N2CCCCC2CO)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), Piperidin-2-yl-methanol (44.06 mg; 0.38 mmol; 1.20 eq.), (3-Dimethylamino-propyl)-ethyl-carbodiimide hydrochloride (73.34 mg; 0.38 mmol; 1.20 eq.) (EDCI), Benzotriazol-1-ol (51.70 mg; 0.38 mmol; 1.20 eq.) (HOBt) and Ethyl-diisopropyl-amine (0.28 ml; 1.59 mmol; 5.00 eq.) in DMF (3.0 mL) (96 mg, 53%). MS: m/z=568 (M+H)$^+$.

Example 223: 5-{2-[2-Methoxy-4-(4-methoxy-piperidine-1-carbonyl)-phenyl]-furo[3,2-b]pyridin-7-yl}-2-(tetrahydro-pyran-4-yloxy)-benzonitrile (12)

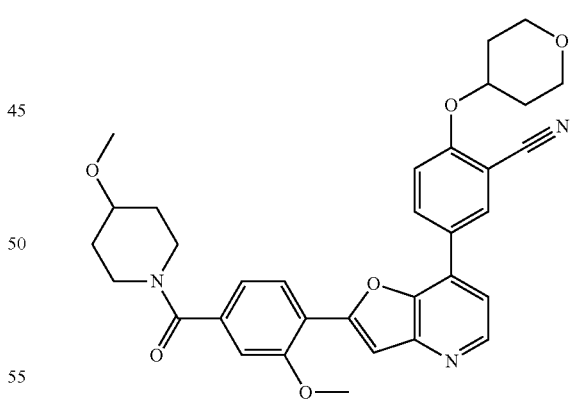

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 4-Methoxy-piperidine (44.06 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) (128 mg, 71%). MS: m/z=568 (M+H)$^+$.

Example 224: 4-{7-[3-Cyano-4-(tetrahydro-pyran-4-yloxy)-phenyl]-furo[3,2-b]pyridin-2-yl}-N-((1R,2S,3R)-2,3-dihydroxy-cyclohexyl)-3-methoxy-benzamide (54)

Chiral

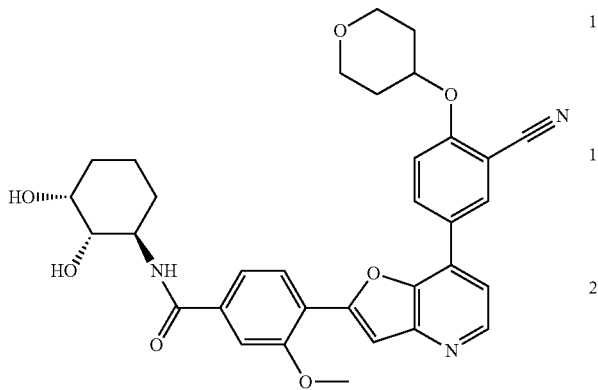

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (75.00 mg; 0.16 mmol; 1.00 eq.), (1R,2S,3R)-3-Amino-cyclohexane-1,2-diol (32.07 mg; 0.19 mmol; 1.20 eq.), (3-Dimethylamino-propyl)-ethyl-carbodiimide hydrochloride (36.67 mg; 0.19 mmol; 1.20 eq.) (EDCI), Benzotriazol-1-ol (25.85 mg; 0.19 mmol; 1.20 eq.) (HOBt) and Ethyl-diisopropyl-amine (0.14 ml; 0.80 mmol; 5.00 eq.) in DMF (3.0 mL) (31 mg, 33%). MS: m/z=584 (M+H)+.

Example 225: 4-{7-[3-Cyano-4-(tetrahydro-pyran-4-yloxy)-phenyl]-furo[3,2-b]pyridin-2-yl}-3-methoxy-N-methyl-N-(1-methyl-pyrrolidin-3-yl)-benzamide (61)

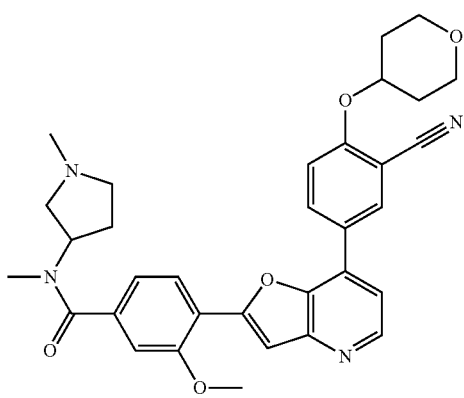 [SMILES: COc1cc(C(=O)N(C)C2CCN(C)C2)ccc1-c1cc2nccc(-c3ccc(OC4CCOCC4)c(C#N)c3)c2o1]

The title compound was synthesized according to the procedure described in example 79 using 4-{7-[3-Cyano-4-(tetrahydro-pyran-4-yloxy)-phenyl]-furo[3,2-b]pyridin-2-yl}-3-methoxy-N-methyl-N-pyrrolidin-3-yl-benzamide hydrochloride (50.00 mg; 0.08 mmol; 1.00 eq.), Formaldehyde (37% w/w Aq. solution) (0.50 ml) and palladium on activated carbon (dry) (18.07 mg; 0.02 mmol; 0.20 eq.) in Methanol (30.00 ml) under hydrogen atmosphere (37 mg, 77%). MS: m/z=567 (M+H).

Example 226: 4-{7-[3-Cyano-4-(tetrahydro-pyran-4-yloxy)-phenyl]-furo[3,2-b]pyridin-2-yl}-3-methoxy-N-methyl-N-piperidin-4-yl-benzamide hydrochloride (41)

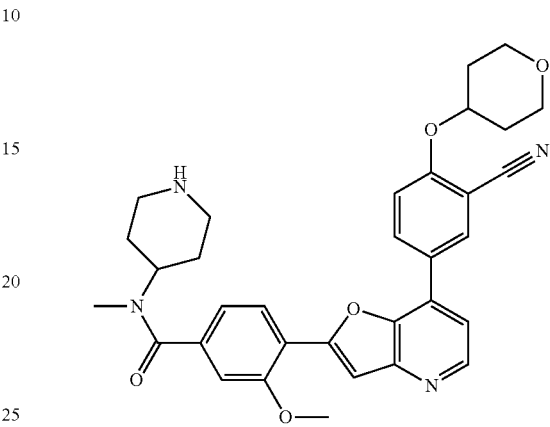

The title compound was synthesized according to the procedure described in example 201 by stirring a mixture of 4-{7-[3-Cyano-4-(tetrahydro-pyran-4-yloxy)-phenyl]-furo[3,2-b]pyridin-2-yl}-3-methoxy-benzoic acid (200.00 mg; 0.43 mmol; 1.00 eq.), 4-Methylamino-piperidine-1-carboxylic acid tert-butyl ester (109.32 mg; 0.51 mmol; 1.20 eq.), [Dimethylamino-([1,2,3]triazolo[4,5-b]pyridin-3-yloxy)-methylene]-dimethyl-ammonium; hexafluoro phosphate (HATU) (193.96 mg; 0.51 mmol; 1.20 eq.), (HATU), and Ethyl-diisopropyl-amine (0.37 ml; 2.13 mmol; 5.00 eq.) in DMF (3.0 mL) at room temperature overnight followed by treatment of 4-[(4-{7-[3-Cyano-4-(tetrahydro-pyran-4-yloxy)-phenyl]-furo[3,2-b]pyridin-2-yl}-3-methoxy-benzoyl)-methyl-amino]-piperidine-1-carboxylic acid tert-butyl ester (350.00 mg; 0.52 mmol; 1.00 eq.) with hydrogen chloride in Ether (2.62 ml; 5.25 mmol; 10.00 eq.) in Dichloro-methane (15.00 ml) to obtain an yellow solid (250 mg, 79%). MS: m/z=567 (M+H)+.

Example 227: 5-{2-[2-Methoxy-4-(4-methyl-[1,4]diazepane-1-carbonyl)-phenyl]-furo[3,2-b]pyridin-7-yl}-2-(tetrahydro-pyran-4-yloxy)-benzonitrile (209)

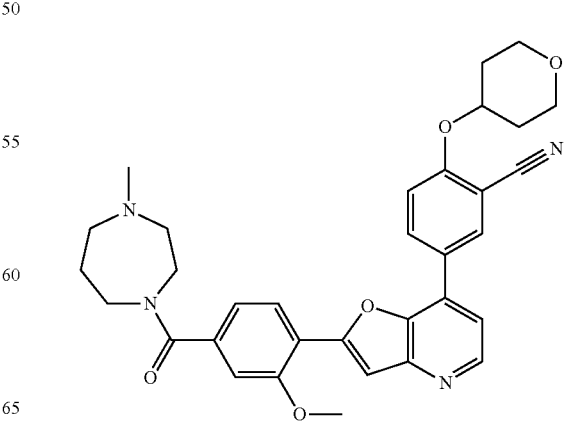

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 1-Methyl-[1,4]diazepane (43.69 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) (105 mg, 58%). MS: m/z=567 (M+H)⁺.

Example 228: 5-{2-[4-(2,5-Diaza-spiro[3.4]octane-2-carbonyl)-2-methoxy-phenyl]-furo[3,2-b]pyridin-7-yl}-2-(tetrahydro-pyran-4-yloxy)-benzonitrile hydrochloride (29)

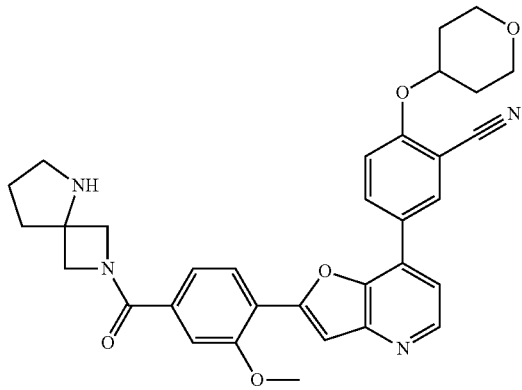 [SMILES: COc1cc(C(=O)N2CC3(CCCN3)C2)ccc1-c1cc2nccc(-c3ccc(OC4CCOCC4)c(C#N)c3)c2o1]

The title compound was synthesized according to the procedure described in example 201 by stirring a mixture of 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 2,5-Diaza-spiro[3.4]octane-5-carboxylic acid tert-butyl ester (81.22 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) was stirred at room temperature overnight followed by treatment of 2-(4-{7-[3-Cyano-4-(tetrahydro-pyran-4-yloxy)-phenyl]-furo[3,2-b]pyridin-2-yl}-3-methoxy-benzoyl)-2,5-diaza-spiro[3.4]octane-5-carboxylic acid tert-butyl ester (80.00 mg; 0.12 mmol; 1.00 eq.) with hydrogen chloride in Ether (0.60 ml; 1.20 mmol; 10.00 eq.) in Dichloro-methane (15.00 ml) to obtain a yellow colored solid (65 mg, 90%). MS: m/z=565 (M+H)⁺.

Example 229: 4-{7-[3-Cyano-4-(tetrahydro-pyran-4-yloxy)-phenyl]-furo[3,2-b]pyridin-2-yl}-3-methoxy-N-piperidin-4-ylmethyl-benzamide hydrochloride (92)

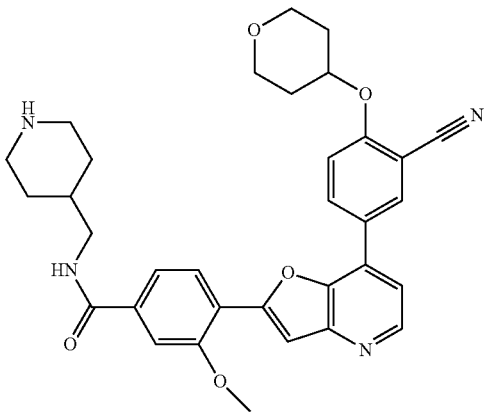 [SMILES: COc1cc(C(=O)NCC2CCNCC2)ccc1-c1cc2nccc(-c3ccc(OC4CCOCC4)c(C#N)c3)c2o1]

The title compound was synthesized according to the procedure described in example 109 by stirring a mixture of 4-{7-[3-Cyano-4-(tetrahydro-pyran-4-yloxy)-phenyl]-furo[3,2-b]pyridin-2-yl}-3-methoxy-benzoic acid (200.00 mg; 0.43 mmol; 1.00 eq.), 4-Aminomethyl-piperidine-1-carboxylic acid tert-butyl ester (109.32 mg; 0.51 mmol; 1.20 eq.), (3-Dimethylamino-propyl)-ethyl-carbodiimide hydrochloride (97.79 mg; 0.51 mmol; 1.20 eq.) (EDCI), Benzotriazol-1-ol (68.93 mg; 0.51 mmol; 1.20 eq.) (HOBt) and Ethyl-diisopropyl-amine (0.37 ml; 2.13 mmol; 5.00 eq.) in DMF (3.0 mL) was stirred at room temperature overnight followed by treatment of 4-[(4-{7-[3-Cyano-4-(tetrahydro-pyran-4-yloxy)-phenyl]-furo[3,2-b]pyridin-2-yl}-3-methoxy-benzoylamino)-methyl]-piperidine-1-carboxylic acid tert-butyl ester (208.00 mg; 0.31 mmol; 1.00 eq.) with hydrogen chloride in Ether (1.56 ml; 3.12 mmol; 10.00 eq.) in Dichloro-methane (10.00 ml) to obtain an yellow colored solid (163 mg, 87%). MS: m/z=567 (M+H)⁺.

Example 230: 5-(2-{4-[4-(2-Hydroxy-ethyl)-piperazine-1-carbonyl]-2-methoxy-phenyl}-furo[3,2-b]pyridin-7-yl)-2-(tetrahydro-pyran-4-yloxy)-benzonitrile (13)

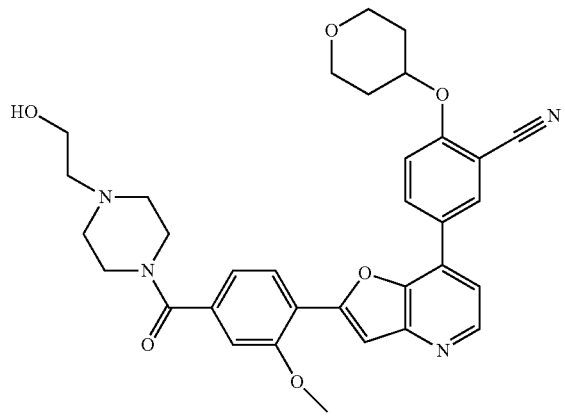 [SMILES: COc1cc(C(=O)N2CCN(CCO)CC2)ccc1-c1cc2nccc(-c3ccc(OC4CCOCC4)c(C#N)c3)c2o1]

The title compound was synthesized according to the procedure described in example 109 by using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.) 2-Piperazin-1-yl-ethanol (49.81 mg; 0.38 mmol; 1.20 eq.), (3-Dimethylamino-propyl)-ethyl-carbodiimide hydrochloride (73.34 mg; 0.38 mmol; 1.20 eq.) (EDCI), Benzotriazol-1-ol (51.70 mg; 0.38 mmol; 1.20 eq.) (HOBt) and Ethyl-diisopropyl-amine (0.28 ml; 1.59 mmol; 5.00 eq.) in DMF (3.0 mL). 70 mg, (38%). MS: m/z=583 (M+H)+.

Example 231: 5-{2-[2-Methoxy-4-(3-pyrrolidin-1-yl-azetidine-1-carbonyl)-phenyl]-furo[3,2-b]pyridin-7-yl}-2-(tetrahydro-pyran-4-yloxy)-benzonitrile (20)

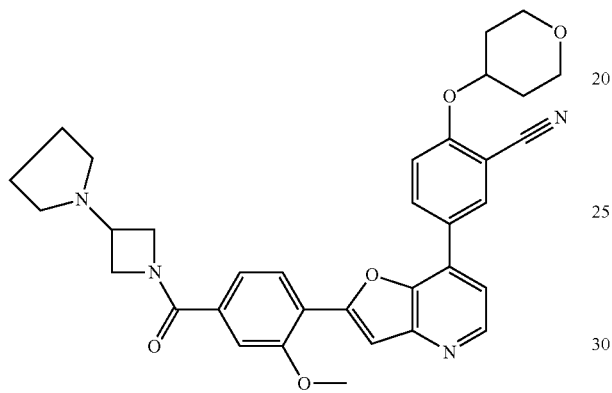

The title compound was synthesized according to the procedure described in example 201 by using of 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 1-(azetidin-3-yl)pyrrolidine dihydrochloride (76.18 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) (95 mg, 51%). MS: m/z=579 (M+H)+.

Example 232: N-(1-Aza-bicyclo[2.2.2]oct-3-yl)-4-{7-[3-cyano-4-(tetrahydro-pyran-4-yloxy)-phenyl]-furo[3,2-b]pyridin-2-yl}-3-methoxy-benzamide (79)

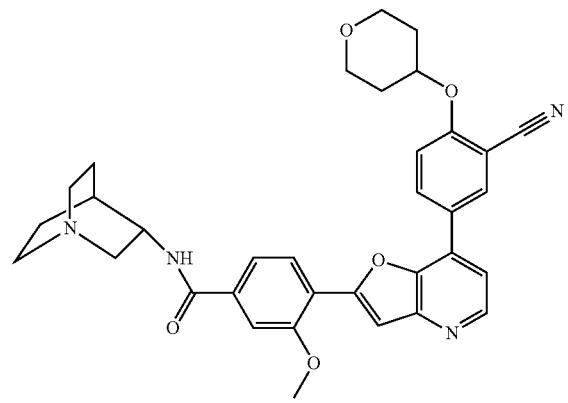 [SMILES: COc1cc(C(=O)NC2CN3CCC2CC3)ccc1-c1cc2nccc(-c3ccc(OC4CCOCC4)c(C#N)c3)c2o1]

The title compound was synthesized according to the procedure described in example 109 by using 4-{7-[3-Cyano-4-(tetrahydro-pyran-4-yloxy)-phenyl]-furo[3,2-b]pyridin-2-yl}-3-methoxy-benzoic acid (50.00 mg; 0.11 mmol; 1.00 eq.), 1-Aza-bicyclo[2.2.2]oct-3-ylamine hydrochloride (2) (27.51 mg; 0.14 mmol; 1.30 eq.), (3-Dimethylamino-propyl)-ethyl-carbodiimide hydrochloride (24.45 mg; 0.13 mmol; 1.20 eq.) (EDCI), Benzotriazol-1-ol (17.23 mg; 0.13 mmol; 1.20 eq.) (HOBt) and Ethyl-diisopropyl-amine (0.09 ml; 0.53 mmol; 5.00 eq.) in DMF (3.0 mL) (15 mg, 24%). MS: m/z=579 (M+H)+.

Example 233: 4-{7-[3-Cyano-4-(tetrahydro-pyran-4-yloxy)-phenyl]-furo[3,2-b]pyridin-2-yl}-3-methoxy-N-(2-piperidin-4-yl-ethyl)-benzamide hydrochloride (118)

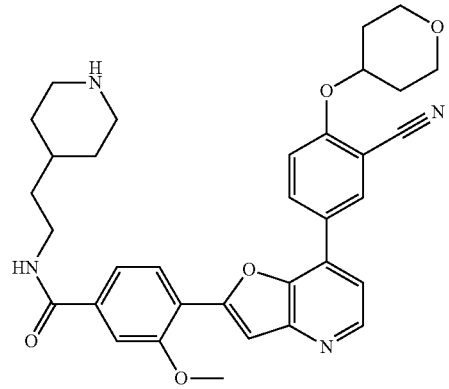 [SMILES: COc1cc(C(=O)NCCC2CCNCC2)ccc1-c1cc2nccc(-c3ccc(OC4CCOCC4)c(C#N)c3)c2o1]

The title compound was synthesized according to the procedure described in example 109 by stirring a mixture of 4-{7-[3-Cyano-4-(tetrahydro-pyran-4-yloxy)-phenyl]-furo[3,2-b]pyridin-2-yl}-3-methoxy-benzoic acid (200.00 mg; 0.43 mmol; 1.00 eq.), 4-(2-Amino-ethyl)-piperidine-1-carboxylic acid tert-butyl ester (116.48 mg; 0.51 mmol; 1.20 eq.), (3-Dimethylamino-propyl)-ethyl-carbodiimide hydrochloride (97.79 mg; 0.51 mmol; 1.20 eq.) (EDCI), Benzotriazol-1-ol (68.93 mg; 0.51 mmol; 1.20 eq.) (HOBt) and Ethyl-diisopropyl-amine (0.37 ml; 2.13 mmol; 5.00 eq.) in DMF (3.0 mL) at room temperature overnight followed by treatment of 4-[2-(4-{7-[3-Cyano-4-(tetrahydro-pyran-4-yloxy)-phenyl]-furo[3,2-b]pyridin-2-yl}-3-methoxy-benzoylamino)-ethyl]-piperidine-1-carboxylic acid tert-butyl ester (270.00 mg; 0.40 mmol; 1.00 eq.) with hydrogen chloride in Ether (1.98 ml; 3.97 mmol; 10.00 eq.) in Dichloro-methane (10.00 ml) to get an yellow colored solid (226 mg). MS: m/z=581 (M+H)+.

Example 234: 5-{2-[2-Methoxy-4-(3-morpholin-4-yl-azetidine-1-carbonyl)-phenyl]-furo[3,2-b]pyridin-7-yl}-2-(tetrahydro-pyran-4-yloxy)-benzonitrile (8)

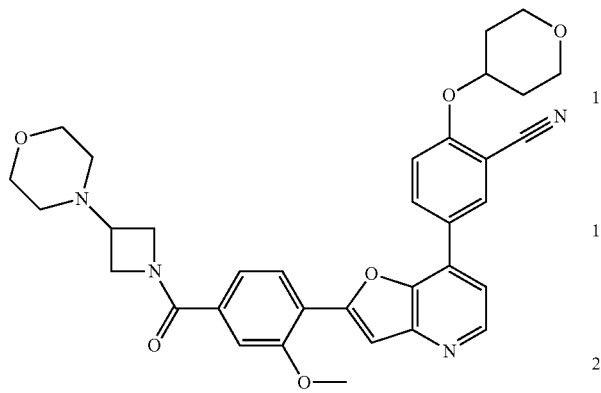

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 4-Azetidin-3-yl-morpholine; Hydrochloride (68.35 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) (95 mg, 50%). MS: m/z=595 (M+H)$^+$.

Example 235: 5-{2-[4-(2,7-Diaza-spiro[4.5]decane-7-carbonyl)-2-methoxy-phenyl]-furo[3,2-b]pyridin-7-yl}-2-(tetrahydro-pyran-4-yloxy)-benzonitrile (25)

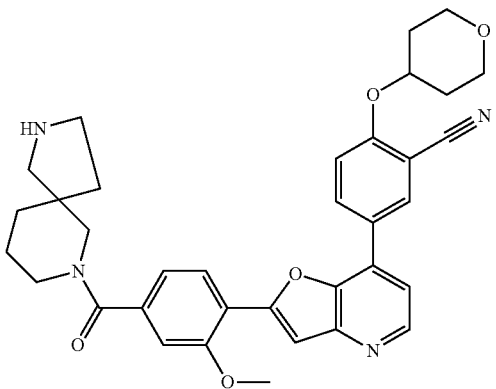 [SMILES: COc1cc(C(=O)N2CCCC3(CCNC3)C2)ccc1-c1cc2nccc(-c3ccc(OC4CCOCC4)c(C#N)c3)c2o1]

The title compound was synthesized according to the procedure described in example 201 by stirring a mixture of 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 2,7-Diaza-spiro[4.5]decane-2-carboxylic acid tert-butyl ester (91.95 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), and Ethyl-diisopropyl-amine (0.28 ml; 1.59 mmol; 5.00 eq.) in DMF (3.0 mL) at room temperature overnight followed by treatment of 7-(4-{7-[3-Cyano-4-(tetrahydro-pyran-4-yloxy)-phenyl]-furo[3,2-b]pyridin-2-yl}-3-methoxy-benzoyl)-2,7-diaza-spiro[4.5]decane-2-carboxylic acid tert-butyl ester (225.00 mg; 0.29 mmol; 1.00 eq.) with hydrogen chloride in Ether (1.45 ml; 2.89 mmol; 10.00 eq.) in Dichloro-methane (30.00 ml) to get an yellow colored solid (150 mg). MS: m/z=593 (M+H)$^+$.

Example 236: 4-{7-[6-Cyano-5-(tetrahydro-pyran-4-yloxy)-pyridin-2-yl]-furo[3,2-b]pyridin-2-yl}-3-methoxy-N,N-dimethyl-benzamide (31)

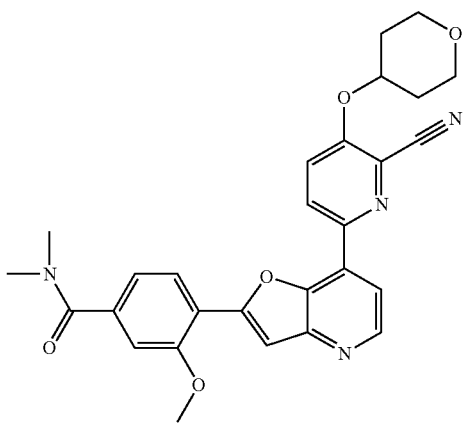 [SMILES: COc1cc(C(=O)N(C)C)ccc1-c1cc2nccc(-c3ccc(OC4CCOCC4)c(C#N)n3)c2o1]

The title compound was synthesized according to the procedure described in example 64 using 4-(7-Chloro-furo[3,2-b]pyridin-2-yl)-3-methoxy-N,N-dimethyl-benzamide (150.00 mg; 0.45 mmol; 1.00 eq.), (6-cyano-5-tetrahydro-pyran-4-yloxy-2-pyridyl)boronic acid (134.98 mg; 0.54 mmol; 1.20 eq.), Dicyclohexyl-(2',6'-dimethoxy-biphenyl-2-yl)-phosphane (55.85 mg; 0.14 mmol; 0.30 eq.), dipotassium carbonate (125.35 mg; 0.91 mmol; 2.00 eq.) and diacetoxypalladium (20.36 mg; 0.09 mmol; 0.20 eq.), 1,4-dioxane (20 ml) and water (2 ml) (50 mg, 22%). MS: m/z=499 (M+H)$^+$. $^1$H NMR (400 MHz, Chloroform-d) δ 8.71 (s, 1H), 8.61 (d, J=5.3 Hz, 1H), 8.19 (d, J=4.7 Hz, 1H), 8.06 (d, J=6.9 Hz, 1H), 7.80 (d, J=4.3 Hz, 1H), 7.69 (d, J=8.0 Hz, 1H), 7.16 (s, 2H), 4.86 (br s, 1H), 4.08 (s, 3H), 4.13-4.02 (m, 2H), 3.71 (m, 2H), 3.18 (s, 3H), 3.07 (s, 3H), 2.16 (m, 2H), 2.01 (s, 2H).

Example 237: 4-{7-[4-Cyano-5-(tetrahydro-pyran-4-yloxy)-pyridin-2-yl]-furo[3,2-b]pyridin-2-yl}-3-methoxy-N,N-dimethyl-benzamideb (161)

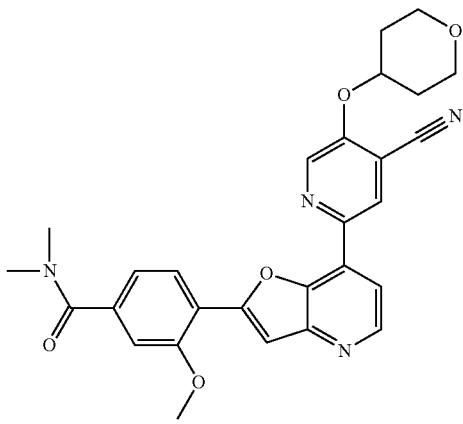 [SMILES: COc1cc(C(=O)N(C)C)ccc1-c1cc2nccc(-c3cc(C#N)c(OC4CCOCC4)cn3)c2o1]

The title compound was synthesized according to the procedure described in example 64 using 4-(7-Chloro-furo[3,2-b]pyridin-2-yl)-3-methoxy-N,N-dimethyl-benzamide (200.00 mg; 0.60 mmol; 1.00 eq.), (4-cyano-5-tetrahydropyran-4-yloxy-2-pyridyl)boronic acid (179.98 mg; 0.73 mmol; 1.20 eq.) (Crude used 500 mg), Dicyclohexyl-(2',6'-dimethoxy-biphenyl-2-yl)-phosphane (74.47 mg; 0.18 mmol; 0.30 eq.), dipotassium carbonate (167.13 mg; 1.21 mmol; 2.00 eq.) and diacetoxypalladium (27.15 mg; 0.12 mmol; 0.20 eq.) in 1,4-dioxane (20 ml) and water (2 ml). (12 mg, 4%). MS: m/z=499 (M+H)+. 1H NMR (400 MHz, Chloroform-d) δ 8.72 (s, 1H), 8.68 (d, J=2.3 Hz, 1H), 8.09 (m, 2H), 7.78 (s, 1H), 7.29 (m, 2H), 7.23 (d, J=6.7 Hz, 2H), 5.08-4.85 (m, 1H), 4.07 (s, 3H) 4.22-4.01 (m, 2H), 3.72 (m, 2H), 3.19 (s, 3H), 3.10 (s, 3H), 2.20 (m, 2H), 2.02 (m, 2H).

Example 238: Synthesis of 4-[7-(3-cyano-4-[4-oxaspiro[2.5]octan-7-yloxy]phenyl)furo[3,2-b]pyridin-2-yl]-N,N-dimethylbenzamide (285)

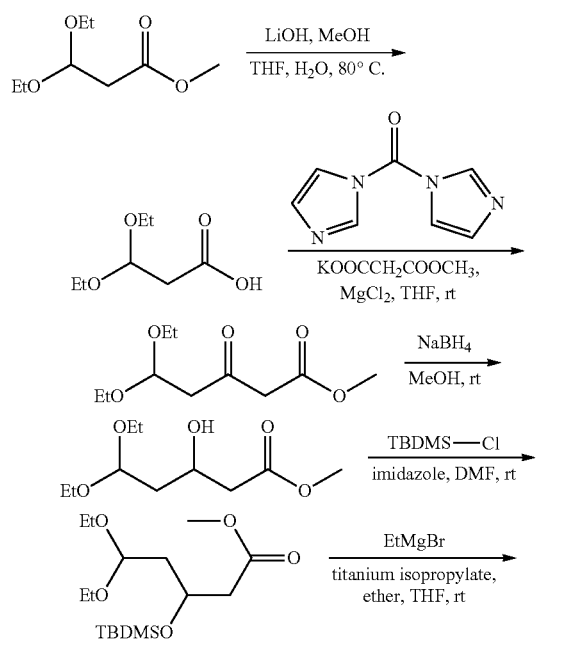

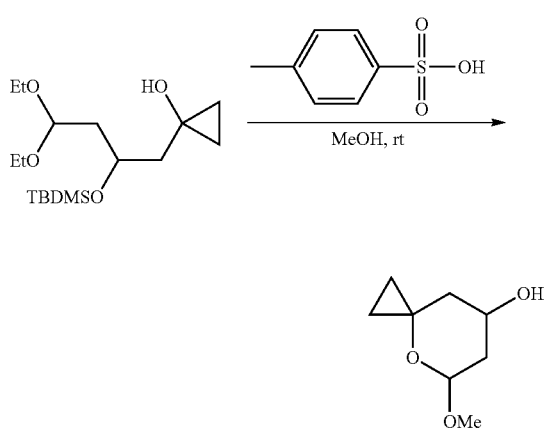

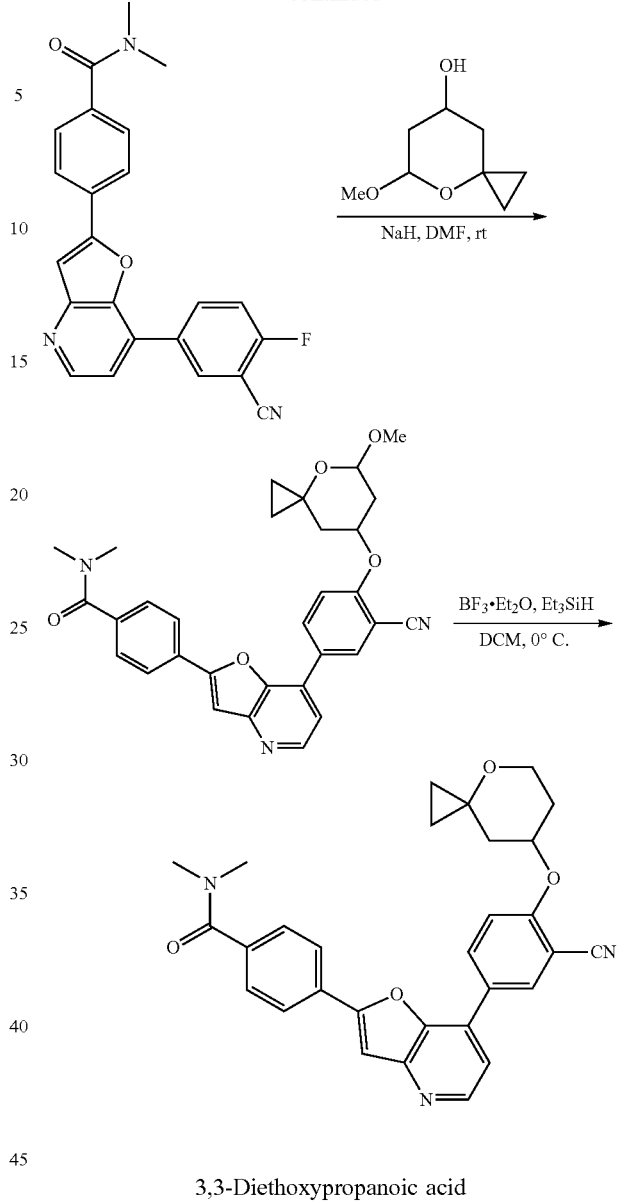

3,3-Diethoxypropanoic acid

To a solution of ethyl 3,3-diethoxypropanoate (24.40 g, 128.24 mmol) in methanol (80 mL) and THF (80 mL) was added a solution of LiOH (16.16 g, 674.80 mmol) in water (80 mL) at room temperature. The resulting mixture was stirred for 3 h at 80° C. After the reaction was done, the reaction mixture was concentrated under reduced pressure, and then the pH value of the remaining aqueous mixture was adjusted to 3 with hydrogen chloride solution (1 M). The resulting mixture was extracted with ethyl acetate (150 mL×3). The organic phases were combined, washed with brine and dried over sodium sulfate. The solvent was removed under reduced pressure to yield 3,3-diethoxypropanoic acid as a light brown liquid (6.82 g, 33%).

Methyl 5,5-diethoxy-3-oxopentanoate

To a solution of 3,3-diethoxypropanoic acid (6.82 g, 41.94 mmol) in THF (60 mL) was added a solution of N,N'-carbonyldiimidazole (9.87 g, 60.87 mmol) in THF (60 mL) dropwise at room temperature. The reaction mixture turned yellow and gas evolution was observed. The mixture was stirred at room temperature for 2 h. At the same time, another reaction flask equipped with monomethyl monopotassium malonate (11.9 g, 76.16 mmol) and magnesium chloride (5.29 g, 55.78 mmol) in THF (80 mL) was stirred at room temperature for 2 h. The imidazolide solution was then transferred into the Mg(OOCCH$_2$COOMe)$_2$ solution by syringe and the resulting mixture was stirred at room temperature for 16 h. The reaction mixture was then acidified with NaHSO$_4$ solution (2 M in water, 90 mL) and extracted with EtOAc (250 mL×3). The combined organic phases were washed with sat. NaHCO$_3$ aqueous solution and brine, dried over sodium sulfate and concentrated to yield methyl 5,5-diethoxy-3-oxopentanoate as a light brown oil (5.95 g, 65%). The oil was used in the next step without further purification. $^1$H NMR (400 MHz, CDCl$_3$, ppm) δ 4.89 (t, J=5.6 Hz, 1H), 3.76 (s, 3H), 3.71-3.65 (m, 2H), 3.59-3.51 (m, 4H), 2.88 (d, J=5.6 Hz, 2H), 1.33-1.18 (m, 6H).

Methyl 5,5-diethoxy-3-hydroxypentanoate

To a solution of methyl 5,5-diethoxy-3-oxopentanoate (5.95 g, 27.26 mmol) in methanol (100 mL) was added NaBH$_4$ (1.38 g, 36.41 mmol) in portions at room temperature. The resulting solution was stirred for 3 h at room temperature. After the reaction was done, the pH value of the reaction mixture was adjusted to 7 with hydrogen chloride solution (1 mol/L). The resulting mixture was extracted with ethyl acetate (150 mL×3) and the organic layers were combined and dried over anhydrous magnesium sulfate. The solvent was removed under reduced pressure to yield methyl 5,5-diethoxy-3-hydroxypentanoate as a light yellow oil (6.08 g, 99%). The oil was used in the next step without further purification. $^1$H NMR (400 MHz, CDCl$_3$, ppm) δ 4.75 (t, J=5.6 Hz, 1H), 4.30-4.20 (m, 1H), 4.13-3.95 (m, 1H), 3.79-3.61 (m, 5H), 3.60-3.41 (m, 2H), 2.62-2.45 (m, 1H), 1.97-1.67 (m, 2H), 1.33-1.17 (m, 6H).

Methyl 3-(tert-butyldimethylsilyloxy)-5,5-diethoxypentanoate

To a solution of methyl 5,5-diethoxy-3-hydroxypentanoate (5.63 g, 25.54 mmol) in DMF (62 mL) was added 1H-imidazole (3.66 g, 53.87 mmol), tert-butyl(chloro)dimethylsilane (6.51 g, 43.18 mmol) at room temperature. The resulting solution was stirred for 24 h at room temperature. After the reaction was done, the reaction mixture was diluted with DCM (300 mL), washed with water and dried over anhydrous magnesium sulfate. The solvent was removed under reduced pressure and the residue was purified by flash chromatography eluting with EtOAc in petroleum ether (0% to 5% gradient) to yield methyl 3-[(tert-butyldimethylsilyl)oxy]-5,5-diethoxypentanoate as a light yellow oil (3.90 g, 46%). $^1$H NMR (400 MHz, CDCl$_3$, ppm) δ 4.69-4.62 (m, 1H), 4.32-4.25 (m, 1H), 3.72-3.60 (m, 5H), 3.57-3.42 (m, 2H), 2.58-2.50 (m, 2H), 1.86 (t, J=5.6 Hz, 2H), 1.26-1.19 (m, 6H), 0.95-0.80 (m, 9H), 0.12-0.05 (m, 6H).

1-(2-(tert-Butyldimethylsilyloxy)-4,4-diethoxybutyl)cyclopropanol:

To a solution of methyl 3-[(tert-butyldimethylsilyl)oxy]-5,5-diethoxypentanoate (424 mg, 1.27 mmol) in diethyl ether (10 mL) was added tetrakis(propan-2-yloxy)titanium (84 mg, 0.29 mmol) at room temperature. The resulting solution was stirred for 10 minutes at room temperature, and then was added by a solution of ethyl magnesium bromide (1M in tetrahydrofuran, 3.8 mL, 3.8 mmol) slowly using a syringe pump over 5 min period. The resulting solution was stirred for 4 h at room temperature. After the reaction was done, the reaction mixture was diluted with diethyl ether (50 mL) and quenched by the addition of sat. NH$_4$Cl solution (30 mL). The insoluble solids were filtered out and the filtrate was extracted with dithyl ether (50 mL×3). The organic layers combined and dried over anhydrous magnesium sulfate. The solvent was removed under reduced pressure and the residue was purified by flash chromatography eluting with EtOAc in petroleum ether (0% to 20% gradient) to yield of 1-[2-[(tert-butyldimethylsilyl)oxy]-4,4-diethoxybutyl]cyclopropan-1-ol as a light yellow solid (189 mg, 45%). $^1$H NMR (400 MHz, CDCl$_3$, ppm) δ 4.91 (t, J=5.6 Hz, 1H), 4.30-4.22 (m, 1H), 3.80-3.62 (m, 3H), 3.48-3.32 (m, 2H), 1.91-1.75 (m, 2H), 1.63-1.50 (m, 2H), 1.25-1.15 (m, 6H), 0.95-0.80 (m, 9H), 0.76-0.65 (m, 2H), 0.57-0.36 (m, 2H), 0.12-0.05 (m, 6H).

5-methoxy-4-oxaspiro[2.5]octan-7-ol:

To a solution of 1-[2-[(tert-butyldimethylsilyl)oxy]-4,4-diethoxybutyl]cyclopropan-1-ol (189 mg, 0.57 mmol) in methanol (8 mL) was added 4-methylbenzene-1-sulfonic acid hydrate (158 mg, 0.92 mmol) at room temperature. The resulting solution was stirred for 16 h at room temperature. When the reaction was done, it was quenched by the addition of sat. sodium bicarbonate solution (30 mL). The resulting mixture was extracted with DCM (50 mL×3). The organic layers were combined, washed with brine and dried over anhydrous magnesium sulfate. The solvent was removed under reduced pressure and the residue was purified by flash chromatography eluting with EtOAc in petroleum ether (20% to 35% gradient) to yield 5-methoxy-4-oxaspiro[2.5]octan-7-ol as a light yellow oil (65 mg, 72%). $^1$H NMR (400 MHz, CDCl$_3$, ppm) δ 4.81 (t, J=3.7 Hz, 1H), 4.61 (dd, J=5.2, 3.0 Hz, 1H), 4.30-4.22 (m, 1H), 4.03 (br s, 1H), 3.36 (s, 3H), 3.32 (s, 3H), 2.10-2.03 (m, 1H), 2.00-1.95 (m, 1H), 1.89 (dd, J=13.2, 4.0 Hz, 1H), 1.84-1.60 (m, 7H), 0.95-0.88 (m, 1H), 0.87-0.75 (m, 1H), 0.74-0.59 (m, 1H), 0.65-0.55 (m, 2H), 0.45-0.40 (m, 2H), 0.38-0.29 (m, 1H).

4-[7-[3-cyano-4-([5-methoxy-4-oxaspiro[2.5]octan-7-yl]oxy)phenyl]furo[3,2-b]pyridin-2-yl]-N,N-dimethylbenzamide To a solution of 5-methoxy-4-oxaspiro[2.5]octan-7-ol (23 mg, 0.15 mmol) in DMF (2 mL) was added sodium hydride (5 mg, 0.19 mmol) at room temperature. The resulting mixture was stirred for 10 min at room temperature, and then was added by 4-[7-(3-cyano-4-fluorophenyl)furo[3,2-b]pyridin-2-yl]-N,N-dimethylbenzamide (45 mg, 0.12 mmol) at room temperature. The resulting solution was then stirred for 4 h at 50° C. After cooling to room temperature, the reaction mixture was quenched by H$_2$O (5 mL). The resulting mixture was extracted with DCM (30 mL×3). The organic phases were combined, washed with brine and dried over sodium sulfate. The solvent was removed under reduced pressure and the residue was purified by reverse phase flash chromatography eluting with MeOH in H$_2$O (0% to 80% gradient) to yield 4-[7-[3-cyano-4-([5-methoxy-4-oxaspiro[2.5]octan-7-yl]oxy)phenyl]furo[3,2-b]pyridin-2-yl]-N,N-dimethylbenzamide as a light yellow solid (55 mg, 73%). MS: m/z=524.2 [M+H]$^+$.

4-[7-(3-cyano-4-[4-oxaspiro[2.5]octan-7-yloxy]phenyl)furo[3,2-b]pyridin-2-yl]-N,N-dimethylbenzamide At −10° C., Et$_3$SiH (118 mg, 1.02 mmol) and BF$_3$.Et$_2$O (98 mg, 0.69 mmol) were added in sequence to a solution of 4-[7-[3-cyano-4-([5-methoxy-4-oxaspiro[2.5]octan-7-yl]oxy)phenyl]furo[3,2-b]pyridin-2-yl]-N,N-dimethylbenzamide (48 mg, 0.09 mmol) in DCM (5 mL). The resulting solution was stirred for 8 h at 0° C. When the reaction was done, it was quenched by H₂O (10 mL). The pH value of the solution was adjusted to 8 with sat. sodium bicarbonate solution. The resulting mixture was extracted with DCM (30 mL×3). The organic phases were combined, washed with brine and dried over sodium sulfate. The solvent was removed under reduced pressure and the residue was purified by prep-HPLC under the following conditions: column, Gemini-NX C18, 21.2×150 mm 5 um; mobile phase, acetonitrile in water (with 10 mmol/L NH₄HCO₃), 20% to 50% gradient in 10 min; detector, UV 254/220 nm. 4-[7-(3-cyano-4-[4-oxaspiro[2.5]octan-7-yloxy]phenyl)furo[3,2-b]pyridin-2-yl]-N,N-dimethylbenzamide was obtained as a white solid (15 mg, 33%). HPLC: 99.6% purity, RT=1.57 min. MS: m/z=494.2 [M+H]⁺. ¹H NMR (300 MHz, DMSO-d₆, ppm) δ 8.58 (d, J=5.1 Hz, 1H), 8.52-8.42 (m, 2H), 8.14-8.03 (m, 2H), 7.83 (s, 1H), 7.73-7.55 (m, 4H), 5.10-4.95 (m, 1H), 3.98-3.82 (m, 1H), 3.70-3.55 (m, 1H), 3.02 (s, 3H), 2.96 (s, 3H), 2.20-2.09 (m, 1H), 2.03-1.70 (m, 3H), 0.82-0.46 (m, 4H).

Example 239: 4-[7-[3-cyano-4-([4-oxaspiro[2.5]octan-7-yl]amino)phenyl]furo[3,2-b]pyridin-2-yl]-N,N-dimethylbenzamide (286)

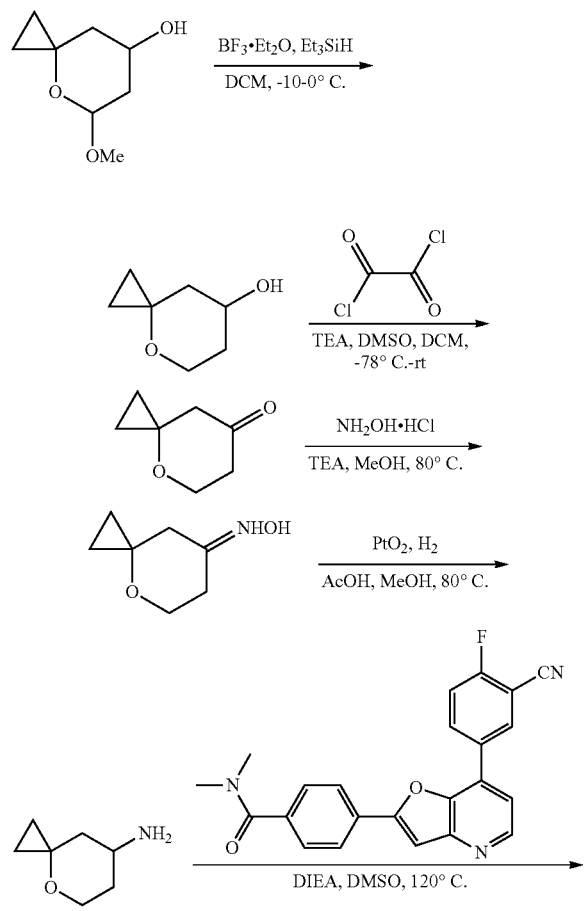

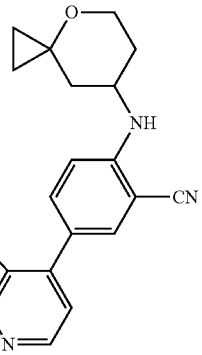

4-oxaspiro[2.5]octan-7-ol

To a solution of 5-methoxy-4-oxaspiro[2.5]octan-7-ol (280 mg, 1.77 mmol) in DCM (10 mL) was added Et₃SiH (3.35 g, 28.84 mmol) at −10° C. The resulting solution was stirred for 5 minutes at −10° C., and then was added by diethyl trifluoroborinate (2.76 g, 19.48 mmol) dropwise at −10° C. The resulting solution was stirred for 3 h at 0° C. When the reaction was done, it was quenched by the addition of aqueous sodium bicarbonate solution (30 mL). The resulting mixture was extracted with DCM (50 mL×3). The organic phases were combined, washed with brine and dried over sodium sulfate. The solvent was removed under reduced pressure to yield 4-oxaspiro[2.5]octan-7-ol as a light brown oil (230 mg, crude). The oil was used in the next step without further purification.

4-oxaspiro[2.5]octan-7-one

At −78° C., to a solution of oxalic dichloride (294 mg, 2.31 mmol) in DCM (5 mL) was added a solution of DMSO (362 mg, 4.63 mmol) in DCM (1 mL) dropwise. The resulting solution was stirred at −78° C. for 20 min, and then was added by a solution of 4-oxaspiro[2.5]octan-7-ol (230 mg, crude) in DCM (1 mL) dropwise. The resulting solution was stirred for another 20 min at −78° C., and then was added by TEA (1.02 g, 10.05 mmol). The reaction mixture was then slowly warmed up to room temperature in 3 h period. When the reaction was done, it was quenched by H₂O (30 mL). The resulting mixture was extracted with DCM (50 mL×3). The organic phases were combined, washed with brine and dried over sodium sulfate. The solvent was removed under reduced pressure and the residue was purified by flash chromatography eluting with ether in pentane (0% to 40% gradient) to yield 4-oxaspiro[2.5]octan-7-one as a yellow oil (48 mg, 21% for 2 steps). GC-MS: m/z=126.0 [M]⁺.

N-[(7Z)-4-oxaspiro[2.5]octan-7-ylidene]hydroxylamine

To a solution of 4-oxaspiro[2.5]octan-7-one (54 mg, 0.43 mmol) in MeOH (3 mL) was added hydroxylamine hydrochloride (229 mg, 3.29 mmol) and triethylamine (137 mg, 1.35 mmol) at room temperature. The resulting solution was stirred for 24 h at 80° C. After cooling to room temperature, the reaction mixture was concentrated under reduced pressure. The residue was diluted with THF (30 mL) and the insoluble solids were filtered out. The filtrate was concentrated under reduced pressure to yield N-[(7Z)-4-oxaspiro

[2.5]octan-7-ylidene]hydroxylamine as a light yellow syrup (130 mg, crude). GC-MS: m/z=142.0 [M]+.

4-oxaspiro[2.5]octan-7-amine

To a solution of N-[(7Z)-4-oxaspiro[2.5]octan-7-ylidene]hydroxylamine (130 mg, crude) in ethanol (15 mL) was added PtO$_2$ (57 mg, 0.25 mmol) and AcOH (1.5 mL) at room temperature under nitrogen atmosphere. The reaction flask was vacuumed and flushed with hydrogen. The reaction mixture was hydrogenated for 16 h at 60° C. under H$_2$ atmosphere using a hydrogen balloon. After the reaction was done, the pH value of the reaction mixture was adjusted to 9 with sodium hydroxide solution (1 mol/L). Then the resulting mixture was concentrated under reduced pressure. The residue was diluted with THF (40 mL) and the insoluble solids were filtered out. The filtrate was concentrated under reduced pressure to yield 4-oxaspiro[2.5]octan-7-amine as a yellow oil (130 mg, crude).

4-[7-[3-cyano-4-([4-oxaspiro[2.5]octan-7-yl]amino)phenyl]furo[3,2-b]pyridin-2-yl]-N,N-dimethylbenzamide To a solution of 4-oxaspiro[2.5]octan-7-amine (65 mg, crude) in DMSO (2 mL) was added 4-[7-(3-cyano-4-fluorophenyl)furo[3,2-b]pyridin-2-yl]-N,N-dimethylbenzamide (36 mg, 0.09 mmol) and DIEA (38 mg, 0.29 mmol) at room temperature. The resulting solution was stirred for 16 h at 120° C. After cooling to room temperature, the reaction mixture was quenched by the addition of water (10 mL). The resulting mixture was extracted with DCM (30 mL×3). The organic phases were combined, washed with brine and dried over sodium sulfate. The solvent was removed under reduced pressure and the residue was purified by prep-HPLC under the following conditions: column, XBridge C18 OBD Prep Column, 10 um, 19 mm×250 mm; mobile phase, acetonitrile in water (with 10 mmol/L NH$_4$HCO$_3$), 36% to 49% gradient in 12 min; detector, UV 254/220 nm. 4-[7-[3-cyano-4-([4-oxaspiro[2.5]octan-7-yl]amino)phenyl]furo[3,2-b]pyridin-2-yl]-N,N-dimethylbenzamide was obtained as a yellow solid (12.9 mg, 12% for 3 steps). HPLC: 99.2% purity, RT=1.51 min. MS: m/z=493.2 [M+H]+. $^1$H NMR (300 MHz, CD$_3$OD, ppm) δ 8.32 (br s, 1H), 8.15-8.05 (m, 2H), 8.00-7.94 (m, 2H), 7.60-7.30 (m, 4H), 6.98 (d, J=8.6 Hz, 1H), 3.97-3.75 (m, 2H), 3.70-3.55 (m, 1H), 3.04 (s, 3H), 2.97 (s, 3H), 2.07-1.87 (m, 2H), 1.73-1.55 (m, 2H), 0.78-0.70 (m, 1H), 0.69-0.60 (m, 1H), 0.56-0.44 (m, 2H).

Example 240: 4-(7-[3-cyano-4-[1-(morpholin-4-yl)cyclopropyl]phenyl]furo[3,2-b]pyridin-2-yl)-N,N-dimethylbenzamide hydrochloride (287)

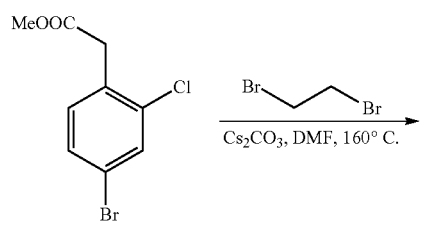

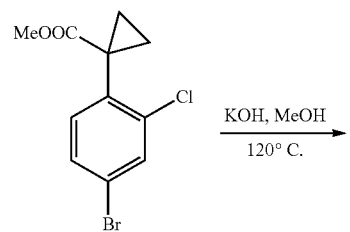

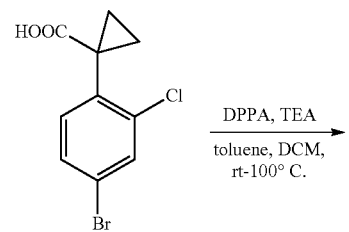

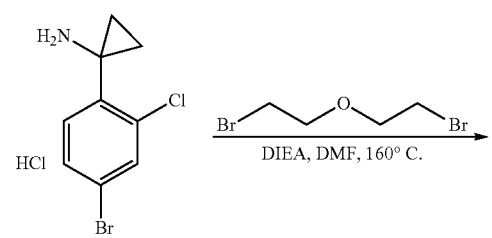

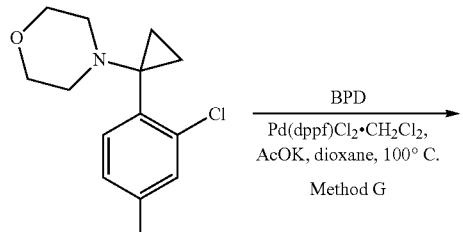

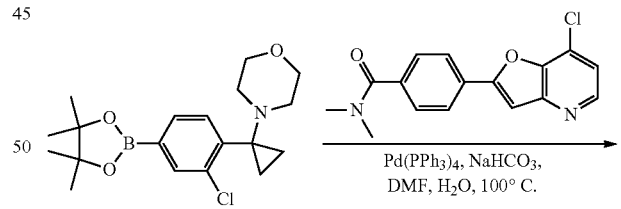

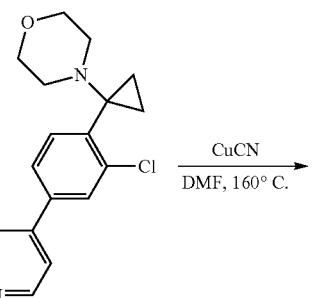

-continued

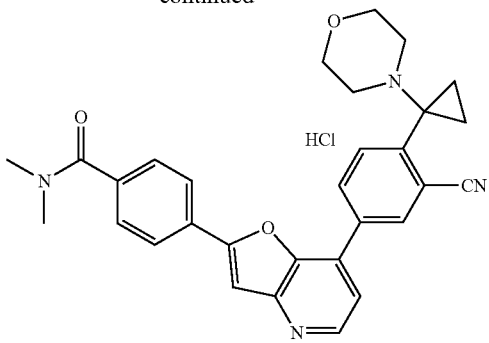

Methyl 1-(4-bromo-2-chlorophenyl)cyclopropanecarboxylate

To a solution of methyl 2-(4-bromo-2-chlorophenyl)acetate (264 mg, 1.00 mmol) in DMF (4 mL) was added 1,2-dibromoethane (282 mg, 1.50 mmol) and Cs$_2$CO$_3$ (975 mg, 2.99 mmol) at room temperature. The resulting mixture was stirred for 10 h at 160° C. After cooling to room temperature, the reaction mixture was quenched by the addition of water (30 mL). The resulting mixture was extracted with ethyl acetate (50 mL×3). The organic phases were combined, washed with brine and dried over sodium sulfate. The solvent was removed under reduced pressure and the residue was purified by flash chromatography eluting with EtOAc in hexane (0% to 2% gradient) to yield methyl 1-(4-bromo-2-chlorophenyl)cyclopropane-1-carboxylate as a off-white solid (100 mg, 34%). MS: m/z=290.0 [M+H]$^+$.

1-(4-Bromo-2-chlorophenyl)cyclopropanecarboxylic acid

To a solution of methyl 1-(4-bromo-2-chlorophenyl)cyclopropane-1-carboxylate (1000 mg, 0.35 mmol) in EtOH (20 mL) was added potassium hydroxide (580 mg, 1.05 mmol) at room temperature. The resulting solution was stirred for 8 h at 120° C. After the reaction was done, the pH value of the reaction mixture was adjusted to 1 with hydrogen chloride solution (3 M). Precipitation happened. The precipitates were collected by filtration and dried in oven under vacuum to yield 1-(4-bromo-2-chlorophenyl)cyclopropane-1-carboxylic acid as a off-white solid (640 mg, 79%). $^1$H NMR (400 MHz, DMSO, ppm) δ 12.49 (br s, 1H), 7.72 (s, 1H), 7.50 (d, J=6.4 Hz, 1H), 7.37 (d, J=7.6 Hz, 1H), 1.55 (d, J=3.2 Hz, 2H), 1.16 (d, J=2.8 Hz, 2H).

1-(4-Bromo-2-chlorophenyl)cyclopropanamine hydrochloride

To a solution of 1-(4-bromo-2-chlorophenyl)cyclopropane-1-carboxylic acid (300 mg, 1.09 mmol) in DCM (10 mL) was added triethylamine (143 mg, 1.41 mmol) at 0° C. The resulting solution was stirred for 15 min at room temperature, and then was added by DPPA (390 mg, 1.42 mmol). The mixture was stirred for 4 h at room temperature. After the reaction was done, the reaction mixture was concentrated and the residue was diluted with toluene (10 mL). The resulting mixture was stirred for another 2 h at 110° C. After cooling to room temperature, the reaction mixture was quenched by HCl solution (6 N in water, 15 mL). The resulting mixture was extracted with ethyl acetate (20 mL×3). The organic phases were combined, washed with brine and dried over sodium sulfate. The solvent was removed under reduced pressure to yield 1-(4-bromo-2-chlorophenyl)cyclopropanamine hydrochloride as a off-white solid (200 mg, crude). The product was used to next step without further purification.

4-(1-(4-Bromo-2-chlorophenyl)cyclopropyl)morpholine

To a solution of 1-(4-bromo-2-chlorophenyl)cyclopropan-1-amine (72 mg, 0.29 mmol) in DMF (1 mL) were added 1-bromo-2-(2-bromoethoxy)ethane (81 mg, 0.35 mmol) and DIEA (151 mg, 1.17 mmol) at room temperature. The resulting solution was stirred for 12 h at 160° C. After cooling to room temperature, the reaction mixture was quenched by the addition of water (15 mL). The resulting mixture was extracted with ethyl acetate (20 mL×3). The organic phases were combined, washed with brine and dried over sodium sulfate. The solvent was removed under reduced pressure to yield 4-[1-(4-bromo-2-chlorophenyl)cyclopropyl]morpholine as a off-white solid (80 mg, crude). The product was used to next step without further purification.

4-[1-[2-Chloro-4-(tetramethyl-1,3,2-dioxaborolan-2-yl)phenyl]cyclopropyl]morpholine 4-[1-[2-chloro-4-(tetramethyl-1,3,2-dioxaborolan-2-yl)phenyl]cyclopropyl]morpholine was prepared from 4-[1-(4-bromo-2-chlorophenyl)cyclopropyl]morpholine (80 mg, crude) using Method G. 4-[1-[2-chloro-4-(tetramethyl-1,3,2-dioxaborolan-2-yl)phenyl]cyclopropyl]morpholine was obtained as a light brown solid (190 mg, crude). MS: m/z=364.2 [M+H]$^+$. The product was used to next step without further purification.

Method 1

4-(7-(3-Chloro-4-(1-morpholinocyclopropyl)phenyl)furo[3,2-b]pyridin-2-yl)-N,N-dimethylbenzamide To a solution of 4-[7-chlorofuro[3,2-b]pyridin-2-yl]-N,N-dimethylbenzamide (21 mg, 0.07 mmol) in DMF (3 mL) was added 4-[1-[2-chloro-4-(tetramethyl-1,3,2-dioxaborolan-2-yl)phenyl]cyclopropyl]morpholine (70 mg, crude), Pd(PPh$_3$)$_4$ (16 mg, 0.01 mmol), sodium bicarbonate (19 mg, 0.23 mmol) and water (0.75 mL) at room temperature under nitrogen atmosphere. The resulting mixture was stirred for 2 h at 100° C. under nitrogen atmosphere. After cooling to room temperature, the reaction mixture was quenched by the addition of water (10 mL). The resulting mixture was extracted with ethyl acetate (30 mL×3). The organic phases were combined, washed with brine and dried over sodium sulfate. The solvent was removed under reduced pressure and the residue was purified by flash chromatography eluting with EtOAc in hexane (0% to 100% gradient) to yield 4-(7-[3-chloro-4-[1-(morpholin-4-yl)cyclopropyl]phenyl]furo[3,2-b]pyridin-2-yl)-N,N-dimethylbenzamide as a light brown solid (36 mg, 53% for 4 steps). MS: m/z=502.2 [M+H]$^+$.

4-(7-[3-Cyano-4-[1-(morpholin-4-yl)cyclopropyl]phenyl]furo[3,2-b]pyridin-2-yl)-N,N-dimethylbenzamide hydrochloride To a solution of 4-(7-[3-chloro-4-[1-(morpholin-4-yl)cyclopropyl]phenyl]furo[3,2-b]pyridin-2-yl)-N,N-dimethylbenzamide (90 mg, 0.18 mmol) in DMF (5 mL) was added CuCN (81 mg, 0.90 mmol) at room temperature. The resulting solution was stirred for 16 h at 160° C. After the reaction was done, the insoluble solids in the reaction mixture were filtered out and the filtrate was diluted with water (10 mL). The resulting mixture was extracted with DCM (30 mL×3). The organic phases were combined, washed with brine and dried over sodium sulfate. The solvent was removed under reduced pressure and the residue was purified by prep-HPLC under the following conditions: column, Gemini-NX C18, 21.2×150 mm 5 um; mobile phase, acetonitrile in water (with 0.02% HCl), 20% to 45% gradient in 10 min; detector, UV 254/220 nm. 4-(7-[3-cyano-4-[1-(morpholin-4-yl)cyclopropyl]phenyl]furo[3,2-b]pyridin-2-yl)-N,N-dimethylbenzamide hydrochloride was obtained as a light yellow solid (10 mg, 11%). HPLC: 99.9% purity, RT=0.83 min. MS: m/z=493.1 [M+H]$^+$. $^1$H NMR (300 MHz, CD$_3$OD, ppm) δ 8.82 (br s, 1H), 8.71 (d, J=1.5 Hz, 1H), 8.63 (d, J=8.1 Hz, 1H), 8.22 (d, J=7.8 Hz, 2H), 8.19-8.08 (m, 2H), 7.88 (s, 1H), 7.65 (d, J=8.4 Hz, 2H), 3.93 (br s, 4H), 3.47 (br s, 4H), 3.12 (s, 3H), 3.01 (s, 3H), 1.95-1.83 (m, 2H), 1.62-1.50 (m, 2H).

Example 241: 4-[7-(3-cyano-5-fluoro-4-[4-oxaspiro[2.5]octan-7-yloxy]phenyl)furo[3,2-b]pyridin-2-yl]-N,N-dimethylbenzamide hydrochloride (288)

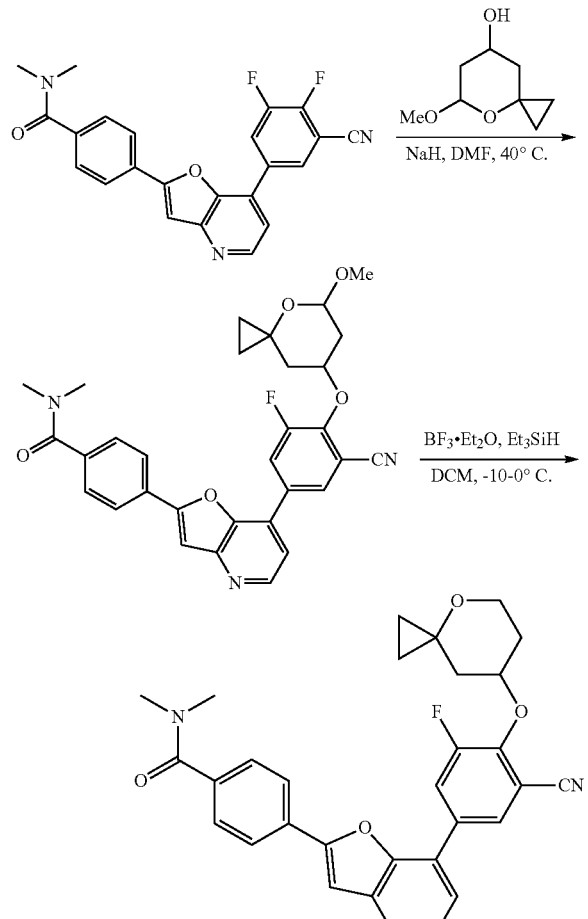

4-[7-[3-cyano-5-fluoro-4-([5-methoxy-4-oxaspiro[2.5]octan-7-yl]oxy)phenyl]furo[3,2-b]pyridin-2-yl]-N,N-dimethylbenzamide To a solution of 5-methoxy-4-oxaspiro[2.5]octan-7-ol (11 mg, 0.07 mmol) in N,N-dimethylformamide (1.5 mL) was added sodium hydride (6 mg, 0.23 mmol) at room temperature. The resulting mixture was stirred at room temperature for 10 min, and then was added by 4-[7-(3-cyano-4,5-difluorophenyl)furo[3,2-b]pyridin-2-yl]-N,N-dimethylbenzamide (43 mg, 0.11 mmol) at room temperature. The reaction mixture was stirred for additional 2 h while the temperature was maintained at 40° C. After cooling to room temperature, the reaction mixture was quenched by the addition of water (10 mL). The resulting mixture was extracted with ethyl acetate (30 mL×3). The organic phases were combined, washed with brine and dried over sodium sulfate. The solvent was removed under reduced pressure and the residue was purified by reverse phase flash chromatography eluting with acetonitrile in water (with 10 mmol/L NH$_4$HCO$_3$), (0% to 90% gradient in 30 min) to yield 4-[7-[3-cyano-5-fluoro-4-([5-methoxy-4-oxaspiro[2.5]octan-7-yl]oxy)phenyl]furo[3,2-b]pyridin-2-yl]-N,N-dimethylbenzamide as gray solid (10 mg, 68%). MS: m/z=542.2 [M+H]$^+$.

4-[7-(3-cyano-5-fluoro-4-[4-oxaspiro[2.5]octan-7-yloxy]phenyl)furo[3,2-b]pyridin-2-yl]-N,N-dimethylbenzamide hydrochloride At −10° C., to a solution of 4-[7-[3-cyano-5-fluoro-4-([5-methoxy-4-oxaspiro[2.5]octan-7-yl]oxy)phenyl]furo[3,2-b]pyridin-2-yl]-N,N-dimethylbenzamide (33 mg, 0.06 mmol) in dichloromethane (10 mL) was added Et$_3$SiH (734 mg, 6.32 mmol) and BF$_3$.Et$_2$O (605 mg, 4.26 mmol) in sequence. The resulting solution was then stirred for 1 h at 0° C. When the reaction was done, it was quenched by the addition of water (10 mL). The resulting mixture was extracted with DCM (30 mL×3). The organic phases were combined, washed with brine and dried over sodium sulfate. The solvent was removed under reduced pressure and the residue was purified by prep-HPLC under the following conditions: column, XBridge Prep C18 OBD Column, 5 um, 19×150 mm; mobile phase, acetonitrile in water (with 10 mmol/L NH$_4$HCO$_3$), 35% to 55% gradient in 10 min; detector, UV 254/220 nm. 4-[7-(3-cyano-5-fluoro-4-[4-oxaspiro[2.5]octan-7-yloxy]phenyl)furo[3,2-b]pyridin-2-yl]-N,N-dimethylbenzamide hydrochloride was obtained as a yellow solid (12 mg, 32%). HPLC: 89.6% purity, RT=2.07 min. MS: m/z=512.2 [M+H]$^+$. $^1$H NMR (400 MHz, CD$_3$OD, ppm) δ 8.85 (d, J=5.8 Hz, 1H), 8.17 (d, J=8.0 Hz, 2H), 8.04 (dd, J=6.1, 3.1 Hz, 1H), 7.96-7.88 (m, 1H), 7.82 (dd, J=11.1, 8.5 Hz, 1H), 7.73 (dd, J=8.4, 4.0 Hz, 1H), 7.64 (d, J=7.9 Hz, 2H), 5.00-4.90 (m, 1H), 4.10-4.00 (m, 1H), 3.70-3.60 (m, 1H), 3.13 (s, 3H), 3.02 (s, 3H), 2.27-2.12 (m, 2H), 2.06-1.86 (m, 2H), 0.91-0.81 (m, 1H), 0.75-0.63 (m, 1H), 0.66-0.56 (m, 1H), 0.51-0.42 (m, 1H).

Example 242: 4-(7-[3-cyano-4-[(3,5-dimethyloxan-4-yl)oxy]-5-fluorophenyl]furo[3,2-b]pyridin-2-yl)-N,N-dimethylbenzamide (289)

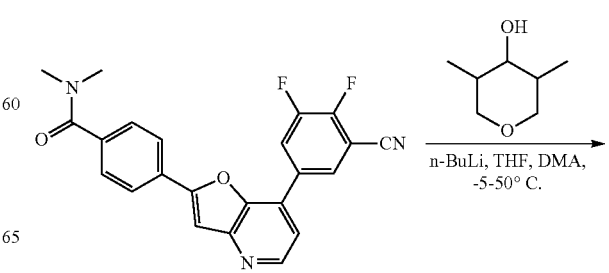

437
-continued

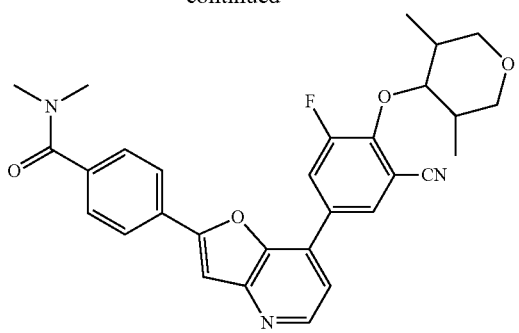

At −5° C., to a solution of 3,5-dimethyloxan-4-ol (19 mg, 0.15 mmol) in THF (3 mL) was added n-BuLi (1 M in THF, 0.95 mL) dropwise. The resulting solution was stirred for 15 min at −5° C., and then was added by a solution of 4-[7-(3-cyano-4,5-difluorophenyl)furo[3,2-b]pyridin-2-yl]-N,N-dimethylbenzamide (84 mg, 0.21 mmol) in DMA (1.5 mL) dropwise. The reaction mixture was allowed to react for additional 20 min while the temperature was maintained at 50° C. After cooling to room temperature, the reaction mixture was quenched by the addition of water (10 mL). The resulting mixture was extracted with DCM (30 mL×3). The organic phases were combined, washed with brine and dried over sodium sulfate. The solvent was removed under reduced pressure and the residue was purified by prep-HPLC under the following conditions: column, Gemini-NX C18, 21.2×150 mm 5 um; mobile phase, acetonitrile in water (with 10 mmol/L NH$_4$HCO$_3$), 20% to 50% gradient in 10 min; detector, UV 254/220 nm. 4-(7-[3-cyano-4-[(3,5-dimethyloxan-4-yl)oxy]-5-fluorophenyl]furo[3,2-b]pyridin-2-yl)-N,N-dimethylbenzamide was obtained as a light yellow solid (12 mg, 14%). HPLC: 91.3% purity, RT=4.66 min. MS: m/z=514.1 [M+H]$^+$. $^1$H NMR (400 MHz, CD$_3$OD, ppm) δ 8.53 (s, 1H), 7.94 (d, J=7.8 Hz, 2H), 7.73-7.32 (m, 6H), 4.60-4.30 (m, 1H), 4.10-3.94 (m, 1H), 3.66-3.57 (m, 2H), 3.35-3.25 (m, 1H), 3.04 (s, 3H), 2.95 (s, 3H), 2.21-1.80 (m, 2H), 1.31-0.75 (m, 6H).

Example 243: 4-[7-(3-cyano-4-[4-oxaspiro[2.5]octan-7-yloxy]phenyl)furo[3,2-b]pyridin-2-yl]-3-methoxy-N,N-dimethylbenzamide (290)

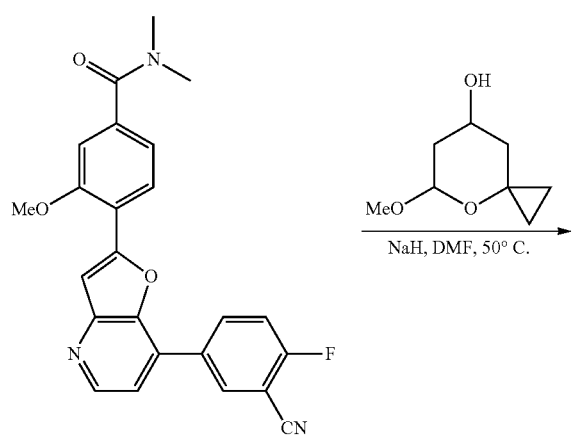

438
-continued

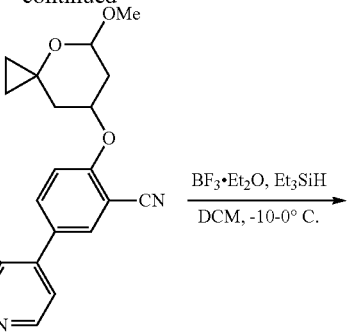

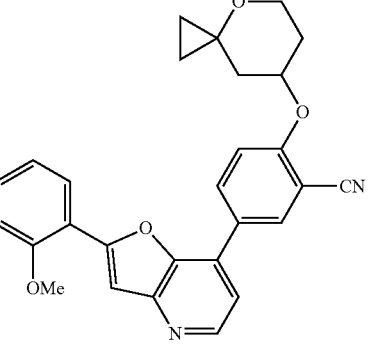

4-[7-[3-cyano-4-([5-methoxy-4-oxaspiro[2.5]octan-7-yl]oxy)phenyl]furo[3,2-b]pyridin-2-yl]-3-methoxy-N,N-dimethylbenzamide To a solution of 5-methoxy-4-oxaspiro[2.5]octan-7-ol (32 mg, 0.20 mmol) in N,N-dimethylformamide (1.5 mL) was added sodium hydride (28 mg, 1.17 mmol) at room temperature. The resulting mixture was stirred for 10 min at room temperature, and then was added by a solution of 4-[7-(3-cyano-4-fluorophenyl)furo[3,2-b]pyridin-2-yl]-3-methoxy-N,N-dimethylbenzamide (58 mg, 0.14 mmol) in N,N-dimethylformamide (1.5 mL). The reaction mixture was then stirred for 3.5 h at 50° C. After cooling to room temperature, the reaction mixture was quenched by the addition of water (10 mL). The resulting mixture was extracted with ethyl acetate (30 mL×3). The organic phases were combined, washed with brine and dried over sodium sulfate. The solvent was removed under reduced pressure and the residue was purified by flash chromatography eluting with acetonitrile in water (0% to 62% gradient in 30 min) to yield 4-[7-[3-cyano-4-([5-methoxy-4-oxaspiro[2.5]octan-7-yl]oxy)phenyl]furo[3,2-b]pyridin-2-yl]-3-methoxy-N,N-dimethylbenzamide as a light brown solid (70 mg, 64%). MS: m/z=554.2 [M+H]$^+$.

4-[7-(3-cyano-4-[4-oxaspiro[2.5]octan-7-yloxy]phenyl)furo[3,2-b]pyridin-2-yl]-3-methoxy-N,N-dimethylbenzamide At −10° C., to a solution of 4-[7-[3-cyano-4-([5-methoxy-4-oxaspiro[2.5]octan-7-yl]oxy)phenyl]furo[3,2-b]pyridin-2-yl]-3-methoxy-N,N-dimethylbenzamide (63 mg, 0.11 mmol) in dichloromethane (9 mL) were added Et$_3$SiH (72 mg, 0.62 mmol) and BF$_3$·Et$_2$O (59 mg, 0.42 mmol) in sequence. The resulting solution was stirred for 4 h at 0° C. When the reaction was done, it was quenched by the addition of water (10 mL). The resulting mixture was extracted with DCM (30 mL×3). The organic phases were combined, washed with brine and dried over sodium sulfate. The solvent was removed under reduced pressure and the residue was purified by prep-HPLC under the following conditions: column, Gemini-NX 5u C18 110A, AXIA Packed, 150×21.2 mm; mobile phase, acetonitrile in water (with 10 mmol/L NH$_4$HCO$_3$), 20% to 50% gradient in 8 min; detector, UV 254/220 nm. 4-[7-(3-cyano-4-[4-oxaspiro [2.5]octan-7-yloxy]phenyl)furo[3,2-b]pyridin-2-yl]-3-methoxy-N,N-dimethylbenzamide was obtained as a white solid (35 mg, 55%). HPLC: 93.4% purity, RT=1.81 min. MS: m/z=524.2 [M+H]$^+$. $^1$H NMR (400 MHz, CD$_3$OD, ppm) δ 8.57 (d, J=5.1 Hz, 1H), 8.52-8.41 (m, 2H), 8.03 (d, J=8.0 Hz, 1H), 7.72-7.59 (m, 3H), 7.29-7.13 (m, 2H), 5.03 (s, 1H), 4.06 (s, 3H), 3.97-3.83 (m, 1H), 3.62 (dd, J=11.5, 8.6, Hz, 1H), 3.02 (s, 3H), 2.96 (s, 3H), 2.20-2.08 (m, 1H), 2.03-1.73 (m, 3H), 0.77 (dd, J=9.7, 3.1 Hz, 1H), 0.67-0.49 (m, 3H).

Example 244: 4-(7-[3-cyano-4-[2-(morpholin-4-yl) propan-2-yl]phenyl]furo[3,2-b]pyridin-2-yl)-3-methoxy-N,N-dimethylbenzamide hydrochloride (291)

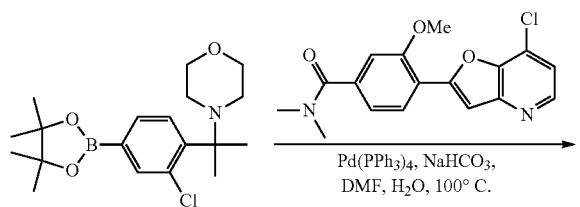

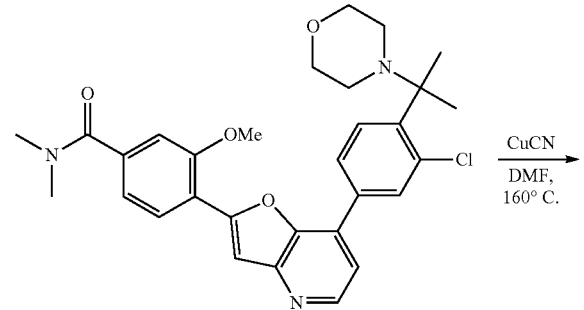

4-(7-[3-chloro-4-[2-(morpholin-4-yl)propan-2-yl] phenyl]furo[3,2-b]pyridin-2-yl)-3-methoxy-N,N-dimethylbenzamide 4-(7-[3-chloro-4-[2-(morpholin-4-yl)propan-2-yl]phenyl] furo[3,2-b]pyridin-2-yl)-3-methoxy-N,N-dimethylbenzamide was prepared from 4-(2-(2-chloro-4-(4,4,5,5-tetramethyl-1,3,2-dioxaborolan-2-yl)phenyl)propan-2-yl) morpholine and 4-(7-chlorofuro[3,2-b]pyridin-2-yl)-3-methoxy-N,N-dimethylbenzamide using Method 1. The product was purified by flash chromatography eluting with EtOAc in hexane (0% to 1% gradient) to yield 4-(7-[3-chloro-4-[2-(morpholin-4-yl)propan-2-yl]phenyl]furo[3,2-b]pyridin-2-yl)-3-methoxy-N,N-dimethylbenzamide as a light brown solid (180 mg, 84%). MS: m/z=534.2 [M+H]$^+$.

4-(7-[3-cyano-4-[2-(morpholin-4-yl)propan-2-yl] phenyl]furo[3,2-b]pyridin-2-yl)-3-methoxy-N,N-dimethylbenzamide hydrochloride To a solution of 4-(7-[3-chloro-4-[2-(morpholin-4-yl)propan-2-yl]phenyl]furo[3,2-b]pyridin-2-yl)-3-methoxy-N,N-dimethylbenzamide (175 mg, 0.33 mmol) in DMF (4 mL) was added CuCN (200 mg, 2.23 mmol) at room temperature. The resulting mixture was stirred for 16 h at 160° C. After the reaction was done, the insoluble solids in the reaction mixture were filtered out and the filtrate was diluted with water (10 mL). The resulting mixture was extracted with DCM (30 mL×3). The organic phases were combined, washed with brine and dried over sodium sulfate. The solvent was removed under reduced pressure and the residue was purified by prep-HPLC under the following conditions: column, Gemini-NX C18 AXAI Packed 21.2×150 mm 5 um 11 nm; mobile phase, acetonitrile in water (with 0.02% HCl), 20% to 45% gradient in 10 min; detector, UV 254/220 nm. 4-(7-[3-cyano-4-[2-(morpholin-4-yl)propan-2-yl]phenyl]furo[3,2-b]pyridin-2-yl)-3-methoxy-N,N-dimethylbenzamide hydrochloride was obtained as a yellow solid (30 mg, 16%). HPLC: 95.1% purity, RT=1.28 min. MS: m/z=525.3 [M+H]$^+$. $^1$H NMR (300 MHz, CD$_3$OD, ppm) δ 8.90-8.45 (m, 4H), 8.35-8.10 (br s, 2H), 7.89 (s, 1H), 7.33 (s, 1H), 7.24 (br s, 1H), 4.14 (s, 3H), 4.04 (br s, 4H), 3.14 (br s, 4H), 3.12 (s, 3H), 3.02 (s, 3H), 2.23 (s, 6H).

Example 245: 4-(7-[3-cyano-4-[1-(morpholin-4-yl) cyclopropyl]phenyl]furo[3,2-b]pyridin-2-yl)-3-methoxy-N,N-dimethylbenzamide hydrochloride (292)

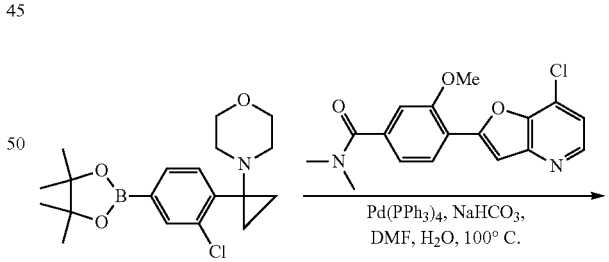

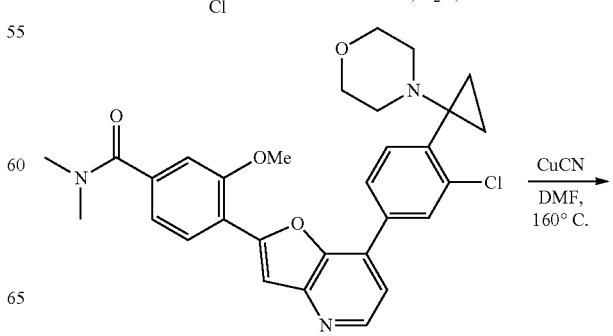

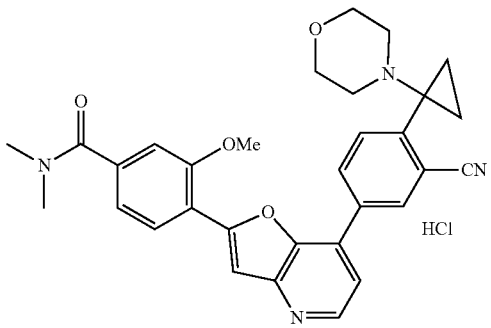

4-(7-[3-chloro-4-[1-(morpholin-4-yl)cyclopropyl]phenyl]furo[3,2-b]pyridin-2-yl)-3-methoxy-N,N-dimethylbenzamide 4-(7-[3-chloro-4-[1-(morpholin-4-yl)cyclopropyl]phenyl]furo[3,2-b]pyridin-2-yl)-3-methoxy-N,N-dimethylbenzamide was prepared from 4-(1-(2-chloro-4-(4,4,5,5-tetramethyl-1,3,2-dioxaborolan-2-yl)phenyl)cyclopropyl)morpholine and 4-(7-chlorofuro[3,2-b]pyridin-2-yl)-3-methoxy-N,N-dimethylbenzamide using Method 1. The product was purified by flash chromatography eluting with MeOH in DCM (0% to 5% gradient) to yield 4-(7-[3-chloro-4-[1-(morpholin-4-yl)cyclopropyl]phenyl]furo[3,2-b]pyridin-2-yl)-3-methoxy-N,N-dimethylbenzamide as a light yellow solid (250 mg, 49%). MS: m/z=532.2 [M+H]$^+$.

4-(7-[3-cyano-4-[1-(morpholin-4-yl)cyclopropyl]phenyl]furo[3,2-b]pyridin-2-yl)-3-methoxy-N,N-dimethylbenzamide hydrochloride To a solution of 4-(7-[3-chloro-4-[1-(morpholin-4-yl)cyclopropyl]phenyl]furo[3,2-b]pyridin-2-yl)-3-methoxy-N,N-dimethylbenzamide (213 mg, 0.40 mmol) in DMF (4 mL) was added CuCN (210 mg, 2.34 mmol) at room temperature. The resulting solution was stirred for 16 h at 160° C. After cooling to room temperature the solids were filtered out, the reaction mixture was quenched by the addition of water (10 mL). The resulting mixture was extracted with DCM (30 mL×3). The organic phases were combined, washed with brine and dried over sodium sulfate. The solvent was removed under reduced pressure and the residue was purified by prep-HPLC under the following conditions: column, Gemini-NX C18 AXAI Packed 21.2×150 mm 5 um 11 nm; mobile phase, acetonitrile in water (with 0.02% HCl), 20% to 45% gradient in 10 min; detector, UV 254/220 nm. 4-(7-[3-cyano-4-[1-(morpholin-4-yl)cyclopropyl]phenyl]furo[3,2-b]pyridin-2-yl)-3-methoxy-N,N-dimethylbenzamide hydrochloride as a yellow solid (20 mg, 8%). HPLC: 93.2% purity, RT=1.17 min. MS: m/z=523.2 [M+H]$^+$. $^1$H NMR (300 MHz, CD$_3$OD, ppm) δ 8.90-8.60 (m, 3H), 8.40-8.10 (m, 3H), 7.88 (s, 1H), 7.40-7.10 (m, 2H), 4.30-3.60 (m, 10H), 3.20-2.90 (m, 7H), 2.20-1.90 (br s, 2H), 1.70-1.50 (br s, 2H).

Example 246: 4-[7-(3-cyano-5-fluoro-4-[4-oxaspiro[2.5]octan-7-yloxy]phenyl)furo[3,2-b]pyridin-2-yl]-3-methoxy-N,N-dimethylbenzamide (293)

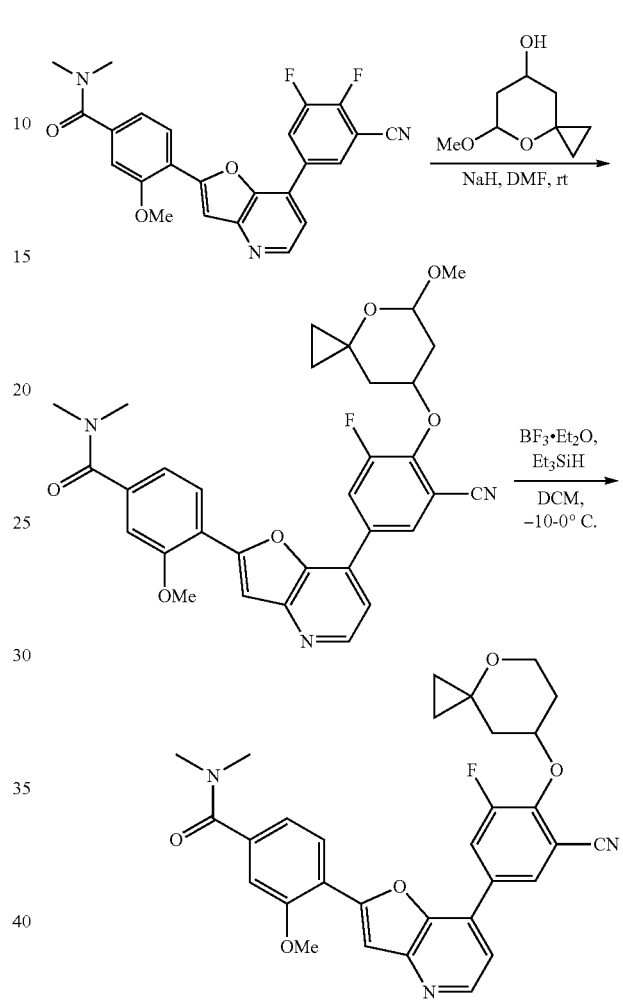

4-[7-[3-cyano-5-fluoro-4-([5-methoxy-4-oxaspiro[2.5]octan-7-yl]oxy)phenyl]furo[3,2-b]pyridin-2-yl]-3-methoxy-N,N-dimethylbenzamide To a solution of 5-methoxy-4-oxaspiro[2.5]octan-7-ol (16 mg, 0.10 mmol) in N,N-dimethylformamide (2 mL) was added sodium hydride (4 mg, 0.17 mmol) at room temperature. The resulting mixture was stirred at room temperature for 10 min, and then was added by a solution of 4-[7-(3-cyano-4,5-difluorophenyl)furo[3,2-b]pyridin-2-yl]-3-methoxy-N,N-dimethylbenzamide (67 mg, 0.15 mmol) in DMF (1 mL). The reaction mixture was stirred at room temperature for 1 h. When the reaction was done, it was quenched by the addition of water (10 mL). The resulting mixture was extracted with ethyl acetate (30 mL×3). The organic phases were combined, washed with brine and dried over sodium sulfate. The solvent was removed under reduced pressure and the residue was purified by reverse phase flash chromatography eluting with acetonitrile in water (with 10 mmol/L NH$_4$HCO$_3$), (0% to 60% gradient in 30 min) to yield 4-[7-[3-cyano-5-fluoro-4-([5-methoxy-4-oxaspiro[2.5]octan-7-yl]oxy)phenyl]furo[3,2-b]pyridin-2- yl]-3-methoxy-N,N-dimethylbenzamide as a brown solid (33 mg, 54%). MS: m/z=572.2 [M+H]+.

4-[7-(3-cyano-5-fluoro-4-[4-oxaspiro[2.5]octan-7-yloxy]phenyl)furo[3,2-b]pyridin-2-yl]-3-methoxy-N,N-dimethylbenzamidE At −10° C., to a solution of 4-[7-[3-cyano-5-fluoro-4-([5-methoxy-4-oxaspiro[2.5]octan-7-yl]oxy)phenyl]furo[3,2-b]pyridin-2-yl]-3-methoxy-N,N dimethylbenzamide (64 mg, 0.11 mmol) in dichloromethane (5 mL) were added Et$_3$SiH (232 mg, 1.99 mmol) and BF$_3$.Et$_2$O (191 mg, 1.35 mmol) in sequence. The resulting solution was then stirred for 3.5 h at 0° C. When the reaction was done, it was quenched by the addition of water (10 mL). The resulting mixture was extracted with DCM (30 mL×3). The organic phases were combined, washed with brine and dried over sodium sulfate. The solvent was removed under reduced pressure and the residue was purified by prep-HPLC under the following conditions: column, Gemini-NX 5u C18 110A, AXIA Packed, 150×21.2 mm; mobile phase, acetonitrile in water (with 10 mmol/L NH$_4$HCO$_3$), 35% to 65% gradient in 8 min; detector, UV 254/220 nm. 4-[7-(3-cyano-5-fluoro-4-[4-oxaspiro[2.5]octan-7-yloxy]phenyl)furo[3,2-b]pyridin-2-yl]-3-methoxy-N,N-dimethylbenzamide was obtained as a off-white solid (50 mg, 56%). HPLC: 87.7% purity, RT=2.57 min. MS: m/z=542.3 [M+H]+. $^1$H NMR (400 MHz, CD$_3$OD, ppm) δ 8.60 (d, J=5.1 Hz, 1H), 8.04 (d, J=8.0 Hz, 1H), 7.80-7.64 (m, 2H), 7.60 (dd, J=8.7, 4.4 Hz, 1H), 7.51 (d, J=5.1 Hz, 1H), 7.28 (d, J=1.4 Hz, 1H), 7.14 (dd, J=8.0, 1.4 Hz, 1H), 4.96-4.89 (m, 1H), 4.13 (s, 3H), 4.10-4.00 (m, 1H), 3.70-3.60 (m, 1H), 3.15 (s, 3H), 3.06 (s, 3H), 2.25-2.10 (m, 2H), 2.07-1.89 (m, 2H), 0.91-0.81 (m, 1H), 0.77-0.56 (m, 2H), 0.50-0.42 (m, 1H).

Example 247: 4-(7-[3-cyano-4-[(3,5-dimethyloxan-4-yl)oxy]-5-fluorophenyl]furo[3,2-b]pyridin-2-yl)-3-methoxy-N,N-dimethylbenzamide (294)

4-(7-[3-cyano-4-[(3,5-dimethyloxan-4-yl)oxy]-5-fluorophenyl]furo[3,2-b]pyridin-2-yl)-3-methoxy-N,N-dimethylbenzamide To a solution of 3,5-dimethyloxan-4-ol (14 mg, 0.11 mmol) in DMA (2 mL) was added sodium hydride (4 mg, 0.16 mmol) at room temperature. The resulting mixture was stirred for 10 minutes at room temperature, and then was added by a solution of 4-[7-(3-cyano-4,5-difluorophenyl)furo[3,2-b]pyridin-2-yl]-3-methoxy-N,N-dimethylbenzamide (55 mg, 0.13 mmol) in DMA (1 mL) at room temperature. The reaction mixture was stirred for 16 h while the temperature was maintained at 30° C. When the reaction was done, it was quenched by the addition of water (10 mL). The resulting mixture was extracted with DCM (30 mL×3). The organic phases were combined, washed with brine and dried over sodium sulfate. The solvent was removed under reduced pressure and the residue was purified by prep-HPLC under the following conditions: column, XBridge Prep C18 OBD Column, 5 um, 19×150 mm; mobile phase, acetonitrile in water (with 10 mmol/L NH$_4$HCO$_3$), 30% to 50% gradient in 10 min; detector, UV 254/220 nm. 4-(7-[3-cyano-4-[(3,5-dimethyloxan-4-yl)oxy]-5-fluorophenyl]furo[3,2-b]pyridin-2-yl)-3-methoxy-N,N-dimethylbenzamide was obtained as a light yellow solid (5 mg, 8%). HPLC: 99.0% purity, RT=1.95 min. MS: m/z=544.1 [M+H]+. $^1$H NMR (300 MHz, CD$_3$OD, ppm) δ 8.62 (d, J=5.2 Hz, 1H), 8.03 (d, J=8.0 Hz, 1H), 7.75-7.67 (m, 2H), 7.55-7.51 (m, 2H), 7.27 (d, J=1.4 Hz, 1H), 7.12 (dd, J=8.0, 1.9 Hz, 1H), 4.86-4.68 (m, 1H), 4.15 (s, 3H), 4.07 (dd, J=11.4, 3.6 Hz, 1H), 3.79-3.63 (m, 2H), 3.39-3.30 (m, 1H), 3.13 (s, 3H), 3.04 (s, 3H), 2.30-2.17 (m, 2H), 1.36-1.24 (m, 2H), 1.18-0.87 (m, 4H).

Example 248: 4-(7-[3-cyano-4-[(oxan-4-yl)amino]phenyl]furo[3,2-b]pyridin-2-yl)-3,5-difluoro-N,N-dimethylbenzamide hydrochloride (295)

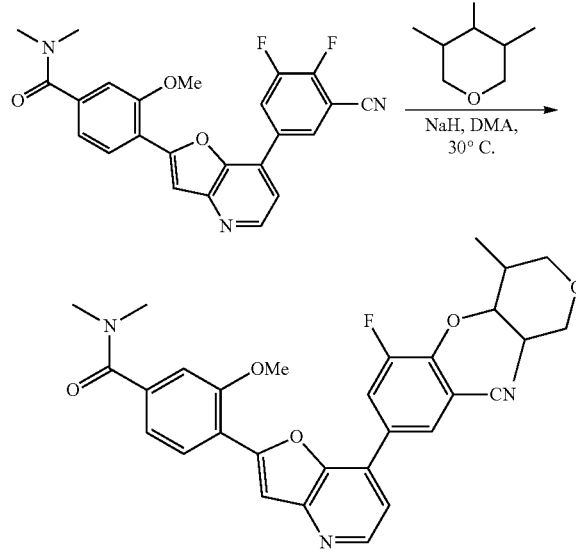

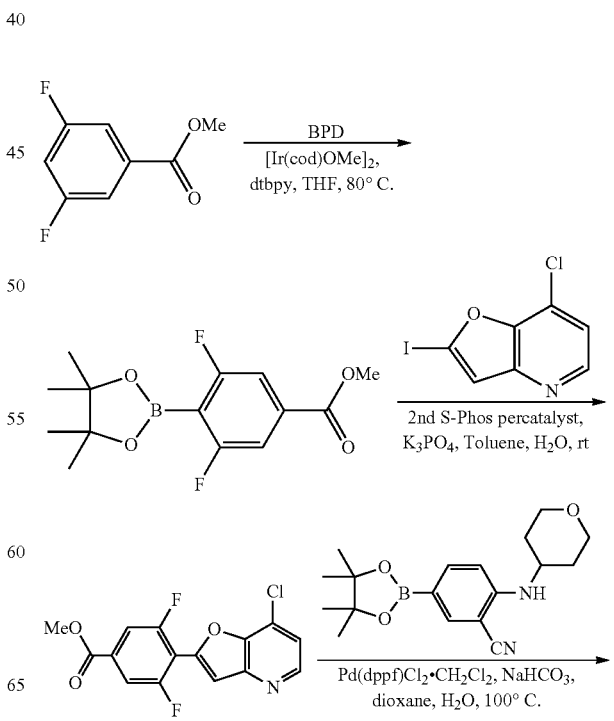

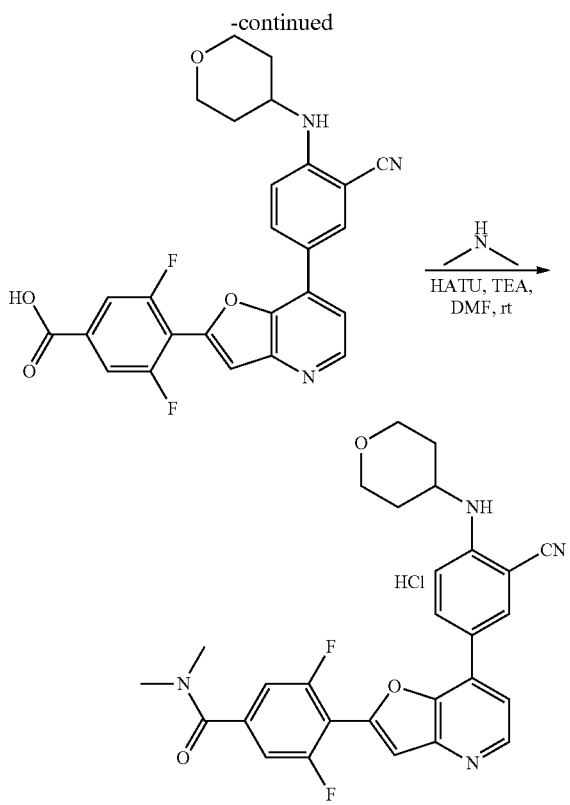

Methyl 3,5-difluoro-4-(4,4,5,5-tetramethyl-1,3,2-dioxaborolan-2-yl)benzoate

To a solution of methyl 3,5-difluorobenzoate (1.63 g, 9.49 mmol) in THF (12 mL) were added [Ir(Cod)OMe]₂ (65 mg, 0.10 mmol), 4,4-di-tert-butyl bipyridine (53 mg, 0.20 mmol) and 4,4,5,5-tetramethyl-2-(tetramethyl-1,3,2-dioxaborolan-2-yl)-1,3,2-dioxaborolane (4.75 g, 18.71 mmol) at room temperature under nitrogen atmosphere. The resulting solution was stirred for 16 h at 80° C. under nitrogen atmosphere. After cooling to room temperature, the reaction mixture was quenched by the addition of water (50 mL). The resulting mixture was extracted with ethyl acetate (100 mL×3). The organic phases were combined, washed with brine and dried over sodium sulfate. The solvent was removed under reduced pressure and the residue was purified by flash chromatography eluting with EtOAc in hexane (0% to 1% gradient) to yield methyl 3,5-difluoro-4-(tetramethyl-1,3,2-dioxaborolan-2-yl)benzoate as a white solid (1.83 g, 65%). ¹H NMR (300 MHz, CDCl₃, ppm) δ 7.50 (d, J=7.8 Hz, 2H), 3.93 (s, 3H), 1.39 (s, 12H).

Methyl 4-(7-chlorofuro[3,2-b]pyridin-2-yl)-3,5-difluorobenzoate

To a solution of methyl 3,5-difluoro-4-(tetramethyl-1,3,2-dioxaborolan-2-yl)benzoate (40 mg, 0.13 mmol) in toluene (1 mL) were added 2nd Generation SPhos precatalyst (10 mg, 0.01 mmol), a solution of K₃PO₄ (95 mg, 0.45 mmol) in water (0.5 mL) and a solution of 7-chloro-2-iodofuro[3,2-b]pyridine (26 mg, 0.09 mmol) in toluene (0.5 mL) at room temperature under nitrogen atmosphere. The resulting mixture was stirred for 5 h at room temperature under nitrogen atmosphere. When the reaction was done, it was quenched by the addition of water (10 mL). The resulting mixture was extracted with ethyl acetate (30 mL×3). The organic phases were combined, washed with brine and dried over sodium sulfate. The solvent was removed under reduced pressure and the residue was purified by reverse phase flash chromatography eluting with acetonitrile in water (with 10 mmol/L NH₄HCO₃) (5% to 70% gradient in 55 min) to yield methyl 4-[7-chlorofuro[3,2-b]pyridin-2-yl]-3,5-difluorobenzoate as a yellow solid (25 mg, 82%). MS: m/z=324.0 [M+H]⁺

4-(7-(3-cyano-4-(tetrahydro-2H-pyran-4-ylamino) phenyl)furo[3,2-b]pyridin-2-yl)-3,5-difluorobenzoic acid To a solution of methyl 4-[7-chlorofuro[3,2-b]pyridin-2-yl]-3,5-difluorobenzoate (20 mg, 0.04 mmol) in dioxane (3 mL) was added 2-[(oxan-4-yl)amino]-5-(tetramethyl-1,3,2-dioxaborolan-2-yl)benzonitrile (31 mg, 0.09 mmol), Pd(dppf)Cl₂.CH₂Cl₂ (10 mg, 0.01 mmol) and a solution of sodium bicarbonate (5 mg, 0.06 mmol) in water (0.1 mL) at room temperature. The resulting mixture was stirred for 16 h at 100° C. After cooling to room temperature, the reaction mixture was quenched by the addition of water (10 mL). The resulting mixture was extracted with ethyl acetate (30 mL×3). The organic phases were combined, washed with brine and dried over sodium sulfate. The solvent was removed under reduced pressure and the residue was purified by reverse phase flash chromatography eluting with acetonitrile in water (5% to 70% gradient in 55 min) to yield 4-(7-[3-cyano-4-[(oxan-4-yl)amino]phenyl]furo[3,2-b]pyridin-2-yl)-3,5-difluorobenzoic acid as a yellow oil (21 mg, 73%). MS: m/z=476.1 [M+H]⁺.

4-(7-(3-cyano-4-(tetrahydro-2H-pyran-4-ylamino) phenyl)furo[3,2-b]pyridin-2-yl)-3,5-difluoro-N,N-dimethylbenzamide To a solution of 4-(7-[3-cyano-4-[(oxan-4-yl)amino]phenyl]furo[3,2-b]pyridin-2-yl)-3,5-difluorobenzoic acid (61 mg, 0.13 mmol) in DMF (5 mL) were added dimethylamine hydrochloride (15 mg, 0.17 mmol), HATU (70 mg, 0.17 mmol) and DIEA (52 mg, 0.40 mmol) at room temperature. The resulting solution was stirred for 16 h at room temperature. When the reaction was done, it was quenched by the addition of water (10 mL). The resulting mixture was extracted with DCM (30 mL×3). The organic phases were combined, washed with brine and dried over sodium sulfate. The solvent was removed under reduced pressure and the residue was purified by prep-HPLC under the following conditions: column, Gemini-NX 5u C18 110A, AXIA Packed, 150×21.2 mm; mobile phase, acetonitrile in water (with 10 mmol/L NH₄HCO₃), 20% to 50% gradient in 10 min; detector, UV 254/220 nm. 4-(7-[3-cyano-4-[(oxan-4-yl)amino]phenyl]furo[3,2-b]pyridin-2-yl)-3,5-difluoro-N,N-dimethylbenzamide hydrochloride was obtained as a yellow solid (9 mg, 14%). HPLC: 97.8% purity, RT=1.28 min. MS: m/z=503.1 [M+H]⁺. ¹H NMR (300 MHz, CD₃OD, ppm) δ 8.70 (d, J=6.6 Hz, 1H), 8.62 (d, J=2.1 Hz, 1H), 8.45 (dd, J=9.3, 2.1 Hz, 1H), 8.18 (d, J=6.6 Hz, 1H), 7.74 (s, 1H), 7.43 (d, J=9.6 Hz, 2H), 7.20 (d, J=9.3 Hz, 1H), 4.10-3.85 (m, 3H), 3.69-3.50 (m, 2H), 3.14 (s, 3H), 3.06 (s, 3H), 2.09-1.97 (m, 2H), 1.82-1.65 (m, 2H).

Example 249: 4-(7-[3-cyano-4-[(oxan-4-yl)amino]phenyl]-6-fluorofuro[3,2-b]pyridin-2-yl)-N-(2-hydroxyethyl)-3-methoxy-N-methylbenzamide (296)

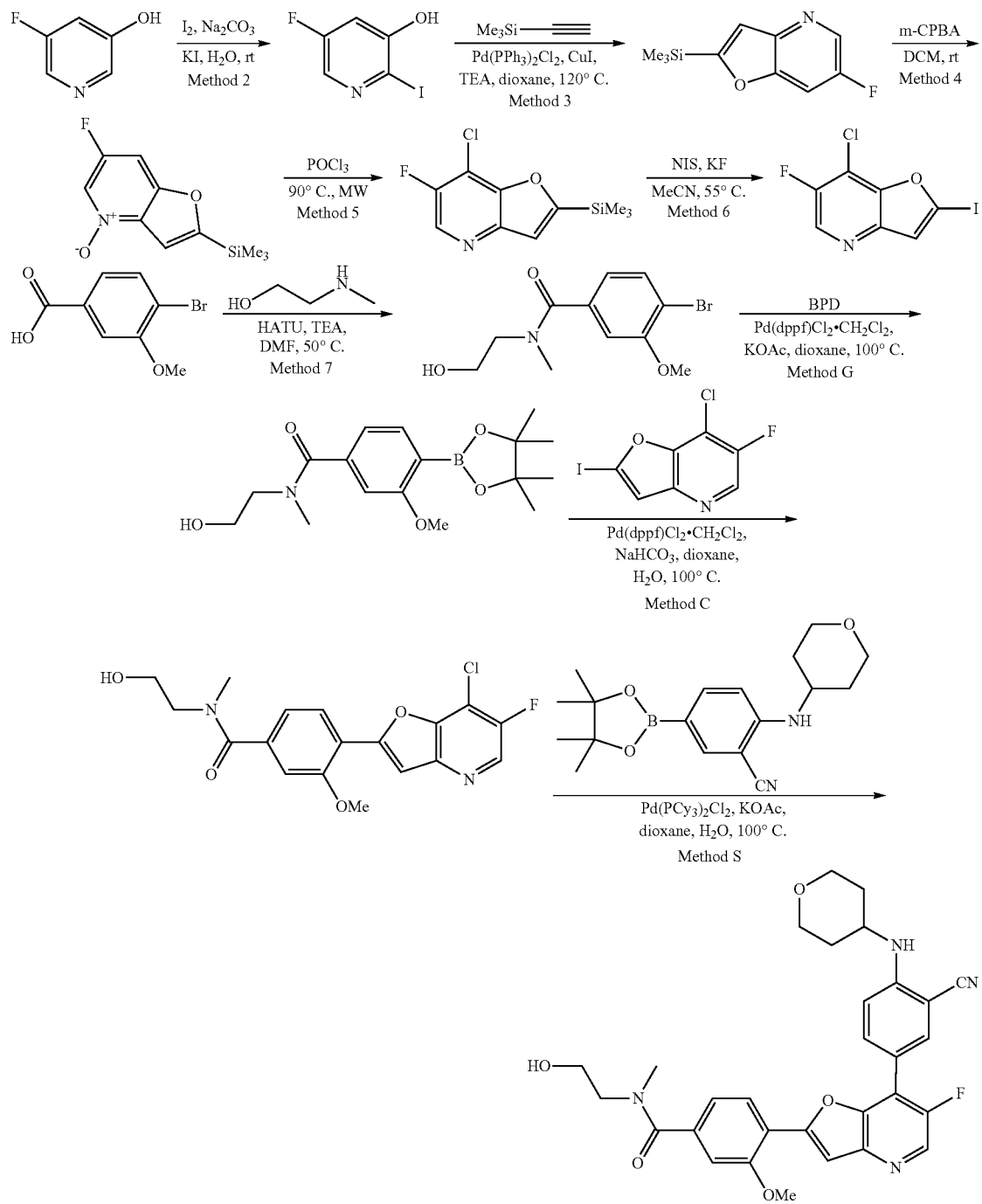

Method 2

5-fluoro-2-iodopyridin-3-ol

To a solution of 5-fluoropyridin-3-ol (3.80 g, 33.60 mmol) in H₂O (92 mL) was added sodium carbonate (7.13 g, 67.22 mmol), KI (11.15 g, 67.19 mmol) at room temperature. The mixture was stirring while a solution of iodine (11.94 g, 47.05 mmol) in water (13 mL) was added dropwise over a period of 1.5 h. Then reaction mixture was stirred for additional 2 h at room temperature. After the reaction was done, the pH value of the reaction mixture was adjusted to 5-6 using hydrogen chloride solution (4 M) to get a precipitate which was collected by filtration and dried in oven under vacuum to yield 5-fluoro-2-iodopyridin-3-ol as a white solid (2.97 g, 37%). MS: m/z=239.9 [M+H]$^+$.

Method 3

6-fluoro-2-(trimethylsilyl)furo[3,2-b]pyridine

To a solution of 5-fluoro-2-iodopyridin-3-ol (2.96 g, 12.55 mmol) in dioxane (50 mL) was added ethynyltrimethylsilane (2.5 g, 25.45 mmol), Pd(PPh$_3$)$_2$Cl$_2$ (1.25 g, 1.78 mmol), CuI (240 mg, 1.26 mmol) and TEA (6.33 g, 62.56 mmol) at room temperature under nitrogen atmosphere. The resulting solution was stirred for 5 h at 120° C. under nitrogen atmosphere. After cooling to room temperature, the reaction mixture was quenched by the addition of water (50 mL). The resulting mixture was extracted with ethyl acetate (100 mL×3). The organic phases were combined, washed with brine and dried over sodium sulfate. The solvent was removed under reduced pressure and the residue was purified by flash chromatography eluting with EtOAc in hexane (0% to 10% gradient) to yield 6-fluoro-2-(trimethylsilyl) furo[3,2-b]pyridine as a brown oil (1.27 g, 49%). MS: m/z=210.1 [M+H]$^+$.

Method 4

6-fluoro-2-(trimethylsilyl)furo[3,2-b]pyridine 4-oxide

To a solution of 6-fluoro-2-(trimethylsilyl)furo[3,2-b] pyridine (3.96 g, 18.92 mmol) in DCM (100 mL) was added m-CPBA (4.86 g, 28.16 mmol) at room temperature. The resulting solution was stirred for 16 h at room temperature. After the reaction was done, the insoluble solids in the reaction mixture were filtered out, and the filtrate was washed with sat. sodium bicarbonate solution (30 mL×3), dried over anhydrous sodium sulfate and concentrated under reduced pressure to yield 6-fluoro-2-(trimethylsilyl)furo[3,2-b]pyridin-4-ium-4-olate as a yellow oil (4.5 g, crude). MS: m/z=226.1 [M+H]$^+$. The product was used to next step without further purification.

Method 5

7-chloro-6-fluoro-2-(trimethylsilyl)furo[3,2-b]pyridine

A solution of 6-fluoro-2-(trimethylsilyl)furo[3,2-b]pyridin-4-ium-4-olate (2.00 g, crude) in POCl$_3$ (20 mL) was irradiated with microwave for 20 min at 90° C. After cooling to room temperature, the reaction mixture was quenched by the addition of water (50 mL). The pH value of the mixture was adjusted to 9 with sat. sodium carbonate solution. The resulting mixture was extracted with DCM (50 mL×3). The organic phases were combined, washed with brine and dried over sodium sulfate. The solvent was removed under reduced pressure and the residue was purified by flash chromatography eluting with EtOAc in hexane (0% to 2% gradient) to yield 7-chloro-6-fluoro-2-(trimethylsilyl)furo[3,2-b]pyridine as a yellow oil (1.50 g, 73% for 2 steps). MS: m/z=244.0 [M+H]$^+$.

Method 6

7-chloro-6-fluoro-2-iodofuro[3,2-b]pyridine

To a solution of 7-chloro-6-fluoro-2-(trimethylsilyl)furo [3,2-b]pyridine (1.33 g, 5.48 mmol) in CH$_3$CN (50 mL) was added KF (504 mg, 8.67 mmol) and NIS (12.35 g, 54.89 mmol) at room temperature. The resulting solution was stirred for 2 h at 55° C. After the reaction was done, the insoluble solids in the reaction mixture were filtered out, and the filtrate was washed with NaHSO$_3$ solution (20%, 50 mL). Precipitation happened. The precipitates were collected by filtration and dried in oven under vacuum to yield 7-chloro-6-fluoro-2-iodofuro[3,2-b]pyridine as a off-white solid (900 mg, 55%). MS: m/z=297.9 [M+H]$^+$.

Method 7

4-bromo-N-(2-hydroxyethyl)-3-methoxy-N-methylbenzamide

To a solution of 4-bromo-3-methoxybenzoic acid (4.75 g, 20.56 mmol) in DMF (50 mL) was added 2-(methylamino) ethan-1-ol (1.70 g, 22.64 mmol), HATU (9.38 g, 24.66 mmol) and DIEA (13.28 g, 102.76 mmo) at room temperature. The resulting mixture was stirred for 2 h at 50° C. After cooling to room temperature, the reaction mixture was quenched by the addition of water (60 mL). The resulting mixture was extracted with ethyl acetate (100 mL×3). The organic phases were combined, washed with brine and dried over sodium sulfate. The solvent was removed under reduced pressure and the residue was purified by flash chromatography eluting with EtOAc in hexane (0% to 50% gradient) to yield 4-bromo-N-(2-hydroxyethyl)-3-methoxy-N-methylbenzamide as a yellow oil (4.99 g, 84%).

4-(7-(3-cyano-4-(tetrahydro-2H-pyran-4-ylamino) phenyl)-6-fluorofuro[3,2-b]pyridin-2-yl)-N-(2-hydroxyethyl)-3-methoxy-N-methylbenzamide 4-(7-(3-cyano-4-(tetrahydro-2H-pyran-4-ylamino)phenyl)-6-fluorofuro[3,2-b]pyridin-2-yl)-N-(2-hydroxyethyl)-3-methoxy-N-methylbenzamide was prepared from 4-bromo-N-(2-hydroxyethyl)-3-methoxy-N-methylbenzamide, 4,4,5,5-tetramethyl-2-(tetramethyl-1,3,2-dioxaborolan-2-yl)-1,3,2-dioxaborolane, 7-chloro-6-fluoro-2-iodofuro [3,2-b]pyridine, and 2-(tetrahydro-2H-pyran-4-ylamino)-5-(4,4,5,5-tetramethyl-1,3,2-dioxaborolan-2-yl)benzonitrile using Method G, C, and S. The final product was purified by prep-HPLC under the following conditions: column, Gemini-NX 5u C18, 110A, AXIA Packed 150×21.2 mm; mobile phase, acetonitrile in water (with 10 mmol/L NH$_4$HCO$_3$), 20% to 50% gradient in 8 min; detector, UV 254/220 nm. 4-(7-[3-cyano-4-[(oxan-4-yl)amino]phenyl]-6-fluorofuro[3,2-b]pyridin-2-yl)-N-(2-hydroxyethyl)-3-methoxy-N-methylbenzamide was obtained as a white solid (24 mg, 8.9% for 3 steps). HPLC: 99.9% purity, RT=2.60 min. MS: m/z=545.2 [M+H]$^+$. $^1$H NMR (400 MHz, DMSO-d$_6$, ppm) δ 8.63 (d, J=3.2 Hz, 1H), 8.04 (s, 1H), 8.00 (d, J=8.4 Hz, 1H), 7.90 (d, J=4.0 Hz, 1H), 7.59 (s, 1H), 7.31-7.13 (m, 3H), 6.36 (d, J=8.0 Hz, 1H), 4.90-4.80 (m, 1H), 4.04 (s, 3H), 3.92 (d, J=9.2 Hz, 2H), 3.87-3.72 (m, 1H), 3.70-3.40 (m, 5H), 3.40-3.30 (m, 1H), 3.00 (d, J=9.2 Hz, 3H), 1.89 (d, J=10.4 Hz, 2H), 1.75-1.60 (m, 2H).

Example 250: 4-[7-[3-cyano-4-(oxan-4-yloxy)phenyl]-6-fluorofuro[3,2-b]pyridin-2-yl]-N-(2-hydroxyethyl)-3-methoxy-N-methylbenzamide (297)

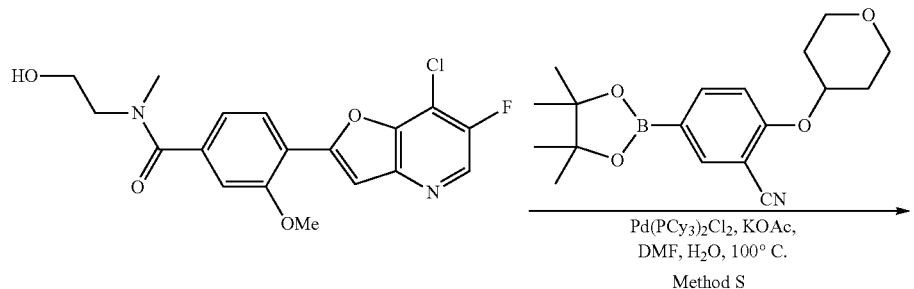

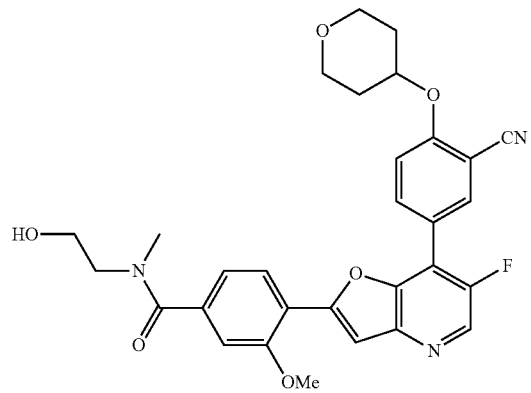

4-[7-[3-cyano-4-(oxan-4-yloxy)phenyl]-6-fluorofuro[3,2-b]pyridin-2-yl]-N-(2-hydroxyethyl)-3-methoxy-N-methylbenzamide was prepared from 4-(7-chloro-6-fluorofuro[3,2-b]pyridin-2-yl)-N-(2-hydroxyethyl)-3-methoxy-N-methylbenzamide, 2-(tetrahydro-2H-pyran-4-yloxy)-5-(4,4,5,5-tetramethyl-1,3,2-dioxaborolan-2-yl)benzonitrile using Method S. The product was purified by prep-HPLC under the following conditions: column, Gemini-NX 5u C18, 110A, AXIA Packed 150×21.2 mm; mobile phase, acetonitrile in water (with 10 mmol/L NH$_4$HCO$_3$), 20% to 50% gradient in 8 min; detector, UV 254/220 nm. 4-[7-[3-cyano-4-(oxan-4-yloxy)phenyl]-6-fluorofuro[3,2-b]pyridin-2-yl]-N-(2-hydroxyethyl)-3-methoxy-N-methylbenzamide was obtained as a white solid (7 mg, 5%). HPLC: 99.8% purity, RT=1.78 min. MS: m/z=546.2 [M+H]$^+$. $^1$H NMR (400 MHz, DMSO-d$_6$, ppm) δ 8.70 (d, J=2.8 Hz, 1H), 8.28 (s, 1H), 8.21 (d, J=8.4 Hz, 1H), 7.89 (d, J=7.6 Hz, 1H), 7.75-7.60 (m, 2H), 7.33-7.10 (m, 3H), 5.04-4.94 (m, 1H), 4.90-4.80 (m, 1H), 4.04 (s, 3H), 3.95-0.85 (m, 2H), 3.60-3.42 (m, 5H), 3.40-3.30 (m, 1H), 2.99 (d, J=11.2 Hz, 3H), 2.15-2.05 (m, 2H), 1.80-1.68 (m, 2H).

Example 251: 4-[7-[3-cyano-4-(oxan-4-yloxy)phenyl]-6-fluorofuro[3,2-b]pyridin-2-yl]-3-methoxy-N,N-dimethylbenzamide (298)

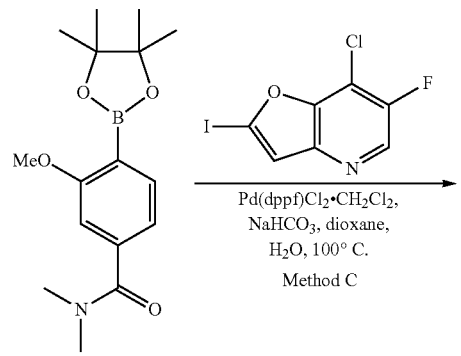

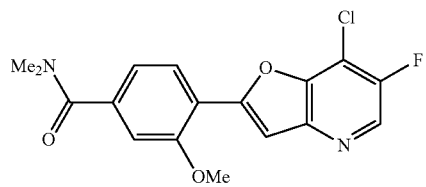 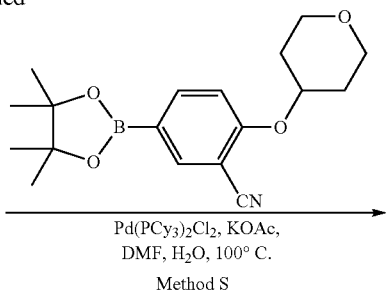

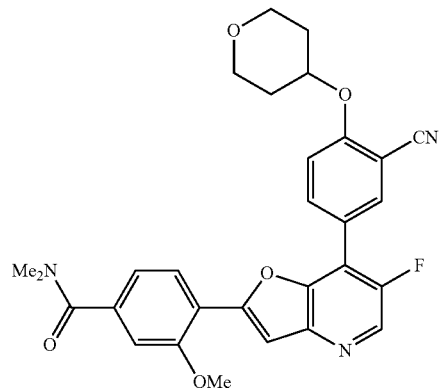

4-[7-[3-cyano-4-(oxan-4-yloxy)phenyl]-6-fluorofuro[3,2-b]pyridin-2-yl]-3-methoxy-N,N-dimethylbenzamide was prepared from 3-methoxy-N,N-dimethyl-4-(4,4,5,5-tetramethyl-1,3,2-dioxaborolan-2-yl)benzamide, 7-chloro-6-fluoro-2-iodofuro[3,2-b]pyridine, 2-(tetrahydro-2H-pyran-4-yloxy)-5-(4,4,5,5-tetramethyl-1,3,2-dioxaborolan-2-yl)benzonitrile using Method C and S. The product was purified by prep-HPLC under the following conditions: column, Gemini-NX 5u C18, 110A, AXIA Packed 150×21.2 mm; mobile phase, acetonitrile in water (with 10 mmol/L NH$_4$HCO$_3$), 25% to 55% gradient in 8 min; detector, UV 254/220 nm. 4-[7-[3-cyano-4-(oxan-4-yloxy)phenyl]-6-fluorofuro[3,2-b]pyridin-2-yl]-3-methoxy-N,N-dimethylbenzamide was obtained as a white solid (45 mg, 26%). HPLC: 91.0% purity, RT=3.11 min. MS: m/z=516.2 [M+H]$^+$. $^1$H NMR (300 MHz, DMSO-d$_6$, ppm) δ 8.70 (s, 1H), 8.40-8.10 (s, 2H), 7.90 (d, J=7.8 Hz, 1H), 7.76-7.50 (m, 2H), 7.35-7.00 (m, 2H), 4.99 (br s, 1H), 4.20-3.80 (m, 5H), 3.70-3.50 (m, 2H), 3.02 (s, 3H), 2.95 (s, 3H), 2.20-1.95 (m, 2H), 1.89-1.50 (m, 2H).

Example 252: 4-(7-[3-cyano-4-[(oxan-4-yl)amino]phenyl]-6-fluorofuro[3,2-b]pyridin-2-yl)-3-methoxy-N,N-dimethylbenzamide (299)

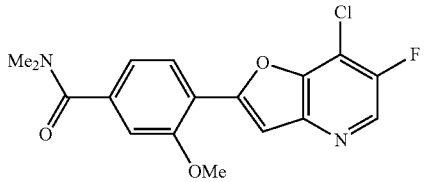 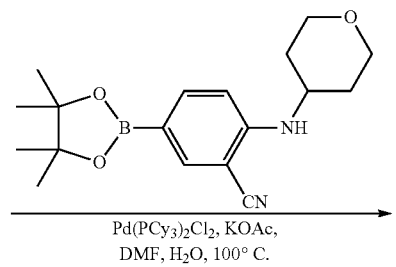

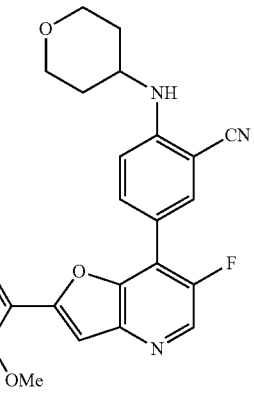

4-(7-[3-cyano-4-[(oxan-4-yl)amino]phenyl]-6-fluorofuro[3,2-b]pyridin-2-yl)-3-methoxy-N,N-dimethylbenzamide was prepared from 4-(7-chloro-6-fluorofuro[3,2-b]pyridin-2-yl)-3-methoxy-N,N-dimethylbenzamide, 2-(tetrahydro-2H-pyran-4-ylamino)-5-(4,4,5,5-tetramethyl-1,3,2-dioxaborolan-2-yl)benzonitrile using Method S. The product was purified by prep-HPLC under the following conditions: column, Gemini-NX 5u C18, 110A, AXIA Packed 150×21.2 mm; mobile phase, acetonitrile in water (with 10 mmol/L NH$_4$HCO$_3$), 20% to 50% gradient in 8 min; detector, UV 254/220 nm. 4-[7-[3-cyano-4-(oxan-4-yloxy)phenyl]-6-fluorofuro[3,2-b]pyridin-2-yl]-3-methoxy-N,N-dimethylbenzamide was obtained as a white solid (40 mg, 31%).

HPLC: 94.5% purity, RT=2.40 min. MS: m/z=515.4 [M+H]$^+$. $^1$H NMR (400 MHz, DMSO-d$_6$, ppm) δ 8.62 (d, J=3.2 Hz, 1H), 8.07-7.97 (m, 2H), 7.90 (d, J=8.0 Hz, 1H), 7.59 (s, 1H), 7.30-7.10 (m, 3H), 6.36 (d, J=8.4 Hz, 1H), 4.05 (s, 3H), 3.91 (d, J=9.2 Hz, 2H), 3.87-3.74 (m, 1H), 3.50-3.40 (m, 2H), 3.01 (s, 3H), 2.95 (s, 3H), 1.89 (d, J=10.8 Hz, 2H), 1.75-1.60 (m, 2H).

Example 253: 4-(7-[3-cyano-4-[(oxan-4-yl)amino]phenyl]-6-fluorofuro[3,2-b]pyridin-2-yl)-3-fluoro-N,N-dimethylbenzamide (300)

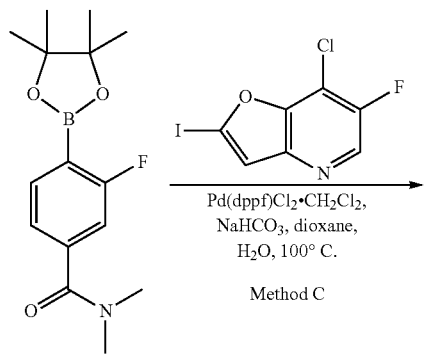

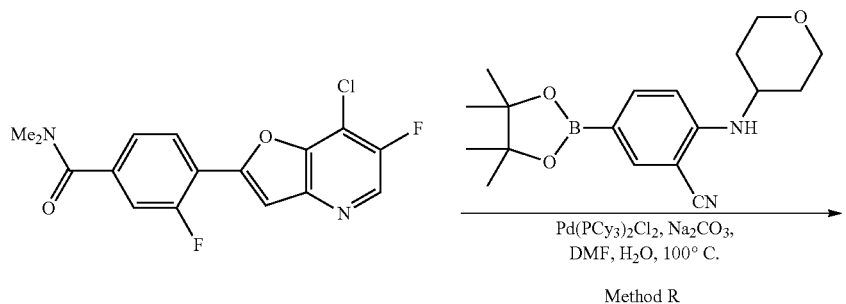

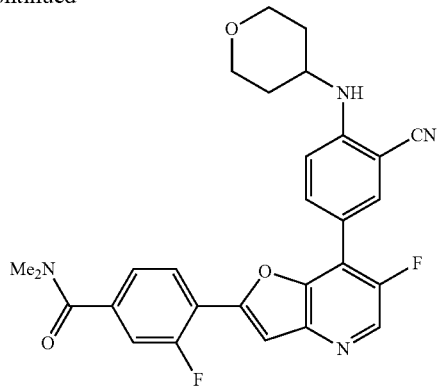

4-(7-[3-cyano-4-[(oxan-4-yl)amino]phenyl]-6-fluorofuro[3,2-b]pyridin-2-yl)-3-fluoro-N,N-dimethylbenzamide was prepared from 3-fluoro-N,N-dimethyl-4-(4,4,5,5-tetramethyl-1,3,2-dioxaborolan-2-yl)benzamide, 7-chloro-6-fluoro-2-iodofuro[3,2-b]pyridine, 2-(tetrahydro-2H-pyran-4-ylamino)-5-(4,4,5,5-tetramethyl-1,3,2-dioxaborolan-2-yl)benzonitrile using Methods C and R. The final product was purified by prep-HPLC under the following conditions: column, Gemini-NX 5u C18, 110A, AXIA Packed 150×21.2 mm; mobile phase, acetonitrile in water (with 10 mmol/L NH$_4$HCO$_3$), 20% to 50% gradient in 8 min; detector, UV 254/220 nm. 4-(7-[3-cyano-4-[(oxan-4-yl)amino]phenyl]-6-fluorofuro[3,2-b]pyridin-2-yl)-3-fluoro-N,N-dimethylbenzamide was obtained as a light yellow solid (25 mg, 12%). HPLC: 99.6% purity, RT=1.39 min. MS: m/z=503.0 [M+H]$^+$. $^1$H NMR (400 MHz, DMSO-d$_6$, ppm) δ 8.66 (d, J=3.2 Hz, 1H), 8.10-7.90 (m, 3H), 7.60-7.40 (m, 3H), 7.17 (d, J=9.2 Hz, 1H), 6.37 (d, J=8.0 Hz, 1H), 4.00-3.70 (m, 3H), 3.52-3.40 (m, 2H), 3.01 (s, 3H), 2.95 (s, 3H), 1.88 (dd, J=12.4, 2.0 Hz, 2H), 1.76-1.60 (m, 2H).

Example 254: 4-[7-[3-cyano-4-(oxan-4-yloxy)phenyl]-6-fluorofuro[3,2-b]pyridin-2-yl]-3-fluoro-N,N-dimethylbenzamide (301)

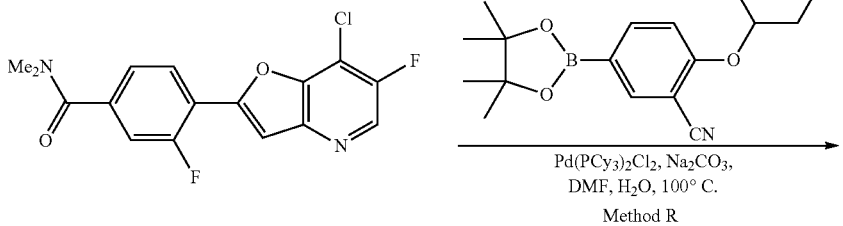

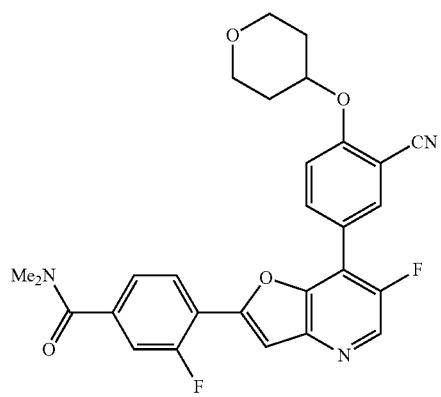

4-(7-[3-cyano-4-[(oxan-4-yl)amino]phenyl]-6-fluorofuro[3,2-b]pyridin-2-yl)-3-fluoro-N,N-dimethylbenzamide was prepared from 4-(7-chloro-6-fluorofuro[3,2-b]pyridin-2-yl)-3-fluoro-N,N-dimethylbenzamide, 2-(tetrahydro-2H-pyran-4-yloxy)-5-(4,4,5,5-tetramethyl-1,3,2-dioxaborolan-2-yl)benzonitrile using Method R. The product was purified by prep-HPLC under the following conditions: column, Gemini-NX 5u C18, 110A, AXIA Packed 150×21.2 mm; mobile phase, acetonitrile in water (with 10 mmol/L NH$_4$HCO$_3$), 20% to 50% gradient in 8 min; detector, UV 254/220 nm. 4-(7-[3-cyano-4-[(oxan-4-yl)amino]phenyl]-6-fluorofuro[3,2-b]pyridin-2-yl)-3-fluoro-N,N-dimethylbenzamide was obtained as a white solid (28 mg, 35%). HPLC: 99.9% purity, RT=1.37 min. MS: m/z=504.0 [M+H]$^+$. $^1$H NMR (400 MHz, DMSO-d$_6$, ppm) δ 8.74 (d, J=2.8 Hz, 1H), 8.28 (d, J=1.2 Hz, 1H), 8.20 (d, J=8.8 Hz, 1H), 8.04-7.94 (m, 1H), 7.70-7.60 (m, 2H), 7.53 (dd, J=11.5, 1.5 Hz, 1H), 7.44 (dd, J=8.0, 1.5 Hz, 1H), 5.03-4.93 (m, 1H), 3.98-3.80 (m, 2H), 3.65-3.50 (m, 2H), 3.01 (s, 3H), 2.94 (s, 3H), 2.12-2.02 (m, 2H), 1.80-1.65 (m, 2H).

Example 255: 4-[7-[3-cyano-4-(oxan-4-yloxy)phenyl]-6-fluorofuro[3,2-b]pyridin-2-yl]-3-fluoro-N-(2-hydroxyethyl)-N-methylbenzamide (302)

4-[7-[3-cyano-4-(oxan-4-yloxy)phenyl]-6-fluorofuro[3,2-b]pyridin-2-yl]-3-fluoro-N-(2-hydroxyethyl)-N-methylbenzamide was prepared from 3-fluoro-N-(2-hydroxyethyl)-N-methyl-4-(4,4,5,5-tetramethyl-1,3,2-dioxaborolan-2-yl)benzamide, 7-chloro-6-fluoro-2-iodofuro[3,2-b]pyridine, 2-(tetrahydro-2H-pyran-4-yloxy)-5-(4,4,5,5-tetramethyl-1,3,2-dioxaborolan-2-yl)benzonitrile using Methods C and S. The product was purified by prep-HPLC under the following conditions: column, Gemini-NX 5u C18, 110A, AXIA Packed 150×21.2 mm; mobile phase, acetonitrile in water (with 10 mmol/L NH$_4$HCO$_3$), 20% to 50% gradient in 8 min; detector, UV 254/220 nm. 4-[7-[3-cyano-4-(oxan-4-yloxy)phenyl]-6-fluorofuro[3,2-b]pyridin-2-yl]-3-fluoro-N-(2-hydroxyethyl)-N-methylbenzamide as a white solid (25 mg, 15%). HPLC: 99.3% purity, RT=1.77 min. MS: m/z=534.2 [M+H]$^+$. $^1$H NMR (400 MHz, DMSO-d$_6$, ppm) δ 8.74 (d, J=2.8 Hz, 1H), 8.29 (s, 1H), 8.25-8.17 (m, 1H), 8.05-7.95 (m, 1H), 7.70-7.59 (m, 2H), 7.53 (d, J=11.2 Hz, 1H), 7.44 (d, J=8.0 Hz, 1H), 5.05-4.05 (m, 1H), 4.91-4.79 (m, 1H), 3.98-3.85 (m, 2H), 3.70-3.45 (m, 5H), 3.35-3.25 (m, 1H), 2.99 (d, J=10.8 Hz, 3H), 2.15-2.00 (m, 2H), 1.80-1.78 (m, 2H).

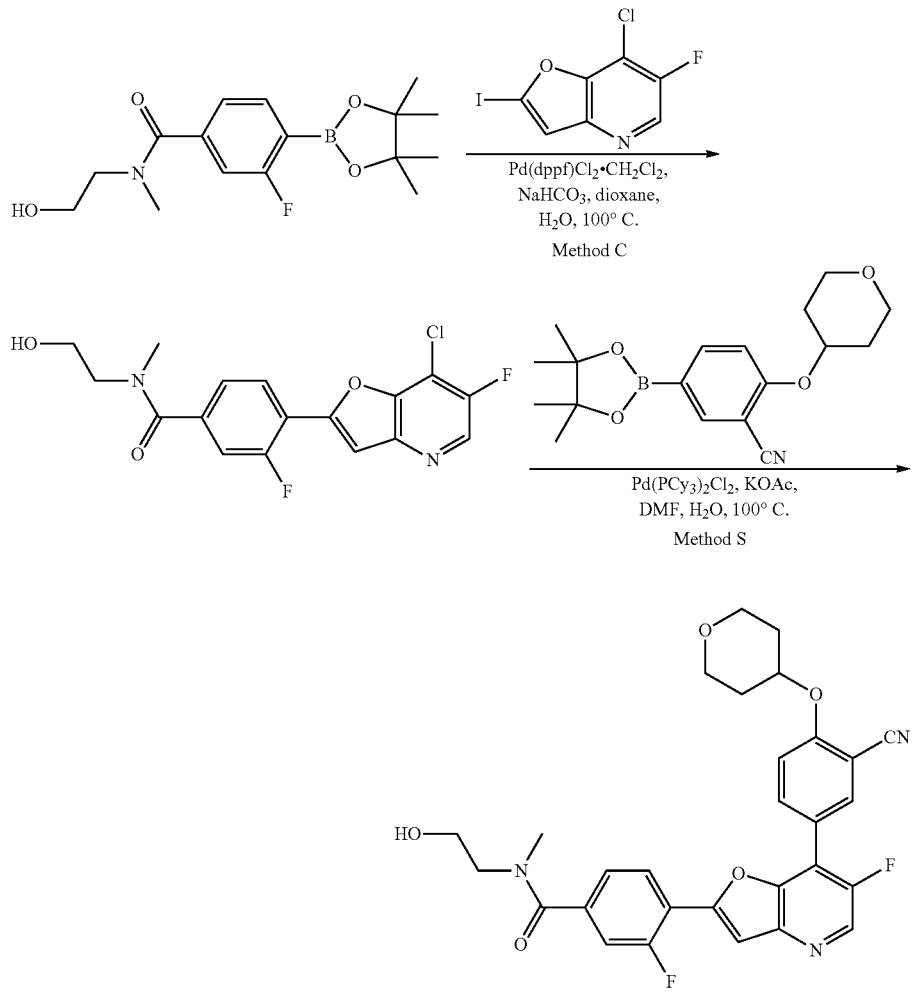

Example 256: 4-(7-[3-cyano-4-[(oxan-4-yl)amino]
phenyl]-6-fluorofuro[3,2-b]pyridin-2-yl)-3-fluoro-N-
(2-hydroxyethyl)-N-methylbenzamide (303)

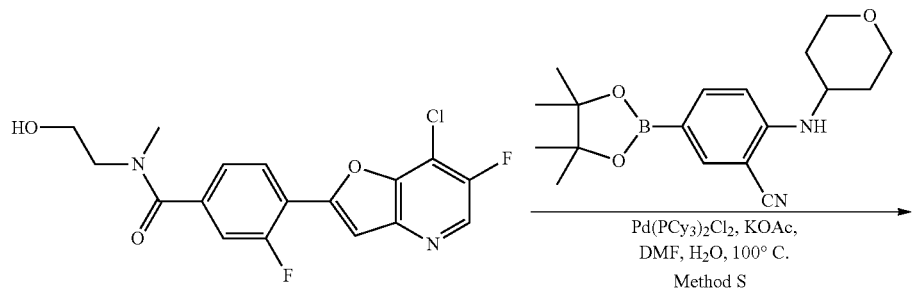

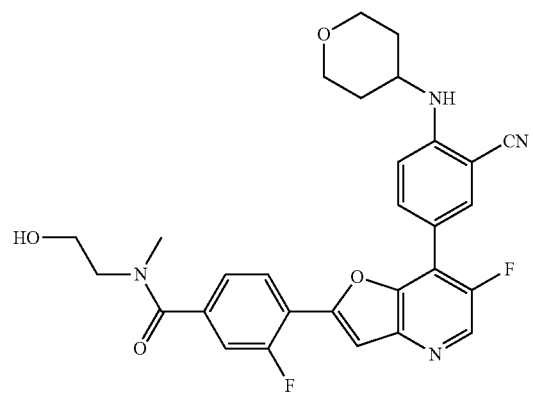

4-(7-[3-cyano-4-[(oxan-4-yl)amino]phenyl]-6-fluorofuro[3,2-b]pyridin-2-yl)-3-fluoro-N-(2-hydroxyethyl)-N-methylbenzamide was prepared from 4-(7-chloro-6-fluorofuro[3,2-b]pyridin-2-yl)-3-fluoro-N-(2-hydroxyethyl)-N-methylbenzamide, 2-(tetrahydro-2H-pyran-4-ylamino)-5-(4,4,5,5-tetramethyl-1,3,2-dioxaborolan-2-yl)benzonitrile using Method S. The product was purified by prep-HPLC under the following conditions: column, Gemini-NX 5u C18, 110A, AXIA Packed 150×21.2 mm; mobile phase, acetonitrile in water (with 10 mmol/L $NH_4HCO_3$), 20% to 50% gradient in 8 min; detector, UV 254/220 nm. 4-(7-[3-cyano-4-[(oxan-4-yl)amino]phenyl]-6-fluorofuro[3,2-b]pyridin-2-yl)-3-fluoro-N-(2-hydroxyethyl)-N methylbenzamide as a white solid (45 mg, 30%). HPLC: 99.5% purity, RT=1.22 min. MS: m/z=533.2 [M+H]$^+$. $^1$H NMR (300 MHz, DMSO-$d_6$, ppm) δ 8.65 (d, J=3.2 Hz, 1H), 8.07-7.91 (m, 3H), 7.59-7.38 (m, 3H), 7.17 (d, J=8.8 Hz, 1H), 6.35 (d, J=8.0 Hz, 1H), 4.82-4.79 (m, 1H), 3.97-3.86 (m, 2H), 3.83-3.70 (m, 1H), 3.63 (s, 1H), 3.59-3.35 (m, 4H), 3.35-3.25 (m, 1H), 2.98 (d, J=5.8 Hz, 3H), 1.93-1.82 (m, 2H), 1.78-1.59 (m, 2H).

Example 257: 4-[6-chloro-7-[3-cyano-4-(oxan-4-yloxy)phenyl]furo[3,2-b]pyridin-2-yl]-N-(2-hydroxyethyl)-3-methoxy-N-methylbenzamide (304)

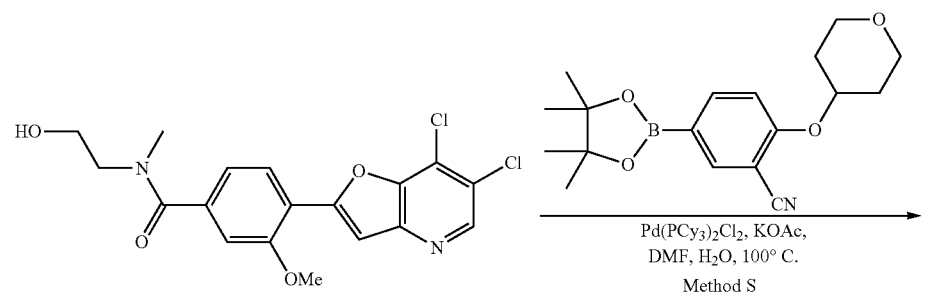

-continued

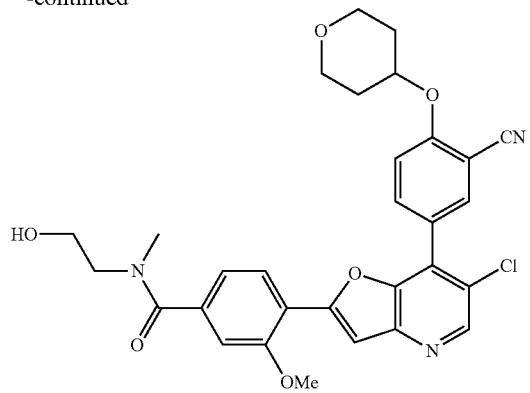

4-[6-chloro-7-[3-cyano-4-(oxan-4-yloxy)phenyl]furo[3,2-b]pyridin-2-yl]-N-(2-hydroxyethyl)-3-methoxy-N-methylbenzamide was prepared from 4-(6,7-dichlorofuro[3,2-b]pyridin-2-yl)-N-(2-hydroxyethyl)-3-methoxy-N-methylbenzamide, 2-(tetrahydro-2H-pyran-4-yloxy)-5-(4,4,5,5-tetramethyl-1,3,2-dioxaborolan-2-yl)benzonitrile using Method S. The product was purified by prep-HPLC under the following conditions: column, Gemini-NX 5u C18, 110A, AXIA Packed 150×21.2 mm; mobile phase, acetonitrile in water (with 10 mmol/L $NH_4HCO_3$), 20% to 50% gradient in 8 min; detector, UV 254/220 nm. 4-[6-chloro-7-[3-cyano-4-(oxan-4-yloxy)phenyl]furo[3,2-b]pyridin-2-yl]-N-(2-hydroxyethyl)-3-methoxy-N-methylbenzamide as a white solid (15 mg, 8%). HPLC: 99.4% purity, RT=2.02 min. MS: m/z=562.1 $[M+H]^+$. $^1$H NMR (400 MHz, DMSO-$d_6$, ppm) δ 8.70 (s, 1H), 8.18 (s, 1H), 8.04 (d, J=9.2 Hz, 1H), 7.83-7.73 (m, 1H), 7.68-7.60 (m, 2H), 7.25 (d, J=18.8 Hz, 1H), 7.12 (d, J=8.0 Hz, 1H), 5.01-4.82 (m, 2H), 4.04 (d, J=6.4 Hz, 3H), 3.95-3.87 (m, 2H), 3.70-3.50 (m, 6H), 2.98 (d, J=15.6 Hz, 3H), 2.15-2.05 (m, 2H), 1.80-1.68 (m, 2H).

Example 258: 4-(7-[3-cyano-4-[(oxan-4-yl)amino]phenyl]-6-cyclopropylfuro[3,2-b]pyridin-2-yl)-N-(2-hydroxyethyl)-3-methoxy-N-methylbenzamide (305)

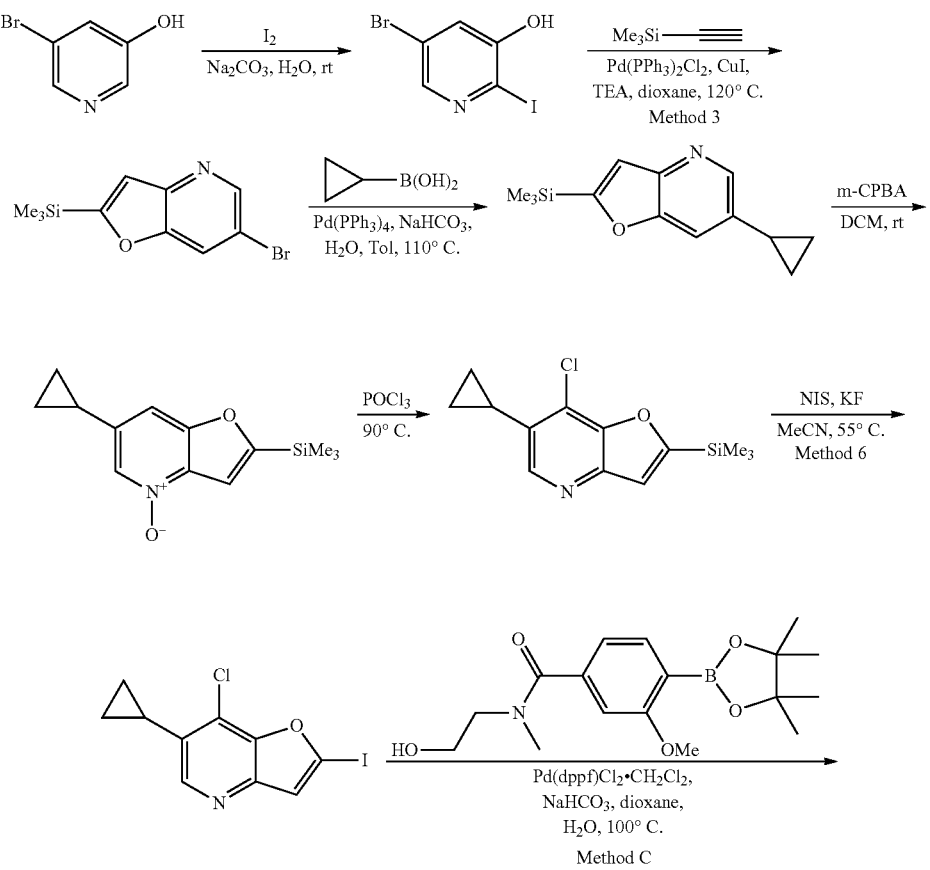

-continued

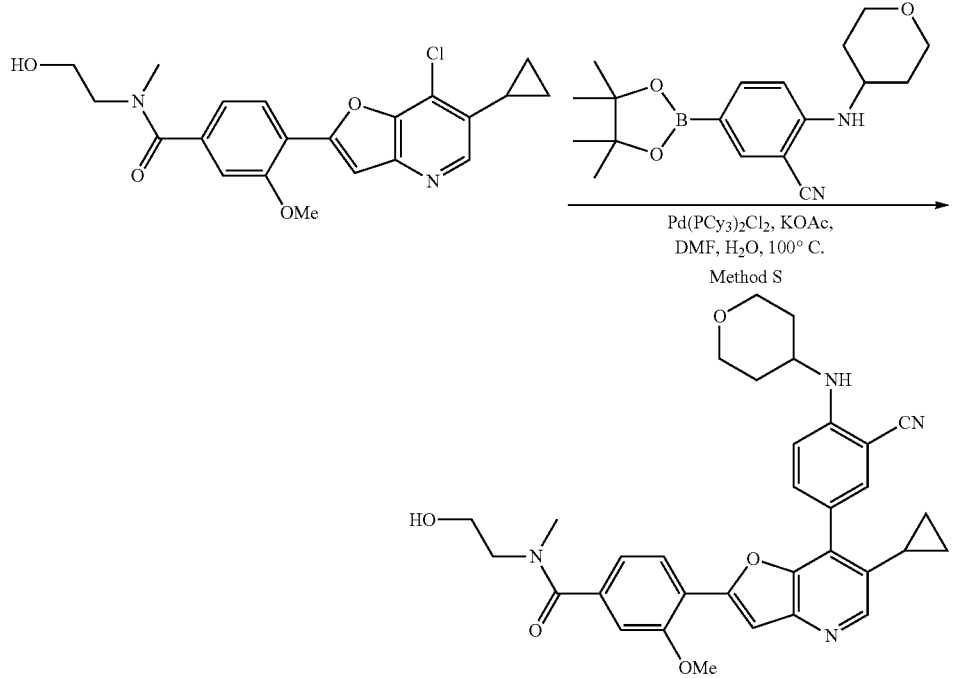

Method S

5-bromo-2-iodopyridin-3-ol

To a solution of 5-bromopyridin-3-ol (20.00 g, 114.95 mmol) in water (400 mL) was added sodium carbonate (40.00 g, 377.40 mmol) and iodine (30.00 g, 118.20 mmol) at room temperature. The resulting solution was stirred for 6 h at room temperature. After the reaction was done, the pH value of the reaction mixture was adjusted to 3 with hydrogen chloride solution (2 M). Precipitation happened. The precipitates were collected by filtration and dried in oven under vacuum to yield 5-bromo-2-iodopyridin-3-ol as a yellow solid (28.00 g, 81%). $^1$H NMR (400 MHz, CD$_3$OD, ppm) δ 7.93 (s, 1H), 7.24 (d, J=2.0 Hz, 1H).

6-bromo-2-(trimethylsilyl)furo[3,2-b]pyridine 6-bromo-2-(trimethylsilyl)furo[3,2-b]pyridine was prepared from 5-bromo-2-iodopyridin-3-ol, ethynyltrimethylsilane using Method 3. The crude product was purified by reverse phase flash chromatography eluting with acetonitrile in water (0% to 60% gradient in 30 min) to yield 6-bromo-2-(trimethylsilyl)furo[3,2-b]pyridine as a brown solid (1.15 g, 34%). $^1$H NMR (400 MHz, DMSO-d$_6$, ppm) δ 8.60 (d, J=1.6 Hz, 1H), 8.41 (d, J=0.8 Hz, 1H), 7.39 (m, 1H).

6-cyclopropyl-2-(trimethylsilyl)furo[3,2-b]pyridine

To a solution of 6-bromo-2-(trimethylsilyl)furo[3,2-b]pyridine (2.34 g, 8.79 mmol) in toluene (55 mL) and water (5.5 mL) were added cyclopropylboronic acid (1.52 g, 17.70 mmol), sodium carbonate (2.79 g, 26.35 mmol) and Pd(PPh$_3$)$_4$ (1.02 g, 0.88 mmol) at room temperature under nitrogen atmosphere. The resulting mixture was stirred for 3 h at 110° C. After cooling to room temperature, the reaction mixture was quenched by the addition of water (100 mL). The resulting mixture was extracted with ethyl acetate (200 mL×3). The organic phases were combined, washed with brine and dried over sodium sulfate. The solvent was removed under reduced pressure to yield 6-cyclopropyl-2-(trimethylsilyl)furo[3,2-b]pyridine as a yellow oil (3.21 g, crude). MS: m/z=232.0 [M+H]$^+$. The crude product was used in next step without further purification.

6-cyclopropyl-2-(trimethylsilyl)furo[3,2-b]pyridine 4-oxide

At 0° C., to a solution 6-cyclopropyl-2-(trimethylsilyl)furo[3,2-b]pyridine (3.21 g, crude) in DCM (100 mL) was added m-CPBA (3.17 g, 17.40 mmol). The resulting solution was stirred for 2 h at 0° C. After the reaction was done, the reaction mixture was washed with brine (25 mL×3), dried over sodium sulfate and concentrated under reduced pressure to yield 6-cyclopropyl-2-(trimethylsilyl)furo[3,2-b]pyridin-4-ium-4-olate as a brown solid (4.10 g, crude). MS: m/z=248.1 [M+H]$^+$.

7-chloro-6-cyclopropyl-2-(trimethylsilyl)furo[3,2-b]pyridine

A solution of 6-cyclopropyl-2-(trimethylsilyl)furo[3,2-b]pyridin-4-ium-4-olate (4.10 g, crude) in POCl$_3$ (30 mL) was stirred overnight at 70° C. After cooling to room temperature, the reaction mixture was concentrated under reduced pressure and the residue was purified by flash chromatography eluting with EtOAc in hexane (0% to 2% gradient) to yield 7-chloro-6-cyclopropyl-2-(trimethylsilyl)furo[3,2-b]pyridine as a yellow oil (800 mg, 35% for 3 steps). MS: m/z=266.1 [M+H]$^+$.

7-chloro-6-cyclopropyl-2-iodofuro[3,2-b]pyridine 7-chloro-6-cyclopropyl-2-iodofuro[3,2-b]pyridine was prepared from 7-chloro-6-cyclopropyl-2-(trimethylsilyl)furo[3,2-b]pyridine using Method 6. 7-chloro-6-cyclopropyl-2-iodofuro[3,2-b]pyridine as a yellow solid (1.31 g, 45%). $^1$H NMR (400 MHz, DMSO, ppm) δ 8.36 (s, 1H), 7.48 (s, 1H), 2.20-2.10 (m, 1H), 1.12-1.02 (m, 2H), 0.92-0.85 (m, 2H).

4-(7-(3-cyano-4-(tetrahydro-2H-pyran-4-ylamino) phenyl)-6-cyclopropylfuro[3,2-b]pyridin-2-yl)-N-(2-hydroxyethyl)-3-methoxy-N-methylbenzamide 4-(7-(3-cyano-4-(tetrahydro-2H-pyran-4-ylamino)phenyl)-6-cyclopropylfuro[3,2-b]pyridin-2-yl)-N-(2-hydroxyethyl)-3-methoxy-N-methylbenzamide was prepared from 7-chloro-6-cyclopropyl-2-iodofuro[3,2-b]pyridine, N-(2-hydroxyethyl)-3-methoxy-N-methyl-4-(4,4,5,5-tetramethyl-1,3,2-dioxaborolan-2-yl)benzamide and 2-(tetrahydro-2H-pyran-4-ylamino)-5-(4,4,5,5-tetramethyl-1,3,2-dioxaborolan-2-yl)benzonitrile using Methods C and S. The final product was purified by prep-HPLC under the following conditions: column, Gemini-NX 5u C18, 110A, AXIA Packed 150×21.2 mm; mobile phase, acetonitrile in water (with 10 mmol/L $NH_4HCO_3$), 20% to 50% gradient in 8 min; detector, UV 254/220 nm. 4-(7-(3-cyano-4-(tetrahydro-2H-pyran-4-ylamino)phenyl)-6-cyclopropylfuro[3,2-b]pyridin-2-yl)-N-(2-hydroxyethyl)-3-methoxy-N-methylbenzamide was obtained as a yellow solid (17 mg, 11% for 2 steps). HPLC: 99.3% purity, RT=1.05 min. MS: m/z=567.3 [M+H]$^+$. $^1$H NMR (400 MHz, DMSO-d$_6$, ppm) δ 8.31 (s, 1H), 8.10 (d, J=2.2 Hz, 1H), 7.98 (dd, J=8.8, 2.3 Hz, 1H), 7.82-7.72 (m, 1H), 7.64-7.53 (m, 2H), 7.22 (d, J=18.5 Hz, 1H), 7.10 (dd, J=7.9, 1.4 Hz, 1H), 5.00-4.75 (m, 2H), 4.02 (d, J=5.8 Hz, 3H), 3.96-3.85 (m, 2H), 3.70-3.43 (m, 5H), 3.30-3.20 (m, 1H), 2.97 (d, J=12.3 Hz, 3H), 2.14-2.04 (m, 2H), 2.00-1.90 (m, 1H), 1.80-1.65 (m, 2H), 1.24 (s, 1H), 1.00-0.70 (m, 4H).

Example 259: 4-(7-(3-cyano-4-(tetrahydro-2H-pyran-4-yloxy)phenyl)-6-cyclopropylfuro[3,2-b]pyridin-2-yl)-N-(2-hydroxyethyl)-3-methoxy-N-methylbenzamide (306)

4-(7-(3-cyano-4-(tetrahydro-2H-pyran-4-yloxy)phenyl)-6-cyclopropylfuro[3,2-b]pyridin-2-yl)-N-(2-hydroxyethyl)-3-methoxy-N-methylbenzamide 4-(7-(3-cyano-4-(tetrahydro-2H-pyran-4-yloxy)phenyl)-6-cyclopropylfuro[3,2-b]pyridin-2-yl)-N-(2-hydroxyethyl)-3-methoxy-N-methylbenzamide was prepared from 4-(7-chloro-6-cyclopropylfuro[3,2-b]pyridin-2-yl)-N-(2-hydroxyethyl)-3-methoxy-N-methylbenzamide and 2-(tetrahydro-2H-pyran-4-yloxy)-5-(4,4,5,5-tetramethyl-1,3,2-dioxaborolan-2-yl)benzonitrile using Method S. The product was purified by prep-HPLC under the following conditions: column, Gemini-NX 5u C18, 110A, AXIA Packed 150×21.2 mm; mobile phase, acetonitrile in water (with 10 mmol/L $NH_4HCO_3$), 20% to 50% gradient in 8 min; detector, UV 254/220 nm. 4-(7-(3-cyano-2H-pyran-4-yloxy)phenyl)-6-cyclopropylfuro[3,2-b]pyridin-2-yl)-N-(2-hydroxyethyl)-3-methoxy-N-methylbenzamide was obtained as a yellow solid (19 mg, 19%). HPLC: 98.6% purity, RT=1.11 min. MS: m/z=568.3 [M+H]$^+$. $^1$H NMR (400 MHz, DMSO-d$_6$, ppm) δ 8.27 (s, 1H), 7.85 (d, J=2.1 Hz, 1H), 7.78 (dd, J=8.7, 2.4 Hz, 2H), 7.53 (s, 1H), 7.22 (d, J=18.8 Hz, 1H), 7.17-7.08 (m, 2H), 6.14 (d, J=8.1 Hz, 1H), 4.83 (s, 1H), 4.03 (d, J=5.8 Hz, 3H), 3.96-3.88 (m, 2H), 3.64 (s, 1H), 3.48-3.40 (m, 4H), 3.33-3.20 (m, 1H), 2.98 (d, J=8.6 Hz, 3H), 2.05-1.86 (m, 3H), 1.81-1.65 (m, 2H), 0.97-0.83 (m, 2H), 0.81-0.72 (m, 2H).

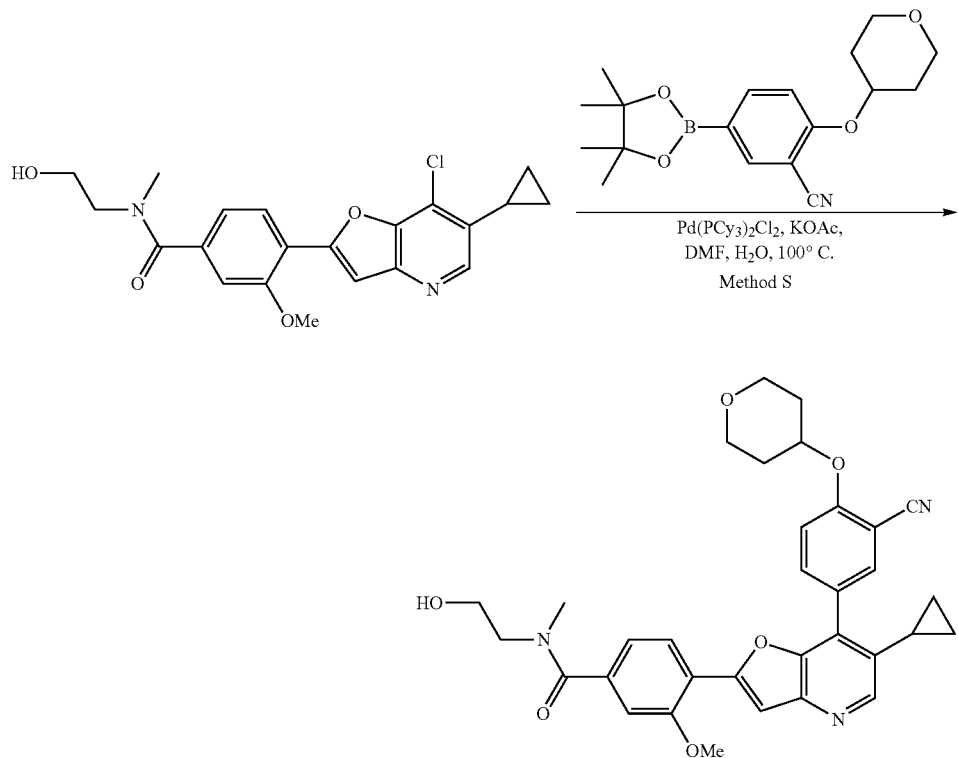

Example 260: 4-(7-(3-cyano-5-cyclopropyl-4-(tetrahydro-2H-pyran-4-yloxy)phenyl)furo[3,2-b]pyridin-2-yl)-3-methoxy-N,N-dimethylbenzamide (307)

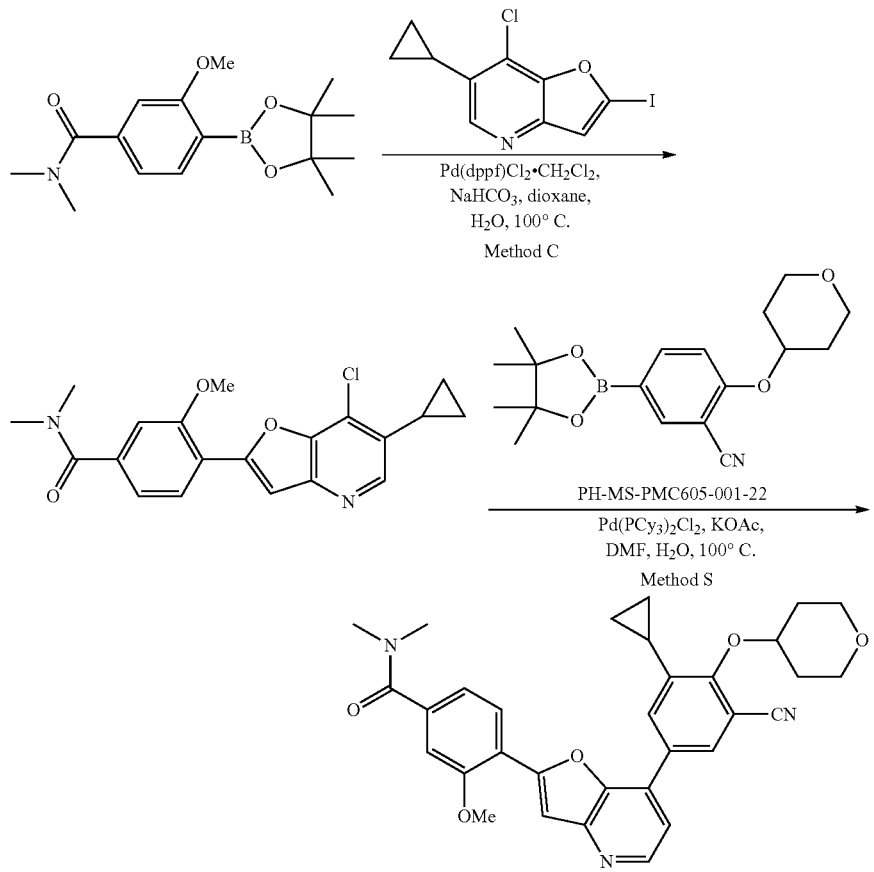

4-(7-(3-cyano-5-cyclopropyl-4-(tetrahydro-2H-pyran-4-yloxy)phenyl)furo[3,2-b]pyridin-2-yl)-3-methoxy-N,N-dimethylbenzamide was prepared from 3-methoxy-N,N-dimethyl-4-(4,4,5,5-tetramethyl-1,3,2-dioxaborolan-2-yl)benzamide, 7-chloro-6-cyclopropyl-2-iodofuro[3,2-b]pyridine and 2-(tetrahydro-2H-pyran-4-yloxy)-5-(4,4,5,5-tetramethyl-1,3,2-dioxaborolan-2-yl)benzonitrile using Methods C and S. The final product was purified by prep-HPLC under the following conditions: column, Gemini-NX 5u C18, 110A, AXIA Packed 150×21.2 mm; mobile phase, acetonitrile in water (with 10 mmol/L $NH_4HCO_3$), 20% to 50% gradient in 8 min; detector, UV 254/220 nm. 4-(7-(3-cyano-5-cyclopropyl-4-(tetrahydro-2H-pyran-4-yloxy)phenyl)furo[3,2-b]pyridin-2-yl)-3-methoxy-N,N-dimethylbenzamide was obtained as a white solid (24 mg, 23% for 2 steps). HPLC: 99.9% purity, RT=1.27 min. MS: m/z=538.3 [M+H]$^+$. $^1$H NMR (400 MHz, DMSO-$d_6$, ppm) δ 8.33 (s, 1H), 8.12 (s, 1H), 8.00 (d, J=8.8 Hz, 1H), 7.79 (s, 1H), 7.61 (d, J=19.4 Hz, 2H), 7.23 (s, 1H), 7.16-7.08 (m, 1H), 4.98 (s, 1H), 4.20-3.80 (m, 5H), 3.60 (br s, 2H), 3.01 (s, 3H), 2.94 (s, 3H), 2.20-1.90 (m, 3H), 1.75 (br s, 2H), 1.00-0.70 (m, 4H).

Example 261: 4-(7-(3-cyano-5-cyclopropyl-4-(tetrahydro-2H-pyran-4-ylamino)phenyl)furo[3,2-b]pyridin-2-yl)-3-methoxy-N,N-dimethylbenzamide (308)

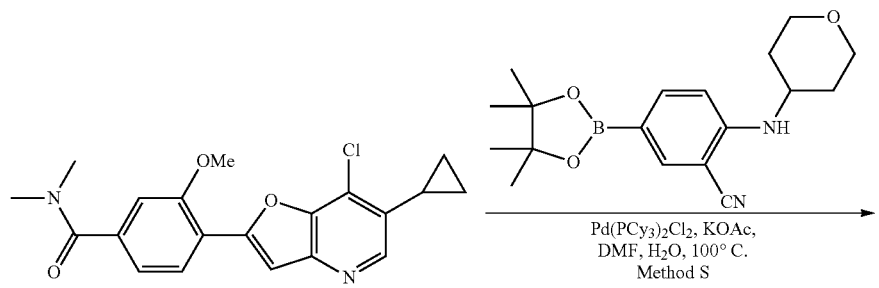

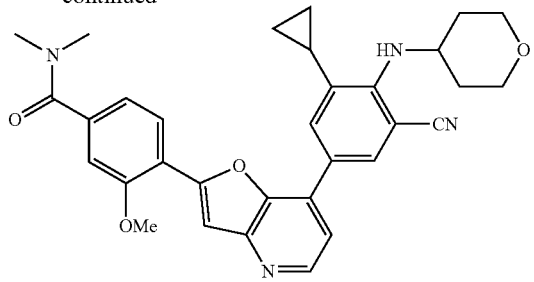

The title compound was prepared from 4-(7-chloro-6-cyclopropylfuro[3,2-b]pyridin-2-yl)-3-methoxy-N,N-dimethylbenzamide, and 2-(tetrahydro-2H-pyran-4-ylamino)-5-(4,4,5,5-tetramethyl-1,3,2-dioxaborolan-2-yl)benzonitrile using Method S. The product was purified by prep-HPLC under the following conditions: column, Gemini-NX 5u C18, 110A, AXIA Packed 150×21.2 mm; mobile phase, acetonitrile in water (with 10 mmol/L NH₄HCO₃), 20% to 50% gradient in 8 min; detector, UV 254/220 nm. 4-(7-(3-cyano-5-cyclopropyl-4-(tetrahydro-2H-pyran-4-ylamino)phenyl)furo[3,2-b]pyridin-2-yl)-3-methoxy-N,N-dimethylbenzamide was obtained as a white solid (17 mg, 39%).

HPLC: 99.7% purity, RT=1.67 min. MS: m/z=537.3 [M+H]⁺. ¹H NMR (400 MHz, DMSO-d₆, ppm) δ 8.26 (s, 1H), 7.85 (s, 1H), 7.82-7.73 (m, 2H), 7.53 (s, 1H), 7.20 (s, 1H), 7.19-7.09 (m, 2H), 6.13 (d, J=8.0 Hz, 1H), 4.03 (s, 3H), 3.96-3.87 (m, 2H), 3.80-3.70 (m, 1H), 3.55-3.40 (m, 2H), 3.00 (s, 3H), 2.93 (s, 3H), 2.04-1.86 (m, 3H), 1.75-1.60 (m, 2H), 0.92 (d, J=8.2 Hz, 2H), 0.76 (d, J=5.3 Hz, 2H).

Example 262: 4-(7-[3-cyano-4-[(oxan-4-yl)amino]phenyl]-6-cyclopropylfuro[3,2-b]pyridin-2-yl)-3-fluoro-N,N-dimethylbenzamide (309)

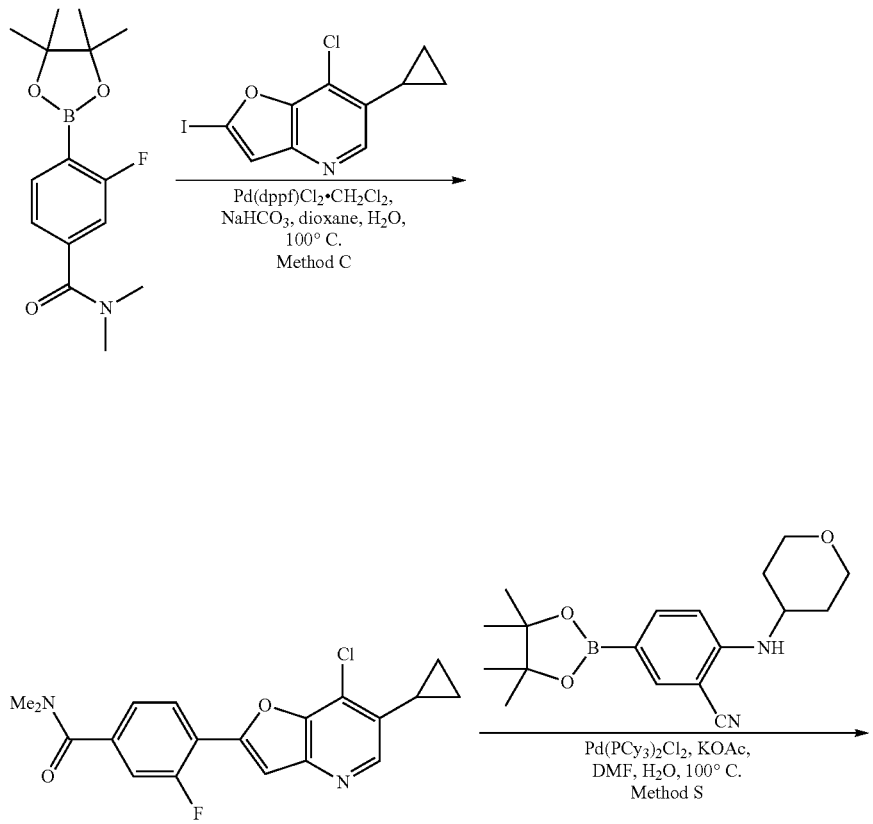

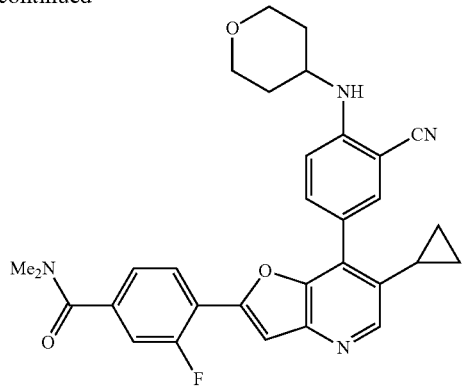

The title compound was prepared from 3-fluoro-N,N-dimethyl-4-(4,4,5,5-tetramethyl-1,3,2-dioxaborolan-2-yl)benzamide, 7-chloro-6-cyclopropyl-2-iodofuro[3,2-b]pyridine, and 2-(tetrahydro-2H-pyran-4-ylamino)-5-(4,4,5,5-tetramethyl-1,3,2-dioxaborolan-2-yl)benzonitrile using Method C and S. The final product was purified by prep-HPLC under the following conditions: column, Gemini-NX 5u C18, 110A, AXIA Packed 150×21.2 mm; mobile phase, acetonitrile in water (with 10 mmol/L $NH_4HCO_3$), 20% to 50% gradient in 8 min; detector, UV 254/220 nm. 4-(7-[3-cyano-4-[(oxan-4-yl)amino]phenyl]-6-cyclopropylfuro[3,2-b]pyridin-2-yl)-3-fluoro-N,N-dimethylbenzamide was obtained as a white solid (24 mg, 19% for 2 steps). HPLC: 99.5% purity, RT=1.30 min. MS: m/z=525.1 [M+H]$^+$. $^1$H NMR (400 MHz, DMSO-d$_6$, ppm) δ 8.31 (s, 1H), 7.91-7.83 (m, 2H), 7.78 (dd, J=9.0, 2.2 Hz, 1H), 7.54-7.45 (m, 2H), 7.40 (dd, J=7.9, 1.5 Hz, 1H), 7.13 (d, J=9.0 Hz, 1H), 6.15 (d, J=8.1 Hz, 1H), 3.95-3.87 (m, 2H), 3.83-3.70 (m, 1H), 3.52-3.40 (m, 2H), 3.01 (s, 3H), 2.94 (s, 3H), 2.07-1.85 (m, 3H), 1.75-1.60 (m, 2H), 0.99-0.89 (m, 2H), 0.83-00.74 (m, 2H).

Example 263: 4-[7-[3-cyano-4-(oxan-4-yloxy)phenyl]-6-cyclopropylfuro[3,2-b]pyridin-2-yl]-3-fluoro-N,N-dimethylbenzamide (310)

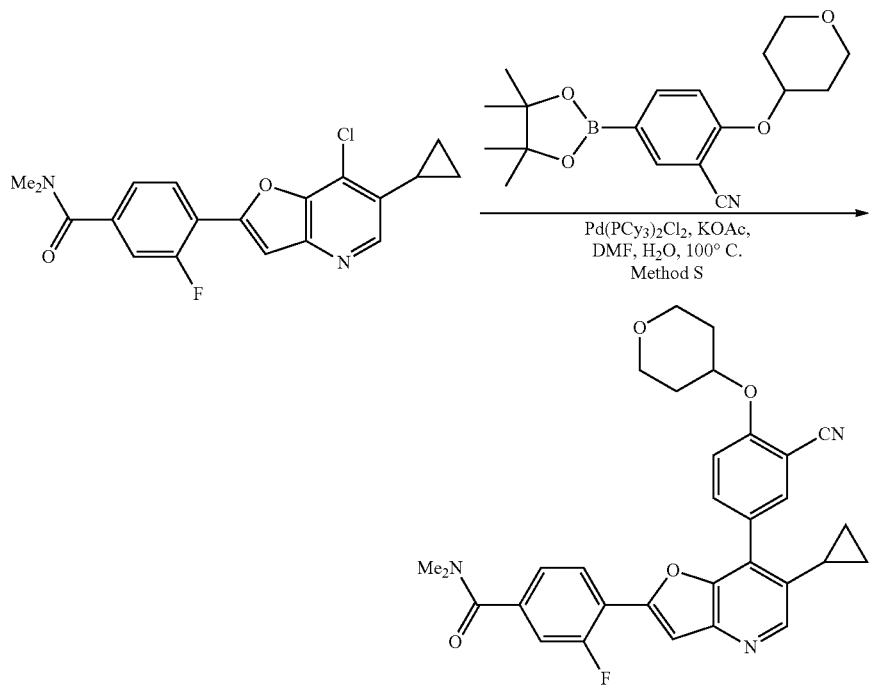

The title compound was prepared from 4-(7-chloro-6-cyclopropylfuro[3,2-b]pyridin-2-yl)-3-fluoro-N,N-dimethylbenzamide and 2-(tetrahydro-2H-pyran-4-yloxy)-5-(4,4,5,5-tetramethyl-1,3,2-dioxaborolan-2-yl)benzonitrile using Method S. The product was purified by prep-HPLC under the following conditions: column, Gemini-NX 5u C18, 110A, AXIA Packed 150×21.2 mm; mobile phase, acetonitrile in water (with 10 mmol/L $NH_4HCO_3$), 20% to 50% gradient in 8 min; detector, UV 254/220 nm. 4-(7-(3-cyano-5-cyclopropyl-4-(tetrahydro-2H-pyran-4-ylamino)phenyl)furo[3,2-b]pyridin-2-yl)-3-methoxy-N,N-dimethylbenzamide was obtained as a white solid (19 mg, 29%). HPLC:

99.8% purity, RT=1.36 min. MS: m/z=526.1 [M+H]⁺. ¹H NMR (400 MHz, DMSO-d₆, ppm) δ 8.35 (s, 1H), 8.11 (d, J=2.1 Hz, 1H), 7.99 (dd, J=8.6, 2.2 Hz, 1H), 7.95-7.82 (m, 1H), 7.60 (d, J=8.9 Hz, 1H), 7.55-7.46 (m, 2H), 7.39 (d, J=8.1 Hz, 1H), 5.00-4.91 (m, 1H), 4.00-3.85 (m, 2H), 3.65-3.50 (m, 2H), 3.01 (s, 3H), 2.92 (s, 3H), 2.08 (d, J=12.9 Hz, 2H), 2.01-1.90 (m, 1H), 1.82-1.65 (m, 2H), 0.97-0.87 (m, 2H), 0.83-0.74 (m, 2H).

Example 264: 4-(7-(3-cyano-4-(tetrahydro-2H-pyran-4-ylamino)phenyl)-6-cyclopropylfuro[3,2-b]pyridin-2-yl)-3-fluoro-N-(2-hydroxyethyl)-N-methylbenzamide (311)

ylamino)-5-(4,4,5,5-tetramethyl-1,3,2-dioxaborolan-2-yl)benzonitrile using Methods C and S. The final product was purified by prep-HPLC under the following conditions: column, Gemini-NX 5u C18, 110A, AXIA Packed 150×21.2 mm; mobile phase, acetonitrile in water (with 10 mmol/L NH₄HCO₃), 20% to 50% gradient in 8 min; detector, UV 254/220 nm. 4-(7-(3-cyano-4-(tetrahydro-2H-pyran-4-ylamino)phenyl)-6-cyclopropylfuro[3,2-b]pyridin-2-yl)-3-fluoro-N-(2-hydroxyethyl)-N-methylbenzamide was obtained as a white solid (17 mg, 5.8% for 2 steps). HPLC: 99.7% purity, RT=1.20 min. MS: m/z=556.3 [M+H]⁺. ¹H NMR (300 MHz, DMSO-d₆, ppm) δ 8.38 (s, 1H), 8.11 (d, J=2.1 Hz, 1 H), 7.99 (dd, J=6.6, 2.1 Hz, 1H), 7.92-7.80 (m,

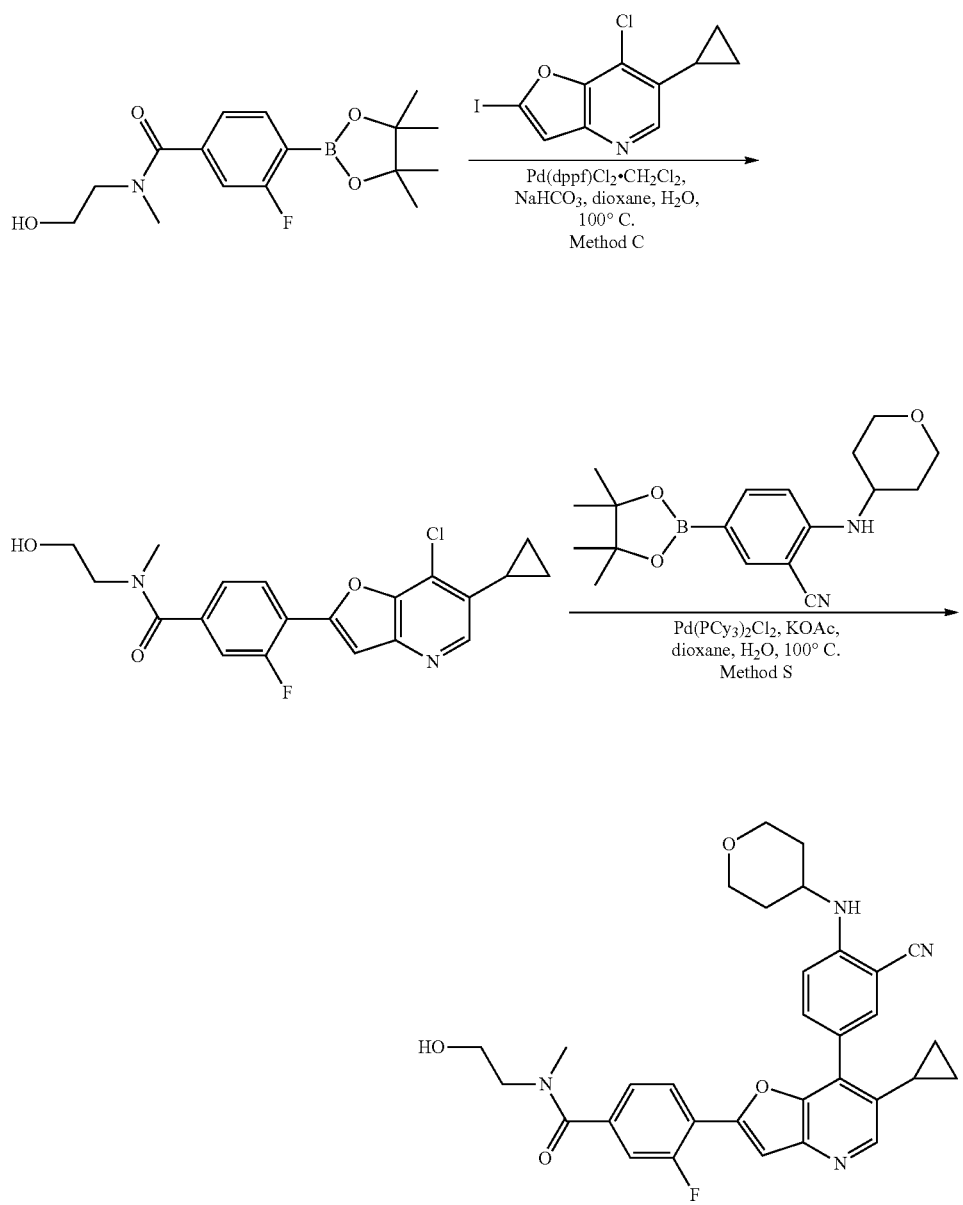

The title compound was prepared from 3-fluoro-N-(2-hydroxyethyl)-N-methyl-4-(4,4,5,5-tetramethyl-1,3,2-dioxaborolan-2-yl)benzamide, 7-chloro-6-cyclopropyl-2-iodofuro[3,2-b]pyridine, and 2-(tetrahydro-2H-pyran-4-

1H), 7.60 (d, J=9.0 Hz, 1H), 7.57-7.45 (m, 2H), 7.40 (d, J=8.1 Hz, 1H), 5.10-4.76 (m, 2H), 4.00-3.85 (m, 2H), 3.70-3.40 (m, 5H), 3.35-3.20 (m, 2H), 3.10-2.90 (m, 3H), 2.18-1.90 (m, 3H), 1.81-1.65 (m, 2H), 1.00-0.70 (m, 4H).

Example 265: 4-(7-(3-cyano-4-(tetrahydro-2H-pyran-4-yloxy)phenyl)-6-cyclopropylfuro[3,2-b]pyridin-2-yl)-3-fluoro-N-(2-hydroxyethyl)-N-methylbenzamide (312)

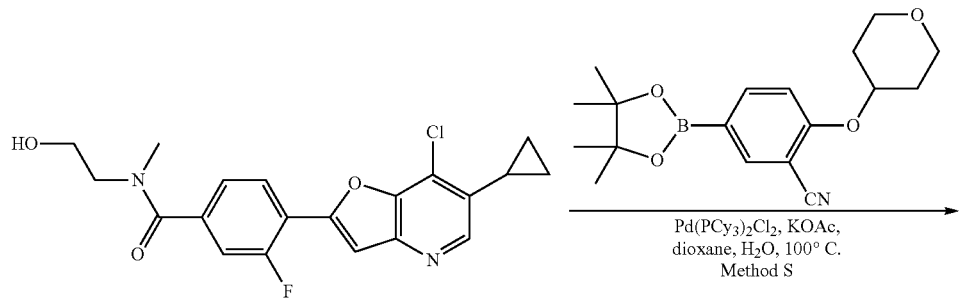

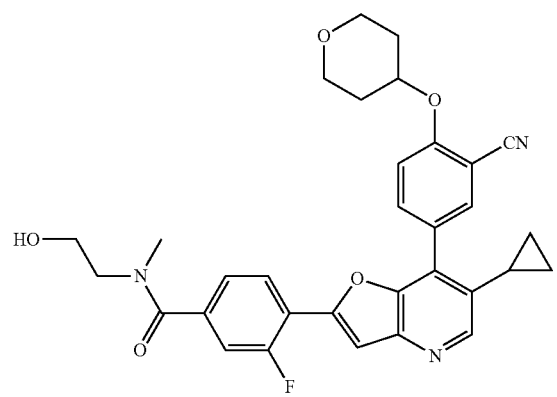

The title compound was prepared from 4-(7-chloro-6-cyclopropylfuro[3,2-b]pyridin-2-yl)-3-fluoro-N-(2-hydroxyethyl)-N-methylbenzamide and 2-(tetrahydro-2H-pyran-4-yloxy)-5-(4,4,5,5-tetramethyl-1,3,2-dioxaborolan-2-yl)benzonitrile using Method S. The product was purified by prep-HPLC under the following conditions: column, Gemini-NX 5u C18, 110A, AXIA Packed 150×21.2 mm; mobile phase, acetonitrile in water (with 10 mmol/L NH$_4$HCO$_3$), 25% to 55% gradient in 8 min; detector, UV 254/220 nm. 4-(7-(3-cyano-4-(tetrahydro-2H-pyran-4-yloxy)phenyl)-6-cyclopropylfuro[3,2-b]pyridin-2-yl)-3-fluoro-N-(2-hydroxyethyl)-N-methylbenzamide was obtained as a white solid (10 mg, 13%). HPLC: 99.3% purity, RT=1.62 min. MS: m/z=555.2 [M+H]$^+$. $^1$H NMR (400 MHz, DMSO-d$_6$, ppm) δ 8.30 (s, 1H), 7.93-7.81 (m, 2H), 7.77 (dd, J=8.9, 2.2 Hz, 1H), 7.54-7.44 (m, 2H), 7.40 (d, J=8.0 Hz, 1H), 7.12 (d, J=8.9 Hz, 1H), 6.14 (d, J=8.1 Hz, 1H), 4.90-4.80 (m, 1H), 3.91 (d, J=10.1 Hz, 2H), 3.83-3.70 (m, 1H), 3.69-3.2 (m, 5H), 2.97 (d, J=9.4 Hz, 3H), 2.08-1.85 (m, 3H), 1.76-1.60 (m, 2H), 1.00-0.67 (m, 4H).

Example 266: 5-(7-(3-cyano-4-(3-fluoropyrrolidin-1-yl)phenyl)furo[3,2-b]pyridin-2-yl)-6-methoxy-N,N-dimethylpicolinamide hydrochloride

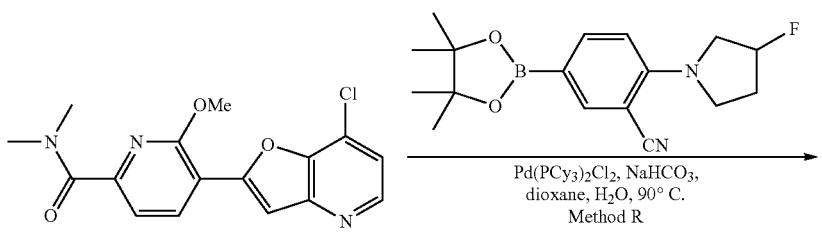

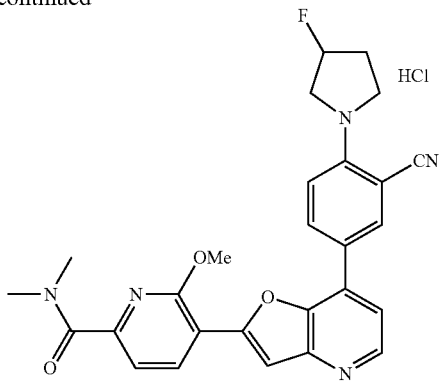

The title compound was prepared from 5-(7-chlorofuro[3,2-b]pyridin-2-yl)-6-methoxy-N,N-dimethylpicolinamide and 2-(3-fluoropyrrolidin-1-yl)-5-(4,4,5,5-tetramethyl-1,3,2-dioxaborolan-2-yl)benzonitrile using Method R. The product was first purified by prep-HPLC under the following conditions: column, Atlantis Prep T$_3$ OBD column, 19×150 mm 5 um 10 nm; mobile phase, acetonitrile in water (with 0.02% HCl), 20% to 50% gradient in 8 min; detector, UV 254/220 nm.

Example 267: 5-{7-[3-Cyano-4-((R)-3-fluoro-pyrrolidin-1-yl)-phenyl]-furo[3,2-b]pyridin-2-yl}-6-methoxy-pyridine-2-carboxylic acid dimethylamide (313)

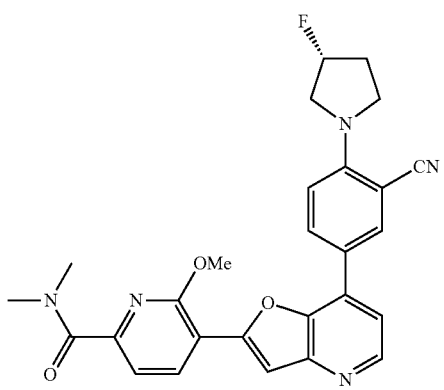 [SMILES: COc1nc(C(=O)N(C)C)ccc1-c1cc2nccc(-c3ccc(N4CC[C@@H](F)C4)c(C#N)c3)c2o1]

The title compound was separated from 5-(7-(3-cyano-4-(3-fluoropyrrolidin-1-yl)phenyl)furo[3,2-b]pyridin-2-yl)-6-methoxy-N,N-dimethylpicolinamide were obtained by separation on a chiral prep-HPLC under the following conditions: column CHIRALPAK AD-H SFC, 5×25 cm, 5 um; mobile phase, EtOH (0.1% DEA) in 20 min; detector, UV 330 nm. (25 mg, 7%, yellow solid) HPLC: 99.7% purity, RT=1.19 min. MS: m/z=486.1 [M+H]$^+$. $^1$H NMR (300 MHz, CD$_3$OD, ppm) δ 8.65-8.47 (m, 3H), 8.39 (dd, J=9.2, 2.4 Hz, 1H), 8.05 (d, J=6.4 Hz, 1H), 7.78 (s, 1H), 7.46 (d, J=7.7 Hz, 1H), 7.08 (d, J=9.2 Hz, 1H), 5.60-5.35 (m, 1H), 4.27-3.86 (m, 7H), 3.17 (s, 6H), 2.55-2.10 (m, 2H).

Example 268: 5-{7-[3-Cyano-4-((S)-3-fluoro-pyrrolidin-1-yl)-phenyl]-furo[3,2-b]pyridin-2-yl}-6-methoxy-pyridine-2-carboxylic acid dimethylamide (314)

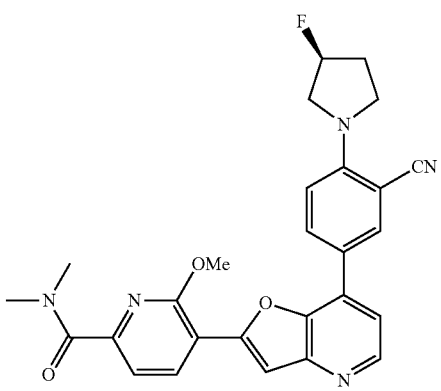 [SMILES: COc1nc(C(=O)N(C)C)ccc1-c1cc2nccc(-c3ccc(N4CC[C@H](F)C4)c(C#N)c3)c2o1]

The title compound was separated from 5-(7-(3-cyano-4-(3-fluoropyrrolidin-1-yl)phenyl)furo[3,2-b]pyridin-2-yl)-6-methoxy-N,N-dimethylpicolinamide were obtained by separation on a chiral prep-HPLC (25 mg, 7%, yellow solid) HPLC: 99.3% purity, RT=1.19 min. MS: m/z=486.1 [M+H]$^+$. $^1$H NMR (300 MHz, CD$_3$OD, ppm) δ 8.57-8.37 (m, 3H), 8.29 (dd, J=9.2, 2.4 Hz, 1H), 7.95 (d, J=6.3 Hz, 1H), 7.69 (s, 1H), 7.39 (d, J=7.8 Hz, 1H), 7.00 (d, J=9.2 Hz, 1H), 5.60-5.35 (m, 1H), 4.20-3.80 (m, 7H), 3.11 (d, J=1.2 Hz, 6H), 2.55-2.10 (m, 2H).

Example 269: 6-(7-[6-cyano-5-[(oxan-4-yl)amino]pyridin-2-yl]furo[3,2-b]pyridin-2-yl)-5-methoxy-N,N-dimethylpyridine-3-carboxamide hydrochloride (315)

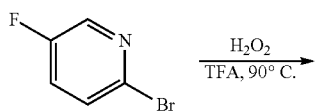

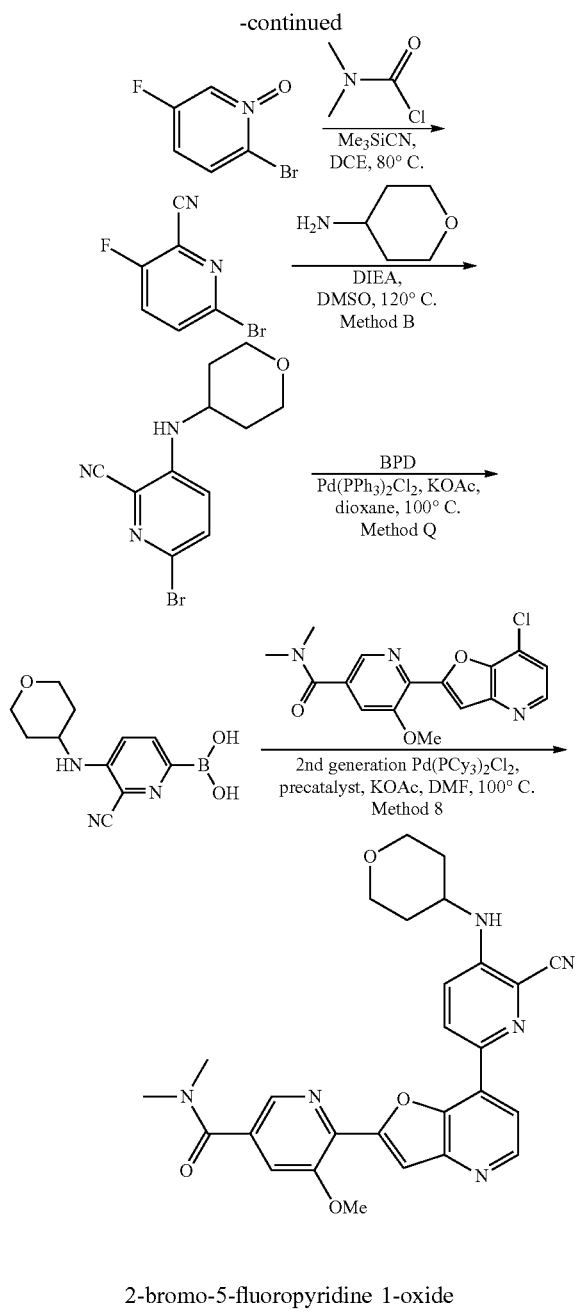

2-bromo-5-fluoropyridine 1-oxide

At 0° C., TFA (10 mL) was added dropwise to a solution of 2-bromo-5-fluoropyridine (5.75 g, 26.99 mmol) in H₂O₂ (30%, 15 mL, 159 mmol). Then resulting solution was stirred for 16 h at 90° C. After cooling to room temperature, the reaction mixture was quenched by the addition of water (25 mL). The resulting mixture was extracted with DCM (50 mL×3). The organic phases were combined, washed with brine and dried over sodium sulfate. The solvent was removed under reduced pressure to yield 2-bromo-5-fluoro-1lambda5-pyridin-1-one as a white solid (4.00 g, 69%). MS: m/z=191.9 [M+H]⁺.

6-bromo-3-fluoropicolinonitrile

To a solution of 2-bromo-5-fluoro-1lambda5-pyridin-1-one (3.00 g, 15.63 mmol) in DCE (30 mL) was added trimethylsilanecarbonitrile (1.86 g, 18.75 mmol) and N,N-dimethylcarbamoyl chloride (2.00 g, 18.60 mmol) at room temperature. The resulting solution was stirred for 16 h at 80° C. After the reaction was done, the pH value of the reaction mixture was adjusted to 9 with sat. sodium bicarbonate solution. The resulting mixture was extracted with DCM (50 mL×3). The organic phases were combined, washed with brine and dried over sodium sulfate. The solvent was removed under reduced pressure and the residue was purified by flash chromatography eluting with EtOAc in hexane (0% to 2% gradient) to yield 6-bromo-3-fluoropyridine-2-carbonitrile as a light yellow solid (1.20 g, 38%).

6-bromo-3-(tetrahydro-2H-pyran-4-ylamino)picolinonitrile 6-bromo-3-(tetrahydro-2H-pyran-4-ylamino)picolinonitrile was prepared from 6-bromo-3-fluoropicolinonitrile and tetrahydro-2H-pyran-4-amine using Method B. The product was purified by flash chromatography eluting with EtOAc in hexane (0% to 50% gradient) to yield 6-bromo-3-[(oxan-4-yl)amino]pyridine-2-carbonitrile as a light yellow solid (1.30 g, 52%). MS: m/z=282.0 [M+H]⁺.

6-cyano-5-(tetrahydro-2H-pyran-4-ylamino)pyridin-2-ylboronic acid 6-cyano-5-(tetrahydro-2H-pyran-4-ylamino)pyridin-2-yl-boronic acid was prepared from 6-bromo-3-(tetrahydro-2H-pyran-4-ylamino)picolinonitrile and 4,4,5,5-tetramethyl-2-(tetramethyl-1,3,2-dioxaborolan-2-yl)-1,3,2-dioxaborolane using Method Q. The crude product was purified by flash chromatography eluting with MeOH in ethyl acetate (0% to 100% gradient) to yield [6-cyano-5-[(oxan-4-yl)amino]pyridin-2-yl]boronic acid as a light yellow solid (80 mg, 74%). MS: m/z=248.1 [M+H]⁺.

Method 8

6-(7-[6-cyano-5-[(oxan-4-yl)amino]pyridin-2-yl]furo[3,2-b]pyridin-2-yl)-5-methoxy-N,N-dimethylpyridine-3-carboxamide hydrochloride To a solution of 6-[7-chlorofuro[3,2-b]pyridin-2-yl]-5-methoxy-N,N-dimethylpyridine-3-carboxamide (24 mg, 0.07 mmol) in DMF (1 mL) was added [6-cyano-5-[(oxan-4-yl)amino]pyridin-2-yl]boronic acid (54 mg, 0.22 mmol), 2nd generation PCy₃ precatalyst (containing 30% Pd(PCy₃)₂Cl₂, 19 mg, 0.03 mmol), KOAc (30 mg, 0.31 mmol) at room temperature under nitrogen atmosphere. The resulting mixture was stirred for 18 h at 100° C. under nitrogen atmosphere. After cooling to room temperature, the reaction mixture was quenched by the addition of water (10 mL). The resulting mixture was extracted with DCM (30 mL×3). The organic phases were combined, washed with brine and dried over sodium sulfate. The solvent was removed under reduced pressure and the residue was purified by prep-HPLC under the following conditions: column, Gemini-NX C18, 21.2×150 mm 5 um; mobile phase, acetonitrile in water (with 0.02% HCl), 20% to 55% gradient in 10 min; detector, UV 254/220 nm. 6-(7-[6-cyano-5-[(oxan-4-yl)amino]pyridin-2-yl]furo[3,2-b]pyridin-2-yl)-5-methoxy-N,N-dimethylpyridine-3-carboxamide hydrochloride was obtained as an orange solid (17 mg, 42%). HPLC: 94.0% purity, RT=1.38 min. MS: m/z=499.2 [M+H]⁺. ¹H NMR (300 MHz, CD₃OD, ppm) δ 8.98 (d, J=9.2 Hz, 1H), 8.72 (d, J=6.4 Hz, 1H), 8.59 (d, J=6.4 Hz, 1H), 8.47 (d, J=1.5 Hz, 1H), 7.96 (s, 1H), 7.86 (d, J=1.5 Hz, 1H), 7.68 (d, J=9.3 Hz, 1H), 4.20 (s, 3H), 4.03

(d, J=10.1 Hz, 2H), 3.90 (s, 1H), 3.67-3.50 (m, 2H), 3.18 (s, 3H), 3.09 (s, 3H), 2.02 (d, J=13.2 Hz, 2H), 1.88-1.70 (m, 2H).

Example 270: 6-[7-[6-cyano-5-(oxan-4-yloxy)pyridin-2-yl]furo[3,2-b]pyridin-2-yl]-5-methoxy-N,N-dimethylpyridine-3-carboxamide (316)

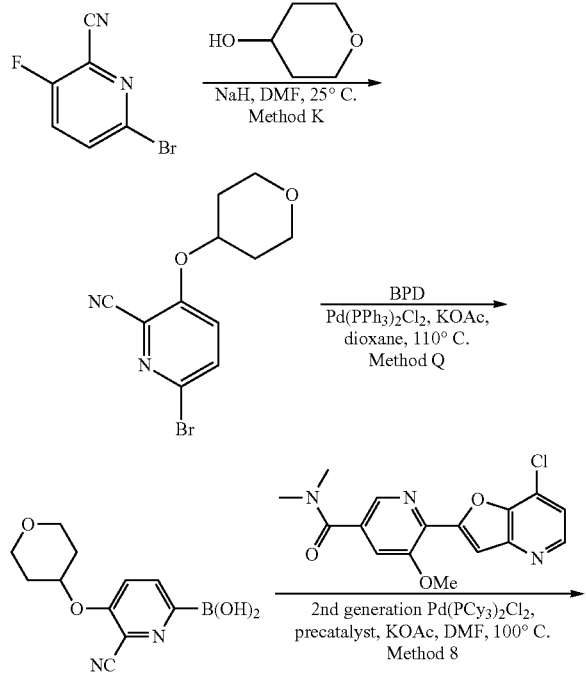

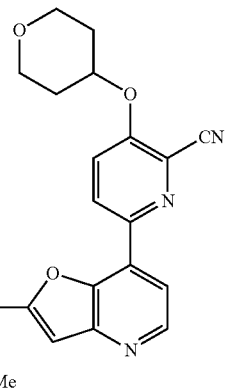

The title compound was prepared from 6-bromo-3-fluoropicolinonitrile, tetrahydro-2H-pyran-4-ol, 4,4,5,5-tetramethyl-2-(tetramethyl-1,3,2-dioxaborolan-2-yl)-1,3,2-dioxaborolane, and 6-(7-chlorofuro[3,2-b]pyridin-2-yl)-5-methoxy-N,N-dimethylnicotinamide using Methods K, Q and 8. The final product was purified by prep-HPLC under the following conditions: column, XBridge Prep C18 OBD Column, 19×150 mm 5 um; mobile phase, acetonitrile in water (with 10 mmol/L $NH_4HCO_3$), 20% to 50% gradient in 8 min; detector, UV 254/220 nm. 6-[7-[6-cyano-5-(oxan-4-yloxy)pyridin-2-yl]furo[3,2-b]pyridin-2-yl]-5-methoxy-N,N-dimethylpyridine-3-carboxamide as a white solid (10 mg, 5.9% for 3 steps). HPLC: 99.8% purity, RT=1.51 min. MS: m/z=500.2 $[M+H]^+$. $^1$H NMR (300 MHz, $CD_3OD$, ppm) δ 8.95 (d, J=9.1 Hz, 1H), 8.60 (d, J=5.2 Hz, 1H), 8.36 (d, J=1.6 Hz, 1H), 8.13 (d, J=5.2 Hz, 1H), 7.93 (d, J=9.1 Hz, 1H), 7.81 (s, 1H), 7.75 (d, J=1.6 Hz, 1H), 5.05-4.95 (m, 1H), 4.15 (s, 3H), 4.10-4.00 (m, 2H), 3.80-3.65 (m, 2H), 3.16 (s, 3H), 3.10 (s, 3H), 2.25-2.10 (m, 2H), 1.98-1.82 (m, 2H).

Example 271: 6-(7-(3-cyano-4-(tetrahydro-2H-pyran-4-yloxy)phenyl)-6-fluorofuro[3,2-b]pyridin-2-yl)-5-methoxy-N,N-dimethylnicotinamide (317)

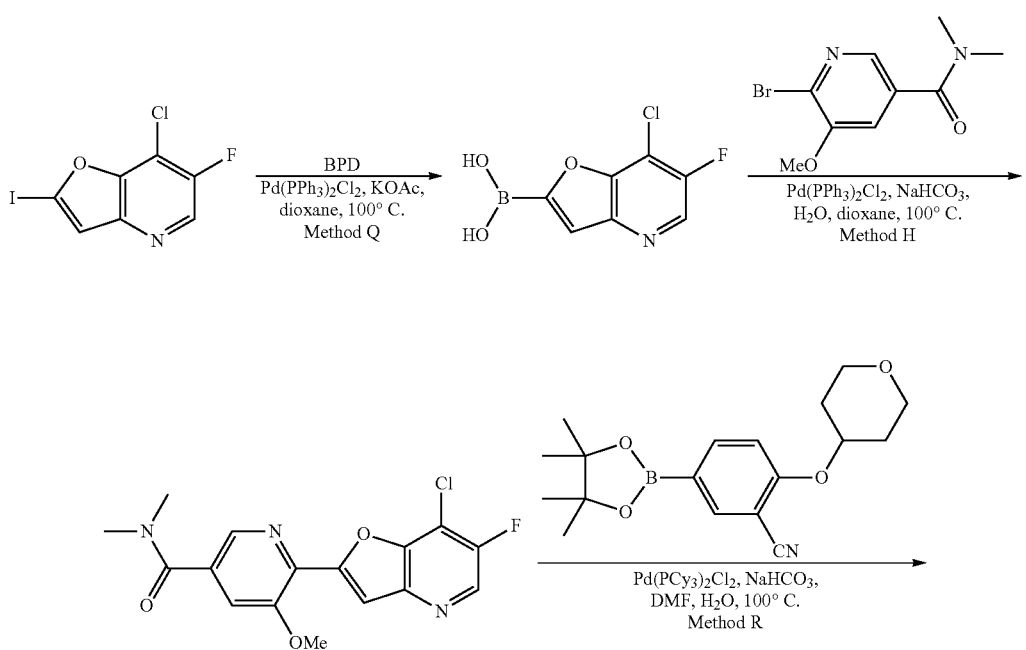

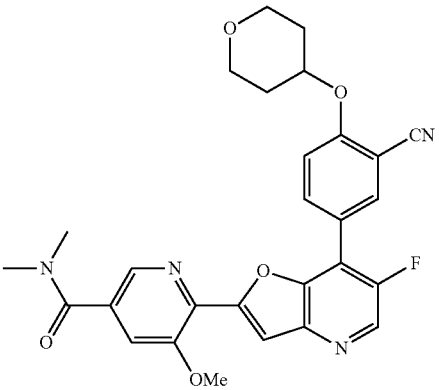

The title compound was prepared from 7-chloro-6-fluoro-2-iodofuro[3,2-b]pyridine, 4,4,5,5-tetramethyl-2-(tetramethyl-1,3,2-dioxaborolan-2-yl)-1,3,2-dioxaborolane, 6-bromo-5-methoxy-N,N-dimethylnicotinamide, and 2-(tetrahydro-2H-pyran-4-yloxy)-5-(4,4,5,5-tetramethyl-1,3,2-dioxaborolan-2-yl)benzonitrile using Methods Q, H, and R. The final product was purified by prep-HPLC under the following conditions: column, Gemini-NX 5u C18, 110A, AXIA Packed 150×21.2 mm; mobile phase, acetonitrile in water (with 10 mmol/L NH$_4$HCO$_3$), 20% to 50% gradient in 8 min; detector, UV 254/220 nm. 6-(7-(3-cyano-4-(tetrahydro-2H-pyran-4-yloxy)phenyl)-6-fluorofuro[3,2-b]pyridin-2-yl)-5-methoxy-N,N-dimethylnicotinamide was obtained as a white solid (9 mg, 5.0% for 3 steps). HPLC: 99.9% purity, RT=1.22 min. MS: m/z=517.2 [M+H]$^+$. $^1$H NMR (400 MHz, DMSO-d$_6$, ppm) δ 8.73 (d, J=2.8 Hz, 1H), 8.32 (d, J=1.6 Hz, 1H), 8.24 (d, J=1.6 Hz, 1H), 8.18-8.10 (m, 1H), 7.82 (s, 1H), 7.75-7.60 (m, 2H), 5.00-4.92 (m, 1H), 4.07 (s, 3H), 3.95-3.80 (m, 2H), 3.65-3.50 (m, 2H), 3.02 (s, 3H), 2.96 (s, 3H), 2.15-2.00 (m, 2H), 1.79-1.62 (m, 2H).

Example 272: 6-(7-(3-cyano-4-(tetrahydro-2H-pyran-4-ylamino)phenyl)furo[3,2-b]pyridin-2-yl)-N-(2-hydroxyethyl)-5-methoxy-N-methylnicotinamide (318)

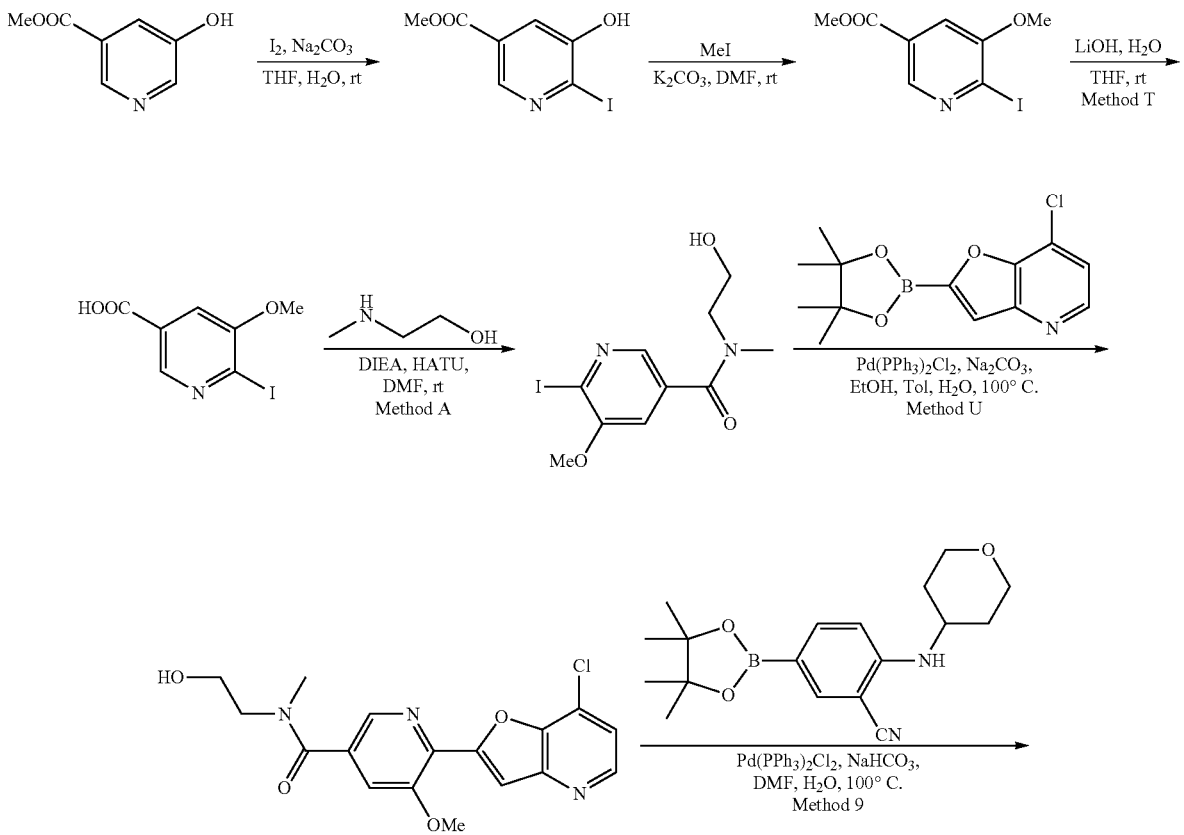

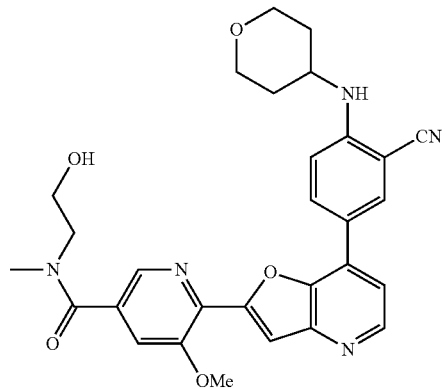

Methyl 5-hydroxy-6-iodonicotinate

To a solution of methyl 5-hydroxypyridine-3-carboxylate (2.38 g, 15.51 mmol) in THF (50 mL) and water (50 mL) were added sodium carbonate (4.93 g, 46.52 mmol) and iodine (9.88 g, 38.93 mmol) at room temperature. The resulting solution was stirred for 4 h at room temperature. After the reaction was done, the reaction mixture was washed with hexane (200 mL×3), and then the pH value of the aqueous phase was adjusted to 7 with hydrogen chloride solution (2 N). The resulting mixture was extracted with ethyl acetate (100 mL×3). The organic phases were combined, washed with brine and dried over sodium sulfate. The solvent was removed under reduced pressure and the residue was purified by flash chromatography eluting with EtOAc in hexane (0% to 40% gradient) to yield methyl 5-hydroxy-6-iodopyridine-3-carboxylate as a yellow solid (3.60 g, 83%). $^1$H NMR (400 MHz, DMSO, ppm) δ 11.42 (s, 1H), 8.33 (d, J=2.0 Hz, 1H), 7.57 (d, J=2.0 Hz, 1H).

Methyl 6-iodo-5-methoxynicotinate

To a solution of methyl 5-hydroxy-6-iodopyridine-3-carboxylate (2.47 g, 8.85 mmol) in DMF (100 mL) was added potassium carbonate (1.58 g, 11.41 mmol) and iodomethane (1.43 g, 10.04 mmol) at room temperature. The resulting solution was stirred for 16 h at room temperature. After the reaction was done, the reaction mixture was diluted with H$_2$O (400 mL). The resulting mixture was extracted with ethyl acetate (150 mL×3). The organic phases were combined, washed with brine and dried over sodium sulfate. The solvent was removed under reduced pressure to yield methyl 6-iodo-5-methoxypyridine-3-carboxylate as a yellow solid (2.70 g, 91%). MS: m/z=294.0 [M+H]$^+$.

6-iodo-5-methoxynicotinic acid 6-iodo-5-methoxynicotinic acid was prepared from methyl 6-iodo-5-methoxynicotinate using Method T to yield 6-iodo-5-methoxypyridine-3-carboxylic acid as a yellow solid (2.30 g, crude). MS: m/z=279.9 [M+H]$^+$.

N-(2-hydroxyethyl)-6-iodo-5-methoxy-N-methylnicotinamide

N-(2-hydroxyethyl)-6-iodo-5-methoxy-N-methylnicotinamide was prepared from 6-iodo-5-methoxynicotinic acid and 2-(methylamino)ethanol using Method A. The crude product was purified by flash chromatography eluting with ethyl acetate in petroleum ether (0% to 60% gradient) to yield N-(2-hydroxyethyl)-6-iodo-5-methoxy-N-methylpyridine-3-carboxamide as a yellow oil (1.42 g, 50% for 2 steps). MS: m/z=337.0 [M+H]$^+$.

6-(7-chlorofuro[3,2-b]pyridin-2-yl)-N-(2-hydroxyethyl)-5-methoxy-N-methylnicotinamide 6-(7-chlorofuro[3,2-b]pyridin-2-yl)-N-(2-hydroxyethyl)-5-methoxy-N-methylnicotinamide was prepared from 6-iodo-5-methoxynicotinic acid and 2-(methylamino)ethanol using Method U. The product was purified by flash chromatography eluting with MeOH in DCM (0% to 20% gradient) to yield 6-(7-chlorofuro[3,2-b]pyridin-2-yl)-N-(2-hydroxyethyl)-5-methoxy-N-methylnicotinamide as a yellow oil (134 mg, 34). MS: m/z=362.0 [M+H]$^+$.

Method 9

6-(7-(3-cyano-4-(tetrahydro-2H-pyran-4-ylamino)phenyl)furo[3,2-b]pyridin-2-yl)-N-(2-hydroxyethyl)-5-methoxy-N-methylnicotinamide To a solution of 6-[7-chlorofuro[3,2-b]pyridin-2-yl]-N-(2-hydroxyethyl)-5-methoxy-N-methylpyridine-3-carboxamide (84 mg, 0.23 mmol) in DMF (5 mL) was added 2-[(oxan-4-yl)amino]-5-(tetramethyl-1,3,2-dioxaborolan-2-yl)benzonitrile (81 mg, 0.25 mmol), Pd(PPh$_3$)$_2$Cl$_2$ (19 mg, 0.03 mmol), sodium carbonate (38 mg, 0.36 mmol) and water (I mL) at room temperature under nitrogen atmosphere. The reaction mixture was then irradiated with microwave for 2 h at 100° C. under nitrogen atmosphere. After cooling to room temperature, the reaction mixture was quenched by the addition of water (10 mL). The resulting mixture was extracted with DCM (30 mL×3). The organic phases were combined, washed with brine and dried over sodium sulfate. The solvent was removed under reduced pressure and the residue was purified by prep-HPLC under the following conditions: column, Gemini-NX 5u C18 110A, AXIA Packed, 150×21.2 mm; mobile phase, acetonitrile in water (with 10 mmol/L NH$_4$HCO$_3$), 20?% to 50% gradient in 8 min; detector, UV 254/220 nm. 6-(7-[3-cyano-4-[(oxan-4-yl)amino]phenyl]furo[3,2-b]pyridin-2-yl)-N-(2-hydroxyethyl)-5-methoxy-N-methylpyridine-3-carboxamide was obtained as a yellow solid (18 mg, 14%). HPLC: 97.4% purity, RT=1.16 min. MS: m n/=528.2 [M+H]$^+$. $^1$H NMR (300 MHz, DMSO-d$_6$, ppm) δ 8.55 (d, J=5.1 Hz, 1H), 8.38 (t, J=2.6 Hz, 2H), 8.34-8.24 (m, 1H), 7.75 (d, J=13.3 Hz, 2H), 7.69 (d, J=5.1 Hz, 1H), 7.18 (d, J=9.2 Hz, 1H), 6.30 (d, J=8.3 Hz, 1H), 4.96-4.80 (m, 1H), 4.11 (d, J=5.6 Hz, 3H), 3.99-3.72 (m, 3H), 3.71-3.30 (m, 6H), 3.04 (s, 3H), 1.93-1.82 (m, 2H), 1.76-1.60 (m, 2H).

Example 273: 6-(7-(3-cyano-4-(tetrahydro-2H-pyran-4-ylamino)phenyl)-6-methylfuro[3,2-b]pyridin-2-yl)-5-methoxy-N,N-dimethylnicotinamide (319)

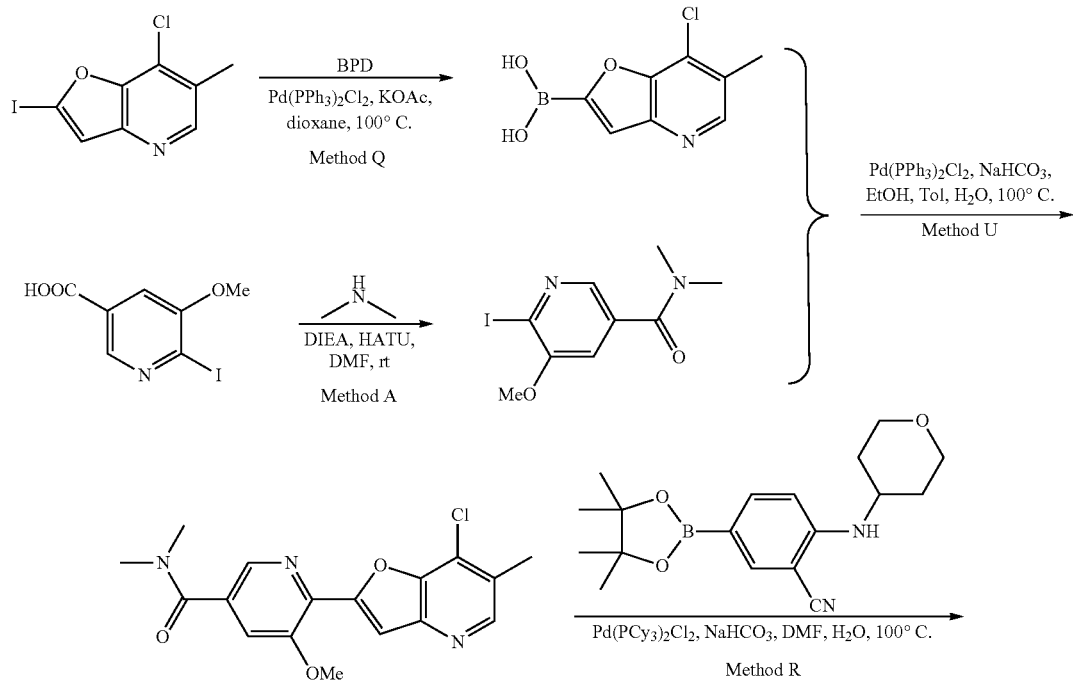

7-chloro-6-methylfuro[3,2-b]pyridin-2-ylboronic acid 7-chloro-6-methylfuro[3,2-b]pyridin-2-ylboronic acid was prepared from 7-chloro-2-iodo-6-methylfuro[3,2-b]pyridine using Method Q to yield 7-chloro-6-methylfuro[3,2-b]pyridin-2-ylboronic acid as a brown solid (300 mg, crude). MS: m/z=212.0 [M+H]+.

6-(7-(3-cyano-4-(tetrahydro-2H-pyran-4-ylamino)phenyl)-6-methylfuro[3,2-b]pyridin-2-yl)-5-methoxy-N,N-dimethylnicotinamide The title compound was prepared from 6-iodo-5-methoxynicotinic acid, dimethylamine, 7-chloro-6-methylfuro[3,2-b]pyridin-2-ylboronic acid, and 2-(tetrahydro-2H-pyran-4-ylamino)-5-(4,4,5,5-tetramethyl-1,3,2-dioxaborolan-2-yl)benzonitrile using Method A, U, and R. The final product was purified by prep-HPLC under the following conditions: column, XBridge Prep C18 OBD Column, 5 um, 19×150 mm; mobile phase, acetonitrile in water (with 10 mmol/L NH$_4$HCO$_3$), 30% to 55% gradient in 8 min; detector, UV 254/220 nm. 6-(7-(3-cyano-4-(tetrahydro-2H-pyran-4-ylamino)phenyl)-6-methylfuro[3,2-b]pyridin-2-yl)-5-methoxy-N,N-dimethylnicotinamide was obtained as a light yellow solid (40 mg, 8.6% for 4 steps). HPLC: 99.7% purity, RT=1.02 min. MS: m/z=513.3 [M+H]+. $^1$H NMR (300 MHz, CD$_3$OD, ppm) δ 8.47 (s, 1H), 8.28 (d, J=1.5 Hz, 1H), 7.79-7.61 (m, 4H), 7.08 (d, J=8.9 Hz, 1H), 4.12 (s, 3H), 4.02 (d, J=11.8 Hz, 2H), 3.90-3.76 (m, 1H), 3.67-3.52 (m, 2H), 3.14 (s, 3H), 3.07 (s, 3H), 2.44 (s, 3H), 2.07 (d, J=13.0 Hz, 2H), 1.77-1.64 (m, 2H).

Example 274: 6-(7-(3-cyano-4-(tetrahydro-2H-pyran-4-yloxy)phenyl)-6-methylfuro[3,2-b]pyridin-2-yl)-5-methoxy-N,N-dimethylnicotinamide (320)

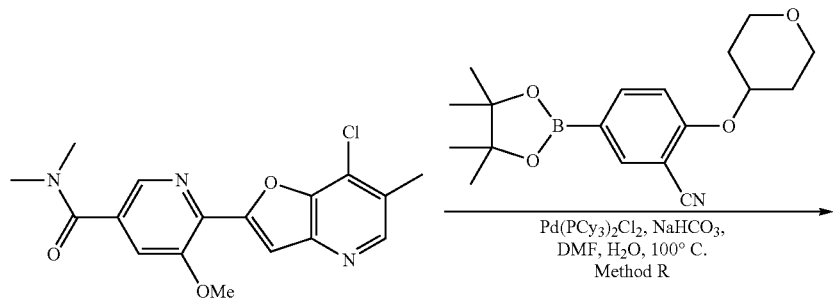

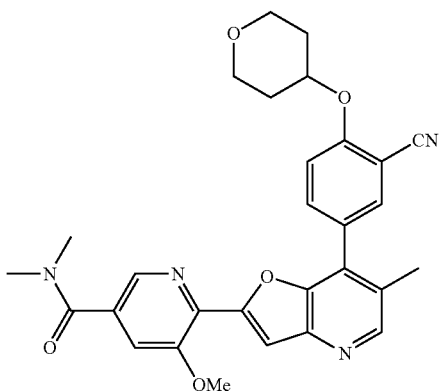

The title compound was prepared from 6-(7-chloro-6-methylfuro[3,2-b]pyridin-2-yl)-5-methoxy-N,N-dimethylnicotinamide and 2-(tetrahydro-2H-pyran-4-yloxy)-5-(4,4,5,5-tetramethyl-1,3,2-dioxaborolan-2-yl)benzonitrile using Method R. The product was purified by prep-HPLC under the following conditions: column, XBridge Prep C18 OBD Column, 10 um, 19×250 mm; mobile phase, acetonitrile in water (with 10 mmol/L $NH_4HCO_3$), 8% to 56% gradient in 8 min; detector, UV 254/220 nm. 6-(7-(3-cyano-4-(tetrahydro-2H-pyran-4-yloxy)phenyl)-6-methylfuro[3,2-b]pyridin-2-yl)-5-methoxy-N,N-dimethylnicotinamide was obtained as a white solid (10 mg, 10%). HPLC: 99.1% purity, RT=1.09 min. MS: m/z=513.2 [M+H]$^+$. $^1$H NMR (300 MHz, CD$_3$OD, ppm) δ 8.52 (s, 1H), 8.28 (d, J=1.6 Hz, 1H), 7.94-7.75 (m, 3H), 7.71 (d, J=1.6 Hz, 1H), 7.45 (d, J=8.9 Hz, 1H), 4.94 (dd, J=7.6, 4.0 Hz, 1H), 4.16-3.97 (m, 5H), 3.75-3.60 (m, 2H), 3.14 (s, 3H), 3.07 (s, 3H), 2.42 (s, 3H), 2.20-2.05 (m, 2H), 1.98-1.83 (m, 2H).

Example 275: 6-[7-[6-cyano-5-(oxan-4-yloxy)pyridin-2-yl]-6-methylfuro[3,2-b]pyridin-2-yl]-5-methoxy-N,N-dimethylpyridine-3-carboxamide hydrochloride (321)

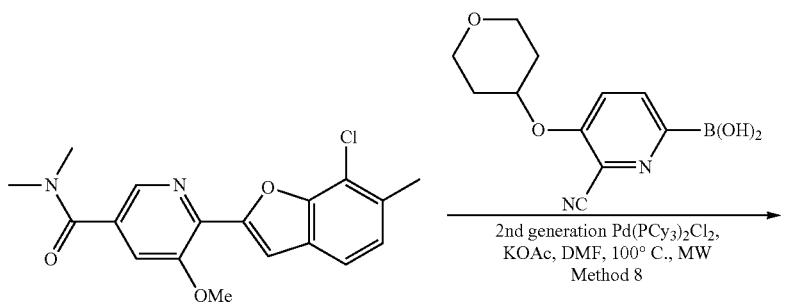

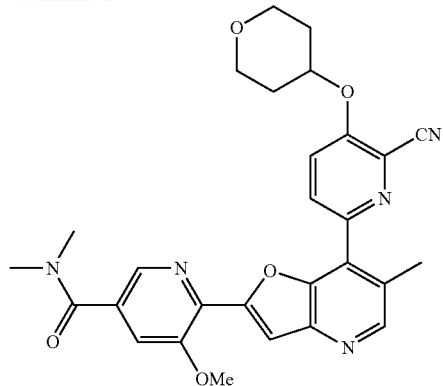

The title compound was prepared from 6-(7-chloro-6-methylbenzofuran-2-yl)-5-methoxy-N,N-dimethylnicotinamide and 6-cyano-5-(tetrahydro-2H-pyran-4-yloxy)pyridin-2-ylboronic acid using Method 8. The product was purified by prep-HPLC under the following conditions: column, XBridge Prep C18 OBD Column, 19×150 mm 5 um; mobile phase, acetonitrile in water (with 0.02% HCl), 20% to 50% gradient in 8 min; detector, UV 254/220 nm. 6-[7-[6-cyano-5-(oxan-4-yloxy)pyridin-2-yl]-6-methyl furo[3,2-b]pyridin-2-yl]-5-methoxy-N,N-dimethylpyridine-3-carboxamide was obtained as a yellow solid (9 mg, 27%). HPLC: 97.4% purity, RT=1.07 min. MS: m/z=514.1 [M+H]+. 1H NMR (300 MHz, CD3OD, ppm) δ 8.79 (s, 1H), 8.31 (d, J=13.9 Hz, 2H), 8.05 (d, J=8.2 Hz, 1H), 7.96 (s, 1H), 7.80 (s, 1H), 5.07-4.95 (m, 1H), 4.14 (s, 3H), 4.10-3.90 (m, 2H), 3.80-3.60 (mz, 2H), 3.12 (s, 3H), 3.03 (s, 3H), 2.65 (s, 3H), 2.25-2.05 (m, 2H), 1.96-1.80 (m, 2H).

Example 276: 6-(7-(6-cyano-5-(tetrahydro-2H-pyran-4-ylamino)pyridin-2-yl)-6-methylfuro[3,2-b]pyridin-2-yl)-5-methoxy-N,N-dimethylnicotinamide (322)

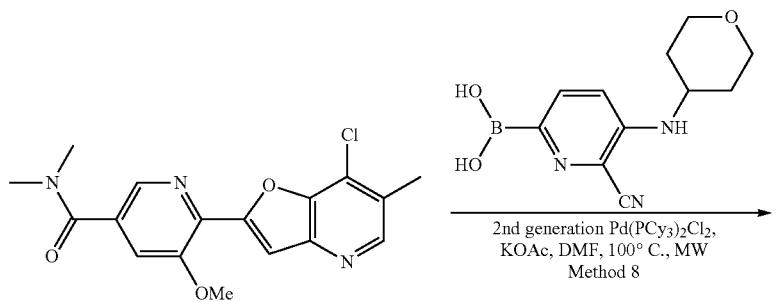

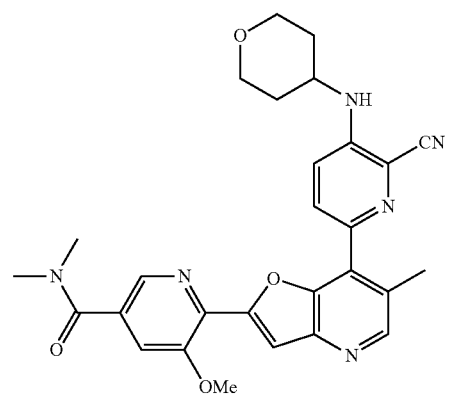

The title compound was prepared from 6-(7-chloro-6-methylfuro[3,2-b]pyridin-2-yl)-5-methoxy-N,N-dimethylnicotinamide and 6-cyano-5-(tetrahydro-2H-pyran-4-ylamino)pyridin-2-ylboronic acid using Method 8. The product was purified by prep-HPLC under the following conditions: column, XBridge Prep C18 OBD Column, 19×150 mm 5 um; mobile phase, acetonitrile in water (with 10 mmol/L NH$_4$HCO$_3$), 20/o to 50% gradient in 8 min; detector, UV 254/220 nm. 6-(7-[6-cyano-5-[(oxan-4-yl)amino]pyridin-2-yl]-6-methylfuro[3,2-b]pyridin-2-yl)-5-methoxy-N,N-dimethylpyridine-3-carboxamide was obtained as a off-white solid (7 mg, 23%). HPLC: 96.4% purity, RT=1.01 min. MS: m % z=513.2 [M+H]$^+$. $^1$H NMR (300 MHz, CD$_3$OD, ppm) δ 8.46 (s, 1H), 8.24 (d, J=1.5 Hz, 1H), 7.93 (d, J=9.0 Hz, 1H), 7.80-7.64 (m, 2H), 7.53 (d, J=9.0 Hz, 1H), 4.09 (s, 3H), 3.99 (dd, J=11.4, 3.4 Hz, 2H), 3.88-3.73 (m, 1H), 3.60-3.49 (m, 2H), 3.11 (s, 3H), 3.03 (s, 3H), 2.48 (s, 3H), 2.01 (dd, J=12.8, 4.4 Hz, 2H), 1.79-1.59 (m, 2H).

Example 277: 6-(7-(3-cyano-4-(tetrahydro-2H-pyran-4-yloxy)phenyl)-6-cyclopropylfuro[3,2-b]pyridin-2-yl)-5-methoxy-N,N-dimethylnicotinamide (323)

The title compound was prepared from 7-chloro-6-cyclopropyl-2-iodofuro[3,2-b]pyridine, 4,4,5,5-tetramethyl-2-(tetramethyl-1,3,2-dioxaborolan-2-yl)-1,3,2-dioxaborolane, 6-bromo-5-methoxy-N,N-dimethylnicotinamide and 2-(tetrahydro-2H-pyran-4-yloxy)-5-(4,4,5,5-tetramethyl-1,3,2-dioxaborolan-2-yl)benzonitrile using Methods Q, 9 and S. The final product was purified by prep-HPLC under the following conditions: column, Gemini-NX 5u C18, 110A, AXIA Packed 150×21.2 mm; mobile phase, acetonitrile in water (with 10 mmol/L NH$_4$HCO$_3$), 20% to 50% gradient in 8 min; detector, UV 254/220 nm. 6-[7-[3-cyano-4-(oxan-4-yloxy)phenyl]-6-cyclopropylfuro[3,2-b]pyridin-2-yl]-5-methoxy-N,N-dimethylpyridine-3-carboxamide was obtained as a white solid (9 mg, 10% for 3 steps). HPLC: 99.8% purity, RT=1.53 min. MS: m/z=539.2 [M+H]$^+$. $^1$H NMR (400 MHz, DMSO-d$_6$, ppm) δ 8.32 (s, 1H), 8.27 (d, J=1.6 Hz, 1H), 8.03 (d, J=2.4 Hz, 1H), 7.90 (dd, J=8.4, 2.0 Hz, 1H), 7.76 (s, 1H), 7.66 (d, J=1.6 Hz, 1H), 7.59 (d, J=9.2 Hz, 1H), 5.00-4.90 (m, 1H), 4.05 (s, 3H), 3.93-3.82 (m, 2H), 3.63-3.50 (m, 2H), 3.01 (s, 3H), 2.95 (s, 3H), 2.13-2.02 (m, 2H), 1.95-1.83 (m, 1H), 1.79-1.65 (m, 2H), 0.95-0.70 (m, 4H).

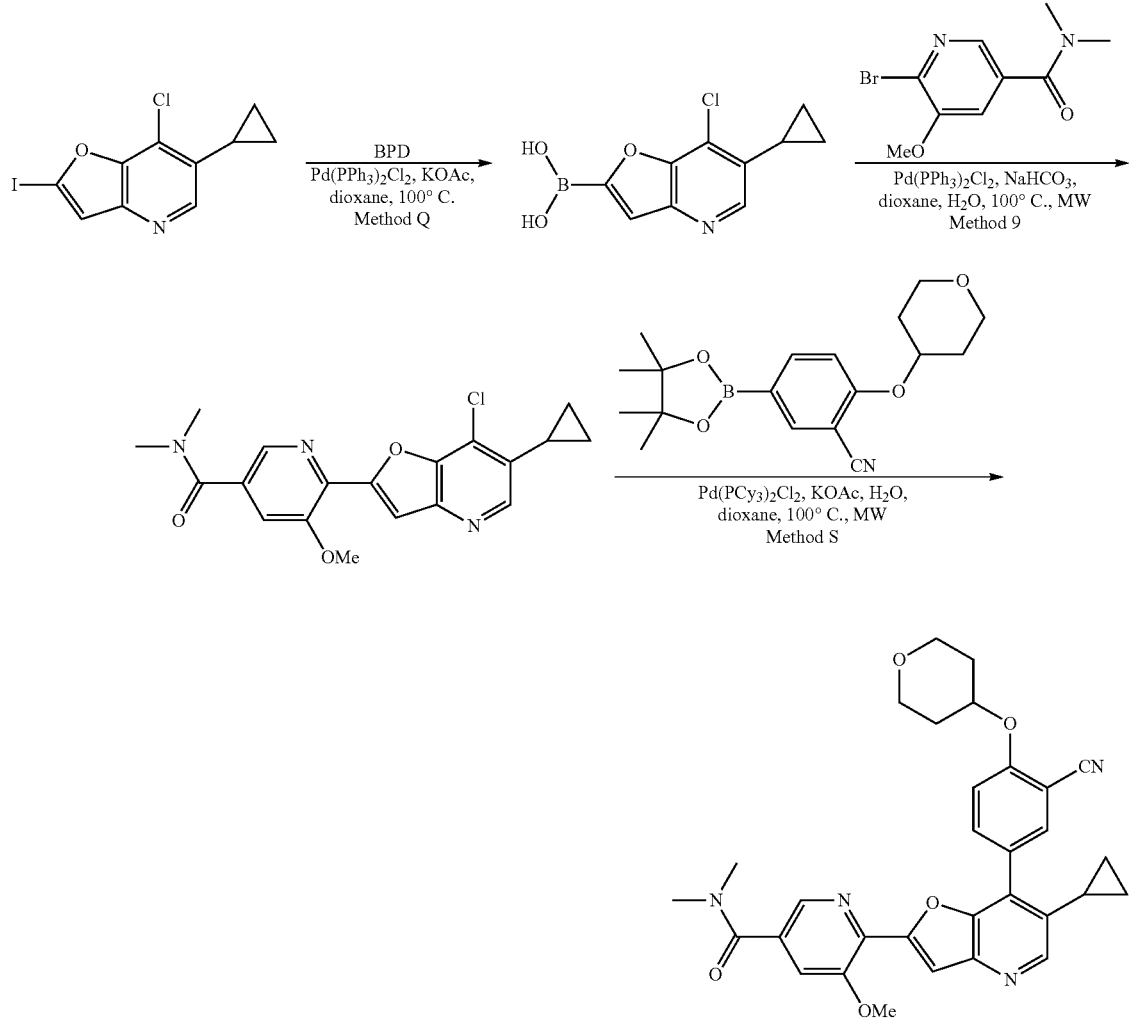

Example 278: 4-(7-(5-cyano-6-(tetrahydro-2H-pyran-4-ylamino)pyridin-3-yl)furo[3,2-b]pyridin-2-yl)-3-methoxy-N,N-dimethylbenzamide (324)

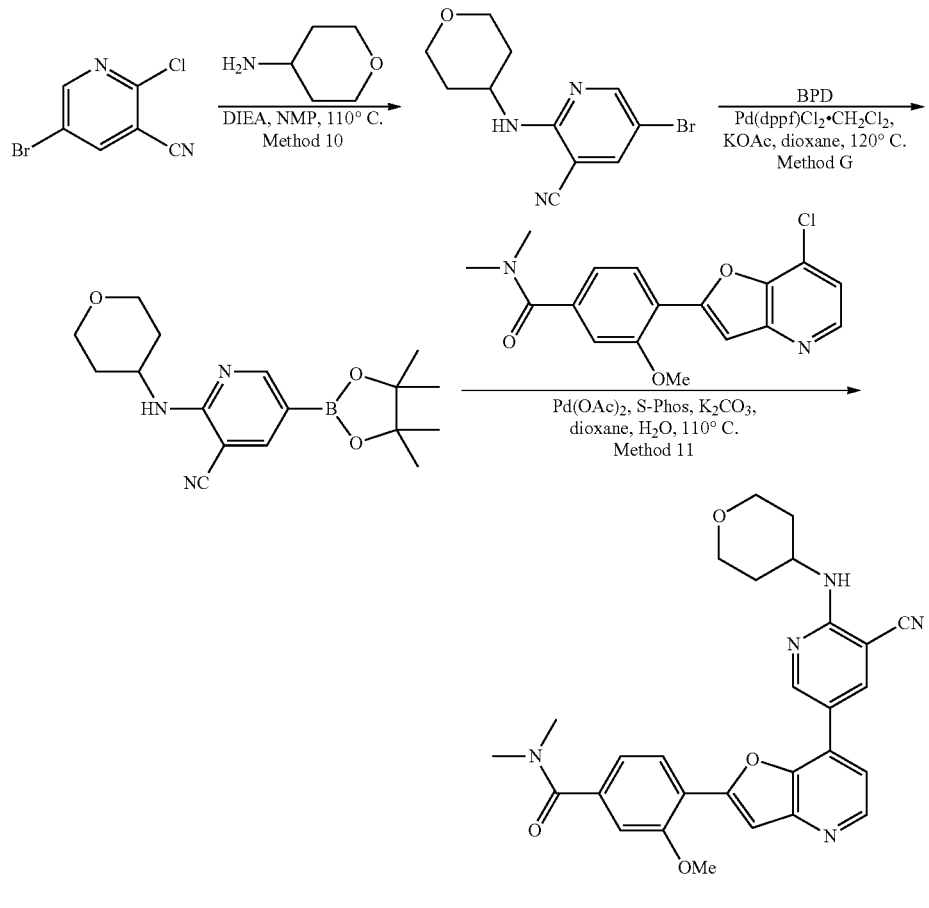

Method 10

5-bromo-2-(tetrahydro-2H-pyran-4-ylamino)nicotinonitrile

To a solution of oxan-4-amine (243 mg, 2.40 mmol) in NMP (6 mL) was added 5-bromo-2-chloropyridine-3-carbonitrile (475 mg, 2.18 mmol) and DIEA (846 mg, 6.54 mmol) at room temperature. The mixture was stirred for 6 h at 100° C. After cooling to room temperature, the reaction mixture was quenched by the addition of water (10 mL). The resulting mixture was extracted with ethyl acetate (30 mL×3). The organic phases were combined, washed with brine and dried over sodium sulfate. The solvent was removed under reduced pressure and the residue was purified by reverse phase flash chromatography eluting with acetonitrile in water (0% to 95% gradient in 30 min) to yield 5-bromo-2-[(oxan-4-yl)amino]pyridine-3-carbonitrile as a yellow solid (310 mg, 49%). MS: m/z=282.0 [M+H]$^+$.

2-(tetrahydro-2H-pyran-4-ylamino)-5-(4,4,5,5-tetramethyl-1,3,2-dioxaborolan-2-yl)nicotinonitrile 2-(tetrahydro-2H-pyran-4-ylamino)-5-(4,4,5,5-tetramethyl-1,3,2-dioxaborolan-2-yl)nicotinonitrile was prepared from 5-bromo-2-(tetrahydro-2H-pyran-4-ylamino)nicotinonitrile and 4,4,5,5-tetramethyl-2-(tetramethyl-1,3,2-dioxaborolan-2-yl)-1,3,2-dioxaborolane using Method G to yield [5-cyano-6-[(oxan-4-yl)amino]pyridin-3-yl]boronic acid as a brown solid (69 mg, crude).

Method 11

4-(7-(5-cyano-6-(tetrahydro-2H-pyran-4-ylamino)pyridin-3-yl)furo[3,2-b]pyridin-2-yl)-3-methoxy-N,N-dimethylbenzamide To a solution of 4-[7-chlorofuro[3,2-b]pyridin-2-yl]-3-methoxy-N,N-dimethylbenzamide (57 mg, 0.17 mmol) in 1,4-dioxane (7 mL) was added [5-cyano-6-[(oxan-4-yl)amino]pyridin-3-yl]boronic acid (69 mg, crude), Pd(OAc)$_2$ (10 mg, 0.05 mmol), S-Phos (56 mg, 0.14 mmol) and a solution of potassium carbonate (63 mg, 0.46 mmol) in water (0.5 mL) at room temperature under nitrogen atmosphere. The resulting solution was stirred for 3.5 h at 110° C. under nitrogen atmosphere. After cooling to room temperature, the reaction mixture was quenched by the addition of water (10 mL). The resulting mixture was extracted with DCM (30 mL×3). The organic phases were combined, washed with brine and dried over sodium sulfate. The solvent was removed under reduced pressure and the residue was purified by prep-HPLC under the following conditions:

column, XBridge Shield RP18 OBD Column, 5 um, 19×150 mm; mobile phase, acetonitrile in water (with 10 mmol/L NH$_4$HCO$_3$), 20% to 50% gradient in 8 min; detector, UV 254. 4-(7-[5-cyano-6-[(oxan-4-yl)amino]pyridin-3-yl]furo[3,2-b]pyridin-2-yl)-3-methoxy-N,N-dimethylbenzamide was obtained as a off-white solid (35 mg, 6.3% for 2 steps). HPLC: 95.7% purity, RT=1.37 min. MS: m/z=498.2 [M+H]$^+$. $^1$H NMR (400 MHz, DMSO-d$_6$, ppm) δ 9.13 (d, J=2.4 Hz, 1H), 8.66 (d, J=2.4 Hz, 1H), 8.53 (d, J=5.1 Hz, 1H), 8.02 (d. J=7.9 Hz, 1H), 7.68-7.51 (m, 2H), 7.43 (d, J=7.7 Hz, 1H), 7.28-7.17 (m, 2H), 4.42-4.30 (m, 1H), 4.06 (s, 3H), 3.97-3.88 (m, 2H), 3.50-3.38 (m, 2H), 3.03 (s, 3H), 2.97 (s, 3H), 1.87-1.67 (m, 4H).

Example 279: 5-(7-[3-cyano-4-[(oxan-4-yl)amino]phenyl]furo[3,2-b]pyridin-2-yl)-4-methoxy-N,N-dimethylpyridine-2-carboxamide (325)

The title compound was prepared from methyl 5-bromo-4-methoxypicolinate, dimethylamine, 7-chloro-2-(4,4,5,5-tetramethyl-1,3,2-dioxaborolan-2-yl)furo[3,2-b]pyridine, and 2-(tetrahydro-2H-pyran-4-ylamino)-5-(4,4,5,5-tetramethyl-1,3,2-dioxaborolan-2-yl)benzonitrile using Method T, 7, 9 and R. The product was purified by prep-HPLC under the following conditions: column, XBridge Shield RP18 OBD column, 19×150 mm 5 um; mobile phase, acetonitrile in water (with 10 mmol/L NH$_4$HCO$_3$), 25% to 50% gradient in 8 min; detector, UV 254/220 nm. 5-(7-[3-cyano-4-[(oxan-4-yl)amino]phenyl]furo[3,2-b]pyridin-2-yl)-4-methoxy-N,N-dimethylpyridine-2-carboxamide was obtained as a light yellow solid (40 mg, 23% for 4 steps). HPLC: 99.7% purity, RT=0.95 min. MS: m/z=498.1 [M+H]$^+$. $^1$H NMR (300 MHz, CD$_3$OD, ppm) δ 9.00 (s, 1H), 8.41 (d, J=5.3 Hz, 1H), 8.16 (d, J=7.4 Hz, 2H), 7.56-7.39 (m, 3H), 7.07 (d, J=9.7 Hz, 1H), 4.16 (s, 3H), 4.05-3.94 (m, 2H), 3.88-3.72 (m, 1H), 3.64-3.50 (m, 2H), 3.14 (s, 3H), 3.06 (s, 3H), 2.09-1.97 (m, 2H), 1.76-1.56 (m, 2H).

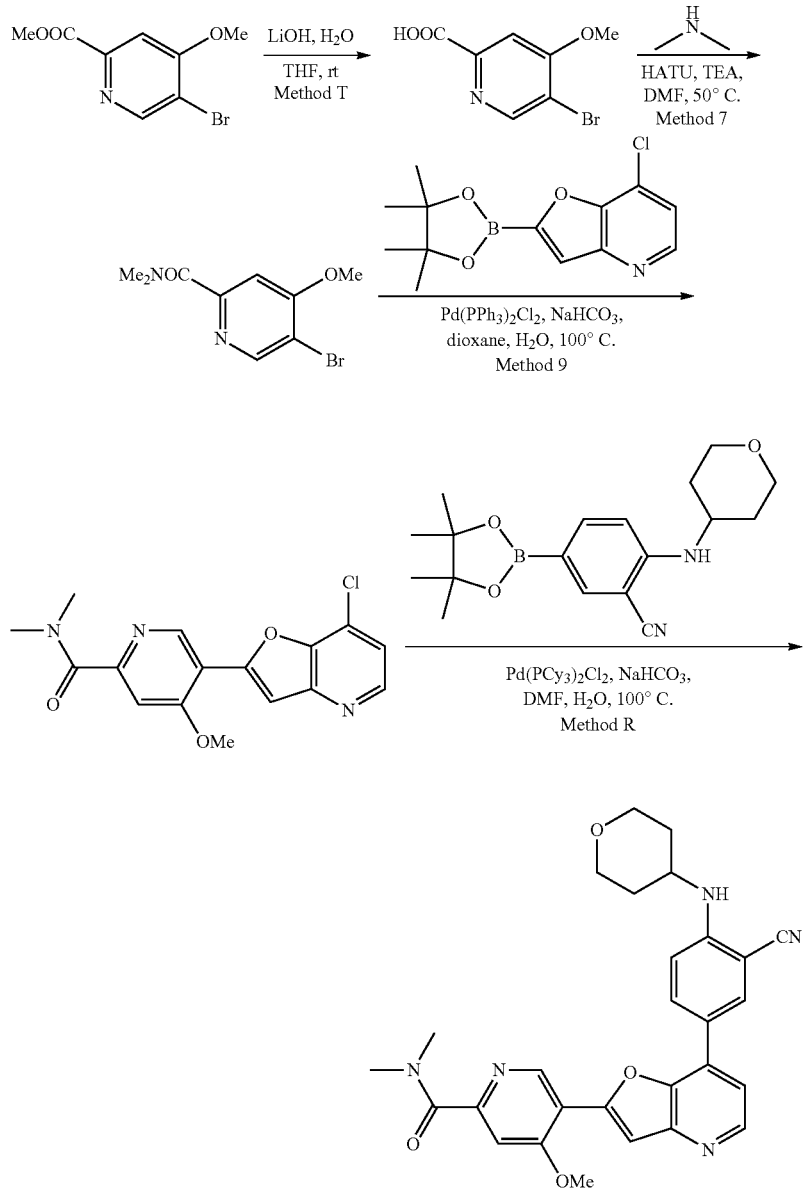

Example 280: 5-[7-[3-cyano-4-(oxan-4-yloxy)phenyl]furo[3,2-b]pyridin-2-yl]-4-methoxy-N,N-dimethylpyridine-2-carboxamide (326)

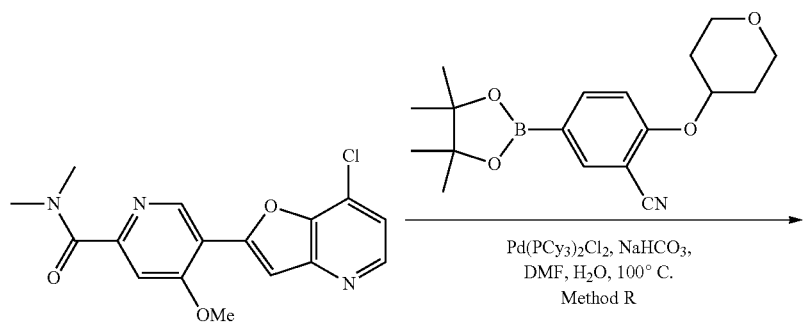

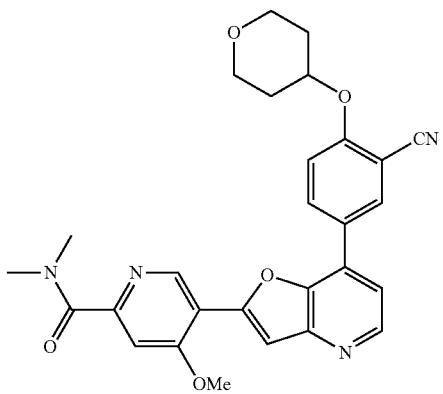

The title compound was prepared from 5-(7-chlorofuro[3,2-b]pyridin-2-yl)-4-methoxy-N,N-dimethylpicolinamide and 2-(tetrahydro-2H-pyran-4-yloxy)-5-(4,4,5,5-tetramethyl-1,3,2-dioxaborolan-2-yl)benzonitrile using Method R. The product was purified by prep-HPLC under the following conditions: column, XBridge Shield RP18 OBD column, 19×150 mm 5 um; mobile phase, acetonitrile in water (with 10 mmol/L $NH_4HCO_3$), 25%0 to 50% gradient in 8 min; detector, UV 254/220 nm. 5-(7-[3-cyano-4-[(oxan-4-yl)amino]phenyl]furo[3,2-b]pyridin-2-yl)-4-methoxy-N,N-dimethylpyridine-2-carboxamide was obtained as a light yellow solid (15 mg, 13%). HPLC: 99.2% purity, RT=1.08 min.

MS: m/z=499.2 [M+H]$^+$. $^1$H NMR (300 MHz, $CD_3OD$, ppm) δ 8.99 (s, 1H), 8.47 (d, J=5.2 Hz, 1H), 8.28-8.38 (m, 2H), 7.55 (d, J=5.6 Hz, 2H), 7.50-7.39 (m, 2H), 4.95-4.85 (m, 1H), 4.16 (s, 3H), 4.05-3.96 (m, 2H), 3.72-3.60 (m, 2H), 3.13 (s, 3H), 3.05 (s, 3H), 2.19-2.05 (m, 2H), 1.90-1.78 (m, 2H).

Example 281: 6-[7-[6-cyano-5-(oxan-4-yloxy)pyridin-2-yl]furo[3,2-b]pyridin-2-yl]-N-(2-hydroxyethyl)-5-methoxy-N-methylpyridine-3-carboxamide hydrochloride (327)

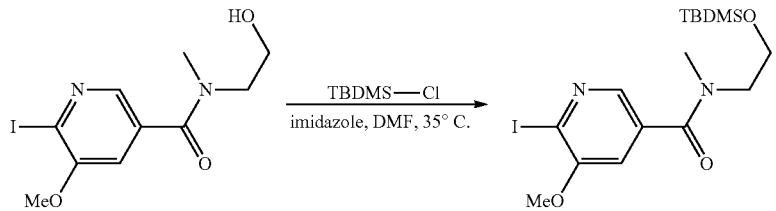

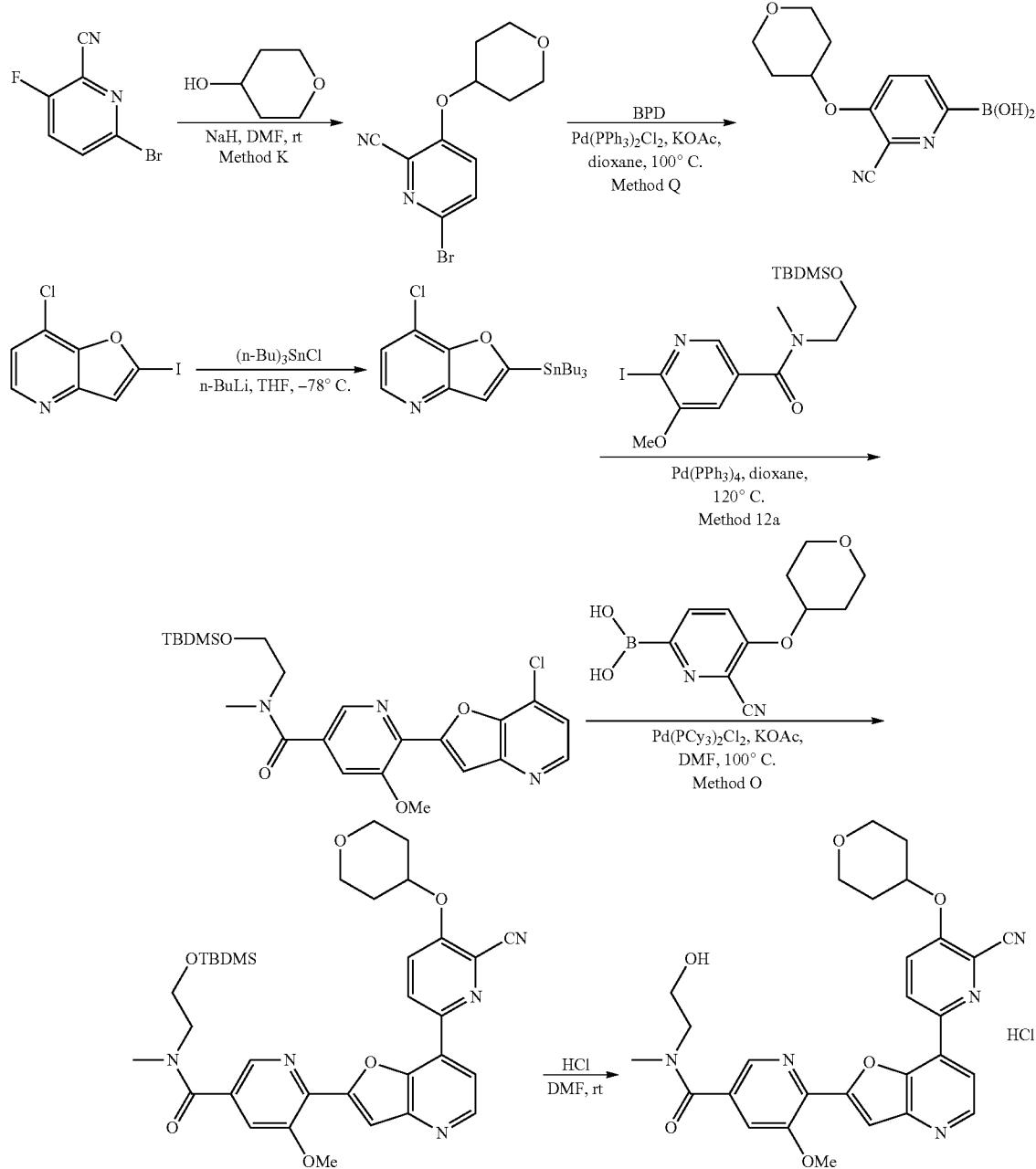

N-(2-(tert-butyldimethylsilyloxy)ethyl)-6-iodo-5-methoxy-N-methylnicotinamide To a solution of N-(2-hydroxyethyl)-6-iodo-5-methoxy-N-methylpyridine-3-carboxamide (8.67 g, 25.79 mmol) in DMF (15 mL) was added TBDMSCl (23.75 g, 157.57 mmol) and imidazole (10.79 g, 158.53 mmol) at room temperature. The resulting solution was stirred for 2.5 h at 35° C. When the reaction was done, it was quenched by the addition of H$_2$O (50 mL). The resulting mixture was extracted with ethyl acetate (30 mL×3). The organic phases were combined, washed with brine and dried over sodium sulfate. The solvent was removed under reduced pressure and the residue was purified by flash chromatography eluting with EtOAc in petroleum ether (0% to 30% gradient) to yield N-[2-[(tert-butyldimethylsilyl)oxy]ethyl]-6-iodo-5-methoxy-N-methylpyridine-3-carboxamide as a light yellow solid (8.01 g, 690%). MS: m/z=451.1 [M+H]$^+$.

6-cyano-5-(tetrahydro-2H-pyran-4-yloxy)pyridin-2-ylboronic acid 6-cyano-5-(tetrahydro-2H-pyran-4-yloxy)pyridin-2-ylboronic acid was prepared from 6-bromo-3-fluoropicolinonitrile, tetrahydro-2H-pyran-4-ol and 4,4,5,5-tetramethyl-2-(tetramethyl-1,3,2-dioxaborolan-2-yl)-1,3,2-dioxaborolane using Method K and Q. The product was purified by flash chromatography eluting with MeOH to yield 6-cyano-5-(tetrahydro-2H-pyran-4-yloxy)pyridin-2-ylboronic acid as gray solid (0.45 g, 48% for 2 steps). MS: m/z=249.1 [M+H]$^+$.

7-chloro-2-(tributylstannyl)furo[3,2-b]pyridine

At −78° C., to a solution of 7-chloro-2-iodofuro[3,2-b]pyridine (4.50 g, 16.10 mmol) in THF (50 mL) was added n-BuLi (3M in THF, 6 mL, 18.00 mmol) dropwise over 15 min period. The resulting solution was stirred for 60 min at −78° C., and then was added by tributyl(chloro)stannane (5.77 g, 17.73 mmol) slowly. The reaction mixture was stirred for 2 h at −78° C. When the reaction was done, it was quenched by the addition of ice water (150 mL). The resulting mixture was extracted with ethyl acetate (200 mL×3). The organic phases were combined, washed with brine and dried over sodium sulfate. The solvent was removed under reduced pressure and the residue was purified by flash chromatography eluting with EtOAc in hexane (0% to 10% gradient) to yield 7-chloro-2-(tributylstannyl)furo[3,2-b]pyridine as colorless oil (4.95 g, 69%). MS: m/z=444.0 [M+H]$^+$.

Method 12a

N-(2-(tert-butyldimethylsilyloxy)ethyl)-6-(7-chlorofuro[3,2-b]pyridin-2-yl)-5-methoxy-N-methylnicotinamide To a solution of 7-chloro-2-(tributylstannyl)furo[3,2-b]pyridine (255 mg, 0.58 mmol) in dioxane (6 mL) was added N-[2-[(tert-butyldimethylsilyl)oxy]ethyl]-6-iodo-5-methoxy-N-methylpyridine-3-carboxamide (270 mg, 0.60 mmol) and Pd(PPh$_3$)$_4$ (133 mg, 0.12 mmol) at room temperature under nitrogen atmosphere. The resulting mixture was stirred for 2 h at 120° C. under nitrogen atmosphere. After the reaction was done, the reaction mixture was concentrated under reduced pressure. The residue was purified by flash chromatography eluting with EtOAc to yield N-[2-[(tert-butyldimethylsilyl)oxy]ethyl]-6-[7-chlorofuro[3,2-b]pyridin-2-yl]-5-methoxy-N-methylpyridine-3-carboxamide as a light yellow solid (208 mg, 76%). MS: m/z=476.2 [M+H]$^+$.

N-(2-(tert-butyldimethylsilyloxy)ethyl)-6-(7-(6-cyano-5-(tetrahydro-2H-pyran-4-yloxy)pyridin-2-yl)furo[3,2-b]pyridin-2-yl)-5-methoxy-N-methylnicotinamide N-(2-(tert-butyldimethylsilyloxy)ethyl)-6-(7-(6-cyano-5-(tetrahydro-2H-pyran-4-yloxy)pyridin-2-yl)furo[3,2-b]pyridin-2-yl)-5-methoxy-N-methylnicotinamide was prepared from N-(2-(tert-butyldimethylsilyloxy)ethyl)-6-(7-chlorofuro[3,2-b]pyridin-2-yl)-5-methoxy-N-methylnicotinamide and 6-cyano-5-(tetrahydro-2H-pyran-4-yloxy)pyridin-2-yl-boronic acid using Method O. The product was purified by flash chromatography eluting with MeOH in EtOAc (0% to 10% gradient) to yield N-[2-[(tert-butyldimethylsilyl)oxy]ethyl]-6-[7-[6-cyano-5-(oxan-4-yloxy)pyridin-2-yl]furo[3,2-b]pyridin-2-yl]-5-methoxy-N-methylpyridine-3-carboxamide as a light yellow solid (400 mg, 72%). MS: m/z=644.3 [M+H]$^+$.

6-[7-[6-cyano-5-(oxan-4-yloxy)pyridin-2-yl]furo[3,2-b]pyridin-2-yl]-N-(2-hydroxyethyl)-5-methoxy-N-methylpyridine-3-carboxamide hydrochloride To a solution of N-[2-[(tert-butyldimethyl silyl)oxy]ethyl]-6-[7-[6-cyano-5-(oxan-4-yloxy)pyridin-2-yl]furo[3,2-b]pyridin-2-yl]-5-methoxy-N-methylpyridine-3-carboxamide (400 mg, 0.62 mmol) in DMF (4 mL) was added hydrogen chloride solution (6 N in water, 4 mL) dropwise at room temperature. The resulting solution was stirred for 30 min at room temperature. After the reaction was done, the reaction mixture was concentrated and the residue was purified by prep-HPLC under the following conditions: column, XBridge Shield RP18 OBD column, 19×150 mm 5 um; mobile phase, acetonitrile in water (with 0.02% HCl), 25% to 40% gradient in 8 min; detector, UV 254/220 nm. 6-[7-[6-cyano-5-(oxan-4-yloxy)pyridin-2-yl]furo[3,2-b]pyridin-2-yl]-N-(2-hydroxyethyl)-5-methoxy-N-methylpyridine-3-carboxamide hydrochloride was obtained as a light yellow solid (229 mg, 65%). HPLC: 95.8% purity, RT=1.24 min. MS: m/z=530.2 [M+H]$^+$. $^1$H NMR (300 MHz, CD$_3$OD, ppm) δ 9.16 (d, J=9.1 Hz, 1H), 8.82 (d, J=6.4 Hz, 1H), 8.65 (d, J=6.4 Hz, 1H), 8.49 (s, 1H), 8.11 (d, J=9.1 Hz, 1H), 8.03-7.86 (m, 2H), 5.03 (dd, J=7.8, 4.1 Hz, 1H), 4.19 (d, J=5.9 Hz, 3H), 4.06-3.94 (m, 2H), 3.92-3.80 (m, 1H), 3.74-3.60 (m, 4H), 3.54-3.40 (m, 1H), 3.14 (d, J=10.9 Hz, 3H), 2.21-2.09 (m, 2H), 1.95-1.81 (m, 2H).

Example 282: 6-[7-[3-cyano-4-(oxan-4-yloxy)phenyl]furo[3,2-b]pyridin-2-yl]-N-(2-hydroxyethyl)-5-methoxy-N-methylpyridine-3-carboxamide (328)

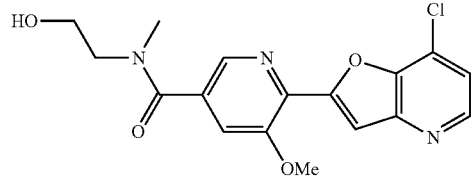
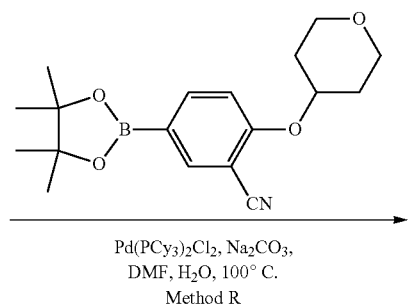

Pd(PCy$_3$)$_2$Cl$_2$, Na$_2$CO$_3$,
DMF, H$_2$O, 100° C.
Method R

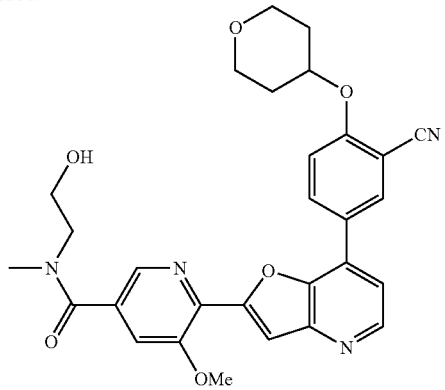

The title compound was prepared from 6-(7-chlorofuro[3,2-b]pyridin-2-yl)-N-(2-hydroxyethyl)-5-methoxy-N-methylnicotinamide and 2-(tetrahydro-2H-pyran-4-yloxy)-5-(4,4,5,5-tetramethyl-1,3,2-dioxaborolan-2-yl)benzonitrile using Method R. The product was purified by prep-HPLC under the following conditions: column, Gemini-NX C18 AXAI Packed, 21.2×150 mm 5 um 11 nm; mobile phase, acetonitrile in water (with 10 mmol/L NH₄HCO₃), 20% to 50% gradient in 8 min; detector, UV 254/220 nm. 6-[7-[3-cyano-4-(oxan-4-yl oxy)phenyl]furo[3,2-b]pyridin-2-yl]-N-(2-hydroxyethyl)-5-methoxy-N-methylpyridine-3-carboxamide was obtained as a yellow solid (10 mg, 7%). HPLC: 95.5% purity, RT=1.44 min. MS: m/z=529.1 [M+H]⁺. ¹H NMR (300 MHz, CD₃OD, ppm) δ 8.58-8.35 (m, 4H), 7.79 (d, J=19.8 Hz, 2H), 7.66-7.58 (m, 1H), 7.44 (dd, J=8.9, 3.8 Hz, 1H), 4.86-4.76 (m, 1H), 4.17-4.09 (m, 3H), 4.07-3.92 (m, 2H), 3.84 (d, J=5.5 Hz, 1H), 3.73-3.59 (m, 4H), 3.53-3.41 (m, 1H), 3.14 (s, 3H), 2.18-2.06 (m, 2H), 1.93-1.77 (m, 2H).

Example 283: 6-(7-[3-cyano-4-[(oxan-4-yl)amino]phenyl]-6-fluorofuro[3,2-b]pyridin-2-yl)-5-methoxy-N,N-dimethylpyridine-3-carboxamide (329)

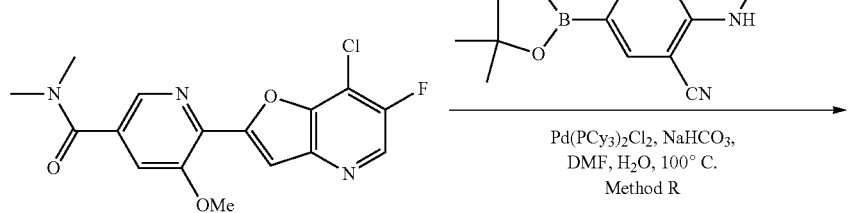

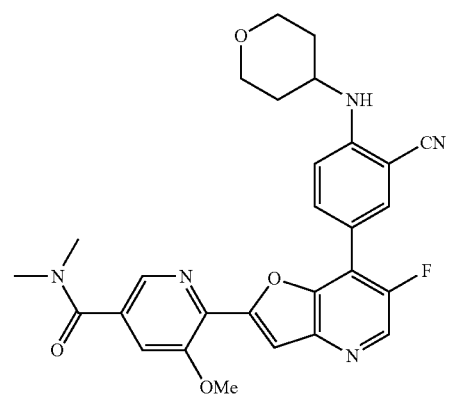

The title compound was prepared from 6-(7-chloro-6-fluorofuro[3,2-b]pyridin-2-yl)-5-methoxy-N,N-dimethylnicotinamide and 2-(tetrahydro-2H-pyran-4-ylamino)-5-(4,4,5,5-tetramethyl-1,3,2-dioxaborolan-2-yl)benzonitrile using Method R. The product were purified by prep-HPLC under the following conditions: column, Gemini-NX 5u C18, 110A, AXIA Packed 150×21.2 mm; mobile phase, acetonitrile in water (with 10 mmol/L $NH_4HCO_3$), 25% to 55% gradient in 8 min; detector, UV 254/220 nm. 6-(7-[3-cyano-4-[(oxan-4-yl)amino]phenyl]-6-fluorofuro[3,2-b]pyridin-2-yl)-5-methoxy-N,N-dimethylpyridine-3-carboxamide was obtained as a light yellow solid (10 mg, 10%). HPLC: 97.9% purity, RT=1.23 min. MS: m % z=516.2 $[M+H]^+$. $^1$H NMR (300 MHz, DMSO-$d_6$, ppm) δ 8.68 (d, J=3.3 Hz, 1H), 8.35 (d, J=1.5 Hz, 1H), 8.05 (dd, J=2.2, 0.9 Hz, 1H), 7.96 (d, J=9.3 Hz, 1H), 7.80 (s, 1H), 7.72 (d, J=1.6 Hz, 1H), 7.18 (d, J=9.2 Hz, 1H), 6.37 (d, J=8.1 Hz, 1H), 4.09 (s, 3H), 3.91 (d, J=12.0 Hz, 2H), 3.87-3.75 (m, 1H), 3.54-3.41 (m, 2H), 3.04 (s, 3H), 2.98 (s, 3H), 1.88 (d, J=12.1 Hz, 2H), 1.76-1.63 (m, 2H).

Example 284: 6-(7-(3-cyano-4-(tetrahydro-2H-pyran-4-yloxy)phenyl)-6-methylfuro[3,2-b]pyridin-2-yl)-N-(2-hydroxyethyl)-5-methoxy-N-methylnicotinamide (330)

The title compound was prepared from 7-chloro-6-methylfuro[3,2-b]pyridin-2-ylboronic acid, N-(2-hydroxyethyl)-6-iodo-5-methoxy-N-methylnicotinamide and 2-(tetrahydro-2H-pyran-4-yloxy)-5-(4,4,5,5-tetramethyl-1,3,2-dioxaborolan-2-yl)benzonitrile using Method U and R. The product was purified by prep-HPLC under the following conditions: column, XBridge Shield RP18 OBD Column, 5 um, 19×150 mm; mobile phase, acetonitrile in water (with 10 mmol/L $NH_4HCO_3$), 25% to 55% gradient in 8 min; detector, UV 254/220 nm. 6-[7-[3-cyano-4-(oxan-4-yloxy)phenyl]-6-methylfuro[3,2-b]pyridin-2-yl]-N-(2-hydroxyethyl)-5-methoxy-N-methylpyridine-3-carboxamide was obtained as a white solid (7.4 mg, 5%). HPLC: 99.4% purity, RT=0.98 min. MS: m/z=543.2 $[M+H]^+$. $^1$H NMR (300 MHz, $CD_3OD$, ppm) δ 8.49 (s, 1H), 8.28 (d, J=1.5 Hz, 1H), 7.91-7.71 (m, 4H), 7.42 (d, J=8.8 Hz, 1H), 4.97-4.85 (m, 1H), 4.54 (br s, 1H), 4.14-3.94 (m, 5H), 3.88-3.76 (m, 1H), 3.74-3.58 (m, 4H), 3.48-3.36 (m, 1H), 3.10 (d, J=7.8 Hz, 3H), 2.39 (s, 3H), 2.20-2.10 (m, 2H), 1.96-1.80 (m, 2H).

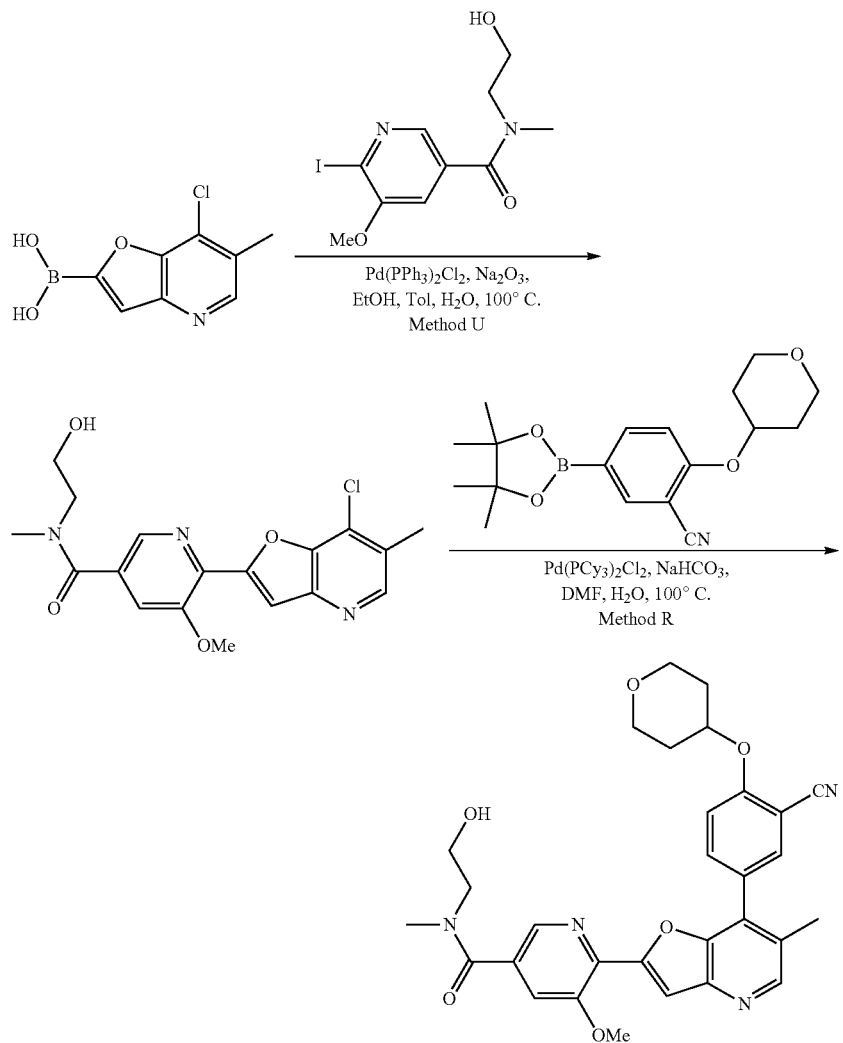

Example 285: 6-[7-[6-cyano-5-(oxan-4-yloxy)pyridin-2-yl]-6-(propan-2-yl)furo[3,2-b]pyridin-2-yl]-5-methoxy-N,N-dimethylpyridine-3-carboxamide hydrochloride (331)

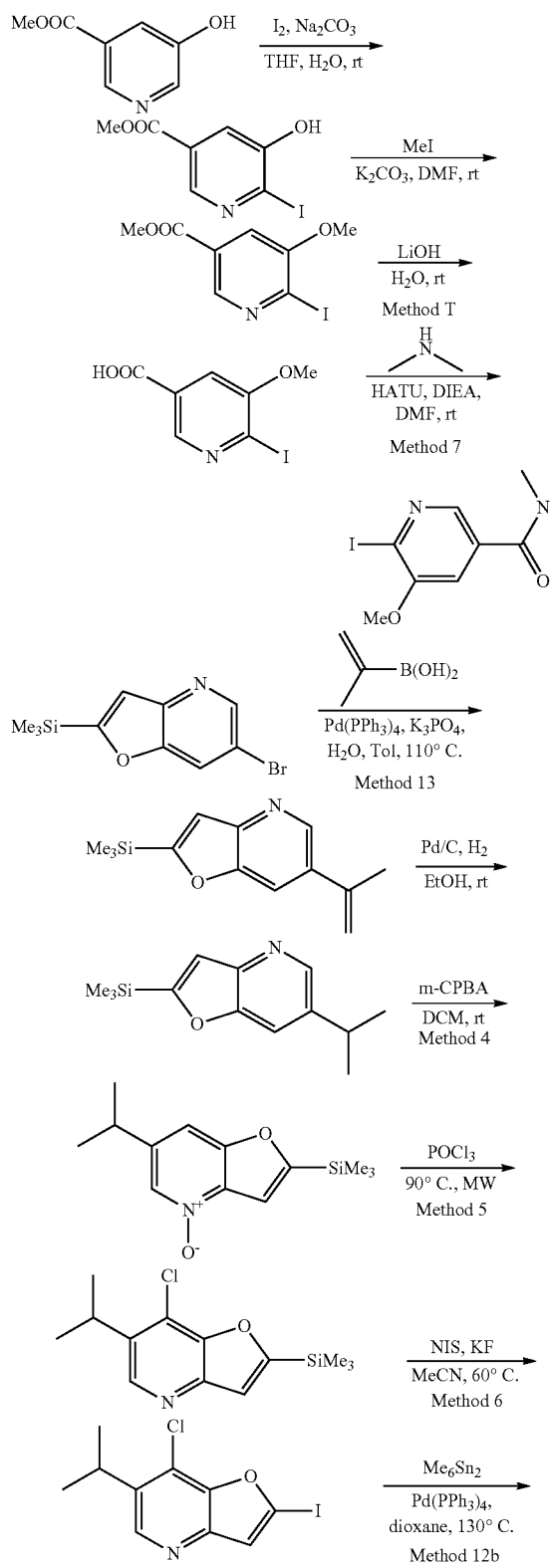

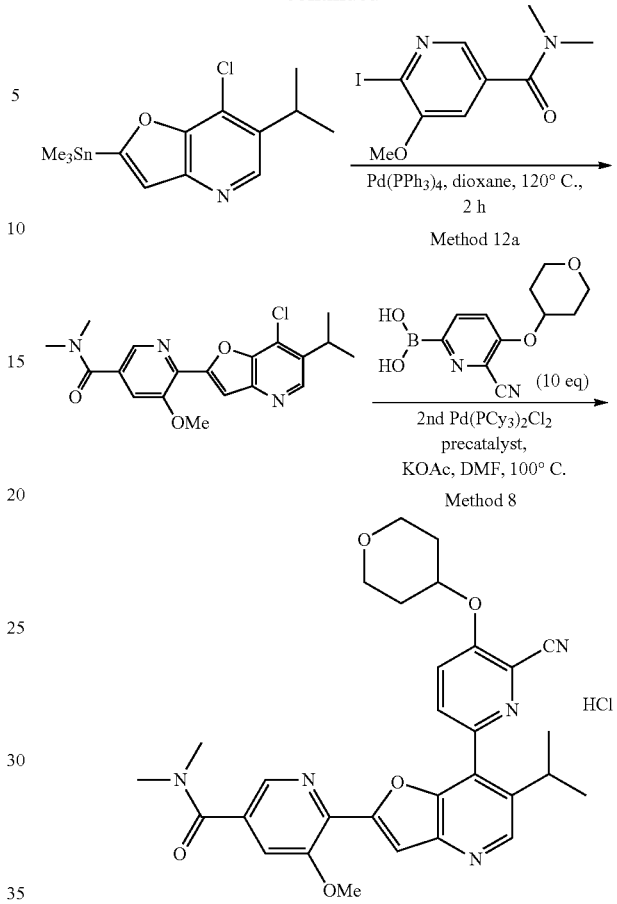

Methyl 5-hydroxy-6-iodonicotinate

To a solution of methyl 5-hydroxypyridine-3-carboxylate (9.50 g, 62.04 mmol) in water (200 mL) was added sodium carbonate (19.72 g, 186.08 mmol) at room temperature. The resulting solution was then added by a solution of $I_2$ (39.35 g, 155.07 mmol) in THF (200 mL) dropwise over 2 h period at room temperature. The reaction mixture was stirred for 20 min at room temperature. When the reaction was done, it was quenched by the addition of $NaHSO_3$ and the pH value of the mixture was adjusted to 4 with hydrogen chloride solution (12 N). The resulting mixture was extracted with ethyl acetate (100 mL×3) and the organic layers were combined, washed with brine and dried over anhydrous sodium sulfate. The solvent was removed under reduced pressure to yield methyl 5-hydroxy-6-iodopyridine-3-carboxylate as a off-white solid (16.28 g, 93%). MS: m/z=279.3 $[M+H]^+$.

Methyl 6-iodo-5-methoxynicotinate

To a solution of methyl 5-hydroxy-6-iodopyridine-3-carboxylate (26.60 g, 95.33 mmol) in DMF (400 mL) was added potassium carbonate (17.13 g, 123.94 mmol) and MeI (15.56 g, 109.63 mmol) at room temperature. The resulting mixture was stirred for 18 h at room temperature. When the reaction was done, it was quenched by the addition of water (1 L) and precipitation happened. The precipitates were collected by filtration, rinsed with water (500 mL×3) and dried in oven under vacuum to yield methyl 6-iodo-5-methoxypyridine-3-carboxylate as a off-white solid (20.24 g, 72%). MS: m/z=294.0 $[M+H]^+$.

6-Iodo-5-methoxy-N,N-dimethylnicotinamide 6-iodo-5-methoxy-N,N-dimethylnicotinamide was prepared from methyl 6-iodo-5-methoxynicotinate and dimethylamine using Method T and 7. 6-iodo-5-methoxy-N,N-dimethylpyridine-3-carboxamide was obtained as a yellow solid (4.40 g, 49% for 2 steps). MS: m/z=307.0 [M+H]⁺.

Method 13

6-(Prop-1-en-2-yl)-2-(trimethylsilyl)furo[3,2-b]pyridine

To a solution of 6-bromo-2-(trimethylsilyl)furo[3,2-b]pyridine (1.70 g, 6.29 mmol) in toluene (46 mL) were added 4,4,5,5-tetramethyl-2-(prop-1-en-2-yl)-1,3,2-dioxaborolane (1.78 g, 10.57 mmol), K₃PO₄ (5.97 g, 28.11 mmol), Pd(PPh₃)₄ (1.43 g, 1.23 mmol) and water (5 mL) at room temperature under nitrogen atmosphere. The resulting mixture was stirred for 2 h at 110° C. under nitrogen atmosphere. When the reaction was done, it was quenched by sat. NH₄Cl solution (30 mL). The resulting mixture was extracted with ethyl acetate (100 mL×3). The organic phases were combined, washed with brine and dried over sodium sulfate. The solvent was removed under reduced pressure and the residue was purified by flash chromatography eluting with EtOAc in hexane (0% to 9% gradient) to yield 6-(prop-1-en-2-yl)-2-(trimethylsilyl)furo[3,2-b]pyridine as a yellow solid (1.20 g, 82%). MS: m/z=232.1 [M+H]⁺.

6-Isopropyl-2-(trimethylsilyl)furo[3,2-b]pyridine

To a solution of 6-(prop-1-en-2-yl)-2-(trimethylsilyl)furo[3,2-b]pyridine (1.2 g, 3.58 mmol, 1.00 equiv, 690/%) in EtOH (25 mL) was added palladium carbon (1.14 g, 10.71 mmol) at room temperature under nitrogen atmosphere. The reaction flask was vacuumed and flushed with hydrogen. The reaction mixture was then hydrogenated for 1 h at room temperature using a hydrogen balloon. After the reaction was done, the reaction mixture was filtered through a Celite pad and the filtrate was concentrated under reduced pressure to yield 6-(propan-2-yl)-2-(trimethylsilyl)furo[3,2-b]pyridine as a yellow solid (0.90 g, 97%). MS: m/z=234.1 [M+H]⁺.

7-Chloro-2-iodo-6-isopropylfuro[3,2-b]pyridine 7-chloro-2-iodo-6-isopropylfuro[3,2-b]pyridine was prepared from 6-isopropyl-2-(trimethylsilyl)furo[3,2-b]pyridine using Method 4, 5 and 6. And 7-chloro-2-iodo-6-isopropylfuro[3,2-b]pyridine was obtained as a brown solid (380 mg, 26% for 3 steps)

Method 12b

7-Chloro-6-isopropyl-2-(trimethylstannyl)furo[3,2-b]pyridine

To a solution of 7-chloro-2-iodo-6-(propan-2-yl)furo[3,2-b]pyridine (164 mg, 0.51 mmol) in dioxane (2 mL) was added hexamethyldistannane (285 mg, 0.87 mmol) and Pd(PPh₃)₄ (139 mg, 0.12 mmol) at room temperature. The resulting solution was stirred for 2 h at 130° C. After the reaction was done, the reaction mixture was concentrated under reduced pressure and the residue was purified by flash chromatography eluting with EtOAc in hexane (0% to 2% gradient) to yield 7-chloro-6-(propan-2-yl)-2-(trimethylstannyl)furo[3,2-b]pyridine as a brown solid (100 mg, 55%). MS: m/z=360.0 [M+H]⁺.

6-[7-[6-cyano-5-(oxan-4-yloxy)pyridin-2-yl]-6-(propan-2-yl)furo[3,2-b]pyridin-2-yl]-5-methoxy-N,N-dimethylpyridine-3-carboxamide hydrochloride The title compound was prepared from 6-iodo-5-methoxy-N,N-dimethylnicotinamide and 6-cyano-5-(tetrahydro-2H-pyran-4-yloxy)pyridin-2-ylboronic acid using Method 12a and 8. The final product was purified by prep-HPLC under the following conditions: column, XBridge Shield RP18 OBD column, 19×150 mm 5 um; mobile phase, acetonitrile in water (with 0.02% HCl), 20% to 50% gradient in 8 min; detector, UV 254/220 nm. 6-[7-[6-cyano-5-(oxan-4-yloxy)pyridin-2-yl]-6-(propan-2-yl)furo[3,2-b]pyridin-2-yl]-5-methoxy-N,N-dimethylpyridine-3-carboxamide hydrochloride was obtained as a yellow solid (15 mg, 14% for 2 steps). HPLC: 91.6% purity, RT=2.83 min. MS: m/z=542.2 [M+H]⁺. ¹H NMR (300 MHz, CD₃OD, ppm) δ 8.92 (s, 1H), 8.34 (s, 1H), 8.19 (d, J=8.4 Hz, 1H), 8.07 (d, J=8.6 Hz, 1H), 7.98 (s, 1H), 7.82 (s, 1H), 5.11-4.97 (m, 1H), 4.18 (s, 3H), 4.11-3.98 (m, 2H), 3.77-3.65 (m, 2H), 3.54-3.40 (m, 1H), 3.16 (s, 3H), 3.06 (s, 3H), 2.24-2.12 (m, 1H), 2.00-1.88 (m, 2H), 1.45-1.35 (m, 7H).

Example 286: 6-[7-[3-cyano-4-(oxan-4-yloxy)phenyl]-6-(propan-2-yl)furo[3,2-b]pyridin-2-yl]-5-methoxy-N,N-dimethylpyridine-3-carboxamide (332)

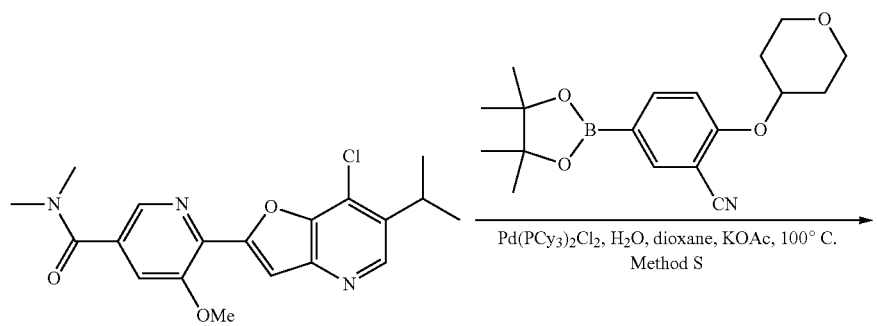

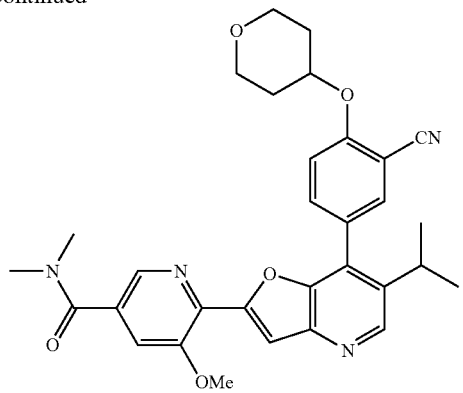

The title compound was prepared from 6-(7-chloro-6-isopropylfuro[3,2-b]pyridin-2-yl)-5-methoxy-N,N-dimethylnicotinamide and 2-(tetrahydro-2H-pyran-4-yloxy)-5-(4,4,5,5-tetramethyl-1,3,2-dioxaborolan-2-yl)benzonitrile using Method S. The crude products were purified by prep-HPLC under the following conditions: column, XBridge Shield RP18 OBD Column, 5 um, 19×150 mm; mobile phase, acetonitrile in water (with 10 mmol/L $NH_4HCO_3$), 20% to 50% gradient in 8 min; detector, UV 254/220 nm. 6-[7-[3-cyano-4-(oxan-4-yl oxy)phenyl]-6-(propan-2-yl)furo[3,2-b]pyridin-2-yl]-5-methoxy-N,N-dimethylpyridine-3-carboxamide was obtained as a white solid (10 mg, 10%). HPLC: 99.8% purity, RT=1.25 min. MS: m/z=542.3 $[M+H]^+$. $^1H$ NMR (300 MHz, $CD_3OD$, ppm) δ 8.61 (s, 1H), 8.23 (s, 1H), 7.81-7.64 (m, 4H), 7.42 (d, J=8.6 Hz, 1H), 4.80-4.70 (m, 1H), 4.20-3.90 (m, 5H), 3.74-3.60 (m, 2H), 3.11 (s, 3H), 3.03 (s, 3H), 2.18-2.06 (m, 2H), 1.93-1.89 (m, 2H), 1.38-1.22 (m, 7H).

Example 287: 6-[7-[3-cyano-4-(oxan-4-yloxy)phenyl]-6-(propan-2-yl)furo[3,2-b]pyridin-2-yl]-N-(2-hydroxyethyl)-5-methoxy-N-methylpyridine-3-carboxamide (333)

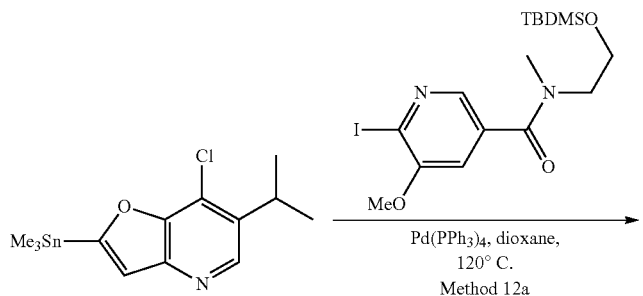

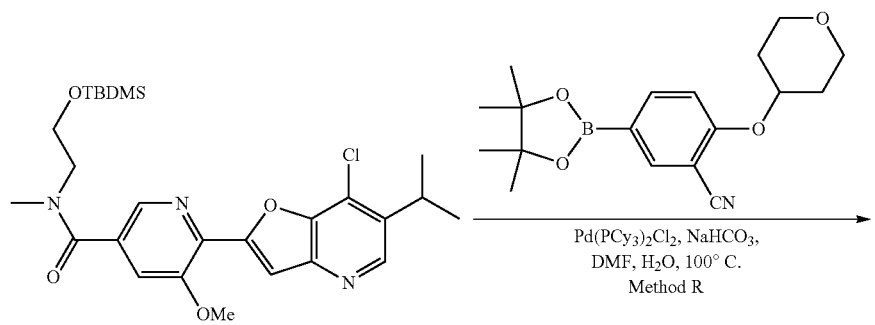

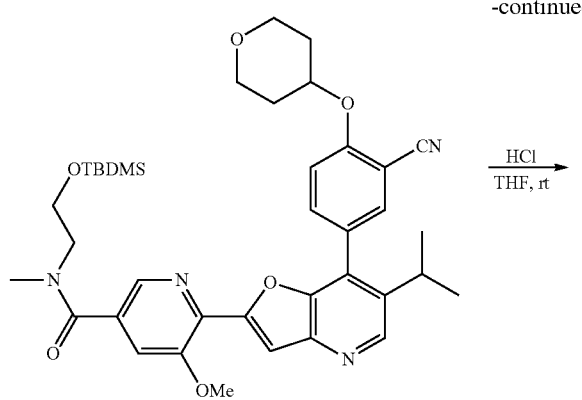

N-(2-(tert-butyldimethylsilyloxy)ethyl)-6-(7-(3-cyano-4-(tetrahydro-2H-pyran-4-yloxy)phenyl)-6-isopropylfuro[3,2-b]pyridin-2-yl)-5-methoxy-N-methylnicotinamide (N-(2-(tert-butyldimethyl silyloxy)ethyl)-6-(7-(3-cyano-4-(tetrahydro-2H-pyran-4-yloxy)phenyl)-6-isopropylfuro[3,2-b]pyridin-2-yl)-5-methoxy-N-methylnicotinamide was prepared from 7-chloro-6-isopropyl-2-(trimethylstannyl)furo[3,2-b]pyridine, N-(2-(tert-butyldimethylsilyloxy)ethyl)-6-iodo-5-methoxy-N-methylnicotinamide and 2-(tetrahydro-2H-pyran-4-yloxy)-5-(4,4,5,5-tetramethyl-1,3,2-dioxaborolan-2-yl)benzonitrile using Methods 12a and R. The obtained crude product (44 mg, brown solid) was used directly in the next step without further purification.

6-[7-[3-cyano-4-(oxan-4-yloxy)phenyl]-6-(propan-2-yl)furo[3,2-b]pyridin-2-yl]-N-(2-hydroxyethyl)-5-methoxy-N-methylpyridine-3-carboxamide (N-(2-(tert-butyl dimethylsilyloxy)ethyl)-6-(7-(3-cyano-4-(tetrahydro-2H-pyran-4-yloxy)phenyl)-6-isopropylfuro[3,2-b]pyridin-2-yl)-5-methoxy-N-methylnicotinamide (44 mg, crude) was added a solution of hydrogen chloride in THF (2 M, 1.5 mL) at room temperature. The resulting solution was stirred for 1 h at room temperature. After the reaction was done, the reaction mixture was concentrated under reduced pressure. The residue was purified by prep-HPLC under the following conditions: column, XBridge Shield RP18 OBD Column, 5 um, 19×150 mm; mobile phase, acetonitrile in water, 25% to 47% gradient in 15 min; detector, UV 254/220 nm. 6-[7-[3-cyano-4-(oxan-4-yloxy)phenyl]-6-(propan-2-yl)furo[3,2-b]pyridin-2-yl]-N-(2-hydroxyethyl)-5-methoxy-N-methylpyridine-3-carboxamide was obtained as a yellow solid (5 mg, 8% for 3 steps). HPLC: 95.4% purity, RT=1.47 min. MS: m/z=571.3 [M+H]$^+$. $^1$H NMR (400 MHz, CD$_3$OD, ppm) δ 8.90 (s, 1H), 8.38 (d, J=1.3 Hz, 1H), 8.00-7.82 (m, 4H), 7.55 (d, J=8.5 Hz, 1H), 5.03-4.93 (m, 1H), 4.21-4.10 (m, 3H), 4.10-4.00 (m, 2H), 3.90-3.80 (m, 1H), 3.78-3.62 (m, 4H), 3.49-3.39 (m, 1H), 3.18-3.06 (m, 3H), 2.24-2.10 (m, 2H), 1.97-1.81 (m, 2H), 1.47-1.25 (m, 7H).

Example 288: 6-[7-[3-cyano-4-(oxan-4-yloxy)phenyl]-6-fluorofuro[3,2-b]pyridin-2-yl]-N-(2-hydroxyethyl)-5-methoxy-N-methylpyridine-3-carboxamide (334)

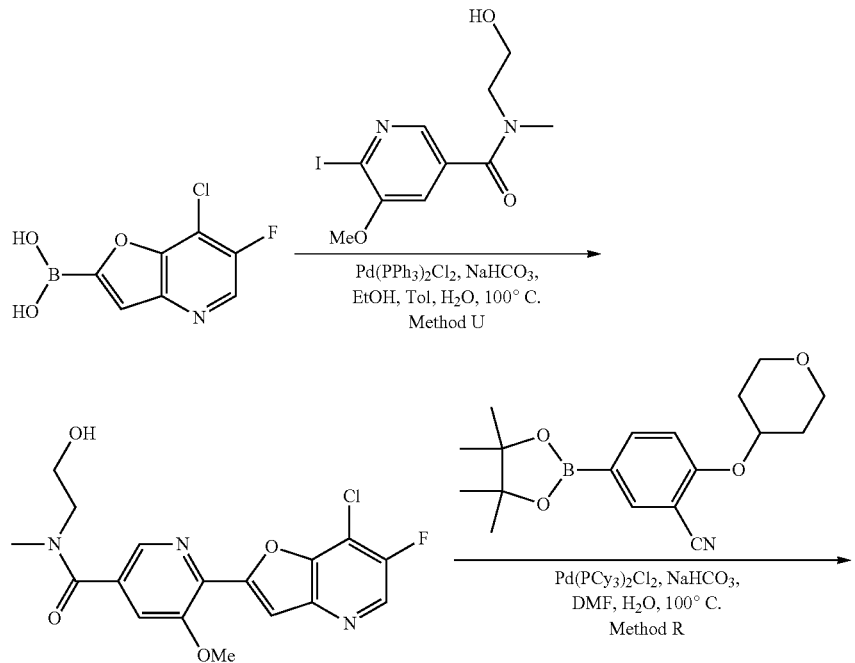

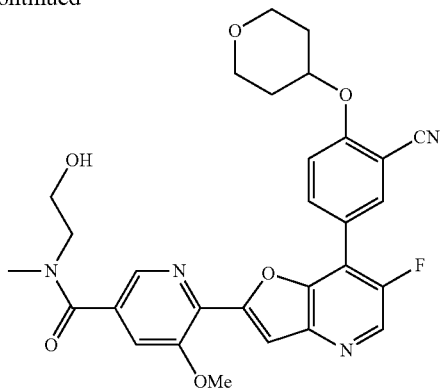

The title compound was prepared from 7-chloro-6-fluorofuro[3,2-b]pyridin-2-ylboronic acid, N-(2-hydroxyethyl)-6-iodo-5-methoxy-N-methylnicotinamide and 2-(tetrahydro-2H-pyran-4-yloxy)-5-(4,4,5,5-tetramethyl-1,3,2-dioxaborolan-2-yl)benzonitrile using Methods U and R. The final product was purified by prep-HPLC under the following conditions: column, Gemini-NX 5u C18, 110A, AXIA Packed 150×21.2 mm; mobile phase, acetonitrile in water (with 10 mmol/L NH$_4$HCO$_3$), 20% to 50% gradient in 8 min; detector, UV 254/220 nm. 6-[7-[3-cyano-4-(oxan-4-yloxy)phenyl]-6-fluorofuro[3,2-b]pyridin-2-yl]-N-(2-hydroxyethyl)-5-methoxy-N-methylpyridine-3-carboxamide was obtained as a white solid (7 mg, 3% for 2 steps). HPLC: 99.9% purity, RT=1.16 min. MS: m/z=547.2 [M+H]$^+$. $^1$H NMR (400 MHz, DMSO-d$_6$, ppm) δ 8.74 (d, J=2.8 Hz, 1H), 8.34 (d, J=1.5 Hz, 1H), 8.26 (s, 1H), 8.21-8.11 (m, 1H), 7.83 (d, J=2.6 Hz, 1H), 7.79-7.64 (m, 2H), 5.05-4.85 (m, 2H), 4.09 (d, J=9.4 Hz, 3H), 3.96-3.80 (m, 2H), 3.70-3.50 (m, 5H), 3.36-3.24 (m, 1H), 3.02 (d, J=5.4 Hz, 3H), 2.13-2.01 (m, 2H), 1.80-1.66 (m, 2H).

Example 289: 6-(7-[3-cyano-4-[(oxan-4-yl)amino]phenyl]-6-(propan-2-yl)furo[3,2-b]pyridin-2-yl)-5-methoxy-N,N-dimethylpyridine-3-carboxamide hydrochloride (335)

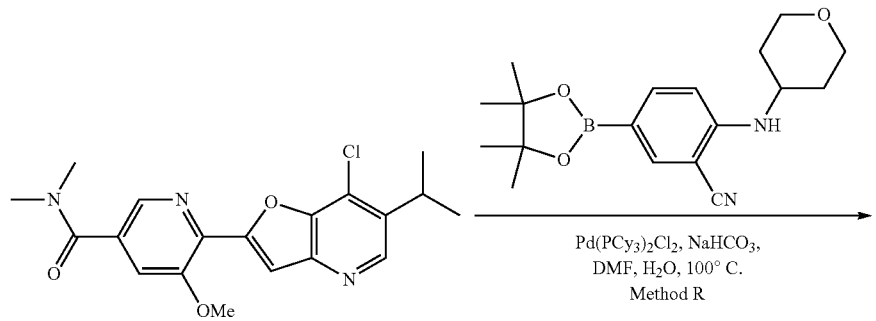

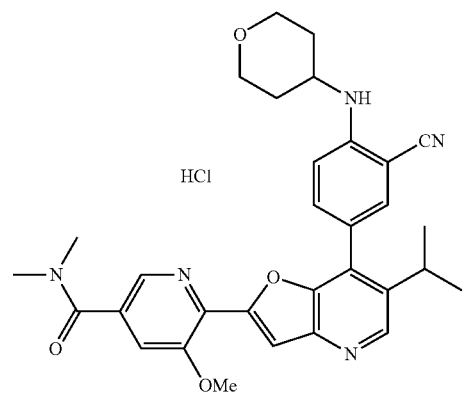

The title compound was prepared from 6-(7-chloro-6-isopropylfuro[3,2-b]pyridin-2-yl)-5-methoxy-N,N-dimethylnicotinamide and 2-(tetrahydro-2H-pyran-4-ylamino)-5-(4,4,5,5-tetramethyl-1,3,2-dioxaborolan-2-yl)benzonitrile using Method R. The product was purified by prep-HPLC under the following conditions: column, XBridge Prep C18 OBD Column, 5 um, 19×150 mm; mobile phase, acetonitrile in water (with 0.02% HCl), 30% to 60% gradient in 8 min; detector, UV 254/220 nm. 6-(7-[3-cyano-4-[(oxan-4-yl)amino]phenyl]-6-(propan-2-yl)furo[3,2-b]pyridin-2-yl)-5-methoxy-N,N-dimethylpyridine-3-carboxamide hydrochloride was obtained as red solid (17 mg, 21%). HPLC: 98.3% purity, RT=1.86 min. MS: m/z=540.2 [M+H]$^+$. $^1$H NMR (300 MHz, CD$_3$OD, ppm) δ 8.76 (s, 1H), 8.32 (d, J=1.5 Hz, 1H), 7.85 (s, 1H), 7.74 (dd, J=7.3, 1.8 Hz, 2H), 7.62 (dd, J=8.9, 2.2 Hz, 1H), 7.12 (d, J=8.9 Hz, 1H), 4.12 (s, 3H), 4.00 (d, J=11.3 Hz, 2H), 3.89-3.75 (m, 1H), 3.64-3.50 (m, 2H), 3.42-3.31 (m, 1H), 3.12 (s, 3H), 3.03 (s, 3H), 2.04 (d, J=13.3 Hz, 2H), 1.77-1.60 (m, 2H), 1.38-1.22 (m, 6H).

Example 290: 6-[6-chloro-7-[3-cyano-4-(oxan-4-yloxy)phenyl]furo[3,2-b]pyridin-2-yl]-5-methoxy-N,N-dimethylpyridine-3-carboxamide hydrochloride (336)

The title compound was prepared from 6,7-dichloro-2-iodofuro[3,2-b]pyridine, 6-iodo-5-methoxy-N,N-dimethylnicotinamide and 2-(tetrahydro-2H-pyran-4-yloxy)-5-(4,4,5,5-tetramethyl-1,3,2-dioxaborolan-2-yl)benzonitrile using Methods 12b, 12a and S. The final product was purified by prep-HPLC under the following conditions: column, XBridge Prep C18 OBD Column, 5 um, 19×150 mm; mobile phase, acetonitrile in water (with 0.02% HCl), 20% to 40% gradient in 8 min; detector, UV 254/220 nm. 6-[6-chloro-7-[3-cyano-4-(oxan-4-yloxy)phenyl]furo[3,2-b]pyridin-2-yl]-5-methoxy-N,N-dimethylpyridine-3-carboxamide hydrochloride was obtained as a yellow solid (13 mg, 4% for 3 steps). HPLC: 96.3% purity, RT=1.30 min. MS: m/z=533.1 [M+H]$^+$. $^1$H NMR (300 MHz, CD$_3$OD, ppm) δ 8.79 (s, 1H), 8.32 (d, J=1.4 Hz, 1H), 8.05 (d, J=2.1 Hz, 1H), 7.98 (dd, J=8.8, 2.3 Hz, 1H), 7.89 (d, J=2.3 Hz, 1H), 7.84 (br s, 1H), 7.47 (d, J=8.9 Hz, 1H), 5.00-4.86 (m, 1H), 4.15 (s, 3H), 4.06-3.94 (m, 2H), 3.73-3.61 (m, 2H), 3.12 (s, 3H), 3.04 (s, 3H), 2.18-2.04 (m, 2H), 1.92-1.78 (m, 2H).

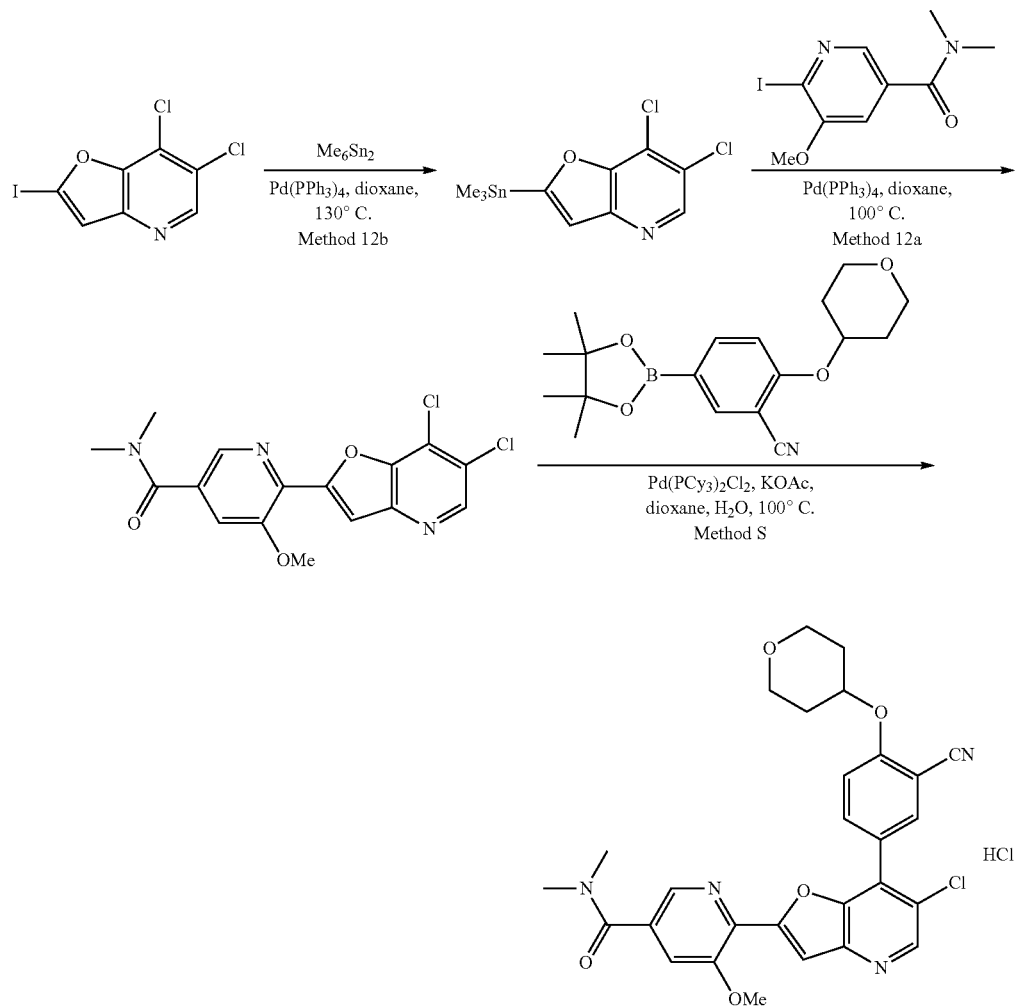

Example 291: 6-(6-chloro-7-[3-cyano-4-[(oxan-4-yl)amino]phenyl]furo[3,2-b]pyridin-2-yl)-5-methoxy-N,N-dimethylpyridine-3-carboxamide (337)

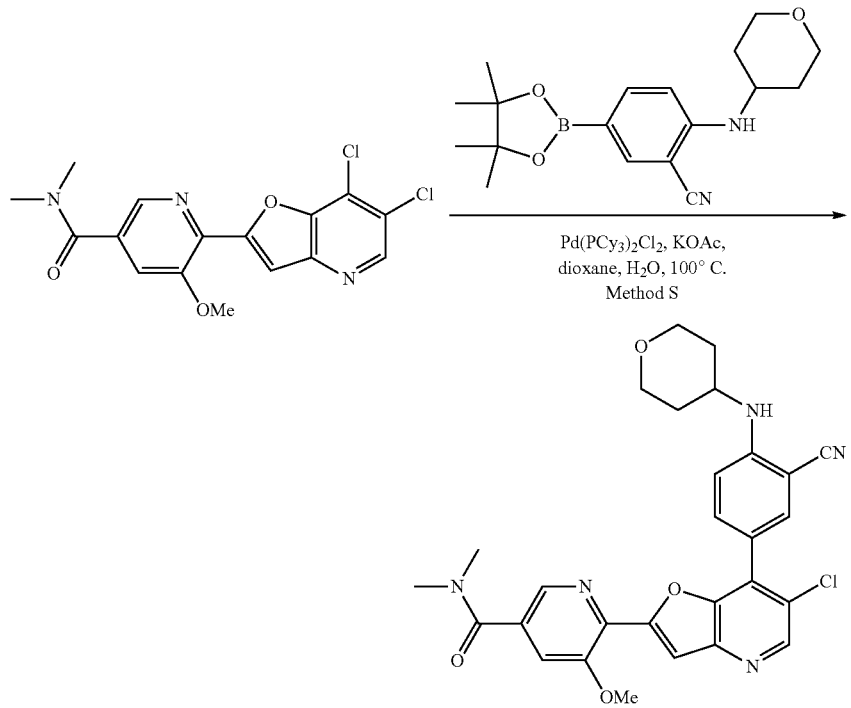

The title compound was prepared from 6-(6,7-dichloro-furo[3,2-b]pyridin-2-yl)-5-methoxy-N,N-dimethylnicotinamide and 2-(tetrahydro-2H-pyran-4-ylamino)-5-(4,4,5,5-tetramethyl-1,3,2-dioxaborolan-2-yl)benzonitrile using Method S. The product was purified by prep-HPLC under the following conditions: column, XBridge Prep C18 OBD Column, 5 um, 19×150 mm; mobile phase, acetonitrile in water, 40% to 60% gradient in 10 min; detector, UV 254/220 nm. 6-(6-chloro-7-[3-cyano-4-[(oxan-4-yl)amino]phenyl]furo[3,2-b]pyridin-2-yl)-5-methoxy-N,N-dimethylpyridine-3-carboxamide was obtained as a yellow solid (7 mg, 7%). HPLC: 97.20 purity, RT=1.31 min. MS: m/z=532.1 [M+H]+.

$^1$H NMR (300 MHz, DMSO-$d_6$, ppm) δ 8.70 (s, 1H), 8.32 (d, J=1.6 Hz, 1H), 7.88-7.78 (i, 2H), 7.78-7.67 (m, 2H), 7.15 (d, J=9.0 Hz, 1H), 6.28 (d, J=8.1 Hz, 1H), 4.08 (s, 3H), 3.96-3.68 (m, 3H), 3.52-3.38 (m, 2H), 3.03 (s, 3H), 2.96 (s, 3H), 1.89 (d, J=12.6 Hz, 2H), 1.73-1.62 (i, 2H).

Example 292: 6-[7-[6-cyano-5-(oxan-4-yloxy)pyridin-2-yl]-6-methoxyfuro[3,2-b]pyridin-2-yl]-5-methoxy-N,N-dimethylpyridine-3-carboxamide hydrochloride (338)

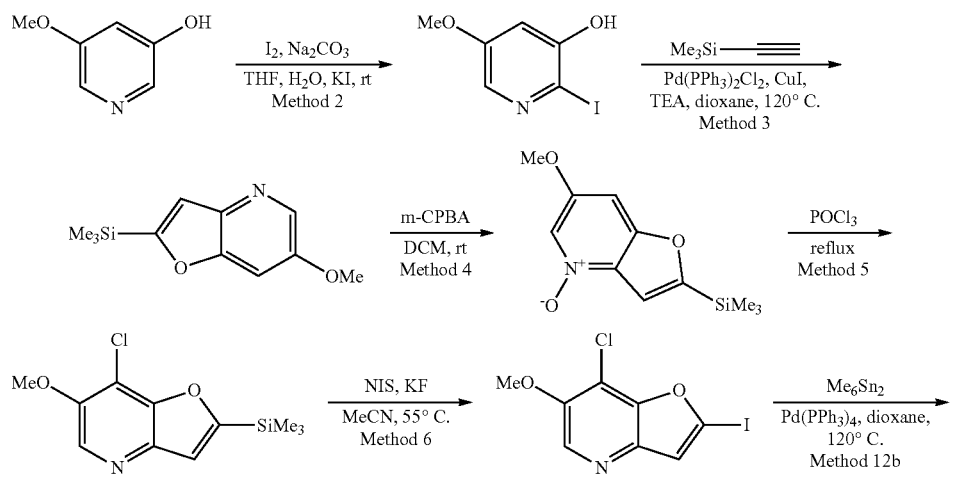

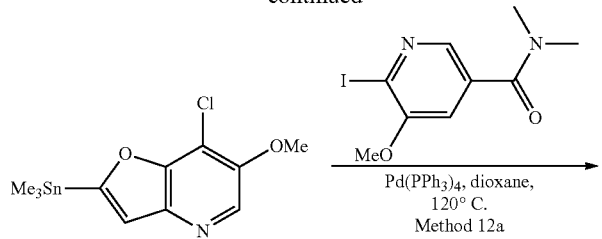

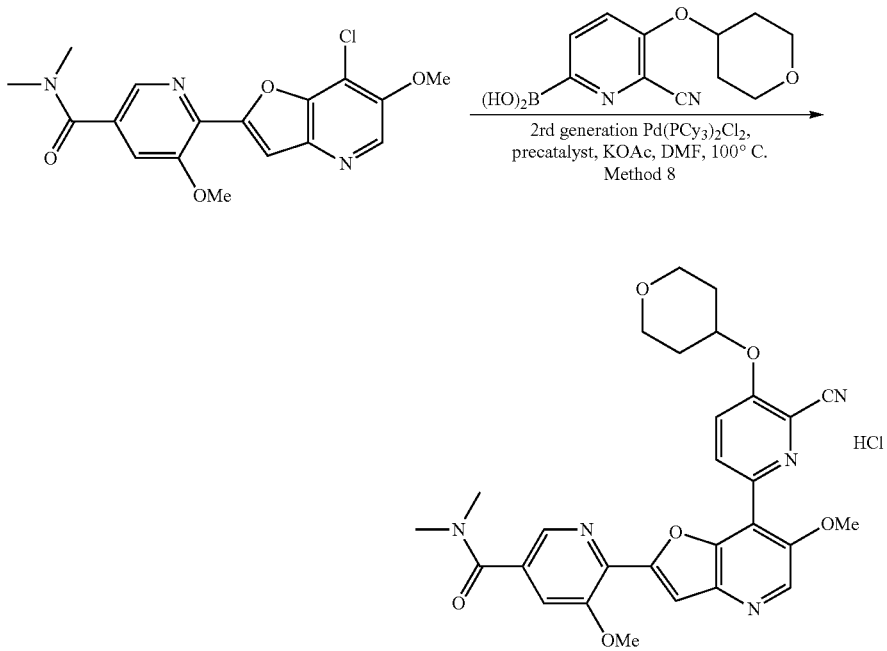

The title compound was prepared from 5-methoxypyridin-3-ol, 6-iodo-5-methoxy-N,N-dimethylnicotinamide, and 6-cyano-5-(tetrahydro-2H-pyran-4-yloxy)pyridin-2-ylboronic acid using Methods 2, 3, 4, 5, 6, 12b, 12a and 8. The final product was purified by prep-HPLC under the following conditions: column, XBridge Prep C18 OBD Column, 5 um, 19×150 mm; mobile phase, acetonitrile in water (with 0.02% HCl), 20% to 40% gradient in 8 min; detector, UV 254/220 nm. 6-[7-[6-cyano-5-(oxan-4-yloxy)pyridin-2-yl]-6-methoxyfuro[3,2-b]pyridin-2-yl]-5-methoxy-N,N-dimethylpyridine-3-carboxamide hydrochloride was obtained as a yellow solid (14 mg, 6% for 8 steps). HPLC: 97.4% purity, RT=1.03 min. MS: m/z=530.2 [M+H]$^+$. $^1$H NMR (300 MHz, CD$_3$OD, ppm) δ 8.82 (s, 1H), 8.38 (d, J=1.5 Hz, 1H), 8.19 (d, J=9.0 Hz, 1H), 8.06-7.92 (m, 2H), 7.86 (d, J=1.5 Hz, 1H), 5.08-4.95 (m, 1H), 4.22-3.97 (m, 8H), 3.78-3.62 (m, 2H), 3.16 (s, 3H), 3.08 (s, 3H), 2.24-2.10 (m, 2H), 2.00-1.82 (m, 2H).

Example 293: 6-[7-[3-cyano-4-(oxan-4-yloxy)phenyl]-6-methoxyfuro[3,2-b]pyridin-2-yl]-5-methoxy-N,N-dimethylpyridine-3-carboxamide (339)

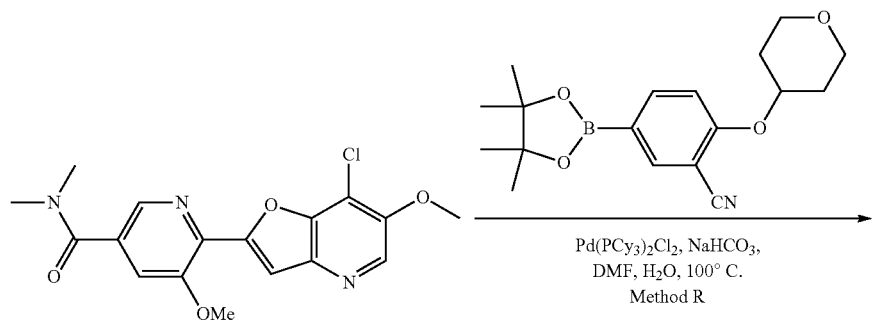

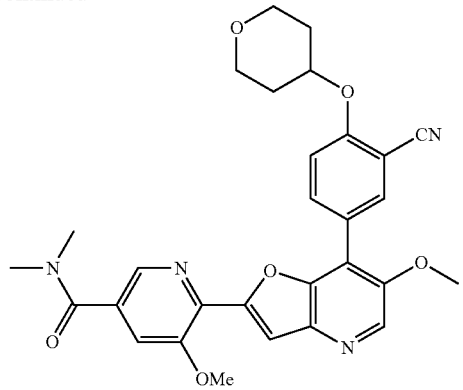

The title compound was prepared from 6-(7-chloro-6-methoxyfuro[3,2-b]pyridin-2-yl)-5-methoxy-N,N-dimethylnicotinamide and 2-(tetrahydro-2H-pyran-4-yloxy)-5-(4,4,5,5-tetramethyl-1,3,2-dioxaborolan-2-yl)benzonitrile using Method R. The product was purified by prep-HPLC under the following conditions: column, Atlantis Prep T$_3$ OBD Column, 19×150 mm 5 um 10 nm; mobile phase, acetonitrile in water (with 10 mmol/L NH$_4$HCO$_3$), 20% to 50% gradient in 8 min; detector, UV 254/220 nm. 6-[7-[3-cyano-4-(oxan-4-yloxy)phenyl]-6-methoxyfuro[3,2-b]pyridin-2-yl]-5-methoxy-N,N-dimethylpyridine-3-carboxamide was obtained as a white solid (10 mg, 9%). HPLC: 99.9% purity, RT=1.55 min. MS: m/z=529.2 [M+H]$^+$. $^1$H NMR (400 MHz, DMSO-d$_6$, ppm) δ 8.58 (s, 1H), 8.28 (d, J=1.5 Hz, 1H), 8.09 (d, J=2.2 Hz, 1H), 8.00 (dd, J=8.8, 2.3 Hz, 1H), 7.75 (s, 1H), 7.66 (d, J=1.6 Hz, 1H), 7.57 (d, J=8.8 Hz, 1H), 5.00-4.90 (m, 1H), 4.06 (s, 3H), 3.96 (s, 3H), 3.94-3.82 (m, 2H), 3.61-3.49 (m, 2H), 3.01 (s, 3H), 2.95 (s, 3H), 2.10-2.01 (m, 2H), 1.78-1.64 (m, 2H).

Example 294: 6-(7-[3-cyano-4-[(oxan-4-yl)amino]phenyl]-6-methoxyfuro[3,2-b]pyridin-2-yl)-5-methoxy-N,N-dimethylpyridine-3-carboxamide (340)

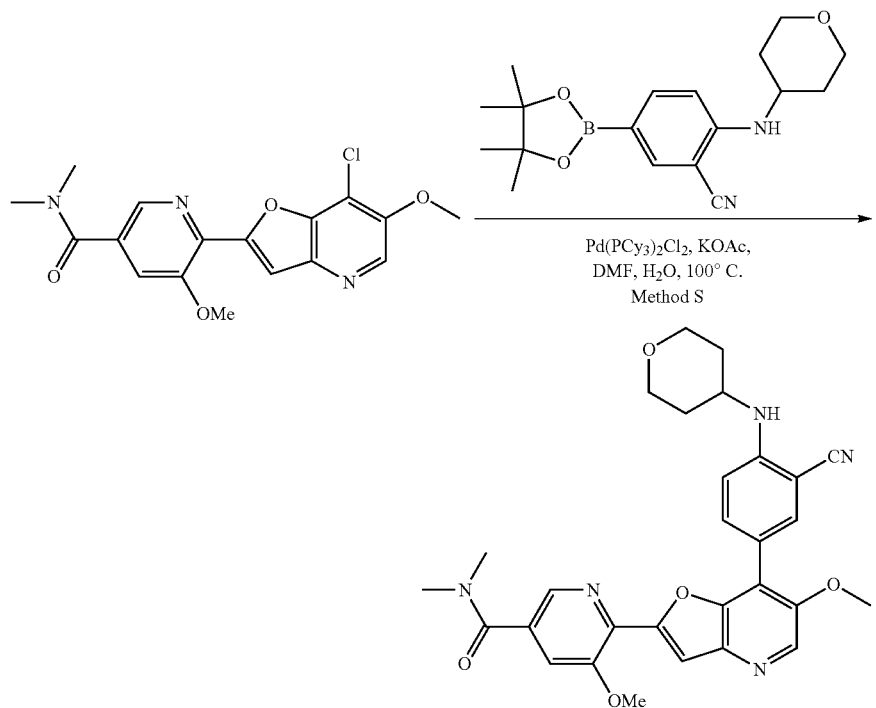

The title compound was prepared from 6-(7-chloro-6-methoxyfuro[3,2-b]pyridin-2-yl)-5-methoxy-N,N-dimethylnicotinamide and 2-(tetrahydro-2H-pyran-4-ylamino)-5-(4,4,5,5-tetramethyl-1,3,2-dioxaborolan-2-yl)benzonitrile using Method S. The product was purified by prep-HPLC under the following conditions: column, XBridge Prep C18 OBD Column, 5 um, 19×150 mm; mobile phase, acetonitrile in water (with 10 mmol/L NH$_4$HCO$_3$), 35% to 65% gradient in 8 min; detector, UV 254/220 nm. 6-(7-[3-cyano-4-[(oxan-4-yl)amino]phenyl]-6-methoxyfuro[3,2-b]pyridin-2-yl)-5-methoxy-N,N-dimethylpyridine-3-carboxamide was obtained as a off-white solid (8 mg, 9%). HPLC: 99.0%, purity, RT=1.10 min. MS: m/z=528.2 [M+H]⁺. ¹H NMR (400 MHz, DMSO-$d_6$, ppm) δ 8.54 (s, 1H), 8.31 (d, J=1.5 Hz, 1H), 7.89 (d, J=2.1 Hz, 1H), 7.83 (dd, J=8.7, 2.2 Hz, 1H), 7.73 (s, 1H), 7.67 (d, J=1.6 Hz, 1H), 7.10 (d, J=9.0 Hz, 1H), 6.15 (d, J=8.2 Hz, 1H), 4.07 (s, 3H), 3.97 (s, 3H), 3.96-3.86 (m, 2H), 3.77 (d, J=10.2 Hz, 1H), 3.50-3.45 (m, 2H), 3.03 (s, 3H), 2.98 (s, 3H), 1.88 (d, J=12.5 Hz, 2H), 1.72-1.58 (m, 2H).

Example 295: 6-[7-[3-cyano-4-(oxan-4-yloxy)phenyl]-6-cyclopropylfuro[3,2-b]pyridin-2-yl]-N-(2-hydroxyethyl)-5-methoxy-N-methylpyridine-3-carboxamide hydrochloride (341)

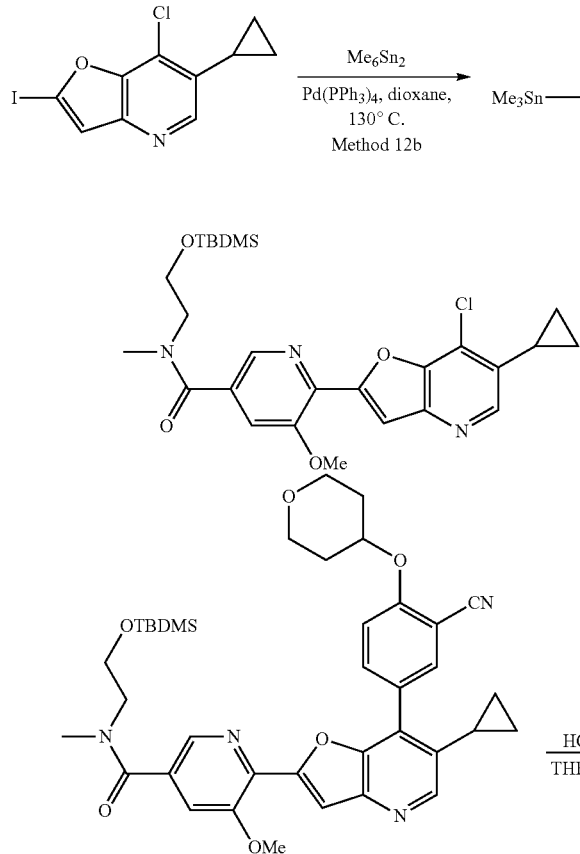

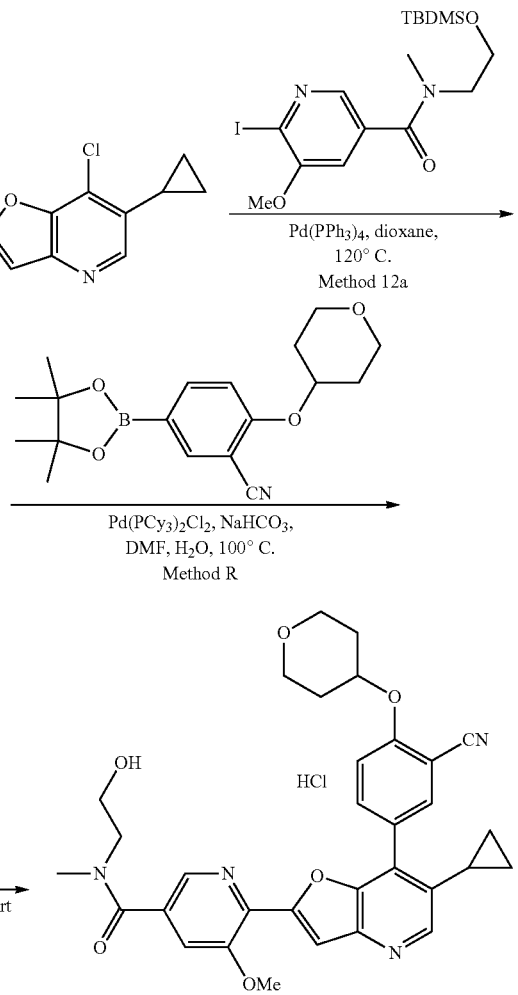

N-(2-(tert-butyldimethylsilyloxy)ethyl)-6-(7-(3-cyano-4-(tetrahydro-2H-pyran-4-yloxy)phenyl)-6-cyclopropylfuro[3,2-b]pyridin-2-yl)-5-methoxy-N-methylnicotinamide The title compound was prepared from 7-chloro-6-cyclopropyl-2-iodofuro[3,2-b]pyridine, N-(2-(tert-butyldimethylsilyloxy)ethyl)-6-iodo-5-methoxy-N-methylnicotinamide and 2-(tetrahydro-2H-pyran-4-yloxy)-5-(4,4,5,5-tetramethyl-1,3,2-dioxaborolan-2-yl)benzonitrile using Methods 12b, 12a, and R. The crude product (80 mg, light brown solid) was used directly in the next step without further purification.

6-[7-[3-cyano-4-(oxan-4-yloxy)phenyl]-6-cyclopropylfuro[3,2-b]pyridin-2-yl]-N-(2-hydroxyethyl)-5-methoxy-N-methylpyridine-3-carboxamide hydrochloride N-(2-(tert-butyldimethylsilyloxy)ethyl)-6-(7-(3-cyano-4-(tetrahydro-2H-pyran-4-yloxy)phenyl)-6-cyclopropylfuro[3,2-b]pyridin-2-yl)-5-methoxy-N-methylnicotinamide (80 mg, crude) was added to a solution of HCl in THF (2 M, 4.5 mL). The resulting solution was stirred for 1 h at room temperature. After the reaction was done, the reaction mixture was concentrated under reduced pressure. The residue was purified by prep-HPLC under the following conditions: column, XBridge Shield RP18 OBD Column, 5 um, 19×150 mm, acetonitrile in water (with 0.02% HCl), 20% to 50% gradient in 15 min; detector, UV 254/220 nm. 6-[7-[3-cyano-4-(oxan-4-yloxy)phenyl]-6-cyclopropylfuro[3,2-b]pyridin-2-yl]-N-(2-hydroxyethyl)-5-methoxy-N-methylpyridine-3-carboxamide hydrochloride was obtained as a yellow solid (20 mg, 5% for 4 steps). HPLC: 98.5% purity, RT=1.08 min. MS: m/z=569.3 [M+H]⁺. ¹H NMR (300 MHz, CD₃OD, ppm) δ 8.40 (s, 1H), 8.31 (d, J=1.5 Hz, 1H), 8.06-7.91 (m, 2H), 7.86-7.70 (m, 2H), 7.46 (d, J=8.8 Hz, 1H), 4.97-4.85 (m, 1H), 4.14-3.93 (m, 5H), 3.86-3.76 (m, 1H), 3.73-3.57 (m, 4H), 3.48-3.38 (m, 1H), 3.09 (d, J=10.5 Hz, 3H), 2.19-1.77 (m, 5H), 1.07-0.94 (m, 2H), 0.90-0.73 (m, 2H).

Example 296: 6-[6-chloro-7-[3-cyano-4-(oxan-4-yloxy)phenyl]furo[3,2-b]pyridin-2-yl]-N-(2-hydroxyethyl)-5-methoxy-N-methylpyridine-3-carboxamide hydrochloride (342)

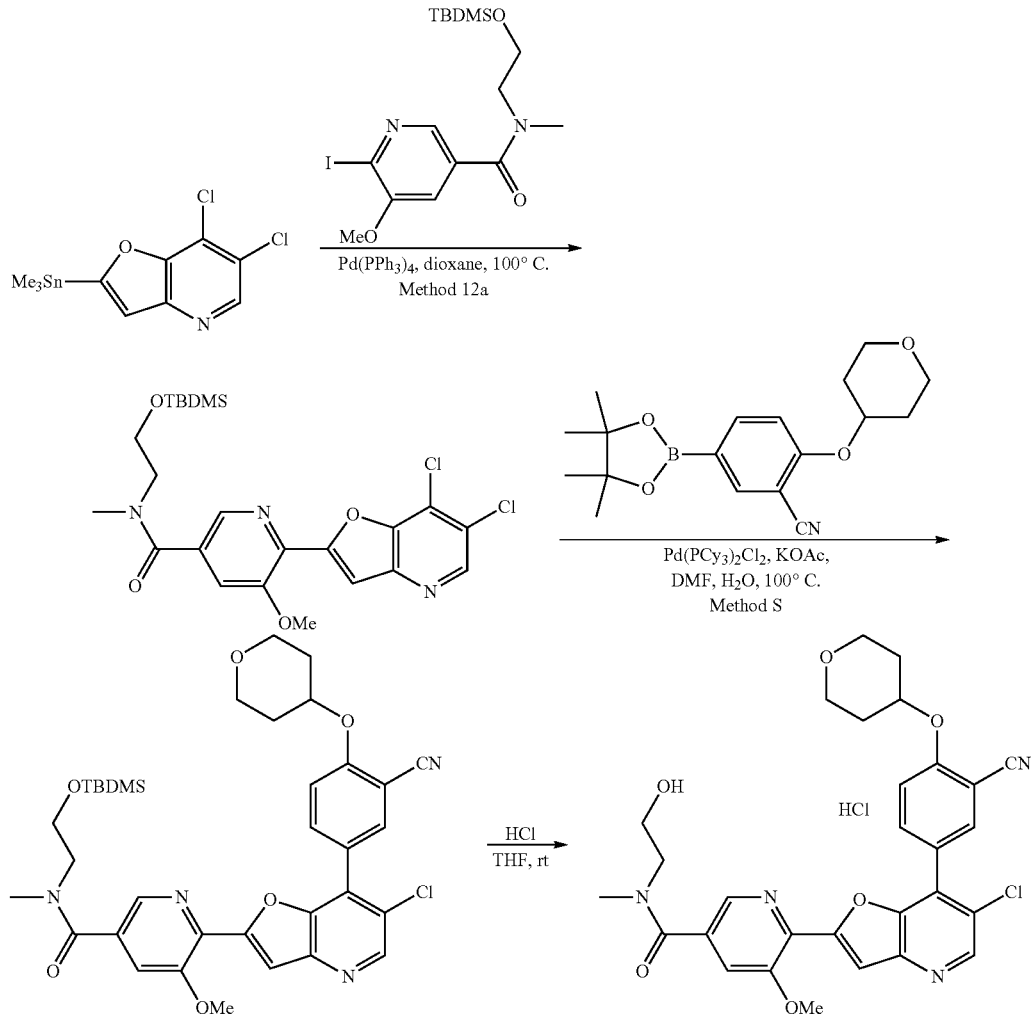

N-(2-((tert-butyldimethylsilyl)oxy)ethyl)-6-(6-chloro-7-(3-cyano-4-((tetrahydro-2H-pyran-4-yl)oxy)phenyl)furo[3,2-b]pyridin-2-yl)-5-methoxy-N-methylnicotinamide The title compound was prepared from 6,7-dichloro-2-(trimethyl stannyl)furo[3,2-b]pyridine, N-(2-(tert-butyldimethylsilyloxy)ethyl)-6-iodo-5-methoxy-N-methylnicotinamide and 2-(tetrahydro-2H-pyran-4-yloxy)-5-(4,4,5,5-tetramethyl-1,3,2-dioxaborolan-2-yl)benzonitrile using Methods 12a and S. The obtained crude final product (180 mg, yellow solid) was used directly in next step without further purification.

6-[6-chloro-7-[3-cyano-4-(oxan-4-yloxy)phenyl]furo[3,2-b]pyridin-2-yl]-N-(2-hydroxyethyl)-5-methoxy-N-methylpyridine-3-carboxamide hydrochloride N-(2-(tert-butyldimethylsilyloxy)ethyl)-6-(6-chloro-7-(3-cyano-4-(tetrahydro-2H-pyran-4-yloxy)phenyl)furo[3,2-b]pyridin-2-yl)-5-methoxy-N-methylnicotinamide (180 mg, crude) was added to a solution of HCl in THF (2 M, 4.5 mL) at room temperature. The resulting solution was stirred for 1 h at room temperature. After the reaction was done, the reaction mixture was concentrated under reduced pressure. The residue was purified by prep-HPLC under the following conditions: column, XBridge Shield RP18 OBD Column, 5 um, 19×150 mm; mobile phase, acetonitrile in water, 25% to 55% gradient in 10 min; detector, UV 254/220 nm. 6-[6-chloro-7-[3-cyano-4-(oxan-4-yloxy)phenyl]furo[3,2-b]pyridin-2-yl]-N-(2-hydroxyethyl)-5-methoxy-N-methylpyridine-3-carboxamide hydrochloride was obtained as a yellow solid (7 mg, 10% for 3 steps). HPLC: 97.3% purity, RT=0.84 min. MS: m/z=563.1 [M+H]$^+$. $^1$H NMR (300 MHz, CD$_3$OD, ppm) δ 8.76 (s, 1H), 8.38 (br s, 1H), 8.09-7.81 (m, 4H), 7.48 (d, J=8.9 Hz, 1H), 5.03-4.91 (m, 1H), 4.25-4.15 (m, 3H), 4.11-3.97 (m, 2H), 3.91-3.79 (m, 1H), 3.77-3.63 (m, 4H), 3.52-3.42 (m, 1H), 3.14 (d, J=10.8 Hz, 3H), 2.25-2.09 (m, 2H), 1.98-1.82 (m, 2H).

Example 297: 6-[7-[3-cyano-4-(oxan-4-yloxy)phenyl]-6-methoxyfuro[3,2-b]pyridin-2-yl]-N-(2-hydroxyethyl)-5-methoxy-N-methylpyridine-3-carboxamide (343)

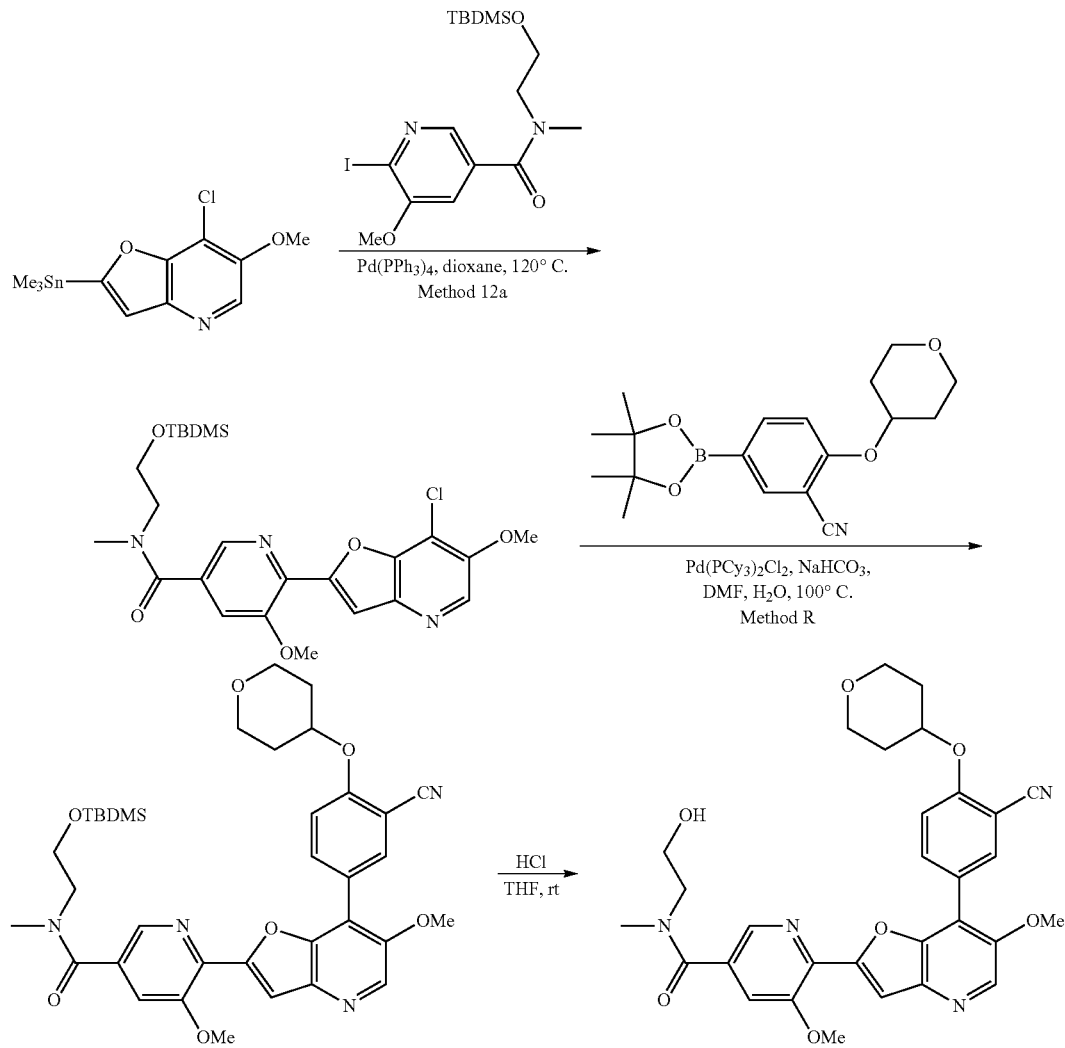

N-(2-(tert-butyldimethylsilyloxy)ethyl)-6-(7-(3-cyano-4-(tetrahydro-2H-pyran-4-yloxy)phenyl)-6-methoxyfuro[3,2-b]pyridin-2-yl)-5-methoxy-N-methylnicotinamide The title compound was prepared from 7-chloro-6-methoxy-2-(trimethylstannyl)furo[3,2-b]pyridine N-(2-(tert-butyldimethylsilyloxy)ethyl)-6-iodo-5-methoxy-N-methylnicotinamide, and 2-(tetrahydro-2H-pyran-4-yloxy)-5-(4,4,5,5-tetramethyl-1,3,2-dioxaborolan-2-yl)benzonitrile using Methods 12a and R. The obtained crude final product (60 mg, yellow solid) was used directly in next step without further purification.

6-[7-[3-cyano-4-(oxan-4-oxy)phenyl]-6-methoxy-furo[3,2-b]pyridin-2-yl]-N-(2-hydroxyethyl)-5-methoxy-N-methylpyridine-3-carboxamide N-(2-(tert-butyldimethyl silyloxy)ethyl)-6-(7-(3-cyano-4-(tetrahydro-2H-pyran-4-yloxy)phenyl)-6-methoxyfuro[3,2-b]pyridin-2-yl)-5-methoxy-N-methylnicotinamide (60 mg, crude) was added to a solution of HCl in THF (2 M, 4.5 mL) at room temperature. The resulting solution was stirred for 1 h at room temperature. After the reaction was done, the reaction mixture was concentrated under reduced pressure. The residue was purified by prep-HPLC under the following conditions: column, XBridge Shield RP18 OBD Column, 5 um, 19×150 mm; acetonitrile in water (with 10 mmol/L $NH_4HCO_3$), 30% to 38% gradient in 10 min; detector, UV 254/220 nm. 6-[7-[3-cyano-4-(oxan-4-yloxy)phenyl]-6-methoxyfuro[3,2-b]pyridin-2-yl]-N-(2-hydroxyethyl)-5-methoxy-N-methylpyridine-3-carboxamide was obtained as a white solid (10 mg, 4.5% for 3 steps). HPLC: 96.0% purity, RT=1.03 min. MS: m/z=559.2 [M+H]$^+$. $^1$H NMR (300 MHz, $CD_3OD$, ppm) δ 8.55-8.25 (m, 2H), 8.18-8.06 (m, 2H), 7.89-7.68 (m, 2H), 7.45-7.30 (m, 1H), 4.20-3.90 (m, 8H), 3.89-3.40 (m, 6H), 3.19-3.05 (s, 4H), 2.21-1.97 (m, 2H), 1.95-1.78 (m, 2H).

Example 298: 4-[7-[3-cyano-4-(oxan-4-yloxy)phenyl]furo[3,2-b]pyridin-2-yl]-N-[3-[(dimethylamino)methyl]cyclobutyl]-3-methoxybenzamide (344)

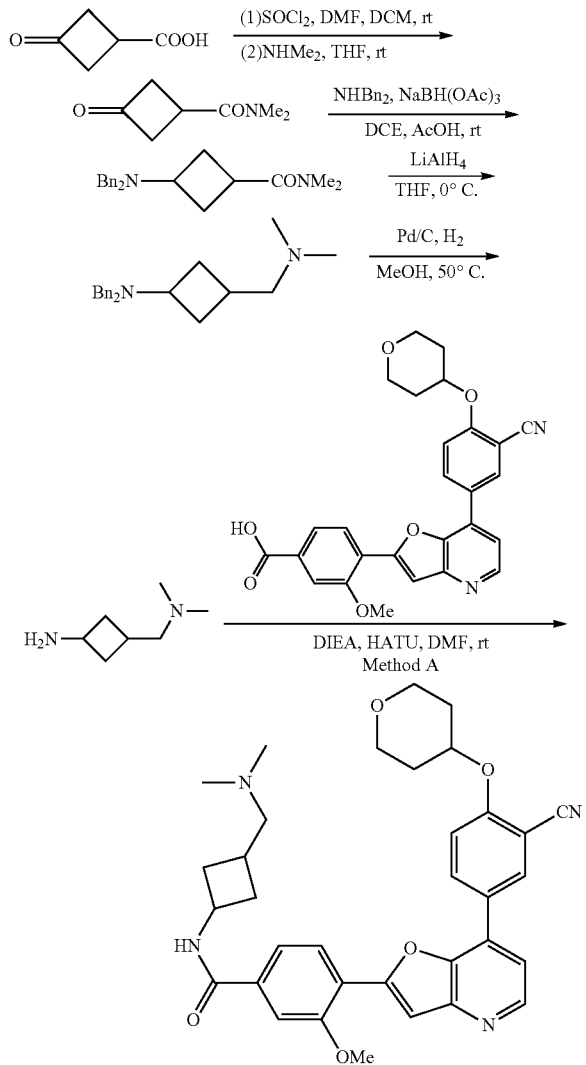

N,N-dimethyl-3-oxocyclobutanecarboxamide

To a solution of 3-oxocyclobutane-1-carboxylic acid (1.00 g, 8.76 mmol) in DCM (10 mL) was added N,N-dimethylformamide (0.05 mL) and oxalic dichloride (3.00 g, 23.64 mmol) in sequence at room temperature. The resulting solution was stirred for 3 h at room temperature, and then was concentrated under reduced pressure. The residue was dissolved in THF (5 mL), to which the dimethylamine gas was bubbled through for 10 min at room temperature. After the reaction was done, the insoluble solids in the reaction mixture were filtered out and the filtrate was concentrated under reduced pressure to yield N,N-dimethyl-3-oxocyclobutane-1-carboxamide as a brown solid (578 mg, 47%).

3-(dibenzylamino)-N,N-dimethylcyclobutanecarboxamide

To a solution of N,N-dimethyl-3-oxocyclobutane-1-carboxamide (462 mg, 3.28 mmol) in DCE (10 mL) was added dibenzylamine (661 mg, 4.67 mmol) at room temperature. The resulting solution was stirred for 1 h at room temperature. Then the reaction mixture was added by acetic acid (350 mg, 5.82 mmol), followed by the addition of sodium triacetoxyborohydride (1.25 g, 5.83 mmol) at room temperature. The resulting solution was allowed to react for additional 2 days at room temperature. After the reaction was done, the pH value of the reaction mixture was adjusted to 8 with sat. sodium bicarbonate solution. The resulting mixture was extracted with DCM (30 mL×3). The organic phases were combined, washed with brine and dried over sodium sulfate. The solvent was removed under reduced pressure to yield 3-(dibenzylamino)-N,N-dimethylcyclobutane-1-carboxamide was obtained as a off-white solid (263 mg, 25%).

N,N-dibenzyl-3-[(dimethylamino)methyl]cyclobutan-1-amine

At 0° C., to a solution of 3-(dibenzylamino)-N,N-dimethylcyclobutane-1-carboxamide (260 mg, 0.81 mmol) in THF (10 mL) was added LiAlH$_4$ (175 mg, 4.60 mmol) in portions. The resulting mixture was stirred for 2 h at 0° C. When the reaction was done, it was quenched by the addition of sat. NH$_4$Cl solution (10 mL). The resulting mixture was extracted with ethyl acetate (20 mL×3). The organic phases were combined, washed with brine and dried over sodium sulfate. The solvent was removed under reduced pressure to yield N,N-dibenzyl-3-[(dimethylamino)methyl]cyclobutan-1-amine was obtained as a white solid (198 mg, 79%).

3-[(dimethylamino)methyl]cyclobutan-1-amine

N,N-dibenzyl-3-[(dimethylamino)methyl]cyclobutan-1-amine (198 mg, 0.64 mmol) was dissolved in methanol (10 mL) at room temperature. The resulting solution was added Pd/C (725 mg, 6.81 mmol) under nitrogen atmosphere. The reaction flask was vacuumed and flushed with hydrogen. The reaction mixture was then hydrogenated for 2 h at 50° C. under hydrogen atmosphere with a hydrogen balloon. After the reaction was done, the reaction mixture was filter through a Celite pad and the filtrate was concentrated under reduced pressure to yield 3-[(dimethylamino)methyl]cyclobutan-1-amine was obtained as a off-white solid (72 mg, 88%).

4-[7-[3-cyano-4-(oxan-4-yloxy)phenyl]furo[3,2-b]pyridin-2-yl]-N-[3-[(dimethylamino)methyl]cyclobutyl]-3-methoxybenzamide The title compound was prepared from 4-(7-(3-cyano-4-(tetrahydro-2H-pyran-4-yloxy)phenyl)furo[3,2-b]pyridin-2-yl)-3-methoxybenzoic acid and 3-[(dimethylamino)methyl]cyclobutan-1-amine using Method A. The product was purified by flash chromatography eluting with MeOH in DCM (0% to 65% gradient) to yield 4-[7-[3-cyano-4-(oxan-4-yloxy)phenyl]furo[3,2-b]pyridin-2-yl]-N-[3-[(dimethylamino)methyl]cyclobutyl]-3-methoxybenzamide as a off-white solid (8 mg, 4%). HPLC: 92.7% purity, RT=1.30 min. MS: m/z=291.4 [M/2+H]$^+$. $^1$H NMR (300 MHz, CD$_3$OD, ppm) δ 8.47 (d, J=5.1 Hz, 1H), 8.39-8.29 (m, 2H), 8.01 (d, J=8.2 Hz, 1H), 7.63-7.42 (m, 5 H), 4.97-4.87 (m, 1H), 4.45-4.35 (m, 1H), 4.13-3.94 (m, 5H), 3.74-3.60 (m, 2H), 2.65-2.46 (m, 4H), 2.28 (s, 6H), 2.20-2.05 (m, 3H), 1.95-1.73 (m, 4H).

Example 299: 4-[7-[3-cyano-4-(oxan-4-yloxy)phenyl]furo[3,2-b]pyridin-2-yl]-N-[3-(hydroxymethyl)-1-methylpyrrolidin-3-yl]-3-methoxybenzamide (345)

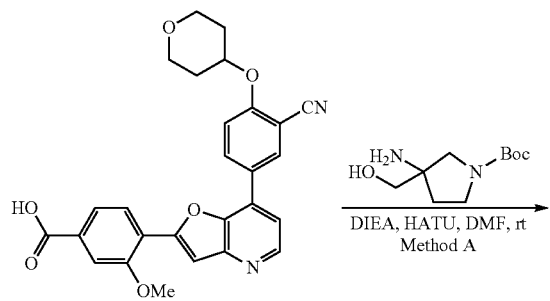

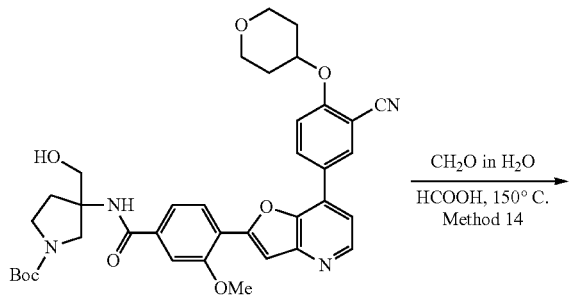

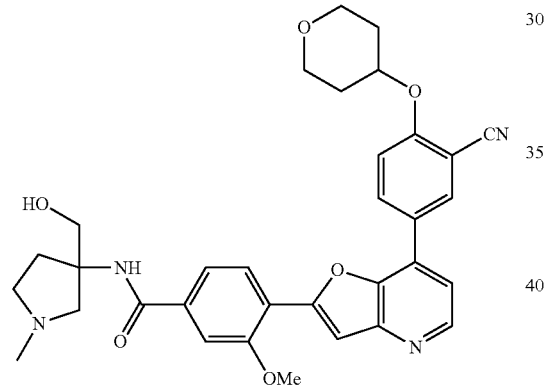

tert-butyl 3-[(4-[7-[3-cyano-4-(oxan-4-yloxy)phenyl]furo[3,2-b]pyridin-2-yl]-3-methoxybenzene)amido]-3-(hydroxymethyl)pyrrolidine-1-carboxylate The title compound was prepared from 4-(7-(3-cyano-4-(tetrahydro-2H-pyran-4-yloxy)phenyl)furo[3,2-b]pyridin-2-yl)-3-methoxybenzoic acid and tert-butyl 3-amino-3-(hydroxymethyl)pyrrolidine-1-carboxylate using Methods A and 14. The product was purified by flash chromatography eluting with MeOH in DCM (0% to 18% gradient) to yield tert-butyl 3-[(4-[7-[3-cyano-4-(oxan-4-yloxy)phenyl]furo[3,2-b]pyridin-2-yl]-3-methoxybenzene)amido]-3-(hydroxymethyl)pyrrolidine-1-carboxylate as a yellow oil (188 mg, 93%). MS: m/z=669.3 [M+H]$^+$.

Method 14

4-[7-[3-cyano-4-(oxan-4-yloxy)phenyl]furo[3,2-b]pyridin-2-yl]-N-[3-(hydroxymethyl)-1-methylpyrrolidin-3-yl]-3-methoxybenzamide To solution of tert-butyl 3-[(4-[7-[3-cyano-4-(oxan-4-yloxy)phenyl]furo[3,2-b]pyridin-2-yl]-3-methoxybenzene)amido]-3-(hydroxymethyl)pyrrolidine-1-carboxylate (150 mg, 0.22 mmol) in formic acid (4 mL) was added formalin (4 mL, 109.24 mmol) at room temperature. The resulting solution was stirred for 1 h at 150° C. After cooling the room temperature, the reaction mixture was concentrated under reduced pressure and the residue was purified by prep-HPLC under the following conditions: column, XBridge Shield RP18 OBD Column, 5 um, 19×150 mm; mobile phase, acetonitrile in water, 25% to 55% gradient in 10 min; detector, UV 254/220 nm. 4-[7-[3-cyano-4-(oxan-4-yloxy)phenyl]furo[3,2-b]pyridin-2-yl]-N-[3-(hydroxymethyl)-1-methylpyrrolidin-3-yl]-3-methoxybenzamide was obtained as a yellow solid (13 mg, 9%). HPLC: 93.3% purity, RT=1.52 min. MS: m/z=583.2 [M+H]$^+$. $^1$H NMR (400 MHz, DMSO-d$_6$, ppm) δ 8.57 (d, J=5.1 Hz, 1H), 8.53-8.41 (m, 2H), 8.17 (s, 1H), 8.02 (d, J=8.1 Hz, 1H), 7.71-7.60 (m, 5H), 5.07-4.87 (m, 2H), 4.09 (s, 3H), 3.96-3.80 (m, 2H), 3.71-3.51 (m, 4H), 2.81-2.69 (m, 2H), 2.60-2.50 (m, 2H), 2.24 (s, 3H), 2.17-1.91 (m, 4H), 1.78-1.64 (m, 2H).

Example 300: 4-[7-[3-cyano-4-(oxan-4-yloxy)phenyl]furo[3,2-b]pyridin-2-yl]-N-[(3R,4R)-4-(dimethylamino)oxolan-3-yl]-3-methoxybenzamide (346)

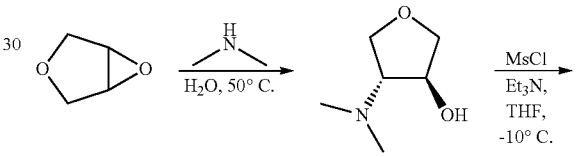

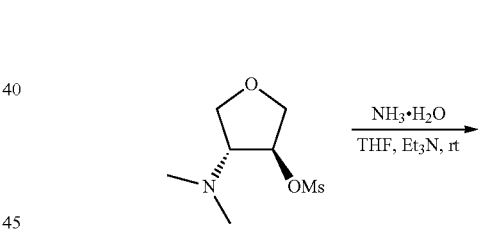

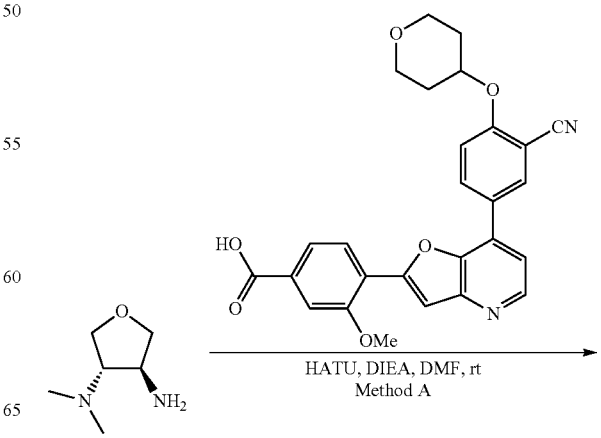

-continued

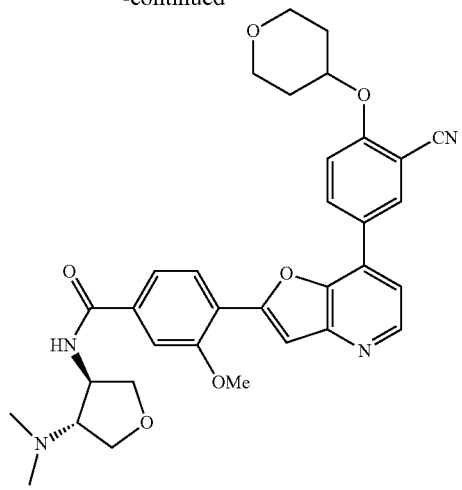

(3S,4R)-4-(dimethylamino)-tetrahydrofuran-3-ol

At 50° C., 3,4-epoxytetrahydrofuran (196 mg, 2.28 mmol) was added to a aqueous dimethylamine solution (33%, 10 mL). The resulting mixture was stirred for 15 h at 50° C. After the reaction was done, the reaction mixture was concentrated under reduced pressure and the residue was purified by flash chromatography eluting with MeOH in DCM (0% to 10% gradient) to yield 4-(dimethylamino) oxolan-3-ol as a yellow oil (200 mg, 67%).

(3S,4R)-4-(dimethylamino)-tetrahydrofuran-3-yl methanesulfonate

At −10° C., to a solution of 4-(dimethylamino)oxolan-3-ol (200 mg, 1.44 mmol) in tetrahydrofuran (5 mL) was added triethylamine (0.45 mL, 6.12 mmol) and MsCl (191 mg, 1.67 mmol) in sequence. The resulting solution was stirred for 2 h at −10° C. After the reaction was done, the reaction mixture was concentrated under reduced pressure. The residue was diluted with EtOAc (20 mL) and washed with water and brine. The solvent was removed to yield 4-(dimethylamino)oxolan-3-yl methanesulfonate as a yellow oil (121 mg, 40%).

(3S,4S)—N,N-dimethyl-tetrahydrofuran-3,4-diamine

To a solution of 4-(dimethylamino)oxolan-3-yl methanesulfonate (115 mg, 0.55 mmol) in tetrahydrofuran (5 mL) were added triethylamine (0.45 mL, 30.76 mmol) and NH$_3$.H$_2$O (4 mL, 33%) at room temperature. The resulting mixture was then stirred for 15 h at room temperature. When the reaction was done, it was quenched by the addition of water (20 mL). The resulting mixture was extracted with ethyl acetate (50 mL×3). The organic phases were combined, washed with brine and dried over sodium sulfate. The solvent was removed under reduced pressure to yield (3S, 4S)—N$^3$,N$^3$-dimethyl-tetrahydrofuran-3,4-diamine as a yellow oil (54 mg, 75%).

4-[7-[3-cyano-4-(oxan-4-yloxy)phenyl]furo[3,2-b] pyridin-2-yl]-N-[(3R,4R)-4-(dimethylamino)oxolan-3-yl]-3-methoxybenzamide The title compound was prepared from 4-(7-(3-cyano-4-(tetrahydro-2H-pyran-4-yloxy)phenyl)furo[3,2-b]pyridin-2-yl)-3-methoxybenzoic acid and (3S,4S)—N$^3$,N$^3$-dimethyl-tetrahydrofuran-3,4-diamine using Method A. The product was purified by prep-HPLC under the following conditions: column, XBridge Shield RP18 OBD Column, 5 um, 19×150 mm; mobile phase, acetonitrile in water (with 10 mmol/L NH$_4$HCO$_3$), 25% to 55% gradient in 8 min; detector, UV 254/220 nm. 4-[7-[3-cyano-4-(oxan-4-yloxy)phenyl]furo[3,2-b]pyridin-2-yl]-N-[(3R,4R)-4-(dimethylamino)oxolan-3-yl]-3-methoxybenzamide was obtained as a yellow solid (27 mg, 8%). HPLC: 93.1% purity, RT=2.35 min. MS: m/z=583.3 [M+H]$^+$. $^1$H NMR (400 MHz, CD$_3$OD, ppm) δ 8.55-8.26 (m, 3H), 8.10-7.90 (m, 1H), 7.70-7.40 (m, 5H), 4.95-4.85 (m, 1H), 4.75-4.65 (m, 1H), 4.21-3.97 (m, 7H), 3.82-3.67 (m, 4H), 3.19-3.09 (m, 1H), 2.38 (s, 6H), 2.21-2.07 (m, 2H), 1.96-1.82 (m, 2H).

Example 301: 4-[7-[3-cyano-4-(oxan-4-yloxy)phenyl]furo[3,2-b]pyridin-2-yl]-N-(3-hydroxy-1-methylpiperidin-4-yl)-3-methoxybenzamide (347)

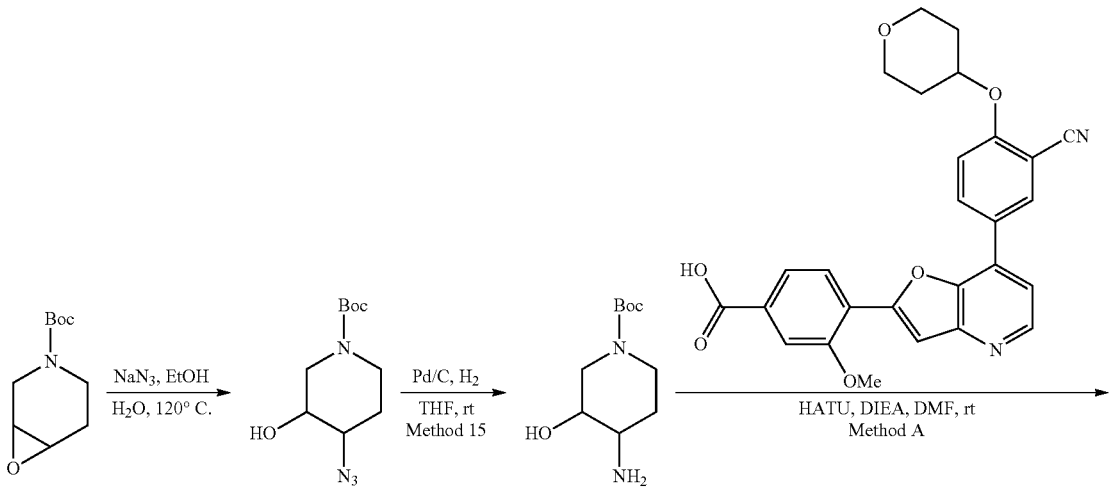

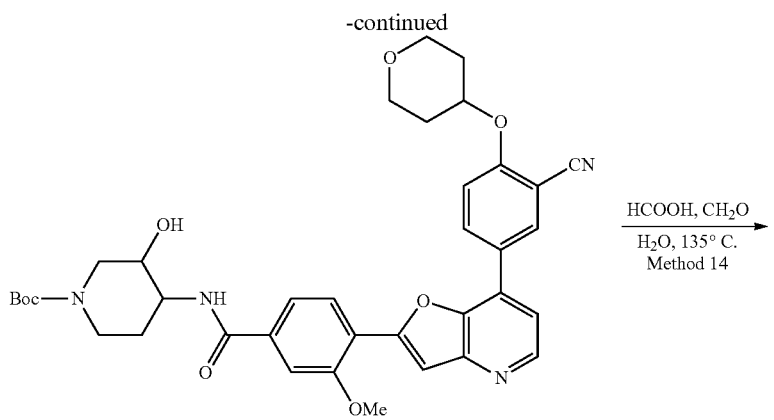

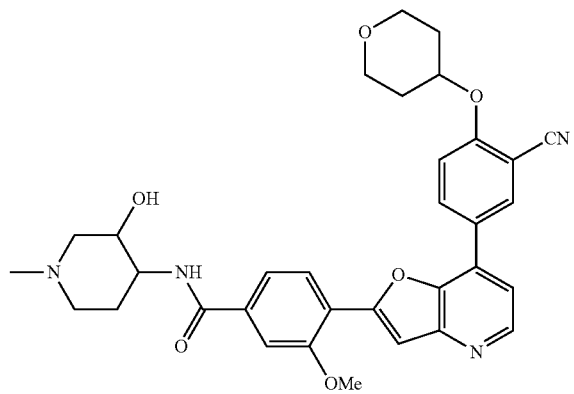

tert-Butyl 4-azido-3-hydroxypiperidine-1-carboxylate

To a solution of tert-butyl 7-oxa-3-azabicyclo[4.1.0]heptane-3-carboxylate (300 mg, 1.51 mmol) in ethanol (2.5 mL) was added a solution of NaN3 (195 mg, 3.00 mmol) in water (2.5 mL) at room temperature. The resulting solution was stirred for 30 min at 120° C. After cooling to room temperature, the reaction mixture was extracted with ethyl acetate (20 mL×3). The organic phases were combined, washed with brine and dried over sodium sulfate. The solvent was removed under reduced pressure and the residue was purified by flash chromatography eluting with EtOAc in hexane (25% to 50% gradient) to yield tert-butyl 4-azido-3-hydroxypiperidine-1-carboxylate as colorless oil (88 mg, 24%). MS: m/z=243.1 [M+H]$^+$.

Method 15 tert-Butyl 4-amino-3-hydroxypiperidine-1-carboxylate

To a solution of tert-butyl 4-azido-3-hydroxypiperidine-1-carboxylate (95 mg, 0.39 mmol) in tetrahydrofuran (5 mL) was added palladium carbon (10%, 10 mg, 0.09 mmol) under nitrogen atmosphere. The reaction flask was vacuumed and flushed with hydrogen gas. The reaction mixture was then hydrogenated for 30 min at room temperature under hydrogen atmosphere with a hydrogen balloon. After the reaction was done, the reaction mixture was filtered through a Celite pad and the filtrate was concentrated under reduced pressure to yield tert-butyl 4-amino-3-hydroxypiperidine-1-carboxylate as colorless oil (80 mg, 94%). MS: m/z=217.1 [M+H]$^+$.

4-[7-[3-Cyano-4-(oxan-4-yloxy)phenyl]furo[3,2-b]pyridin-2-yl]-N-(3-hydroxy-1-methylpiperidin-4-yl)-3-methoxybenzamide The title compound was prepared from 4-(7-(3-cyano-4-(tetrahydro-2H-pyran-4-yloxy)phenyl)furo[3,2-b]pyridin-2-yl)-3-methoxybenzoic acid and tert-butyl 4-amino-3-hydroxypiperidine-1-carboxylate using Methods A and 14. The product was purified by prep-HPLC under the following conditions: column, XBridge Shield RP18 OBD Column, 5 um, 19×150 mm; mobile phase, acetonitrile in water (with 10 mmol/L NH$_4$HCO$_3$), 25% to 55% gradient in 8 min; detector, UV 254/220 nm. 4-[7-[3-cyano-4-(oxan-4-yloxy)phenyl]furo[3,2-b]pyridin-2-yl]-N-(3-hydroxy-1-methylpiperidin-4-yl)-3-methoxybenzamide was obtained as a light yellow solid (15 mg, 37%). HPLC: 97.3% purity, RT=1.18 min. MS: m/z=583.2 [M+H]$^+$. $^1$H NMR (300 MHz, CD$_3$OD, ppm) δ 8.50-8.26 (m, 3H), 7.99 (d, J=8.1 Hz, 1H), 7.68-7.40 (m, 5H), 4.97-4.85 (m, 1H), 4.11 (s, 3H), 4.10-3.81 (m, 4H), 3.73-3.59 (m, 2H), 3.29-2.98 (m, 2H), 2.65-2.20 (m, 4H), 2.20-2.06 (m, 3H), 1.94-1.72 (m, 3H).

Example 302: 4-[7-[3-cyano-4-(oxan-4-yloxy)phenyl]furo[3,2-b]pyridin-2-yl]-N-(4-hydroxy-1-methylpiperidin-3-yl)-3-methoxybenzamide (348)

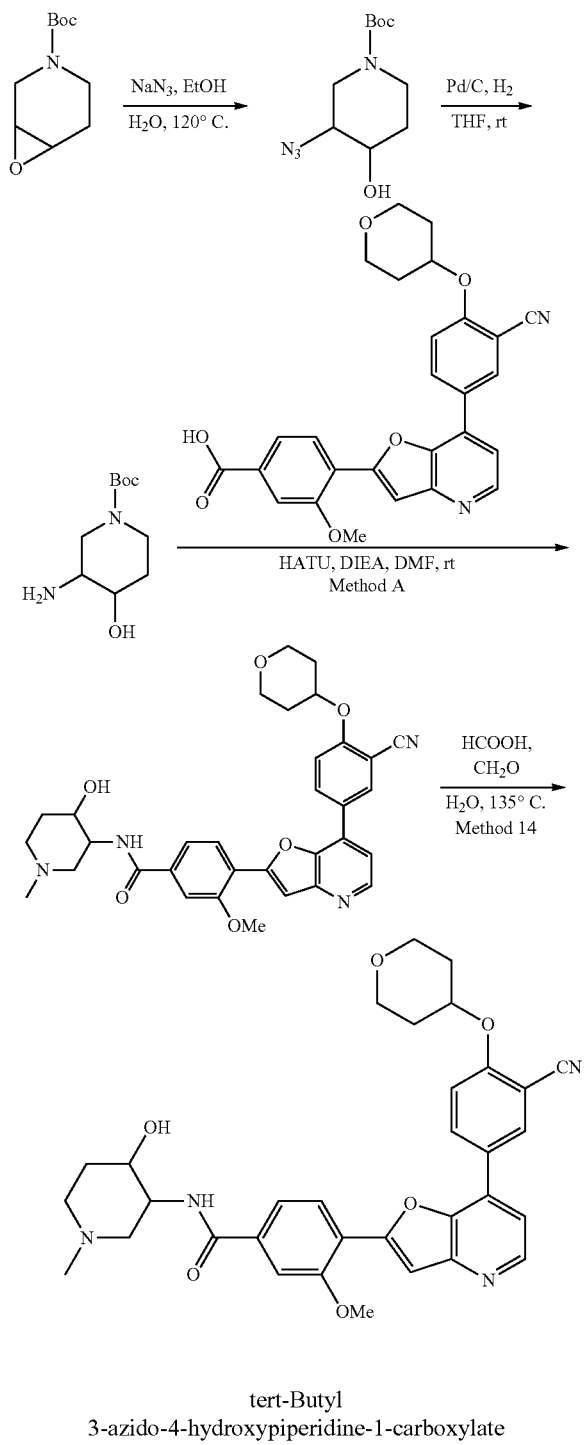

acetate (20 mL×3). The organic phases were combined, washed with brine and dried over sodium sulfate. The solvent was removed under reduced pressure and the residue was purified by flash chromatography eluting with EtOAc in hexane (50% to 67% gradient) to yield tert-butyl 3-azido-4-hydroxypiperidine-1-carboxylate as colorless oil (70 mg, 19%). MS: m/z=243.1 [M+H]$^+$.

tert-Butyl 4-amino-3-hydroxypiperidine-1-carboxylate

To a solution of tert-butyl 4-azido-3-hydroxypiperidine-1-carboxylate (57 mg, 0.23 mmol) in tetrahydrofuran (5 mL) was added palladium carbon (10%, 10 mg, 0.09 mmol) under nitrogen atmosphere. The reaction flask was vacuumed and flushed with hydrogen gas. The reaction mixture was then hydrogenated for 30 min at room temperature under hydrogen atmosphere with a hydrogen balloon. After the reaction was done, the reaction mixture was filtered through a Celite pad and the filtrate was concentrated under reduced pressure to yield tert-butyl 4-amino-3-hydroxypiperidine-1-carboxylate as colorless oil (45 mg, 88%0). MS: m/z=217.1 [M+H]$^+$.

4-[7-[3-Cyano-4-(oxan-4-yloxy)phenyl]furo[3,2-b]pyridin-2-yl]-N-(4-hydroxy-1-methylpiperidin-3-yl)-3-methoxybenzamide The title compound was prepared from 4-(7-(3-cyano-4-(tetrahydro-2H-pyran-4-yloxy)phenyl)furo[3,2-b]pyridin-2-yl)-3-methoxybenzoic acid and tert-butyl 3-amino-4-hydroxypiperidine-1-carboxylate using Methods A and 14. The product was purified by prep-HPLC under the following conditions: column, XBridge Shield RP18 OBD Column, 5 um, 19×150 mm; mobile phase, acetonitrile in water (with 10 mmol/L NH$_4$HCO$_3$), 25% to 55% gradient in 8 min; detector, UV 254/220 nm. 4-[7-[3-cyano-4-(oxan-4-yl oxy)phenyl]furo[3,2-b]pyridin-2-yl]-N-(4-hydroxy-1-methylpiperidin-3-yl)-3-methoxybenzamide was obtained as a white solid (12 mg, 35%0). HPLC: 91.8% purity, RT=1.55 min. MS: m/z=583.2 [M+H]$^+$. $^1$H NMR (300 MHz, CD$_3$OD, ppm) δ 8.47 (d, J=5.2 Hz, 1H), 8.40-8.30 (m, 2H), 8.04 (d, J=8.1 Hz, 1H), 7.69-7.42 (m, 5H), 4.97-4.82 (m, 1H), 4.17-3.93 (m, 6H), 3.74-3.60 (m, 3H), 3.12-2.98 (m, 1H), 2.88-2.74 (m, 1H), 2.32 (s, 3H), 2.28-1.60 (m, 8H).

Example 303: N-(3-cyano-1-methylpyrrolidin-3-yl-4-[7-[3-cyano-4-(oxan-4-yloxy)phenyl]furo[3,2-b]pyridin-2-yl]-3-methoxybenzamide (349)

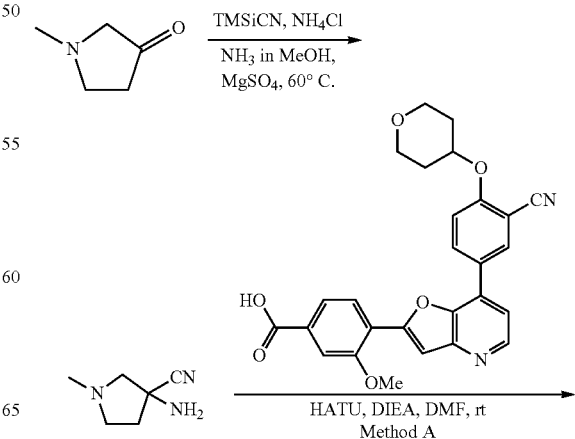

tert-Butyl 3-azido-4-hydroxypiperidine-1-carboxylate

To a solution of tert-butyl 7-oxa-3-azabicyclo[4.1.0]heptane-3-carboxylate (300 mg, 1.51 mmol) in ethanol (2.5 mL) was added a solution of NaN3 (195 mg, 3.00 mmol) in water (2.5 mL) at room temperature. The resulting mixture was stirred for 30 min at 120° C. After cooling to room temperature, the reaction mixture was extracted with ethyl

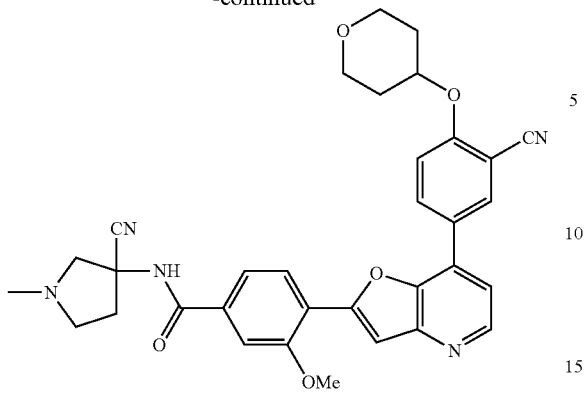

3-Amino-1-methylpyrrolidine-3-carbonitrile

To a solution of 1-methylpyrrolidin-3-one (238 mg, 2.40 mmol) in MeOH (10 mL) was added tert-butylsilanecarbonitrile (542 mg, 4.79 mmol), NH$_4$Cl (270 mg, 5.05 mmol), a solution of NH$_3$ in MeOH (7 M, 1.5 mL, 10.50 mmol) and magnesium sulfate (600 mg, 5.04 mmol) at room temperature. The resulting mixture was stirred for 3 h at 60° C. After the reaction was done, the reaction mixture was concentrated under reduced pressure and the residue was purified by flash chromatography eluting with MeOH in DCM (0% to 15% gradient) to yield 3-amino-1-methylpyrrolidine-3-carbonitrile was obtained as a brown solid (35 mg, 12%). MS: m/z=126.1 [M+H]$^+$.

N-(3-Cyano-1-methylpyrrolidin-3-yl)-4-[7-[3-cyano-4-(oxan-4-yloxy)phenyl]furo[3,2-b]pyridin-2-yl]-3-methoxybenzamide The title compound was prepared from 4-(7-(3-cyano-4-(tetrahydro-2H-pyran-4-yloxy)phenyl)furo[3,2-b]pyridin-2-yl)-3-methoxybenzoic acid and 3-amino-1-methylpyrrolidine-3-carbonitrile using Method A. The product was purified by prep-HPLC under the following conditions: column, XBridge Shield RP18 OBD Column, 5 um, 19×150 mm; mobile phase, acetonitrile in water (with 10 mmol/L NH$_4$HCO$_3$), 200/% to 50% gradient in 8 min; detector, UV 254/220 nm. N-(3-cyano-1-methylpyrrolidin-3-yl)-4-[7-[3-cyano-4-(oxan-4-yloxy)phenyl]furo[3,2-b]pyridin-2-yl]-3-methoxybenzamide was obtained as a off-white solid (15 mg, 13%). HPLC: 99.5% purity, RT=1.33 min. MS: m/z=578.2 [M+H]$^+$. $^1$H NMR (300 MHz, CD$_3$OD, ppm) δ 8.47 (d, J=5.2 Hz, 1H), 8.39-8.28 (m, 2H), 8.03 (d, J=8.1 Hz, 1H), 7.68-7.42 (m, 5H), 4.97-4.87 (m, 1H), 4.14-3.93 (m, 5H), 3.74-3.50 (m, 2H), 3.39-3.29 (m, 1H), 3.08 (d, J=10.6 Hz, 1H), 2.82-2.64 (m, 3H), 2.58-2.40 (m, 4H), 2.20-2.06 (m, 2H), 1.93-1.79 (m, 2H).

Example 304: 4-[7-[3-cyano-4-(oxan-4-yloxy)phenyl]furo[3,2-b]pyridin-2-yl]-N-[(3S,5R)-5-(hydroxymethyl)-1-methylpyrrolidin-3-yl]-3-methoxybenzamide (350)

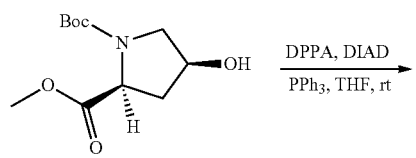

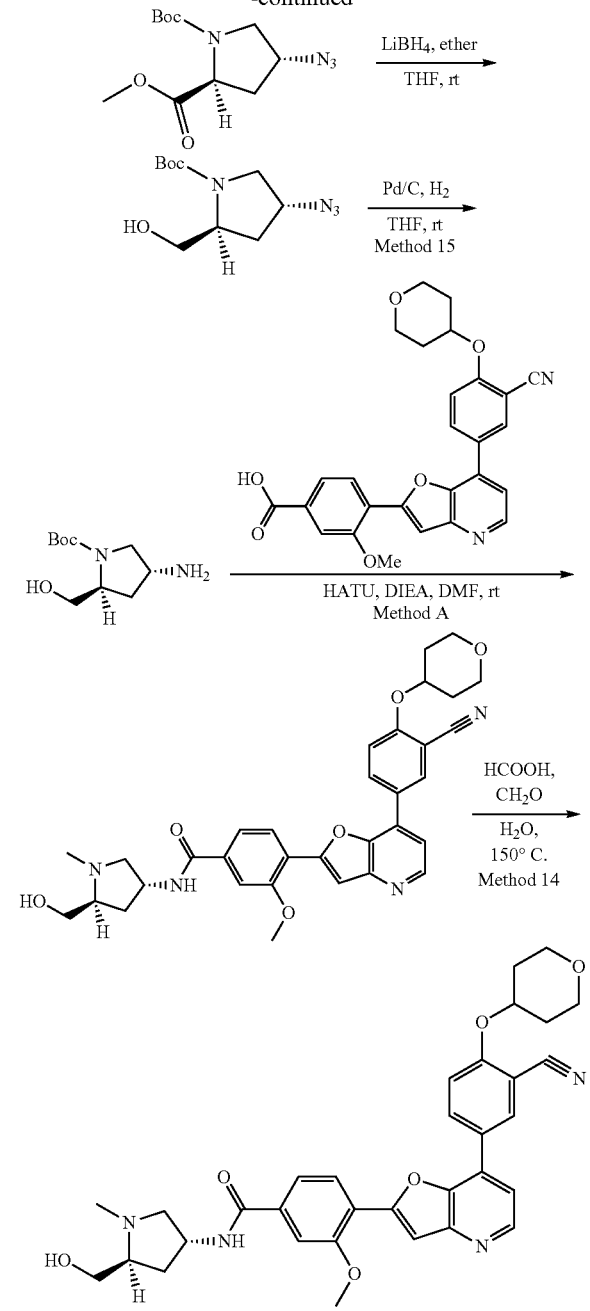

(2S,4S)-1-tert-Butyl 2-methyl 4-hydroxypyrrolidine-1,2-dicarboxylate

At 0° C., to a solution of 1-tert-butyl 2-methyl (2R,4R)-4-hydroxypyrrolidine-1,2-dicarboxylate (500 mg, 2.04 mmol) in tetrahydrofuran (10 mL) was added PPh$_3$ (642 mg, 2.45 mmol). Then DIAD (536 mg, 2.65 mmol) was added in portions at 0° C. The resulting solution was stirred for 30 min at 0° C., and then was added by DPPA (673 mg, 2.45 mmol) slowly. The reaction mixture was stirred for additional 2 h at room temperature. When the reaction was done, it was quenched by the addition of water (20 mL). The mixture was extracted with ethyl acetate (30 mL×3). The organic phases were combined, washed with brine and dried over sodium sulfate. The solvent was removed under reduced pressure and the residue was purified by flash chromatography eluting with EtOAc in hexane (0% to 9% gradient) to yield 1-tert-butyl 2-methyl (2R,4S)-4-azidopyrrolidine-1,2-dicarboxylate as colorless oil (240 mg, 44%). MS: m/z=271.1 [M+H]$^+$.

(2S,4R)-1-tert-butyl 2-methyl 4-azidopyrrolidine-1,2-dicarboxylate

At 0° C., to a solution of 1-tert-butyl 2-methyl (2R,4S)-4-azidopyrrolidine-1,2-dicarboxylate (240 mg, 0.89 mmol) in ether (5 mL) and THF (2 mL) was added LiBH4 (39 mg, 1.79 mmol). The resulting mixture was stirred for 30 min at 0° C., warmed up to room temperature and stirred for 2 h at room temperature. When the reaction was done, it was quenched by the addition of sat. sodium bicarbonate solution (15 mL). The resulting mixture was extracted with ethyl acetate (20 mL×3). The organic phases were combined, washed with brine and dried over sodium sulfate. The solvent was removed under reduced pressure to yield tert-butyl (2R)-4-azido-2-(hydroxymethyl)pyrrolidine-1-carboxylate as colorless oil (183 mg, 85%). MS: m/z=243.1 [M+H]$^+$.

4-[7-[3-cyano-4-(oxan-4-yloxy)phenyl]furo[3,2-b]pyridin-2-yl]-N-[(3S,5R)-5-(hydroxymethyl)-1-methylpyrrolidin-3-yl]-3-methoxybenzamide The title compound was prepared from 4-(7-(3-cyano-4-(tetrahydro-2H-pyran-4-yloxy)phenyl)furo[3,2-b]pyridin-2-yl)-3-methoxybenzoic acid and (2S,4R)-tert-butyl 4-azido-2-(hydroxymethyl)pyrrolidine-1-carboxylate using Methods 15, A and 14. The product was purified by prep-HPLC under the following conditions: column, XBridge Shield RP18 OBD Column, 5 um, 19×150 mm; mobile phase, acetonitrile in water (with 10 mmol/L NH$_4$HCO$_3$), 20% to 50% gradient in 8 min; detector, UV 254/220 nm. 4-[7-[3-cyano-4-(oxan-4-yloxy)phenyl]furo[3,2-b]pyridin-2-yl]-N-[(3S,5R)-5-(hydroxymethyl)-1-methylpyrrolidin-3-yl]-3-methoxybenzamide was obtained as a white solid (44 mg, 26%). HPLC: 96.5% purity, RT=1.23 min. MS: m/z=583.2 [M+H]$^+$. $^1$H NMR (300 MHz, CD$_3$OD, ppm) δ 8.45 (d, J=5.2 Hz, 1H), 8.38-8.26 (m, 2H), 7.99 (d, J=8.1 Hz, 1H), 7.62-7.40 (m, 5H), 4.97-4.85 (m, 1H), 4.60-4.46 (m, 1H), 4.12-3.92 (m, 5H), 3.74-3.45 (m, 5H), 2.89-2.72 (m, 1H), 2.58-2.45 (m, 4H), 2.29-1.97 (m, 4H), 1.94-1.74 (m, 2H).

Example 305: 6-[7-[6-cyano-5-(oxan-4-yloxy)pyridin-2-yl]-6-fluorofuro[3,2-b]pyridin-2-yl]-5-methoxy-N,N-dimethylpyridine-3-carboxamide hydrochloride (351)

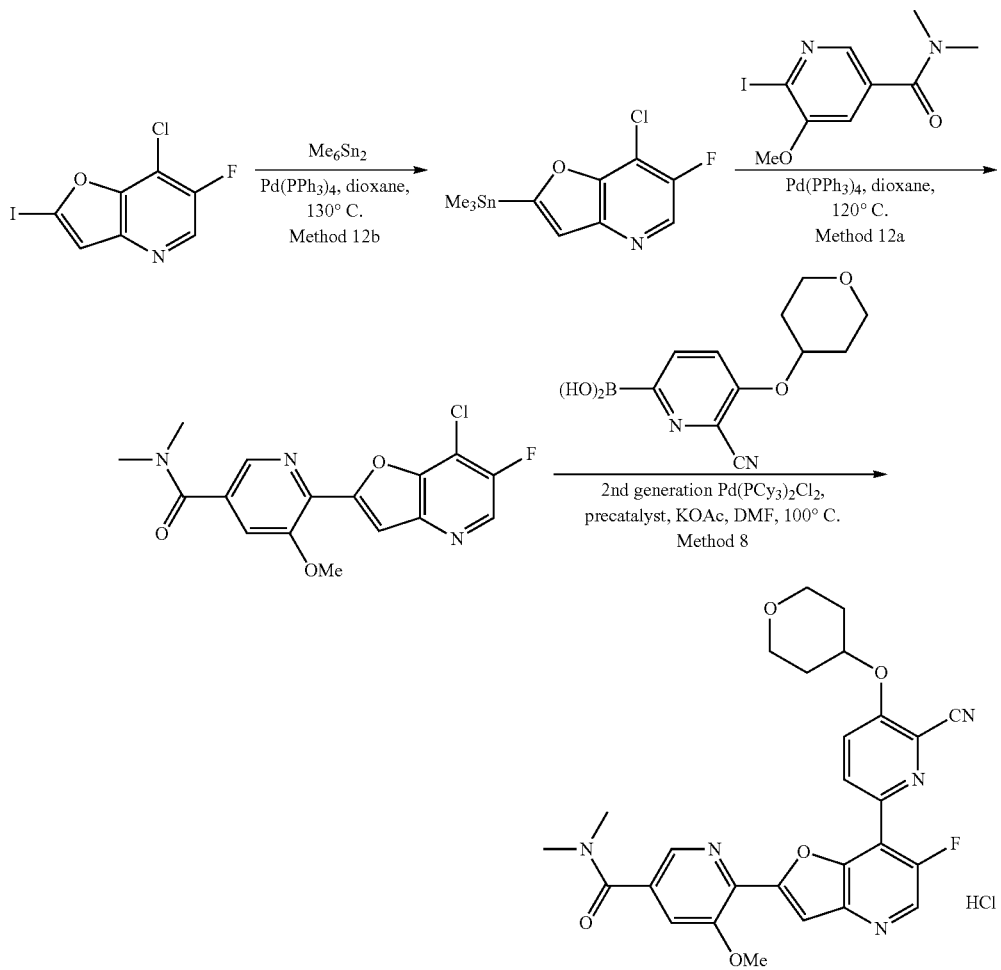

549

The title compound was prepared from 7-chloro-6-fluoro-2-iodofuro[3,2-b]pyridine, 6-iodo-5-methoxy-N,N-dimethylnicotinamide, and 6-cyano-5-(tetrahydro-2H-pyran-4-yloxy)pyridin-2-ylboronic acid using Methods 12a, 12b, and 8. The product was purified by prep-HPLC under the following conditions: column, XBridge Shield RP18 OBD Column, 5 um, 19×150 mm; mobile phase, acetonitrile in water (with 0.02% HCl) 20% to 50% gradient in 8 min; detector, UV 254/220 nm. 4-[7-[3-cyano-4-(oxan-4-yloxy)phenyl]furo[3,2-b]pyridin-2-yl]-N-[(3S,5R)-5-(hydroxymethyl)-1-methylpyrrolidin-3-yl]-3-m ethoxybenzamide was obtained as a yellow solid (15 mg, 23% for 3 steps). HPLC: 99.6% purity, RT=1.25 min. MS: m/z=518.2 [M+H]$^+$. $^1$H NMR (300 MHz, CD$_3$OD, ppm) δ 8.63 (d, J=3.1 Hz, 1H), 8.36-8.18 (m, 2H), 7.96 (d, J=9.0 Hz, 1H), 7.83 (s, 1H), 7.72 (s, 1H), 5.01-4.91 (m, 1H), 4.12 (s, 3H), 4.05-3.91 (m, 2H), 3.74-3.60 (m, 2H), 3.12 (s, 3H), 3.05 (s, 3H), 2.18-2.08 (m, 2H), 1.93-1.83 (m, 2H).

Example 306: 6-(7-[6-cyano-5-[(oxan-4-yl)amino]pyridin-2-yl]-6-fluorofuro[3,2-b]pyridin-2-yl-5-methoxy-N,N-dimethylpyridine-3-carboxamide (352)

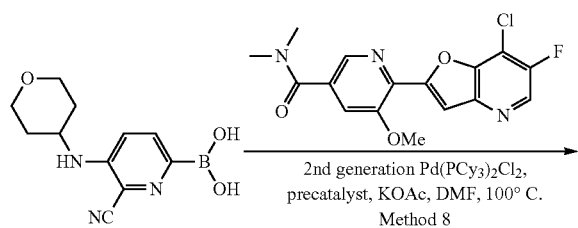

550

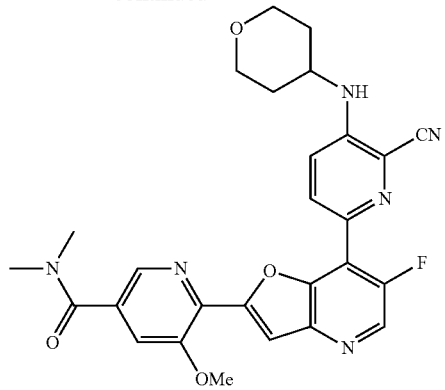

The title compound was prepared from 6-(7-chloro-6-fluorofuro[3,2-b]pyridin-2-yl)-5-methoxy-N,N-dimethylnicotinamide and 6-cyano-5-(tetrahydro-2H-pyran-4-yloxy)pyridin-2-ylboronic acid using Method 8. The product was purified by prep-HPLC under the following conditions: column, XBridge Shield RP18 OBD Column, 5 um, 19×150 mm; mobile phase, acetonitrile in water (with 10 mmol/L NH$_4$HCO$_3$), 20% to 55% gradient in 8 min; detector, UV 254/220 nm. 6-(7-[6-cyano-5-[(oxan-4-yl)amino]pyridin-2-yl]-6-fluorofuro[3,2-b]pyridin-2-yl)-5-methoxy-N,N-dimethylpyridine-3-carboxamide was obtained as a white solid (5 mg, 17%). HPLC: 99.9% purity, RT=1.35 min. MS: m % z=517.3 [M+H]$^+$. $^1$H NMR (300 MHz, CD$_3$OD, ppm) δ 8.61 (d, J=3.3 Hz, 1H), 8.33 (d, J=1.6 Hz, 1H), 8.10 (dd, J=9.1, 1.0 Hz, 1H), 7.83 (s, 1H), 7.75 (d, J=1.6 Hz, 1H), 7.59 (d, J=9.1 Hz, 1H), 4.15 (s, 3H), 4.04 (d, J=10.1 Hz, 2H), 3.92-3.78 (m, 1H), 3.68-3.53 (m, 2H), 3.16 (s, 3H), 3.09 (s, 3H), 2.11-2.00 (m, 2H), 1.85-1.66 (m, 2H).

Example 307: 6-(7-[6-cyano-5-[(oxan-4-yl)amino]pyridin-2-yl]-6-cyclopropylfuro[3,2-b]pyridin-2-yl)-5-methoxy-N,N-dimethylpyridine-3-carboxamide hydrochloride (353)

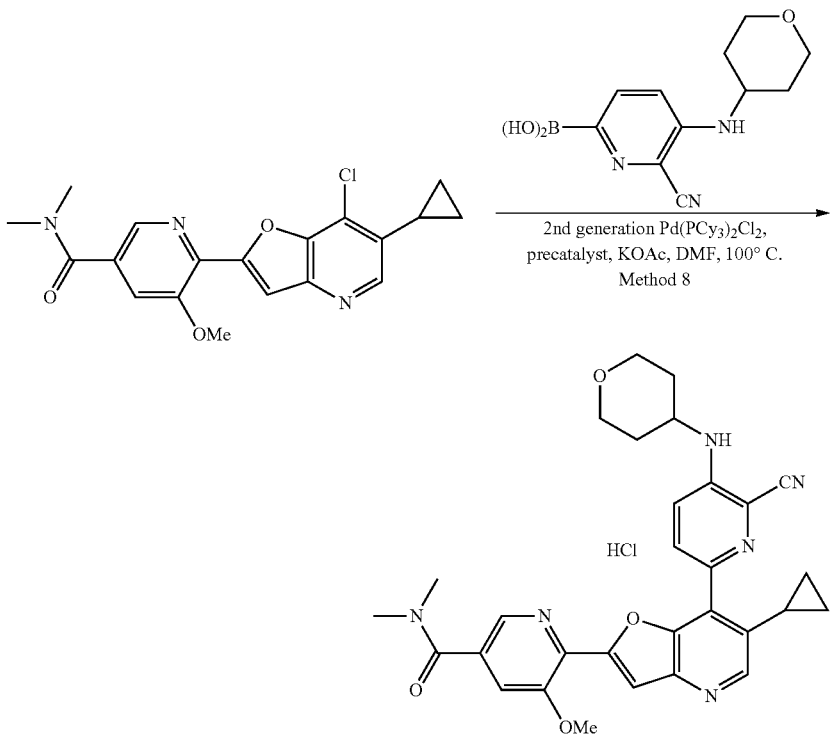

The title compound was prepared from 6-(7-chloro-6-cyclopropylfuro[3,2-b]pyridin-2-yl)-5-methoxy-N,N-dimethylnicotinamide and 6-cyano-5-(tetrahydro-2H-pyran-4-ylamino)pyridin-2-ylboronic acid using Method 8. The product was purified by prep-HPLC under the following conditions: column, XBridge Shield RP18 OBD Column, 5 um, 19×150 mm; mobile phase, acetonitrile in water (with 0.02% HCl) 20% to 50% gradient in 8 min; detector, UV 254/220 nm. 6-(7-[6-cyano-5-[(oxan-4-yl)amino]pyridin-2-yl]-6-cyclopropylfuro[3,2-b]pyridin-2-yl)-5-methoxy-N,N-dimethylpyridine-3-carboxamide hydrochloride was obtained as a yellow solid (10 mg, 32%). HPLC: 96.1% purity, RT=1.09 min. MS: m/z=539.2 [M+H]$^+$. $^1$H NMR (300 MHz, CD$_3$OD, ppm) δ 8.59 (s, 1H), 8.38 (s, 1H), 8.14 (d, J=8.6 Hz, 1H), 7.93 (s, 1H), 7.82 (s, 1H), 7.66 (d, J=8.7 Hz, 1H), 4.17 (s, 3H), 4.10-3.99 (m, 2H), 3.95-3.83 (m, 1H), 3.69-3.53 (m, 2H), 3.16 (s, 3H), 3.08 (s, 3H), 2.55-2.43 (m, 1H), 2.11-1.92 (m, 2H), 1.82-1.70 (m, 2H), 1.09 (d, J=8.2 Hz, 2H), 0.86-0.59 (m, 2H).

Example 308: 6-[7-[6-cyano-5-(oxan-4-yloxy)pyridin-2-yl]-6-fluorofuro[3,2-b]pyridin-2-yl]-N-(2-hydroxyethyl)-5-methoxy-N-methylpyridine-3-carboxamide hydrochloride (354)

N-[2-[(tert-butyldimethylsilyl)oxy]ethyl]-6-[7-[6-cyano-5-(oxan-4-yloxy)pyridin-2-yl]-6-fluorofuro[3,2-b]pyridin-2-yl]-5-methoxy-N-methylpyridine-3-carboxamide The title compound was prepared from 7-chloro-6-fluoro-2-(trimethylstannyl)furo[3,2-b]pyridine, N-(2-(tert-butyldimethylsilyloxy)ethyl)-6-iodo-5-methoxy-N-methylnicotinamide and 6-cyano-5-(tetrahydro-2H-pyran-4-yloxy)pyridin-2-ylboronic acid using Methods 12a and 8. The obtained crude final product (20 mg, yellow solid) was used directly in next step without further purification.

6-[7-[6-cyano-5-(oxan-4-yloxy)pyridin-2-yl]-6-fluorofuro[3,2-b]pyridin-2-yl]-N-(2-hydroxyethyl)-5-methoxy-N-methylpyridine-3-carboxamide hydrochloride N-[2-[(tert-butyldimethylsilyl)oxy]ethyl]-6-[7-[6-cyano-5-(oxan-4-yloxy)pyridin-2-yl]-6-fluorofuro[3,2-b]pyridin-2-yl]-5-methoxy-N-methylpyridine-3-carboxamide (20 mg, crude) was added to a solution of HCl in THF (4.5 mL, 2 M) at room temperature. The resulting solution was stirred for 1 h at room temperature. After the reaction was done, the reaction mixture was concentrated under reduced pressure.

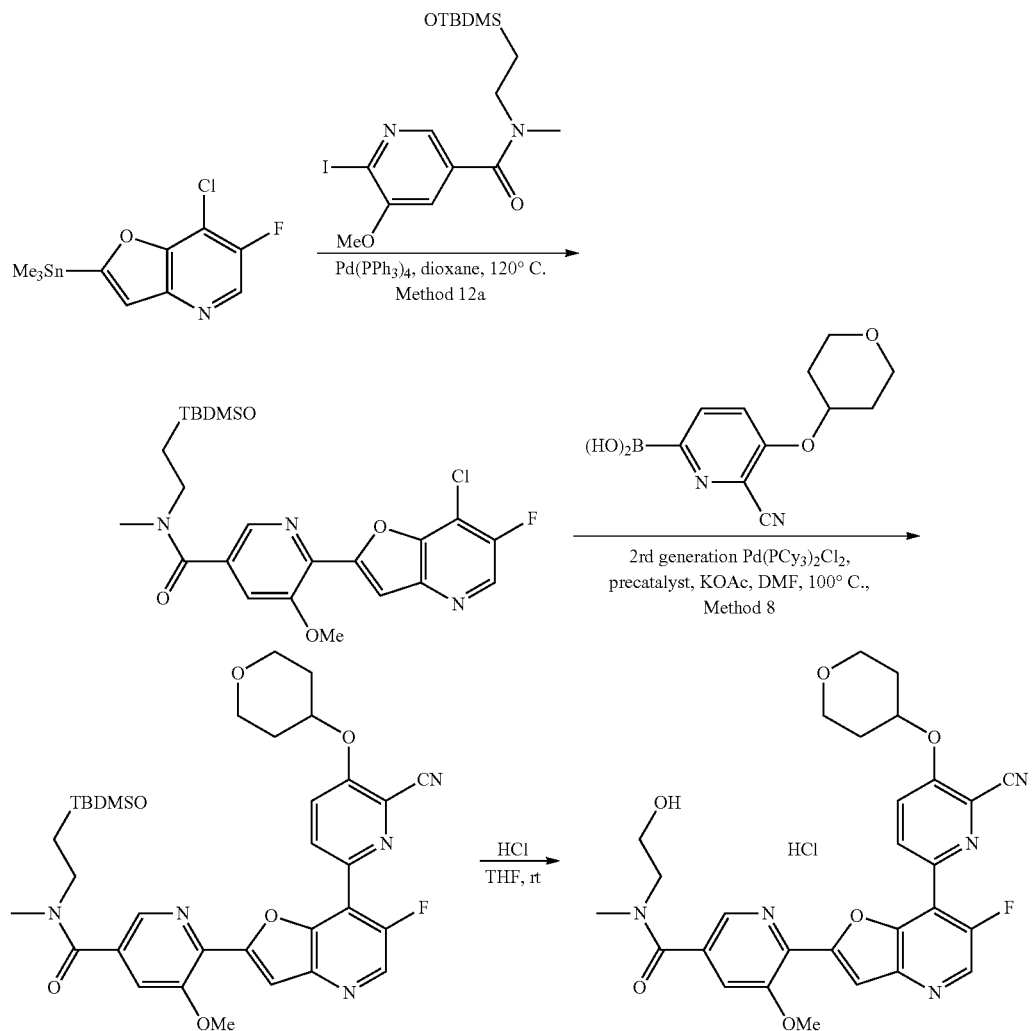

The residue was purified by prep-HPLC under the following conditions: column, XBridge Shield RP18 OBD Column, 5 um, 19×150 mm, mobile phase, acetonitrile in water (with 0.02% HCl), 20%0, to 50% gradient in 8 min; detector, UV 254/220 nm. 6-[7-[6-cyano-5-(oxan-4-yloxy)pyridin-2-yl]-6-fluorofuro[3,2-b]pyridin-2-yl]-N-(2-hydroxyethyl)-5-methoxy-N-methylpyridine-3-carboxamide hydrochloride was obtained as a light yellow solid (9 mg, 8% for 3 steps). HPLC: 95.7% purity, RT=1.04 min. MS: m/z=548.2 [M+H]$^+$. $^1$H NMR (300 MHz, CD$_3$OD, ppm) δ8.608 (s, 1H), 8.35-8.19 (m, 2H), 7.94 (d, J=9.0 Hz, 1H), 7.87-7.72 (m, 2H), 5.01-4.89 (m, 1H), 4.11 (s, 3H), 4.06-3.94 (m, 2H), 3.88-3.76 (m, 1H), 3.74-3.60 (m, 4H), 3.51-3.39 (m, 1H), 3.11 (d, J=7.0 Hz, 3H), 2.21-2.05 (m, 2H), 2.03-1.78 (m, 2H).

Example 309: 4-[7-[3-cyano-4-(oxan-4-yloxy)phenyl]furo[3,2-b]pyridin-2-yl]-3-methoxy-N-[1-(2-methylpropyl)azetidin-3-yl]benzamide (355)

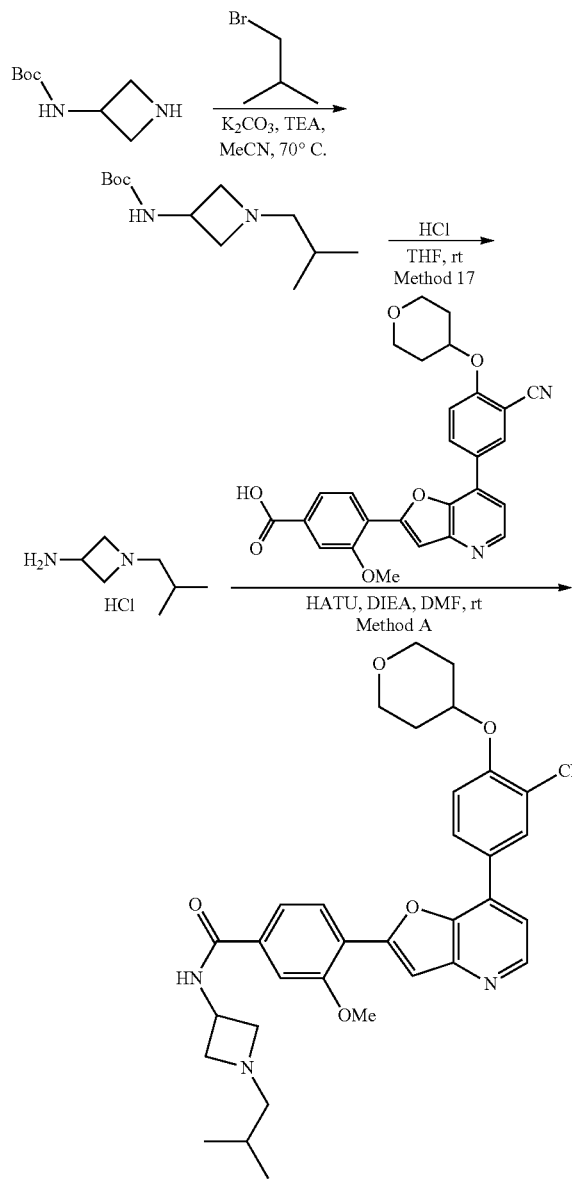

tert-Butyl 1-isobutylazetidin-3-ylcarbamate

To a solution of tert-butyl N-(azetidin-3-yl)carbamate (285 mg, 1.65 mmol) in acetonitrile (15 mL) were added 1-bromo-2-methylpropane (398 mg, 2.91 mmol), potassium carbonate (670 mg, 4.85 mmol) and TEA (466 mg, 4.61 mmol) at room temperature. The resulting mixture was stirred overnight at 70° C. After the reaction was done, the insoluble solids in the reaction mixture were filtered out and The filtrate was concentrated under reduced pressure. The residue was purified by flash chromatography eluting with MeOH in DCM (0% to 5% gradient) to yield tert-butyl N-[1-(2-methylpropyl)azetidin-3-yl]carbamate as a brown solid (200 mg, 53%).

Method 17

1-isobutylazetidin-3-amine hydrochloride

To a solution of tert-butyl N-[1-(2-methylpropyl)azetidin-3-yl]carbamate (80 mg, 0.35 mmol) in THF (10 mL) was added hydrogen chloride solution (12 M, 0.5 mL) at room temperature. The resulting mixture was stirred for 2 h at room temperature. When the reaction was done, the resulting mixture was concentrated under reduced pressure to yield 1-isobutylazetidin-3-amine hydrochloride as a brown solid (90 mg, crude).

4-[7-[3-cyano-4-(oxan-4-yloxy)phenyl]furo[3,2-b]pyridin-2-yl]-3-methoxy-N-[1-(2-methylpropyl)azetidin-3-yl]benzamide The title compound was prepared from 4-(7-(3-cyano-4-(tetrahydro-2H-pyran-4-yloxy)phenyl)furo[3,2-b]pyridin-2-yl)-3-methoxybenzoic acid and 1-isobutylazetidin-3-amine hydrochloride using Method A. The product was first purified by prep-HPLC under the following conditions: column, XBridge Prep C18 OBD Column, 5 um, 19×150 mm; mobile phase, acetonitrile in water (with 10 mmol/L NH$_4$HCO$_3$), 25% to 55% gradient in 8 min; detector, UV 254/220 nm. 4-[7-[3-cyano-4-(oxan-4-yloxy)phenyl]furo[3,2-b]pyridin-2-yl]-3-methoxy-N-[1-(2-methylpropyl)azetidin-3-yl]benzamide was obtained as a white solid (28 mg, 8% for 2 steps). HPLC: 99.5% purity, RT=1.36 min. MS: m/z=581.3 [M+H]$^+$. $^1$H NMR (300 MHz, CD$_3$OD, ppm) δ 8.40 (d, J=5.2 Hz, 1H), 8.32-8.22 (m, 2H), 7.91 (d, J=8.1 Hz, 1H), 7.59-7.36 (m, 5H), 4.95-4.823 (m, 1H), 4.70-4.58 (m, 1H), 4.09-3.92 (m, 5H), 3.83-3.59 (m, 4H), 3.17 (dd, J=8.5, 6.7 Hz, 2H), 2.39 (d, J=7.0 Hz, 2H), 2.19-2.03 (m, H), 1.93-1.76 (m, 2H), 1.75-1.61 (m, 1H), 0.91 (d, J=6.7 Hz, 6H).

Example 310: 6-(7-[6-cyano-5-[(oxan-4-yl)amino]pyridin-2-yl]furo[3,2-b]pyridin-2-yl)-N-(2-hydroxyethyl)-5-methoxy-N-methylpyridine-3-carboxamide (356)

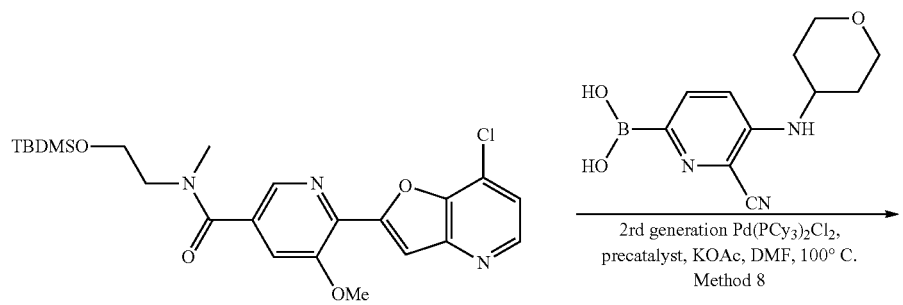

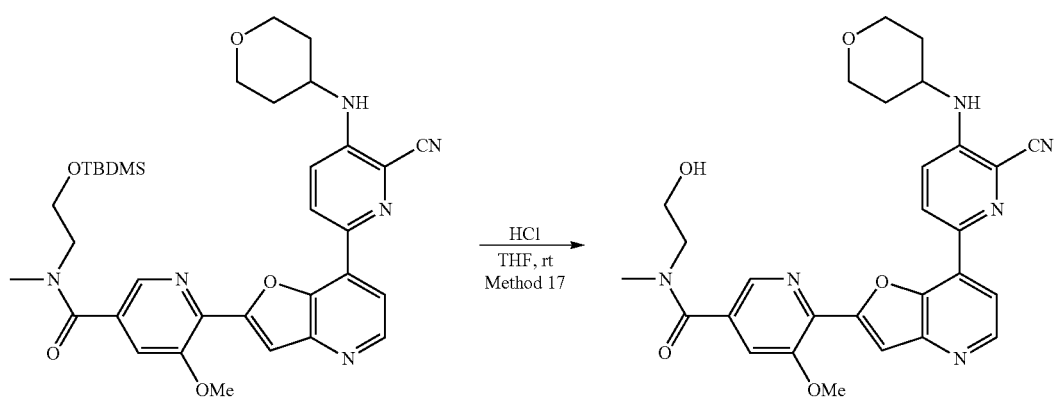

The title compound was prepared from N-(2-(tert-butyldimethylsilyloxy)ethyl)-6-(7-chlorofuro[3,2-b]pyridin-2-yl)-5-methoxy-N-methylnicotinamide and 6-cyano-5-(tetrahydro-2H-pyran-4-ylamino)pyridin-2-ylboronic acid using Methods 8 and 17. The crude products were purified by the separation on prep-HPLC under the following conditions: Column XBridge Shield RP18 OBD Column, 5 um, 19×150 mm; MeCN in water (with 10 mmol/L $NH_4HCO_3$), 20% to 40% gradient in 10 min; Detector, UV 254/220 nm. 6-(7-[6-cyano-5-[(oxan-4-yl)amino]pyridin-2-yl]furo[3,2-b]pyridin-2-yl)-N-(2-hydroxyethyl)-5-methoxy-N-methylpyridine-3-carboxamide was obtained as a off-white solid (7.5 mg, 21%). HPLC: 99.7% purity, RT=0.90 min. MS: m/z=529.2 $[M+H]^+$. $^1$H NMR (300 MHz, $CD_3OD$, ppm) δ 8.64 (d, J=9.0 Hz, 1H), 8.44 (d, J=5.3 Hz, 1H), 8.36 (s, 1H), 7.97 (d, J=5.2 Hz, 1H), 7.87-7.60 (m, 2H), 7.42 (d, J=9.2 Hz, 1H), 4.11 (d, J=5.8 Hz, 3H), 4.06-3.95 (m, 2H), 3.91-3.66 (m, 4H), 3.65-3.45 (m, 3H), 3.15 (s, 3H), 2.06-1.94 (m, 2H), 1.78-1.58 (m, 2H).

Example 311: 6-[7-[6-cyano-5-(oxan-4-yloxy)pyridin-2-yl]-6-cyclopropylfuro[3,2-b]pyridin-2-yl]-5-methoxy-N,N-dimethylpyridine-3-carboxamide hydrochloride (357)

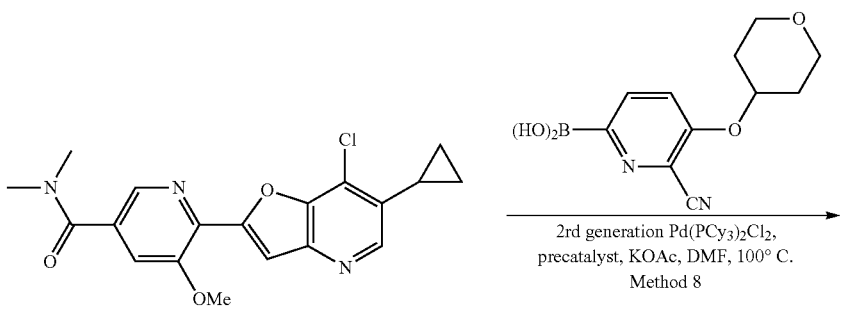

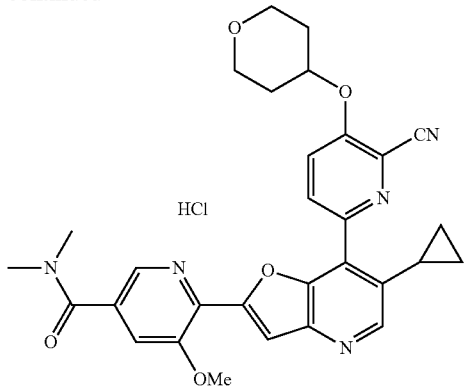

The title compound was prepared from 6-(7-chloro-6-cyclopropylfuro[3,2-b]pyridin-2-yl)-5-methoxy-N,N-dimethylnicotinamide and 6-cyano-5-(tetrahydro-2H-pyran-4-yloxy)pyridin-2-ylboronic acid using Method 8. The product was purified by prep-HPLC under the following conditions: column, XBridge Shield RP18 OBD Column, 5 um, 19×150 mm; mobile phase, acetonitrile in water (with 0.02% HCl), 20% to 50% gradient in 8 min; detector, UV 254/220 nm. 6-[7-[6-cyano-5-(oxan-4-yloxy)pyridin-2-yl]-6-cyclopropylfuro[3,2-b]pyridin-2-yl]-5-methoxy-N,N-dimethylpyridine-3-carboxamide hydrochloride was obtained as a light yellow solid (10 mg, 32%). HPLC: 98.9% purity, RT=1.15 min. MS: m/z=540.2 [M+H]+. 1H NMR (300 MHz, CD3OD, ppm) δ 8.64 (s, 1H), 8.37 (d, J=1.4 Hz, 1H), 8.27 (d, J=8.8 Hz, 1H), 8.08 (d, J=8.8 Hz, 1H), 7.96 (s, 1H), 7.83 (d, J=1.5 Hz, 1H), 5.10-5.00 (m, 1H), 4.18 (s, 3H), 4.10-4.00 (m, 2H), 3.77-3.65 (m, 2H), 3.16 (s, 3H), 3.10 (s, 3H), 2.44-2.32 (m, 1H), 2.25-2.13 (m, 2H), 2.00-1.86 (m, 2H), 1.15-0.94 (m, 2H), 0.90-0.80 (m, 2H).

Example 312: 6-(7-[6-cyano-5-[(oxan-4-yl)amino]pyridin-2-yl]-6-methoxyfuro[3,2-b]pyridin-2-yl)-5-methoxy-N,N-dimethylpyridine-3-carboxamide (358)

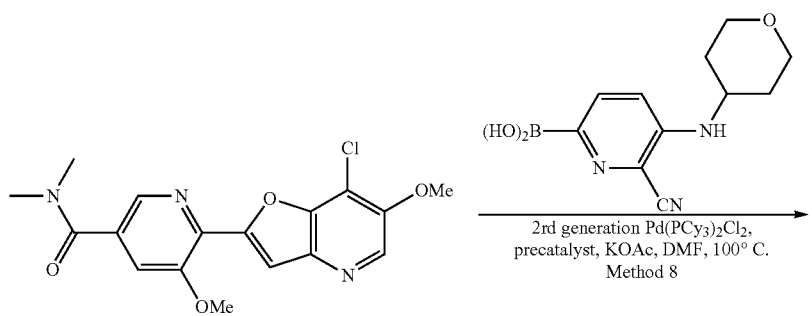

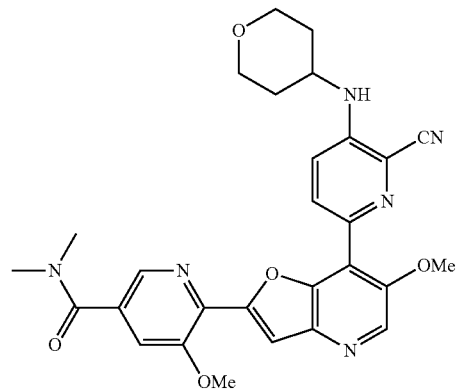

The title compound was prepared from 6-(7-chloro-6-methoxyfuro[3,2-b]pyridin-2-yl)-5-methoxy-N,N-dimethylnicotinamide and 6-cyano-5-(tetrahydro-2H-pyran-4-ylamino)pyridin-2-ylboronic acid using Method 8. The product was purified by prep-HPLC under the following conditions: column, XBridge Shield RP18 OBD Column, 5 um, 19×150 mm; mobile phase, acetonitrile in water (with 10 mmol/L NH$_4$HCO$_3$), 20% to 50% N gradient in 8 min; detector, UV 254/220 nm. 6-(7-[6-cyano-5-[(oxan-4-yl)amino]pyridin-2-yl]-6-methoxyfuro[3,2-b]pyridin-2-yl)-5-methoxy-N,N-dimethylpyridine-3-carboxamide was obtained as a light yellow solid (12 mg, 17%). HPLC: 97.3% purity, RT=3.59 min. MS: m/z=529.2 [M+H]$^+$. $^1$H NMR (300 MHz, DMSO-d$_6$, ppm) δ 8.59 (s, 1H), 8.29 (d, J=1.5 Hz, 1H), 7.80-7.55 (m, 4H), 6.48 (d, J=8.1 Hz, 1H), 4.07 (s, 3H), 4.00-3.85 (m, 5H), 3.82-3.70 (m, 1H), 3.51-3.36 (m, 2H), 3.02 (s, 3H), 2.97 (s, 3H), 1.92-1.81 (m, 2H), 1.76-1.60 (m, 2H).

Example 313: 6-[7-[6-cyano-5-(oxan-4-yloxy)pyridin-2-yl]-6-(propan-2-yl)furo[3,2-b]pyridin-2-yl]-N-(2-hydroxyethyl)-5-methoxy-N-methylpyridine-3-carboxamide hydrochloride (359)

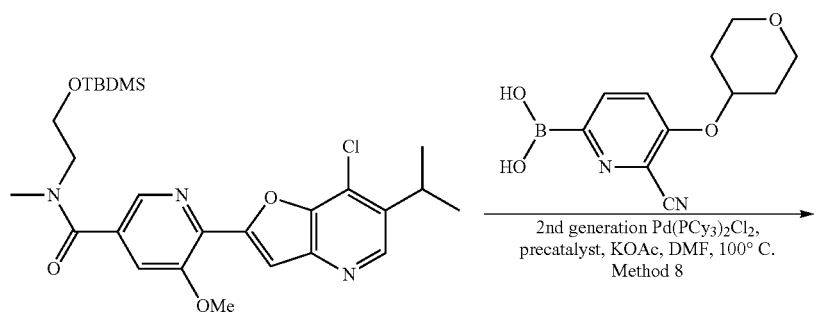

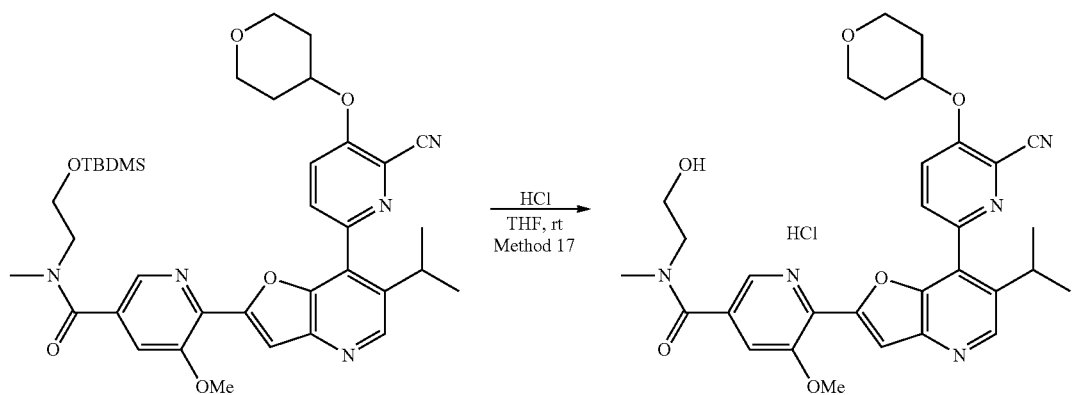

The title compound was prepared from N-(2-(tert-butyldimethylsilyloxy)ethyl)-6-(7-chloro-6-isopropylfuro[3,2-b]pyridin-2-yl)-5-methoxy-N-methylnicotinamide and 6-cyano-5-(tetrahydro-2H-pyran-4-yloxy)pyridin-2-ylboronic acid using Methods 8 and 17. The crude products were purified by the separation on prep-HPLC under the following conditions: Column XBridge Shield RP18 OBD Column, 5 um, 19×150 mm; MeCN in water (with 0.02% HCl), 20% to 50% gradient in 8 min; Detector, UV 254/220 nm. 6-[7-[6-cyano-5-(oxan-4-yloxy)pyridin-2-yl]-6-(propan-2-yl)furo[3,2-b]pyridin-2-yl]-N-(2-hydroxyethyl)-5-methoxy-N-methylpyridine-3-carboxamide hydrochloride was obtained as a yellow solid (10 mg, 66%). HPLC: 95.0%, purity, RT=2.05 min. MS: m/z=572.2 [M+H]$^+$. $^1$H NMR (300 MHz, CD$_3$OD, ppm) δ 8.94 (s, 1H), 8.38 (s, 1H), 8.21 (d, J=8.6 Hz, 1H), 8.09 (d, J=8.6 Hz, 1H), 8.03-7.84 (m, 2H), 5.10-4.95 (m, 1H), 4.18 (d, 0.1=5.2 Hz, 3H), 4.10-3.99 (m, 2H), 3.93-3.81 (m, 1H), 3.78-3.65 (m, 4H), 3.56-3.40 (m, 2H), 3.14 (d, J=14.3 Hz, 3H), 2.25-2.13 (m, 2H), 2.00-1.80 (m, 2H), 1.40 (d, J=6.7 Hz, 6H).

Example 314: 6-[7-[6-cyano-5-(oxan-4-yloxy)pyridin-2-yl]-6-methylfuro[3,2-b]pyridin-2-yl]-N-(2-hydroxyethyl)-5-methoxy-N-methylpyridine-3-carboxamide hydrochloride (360)

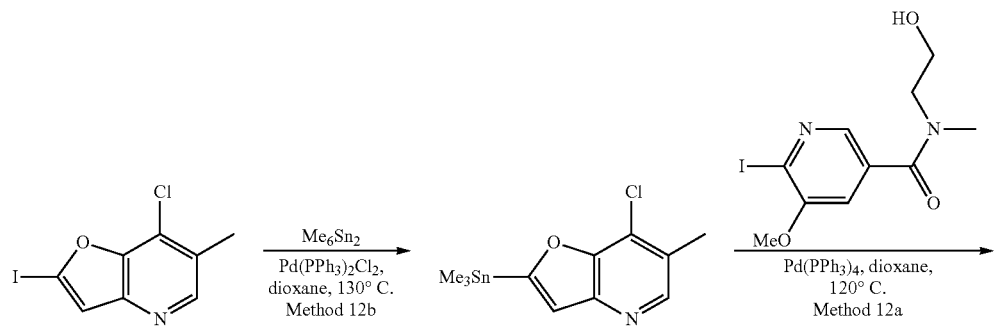

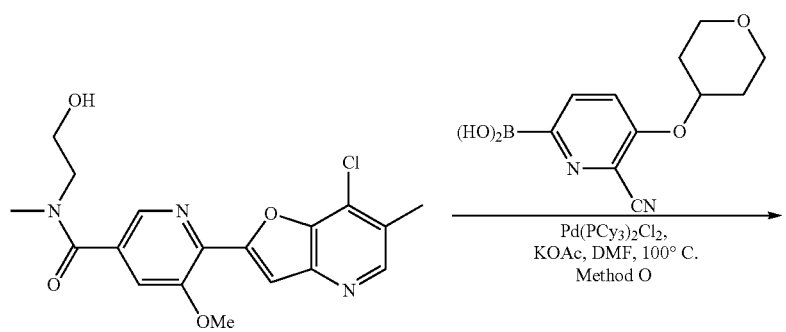

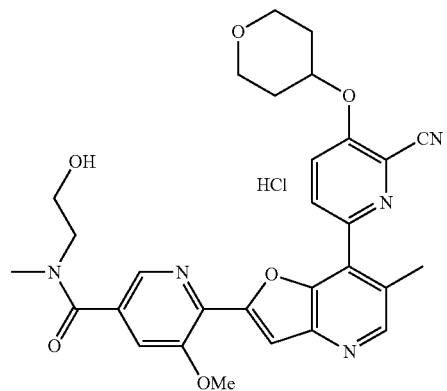

The title compound was prepared from 7-chloro-2-iodo-6-methylfuro[3,2-b]pyridine, N-(2-hydroxyethyl)-6-iodo-5-methoxy-N-methylnicotinamide and 6-cyano-5-(tetrahydro-2H-pyran-4-yloxy)pyridin-2-ylboronic acid using Methods 12a, 12b and O. The product was purified by prep-HPLC under the following conditions: column, XBridge Shield RP18 OBD Column, 5 um, 19×150 mm; mobile phase, acetonitrile in water (with 0.02% HCl), 20% to 35% gradient in 10 min; detector, UV 254/220 nm. 6-[7-[6-cyano-5-(oxan-4-yloxy)pyridin-2-yl]-6-methylfuro[3,2-b]pyridin-2-yl]-N-(2-hydroxyethyl)-5-methoxy-N-methylpyridine-3-carboxamide hydrochloride was obtained as a yellow solid (22 mg, 16%). HPLC: 99.7% purity, RT=0.97 min. MS: m/z=544.2 [M+H]$^+$. $^1$H NMR (300 MHz, CD$_3$OD, ppm) δ 8.95-8.70 (m, 1H), 8.42-8.26 (m, 2H), 8.13-7.90 (m, 3H), 5.10-4.94 (m, 1H), 4.26-4.12 (m, 3H), 4.07-3.78 (m, 3H), 3.75-3.59 (m, 4H), 3.53-3.49 (m, 1H), 3.11 (d, J=13.3 Hz, 2H), 2.80 (s, 1H), 2.66 (s, 3H), 2.22-2.08 (m, 2H), 1.95-1.81 (m, 2H).

Example 315: 6-(7-[6-cyano-5-[(oxan-4-yl)amino]
pyridin-2-yl]-6-(propan-2-yl)furo[3,2-b]pyridin-2-
yl)-5-methoxy-N,N-dimethylpyridine-3-carboxam-
ide (361)

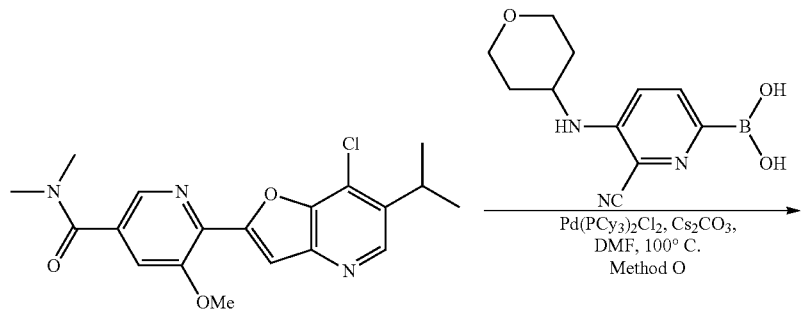

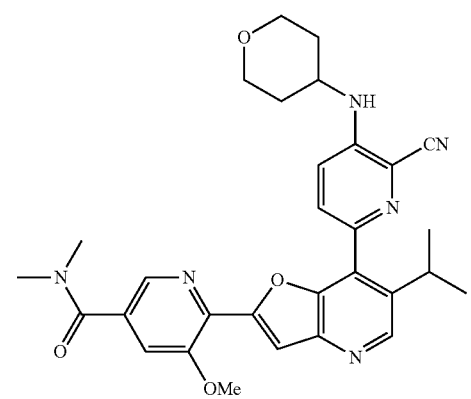

The title compound was prepared from 6-(7-chloro-6-isopropylfuro[3,2-b]pyridin-2-yl)-5-methoxy-N,N-dimethylnicotinamide and 6-cyano-5-(tetrahydro-2H-pyran-4-ylamino)pyridin-2-ylboronic acid using Method O. The product was purified by prep-HPLC under the following conditions: column, XBridge Shield RP18 OBD Column, 5 um, 19×150 mm; mobile phase, acetonitrile in water (with 10 mmol/L $NH_4HCO_3$), 20% to 40% gradient in 10 min; detector, UV 254/220 nm. 6-(7-[6-cyano-5-[(oxan-4-yl)amino]pyridin-2-yl]-6-(propan-2-yl)furo[3,2-b]pyridin-2-yl)-5-methoxy-N,N-dimethylpyridine-3-carboxamide was obtained as a white solid (3 mg, 14%). HPLC: 94.6% purity, RT=2.63 min. MS: m/z=541.2 $[M+H]^+$. $^1$H NMR (300 MHz, $CD_3OD$, ppm) δ 8.62 (s, 1H), 8.23 (d, J=1.5 Hz, 1H), 7.81-7.65 (m, 3H), 7.55 (d, J=9.0 Hz, 1H), 4.10 (s, 3H), 4.01 (d, J=11.8 Hz, 2H), 3.87-3.73 (m, 1H), 3.64-3.48 (m, 2H), 3.11 (s, 3H), 3.04 (s, 3H), 2.10-1.60 (m, 5H), 1.31 (d, J=6.9 Hz, 6H).

Example 316: 6-[7-[6-cyano-5-(oxan-4-yloxy)pyri-
din-2-yl]-6-methoxyfuro[3,2-b]pyridin-2-yl]-N-(2-
hydroxyethyl)-5-methoxy-N-methylpyridine-3-car-
boxamide (362)

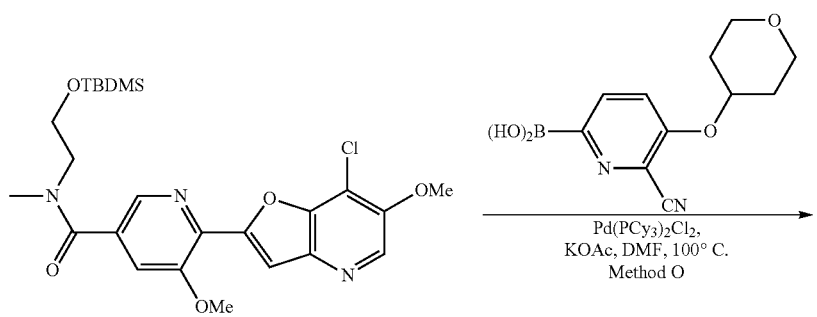

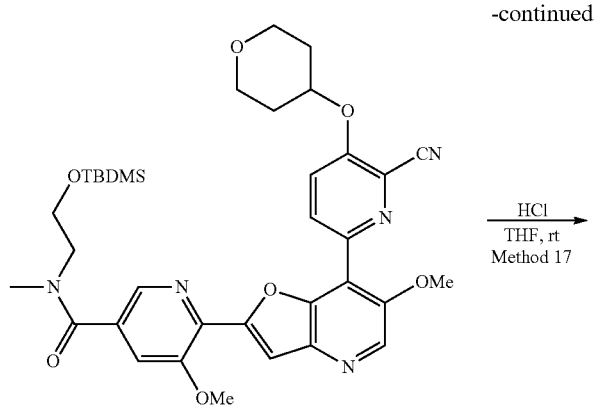

565

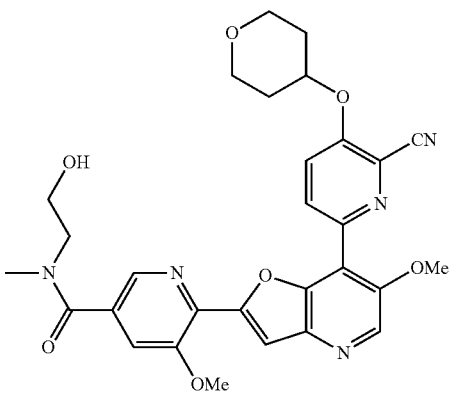

566

The title compound was prepared from N-(2-(tert-butyldimethylsilyloxy)ethyl)-6-(7-chloro-6-methoxyfuro[3,2-b]pyridin-2-yl)-5-methoxy-N-methylnicotinamide and 6-cyano-5-(tetrahydro-2H-pyran-4-yloxy)pyridin-2-ylboronic acid using Methods O and 17. The crude products were purified by the separation on prep-HPLC under the following conditions: Column XBridge Shield RP18 OBD Column, 5 um, 19×150 mm; MeCN in water (with 10 mmol/L NH$_4$HCO$_3$), 20% to 45% gradient in 10 min; Detector, UV 254/220 nm. 6-[7-[6-cyano-5-(oxan-4-yloxy)pyridin-2-yl]-6-methoxyfuro[3,2-b]pyridin-2-yl]-N-(2-hydroxyethyl)-5-methoxy-N-methylpyridine-3-carboxamide was obtained as a light yellow solid (20 mg, 29%). HPLC: 98.4% purity, RT=0.93 min. MS: m/z=560.1 [M+H]$^+$. $^1$H NMR (300 MHz, CD$_3$OD, ppm) δ 8.56 (s, 1H), 8.31 (d, J=1.6 Hz, 1H), 8.07-7.88 (m, 2H), 7.87-7.71 (m, 2H), 5.05-4.93 (m, 1H), 4.18-3.97 (m, 8H), 3.91-3.81 (m, 1H), 3.78-3.61 (m, 4H), 3.54-3.42 (m, 1H), 3.14 (d, J=5.9 Hz, 3H), 2.23-2.12 (m, 2H), 2.00-1.82 (m, 2H).

Example 317: 6-[7-[6-cyano-5-(oxan-4-yloxy)pyridin-2-yl]-6-cyclopropylfuro[3,2-b]pyridin-2-yl]-N-(2-hydroxyethyl)-5-methoxy-N-methylpyridine-3-carboxamide hydrochloride (363)

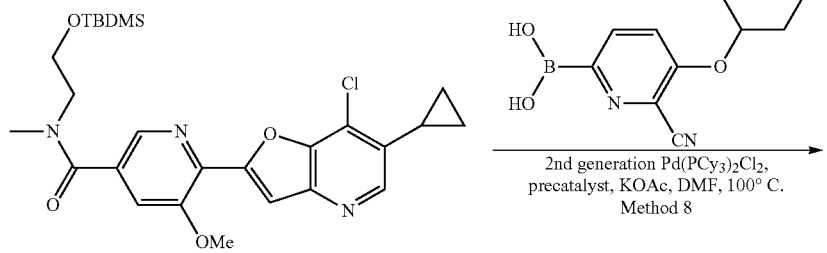

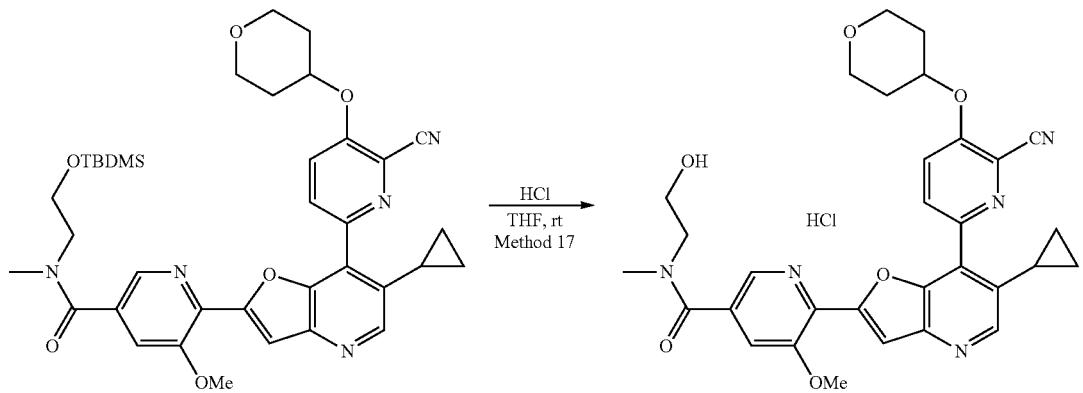

The title compound was prepared from N-(2-(tert-butyldimethylsilyloxy)ethyl)-6-(7-chloro-6-cyclopropylfuro[3,2-b]pyridin-2-yl)-5-methoxy-N-methylnicotinamide and 6-cyano-5-(tetrahydro-2H-pyran-4-yloxy)pyridin-2-ylboronic acid using Methods O and 17. The crude was added a solution of HCl in THF (4.5 mL, 2 M), and the resulting solution was stirred for 1 h at room temperature. When the reaction was done, the resulting mixture was concentrated under vacuum. The crude products were purified by the separation on prep-HPLC under the following conditions: Column XBridge Shield RP18 OBD Column, 5 um, 19×150 mm; MeCN in water (with 0.02% HCl), 20% to 40% gradient in 10 min; Detector, UV 254/220 nm. 6-[7-[6-cyano-5-(oxan-4-yloxy)pyridin-2-yl]-6-cyclopropylfuro[3,2-b]pyridin-2-yl]-N-(2-hydroxyethyl)-5-methoxy-N-methylpyridine-3-carboxamide hydrochloride was obtained as a yellow solid (15 mg, 23%). HPLC: 90.9% purity, RT=2.38 min. MS: m/z=570.2 [M+H]+. 1H NMR (300 MHz, CD3OD, ppm) δ 8.60 (s, 1H), 8.39 (d, J=1.6 Hz, 1H), 8.24 (d, J=9.0 Hz, 1H), 8.06 (d, J=9.0 Hz, 1H), 7.92 (s, 2H), 5.10-4.98 (m, 1H), 4.17 (d, J=5.0 Hz, 3H), 4.10-3.80 (m, 3H), 3.79-3.63 (m, 4H), 3.51-3.41 (m, 1H), 3.14 (d, J=13.1 Hz, 3H), 2.40-2.28 (m, 1H), 2.28-1.85 (m, 4H), 1.12-0.99 (m, 2H), 0.88-0.78 (m, 2H).

Example 318: 4-(7-(3-cyano-4-(tetrahydro-2H-pyran-4-yloxy)phenyl)furo[3,2-b]pyridin-2-yl)-N-(1-isopropylazetidin-3-yl)-3-methoxybenzamide (364)

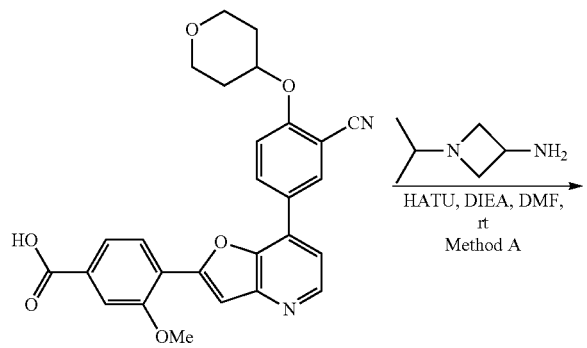

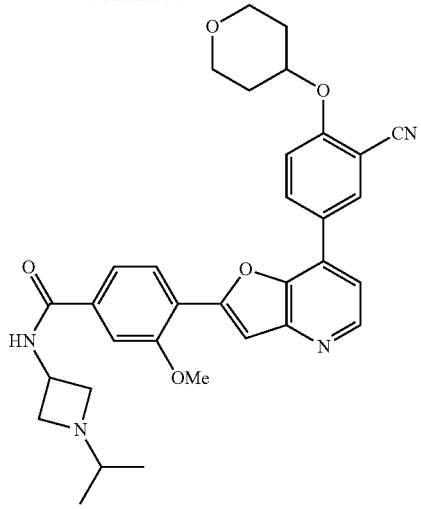

The title compound was prepared from 4-(7-(3-cyano-4-(tetrahydro-2H-pyran-4-yloxy)phenyl)furo[3,2-b]pyridin-2-yl)-3-methoxybenzoic acid and 1-isopropylazetidin-3-amine using Method A. The product was purified by prep-HPLC under the following conditions: column, XBridge Prep C18 OBD Column, 5 um, 19×150 mm; mobile phase, acetonitrile in water (with 0.02% HCl), 20% to 64% gradient in 8 min, and then isocratic at 64% for 12 min; detector, UV 254/220 nm. 4-(7-(3-cyano-4-(tetrahydro-2H-pyran-4-yloxy)phenyl)furo[3,2-b]pyridin-2-yl)-N-(1-isopropylazetidin-3-yl)-3-methoxybenzamide was obtained as a white solid (15 mg, 8%) HPLC: 96.5% purity, RT=1.28 min. MS: m/z=567.3 [M+H]+. 1H NMR (300 MHz, CD3OD, ppm) δ 8.38 (s, 1H), 8.24 (d, J=5.2 Hz, 2H), 7.88 (s, 1H), 7.57-7.34 (m, 5H), 4.95-4.82 (m, 1H), 4.48-4.38 (m, 1H), 4.09-3.93 (m, 5H), 3.71-3.61 (m, 2H), 3.11-3.09 (m, 1H), 2.50-2.27 (m, 4H), 2.23 (s, 6H), 2.18-2.04 (m, 2H), 1.93-1.76 (m, 2H).

Example 319: 4-(7-(3-cyano-4-(tetrahydro-2H-pyran-4-yloxy)phenyl)furo[3,2-b]pyridin-2-yl)-3-methoxy-N-(3-methyl-3-aza-bicyclo[3.1.1]heptan-6-yl)benzamide

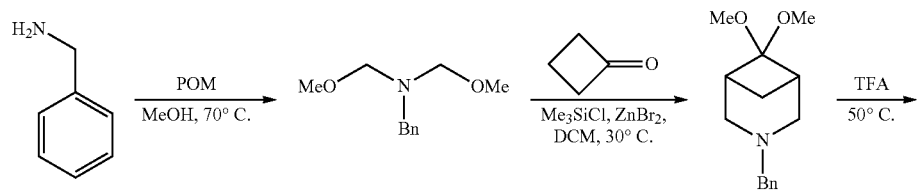

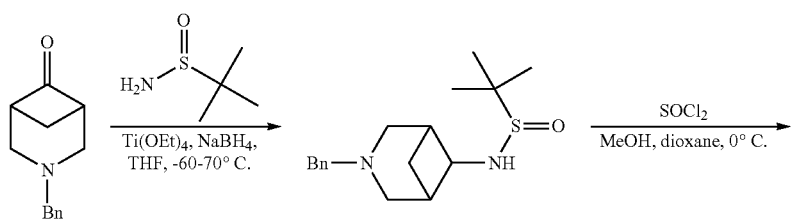

-continued
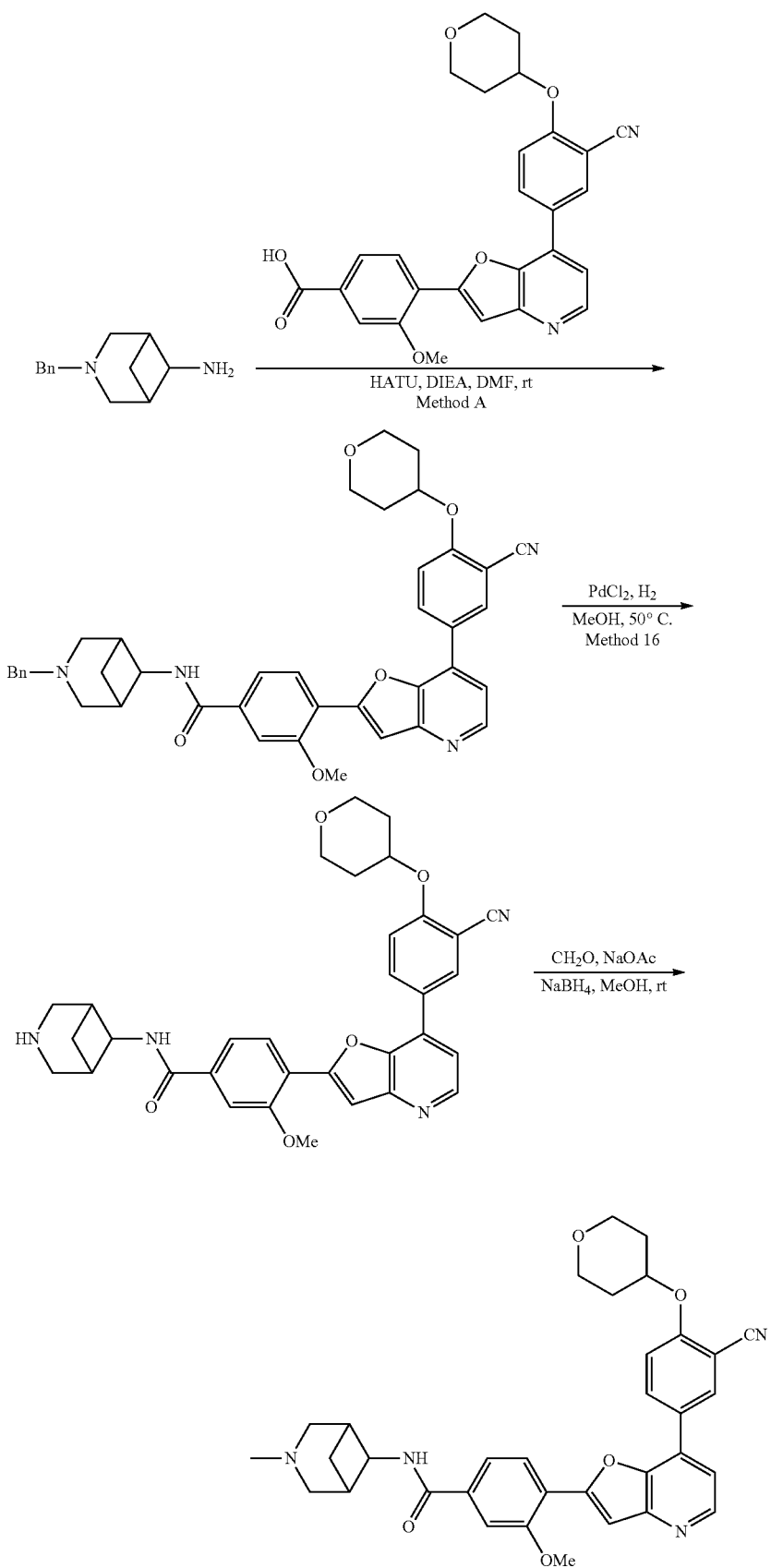

Benzylbis(methoxymethyl)amine

To a solution of benzyl amine (95.00 g, 886.58 mmol) in MeOH (500 mL) was added polyformaldehyde (78.34 g, 870.08 mmol) at room temperature. The resulting solution was then stirred overnight at 70° C. After the reaction was done, the reaction mixture was concentrated under reduced pressure. The residue was purified by distillation under reduced pressure (10 mmHg) and the fractions were collected at 82-84° C. to yield benzylbis(methoxymethyl)amine as colorless liquid (90.21 g, 47%).

3-Benzyl-6,6-dimethoxy-3-azabicyclo[3.1.1]heptane

At 0° C., to a solution of cyclobutanone (17.10 g, 243.97 mmol) in DCM (200 mL) was added chlorotrimethylsilane (58.91 g, 542.15 mmol) dropwise over 20 min period. The resulting solution was added by zinc bromide (55.33 g, 244.65 mmol) in portions at 0° C., followed by the addition of benzylbis(methoxymethyl)amine (50.4 g, 232.31 mmol, 1.00 equiv, 90%) dropwise over 5 min period. The resulting mixture was then stirred overnight at 30° C. After cooling to room temperature, the reaction mixture was quenched by the addition of sat. sodium carbonate solution (500 mL). The resulting mixture was extracted with ethyl acetate (200 mL×3). The organic phases were combined, washed with brine and dried over sodium sulfate. The solvent was removed under reduced pressure and the residue was purified by flash chromatography eluting with EtOAc in hexane (0% to 2% gradient) to yield 3-benzyl-6,6-dimethoxy-3-azabicyclo[3.1.1]heptane as a yellow oil (10.75 g, 19%). MS: m/z=248.2 [M+H]$^+$.

3-Benzyl-3-azabicyclo[3.1.1]heptan-6-one

At room temperature, 3-benzyl-6,6-dimethoxy-3-azabicyclo[3.1.1]heptane (5.48 g, 22.14 mmol) was added to trifluoroacetic acid (45 g, 374.92 mmol) slowly. The resulting solution was stirred overnight at 50° C. After the reaction was done, the reaction mixture was concentrated under reduced pressure. The pH value of the remaining solution was adjusted to 8-9 with sat. sodium bicarbonate solution. The resulting mixture was extracted with DCM (200 mL×3). The organic phases were combined, washed with brine and dried over sodium sulfate. The solvent was removed under reduced pressure and the residue was purified by flash chromatography eluting with EtOAc in hexane (0% to 5% gradient) to yield 3-benzyl-3-azabicyclo[3.1.1]heptan-6-one was obtained as a yellow liquid (3.26 g, 73%). MS: min=202.1 [M+H]$^+$.

N-[3-benzyl-3-azabicyclo[3.1.1]heptan-6-yl]-2-methylpropane-2-sulfinamide

To a solution of 3-benzyl-3-azabicyclo[3.1.1]heptan-6-one (1.86 g, 9.24 mmol) in tetrahydrofuran (37 mL) was added 2-methylpropane-2-sulfinamide (1.14 g, 9.41 mmol) and Ti(OEt)$_4$ (4.27 g, 18.74 mmol) at room temperature. The resulting solution was stirred overnight at 70° C. Then the reaction mixture was cooled to −60° C., and was added by NaBH$_4$ (1.43 g, 37.67 mmol) in portions. The resulting mixture was stirred overnight at room temperature. When the reaction was done, it was quenched by the addition of ice water (300 mL). The insoluble solids from the mixture were filtered out and the filtrate was extracted with DCM (150 mL×3). The organic phases were combined, washed with brine and dried over sodium sulfate. The solvent was removed under reduced pressure and the residue was purified by flash chromatography eluting with EtOAc in hexane (0% to % gradient) to yield N-[3-benzyl-3-azabicyclo[3.1.1]heptan-6-yl]-2-methylpropane-2-sulfinamide as a yellow oil (1.54 g, 54%). MS: m/z=307.2 [M+H]$^+$.

3-Benzyl-3-azabicyclo[3.1.1]heptan-6-amine

At 0° C., to a solution of N-[3-benzyl-3-azabicyclo[3.1.1]heptan-6-yl]-2-methylpropane-2-sulfinamide (1 g, 2.28 mmol, 1.00 equiv, 70%) in dioxane (10 mL) and methanol (10 mL) was added thionyl chloride (380 mg, 3.19 mmol) dropwise at 0° C. The resulting solution was then stirred for 1 h at room temperature. After the reaction was done, the reaction mixture was concentrated under reduced pressure. The pH value of the remaining mixture was adjusted to 10 with sat. sodium carbonate solution. The resulting mixture was extracted with ethyl acetate (20 mL×3). The organic phases were combined, washed with brine and dried over sodium sulfate. The solvent was removed under reduced pressure and the residue was purified by reverse phase flash chromatography eluting with acetonitrile in water (with 10 mmol/L NH$_4$HCO$_3$) (0% to 30% gradient in 30 min) to yield 3-benzyl-3-azabicyclo[3.1.1]heptan-6-amine as a yellow oil (300 mg, 55%). MS: m/z=203.1 [M+H]$^+$.

N-(3-benzyl-3-aza-bicyclo[3.1.1]heptan-6-yl)-4-(7-(3-cyano-4-(tetrahydro-2H-pyran-4-yloxy)phenyl)furo[3,2-b]pyridin-2-yl)-3-methoxybenzamide The title compound was prepared from 4-(7-(3-cyano-4-(tetrahydro-2H-pyran-4-yloxy)phenyl)furo[3,2-b]pyridin-2-yl)-3-methoxybenzoic acid and 3-benzyl-3-aza-bicyclo[3.1.1]heptan-6-amine using Method A. The product was purified by reverse phase flash chromatography eluting with acetonitrile in water (0% to 95% gradient in 30 min) to yield N-(3-benzyl-3-aza-bicyclo[3.1.1]heptan-6-yl)-4-(7-(3-cyano-4-(tetrahydro-2H-pyran-4-yloxy)phenyl)furo[3,2-b]pyridin-2-yl)-3-methoxybenzamide as a brown solid (163 mg, 69%). MS: m/z=655.3 [M+H]$^+$.

N-(3-aza-bicyclo[3.1.1]heptan-6-yl)-4-(7-(3-cyano-4-(tetrahydro-2H-pyran-4-yloxy)phenyl)furo[3,2-b]pyridin-2-yl)-3-methoxybenzamide To a solution of N-(3-benzyl-3-aza-bicyclo[3.1.1]heptan-6-yl)-4-(7-(3-cyano-4-(tetrahydro-2H-pyran-4-yloxy)phenyl)furo[3,2-b]pyridin-2-yl)-3-methoxybenzamide (75 mg, 0.11 mmol) in methanol (50 ml) was added PdCl$_2$ (50.5 mg, 0.28 mmol) at room temperature under nitrogen atmosphere. The reaction flask was vacuumed and flushed with hydrogen. The reaction mixture was hydrogenated for 2 h at 50° C. under hydrogen atmosphere with a hydrogen balloon. After cooling to room temperature, the reaction mixture were filtered through a Celite pad and the filtrate was concentrated under reduced pressure to yield N-(3-aza-bicyclo[3.1.1]heptan-6-yl)-4-(7-(3-cyano-4-(tetrahydro-2H-pyran-4-yloxy)phenyl)furo[3,2-b]pyridin-2-yl)-3-methoxybenzamide as an orange solid (50 mg, 72%). MS: m/z=565.2 [M+H]$^+$.

4-(7-(3-cyano-4-(tetrahydro-2H-pyran-4-yloxy)phenyl)furo[3,2-b]pyridin-2-yl)-3-methoxy-N-(3-methyl-3-aza-bicyclo[3.1.1]heptan-6-yl)benzamide To a solution of N-(3-aza-bicyclo[3.1.1]heptan-6-yl)-4-(7-(3-cyano-4-(tetrahydro-2H-pyran-4-yloxy)phenyl)furo

[3,2-b]pyridin-2-yl)-3-methoxybenzamide (50 mg, 0.08 mmol) in methanol (10 mL) was added formaldehyde (0.42 mL, 5.99 mmol, 40%, 14.4 mol/L) at room temperature. Then NaOAc (100 mg, 1.22 mmol) was added. The resulting mixture was stirred at room temperature for 1.5 h, and then was added NaBH$_4$ (76 mg, 2.01 mmol) at room temperature. Stirred for an additional 1 h at room temperature. When the reaction was done, it was quenched by the addition of sat. NH$_4$C solution (30 mL). The resulting mixture was extracted with DCM (50 mL×3). The organic phases were combined, washed with brine and dried over sodium sulfate. The solvent was removed under reduced pressure and the residue was purified by prep-HPLC under the following conditions: column, XBridge Prep C18 OBD Column, 19×150 mm 5 um; mobile phase, acetonitrile in water (with 10 mmol/L NH$_4$HCO$_3$), 20% to 50% gradient in 8 min; detector, UV 254/220 nm. The cis and trans isomers of 4-(7-(3-cyano-4-(tetrahydro-2H-pyran-4-yl oxy)phenyl)furo[3,2-b]pyridin-2-yl)-3-methoxy-N-(3-methyl-3-aza-bicyclo[3.1.1]heptan-6-yl)benzamide were separated and obtained.

Example 320: 4-{7-[3-Cyano-4-(tetrahydro-pyran-4-yloxy)-phenyl]-furo[3,2-b]pyridin-2-yl}-3-methoxy-N-((1S,5R,6R)-3-methyl-3-aza-bicyclo[3.10.1]hept-6-yl)-benzamide (365)

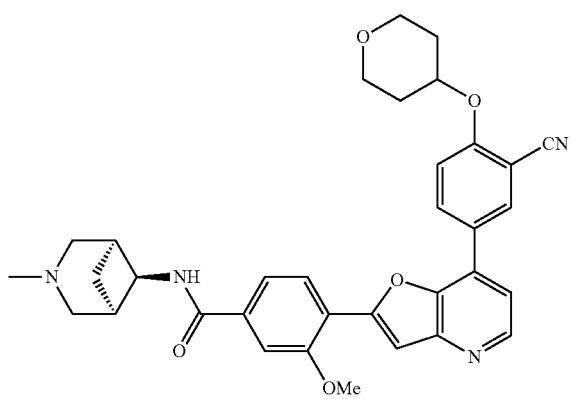 [SMILES: COc1cc(C(=O)N[C@H]2[C@@H]3C[C@H]2CN(C)C3)ccc1-c1cc2nccc(-c3ccc(OC4CCOCC4)c(C#N)c3)c2o1]

The title compound was separated from 4-(7-(3-cyano-4-(tetrahydro-2H-pyran-4-yl oxy)phenyl)furo[3,2-b]pyridin-2-yl)-3-methoxy-N-(3-methyl-3-aza-bicyclo[3.1.1]heptan-6-yl)benzamide. (12 mg, 24%, light yellow solid) HPLC: 99.9% purity, RT=2.08 min. MS: m/z=579.3 [M+H]$^+$. $^1$H NMR (300 MHz, DMSO-d$_6$, ppm) δ 8.89 (d, J=4.8 Hz, 1H), 8.63-8.41 (m, 3H), 8.06 (d, J=8.0 Hz, 1H), 7.76-7.60 (m, 5H), 5.04-4.94 (m, 1H), 4.11 (s, 3H), 3.97-3.83 (m, 2H), 3.70-3.51 (m, 3H), 3.00 (d, J=10.0 Hz, 2H), 2.76 (d, J=9.9 Hz, 2H), 2.45-2.29 (m, 6H), 2.08 (d. J=13.1 Hz, 2H), 1.81-1.61 (m, 3H).

Example 321: 4-{7-[3-Cyano-4-(tetrahydro-pyran-4-yloxy)-phenyl]-furo[3,2-b]pyridin-2-yl}-3-methoxy-N-((1S,5R,6R)-3-methyl-3-aza-bicyclo[3.10.1]hept-6-yl)-benzamide (366)

The title compound was separated from 4-(7-(3-cyano-4-(tetrahydro-2H-pyran-4-yloxy)phenyl)furo[3,2-b]pyridin-2-yl)-3-methoxy-N-(3-methyl-3-aza-bicyclo[3.1.1]heptan-6-yl)benzamide. (14 mg, 15.%, off-white solid) HPLC: 94.1% purity, RT=2.66 min. MS: m/z=579.3 [M+H]$^+$. $^1$H NMR (300 MHz, DMSO-d$_6$, ppm) δ 8.61-8.38 (m, 4H), 8.07 (d, J=8.1 Hz, 1H), 7.75-7.46 (m, 5H), 5.00-4.90 (m, 1H), 4.30-4.28 (m, 1H), 4.09 (s, 3H), 3.96-3.80 (m, 2H), 3.62-3.60 (m, 2H), 3.04 (d, J=10.2 Hz, 2H), 2.79-2.68 (m, 2H), 2.57 (d, J=6.0 Hz, 2H), 2.31 (s, 3H), 2.13-2.01 (m, 2H), 1.85-1.65 (m, 3H), 1.40-1.30 (m, 1H).

Example 322: 4-[7-[3-cyano-4-(oxan-4-yloxy)phenyl]furo[3,2-b]pyridin-2-yl]-N-(1,3-dimethylpiperidin-3-yl)-3-methoxybenzamide (367)

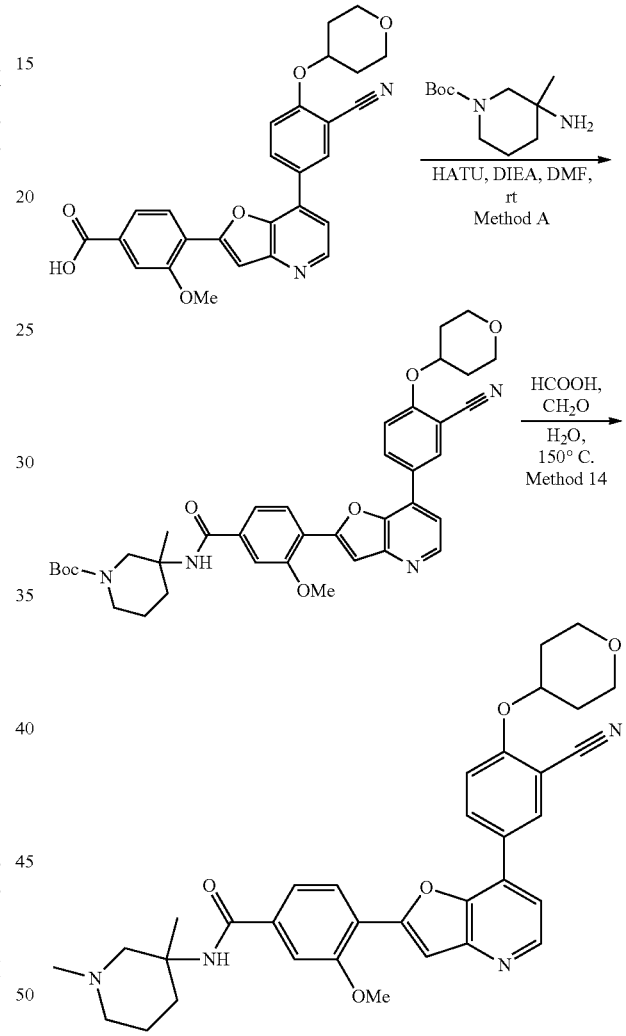

The Title compound was prepared from 4-(7-(3-cyano-4-(tetrahydro-2H-pyran-4-yloxy)phenyl)furo[3,2-b]pyridin-2-yl)-3-methoxybenzoic acid and tert-butyl 3-amino-3-methylpiperidine-1-carboxylate using Methods A and 14. The final product was purified by prep-HPLC under the following conditions: column. XBridge Prep C18 OBD Column, 5 um, 19×150 mm; mobile phase, acetonitrile in water (with 10 mmol/L NH$_4$HCO$_3$), 25% to 55% gradient in 8 min; detector, UV 254/220 nm. 4-[7-[3-cyano-4-(oxan-4-yloxy)phenyl]furo[3,2-b]pyridin-2-yl]-N-(1,3-dimethylpiperidin-3-yl)-3-methoxybenzamide was obtained as a white solid (25 mg, 31% for 2 steps). HPLC: 97.5% purity, RT=1.97 min. MS: m/z=581.3 [M+H]$^+$. $^1$H NMR (300 MHz, CD$_3$OD, ppm) δ 8.42 (d, J=5.2 Hz, 1H), 8.30 (d, J=7.9 Hz, 2H), 7.96

(d, J=8.1 Hz, 1H), 7.61-7.38 (m, 5H), 4.94-4.84 (m, 1H), 4.11-3.92 (m, 5H), 3.72-3.60 (m, 2H), 3.28-3.12 (m, 1H), 2.86-2.70 (m, 1H), 2.41 (d, J=13.6 Hz, 1H), 2.32 (s, 3H), 2.20-2.00 (m, 4H), 1.93-1.55 (m, 4H), 1.48 (s, 3H), 1.36-1.20 (m, 1H).

Example 323: 4-[7-[3-cyano-4-(oxan-4-yloxy)phenyl]furo[3,2-b]pyridin-2-yl]-N-[1-[(dimethylamino)methyl]cyclobutyl]-3-methoxybenzamide (368)

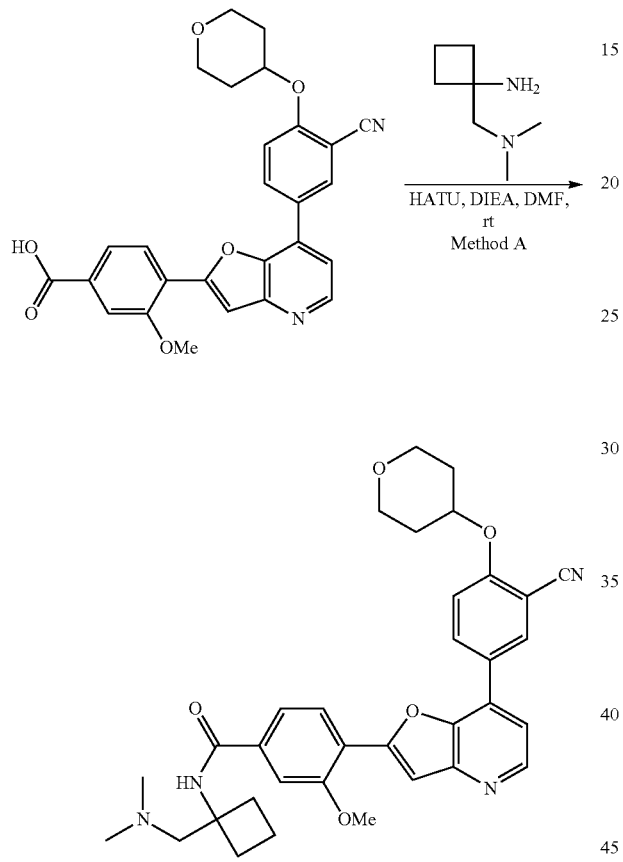

The title compound was prepared from 4-(7-(3-cyano-4-(tetrahydro-2H-pyran-4-yloxy)phenyl)furo[3,2-b]pyridin-2-yl)-3-methoxybenzoic acid and 1-((dimethylamino)methyl)cyclobutanamine using Method A. The product was purified by prep-HPLC under the following conditions: column, XBridge Prep C18 OBD Column, 5 um, 19×150 mm; mobile phase, acetonitrile in water (with 10 mmol/L NH$_4$HCO$_3$), 25% to 55% gradient in 8 min; detector, UV 254/220 nm. 4-[7-[3-cyano-4-(oxan-4-yloxy)phenyl]furo[3,2-b]pyridin-2-yl]-N-[1-[(dimethylamino)methyl]cyclobutyl]-3-methoxybenzamide was obtained as a off-white solid (50 mg, 61%). HPLC: 93.5% purity, RT=2.81 min. MS: m/z=581.3 [M+H]$^+$. $^1$H NMR (300 MHz, DMSO-d, ppm) δ 8.62-8.40 (m, 4H), 8.04 (d, J=8.4 Hz, 1H), 7.73-7.59 (m, 5H), 5.02-4.92 (m, 1H), 4.10 (s, 3H), 3.95-3.83 (m, 2H), 3.63-3.59 (m, 2H), 3.50-3.35 (m, 1H), 2.73 (s, 2H), 2.41-2.24 (m, 2H), 2.21-2.02 (m, 10H), 1.95-1.63 (m, 4H).

Example 324: 4-[7-[3-cyano-4-(oxan-4-yloxy)phenyl]furo[3,2-b]pyridin-2-yl]-3-methoxy-N-(2-methyl-6-oxopiperidin-3-yl)benzamide (369)

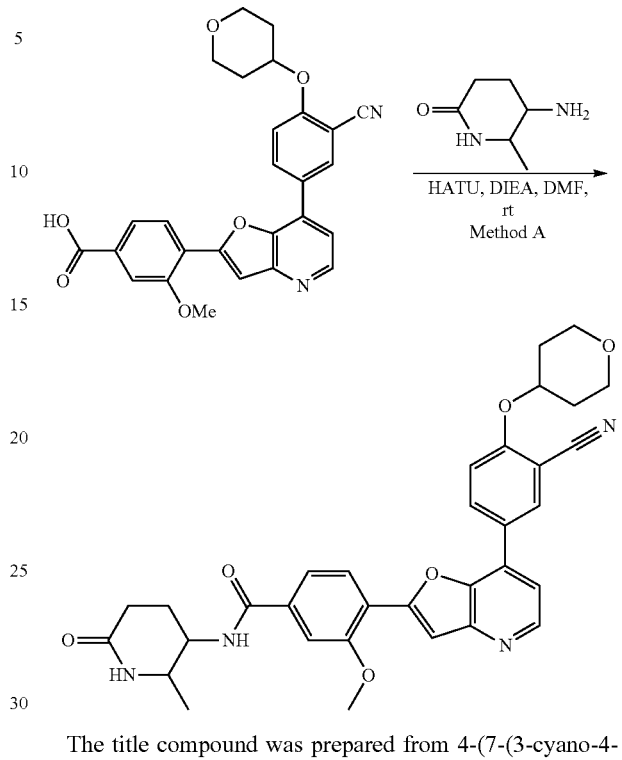

The title compound was prepared from 4-(7-(3-cyano-4-(tetrahydro-2H-pyran-4-yloxy)phenyl)furo[3,2-b]pyridin-2-yl)-3-methoxybenzoic acid and 5-amino-6-methylpiperidin-2-one using Method A. The product was purified by prep-HPLC under the following conditions: column, XBridge Prep C18 OBD Column, 5 um, 19×150 mm; mobile phase, acetonitrile in water (with 10 mmol/L NH$_4$HCO$_3$), 20% to 50% gradient in 8 min; detector, UV 254/220 nm. 4-[7-[3-cyano-4-(oxan-4-yloxy)phenyl]furo[3,2-b]pyridin-2-yl]-N-[1-[(dimethylamino)methyl]cyclobutyl]-3-methoxybenzamide was obtained as a off-white solid (15 mg, 18%). HPLC: 98.7% purity, RT=1.40 min. MS: m/z=581.0 [M+H]$^+$. $^1$H NMR (300 MHz, DMSO-d$_6$, ppm) δ 8.38-8.27 (m, 1H), 8.26-8.10 (m, 2H), 7.86-7.71 (m, 1H), 7.55-7.29 (m, 5H), 4.96-4.86 (m, 1H), 4.53-4.43 (m, 1H), 4.15-3.86 (m, 6H), 3.82-3.54 (m, 2H), 2.60-2.44 (m, 2H), 2.29-1.78 (m, 6H), 1.28 (dd, J=16.9, 6.5 Hz, 3H).

Example 325: 4-[7-[3-cyano-4-(oxan-4-yloxy)phenyl]furo[3,2-b]pyridin-2-yl]-N-(1,4-dimethylpiperidin-4-yl)-3-methoxybenzamide hydrochloride (370)

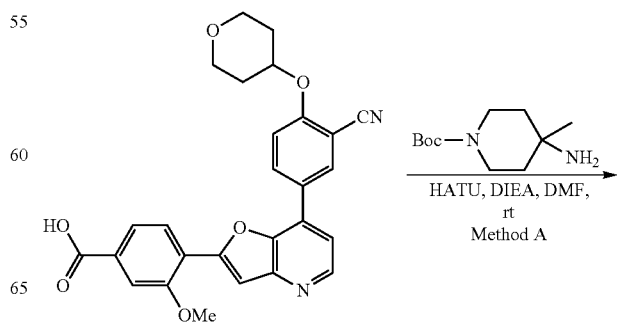

-continued

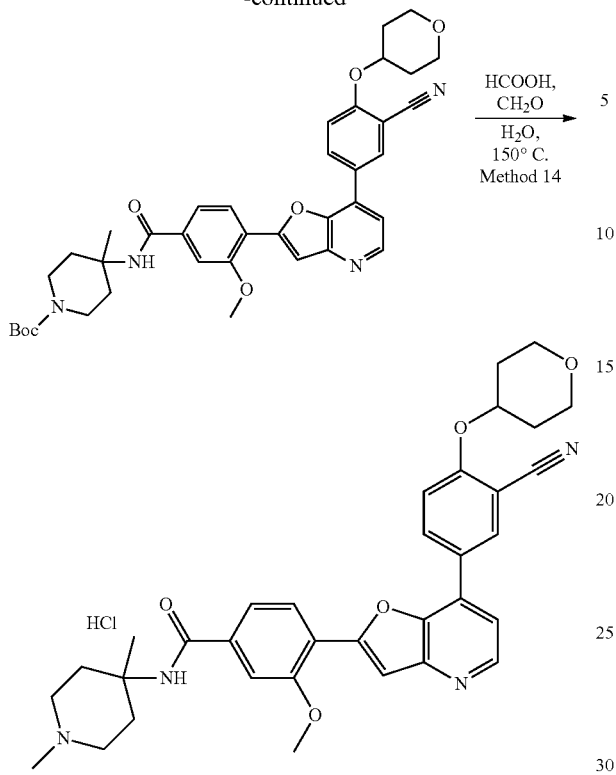

The title compound was prepared from 4-(7-(3-cyano-4-(tetrahydro-2H-pyran-4-yloxy)phenyl)furo[3,2-b]pyridin-2-yl)-3-methoxybenzoic acid and tert-butyl 4-amino-4-methylpiperidine-1-carboxylate using Methods A and 14. The product was purified by prep-HPLC under the following conditions: column, XBridge Prep C18 OBD Column, 5 um, 19×150 mm; mobile phase, acetonitrile in water (with 0.02% HCl), 18% to 45% gradient in 8 min; detector, UV 254/220 nm. 4-[7-[3-cyano-4-(oxan-4-yloxy)phenyl]furo[3,2-b]pyridin-2-yl]-N-(1,4-dimethylpiperidin-4-yl)-3-methoxybenzamide hydrochloride was obtained as a yellow solid (20 mg, 20% for 2 steps). HPLC: 99.9% purity, RT=1.00 min. MS: m/z=581.3 [M+H]$^+$. $^1$H NMR (400 MHz, CD$_3$OD, ppm) δ 8.90-8.39 (m, 3H), 8.20-8.10 (m, 1H), 8.06-7.90 (m, 1H), 7.81-7.56 (m, 4H), 5.00 (s, 1H), 4.17 (s, 3H), 4.06-3.96 (m, 2H), 3.78-3.62 (m, 2H), 3.58-3.42 (m, 2H), 3.35-3.22 (m, 2H), 3.00-2.78 (m, 5H), 2.50-2.30 (m, 1H), 2.23-2.07 (m, 2H), 1.92-1.80 (m, 4H), 1.55 (s, 2H).

Example 326: 4-(7-(3-cyano-4-(tetrahydro-2H-pyran-4-yloxy)phenyl)furo[3,2-b]pyridin-2-yl)-3-methoxy-N-(3-(pyrrolidin-1-yl)cyclobutyl)benzamide (371)

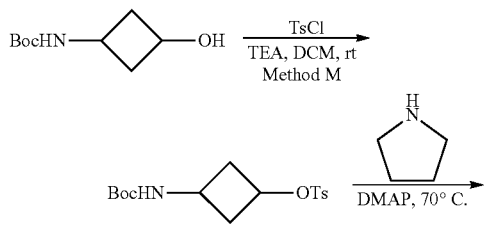

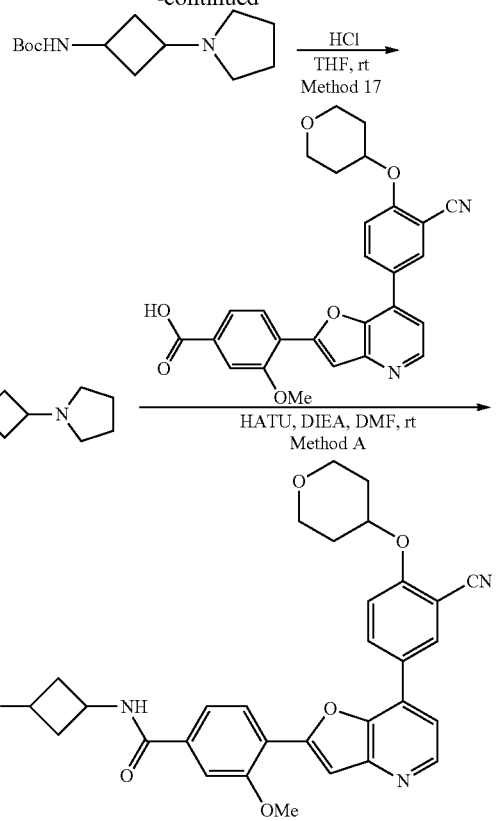

3-(tert-butoxycarbonylamino)cyclobutyl 4-methylbenzenesulfonate 3-(tert-butoxycarbonyl amino)cyclobutyl 4-methylbenzenesulfonate was prepared from tert-butyl 3-hydroxycyclobutylcarbamate and 4-methylbenzene-1-sulfonyl chloride using Method M. The product was purified by flash chromatography eluting with EtOAc in hexane (0% to 17% gradient) to yield tert-butyl N-(3-[[(4-methylbenzene)sulfonyl]oxy]cyclobutyl)carbamate as a yellow solid (915 mg, 53%).

tert-butyl 3-(pyrrolidin-1-yl)cyclobutylcarbamate

To a solution of tert-butyl N-(3-[[(4-methylbenzene)sulfonyl]oxy]cyclobutyl)carbamate (774 mg, 2.27 mmol) in pyrrolidine (22 mL) was added 4-dimethylaminopyridine (33 mg, 0.27 mmol) at room temperature. The resulting solution was then stirred overnight at 70° C. After cooling to room temperature, the reaction mixture was quenched by the addition of water (30 mL). The resulting mixture was extracted with ethyl acetate (50 mL×3). The organic phases were combined, washed with brine and dried over sodium sulfate. The solvent was removed under reduced pressure and the residue was purified by flash chromatography eluting with MeOH in DCM (0% to 100% gradient) to yield tert-butyl N-[3-(pyrrolidin-1-yl)cyclobutyl]carbamate as a brown solid (510 mg, 94%).

4-(7-(3-cyano-4-(tetrahydro-2H-pyran-4-yloxy)phenyl)furo[3,2-b]pyridin-2-yl)-3-methoxy-N-(3-(pyrrolidin-1-yl)cyclobutyl)benzamide The title compound was prepared from 4-(7-(3-cyano-4-(tetrahydro-2H-pyran-4-yloxy)phenyl)furo[3,2-b]pyridin-2- yl)-3-methoxybenzoic acid and tert-butyl 3-(pyrrolidin-1-yl) cyclobutylcarbamate using Methods 17 and A. The final product was purified by prep-HPLC under the following conditions: column, XBridge Prep C18 OBD Column, 5 um, 19×150 mm; mobile phase, acetonitrile in water (with 10 mmol/L NH$_4$HCO$_3$), 20% to 64% gradient in 8 min, and then isocratic at 64% for 12 min; detector, UV 254/220 nm. The cis and trans isomers of 4-(7-(3-cyano-4-(tetrahydro-2H-pyran-4-yloxy)phenyl)furo[3,2-b]pyridin-2-yl)-3-methoxy-N-(3-(pyrrolidin-1-yl)cyclobutyl)benzamide were separated and obtained. (16 mg, 11% for 2 steps, white solid) HPLC: 96.5% purity, RT=1.28 min. MS: m/z=593.3 [M+H]$^+$. $^1$H NMR (400 MHz, CD$_3$OD, ppm) δ 8.52-8.28 (m, 3H), 8.10-7.95 (m, 1H), 7.64-7.44 (m, 5H), 4.98-4.89 (m, 1H), 4.69-4.54 (m, 1H), 4.15-3.98 (m, 5H), 3.77-3.61 (m, 2H), 3.24-3.16 (m, 1H), 2.59 (d, J=6.1 Hz, 4H), 2.54-2.43 (m, 2H), 2.40-2.28 (m, 2H), 2.15 (d, J=9.8 Hz, 2H), 1.88 (d, J=6.8 Hz, 6H).

Example 327: 4-[7-[3-cyano-4-(oxan-4-yloxy)phenyl]furo[3,2-b]pyridin-2-yl]-3-methoxy-N-[(1S,5R)-3-(propan-2-yl)-3-azabicyclo[3.1.0]hexan-1-yl]benzamide (372)

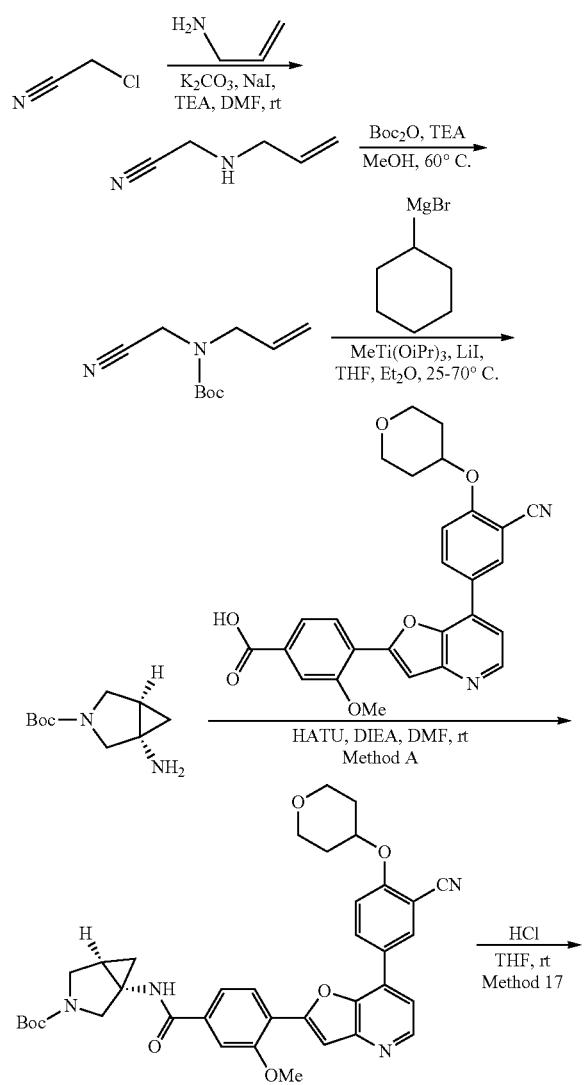

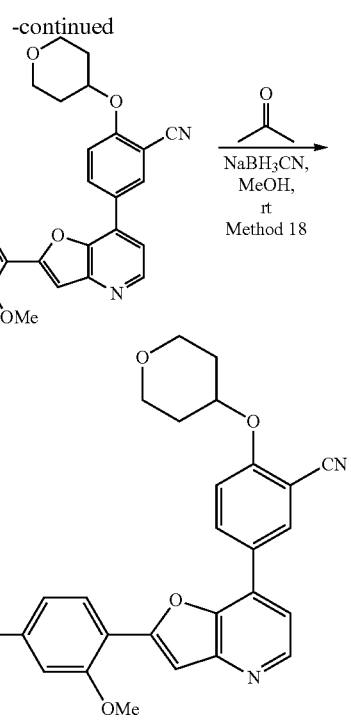

2-(Allylamino)acetonitrile

To a solution of 2-chloroacetonitrile (9.50 g, 125.83 mmol) in DMF (200 mL) was added potassium carbonate (34.78 g, 251.66 mmol), NaI (37.72 g, 251.67 mmol), triethylamine (50.93 g, 503.33 mmol) and prop-2-en-1-amine (7.18 g, 125.82 mmol) at room temperature. The resulting solution was stirred overnight at room temperature. After the reaction was done, the insoluble solids in reaction mixture were filtered out and the filtrate was quenched water (100 mL). The resulting mixture was extracted with ethyl acetate (100 mL×3). The organic phases were combined, washed with brine and dried over sodium sulfate. The solvent was removed under reduced pressure to yield 2-(allylamino)acetonitrile as a yellow oil (7.4 g, 61%).

tert-Butyl N-(cyanomethyl)-N-(prop-2-en-1-yl)carbamate

To a solution of 2-[(prop-2-en-1-yl)amino]acetonitrile (6.29 g, 65.43 mmol) in MeOH (50 mL) was added triethylamine (15 mL, 109.35 mmol) and di-tert-butyl dicarbonate (17.58 g, 80.53 mmol) at room temperature. The resulting solution was stirred for 2 h at 60° C. After cooling to room temperature, the reaction was then quenched by the addition of water (50 mL). The resulting mixture was extracted with ethyl acetate (150 mL×3). The organic phases were combined, washed with brine and dried over sodium sulfate. The solvent was removed under reduced pressure and the residue was purified by flash chromatography eluting with EtOAc in hexane (0% to 100% gradient) to yield tert-butyl N-(cyanomethyl)-N-(prop-2-en-1-yl)carbamate as colorless oil (5.00 g, 39%).

tert-Butyl (1S,5R)-1-amino-3-azabicyclo[3.1.0] hexane-3-carboxylate

At 0° C., methyltris(propan-2-yloxy)titanium (1 M solution in Et$_2$O, 5.6 mL, 5.6 mmol) was added to a solution of tert-butyl N-(cyanomethyl)-N-(prop-2-en-1-yl)carbamate (0.85 g, 4.3 mmol) in THF (60 mL). Then bromo(cyclohexyl)magnesium (1M in THF, 10.2 mL, 10.2 mmol) was added dropwise over 5 min period at 0° C. The resulting solution was stirred for 2 h at room temperature, and then was added by LiI (1.30 g, 9.72 mmol) in portions at room temperature. The resulting mixture was heated to 70° C. and stirred for additional 3 h. After cooling to room temperature, the reaction mixture was quenched by the addition of NaOH solution (40 mL, 10%). The insoluble solids in the mixture were filtered out and the filtrate was extracted with ethyl acetate (100 mL×3). The organic phases were combined, washed with brine and dried over sodium sulfate. The solvent was removed under reduced pressure to yield tert-butyl (1S,5R)-1-amino-3-azabicyclo[3.1.0]hexane-3-carboxylate as a yellow oil (0.46 g, 53%).

tert-butyl (1S,5R)-1-[(4-[7-[3-cyano-4-(oxan-4-yloxy)phenyl]furo[3,2-b]pyridin-2-yl]-3-methoxybenzene)amido]-3-azabicyclo[3.1.0]hexane-3-carboxylate tert-butyl (1S,5R)-1-[(4-[7-[3-cyano-4-(oxan-4-yloxy)phenyl]furo[3,2-b]pyridin-2-yl]-3-methoxybenzene)amido]-3-azabicyclo[3.1.0]hexane-3-carboxylate was prepared from 4-(7-(3-cyano-4-(tetrahydro-2H-pyran-4-yloxy)phenyl)furo[3,2-b]pyridin-2-yl)-3-methoxybenzoic acid and (1S,5R)-tert-butyl 1-amino-3-aza-bicyclo[3.1.0]hexane-3-carboxylate using Methods 17 and A. The final product was purified by flash chromatography eluting with MeOH in EtOAc (0% to 20% gradient) to yield tert-butyl (1S,5R)-1-[(4-[7-[3-cyano-4-(oxan-4-yloxy)phenyl]furo[3,2-b]pyridin-2-yl]-3-methoxybenzene)amido]-3-azabicyclo[3.1.0]hexane-3-carboxylate as a yellow oil (85 mg, 73%). MS: m/z=551.2 [M+H]$^+$.

Method 18

4-[7-[3-cyano-4-(oxan-4-yloxy)phenyl]furo[3,2-b]pyridin-2-yl]-3-methoxy-N-[(1S,5R)-3-(propan-2-yl)-3-azabicyclo[3.1.0]hexan-1-yl]benzamide To a solution of N-[(1S,5R)-3-azabicyclo[3.1.0]hexan-1-yl]-4-[7-[3-cyano-4-(oxan-4-yloxy)phenyl]furo[3,2-b]pyridin-2-yl]-3-methoxybenzamide (81 mg, 0.15 mmol) in MeOH (2 mL) was added propan-2-one (2 mL, 27.20 mmol) at room temperature. The mixture was stirred for 3 h at room temperature, and then was added by NaBH$_3$CN (104 mg, 1.65 mmol) in portions at room temperature. The resulting mixture was then stirred overnight at room temperature. When the reaction was done, it was then quenched by the addition of sat. sodium bicarbonate solution (5 mL). The resulting mixture was extracted with ethyl acetate (20 mL×3). The organic phases were combined, washed with brine and dried over sodium sulfate. The solvent was removed under reduced pressure and the residue was purified by prep-HPLC under the following conditions: column, XBridge Prep C18 OBD Column, 150 mm 5 um; mobile phase, acetonitrile in water (with 10 mmol/L NH$_4$HCO$_3$), 20% to 50% gradient in 10 min; detector, UV 254 nm. 4-[7-[3-cyano-4-(oxan-4-yloxy)phenyl]furo[3,2-b]pyridin-2-yl]-3-methoxy-N-[(1S,5R)-3-(propan-2-yl)-3-azabicyclo[3.1.0]hexan-1-yl]benzamide was obtained as a white solid (35 mg, 40%). HPLC: 95.2% purity, RT=1.32 min. MS: m/z=593.3 [M+H]$^+$. $^1$H NMR (400 MHz, DMSO-d$_6$, ppm) δ 9.02 (s, 1H), 8.56 (d, =5.2 Hz, 1H), 8.52-8.38 (m, 2H), 8.02 (d, J=8.1 Hz, 1H), 7.71-7.57 (m, 5H), 5.01-4.91 (m, 1H), 4.08 (s, 3H), 3.95-3.83 (m, 2H), 3.64-3.50 (m, 3H), 3.17 (d, J=7.8 Hz, 1H), 2.92 (d, J=8.6 Hz, 1H), 2.64-2.37 (m, 2H), 2.07 (d, J=10.9 Hz, 2H), 1.80-1.65 (m, 3H), 1.25-1.10 (m, 1H), 0.98 (d, J=6.2 Hz, 6H), 0.75 (dd, J=8.4, 4.4 Hz, 1H).

Example 328: N-[(3aR,4R,6aS)-2-methyl-octahydrocyclopenta[c]pyrrol-4-yl]-4-[7-[3-cyano-4-(oxan-4-yloxy)phenyl]furo[3,2-b]pyridin-2-yl]-3-methoxybenzamide (373)

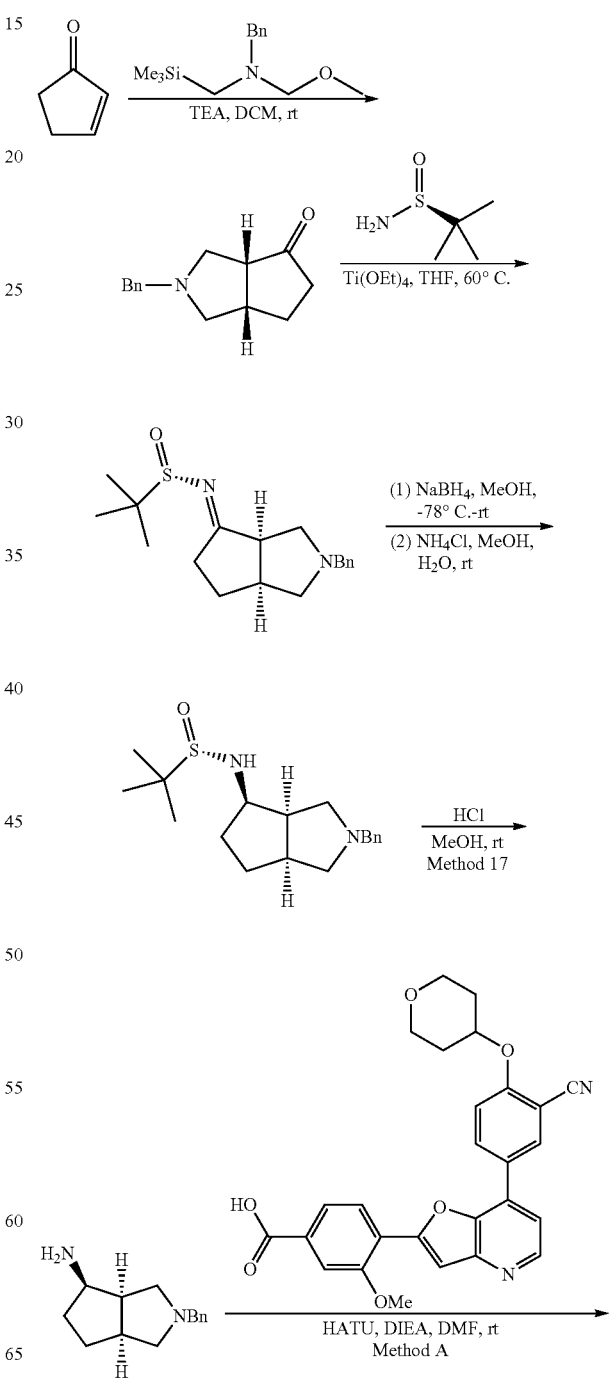

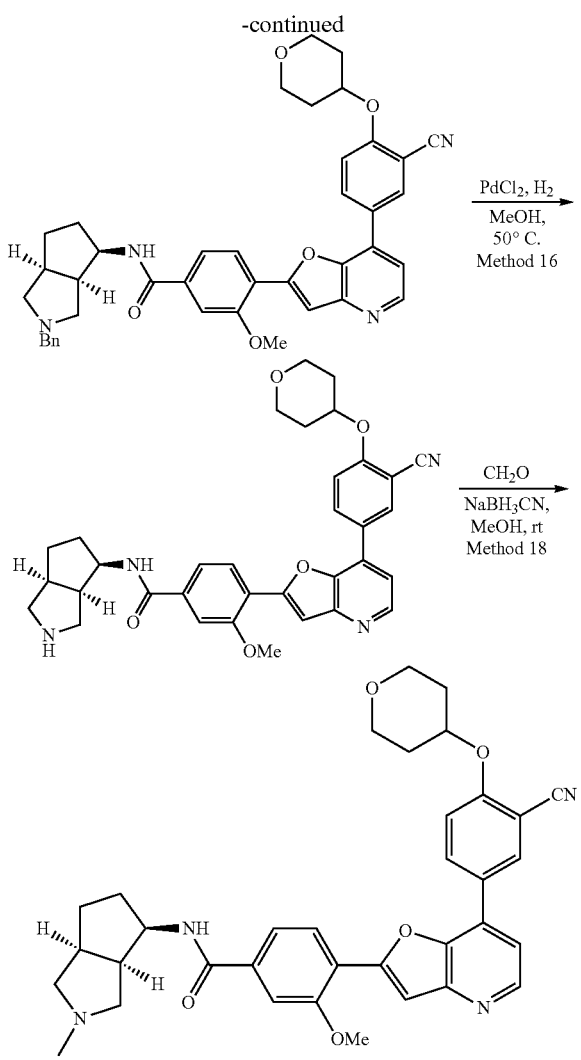

(3aR,6aS)-2-benzyl-tetrahydrocyclopenta[c]pyrrol-4(1H,2H,5H)-one

At room temperature, trifluoroacetic acid (43.9 mg, 0.39 mmol) was added to a solution of cyclopent-2-en-1-one (3.16 g, 38.49 mmol) in dichloromethane (45 mL), to which was added a solution of benzyl(methoxymethyl)[(trimethylsilyl)methyl]amine (8.23 g, 34.65 mmol) in dichloromethane (15 mL) dropwise over 1 h period. The resulting solution was then stirred for 40 min at room temperature. When the reaction was done, it was then quenched by the addition of sat. sodium bicarbonate solution (120 mL). The resulting mixture was extracted with DCM (100 mL×3). The organic phases were combined, washed with brine and dried over sodium sulfate. The solvent was removed under reduced pressure to yield 2-benzyl-octahydrocyclopenta[c]pyrrol-4-one as a yellow syrup (3.28 g, 40%). MS: m/z=216.1 [M+H]⁺.

(S,E)-N-((3aR,6aS)-2-benzyl-hexahydrocyclopenta[c]pyrrol-4(5H)-ylidene)-2-methylpropane-2-sulfinamide To a solution of 2-benzyl-octahydrocyclopenta[c]pyrrol-4-one (0.77 g, 3.55 mmol) in tetrahydrofuran (30 mL) was added (S)-2-methylpropane-2-sulfinamide (1.21 g, 9.98 mmol) and tetraethoxytitanium (3.19 g, 13.98 mmol) at room temperature. The resulting solution was then stirred for 32 h at 60° C. After cooling to room temperature, the reaction mixture was quenched by the addition of water (60 mL). The resulting mixture was extracted with ethyl acetate (100 mL×3). The organic phases were combined, washed with brine and dried over sodium sulfate. The solvent was removed under reduced pressure and the residue was purified by flash chromatography eluting with EtOAc in hexane (0% to 30% gradient) to yield (S)—N-[(3aR,4E,6aS)-2-benzyl-octahydrocyclopenta[c]pyrrol-4-ylidene]-2-methylpropane-2-sulfinamide as a light brown syrup (397 mg, 35%). MS: m/z=319.2 [M+H]⁺.

(S)—N-[(3aR,4R,6aS)-2-benzyl-octahydrocyclopenta[c]pyrrol-4-yl]-2-methylpropane-2-sulfinamide At −78° C., to a solution of (S)—N-[(3aR,4E,6aS)-2-benzyl-octahydrocyclopenta[c]pyrrol-4-ylidene]-2-methylpropane-2-sulfinamide (284 mg, 0.89 mmol) in methanol (10 mL) was followed by the addition of NaBH₄ (125 mg, 3.30 mmol). The resulting solution was stirred for 1 h at −78° C., slowly warmed up to room temperature, and stirred for additional 12 h at room temperature. When the reaction was done, it was quenched by sat. NH₄Cl solution (20 mL). The resulting mixture was extracted with ethyl acetate (30 mL×3). The organic phases were combined, washed with brine and dried over sodium sulfate. The solvent was removed under reduced pressure to yield (S)—N-[(3aR,4R,6aS)-2-benzyl-octahydrocyclopenta[c]pyrrol-4-yl]-2-methylpropane-2-sulfinamide as a brown oil (264 mg, 92%). MS: m/z=321.2 [M+H]⁺.

N-[(3aR,4R,6aS)-2-methyl-octahydrocyclopenta[c]pyrrol-4-yl]-4-[7-[3-cyano-4-(oxan-4-yloxy)phenyl]furo[3,2-b]pyridin-2-yl]-3-methoxybenzamide The title compound was prepared from (S)—N-((3aR,4R,6aS)-2-benzyl-octahydrocyclopenta[c]pyrrol-4-yl)-2-methylpropane-2-sulfinamide, 4-(7-(3-cyano-4-(tetrahydro-2H-pyran-4-yloxy)phenyl)furo[3,2-b]pyridin-2-yl)-3-methoxybenzoic acid and formaldehyde using Methods 17, A, 16 and 18. The final product was purified by prep-HPLC under the following conditions: column, XBridge Prep C18 OBD Column, 150 mm 5 um; mobile phase, acetonitrile in water (with 10 mmol/L NH₄HCO₃), 20% to 45% gradient in 8 min; detector, UV 254 nm. N-[(3aR,4R,6aS)-2-methyl-octahydrocyclopenta[c]pyrrol-4-yl]-4-[7-[3-cyano-4-(oxan-4-yloxy)phenyl]furo[3,2-b]pyridin-2-yl]-3-methoxybenzamide was obtained as a off-white solid (7 mg, 5.5% for 4 steps). HPLC: 92.8% purity, RT=1.32 min. MS: m/z=593.3 [M+H]⁺. ¹H NMR (300 MHz, DMSO-d₆, ppm) δ 8.60 (dd, J=13.3, 5.9 Hz, 2H), 8.56-8.39 (m, 2H), 8.17-8.00 (m, 1H), 7.72-7.56 (m, 4H), 5.02-4.92 (m, 1H), 4.26-4.03 (m, 4H), 3.97-3.83 (m, 2H), 3.65-3.42 (m, 2H), 2.88-2.76 (m, 1H), 2.71-2.50 (m, 4H), 2.38-2.16 (m, 5H), 2.16-1.98 (m, 2H), 1.97-1.60 (m, 5H), 1.51-1.34 (m, 1H).

Example 329: 4-[7-[3-cyano-4-(oxan-4-yloxy)phenyl]furo[3,2-b]pyridin-2-yl]-N-[(3S,5S)-5-(hydroxymethyl)-1-methylpyrrolidin-3-yl]-3-methoxybenzamide (374)

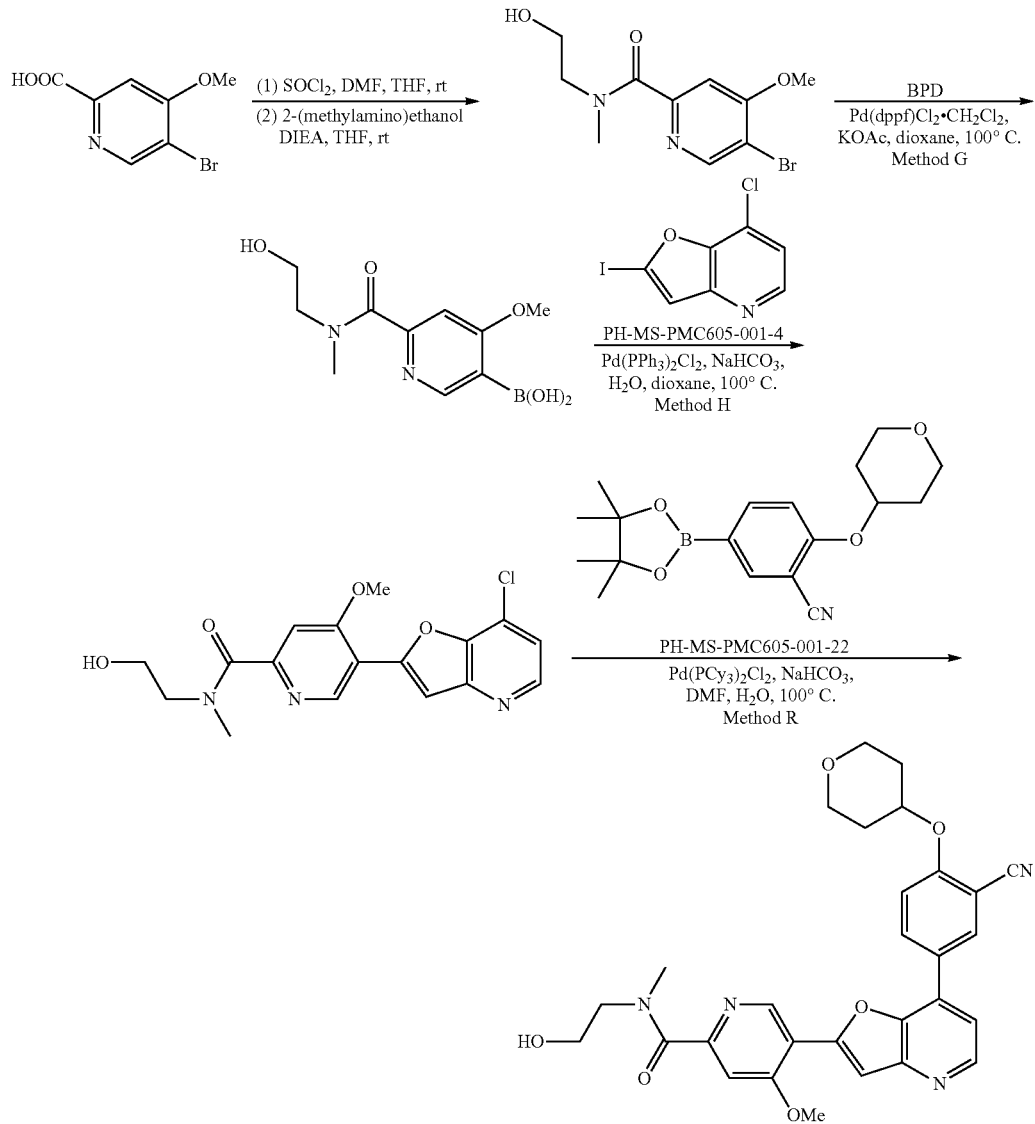

5-bromo-N-(2-hydroxyethyl)-4-methoxy-N-methylpyridine-2-carboxamide

At 0 OC, N,N-dimethylformamide (0.01 mL) was added to a solution of 5-bromo-4-methoxypyridine-2-carboxylic acid (495 mg, 2.13 mmol) in tetrahydrofuran (10 mL). Then oxalyl chloride (5.7 mL, 66.91 mmol) was added dropwise at 0° C. The resulting solution was then stirred for 1 h at room temperature. After the reaction was done, the reaction mixture was concentrated under reduced pressure to yield 5-bromo-4-methoxypyridine-2-carbonyl chloride (500 mg, crude), which was used directly in next step without further purification.

To a solution of 5-bromo-4-methoxypyridine-2-carbonyl chloride (500 mg, crude) in THF (10 mL) was added 2-(methylamino)ethan-1-ol (475 mg, 6.32 mmol) and DIEA (6.7 mL, 40.24 mmol) at room temperature. The resulting solution was stirred for 1.5 h at room temperature. When the reaction was done, it was quenched by the addition of water (10 mL). The resulting mixture was extracted with ethyl acetate (30 mL×3). The organic phases were combined, washed with brine and dried over sodium sulfate. The solvent was removed under reduced pressure to yield 5-bromo-N-(2-hydroxyethyl)-4-methoxy-N-methylpyridine-2-carboxamide as a light yellow solid (110 mg, 18%). MS: m/z=289.0 [M+H]$^+$.

4-[7-[3-cyano-4-(oxan-4-yloxy)phenyl]furo[3,2-b]pyridin-2-yl]-N-[(3S,5S)-5-(hydroxymethyl)-1-methylpyrrolidin-3-yl]-3-methoxybenzamide The title compound was prepared from 5-bromo-N-(2-hydroxyethyl)-4-methoxy-N-methylpicolinamide, 4,4,4',4', 5,5,5',5'-octamethyl-2,2'-bi(1,3,2-dioxaborolane), 7-chloro-2-iodofuro[3,2-b]pyridine and 2-(tetrahydro-2H-pyran-4-yloxy)-5-(4,4,5,5-tetramethyl-1,3,2-dioxaborolan-2-yl)benzonitrile using Methods G, H and R. The final product was purified by prep-HPLC under the following conditions: column, XBridge Prep C18 OBD Column, 150 mm 5 um; mobile phase, acetonitrile in water (with 10 mmol/L NH$_4$HCO$_3$), 20% to 50% gradient in 8 min; detector, UV 254 nm. 4-[7-[3-cyano-4-(oxan-4-yloxy)phenyl]furo[3,2-b]pyridin-2-yl]-N-[(3S,5S)-5-(hydroxymethyl)-1-methylpyrrolidin-3-yl]-3-methoxybenzamide was obtained as a white solid (22 mg, 1.9% for 3 steps). HPLC: 99.2% purity, RT=0.97 min. MS: m/z=529.0 [M+H]$^+$. $^1$H NMR (300 MHz, CD$_3$OD, ppm) δ 9.01 (d, J=10.5 Hz, 1H), 8.50 (d, J=5.2 Hz, 1H), 8.41-8.30 (m, 2H), 7.63-7.53 (m, 2H), 7.52-7.42 (m, 2H), 4.99-4.82 (m, 1H), 4.17 (d, J=4.0 Hz, 3H), 4.06-3.94 (m, 2H), 3.89-3.49 (m, 6H), 3.13 (d, J=18.5 Hz, 3H), 2.20-2.04 (m, 2H), 1.93-1.77 (m, 2H).

Example 330: 5-[7-[3-cyano-4-(oxan-4-yloxy)phenyl]furo[3,2-b]pyridin-2-yl]-N-(2-hydroxyethyl)-4-methoxy-N-methylpyridine-2-carboxamide (375)

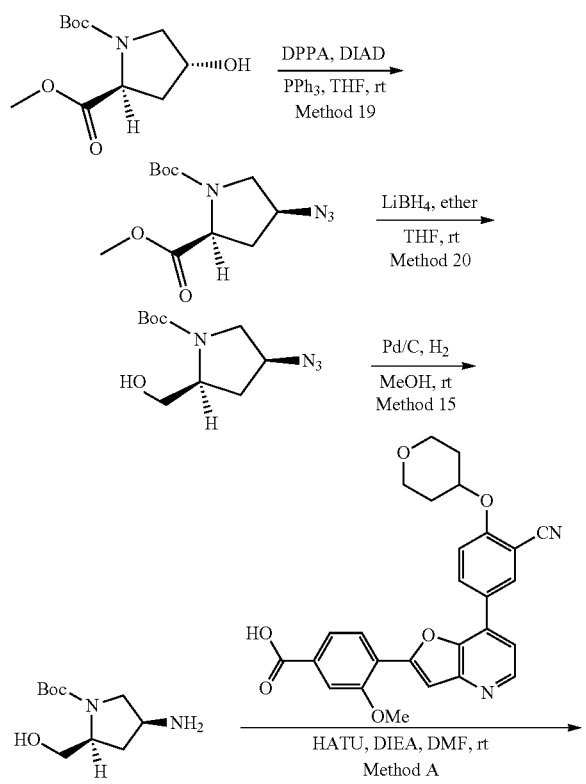

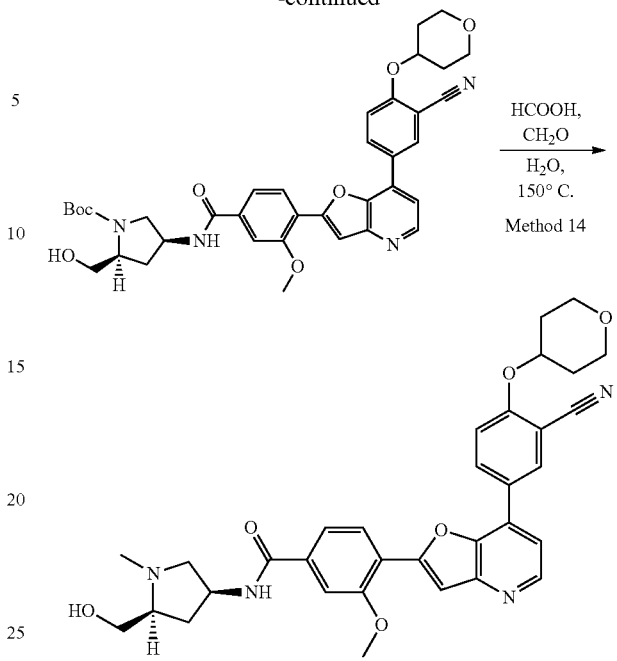

The title compound was prepared from (2S,4R)-1-tert-butyl 2-methyl 4-hydroxypyrrolidine-1,2-dicarboxylate, 4-(7-(3-cyano-4-(tetrahydro-2H-pyran-4-yloxy)phenyl)furo[3,2-b]pyridin-2-yl)-3-methoxybenzoic acid and formaldehyde using Methods 19, 20, 15, A and 14. The final product was purified by prep-HPLC under the following conditions: column, XBridge Prep C18 OBD Column, 150 mm 5 um; mobile phase, acetonitrile in water (with 10 mmol/L NH$_4$HCO$_3$), 25% to 55% gradient in 8 min; detector, UV 254 nm. 4-[7-[3-cyano-4-(oxan-4-yloxy)phenyl]furo[3,2-b]pyridin-2-yl]-N-[(3S,5S)-5-(hydroxymethyl)-1-methylpyrrolidin-3-yl]-3-methoxybenzamide was obtained as a white solid (16 mg, 1.7% for 5 steps). HPLC: 92.4% purity, RT=2.26 min. MS: m/z=583.2 [M+H]$^+$. $^1$H NMR (300 MHz, DMSO-d$_6$, ppm) δ 8.52-8.40 (m, 1H), 8.39-8.27 (m, 2H), 8.08-7.96 (m, 1H), 7.65-7.40 (m, 5H), 4.95-4.83 (m, 1H), 4.57-4.45 (m, 1H), 4.133.95 (m, 5H), 3.77-3.58 (m, 4H), 3.14 (d, J=10.0 Hz, 1H), 2.78-2.58 (m, 2H), 2.55-2.42 (m, 4H), 2.19-2.06 (m, 2H), 1.92-1.79 (m, 3H).

Example 331: 5-[7-[6-cyano-5-(oxan-4-yloxy)pyridin-2-yl]furo[3,2-b]pyridin-2-yl]-N-(2-hydroxyethyl)-4-methoxy-N-methylpyridine-2-carboxamide (376)

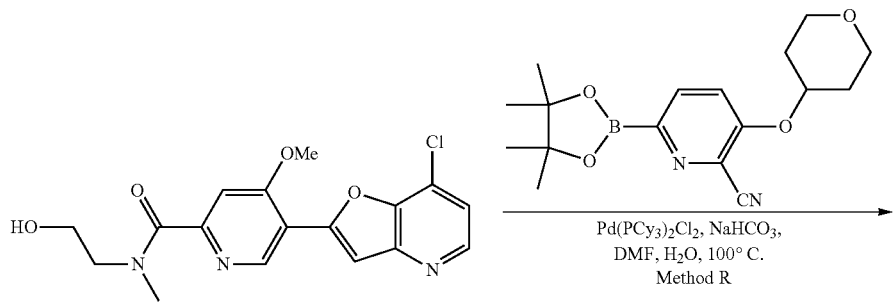

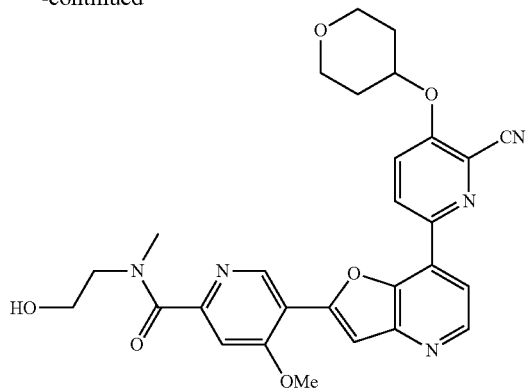

The title compound was prepared from 5-(7-chlorofuro[3,2-b]pyridin-2-yl)-N-(2-hydroxyethyl)-4-methoxy-N-methylpicolinamide and 3-(tetrahydro-2H-pyran-4-yloxy)-6-(4,4,5,5-tetramethyl-1,3,2-dioxaborolan-2-yl)picolinonitrile using Method R. The product was purified by prep-HPLC under the following conditions: column, XBridge Prep C18 OBD Column, 150 mm 5 um; mobile phase, acetonitrile in water (with 10 mmol/L $NH_4HCO_3$), 20% to 50% gradient in 8 min; detector, UV 254 nm. 5-[7-[6-cyano-5-(oxan-4-yloxy)pyridin-2-yl]furo[3,2-b]pyridin-2-yl]-N-(2-hydroxyethyl)-4-methoxy-N-methylpyridine-2-carboxamide was obtained as a white solid (22 mg, 18%). HPLC: 97.8% purity, RT=1.27 min. MS: m % z=529.9 [M+H]$^+$. $^1$H NMR (300 MHz, CD$_3$OD, ppm) δ 9.14 (d, J=8.7 Hz, 1H), 8.74 (d, J=9.3 Hz, 1H), 8.59 (d, J=5.2 Hz, 1H), 8.07 (d, J=4.9 Hz, 1H), 7.99 (d, J=8.9 Hz, 1H), 7.64 (s, 1 H), 7.49 (d, J=8.0 Hz, 1H), 5.02-4.90 (m, 1H), 4.18 (d, J=3.1 Hz, 3H), 4.06-3.92 (m, 2H), 3.90-3.51 (m, 6H), 3.14 (d, J=18.0 Hz, 3H), 2.20-2.08 (m, 2H), 1.96-1.80 (m, 2H).

Example 332: 5-[7-[4-cyano-5-(oxan-4-yloxy)pyridin-2-yl]furo[3,2-b]pyridin-2-yl]-N-(2-hydroxyethyl)-4-methoxy-N-methylpyridine-2-carboxamide (377)

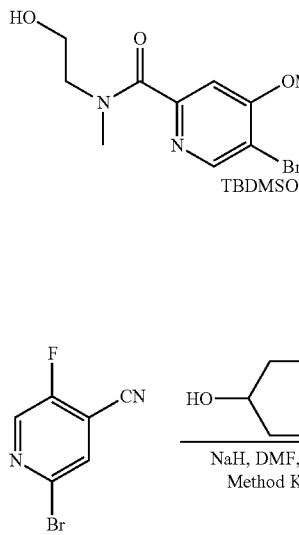

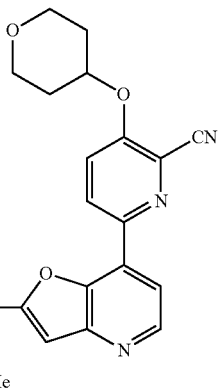

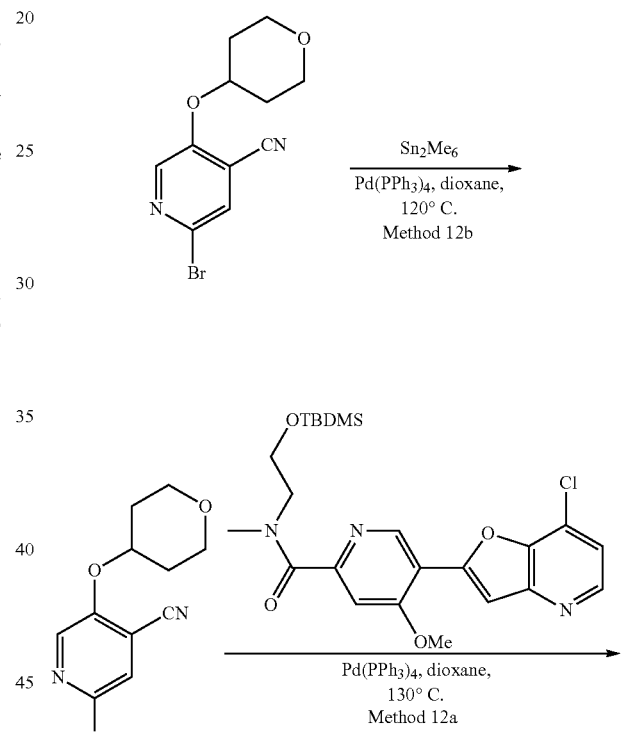

-continued

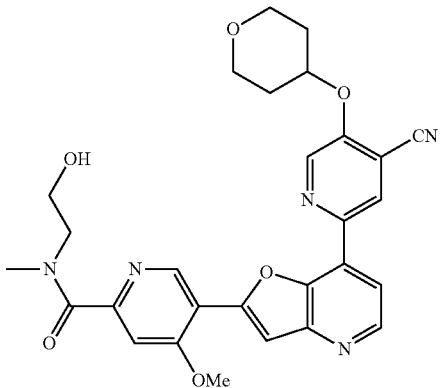 [SMILES: COc1cc(C(=O)N(C)CCO)ncc1-c1cc2nccc(-c3cc(C#N)c(OC4CCOCC4)cn3)c2o1]

The title compound was prepared from 2-bromo-5-fluoroisonicotinonitrile, tetrahydro-2H-pyran-4-ol and N-(2-(tert-butyldimethylsilyloxy)ethyl)-5-(7-chlorofuro[3,2-b]pyridin-2-yl)-4-methoxy-N-methylpicolinamide using Methods 21, K, 12a, 12b, and I. The final product was purified by prep-HPLC under the following conditions: column, XBridge Prep C18 OBD Column, 150 mm 5 um; mobile phase, acetonitrile in water (with 10 mmol/L $NH_4HCO_3$), 25% to 55% gradient in 8 min; detector, UV 254 nm. 5-[7-[4-cyano-5-(oxan-4-yloxy)pyridin-2-yl]furo[3,2-b]pyridin-2-yl]-N-(2-hydroxyethyl)-4-methoxy-N-methylpyridine-2-carboxamide was obtained as a white solid (13 mg, 3.2% for 5 steps). HPLC: 98.7% purity, RT=2.66 min. MS: m/z=530.2 [M+H]$^+$. $^1$H NMR (400 MHz, DMSO-d$_6$, ppm) δ 9.17 (d, J=11.0 Hz, 1H), 9.08 (d, J=1.4 Hz, 1H), 8.80 (s, 1H), 8.70-8.64 (m, 1H), 7.98 (d, J=5.1 Hz, 1H), 7.72 (d, J=2.0 Hz, 1H), 7.43 (d, J=3.9 Hz, 1H), 5.22-5.12 (m, 1H), 4.88-4.72 (m, 1H), 4.15 (d, J=7.4 Hz, 3H), 3.96-3.84 (m, 2H), 3.69-3.50 (m, 5H), 3.46-3.36 (m, 1H), 3.04 (d, J=7.8 Hz, 3H), 2.19-2.03 (m, 2H), 1.82-1.68 (m, 2H).

Example 333: 5-(7-(3-cyano-4-(3-fluoropyrrolidin-1-yl)phenyl)furo[3,2-b]pyridin-2-yl)-N-(2-hydroxyethyl)-4-methoxy-N-methylpicolinamide (378)

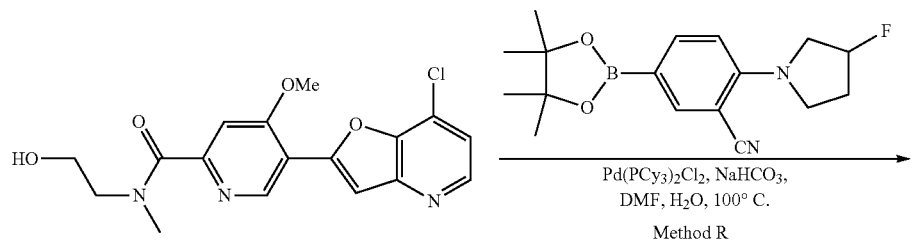

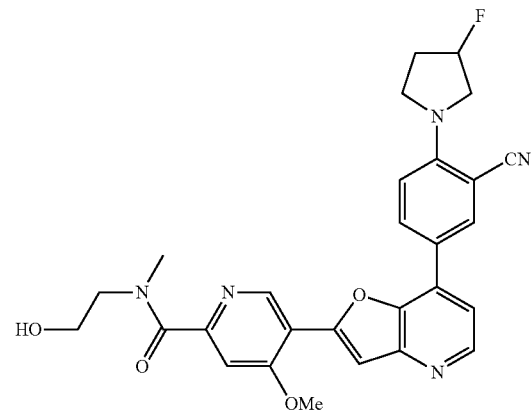

The title compound was prepared from 5-(7-chlorofuro[3,2-b]pyridin-2-yl)-N-(2-hydroxyethyl)-4-methoxy-N-methylpicolinamide and 2-(3-fluoropyrrolidin-1-yl)-5-(4,4,5,5-tetramethyl-1,3,2-dioxaborolan-2-yl)benzonitrile using Method R. The product was first purified by prep-HPLC under the following conditions: column, XBridge Prep C18 OBD Column, 150 mm 5 um; mobile phase, acetonitrile in water (with 10 mmol/L NH₄HCO₃), 200/% to 50% gradient in 8 min; detector, UV 254/220 nm.

Example 334: 5-{7-[3-Cyano-4-((S)-3-fluoro-pyrrolidin-1-yl)-phenyl]-furo[3,2-b]pyridin-2-yl}-4-methoxy-pyridine-2-carboxylic acid (2-hydroxyethyl)-methyl-amide (379)

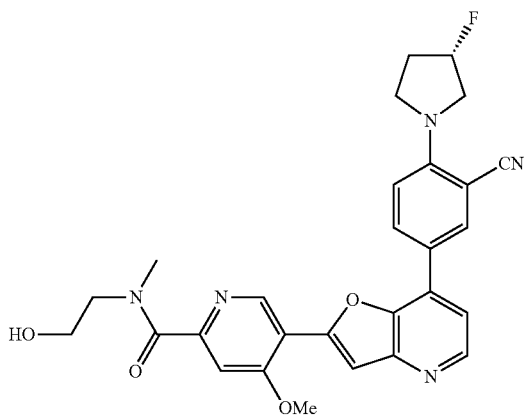 [SMILES: COc1cc(C(=O)N(C)CCO)ncc1-c1cc2nccc(-c3ccc(N4CC[C@H](F)C4)c(C#N)c3)c2o1]

The title compound was separated from 5-(7-(3-cyano-4-(3-fluoropyrrolidin-1-yl)phenyl)furo[3,2-b]pyridin-2-yl)-N-(2-hydroxyethyl)-4-methoxy-N-methylpicolinamide on a chiral prep-HPLC under the following conditions: column CHIRALPAK IA, 0.46×10 cm, 5 um; mobile phase, EtOH in MeCN (0.1% DEA), 50% isocratic in 10 min; detector, UV 330 nm. (40 mg, 17%, yellow solid) HPLC: 94.1% purity, RT=3.42 min. MS: m, =516.2 [M+H]⁺. ¹H NMR (300 MHz, CD₃OD, ppm) δ 8.98 (d, J=12.5 Hz, 1H), 8.42 (d, J=5.2 Hz, 1H), 8.27-8.07 (m, 2H), 7.57-7.42 (m, 3H), 6.94 (d, J=9.1 Hz, 1H), 5.53-5.28 (m, 1H), 4.17 (d, J=4.1 Hz, 3H), 4.10-3.50 (m, 8H), 3.13 (d, J=17.2 Hz, 3H), 2.48-2.08 (m, 2H).

Example 335: 5-{7-[3-Cyano-4-((R)-3-fluoro-pyrrolidin-1-yl)-phenyl]-furo[3,2-b]pyridin-2-yl}-4-methoxy-pyridine-2-carboxylic acid (2-hydroxyethyl)-methyl-amide (380)

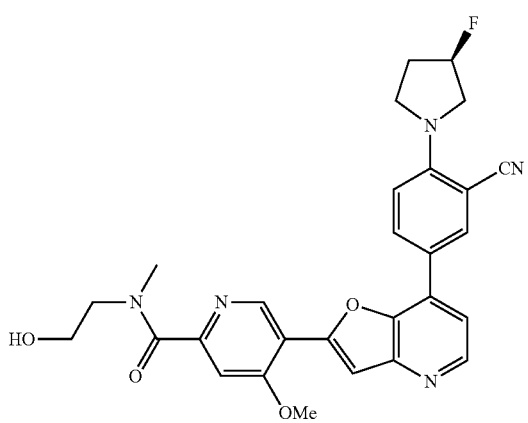 [SMILES: COc1cc(C(=O)N(C)CCO)ncc1-c1cc2nccc(-c3ccc(N4CC[C@@H](F)C4)c(C#N)c3)c2o1]

The title compound was separated from 5-(7-(3-cyano-4-(3-fluoropyrrolidin-1-yl)phenyl)furo[3,2-b]pyridin-2-yl)-N-(2-hydroxyethyl)-4-methoxy-N-methylpicolinamide on a chiral prep-HPLC. (15 mg, 3.3% for 3 steps, yellow solid) HPLC: 98.6% purity, RT=3.42 min. MS: mm/z=516.2 [M+H]⁺. ¹H NMR (300 MHz, CD₃OD, ppm) δ 9.02 (d, J=11.5 Hz, 1H), 8.44 (d, J=5.3 Hz, 1H), 8.31-8.11 (m, 2H), 7.60-7.42 (m, 3H), 6.98 (d, J=9.2 Hz, 1H), 5.55-5.27 (m, 1H), 4.22-3.50 (m, 11H), 3.13 (d, J=17.5 Hz, 3H), 2.40-2.10 (m, 2H).

Example 336: 5-(2-[4-methoxy-6-[(piperidin-1-yl)carbonyl]pyridin-3-yl]furo[3,2-b]pyridin-7-yl)-2-(oxan-4-yloxy)benzonitrile hydrochloride (381)

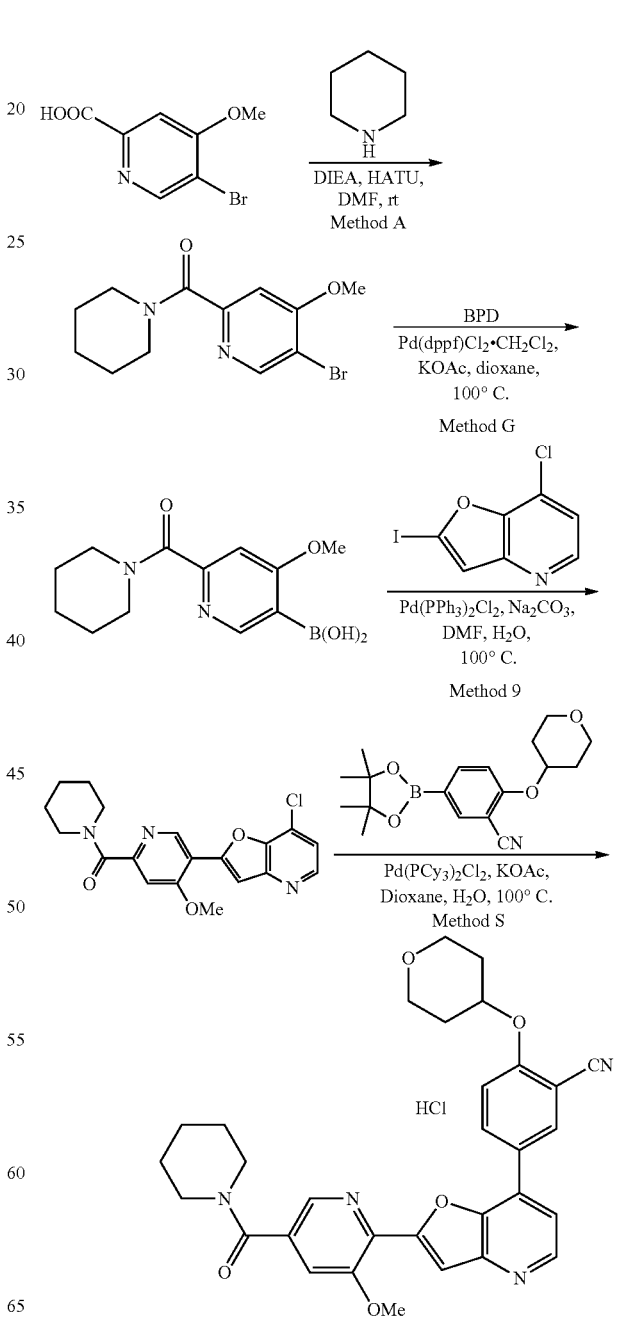

The title compound was prepared from 5-bromo-4-methoxypicolinic acid, piperidine, 4,4,4',4',5,5,5',5'-octamethyl-2,2'-bi(1,3,2-dioxaborolane), 7-chloro-2-iodofuro[3,2-b]pyridine and 2-(tetrahydro-2H-pyran-4-yloxy)-5-(4,4,5,5-tetramethyl-1,3,2-dioxaborolan-2-yl)benzonitrile using Methods A, G, 9 and S. The final product was purified by prep-HPLC under the following conditions: column, XBridge Prep C18 OBD Column, 150 mm 5 um; mobile phase, acetonitrile in water (with 0.02% HCl), 20% to 50% gradient in 8 min; detector, UV 254 nm. 5-(2-[4-methoxy-6-[(piperidin-1-yl)carbonyl]pyridin-3-yl]furo[3,2-b]pyridin-7-yl)-2-(oxan-4-yloxy)benzonitrile hydrochloride was obtained as a yellow solid (35 mg, 7.8% for 4 steps). HPLC: 99.3% purity, RT=1.41 min. MS: m/z=539.2 [M+H]⁺. ¹H NMR (300 MHz, DMSO-d₆, ppm) δ 9.12 (s, 1H), 8.74 (d, J=5.6 Hz, 1H), 8.68-8.51 (m, 2H), 7.96 (d, J=5.5 Hz, 1H), 7.80-7.65 (m, 2H), 7.49 (s, 1H), 5.05-4.95 (m, 1H), 4.17 (s, 3H), 3.95-3.30 (m, 8H), 2.16-2.00 (m, 2H), 1.82-1.48 (m, 8H).

Example 337: 6-(2-[4-methoxy-6-[(piperidin-1-yl)carbonyl]pyridin-3-yl]furo[3,2-b]pyridin-7-yl)-3-(oxan-4-yloxy)pyridine-2-carbonitrile (382)

The title compound was prepared from (5-(7-chlorofuro[3,2-b]pyridin-2-yl)-4-methoxypyridin-2-yl)(piperidin-1-yl)methanone and 6-cyano-5-(tetrahydro-2H-pyran-4-yloxy)pyridin-2-ylboronic acid using Method O. The product was purified by prep-HPLC under the following conditions: column, XBridge Prep C18 OBD Column, 150 mm 5 um; mobile phase, acetonitrile in water (with 10 mmol/L NH₄HCO₃), 20% to 50% gradient in 8 min; detector, UV 254 nm. 6-(2-[4-methoxy-6-[(piperidin-1-yl)carbonyl]pyridin-3-yl]furo[3,2-b]pyridin-7-yl)-3-(oxan-4-yloxy)pyridine-2-carbonitrile was obtained as a off-white solid (20 mg, 23%). HPLC: 98.9% purity, RT=1.69 min. MS: m/z=540.2 [M+H]⁺. ¹H NMR (300 MHz, DMSO-d₆, ppm) δ 9.16 (s, 1H), 8.81 (d, J=9.6 Hz, 1H), 8.66 (d, J=5.3 Hz, 1H), 8.21 (d, J=9.6 Hz, 1H), 7.98 (d, J=5.2 Hz, 1H), 7.70 (s, 1H), 7.45 (S, 1H), 5.05-4.95 (m, 1H), 4.16 (s, 3H), 3.98-3.85 (m, 2H), 3.72-3.58 (m, 5H), 3.39-3.29 (m, 1H), 2.18-2.02 (m, 2H), 1.85-1.40 (m, 8H).

Example 338: 2-(2-[4-methoxy-6-[(piperidin-1-yl)carbonyl]pyridin-3-yl]furo[3,2-b]pyridin-7-yl)-5-(oxan-4-yloxy)pyridine-4-carbonitrile (383)

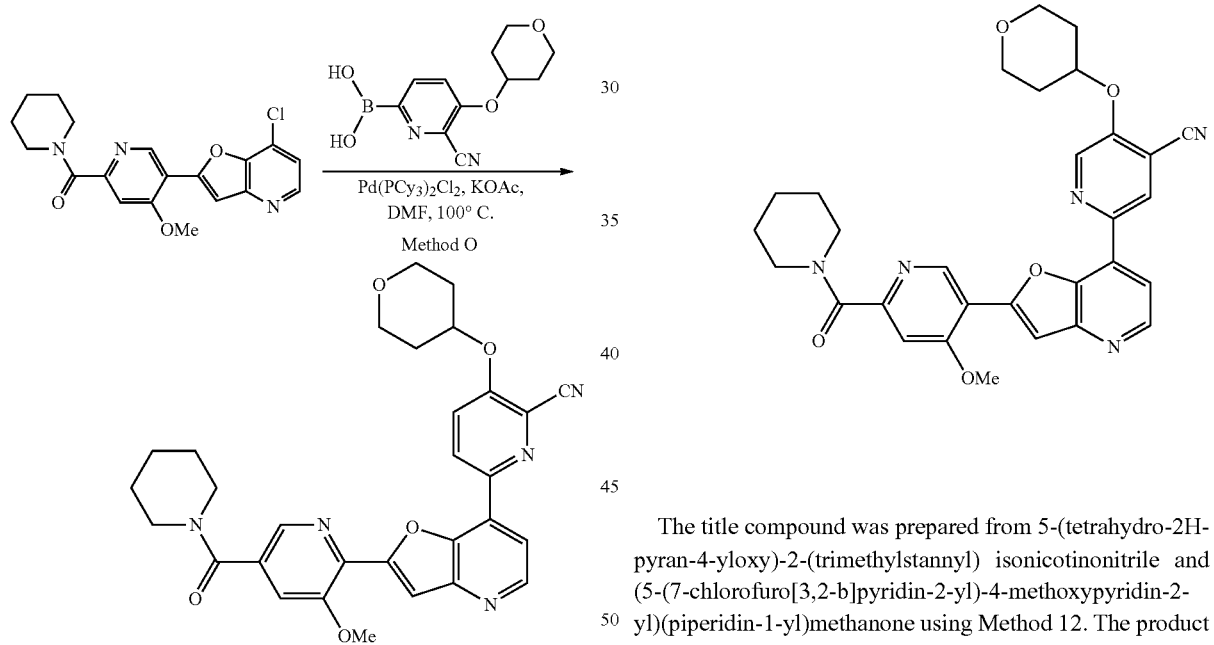

The title compound was prepared from 5-(tetrahydro-2H-pyran-4-yloxy)-2-(trimethylstannyl) isonicotinonitrile and (5-(7-chlorofuro[3,2-b]pyridin-2-yl)-4-methoxypyridin-2-yl)(piperidin-1-yl)methanone using Method 12. The product was purified by prep-HPLC under the following conditions: column, XBridge Prep C18 OBD Column, 150 mm 5 um; mobile phase, acetonitrile in water (with 10 mmol/L NH₄HCO₃), 20% to 50% gradient in 8 min; detector, UV 254 nm. 2-(2-[4-methoxy-6-[(piperidin-1-yl)carbonyl]pyridin-3-yl]furo[3,2-b]pyridin-7-yl)-5-(oxan-4-yloxy)pyridine-4-carbonitrile was obtained as a off-white solid (11 mg, 8%). HPLC: 93.5% purity, RT=1.62 min. MS: m/z=540.2 [M+H]⁺. ¹H NMR (400 MHz, DMSO-d₆, ppm) δ 9.18 (s, 1H), 9.08 (s, 1H), 8.81 (s, 1H), 8.67 (d, J=5.1 Hz, 1H), 7.99 (d, J=5.1 Hz, 1H), 7.72 (s, 1H), 7.44 (s, 1H), 5.22-5.12 (m, 1H), 4.16 (s, 3H), 3.96-3.84 (m, 2H), 3.68-3.52 (m, 4H), 3.36-3.25 (m, 2H), 2.11 (dd, J=9.7, 5.5 Hz, 2H), 1.82-1.45 (m, 8H).

Example 339: 2-(3-fluoropyrrolidin-1-yl)-5-(2-(4-methoxy-6-(piperidine-1-carbonyl)pyridin-3-yl)furo[3,2-b]pyridin-7-yl)benzonitrile

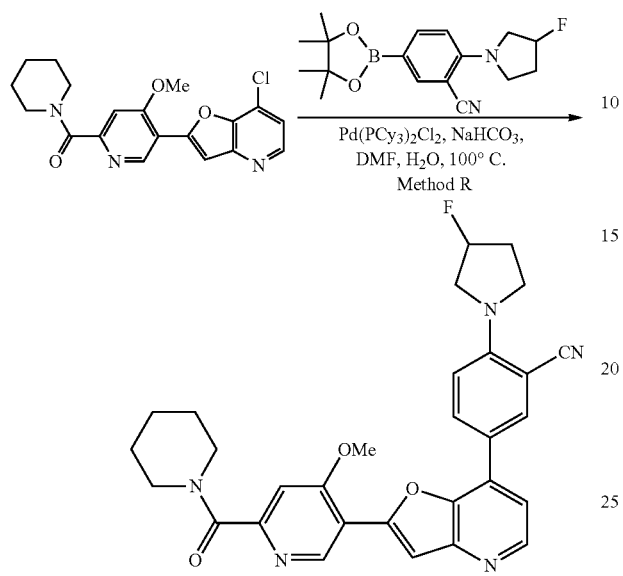

The title compound was prepared from (5-(7-chlorofuro[3,2-b]pyridin-2-yl)-4-methoxypyridin-2-yl)(piperidin-1-yl)methanone and 2-(3-fluoropyrrolidin-1-yl)-5-(4,4,5,5-tetramethyl-1,3,2-dioxaborolan-2-yl)benzonitrile using Method R. The product was first purified by prep-HPLC under the following conditions: column, XBridge Prep C18 OBD Column, 150 mm 5 um; mobile phase, acetonitrile in water (with 10 mmol/L NH$_4$HCO$_3$), 25% to 55% gradient in 8 min; detector, UV 254/220 nm.

Example 340: 2-((S)-3-Fluoro-pyrrolidin-1-yl)-5-{2-[4-methoxy-6-(piperidine-1-carbonyl)-pyridin-3-yl]-furo[3,2-b]pyridin-7-yl}-benzonitrile (384)

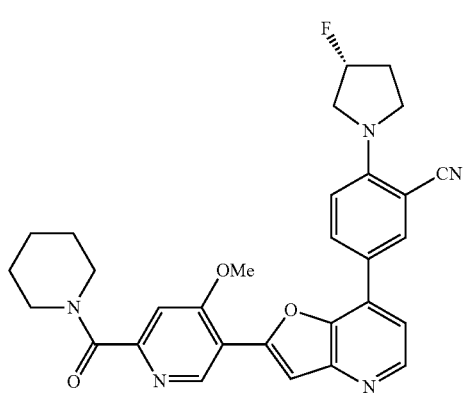 [SMILES: COc1cc(C(=O)N2CCCCC2)ncc1-c1cc2nccc(-c3ccc(N4CC[C@@H](F)C4)c(C#N)c3)c2o1]

The title compound was separated from 2-(3-fluoropyrrolidin-1-yl)-5-(2-(4-methoxy-6-(piperidine-1-carbonyl)pyridin-3-yl)furo[3,2-b]pyridin-7-yl)benzonitrile on a chiral prep-HPLC under the following conditions: column CHIRALPAK AD-H SFC, 0.46×10 cm, 5 um; mobile phase, EtOH in MeCN (0.1% DEA), 50% isocatic in 10 min; detector, UV 330 nm. (25 mg, 18%, yellow solid) HPLC: 94.1° % purity, RT=3.42 min. MS: m/z=526.2 [M+H]$^+$. $^1$H NMR (300 MHz, DMSO-d$_6$, ppm) δ 9.20 (s, 1H), 8.80 (d, J=6.2 Hz, 1H), 8.59 (d, J=2.2 Hz, 1H), 8.51-8.43 (m, 1H), 8.25 (d, J=6.2 Hz, 1H), 7.85 (s, 1H), 7.62 (s, 1H), 7.14 (d, J=9.3 Hz, 1H), 5.64-5.50 (m, 1H), 4.23 (s, 3H), 4.14-3.74 (m, 4H), 3.70-3.59 (m, 2H), 3.40-3.28 (m, 2H), 2.41-2.27 (m, 2H), 1.70-1.45 (m, 6H).

Example 341: 2-((R)-3-Fluoro-pyrrolidin-1-yl)-5-{2-[4-methoxy-6-(piperidine-1-carbonyl)-pyridin-3-yl]-furo[3,2-b]pyridin-7-yl}-benzonitrile (385)

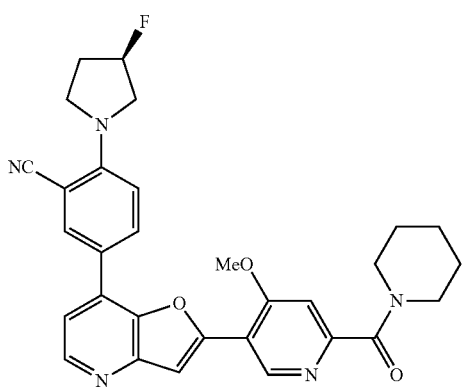 [SMILES: COc1cc(C(=O)N2CCCCC2)ncc1-c1cc2nccc(-c3ccc(N4CC[C@@H](F)C4)c(C#N)c3)c2o1]

The title compound was separated from 2-(3-fluoropyrrolidin-1-yl)-5-(2-(4-methoxy-6-(piperidine-1-carbonyl)pyridin-3-yl)furo[3,2-b]pyridin-7-yl)benzonitrile on a chiral prep-HPLC. (25 mg, 18%, yellow solid) HPLC: 98.90/% purity, RT=1.29 min. MS: m/z=526.2 [M+H]$^+$. $^1$H NMR (300 MHz, DMSO-d$_6$, ppm) δ 9.16 (s, 1H), 8.78 (d, 0.1=6.3 Hz, 1H), 8.59 (d, J=2.4 Hz, 1H), 8.47 (dd, J=9.3, 2.4 Hz, 1H), 8.22 (d, J=6.4 Hz, 1H), 7.79 (s, 1H), 7.54 (s, 1H), 7.14 (d, J=9.3 Hz, 1H), 5.67-5.39 (m, 1H), 4.19 (s, 3H), 4.15-3.75 (m, 4H), 3.70-3.58 (m, 2H), 3.39-3.25 (m, 2H), 2.40-2.25 (m, 2H), 1.70-1.45 (m, 6H).

Example 342: 5-[7-[4-cyano-5-(oxan-4-yloxy)pyridin-2-yl]furo[3,2-b]pyridin-2-yl]-4-methoxy-N,N-dimethylpyridine-2-carboxamide (386)

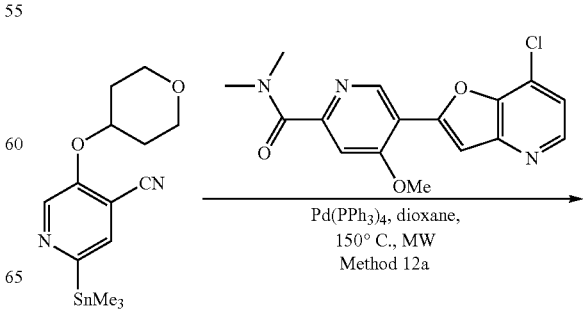

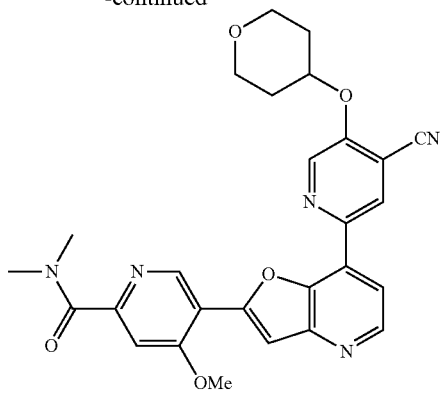

The title compound was prepared from 5-(tetrahydro-2H-pyran-4-yloxy)-2-(trimethylstannyl) isonicotinonitrile and (5-(7-chlorofuro[3,2-b]pyridin-2-yl)-4-methoxypyridin-2-yl)(piperidin-1-yl)methanone using Method 12. The product was purified by prep-HPLC under the following conditions: column, XBridge Prep C18 OBD Column, 150 mm 5 um; mobile phase, acetonitrile in water (with 10 mmol/L NH$_4$HCO$_3$), 20% to 50% gradient in 8 min; detector, UV 254 nm. 5-[7-[4-cyano-5-(oxan-4-yloxy)pyridin-2-yl]furo[3,2-b]pyridin-2-yl]-4-methoxy-N,N-dimethylpyridine-2-carboxamide was obtained as a white solid (10 mg, 11%0). HPLC: 99.8% purity, RT=1.46 min. MS: m/z=500.1 [M+H]$^+$. $^1$H NMR (300 MHz, CD$_3$OD, ppm) δ 9.15 (d, J=11.0 Hz, 1H), 8.91 (d, J=4.6 Hz, 1H), 8.79-8.50 (m, 2H), 8.08 (dd, J=9.3, 5.1 Hz, 1H), 7.66 (d, J=10.4 Hz, 1H), 7.49 (d, J=2.0 Hz, 1H), 5.19-5.07 (m, 1H), 4.23 (d, J=1.6 Hz, 3H), 4.10-3.98 (m, 2H), 3.78-3.64 (m, 2H), 3.18 (s, 3H), 3.11 (s, 3H), 2.27-2.13 (m, 2H), 1.99-1.85 (m, 2H).

Example 343: 5-[7-[6-cyano-5-(oxan-4-yloxy)pyridin-2-yl]furo[3,2-b]pyridin-2-yl]-4-methoxy-N,N-dimethylpyridine-2-carboxamide hydrochloride (387)

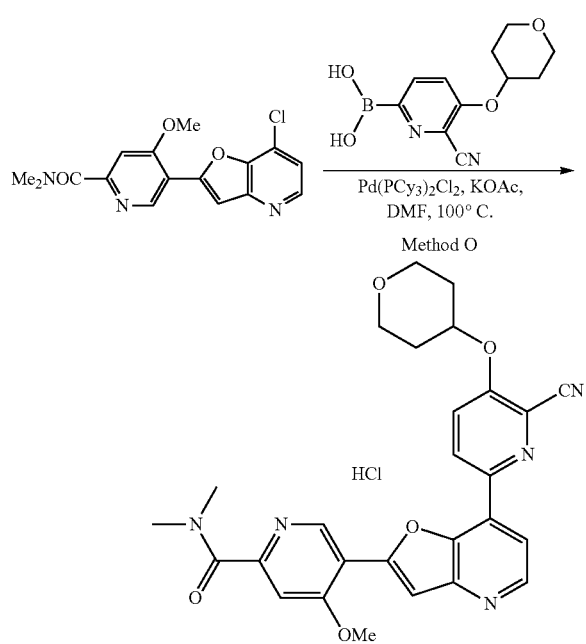

The title compound was prepared from 5-(7-chlorofuro[3,2-b]pyridin-2-yl)-4-methoxy-N,N-dimethylpicolinamide and 6-cyano-5-(tetrahydro-2H-pyran-4-yloxy)pyridin-2-ylboronic acid using Method O. The product was purified by prep-HPLC under the following conditions: column, XBridge Prep C18 OBD Column, 150 mm 5 um; mobile phase, acetonitrile in water (with 0.05% HCl), 20% to 45% gradient in 8 min; detector, UV 254 nm. 5-[7-[6-cyano-5-(oxan-4-yloxy)pyridin-2-yl]furo[3,2-b]pyridin-2-yl]-4-methoxy-N,N-dimethylpyridine-2-carboxamide hydrochloride was obtained as a yellow solid (18 mg, 21%). HPLC: 95.9% purity, RT=2.09 min. MS: m/z=500.2 [M+H]$^+$. $^1$H NMR (300 MHz, CD$_3$OD, ppm) δ 9.26 (s, 1H), 8.88 (d, J=9.0 Hz, 1H), 8.74 (d, J=5.8 Hz, 1H), 8.39 (d, J=5.9 Hz, 1H), 8.08 (d, J=9.1 Hz, 1H), 7.80 (s, 1H), 7.55 (s, 1H), 5.08-4.98 (m, 1H), 4.25 (s, 3H), 4.10-3.98 (m, 2H), 3.77-3.65 (m, 2H), 3.19 (s, 3H), 3.10 (s, 3H), 2.26-2.12 (m, 2H), 2.00-1.83 (m, 2H).

Example 344: 5-[7-[5-cyano-6-(oxan-4-yloxy)pyridin-3-yl]furo[3,2-b]pyridin-2-yl]-4-methoxy-N,N-dimethylpyridine-2-carboxamide (388)

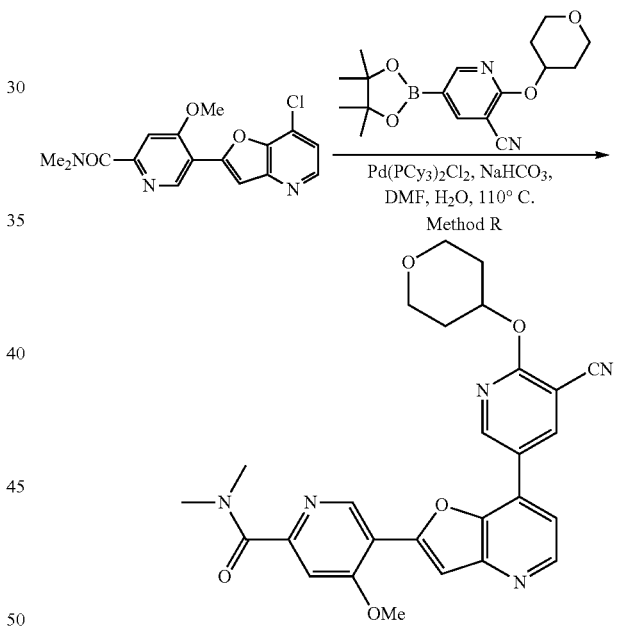

The title compound was prepared from 2-(tetrahydro-2H-pyran-4-yloxy)-5-(4,4,5,5-tetramethyl-1,3,2-dioxaborolan-2-yl)nicotinonitrile and 5-(7-chlorofuro[3,2-b]pyridin-2-yl)-4-methoxy-N,N-dimethylpicolinamide using Method R. The product was purified by prep-HPLC under the following conditions: column, XBridge Prep C18 OBD Column, 150 mm 5 um; mobile phase, acetonitrile in water (with 10 mmol/L NH$_4$HCO$_3$), 30% to 60% gradient in 8 min; detector, UV 254 nm. 5-[7-[5-cyano-6-(oxan-4-yloxy)pyridin-3-yl]furo[3,2-b]pyridin-2-yl]-4-methoxy-N,N-dimethylpyridine-2-carboxamide was obtained as a white solid (29 mg, 22%). HPLC: 97.7% purity, RT=1.69 min. MS: m %z=500.2 [M+H]$^+$. $^1$H NMR (400 MHz, DMSO-d$_6$, ppm) δ 9.26 (d, J=2.5 Hz, 1H), 9.09 (s, 1H), 9.03 (d, J=2.5 Hz, 1H), 8.64 (d, J=5.1 Hz, 1H), 7.75 (d, J=5.1 Hz, 1H), 7.70 (s, 1H), 7.45 (s, 1H), 5.55-5.45 (m, 1H), 4.15 (s, 3H), 3.96-3.86 (m, 2H), 3.66-3.52 (m, 2H), 3.05 (s, 3H), 3.00 (s, 3H), 2.16-2.06 (m, 2H), 1.85-1.71 (m, 2H).

Example 345: 5-(7-(3-cyano-4-(3-fluoropyrrolidin-1-yl)phenyl)furo[3,2-b]pyridin-2-yl)-4-methoxy-N,N-dimethylpicolinamide

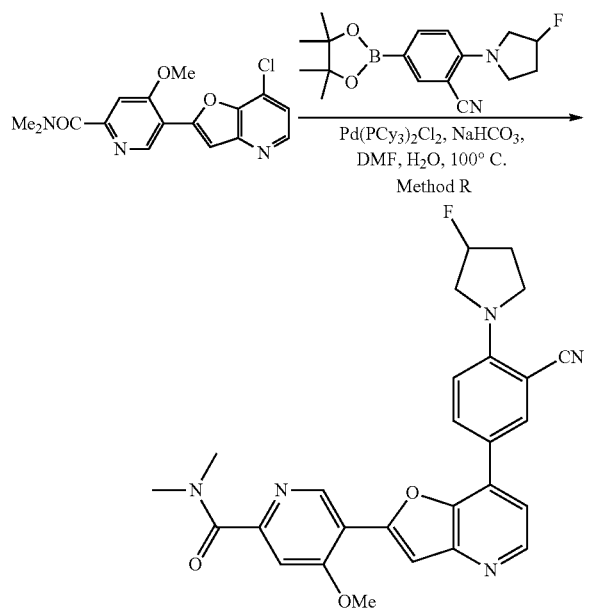

The title compound was prepared from 5-(7-chlorofuro[3,2-b]pyridin-2-yl)-4-methoxy-N,N-dimethylpicolinamide and 2-(3-fluoropyrrolidin-1-yl)-5-(4,4,5,5-tetramethyl-1,3,2-dioxaborolan-2-yl)benzonitrile using Method R. The product was first purified by prep-HPLC under the following conditions: column, XBridge Prep C18 OBD Column, 150 mm 5 um; mobile phase, acetonitrile in water (with 10 mmol/L NH$_4$HCO$_3$), 20% to 50% gradient in 8 min; detector, UV 254/220 nm.

Example 346: 5-{7-[3-Cyano-4-((S)-3-fluoro-pyrrolidin-1-yl)-phenyl]-furo[3,2-b]pyridin-2-yl}-4-methoxy-pyridine-2-carboxylic acid dimethylamide (389)

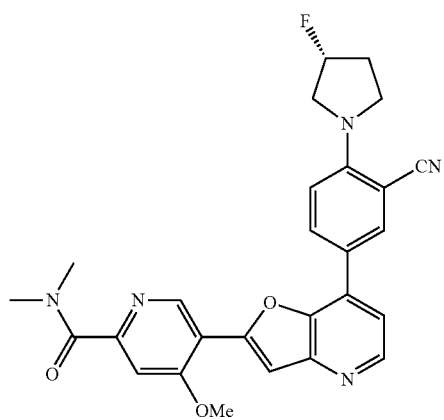 [SMILES: COc1cc(C(=O)N(C)C)ncc1-c1cc2nccc(-c3ccc(N4CC[C@@H](F)C4)c(C#N)c3)c2o1]

The title compound was separated from 5-(7-(3-cyano-4-(3-fluoropyrrolidin-1-yl)phenyl)furo[3,2-b]pyridin-2-yl)-4-methoxy-N,N-dimethylpicolinamide on a chiral prep-HPLC under the following conditions: column CHIRALPAK AD-H SFC, 0.46×10 cm, 5 um; mobile phase, EtOH (0.1% DEA) in 10 min; detector, UV 320 nm. (15 mg, 8%, light yellow solid) HPLC: 92.8% purity, RT=1.46 min. MS: m/z=486.3 [M+H]$^+$. $^1$H NMR (400 MHz, CD$_3$OD, ppm) δ 9.01 (s, 1H), 8.43 (d, J=5.2 Hz, 1H), 8.22 (d, J=2.3 Hz, 1H), 8.14 (dd, J=9.1, 2.3 Hz, 1H), 7.60-7.49 (m, 2H), 7.45 (s, 1H), 6.95 (d, J=9.1 Hz, 1H), 5.56-5.32 (m, 1H), 4.19 (s, 3H), 4.07-3.80 (m, 4H), 3.16 (s, 3H), 3.09 (s, 3H), 2.45-2.15 (m, 2H).

Example 347: 5-{7-[3-Cyano-4-((R)-3-fluoro-pyrrolidin-1-yl)-phenyl]-furo[3,2-b]pyridin-2-yl}-4-methoxy-pyridine-2-carboxylic acid dimethylamide (390)

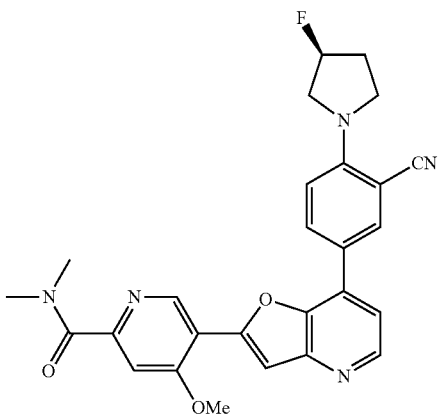 [SMILES: COc1cc(C(=O)N(C)C)ncc1-c1cc2nccc(-c3ccc(N4CC[C@H](F)C4)c(C#N)c3)c2o1]

The title compound was separated from 5-(7-(3-cyano-4-(3-fluoropyrrolidin-1-yl)phenyl)furo[3,2-b]pyridin-2-yl)-4-methoxy-N,N-dimethylpicolinamide on a chiral prep-HPLC (17 mg, 9%, light brown solid) HPLC: 93.1% purity, RT=1.55 min. MS: m/z=486.1 [M+H]$^+$. $^1$H NMR (300 MHz, CD$_3$OD, ppm) δ 9.01 (s, 1H), 8.44 (d, J=5.3 Hz, 1H), 8.28-8.04 (m, 2H), 7.69-7.28 (m, 3H), 6.95 (d, J=9.1 Hz, 1H), 5.52-5.39 (m, 1H), 4.21 (s, 3H), 4.15-3.79 (m, 4H), 3.18 (s, 3H), 3.11 (s, 3H), 2.55-1.99 (m, 2H).

Example 348: 6-[7-[3-cyano-4-(oxan-4-yloxy)phenyl]furo[3,2-b]pyridin-2-yl]-4-methoxy-N,N-dimethylpyridine-3-carboxamide (391)

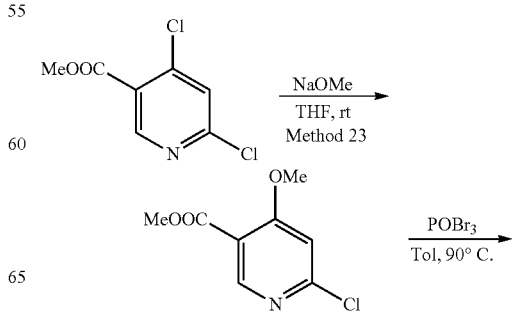

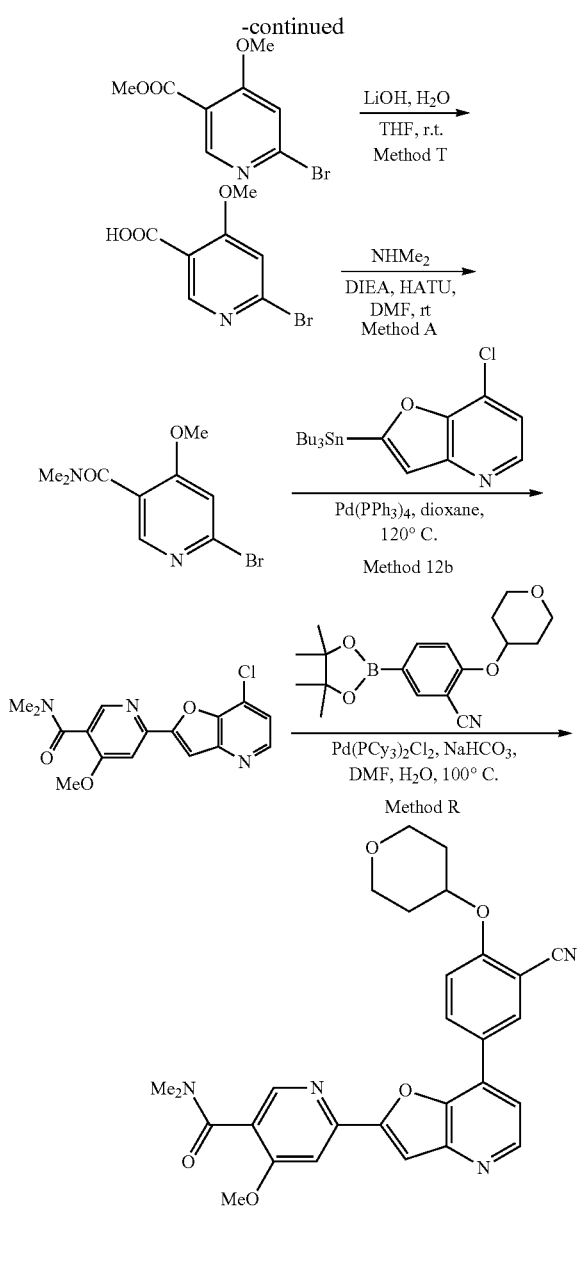

Method 23

Methyl 6-chloro-4-methoxynicotinate

At 0° C., to a solution of sodium methoxide (373 mg, 6.91 mmol) in THF (10 mL) was added a solution of methyl 4,6-dichloropyridine-3-carboxylate (0.95 g, 4.61 mmol) in tetrahydrofuran (5 mL) dropwise. The resulting solution was stirred overnight at room temperature. When the reaction was done, it was quenched by the addition of water (30 mL). The resulting mixture was extracted with ethyl acetate (100 mL×3). The organic phases were combined, washed with brine and dried over sodium sulfate. The solvent was removed under reduced pressure to yield methyl 6-chloro-4-methoxypyridine-3-carboxylate as a white solid (0.35 g, 38%). MS: m/z=202.0 [M+H]$^+$.

Methyl 6-bromo-4-methoxynicotinate

To a solution of methyl 6-chloro-4-methoxypyridine-3-carboxylate (326 mg, 1.61 mmol) in toluene (6 mL) was added POBr$_3$ (1.90 g, 6.63 mmol) at room temperature. The resulting solution was then stirred overnight at 90° C. After the reaction was done, the pH value of reaction mixture was adjusted to 7-8 with sat. sodium carbonate solution. The resulting mixture was extracted with ethyl acetate (30 mL×3). The organic phases were combined, washed with brine and dried over sodium sulfate. The solvent was removed under reduced pressure and the residue was purified by flash chromatography eluting with EtOAc in hexane (0% to % gradient) to yield methyl 6-bromo-4-methoxy pyridine-3-carboxylate as a yellow oil (350 mg, 88%). MS: m/z=246.0 [M+H]$^+$.

6-[7-[3-Cyano-4-(oxan-4-yloxy)phenyl]furo[3,2-b]pyridin-2-yl]-4-methoxy-N,N-dimethylpyridine-3-carboxamide 6-[7-[3-cyano-4-(oxan-4-yloxy)phenyl]furo[3,2-b]pyridin-2-yl]-4-methoxy-N,N-dimethylpyridine-3-carboxamide was prepared from methyl 6-bromo-4-methoxynicotinate, dimethylamine, 7-chloro-2-(tributylstannyl)furo[3,2-b]pyridine and 2-(tetrahydro-2H-pyran-4-yloxy)-5-(4,4,5,5-tetramethyl-1,3,2-dioxaborolan-2-yl)benzonitrile using Methods T, A, 12b, and R. The final product was purified by prep-HPLC under the following conditions: column, XBridge Prep C18 OBD Column, 150 mm 5 um; mobile phase, acetonitrile in water (with 10 mmol/L NH$_4$HCO$_3$), 30% to 55% gradient in 8 min; detector, UV 254 nm. 6-[7-[3-cyano-4-(oxan-4-yl oxy)phenyl]furo[3,2-b]pyridin-2-yl]-4-methoxy-N, N-dimethyl pyridine-3-carboxamide was obtained as a white solid (35 mg, 69%). HPLC: 99.1% purity, RT=1.49 min. MS: m/z=499.3 [M+H]$^+$. $^1$H NMR (300 MHz, DMSO-d$_6$, ppm) δ 8.59 (dd, J=10.3, 3.7 Hz, 2H), 8.41 (d, J=5.9 Hz, 2H), 7.84 (s, 1H), 7.74 (d, 0.1=3.3 Hz, 2H), 7.61 (d, J=9.0 Hz, 1H), 5.03-4.93 (m, 1H), 4.05 (s, 3H), 3.95-3.81 (m, 2H), 3.64-3.50 (m, 2H), 3.01 (s, 3H), 2.84 (s, 3H), 2.12-1.98 (m, 2H), 1.78-1.62 (m, 2H).

Example 349: 6-(7-[3-cyano-4-[(oxan-4-yl)amino]phenyl]furo[3,2-b]pyridin-2-yl)-4-methoxy-N,N-dimethylpyridine-3-carboxamide (392)

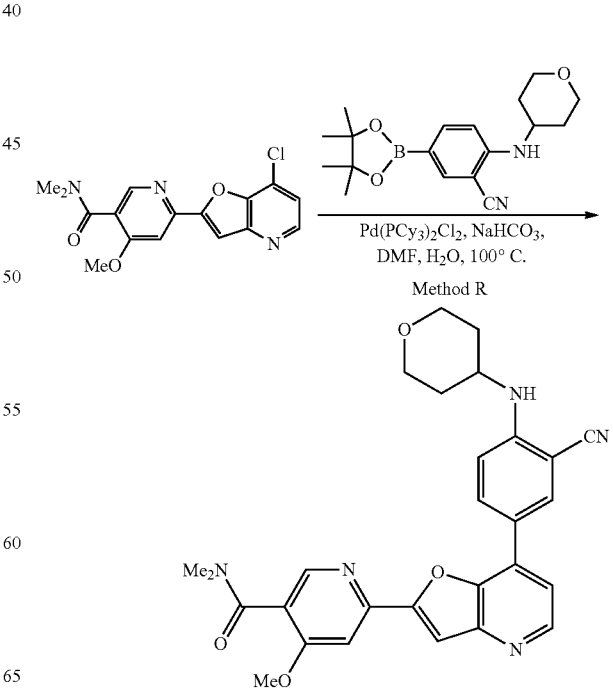

The title compound was prepared from 6-(7-chlorofuro[3,2-b]pyridin-2-yl)-4-methoxy-N,N-dimethylnicotinamide and 2-(tetrahydro-2H-pyran-4-ylamino)-5-(4,4,5,5-tetramethyl-1,3,2-dioxaborolan-2-yl)benzonitrile using Method R. The product was purified by prep-HPLC under the following conditions: column, XBridge Prep C18 OBD Column, 150 mm 5 um; mobile phase, acetonitrile in water (with 10 mmol/L $NH_4HCO_3$), 20% to 50% gradient in 8 min; detector, UV 254 nm. 6-(7-[3-cyano-4-[(oxan-4-yl)amino]phenyl]furo[3,2-b]pyridin-2-yl)-4-methoxy-N,N-dimethylpyridine-3-carboxamide was obtained as a yellow solid (70 mg, 77%). HPLC: 99.9% purity, RT=1.30 min. MS: m/z=498.3 $[M+H]^+$. $^1H$ NMR (300 MHz, DMSO-$d_6$, ppm) δ 8.56 (d, J=5.1 Hz, 1H), 8.43 (d, J=2.0 Hz, 2H), 8.23 (dd, J=9.0, 2.3 Hz, 1H), 7.82 (s, 1H), 7.78-7.66 (m, 2H), 7.15 (d, J=9.2 Hz, 1H), 6.35 (d, J=8.1 Hz, 1H), 4.06 (s, 3H), 3.96-3.71 (m, 3H), 3.52-3.37 (m, 2H), 3.01 (s, 3H), 2.84 (s, 3H), 1.87 (dd, J=12.9, 3.7 Hz, 2H), 1.75-1.55 (m, 2H).

Example 350: 5-[7-[3-cyano-4-(oxan-4-yloxy)phenyl]furo[3,2-b]pyridin-2-yl]-3-methoxy-N,N-dimethylpyridine-2-carboxamide (393)

5-bromo-3-methoxypicolinonitrile

To a solution of 5-bromo-3-fluoropyridine-2-carbonitrile (2.00 g, 9.93 mmol) in THF (80 mL) was added sodium methoxide (2.68 g, 49.59 mmol) at room temperature. The resulting solution was then stirred for 3 h at 70° C. When the reaction was done, the pH value of the reaction mixture was adjusted to 7 with hydrogen chloride solution (3 M). The resulting mixture was extracted with ethyl acetate (100 mL×3). The organic phases were combined, washed with brine and dried over sodium sulfate. The solvent was removed under reduced pressure to yield 5-bromo-3-methoxypyridine-2-carbonitrile as a brown solid (2.00 g, 95%). MS: m/z=213.0 $[M+H]^+$.

5-bromo-3-methoxypicolinic acid

To a solution of 5-bromo-3-methoxypyridine-2-carbonitrile (1.49 g, 7.00 mmol) in ethanol (28 mL) was added sodium hydroxide (10 M, 3.5 mL, 30 mmol). The resulting mixture was then stirred for 1 h at 100° C. When the reaction was done, it was quenched by the addition of water (30 mL). The pH value of the mixture was adjusted to 7 with

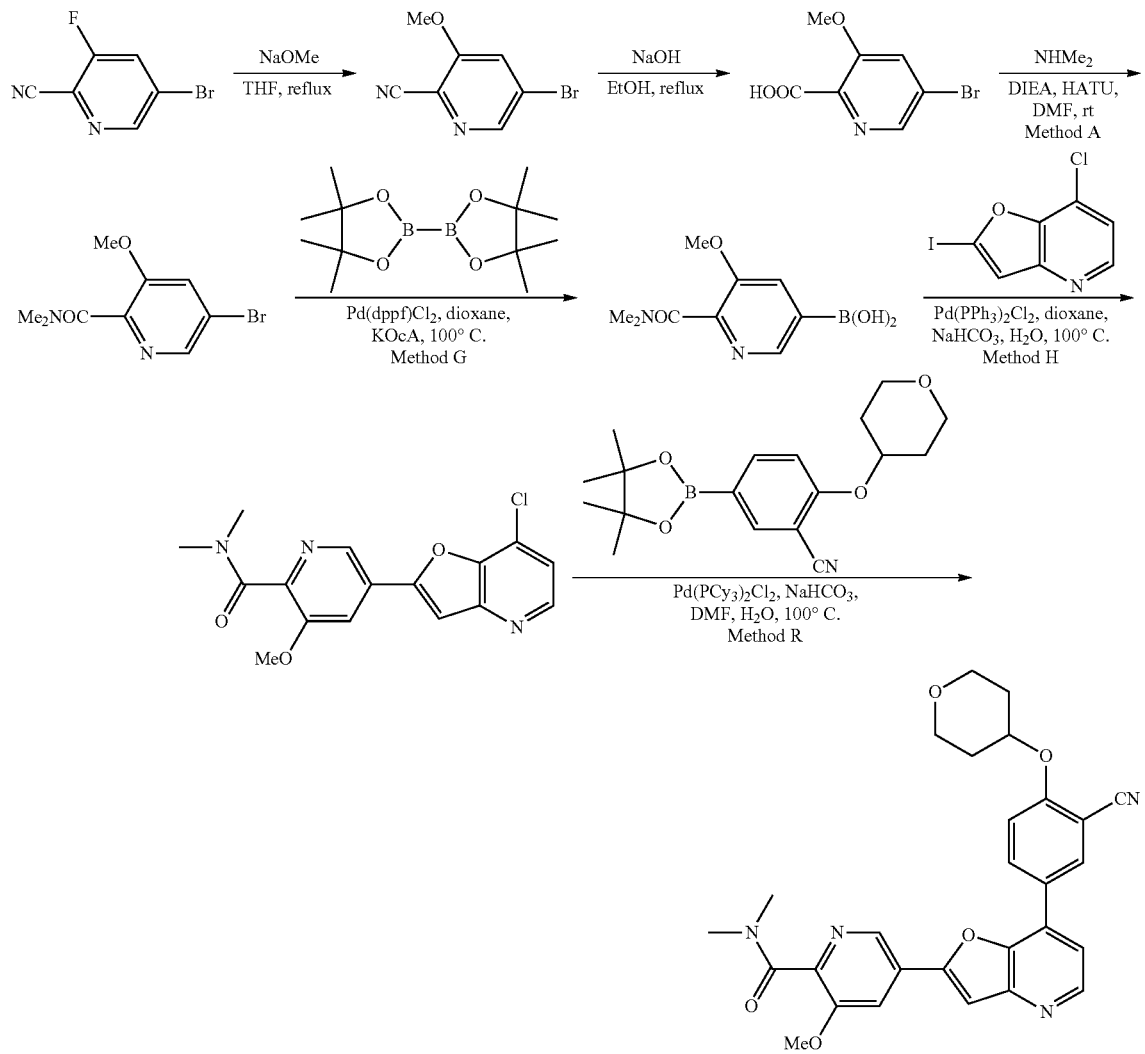

hydrogen chloride solution (3 M). The resulting mixture was extracted with ethyl acetate (100 mL×3). The organic phases were combined, washed with brine and dried over sodium sulfate. The solvent was removed under reduced pressure to yield 5-bromo-3-methoxypyridine-2-carboxylic acid as a brown solid (1.51 g, 92%). MS: m/z=232.0 [M+H]$^+$.

5-[7-[3-cyano-4-(oxan-4-yloxy)phenyl]furo[3,2-b]pyridin-2-yl]-3-methoxy-N,N-dimethylpyridine-2-carboxamide The title compound was prepared from 5-bromo-3-methoxypicolinic acid, dimethylamine, 4,4,4',4',5,5,5',5'-octamethyl-2,2'-bi(1,3,2-dioxaborolane) and 7-chloro-2-iodofuro[3,2-b]pyridine and 2-(tetrahydro-2H-pyran-4-yloxy)-5-(4,4,5,5-tetramethyl-1,3,2-dioxaborolan-2-yl)benzonitrile using Methods A, G, H and R. The final product was purified by prep-HPLC under the following conditions: column, XBridge Prep C18 OBD Column, 150 mm 5 um, mobile phase, acetonitrile in water (with 10 mmol/L NH$_4$HCO$_3$), 25% to 50% gradient in 8 min; detector, UV 254 nm. 5-[7-[3-cyano-4-(oxan-4-yloxy) phenyl]furo[3,2-b]pyridin-2-yl]-3-methoxy-N,N-dimethylpyridine-2-carboxamide was obtained as a off-white solid (25 mg, 6% for 4 steps). HPLC: 98.6% purity, RT=2.83 min. MS: m/z=499.2 [M+H]$^+$. $^1$H NMR (300 MHz, CD$_3$OD, ppm) δ 8.79-8.63 (m, 1H), 8.59-8.20 (m, 3H), 8.12-7.96 (m, 1H), 7.70-7.30 (m, 3H), 4.95-4.85 (m, 1H), 4.06-3.92 (m, 5H), 3.73-3.59 (m, 2H), 3.13 (s, 3H), 2.89 (s, 3H), 2.10-2.05 (m, 2H), 1.91-1.77 (m, 2H).

Example 351: 5-(7-[3-cyano-4-[(oxan-4-yl)amino]phenyl]furo[3,2-b]pyridin-2-yl)-3-methoxy-N,N-dimethylpyridine-2-carboxamide (394)

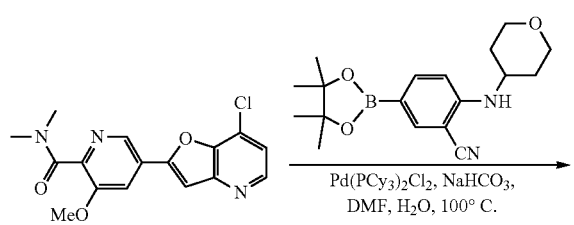

The title compound was prepared from 5-(7-chlorofuro[3,2-b]pyridin-2-yl)-3-methoxy-N,N-dimethylpicolinamide and 2-(tetrahydro-2H-pyran-4-ylamino)-5-(4,4,5,5-tetramethyl-1,3,2-dioxaborolan-2-yl)benzonitrile using Method R. The product was purified by prep-HPLC under the following conditions: column, XBridge Prep C18 OBD Column, 150 mm 5 um; mobile phase, acetonitrile in water (with 10 mmol/L NH$_4$HCO$_3$), 25% to 50% gradient in 8 min; detector, UV 254 nm. 5-(7-[3-cyano-4-[(oxan-4-yl)amino]phenyl]furo[3,2-b]pyridin-2-yl)-3-methoxy-N,N-dimethylpyridine-2-carboxamide was obtained as a off-white solid (25 mg, 10%). HPLC: 98.7% purity, RT=1.32 min. MS: m%z=498.3 [M+H]$^+$. $^1$H NMR (300 MHz, CD$_3$OD, ppm) δ 8.74-8.58 (m, 1H), 8.37 (d, J=9.9 Hz, 1H), 8.27-7.85 (m, 3H), 7.62-7.45 (m, 2H), 7.06-6.94 (m, 1H), 4.06-3.93 (m, 5H), 3.86-370 (m, 1H), 3.64-3.50 (m, 2H), 3.13 (s, 3H), 2.90 (s, 3H), 2.01 (d, J=12.4 Hz, 2H), 1.72-1.56 (m, 2H).

Example 352: 6-[7-[3-cyano-4-(oxan-4-yloxy)phenyl]furo[3,2-b]pyridin-2-yl]-5-methoxy-N,N-dimethylpyridazine-3-carboxamide (395)

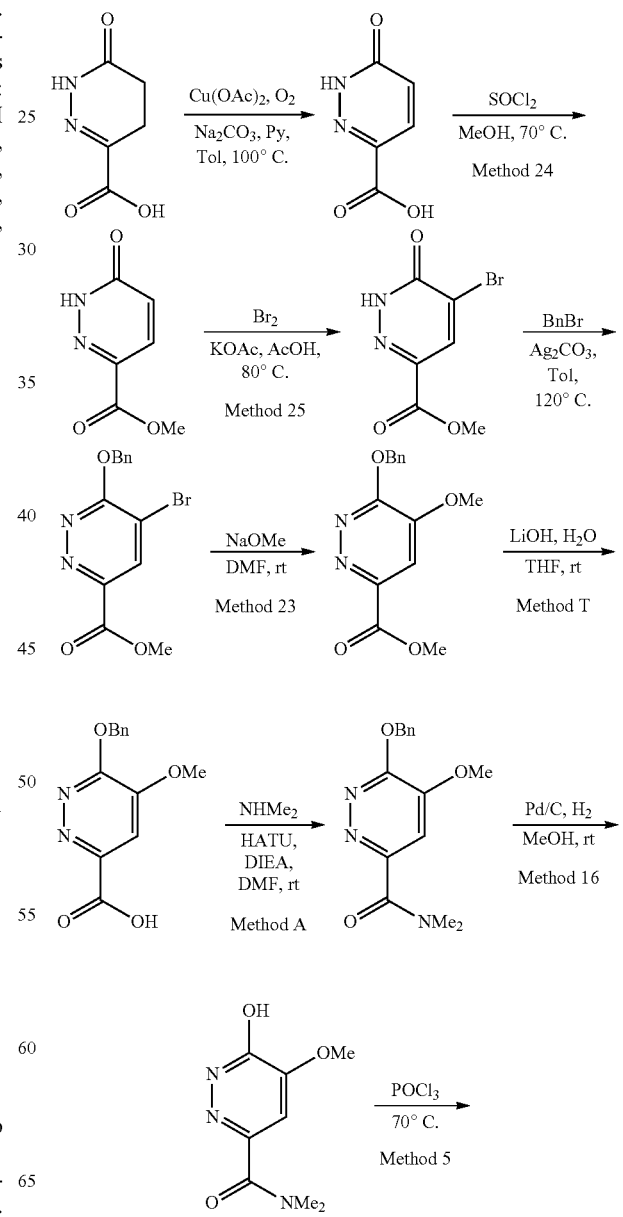

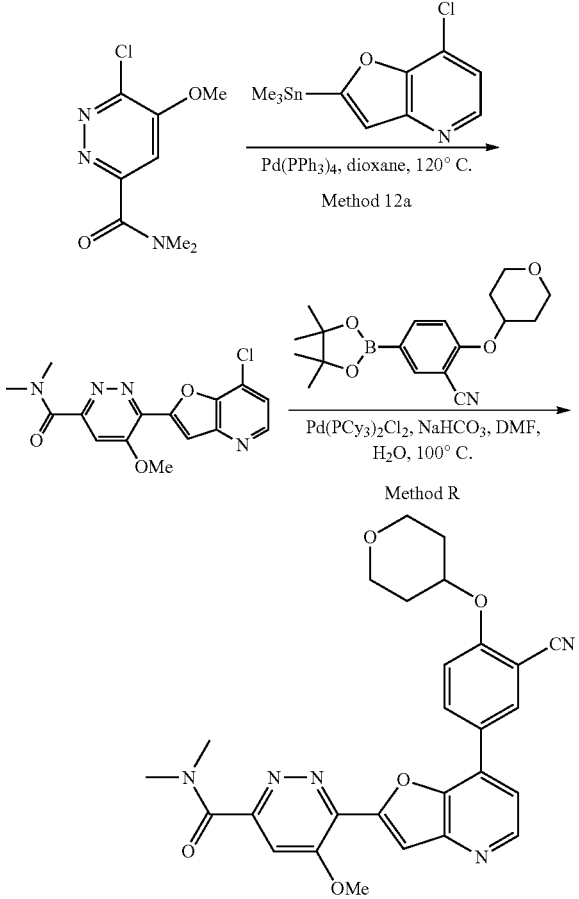

6-oxo-1,6-dihydropyridazine-3-carboxylic acid

To a solution of 6-oxo-1,4,5,6-tetrahydropyridazine-3-carboxylic acid (2.50 g, 17.59 mmol) in toluene (44 mL) was added Cu(OAc)$_2$ (450 mg, 2.48 mmol), sodium carbonate (7.01 g, 66.14 mmol) and pyridine (4.4 mL) at room temperature. The resulting solution was stirred for 16 h at 100° C. After the reaction was done, the insoluble solids in the reaction mixture were filtered out and the filtrate was concentrated under reduced pressure to yield 6-oxo-1,6-dihydropyridazine-3-carboxylic acid as a off-white solid (1.80 g, 73%). MS: m/z=177.0 [M+H]$^+$.

Method 24

Methyl 6-oxo-1,6-dihydropyridazine-3-carboxylate

To a solution of 6-oxo-1,6-dihydropyridazine-3-carboxylic acid (1.80 g, 12.85 mmol) in methanol (24 mL) was added thionyl chloride (6 mL, 82.71 mmol) at room temperature. The resulting solution was then stirred for 16 h at 70° C. When the reaction was done, it was quenched by the addition of water (30 mL). The resulting mixture was extracted with ethyl acetate (60 mL×3). The organic phases were combined, washed with brine and dried over sodium sulfate. The solvent was removed under reduced pressure and the residue was purified by flash chromatography eluting with EtOAc in hexane (0% to 80% gradient) to yield methyl 6-oxo-1,6-dihydropyridazine-3-carboxylate as a light yellow solid (1.31 g, 66%). MS: m/z=155.0 [M+H]$^+$.

Method 25

Methyl 5-bromo-6-oxo-1,6-dihydropyridazine-3-carboxylate

To a solution of methyl 6-oxo-1,6-dihydropyridazine-3-carboxylate (456 mg, 4.52 mmol) in AcOH (10 mL) was added KOAc (1.58 g, 16.10 mmol) and Br$_2$ (1.58 g, 9.89 mmol) at room temperature. The resulting solution was then stirred for 6 h at 80° C. When the reaction was done, it was quenched by the addition of NaHSO$_3$ solution (100 mL, 3 mol/L). The resulting mixture was extracted with ethyl acetate (100 mL×3). The organic phases were combined, washed with brine and dried over sodium sulfate. The solvent was removed under reduced pressure to yield methyl 5-bromo-6-oxo-1,6-dihydropyridazine-3-carboxylate as a light yellow solid (490 mg, 53%). MS: m/z=232.0 [M+H]f.

Methyl 6-(benzyloxy)-5-bromopyridazine-3-carboxylate

To a solution of methyl 5-bromo-6-oxo-1,6-dihydropyridazine-3-carboxylate (490 mg, 2.10 mmol) in toluene (12 mL) was added (bromomethyl)benzene (722 mg, 4.22 mmol) and Ag$_2$CO$_3$ (1.04 g, 3.76 mmol) at room temperature. The resulting mixture was then stirred for 4 h at 120° C. After cooling to room temperature, the reaction mixture was quenched by the addition of water (30 mL). The resulting mixture was extracted with ethyl acetate (60 mL×3). The organic phases were combined, washed with brine and dried over sodium sulfate. The solvent was removed under reduced pressure and the residue was purified by flash chromatography eluting with EtOAc in hexane (0% to 70% gradient) to yield methyl 6-(benzyloxy)-5-bromopyridazine-3-carboxylate as a brown solid (540 mg, 79%). MS: m/z=323.0 [M+H]f.

6-[7-[3-cyano-4-(oxan-4-yloxy)phenyl]furo[3,2-b]pyridin-2-yl]-5-methoxy-N,N-dimethylpyridazine-3-carboxamide The title compound was prepared from methyl 6-(benzyloxy)-5-bromopyridazine-3-carboxylate, dimethylamine, 7-chloro-2-(trimethylstannyl)furo[3,2-b]pyridine and 2-(tetrahydro-2H-pyran-4-yloxy)-5-(4,4,5,5-tetramethyl-1,3,2-dioxaborolan-2-yl)benzonitrile using Methods 23, T, A, 16, 5, 12a and R. The final product was purified by prep-HPLC under the following conditions: column, XBridge Prep C18 OBD Column, 150 mm 5 um; mobile phase, acetonitrile in water (with 0.05% NH$_3$.H$_2$O), 30% to 45% gradient in 8 min; detector, UV 254 nm. 6-[7-[3-cyano-4-(oxan-4-yl oxy)phenyl]furo[3,2-b]pyridin-2-yl]-5-methoxy-N,N-dimethylpyridazine-3-carboxamide was obtained as a light yellow solid (16 mg, 1.7% for 7 steps). HPLC: 98.3% purity, RT=1.56 min. MS: m/z=500.1 [M+H]$^+$. $^1$H NMR (300 MHz, CD$_3$OD, ppm) δ 8.52 (d, J=5.2 Hz, 1H), 8.40 (d, J=7.4 Hz, 2H), 7.83 (s, 1H), 7.66-7.58 (m, 2H), 7.39 (d, J=9.2 Hz, 1H), 4.95-4.85 (m, 1H), 4.21 (s, 3H), 4.05-3.93 (m, 2H), 3.73-3.59 (m, 2H), 3.19 (s, 3H), 3.12 (s, 3H), 2.19-2.03 (m, 2H), 1.92-1.75 (m, 2H).

Example 353: 6-[7-[4-cyano-5-(oxan-4-yloxy)pyrimidin-2-yl]furo[3,2-b]pyridin-2-yl]-5-methoxy-N,N-dimethylpyridine-3-carboxamide (396)

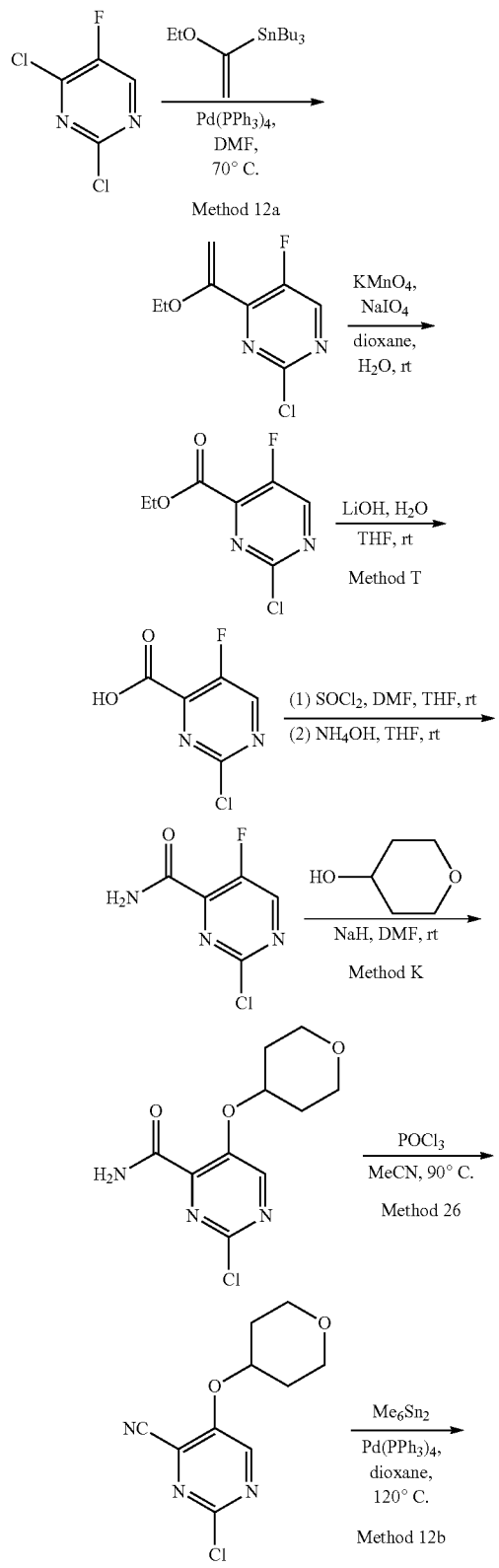

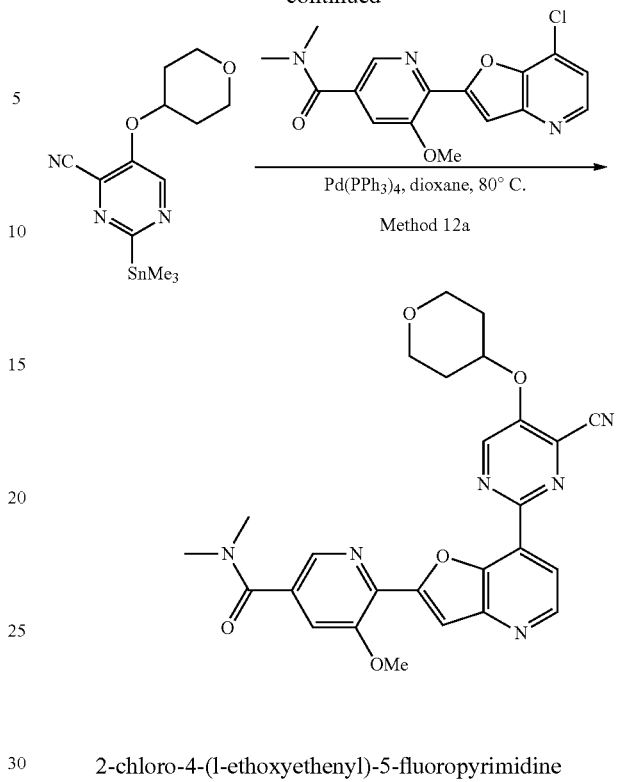

2-chloro-4-(1-ethoxyethenyl)-5-fluoropyrimidine 2-chloro-4-(1-ethoxyethenyl)-5-fluoropyrimidine was prepared from 2,4-dichloro-5-fluoropyrimidine and tributyl (1-ethoxyvinyl)stannane using Method 12a. The product was purified by flash chromatography eluting with EtOAc in hexane (0% to 10% gradient) to yield 2-chloro-4-(1-ethoxyethenyl)-5-fluoropyrimidine as a light brown oil (3.06 g, 91%). MS: m/z=203.0 [M+H]$^+$.

ethyl 2-chloro-5-fluoropyrimidine-4-carboxylate

To a solution of 2-chloro-4-(1-ethoxyethenyl)-5-fluoropyrimidine (2.56 g, 10.22 mmol) in dioxane (70 mL) was added NaIO$_4$ (3.50 g, 16.34 mmol), water (40 mL) and KMnO$_4$ (656 mg, 4.15 mmol) at room temperature. The resulting mixture was stirred for 4 h at room temperature. After the reaction was done, the pH value of the mixture was adjusted to 7-8 with sat. potassium carbonate solution. The insoluble solids from the mixture were filtered out and the filtrate was extracted with ethyl acetate (30 mL×3). The organic phases were combined, washed with brine and dried over sodium sulfate. The solvent was removed under reduced pressure and the residue was purified by flash chromatography eluting with EtOAc in hexane (0% to 100% gradient) to yield ethyl 2-chloro-5-fluoropyrimidine-4-carboxylate as a light yellow oil (882 mg, 42%). MS: m/z=205.0 [M+H]$^+$.

2-chloro-5-fluoropyrimidine-4-carboxylic acid 2-chloro-5-fluoropyrimidine-4-carboxylic acid was prepared from ethyl 2-chloro-5-fluoropyrimidine-4-carboxylate using Method T. 2-chloro-5-fluoropyrimidine-4-carboxylic acid was obtained as a white solid (1.37 g, 88%). MS: m/z=177.0 [M+H]$^+$.

2-chloro-5-fluoropyrimidine-4-carboxamide

At 0° C., N,N-dimethylformamide (0.1 mL) was added to a solution of 2-chloro-5-fluoropyrimidine-4-carboxylic acid (684 mg, 3.87 mmol) in tetrahydrofuran (15 mL), followed by the addition of oxalic dichloride (1.84 g, 14.53 mmol) dropwise. The resulting solution was stirred for 2 h at 0° C. When the reaction was done, the reaction mixture was concentrated under reduced pressure to yield 2-chloro-5-fluoropyrimidine-4-carbonyl chloride as a yellow solid (1.20 g, crude), which was used in next step without further purification.

At 0° C., to a solution of NH$_4$OH (8 mL, 51.36 mmol, 25%) in tetrahydrofuran (20 mL) was added a solution of 2-chloro-5-fluoropyrimidine-4-carbonyl chloride (1.20 g, crude) in THF (5 mL). The resulting solution was stirred for 30 min at 0° C. When the reaction was done, it was quenched by the addition of water (20 mL). The resulting mixture was extracted with ethyl acetate (50 mL×3). The organic phases were combined, washed with brine and dried over sodium sulfate. The solvent was removed under reduced pressure to yield 2-chloro-5-fluoropyrimidine-4-carboxamide as a yellow solid (644 mg, 94% for 2 steps). MS: m/z=176.0 [M+H]$^+$.

6-[7-[4-cyano-5-(oxan-4-yloxy)pyrimidin-2-yl]furo[3,2-b]pyridin-2-yl]-5-methoxy-N,N-dimethylpyridine-3-carboxamide The title compound was prepared from 2-chloro-5-fluoropyrimidine-4-carboxamide, tetrahydro-2H-pyran-4-ol, 1,1,1,2,2,2-hexamethyldistannane and 6-(7-chlorofuro[3,2-b]pyridin-2-yl)-5-methoxy-N,N-dimethylnicotinamide using Methods K, 26, 12a, and 12b. The final product was purified by prep-HPLC under the following conditions: column, XBridge Prep C18 OBD Column, 150 mm 5 um; mobile phase, acetonitrile in water (with 0.05% NH$_3$.H$_2$O), 30% to 50% gradient in 8 min; detector, UV 254 nm. 6-[7-[4-cyano-5-(oxan-4-yloxy)pyrimidin-2-yl]furo[3,2-b]pyridin-2-yl]-5-methoxy-N,N-dimethylpyridine-3-carboxamide was obtained as a white solid (10 mg, 0.6% for 4 steps). HPLC: 96.8% purity, RT=2.44 min. MS: m/z=501.2 [M+H]$^+$. $^1$H NMR (300 MHz, CD$_3$OD, ppm) δ 9.21 (s, 1H), 8.68 (d, J=5.0 Hz, 1H), 8.40 (d, J=1.6 Hz, 1H), 8.14 (d, J=4.9 Hz, 1H), 7.85 (s, 1H), 7.76 (d, J=1.6 Hz, 1H), 5.20-5.10 (m, 1H), 4.17 (s, 3H), 4.10-3.98 (m, 2H), 3.76-3.64 (m, 2H), 3.17 (s, 3H), 3.11 (s, 3H), 2.29-2.13 (m, 2H), 2.02-1.84 (m, 2H).

Example 354: 6-(7-(3-cyano-4-(tetrahydro-2H-pyran-4-yloxy)phenyl)furo[3,2-b]pyridin-2-yl)-5-methoxy-N-(3-methyl-3-aza-bicyclo[3.1.1]heptan-6-yl)nicotinamide

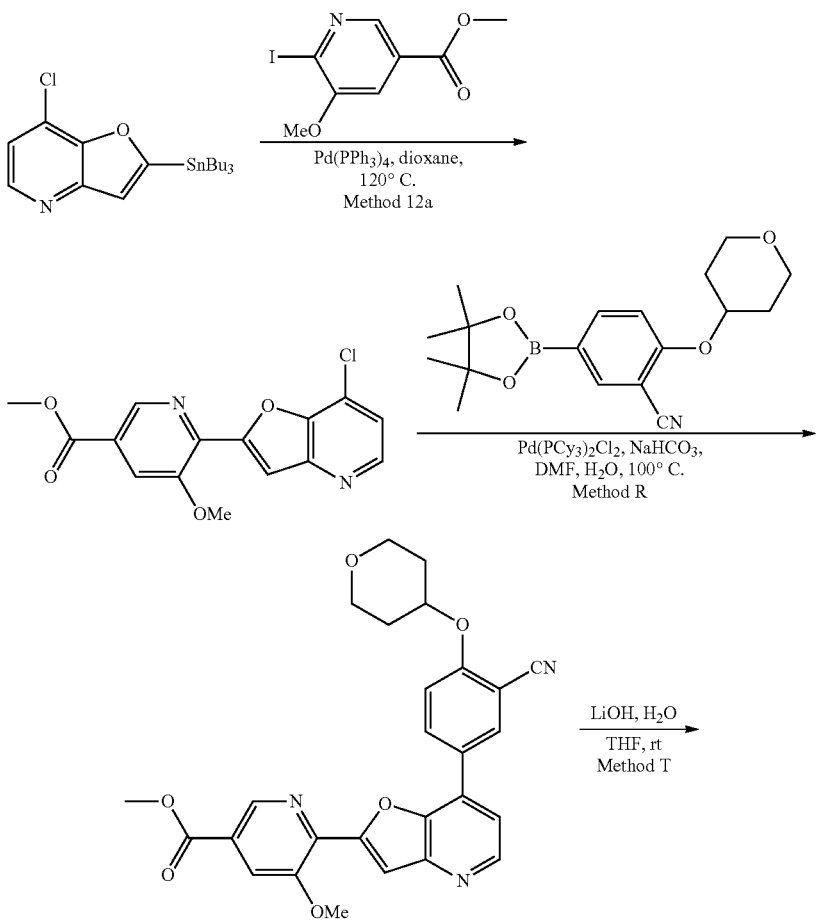

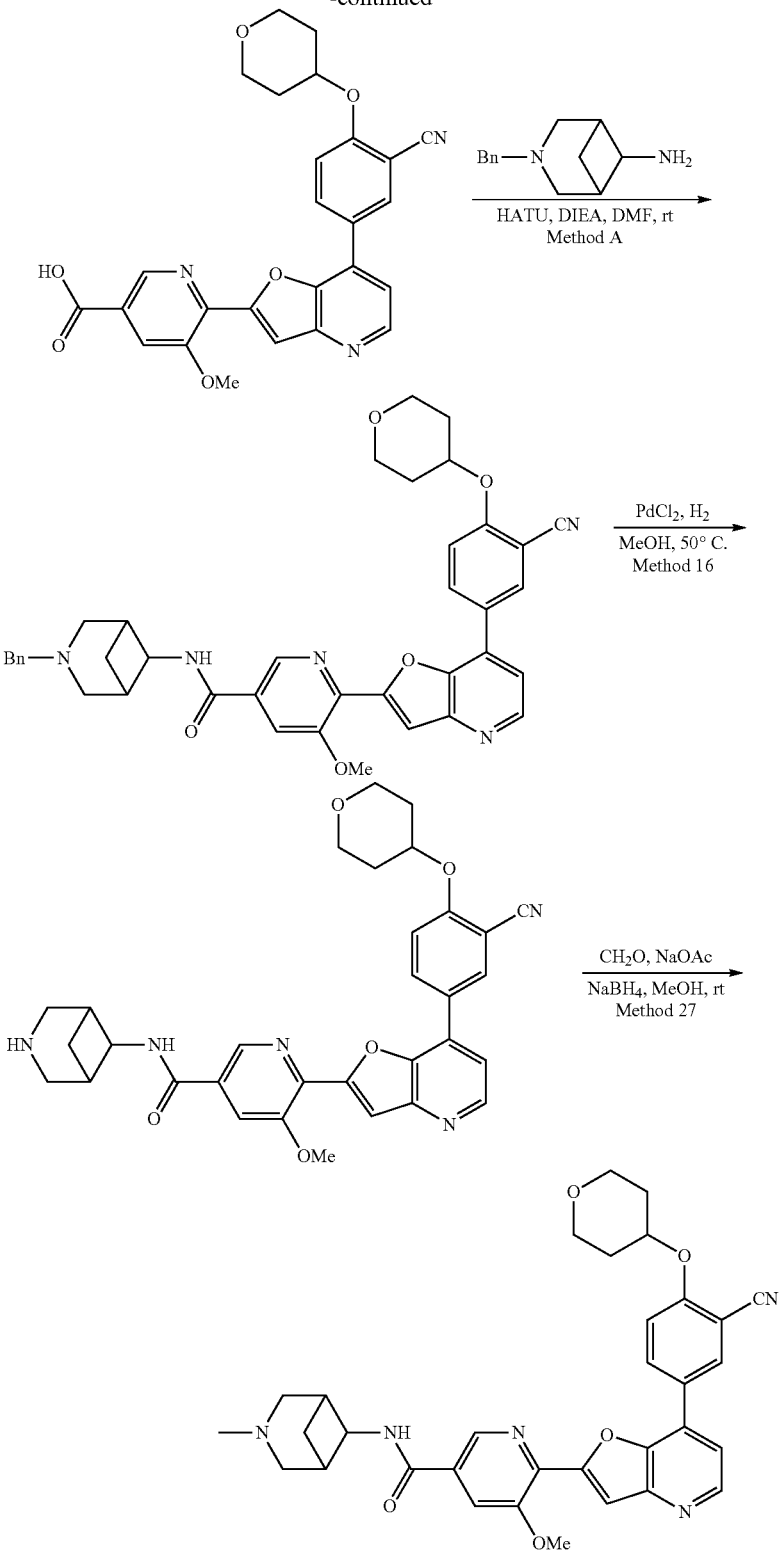

The title compound was prepared from 7-chloro-2-(tributylstannyl)furo[3,2-b]pyridine, methyl 6-iodo-5-methoxynicotinate, 2-(tetrahydro-2H-pyran-4-yloxy)-5-(4,4,5,5-tetramethyl-1,3,2-dioxaborolan-2-yl)benzonitrile, 3-benzyl-3-aza-bicyclo[3.1.1]heptan-6-amine and formaldehyde using Methods 12a, R, T, A, 16, and 27. The final product was purified by prep-HPLC under the following conditions: column, XBridge Prep C18 OBD Column, 150 mm 5 um; mobile phase, acetonitrile in water (with 0.05% NH₃H₂O), 25% to 50% gradient in 10 min; detector, UV 254/220 nm.

Example 355: 6-{7-[3-Cyano-4-(tetrahydro-pyran-4-yloxy)-phenyl]-furo[3,2-b]pyridin-2-yl}-5-methoxy-N-((1S,5R,6R)-3-methyl-3-aza-bicyclo[3.10.1]hept-6-yl)-nicotinamide (397)

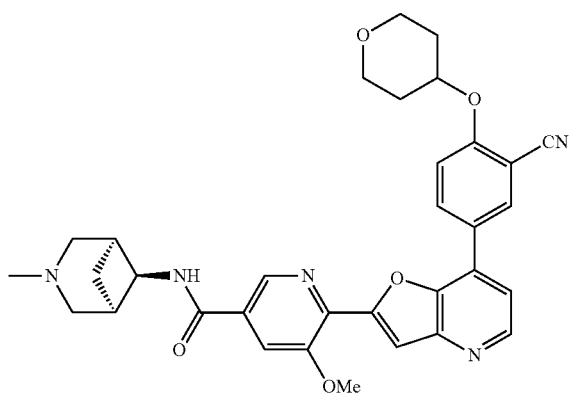 [SMILES: COc1cc(C(=O)N[C@H]2[C@@H]3C[C@H]2CN(C)C3)cnc1-c1cc2nccc(-c3ccc(OC4CCOCC4)c(C#N)c3)c2o1]

The title compound was separated from of 6-(7-(3-cyano-4-(tetrahydro-2H-pyran-4-yloxy)phenyl)furo[3,2-b]pyridin-2-yl)-5-methoxy-N-(3-methyl-3-aza-bicyclo[3.1.1]heptan-6-yl)nicotinamide. (18 mg, 8.4% for 6 steps, yellow solid) HPLC: 92.8% purity, RT=1.26 min. MS: m/z=580.3 [M+H]$^+$. $^1$H NMR (400 MHz, CD$_3$OD, ppm) δ 8.91 (d, J=1.6 Hz, 1H), 8.81-8.74 (m, 2H), 8.62 (dd, J=9.1, 2.4 Hz, 1H), 8.22 (d, J=1.7 Hz, 1H), 8.15 (d, J=6.2 Hz, 1H), 8.01 (s, 1H), 7.61 (d, J=9.0 Hz, 1H), 5.09-4.99 (m, 1H), 4.29 (s, 3H), 4.14-3.96 (m, 5H), 3.77-3.67 (m, 2H), 3.66-3.56 (m, 2H), 3.04 (s, 3H), 2.89-2.74 (m, 3H), 2.24-2.13 (m, 2H), 2.06-1.85 (m, 3H).

Example 356: 6-{7-[3-Cyano-4-(tetrahydro-pyran-4-yloxy)-phenyl]-furo[3,2-b]pyridin-2-yl}-5-methoxy-N-((1R,5S,6S)-3-methyl-3-aza-bicyclo[3.1.1]hept-6-yl)-nicotinamide (398)

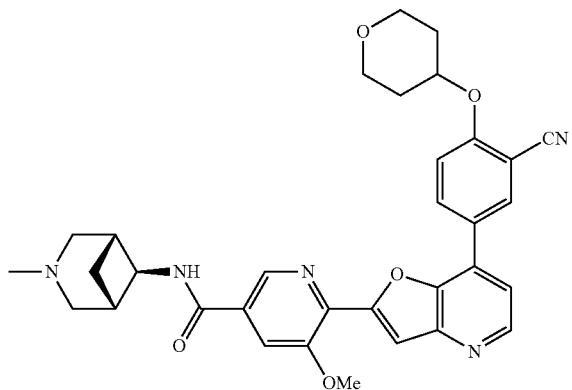 [SMILES: COc1cc(C(=O)N[C@@H]2[C@@H]3C[C@H]2CN(C)C3)cnc1-c1cc2nccc(-c3ccc(OC4CCOCC4)c(C#N)c3)c2o1]

The title compound was separated from of 6-(7-(3-cyano-4-(tetrahydro-2H-pyran-4-yloxy)phenyl)furo[3,2-b]pyridin-2-yl)-5-methoxy-N-(3-methyl-3-aza-bicyclo[3.1.1]heptan-6-yl)nicotinamide. (12 mg, 6.8% for 6 steps, light yellow solid) HPLC: 92.2% purity, RT=1.26 min. MS: m/z=580.2 [M+H]$^+$. $^1$H NMR (300 MHz, DMSO-d$_6$, ppm) δ 8.80-8.59 (m, 3H), 8.60-8.42 (m, 2H), 7.92 (d, J=1.6 Hz, 1H), 7.86 (s, 1H), 7.76 (d, J=5.1 Hz, 1H), 7.65 (d, J=9.0 Hz, 1H), 5.04-4.95 (m, 1H), 4.28-4.18 (m, 1H), 4.15 (s, 3H), 3.95-3.83 (m, 2H), 3.63-3.51 (m, 2H), 3.09-2.98 (m, 2H), 2.80-2.68 (m, 2H), 2.64-2.52 (m, 2H), 2.32 (s, 3H), 2.14-2.00 (m, 3H), 1.82-1.66 (m, 3H).

Example 357: 4-(7-1 [[13-cyano-4-(oxan-4-yloxy)phenyl]amino]furo[3,2-b]pyridin-2-yl)-3-methoxy-N,N-dimethylbenzamide (399)

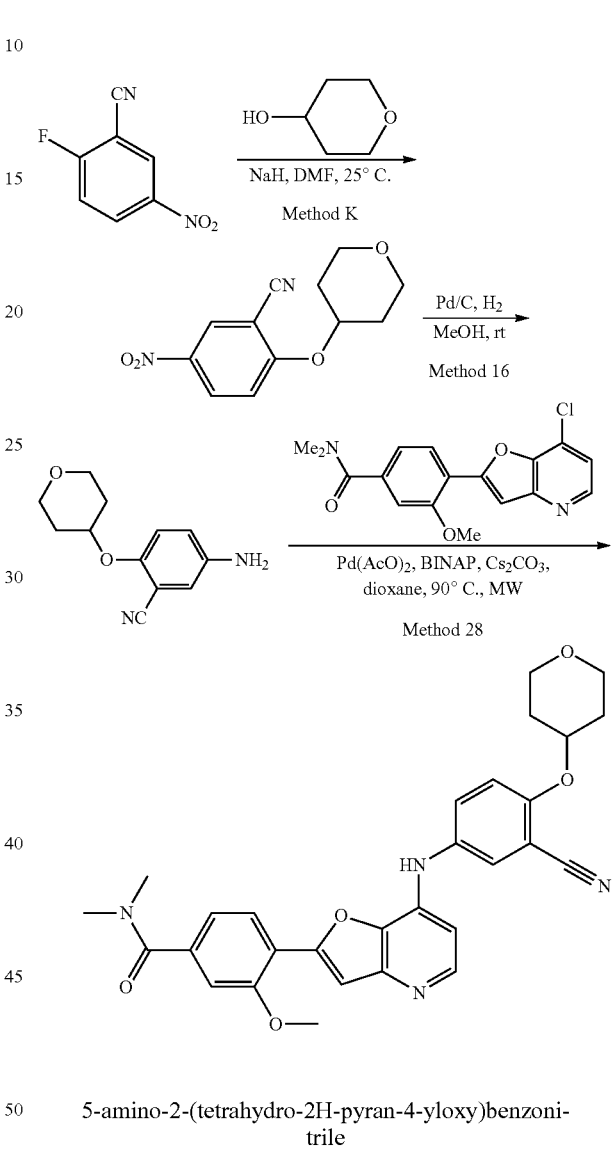

5-amino-2-(tetrahydro-2H-pyran-4-yloxy)benzonitrile 5-amino-2-(tetrahydro-2H-pyran-4-yloxy)benzonitrile was prepared from 2-fluoro-5-nitrobenzonitrile and 2-fluoro-5-nitrobenzonitrile using Methods K and 15. And 5-amino-2-(tetrahydro-2H-pyran-4-yloxy)benzonitrile was obtained as a light yellow solid (2.31 g, 77% for 2 steps). MS: m/z=249.0 [M+H]$^+$.

Method 28

4-(7-[[3-cyano-4-(oxan-4-yloxy)phenyl]amino]furo[3,2-b]pyridin-2-yl)-3-methoxy-N,N-dimethylbenzamide To a solution of 4-[7-chlorofuro[3,2-b]pyridin-2-yl]-3-methoxy-N,N-dimethylbenzamide (90 mg, 0.27 mmol) in dioxane (3 mL) was added 5-amino-2-(oxan-4-yloxy)benzonitrile (119 mg, 0.55 mmol), Pd(OAc)₂ (6 mg, 0.03 mmol), BINAP (34 mg, 0.05 mmol) and Cs₂CO₃ (177 mg, 0.54 mmol) at room temperature under nitrogen atmosphere. The reaction mixture was irradiated with microwave for 1 h at 90° C. After cooling to room temperature, the reaction mixture was quenched by the addition of water (10 mL). The resulting mixture was extracted with DCM (30 mL×3). The organic phases were combined, washed with brine and dried over sodium sulfate. The solvent was removed under reduced pressure and the residue was purified by prep-HPLC under the following conditions: column, XBridge Prep Phenyl OBD Column, 19×150 mm 5 um; mobile phase, acetonitrile in water (with 10 mmol/L NH₄HCO₃), 30% to 60% gradient in 8 min; detector, UV 254 nm. 4-(7-[[3-cyano-4-(oxan-4-yloxy)phenyl]amino]furo[3,2-b]pyridin-2-yl)-3-methoxy-N,N-dimethylbenzamide was obtained as a off-white solid (50 mg, 35%). HPLC: 99.8% purity, RT=1.38 min. MS: m/z=513.3 [M+H]⁺. ¹H NMR (300 MHz, CD₃OD, ppm) δ 8.12-7.98 (m, 2H), 7.64-7.50 (m, 2H), 7.41 (s, 1H), 7.32-7.16 (m, 2H), 7.08 (dd, J=8.0, 1.4 Hz, 1H), 6.81 (d, J=5.7 Hz, 1H), 4.81-4.71 (m, 1H), 4.08-3.91 (m, 5H), 3.70-3.54 (m, 2H), 3.10 (s, 3H), 3.03 (s, 3H), 2.15-1.99 (m, 2H), 1.88-1.74 (m, 2H).

Example 358: 5-[7-[3-cyano-4-(oxan-4-yloxy)phenyl]furo[3,2-b]pyridin-2-yl]-N,N,1-trimethyl-1H-pyrrole-3-carboxamide (400)

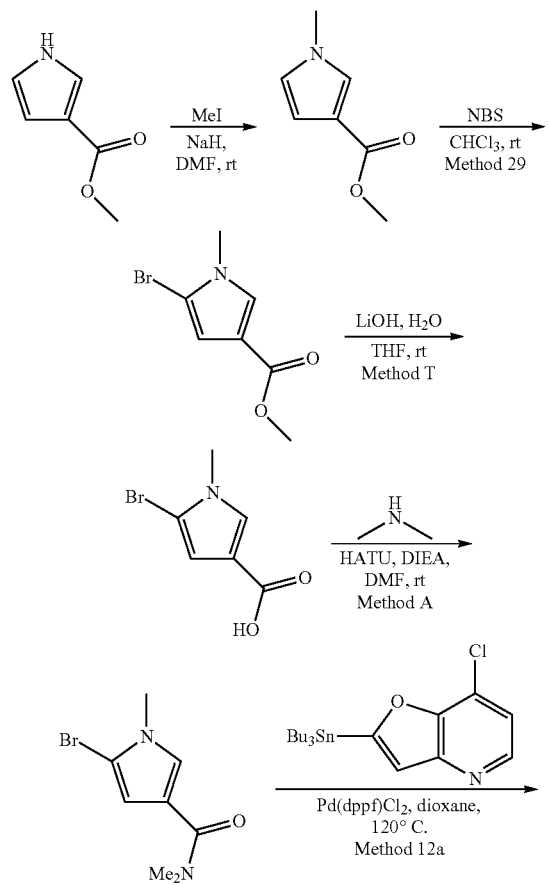

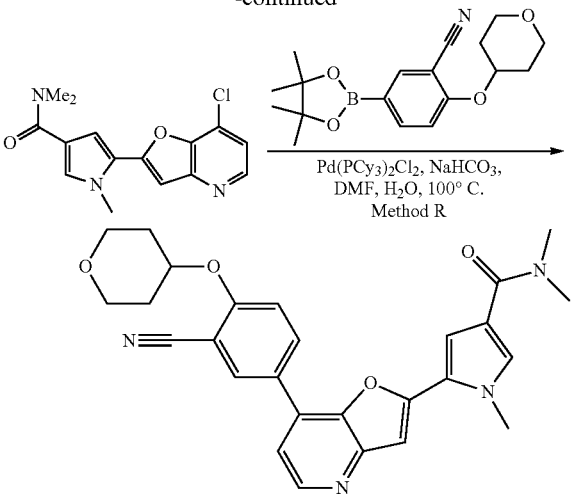

Methyl 1-methyl-1H-pyrrole-3-carboxylate

At 0° C., to a solution of methyl 1H-pyrrole-3-carboxylate (0.95 g, 7.59 mmol) in N,N-dimethylformamide (10 mL) was added sodium hydride (173 mg, 7.20 mmol) in portions. The resulting mixture was stirred for 15 min at 0° C., and then was added by CH₃I (1.62 g, 11.39 mmol) dropwise at 0° C. The reaction mixture was stirred for 1 h at room temperature. When the reaction was done, it was quenched by the addition of water (30 mL). The resulting mixture was extracted with ethyl acetate (30 mL×3). The organic phases were combined, washed with brine and dried over sodium sulfate. The solvent was removed under reduced pressure to yield methyl 1-methyl-1H-pyrrole-3-carboxylate as a yellow oil (1.00 g, 95%). MS: m/z=140.0 [M+H]⁺.

Method 29

Methyl 5-bromo-1-methyl-1H-pyrrole-3-carboxylate

To a solution of methyl 1-methyl-1H-pyrrole-3-carboxylate (465 mg, 3.34 mmol) in CHCl₃ was added NBS (608 mg, 3.42 mmol) at room temperature. The resulting solution was then stirred for 1 h at room temperature. When the reaction was done, it was quenched by the addition of water (30 mL). The resulting mixture was extracted with ethyl acetate (30 mL×3). The organic phases were combined, washed with brine and dried over sodium sulfate. The solvent was removed under reduced pressure and the residue was purified by flash chromatography eluting with EtOAc in hexane (0% to 10% gradient) to yield methyl 5-bromo-1-methyl-1H-pyrrole-3-carboxylate as a off-white solid (600 mg, 82%). MS: m/z=218.0 [M+H]⁺.

5-[7-[3-cyano-4-(oxan-4-yloxy)phenyl]furo[3,2-b]pyridin-2-yl]-N,N,1-trimethyl-1H-pyrrole-3-carboxamide The title compound was prepared from methyl 1H-pyrrole-3-carboxylate, iodomethane, dimethylamine, 7-chloro-2-(tributylstannyl)furo[3,2-b]pyridine and 2-(tetrahydro-2H-pyran-4-yloxy)-5-(4,4,5,5-tetramethyl-1,3,2-dioxaborolan-2-yl)benzonitrile using Methods T, A, 12a and R. The final product was purified by prep-HPLC under the following conditions: column, XBridge Prep C18 OBD Column, 150 mm 5 um; mobile phase, acetonitrile in water (with 0.05% NH₃H₂O), 25% to 45% gradient in 8 min; detector, UV 254 nm. 5-[7-[3-cyano-4-(oxan-4-yloxy)phenyl]furo[3,2-b]pyridin-2-yl]-N,N, 1-trimethyl-1H-pyrrole-3-carboxamide as a yellow solid (52 mg, 20% 4 steps). HPLC: 98.8% purity, RT=1.04 min. MS: m/z=471.2 [M+H]⁺. ¹H NMR (300 MHz, DMSO-d₆, ppm) δ 8.57-8.33 (m, 3H), 7.62 (dd, J=7.0, 1.9 Hz, 2H), 7.50 (d, J=1.9 Hz, 1H), 7.34 (s, 1H), 7.02 (d, J=1.9 Hz, 1H), 5.00-4.90 (m, 1H), 4.00-3.81 (m, 5H), 3.64-3.48 (m, 2H), 3.20-2.80 (m, 6H), 2.10-1.98 (m, 2H), 1.78-1.62 (m, 2H).

Example 359: 5-[7-[3-cyano-4-(oxan-4-yloxy)phenyl]furo[3,2-b]pyridin-2-yl]-4-methoxy-N,N,1-trimethyl-1H-pyrazole-3-carboxamide hydrochloride (401)

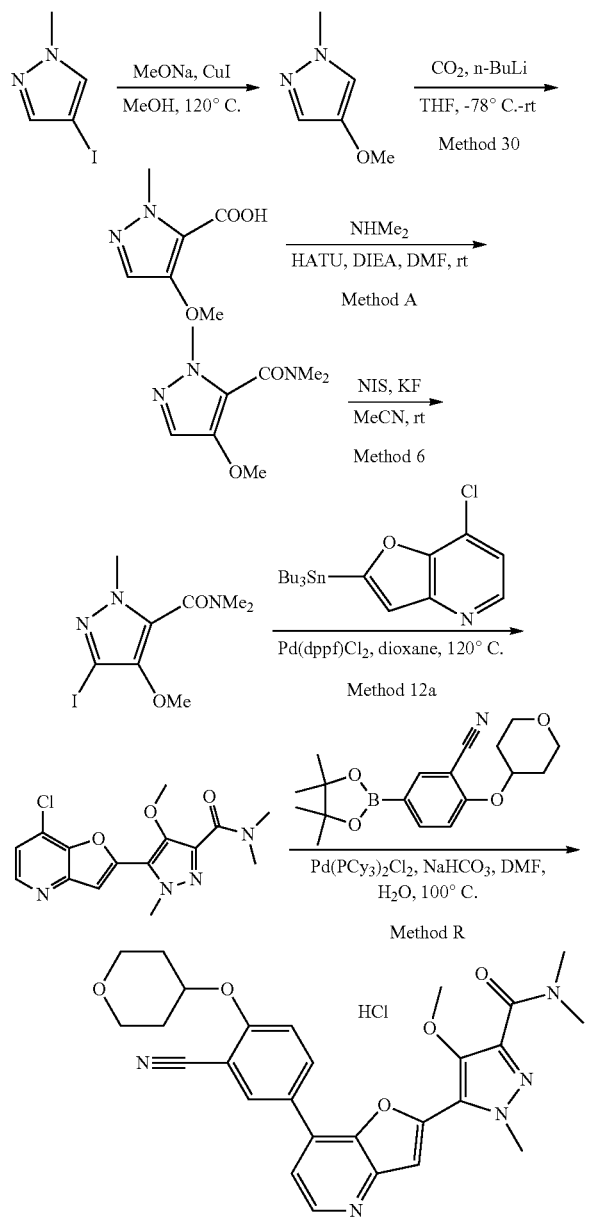

Methyl 1-methyl-1H-pyrrole-3-carboxylate

To a solution of 4-iodo-1-methyl-1H-pyrazole (475 mg, 2.28 mmol) in MeOH (8 mL) was added CuI (120 mg, 0.63 mmol) and NaOMe solution (2 M in MeOH, 1.7 mL, 3.42 mmol) at room temperature. The resulting solution was stirred overnight at 120° C. After cooling to room temperature, the reaction mixture was quenched by the addition of water (30 mL). The resulting mixture was extracted with ethyl acetate (50 mL×3). The organic phases were combined, washed with brine and dried over sodium sulfate. The solvent was removed under reduced pressure to yield 4-methoxy-1-methyl-1H-pyrazole as a yellow solid (130 mg, 51%). MS: m/z=113.0 [M+H]⁺.

Method 30

4-methoxy-1-methyl-1H-pyrazole-5-carboxylic acid

At -78° C., to a solution of 4-methoxy-1-methyl-1H-pyrazole (665 mg, 5.93 mmol) in tetrahydrofuran (40 mL) was added n-BuLi solution (1 M in THF, 11.9 mL, 11.9 mmol) dropwise. The resulting solution was stirred for 20 min, and then was added by dry ice (3 g, 68.17 mmol) in portions at -78° C. The resulting solution was stirred for 1 h at -78° C., warmed up to room temperature and then stirred for additional 1 h at room temperature. When the reaction was done, it was quenched by the addition of sat. NH₄Cl solution (40 mL). The pH value of the resulting mixture was adjusted to 5 with hydrogen chloride solution (6 M). Then the mixture was extracted with ethyl acetate (40 mL×3). The organic phases were combined, washed with brine and dried over sodium sulfate. The solvent was removed under reduced pressure to yield 4-methoxy-1-methyl-1H-pyrazole-3-carboxylic acid as a brown solid (700 mg, 76%). MS: m/z=157.0 [M+H]⁺

5-[7-[3-cyano-4-(oxan-4-yloxy)phenyl]furo[3,2-b]pyridin-2-yl]-4-methoxy-N,N,1-trimethyl-1H-pyrazole-3-carboxamide hydrochloride The title compound was prepared from 4-methoxy-1-methyl-1H-pyrazole-5-carboxylic acid, dimethylamine, 7-chloro-2-(tributyl stannyl)furo[3,2-b]pyridine and 2-(tetrahydro-2H-pyran-4-yloxy)-5-(4,4,5,5-tetramethyl-1,3,2-dioxaborolan-2-yl)benzonitrile using Methods T, A, 12a and R. The final product was purified by prep-HPLC under the following conditions: column, XBridge Prep C18 OBD Column, 150 mm 5 um; mobile phase, acetonitrile in water (with 0.05% HCl), 25% to 50% gradient in 8 min; detector, UV 254 nm. 5-[7-[3-cyano-4-(oxan-4-yloxy)phenyl]furo[3,2-b]pyridin-2-yl]-4-methoxy-N,N,1-trimethyl-1H-pyrazole-3-carboxamide hydrochloride was obtained as a yellow solid (40 mg, 4.1% 4 steps). HPLC: 99.9% purity, RT=1.00 min. MS: m/z=502.1 [M+H]⁺. ¹H NMR (300 MHz, CD₃OD, ppm) δ 8.71-8.61 (m, 2H), 8.53 (dd, J=9.0, 2.4 Hz, 1H), 8.08 (d, J=6.4 Hz, 1H), 7.56 (d, J=9.0 Hz, 1H), 7.46 (s, 1H), 5.03-4.93 (m, 1H), 4.06-3.89 (m, 8H), 3.75-3.59 (m, 2H), 3.16 (s, 3H), 3.12 (s, 3H), 2.21-2.05 (m, 2H), 1.93-1.77 (m, 2H).

Example 360: 5-[7-[3-cyano-4-(oxan-4-yloxy)phenyl]furo[3,2-b]pyridin-2-yl]-4-methoxy-N,N,1-trimethyl-1H-pyrrole-2-carboxamide (402)

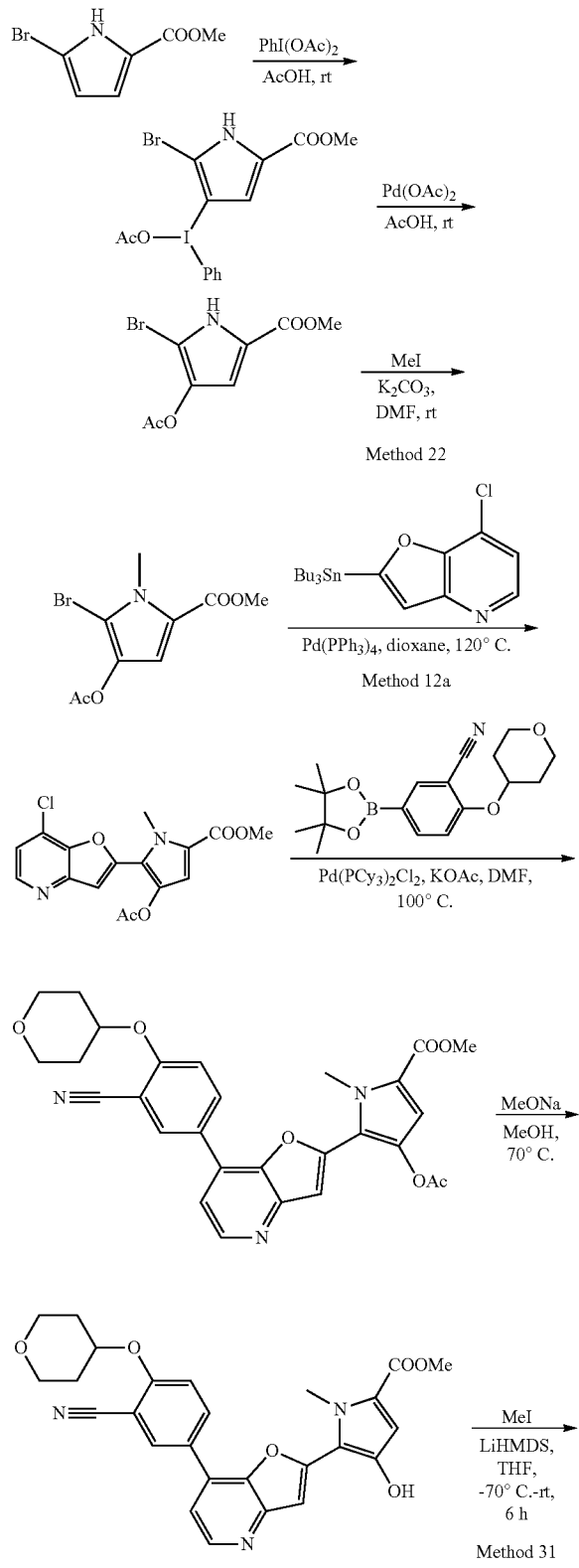

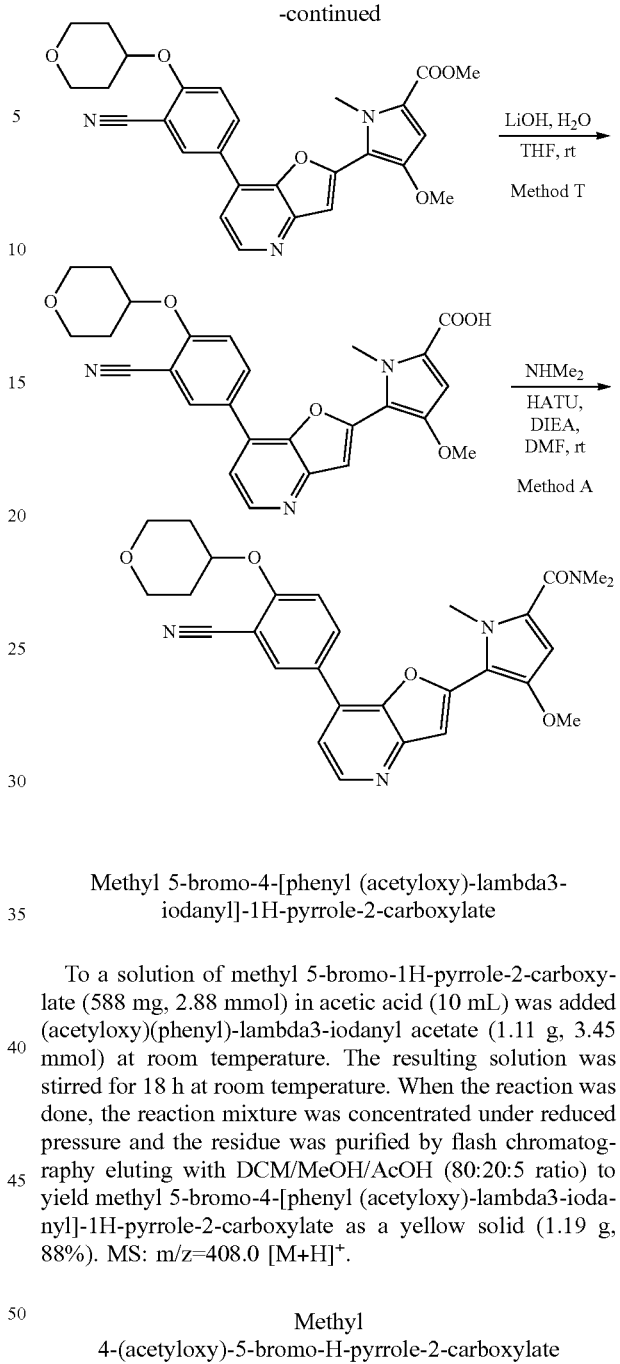

Methyl 5-bromo-4-[phenyl (acetyloxy)-lambda3-iodanyl]-1H-pyrrole-2-carboxylate To a solution of methyl 5-bromo-1H-pyrrole-2-carboxylate (588 mg, 2.88 mmol) in acetic acid (10 mL) was added (acetyloxy)(phenyl)-lambda3-iodanyl acetate (1.11 g, 3.45 mmol) at room temperature. The resulting solution was stirred for 18 h at room temperature. When the reaction was done, the reaction mixture was concentrated under reduced pressure and the residue was purified by flash chromatography eluting with DCM/MeOH/AcOH (80:20:5 ratio) to yield methyl 5-bromo-4-[phenyl (acetyloxy)-lambda3-iodanyl]-1H-pyrrole-2-carboxylate as a yellow solid (1.19 g, 88%). MS: m/z=408.0 [M+H]$^+$.

Methyl 4-(acetyloxy)-5-bromo-H-pyrrole-2-carboxylate

To a solution of methyl 5-bromo-4-[phenyl (acetyloxy)-lambda3-iodanyl]-1H-pyrrole-2-carboxylate (0.99 g, 2.12 mmol) in acetic acid (30 mL) was added Pd(OAc)$_2$ (48 mg, 0.21 mmol) at room temperature. The resulting solution was stirred for 18 h at room temperature. When the reaction was done, it was quenched by the addition of water (20 mL). The resulting mixture was extracted with ethyl acetate (50 mL×3). The organic phases were combined, washed with brine and dried over sodium sulfate. The solvent was removed under reduced pressure and the residue was purified by flash chromatography eluting with EtOAc in hexane (0% to 70% gradient) to yield methyl 4-(acetyloxy)-5-bromo-1H-pyrrole-2-carboxylate as a off-white solid (396 mg, 71%). MS: m/z=262.0 [M+H]$^+$.

Methyl 4-(acetyloxy)-5-[7-[3-cyano-4-(oxan-4-yloxy)phenyl]furo[3,2-b]pyridin-2-yl]-1-methyl-1H-pyrrole-2-carboxylate The title compound was prepared from methyl 4-acetoxy-5-bromo-1H-pyrrole-2-carboxylate, iodomethane, 7-chloro-2-(tributylstannyl)furo[3,2-b]pyridine and 2-(tetrahydro-2H-pyran-4-yloxy)-5-(4,4,5,5-tetramethyl-1,3,2-dioxaborolan-2-yl)benzonitrile using Methods 22, 12a and O. The product was purified by flash chromatography eluting with MeOH in EtOAc (0% to 10% gradient) to yield methyl 4-(acetyloxy)-5-[7-[3-cyano-4-(oxan-4-yloxy)phenyl]furo[3,2-b]pyridin-2-yl]-1-methyl-1H-pyrrole-2-carboxylate as a light yellow solid (120 mg, 64% for 3 steps). MS: m/z=516.0 [M+H]$^+$.

Methyl 5-(7-(3-cyano-4-(tetrahydro-2H-pyran-4-yloxy)phenyl)furo[3,2-b]pyridin-2-yl)-4-hydroxy-1-methyl-1H-pyrrole-2-carboxylate To a solution of methyl 4-(acetyloxy)-5-[7-[3-cyano-4-(oxan-4-yloxy)phenyl]furo[3,2-b]pyridin-2-yl]-1-methyl-1H-pyrrole-2-carboxylate (88 mg, 0.17 mmol) in methanol (5 mL) was added MeONa (42 mg, 0.77 mmol) at room temperature. The resulting solution was stirred for 3 h at 70° C. After cooling to room temperature, the reaction mixture was quenched by the addition of water (15 mL). The resulting mixture was extracted with ethyl acetate (50 mL×3). The organic phases were combined, washed with brine and dried over sodium sulfate. The solvent was removed under reduced pressure to yield methyl 5-[7-[3-cyano-4-(oxan-4-yloxy)phenyl]furo[3,2-b]pyridin-2-yl]-4-hydroxy-1-methyl-1H-pyrrole-2-carboxylate as a light yellow solid (100 mg, 99%). MS: m/z=474.0 [M+H]$^+$.

Method 31

4-methoxy-1-methyl-1H-pyrazole-5-carboxylic acid

At −78° C., to a solution of methyl 5-[7-[3-cyano-4-(oxan-4-yloxy)phenyl]furo[3,2-b]pyridin-2-yl]-4-hydroxy-1-methyl-1H-pyrrole-2-carboxylate (69 mg, 0.15 mmol) in tetrahydrofuran (5 mL) was added Li-HMDS solution (1 M in THF, 0.45 mL, 0.45 mmol) dropwise over 5 min period. The resulting solution was stirred for 0.5 h at −78° C., and then was added by iodomethane (70 mg, 0.49 mmol) at −78° C. The resulting solution was stirred for additional 2 h at room temperature. When the reaction was done, it was quenched by the addition of sat. NH$_4$Cl solution (3 mL). The resulting mixture was extracted with ethyl acetate (20 mL×3). The organic phases were combined, washed with brine and dried over sodium sulfate. The solvent was removed under reduced pressure to yield methyl 5-[7-[3-cyano-4-(oxan-4-yloxy)phenyl]furo[3,2-b]pyridin-2-yl]-4-methoxy-1-methyl-1H-pyrrole-2-carboxylate as a light brown solid (67 mg, 93%). MS: m/z=157.0 [M+H]f.

5-[7-[3-cyano-4-(oxan-4-yloxy)phenyl]furo[3,2-b]pyridin-2-yl]-4-methoxy-N,N,1-trimethyl-1H-pyrrole-2-carboxamide The title compound was prepared from methyl 5-(7-(3-cyano-4-(tetrahydro-2H-pyran-4-yloxy)phenyl)furo[3,2-b]pyridin-2-yl)-4-methoxy-1-methyl-1H-pyrrole-2-carboxylate and dimethylamine using Methods T and A. The final product was purified by prep-HPLC under the following conditions: column, XBridge Prep C18 OBD Column, 150 mm 5 um; mobile phase, acetonitrile in water (with 0.05% NH$_3$H$_2$O), 30% to 55% gradient in 8 min; detector, UV 254 nm. 5-[7-[3-cyano-4-(oxan-4-yloxy)phenyl]furo[3,2-b]pyridin-2-yl]-4-methoxy-N,N, 1-trimethyl-1H-pyrrole-2-carboxamide was obtained as a yellow solid (29 mg, 21% 2 steps). HPLC: 98.5% purity, RT=1.47 min. MS: m/z=501.3 [M+H]$^+$. $^1$H NMR (300 MHz, CD$_3$OD, ppm) δ 8.57-8.47 (m, 2H), 8.38 (dd, J=8.9, 2.4 Hz, 1H), 7.65-7.55 (m, 2H), 7.12 (s, 1H), 6.37 (s, 1H), 5.02-4.92 (m, 1H), 3.95-3.81 (m, 8H), 3.63-3.59 (m, 2H), 3.06 (br s, 6H), 2.12-1.96 (m, 2H), 1.77-1.62 (m, 2H).

Example 361: 6-(7-[3-cyano-4-[(3,3-difluoropiperidin-4-yl)oxy]phenyl]furo[3,2-b]pyridin-2-yl)-5-methoxy-N,N-dimethylpyridine-3-carboxamide (403)

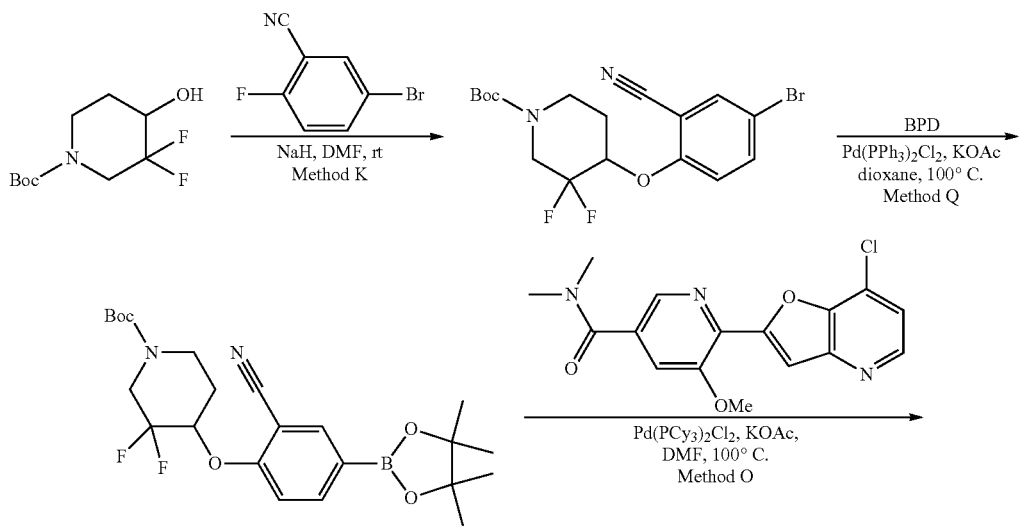

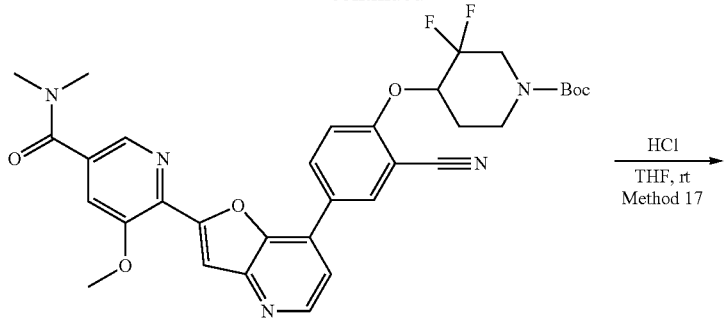

6-(7-[3-cyano-4-[(3,3-difluoropiperidin-4-yl)oxy]phenyl]furo[3,2-b]pyridin-2-yl)-5-methoxy-N,N-dimethylpyridine-3-carboxamide The title compound was prepared from tert-butyl 3,3-difluoro-4-hydroxypiperidine-1-carboxylate, 5-bromo-2-fluorobenzonitrile, 4,4,5,5-tetramethyl-2-(tetramethyl-1,3,2-dioxaborolan-2-yl)-1,3,2-dioxaborolane and 6-(7-chlorofuro[3,2-b]pyridin-2-yl)-5-methoxy-N,N-dimethylnicotinamide using Methods K, Q, O and 17. The final product was purified by prep-HPLC under the following conditions: column, XBridge Prep C18 OBD Column, 150 mm 5 um; mobile phase, acetonitrile in water (with 10 mmol/L $NH_4HCO_3$), 30% to 60% gradient in 8 min; detector, UV 254 nm. 6-(7-[3-cyano-4-[(3,3-difluoropiperidin-4-yl)oxy]phenyl]furo[3,2-b]pyridin-2-yl)-5-methoxy-N,N-dimethylpyridine-3-carboxamide was obtained as a white solid (20 mg, 9.2% 4 steps). HPLC: 93.0% purity, RT=1.74 min. MS: m/z=534.3 [M+H]$^+$. $^1$H NMR (300 MHz, $CD_3OD$, ppm) δ 8.57 (d, J=5.2 Hz, 1H), 8.53-8.43 (m, 2H), 8.37 (d, J=1.6 Hz, 1H), 7.81 (s, 1H), 7.73 (d, J=1.6 Hz, 1H), 7.66 (d, J=5.2 Hz, 1H), 7.55 (d, J=8.9 Hz, 1H), 5.14-5.04 (m, 1H), 4.14 (s, 3H), 3.40-3.30 (m, 1H), 3.20-2.95 (m, 8H), 2.92-2.78 (m, 1H), 2.22-2.06 (m, 2H).

Example 362: 6-(7-[3-cyano-4-[(3,3-difluoro-1-methylpiperidin-4-yl)oxy]phenyl]furo[3,2-b]pyridin-2-yl)-5-methoxy-N,N-dimethylpyridine-3-carboxamide (404)

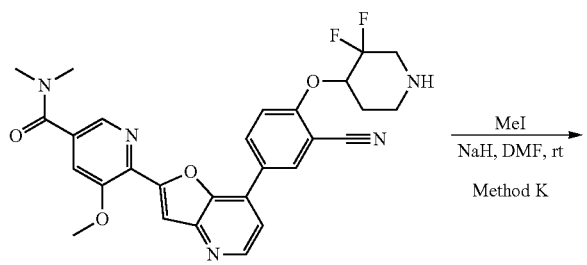

The title compound was prepared from 6-(7-(3-cyano-4-(3,3-difluoropiperidin-4-yloxy)phenyl)furo[3,2-b]pyridin-2-yl)-5-methoxy-N,N-dimethylnicotinamide and iodomethane using Method K. The product was purified by prep-HPLC under the following conditions: column, XBridge Prep C18 OBD Column, 150 mm 5 um; mobile phase, acetonitrile in water (with 10 mmol/L $NH_4HCO_3$), 30% to 50% gradient in 8 min; detector, UV 254 nm. 6-(7-[3-cyano-4-[(3,3-difluoro-1-methylpiperidin-4-yl)oxy]phenyl]furo[3,2-b]pyridin-2-yl)-5-methoxy-N,N-dimethylpyridine-3-carboxamide was obtained as a light yellow solid (18 mg, 25%). HPLC: 92.5% purity, RT=1.80 min. MS: m/z=548.3 [M+H]$^+$. $^1$H NMR (300 MHz, $CD_3OD$, ppm) δ 8.60-8.42 (m, 3H), 8.36 (d, J=1.6 Hz, 1H), 7.83-7.70 (m, 2H), 7.65 (d, J=5.0 Hz, 1H), 7.55 (d, J=9.0 Hz, 1H), 5.07-4.97 (m, 1H), 4.14 (s, 3H), 3.14 (s, 3H), 3.08 (s, 3H), 3.00-2.85 (m, 2H), 2.71-2.55 (m, 2H), 2.37 (s, 3H), 2.24-2.10 (m, 2H).

Example 363: 5-[2-[3-methoxy-5-([2-methyl-2,6-diazabicyclo[3.2.0]heptan-6-yl]carbonyl)pyridin-2-yl]furo[3,2-b]pyridin-7-yl]-2-(oxan-4-yloxy)benzonitrile hydrochloride (405)

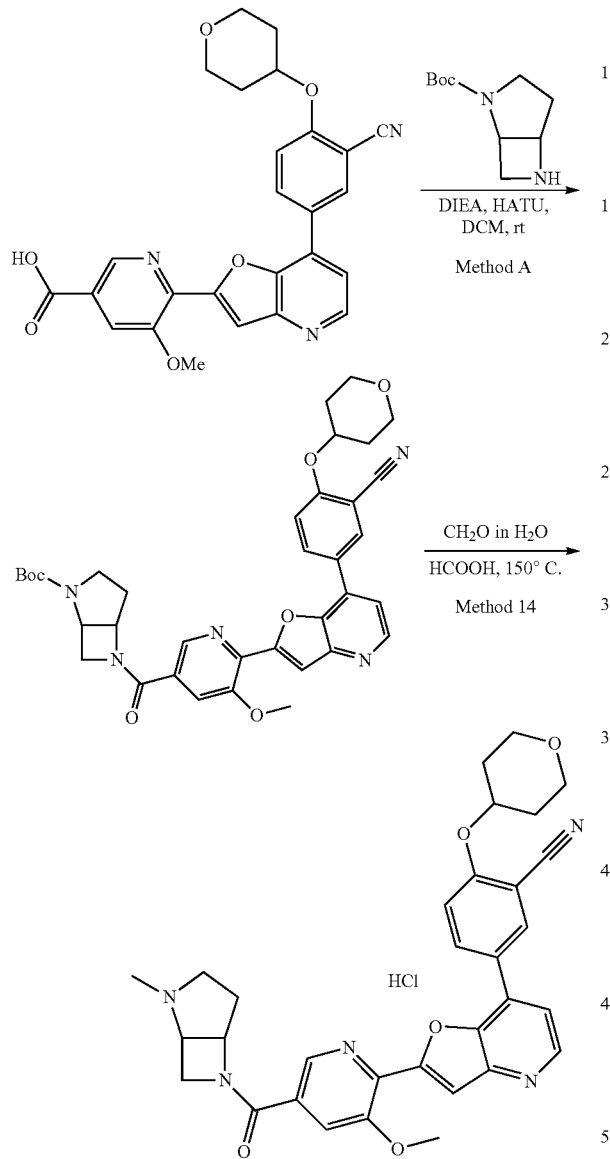

The title compound was prepared from 6-(7-(3-cyano-4-(tetrahydro-2H-pyran-4-yloxy)phenyl)furo[3,2-b]pyridin-2-yl)-5-methoxynicotinic acid, tert-butyl 2,6-diaza-bicyclo[3.2.0]heptane-2-carboxylate and formaldehyde using Methods A and 14. The product was purified by prep-HPLC under the following conditions: column, XBridge Prep C18 OBD Column, 150 mm 5 um; mobile phase, acetonitrile in water (with 0.05% HCl), 20% to 50% gradient in 8 min; detector, UV 254 nm. 5-[2-[3-methoxy-5-([2-methyl-2,6-diazabicyclo[3.2.0]heptan-6-yl]carbonyl)pyridin-2-yl]furo[3,2-b]pyridin-7-yl]-2-(oxan-4-yloxy)benzonitrile hydrochloride was obtained as a yellow solid (8 mg, 7.4% for 2 steps). HPLC: 94.8% purity, RT=0.93 min. MS: m/z=566.3 [M+H]$^+$. $^1$H NMR (300 MHz, CD$_3$OD, ppm) δ 8.92-8.45 (m, 4H), 8.13 (d, J=6.1 Hz, 1H), 7.99 (s, 2H), 7.59 (d, J=8.9 Hz, 1H), 5.39-5.27 (m, 1H), 5.07-4.97 (m, 1H), 4.75-4.30 (m, 2H), 4.26 (s, 3H), 4.10-3.60 (m, 5H), 3.10-2.90 (m, 3H), 2.81-2.00 (m, 4H), 1.96-1.81 (m, 2H), 1.40-1.22 (m, 2H).

Example 364: 5-[2-[3-methoxy-5-([5-methyl-2,5-diazabicyclo[2.2.2]octan-2-yl]carbonyl)pyridin-2-yl]furo[3,2-b]pyridin-7-yl]-2-(oxan-4-yloxy)benzonitrile hydrochloride (406)

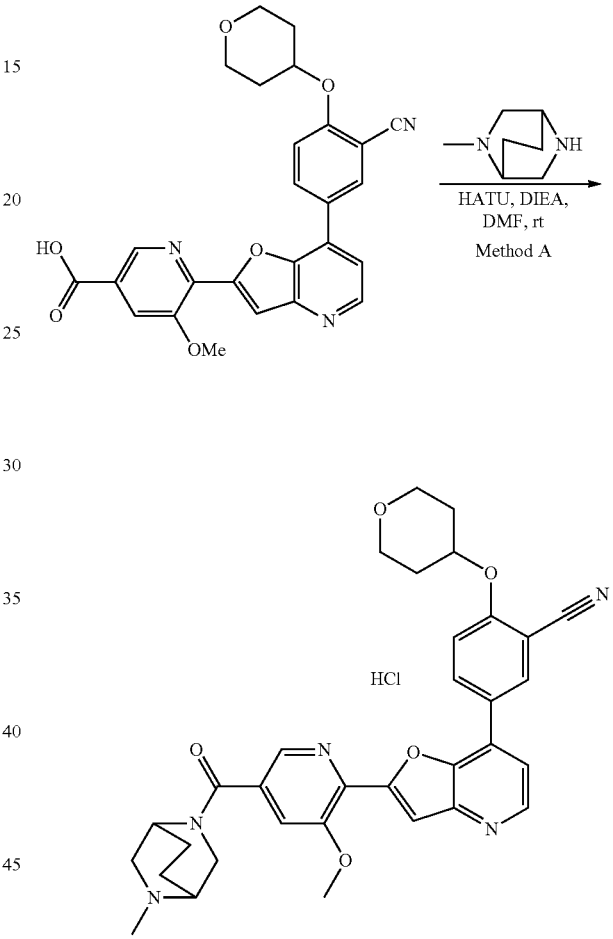

The title compound was prepared from 6-(7-(3-cyano-4-(tetrahydro-2H-pyran-4-yloxy)phenyl)furo[3,2-b]pyridin-2-yl)-5-methoxynicotinic acid and 2-methyl-2,5-diaza-bicyclo[2.2.2]octane using Method A. The product was purified by prep-HPLC under the following conditions: column, XBridge Prep C18 OBD Column, 150 mm 5 um; mobile phase, acetonitrile in water (with 0.05% HCl), 20% to 50% gradient in 8 min; detector, UV 254 nm. 5-[2-[3-methoxy-5-([5-methyl-2,5-diazabicyclo[2.2.2]octan-2-yl]carbonyl)pyridin-2-yl]furo[3,2-b]pyridin-7-yl]-2-(oxan-4-yloxy)benzonitrile hydrochloride was obtained as a yellow solid (17 mg, 13%). HPLC: 96.8% purity, RT=1.59 min. MS: m % z=580.2 [M+H]$^+$. $^1$H NMR (300 MHz, CD$_3$OD, ppm) δ 8.77-8.65 (m, 2H), 8.62-8.41 (m, 2H), 8.06 (d, J=6.0 Hz, 1H), 7.99-7.76 (m, 2H), 7.55 (d, J=9.1 Hz, 1H), 5.03-4.91 (m, 1H), 4.21 (d. J=6.6 Hz, 3H), 4.15-3.79 (m, 6H), 3.77-3.36 (m, 4H), 3.04 (s, 3H), 2.43-1.70 (m, 8H).

Example 365: 5-(2-[5-[(1,2-diazinan-1-yl)carbonyl]-3-methoxypyridin-2-yl]furo[3,2-b]pyridin-7-yl)-2-(oxan-4-yloxy)benzonitrile hydrochloride (407)

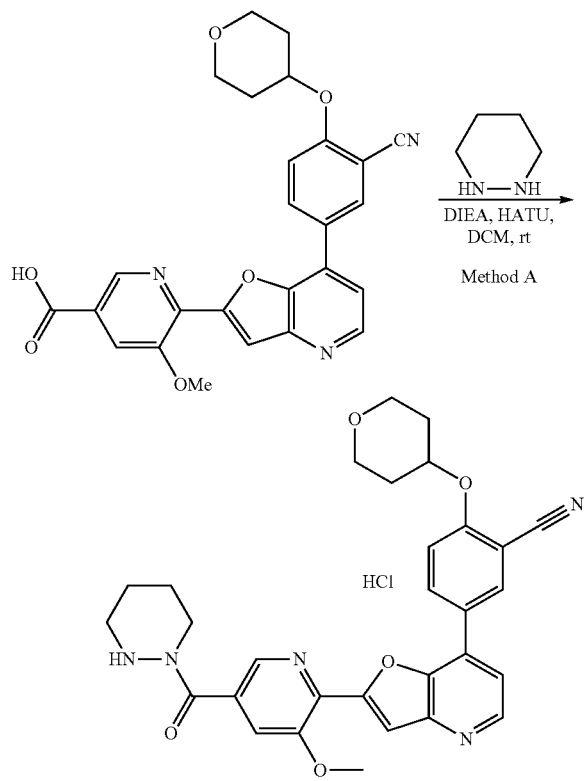

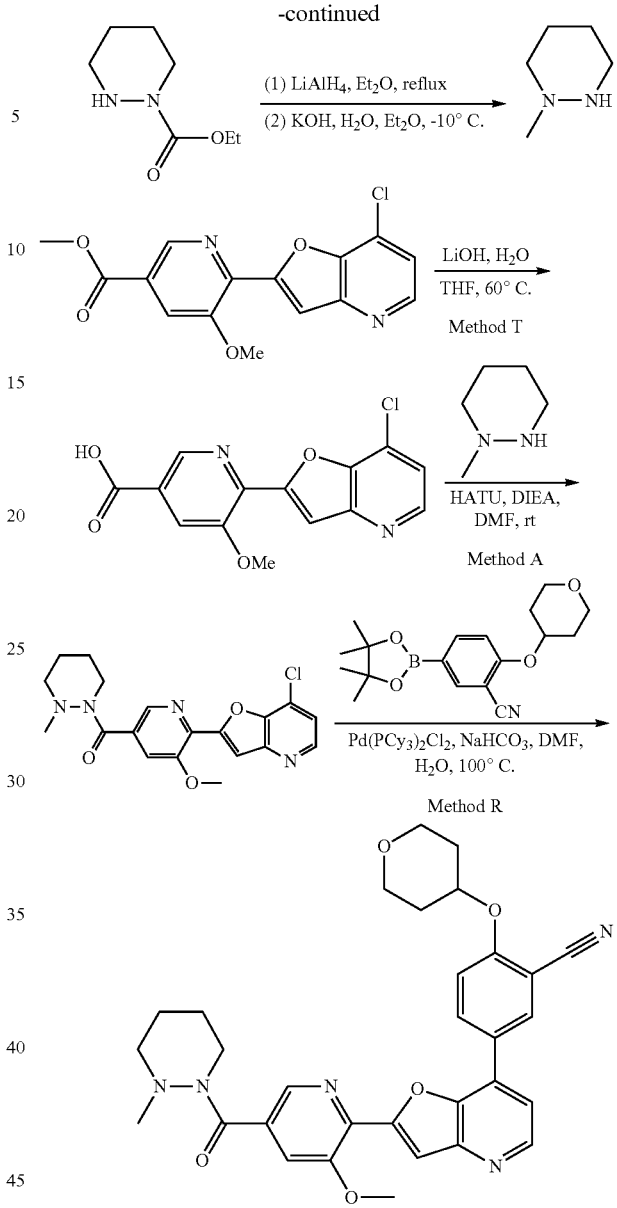

The title compound was prepared from 6-(7-(3-cyano-4-(tetrahydro-2H-pyran-4-yloxy)phenyl)furo[3,2-b]pyridin-2-yl)-5-methoxynicotinic acid and piperazine using Method A. The product was purified by prep-HPLC under the following conditions: column, XBridge Prep C18 OBD Column, 150 mm 5 um; mobile phase, acetonitrile in water (with 0.05% HCl), 20% to 50% gradient in 8 min; detector, UV 254 nm. 5-(2-[5-[(1,2-diazinan-1-yl)carbonyl]-3-methoxypyridin-2-yl]furo[3,2-b]pyridin-7-yl)-2-(oxan-4-yloxy)benzonitrile hydrochloride was obtained as a yellow solid (15 mg, 13%). HPLC: 97.7% purity, RT=1.43 min. MS: m/z=540.3 [M+H]$^+$. $^1$H NMR (300 MHz, CD$_3$OD, ppm) δ 8.79-8.71 (m, 2H), 8.65 (dd, J=9.0, 2.5 Hz, 1H), 8.58 (d, J=1.5 Hz, 1H), 8.13 (d, J=6.2 Hz, 1H), 7.99-7.88 (m, 2H), 7.60 (d, J=9.1 Hz, 1H), 5.07-4.97 (m, 1H), 4.21 (s, 3H), 4.11-3.97 (m, 2H), 3.90-3.62 (m, 4H), 2.94 (s, 2H), 2.26-2.11 (m, 2H), 1.99-1.65 (m, 6H).

Example 366: 5-(2-[3-methoxy-5-[(2-methyl-1,2-diazinan-1-yl)carbonyl]pyridin-2-yl]furo[3,2-b]pyridin-7-yl)-2-(oxan-4-yloxy)benzonitrile (408)

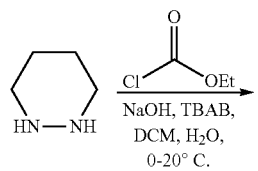

Ethyl piperazine-1-carboxylate

At 0° C., to a solution of 1,2-diazinane (2.85 g, 33.09 mmol) in dichloromethane (35 mL) was added tetra-n-butylammonium bromide (100 mg, 0.31 mmol) and water (32 mL). The resulting mixture was then added by a solution of sodium hydroxide (34 mL, 102 mmol, 3 mol/L), followed by the dropwise addition of a solution of chloro(ethoxy)methanone (4.75 g, 43.77 mmol) in dichloromethane (30 mL) over 15 min period at 0° C. The reaction mixture was stirred for 2 h at 0° C., warmed up to room temperature and stirred overnight at room temperature. After the reaction was done, the reaction mixture was diluted with water (15 mL) and the pH value of the mixture was adjusted to 5 with hydrogen chloride solution (2 M). The resulting mixture was extracted with ether (30 mL×3) and the two phases were separated. The pH value of aqueous phase was adjusted to 7 with sat. NaHCO$_3$ solution. The resulting mixture was extracted with DCM (50 mL×3). The organic layers were combined, washed with brine and dried over sodium sulfate. The solvent was removed under reduced pressure to yield ethyl 1,2-diazinane-1-carboxylate as a yellow oil (3.70 g, 53%). MS: m/z=159.0 [M+H]⁺. ¹H NMR (400 MHz, CDCl₃, ppm) δ 4.26-4.14 (m, 2H), 3.61-3.49 (m, 2H), 2.98-2.82 (m, 2H), 1.73-1.57 (m, 4H), 1.36-1.24 (m, 3H).

1-Methylpiperazine

At 0° C., to a solution of ethyl 1,2-diazinane-1-carboxylate (85 mg, 0.54 mmol) in ether (30 mL) was added LiAlH₄ (120 mg, 3.16 mmol) in portions over 20 min period. The resulting mixture was stirred for 2 h at room temperature and then heated to 40° C. and stirred for 4 h at 40° C. After cooling to room temperature, the reaction mixture was quenched by the addition of aqueous KOH solution (40%, 0.5 mL). The two phases were separated. The organic phase was dried over sodium sulfate and concentrated under reduced pressure to yield 1-methyl-1,2-diazinane as a white oil (30 mg, 56%). MS: m/z=101.0 [M+H]⁺.

5-(2-[3-methoxy-5-[(2-methyl-1,2-diazinan-1-yl)carbonyl]pyridin-2-yl]furo[3,2-b]pyridin-7-yl)-2-(oxan-4-yloxy)benzonitrile The title compound was prepared from methyl 6-(7-chlorofuro[3,2-b]pyridin-2-yl)-5-methoxynicotinate, 1-methylpiperazine and 2-(tetrahydro-2H-pyran-4-yloxy)-5-(4,4,5,5-tetramethyl-1,3,2-dioxaborolan-2-yl)benzonitrile using Methods T, A and R. The final product was purified by prep-HPLC under the following conditions: column, XBridge Prep C18 OBD Column, 150 mm 5 um; mobile phase, acetonitrile in water (with 0.05% NH₃H₂O), 45% to 70% gradient in 8 min; detector, UV 254 nm. 5-[7-[3-cyano-4-(oxan-4-yloxy)phenyl]furo[3,2-b]pyridin-2-yl]-4-methoxy-N,N,1-trimethyl-1H-pyrrole-2-carboxamide was obtained as a yellow solid (15 mg, 9% 3 steps). HPLC: 98.3% purity, RT=3.41 min. MS: m/z=554.3 [M+H]⁺. ¹H NMR (300 MHz, DMSO-d₆, ppm) δ 8.63 (d, J=5.0 Hz, 1H), 8.58-8.41 (m, 3H), 7.83-7.63 (m, 4H), 5.06-4.96 (m, 1H), 4.20-4.02 (m, 4H), 3.96-3.84 (m, 2H), 3.64-3.52 (m, 2H), 3.30-3.15 (m, 1H), 3.11-2.99 (m, 1H), 2.78 (d, J=13.9 Hz, 1H), 2.62 (s, 3H), 2.14-1.92 (m, 3H), 1.86-1.60 (m, 4H), 1.40-1.28 (m, 1H).

Example 367: (R)-6-(7-(3-cyano-4-(3-fluoropyrrolidin-1-yl)phenyl)furo[3,2-b]pyridin-2-yl)-N-(2-hydroxyethyl)-5-methoxy-N-methylnicotinamide (409)

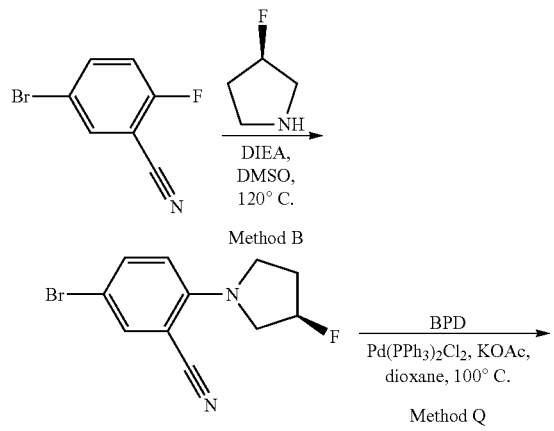

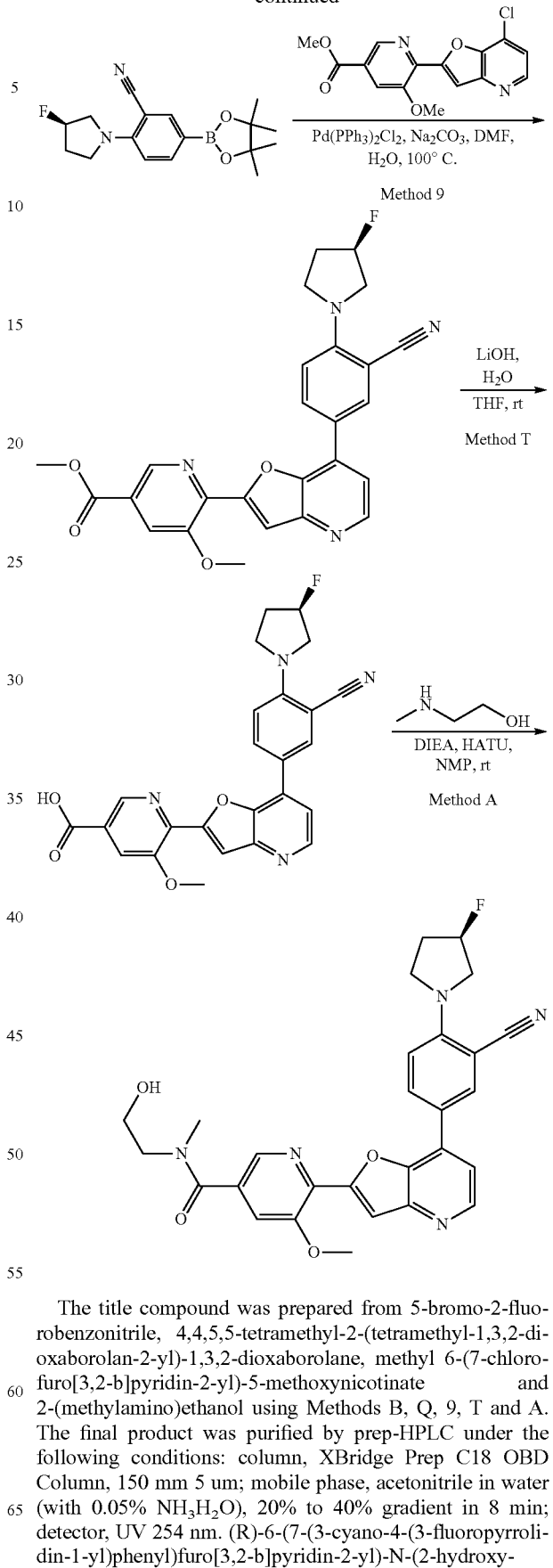

The title compound was prepared from 5-bromo-2-fluorobenzonitrile, 4,4,5,5-tetramethyl-2-(tetramethyl-1,3,2-dioxaborolan-2-yl)-1,3,2-dioxaborolane, methyl 6-(7-chlorofuro[3,2-b]pyridin-2-yl)-5-methoxynicotinate and 2-(methylamino)ethanol using Methods B, Q, 9, T and A. The final product was purified by prep-HPLC under the following conditions: column, XBridge Prep C18 OBD Column, 150 mm 5 um; mobile phase, acetonitrile in water (with 0.05% NH₃H₂O), 20% to 40% gradient in 8 min; detector, UV 254 nm. (R)-6-(7-(3-cyano-4-(3-fluoropyrrolidin-1-yl)phenyl)furo[3,2-b]pyridin-2-yl)-N-(2-hydroxyethyl)-5-methoxy-N-methylnicotinamide was obtained as a yellow solid (23 mg, 17% 5 steps). HPLC: 99.0% purity, RT=2.10 min. MS: m/z=516.3 [M+H]+. 1H NMR (300 MHz, CD3OD, ppm) δ 8.48 (d, J=5.3 Hz, 1H), 8.40 (d, J=1.6 Hz, 2H), 8.29 (dd, J=9.1, 2.3 Hz, 1H), 7.82 (s, 1H), 7.74 (s, 1H), 7.61 (d, J=5.2 Hz, 1H), 6.98 (d, J=9.1 Hz, 1H), 5.55-5.27 (m, 1H), 4.20-4.04 (m, 4H), 4.03-3.79 (m, 4H), 3.77-3.63 (m, 2H), 3.53-3.41 (m, 1H), 3.14 (d, J=2.4 Hz, 3H), 2.42-2.10 (m, 2H).

Example 368: 2-[(3R)-3-fluoropyrrolidin-1-yl]-5-(2-[3-methoxy-5-[(piperidin-1-yl)carbonyl]pyridin-2-yl]furo[3,2-b]pyridin-7-yl)benzonitrile (410)

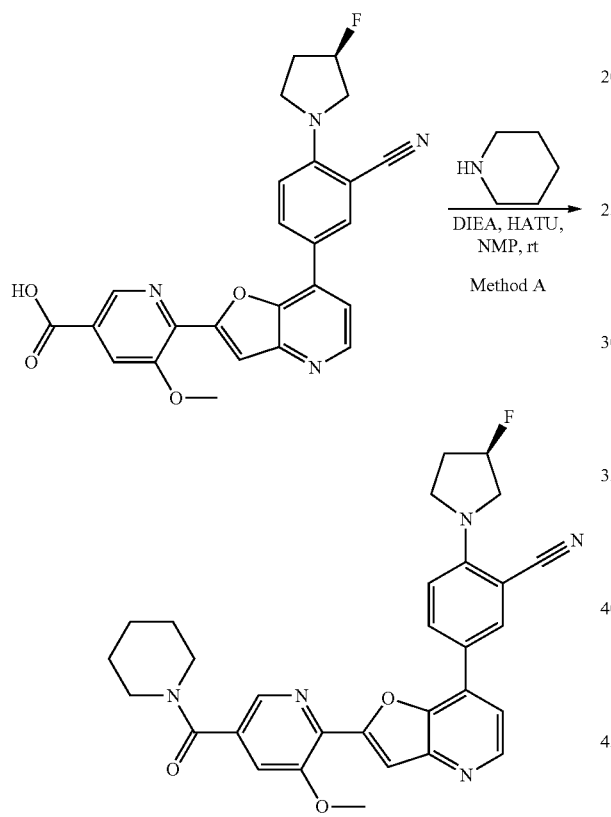

Example 369: 5-[2-[3-methoxy-5-([8-oxa-3-azabicyclo[3.2.1]octan-3-yl]carbonyl)pyridin-2-yl]furo[3,2-b]pyridin-7-yl]-2-(oxan-4-yloxy)benzonitrile hydrochloride (411)

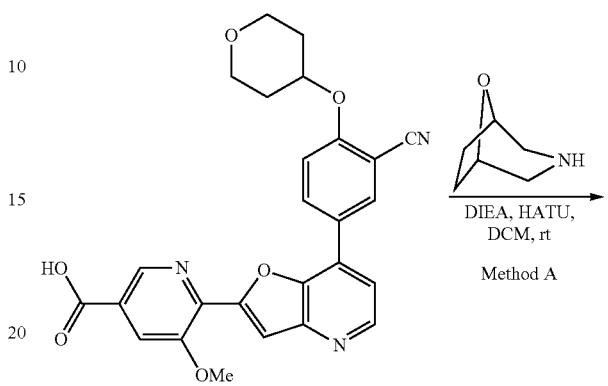

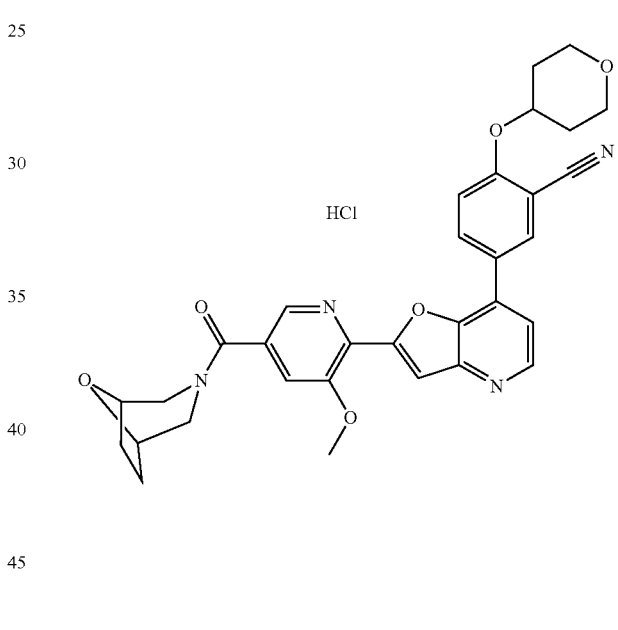

The title compound was prepared from (R)-6-(7-(3-cyano-4-(3-fluoropyrrolidin-1-yl)phenyl)furo[3,2-b]pyridin-2-yl)-5-methoxynicotinic acid and piperidine using Method A. The product was purified by prep-HPLC under the following conditions: column, XBridge Prep C18 OBD Column, 150 mm 5 um; mobile phase, acetonitrile in water (with 0.05% NH3H2O), 20% to 40% gradient in 8 min; detector, UV 254 nm. 2-[(3R)-3-fluoropyrrolidin-1-yl]-5-(2-[3-methoxy-5-[(piperidin-1-yl)carbonyl]pyridin-2-yl]furo[3,2-b]pyridin-7-yl)benzonitrile was obtained as a yellow solid (23 mg, 31%). HPLC: 96.3% purity, RT=1.21 min. MS: m/z=526.3 [M+H]+. 1H NMR (300 MHz, CD3OD, ppm) δ 8.48 (d, J=5.2 Hz, 1H), 8.41 (d, J=2.3 Hz, 1H), 8.36-8.24 (m, 2H), 7.74 (s, 1H), 7.68 (d, J=1.6 Hz, 1H), 7.61 (d, J=5.2 Hz, 1H), 6.99 (d, J=9.2 Hz, 1H), 5.57-5.24 (m, 1H), 4.14 (s, 3H), 4.01-3.67 (m, 6H), 3.55-3.39 (m, 2H), 2.48-2.20 (m, 2H), 1.74-1.58 (m, 6H).

The title compound was prepared from 6-(7-(3-cyano-4-(tetrahydro-2H-pyran-4-yloxy)phenyl)furo[3,2-b]pyridin-2-yl)-5-methoxynicotinic acid and 8-oxa-3-aza-bicyclo[3.2.1]octane using Method A. The product was purified by prep-HPLC under the following conditions: column, XBridge Prep C18 OBD Column, 150 mm 5 um; mobile phase, acetonitrile in water (with 0.02% HCl), 20% to 50% gradient in 8 min; detector, UV 254 nm. 5-[2-[3-methoxy-5-([8-oxa-3-azabicyclo[3.2.1]octan-3-yl]carbonyl)pyridin-2-yl]furo[3,2-b]pyridin-7-yl]-2-(oxan-4-yloxy)benzonitrile hydrochloride was obtained as a yellow solid (8 mg, 5%). HPLC: 99.9% purity, RT=1.39 min. MS: m/z=567.3 [M+H]+. 1H NMR (300 MHz, CD3OD, ppm) δ 8.81-8.59 (m, 3H), 8.46 (d, J=1.5 Hz, 1H), 8.15 (d, J=6.3 Hz, 1H), 7.96 (s, 1H), 7.84 (d, l=1.5 Hz, 1H), 7.60 (d, J=9.1 Hz, 1H), 5.07-4.98 (m, 1H), 4.55-4.20 (m, 6H), 4.11-3.96 (m, 2H), 3.78-3.57 (m, 3H), 3.45-3.20 (m, 2H), 2.15-1.70 (m, 8H).

Example 370: 5-[2-[5-([7-hydroxy-3-oxa-9-azabicyclo[3.3.1]nonan-9-yl]carbonyl)-3-methoxypyridin-2-yl]furo[3,2-b]pyridin-7-yl]-2-(oxan-4-yloxy)benzonitrile (412)

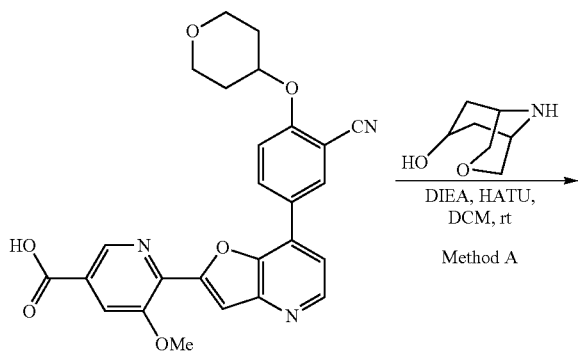

Example 371: 5-[2-[4-methoxy-6-([2-oxa-5-azabicyclo[2.2.2]octan-5-yl]carbonyl)pyridin-3-yl]furo[3,2-b]pyridin-7-yl]-2-(oxan-4-yloxy)benzonitrile hydrochloride (413)

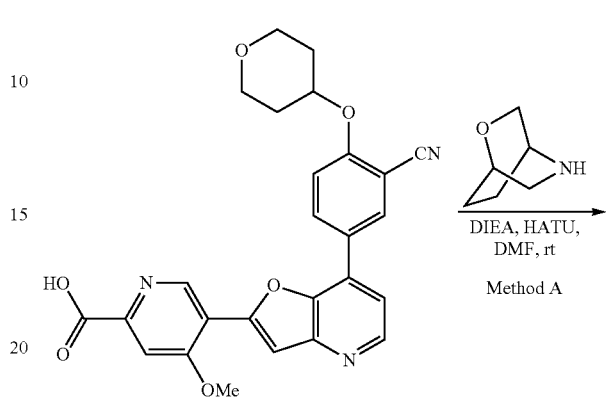

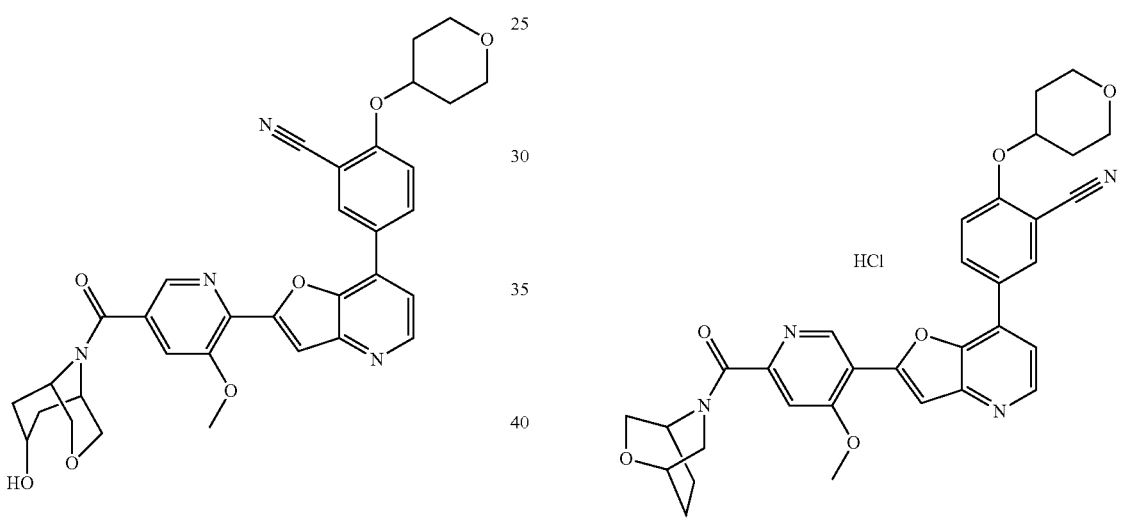

The title compound was prepared from 6-(7-(3-cyano-4-(tetrahydro-2H-pyran-4-yloxy)phenyl)furo[3,2-b]pyridin-2-yl)-5-methoxynicotinic acid and 3-oxa-9-aza-bicyclo[3.3.1]nonan-7-ol using Method A. The product was purified by prep-HPLC under the following conditions: column, XBridge Prep C18 OBD Column, 150 mm 5 um; mobile phase, acetonitrile in water (with 10 mmol/L $NH_4HCO_3$), 20% to 50% gradient in 8 min; detector, UV 254 nm. 5-[2-[5-([7-hydroxy-3-oxa-9-azabicyclo[3.3.1]nonan-9-yl]carbonyl)-3-methoxypyridin-2-yl]furo[3,2-b]pyridin-7-yl]-2-(oxan-4-yloxy)benzonitrile was obtained as a white solid (50 mg, 43%). HPLC: 97.7% purity, RT=1.59 min. MS: m/z=597.2 [M+H]$^+$. $^1$H NMR (300 MHz, DMSO-d$_6$, ppm) δ 8.63 (d, J=5.1 Hz, 1H), 8.54 (d, J=2.3 Hz, 1H), 8.47 (dd, J=8.9, 2.4 Hz, 1H), 8.40 (d, J=1.5 Hz, 1H), 7.83 (s, 1H), 7.79-7.71 (m, 2H), 7.67 (d, J=9.1 Hz, 1H), 5.10 (d, J=11.1 Hz, 1H), 5.05-4.93 (m, 1H), 4.62-4.50 (m, 1H), 4.13 (s, 3H), 3.98-3.49 (m, 10H), 2.33-1.99 (m, 4H), 1.88-1.54 (m, 4H).

The title compound was prepared from 5-(7-(3-cyano-4-(tetrahydro-2H-pyran-4-yloxy)phenyl)furo[3,2-b]pyridin-2-yl)-4-methoxypicolinic acid and 5-oxa-2-aza-bicyclo[2.2.2]octane using Method A. The product was purified by prep-HPLC under the following conditions: column, XBridge Prep C18 OBD Column, 150 mm 5 um; mobile phase, acetonitrile in water (with 0.02% HCl), 20% to 50% gradient in 8 min, detector, UV 254 nm. 5-[2-[4-methoxy-6-([2-oxa-5-azabicyclo[2.2.2]octan-5-yl]carbonyl)pyridin-3-yl]furo[3,2-b]pyridin-7-yl]-2-(oxan-4-yloxy)benzonitrile hydrochloride was obtained as a yellow solid (44 mg, 47%). HPLC: 91.6% purity, RT=2.78 min. MS: m/z=567.1 [M+H]$^+$. $^1$H NMR (300 MHz, CD$_3$OD, ppm) δ 9.25 (s, 1H), 8.80 (dd, J=6.4, 2.3 Hz, 1H), 8.70-8.57 (m, 2H), 8.21 (dd, J=6.4, 2.1 Hz, 1H), 7.91 (d, J=5.8 Hz, 1H), 7.76-7.60 (m, 2H), 5.08-4.98 (m, 1H), 4.36-3.91 (m, 10H), 3.84-3.64 (m, 3H), 2.27-2.11 (m, 4H), 2.09-1.82 (m, 4H).

Example 372: 5-[2-[2-methoxy-4-([2-oxa-5-azabicyclo[2.2.2]octan-5-yl]carbonyl)phenyl]furo[3,2-b]pyridin-7-yl]-2-(oxan-4-yloxy)benzonitrile hydrochloride (414)

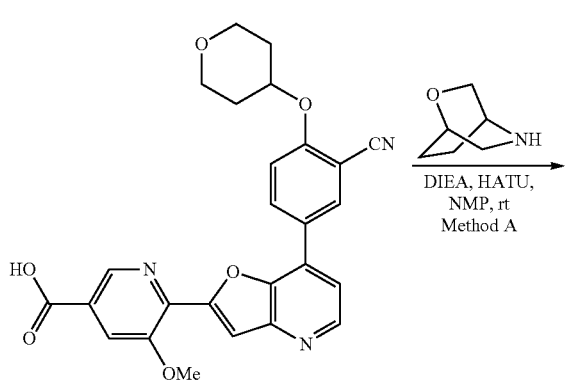

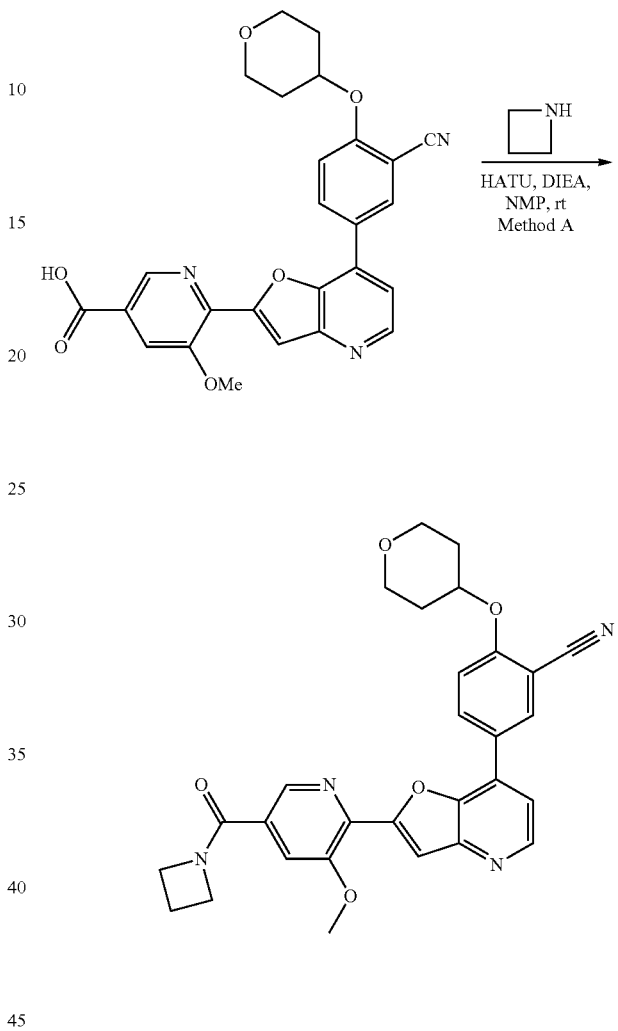

Example 373: 5-(2-[5-[(azetidin-1-yl)carbonyl]-3-methoxypyridin-2-yl]furo[3,2-b]pyridin-7-yl)-2-(oxan-4-yloxy)benzonitrile (415)

The title compound was prepared from 6-(7-(3-cyano-4-(tetrahydro-2H-pyran-4-yloxy)phenyl)furo[3,2-b]pyridin-2-yl)-5-methoxynicotinic acid and 5-oxa-2-aza-bicyclo[2.2.2]octane using Method A. The product was purified by prep-HPLC under the following conditions: column, XBridge Prep C18 OBD Column, 150 mm 5 um; mobile phase, acetonitrile in water (with 0.02% HCl), 20% to 50% gradient in 8 min; detector, UV 254 nm. 5-[2-[2-methoxy-4-([2-oxa-5-azabicyclo[2.2.2]octan-5-yl]carbonyl)phenyl]furo[3,2-b]pyridin-7-yl]-2-(oxan-4-yloxy)benzonitrile hydrochloride was obtained as a yellow solid (50 mg, 43%). HPLC: 99.8% purity, RT=1.67 min. MS: m/z=567.2 [M+H]$^+$. $^1$H NMR (300 MHz, CD$_3$OD, ppm) δ 8.72-8.61 (m, 2H), 8.60-8.39 (m, 2H), 7.99 (d, 0.1=5.9 Hz, 1H), 7.92-7.78 (m, 2H), 7.53 (d, J=9.1 Hz, 1H), 5.01-4.91 (m, 1H), 4.30-3.86 (m, 9H), 3.85-3.60 (m, 4H), 2.31-1.69 (m, 8H).

The title compound was prepared from 6-(7-(3-cyano-4-(tetrahydro-2H-pyran-4-yloxy)phenyl)furo[3,2-b]pyridin-2-yl)-5-methoxynicotinic acid and azetidine using Method A. The final product was purified by prep-HPLC under the following conditions: column, XBridge Prep C18 OBD Column, 150 mm 5 um; mobile phase, acetonitrile in water (with 10 mmol/L NH$_4$HCO$_3$), 30% to 60% gradient in 8 min; detector, UV 254 nm. 5-(2-[5-[(azetidin-1-yl)carbonyl]-3-methoxypyridin-2-yl]furo[3,2-b]pyridin-7-yl)-2-(oxan-4-yloxy)benzonitrile was obtained as a white solid (16 mg, 16%). HPLC: 95.8% purity, RT=1.66 min. MS: m/z=511.1 [M+H]$^+$. $^1$H NMR (300 MHz, DMSO-d$_6$, ppm) δ 8.63 (d, J=5.1 Hz, 1H), 8.54 (dd, J=4.7, 1.9 Hz, 2H), 8.47 (dd, J=8.9, 2.4 Hz, 1H), 5.04-4.94 (mz, 1H), 4.42 (t, J=7.6 Hz, 2H), 4.20-4.04 (m, 5H), 3.95-3.83 (m, 2H), 3.64-3.60 (m, 2H), 2.43-2.21 (m, 2H), 2.13-1.97 (m, 2H), 1.78-1.64 (m, 2H).

Example 374: 5-(2-[3-methoxy-5-[(pyrrolidin-1-yl)carbonyl]pyridin-2-yl]furo[3,2-b]pyridin-7-yl)-2-(oxan-4-yloxy)benzonitrile hydrochloride (416)

Example 375: 5-(2-[6-[(1,2-diazinan-1-yl)carbonyl]-4-methoxypyridin-3-yl]furo[3,2-b]pyridin-7-yl)-2-(oxan-4-yloxy)benzonitrile (417)

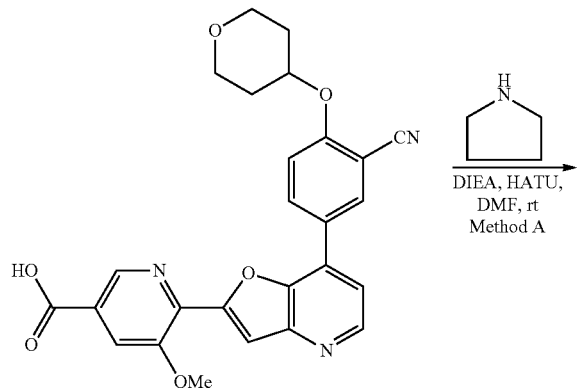

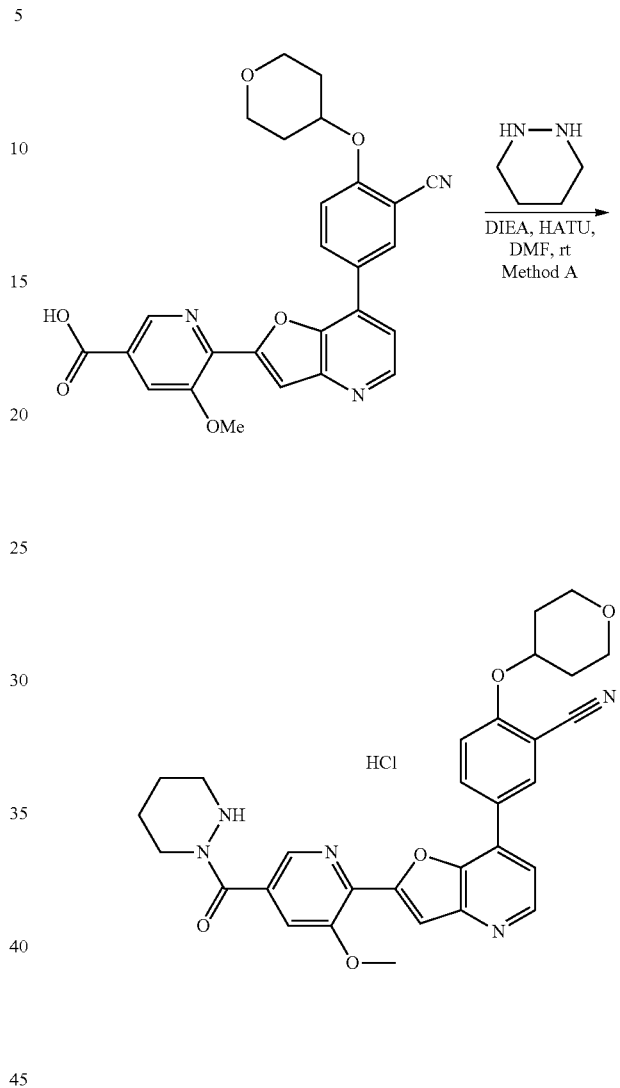

The title compound was prepared from 6-(7-(3-cyano-4-(tetrahydro-2H-pyran-4-yloxy)phenyl)furo[3,2-b]pyridin-2-yl)-5-methoxynicotinic acid and pyrrolidine using Method A. The product was purified by prep-HPLC under the following conditions: column, XBridge Prep C18 OBD Column, 150 mm 5 um; mobile phase, acetonitrile in water (with 0.05% HCl), 20% to 50% gradient in 8 min; detector, UV 254 nm. 5-(2-[3-methoxy-5-[(pyrrolidin-1-yl)carbonyl]pyridin-2-yl]furo[3,2-b]pyridin-7-yl)-2-(oxan-4-yloxy)benzonitrile hydrochloride was obtained as a yellow solid (17 mg, 16%). HPLC: 99.8% purity, RT=1.13 min. MS: m/z=525.3 [M+H]$^+$. $^1$H NMR (300 MHz, DMSO-$d_6$, ppm) δ 8.72-8.47 (m, 4H), 8.00-7.82 (m, 3H), 7.53 (d, J=9.0 Hz, 1H), 5.02-4.92 (m, 1H), 4.17 (s, 3H), 3.98 (dd, J=6.6, 4.3 Hz, 2H), 3.74-3.50 (m, 6H), 2.13-1.84 (m, 8H).

The title compound was prepared from 5-(7-(3-cyano-4-(tetrahydro-2H-pyran-4-yloxy)phenyl)furo[3,2-b]pyridin-2-yl)-4-methoxypicolinic acid and piperazine using Method A. The product was purified by prep-HPLC under the following conditions: column, XBridge Prep C18 OBD Column, 150 mm 5 um; mobile phase, acetonitrile in water (with 10 mmol/L NH$_4$HCO$_3$), 25% to 50% gradient in 8 min; detector, UV 254 nm. 5-(2-[6-[(1,2-diazinan-1-yl)carbonyl]-4-methoxypyridin-3-yl]furo[3,2-b]pyridin-7-yl)-2-(oxan-4-yloxy)benzonitrile was obtained as a white solid (30 mg, 36%). HPLC: 99.2% purity, RT=1.42 min. MS: m/z=540.3 [M+H]$^+$. $^1$H NMR (300 MHz, DMSO-$d_6$, ppm) δ 9.03-8.93 (m, 1H), 8.64-8.43 (m, 3H), 7.75-7.57 (m, 3H), 7.27 (s, 1H), 4.97 (t, J=6.8 Hz, 2H), 4.20-4.06 (m, 3H), 3.96-3.82 (m, 2H), 3.71-3.49 (m, 4H), 2.95-2.68 (m, 2H), 2.13-1.99 (m, 2H), 1.80-1.54 (m, 6H).

Example 376: 5-(7-[3-cyano-4-[(3,3-difluoropiperidin-4-yl)oxy]phenyl]furo[3,2-b]pyridin-2-yl)-4-methoxy-N,N-dimethylpyridine-2-carboxamide hydrochloride (418)

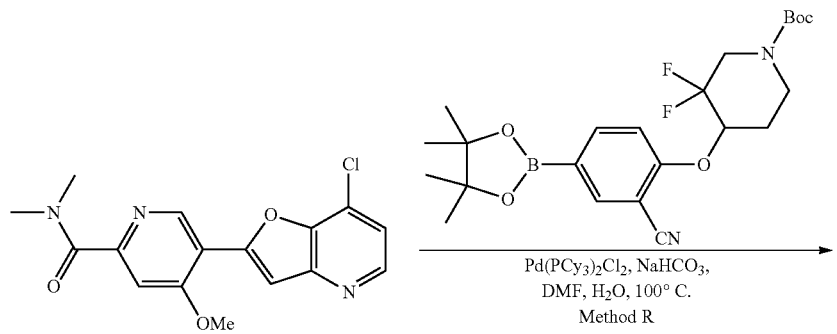

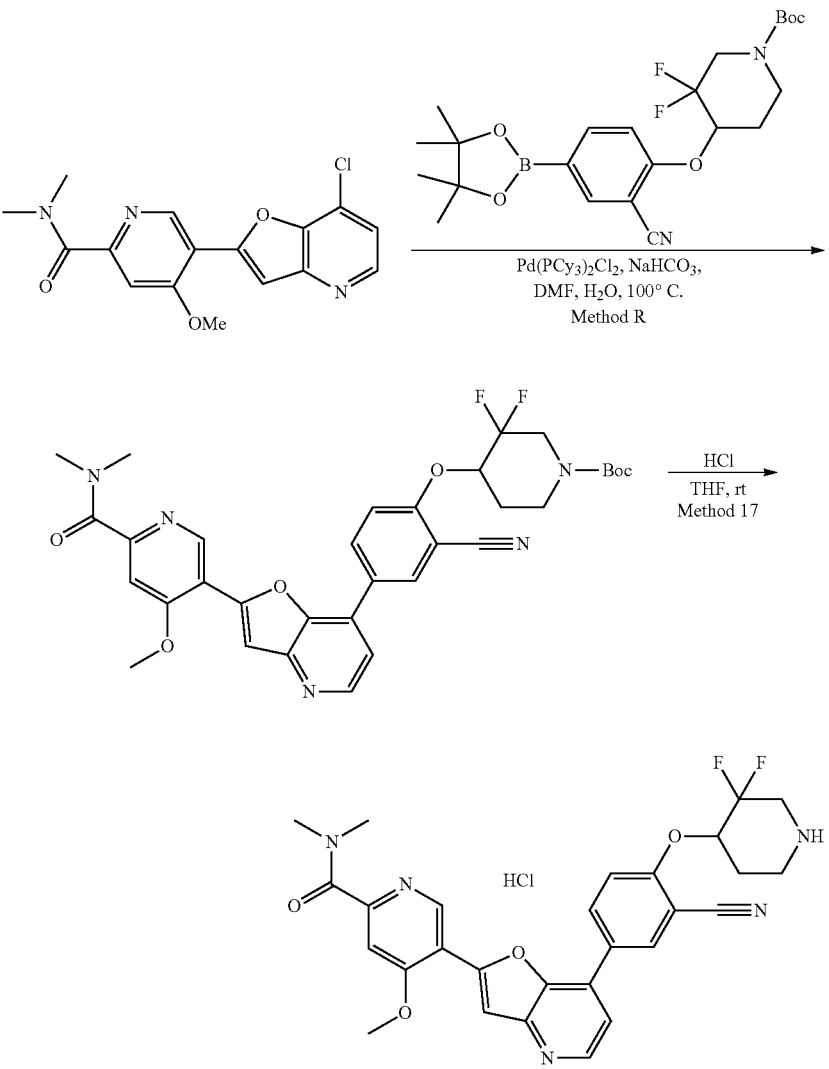

The title compound was prepared from 5-(7-chlorofuro[3,2-b]pyridin-2-yl)-4-methoxy-N,N-dimethylpicolinamide and tert-butyl 4-(2-cyano-4-(4,4,5,5-tetramethyl-1,3,2-dioxaborolan-2-yl)phenoxy)-3,3-difluoropiperidine-1-carboxylate using Methods R and 17. The final product was purified by prep-HPLC under the following conditions: column, XBridge Prep C18 OBD Column, 150 mm 5 um; mobile phase, acetonitrile in water (with 0.05% HCl), 20% to 50% gradient in 8 min; detector, UV 254 nm. 5-(7-[3-cyano-4-[(3,3-difluoropiperidin-4-yl)oxy]phenyl]furo[3,2-b]pyridin-2-yl)-4-methoxy-N,N-dimethylpyridine-2-carboxamide hydrochloride was obtained as a yellow solid (45 mg, 31%). HPLC: 92.8% purity, RT=2.46 min. MS: m/z=534.4 [M+H]$^+$. $^1$H NMR (300 MHz, CD$_3$OD, ppm) δ 9.33 (s, 1H), 8.85 (d, J=6.2 Hz, 1H), 8.71-8.60 (m, 2H), 8.23 (d, J=6.3 Hz, 1H), 8.00 (s, 1H), 7.90-7.78 (m, 2H), 5.51 (dd, J=10.3, 5.1 Hz, 1H), 4.37 (s, 3H), 3.95-3.74 (m, 2H), 3.47 (t, J=6.0 Hz, 2H), 3.20-3.07 (m, 6H), 2.55-2.41 (m, 2H).

Example 377: 5-(7-[3-cyano-4-[(3,3-difluoro-1-methylpiperidin-4-yl)oxy]phenyl]furo[3,2-b]pyridin-2-yl)-4-methoxy-N,N-dimethylpyridine-2-carboxamide (419)

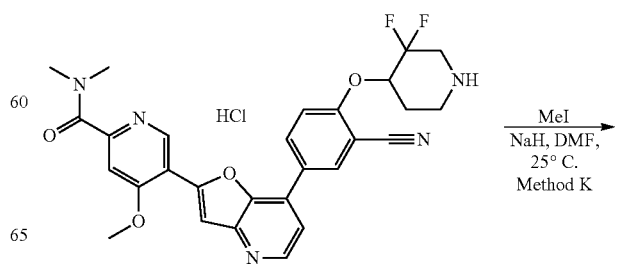

-continued

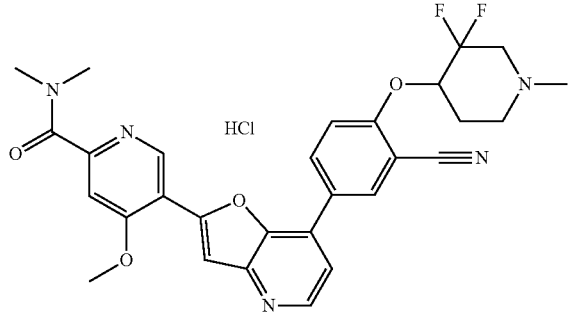

The title compound was prepared from 5-(7-(3-cyano-4-(3,3-difluoropiperidin-4-yloxy)phenyl)furo[3,2-b]pyridin-2-yl)-4-methoxy-N,N-dimethylpicolinamide and iodomethane using Method K. The final product was purified by prep-HPLC under the following conditions: column, XBridge Prep C18 OBD Column, 150 mm 5 um; mobile phase, acetonitrile in water (with 10 mmol/L $NH_4HCO_3$), 20% to 50% gradient in 8 min; detector, UV 254 nm. 5-(7-[3-cyano-4-[(3,3-difluoro-1-methylpiperidin-4-yl)oxy]phenyl]furo[3,2-b]pyridin-2-yl)-4-methoxy-N,N-dimethyl-pyridine-2-carboxamide was obtained as a white solid (27 mg, 18%). HPLC: 97.5% purity, RT=0.87 min. MS: m/z=548.3 $[M+H]^+$. $^1$H NMR (300 MHz, $CD_3OD$, ppm) δ 9.07 (s, 1H), 8.55 (d, J=5.3 Hz, 1H), 8.41 (d, J=7.4 Hz, 2H), 7.68-7.54 (m, 3H), 7.45 (s, 1H), 5.05-4.95 (m, 1H), 4.18 (s, 3H), 3.13 (s, 3H), 3.05 (s, 3H), 2.96-2.80 (m, 2H), 2.70-2.56 (m, 2H), 2.38 (s, 3H), 2.26-2.10 (m, 2H).

Example 378: 5-[2-[5-([hexahydro-1H-furo[3,4-c]pyrrol-5-yl]carbonyl)-3-methoxypyridin-2-yl]furo[3,2-b]pyridin-7-yl]-2-[(oxan-4-yl)amino]benzonitrile (420)

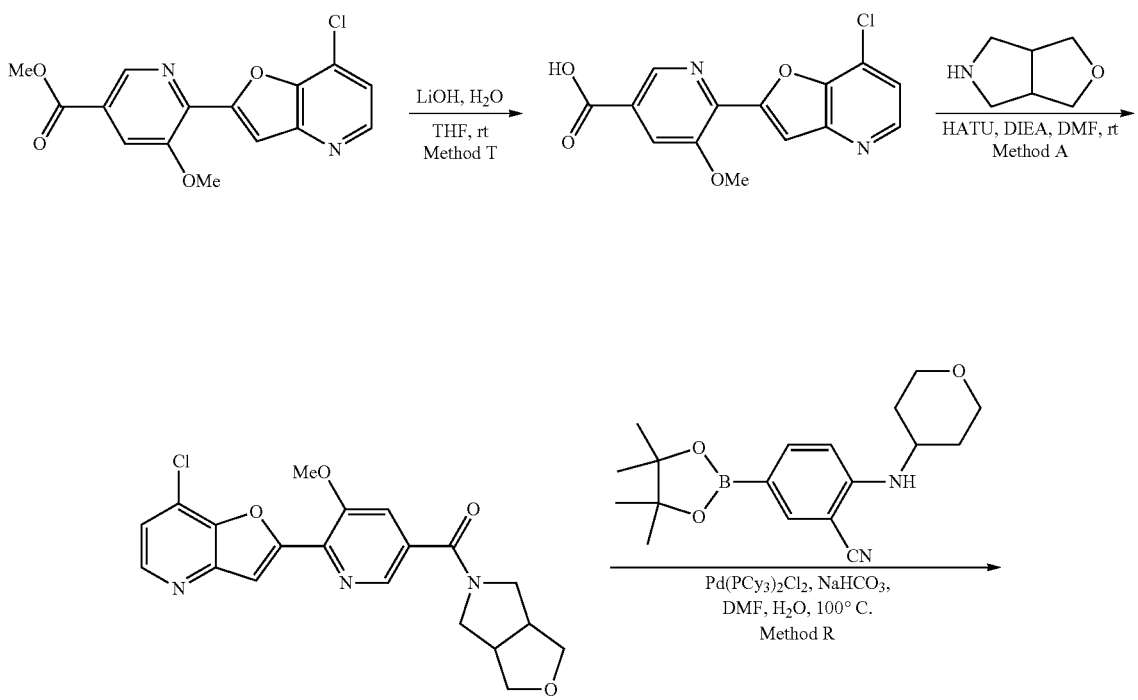

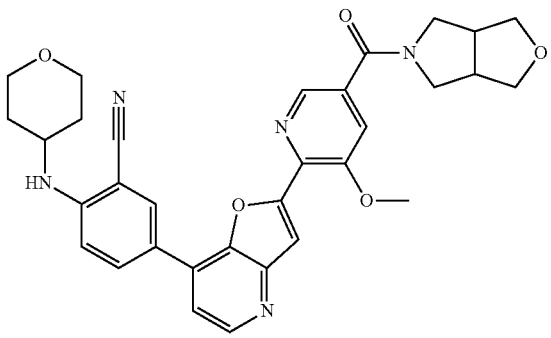

The title compound was prepared from methyl 6-(7-chlorofuro[3,2-b]pyridin-2-yl)-5-methoxynicotinate, hexahydro-1H-furo[3,4-c]pyrrole and 2-(tetrahydro-2H-pyran-4-ylamino)-5-(4,4,5,5-tetramethyl-1,3,2-dioxaborolan-2-yl)benzonitrile using Methods T, A, and R. The final product was purified by prep-HPLC under the following conditions: column, XBridge Prep C18 OBD Column, 150 mm 5 um; mobile phase, acetonitrile in water (with 10 mmol/L $NH_4HCO_3$), 30% to 55% gradient in 8 min; detector, UV 254 nm. 5-[2-[5-([hexahydro-1H-furo[3,4-c]pyrrol-5-yl]carbonyl)-3-methoxypyridin-2-yl]furo[3,2-b]pyridin-7-yl]-2-[(oxan-4-yl)amino]benzonitrile was obtained as a light yellow solid (35 mg, 23% for 2 steps). HPLC: 99.8% purity, RT=1.32 min. MS: m/z=566.3 [M+H]$^+$. $^1$H NMR (300 MHz, DMSO-$d_6$, ppm) δ 8.55 (d, J=5.1 Hz, 1H), 8.46 (d, J=1.6 Hz, 1H), 8.41-8.24 (m, 2H), 7.78 (d, J=2.1 Hz, 2H), 7.69 (d, J=5.2 Hz, 1H), 7.17 (d, J=9.2 Hz, 1H), 6.32 (d, J=8.1 Hz, 1H), 4.12 (s, 3H), 3.97-3.71 (m, 7H), 3.53-3.27 (m, 6H), 2.95 (s, 2H), 1.93-1.82 (m, 2H), 1.73-1.61 (m, 2H).

Example 379: 5-[2-[6-([hexahydro-1H-furo[3,4-c]pyrrol-5-yl]carbonyl)-4-methoxypyridin-3-yl]furo[3,2-b]pyridin-7-yl]-2-[(oxan-4-yl)amino]benzonitrile (421)

The title compound was prepared from methyl 5-(7-chlorofuro[3,2-b]pyridin-2-yl)-4-methoxypicolinate, hexahydro-1H-furo[3,4-c]pyrrole and 2-(tetrahydro-2H-pyran-4-ylamino)-5-(4,4,5,5-tetramethyl-1,3,2-dioxaborolan-2-yl)benzonitrile using Methods T, A, and R. The final product was purified by prep-HPLC under the following conditions: column, XBridge Prep C18 OBD Column, 150 mm 5 um; mobile phase, acetonitrile in water (with 10 mmol/L $NH_4HCO_3$), 30% to 50% gradient in 8 min; detector, UV 254 nm. 5-[2-[6-([hexahydro-1H-furo[3,4-c]pyrrol-5-yl]carbonyl)-4-methoxypyridin-3-yl]furo[3,2-b]pyridin-7-yl]-2-[(oxan-4-yl)amino]benzonitrile was obtained as a white solid (17 mg, 9.3% for 3 steps). HPLC: 99.8% purity, RT=1.00 min. MS: m/z=566.1 [M+H]$^+$. $^1$H NMR (300 MHz, DMSO-$d_6$, ppm) δ 9.07 (s, 1H), 8.53 (d, J=5.2 Hz, 1H), 8.36-8.26 (m, 2H), 7.67 (d, J=5.0 Hz, 2H), 7.57 (s, 1H), 7.20 (d, J=9.7 Hz, 1H), 6.31 (d, J=8.1 Hz, 1H), 4.16 (s, 3H), 3.97-3.69 (m, 7H), 3.66-3.38 (m, 6H), 2.96 (s, 2H), 1.89 (d, J=11.2 Hz, 2H), 1.74-1.60 (m, 2H).

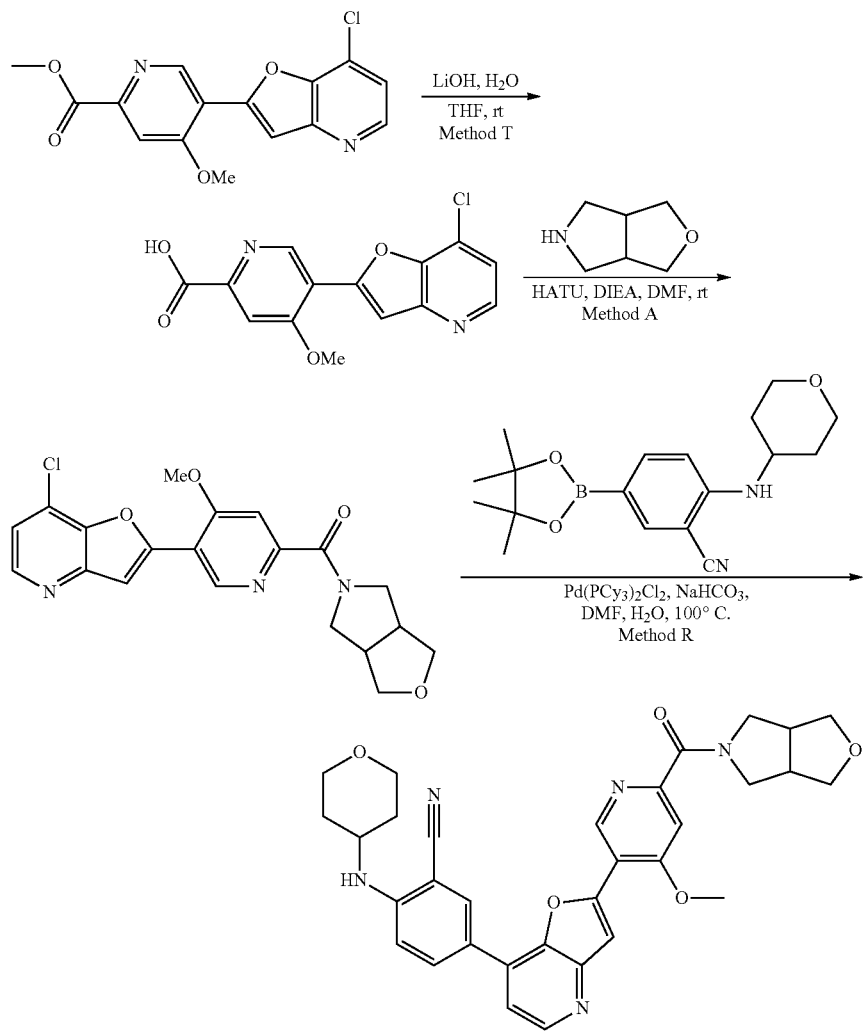

Example 380: 6-(7-[3-cyano-4-[(oxan-4-yl)amino]
phenyl]furo[3,2-b]pyridin-2-yl)-N-[4-(dimethyl-
amino)-2-methylbutan-2-yl]-5-methoxypyridine-3-
carboxamide (422)

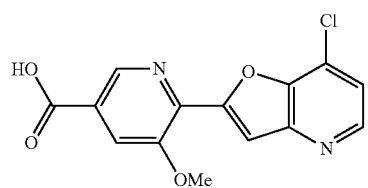 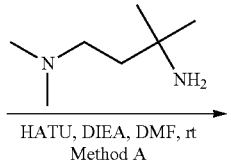

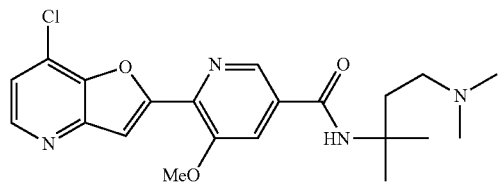 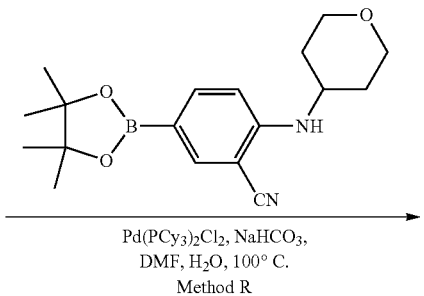

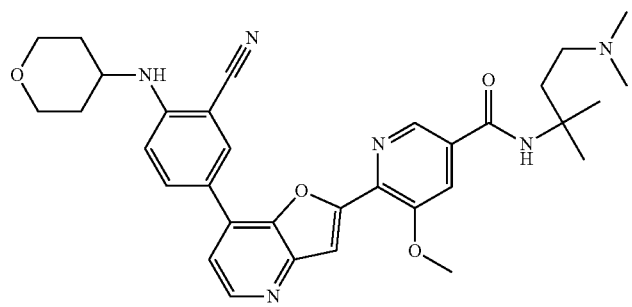

The title compound was prepared from 6-(7-chlorofuro
[3,2-b]pyridin-2-yl)-5-methoxynicotinic acid, N1,N1,3-
trimethylbutane-1,3-diamine and 2-(tetrahydro-2H-pyran-4-
ylamino)-5-(4,4,5,5-tetramethyl-1,3,2-dioxaborolan-2-yl)
benzonitrile using Methods A and R. The final product was
purified by prep-HPLC under the following conditions:
column, XBridge Prep C18 OBD Column, 150 mm 5 um;
mobile phase, acetonitrile in water (with 10 mmol/L
NH$_4$HCO$_3$), 35% to 55% gradient in 8 min; detector, UV
254 nm. 6-(7-[3-cyano-4-[(oxan-4-yl)amino]phenyl]furo[3,
2-b]pyridin-2-yl)-N-[4-(dimethylamino)-2-methylbutan-2-
yl]-5-methoxypyridine-3-carboxamide was obtained as a
light yellow solid (40 mg, 6.7% for 2 steps). HPLC: 98.1%
purity, RT=1.42 min. MS: m/z=583.3 [M+H]$^+$. $^1$H NMR
(300 MHz, CD$_3$OD, ppm) δ 8.55 (d, J=1.7 Hz, 1H), 8.36 (d,
J=5.2 Hz, 1H), 8.25 (d, 0.1=2.3 Hz, 1H), 8.15 (dd, J=9.0, 2.3
Hz, 1H), 7.82 (d, J=1.7 Hz, 1H), 7.60 (s, 1H), 7.45 (d, J=5.2
Hz, 1H), 6.95 (d, J=9.1 Hz, 1H), 4.10 (s, 3H), 3.99 (dd,
J=11.8, 4.1 Hz, 2H), 3.74 (tt, J=10.8, 4.1 Hz, 1H), 3.61-2.49
(m, 2H), 2.49 (t, J=7.3 Hz, 2H), 2.29 (s, 6H), 2.06-1.92 (m,
5H), 1.74-1.54 (m, 2H), 1.49 (s, 6H).

Example 381: 5-(7-[3-cyano-4-[(oxan-4-yl)amino]
phenyl]furo[3,2-b]pyridin-2-yl)-N-[4-(dimethyl-
amino)-2-methylbutan-2-yl]-4-methoxypyridine-2-
carboxamide (423)

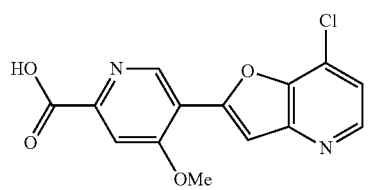 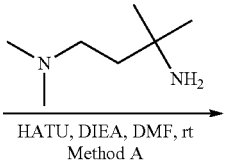

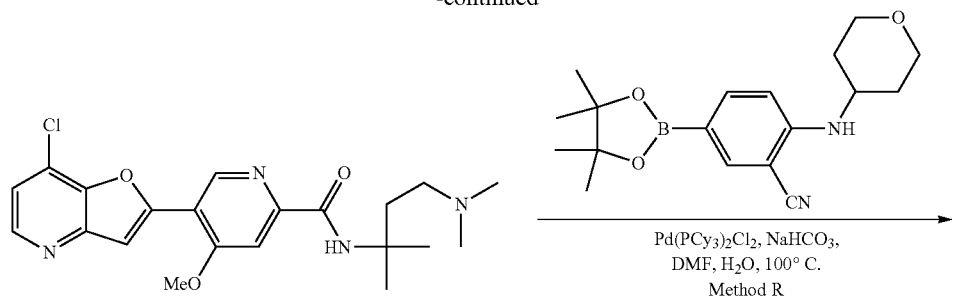

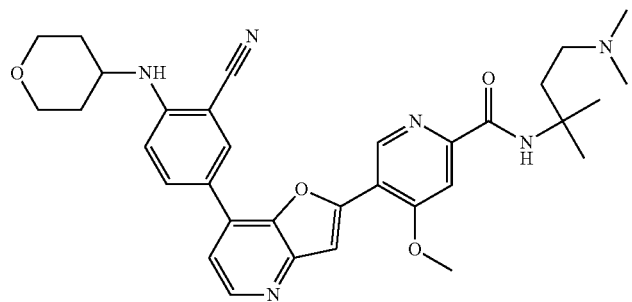

The title compound was prepared from 5-(7-chlorofuro[3,2-b]pyridin-2-yl)-4-methoxypicolinic acid, N1,N1,3-trimethylbutane-1,3-diamine and 2-(tetrahydro-2H-pyran-4-ylamino)-5-(4,4,5,5-tetramethyl-1,3,2-dioxaborolan-2-yl)benzonitrile using Methods A and R. The final product was purified by prep-HPLC under the following conditions: column, XBridge Prep C18 OBD Column, 150 mm 5 um; mobile phase, acetonitrile in water (with 10 mmol/L NH$_4$HCO$_3$), 35% to 55% gradient in 8 min; detector, UV 254 nm. 5-(7-[3-cyano-4-[(oxan-4-yl)amino]phenyl]furo[3,2-b]pyridin-2-yl)-N-[4-(dimethylamino)-2-methylbutan-2-yl]-4-methoxypyridine-2-carboxamide was obtained as a light yellow solid (40 mg, 12% for 2 steps). HPLC: 96.2% purity, RT=1.25 min. MS: m/z=583.2 [M+H]$^+$. $^1$H NMR (300 MHz, CD$_3$OD, ppm) δ 8.76 (s, 1H), 8.27 (d, J=5.2 Hz, 1H), 8.06-7.93 (m, 2H), 7.65 (s, 1H), 7.36-7.28 (m, 2H), 6.96 (d, J=9.0 Hz, 1H), 4.14-3.94 (m, 5H), 3.80-3.66 (m, 1H), 3.65-3.49 (m, 2H), 2.43 (dd, J=9.6, 6.1 Hz, 2H), 2.26 (s, 6H), 2.09-1.95 (m, 4H), 1.75-1.55 (m, 2H), 1.48 (s, 6H).

Example 382: 5-(7-[3-cyano-4-[(1-methylazetidin-3-yl)oxy]phenyl]furo[3,2-b]pyridin-2-yl)-4-methoxy-N,N-dimethylpyridine-2-carboxamide (424)

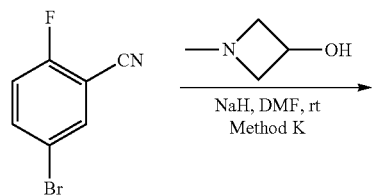

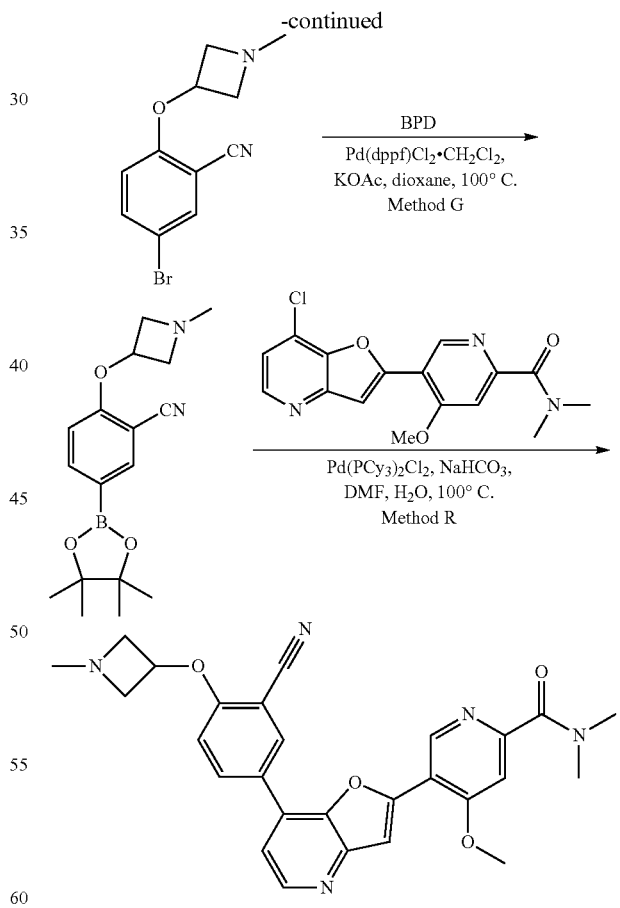

The title compound was prepared from 5-bromo-2-fluorobenzonitrile, 1-methylazetidin-3-ol, 4,4,5,5-tetramethyl-2-(tetramethyl-1,3,2-dioxaborolan-2-yl)-1,3,2-dioxaborolane and 5-(7-chlorofuro[3,2-b]pyridin-2-yl)-4-methoxy-N,N-dimethylpicolinamide using Methods K, G and R. The final product was purified by prep-HPLC under the following conditions: column, XBridge Prep C18 OBD Column, 150 mm 5 um; mobile phase, acetonitrile in water (with 0.05% NH₃H₂O), 28% to 48° % gradient in 8 min; detector, UV 254 nm. 5-(7-[3-cyano-4-[(1-methylazetidin-3-yl)oxy]phenyl]furo[3,2-b]pyridin-2-yl)-4-methoxy-N,N-dimethyl-pyridine-2-carboxamide was obtained as a light yellow solid (20 mg, 17% for 3 steps). HPLC: 99.1% purity, RT=1.15 min. MS: m/z=506.3 [M+H]⁺. ¹H NMR (300 MHz, DMSO-d₆, ppm) δ 9.08 (s, 1H), 8.65-8.44 (m, 3H), 7.77-7.65 (m, 2H), 7.45 (s, 1H), 7.32 (d, J=8.9 Hz, 1H), 5.10-5.00 (m, 1H), 4.15 (s, 3H), 3.82 (dd, J=8.4, 6.0 Hz, 2H), 3.17-2.96 (m, 8H), 2.33 (s, 3H).

Example 383: 6-(7-[3-cyano-4-[(1-methylazetidin-3-yl)oxy]phenyl]furo[3,2-b]pyridin-2-yl)-5-methoxy-N,N-dimethylpyridine-3-carboxamide (425)

Example 384: 6-(7-[3-cyano-4-[(1-methylpyrrolidin-3-yl)oxy]phenyl]furo[3,2-b]pyridin-2-yl)-5-methoxy-N,N-dimethylpyridine-3-carboxamide (426)

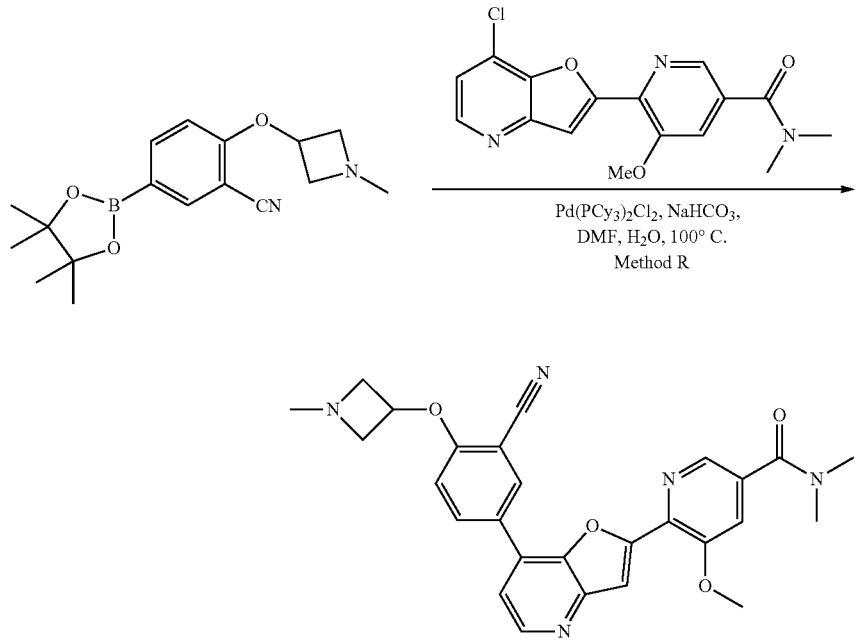

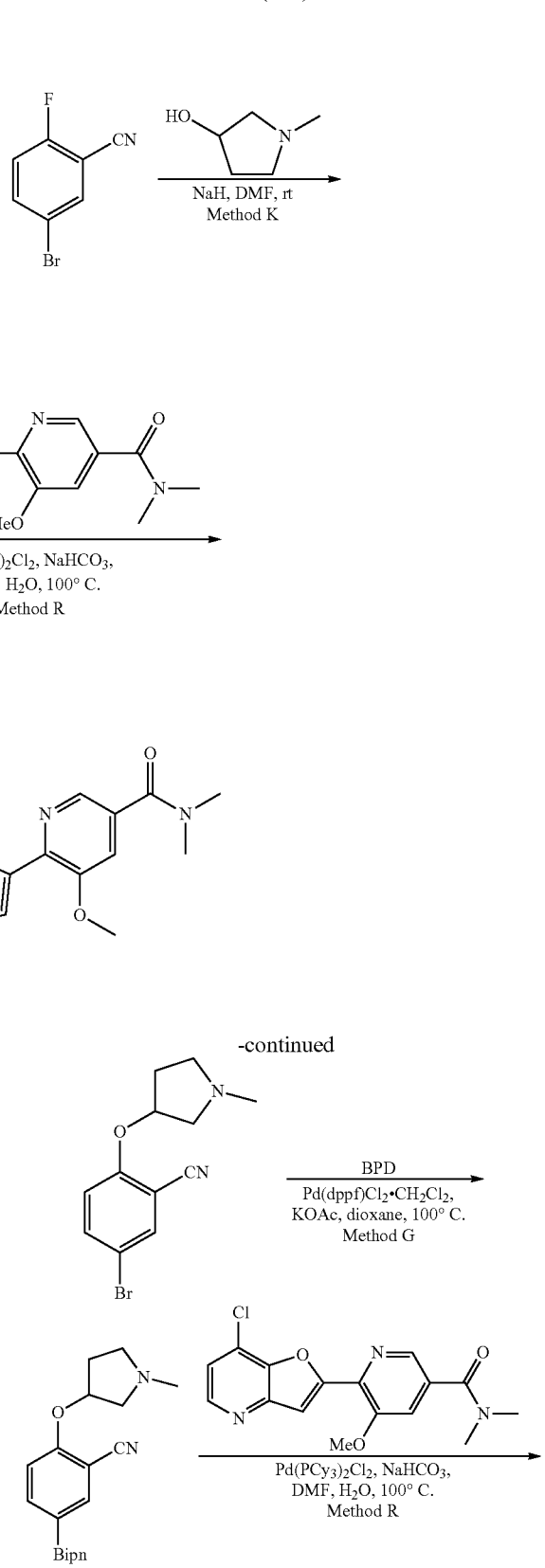

The title compound was prepared from 2-(1-methylazetidin-3-yloxy)-5-(4,4,5,5-tetramethyl-1,3,2-dioxaborolan-2-yl)benzonitrile and 6-(7-chlorofuro[3,2-b]pyridin-2-yl)-5-methoxy-N,N-dimethylnicotinamide using Method R. The final product was purified by prep-HPLC under the following conditions: column, XBridge Prep C18 OBD Column, 150 mm 5 um; mobile phase, acetonitrile in water (with 0.05% NH₃H₂O), 25% to 55% gradient in 8 min; detector, UV 254 nm. 6-(7-[3-cyano-4-[(1-methylazetidin-3-yl)oxy]phenyl]furo[3,2-b]pyridin-2-yl)-5-methoxy-N,N-dimethyl-pyridine-3-carboxamide was obtained as a yellow solid (20 mg, 15%). HPLC: 99.2% purity, RT=0.82 min. MS: m/z=484.2 [M+H]⁺. ¹H NMR (300 MHz, DMSO-d₆, ppm) δ 8.66 (d, J=5.0 Hz, 1H), 8.58 (d, J=2.3 Hz, 1H), 8.53-8.39 (m, 2H), 7.89-7.74 (m, 3H), 7.35 (d, J=8.9 Hz, 1H), 5.16-4.96 (m, 1H), 4.15 (s, 3H), 3.85 (t, J=6.1 Hz, 2H), 3.20-3.00 (m, 8H), 2.36 (s, 3H).

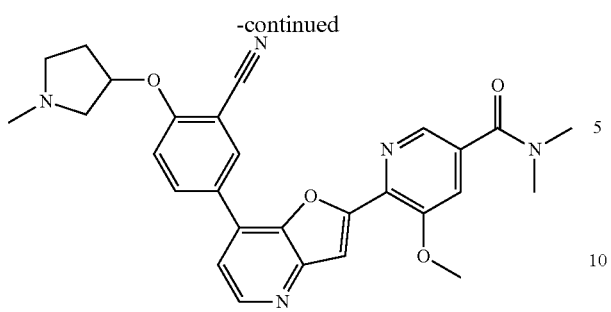

The title compound was prepared from 5-bromo-2-fluorobenzonitrile, 1-methylpyrrolidin-3-ol, 4,4,5,5-tetramethyl-2-(tetramethyl-1,3,2-dioxaborolan-2-yl)-1,3,2-dioxaborolane and 6-(7-chlorofuro[3,2-b]pyridin-2-yl)-5-methoxy-N,N-dimethylnicotinamide using Methods K, G and R. The final product was purified by prep-HPLC under the following conditions: column, XBridge Prep C18 OBD Column, 150 mm 5 um; mobile phase, acetonitrile in water (with 0.05° % $NH_3H_2O$), 25% to 55° % gradient in 8 min; detector, UV 254 nm. 6-(7-[3-cyano-4-[(1-methylpyrrolidin-3-yl)oxy]phenyl]furo[3,2-b]pyridin-2-yl)-5-methoxy-N,N-dimethylpyridine-3-carboxamide was obtained as a yellow solid (39 mg, 25% for 3 steps). HPLC: 97.0% purity, RT=1.24 min. MS: m/z=498.2 $[M+H]^+$. $^1$H NMR (300 MHz, DMSO-$d_6$, ppm) δ 8.60 (d, J=5.0 Hz, 1H), 8.55-8.33 (m, 3H), 7.83-7.69 (m, 3H), 7.45 (d, J=8.9 Hz, 1H), 5.20-5.10 (m, 1H), 4.09 (s, 3H), 3.02 (s, 3H), 2.98 (s, 3H), 2.89-2.67 (m, 3H), 2.47-2.25 (m, 5H), 1.92-1.78 (m, 1H).

Example 385: 6-(7-(3-cyano-4-(1-isopropylpyrrolidin-3-yloxy)phenyl)furo[3,2-b]pyridin-2-yl)-5-methoxy-N,N-dimethylnicotinamide (427)

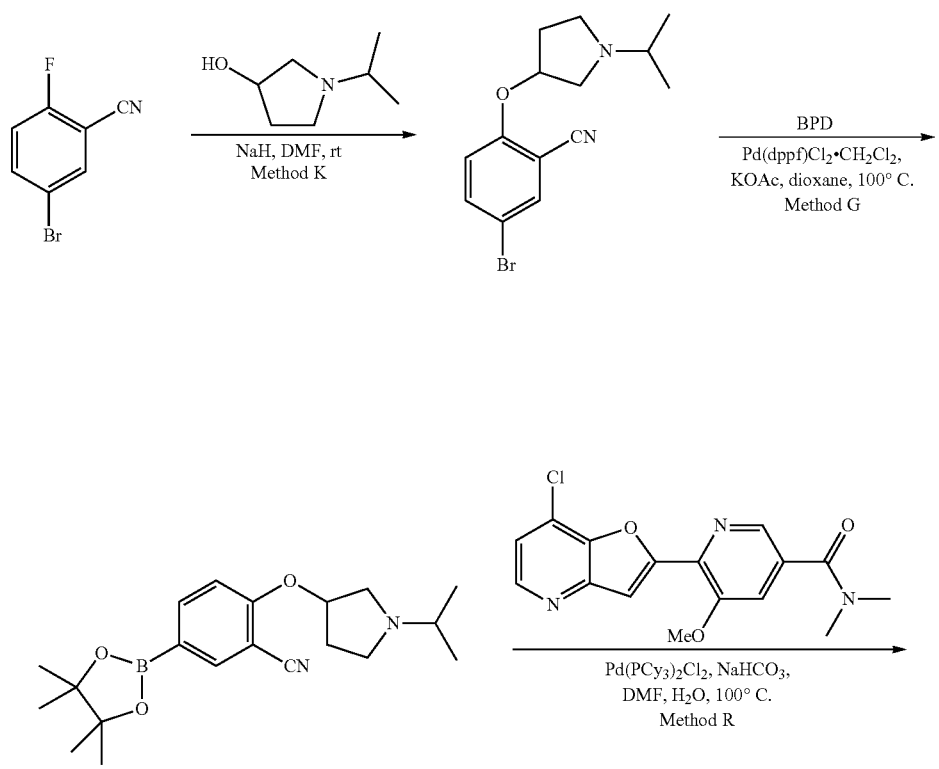

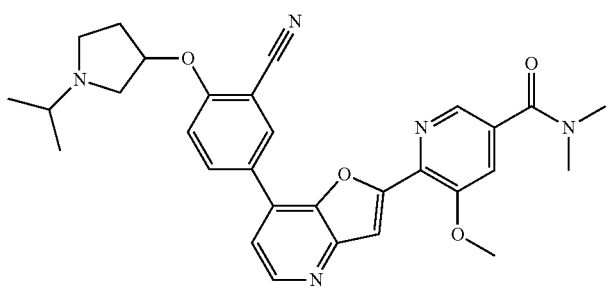

The title compound was prepared from 5-bromo-2-fluorobenzonitrile, 1-isopropylpyrrolidin-3-ol, 4,4,5,5-tetramethyl-2-(tetramethyl-1,3,2-dioxaborolan-2-yl)-1,3,2-dioxaborolane and 6-(7-chlorofuro[3,2-b]pyridin-2-yl)-5-methoxy-N,N-dimethylnicotinamide using Methods K, G and R. The final product was purified by prep-HPLC under the following conditions: column, XBridge Prep C18 OBD Column, 150 mm 5 um; mobile phase, acetonitrile in water (with 0.05% $NH_3H_2O$), 30% to 55% gradient in 8 min; detector, UV 254 nm. 6-[7-(3-cyano-4-[[1-(propan-2-yl)pyrrolidin-3-yl]oxy]phenyl)furo[3,2-b]pyridin-2-yl]-5-methoxy-N,N-dimethylpyridine-3-carboxamide was obtained as a yellow solid (40 mg, 12% for 3 steps). HPLC: 99.2% purity, RT=0.87 min. MS: m/z=526.3 [M+H]$^+$. $^1$H NMR (300 MHz, $CD_3OD$, ppm) δ 8.56-8.32 (m, 4H), 7.73 (dd, J=10.3, 1.2 Hz, 1H), 7.61 (dd, J=5.2, 2.8 Hz, 1H), 7.30 (d, J=8.8 Hz, 1H), 5.17-5.07 (s, 1H), 4.13 (s, 3H), 3.21-3.04 (m, 7H), 3.03-2.88 (m, 2H), 2.75-2.61 (m, 1H), 2.60-2.34 (m, 2H), 2.16-2.02 (m, 1H), 1.14 (d, J=6.3 Hz, 6H).

Example 386: 5-[7-(3-cyano-4-[[1-(propan-2-yl)pyrrolidin-3-yl]oxy]phenyl)furo[3,2-b]pyridin-2-yl]-4-methoxy-N,N-dimethylpyridine-2-carboxamide (428)

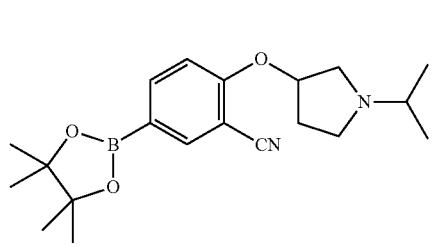
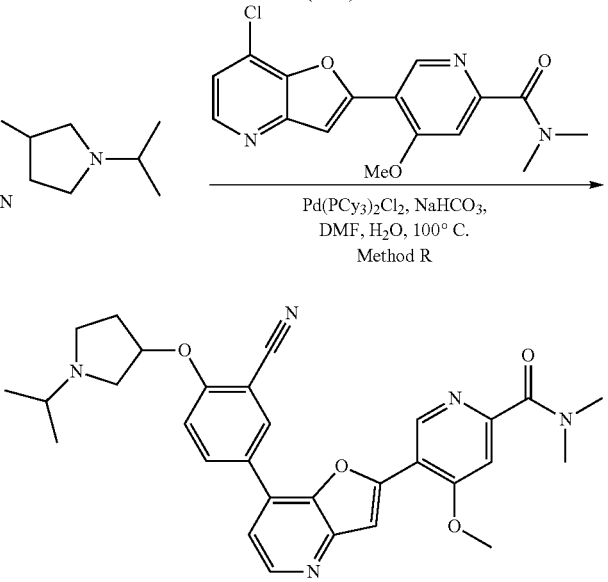

The title compound was prepared from 2-(1-isopropylpyrrolidin-3-yloxy)-5-(4,4,5,5-tetramethyl-1,3,2-dioxaborolan-2-yl)benzonitrile and 5-(7-chlorofuro[3,2-b]pyridin-2-yl)-4-methoxy-N,N-dimethylpicolinamide using Method R. The final product was purified by prep-HPLC under the following conditions: column, XBridge Prep C18 OBD Column, 150 mm 5 um; mobile phase, acetonitrile in water (with 0.05% $NH_3H_2O$), 25% to 55% gradient in 8 min; detector, UV 254 nm. 5-[7-(3-cyano-4-[[1-(propan-2-yl)pyrrolidin-3-yl]oxy]phenyl)furo[3,2-b]pyridin-2-yl]-4-methoxy-N,N-dimethylpyridine-2-carboxamide was obtained as a yellow solid (30 mg, 29%). HPLC: 96.8% purity, RT=0.94 min. MS: m/z=526.3 [M+H]$^+$. $^1$H NMR (300 MHz, $CD_3OD$, ppm) δ 9.05 (s, 1H), 8.56 (d, J=5.3 Hz, 1H), 8.45 (h, J=2.4 Hz, 2H), 7.66 (d, J=5.0 Hz, 2H), 7.55-7.39 (m, 2H), 5.49 (s, 1H), 4.19 (s, 3H), 4.14-3.34 (m, 5H), 3.14 (s, 3H), 3.05 (s, 3H), 2.90-2.30 (m, 2H), 1.50-1.36 (m, 6H).

Example 387: 5-[7-[3-cyano-4-(pyrrolidin-3-yloxy)phenyl]furo[3,2-b]pyridin-2-yl]-4-methoxy-N,N-dimethylpyridine-2-carboxamide (429)

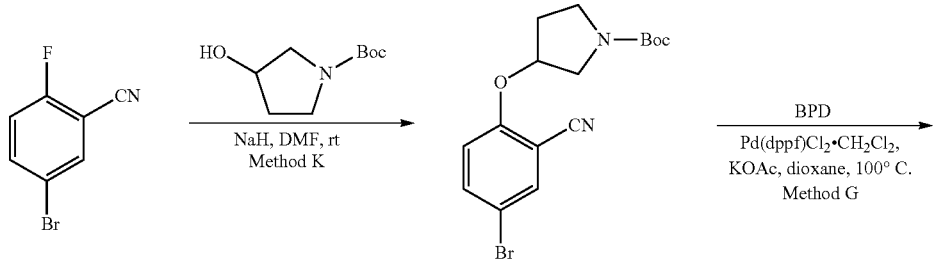

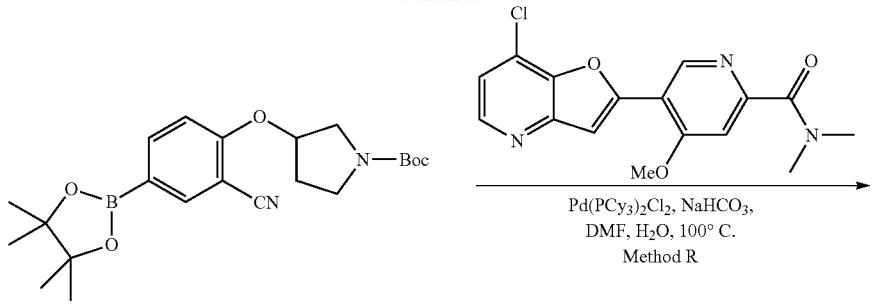

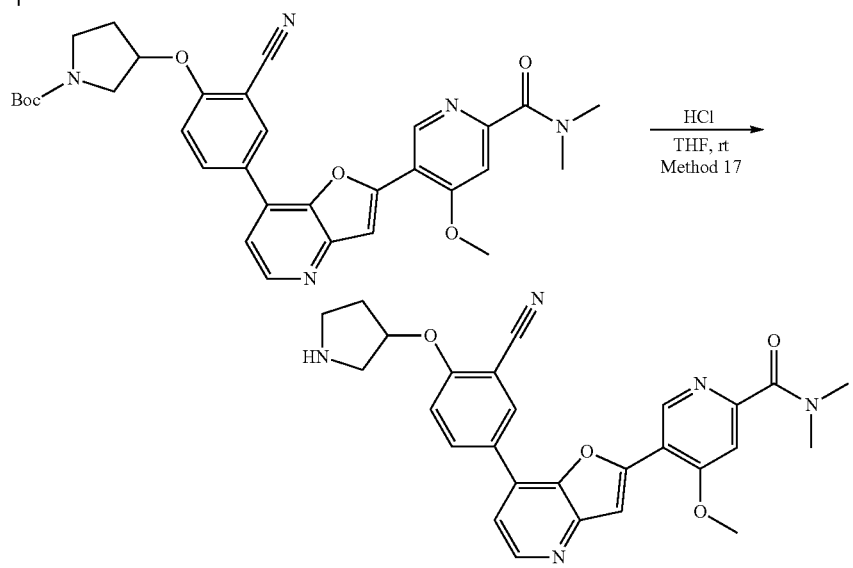

The title compound was prepared from 5-bromo-2-fluorobenzonitrile, tert-butyl 3-hydroxypyrrolidine-1-carboxylate, 4,4,5,5-tetramethyl-2-(tetramethyl-1,3,2-dioxaborolan-2-yl)-1,3,2-dioxaborolane and 5-(7-chlorofuro[3,2-b]pyridin-2-yl)-4-methoxy-N,N-dimethylpicolinamide using Methods K, G, R and 17. The final product was purified by prep-HPLC under the following conditions: column, XBridge Prep C18 OBD Column, 150 mm 5 um; mobile phase, acetonitrile in water (with 0.05% $NH_3H_2O$), 25% to 55% gradient in 8 min; detector, UV 254 nm. 5-[7-[3-cyano-4-(pyrrolidin-3-yloxy)phenyl]furo[3,2-b]pyridin-2-yl]-4-methoxy-N,N-dimethylpyridine-2-carboxamide was obtained as a yellow solid (18 mg, 6% for 4 steps). HPLC: 97.4% purity, RT=1.61 min. MS: m/z=484.2 $[M+H]^+$. $^1H$ NMR (300 MHz, DMSO-$d_6$, ppm) δ 9.08 (s, 1H), 8.60 (d, J=5.1 Hz, 1H), 8.51 (d, J=7.2 Hz, 2H), 7.78-7.64 (m, 2H), 7.62-7.48 (m, 1H), 7.45 (s, 1H), 5.35-5.10 (m, 1H), 4.15 (s, 3H), 3.70-3.10 (m, 3H), 3.25-2.70 (m, 8H), 2.30-2.09 (m, 1H), 1.95-1.75 (m, 1H).

Example 388: 5-(7-[3-cyano-4-[(1-methylpyrrolidin-3-yl)oxy]phenyl]furo[3,2-b]pyridin-2-yl)-4-methoxy-N,N-dimethylpyridine-2-carboxamide (430)

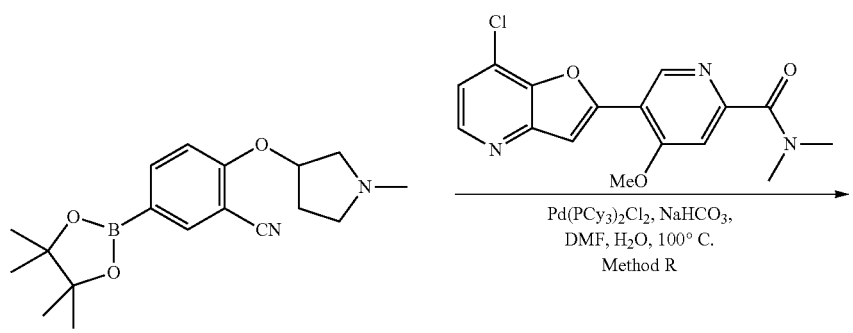

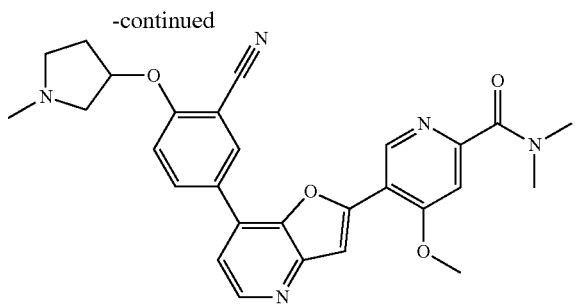

The title compound was prepared from 2-(1-methylpyrrolidin-3-yloxy)-5-(4,4,5,5-tetramethyl-1,3,2-dioxaborolan-2-yl)benzonitrile and 5-(7-chlorofuro[3,2-b]pyridin-2-yl)-4-methoxy-N,N-dimethylpicolinamide using Method R. The product was purified by prep-HPLC under the following conditions: column, XBridge Prep C18 OBD Column, 150 mm 5 um; mobile phase, acetonitrile in water (with 0.05% NH$_3$H$_2$O), 25% to 55% gradient in 8 min; detector, UV 254 nm. 5-(7-[3-cyano-4-[(1-methylpyrrolidin-3-yl)oxy]phenyl]furo[3,2-b]pyridin-2-yl)-4-methoxy-N,N-dimethylpyridine-2-carboxamide was obtained as a yellow solid (40 mg, 37%). HPLC: 95.5% purity, RT=1.56 min. MS: m/z=498.2 [M+H]$^+$. $^1$H NMR (300 MHz, DMSO-d$_6$, ppm) δ 9.05 (s, 1H), 8.58 (d, J=5.1 Hz, 1H), 8.54-8.43 (m, 2H), 7.75-7.63 (m, 2H), 7.51-7.41 (m, 2H), 5.20-5.10 (m, 1H), 4.14 (s, 3H), 3.05 (s, 3H), 3.00 (s, 3H), 2.91-2.69 (m, 3H), 2.50-2.27 (m, 5H), 1.96-1.82 (m, 1H).

Example 389: 5-(7-[3-cyano-4-[(pyrrolidin-3-yl)amino]phenyl]furo[3,2-b]pyridin-2-yl)-4-methoxy-N,N-dimethylpyridine-2-carboxamide (431)

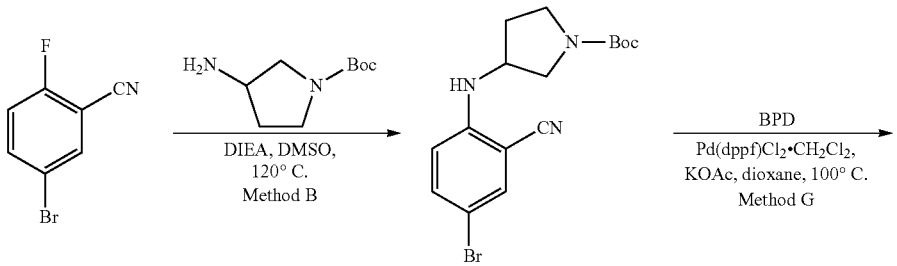

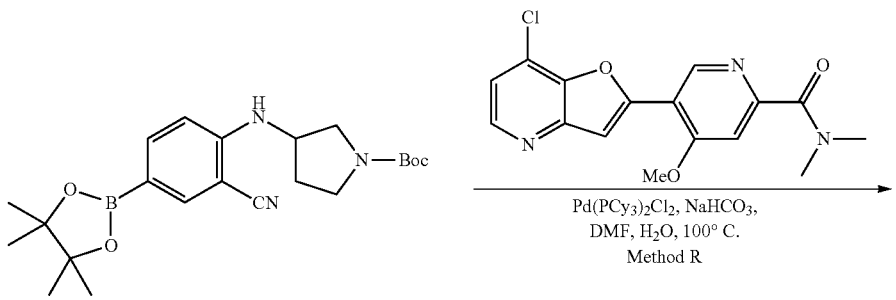

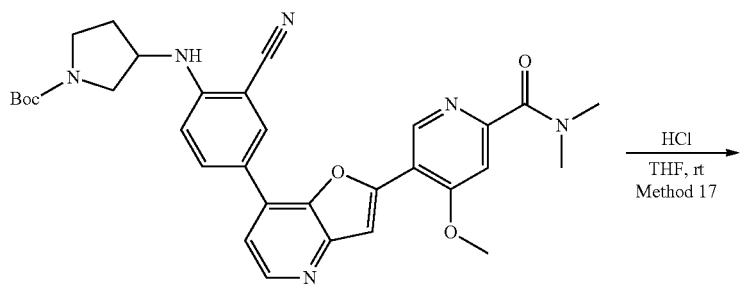

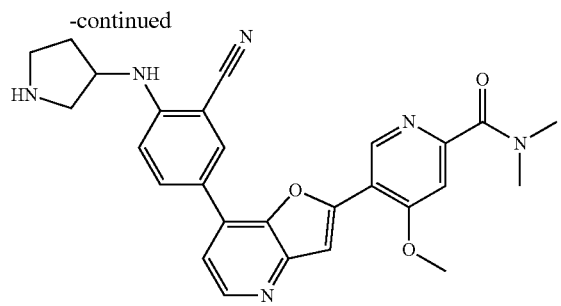

The title compound was prepared from 5-bromo-2-fluorobenzonitrile, tert-butyl 3-aminopyrrolidine-1-carboxylate, 4,4,5,5-tetramethyl-2-(tetramethyl-1,3,2-dioxaborolan-2-yl)-1,3,2-dioxaborolane and 5-(7-chlorofuro[3,2-b]pyridin-2-yl)-4-methoxy-N,N-dimethylpicolinamide using Methods B, G, R and 17. The final product was purified by prep-HPLC under the following conditions: Column, Atlantis Prep T$_3$ OBD 19×250 mm 10 um; mobile phase, acetonitrile in water (with 0.05% NH$_3$H$_2$O), 3% to 30% gradient in 10 min; detector, UV 254 nm. 5-(7-[3-cyano-4-[(pyrrolidin-3-yl)amino]phenyl]furo[3,2-b]pyridin-2-yl)-4-methoxy-N,N-dimethylpyridine-2-carboxamide was obtained as a yellow solid (20 mg, 11% for 4 steps). HPLC: 96.7% purity, RT=0.76 min. MS: m/z=483.3 [M+H]$^+$. $^1$H NMR (300 MHz, DMSO-d$_6$, ppm) δ 9.62-9.20 (m, 2H), 9.13 (s, 1H), 8.77-8.65 (m, 1H), 8.57-8.41 (m, 2H), 8.12-7.94 (m, 1H), 7.74 (s, 1H), 7.52 (s, 1H), 7.22 (d, J=9.1 Hz, 1H), 7.13-7.01 (m, 1H), 4.47 (d, J=8.5 Hz, 1H), 4.18 (s, 3H), 3.50-3.20 (m, 4H), 3.05 (s, 3H), 3.00 (s, 3H), 2.41-2.29 (m, 1H), 2.15-1.99 (m, 1H).

Example 390: 6-(7-[3-cyano-4-[(pyrrolidin-3-yl)amino]phenyl]furo[3,2-b]pyridin-2-yl)-5-methoxy-N,N-dimethylpyridine-3-carboxamide (432)

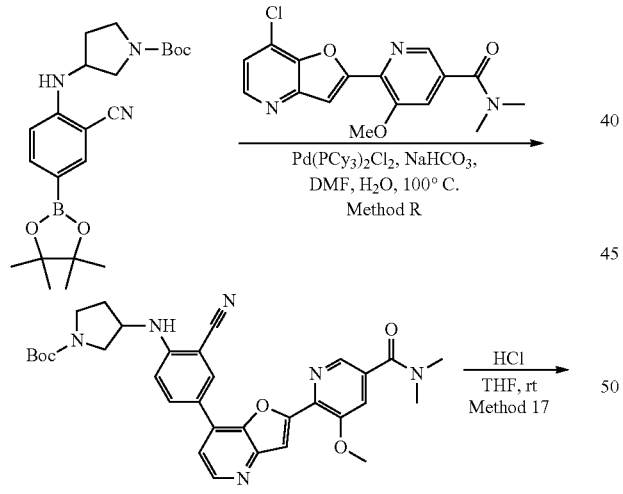

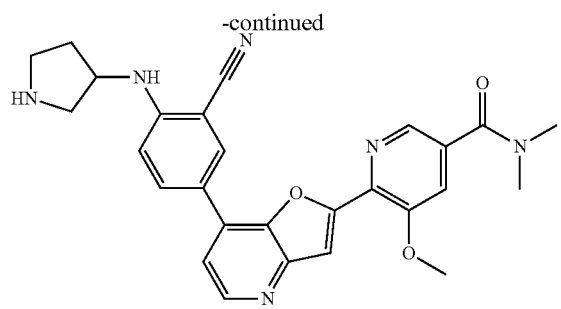

The title compound was prepared from tert-butyl 3-(2-cyano-4-(4,4,5,5-tetramethyl-1,3,2-dioxaborolan-2-yl)phenylamino)pyrrolidine-1-carboxylate and 6-(7-chlorofuro[3,2-b]pyridin-2-yl)-5-methoxy-N,N-dimethylnicotinamide using Methods R and 17. The final product was purified by prep-HPLC under the following conditions: column, XBridge Prep C18 OBD Column, 150 mm 5 um; mobile phase, acetonitrile in water (with 0.05% NH$_3$H$_2$O), 30% to 55% gradient in 10 min; detector, UV 254 nm. 6-(7-[3-cyano-4-[(pyrrolidin-3-yl)amino]phenyl]furo[3,2-b]pyridin-2-yl)-5-methoxy-N,N-dimethylpyridine-3-carboxamide was obtained as a yellow solid (37 mg, 50% for 2 steps). HPLC: 96.1% purity, RT=1.07 min. MS: m/z=483.2 [M+H]$^+$. $^1$H NMR (400 MHz, DMSO-d$_6$, ppm) δ 8.56 (d, J=5.1 Hz, 1H), 8.39 (dd, J=6.4, 1.9 Hz, 2H), 8.31 (d, J=8.7 Hz, 1H), 7.84-7.66 (m, 3H), 7.11 (dd, J=28.8, 9.1 Hz, 1 H), 6.38 (d, J=6.8 Hz, 1H), 4.11 (s, 4H), 3.50-3.35 (m, 1H), 3.10-2.90 (m, 7H), 2.83-2.66 (m, 2H), 2.35-210 (m, 2H), 1.75-1.60 (m, 1H).

Example 391: 6-(7-[3-cyano-4-[(1-methylpyrrolidin-3-yl)amino]phenyl]furo[3,2-b]pyridin-2-yl)-5-methoxy-N,N-dimethylpyridine-3-carboxamide (433)

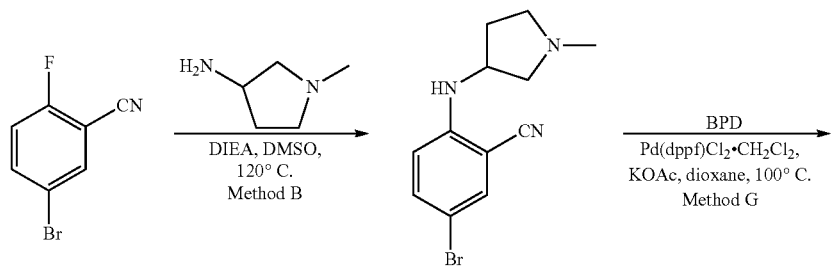

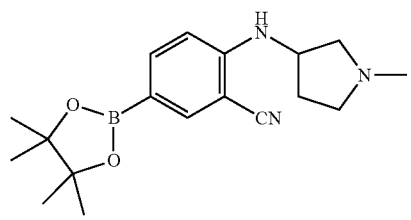
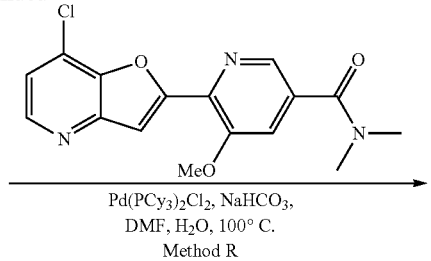

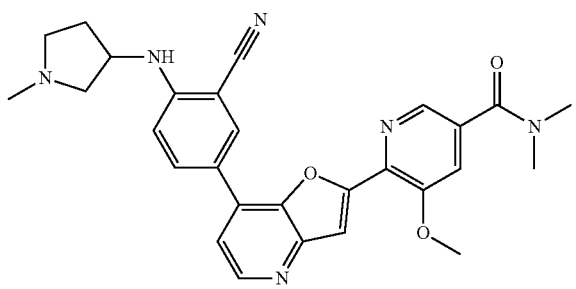

The title compound was prepared from 5-bromo-2-fluorobenzonitrile, 1-methylpyrrolidin-3-amine, 4,4,5,5-tetramethyl-2-(tetramethyl-1,3,2-dioxaborolan-2-yl)-1,3,2-dioxaborolane and 6-(7-chlorofuro[3,2-b]pyridin-2-yl)-5-methoxy-N,N-dimethylnicotinamide using Methods B, G and R. The final product was purified by prep-HPLC under the following conditions: column, XBridge Prep C18 OBD Column, 150 mm 5 um; mobile phase, acetonitrile in water (with 0.05% NH$_3$H$_2$), 28% to 58% gradient in 10 min; detector, UV 254 nm. 6-(7-[3-cyano-4-[(1-methylpyrrolidin-3-yl)amino]phenyl]furo[3,2-b]pyridin-2-yl)-5-methoxy-N,N-dimethylpyridine-3-carboxamide was obtained as a yellow solid (13 mg, 20% for 3 steps). HPLC: 98.7% purity, RT=1.43 min. MS: m/z=497.2 [M+H]$^+$. $^1$H NMR (300 MHz, DMSO-d$_6$, ppm) δ 8.55 (d, J=5.0 Hz, 1H), 8.43-8.23 (m, 3H), 7.79-7.63 (m, 3H), 7.05 (d, J=9.0 Hz, 1H), 6.32 (d, J=6.9 Hz, 1H), 4.27-4.07 (m, 4H), 3.05 (s, 3H), 3.01 (m, 3H), 2.83-2.61 (m, 2H), 2.48-2.20 (m, 6H), 1.86-1.69 (m, 1H).

Example 392: 5-(7-[3-cyano-4-[(1-methylpyrrolidin-3-yl)amino]phenyl]furo[3,2-b]pyridin-2-yl)-4-methoxy-N,N-dimethylpyridine-2-carboxamide (434)

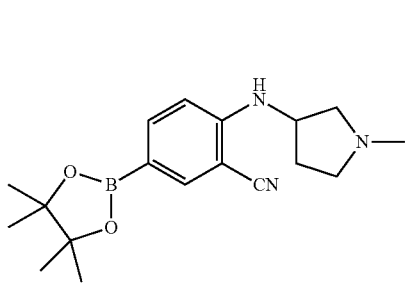
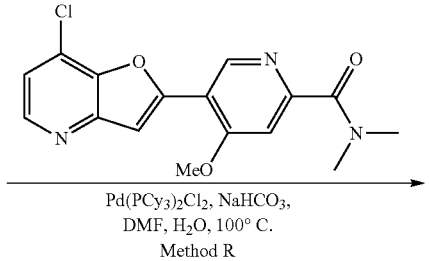

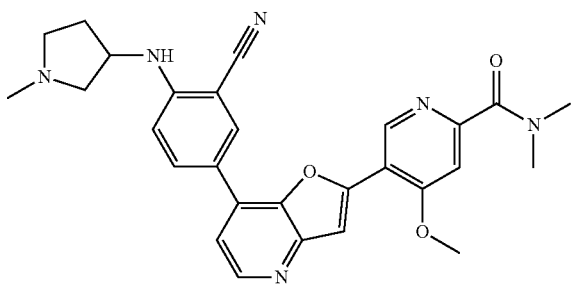

The title compound was prepared from 2-(1-methylpyrrolidin-3-ylamino)-5-(4,4,5,5-tetramethyl-1,3,2-dioxaborolan-2-yl)benzonitrile and 5-(7-chlorofuro[3,2-b]pyridin-2-yl)-4-methoxy-N,N-dimethylpicolinamide using Method R. The final product was purified by prep-HPLC under the following conditions: column, XBridge Prep C18 OBD Column, 150 mm 5 um; mobile phase, acetonitrile in water (with 0.05% $NH_3H_2O$), 28% to 48% gradient in 8 min; detector, UV 254 nm. 5-(7-[3-cyano-4-[(1-methylpyrrolidin-3-yl)amino]phenyl]furo[3,2-b]pyridin-2-yl)-4-methoxy-N,N-dimethylpyridine-2-carboxamide was obtained as a yellow solid (30 mg, 24%). HPLC: 99.5% purity, RT=1.44 min. MS: m/z=497.3 [M+H]$^+$. $^1$H NMR (300 MHz, DMSO-$d_6$, ppm) δ 9.03 (d, J=1.9 Hz, 1H), 8.51 (dd, J=4.9, 1.9 Hz, 1H), 8.34-8.22 (m, 2H), 7.70-7.58 (m, 2H), 7.44 (d, J=2.0 Hz, 1H), 7.06 (d, J=9.4 Hz, 1H), 6.35-6.26 (m, 1H), 4.27-4.10 (m, 4H), 3.05 (s, 3H), 3.01 (m, 3H), 2.85-2.63 (m, 2H), 2.49-2.22 (m, 6H), 1.79 (dd, J=12.1, 6.1 Hz, 1H).

Example 393: 5-[2-[3-methoxy-5-([6-oxa-3-azabicyclo[3.1.1]heptan-3-yl]carbonyl)pyridin-2-yl]furo[3,2-b]pyridin-7-yl]-2-(oxan-4-yloxy)benzonitrile (435)

The title compound was prepared from 6-(7-chlorofuro[3,2-b]pyridin-2-yl)-5-methoxynicotinic acid, 6-oxa-3-azabicyclo[3.1.1]heptanes and 2-(tetrahydro-2H-pyran-4-yloxy)-5-(4,4,5,5-tetramethyl-1,3,2-dioxaborolan-2-yl)benzonitrile using Methods A and R. The final product was purified by prep-HPLC under the following conditions: column, XBridge Prep C18 OBD Column, 150 mm 5 um; mobile phase, acetonitrile in water (with 0.05% $NH_3H_2O$), 28% to 48% gradient in 8 min; detector, UV 254 nm. 5-[2-[3-methoxy-5-([6-oxa-3-azabicyclo[3.1.1]heptan-3-yl]carbonyl)pyridin-2-yl]furo[3,2-b]pyridin-7-yl]-2-(oxan-4-yloxy)benzonitrile was obtained as a off-white solid (30 mg, 22%). HPLC: 99.8% purity, RT=1.30 min. MS: m/z=553.3 [M+H]$^+$. $^1$H NMR (300 MHz, DMSO-$d_6$, ppm) δ 8.63 (d, J=5.1 Hz, 1H), 8.58-8.42 (m, 3H), 7.89-7.72 (m, 3H), 7.67 (d, J=9.1 Hz, 1H), 5.05-4.95 (m, 1H), 4.75-4.65 (m, 1H), 4.55-4.45 (m, 1H), 4.13 (s, 3H), 4.05-3.79 (m, 4H), 3.70-3.50 (m, 4H), 3.16-3.04 (m, 1H), 2.07 (d, J=11.9 Hz, 2H), 1.92 (d, J=9.0 Hz, 1H), 1.80-1.64 (m, 2H).

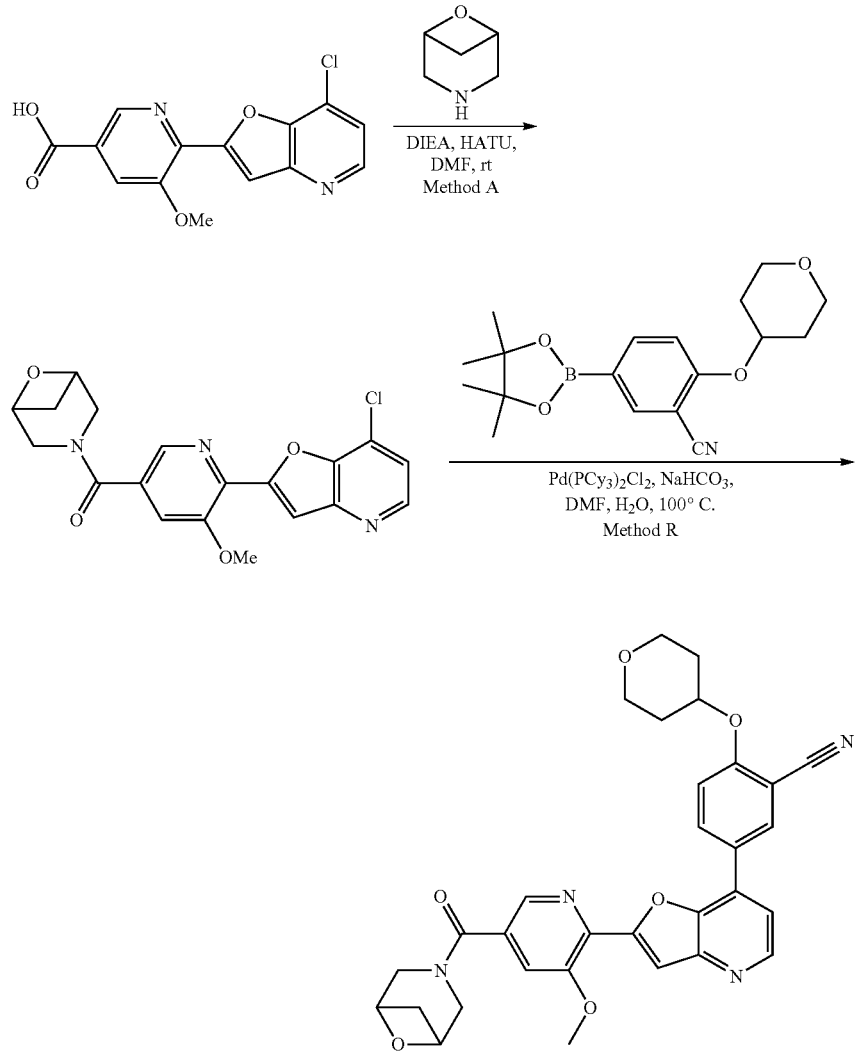

Example 394: 6-[7-[3-cyano-4-([3-oxabicyclo[3.1.0]
hexan-6-yl]amino)phenyl]furo[3,2-b]pyridin-2-yl]-5-
methoxy-N,N-dimethylpyridine-3-carboxamide
(436)

Example 395: 5-[7-[3-cyano-4-([3-oxabicyclo[3.1.0]
hexan-6-yl]amino)phenyl]furo[3,2-b]pyridin-2-yl]-4-
methoxy-N,N-dimethylpyridine-2-carboxamide
(437)

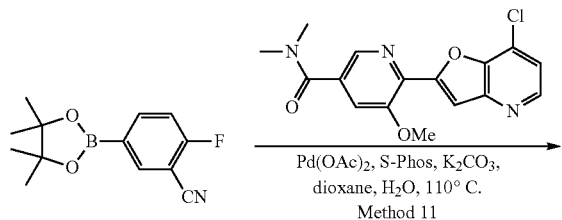
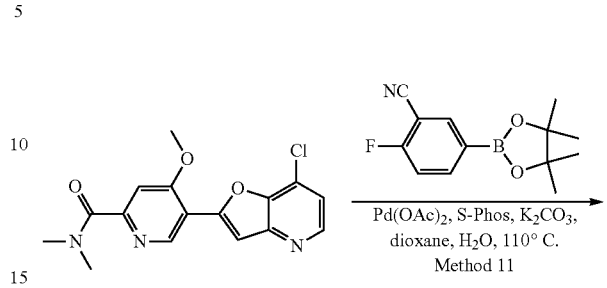

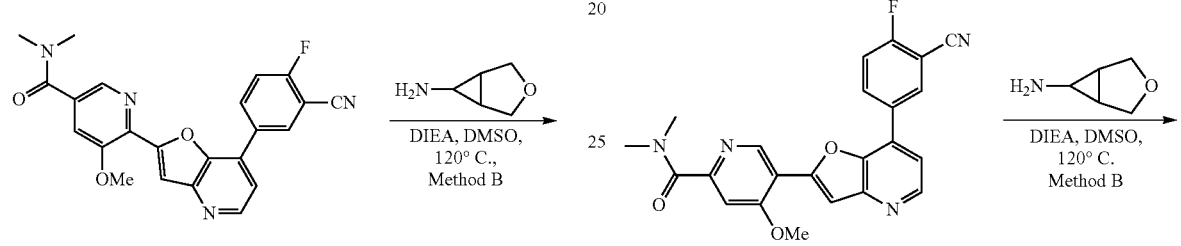

The title compound was prepared from 2-fluoro-5-(4,4,5,5-tetramethyl-1,3,2-dioxaborolan-2-yl)benzonitrile, 6-(7-chlorofuro[3,2-b]pyridin-2-yl)-5-methoxy-N,N-dimethylnicotinamide and 3-oxa-bicyclo[3.1.0]hexan-6-amine using Methods 11 and B. The final product was purified by prep-HPLC under the following conditions: column, XBridge Prep C18 OBD Column, 150 mm 5 um; mobile phase, acetonitrile in water (with 0.05% NH$_3$H$_2$O), 30% to 50% gradient in 8 min; detector, UV 254 nm. 6-[7-[3-cyano-4-([3-oxabicyclo[3.1.0]hexan-6-yl]amino)phenyl]furo[3,2-b]pyridin-2-yl]-5-methoxy-N,N-dimethylpyridine-3-carboxamide was obtained as a yellow solid (15 mg, 15% for 2 steps). HPLC: 98.6% purity, RT=2.63 min. MS: m/z=496.2 [M+H]$^+$. $^1$H NMR (300 MHz, CD$_3$OD, ppm) δ 8.51 (d, J=5.2 Hz, 1H), 8.44-8.32 (m, 3H), 7.82-7.72 (m, 2H), 7.63 (d, J=5.3 Hz, 1H), 7.20 (d, J=9.6 Hz, 1H), 4.20-4.06 (m, 5H), 3.81 (d, J=8.4 Hz, 2H), 3.17 (s, 3H), 3.11 (s, 3H), 2.42 (s, 1H), 1.99 (s, 2H).

The title compound was prepared from 2-fluoro-5-(4,4,5,5-tetramethyl-1,3,2-dioxaborolan-2-yl)benzonitrile, 6-(7-chlorofuro[3,2-b]pyridin-2-yl)-5-methoxy-N,N-dimethylnicotinamide and 3-oxa-bicyclo[3.1.0]hexan-6-amine using Methods 11 and B. The final product was purified by prep-HPLC under the following conditions: column, XBridge Prep C18 OBD Column, 150 mm 5 um: mobile phase, acetonitrile in water (with 0.05% NH$_3$H$_2$O), 20% to 55% gradient in 8 min; detector, UV 254 nm. 5-[7-[3-cyano-4-([3-oxabicyclo[3.1.0]hexan-6-yl]amino)phenyl]furo[3,2-b]pyridin-2-yl]-4-methoxy-N,N-dimethylpyridine-2-carboxamide was obtained as a off-white solid (14 mg, 11% for 2 steps). HPLC: 96.8% purity, RT=0.94 min. MS: m/z=496.0 [M+H]$^+$. $^1$H NMR (300 MHz, Chloroform-d, ppm) δ 9.16 (s, 1H), 8.58 (d, J=5.4 Hz, 1H), 8.25 (dd, J=9.0, 2.2 Hz, 1H), 8.09 (d, J=2.2 Hz, 1H), 7.74 (s, 1H), 7.41 (d, J=4.0 Hz, 2H), 7.15 (d, J=8.9 Hz, 1H), 5.19 (s, 1H), 4.20-4.10 (m, 5H), 3.87 (d, J=8.5 Hz, 2H), 3.19 (d, J=3.7 Hz, 6H), 2.54 (s, 1H), 1.97 (s, 2H).

Example 396: N-[1-azabicyclo[2.2.2]octan-3-yl]-6-[7-[3-cyano-4-(3-fluoropyrrolidin-1-yl)phenyl]furo[3,2-b]pyridin-2-yl]-5-methoxypyridine-3-carboxamide (438)

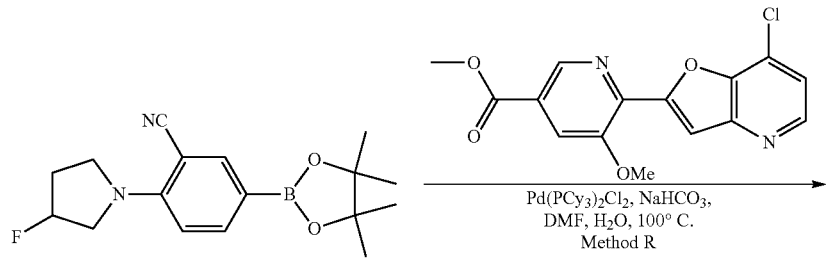

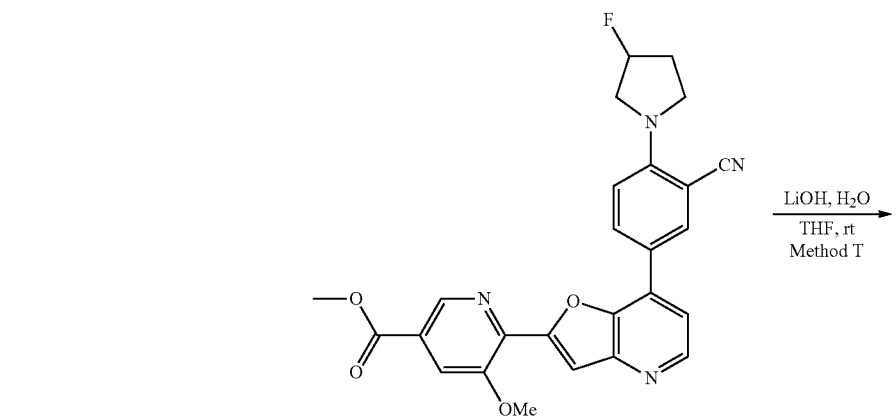

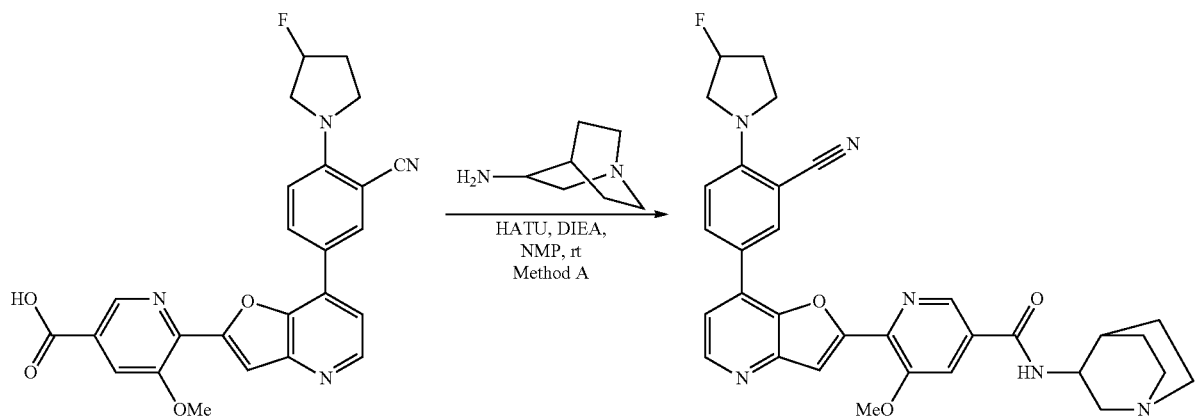

The title compound was prepared from 2-(3-fluoropyrrolidin-1-yl)-5-(4,4,5,5-tetramethyl-1,3,2-dioxaborolan-2-yl)benzonitrile, methyl 6-(7-chlorofuro[3,2-b]pyridin-2-yl)-5-methoxynicotinate and quinuclidin-3-amine using Methods R, T and A. The final product was purified by prep-HPLC under the following conditions: column, XBridge Prep C18 OBD Column, 150 mm 5 um; mobile phase, acetonitrile in water (with 0.05% $NH_3H_2O$), 25% to 55% gradient in 8 min; detector, UV 254 nm. N-[1-azabicyclo[2.2.2]octan-3-yl]-6-[7-[3-cyano-4-(3-fluoropyrrolidin-1-yl)phenyl]furo[3,2-b]pyridin-2-yl]-5-methoxypyridine-3-carboxamide was obtained as a yellow solid (25 mg, 3.7% for 3 steps). HPLC: 94.5% purity, RT=1.78 min. MS: m/z=567.2 [M+H]$^+$. $^1$H NMR (300 MHz, DMSO-$d_6$, ppm) δ 8.83 (d, J=1.6 Hz, 1H), 8.59 (dd, J=8.3, 5.8 Hz, 2H), 8.48 (d, J=2.3 Hz, 1H), 8.33 (dd, J=9.1, 2.4 Hz, 1H), 7.98 (d, J=1.6 Hz, 1H), 7.83 (s, 1H), 7.75 (d, l=5.1 Hz, 1H), 7.05 (d, J=9.2 Hz, 1H), 5.65-5.38 (m, 1H), 4.20-3.76 (m, 8H), 3.26-3.10 (m, 1H), 2.98-2.60 (m, 5H), 2.40-2.10 (m, 2H), 1.98-1.78 (m, 2H), 1.68-1.56 (m, 2H), 1.42-1.32 (m, 1H).

Example 397: N—(S)-1-Aza-bicyclo[2.20.2]oct-3-yl-6-{7-[3-cyano-4-((S)-3-fluoro-pyrrolidin-1-yl)-phenyl]-furo[3,2-b]pyridin-2-yl}-5-methoxy-nicotinamide (439)

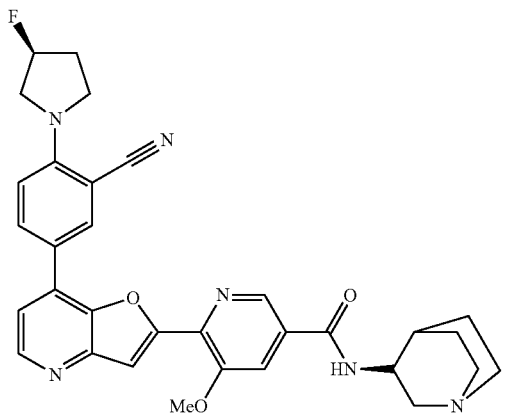

The title compound was separated from N-[1-azabicyclo[2.2.2]octan-3-yl]-6-[7-[3-cyano-4-(3-fluoropyrrolidin-1-yl)phenyl]furo[3,2-b]pyridin-2-yl]-5-methoxypyridine-3-carboxamide on a chiral prep-HPLC under the following conditions: column CHIRALPAK IC-3, 0.46×10 cm, 5 um; mobile phase, EtOH (0.1% DEA) in DCM, 70% isocratic in 15 min; detector, UV 254 nm. (35 mg, 10%, yellow solid) HPLC: 90.8% purity, RT=5.71 min. MS: m/z=567.3 [M+H]$^+$. $^1$H NMR (300 MHz, DMSO-d$_6$, ppm) δ 8.83 (d, J=1.6 Hz, 1H), 8.62-8.53 (m, 2H), 8.48 (d, J=2.3 Hz, 1H), 8.32 (dd, J=9.2, 2.4 Hz, 1H), 7.97 (d, J=1.7 Hz, 1H), 7.82 (s, 1H), 7.74 (d, J=5.2 Hz, 1H), 7.05 (d, J=9.2 Hz, 1H), 5.65-5.38 (m, 1H), 4.19-3.76 (m, 8H), 3.23-3.09 (m, 1H), 3.08-2.61 (m, 5H), 2.40-2.10 (m, 2H), 1.99-1.78 (m, 2H), 1.68-1.58 (m, 2H), 1.41-1.30 (m, 1H).

Example 398: N—(S)-1-Aza-bicyclo[2.20.2]oct-3-yl-6-{7-[3-cyano-4-((R)-3-fluoro-pyrrolidin-1-yl)-phenyl]-furo[3,2-b]pyridin-2-yl}-5-methoxy-nicotinamide (440)

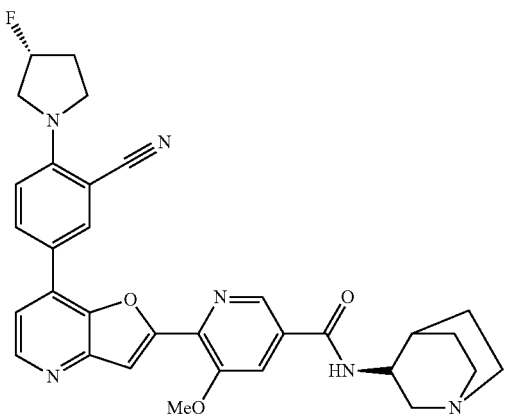

The title compound was separated from N-[1-azabicyclo[2.2.2]octan-3-yl]-6-[7-[3-cyano-4-(3-fluoropyrrolidin-1-yl)phenyl]furo[3,2-b]pyridin-2-yl]-5-methoxypyridine-3-carboxamide on a chiral prep-HPLC. (25 mg, 7%, yellow solid) HPLC: 90.4% purity, RT=5.69 min. MS: m/z=567.3 [M+H]$^+$. $^1$H NMR (300 MHz, DMSO-d$_6$, ppm) δ 8.83 (d, J=1.6 Hz, 1H), 8.62-8.53 (m, 2H), 8.48 (d, J=2.3 Hz, 1H), 8.33 (dd, J=9.2, 2.4 Hz, 1H), 7.97 (d, J=1.7 Hz, 1H), 7.83 (s, 1H), 7.74 (d, J=5.2 Hz, 1H), 7.05 (d, J=9.2 Hz, 1H), 5.65-5.38 (m, 1H), 4.19-3.76 (m, 8H), 3.24-3.10 (m, 1H), 3.08-2.61 (m, 5H), 2.40-2.10 (m, 2H), 1.95-1.75 (m, 2H), 1.68-1.58 (m, 2H), 1.41-1.28 (m, 1H).

Example 399: N—(R)-1-Aza-bicyclo[2.20.2]oct-3-yl-6-{7-[3-cyano-4-((S)-3-fluoro-pyrrolidin-1-yl)-phenyl]-furo[3,2-b]pyridin-2-yl}-5-methoxy-nicotinamide (441)

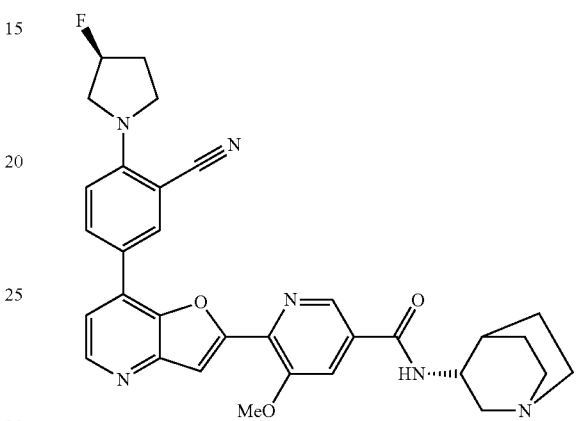

The title compound was separated from N-[1-azabicyclo[2.2.2]octan-3-yl]-6-[7-[3-cyano-4-(3-fluoropyrrolidin-1-yl)phenyl]furo[3,2-b]pyridin-2-yl]-5-methoxypyridine-3-carboxamide on a chiral prep-HPLC. (25 mg, 7%, yellow solid) HPLC: 95.7% purity, RT=5.70 min. MS: m/z=567.3 [M+H]$^+$. $^1$H NMR (300 MHz, DMSO-d$_6$, ppm) δδ 8.83 (d, J=1.6 Hz, 1H), 8.62-8.53 (m, 2H), 8.48 (d, J=2.3 Hz, 1H), 8.32 (dd, J=9.2, 2.4 Hz, 1H), 7.97 (d, J=1.7 Hz, 1H), 7.82 (s, 1H), 7.74 (d, J=5.2 Hz, 1H), 7.05 (d, J=9.2 Hz, 1H), 5.65-5.38 (m, 1H), 4.19-3.76 (m, 8H), 3.23-3.09 (m, 1H), 3.08-2.61 (m, 5H), 2.40-2.10 (m, 2H), 1.99-1.78 (m, 2H), 1.68-1.58 (m, 2H), 1.41-1.30 (m, 1H).

Example 400: N—(R)-1-Aza-bicyclo[2.20.2]oct-3-yl-6-{7-[3-cyano-4-((R)-3-fluoro-pyrrolidin-1-yl)-phenyl]-furo[3,2-b]pyridin-2-yl}-5-methoxy-nicotinamide (442)

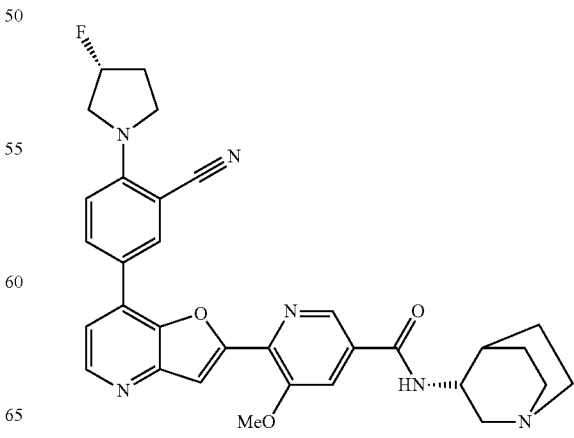

The title compound was separated from N-[1-azabicyclo[2.2.2]octan-3-yl]-6-[7-[3-cyano-4-(3-fluoropyrrolidin-1-yl)phenyl]furo[3,2-b]pyridin-2-yl]-5-methoxypyridine-3-carboxamide on a chiral prep-HPLC. (35 mg, 10%, yellow solid) HPLC: 96.5% purity, RT=6.60 min. MS: m/z=567.3 [M+H]$^+$. $^1$H NMR (300 MHz, DMSO-d$_6$, ppm) 58.83 (d, J=1.6 Hz, 1H), 8.62-8.53 (m, 2H), 8.48 (d, J=2.3 Hz, 1H), 8.33 (dd, J=9.2, 2.4 Hz, 1H), 7.97 (d, J=1.7 Hz, 1H), 7.83 (s, 1H), 7.74 (d. J=5.2 Hz, 1H), 7.05 (d, J=9.2 Hz, 1H), 5.65-5.38 (m, 1 H), 4.19-3.76 (m, 8H), 3.24-3.10 (m, 1H), 3.08-2.61 (m, 5H), 2.40-2.10 (m, 2H), 1.95-1.75 (m, 2H), 1.68-1.58 (m, 2H), 1.41-1.28 (m, 1H).

Example 401: N-[1-azabicyclo[2.2.2]octan-3-yl]-5-[7-[3-cyano-4-(3-fluoropyrrolidin-1-yl)phenyl]furo[3,2-b]pyridin-2-yl]-4-methoxypyridine-2-carboxamide (443)

The title compound was prepared from 2-(3-fluoropyrrolidin-1-yl)-5-(4,4,5,5-tetramethyl-1,3,2-dioxaborolan-2-yl)benzonitrile, methyl 5-(7-chlorofuro[3,2-b]pyridin-2-yl)-4-methoxypicolinate and quinuclidin-3-amine using Methods R, T and A. The final product was purified by prep-HPLC under the following conditions: column, XBridge Prep C18 OBD Column, 150 mm 5 um; mobile phase, acetonitrile in water (with 0.05% NH$_3$H$_2$O), 20% to 50% gradient in 8 min; detector, UV 254 nm. N-[1-azabicyclo[2.2.2]octan-3-yl]-5-[7-[3-cyano-4-(3-fluoropyrrolidin-1-yl)phenyl]furo[3,2-b]pyridin-2-yl]-4-methoxypyridine-2-carboxamide was obtained as a yellow solid (50 mg, 13% for 3 steps). HPLC: 90.7% purity, RT=9.15 min. MS: m/z=567.3 [M+H]$^+$. $^1$H NMR (300 MHz, CD$_3$OD, ppm) δ 9.27 (s, 1H), 8.69-8.60 (m, 2H), 8.39-8.29 (m, 1H), 8.16-8.01 (m, 2H), 7.85 (s, 1H), 7.10 (d, J=9.4 Hz, 1H), 5.55-5.30 (m, 1H), 4.58-4.48 (s, 1H), 4.29 (s, 3H), 4.20-3.80 (m, 5H), 3.55-3.25 (m, 5H), 2.51-1.89 (m, 7H).

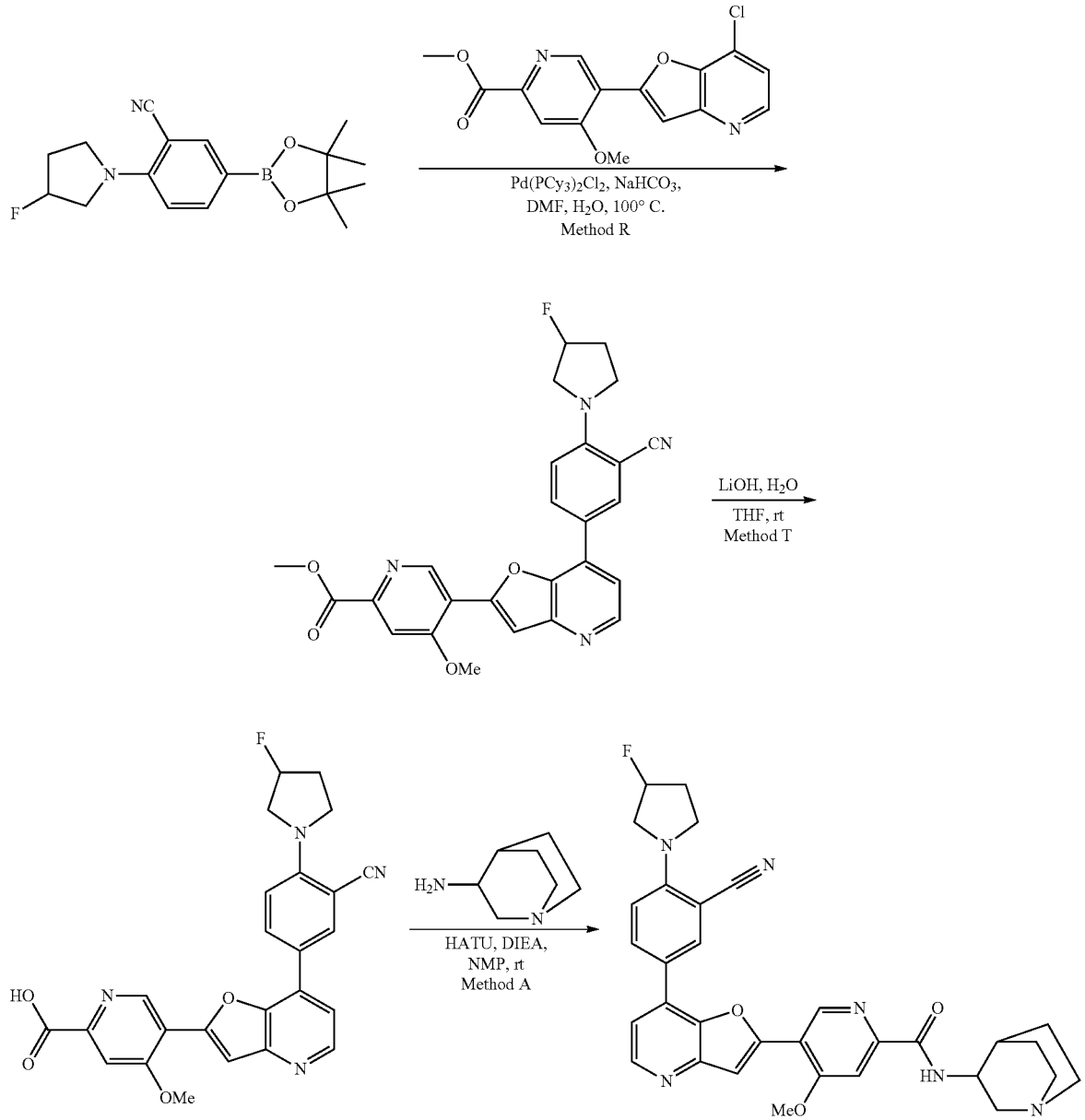

Example 402: 5-{7-[3-Cyano-4-((S)-3-fluoro-pyrrolidin-1-yl)-phenyl]-furo[3,2-b]pyridin-2-yl}-4-methoxy-pyridine-2-carboxylic acid (1-aza-bicyclo[2.20.2]oct-3-yl)-amide (444)

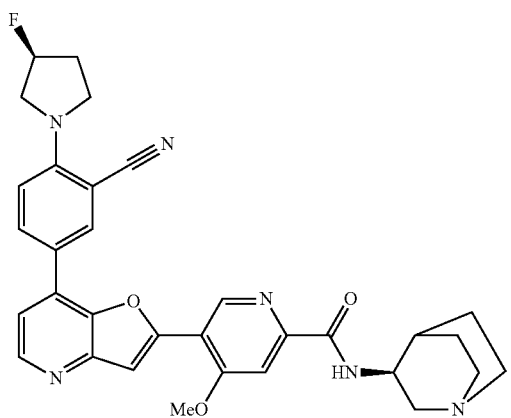 [SMILES: COc1cc(C(=O)N[C@@H]2CN3CCC2CC3)ncc1-c1cc2nccc(-c3ccc(N4CC[C@H](F)C4)c(C#N)c3)c2o1]

The title compound was separated from N-[1-azabicyclo[2.2.2]octan-3-yl]-5-[7-[3-cyano-4-(3-fluoropyrrolidin-1-yl)phenyl]furo[3,2-b]pyridin-2-yl]-4-methoxypyridine-2-carboxamide on a chiral prep-HPLC under the following conditions: column CHIRALPAK IC-3, 0.46×10 cm, 5 um; mobile phase, EtOH (0.1% DEA) in DCM, 85% isocratic in 15 min; detector, UV 254 nm. (60 mg, 39%, yellow solid) HPLC: 96.3% purity, RT=11.3 min. MS: m/z=567.1 [M+H]$^+$. $^1$H NMR (300 MHz, CD$_3$OD, ppm) δ 8.99 (s, 1H), 8.39 (d, J=5.3 Hz, 1H), 8.23 (s, 1H), 8.08 (d, J=9.5 Hz, 1H), 7.80 (s, 1H), 7.48 (d, J=4.4 Hz, 2H), 6.93 (d, J=9.2 Hz, 1H), 5.55-5.30 (m, 1H), 4.17 (s, 3H), 4.10-3.77 (m, 6H), 3.50-3.25 (m, 1H), 3.00-2.80 (m, 4H), 2.45-2.01 (m, 3H), 1.99-1.75 (m, 3H), 1.70-1.55 (m, 1H).

Example 403: 5-{7-[3-Cyano-4-((R)-3-fluoro-pyrrolidin-1-yl)-phenyl]-furo[3,2-b]pyridin-2-yl}-4-methoxy-pyridine-2-carboxylic acid (1-aza-bicyclo[2.20.2]oct-3-yl)-amide (445)

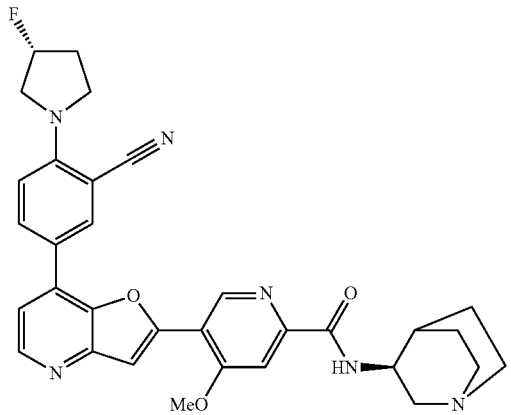 [SMILES: COc1cc(C(=O)N[C@@H]2CN3CCC2CC3)ncc1-c1cc2nccc(-c3ccc(N4CC[C@@H](F)C4)c(C#N)c3)c2o1]

The title compound was separated from N-[1-azabicyclo[2.2.2]octan-3-yl]-5-[7-[3-cyano-4-(3-fluoropyrrolidin-1-yl)phenyl]furo[3,2-b]pyridin-2-yl]-4-methoxypyridine-2-carboxamide on a chiral prep-HPLC. (15 mg, 10%, yellow solid) HPLC: 96.0% purity, RT=11.3 min. MS: m/z=567.2 [M+H]$^+$. $^1$H NMR (300 MHz, CD$_3$OD, ppm) δ 8.99 (s, 1H), 8.39 (d, J=5.3 Hz, 1H), 8.23 (s, 1H), 8.08 (d, J=9.5 Hz, 1H), 7.80 (s, 1H), 7.48 (d, J=4.4 Hz, 2H), 6.93 (d, J=9.2 Hz, 1H), 5.58-5.31 (m, 1H), 4.17 (s, 3H), 4.09-3.76 (m, 6H), 3.52-3.26 (m, 1H), 3.00-2.79 (m, 4H), 2.49-2.01 (m, 3H), 1.99-1.74 (m, 3H), 1.70-1.58 (m, 1H).

Example 404: 5-(2-(5-((S)-3-(dimethylamino)pyrrolidine-1-carbonyl)-3-methoxypyridin-2-yl)furo[3,2-b]pyridin-7-yl)-2-(3-fluoropyrrolidin-1-yl)benzonitrile (446)

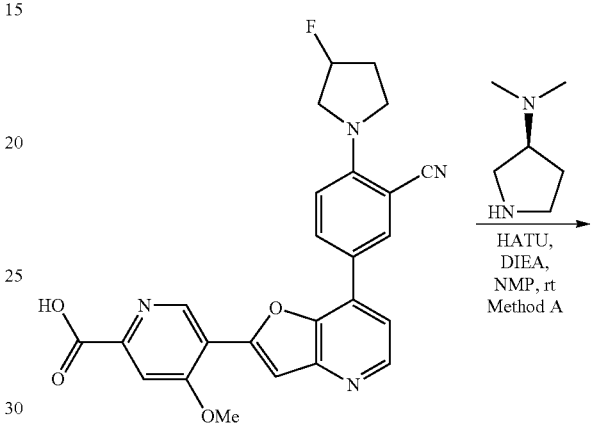

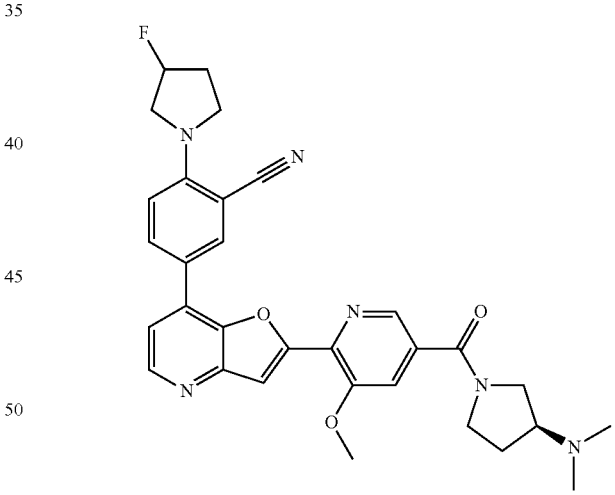

The title compound was prepared from 5-(7-(3-cyano-4-(3-fluoropyrrolidin-1-yl)phenyl)furo[3,2-b]pyridin-2-yl)-4-methoxypicolinic acid and (S)—N,N-dimethylpyrrolidin-3-amine using Method A. The product was first purified by prep-HPLC under the following conditions: column Atlantis Prep T$_3$ OBD column, 19×150 mm 5 um 10 nm; mobile phase, acetonitrile in water (0.05% NH$_3$H$_2$O), 30% to 55% gradient in 8 min; detector, UV 254/220 nm.

Example 405: 5-{2-[5-((S)-3-Dimethylamino-pyrrolidine-1-carbonyl)-3-methoxy-pyridin-2-yl]-furo[3,2-b]pyridin-7-yl}-2-((S)-3-fluoro-pyrrolidin-1-yl)-benzonitrile (447)

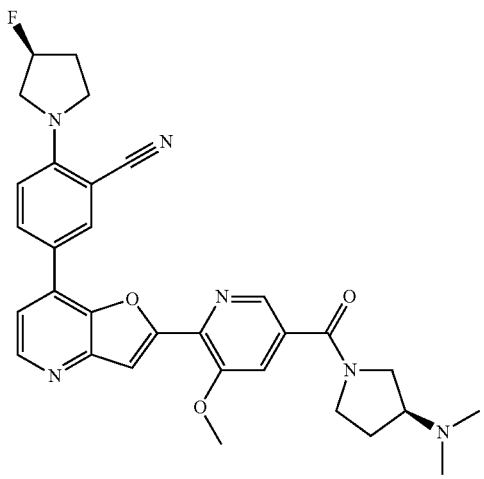 [SMILES: COc1cc(C(=O)N2CC[C@H](N(C)C)C2)cnc1-c1cc2nccc(-c3ccc(N4CC[C@H](F)C4)c(C#N)c3)c2o1]

The title compound was separated from 5-(2-(5-((S)-3-(dimethylamino)pyrrolidine-1-carbonyl)-3-methoxypyridin-2-yl)furo[3,2-b]pyridin-7-yl)-2-(3-fluoropyrrolidin-1-yl)benzonitrile on a chiral prep-HPLC under the following conditions: column CHIRALPAK IC-3, 0.46×10 cm, 3 um; mobile phase, MeOH (0.1% DEA) in DCM, 70% isocratic in 20 min; detector, UV 254 nm. (40 mg, 17%, yellow solid) HPLC: 96.6% purity, RT=2.82 min. MS: m/z=555.3 [M+H]+. 1H NMR (300 MHz, CD3OD, ppm) δ 8.47-8.39 (m, 1H), 8.34 (d, J=5.2 Hz, 1H), 8.20 (dd, J=4.2, 2.2 Hz, 1H), 8.12-8.01 (m, 1H), 7.72 (d, J=2.1 Hz, 1H), 7.59 (d, J=1.4 Hz, 1H), 7.42 (d, J=5.3 Hz, 1H), 6.72 (dd, J=9.2, 5.2 Hz, 1H), 5.52-5.20 (m, 1H), 4.10 (s, 3H), 4.04-3.58 (m, 7H), 3.48 (dd, J=13.1, 8.0 Hz, 1H), 3.10-2.90 (m, 1H), 2.45-2.05 (m, 9H), 2.00-1.84 (m, 1H).

Example 406: 5-{2-[5-((S)-3-Dimethylamino-pyrrolidine-1-carbonyl)-3-methoxy-pyridin-2-yl]-furo[3,2-b]pyridin-7-yl}-2-((R)-3-fluoro-pyrrolidin-1-yl)-benzonitrile (448)

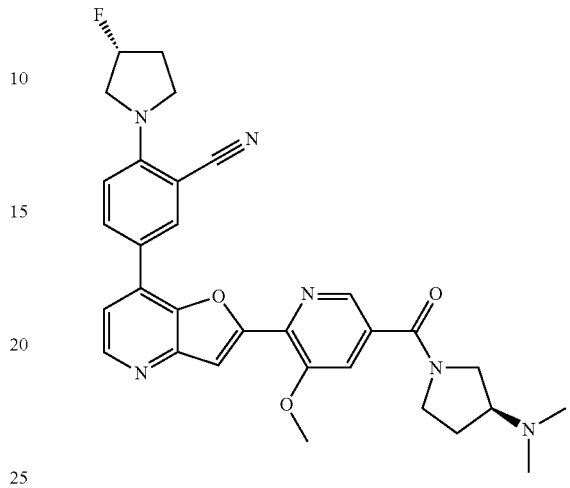

The title compound was separated from 5-(2-(5-((S)-3-(dimethylamino)pyrrolidine-1-carbonyl)-3-methoxypyridin-2-yl)furo[3,2-b]pyridin-7-yl)-2-(3-fluoropyrrolidin-1-yl)benzonitrile on a chiral prep-HPLC (25 mg, 11%, yellow solid) HPLC: 94.9% purity, RT=1.39 min. MS: m/z=555.3 [M+H]+. 1H NMR (300 MHz, CD3OD, ppm) δ 8.42 (d, J=7.3 Hz, 1H), 8.31 (d, J=5.2 Hz, 1H), 8.13 (dd, J=5.8, 2.3 Hz, 1H), 8.05-7.95 (m, 1H), 7.71 (t, J=2.5 Hz, 1H), 7.55 (d, J=1.7 Hz, 1H), 7.37 (d, J=5.3 Hz, 1H), 6.64 (t, J=8.3 Hz, 1H), 5.52-5.20 (m, 1H), 4.11 (d, J=3.6 Hz, 3H), 4.02-3.60 (m, 7H), 3.50 (dd, J=13.0, 8.3 Hz, 1H), 3.10-2.90 (m, 1H), 2.45-2.05 (m, 9H), 2.00-1.84 (m, 1H).

Example 407: 5-[2-(6-[[(3S)-3-(dimethylamino)pyrrolidin-1-yl]carbonyl]-4-methoxypyridin-3-yl)furo[3,2-b]pyridin-7-yl]-2-[(3S)-3-fluoropyrrolidin-1-yl]benzonitrile (449)

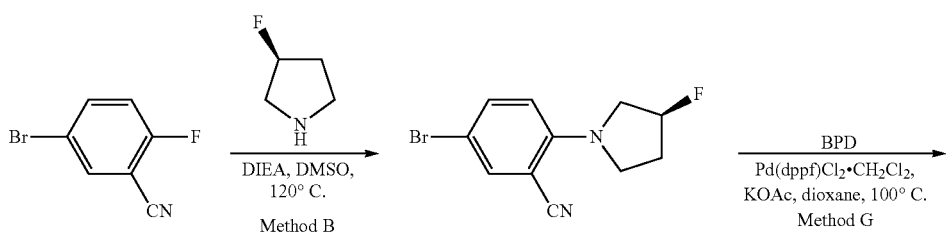

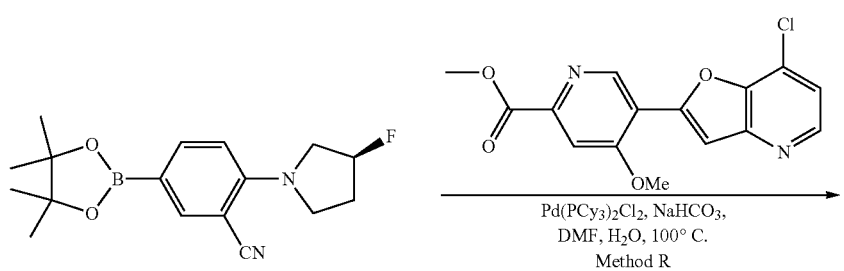

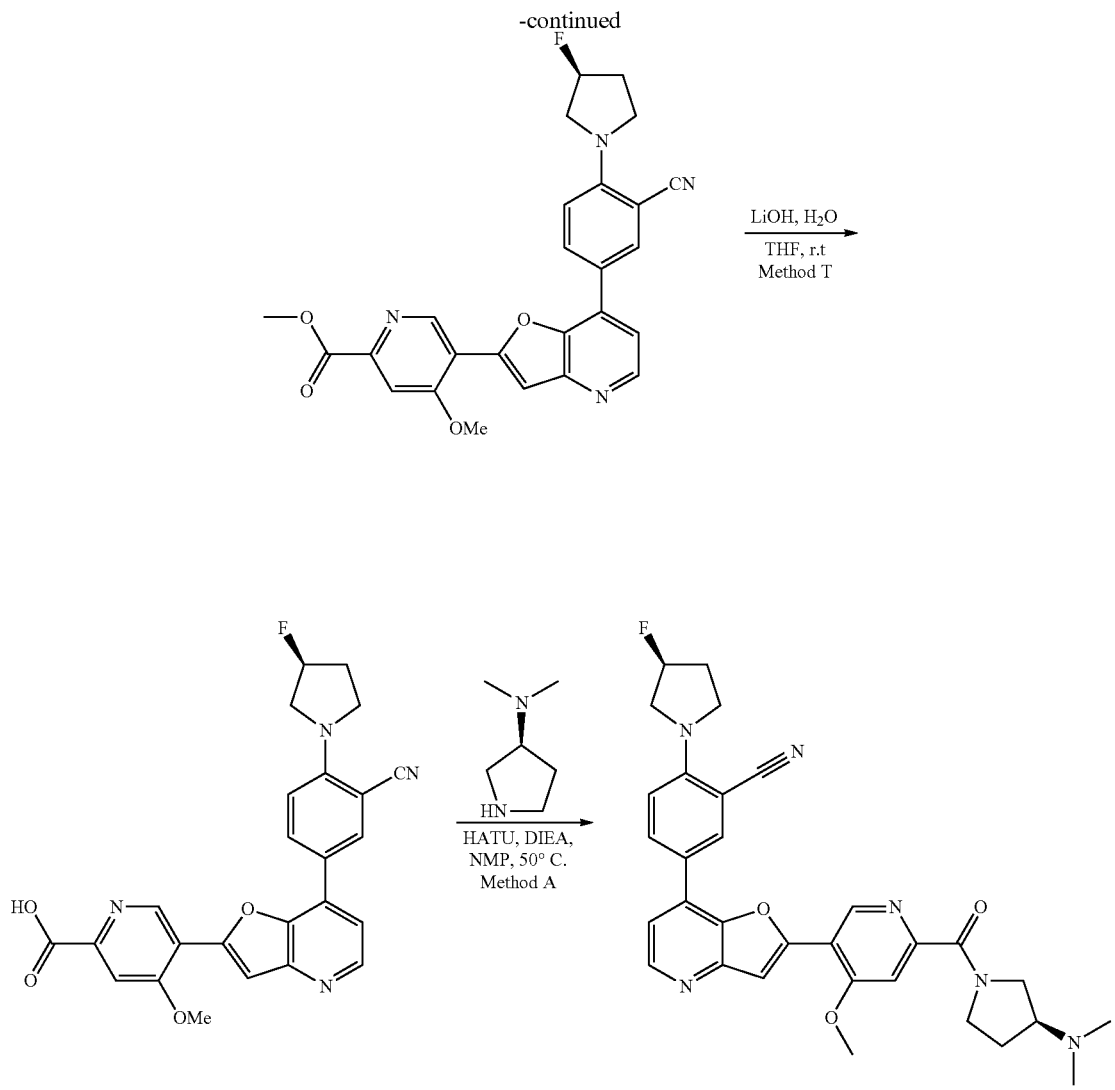

The title compound was prepared from 5-bromo-2-fluorobenzonitrile, 4,4,5,5-tetramethyl-2-(tetramethyl-1,3,2-dioxaborolan-2-yl)-1,3,2-dioxaborolane, methyl 5-(7-chlorofuro[3,2-b]pyridin-2-yl)-4-methoxypicolinate and (S)—N,N-dimethylpyrrolidin-3-amine using Methods B, G, R, T and A. The final product was purified by prep-HPLC under the following conditions: column, XBridge Prep C18 OBD Column, 150 mm 5 um; mobile phase, acetonitrile in water (with 0.05% NH$_4$OH), 30% to 50% gradient in 8 min; detector, UV 254 nm. 5-[2-(6-[[(3 S)-3-(dimethylamino) pyrrolidin-1-yl]carbonyl]-4-methoxypyridin-3-yl)furo[3,2-b]pyridin-7-yl]-2-[(3S)-3-fluoropyrrolidin-1-yl]benzonitrile was obtained as a off-white solid (25 mg, 7.6% for 5 steps). HPLC: 97.3% purity, RT=1.23 min. MS: m/z=555.3 [M+H]$^+$. $^1$H NMR (300 MHz, DMSO-d$_6$, ppm) δ 9.07 (d, J=7.8 Hz, 1H), 8.55 (d, J=5.1 Hz, 1H), 8.40-8.26 (m, 2H), 7.74-7.54 (m, 3H), 7.10 (d, J=9.1 Hz, 1H), 5.65-5.40 (m, 1H), 4.16 (s, 3H), 4.10-3.63 (m, 6H), 3.55-3.20 (m, 2H), 2.75-2.61 (m, 1H), 2.32 (d, J=18.3 Hz, 2H), 2.20 (s, 3H), 2.18-2.00 (m, 4H), 1.73 (dd, J=15.2, 6.4 Hz, 1H).

Example 408: 5-[2-(6-[[(3R)-3-(dimethylamino)pyrrolidin-1-yl]carbonyl]-4-methoxypyridin-3-yl)furo[3,2-b]pyridin-7-yl]-2-[(3S)-3-fluoropyrrolidin-1-yl]benzonitrile (450)

Example 409: 5-(7-[3-cyano-4-[(3S)-3-fluoropyrrolidin-1-yl]phenyl]furo[3,2-b]pyridin-2-yl)-4-methoxy-N-[3-oxabicyclo[3.1.0]hexan-6-yl]pyridine-2-carboxamide (451)

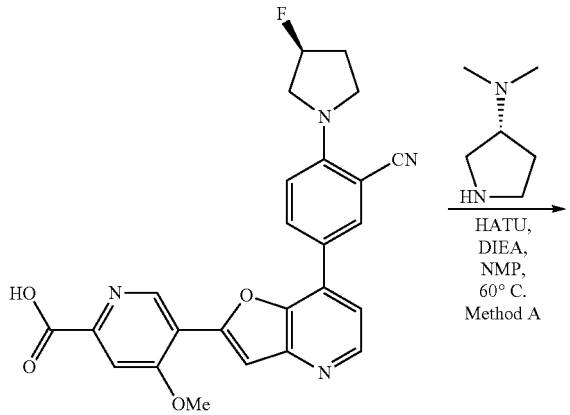

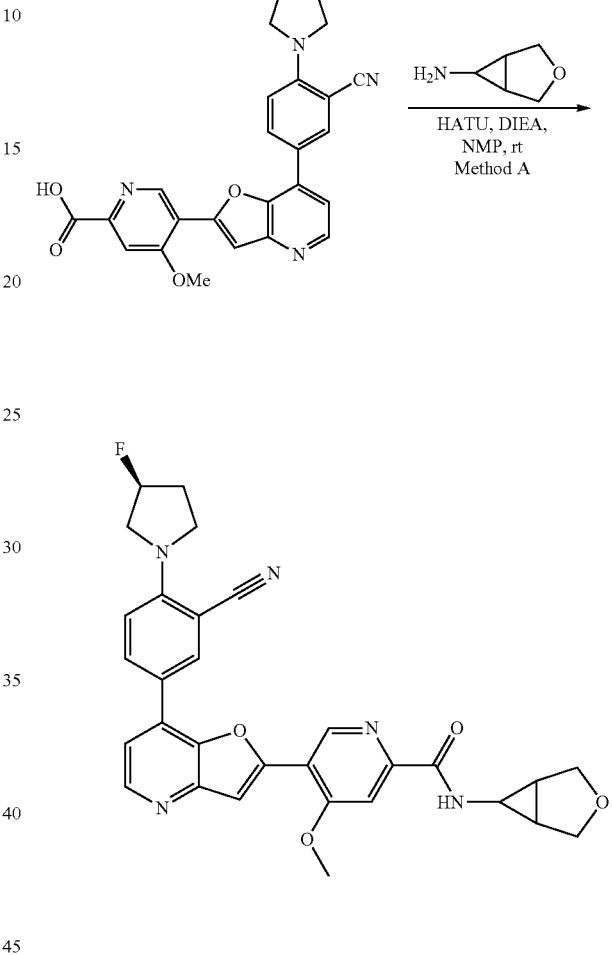

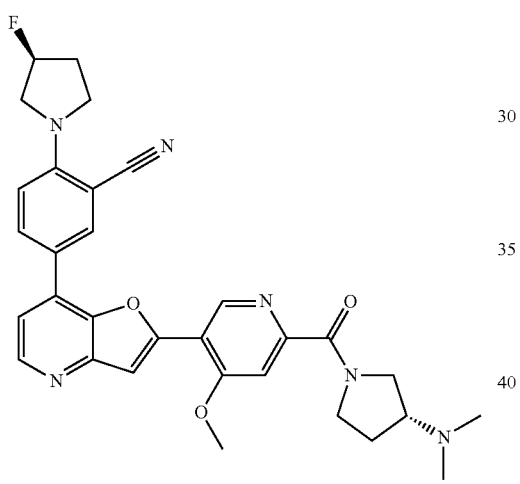

The title compound was prepared from (S)-5-(7-(3-cyano-4-(3-fluoropyrrolidin-1-yl)phenyl)furo[3,2-b]pyridin-2-yl)-4-methoxypicolinic acid and (R)—N,N-dimethylpyrrolidin-3-amine using Method A. The product was purified by prep-HPLC under the following conditions: column, XBridge Prep C18 OBD Column, 150 mm 5 um; mobile phase, acetonitrile in water (with 0.05% $NH_4OH$), 35% to 65% gradient in 8 min; detector, UV 254 nm. 5-[2-(6-[[(3R)-3-(dimethylamino)pyrrolidin-1-yl]carbonyl]-4-methoxypyridin-3-yl)furo[3,2-b]pyridin-7-yl]-2-[(3S)-3-fluoropyrrolidin-1-yl]benzonitrile was obtained as a yellow solid (19 mg, 16%). HPLC: 96.9% purity, RT=1.72 min. MS: m/z=555.3 $[M+H]^+$. $^1$H NMR (300 MHz, DMSO-$d_6$, ppm) δ 9.07 (d, J=7.7 Hz, 1H), 8.55 (d, J=5.1 Hz, 1H), 8.40-8.26 (m, 2H), 7.74-7.65 (m, 2H), 7.58 (d, J=2.1 Hz, 1H), 7.10 (d, 0.1=9.1 Hz, 1H), 5.64-5.39 (m, 1H), 4.16 (s, 3H), 4.00-3.75 (m, 6H), 3.53-3.20 (m, 2H), 2.74-2.64 (m, 1H), 2.32 (d, J=18.2 Hz, 2H), 2.20-2.00 (m, 7H), 1.76 (d, J=10.3 Hz, 1H).

The title compound was prepared from (S)-5-(7-(3-cyano-4-(3-fluoropyrrolidin-1-yl)phenyl)furo[3,2-b]pyridin-2-yl)-4-methoxypicolinic acid and 3-oxa-bicyclo[3.1.0]hexan-6-amine using Method A. The product was purified by prep-HPLC under the following conditions: column, XBridge Prep C18 OBD Column, 150 mm 5 um; mobile phase, acetonitrile in water (with 0.05% $NH_4OH$), 40% to 65% gradient in 8 min; detector, UV 254 nm. 5-(7-[3-cyano-4-[(3S)-3-fluoropyrrolidin-1-yl]phenyl]furo[3,2-b]pyridin-2-yl)-4-methoxy-N-[3-oxabicyclo[3.1.0]hexan-6-yl]pyridine-2-carboxamide was obtained as a yellow solid (25 mg, 21%). HPLC: 95.9% purity, RT=1.55 min. MS: m/z=540.2 $[M+H]^+$. $^1$H NMR (300 MHz, DMSO-$d_6$, ppm) δ 9.08-8.96 (m, 2H), 8.55 (d, J=5.1 Hz, 1H), 8.38 (d, J=2.2 Hz, 1H), 8.23 (dd, J=9.1, 2.4 Hz, 1H), 7.81 (s, 1H), 7.74-7.64 (m, 2H), 7.04 (d, J=9.2 Hz, 1H), 5.65-5.40 (m, 1H), 4.20 (s, 3H), 4.11-3.78 (m, 6H), 3.64 (d, J=8.3 Hz, 2H), 2.77-2.67 (m, 1H), 2.40-2.10 (m, 2H), 2.09-1.99 (m, 2H).

Example 410: 2-[(3R)-3-fluoropyrrolidin-1-yl]-5-[2-[3-methoxy-5-([5-methyl-octahydropyrrolo[3,4-c]pyrrol-2-yl]carbonyl)pyridin-2-yl]furo[3,2-b]pyridin-7-yl]benzonitrile (452)

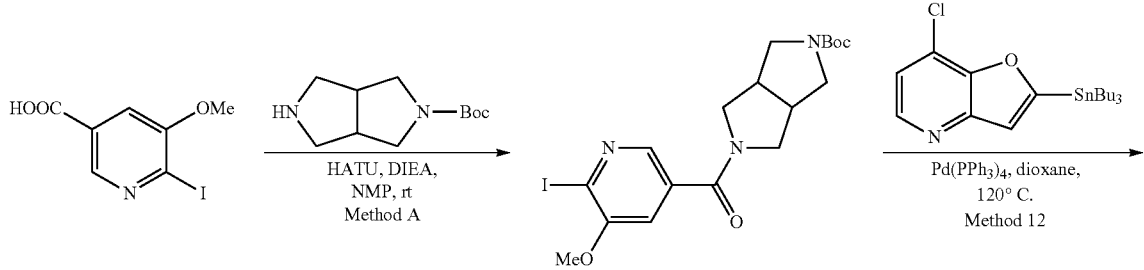

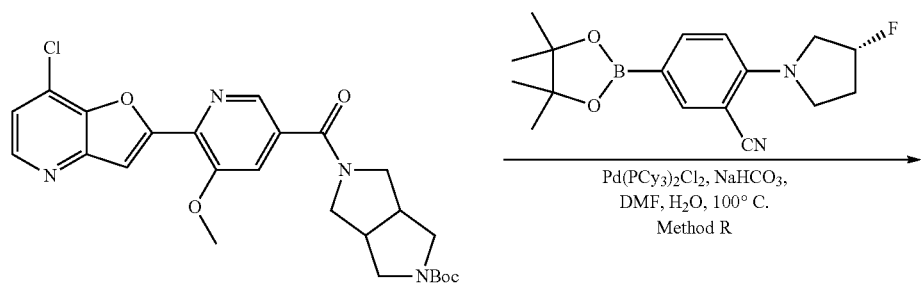

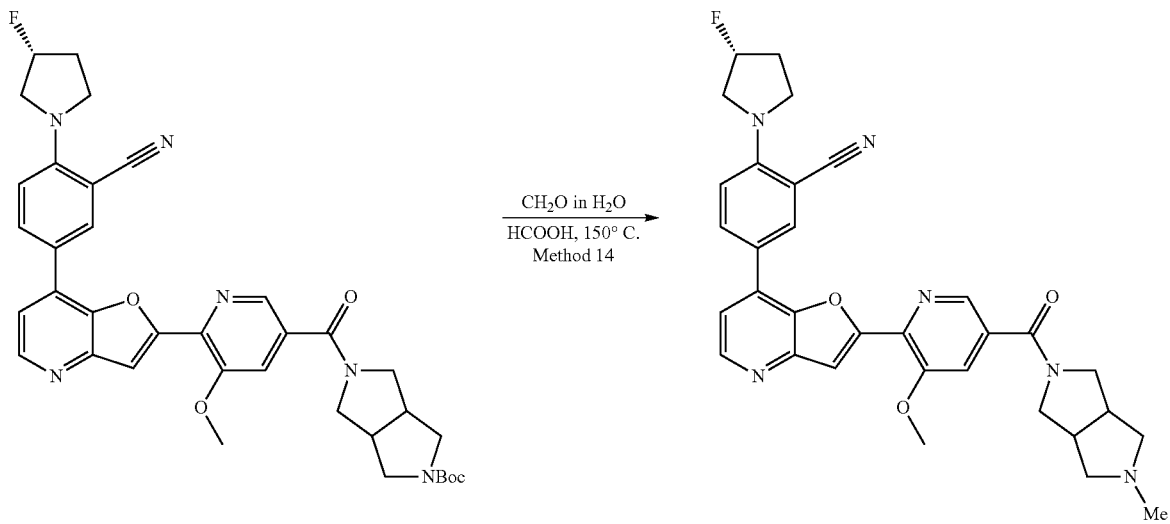

The title compound was prepared from 2-[(3R)-3-fluoropyrrolidin-1-yl]-5-[2-[3-methoxy-5-([5-methyl-octahydropyrrolo[3,4-c]pyrrol-2-yl]carbonyl)pyridin-2-yl]furo[3,2-b]pyridin-7-yl]benzonitrile, tert-butyl hexahydropyrrolo[3,4-c]pyrrole-2(1H)-carboxylate, 7-chloro-2-(tributylstannyl)furo[3,2-b]pyridine, (R)-2-(3-fluoropyrrolidin-1-yl)-5-(4,4,5,5-tetramethyl-1,3,2-dioxaborolan-2-yl)benzonitrile and formaldehyde using Methods A, 12, R and 14. The final product was purified by prep-HPLC under the following conditions: column, XBridge Prep C18 OBD Column, 150 mm 5 um; mobile phase, acetonitrile in water (with 0.05% NH$_4$OH), 30% to 55% gradient in 8 min; detector, UV 254 nm. 2-[(3R)-3-fluoropyrrolidin-1-yl]-5-[2-[3-methoxy-5-([5-methyl-octahydropyrrolo[3,4-c]pyrrol-2-yl]carbonyl)pyridin-2-yl]furo[3,2-b]pyridin-7-yl]benzonitrile was obtained as a yellow solid (15 mg, 9.3% for 4 steps). HPLC: 92.8% purity, RT=2.82 min. MS: m/z=567.3 [M+H]$^+$. $^1$H NMR (300 MHz, CD$_3$OD, ppm) δ 8.53-8.37 (m, 3H), 8.29 (dd, J=9.2, 2.4 Hz, 1H), 7.81-7.72 (m, 2H), 7.61 (d, J=5.2 Hz, 1H), 6.98 (d, J=9.1 Hz, 1H), 5.55-5.27 (m, 1H), 4.15 (s, 3H), 4.10-3.80 (m, 6H), 3.75-3.65 (m, 1H), 3.52-3.348 (m, 1H), 3.00-2.90 (m, 2H), 2.80-2.10 (m, 9H).

Example 411: 2-[(3R)-3-fluoropyrrolidin-1-yl]-5-[2-[4-methoxy-6-([5-methyl-octahydropyrrolo[3,4-c]pyrrol-2-yl]carbonyl)pyridin-3-yl]furo[3,2-b]pyridin-7-yl]benzonitrile (453)

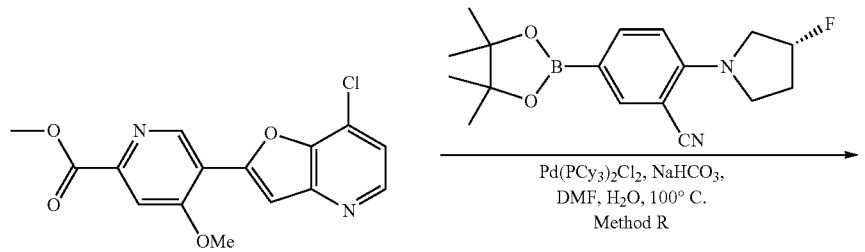

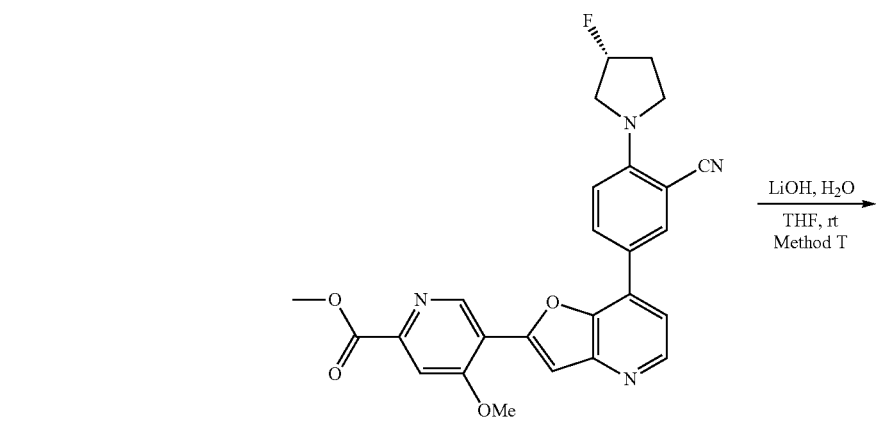

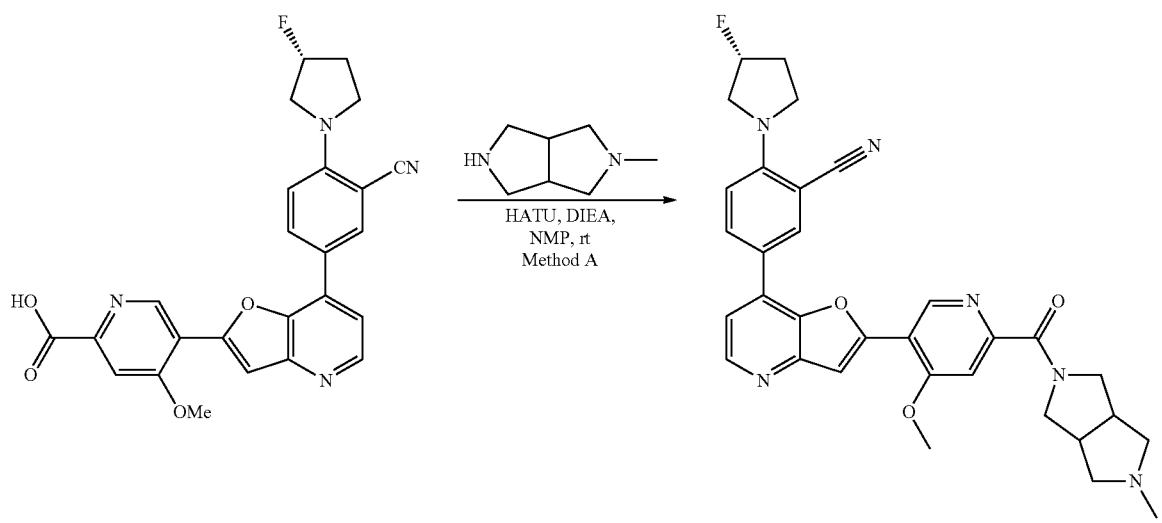

The title compound was prepared from methyl 5-(7-chlorofuro[3,2-b]pyridin-2-yl)-4-methoxypicolinate, (R)-2-(3-fluoropyrrolidin-1-yl)-5-(4,4,5,5-tetramethyl-1,3,2-dioxaborolan-2-yl)benzonitrile and 2-methyl-octahydropyrrolo[3,4-c]pyrrole using Methods T, R and A. The final product was purified by prep-HPLC under the following conditions: column, XBridge Prep C18 OBD Column, 150 mm 5 um; mobile phase, acetonitrile in water (with 0.05° % NH₃H₂O), 28% to 55% gradient in 8 min; detector, UV 254 nm. 2-[(3R)-3-fluoropyrrolidin-1-yl]-5-[2-[4-methoxy-6-([5-methyl-octahydropyrrolo[3,4-c]pyrrol-2-yl]carbonyl)pyridin-3-yl]furo[3,2-b]pyridin-7-yl]benzonitrile was obtained as a yellow solid (15 mg, 10% for 3 steps). HPLC: 98.7% purity, RT=1.24 min. MS: m/z=567.2 [M+H]⁺. ¹H NMR (300 MHz, DMSO-d₆, ppm) δ 9.06 (s, 1H), 8.55 (d, J=5.1 Hz, 1H), 8.40-8.27 (m, 2H), 7.74-7.64 (m, 2H), 7.55 (s, 1H), 7.10 (d, J=9.1 Hz, 1H), 5.65-5.40 (m, 1H), 4.16 (s, 3H), 4.10-3.72 (m, 6H), 3.60-3.42 (m, 2H), 2.88-2.77 (m, 2H), 2.51-2.10 (m, 7H), 2.08 (s, 2H).

Example 412: 5-[2-(5-[[(3R)-3-(dimethylamino) pyrrolidin-1-yl]carbonyl]-3-methoxypyridin-2-yl) furo[3,2-b]pyridin-7-yl]-2-(3-fluoropyrrolidin-1-yl) benzonitrile (454)

Example 413: 5-[2-(5-[[(3R)-3-(dimethylamino) pyrrolidin-1-yl]carbonyl]-3-methoxypyridin-2-yl) (S)-furo[3,2-b]pyridin-7-yl]-2-(3-fluoropyrrolidin-1-yl)benzonitrile (455)

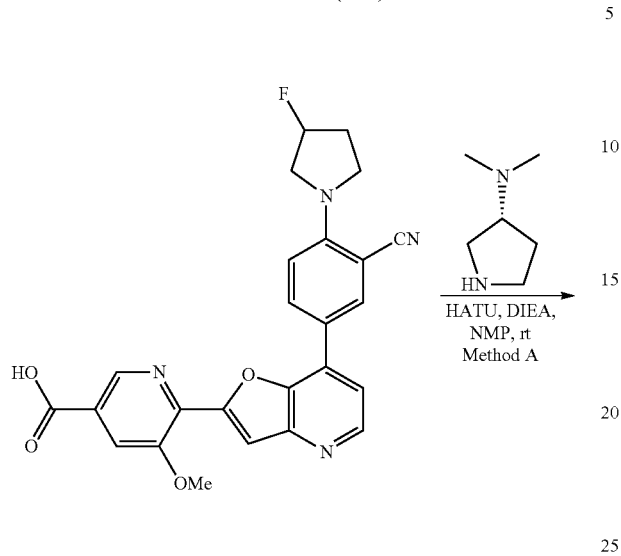

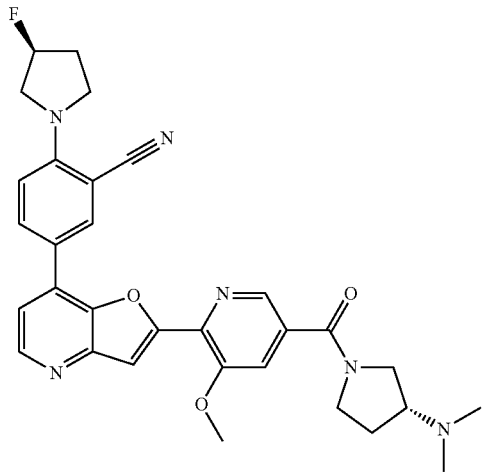 [SMILES: COc1cc(C(=O)N2CC[C@@H](N(C)C)C2)cnc1-c1cc2nccc(-c3ccc(N4CC[C@H](F)C4)c(C#N)c3)c2o1]

The title compound was separated from 5-[2-(5-[[(3R)-3-(dimethylamino)pyrrolidin-1-yl]carbonyl]-3-methoxy-pyridin-2-yl)furo[3,2-b]pyridin-7-yl]-2-(3-fluoropyrrolidin-1-yl)benzonitrile on a chiral prep-HPLC under the following conditions: column CHIRALPAK IC-3, 0.46×10 cm, 5 um; mobile phase, MeOH (0.5% i-PrNH$_2$) in DCM, 60% isocratic in 20 min; detector, UV 254 nm. (40 mg, 12%, yellow solid) HPLC: 97.0% purity, RT=2.84 min. MS: m/z=555.3 [M+H]$^+$. $^1$H NMR (300 MHz, CD$_3$OD, ppm) δ 8.47-8.30 (m, 2H), 8.20 (dd, 0.1=4.7, 2.3 Hz, 1H), 8.13-8.02 (m, 1H), 7.72 (s, 1H), 7.60 (d, J=2.1 Hz, 1H), 7.42 (d, J=5.3 Hz, 1H), 6.72 (dd, J=9.1, 5.4 Hz, 1H), 5.53-5.25 (m, 1H), 4.11 (s, 3H), 4.04-3.57 (m, 7H), 3.50-3.38 (m, 1H), 2.92-2.80 (m, 1H), 2.45-2.08 (m, 9H), 1.95-1.79 (m, 1H).

Example 414: 5-[2-(5-1[[(3R)-3-(dimethylamino) pyrrolidin-1-yl]carbonyl]-3-methoxypyridin-2-yl) (R)-furo[3,2-b]pyridin-7-yl]-2-(3-fluoropyrrolidin-1-yl)benzonitrile (456)

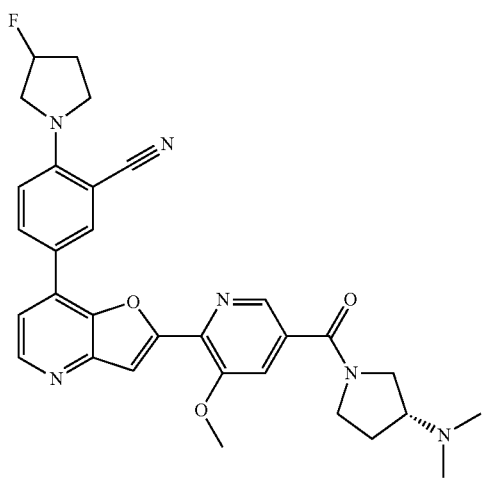

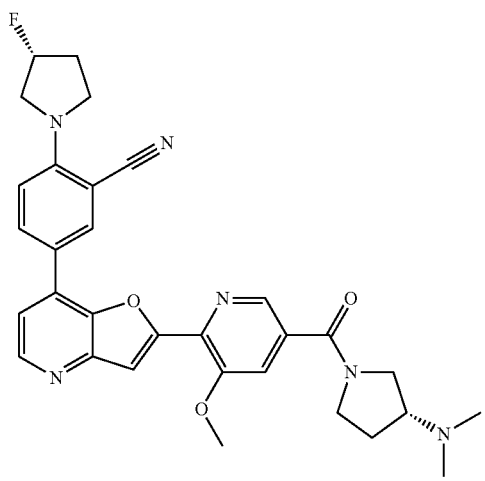 [SMILES: COc1cc(C(=O)N2CC[C@@H](N(C)C)C2)cnc1-c1cc2nccc(-c3ccc(N4CC[C@@H](F)C4)c(C#N)c3)c2o1]

The title compound was prepared from 6-(7-(3-cyano-4-(3-fluoropyrrolidin-1-yl)phenyl)furo[3,2-b]pyridin-2-yl)-5-methoxynicotinic acid and (R)—N,N-dimethylpyrrolidin-3-amine using Method A. The product was purified by prep-HPLC under the following conditions: column, XBridge Prep C18 OBD Column, 150 mm 5 um; mobile phase, acetonitrile in water (with 0.05% NH$_3$H$_2$O), 30% to 50% gradient in 8 min; detector, UV 254 nm. 5-[2-(5-[[(3R)-3-(dimethylamino)pyrrolidin-1-yl]carbonyl]-3-methoxypyridin-2-yl)furo[3,2-b]pyridin-7-yl]-2-(3-fluoropyrrolidin-1-yl)benzonitrile was obtained as a yellow solid (30 mg, 9%). HPLC: 99.7% purity, RT=0.70 min. MS: m/z=555.2 [M+H]$^+$. $^1$H NMR (300 MHz, CD$_3$OD, ppm) δ 8.50-8.36 (m, 2H), 8.34-8.24 (t, J=2.7 Hz, 1H), 8.17 (dd, J=9.2, 2.4 Hz, 1H), 7.75 (s, 1H), 7.67 (d, J=1.7 Hz, 1H), 7.51 (dd, J=5.3, 0.9 Hz, 1H), 6.84 (dd, J=9.1, 3.4 Hz, 1H), 5.54-5.39 (m, 1H), 4.13 (s, 3H), 4.10-3.57 (m, 7H), 3.51-3.37 (m, 1H), 2.94-2.78 (m, 1H), 2.45-2.05 (m, 9H), 1.96-1.79 (m, 1H).

The title compound was separated from 5-[2-(5-[[(3R)-3-(dimethylamino)pyrrolidin-1-yl]carbonyl]-3-methoxy-pyridin-2-yl)furo[3,2-b]pyridin-7-yl]-2-(3-fluoropyrrolidin-1-yl)benzonitrile on a chiral prep-HPLC. (40 mg, 12%, yellow solid) HPLC: 96.2% purity, RT=2.83 min. MS: m/z=555.3 [M+H]⁺. ¹H NMR (300 MHz, CD₃OD, ppm) δ 8.49 (d, J=8.1 Hz, 1H), 8.31 (d, J=5.0 Hz, 1H), 8.10 (s, 1H), 8.01-7.90 (m, 1H), 7.76 (d, J=5.9 Hz, 1H), 7.55 (s, 1H), 7.34 (d, J=5.5 Hz, 1H), 6.63-6.52 (m, 1H), 5.62-5.22 (m, 1H), 4.16 (s, 3H), 4.00-3.30 (m, 8H), 2.95-2.75 (m, 1H), 2.40-2.02 (m, 9H), 2.00-1.80 (m, 1H).

Example 415: 5-[2-(6-[[(3R)-3-(dimethylamino)pyrrolidin-1-yl]carbonyl]-4-methoxypyridin-3-yl)furo[3,2-b]pyridin-7-yl]-2-(3-fluoropyrrolidin-1-yl)benzonitrile (457)

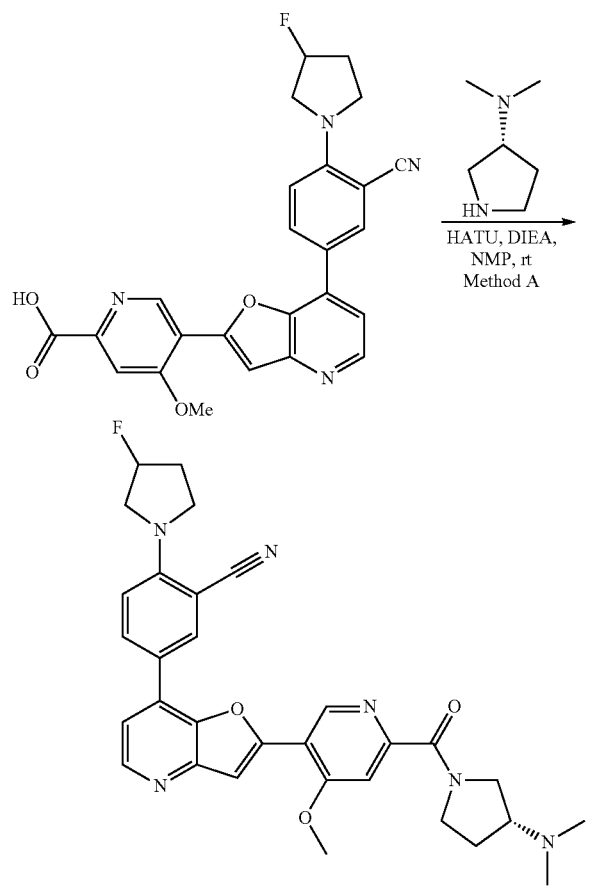

The title compound was prepared from 5-(7-(3-cyano-4-(3-fluoropyrrolidin-1-yl)phenyl)furo[3,2-b]pyridin-2-yl)-4-methoxypicolinic acid and (R)—N,N-dimethylpyrrolidin-3-amine using Method A. The final product was purified by prep-HPLC under the following conditions: column, XBridge Prep C18 OBD Column, 150 mm 5 um; mobile phase, acetonitrile in water (with 0.05% NH₃H₂O), 28% to 55% gradient in 8 min; detector, UV 254 nm. 5-[2-(6-[[(3R)-3-(dimethylamino)pyrrolidin-1-yl]carbonyl]-4-methoxy-pyridin-3-yl)furo[3,2-b]pyridin-7-yl]-2-(3-fluoropyrrolidin-1-yl)benzonitrile was obtained as a yellow solid (25 mg, 15%). HPLC: 95.4% purity, RT=1.45 min. MS: m/z=555.3 [M+H]⁺. ¹H NMR (300 MHz, CD₃OD, ppm) δ 8.96 (dd, J=11.5, 1.6 Hz, 1H), 8.44-8.33 (m, 1H), 8.19-8.03 (m, 2H), 7.58 (d, J=5.3 Hz, 1H), 7.51-7.39 (m, 2H), 6.90 (dd, J=9.1, 3.4 Hz, 1H), 5.55-5.27 (m, 1H), 4.15 (s, 3H), 4.12-3.75 (m, 6H), 3.70-3.52 (m, 1H), 3.48-3.34 (m, 1H), 2.91-2.79 (m, 1H), 2.45-2.10 (m, 9H), 1.94-1.77 (m, 1H).

Example 416: 5-[2-(6-[[(3R)-3-(dimethylamino)pyrrolidin-1-yl]carbonyl]-4-methoxy pyridin-3-yl)furo[3,2-b]pyridin-7-yl]-2-[(3S)-3-fluoropyrrolidin-1-yl]benzonitrileb (458)

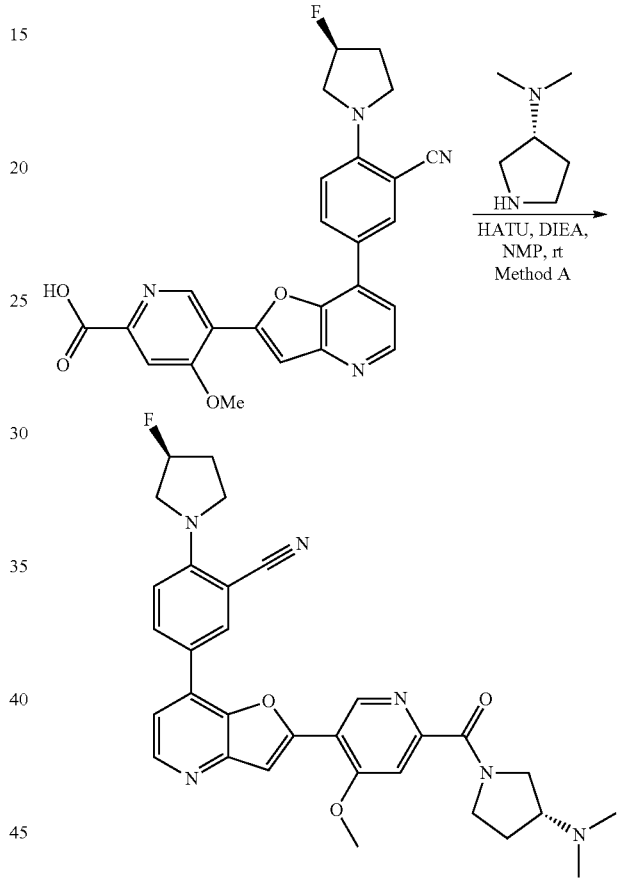

The title compound was prepared from (S)-5-(7-(3-cyano-4-(3-fluoropyrrolidin-1-yl)phenyl)furo[3,2-b]pyridin-2-yl)-4-methoxypicolinic acid and (R)—N,N-dimethylpyrrolidin-3-amine using Method A. The final product was purified by prep-HPLC under the following conditions: column, XBridge Prep C18 OBD Column, 150 mm 5 um; mobile phase, acetonitrile in water (with 0.05% NH4OH), 35% to 65% gradient in 8 min; detector, UV 254 nm. 5-[2-(6-[[(3R)-3-(dimethylamino)pyrrolidin-1-yl]carbonyl]-4-methoxy-pyridin-3-yl)furo[3,2-b]pyridin-7-yl]-2-[(3S)-3-fluoropyrrolidin-1-yl]benzonitrile was obtained as a yellow solid (19 mg, 16%). HPLC: 96.9% purity, RT=2.72 min. MS: m/z=555.3 [M+H]⁺. ¹H NMR (300 MHz, DMSO-d₆, ppm) δ 9.07 (d, J=7.7 Hz, 1H), 8.54 (d, J=5.1 Hz, 1H), 8.40-8.26 (m, 2H), 7.74-7.65 (m, 2H), 7.58 (d, J=2.1 Hz, 1H), 7.10 (d, J=9.1 Hz, 1H), 5.66-5.38 (m, 1H), 4.16 (s, 3H), 4.00-3.60 (m, 6H), 3.65-3.40 (m, 1H), 3.43-3.20 (m, 1H), 2.76-2.62 (m, 1H), 2.32 (d, J=18.2 Hz, 2H), 2.17-2.00 (m, 7H), 1.83-1.69 (m, 1H).

Example 417: 5-[2-(6-[[(3R)-3-(dimethylamino)
pyrrolidin-1-yl]carbonyl]-4-methoxy pyridin-3-yl)
furo[3,2-b]pyridin-7-yl]-2-[(3R)-3-fluoropyrrolidin-
1-yl]benzonitrile (459)

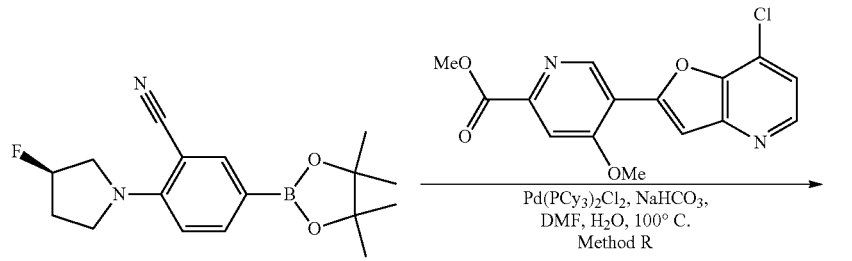

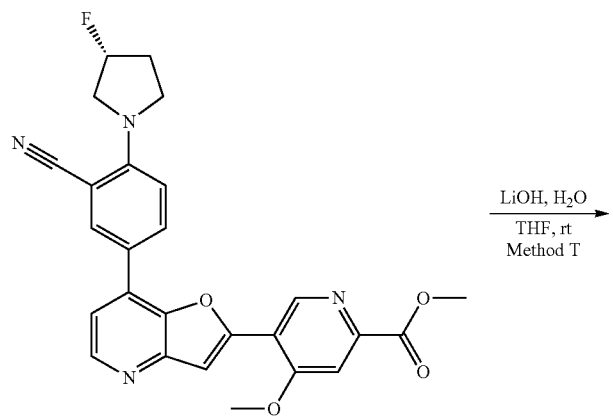

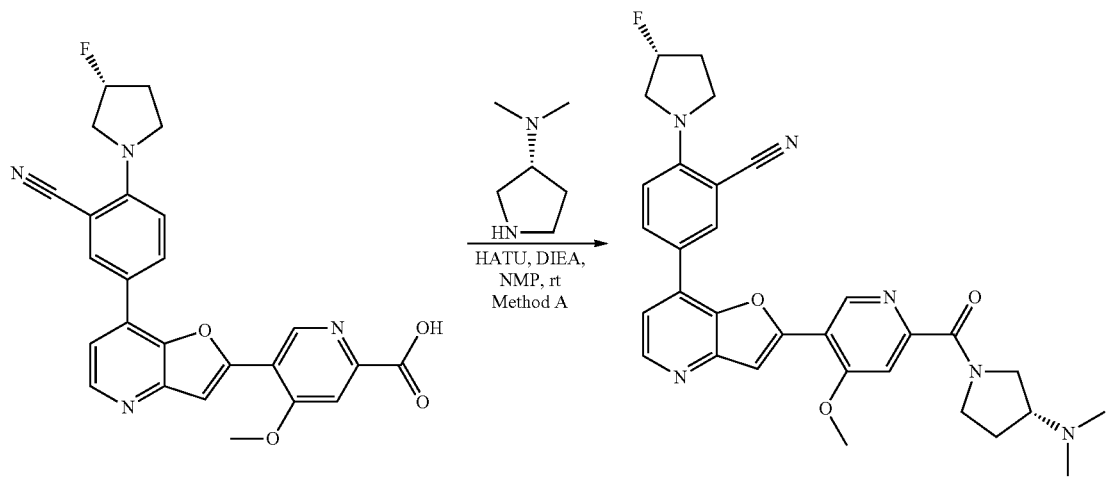

The title compound was prepared from (R)-2-(3-fluoro-pyrrolidin-1-yl)-5-(4,4,5,5-tetramethyl-1,3,2-dioxaborolan-2-yl)benzonitrile, methyl 5-(7-chlorofuro[3,2-b]pyridin-2-yl)-4-methoxypicolinate and (R)—N,N-dimethylpyrrolidin-3-amine using Methods R, T and A. The final product was purified by prep-HPLC under the following conditions: column, XBridge Prep C18 OBD Column, 150 mm 5 um; mobile phase, acetonitrile in water (with 0.05% $NH_3H_2O$), 30 O/o to 60% gradient in 8 min, detector, UV 254 nm. 5-[2-(6-[[(3R)-3-(dimethylamino)pyrrolidin-1-yl]carbonyl]-4-methoxypyridin-3-yl)furo[3,2-b]pyridin-7-yl]-2-[(3R)-3-fluoropyrrolidin-1-yl]benzonitrile was obtained as a yellow solid (20 mg, 6.3% for 3 steps). HPLC: 94.0% purity, RT=1.24 min. MS: m/z=555.3 [M+H]$^+$. $^1$H NMR (300 MHz, CD$_3$OD, ppm) δ 9.03 (d, J=9.2 Hz, 1H), 8.43 (d, J=5.3 Hz, 1H), 8.27-8.10 (m, 2H), 7.63-7.48 (m, 3H), 6.96 (dd, J=9.2, 2.5 Hz, 1H), 5.55-5.28 (m, 1H), 4.20-3.78 (m, 9H), 3.69-3.35 (m, 2H), 2.92-2.82 (m, 1H), 2.45-2.05 (m, 9H), 1.92-1.80 (m, 1H).

Example 418: 2-(3-fluoropyrrolidin-1-yl)-5-(2-[3-methoxy-5-[(4-methylpiperazin-1-yl)carbonyl]pyridin-2-yl]furo[3,2-b]pyridin-7-yl)benzonitrile (460)

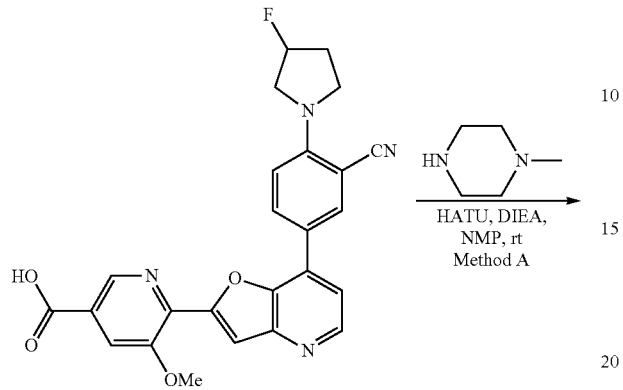

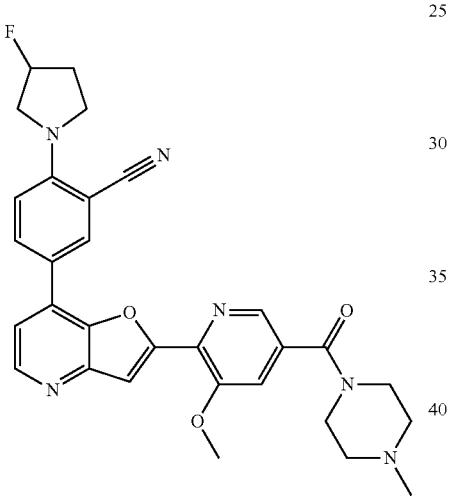

The title compound was prepared from 6-(7-(3-cyano-4-(3-fluoropyrrolidin-1-yl)phenyl)furo[3,2-b]pyridin-2-yl)-5-methoxynicotinic acid and (1-methylpiperazine using Method A. The product was purified by prep-HPLC under the following conditions: column, XBridge Prep C18 OBD Column, 150 mm 5 um; mobile phase, acetonitrile in water (with 0.05% NH₄OH), 15% to 45% gradient in 8 min; detector, UV 254 nm. 2-(3-fluoropyrrolidin-1-yl)-5-(2-[3-methoxy-5-[(4-methylpiperazin-1-yl)carbonyl]pyridin-2-yl]furo[3,2-b]pyridin-7-yl)benzonitrile was obtained as a yellow solid (15 mg, 22%). HPLC: 96.4% purity, RT=1.22 min. MS: m/z=541.2 [M+H]⁺. ¹H NMR (300 MHz, CD₃OD, ppm) δ 8.39 (d, J=5.2 Hz, 1H), 8.33 (d, J=1.5 Hz, 1H), 8.27 (d, J=2.3 Hz, 1H), 8.14 (dd, J=9.1, 2.4 Hz, 1H), 7.70-7.61 (m, 2H), 7.49 (d, J=5.2 Hz, 1H), 6.81 (d, J=9.1 Hz, 1H), 5.55-5.26 (m, 1H), 4.12 (s, 3H), 4.07-3.68 (m, 6H), 3.65-3.45 (m, 2H), 2.63-2.08 (m, 9H).

Example 419: 2-(3(S)-fluoropyrrolidin-1-yl)-5-(2-[3-methoxy-5-[(4-methylpiperazin-1-yl)carbonyl]pyridin-2-yl]furo[3,2-b]pyridin-7-yl)benzonitrile (461)

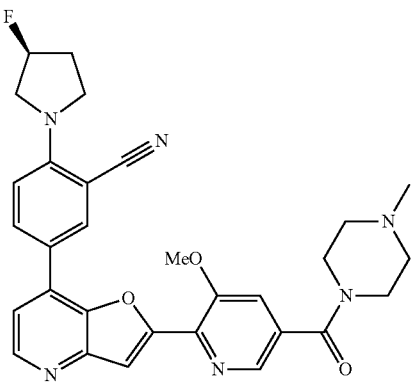

The title compound was separated from 2-(3-fluoropyrrolidin-1-yl)-5-(2-[3-methoxy-5-[(4-methylpiperazin-1-yl)carbonyl]pyridin-2-yl]furo[3,2-b]pyridin-7-yl)benzonitrile on a chiral prep-HPLC under the following conditions: column CHIRAL Cellulose-SB, 0.46×15 cm, 5 um; mobile phase, MeOH (0.1% DEA) in MTBE, 10% isocratic in 15 min; detector, UV 254 nm. (40 mg, 14%, yellow solid) HPLC: 98.7% purity, RT=1.38 min. MS: m/z=541.3 [M+H]⁺. ¹H NMR (300 MHz, CD₃OD, ppm) δ 8.35-8.29 (m, 2H), 8.15 (d, J=2.3 Hz, 1H), 8.01 (dd, J=9.1, 2.4 Hz, 1H), 7.64 (d, J=1.6 Hz, 1H), 7.56 (s, 1H), 7.38 (d, J=5.3 Hz, 1H), 6.65 (d, J=9.2 Hz, 1H), 5.53-5.30 (m, 1H), 4.11 (s, 3H), 3.99-3.50 (m, 8H), 2.68-2.48 (m, 4H), 2.42-2.10 (m, 5H).

Example 420: 2-(3(R)-fluoropyrrolidin-1-yl)-5-(2-[3-methoxy-5-[(4-methylpiperazin-1-yl)carbonyl]pyridin-2-yl]furo[3,2-b]pyridin-7-yl)benzonitrile (462)

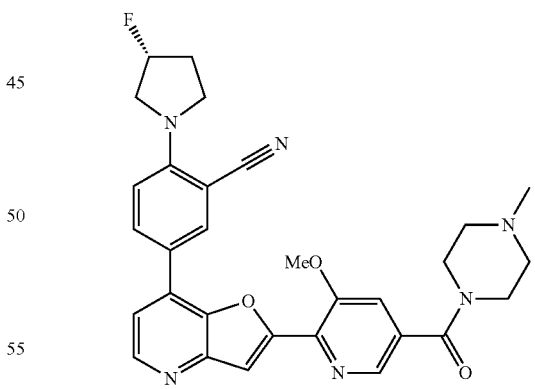

The title compound was separated from 2-(3-fluoropyrrolidin-1-yl)-5-(2-[3-methoxy-5-[(4-methylpiperazin-1-yl)carbonyl]pyridin-2-yl]furo[3,2-b]pyridin-7-yl)benzonitrile on a chiral prep-HPLC. (40 mg, 14%, yellow solid) HPLC: 98.3% purity, RT=1.37 min. MS: m/z=541.3 [M+H]⁺. ¹H NMR (300 MHz, CD₃OD, ppm) δ 8.39-8.26 (m, 2H), 8.14 (d, J=2.3 Hz, 1H), 8.00 (dd, J=9.1, 2.4 Hz, 1H), 7.65-7.51 (m, 2H), 7.37 (d, J=5.3 Hz, 1H), 6.65 (d, J=9.2 Hz, 1H), 5.52-5.25 (m, 1H), 4.08 (s, 3H), 3.99-3.45 (m, 8H), 2.66-2.46 (m, 4H), 2.42-2.06 (m, 5H).

Example 421: 2-(3-fluoropyrrolidin-1-yl)-5-(2-(4-methoxy-6-(4-methylpiperazine-1-carbonyl)pyridin-3-yl)furo[3,2-b]pyridin-7-yl)benzonitrile

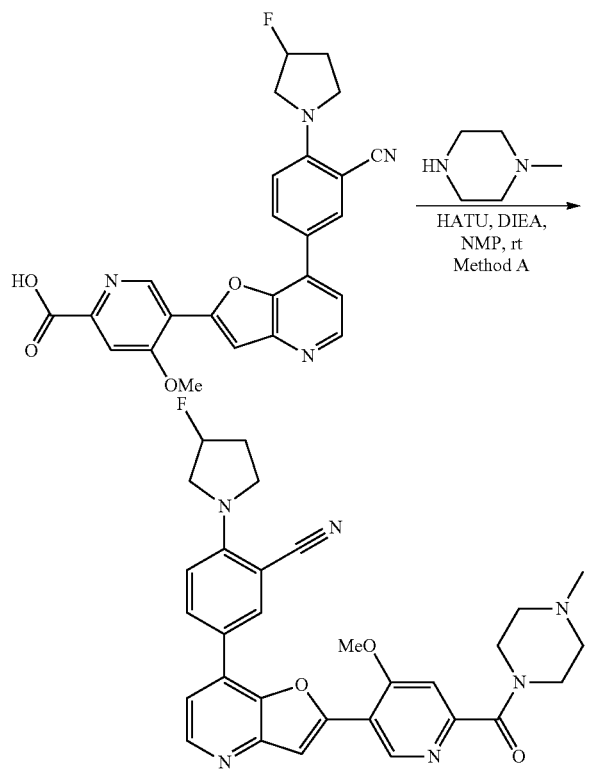

The title compound was prepared from 5-(7-(3-cyano-4-(3-fluoropyrrolidin-1-yl)phenyl)furo[3,2-b]pyridin-2-yl)-4-methoxypicolinic acid and 1-methylpiperazine using Method A. The product was first purified by prep-HPLC under the following conditions: column, XBridge Prep C18 OBD Column, 150 mm 5 um; mobile phase, acetonitrile in water (with 0.05% NH₄OH), 28% to 55% gradient in 8 min; detector, UV 254 nm.

Example 422: 2-((S)-3-Fluoro-pyrrolidin-1-yl)-5-{2-[4-methoxy-6-(4-methyl-piperazine-1-carbonyl)-pyridin-3-yl]-furo[3,2-b]pyridin-7-yl})-benzonitrile (463)

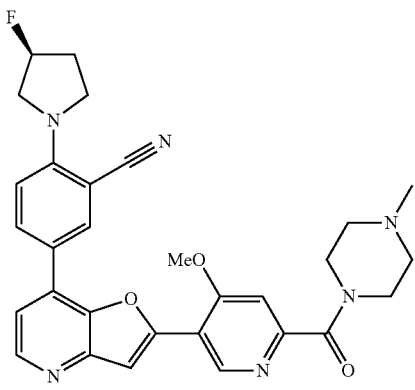 [SMILES: COc1cc(C(=O)N2CCN(C)CC2)ncc1-c1cc2nccc(-c3ccc(N4CC[C@H](F)C4)c(C#N)c3)c2o1]

The title compound was separated from 2-(3-fluoropyrrolidin-1-yl)-5-(2-(4-methoxy-6-(4-methylpiperazine-1-carbonyl)pyridin-3-yl)furo[3,2-b]pyridin-7-yl)benzonitrile on a chiral prep-HPLC under the following conditions: column CHIRALPAK IA-3, 100×3 mm, 3 um; mobile phase, EtOH (0.1% DEA) in MeOH, 50% isocratic in 15 min; detector, UV 310 nm. (15 mg, 7%, yellow solid) HPLC: 96.7% purity, RT=0.93 min. MS: m/z=541.3 [M+H]⁺. ¹H NMR (300 MHz, DMSO-d₆, ppm) δ 9.06 (s, 1H), 8.55 (d, J=5.2 Hz, 1H), 8.41-8.27 (m, 2H), 7.74-7.63 (m, 2H), 7.46 (s, 1H), 7.10 (d, J=9.1 Hz, 1H), 5.65-5.38 (m, 1H), 4.15 (s, 3H), 4.10-3.72 (m, 4H), 3.67 (t, 0.1=4.8 Hz, 2H), 3.44 (t, J=4.8 Hz, 2H), 2.45-2.10 (m, 9H).

Example 423: 2-((R)-3-Fluoro-pyrrolidin-1-yl)-5-{2-[4-methoxy-6-(4-methyl-piperazine-1-carbonyl)-pyridin-3-yl]-furo[3,2-b]pyridin-7-yl}-benzonitrile (464)

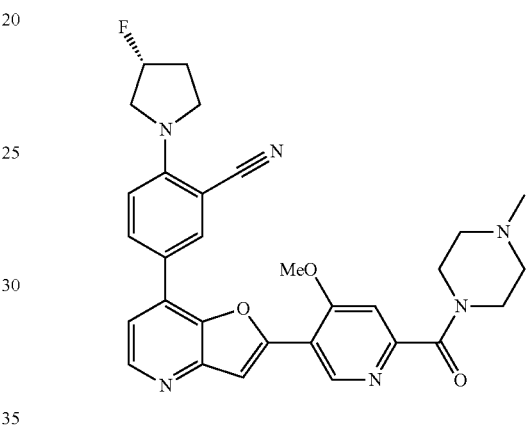

The title compound was separated from 2-(3-fluoropyrrolidin-1-yl)-5-(2-(4-methoxy-6-(4-methylpiperazine-1-carbonyl)pyridin-3-yl)furo[3,2-b]pyridin-7-yl)benzonitrile on a chiral prep-HPLC. (15 mg, 7%, yellow solid) HPLC: 90.9% purity, RT=0.93 min. MS: m/z=541.2 [M+H]⁺. ¹H NMR (300 MHz, DMSO-d₆, ppm) δ 9.06 (s, 1H), 8.55 (d, J=5.2 Hz, 1H), 8.40-8.25 (m, 2H), 7.75-7.62 (m, 2H), 7.46 (s, 1H), 7.10 (d, J=9.1 Hz, 1H), 5.65-5.38 (m, 1H), 4.15 (s, 3H), 4.10-3.70 (m, 4H), 3.66 (t, J=4.8 Hz, 2H), 3.44 (t, J=4.8 Hz, 2H), 2.46-2.03 (m, 9H).

Example 424: 6-[7-[3-cyano-4-(3-fluoropyrrolidin-1-yl)phenyl]furo[3,2-b]pyridin-2-yl]-5-methoxy-N-[3-oxabicyclo[3.1.0]hexan-6-yl]pyridine-3-carboxamide (465)

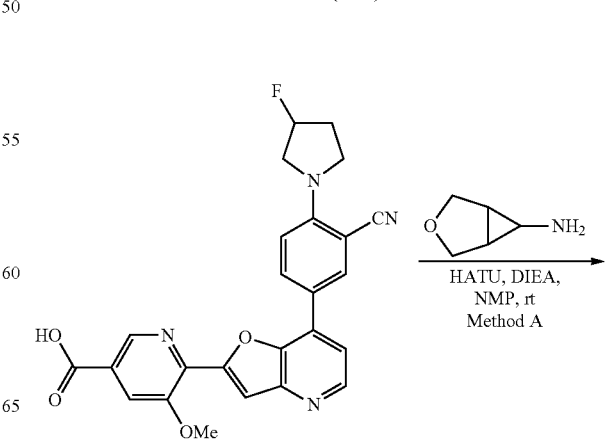

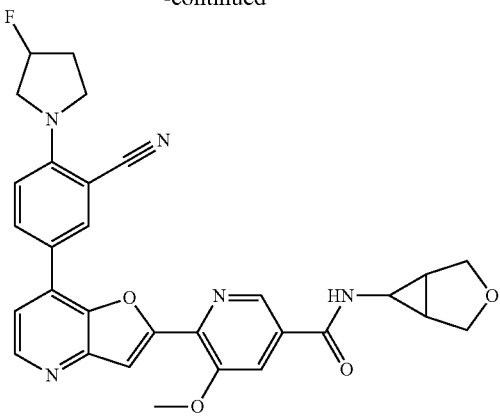

The title compound was prepared from 6-(7-(3-cyano-4-(3-fluoropyrrolidin-1-yl)phenyl)furo[3,2-b]pyridin-2-yl)-5-methoxynicotinic acid and 3-oxa-bicyclo[3.1.0]hexan-6-amine using Method A. The final product was purified by prep-HPLC under the following conditions: column, XBridge Prep C18 OBD Column, 150 mm 5 um; mobile phase, acetonitrile in water (with 0.05% $NH_3H_2O$), 30% to 55% gradient in 8 min; detector, UV 254 nm. 6-[7-[3-cyano-4-(3-fluoropyrrolidin-1-yl)phenyl]furo[3,2-b]pyridin-2-yl]-5-methoxy-N-[3-oxabicyclo[3.1.0]hexan-6-yl]pyridine-3-carboxamide was obtained as a yellow solid (25 mg, 7%). HPLC: 93.7% purity, RT=2.95 min. MS: m/z=540.2 [M+H]$^+$. $^1$H NMR (300 MHz, DMSO-d$_6$, ppm) δ 8.88-8.72 (m, 2H), 8.57 (d, J=5.1 Hz, 1H), 8.48 (d, J=2.3 Hz, 1H), 8.31 (dd, J=9.2, 2.4 Hz, 1H), 7.99 (d, J=1.7 Hz, 1H), 7.82 (s, 1H), 7.74 (d, J=5.1 Hz, 1H), 7.06 (d, J=9.2 Hz, 1H), 5.65-5.38 (m, 1H), 4.15 (s, 3H), 4.10-3.76 (m, 7H), 3.67 (dd, J=8.4, 1.7 Hz, 2H), 2.71-2.61 (m, 1H), 2.40-2.10 (m, 2H), 1.96 (s, 2H).

Example 425: 6-{7-[3-Cyano-4-((R)-3-fluoro-pyrrolidin-1-yl)-phenyl]-furo[3,2-b]pyridin-2-yl}-5-methoxy-N-(3-oxa-bicyclo[3.1.0]hex-6-yl)-nicotinamide (466)

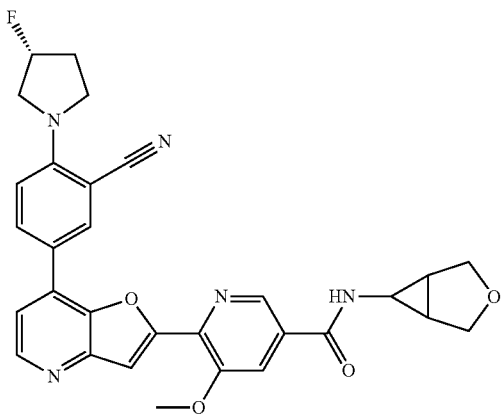

The title compound was separated from 6-[7-[3-cyano-4-(3-fluoropyrrolidin-1-yl)phenyl]furo[3,2-b]pyridin-2-yl]-5-methoxy-N-[3-oxabicyclo[3.1.0]hexan-6-yl]pyridine-3-carboxamide were obtained by separation on a chiral prep-HPLC under the following conditions: column Repaired Chiral-IC, 0.46×10 cm, 5 um; mobile phase, DCM (0.1% DEA) in MeOH, 30% isocratic in 30 min; detector, UV 254 nm. (25 mg, 7%, yellow solid) HPLC: 96.8% purity, RT=1.45 min. MS: m/z=540.2 [M+H]$^+$. $^1$H NMR (300 MHz, DMSO-d$_6$, ppm) δ 8.83 (d, J=4.1 Hz, 1H), 8.77 (d, J=1.6 Hz, 1H), 8.57 (d, J=5.1 Hz, 1H), 8.48 (d, J=2.3 Hz, 1H), 8.31 (dd, J=9.2, 2.4 Hz, 1H), 7.99 (d, J=1.7 Hz, 1H), 7.82 (s, 1H), 7.74 (d, J=5.1 Hz, 1H), 7.05 (d, J=9.2 Hz, 1H), 5.67-5.38 (m, 1H), 4.15 (s, 3H), 4.12-3.76 (m, 7H), 3.68 (d, J=8.3 Hz, 2H), 2.72-2.62 (m, 1H), 2.40-2.11 (m, 2H), 2.03-1.92 (m, 2H).

Example 426: 6-{7-[3-Cyano-4-((S)-3-fluoro-pyrrolidin-1-yl)-phenyl]-furo[3,2-b]pyridin-2-yl}-5-methoxy-N-(3-oxa-bicyclo[3.1.0]hex-6-yl)-nicotinamide (467)

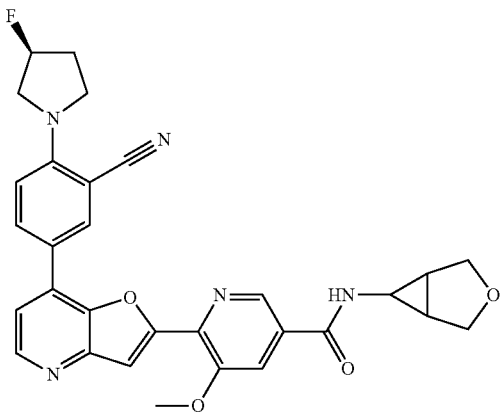

The title compound was separated from 6-[7-[3-cyano-4-(3-fluoropyrrolidin-1-yl)phenyl]furo[3,2-b]pyridin-2-yl]-5-methoxy-N-[3-oxabicyclo[3.1.0]hexan-6-yl]pyridine-3-carboxamide were obtained by separation on a chiral prep-HPLC. (25 mg, 7%, yellow solid) HPLC: 94.2% purity, RT=2.98 min. MS: m % z=540.2 [M+H]$^+$. $^1$H NMR (300 MHz, DMSO-d$_6$, ppm) δ 8.83 (d, J=4.1 Hz, 1H), 8.77 (d, J=1.6 Hz, 1H), 8.57 (d, J=5.1 Hz, 1H), 8.47 (d, J=2.3 Hz, 1H), 8.30 (dd, J=9.2, 2.4 Hz, 1H), 7.99 (d, J=1.7 Hz, 1H), 7.82 (s, 1H), 7.73 (d, J=5.1 Hz, 1H), 7.05 (d, J=9.2 Hz, 1H), 5.67-5.38 (m, 1H), 4.14 (s, 3H), 4.12-3.76 (m, 7H), 3.68 (d, J=8.3 Hz, 2H), 2.72-2.62 (m, 1H), 2.40-2.10 (m, 2H), 2.03-1.90 (m, 2H).

701

Example 427: 5-[7-[3-cyano-4-(3-fluoropyrrolidin-1-yl)phenyl]furo[3,2-b]pyridin-2-yl]-4-methoxy-N-[3-oxabicyclo[3.1.0]hexan-6-yl]pyridine-2-carboxamide (468)

702

Example 428: 5-(7-[3-cyano-4-[(3R)-3-fluoropyrrolidin-1-yl]phenyl]furo[3,2-b]pyridin-2-yl)-4-methoxy-N-[3-oxabicyclo[3.1.0]hexan-6-yl]pyridine-2-carboxamide (469)

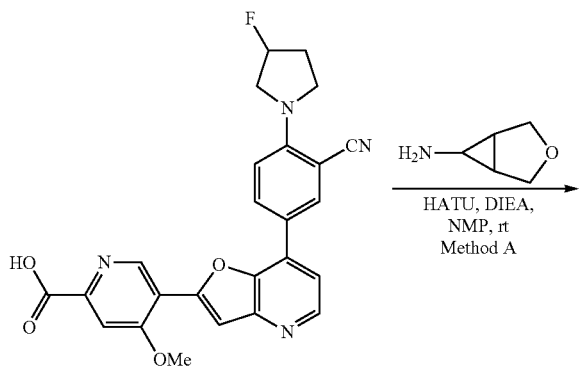

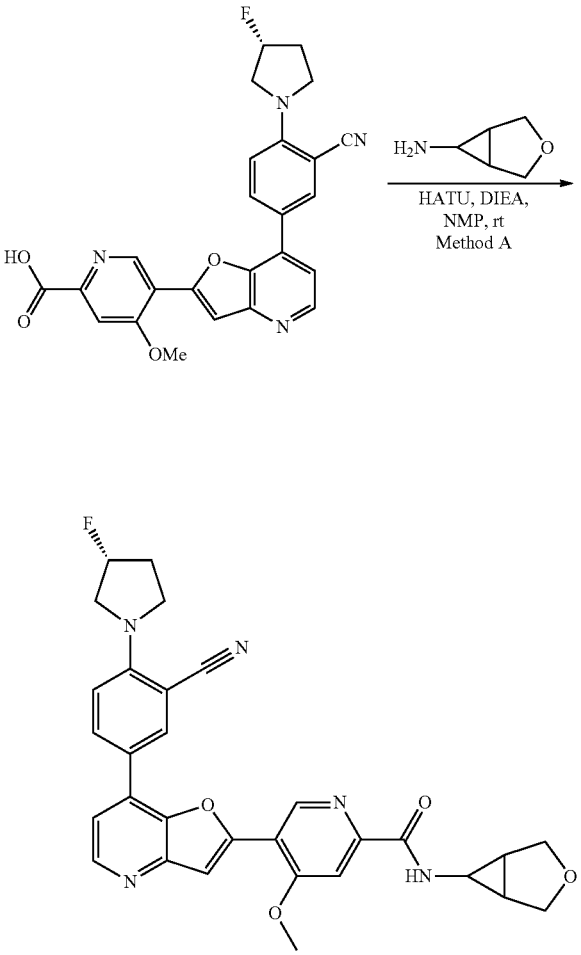

The title compound was prepared from 5-(7-(3-cyano-4-(3-fluoropyrrolidin-1-yl)phenyl)furo[3,2-b]pyridin-2-yl)-4-methoxypicolinic acid and 3-oxa-bicyclo[3.1.0]hexan-6-amine using Method A. The product was purified by prep-HPLC under the following conditions: column, XBridge Prep C18 OBD Column, 150 mm 5 um; mobile phase, acetonitrile in water (with 0.05% $NH_3H_2O$), 40% to 70% gradient in 8 min; detector, UV 254 nm. 5-[7-[3-cyano-4-(3-fluoropyrrolidin-1-yl)phenyl]furo[3,2-b]pyridin-2-yl]-4-methoxy-N-[3-oxabicyclo[3.1.0]hexan-6-yl]pyridine-2-carboxamide was obtained as a yellow solid (15 mg, 14%). HPLC: 94.0% purity, RT=2.86 min. MS: m/z=540.2 [M+H]$^+$. $^1$H NMR (300 MHz, DMSO-d$_6$, ppm) δ 9.10-9.01 (m, 2H), 8.56 (d, J=5.1 Hz, 1H), 8.40 (d, J=2.3 Hz, 1H), 8.25 (dd, J=9.1, 2.4 Hz, 1H), 7.82 (s, 1H), 7.76-7.65 (m, 2H), 7.05 (d, J=9.2 Hz, 1H), 5.66-5.38 (m, 1H), 4.20 (s, 3H), 4.00-3.75 (m, 6H), 3.69-3.59 (m, 2H), 2.75-2.65 (m, 1H), 2.40-1.95 (m, 4H).

The title compound was prepared from (R)-5-(7-(3-cyano-4-(3-fluoropyrrolidin-1-yl)phenyl)furo[3,2-b]pyridin-2-yl)-4-methoxypicolinic acid and 3-oxa-bicyclo[3.1.0]hexan-6-amine using Method A. The product was purified by prep-HPLC under the following conditions: column, XBridge Prep C18 OBD Column, 150 mm 5 um; mobile phase, acetonitrile in water (with 0.05% $NH_3H_2O$), 30% to 60% gradient in 8 min; detector, UV 254 nm. 5-(7-[3-cyano-4-[(3R)-3-fluoropyrrolidin-1-yl]phenyl]furo[3,2-b]pyridin-2-yl)-4-methoxy-N-[3-oxabicyclo[3.1.0]hexan-6-yl]pyridine-2-carboxamide was obtained as a yellow solid (12 mg, 19%). HPLC: 94.5% purity, RT=1.11 min. MS: m/z=540.0 [M+H]$^+$. $^1$H NMR (300 MHz, DMSO-d$_6$, ppm) δ 9.06 (s, 1H), 9.01 (d, J=5.2 Hz, 1H), 8.55 (d, J=5.1 Hz, 1H), 8.39 (d, J=2.3 Hz, 1H), 8.24 (dd, J=9.2, 2.4 Hz, 1H), 7.82 (s, 1H), 7.75-7.64 (m, 2H), 7.05 (d, J=9.2 Hz, 1H), 5.67-5.39 (m, 1H), 4.20 (s, 3H), 4.12-3.75 (m, 6H), 3.69-3.60 (m, 2H), 2.76-2.66 (m, 1H), 2.39-2.10 (m, 2H), 2.08-1.97 (m, 2H).

Example 429: 4-[7-[3-cyano-4-(oxan-4-yloxy)phenyl]furo[3,2-b]pyridin-2-yl]-2-methoxy-N,N-dimethylbenzamide (470)

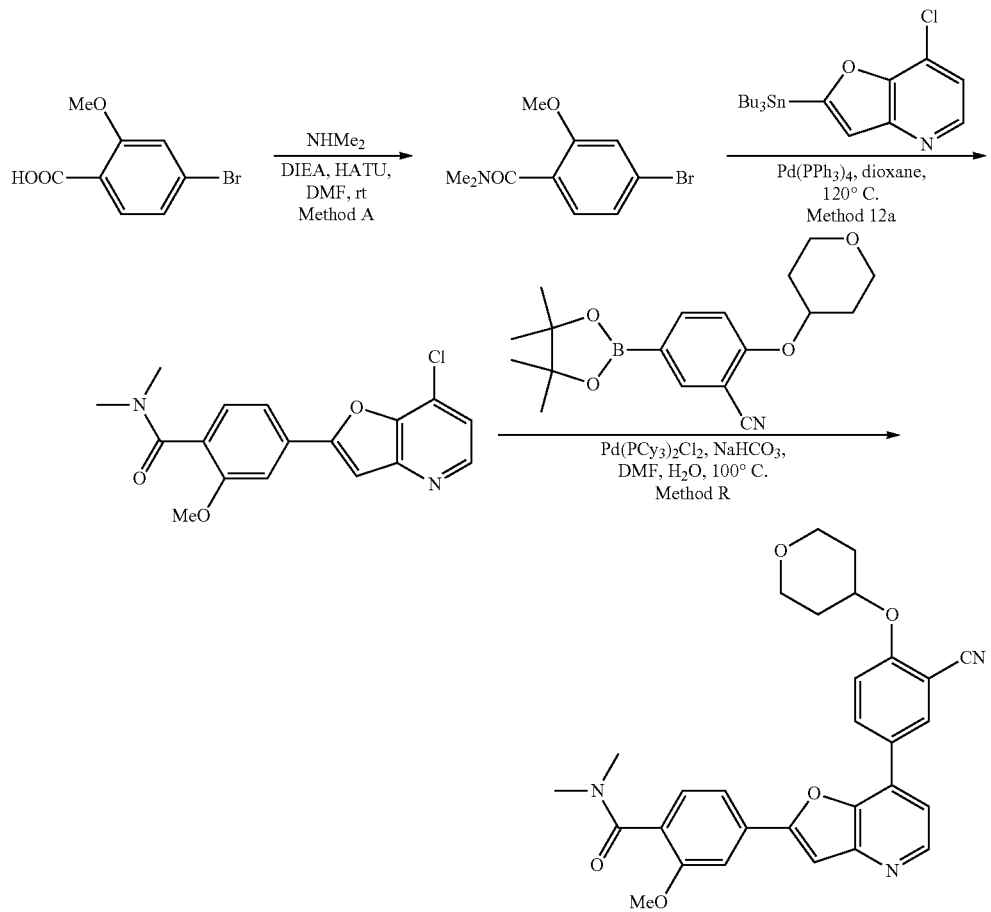

The title compound was prepared from 4-bromo-2-methoxybenzoic acid, dimethylamine, 7-chloro-2-(tributylstannyl)furo[3,2-b]pyridine, and 2-(tetrahydro-2H-pyran-4-yloxy)-5-(4,4,5,5-tetramethyl-1,3,2-dioxaborolan-2-yl)benzonitrile using Methods A, 12 and R. The final product was purified by prep-HPLC under the following conditions: column, XBridge Prep C18 OBD Column, 150 mm 5 um; mobile phase, acetonitrile in water (with 0.05% $NH_3H_2O$), 30% to 60% gradient in 8 min; detector, UV 254 nm. 4-[7-[3-cyano-4-(oxan-4-yloxy)phenyl]furo[3,2-b]pyridin-2-yl]-2-methoxy-N,N-dimethylbenzamide was obtained as a yellow solid (28 mg, 21% for 3 steps). HPLC: 99.6% purity, RT=2.96 min. MS: m/z=498.2 [M+H]+. $^1$H NMR (300 MHz, $CD_3OD$, ppm) δ 8.53-8.43 (m, 2H), 8.34 (dd, J=9.0, 2.4 Hz, 1H), 7.69-7.42 (m, 5H), 7.35 (d, J=8.1 Hz, 1H), 4.96-4.86 (m, 1H), 4.06-3.92 (m, 5H), 3.72-3.58 (m, 2H), 3.09 (s, 3H), 2.90 (s, 3H), 2.17-2.05 (m, 2H), 1.93-1.76 (m, 2H).

Example 430: 4-(7-[3-cyano-4-[(2,2,6,6-tetramethyloxan-4-yl)amino]phenyl]furo[3,2-b]pyridin-2-yl)-3-methoxy-N,N-dimethylbenzamide (471)

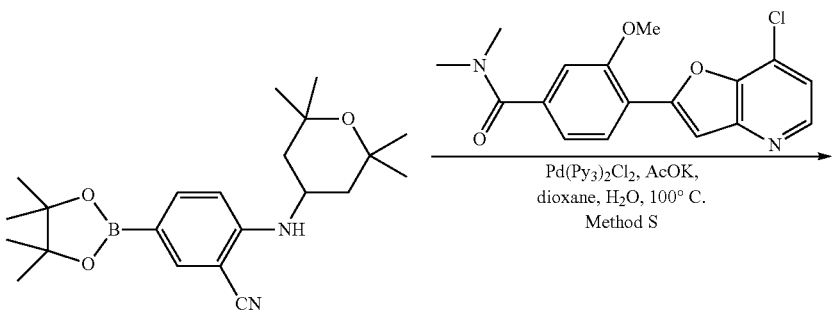

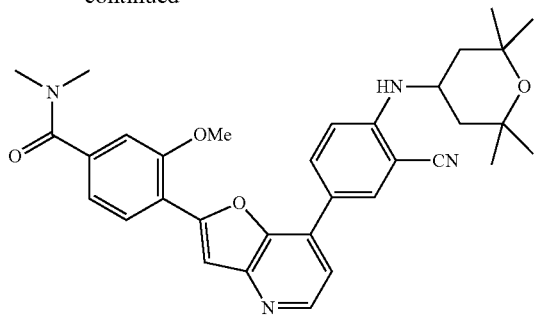

The title compound was prepared from 4-(7-chlorofuro[3,2-b]pyridin-2-yl)-3-methoxy-N,N-dimethylbenzamide and 5-(4,4,5,5-tetramethyl-1,3,2-dioxaborolan-2-yl)-2-(2,2,6,6-tetramethyl-tetrahydro-2H-pyran-4-ylamino)benzonitrile using Method S. The product was purified by prep-HPLC under the following conditions: column, Gemini-NX C18 AXAI Packed, 21×150 mm 5 um; mobile phase, acetonitrile in water (with 10 mmol/L $NH_4HCO_3$), 20% to 50% gradient in 8 min; detector, UV 254 nm. 4-(7-[3-cyano-4-[(2,2,6,6-tetramethyloxan-4-yl)amino]phenyl]furo[3,2-b]pyridin-2-yl)-3-methoxy-N,N-dimethylbenzamide was obtained as a light yellow solid (25 mg, 7%). HPLC: 98.3% purity, RT=1.33 min. MS: m/z=553.0 [M+H]$^+$. $^1$H NMR (400 MHz, CD$_3$OD, ppm) δ 8.45-8.35 (m, 1H), 8.25-8.15 (m, 2H), 8.10-8.00 (m, 1H), 7.52-7.42 (m, 2H), 7.22 (s, 1H), 7.18 (d, J=5.2 Hz, 1H), 7.10-7.00 (m, 1H), 4.20-4.05 (m, 4H), 3.14 (s, 3H), 3.07 (s, 3H), 2.06 (dd, J=12.4, 2.8 Hz, 2H), 1.48-1.38 (m, 8H), 1.27 (s, 6H).

Example 431: N-(1-Aza-bicyclo[2.2.2]oct-3-yl)-4-(7-[3-cyano-4-(tetrahydro-pyran-4-yloxy)-phenyl]-furo[3,2-b]pyridin-2-yl)-3-methoxy-N-methyl-benzamide (472)

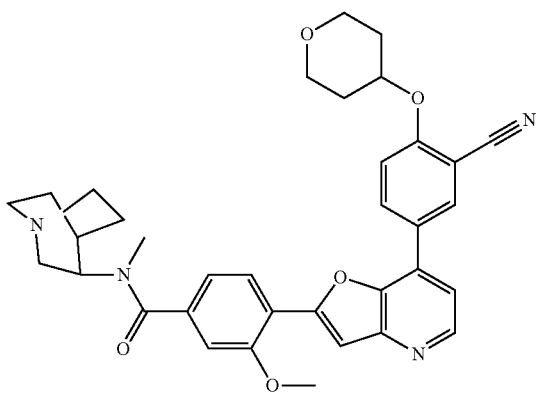 [SMILES: CCCC1CCNCC1N(C)C(=O)c1ccc(-c2cc3nccc(-c4ccc(OC5CCOCC5)c(C#N)c4)c3o2)c(OC)c1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), (1-Aza-bicyclo[2.2.2]oct-3-yl)-methyl-amine (53.65 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), (HATU), and Ethyl-diisopropyl-amine (0.28 ml; 1.59 mmol; 5.00 eq.) in DMF (3.0 mL) 70 mg (37%). MS: m/z=594.2 [M+H]$^+$. $^1$H NMR (400 MHz, Chloroform-d) δ 8.54-8.38 (m, 2H), 8.27-8.09 (m, 2H), 7.95 (t, J=6.9 Hz, 1H), 7.61-7.46 (m, 1H), 7.31-7.18 (m, 2H), 7.11 (d, J=4.8 Hz, 2H), 4.77 (m, 1H), 4.38 (m, 1H), 4.02 (s, 3H), 4.01 (m, 2H), 3.79-3.54 (m, 4H), 3.42 (m, 2H), 3.28-3.11 (m, 2H), 3.07 (s, 3H), 2.21 (d, J=13.8 Hz, 1H), 2.08 (t, J=7.8 Hz, 2H), 2.02-1.80 (m, 5H).

Example 432: 4-{7-[3-Cyano-4-(tetrahydro-pyran-4-yloxy)-phenyl]-furo[3,2-b]pyridin-2-yl}-3-methoxy-N-methyl-N-(2-pyrrolidin-1-yl-ethyl)-benzamide (473)

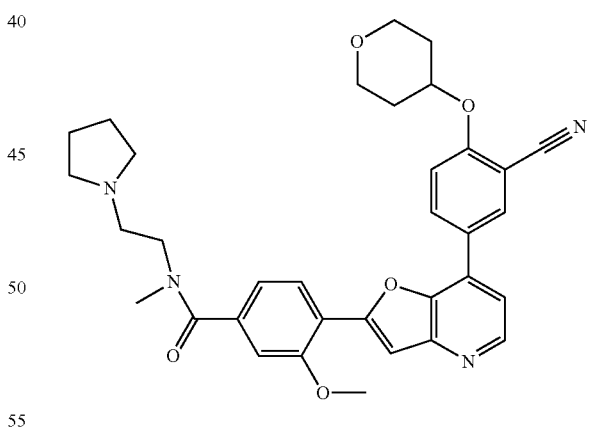

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), Methyl-(2-pyrrolidin-1-yl-ethyl)-amine (49.05 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), (HATU), and Ethyl-diisopropyl-amine (0.28 ml; 1.59 mmol; 5.00 eq.) in DMF (3.0 mL) (80 mg, 43%). MS: m/z=581.2 [M+H]+.

Example 433: 5-(2-[2-Methoxy-4-(2-methyl-2,6-diaza-bicyclo[3.2.0]heptane-6-carbonyl)-phenyl]-furo[3,2-b]pyridin-7-yl)-2-(tetrahydro-pyran-4-yloxy)-benzonitrile (474)

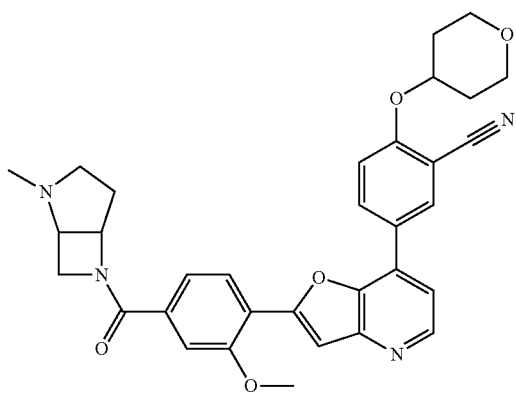 [SMILES: COc1cc(C(=O)N2CC3C2CCN3C)ccc1-c1cc2nccc(-c3ccc(OC4CCOCC4)c(C#N)c3)c2o1]

The title compound was synthesized according to the procedure described in example 79 using 5-{2-[4-(2,6-Di-aza-bicyclo[3.2.0]heptane-6-carbonyl)-2-methoxy-phenyl]-furo[3,2-b]pyridin-7-yl}-2-(tetrahydro-pyran-4-yloxy)-benzonitrile hydrochloride (50.00 mg; 0.09 mmol; 1.00 eq.), Formaldehyde (0.50 ml) solution, palladium on activated carbon (dry) (18.13 mg; 0.02 mmol; 0.20 eq.) in Methanol (30.00 ml) under hydrogen atmosphere. (19 mg, 40%). MS: m/z=566.2 [M+H]+. $^1$H NMR (400 MHz, Chloroform-d) δ 8.62 (d, J=3.7 Hz, 1H), 8.33 (s, 1H), 8.19 (d, J=9.1 Hz, 1H), 8.03 (d, J=8.0 Hz, 1H), 7.72 (d, J=2.7 Hz, 1H), 7.46 (s, 1H), 7.39-7.29 (m, 2H), 7.23 (m 1H), 5.18 (s, 1H), 4.82 (m, 1H), 4.17-3.94 (m, 5H), 3.71 (m, 2H), 3.26-2.80 (m, 2H), 2.50 (s, 3H), 2.33 (m, 2H), 2.22-2.06 (m, 4H), 2.05-1.90 (m, 3H).

Example 434: 4-{7-[3-Cyano-4-(tetrahydro-pyran-4-yloxy)-phenyl]-furo[3,2-b]pyridin-2-yl}-N-(1-hydroxymethyl-cyclopentyl)-3-methoxy-benzamide (475)

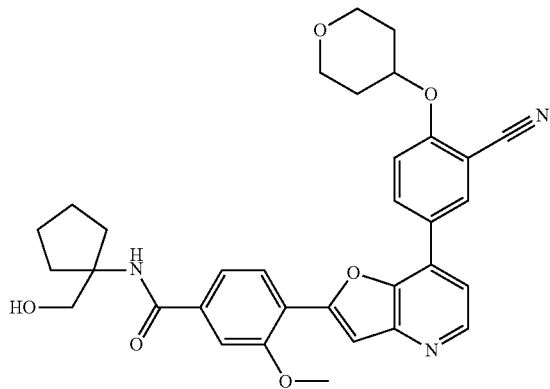 [SMILES: COc1cc(C(=O)NC2(CO)CCCC2)ccc1-c1cc2nccc(-c3ccc(OC4CCOCC4)c(C#N)c3)c2o1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), (1-Amino-cyclopentyl)-methanol (44.06 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), (HATU), and Ethyl-diisopropyl-amine (0.28 ml; 1.59 mmol; 5.00 eq.) in DMF (3.0 mL) 132 mg, 72%). MS: m/z=569.2 [M+H]+. $^1$H NMR (400 MHz, DMSO-d$_6$) δ 8.56 (d, J=5.1 Hz, 1H), 8.51-8.39 (m, 2H), 8.00 (m, 1H), 7.89 (s, 1H), 7.63 (m, 5H), 5.01-4.91 (m, 1H), 4.87 (m, 1H), 4.10 (s, 3H), 3.91 (m, 2H), 3.68-3.52 (m, 4H), 3.18 (m, 1H), 2.06 (m, 4H), 1.85-1.66 (m, 4H), 1.60 (d, J=8.4 Hz, 2H).

Example 435: 4-{7-[3-Cyano-4-(tetrahydro-pyran-4-yloxy)-phenyl]-furo[3,2-b]pyridin-2-yl}-N-((1S,2R)-2-hydroxy-cyclohexyl)-3-methoxy-benzamide (476)

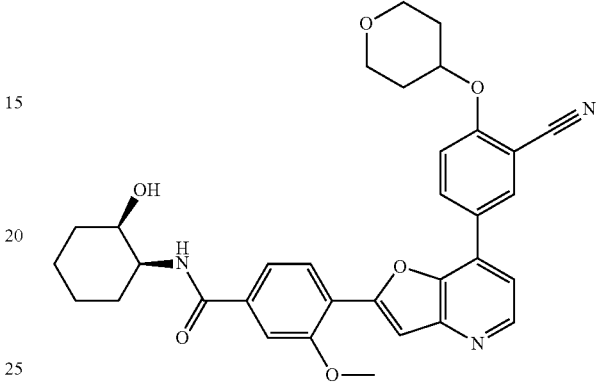

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), cis-2-Amino-cyclohexanol hydrochloride (58.01 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), (HATU), and Ethyl-diisopropyl-amine (0.28 ml; 1.59 mmol; 5.00 eq.) in DMF (3.0 mL) (113 mg, 62%). MS: m/z=568.3 [M+H]+. $^1$H NMR (400 MHz, Chloroform-d) δ 8.62-8.44 (m, 1H), 8.27 (d. J=2.5 Hz, 1H), 8.16 (dd, J=8.8, 2.6 Hz, 1H), 7.95 (dd, J=8.1, 2.0 Hz, 1H), 7.63 (d, J=2.0 Hz, 1H), 7.57 (s, 1H), 7.39 (d, J=8.1 Hz, 1H), 7.29 (s, 1H), 7.24-7.08 (m, 1H), 6.76 (d, J=8.1 Hz, 1H), 4.80 (m, 1H), 4.07 (s, 3H), 4.27-3.95 (m, 3H), 3.70 (m, 2H), 2.15 (m, 2H), 1.98 (m, 3H), 1.85 (m, 2H), 1.81-1.62 (m, 4H), 1.57-1.43 (m, 2H).

Example 436: N-(2-Azetidin-1-yl-ethyl)-4-(7-[3-cyano-4-(tetrahydro-pyran-4-yloxy)-phenyl]-furo[3,2-b]pyridin-2-yl)-3-methoxy-benzamide (477)

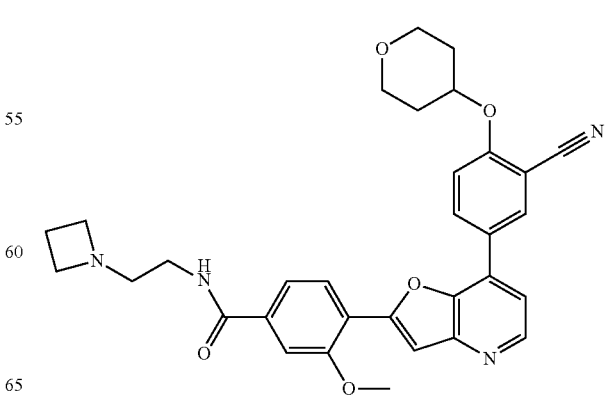

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 2-Azetidin-1-yl-ethylamine (38.32 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), (HATU), and Ethyl-diisopropyl-amine (0.28 ml; 1.59 mmol; 5.00 eq.) in DMF (3.0 mL) (92 mg, 52%). MS: m/z=554.1 [M+H]+.
$^1$H NMR (400 MHz, Chloroform-d) δ 8.60 (t, J=3.7 Hz, 1H), 8.30 (d, J=3.0 Hz, 1H), 8.21 (d, J=8.7 Hz, 1H), 8.04 (dd, J=8.1, 2.5 Hz, 1H), 7.69 (d, J=2.6 Hz, 1H), 7.65 (s, 1H), 7.47 (d, J=8.1 Hz, 1H), 7.32 (t, J=3.7 Hz, 1H), 7.22 (dd, J=9.1, 2.5 Hz, 1H), 7.03 (s, 1H), 4.87-4.75 (m, 1H), 4.07 (s, 3H) 4.16-3.98 (m, 2H), 3.70 (m, 2H), 3.47 (m, 2H), 3.29 (m, 4H), 2.69 (d, J=6.0 Hz, 2H), 2.15 (m, 6H).

Example 437: 5-(2-[2-Methoxy-4-(2-methyl-tetrahydro-pyridazine-1-carbonyl)-phenyl]-furo[3,2-b]pyridin-7-yl)-2-(tetrahydro-pyran-4-yloxy)-benzonitrile (478)

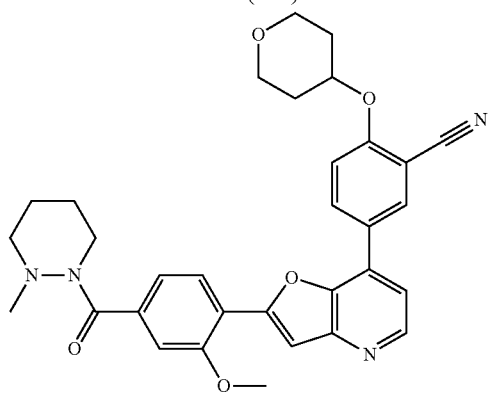

The title compound was synthesized according to the procedure described in example 79 using 5-{2-[2-Methoxy-4-(tetrahydro-pyridazine-1-carbonyl)-phenyl]-furo[3,2-b]pyridin-7-yl}-2-(tetrahydro-pyran-4-yloxy)-benzonitrile (60.00 mg; 0.11 mmol; 1.00 eq.), Formaldehyde (37% w/w Aq. solution) (0.50 ml 1.11 mmol), palladium on activated carbon (dry) (23.71 mg; 0.02 mmol; 0.20 eq.) in Methanol (30.00 ml) under H2 atmosphere (10 mg, 16%). MS: m/z=553.2 [M+H]+

Example 438: N-(1,1-Bis-hydroxymethyl-propyl)-4-(7-[3-cyano-4-(tetrahydro-pyran-4-yloxy)-phenyl]-furo[3,2-b]pyridin-2-yl)-3-methoxy-benzamide (479)

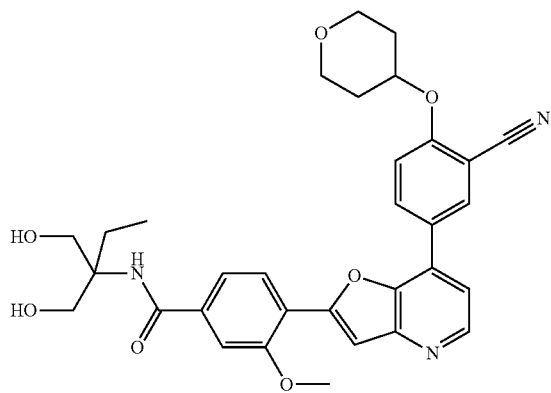 [SMILES: CCC(CO)(CO)NC(=O)c1ccc(-c2cc3nccc(-c4ccc(OC5CCOCC5)c(C#N)c4)c3o2)c(OC)c1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.38 mmol; 1.00 eq.), 2-Amino-2-ethyl-propane-1,3-diol (45.59 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), (HATU), and Ethyl-diisopropyl-amine (0.28 ml; 1.59 mmol; 5.00 eq.) in DMF (3.0 mL) (90 mg, 49%). MS: m/z=572.2 [M+H]+.

Example 439: 4-(7-[3-Cyano-4-(tetrahydro-pyran-4-yloxy)-phenyl]-furo[3,2-b]pyridin-2-yl)-N-(2-hydroxy-1,1-dimethyl-ethyl)-3-methoxy-N-methyl-benzamide (480)

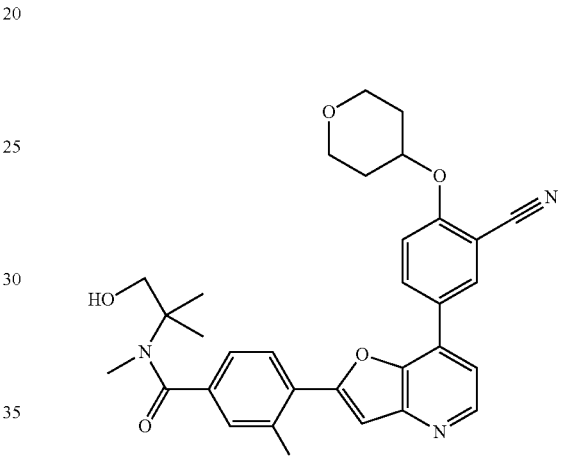

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), 2-Methyl-2-methylamino-propan-1-ol (39.47 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), (HATU), and Ethyl-diisopropyl-amine (0.28 ml; 1.59 mmol; 5.00 eq.) in DMF (3.0 mL) (30 mg, 17%). MS: m/z=557.2 [M+H]+. $^1$H NMR (400 MHz, Chloroform-d) δ 8.59 (d, J=3.8 Hz, 1H), 8.26 (m, 1H), 8.19 (d, J=9.0 Hz, 1H), 8.04 (d, J=8.7, 1H), 7.78 (dd, J=8.3, 2.7 Hz, 1H), 7.72 (d, J=3.8 Hz, 2H), 7.30 (dd, J=8.7, 4.9 Hz, 1H), 7.20 (m, 1H), 4.88-4.71 (m, 1H), 4.23 (d, J=2.7 Hz, 2H), 4.1 (s, 3H), (3.98, 2H), 3.69 (m, 2H), 2.42 (m, 3H), 2.13 (m, 2H), 2.03-1.83 (m, 4H), 1.22 (d, J=2.7 Hz, 6H).

Example 440: N-tert-Butyl-4-{7-[3-cyano-4-(tetra-hydro-pyran-4-yloxy)-phenyl]-furo[3,2-b]pyridin-2-yl}-3-methoxy-N-methyl-benzamide (481)

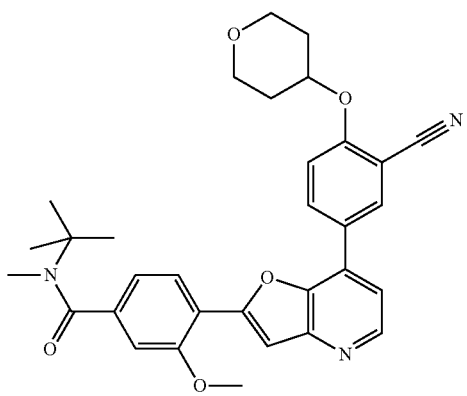 [SMILES: COc1cc(C(=O)N(C)C(C)(C)C)ccc1-c1cc2nccc(-c3ccc(OC4CCOCC4)c(C#N)c3)c2o1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), tert-Butyl-methyl-amine (33.35 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), (HATU), and Ethyl-diisopropyl-amine (0.28 ml; 1.59 mmol; 5.00 eq.) in DMF (3.0 mL) (100 mg, 58%). MS: m/z=541.1 [M+H]+. $^1$H NMR (400 MHz, Chloroform-d) δ 8.56 (d, J=5.1, 1H), 8.29 (d, J=2.6 Hz, 1H), 8.21-8.15 (m, 1H), 7.97 (d, J=8.1, 1H), 7.62 (d, J=2.7 Hz, 1H), 7.29 (d, J=5.0, 1H), 7.22-7.11 (m, 3H), 4.89-4.65 (m, 1H), 4.01 (s, 3H), 4.06 (m, 2H), 3.69 (m, 2H), 3.03-2.80 (m, 2H), 2.05 (m, 5H), 1.64-1.42 (m, 9H).

Example 441: 5-(2-[2-Methoxy-4-(tetrahydro-pyridazine-1-carbonyl)-phenyl]-furo[3,2-b]pyridin-7-yl)-2-(tetrahydro-pyran-4-yloxy)-benzonitrile (482)

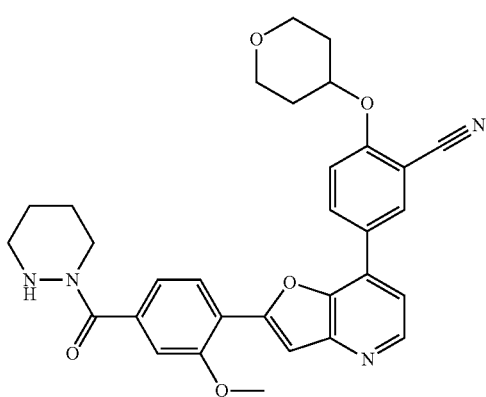 [SMILES: COc1cc(C(=O)N2CCCCN2)ccc1-c1cc2nccc(-c3ccc(OC4CCOCC4)c(C#N)c3)c2o1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), Hexahydro-pyridazine hydrochloride (2) (60.85 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), (HATU), and Ethyl-diisopropyl-amine (0.28 ml; 1.59 mmol; 5.00 eq.) in DMF (3.0 mL) (70 mg, 41%). MS: m/z=540.1 [M+H]+. $^1$H NMR (400 MHz, Chloroform-d) δ 8.58 (d, J=4.7 Hz, 1H), 8.27 (s, 1H), 8.19 (d, J=8.9 Hz, 1H), 7.99 (d, J=7.9 Hz, 1H), 7.64 (s, 1H), 7.29 (t, J=3.9 Hz, 2H), 7.24-7.16 (m, 2H), 4.91-4.69 (m, 1H), 4.01 (s, 3H) 4.06 (m, 2H), 3.69 (m, 4H), 3.03 (m, 2H), 2.28-1.49 (m, 8H).

Example 442: 4-{7-[3-Cyano-4-(tetrahydro-pyran-4-yloxy)-phenyl]-furo[3,2-b]pyridin-2-yl}-N-(2-methanesulfonyl-ethyl)-3-methoxy-N-methyl-benzamide (483)

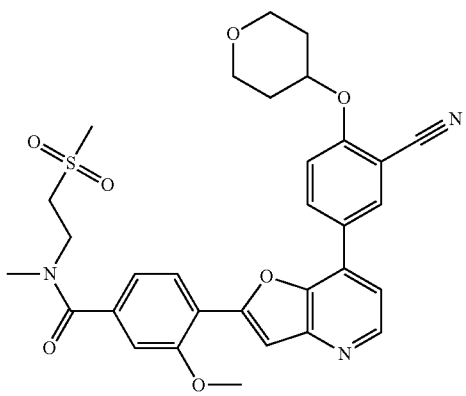 [SMILES: COc1cc(C(=O)N(C)CCS(C)(=O)=O)ccc1-c1cc2nccc(-c3ccc(OC4CCOCC4)c(C#N)c3)c2o1]

The title compound was synthesized according to the procedure described in example 201 using 4-{7-[3-Cyano-4-(tetrahydro-pyran-4-yloxy)-phenyl]-furo[3,2-b]pyridin-2-yl}-3-methoxy-benzoic acid (150.00 mg; 0.32 mmol; 1.00 eq.), (2-Methanesulfonyl-ethyl)-methyl-amine (52.49 mg; 0.38 mmol; 1.20 eq.), [Dimethylamino-([1,2,3]triazolo[4,5-b]pyridin-3-yloxy)-methylene]-dimethyl-ammonium; hexafluoro phosphate (HATU) (145.47 mg; 0.38 mmol; 1.20 eq.), (HATU), and Ethyl-diisopropyl-amine (0.28 ml; 1.59 mmol; 5.00 eq.) in DMF (3.0 mL) (85 mg, 45%). $^1$H NMR (400 MHz, Chloroform-d) δ 8.54 (d, J=4.9 Hz, 1H), 8.22 (d, J=4.4 Hz, 1H), 8.17 (d, J=8.6 Hz, 1H), 7.99 (d, J=8.5, 1H), 7.61 (d, J=5.1 Hz, 1H), 7.28 (t, J=4.5 Hz, 1H), 7.20 (s, 1H), 7.1 (d. J=7.8 Hz, 2H), 4.77 (m, 1H), 4.03 (s, 3H), 3.94-4.10 (m, 4H), 3.66 (m, 2H), 3.48 (m, 2H), 3.13 (s, 3H), 3.05 (m, 3H), 2.11 (m, 2H), 1.95 (m, 2H).

Example 443: 4-{7-[3-Cyano-4-(1-methyl-azetidin-3-yloxy)-phenyl]-furo[3,2-b]pyridin-2-yl}-3-methoxy-N,N-dimethyl-benzamide (484)

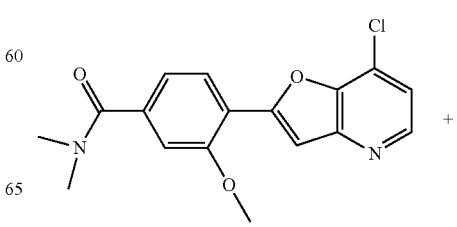

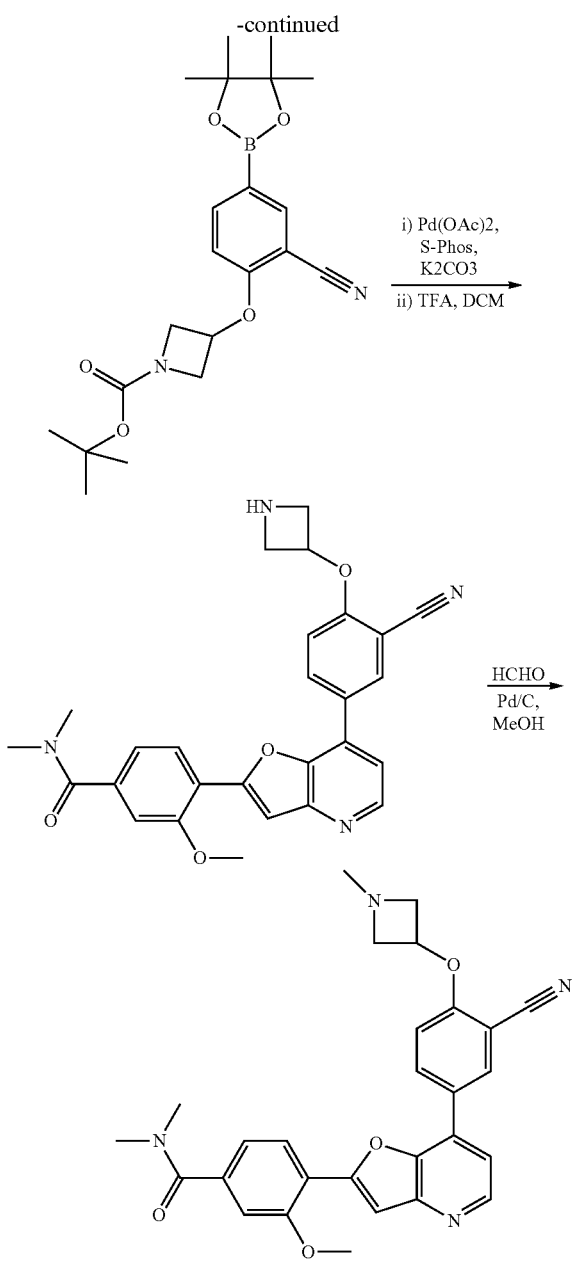

4-{7-[4-(Azetidin-3-yloxy)-3-cyano-phenyl]-furo[3,2-b]pyridin-2-yl}-3-methoxy-N,N-dimethyl-benzamide 3-{2-Cyano-4-[2-(4-dimethylcarbamoyl-2-methoxy-phenyl)-furo[3,2-b]pyridin-7-yl]-phenoxy}-azetidine-1-carboxylic acid tert-butyl ester was synthesized according to the procedure described in example 64 using 4-(7-Chloro-furo[3,2-b]pyridin-2-yl)-3-methoxy-N,N-dimethyl-benzamide (200.00 mg; 0.60 mmol; 1.00 eq.), 3-[2-Cyano-4-(4,4,5,5-tetramethyl-[1,3,2]dioxaborolan-2-yl)-phenoxy]-azetidine-1-carboxylic acid tert-butyl ester (290.44 mg; 0.73 mmol; 1.20 eq.), Dicyclohexyl-(2',6'-dimethoxy-biphenyl-2-yl)-phosphane (74.47 mg; 0.18 mmol; 0.30 eq.), dipotassium carbonate (167.13 mg; 1.21 mmol; 2.00 eq.) and diacetoxy-palladium (27.15 mg; 0.12 mmol; 0.20 eq.) using a MW oven vial in 1,4-dioxane (20 ml) and water (2 ml). (203 mg, 48%). MS: m/z=469.1 [M+H]+. The boc group was deprotected in DCM by treating a solution of 3-{2-Cyano-4-[2-(4-dimethylcarbamoyl-2-methoxy-phenyl)-furo[3,2-b]pyridin-7-yl]-phenoxy}-azetidine-1-carboxylic acid tert-butyl ester (203.00 mg; 0.36 mmol; 1.00 eq.) in Dichloro-methane (15.00 ml) with Trifluoro-acetic acid (0.14 ml; 1.79 mmol; 5.00 eq.) to obtain 4-{7-[4-(Azetidin-3-yloxy)-3-cyano-phenyl]-furo[3,2-b]pyridin-2-yl}-3-methoxy-N,N-dimethyl-benzamide (88 mg, 42%)

4-{7-[3-Cyano-4-(1-methyl-azetidin-3-yloxy)-phenyl]-furo[3,2-b]pyridin-2-yl}-3-methoxy-N,N-dimethyl-benzamide The title compound was synthesized according to the procedure described in example 79 using 4-{7-[4-(Azetidin-3-yloxy)-3-cyano-phenyl]-furo[3,2-b]pyridin-2-yl}-3-methoxy-N,N-dimethyl-benzamide trifluoroacetate (60.00 mg; 0.10 mmol; 1.00 eq.), Formaldehyde (37% w/w Aq. solution) (0.50 ml) palladium on activated carbon (dry) (21.92 mg; 0.02 mmol; 0.20 eq. in Methanol (30.00 ml) under H2 atmosphere. MS: m/z=483.1 [M+H]+.

Example 444: 4-{7-[3-Cyano-4-(1-isopropyl-azetidin-3-yloxy)-phenyl]-furo[3,2-b]pyridin-2-yl}-3-methoxy-N,N-dimethyl-benzamide (485)

3-{2-Cyano-4-[2-(4-dimethylcarbamoyl-2-methoxy-phenyl)-furo[3,2-b]pyridin-7-yl]-phenoxy}-azetidine-1-carboxylic acid tert-butyl ester was synthesized according to the procedure described in example 64 using 4-(7-Chloro-furo[3,2-b]pyridin-2-yl)-3-methoxy-N,N-dimethyl-benzamide (300.00 mg; 0.91 mmol; 1.00 eq.), 3-[2-Cyano-4-(4,4,5,5-tetramethyl-[1,3,2]dioxaborolan-2-yl)-phenoxy]-azetidine-1-carboxylic acid tert-butyl ester (435.65 mg; 1.09 mmol; 1.20 eq.), Dicyclohexyl-(2',6'-dimethoxy-biphenyl-2-yl)-phosphane (111.70 mg; 0.27 mmol; 0.30 eq.), dipotassium carbonate (250.70 mg; 1.81 mmol; 2.00 eq.) and diacetoxy-palladium (40.73 mg; 0.18 mmol; 0.20 eq.) in 1,4-dioxane (20 ml) and water (2 ml). (400 mg, 71%). MS: m/z=569.2 [M+H]+. The boc group was deprotected in DCM by treating a solution of 3-{2-Cyano-4-[2-(4-dimethylcarbamoyl-2-methoxy-phenyl)-furo[3,2-b]pyridin-7-yl]-phenoxy}-azetidine-1-carboxylic acid tert-butyl ester (400.00 mg; 0.70 mmol; 1.00 eq.) in Dichloro-methane (15.00 ml) with Trifluoro-acetic acid (0.54 ml; 7.03 mmol; 10.00 eq.) to obtain 4-{7-[4-(Azetidin-3-yloxy)-3-cyano-phenyl]-furo[3,2-b]pyridin-2-yl}-3-methoxy-N,N-dimethyl-benzamide. MS: m/z=469.2 [M+H]+.

4-{7-[3-Cyano-4-(1-isopropyl-azetidin-3-yloxy)-phenyl]-furo[3,2-b]pyridin-2-yl}-3-methoxy-N,N-dimethyl-benzamide The title compound was synthesized according to the procedure described in example 79 using 4-{7-[4-(Azetidin-3-yloxy)-3-cyano-phenyl]-furo[3,2-b]pyridin-2-yl}-3-methoxy-N,N-dimethyl-benzamide trifluoroacetate (50.00 mg; 0.09 mmol; 1.00 eq.), Propan-2-one (0.50 ml; 0.86 mmol), palladium on activated carbon (18.27 mg; 0.02 mmol; 0.20 eq.) in Methanol (30.00 ml) under hydrogen atmosphere. (15 mg, 34%). MS: m/z=511.2 [M+H]+. $^1$H NMR (400 MHz, Chloroform-d) δ 8.58 (d, J=4.9, 1H), 8.27 (s, 1H), 8.18 (d, J=8.6 Hz, 1H), 8.00 (d, J=7.9, 1H), 7.65 (d, J=2.4 Hz, 1H), 7.29 (s, 1H), 7.15 (d, J=9.0 Hz, 2H), 6.97 (dd, J=8.9, 2.3 Hz, 1H), 4.96 (m, 1H), 4.07 (s, 3H), 3.94 (m, 2H), 3.24 (m, 2H), 3.16 (s, 3H), 3.06 (s, 3H), 2.55-2.41 (m, 1H), 1.02 (d, J=6.4, 6H).

Example 445: 6-{7-[3-Cyano-4-(3-fluoro-tetrahydro-pyran-4-yloxy)-phenyl]-furo[3,2-b]pyridin-2-yl}-5-methoxy-N,N-dimethyl-nicotinamide (486)

The title compound was synthesized according to the procedure described in example 49 from 6-(7-Chloro-furo[3,2-b]pyridin-2-yl)-5-methoxy-nicotinic acid ethyl ester (200.00 mg; 0.60 mmol; 1.00 eq.), 2-(3-Fluoro-tetrahydro-pyran-4-yloxy)-5-(4,4,5,5-tetramethyl-[1,3,2]dioxaborolan-2-yl)-benzonitrile (417.37 mg; 1.20 mmol; 2.00 eq.), Dicyclohexyl-(2',6'-dimethoxy-biphenyl-2-yl)-phosphane (74.03 mg; 0.18 mmol; 0.30 eq.), dipotassium carbonate (166.14 mg; 1.20 mmol; 2.00 eq.) diacetoxypalladium (26.99 mg; 0.12 mmol; 0.20 eq) in 1,4-dioxane (15 ml) and water (2 ml) to obtain 6-{7-[3-Cyano-4-(3-fluoro-tetrahydro-pyran-4-yloxy)-phenyl]-furo[3,2-b]pyridin-2-yl}-5-methoxy-nicotinic acid ethyl ester which was hydrolyzed and coupled with Dimethyl-amine in THF (0.08 ml; 0.16 mmol; 1.20 eq.) (20.00 mg, (29%). MS: m/z=517.2 [M+H]+.

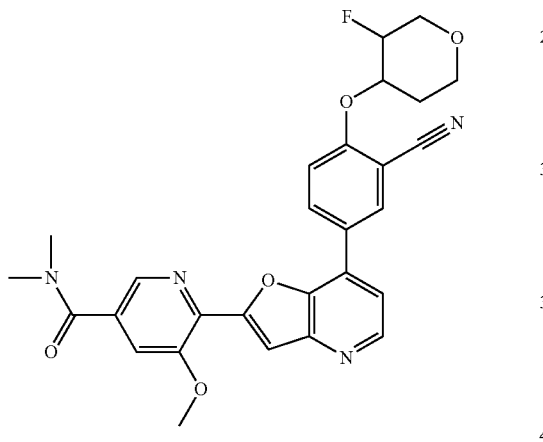

Example 446: 6-{7-[3-Cyano-4-(pyrrolidin-3-yloxy)-phenyl]-furo[3,2-b]pyridin-2-yl}-5-methoxy-N,N-dimethyl-nicotinamide (487)

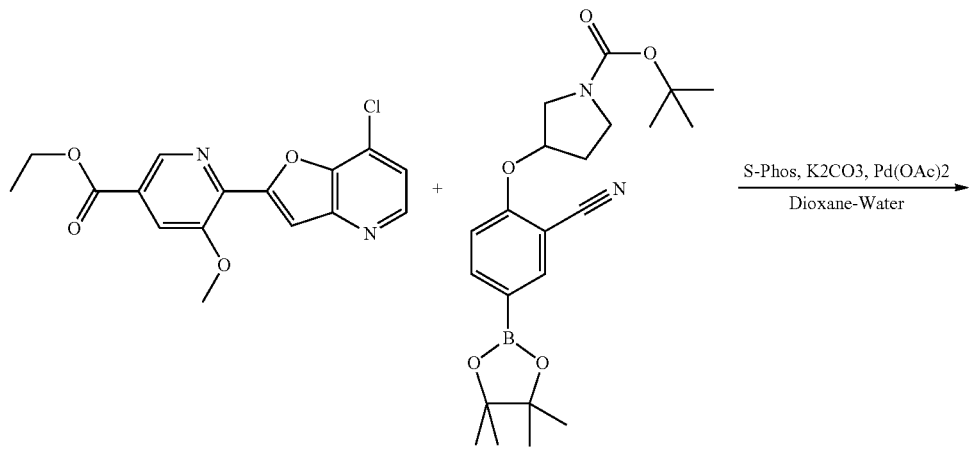

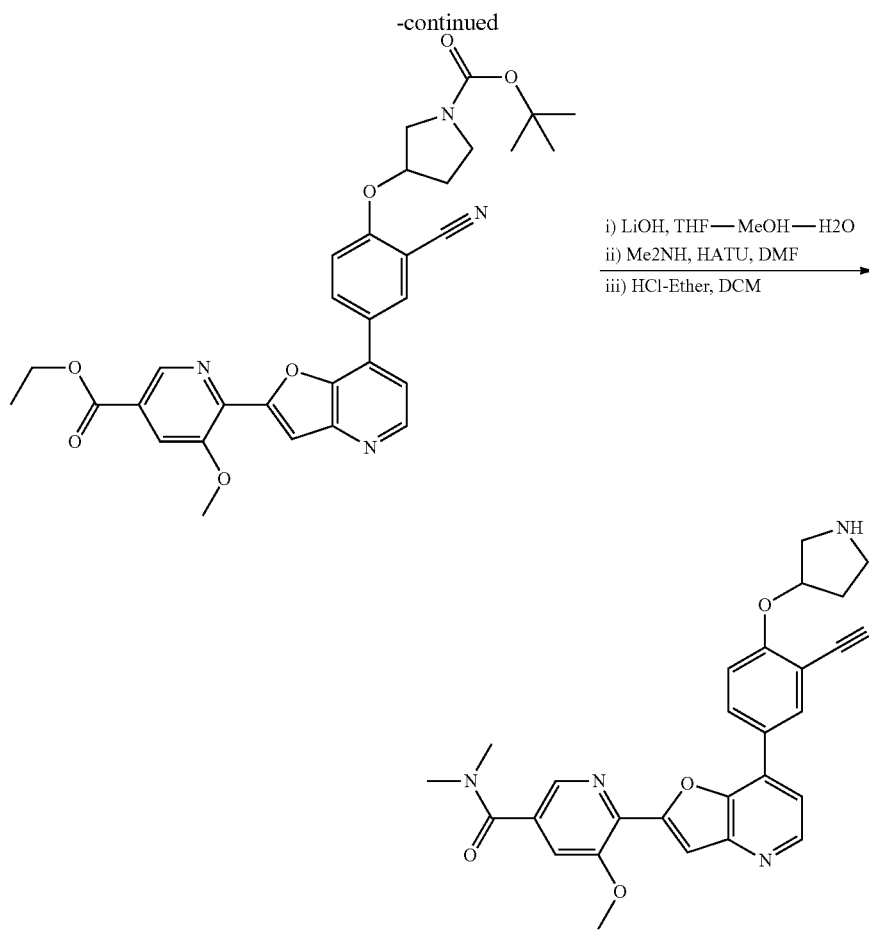

The title compound was synthesized according to the procedure described in example 49 from 6-(7-Chloro-furo[3,2-b]pyridin-2-yl)-5-methoxy-nicotinic acid ethyl ester (200.00 mg; 0.60 mmol; 1.00 eq.), 3-[2-Cyano-4-(4,4,5,5-tetramethyl-[1,3,2]dioxaborolan-2-yl)-phenoxy]-pyrrolidine-1-carboxylic acid tert-butyl ester (498.05 mg; 1.20 mmol; 2.00 eq.), Dicyclohexyl-(2',6'-dimethoxy-biphenyl-2-yl)-phosphane (74.03 mg; 0.18 mmol; 0.30 eq.), dipotassium carbonate (166.14 mg; 1.20 mmol; 2.00 eq.) and diacetoxypalladium (26.99 mg; 0.12 mmol; 0.20 eq.) and Dimethyl-amine in THF (0.08 ml; 0.16 mmol; 1.20 eq.) (20.00 mg, (290%). MS: m/z=484.1 [M+H]+. ¹H NMR (400 MHz, Chloroform-d) δ 8.66 (d, 1H), 8.45 (s, 1H), 8.37 (s, 1H), 8.32 (d, J=8.7, 1H), 7.87 (s, 1H), 7.54 (s, 1H), 7.40 (d. J=4.4, 1H), 7.19 (d. J=8.8, 1H), 5.05 (m, 1H), 4.13 (s, 3H), 3.34 (m, 2H), 3.19 (s, 3H), 3.13 (s, 3H), 3.05-2.93 (m, 2H), 2.32-2.04 (m, 2H).

Example 447: 2-{7-[6-Cyano-6-5-(3-fluoro-pyrrolidin-1-yl)-pyridin-3-yl]-furo[3,2-b]pyridin-2-yl}-5-methoxy-N,N-dimethyl-nicotinamide (488)

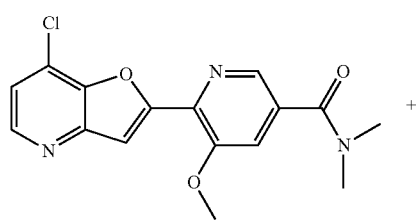

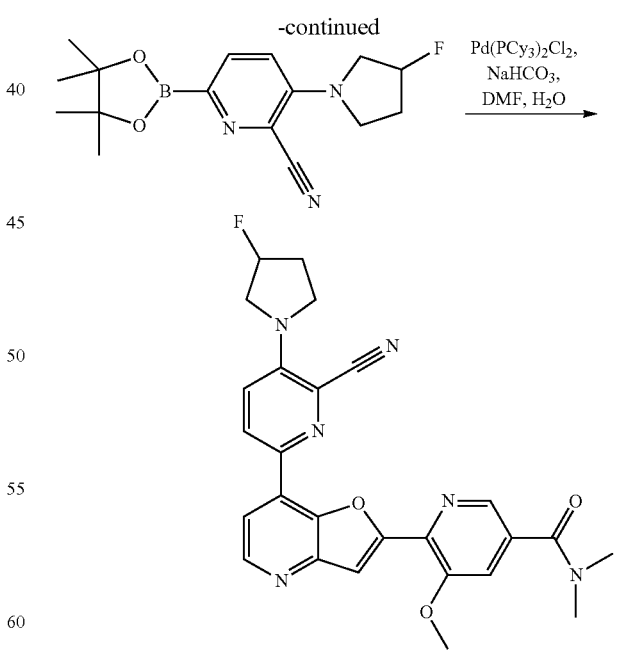

The title compound was synthesized according to the procedure described in example 32 using 6-(7-Chloro-furo[3,2-b]pyridin-2-yl)-5-methoxy-N,N-dimethyl-nicotinamide (70.00 mg; 0.21 mmol; 1.00 eq.), 2-(3-fluro-pyrrolidin-1-yl)-5-(4,4,5,5-tetramethyl-[1,3,2]dioxaborolan-2-yl)- nicotinonitrile (104.19 mg; 0.32 mmol; 1.50 eq.), sodium bicarbonate (53.18 mg; 0.63 mmol; 3.00 eq.) and dichloropalladium tricyclohexylphosphane (77.88 mg; 0.11 mmol; 0.50 eq.) in DMF (5 mL), water (1 mL) in the sealed vial under microwave irradiation. (63 mg, 61% yield). MS: 487 (M+H). $^1$H NMR (DMSO-d6): 8.61 (2H), 8.41 (1H), 7.98 (1H), 7.83 (1H), 7.75 (1H), 7.67 (1H), 5.56 (1H), 5.49 (1H), 4.32 (1H), 4.08 (3H), 3.83 (2H), 3.40 (2H), 3.02 (3H).

Example 448: 2-(7-[5-Cyano-6-(3-fluoro-pyrrolidin-1-yl)-pyridin-3-yl]-furo[3,2-b]pyridin-2-yl)-5-methoxy-N,N-dimethyl-nicotinamide (489)

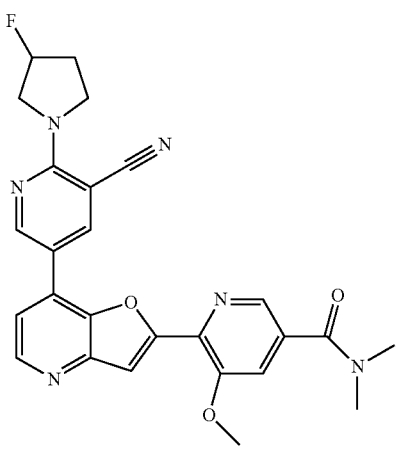 [SMILES: COc1cc(C(=O)N(C)C)cnc1-c1cc2nccc(-c3cnc(N4CCC(F)C4)c(C#N)c3)c2o1]

The title compound was synthesized according to the procedure described in example 32 using 6-(7-Chloro-furo[3,2-b]pyridin-2-yl)-5-methoxy-N,N-dimethyl-nicotinamide (70.00 mg; 0.21 mmol; 1.00 eq.), 6-(3-fluro-pyrrolidin-1-yl)-3-(4,4,5,5-tetramethyl-[1,3,2]dioxaborolan-2-yl)-nicotinonitrile (104.19 mg; 0.32 mmol; 1.50 eq.), sodium hydrogen carbonate (53.18 mg; 0.63 mmol; 3.00 eq.) and dichloropalladium tricyclohexylphosphane (77.88 mg; 0.11 mmol; 0.50 eq.) in DMF (5 mL) and water (1 mL) in a sealed vial under microwave irradiation. (21 mg, 20% yield). MS: 487 (M+H). $^1$H NMR (DMSO-d6): 9.28 (1H), 8.71 (1H), 8.62 (1H), 8.42 (1H), 7.84 (1H), 7.77 (1H), 7.57 (1H), 5.56 (1H), 5.49 (1H), 4.32 (1H), 4.08 (3H), 3.83 (2H), 3.40 (2H), 3.02 (3H).

Example 449: 6-{7-[5-Cyano-2-methoxy-phenyl)-furo[3,2-b]pyridin-2-yl}-5-methoxy-N,N-dimethyl-nicotinamide (490)

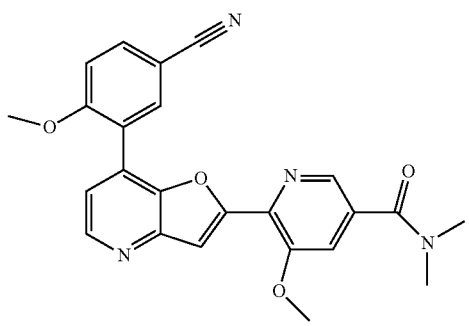

The title compound was synthesized according to the procedure described in example 32 using 6-(7-Chloro-furo[3,2-b]pyridin-2-yl)-5-methoxy-N,N-dimethyl-nicotinamide (100.00 mg; 0.30 mmol; 1.00 eq.), 5-cyano-2-methoxy phenyl boronic acid (64 mg; 0.36 mmol; 1.20 eq.), sodium hydrogen carbonate (83.18 mg; 0.60 mmol; 2.00 eq.) and dichloropalladium tricyclohexylphosphane (111 mg; 0.15 mmol; 0.50 eq.) in DMF (5 mL), water (1 mL) in a sealed vial under microwave irradiation. (31 mg, 24% yield). MS: 429 (M+H). $^1$H NMR (DMSO-d6): 9.28 (1H), 8.71 (1H), 8.62 (1H), 8.42 (1H), 7.84 (1H), 7.77 (1H), 7.57 (1H), 4.10 (3H), 4.08 (3H), 3.06 (3H), 2.97 (3H).

Example 450: 6-{7-[5-Cyano-2-methoxy-phenyl)-furo[3,2-b]pyridin-2-yl}-3-methoxy-N,N-dimethyl-benzamide (491)

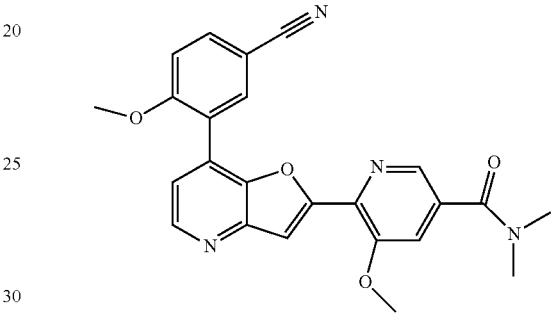

The title compound was synthesized according to the procedure described in example 32 using 6-(7-Chloro-furo[3,2-b]pyridin-2-yl)-5-methoxy-N,N-dimethyl-benzamide (100.00 mg; 0.30 mmol; 1.00 eq.), 5-cyano-2-methoxy phenyl boronic acid (64 mg; 0.36 mmol; 1.20 eq.), sodium hydrogen carbonate (83.18 mg; 0.60 mmol; 2.00 eq.) and dichloropalladium tricyclohexylphosphane (111 mg; 0.15 mmol; 0.50 eq.) in DMF (5 mL), water (1 mL) in a sealed vial under microwave irradiation. (100 mg, 78% yield). MS: 428 (M+H). $^1$H NMR (DMSO-d6): 9.28 (1H), 8.71 (1H), 8.62 (1H), 8.42 (1H), 7.84 (1H), 7.77 (1H), 7.57 (1H), 4.10 (3H), 4.08 (3H), 3.06 (3H), 2.97 (3H).

Example 451: 5-{2-[4-(3-Hydroxy-pyrrolidine-1-carbonyl)-2-methoxy-phenyl]-furo[3,2-b]pyridin-7-yl}-2-(tetrahydro-pyran-4-yloxy)-benzonitrile (492)

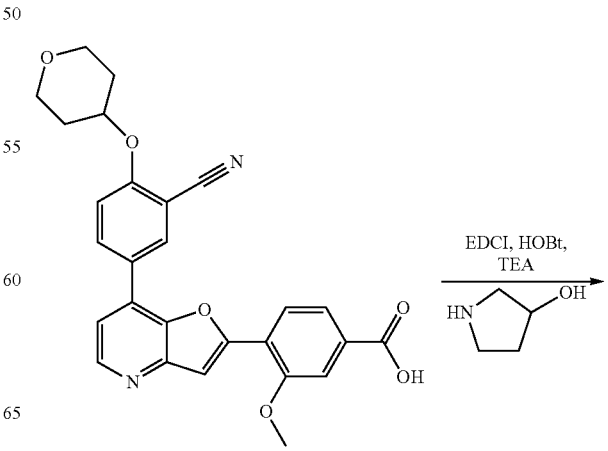

-continued

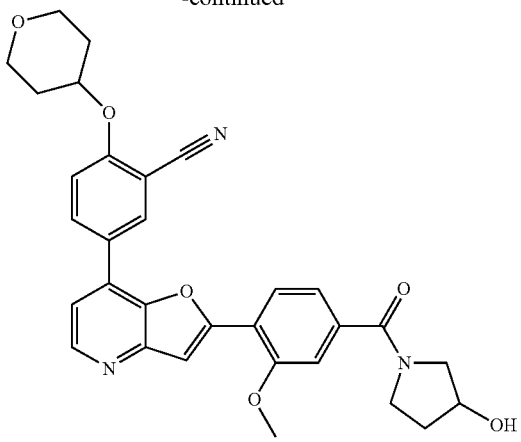

The title compound was synthesized according to the procedure described in example 109 using 4-(7-[3-Cyano-4-(tetrahydro-pyran-4-yloxy)-phenyl]-furo[3,2-b]pyridin-2-yl)-3-methoxy-benzoic acid (100.00 mg; 0.21 mmol; 1.00 eq.), Pyrrolidin-3-ol (34.47 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (95 mg, 82% yield). MS: 540 (M+H). $^1$H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.40 (1H), 2.61 (2H), 2.09 (2H0, 1.75 (2H), 1.32 (2H).

Example 452: 5-{2-[4-(N—((S)-methyl-pyrrolidin-3-yl)-1-carbonyl)-2-methoxy-phenyl]-furo[3,2-b]pyridin-7-yl}-2-(tetrahydro-pyran-4-yloxy)-benzonitrile (493)

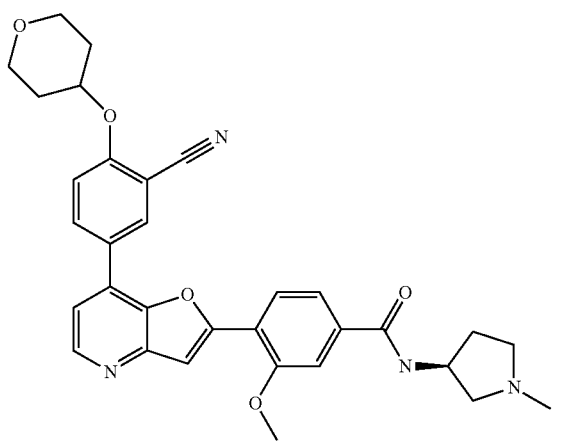

The title compound was synthesized as the protocol described as Example using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), (S)-1-methylPyrrolidin-3-yl-amine (42.58 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (55 mg, 49% yield). MS: 553 (M+H). $^1$H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.40 (1H), 2.61 (2H), 2.30 (3H), 2.09 (2H), 1.75 (2H).

Example 452: 5-{2-[4-(N—((R)-methyl-pyrrolidin-3-yl)-1-carbonyl)-2-methoxy-phenyl]-furo[3,2-b]pyridin-7-yl}-2-(tetrahydro-pyran-4-yloxy)-benzonitrile (494)

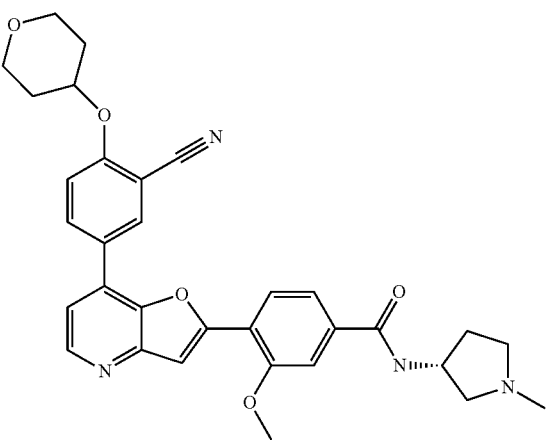 [SMILES: COc1cc(C(=O)N[C@@H]2CCN(C)C2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), (R)-1-methylPyrrolidin-3-yl-amine (42.58 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (59 mg, 50% yield). MS: 553 (M+H). $^1$H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.40 (1H), 2.61 (2H), 2.30 (3H), 2.09 (2H), 1.75 (2H).

Example 453: N-Bicyclo[2.2.2]oct-2-yl-4-{7-[3-cyano-4-(tetrahydro-pyran-4-yloxy)-phenyl]-furo[3.2-b]pyridine-3-yl}-3-methoxy-benzamide (495)

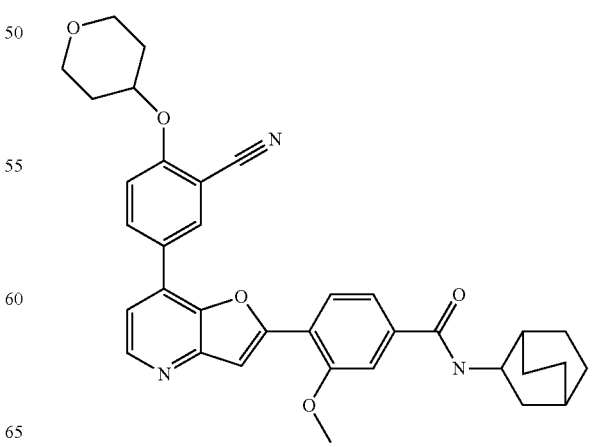

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), Bicyclo[2.2.2]oct-2-ylamine (53.23 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (96 mg, 78% yield). MS: 577 (M+H). $^1$H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.40 (1H), 2.10 (2H), 1.84-1.71 (4H), 1.51 (2H).

Example 455: N-Bicyclo[2.2.1]hept-2-yl-4-{7-[3-cyano-4-(tetrahydro-pyran-4-yloxy)-phenyl]-furo[3.2-b]pyridine-3-yl}-3-methoxy-benzamide (496)

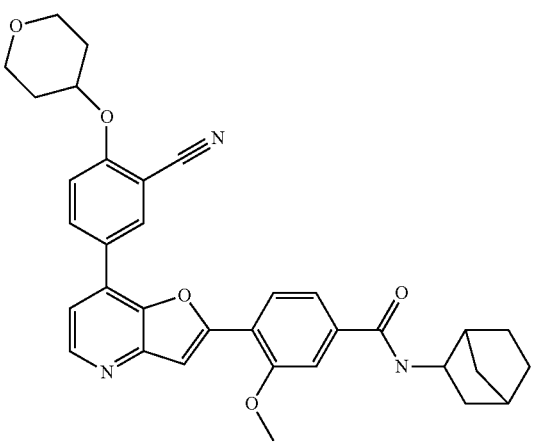 [SMILES: COc1cc(C(=O)NC2CC3CCC2C3)ccc1-c1cc2nccc(-c3ccc(OC4CCOCC4)c(C#N)c3)c2o1]

The title compound was synthesized as the protocol described as Example using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), Bicyclo[2.2.1]hept-2-ylamine (47.23 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg 0.64 mmol; 3.00 eq.) in DMF (5.0 mL) (91 mg, 76% yield). MS: 564 (M+H). $^1$H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.40 (1H), 2.10 (2H), 1.84-1.71 (4H), 1.51 (2H), 1.14 (2H).

Example 456: 2-((R)-3-Fluoro-pyrrolidin-1-yl)-5-{2-[4-(3-hydroxy-azetidine-1-carbonyl)-2-methoxy-phenyl]-furo[3,2-b]pyridin-7-yl}-benzonitrile (497)

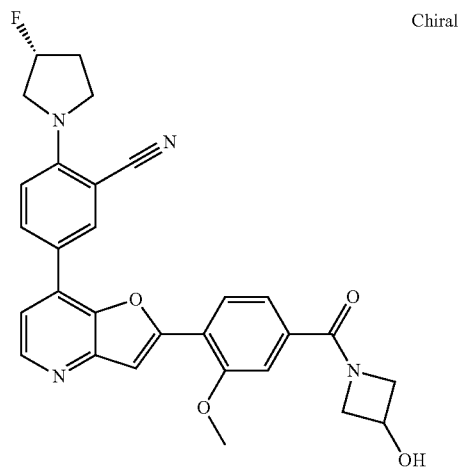 [SMILES: COc1cc(C(=O)N2CC(O)C2)ccc1-c1cc2nccc(-c3ccc(N4CC[C@@H](F)C4)c(C#N)c3)c2o1]

The title compound was synthesized according to the procedure described in example 109 using 4-{7-[3-Cyano-4-((R)-3-fluoro-pyrrolidin-1-yl)-phenyl]-furo[3,2-b]pyridin-2-yl}-3-methoxy-benzoic acid (30.00 mg; 0.07 mmol; 1.00 eq.), 3-hydroxy-azetidine (15.98 mg; 0.20 mmol; 3.00 eq.), (3-Dimethylamino-propyl)-ethyl-carbodiimide hydrochloride (15.09 mg; 0.08 mmol; 1.20 eq.) (EDCI), Benzotriazol-1-ol (10.63 mg; 0.08 mmol; 1.20 eq.) (HOBt) and Ethyl-diisopropyl-amine (25.43 mg; 0.20 mmol; 3.00 eq.) in DMF (5.0 mL), (5 mg, 9% yield). MS: 513 (M+H).

Example 457: 2-((R)-3-Fluoro-pyrrolidin-1-yl)-3-methoxy-N-(3-oxa-bicyclo[3.1.0]hex-6-yl)-benzamide (498)

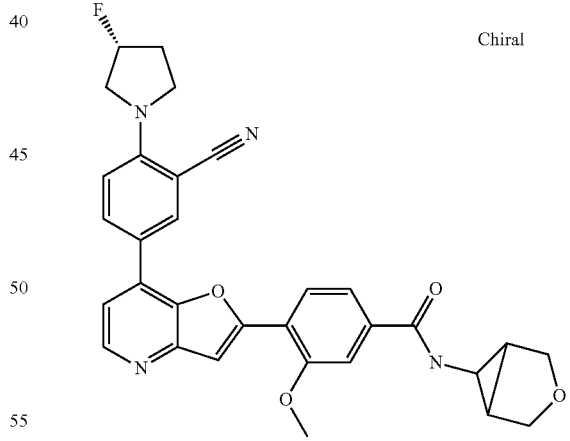

The title compound was synthesized as the protocol described as Example 2 using 4-{7-[3-Cyano-4-((R)-3-fluoro-pyrrolidin-1-yl)-phenyl]-furo[3,2-b]pyridin-2-yl}-3-methoxy-benzoic acid (30.00 mg; 0.07 mmol; 1.00 eq.), 3-oxa-bicyclo[3.1.0]hex-6-yl amine (21.67 mg; 0.20 mmol; 3.00 eq.), (3-Dimethylamino-propyl)-ethyl-carbodiimide hydrochloride (15.09 mg; 0.08 mmol; 1.20 eq.) (EDCI), Benzotriazol-1-ol (10.63 mg; 0.08 mmol; 1.20 eq.) (HOBt) and Ethyl-diisopropyl-amine (25.43 mg; 0.20 mmol; 3.00 eq.) in DMF (5.0 mL), (11.6 mg, 19% yield). MS: 539 (M+H).

Example 458: 4-{7-[3-Cyano-4-(tetrahydro-pyran-4-ylamino)-phenyl]-furo[3,2-b]pyridin-2-yl}-N-(2-dimethylamino-2-methyl-propyl)-3-methoxy-benzamide (499)

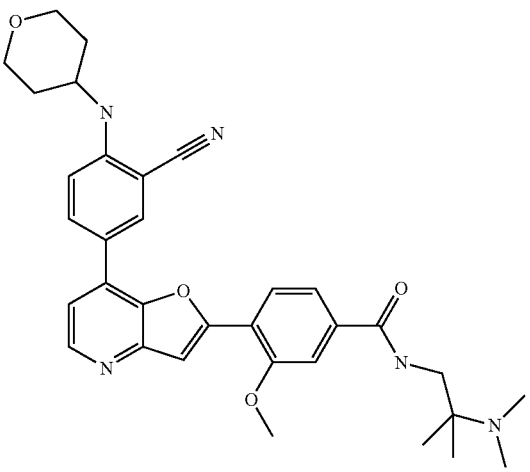 [SMILES: COc1cc(C(=O)NCC(C)(C)N(C)C)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 2-dimethylamino-2-methyl-propylamine dihydrochloride (31.63 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol, 3.00 eq.) in DMF (5.0 mL) (17 mg, 35% yield). MS: 568 (M+H). $^1$H NMR (DMSO-d6): 8.55 (1H), 8.30 (2H), 8.05 (1H), 7.66 (2H), 7.43 (2H), 7.20 (1H), 6.27 (111H), 4.97 (2H), 4.34-4.28 (1H), 4.08 (3H), 3.92 (2H), 3.81 (2H), 3.61 (2H), 3.47 (2H), 2.18 (6H), 2.09 (2H), 1.74 (2H), 1.66 (2H), 1.00 (6H).

Example 459: 4-{7-[3-Cyano-4-(tetrahydro-pyran-4-yloxy)-phenyl]-furo[3,2-b]pyridin-2-yl}-N-(2-dimethylamino-2-methyl-propyl)-3-methoxy-benzamide (500)

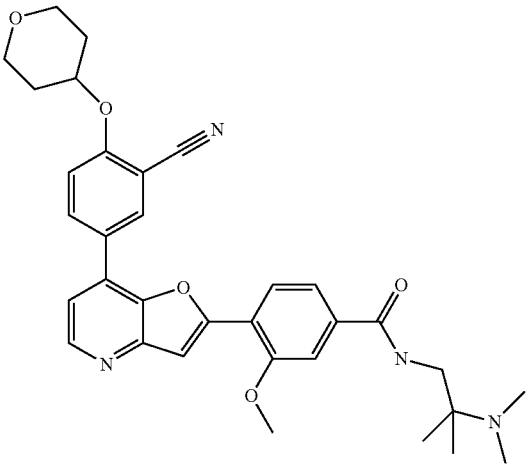 [SMILES: COc1cc(C(=O)NCC(C)(C)N(C)C)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (40.00 mg; 0.09 mmol; 1.00 eq.), 2-dimethylamino-2-methyl-propylamine dihydrochloride (31.63 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (51 mg, 42% yield). MS: 569 (M+H). $^1$H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.18 (6H), 2.09 (2H), 1.74 (2H), 1.66 (2H), 1.00 (6H).

Example 460: 2-((R)-3-Fluoro-pyrrolidin-1-yl)-3-methoxy-4-(5-methyl-hexahydro-pyrrolo[3,4-c]pyrrolo-2-carbonyl)-phenyl]-furo[3,2-b]pyridine-7-yl}-benzonitrile (501)

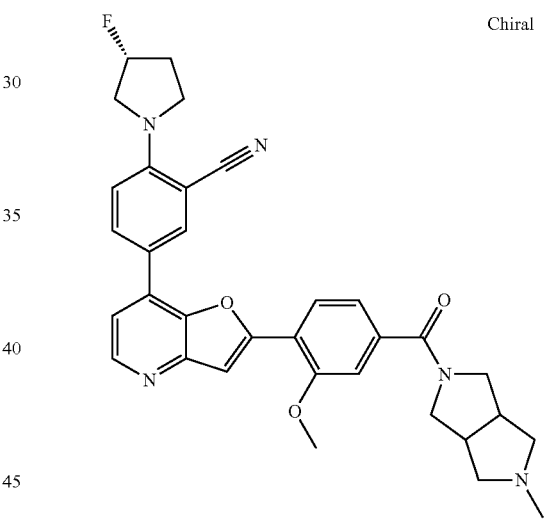

The title compound was synthesized according to the procedure described in example 109 using 4-{7-[3-Cyano-4-((R)-3-fluoro-pyrrolidin-1-yl)-phenyl]-furo[3,2-b]pyridin-2-yl}-3-methoxy-benzoic acid (30.00 mg; 0.07 mmol; 1.00 eq.), 5-methyl-hexahydro-pyrrolo[3,4-c]pyrrole (27.59 mg; 0.20 mmol; 3.00 eq.), (3-Dimethylamino-propyl)-ethyl-carbodiimide hydrochloride (15.09 mg; 0.08 mmol; 1.20 eq.) (EDCI), Benzotriazol-1-ol (10.63 mg; 0.08 mmol; 1.20 eq.) (HOBt) and Ethyl-diisopropyl-amine (25.43 mg; 0.20 mmol; 3.00 eq.) in DMF (5.0 mL), (16.7 mg, 27% yield). MS: 566 (M+H). $^1$H NMR (DMSO-d6): 8.51 (1H), 8.31 (2H), 8.01 (2H), 7.67 (1H), 7.60 (1H), 7.26 (1H), 7.17 (1H), 7.08 (1H), 5.59-5.45 (1H), 4.05 (3H), 3.82-4.04 (4H), 3.82 (4H), 3.69 (2H), 3.41 (2H), 2.81 (3H), 2.43 (2H), 2.21 (4H).

Example 461: N-(2-dimethylamino-1,1-dimethyl-ethyl)-4-{7-[3-cyano-4-(3-oxa-bicyclo[3.1.0]hex-6-ylamino)-phenyl]-furo[3,2-b]pyridin-2-yl}-3-methoxy-benzamide (502)

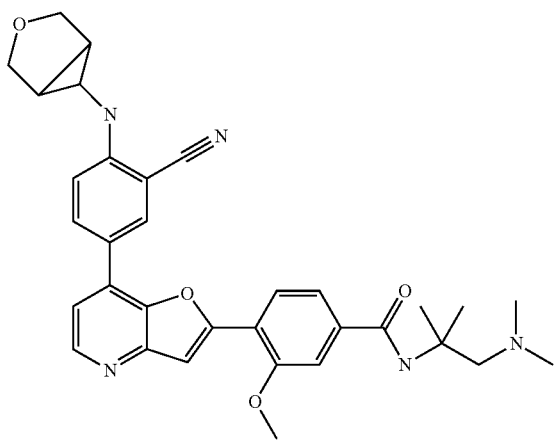 [SMILES: COc1cc(C(=O)NC(C)(C)CN(C)C)ccc1-c1cc2nccc(-c3ccc(NC4C5COCC54)c(C#N)c3)c2o1]

The title compound was synthesized according to the procedure described in example 109 using 4-{7-[3-Cyano-4-(3-oxa-bicyclo[3.1.0]hex-6-ylamino)-phenyl]-furo[3,2-b]pyridin-2-yl}-3-methoxy-benzoic acid (40.00 mg; 0.09 mmol; 1.00 eq.), 2-dimethylamino-1,1-dimethyl-ethylamine (21.60 mg; 0.17 mmol; 2.00 eq.), (3-Dimethylamino-propyl)-ethyl-carbodiimide hydrochloride (19.68 mg; 0.10 mmol; 1.20 eq.) (EDCI), Benzotriazol-1-ol (13.87 mg; 0.10 mmol; 1.20 eq.) (HOBt) and Ethyl-diisopropyl-amine (33.18 mg; 0.26 mmol; 3.00 eq.) in DMF (5.0 mL) (18 mg, 30% yield). MS: 566 (M+H). $^1$H NMR (DMSO-d6): 8.51 (1H), 8.40 (1H), 8.30 (2H), 8.09 (1H), 7.72 (1H), 7.63 (2H), 7.20 (1H), 7.06 (1H), 4.11 (3H), 4.03 (4H), 3.71 (4H), 2.62 (2H), 2.22 (6H), 1.99 (2H), 1.37 (6H).

Example 462: 5-{2-[2-Methoxy-4-(5-methyl-2,5-diaza-bicyclo[2.2.2]octane-2-carbonyl-phenyl]-{7-[3-cyano-4-(tetrahydro-pyran-4-yloxy)-phenyl]-furo[3.2-b]pyridine-3-yl}-benzonitrile (503)

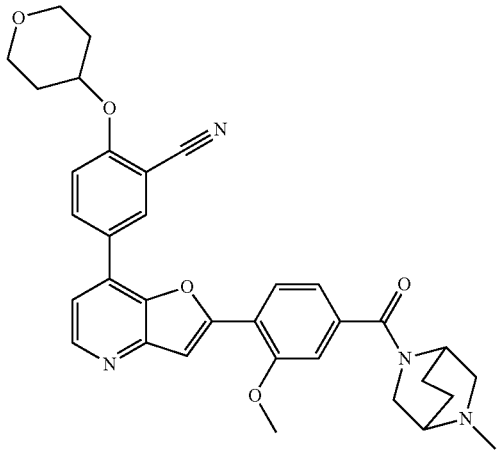 [SMILES: COc1cc(C(=O)N2CC3CCC2CN3C)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), 5-methyl-2,5-diaza-bicyclo[2.2.2]octane (84.68 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (77 mg, 63% yield). MS: 579 (M+H). $^1$H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.40 (1H), 2.86 (2H), 2.71 (2H), 2.34 (3H), 2.10 (2H), 1.84-1.71 (2H), 1.61 (2H).

Example 463: 5-{2-[2-Methoxy-4-(tetrahydro-furo[3,4-c]pyrrole-5-carbonyl-phenyl]-{7-[3-cyano-4-(tetrahydro-pyran-4-yloxy)-phenyl]-furo[3.2-b]pyridine-3-yl}-benzonitrile (504)

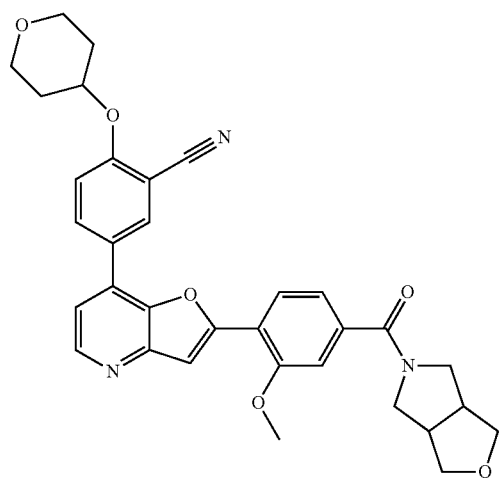 [SMILES: COc1cc(C(=O)N2CC3COCC3C2)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), tetrahydro-furo[3,4-c]pyrrole (48.10 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (105 mg, 87% yield). MS: 566 (M+H). $^1$H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.40 (1H), 2.94 (2H), 2.86 (1H), 2.10 (2H), 1.71 (2H).

Example 464: 4-{7-[3-Cyano-4-(tetrahydro-pyran-4-yloxy)-phenyl]-furo[3,2-b]pyridin-2-yl}-N-(3-dimethylamino-1,1-dimethyl-propyl)-3-methoxy-benzamide (505)

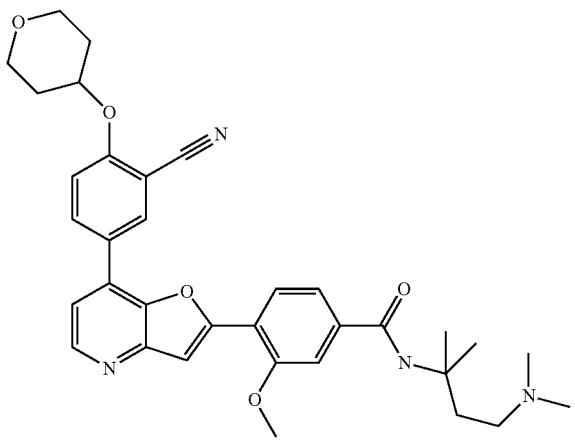 [SMILES: COc1cc(C(=O)NC(C)(C)CCN(C)C)ccc1-c1cc2nccc(-c3ccc(OC4CCOCC4)c(C#N)c3)c2o1]

The title compound was synthesized as the protocol described as Example 2 using 4-{7-[3-Cyano-4-(tetrahydro-pyran-4-yloxy)-phenyl]-furo[3,2-b]pyridin-2-yl}-3-methoxy-benzoic acid (40.00 mg; 0.09 mmol; 1.00 eq.), 3-dimethylamino-1,1-dimethyl-propylamine dihydrochloride (55.36 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (54 mg, 43% yield). MS: 583 (M+H). $^1$H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.18 (6H), 2.09 (2H), 1.74 (2H), 1.66 (2H), 1.00 (6H).

Example 465: 4-{7-[3-Cyano-4-(tetrahydro-pyran-4-yloxy)-phenyl]-furo[3,2-b]pyridin-2-yl}-N-(3-dimethylamino-2,2-dimethyl-propyl)-3-methoxy-benzamide (506)

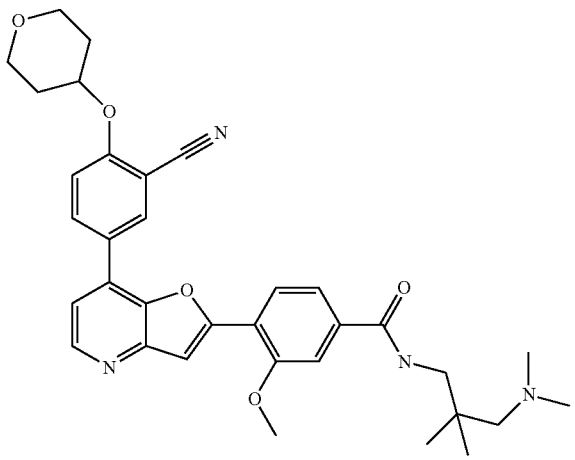 [SMILES: COc1cc(C(=O)NCC(C)(C)CN(C)C)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (40.00 mg; 0.09 mmol; 1.00 eq.), 3-dimethylamino-2,2-dimethyl-propylamine dihydrochloride (55.36 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (93 mg, 75% yield). MS: 583 (M+H). $^1$H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.28 (6H), 2.09 (2H), 1.74 (2H), 1.66 (2H), 0.88 (6H).

Example 466: 5-{2-[2-Methoxy-4-((1S,4S)-5-methyl-2,5-diaza-bicyclo[2.2.2]heptane-2-carbonyl-phenyl]-{7-[3-cyano-4-(tetrahydro-pyran-4-yloxy)-phenyl]-furo[3.2-b]pyridine-3-yl}-benzonitrile (507)

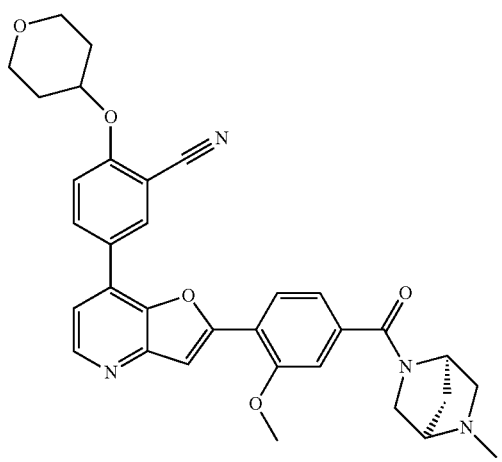

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), (1S,4S)-5-methyl-2,5-diaza-bicyclo[2.2.2]heptane hydrobromide (116.48 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (35 mg, 29% yield). MS: 565 (M+H). $^1$H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.46 (3H), 2.86 (2H), 2.71 (2H), 2.34 (3H), 2.10 (2H), 1.84-1.71 (4H).

Example 467: 5-(2-[2-Methoxy-4-((1R,4R)-5-methyl-2,5-diaza-bicyclo[2.2.2]heptane-2-carbonyl-phenyl]-(7-[3-cyano-4-(tetrahydro-pyran-4-yloxy)-phenyl]-furo[3.2-b]pyridine-3-yl)-benzonitrile (508)

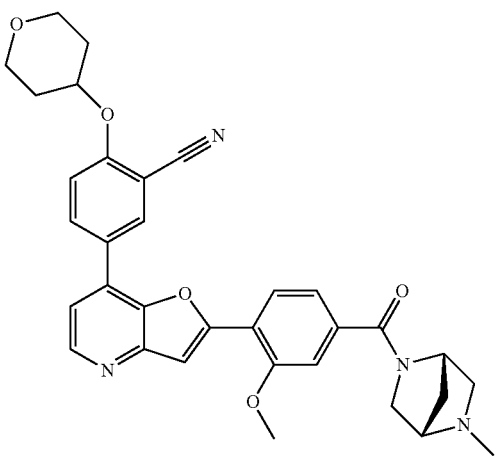 [SMILES: COc1cc(C(=O)N2C[C@@H]3C[C@H]2CN3C)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), (1R,4R)-5-methyl-2,5-diaza-bicyclo[2.2.2]heptane hydrobromide (116.48 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (43 mg, 35% yield). MS: 565 (M+H). $^1$H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.46 (3H), 2.86 (2H), 2.71 (2H), 2.34 (3H), 2.10 (2H), 1.84-1.71 (4H).

Example 468: 5-{2-[4-(8-Aza-bicyclo[3.2.1]octane-8-carbonyl)-2-methoxy-phenyl]-{7-[3-cyano-4-(tetrahydro-pyran-4-yloxy)-phenyl]-furo[3.2-b]pyridine-3-yl}-benzonitrile (509)

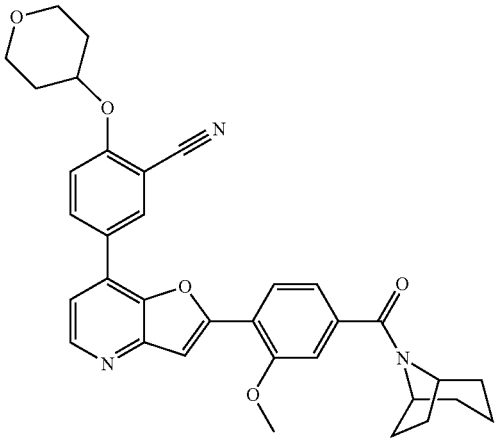 [SMILES: COc1cc(C(=O)N2C3CCCC2CC3)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.21 mmol; 1.00 eq.), 8-Aza-bicyclo[3.2.1]octane hydrocholoride (62.76 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (63 mg, 56% yield). MS: 564 (M+H). $^1$H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.40 (1H), 2.86 (2H), 2.71 (2H), 2.34 (3H), 2.10 (2H), 1.84-1.71 (4H), 1.57 (2H), 1.47 (1H).

Example 469: 5-{2-[2-Methoxy-4-(5-methyl-2,5-diaza-bicyclo[2.2.2]octane-2-carbonyl-phenyl]-{7-[3-cyano-4-(tetrahydro-pyran-4-ylamino)-phenyl]-furo[3.2-b]pyridine-3-yl}-benzonitrile (510)

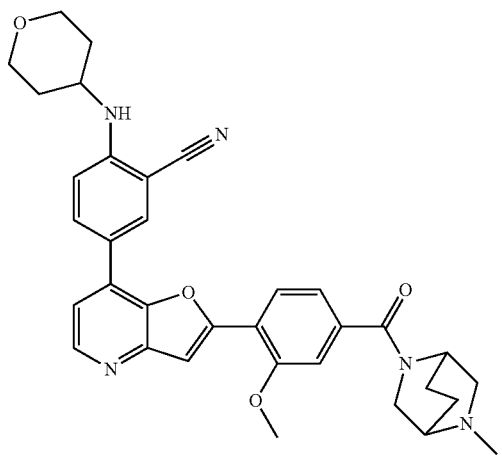 [SMILES: COc1cc(C(=O)N2CC3CCC2CN3C)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (100.00 mg; 0.21 mmol; 1.00 eq.), 5-methyl-2,5-diaza-bicyclo[2.2.2]octane (84.68 mg; 0.43 mmol; 2.00 eq.), (3-Dimethylamino-propyl)-ethyl-carbodiimide hydrochloride (48.90 mg 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg 0.64 mmol; 3.00 eq.) in DMF (5.0 mL) (37 mg, 30% yield). MS: 578 (M+H). $^1$H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.40 (1H), 2.86 (2H), 2.71 (2H), 2.34 (3H), 2.10 (2H), 1.84-1.71 (2H), 1.61 (2H).

Example 470: 5-{2-[2-Methoxy-4-(6-oxa-3-aza-bicyclo[3.1.1]heptane-3-carbonyl)-pyridin-3-yl]-furo[3,2-b]pyridin-7-yl}-2-(tetrahydro-pyran-4-yloxy)-benzonitrile (511)

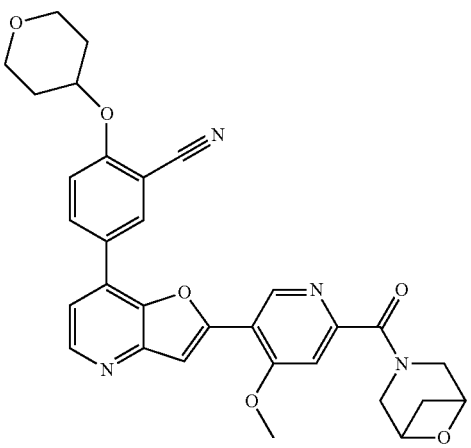

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-pyridine-2-carboxylic acid (50.00 mg; 0.11 mmol; 1.00 eq.), 6-Oxa-3-aza-bicyclo[3.1.1]heptane (16.89 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg 0.26 mmol; 3.00 eq.) in DMF (5.0 mL) (43 mg, 730% yield). MS: 553 (M+H). $^1$H NMR (DMSO-d6): 8.55 (1H), 8.30 (2H), 8.05 (1H), 7.66 (2H), 7.43 (2H), 7.20 (1H), 6.27 (1H), 4.97 (2H), 4.70 (1H), 4.51 (1H), 4.08 (3H), 4.00 (1H), 3.92 (2H), 3.81 (1H), 3.61 (2H), 3.47 (2H), 3.07 (1H), 1.89 (2H), 1.69 (2H).

Example 471: 5-{2-[4-(7-Hydroxy-3-oxa-9-aza-bicyclo[3.3.1]nonane-9-carbonyl)-4-methoxy-pyridin-3-yl]-furo[3,2-b]pyridin-7-yl}-2-(tetrahydro-pyran-4-ylamino)-benzonitrile (512)

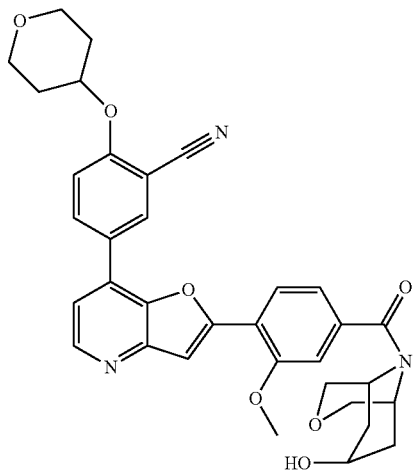 [SMILES: COc1cc(C(=O)N2C3COCC2CC(O)C3)ccc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-4-methoxy-pyridine-3-carboxylic acid (40.00 mg; 0.09 mmol; 1.00 eq.), 3-Oxa-9-aza-bicyclo[3.3.1]nonan-7-ol hydrochloride (30.61 mg; 0.17 mmol; 2.00 eq.)), (3-Dimethylamino-propyl)-ethyl-carbodiimide hydrochloride (19.60 mg; 0.10 mmol; 1.20 eq.)(EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (40 mg, 63% yield). MS: 597 (M+H). $^1$H NMR (DMSO-d6): 8.55 (1H), 8.30 (2H), 8.05 (1H), 7.66 (2H), 7.43 (2H), 7.20 (1H), 6.27 (1H), 4.97 (2H), 4.70 (1H), 4.51 (1H), 4.08 (3H), 4.00 (1H), 3.92 (2H), 3.81 (1H), 3.61 (2H), 3.47 (2H), 3.10 (1H), 2.22 (1H), 2.09 (3H), 1.90-1.74 (4H).

Example 472: 5-{2-[2-Methoxy-4-(tetrahydro-furo[3,4-c]pyrrole-5-carbonyl-phenyl]-{7-[3-cyano-4-(tetrahydro-pyran-4-ylamino)-phenyl]-furo[3.2-b]pyridine-3-yl}-benzonitrile (513)

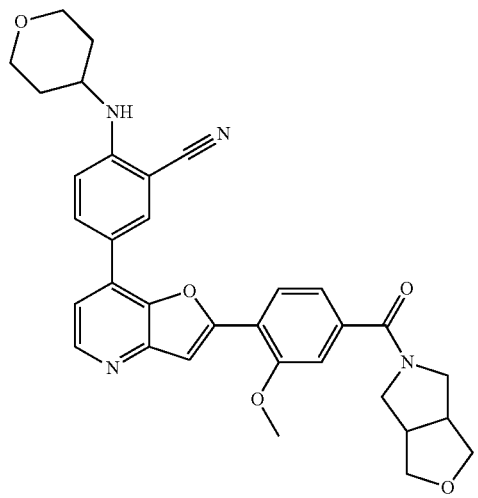 [SMILES: COc1cc(C(=O)N2CC3COCC3C2)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (100.00 mg; 0.21 mmol; 1.00 eq.), tetrahydro-furo[3,4-c]pyrrole (48.10 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (43 mg, 36% yield). MS: 565 (M+H). $^1$H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.40 (1H), 2.94 (2H), 2.86 (1H), 2.10 (2H), 1.71 (2H).

735

Example 473: 4-{7-[3-Cyano-4-(tetrahydro-pyran-4-ylamino)-phenyl]-furo[3,2-b]pyridin-2-yl}-N-(3-dimethylamino-1,1-dimethyl-propyl)-3-methoxy-benzamide (514)

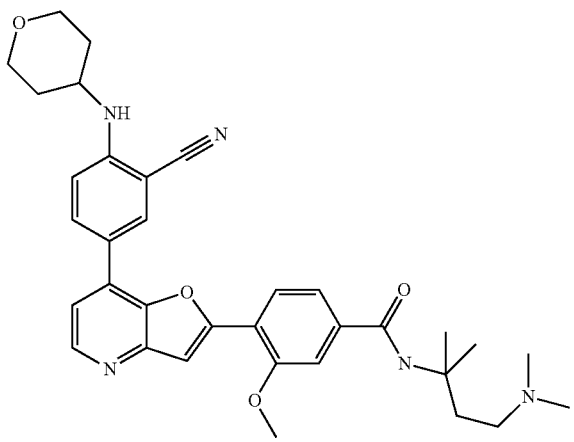 [SMILES: COc1cc(C(=O)NC(C)(C)CCN(C)C)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-benzoic acid (100.00 mg; 0.18 mmol; 1.00 eq.), 3-dimethylamino-1,1-dimethyl-propylamine dihydrochloride (111 mg; 0.34 mmol; 2.00 eq.), (3-Dimethylamino-propyl)-ethyl-carbodiimide hydrochloride (40 mg; 0.20 mmol; 1.20 eq.) (EDCI), Benzotriazol-1-ol (27 mg; 0.20 mmol; 1.20 eq.) (HOBt) and Ethyl-diisopropyl-amine (33.03 mg; 0.52 mmol; 3.00 eq.) in DMF (5.0 mL) (59 mg, 47% yield). MS: 582 (M+H). $^1$H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.18 (6H), 2.09 (2H), 1.74 (2H), 1.66 (2H), 1.00 (6H).

Example 474: 5-{2-[2-Methoxy-4-((1R,4R)-5-methyl-2, 5-diaza-bicyclo[2.2.2]heptane-2-carbonyl-phenyl]-{7-[3-cyano-4-(tetrahydro-pyran-4-ylamino)-phenyl]-furo[3.2-b]pyridine-3-yl}-benzonitrile (515)

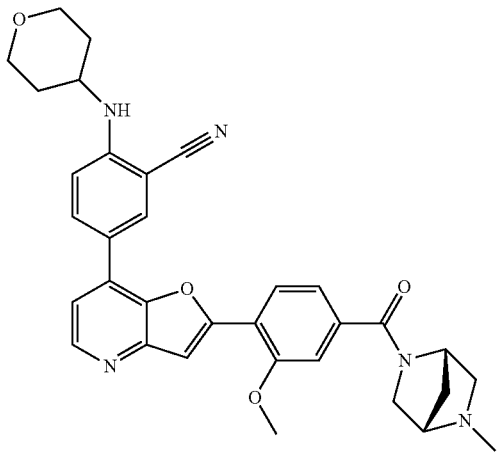 [SMILES: COc1cc(C(=O)N2C[C@@H]3C[C@H]2CN3C)ccc1-c1cc2nccc(-c3ccc(NC4CCOCC4)c(C#N)c3)c2o1]

736

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (100.00 mg; 0.21 mmol; 1.00 eq.), (1R,4R)-5-methyl-2,5-diaza-bicyclo[2.2.2]heptane hydrobromide (116.48 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (51 mg, 42% yield). MS: 564 (M+H). $^1$H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.46 (3H), 2.86 (2H), 2.71 (2H), 2.34 (3H), 2.10 (2H), 1.84-1.71 (4H).

Example 475: 4-(7-[3-Cyano-4-(tetrahydro-pyran-4-ylamino)-phenyl]-furo[3,2-b]pyridin-2-yl)-N-(3-dimethylamino-2,2-dimethyl-propyl)-3-methoxy-benzamide (516)

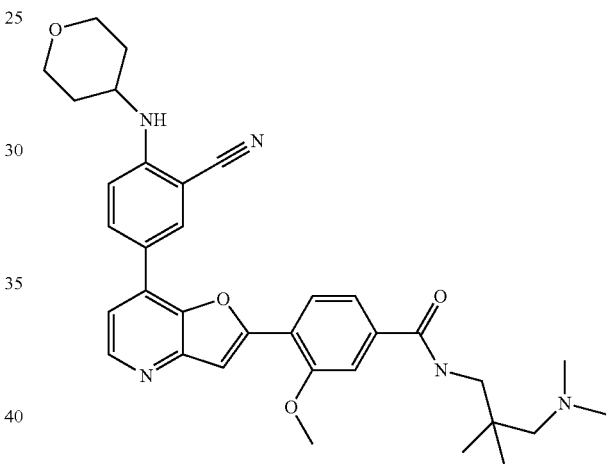

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (40.00 mg; 0.09 mmol; 1.00 eq.), 3-dimethylamino-2,2-dimethyl-propylamine dihydrochloride (55.36 mg; 0.17 mmol; 2.00 eq.), (3-Dimethylamino-propyl)-ethyl-carbodiimide hydrochloride (19.60 mg; 0.10 mmol; 1.20 eq.) (EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (93 mg, 75% yield). MS: 582 (M+H). $^1$H NMR (DMSO-d6): 8.55 (1H), 8.30 (2H), 8.05 (1H), 7.66 (2H), 7.43 (2H), 7.20 (1H), 6.27 (1H), 4.97 (2H), 4.34-4.28 (1H), 4.08 (3H), 3.92 (2H), 3.81 (2H), 3.61 (2H), 3.47 (2H), 2.28 (6H), 2.09 (2H), 1.74 (2H), 1.66 (2H), 0.88 (6H).

Example 476: 5-{2-[2-Methoxy-4-((1S,4S)-5-methyl-2, 5-diaza-bicyclo[2.2.2]heptane-2-carbonyl-phenyl]-{7-[3-cyano-4-(tetrahydro-pyran-4-ylamino)-phenyl]-furo[3.2-b]pyridine-3-yl}-benzonitrile (517)

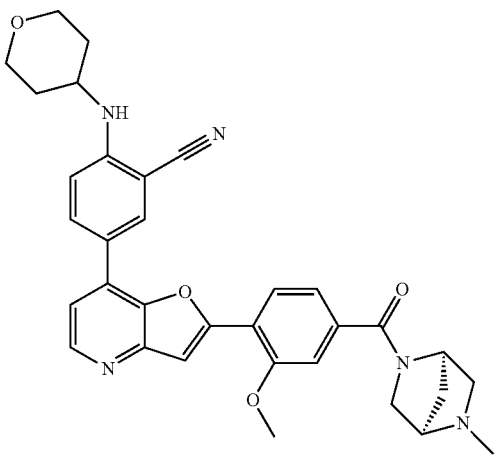 [SMILES: COc1cc(C(=O)N2C[C@H]3C[C@@H]2CN3C)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (100.00 mg; 0.21 mmol; 1.00 eq.), (1S,4S)-5-methyl-2,5-diaza-bicyclo[2.2.2]heptane hydrobromide (116.48 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (31 mg, 26% yield). MS: 564 (M+H). $^1$H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.46 (3H), 2.86 (2H), 2.71 (2H), 2.34 (3H), 2.10 (2H), 1.84-1.71 (4H).

Example 477: 5-{2-[2-Methoxy-4-(1-aza-bicyclo[2.2.2]octane-3-yl)-pyridin-3-yl]-furo[3,2-b]pyridin-7-yl}-2-(tetrahydro-pyran-4-yloxy)phenyl-5-methoxy-nictotiamide (518)

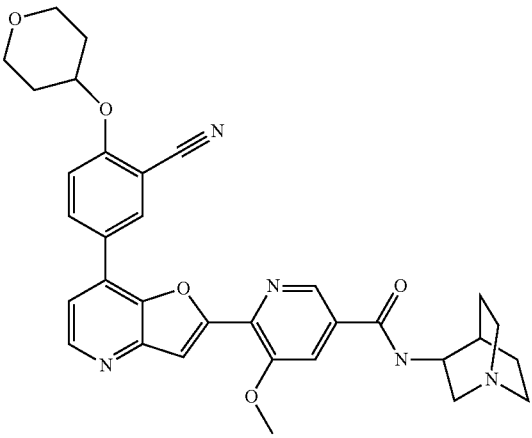 [SMILES: COc1cc(C(=O)NC2CN3CCC2CC3)cnc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-phenyl]-furo[3,2-b]pyridin-2-yl}-3-methoxy-pyridine-2-carboxylic acid (50.00 mg; 0.11 mmol; 1.00 eq.), 6-Oxa-3-aza-bicyclo[3.1.1]heptane (16.89 mg; 0.17 mmol; 2.00 eq.), (3-Dimethylamino-propyl)-ethyl-carbodiimide hydrochloride (19.60 mg; 0.10 mmol; 1.20 eq.)(EDCI), Benzotriazol-1-ol (13.81 mg; 0.10 mmol; 1.20 eq.) (HOBt) and Ethyl-diisopropyl-amine (33.03 mg; 0.26 mmol; 3.00 eq.) in DMF (5.0 mL) (28 mg, 11% yield). MS: 553 (M+H). $^1$H NMR (DMSO-d6): 8.55 (1H), 8.30 (2H), 8.05 (1H), 7.66 (2H), 7.43 (2H), 7.20 (1H), 6.27 (1H), 4.97 (2H), 4.70 (1H), 4.51 (1H), 4.03 (3H), 3.72 (2H), 3.17 (2H), 2.96 (2H), 2.72 (4H), 2.32 (1H), 2.02 (2H), 1.94 (1H), 1.89 (1H), 1.61 (2H), 1.32 (2H).

Example 478: 5-{2-[4-(8-Aza-bicyclo[3.2.1]octane-8-carbonyl)-2-methoxy-phenyl]-{7-[3-cyano-4-(tetrahydro-pyran-4-ylamino)-phenyl]-furo[3.2-b]pyridine-3-yl}-benzonitrile (519)

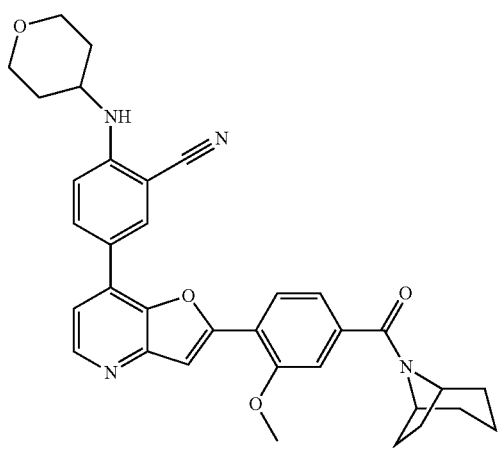 [SMILES: COc1cc(C(=O)N2C3CCCC2CC3)ccc1-c1cc2nccc(-c3ccc(NC4CCOCC4)c(C#N)c3)c2o1]

The title compound was synthesized according to the procedure described in example 109 using 4-{7-[3-Cyano-4-(tetrahydro-pyran-4-ylamino)-phenyl]-furo[3,2-b]pyridin-2-yl}-3-methoxy-benzoic acid (100.00 mg; 0.21 mmol; 1.00 eq.), 8-Aza-bicyclo[3.2.1]octane hydrocholoride (62.76 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (95 mg, 79% yield). MS: 563 (M+H). $^1$H NMR (DMSO-d6): 8.55 (1H), 8.30 (2H), 8.05 (1H), 7.66 (2H), 7.43 (2H), 7.20 (1H), 4.97 (1H), 4.84-4.73 (1H), 4.08 (3H), 3.92 (2H), 3.61 (4H), 3.40 (1H), 2.86 (2H), 2.71 (2H), 2.34 (3H), 2.10 (2H), 1.84-1.71 (4H), 1.57 (2H), 1.47 (1H).

Example 479: 5-{2-[2-Methoxy-4-(8-oxa-3-aza-bicyclo[3.2.1]octane-3-carbonyl)-pyridin-3-yl]-furo[3,2-b]pyridin-7-yl}-2-(tetrahydro-pyran-4-yloxy)-benzonitrile (520)

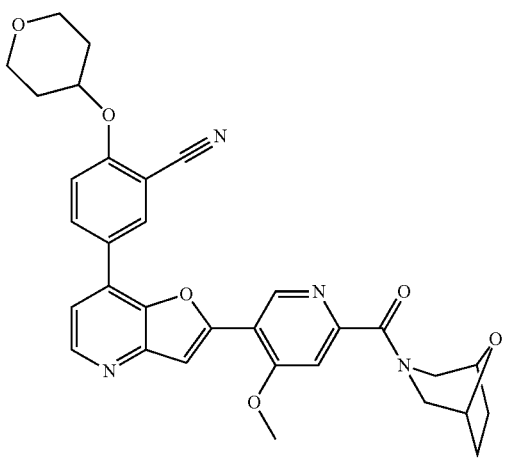 [SMILES: COc1cc(C(=O)N2CC3CCC(C2)O3)ncc1-c1cc2nccc(-c3ccc(OC4CCOCC4)c(C#N)c3)c2o1]

The title compound was synthesized according to the procedure described in example 109 using 4-{7-[3-Cyano-4-(tetrahydro-pyran-4-yloxy)-pyridin-3-yl]-furo[3,2-b]pyridin-2-yl}-3-methoxy-benzoic acid (100.00 mg; 0.21 mmol; 1.00 eq.), 8-Oxa-3-aza-bicyclo[3.2.1]octane (63.60 mg; 0.43 mmol; 2.00 eq.), (3-Dimethylamino-propyl)-ethyl-carbodiimide hydrochloride (48.90 mg; 0.26 mmol; 1.20 eq.) (EDCI), Benzotriazol-1-ol (34.47 mg; 0.26 mmol; 1.20 eq.) (HOBt) and Ethyl-diisopropyl-amine (82.41 mg; 0.64 mmol; 3.00 eq.) in DMF (5.0 mL) (33 mg, 55% yield). MS: 567 (M+H). $^1$H NMR (DMSO-d6): 8.51 (1H), 8.40 (1H), 8.30 (2H), 8.09 (1H), 7.72 (1H), 7.63 (2H), 7.20 (1H), 7.19 (1H), 4.99 (1H), 4.44 (1H), 4.16 (1H), 4.13 (3H), 4.09 (1H), 3.89 (2H), 3.79 (1H), 3.56 (3H), 3.02 (1H), 1.89 (2H), 1.70 (2H).

Example 480: 3-(7-[2-Cyano-4-(pyrrolidine-amino)-phenyl]-furo[3,2-b]pyridin-2-yl)-3-methoxy-N,N-dimethyl-benzamide (521)

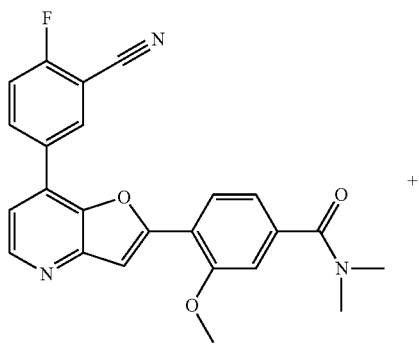

+

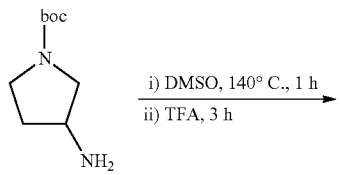

i) DMSO, 140° C., 1 h
ii) TFA, 3 h

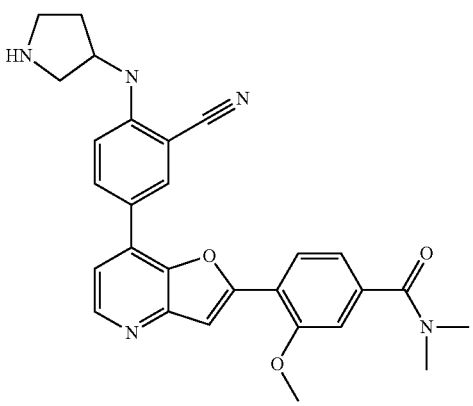

3-{7-[2-Cyano-4-(4-Boc-pyrrolidine-amino)-phenyl]-furo[3,2-b]pyridin-2-yl}-3-methoxy-N,N-dimethyl-benzamide A mixture of 4-[7-(3-Cyano-4-fluoro-phenyl)-furo[3,2-b]pyridin-2-yl]-3-methoxy-N,N-dimethyl-benzamide (50.00 mg; 0.12 mmol; 1.00 eq.) and 3-Boc pyrrolidine-1-amine (89.67 mg; 0.36 mmol; 3.00 eq.) in DMSO (3 mL) was heated at 140° C. for 60 minutes under microwave irradiation. The mixture was poured into water, extracted with ether, dried over MgSO$_4$. The mixture was purified through reverse phase HPLC to obtain the product. (80 mg, 57% yield). MS: 582 (M+H).

3-{7-[2-Cyano-4-(pyrrolidine-amino)-phenyl]-furo[3,2-b]pyridin-2-yl}-3-methoxy-N,N-dimethyl-benzamide A mixture of 3-{7-[2-Cyano-4-(pyrrolidine-amino)-phenyl]-furo[3,2-b]pyridin-2-yl}-3-methoxy-N,N-dimethyl-benzamide (30.00 mg; 0.05 mmol; 1.00 eq.) and 3 mL of TFA was stirred for 10 minutes. The mixture was purified through reverse phase HPLC to provide the product. (4.6 mg, 18% yield). MS: 482 (M+H). $^1$H NMR (DMSO-d6): 8.57 (1H), 8.49 (2H), 8.04 (2H), 7.68 (2H), 7.63 (1H), 7.54 (1H), 7.25 (1H), 7.19 (1H), 4.25 (2H), 4.08 (3H), 3.85 (2H), 3.70 (1H), 3.63 (1H), 3.00 (3H), 2.96 (3H), 2.78 (1H), 2.09 (1H), 1.76 (1H).

Example 481: 6-(7-[3-cyano-4-[(oxan-4-yl)amino]
phenyl]-6-cyclopropylfuro[3,2-b]pyridin-2-yl)-5-
methoxy-N,N-dimethylpyridine-3-carboxamide
(522)

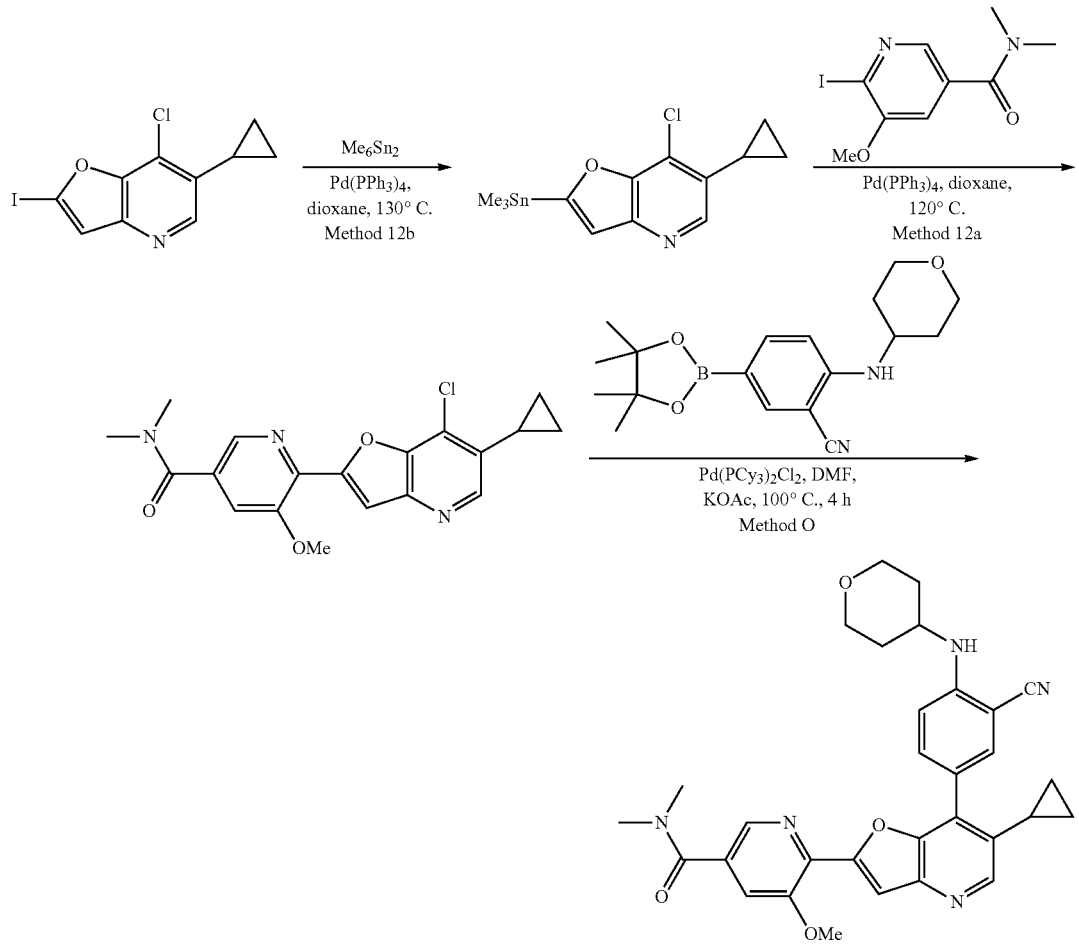

The title compound was prepared from 7-chloro-6-cyclopropyl-2-iodofuro[3,2-b]pyridine, 6-iodo-5-methoxy-N,N-dimethylnicotinamide, and 2-(tetrahydro-2H-pyran-4-ylamino)-5-(4,4,5,5-tetramethyl-1,3,2-dioxaborolan-2-yl) benzonitrile using Methods 12b, 12a and O. The final product were purified by prep-HPLC under the following conditions: column, XBridge Shield RP18 OBD Column, 5 um, 19×150 mm; mobile phase, acetonitrile in water (with 10 mmol/L $NH_4HCO_3$), 20% to 50% gradient in 8 min; detector, UV 254/220 nm. 6-(7-[3-cyano-4-[(oxan-4-yl)amino]phenyl]-6-cyclopropylfuro[3,2-b]pyridin-2-yl)-5-methoxy-N,N-dimethylpyridine-3-carboxamide was obtained as a white solid (4 mg, 7% for 3 steps). HPLC: 99.9% purity, RT=0.82 min. MS: m/z=538.2 $[M+H]^+$. $^1H$ NMR (300 MHz, $CD_3OD$, ppm) δ 8.26 (d, J=1.6 Hz, 2H), 7.83-7.64 (m, 4H), 7.06 (d, J=8.8 Hz, 1H), 4.87 (br s, 2H), 4.56 (s, 1H), 4.09 (s, 3H), 4.05-3.94 (m, 2H), 3.87-3.73 (m, 1H), 3.63-3.51 (m, 2H), 3.11 (s, 3H), 3.04 (s, 3H), 2.10-1.94 (m, 3H), 1.73-1.60 (m, 2H), 1.04-0.91 (m, 2H), 0.80-0.68 (m, 2H).

Example 482: TBK Biochemical Assay

Test compounds were transferred into Labcyte polypropylene 384 well plates (P055-25) and diluted to 3 mM using DMSO. 3 mM test compounds were dispensed using Labcyte ECHO dose response module into Greiner 784075 plates (columns 3-12 and 13-22, 10 point 1:4) so that high concentration was 30 uM final. 100 uM of a reference compound (1 uM final high concentration). Backfilling was performed if necessary so that all wells contain 1% DMSO final:
add 75 nl DMSO/well into columns 1, 2 and 24 using Labcyte Echo.
add 75 nl 1.0 mM staurosporine/well into column 23 using Labcyte Echo (10 uM final)
add 4.5 ul enzyme/well using multidrop dispenser
add 3 ul substrate/well using multidrop dispenser
incubate at 25° C. in Heidolph incubator for 90 min.
add 7.5 ul 2× stop buffer using multidrop dispenser
read on labchip ez reader II using TBK1 job
Raw data files were opened in the Caliper LabChip Reviewer program (Version 3.0.265.0 SP2) and peak assignments were adjusted to reflect "substrate first" with the software's post-run analysis options. A spline-fit baseline was applied using the software's analysis algorithm.

IKKe Biochemical Assay

Test compounds were transferred into Labcyte polypropylene 384 well plates (P055-25) and diluted to 3 mM using DMSO. 3 mM test compounds were dispensed using Labcyte ECHO dose response module into Greiner 784075 plates (columns 3-12 and 13-22, 10 point 1:4) so that high concentration was 30 uM final. 100 uM of a reference compound (1 uM final high concentration). Backfilling was performed if necessary so that all wells contain 1% DMSO final:

add 75 nl DMSO/well into columns 1, 2 and 24 using Labcyte Echo.
add 75 nl 1.0 mM staurosporine/well into column 23 using Labcyte Echo (10 uM final)
add 4.5 ul enzyme/well using multidrop dispenser
add 3 ul substrate/well using multidrop dispenser
incubate at 25° C. for 90 min.
add 7.5 ul 2× stop buffer
read on labchip ez reader II using IKKε. job Raw data files were opened in the Caliper LabChip Reviewer program (Version 3.0.265.0 SP2) and peak assignments were adjusted to reflect "substrate first" with the software's post-run analysis options. A spline-fit baseline was applied using the software's analysis algorithm.

The purpose of the pIRF3 immunocytochemistry cell based assay was to identify small molecules which modulates TBK/IKKε kinase activity through on target substrate phosphorylation of the IRF-3 protein. On the first day of the experiment, MDA-MB-468 cells were plated in 384 well, black, clear-bottom, Poly D lysine coated plates at a density of 5000 cells/well in 45 ul of complete DMEM and allowed to adhere overnight. On the second day compounds were added to cells at a starting concentration of 10 uM with a serial dilution of 3-fold for a total of 10 points. The cells were incubated for 1 hr at 37° C. Cells were then stimulated with Poly(I:C) at a final concentration of 10 ug/ml, and were incubated for 2 hr at 37° C. Following the incubation, media was removed from the wells and the cells were fixed with 4% PFA for 15 min at RT. Cells were washed at least 3 times with PBS, and then permeabilized with ice-cold methanol for 10 min at RT. The washing step was repeated and the cells were then blocked using 10% goat serum/1% BSA, made up in PBS and allowed to incubate at RT for 1 hr. The cells were washed again and then treated with an anti-pIRF3 antibody at 4° C. overnight (1:250 dilution of Abcam ab76493 in PBS containing 1% BSA). On the third day the primary antibody was washed off and pIRF3 was detected by adding the secondary antibody conjugated to AlexaFluor488 (1:200 dilution of secondary antibody in PBS containing 1% BSA) for 1 hr at RT. Cells were washed and then counterstained with PI/RNase staining buffer for 15 min at RT and read on the Acumen Explorer laser scanning cytometer. The percentage of phosphorylation of the IRF-3 protein was calculated using the following algorithm, a modified version of the mean half width intensity (pIRF3 staining)/(PI staining or # of cells)×100%). IC50 curves were generated using the Genedata software.

Results are given in the following table.

| Compound | TBK1 IC50 | IKKε IC50 | pIRF3 IC50 |
|---|---|---|---|
| 1 | A | A | A |
| 2 | A | A |  |
| 3 | A | A | B |
| 4 | A | A |  |
| 5 | A | A | A |
| 6 | A | A |  |
| 7 | A | A | B |
| 8 | A | A | A |
| 9 | A | A | A |
| 10 | A | A | A |
| 11 | A | A | B |
| 12 | A | A |  |
| 13 | A | A | A |
| 14 | A | A | A |
| 15 | A | A | A |
| 16 | A | A | B |
| 17 | A | A | B |
| 18 | A | A | B |
| 19 | A | A |  |
| 20 | A | A | A |
| 21 | A | A | C |
| 22 | A | A |  |
| 23 | A | A | B |
| 24 | A | A | A |
| 25 | A | A | B |
| 26 | A | A |  |
| 27 | A | A | B |
| 28 | A | A | A |
| 29 | A | A | B |
| 30 | A | A | B |
| 31 | A | A | A |
| 32 | A | A | A |
| 33 | A | A | B |
| 34 | A | A | B |
| 35 | A | A | B |
| 36 | A | A | B |
| 37 | A | A | B |
| 38 | A | A | B |
| 39 | A | A | B |
| 40 | A | A | B |
| 41 | A | A |  |
| 42 | A | A | A |
| 43 | A | A | B |
| 44 | A | A |  |
| 45 | A | A | B |
| 46 | A | A | B |
| 47 | A | A | B |
| 48 | A | A |  |
| 49 | A | A | B |
| 50 | A | A | B |
| 51 | A | A | B |
| 52 | A | A | B |
| 53 | A | A | B |
| 54 | A | A | B |
| 55 | A | A | A |
| 56 | A | A |  |
| 57 | A | A | B |
| 58 | A | A | A |
| 59 | A | A | B |
| 60 | A | A |  |
| 61 | A | A |  |
| 62 | A | A | B |
| 63 | A | A | A |
| 64 | A | A | B |
| 65 | A | A | B |
| 66 | A | A |  |
| 67 | A | A | B |
| 68 | A | A | B |
| 69 | A | A | B |
| 70 | A | A | B |
| 71 | A | A | A |
| 72 | A | A | B |
| 73 | A | A | A |
| 74 | A | A | B |
| 75 | A | A | B |
| 76 | A | A | B |
| 77 | A | A | B |

| Compound | TBK1 IC50 | IKKε IC50 | pIRF3 IC50 |
|---|---|---|---|
| 78 | A | A | B |
| 79 | A | A | B |
| 80 | A | A | B |
| 81 | A | A | |
| 82 | A | A | B |
| 83 | A | A | |
| 84 | A | A | B |
| 85 | A | A | |
| 86 | A | A | |
| 87 | A | A | B |
| 88 | A | A | B |
| 89 | A | A | |
| 90 | A | A | B |
| 91 | A | A | B |
| 92 | A | A | B |
| 93 | A | A | B |
| 94 | A | A | |
| 95 | A | A | |
| 96 | A | A | |
| 97 | A | A | |
| 98 | A | A | B |
| 99 | A | A | |
| 100 | A | A | |
| 101 | A | A | B |
| 102 | A | A | |
| 103 | A | A | |
| 104 | A | A | B |
| 105 | A | A | B |
| 106 | A | A | B |
| 107 | A | A | |
| 108 | A | A | A |
| 109 | A | A | B |
| 110 | A | A | B |
| 111 | A | A | B |
| 112 | A | A | B |
| 113 | A | A | |
| 114 | A | A | |
| 115 | A | A | |
| 116 | A | A | B |
| 117 | A | A | B |
| 118 | A | A | B |
| 119 | A | A | A |
| 120 | A | A | B |
| 121 | A | A | |
| 122 | A | A | B |
| 123 | A | A | C |
| 124 | A | A | C |
| 125 | A | A | B |
| 126 | A | A | |
| 127 | A | A | B |
| 128 | A | A | |
| 129 | A | A | B |
| 130 | A | A | B |
| 131 | A | A | B |
| 132 | A | A | |
| 133 | A | A | C |
| 134 | A | A | B |
| 135 | A | A | B |
| 136 | A | A | C |
| 137 | A | A | |
| 138 | A | A | C |
| 139 | A | A | B |
| 140 | A | A | A |
| 141 | A | A | B |
| 142 | A | A | |
| 143 | A | A | B |
| 144 | A | A | |
| 145 | A | A | B |
| 146 | A | A | B |
| 147 | A | A | |
| 148 | A | A | C |
| 149 | A | A | B |
| 150 | A | A | B |
| 151 | A | A | |
| 152 | A | A | |
| 153 | A | A | B |

| Compound | TBK1 IC50 | IKKε IC50 | pIRF3 IC50 |
|---|---|---|---|
| 154 | A | A | C |
| 155 | A | A | B |
| 156 | A | A | C |
| 157 | B | A | |
| 158 | B | A | B |
| 159 | B | B | D |
| 160 | B | A | C |
| 161 | B | B | C |
| 162 | B | A | |
| 163 | B | B | B |
| 164 | B | B | |
| 165 | B | B | |
| 166 | B | A | B |
| 167 | B | B | C |
| 168 | B | B | B |
| 169 | B | B | |
| 170 | B | B | C |
| 171 | B | B | B |
| 172 | B | B | |
| 173 | B | B | C |
| 174 | B | B | |
| 175 | B | B | |
| 176 | B | B | |
| 177 | B | B | C |
| 178 | B | B | |
| 179 | B | B | C |
| 180 | B | B | |
| 181 | B | B | |
| 182 | D | D | |
| 183 | C | B | |
| 184 | C | B | |
| 185 | C | B | |
| 186 | C | B | |
| 187 | C | B | |
| 188 | C | C | |
| 189 | D | C | |
| 190 | D | B | |
| 191 | D | B | |
| 192 | D | D | |
| 193 | | | |
| 194 | B | B | |
| 195 | | | |
| 196 | | | |
| 197 | | | |
| 198 | | | |
| 199 | | | |
| 200 | | D | |
| 201 | | | |
| 202 | | | |
| 203 | | | |
| 204 | | B | |
| 205 | | D | |
| 206 | | | |
| 207 | | | |
| 208 | | | |
| 209 | | | |
| 210 | | | |
| 211 | | B | |
| 212 | | | |
| 213 | | D | |
| 214 | | | |
| 215 | C | B | |
| 216 | D | D | |
| 217 | B | B | |
| 218 | C | C | |
| 219 | B | B | |
| 220 | B | B | |
| 221 | B | B | |
| 222 | B | B | |
| 223 | A | A | |
| 224 | B | A | |
| 225 | B | B | |
| 226 | A | A | |
| 227 | A | A | |
| 228 | B | A | |
| 229 | B | B | |

| Compound | TBK1 IC50 | IKKε IC50 | pIRF3 IC50 |
|---|---|---|---|
| 230 | A | A | |
| 231 | A | A | |
| 232 | A | A | |
| 233 | A | A | |
| 234 | A | A | |
| 235 | B | B | |
| 236 | A | A | |
| 237 | A | A | |
| 238 | A | A | |
| 239 | A | A | |
| 240 | B | B | |
| 241 | A | A | |
| 242 | B | B | |
| 243 | A | A | |
| 244 | B | B | |
| 245 | B | B | |
| 246 | B | B | |
| 247 | B | B | |
| 248 | | B | |
| 249 | B | B | |
| 250 | B | B | |
| 251 | A | A | |
| 252 | B | B | |
| 253 | A | A | |
| 254 | B | A | |
| 255 | A | A | |
| 256 | A | A | |
| 257 | A | A | |
| 258 | A | A | |
| 259 | A | A | |
| 260 | A | A | |
| 261 | A | A | |
| 262 | A | A | |
| 263 | A | A | |
| 264 | A | A | |
| 265 | B | B | |
| 266 | B | B | |
| 267 | C | D | |
| 268 | B | B | |
| 269 | B | B | |
| 270 | A | A | |
| 271 | A | A | |
| 272 | A | A | |
| 273 | A | A | |
| 274 | A | A | |
| 285 | B | B | B |
| 286 | B | B | C |
| 287 | D | D | |
| 288 | D | | |
| 289 | D | | |
| 290 | A | A | B |
| 291 | B | B | D |
| 292 | B | B | B |
| 293 | D | | |
| 294 | D | | |
| 295 | B | A | C |
| 296 | A | A | B |
| 297 | A | A | B |
| 298 | A | A | B |
| 299 | A | A | B |
| 300 | B | B | C |
| 301 | A | A | C |
| 302 | A | A | B |
| 303 | B | B | B |
| 304 | B | B | C |
| 305 | D | D | |
| 306 | D | D | |
| 307 | B | B | |
| 308 | D | D | |
| 309 | D | | |
| 310 | D | | |
| 311 | D | | |
| 312 | D | | |
| 313 | A | A | B |
| 314 | A | A | B |
| 315 | A | A | B |
| 316 | A | A | B |
| 317 | A | A | B |
| 318 | A | A | B |
| 319 | C | C | |
| 320 | C | C | |
| 321 | B | B | |
| 322 | B | C | C |
| 323 | D | D | |
| 324 | A | A | B |
| 325 | A | A | B |
| 326 | A | A | A |
| 327 | A | A | A |
| 328 | A | A | A |
| 329 | A | B | B |
| 330 | C | C | |
| 331 | D | | |
| 332 | D | | |
| 333 | D | D | |
| 334 | A | A | B |
| 335 | D | | |
| 336 | C | C | |
| 337 | D | | |
| 338 | B | B | C |
| 339 | B | | A |
| 340 | B | C | |
| 341 | D | D | |
| 342 | C | C | |
| 343 | B | B | |
| 344 | A | A | B |
| 345 | A | A | B |
| 346 | A | A | B |
| 347 | A | A | B |
| 348 | A | A | B |
| 349 | A | A | B |
| 350 | A | A | B |
| 351 | B | B | |
| 352 | B | C | C |
| 353 | D | | |
| 354 | B | C | |
| 355 | A | A | B |
| 356 | A | A | B |
| 357 | D | D | |
| 358 | C | C | |
| 359 | D | | |
| 360 | B | B | |
| 361 | D | | |
| 362 | B | B | |
| 363 | D | D | |
| 364 | A | A | B |
| 365 | A | A | B |
| 366 | A | A | B |
| 367 | A | A | A |
| 368 | A | A | B |
| 369 | A | A | B |
| 370 | A | A | B |
| 371 | A | A | B |
| 372 | A | A | B |
| 373 | A | A | A |
| 374 | A | A | A |
| 375 | A | A | B |
| 376 | A | A | A |
| 377 | B | B | |
| 379 | A | A | A |
| 380 | A | A | A |
| 381 | A | A | B |
| 382 | A | A | A |
| 383 | B | B | |
| 384 | A | A | A |
| 385 | A | A | A |
| 386 | B | B | |
| 387 | A | A | B |
| 388 | A | A | B |
| 389 | A | A | B |
| 390 | A | A | B |
| 391 | B | A | C |
| 392 | B | B | |

| Compound | TBK1 IC50 | IKKε IC50 | pIRF3 IC50 |
|---|---|---|---|
| 393 | B | A | C |
| 394 | B | B | C |
| 395 | A | A | B |
| 396 | B | B |  |
| 397 | A | A | A |
| 398 | A | A | A |
| 399 | D | D |  |
| 400 | A | A | B |
| 401 | A | A | B |
| 402 | A | A | A |
| 403 | A | A | B |
| 404 | A | A | B |
| 405 | A | A | B |
| 406 | A | A | A |
| 407 | A | A | B |
| 408 | A | A | B |
| 409 | A | A | B |
| 410 | A | A | B |
| 411 | A | A | B |
| 412 | A | A | A |
| 413 | A | A | B |
| 414 | A | A | A |
| 415 | A | A | B |
| 416 | A | A | B |
| 417 | A | A | B |
| 418 | A | A | B |
| 419 | A | A | B |
| 420 | A | A | B |
| 421 | A | A |  |
| 422 | A | A | A |
| 423 | A | A | B |
| 424 | B | B | B |
| 425 | B | B | B |
| 426 | B | B | B |
| 427 | B | B | B |
| 428 | C | C | B |
| 429 | A | A | B |
| 430 | B | B | B |
| 431 | A | A | A |
| 432 | A | A | A |
| 433 | A | A | A |
| 434 | A | A | A |
| 435 | A | A | A |
| 436 | A | A | A |
| 437 | A | A | B |
| 438 | A | A | B |
| 439 | A | A | B |
| 440 | A | A | B |
| 441 | A | A | B |
| 442 | A | A | B |
| 443 | A | A | B |
| 444 | A | A | A |
| 445 | A | A | A |
| 447 | A | A | A |
| 448 | A | A | A |
| 449 | A | A | A |
| 450 | A | A | B |
| 451 | A | A | B |
| 452 | A | A | B |
| 453 | A | A |  |
| 454 | A | A | B |
| 455 | A | A | A |
| 456 | A | A | A |
| 457 | A | A | A |
| 459 | A | A | A |
| 460 | A | A | B |
| 461 | A | A | A |
| 462 | A | A | A |
| 463 | A | A | A |
| 465 | A | A | B |
| 466 | A | A | B |
| 467 | A | A | B |
| 468 | A | A |  |
| 469 | A | A |  |
| 470 | A | A | B |
| 471 | B | B | C |
| 472 | A | A | A |
| 473 | A | A | A |
| 474 | A | A | A |
| 475 | A | A | B |
| 476 | A | A | B |
| 477 | A | A | B |
| 478 | A | A | B |
| 479 | A | A | B |
| 480 | A | A | B |
| 481 | A | A | B |
| 482 | A | A | B |
| 483 | A | A | A |
| 484 | A | A | A |
| 485 | C | C | C |
| 486 | A | A | A |
| 487 | B | B | B |
| 488 | A | A | B |
| 489 | A | A | B |
| 490 | D |  |  |
| 491 | D |  |  |
| 492 | A | A | B |
| 493 | A | A | B |
| 494 | A | A | B |
| 495 | B | A |  |
| 496 | A | A |  |
| 497 | A | A | B |
| 498 | B | A | B |
| 499 | A | A | B |
| 500 | A | A | B |
| 501 | A | A | B |
| 502 | A | A | B |
| 503 | A | A | A |
| 504 | A | A | B |
| 505 | A | A | B |
| 506 | A | A | B |
| 507 | A | A | A |
| 508 | A | A | A |
| 509 | A | A | B |
| 510 | A | A | A |
| 511 | A | A | A |
| 512 | A | A | B |
| 513 | A | A | A |
| 514 | A | A | A |
| 515 | A | A | A |
| 516 | A | A | A |
| 517 | A | A | A |
| 518 | A | A | B |
| 519 | A | A | B |
| 520 | A | A | A |
| 521 | A | A | A |
| 522 | D |  |  |

D $IC_{50} > 5$ μM
C $IC_{50}$ ranges from 1 μM-5 μM
B $IC_{50}$ ranges from 100 nM-1.0 μM
A $IC_{50} < 100$ nM Example 483: Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula I,

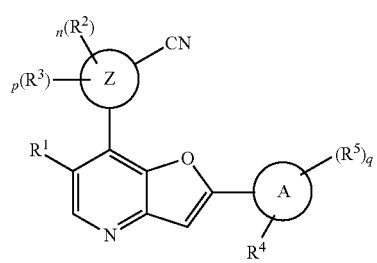

or pharmaceutically acceptable derivatives, solvates, salts, hydrates, or stereoisomers thereof, wherein:
R$^1$ is hydrogen, optionally substituted C$_{1-6}$ aliphatic, optionally substituted 3-8 membered saturated or partially unsaturated carbocyclic ring, —OR, or halogen;
ring Z is phenyl;
each R$^2$ is independently —R, halogen, —OR, or —N(R)$_2$;

each R$^3$ is independently —R, halogen, —OR, SR, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
ring A is

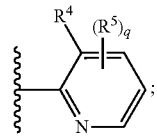

R$^4$ is —R, halogen, —OR, —NRC(O)R, —NRC(O)N(R)$_2$, —NRSO$_2$R, or —N(R)$_2$;
each R$^5$ is independently —R, halogen, —OR, —SR, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
each R is independently hydrogen, C$_{1-6}$ aliphatic, C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, a 5-6 membered monocyclic heteroaryl ring having 1-4 heteroatoms independently selected from nitrogen, oxygen, or sulfur; or a 6-12 membered spiro, fused, or bridged bicyclic carbocyclic or heterocyclic ring having 1-4 heteroatoms independently selected from nitrogen, oxygen, or sulfur; each of which is optionally substituted; or
two R groups on the same atom are taken together with the atom to which they are attached to form a C$_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
n is 1 or 2;
p is 0, 1, or 2; and
q is 0, 1, or 2.
2. The compound of claim 1, wherein each R$^2$ is independently —OH, —OCH$_3$, —F,

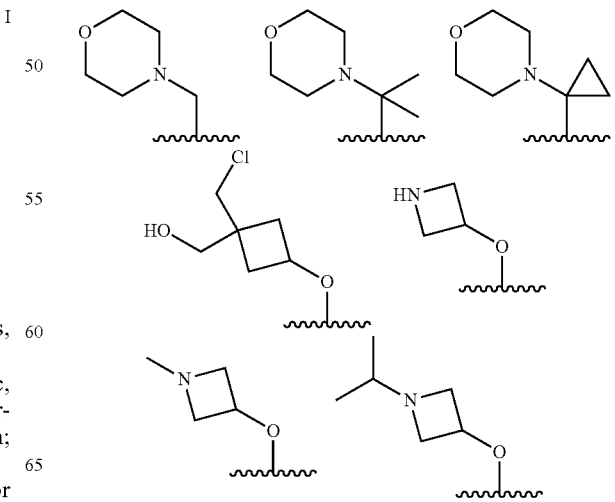

753
-continued
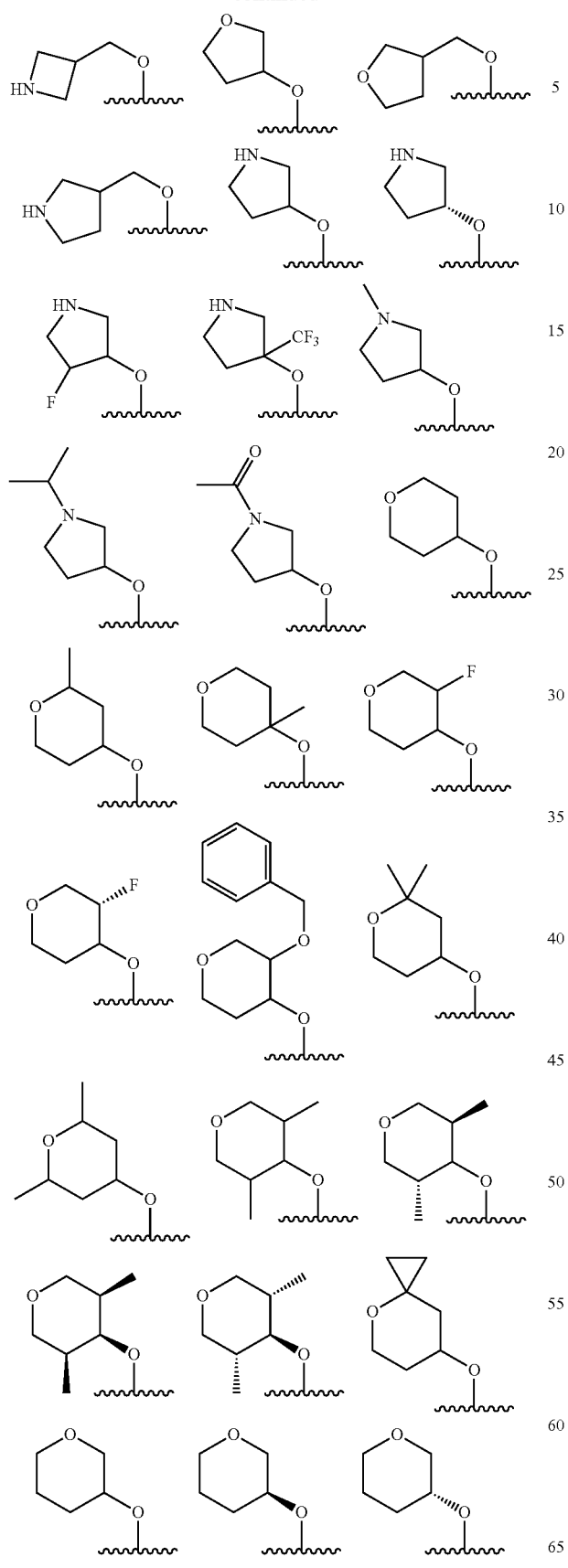
754
-continued
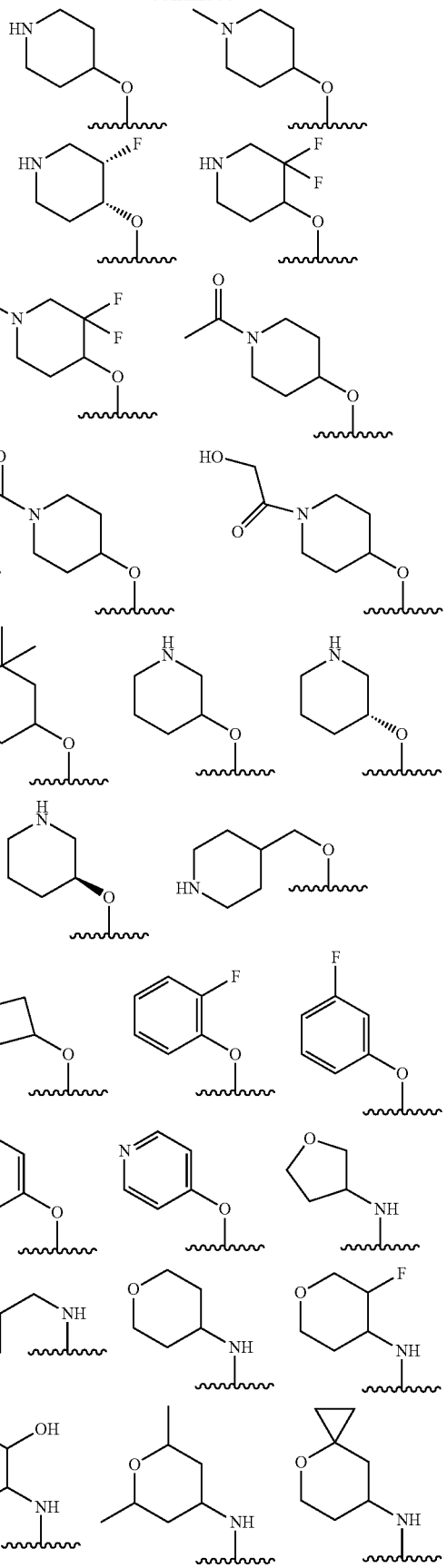

-continued

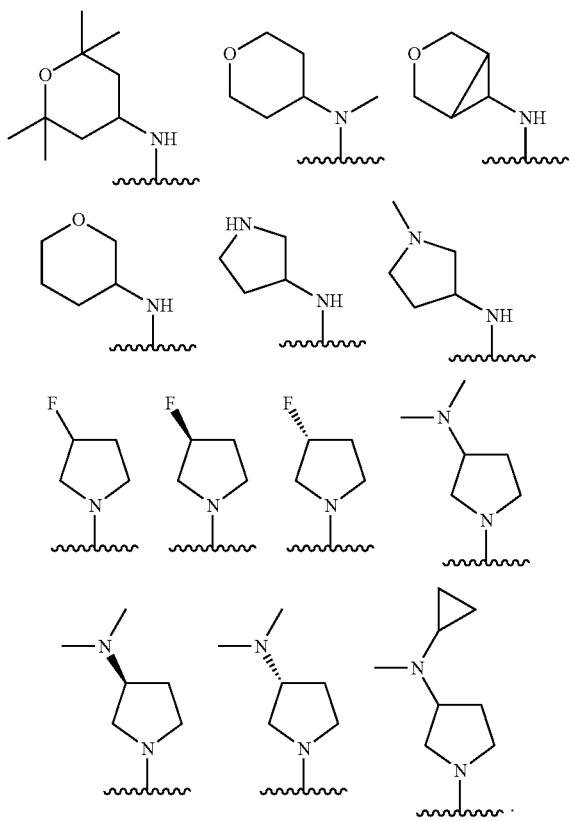

3. The compound of claim 1, wherein each $R^3$ is independently —R, halogen, —OR, or —N(R)$_2$.

4. The compound of claim 1, wherein ring Z is

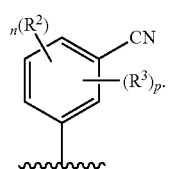

5. The compound of claim 1, wherein $R^4$ is -Me, -Et, —CF$_3$, —OH, —OCH$_3$, —OCF$_3$, —F, or —Cl.

6. The compound of claim 1, wherein each $R^5$ is independently —R, —CO$_2$R, —C(O)N(R)$_2$, —NRC(O)R, or —N(R)$_2$.

7. The compound of claim 6, wherein each $R^5$ is independently —CO$_2$R, —C(O)N(R)$_2$, —NRC(O)R, or —N(R)$_2$.

8. The compound of claim 6, wherein each $R^5$ is independently —NH$_2$, —NHC(O)Me,

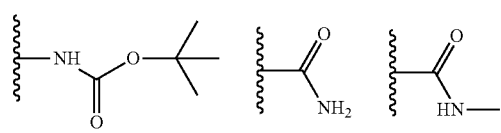

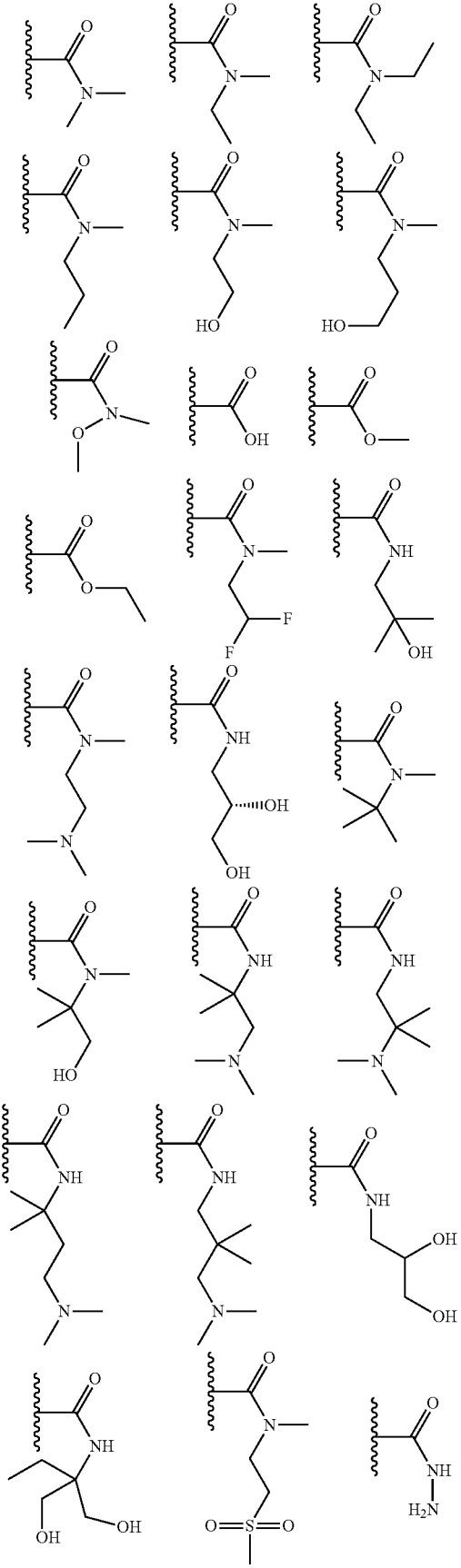

757
-continued
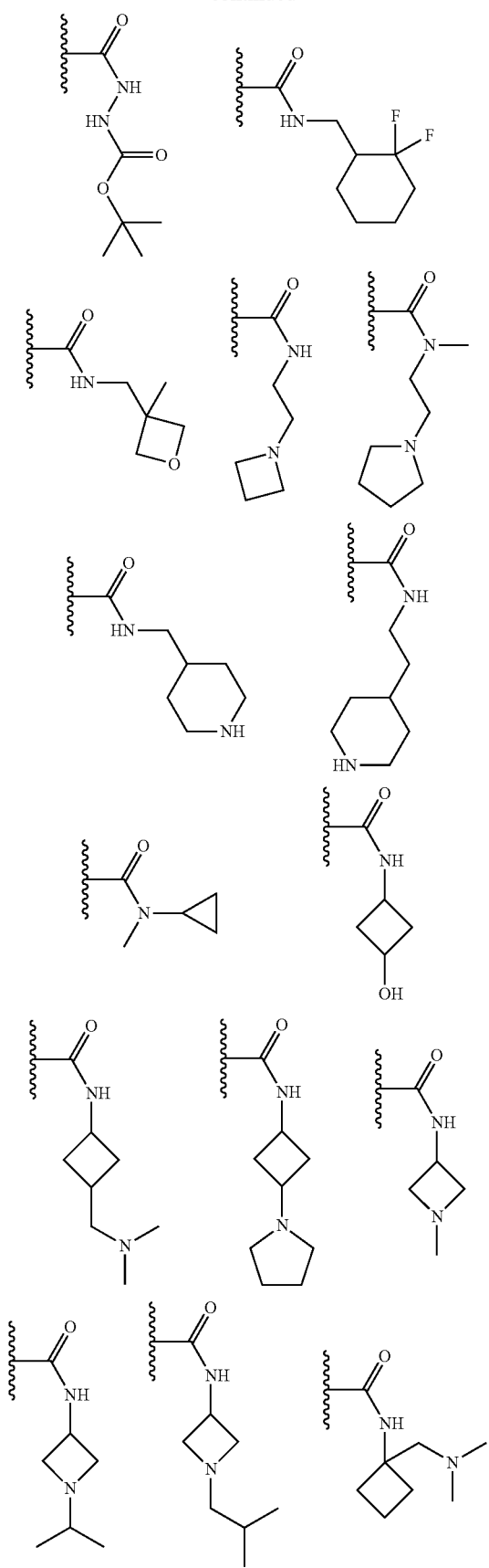
758
-continued
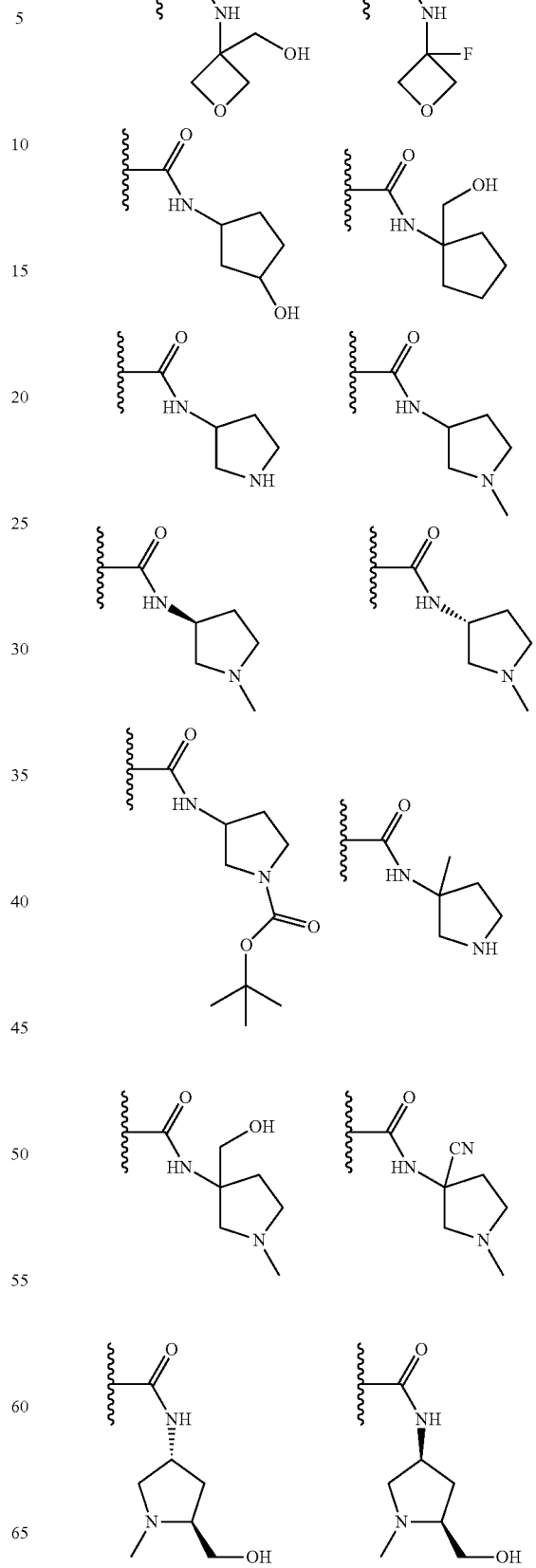

759
-continued
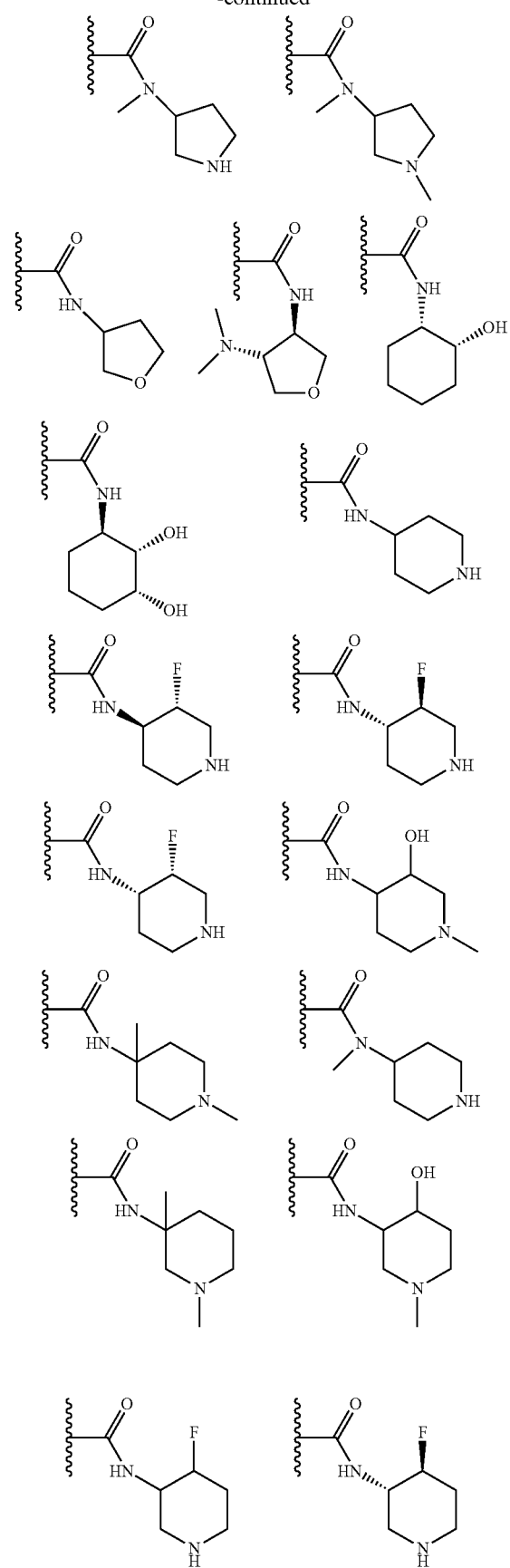
760
-continued
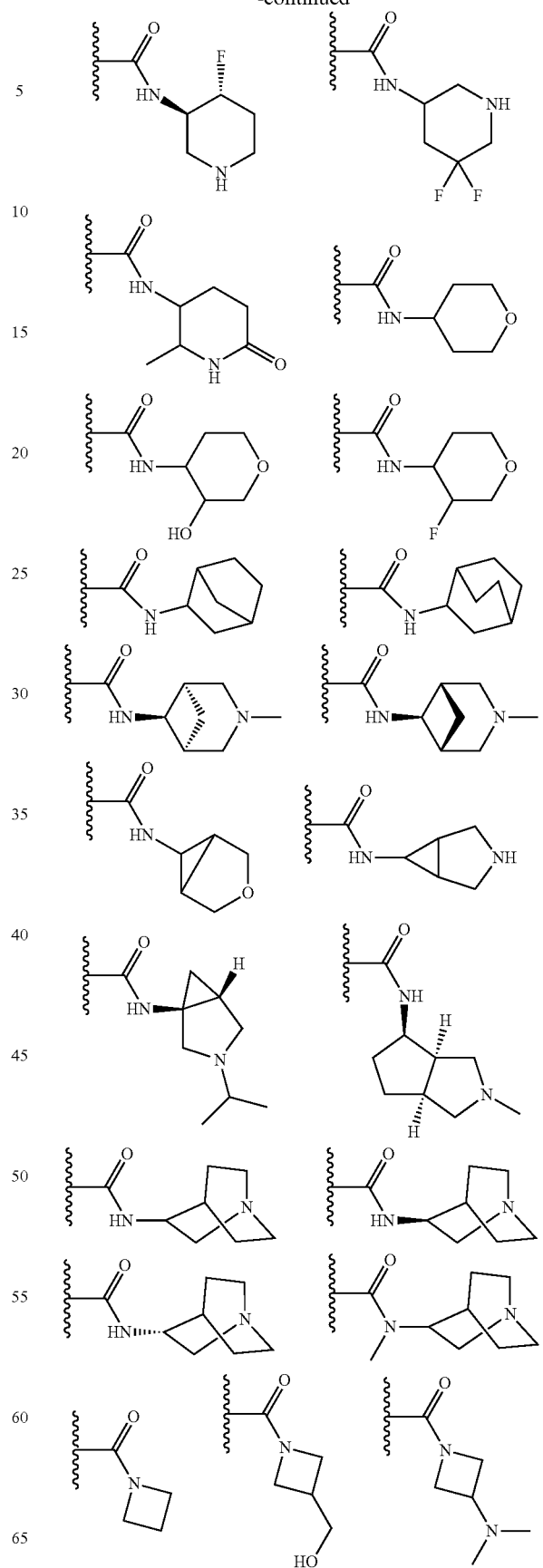

761
-continued
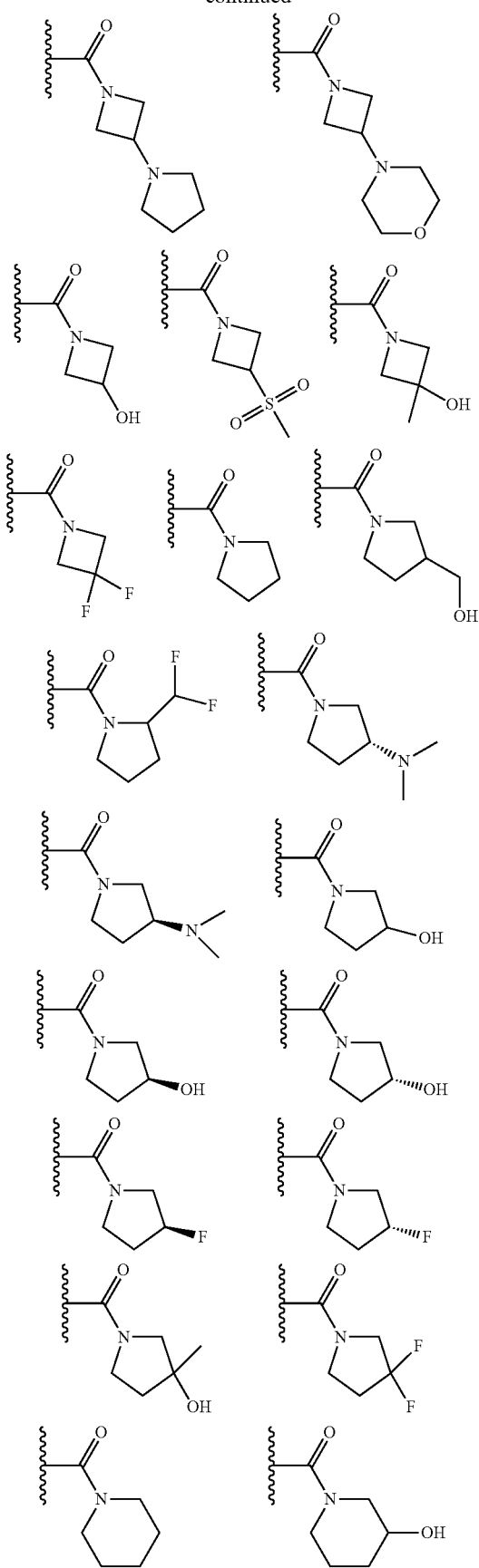
762
-continued
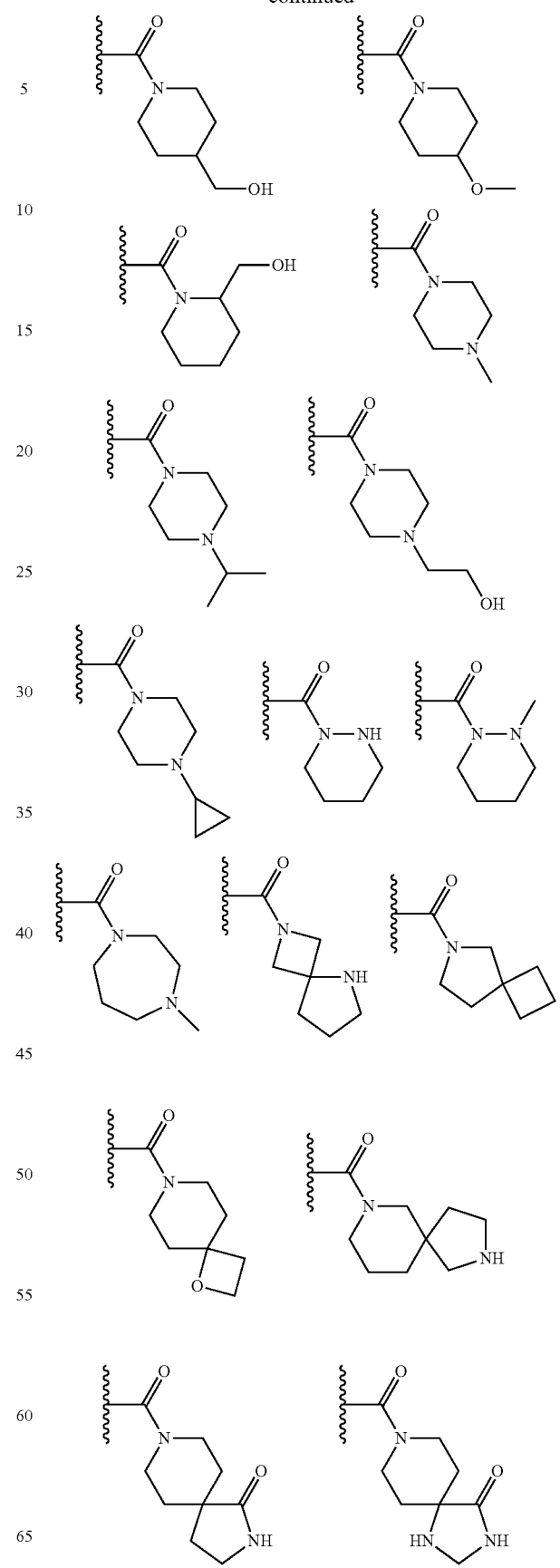

763
-continued
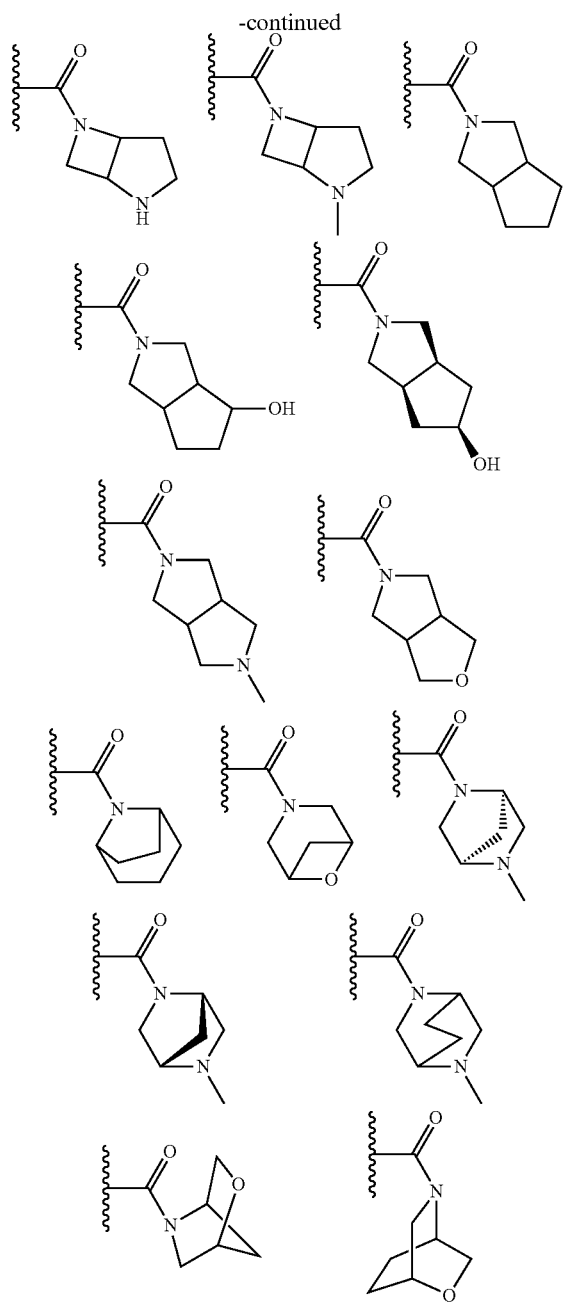
764
-continued
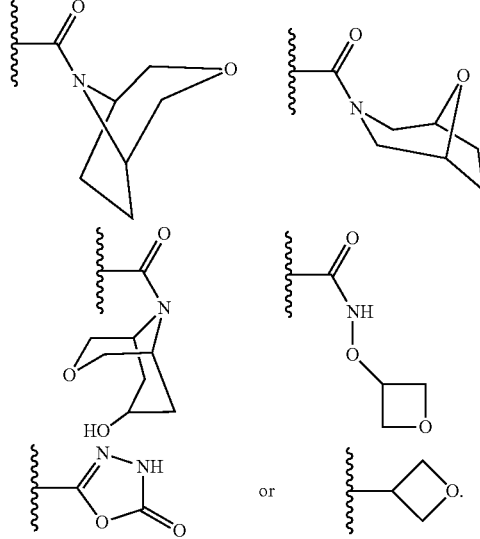
9. The compound of claim 1, of formula VII,
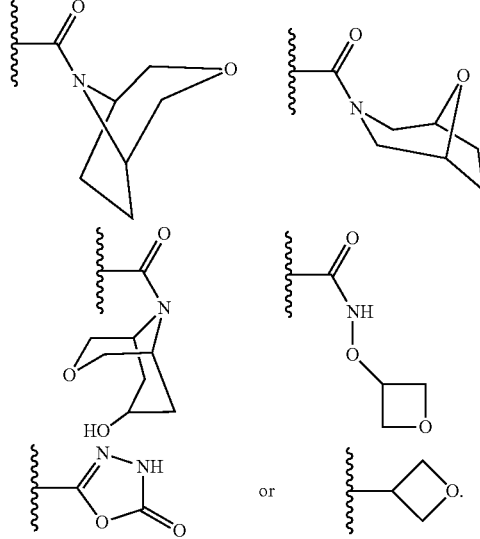
or pharmaceutically acceptable derivatives, solvates, salts, hydrates, or stereoisomers thereof.
10. The compound of claim 1, selected from compounds 190, 210, 243-249, 270, 272-274, 317-320, 323, 328-330, 332-337, 339-343, 381, 391, 392, 397, 398, 403-412, 414-417, 420, 422, 425-427, 432, 433, 435, 436, 438-442, 446-448, 452, 454-456, 460-462, 465-467, 486, 487, 490, 491, 518, and 522.
11. A pharmaceutical composition comprising a compound of claim 1, and a pharmaceutically acceptable adjuvant, carrier, or vehicle.
* * * * *